United States Patent
Kumar KC et al.

(10) Patent No.: US 9,828,372 B2
(45) Date of Patent: Nov. 28, 2017

(54) 2-(1H-INDAZOL-3-YL)-1H-IMIDAZO[4,5-C] PYRIDINE AND THERAPEUTIC USES THEREOF

(71) Applicant: Samumed, LLC, San Diego, CA (US)

(72) Inventors: Sunil Kumar KC, San Diego, CA (US); David Mark Wallace, San Diego, CA (US); Jianguo Cao, San Diego, CA (US); Chandramouli Chiruta, San Diego, CA (US); John Hood, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 15/298,346

(22) Filed: Oct. 20, 2016

(65) Prior Publication Data
US 2017/0260179 A1    Sep. 14, 2017

Related U.S. Application Data

(63) Continuation of application No. 14/847,259, filed on Sep. 8, 2015, now Pat. No. 9,475,807.

(60) Provisional application No. 62/047,324, filed on Sep. 8, 2014.

(51) Int. Cl.
*A61K 31/437*    (2006.01)
*C07D 471/04*    (2006.01)

(52) U.S. Cl.
CPC ................... *C07D 471/04* (2013.01)

(58) Field of Classification Search
CPC .................................................. A61K 31/437
USPC .......................................................... 514/303
See application file for complete search history.

(56) References Cited

U.S. PATENT DOCUMENTS 6,884,890 B2 *    4/2005    Kania ................... C07D 209/18
                                                          546/275.7

* cited by examiner

*Primary Examiner* — Niloofar Rahmani
(74) *Attorney, Agent, or Firm* — Fish & Richardson P.C.

(57) ABSTRACT

Indazole compounds for treating various diseases and pathologies are disclosed. More particularly, the present invention concerns the use of an indazole compound or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

36 Claims, No Drawings

2-(1H-INDAZOL-3-YL)-1H-IMIDAZO[4,5-C] PYRIDINE AND THERAPEUTIC USES THEREOF

RELATED APPLICATIONS

This application is a continuation of U.S. application Ser. No. 14/847,259, filed Sep. 8, 2015, which claims the benefit of U.S. Provisional Application No. 62/047,324, filed Sep. 8, 2014, both of which are incorporated herein by reference in their entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an indazole compound or salts or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic 3-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

SUMMARY

The present disclosure provides methods and reagents, involving contacting a cell with an agent, such as an indazole compound, in a sufficient amount to antagonize a Wnt activity, e.g., to reverse or control an aberrant growth state or correct a genetic disorder due to mutations in Wnt signaling components.

Some embodiments disclosed herein include Wnt inhibitors containing an indazole core. Other embodiments disclosed herein include pharmaceutical compositions and methods of treatment using these compounds.

One embodiment disclosed herein includes a compound having the structure of Formula I:

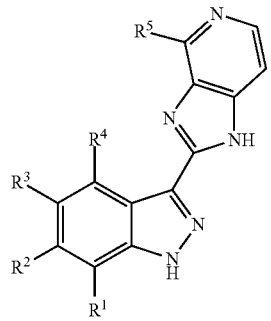

as well as prodrugs and pharmaceutically acceptable salts thereof.

In some embodiments of Formula (I):

$R^1$, $R^2$, and $R^4$ are independently selected from the group consisting of H and halide;

$R^3$ is selected from the group consisting of -heteroaryl $(R^6)_q$ and -heterocyclyl$(R^7)_h$;

$R^5$ is selected from the group consisting of -heteroaryl $(R^8)_q$, -heterocyclyl$(R^9)_h$, and -aryl$(R^{10})_k$;

each $R^6$ is one substituent attached to the heteroaryl and is independently selected from the group consisting of halide, —($C_{1-6}$ alkyl), —($C_{1-4}$ alkylene)$_p$heterocyclyl$(R^{11})_h$, —($C_{1-4}$ alkylene)$_p$carbocyclyl$(R^{12})_j$, —($C_{1-4}$ alkylene)$_p$aryl $(R^{13})_k$, —NHC(=O)$R^{14}$, —NR$^{15}$R$^{16}$, —($C_{1-6}$ alkylene) NR$^{17}$R$^{18}$, and —OR$^{24}$;

each $R^7$ is one substituent attached to the heterocyclyl and is independently selected from the group consisting of —($C_{1-4}$ alkyl), halide, —CF$_3$, and —CN;

each $R^8$ is one substituent attached to the heteroaryl and is independently selected from the group consisting of —($C_{1-6}$ alkyl), halide, —CF$_3$, —OCH$_3$, —CN, and —C(=O)R$^{19}$;

each $R^9$ is one substituent attached to the heterocyclyl and is independently selected from the group consisting of —($C_{1-6}$ alkyl), halide, —CF$_3$, —CN, and —OCH$_3$;

each $R^{10}$ is one substituent attached to the aryl and is independently selected from the group consisting of —($C_{1-6}$ alkyl), halide, —CF$_3$, —CN, —OCH$_3$, —($C_{1-6}$ alkylene)$_p$ NHSO$_2$R$^{19}$, —NR$^{15}$($C_{1-6}$ alkylene)NR$^{15}$R$^{16}$, —($C_{1-6}$ alkylene)$_p$NR$^{15}$R$^{16}$, and —OR$^{27}$;

each $R^{11}$ is one substituent attached to the heterocyclyl and is independently selected from the group consisting of amino, —($C_{1-4}$ alkyl), halide, —CF$_3$, and —CN;

each $R^{12}$ is one substituent attached to the carbocyclyl and is independently selected from the group consisting of —($C_{1-4}$ alkyl), halide, —CF$_3$, and —CN;

each $R^{13}$ is one substituent attached to the aryl and is independently selected from the group consisting of —($C_{1-4}$ alkyl), halide, —CF$_3$, and —CN;

each $R^{14}$ is independently selected from the group consisting of —($C_{1-9}$ alkyl), -heteroaryl$(R^{20})_q$, -aryl$(R^{21})_k$, —CH$_2$aryl$(R^{21})_k$, -carbocyclyl$(R^{22})_j$, —CH$_2$carbocyclyl $(R^{22})_j$, —($C_{1-4}$ alkylene)$_p$NR$^{25}$R$^{26}$, -heterocyclyl$(R^{23})_h$, and —CH$_2$heterocyclyl$(R^{23})_h$;

each $R^{15}$ is independently selected from the group consisting of H and —($C_{1-6}$ alkyl);

each $R^{16}$ is independently selected from the group consisting of H, —($C_{1-6}$ alkyl), —CH$_2$aryl$(R^{21})_k$, and —CH$_2$carbocyclyl$(R^{22})_j$;

each $R^{17}$ is independently selected from the group consisting of H and —($C_{1-6}$ alkyl);

each $R^{18}$ is independently selected from the group consisting of H, —($C_{1-6}$ alkyl), —$CH_2$aryl($R^{21}$)$_k$, and —$CH_2$carbocyclyl($R^{22}$)$_j$;

each $R^{19}$ is a —($C_{1-6}$ alkyl);

each $R^{20}$ is one substituent attached to the heteroaryl and is independently selected from the group consisting of —($C_{1-4}$ alkyl), halide, —$CF_3$, and —CN;

each $R^{21}$ is one substituent attached to the aryl and is independently selected from the group consisting of —($C_{1-4}$ alkyl), halide, —$CF_3$, and —CN;

each $R^{22}$ is one substituent attached to the carbocyclyl and is independently selected from the group consisting of —($C_{1-4}$ alkyl), halide, —$CF_3$, and —CN;

each $R^{23}$ is one substituent attached to the heterocyclyl and is independently selected from the group consisting of —($C_{1-4}$ alkyl), halide, —$CF_3$, and —CN;

each $R^{24}$ is independently selected from the group consisting of H, —($C_{1-6}$ alkyl), —($C_{1-4}$ alkylene)$_p$heterocyclyl($R^{23}$)$_h$, —($C_{1-4}$ alkylene)$_p$carbocyclyl($R^{22}$)$_j$, —($C_{1-4}$ alkylene)$_p$aryl($R^{21}$)$_k$, and —($C_{1-6}$ alkylene)$_p$NR$^{25}$R$^{26}$;

each $R^{25}$ is independently selected from the group consisting of H and —($C_{1-6}$ alkyl);

each $R^{26}$ is independently selected from the group consisting of H and —($C_{1-6}$ alkyl);

each $R^{27}$ is independently selected from the group consisting of H, —($C_{1-6}$ alkyl), —($C_{1-4}$ alkylene)$_p$heterocyclyl($R^{23}$)$_h$, and —($C_{1-6}$ alkylene)$_p$NR$^{25}$R$^{26}$;

each p is independently 0 or 1;

each q is independently 0 to 4;

each h is independently 0 to 10;

each k is independently 0 to 5; and each j is independently 0 to 12.

Some embodiments include stereoisomers and pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-Amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the invention, as claimed.

DETAILED DESCRIPTION

Provided herein are compositions and methods for inhibiting one or more members of the Wnt pathway, including one or more Wnt proteins. Other Wnt inhibitors and methods for using the same are disclosed in U.S. application Ser. Nos. 12/852,706; 12/968,505; 13/552,188; 13/800,963; 13/855,874; 13/887,177 13/938,691; 13/938,692; 14/019,103; 14/019,147; 14/019,940; 14/149,948; 14/178,749; 14/331,427; and Ser. No. 14/334,005; and U.S. Provisional Application Ser. Nos. 61/232,603; 61/288,544; 61/305,459; 61/620,107; 61/642,915; and 61/750,221, all of which are incorporated by reference in their entirety herein.

Some embodiments provided herein relate to a method for treating a disease or disorder including, but not limited to, cancers, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, osteoarthritis, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG) and other eye diseases or syndromes associated with defects or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, bone/osteoporotic (wrist, spine, shoulder and hip) fractures, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. Alkyl groups can be saturated or unsaturated (e.g., containing —C=C— or —C≡C— subunits), at one or several positions. In some embodiments, alkyl groups include 1 to 9 carbon atoms (for example, 1 to 6 carbon atoms, 1 to 4 carbon atoms, or 1 to 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "lower alkyl" means a subset of alkyl having 1 to 3 carbon atoms, which is linear or branched. Examples of lower alkyls include methyl, ethyl, n-propyl and isopropyl. Likewise, radicals using the terminology "lower" refer to radicals having 1 to about 3 carbons in the alkyl portion of the radical.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, and others. In some embodiments, the heteroaryl is selected from thienyl, pyridinyl, furyl, pyrazolyl, imidazolyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —$NH(C_{1-3}$ alkyl), and —$N(C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —$NH(C_{1-3}$ alkyl), and —$N(C_{1-3}$ alkyl)$_2$; —$OPO(OH)_2$; a phosphonate [such as —$PO(OH)_2$ and —$PO(OR')_2$]; —OPO(OR')R''; —NRR'; —C(O)NRR'; —C(NR)NR'R''; —C(NR')R''; a cyano; a nitro; an azido; —SH; —S—R; —$OSO_2(OR)$; a sulfonate [such as —$SO_2$(OH) and —$SO_2(OR)$]; —$SO_2NR'R''$; and —$SO_2R$; in which each occurrence of R, R' and R'' are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracysticalIy, intrapleurally, via wound irrigation, intrabuccally, intraabdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics*, 12*th Ed.*, The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Solvate" refers to the compound formed by the interaction of a solvent and a compound as provided herein or a salt thereof. Suitable solvates are pharmaceutically acceptable solvates including hydrates.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" or "pharmaceutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and/or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present disclosure include compounds of Formula I:

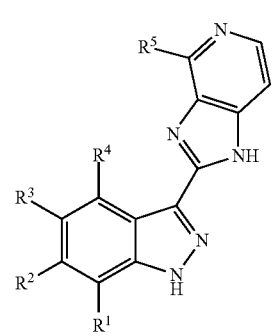

or salts, pharmaceutically acceptable salts, or prodrugs thereof.

In some embodiments, $R^1$, $R^2$, and $R^4$ are independently selected from the group consisting of H and halide.

In some embodiments, $R^3$ is selected from the group consisting of -pyridinyl$(R^6)_q$ and -pyrimidinyl$(R^7)_q$.

In some embodiments, $R^3$ is selected from the group consisting of -piperidinyl$(R^7)_h$ and -tetrahydropyridinyl$(R^7)_h$.

In some embodiments, $R^3$ is selected from the group consisting of -pyridinyl$(R^6)$, -pyrimidinyl$(R^6)_q$, -pyrazinyl$(R^6)_q$, -pyrazolyl$(R^6)_q$, and -imidazolyl$(R^6)_q$.

In some embodiments, $R^3$ is selected from the group consisting of -heteroaryl$(R^6)_q$ and -heterocyclyl$(R^7)_h$.

In some embodiments, $R^5$ is selected from the group consisting of -heteroaryl$(R^8)_q$, -heterocyclyl$(R^9)_h$, and -aryl$(R^{10})_k$.

In some embodiments, $R^5$ is selected from the group consisting of -pyridinyl$(R^8)_q$, -imidazolyl$(R^8)_q$, -furanyl$(R^8)_q$, -thiophenyl$(R^8)_q$, -piperidinyl$(R^9)_h$, -piperazinyl$(R^9)_h$, and -phenyl$(R^{10})_k$.

In some embodiments, each $R^6$ is one substituent attached to the pyridinyl and is independently selected from the group consisting of H, halide, —($C_{1-6}$ alkyl), —($C_{1-4}$ alkylene)$_p$heterocyclyl($R^{11}$)$_h$, —($C_{1-4}$ alkylene)$_p$carbocyclyl($R^{12}$)$_j$, —($C_{1-4}$ alkylene)$_p$aryl($R^{13}$)$_k$, —NHC(=O)$R^{14}$, —N$R^{15}R^{16}$, —($C_{1-6}$ alkylene)N$R^{17}R^{18}$, and —O$R^{24}$.

In some embodiments, each $R^6$ is one substituent attached to the pyridinyl and is independently selected from the group consisting of halide, —($C_{1-6}$ alkyl), —($C_{1-4}$ alkylene)$_p$heterocyclyl($R^{11}$)$_h$, —($C_{1-4}$ alkylene)$_p$carbocyclyl($R^{12}$)$_j$, —($C_{1-4}$ alkylene)$_p$aryl($R^{13}$)$_k$, —NHC(=O)$R^{14}$, —N$R^{15}R^{16}$, —($C_{1-6}$ alkylene)N$R^{17}R^{18}$, and —O$R^{24}$.

In some embodiments, each $R^6$ is one substituent attached to the heteroaryl and is independently selected from the group consisting of H, halide, —($C_{1-6}$ alkyl), —($C_{1-4}$ alkylene)$_p$heterocyclyl($R^{11}$)$_h$, —($C_{1-4}$ alkylene)$_p$carbocyclyl($R^{12}$)$_j$, —($C_{1-4}$ alkylene)$_p$aryl($R^{13}$)$_k$, —NHC(=O)$R^{14}$, —N$R^{15}R^{16}$, —($C_{1-6}$ alkylene)N$R^{17}R^{18}$, and —O$R^{24}$.

In some embodiments, each $R^6$ is one substituent attached to the heteroaryl and is independently selected from the group consisting of halide, —($C_{1-6}$ alkyl), —($C_{1-4}$ alkylene)$_p$heterocyclyl($R^{11}$)$_h$, —($C_{1-4}$ alkylene)$_p$carbocyclyl($R^{12}$)$_j$, —($C_{1-4}$ alkylene)$_p$aryl($R^{13}$)$_k$, —NHC(=O)$R^{14}$, —N$R^{15}R^{16}$, —($C_{1-6}$ alkylene)N$R^{17}R^{18}$, and —O$R^{24}$.

In some embodiments, each $R^6$ is one substituent attached to the heteroaryl and is independently selected from the group consisting of F, -Me, -Et, —(CH$_2$)heterocyclyl($R^{11}$)$_h$, -heterocyclyl($R^{11}$)$_h$, —(CH$_2$)carbocyclyl($R^{12}$)$_j$, —(CH$_2$)aryl($R^{13}$)$_k$, —NHC(=O)($C_{1-5}$ alkyl), —NHC(=O)phenyl($R^{21}$)$_k$, —NHC(=O)(CH$_2$)phenyl($R^{21}$)$_k$, —NHC(=O)carbocyclyl($R^{22}$)$_j$, —NHC(=O)(CH$_2$)heterocyclyl($R^{23}$)$_h$, —NH$_2$, —N($C_{1-3}$ alkyl)$_2$, —NH($C_{1-4}$ alkyl), —(CH$_2$)N($C_{1-3}$ alkyl)$_2$, —(CH$_2$)NH($C_{1-4}$ alkyl), —OH, —O($C_{1-3}$ alkyl), —Ocarbocyclyl($R^{22}$)$_j$, —Oheterocyclyl($R^{23}$)$_h$, —O(CH$_2$CH$_2$)heterocyclyl($R^{23}$)$_h$, —O(CH$_2$CH$_2$)N($C_{1-3}$ alkyl)$_2$, and —O(CH$_2$)phenyl($R^{21}$)$_k$.

In some embodiments, each $R^7$ is one substituent attached to the pyrimidinyl and is independently selected from the group consisting of H, halide, —($C_{1-6}$ alkyl), —($C_{1-4}$ alkylene)$_p$heterocyclyl($R^{11}$)$_h$, —($C_{1-4}$ alkylene)$_p$carbocyclyl($R^{12}$)$_j$, —($C_{1-4}$ alkylene)$_p$aryl($R^{13}$)$_k$, —NHC(=O)$R^{14}$, —N$R^{15}R^{16}$, —($C_{1-6}$ alkylene)N$R^{17}R^{18}$, and —O$R^{24}$.

In some embodiments, each $R^7$ is one substituent attached to the pyrimidinyl and is independently selected from the group consisting of halide, —($C_{1-6}$ alkyl), —($C_{1-4}$ alkylene)$_p$heterocyclyl($R^{11}$)$_h$, —($C_{1-4}$ alkylene)$_p$carbocyclyl($R^{12}$)$_j$, —($C_{1-4}$ alkylene)$_p$aryl($R^{13}$)$_k$, —NHC(=O)$R^{14}$, —N$R^{15}R^{16}$, —($C_{1-6}$ alkylene)N$R^{17}R^{18}$, and —O$R^{24}$.

In some embodiments, each $R^7$ is one substituent attached to the pyrimidinyl and is independently selected from the group consisting of H, —($C_{1-4}$ alkyl), halide, —CF$_3$, and —CN.

In some embodiments, each $R^7$ is one substituent attached to the heterocyclyl and is independently selected from the group consisting of —($C_{1-4}$ alkyl), halide, —CF$_3$, and —CN.

In some embodiments, each $R^8$ is one substituent attached to the heteroaryl and is independently selected from the group consisting of H, —($C_{1-6}$ alkyl), halide, —CF$_3$, —OCH$_3$, —CN, and —C(=O)$R^{19}$.

In some embodiments, each $R^8$ is one substituent attached to the heteroaryl and is independently selected from the group consisting of —($C_{1-6}$ alkyl), halide, —CF$_3$, —OCH$_3$, —CN, and —C(=O)$R^{19}$.

In some embodiments, each $R^8$ is one substituent attached to the heteroaryl and is independently selected from the group consisting of H, -Me, -Et, F, —CF$_3$, —OCH$_3$, —CN, and —C(=O)($C_{1-3}$ alkyl).

In some embodiments, each $R^8$ is one substituent attached to the heteroaryl and is independently selected from the group consisting of -Me, -Et, F, —CF$_3$, —OCH$_3$, —CN, and —C(=O)($C_{1-3}$ alkyl).

In some embodiments, each $R^9$ is one substituent attached to the heterocyclyl and is independently selected from the group consisting of H, —($C_{1-6}$ alkyl), halide, —CF$_3$, —CN, and —OCH$_3$.

In some embodiments, each $R^9$ is one substituent attached to the heterocyclyl and is independently selected from the group consisting of —($C_{1-6}$ alkyl), halide, —CF$_3$, —CN, and —OCH$_3$.

In some embodiments, each $R^{10}$ is one substituent attached to the aryl and is independently selected from the group consisting of H, —($C_{1-6}$ alkyl), halide, —CF$_3$, —CN, —OCH$_3$, —($C_{1-6}$ alkylene)$_p$NHSO$_2R^{19}$, —N$R^{15}$($C_{1-6}$ alkylene)N$R^{15}R^{16}$, —($C_{1-6}$ alkylene)$_p$N$R^{15}R^{16}$, and —O$R^{27}$.

In some embodiments, each $R^{10}$ is one substituent attached to the aryl and is independently selected from the group consisting of —($C_{1-6}$ alkyl), halide, —CF$_3$, —CN, —OCH$_3$, —($C_{1-6}$ alkylene)$_p$NHSO$_2R^{19}$, —N$R^{15}$($C_{1-6}$ alkylene)N$R^{15}R^{16}$, —($C_{1-6}$ alkylene)$_p$N$R^{15}R^{16}$, and —O$R^{27}$.

In some embodiments, each $R^{10}$ is one substituent attached to the aryl and is independently selected from the group consisting of H, -Me, -Et, F, —CF$_3$, —CN, —OCH$_3$, —(CH$_2$CH$_2$)NHSO$_2$($C_{1-3}$ alkyl), —NH(CH$_2$CH$_2$)N($C_{1-3}$ alkyl)$_2$, —OH, —O($C_{1-3}$ alkyl), —O(CH$_2$CH$_2$)heterocyclyl($R^{23}$)$_h$, and —O(CH$_2$CH$_2$)N($C_{1-3}$ alkyl)$_2$.

In some embodiments, each $R^{10}$ is one substituent attached to the aryl and is independently selected from the group consisting of -Me, -Et, F, —CF$_3$, —CN, —OCH$_3$, —(CH$_2$CH$_2$)NHSO$_2$($C_{1-3}$ alkyl), —NH(CH$_2$CH$_2$)N($C_{1-3}$ alkyl)$_2$, —OH, —O($C_{1-3}$ alkyl), —O(CH$_2$CH$_2$)heterocyclyl($R^{23}$)$_h$, and —O(CH$_2$CH$_2$)N($C_{1-3}$ alkyl)$_2$.

In some embodiments, each $R^{11}$ is one substituent attached to the heterocyclyl and is independently selected from the group consisting of H, amino, —($C_{1-4}$ alkyl), halide, —CF$_3$, and —CN.

In some embodiments, each $R^{11}$ is one substituent attached to the heterocyclyl and is independently selected from the group consisting of amino, —($C_{1-4}$ alkyl), halide, —CF$_3$, and —CN.

In some embodiments, each $R^{11}$ is one substituent attached to the heterocyclyl and is independently selected from the group consisting of amino, Me, Et, F, Cl, and —CF$_3$.

In some embodiments, each $R^{12}$ is one substituent attached to the carbocyclyl and is independently selected from the group consisting of H, —($C_{1-4}$ alkyl), halide, —CF$_3$, and —CN.

In some embodiments, each $R^{12}$ is one substituent attached to the carbocyclyl and is independently selected from the group consisting of —($C_{1-4}$ alkyl), halide, —CF$_3$, and —CN.

In some embodiments, each $R^{12}$ is one substituent attached to the carbocyclyl and is independently selected from the group consisting of Me, Et, F, Cl, and —CF$_3$.

In some embodiments, each $R^{13}$ is one substituent attached to the aryl and is independently selected from the group consisting of H, —($C_{1-4}$ alkyl), halide, —CF$_3$, and —CN.

In some embodiments, each $R^{13}$ is one substituent attached to the aryl and is independently selected from the group consisting of —($C_{1-4}$ alkyl), halide, —$CF_3$, and —CN.

In some embodiments, each $R^{13}$ is one substituent attached to the aryl and is independently selected from the group consisting of Me, Et, F, Cl, and —$CF_3$.

In some embodiments, each $R^{14}$ is independently selected from the group consisting of —($C_{1-9}$ alkyl), -heteroaryl($R^{20}$)$_q$, -aryl($R^{21}$)$_k$, —$CH_2$aryl($R^{21}$)$_k$, -carbocyclyl($R^{22}$)$_j$, and —$CH_2$carbocyclyl($R^{22}$)$_j$.

In some embodiments, each $R^{14}$ is independently selected from the group consisting of —($C_{1-9}$ alkyl), -heteroaryl($R^{20}$)$_q$, -aryl($R^{21}$)$_k$, —$CH_2$aryl($R^{21}$)$_k$, -carbocyclyl($R^{22}$)$_j$, —$CH_2$carbocyclyl($R^{22}$)$_j$, —($C_{1-4}$ alkylene)$_p$NR$^{25}$R$^{26}$, -heterocyclyl($R^{23}$)$_h$, and —$CH_2$heterocyclyl($R^{23}$)$_h$.

In some embodiments, each $R^{14}$ is independently selected from the group consisting of —($C_{1-5}$ alkyl), -phenyl($R^{21}$)$_k$, —($CH_2$)phenyl($R^{21}$)$_k$, -carbocyclyl($R^{22}$)$_j$, —($CH_2$)carbocyclyl($R^{22}$)$_j$, —($CH_2$)N($C_{1-3}$ alkyl)$_2$, and —($CH_2$)heterocyclyl($R^{23}$)$_h$.

In some embodiments, each $R^{15}$ is independently selected from the group consisting of H and —($C_{1-6}$ alkyl).

In some embodiments, each $R^{15}$ is independently selected from the group consisting of H and —($C_{1-3}$ alkyl).

In some embodiments, each $R^{16}$ is independently selected from the group consisting of H, —($C_{1-6}$ alkyl), —$CH_2$aryl($R^{21}$)$_k$, and —$CH_2$carbocyclyl($R^{22}$)$_j$.

In some embodiments, each $R^{16}$ is independently selected from the group consisting of H, —($C_{1-3}$ alkyl), —$CH_2$phenyl($R^{21}$)$_k$, and —$CH_2$carbocyclyl($R^{22}$)$_j$.

In some embodiments, each $R^{17}$ is independently selected from the group consisting of H and —($C_{1-6}$ alkyl).

In some embodiments, each $R^{17}$ is independently selected from the group consisting of H and —($C_{1-3}$ alkyl).

In some embodiments, each $R^{18}$ is independently selected from the group consisting of H, —($C_{1-6}$ alkyl), —$CH_2$aryl($R^{21}$)$_k$, and —$CH_2$carbocyclyl($R^{22}$)$_j$.

In some embodiments, each $R^{18}$ is independently selected from the group consisting of H, —($C_{1-3}$ alkyl), —$CH_2$phenyl($R^{21}$)$_k$, and —$CH_2$carbocyclyl($R^{22}$)$_j$.

In some embodiments, each $R^{19}$ is independently a —($C_{1-6}$ alkyl).

In some embodiments, each $R^{19}$ is independently a —($C_{1-3}$ alkyl).

In some embodiments, each $R^{20}$ is one substituent attached to the heteroaryl and is independently selected from the group consisting of H, —($C_{1-4}$ alkyl), halide, —$CF_3$, and —CN.

In some embodiments, each $R^{20}$ is one substituent attached to the heteroaryl and is independently selected from the group consisting of —($C_{1-4}$ alkyl), halide, —$CF_3$, and —CN.

In some embodiments, each $R^{20}$ is one substituent attached to the heteroaryl and is independently selected from the group consisting of Me, Et, F, Cl, and —$CF_3$.

In some embodiments, each $R^{21}$ is one substituent attached to the aryl and is independently selected from the group consisting of H, —($C_{1-4}$ alkyl), halide, —$CF_3$, and —CN.

In some embodiments, each $R^{21}$ is one substituent attached to the aryl and is independently selected from the group consisting of —($C_{1-4}$ alkyl), halide, —$CF_3$, and —CN.

In some embodiments, each $R^{21}$ is one substituent attached to the aryl and is independently selected from the group consisting of Me, Et, F, Cl, and —$CF_3$.

In some embodiments, each $R^{22}$ is one substituent attached to the carbocyclyl and is independently selected from the group consisting of H, —($C_{1-4}$ alkyl), halide, —$CF_3$, and —CN.

In some embodiments, each $R^{22}$ is one substituent attached to the carbocyclyl and is independently selected from the group consisting of —($C_{1-4}$ alkyl), halide, —$CF_3$, and —CN.

In some embodiments, each $R^{22}$ is one substituent attached to the carbocyclyl and is independently selected from the group consisting of Me, Et, F, Cl, and —$CF_3$.

In some embodiments, each $R^{23}$ is one substituent attached to the heterocyclyl and is independently selected from the group consisting of H, —($C_{1-4}$ alkyl), halide, —$CF_3$, and —CN.

In some embodiments, each $R^{23}$ is one substituent attached to the heterocyclyl and is independently selected from the group consisting of —($C_{1-4}$ alkyl), halide, —$CF_3$, and —CN.

In some embodiments, each $R^{23}$ is one substituent attached to the heterocyclyl and is independently selected from the group consisting of Me, Et, F, Cl, and —$CF_3$.

In some embodiments, $R^{24}$ is selected from the group consisting of H, —($C_{1-6}$ alkyl), —($C_{1-4}$ alkylene)$_p$heterocyclyl($R^{23}$)$_h$, —($C_{1-4}$ alkylene)$_p$carbocyclyl($R^{22}$)$_j$, —($C_{1-4}$ alkylene)$_p$aryl($R^{21}$)$_k$, and —($C_{1-6}$ alkylene)$_p$NR$^{25}$R$^{26}$.

In some embodiments, $R^{24}$ is selected from the group consisting of H, -Me, -Et, -iPr, -heterocyclyl($R^{23}$)$_h$, —($CH_2CH_2$)heterocyclyl($R^{23}$)$_h$, -carbocyclyl($R^{22}$)$_j$, —($CH_2$)phenyl($R^{21}$)$_k$, and —($CH_2CH_2$)N($C_{1-3}$ alkyl)$_2$.

In some embodiments, each $R^{25}$ is independently selected from the group consisting of H and —($C_{1-6}$ alkyl).

In some embodiments, each $R^{25}$ is independently selected from the group consisting of Me and Et.

In some embodiments, each $R^{26}$ is independently selected from the group consisting of H and —($C_{1-6}$ alkyl).

In some embodiments, each $R^{26}$ is independently selected from the group consisting of Me and Et.

In some embodiments, $R^{27}$ is selected from the group consisting of H, —($C_{1-6}$ alkyl), —($C_{1-4}$ alkylene)$_p$heterocyclyl($R^{23}$)$_h$, and —($C_{1-6}$ alkylene)$_p$NR$^{25}$R$^{26}$.

In some embodiments, $R^{27}$ is selected from the group consisting of H, -Me, -Et, -iPr, —($CH_2CH_2$)heterocyclyl($R^{23}$)$_h$, and —($CH_2CH_2$)N($C_{1-3}$ alkyl)$_2$.

In some embodiments, each p is independently 0 or 1; in some embodiments, each p is 0; in some embodiments, each p is 1.

In some embodiments, each q is independently 0 to 4; in some embodiments, each q is 0; in some embodiments, each q is 1; in some embodiments, each q is 2; in some embodiments, each q is 3; in some embodiments, each q is 4.

In some embodiments, each h is independently 0 to 10; in some embodiments, each h is 0; in some embodiments, each h is 1; in some embodiments, each h is 2; in some embodiments, each h is 3; in some embodiments, each h is 4.

In some embodiments, each k is independently 0 to 5; in some embodiments, each k is 0; in some embodiments, each k is 1; in some embodiments, each k is 2; in some embodiments, each k is 3.

In some embodiments, each j is independently 0 to 12; in some embodiments, each j is 0; in some embodiments, each j is 1; in some embodiments, each j is 2; in some embodiments, each j is 3; in some embodiments, each j is 4.

In some embodiments, each $R^6$ is one substituent attached to the heteroaryl and is selected from the group consisting of —($C_{1-3}$ alkyl), —$CH_2$heterocyclyl($R^{11}$)$_h$, —NHC(=O)R$^{14}$, —NR$^{15}$R$^{16}$, and —$CH_2$NR$^{17}$R$^{18}$.

In some embodiments, at least one $R^{11}$ is halide.

In some embodiments, $R^{14}$ is selected from the group consisting of —($C_{1-5}$ alkyl), -phenyl$(R^{21})_k$, —$CH_2$phenyl $(R^{21})_k$, and -carbocyclyl$(R^{22})_j$.

In some embodiments, each $R^{15}$ and $R^{16}$ are independently selected from H and —($C_{1-5}$ alkyl).

In some embodiments, each $R^{17}$ and $R^{18}$ are independently selected from H and —($C_{1-5}$ alkyl).

In some embodiments, k is 1 or 2 and each $R^{10}$ is independently a halide.

In some embodiments, k is 2 and one $R^{10}$ is halide and the other $R^{10}$ is —$CH_2NHSO_2R^{19}$.

In some embodiments, $R^{19}$ is —($C_{1-3}$ alkyl).

In some embodiments, k is 2 and one $R^{10}$ is halide and the other $R^{10}$ is —$NHCH_2CH_2NR^{15}R^{16}$.

In some embodiments, each $R^{15}$ and $R^{16}$ are independently selected from H and —($C_{1-3}$ alkyl).

In some embodiments, $R^5$ is selected from the group consisting of -pyridinyl$(R^8)_q$, -imidazolyl$(R^8)_q$, -furanyl$(R^8)_q$, and -thiophenyl$(R^8)_q$.

In some embodiments, q is 1, and $R^8$ is selected from the group consisting of halide, —($C_{1-3}$ alkyl), —C(=O)$R^{19}$, and $R^{19}$ is —($C_{1-2}$ alkyl).

In some embodiments, $R^5$ is selected from the group consisting of -piperidinyl$(R^9)_h$ and -piperazinyl$(R^9)_h$.

In some embodiments, q is 1, and $R^9$ is a —($C_{1-3}$ alkyl).

In some embodiments, $R^1$ is H; in other embodiments, $R^1$ is halide, e.g. F.

In some embodiments, $R^2$ is H; in other embodiments, $R^2$ is halide, e.g. F.

In some embodiments, $R^4$ is H; in other embodiments, $R^4$ is halide, e.g. F.

In some embodiments, $R^2$ and $R^4$ are H, and $R^1$ is F; in some embodiments, $R^1$ and $R^4$ are H, and $R^2$ is F; in some embodiments, $R^1$ and $R^2$ are H, and $R^4$ is F; in some embodiments, $R^2$ and $R^4$ are F, and $R^1$ is H; in some embodiments, $R^1$ and $R^4$ are F, and $R^2$ is H; in some embodiments, $R^1$ and $R^2$ are F, and $R^4$ is H; in some embodiments, $R^1$, $R^2$, and $R^4$ are H; in some embodiments, $R^1$, $R^2$, and $R^4$ are F.

In some embodiments, $R^3$ is -heteroaryl$(R^6)_q$.
In some embodiments, $R^3$ is -pyridinyl$(R^6)_q$.
In some embodiments, $R^3$ is -pyridin-3-yl$(R^6)_q$.
In some embodiments, $R^3$ is -pyrimidinyl$(R^6)_q$.
In some embodiments, $R^3$ is -pyrimidin-5-yl$(R^6)_q$.
In some embodiments, $R^3$ is -pyrimidin-5-yl$(R^6)_q$ and q is 0.
In some embodiments, $R^3$ is -pyrazinyl$(R^6)_q$.
In some embodiments, $R^3$ is -pyrazolyl$(R^6)_q$.
In some embodiments, $R^3$ is -pyrazol-4-yl$(R^6)_q$, q is 1, and $R^6$ is Me.
In some embodiments, $R^3$ is -pyrazol-4-yl$(R^6)_q$ and q is 0.
In some embodiments, $R^3$ is -imidazolyl$(R^6)_q$.
In some embodiments, $R^3$ is -imidazol-5-yl$(R^6)_q$, q is 1, and $R^6$ is Me.
In some embodiments, $R^3$ is -imidazol-5-yl$(R^6)_q$, q is 2, and both $R^6$ are Me.
In some embodiments, $R^3$ is -heterocyclyl$(R^7)_h$.
In some embodiments, $R^3$ is -piperidinyl$(R^7)_h$.
In some embodiments, $R^3$ is -piperidin-4-yl$(R^7)_h$.
In some embodiments, $R^3$ is -piperidin-4-yl$(R^7)_h$, and h is 0.
In some embodiments, $R^3$ is -tetrahydropyridinyl$(R^7)_h$.
In some embodiments, $R^3$ is -1,2,3,6-tetrahydropyridinyl$(R^7)_h$.
In some embodiments, $R^3$ is -1,2,3,6-tetrahydropyridinyl$(R^7)_h$, and h is 0.

In some embodiments, $R^5$ is -heteroaryl$(R^8)_q$.
In some embodiments, $R^5$ is -heterocyclyl$(R^9)_h$.
In some embodiments, $R^5$ is -piperidinyl$(R^9)_h$.
In some embodiments, $R^5$ is -piperazinyl$(R^9)_h$.
In some embodiments, $R^5$ is -aryl$(R^{10})_k$.
In some embodiments, $R^5$ is -phenyl$(R^{10})_k$.
In some embodiments, $R^5$ is -pyridinyl$(R^8)_q$.
In some embodiments, $R^5$ is -pyridin-3-yl$(R^8)_q$.
In some embodiments, $R^5$ is -pyridin-4-yl$(R^8)_q$.
In some embodiments, $R^5$ is -pyridin-5-yl$(R^8)_q$.
In some embodiments, $R^5$ is -pyridin-3-yl$(R^8)_q$ and q is 0.
In some embodiments, $R^5$ is -pyridin-4-yl$(R^8)_q$ and q is 0.
In some embodiments, $R^5$ is -pyridin-5-yl$(R^8)_q$ and q is 0.
In some embodiments, $R^5$ is -imidazolyl$(R^8)_q$.
In some embodiments, $R^5$ is -imidazol-1-yl$(R^8)_q$, q is 1, and $R^8$ is —($C_{1-3}$ alkyl).
In some embodiments, $R^5$ is -imidazol-1-yl$(R^8)_q$, q is 1, and $R^8$ is methyl.
In some embodiments, $R^5$ is -furanyl$(R^8)_q$.
In some embodiments, $R^5$ is -furan-2-yl$(R^8)_q$.
In some embodiments, $R^5$ is -furan-2-yl$(R^8)_q$ and q is 0.
In some embodiments, $R^5$ is -furan-3-yl$(R^8)_q$.
In some embodiments, $R^5$ is -furan-3-yl$(R^8)_q$ and q is 0.
In some embodiments, $R^5$ is -thiophenyl$(R^8)_q$.
In some embodiments, $R^5$ is -thiophen-2-yl$(R^8)_q$.
In some embodiments, $R^5$ is -thiophen-2-yl$(R^8)_q$ and q is 0.
In some embodiments, $R^5$ is -thiophen-2-yl$(R^8)_q$, q is 1 or 2, and each $R^8$ is independently a halide.
In some embodiments, $R^5$ is -thiophen-2-yl$(R^8)_q$, q is 1 or 2, and $R^8$ is F.
In some embodiments, $R^5$ is -thiophen-2-yl$(R^8)_q$, q is 1 or 2, and each $R^8$ is independently a —($C_{1-6}$ alkyl).
In some embodiments, $R^5$ is -thiophen-2-yl$(R^8)_q$, q is 1 or 2, and each $R^8$ is independently a —($C_{1-2}$ alkyl).
In some embodiments, $R^5$ is -thiophen-2-yl$(R^8)_q$, q is 1 or 2, and $R^8$ is methyl.
In some embodiments, $R^5$ is -thiophen-2-yl$(R^8)_q$, q is 1 or 2, and $R^8$ is —$CF_3$.
In some embodiments, $R^5$ is -thiophen-2-yl$(R^8)_q$, q is 1 or 2, and $R^8$ is CN.
In some embodiments, $R^5$ is -thiophen-2-yl$(R^8)_q$, q is 1, and $R^8$ is —C(=O)$R^{19}$.
In some embodiments, $R^5$ is -thiophen-2-yl$(R^8)_q$, q is 1, $R^8$ is —C(=O)$R^{19}$, and $R^{19}$ is —($C_{1-6}$ alkyl).
In some embodiments, $R^5$ is -thiophen-2-yl$(R^8)_q$, q is 1, $R^8$ is —C(=O)$R^9$, and $R^{19}$ is —($C_{1-4}$ alkyl).
In some embodiments, $R^5$ is -thiophen-2-yl$(R^8)_q$, q is 1, $R^8$ is —C(=O)$R^9$, and $R^{19}$ is —($C_{1-2}$ alkyl).
In some embodiments, $R^5$ is -thiophen-2-yl$(R^8)_q$, q is 1, $R^8$ is —C(=O)$R^9$, and $R^{19}$ is methyl.
In some embodiments, $R^5$ is -thiophen-3-yl$(R^8)_q$.
In some embodiments, $R^5$ is -thiophen-3-yl$(R^8)_q$ and q is 0.
In some embodiments, $R^5$ is -thiophen-3-yl$(R^8)_q$, q is 1 or 2, and each $R^8$ is independently a halide.
In some embodiments, $R^5$ is -thiophen-3-yl$(R^8)_q$, q is 1 or 2, and $R^8$ is F.
In some embodiments, $R^5$ is -thiophen-3-yl$(R^8)_q$, q is 1 or 2, and each $R^8$ is independently a —($C_{1-6}$ alkyl).
In some embodiments, $R^5$ is -thiophen-3-yl$(R^8)_q$, q is 1 or 2, and each $R^8$ is independently a —($C_{1-2}$ alkyl).
In some embodiments, $R^5$ is -thiophen-3-yl$(R^8)_q$, q is 1 or 2, and $R^8$ is methyl.
In some embodiments, $R^5$ is -thiophen-3-yl$(R^8)_q$, q is 1 or 2, and $R^8$ is —$CF_3$.

In some embodiments, R⁵ is -thiophen-3-yl(R⁸)_q, q is 1 or 2, and R⁸ is CN.

In some embodiments, R⁵ is -thiophen-3-yl(R⁸)_q, q is 1, and R⁸ is —C(=O)R¹⁹.

In some embodiments, R⁵ is -thiophen-3-yl(R⁸)_q, q is 1, R⁸ is —C(=O)R⁹, and R¹⁹ is —(C_{1-4} alkyl).

In some embodiments, R⁵ is -thiophen-3-yl(R⁸)_q, q is 1, R⁸ is —C(=O)R⁹, and R¹⁹ is —(C_{1-2} alkyl).

In some embodiments, R⁵ is -thiophen-3-yl(R⁸)_q, q is 1, R⁸ is —C(=O)R⁹, and R¹⁹ is methyl.

In some embodiments, R⁵ is selected from the group consisting of:

In some embodiments, R⁵ is -phenyl(R¹⁰)_k.

In some embodiments, R⁵ is -phenyl(R¹⁰)_k and k is 0.

In some embodiments, R⁵ is -phenyl(R¹⁰)_k, k is 1 or 2, and each R¹⁰ is independently a halide.

In some embodiments, R⁵ is -phenyl(R¹⁰)_k, k is 1 or 2, and R¹⁰ is F.

In some embodiments, R⁵ is -phenyl(R¹⁰)_k, k is 1, and R¹⁰ is F.

In some embodiments, R⁵ is -phenyl(R¹⁰)_k, k is 2, one R¹⁰ is a halide and the other R¹⁰ is —(C_{1-6} alkylene)_p NHSO₂R¹⁹.

In some embodiments, R⁵ is -phenyl(R¹⁰)_k, k is 2, one R¹⁰ is a halide and the other R¹⁰ is —(C_{1-4} alkylene)_p NHSO₂R¹⁹, and p is 1.

In some embodiments, R⁵ is -phenyl(R¹⁰)_k, k is 2, one R¹⁰ is a halide and the other R¹⁰ is —(C_{1-2} alkylene)_p NHSO₂R¹⁹, and p is 1.

In some embodiments, R⁵ is -phenyl(R¹⁰)_k, k is 2, one R¹⁰ is a halide and the other R¹⁰ is —CH₂NHSO₂R¹⁹.

In some embodiments, R⁵ is -phenyl(R¹⁰)_k, k is 2, one R¹⁰ is a halide and the other R¹⁰ is —CH₂NHSO₂R¹⁹, and R¹⁹ is —(C_{1-4} alkyl).

In some embodiments, R⁵ is -phenyl(R¹⁰)_k, k is 2, one R¹⁰ is a halide and the other R¹⁰ is —CH₂NHSO₂R¹⁹, and R¹⁹ is —(C_{1-2} alkyl).

In some embodiments, R⁵ is -phenyl(R¹⁰)_k, k is 2, one R¹⁰ is a halide and the other R¹⁰ is —CH₂NHSO₂R¹⁹, and R¹⁹ is methyl.

In some embodiments, R⁵ is -phenyl(R¹⁰)_k, k is 2, one R¹⁰ is F and the other R¹⁰ is —CH₂NHSO₂R¹⁹, and R¹⁹ is —(C_{1-2} alkyl).

In some embodiments, R⁵ is -phenyl(R¹⁰)_k, k is 2, one R¹⁰ is F and the other R¹⁰ is —CH₂NHSO₂R¹⁹, and R¹⁹ is methyl.

In some embodiments, R⁵ is -phenyl(R¹⁰)_k, k is 2, one R¹⁰ is halide and the other R¹⁰ is —NR¹⁵(C_{1-6} alkylene)NR¹⁵R¹⁶.

In some embodiments, R⁵ is -phenyl(R¹⁰)_k, k is 2, one R¹⁰ is halide and the other R¹⁰ is —NR¹⁵(C_{1-5} alkylene)NR¹⁵R¹⁶.

In some embodiments, R⁵ is -phenyl(R¹⁰)_k, k is 2, one R¹⁰ is halide and the other R¹⁰ is —NR¹⁵(C_{1-4} alkylene)NR¹⁵R¹⁶.

In some embodiments, R⁵ is -phenyl(R¹⁰)_k, k is 2, one R¹⁰ is halide and the other R¹⁰ is —NR¹⁵(C_{1-3} alkylene)NR¹⁵R¹⁶.

In some embodiments, R⁵ is -phenyl(R¹⁰)_k, k is 2, one R¹⁰ is halide and the other R¹⁰ is —NR⁵CH₂CH₂NR¹⁵R¹⁶.

In some embodiments, R⁵ is -phenyl(R¹⁰)_k, k is 2, one R¹⁰ is halide and the other R¹⁰ is —NHCH₂CH₂NR¹⁵R¹⁶, and R¹⁵ and R¹⁶ are independently a —(C_{1-6} alkyl).

In some embodiments, R⁵ is -phenyl(R¹⁰)_k, k is 2, one R¹⁰ is halide and the other R¹⁰ is —NHCH₂CH₂NR¹⁵R¹⁶, and R¹⁵ and R¹⁶ are independently a —(C_{1-4} alkyl).

In some embodiments, R⁵ is -phenyl(R¹⁰)_k, k is 2, one R¹⁰ is halide and the other R¹⁰ is —NHCH₂CH₂NR¹⁵R¹⁶, and R¹⁵ and R¹⁶ are independently a —(C_{1-2} alkyl).

In some embodiments, R⁵ is -phenyl(R¹⁰)_k, k is 2, one R¹⁰ is halide and the other R¹⁰ is —NHCH₂CH₂NR¹⁵R¹⁶, and R¹⁵ and R¹⁶ are both methyl.

In some embodiments, R⁵ is -phenyl(R¹⁰)_k, k is 2, one R¹⁰ is F and the other R¹⁰ is —NHCH₂CH₂NR¹⁵R¹⁶, and R¹⁵ and R¹⁶ are independently a —(C_{1-2} alkyl).

In some embodiments, R⁵ is -phenyl(R¹⁰)_k, k is 2, one R¹⁰ is F and the other R¹⁰ is —NHCH₂CH₂NR¹⁵R¹⁶, and R¹⁵ and R¹⁶ are both methyl.

In some embodiments, R⁵ is -phenyl(R¹⁰)_k, k is 2, one R¹⁰ is halide and the other R¹⁰ is —OCH₂CH₂NR²⁵R²⁶.

In some embodiments, R⁵ is -phenyl(R¹⁰)_k, k is 2, one R¹⁰ is halide and the other R¹⁰ is —OCH₂CH₂NR²⁵R²⁶, and R²⁵ and R²⁶ are independently a —(C_{1-2} alkyl).

In some embodiments, R⁵ is -phenyl(R¹⁰)_k, k is 2, one R¹⁰ is halide and the other R¹⁰ is —OCH₂CH₂NR²⁵R²⁶, and R²⁵ and R²⁶ are both methyl.

In some embodiments, R⁵ is -phenyl(R¹⁰)_k, k is 2, one R¹⁰ is F and the other R¹⁰ is —OCH₂CH₂NR²⁵R²⁶, and R²⁵ and R²⁶ are both methyl.

In some embodiments, R⁵ is -phenyl(R¹⁰)_k, k is 2, one R¹⁰ is halide and the other R¹⁰ is —CH₂NHSO₂R¹⁹, and R¹⁹ is —(C_{1-4} alkyl).

In some embodiments, R⁵ is -phenyl(R¹⁰)_k, k is 2, one R¹⁰ is halide and the other R¹⁰ is —CH₂NHSO₂R¹⁹, and R¹⁹ is —(C_{1-2} alkyl).

In some embodiments, R⁵ is -phenyl(R¹⁰)_k, k is 2, one R¹⁰ is halide and the other R¹⁰ is —CH₂NHSO₂R¹⁹, and R¹⁹ is methyl.

In some embodiments, R⁵ is -phenyl(R¹⁰)_k, k is 2, one R¹⁰ is F and the other R¹⁰ is —CH₂NHSO₂R¹⁹, and R¹⁹ is —(C_{1-2} alkyl).

In some embodiments, R⁵ is -phenyl(R¹⁰)_k, k is 2, one R¹⁰ is F and the other R¹⁰ is —CH₂NHSO₂R¹⁹, and R¹⁹ is methyl.

In some embodiments, R⁵ is selected from the group consisting of:

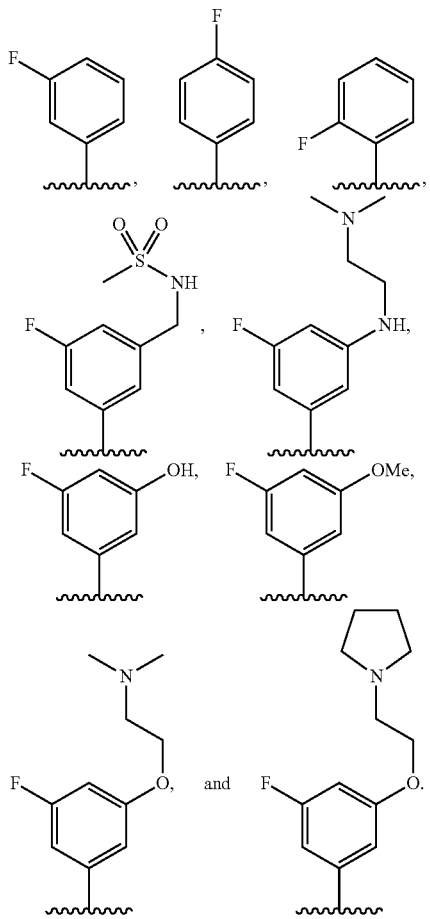

In some embodiments, R⁵ is -piperidinyl(R⁹)$_h$.
In some embodiments, R⁵ is -piperidin-1-yl(R⁹)$_h$.
In some embodiments, R⁵ is -piperidin-1-yl(R⁹)$_h$ and h is 0.
In some embodiments, R⁵ is -piperidin-1-yl(R⁹)$_h$, h is 1 or 2, and each R⁹ is independently selected from a halide.
In some embodiments, R⁵ is -piperazinyl(R⁹)$_h$.
In some embodiments, R⁵ is -piperazin-1-yl(R⁹)$_h$.
In some embodiments, R⁵ is -piperazin-1-yl(R⁹)$_h$, h is 1, and R⁹ is C$_{1-3}$ alkyl.
In some embodiments, R⁵ is -piperazin-1-yl(R⁹)$_h$, h is 1, and R⁹ is methyl.
In some embodiments, R⁵ is -morpholinyl(R⁹)$_h$.
In some embodiments, R⁵ is -morpholin-1-yl(R⁹)$_h$.
In some embodiments, R⁵ is -morpholin-1-yl(R⁹)$_h$ and h is 0.

In some embodiments, R⁵ is selected from the group consisting of:

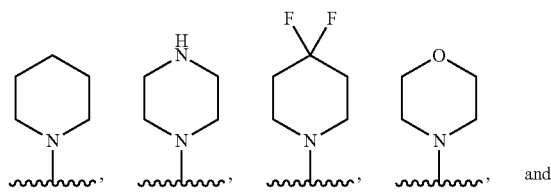

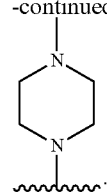

In some embodiments, q is 0.
In some embodiments, at least one R⁶ is a halide.
In some embodiments, at least one R⁶ is a F.
In some embodiments, R⁶ is F.
In some embodiments, at least one R⁶ is —(C$_{1-6}$ alkyl).
In some embodiments, at least one R⁶ is —(C$_{1-5}$ alkyl).
In some embodiments, at least one R⁶ is —(C$_{1-4}$ alkyl).
In some embodiments, at least one R⁶ is —(C$_{1-3}$ alkyl).
In some embodiments, at least one R⁶ is —(C$_{1-2}$ alkyl).
In some embodiments, at least one R⁶ is methyl.
In some embodiments, R⁶ is a methyl.
In some embodiments, at least one R⁶ is —(C$_{1-4}$ alkylene)$_p$heterocyclyl(R¹¹)$_h$ and p is 0 or 1.
In some embodiments, at least one R⁶ is —(C$_{1-3}$ alkylene)$_p$heterocyclyl(R¹¹)$_h$ and p is 0 or 1.
In some embodiments, at least one R⁶ is —(C$_{1-2}$ alkylene)$_p$heterocyclyl(R¹¹)$_h$ and p is 0 or 1.
In some embodiments, at least one R⁶ is —CH$_2$pyrrolidinyl(R⁷)$_h$.
In some embodiments, at least one R⁶ is —CH$_2$pyrrolidinyl(R⁷)$_h$ and h is 0.
In some embodiments, R⁶ is a —CH$_2$pyrrolidinyl(R⁷)$_h$ and h is 0.
In some embodiments, at least one R⁶ is —CH$_2$pyrrolidinyl(R¹¹)$_h$, h is 1 or 2, and at least one R¹¹ is a halide.
In some embodiments, at least one R⁶ is —CH$_2$pyrrolidinyl(R¹¹)$_h$, h is 1 or 2, and at least one R¹¹ is F.
In some embodiments, R⁶ is a —CH$_2$pyrrolidinyl(R⁷)$_h$, h is 1 or 2, and at least one R¹¹ is halide.
In some embodiments, R⁶ is —CH$_2$pyrrolidinyl(R⁷)$_h$, h is 1 or 2, and at least one R¹¹ is F.
In some embodiments, R⁶ is a —CH$_2$pyrrolidinyl(R⁷)$_h$, h is 1 or 2, and each R¹¹ is F.
In some embodiments, at least one R⁶ is —CH$_2$piperidinyl(R¹¹)$_h$.
In some embodiments, at least one R⁶ is —CH$_2$piperidinyl(R¹¹)$_h$ and h is 0.
In some embodiments, R⁶ is a —CH$_2$piperidinyl(R¹¹)$_h$ and h is 0.
In some embodiments, at least one R⁶ is —CH$_2$piperidinyl(R¹¹)$_h$ and at least one R¹¹ is a halide.
In some embodiments, at least one R⁶ is —CH$_2$piperidinyl(R¹¹)$_h$ and at least one R¹¹ is F.
In some embodiments, at least one R⁶ is —CH$_2$piperidinyl(R¹¹)$_h$, h is 1 or 2, and each R¹¹ is a halide.
In some embodiments, at least one R⁶ is —CH$_2$piperidinyl(R$^U$)$_h$, h is 1 or 2, and each R¹¹ is F.
In some embodiments, R⁶ is a —CH$_2$piperidinyl(R⁷)$_h$, h is 1 or 2, and each R¹¹ is a halide.
In some embodiments, R⁶ is a —CH$_2$piperidinyl(R⁷)$_h$, h is 1 or 2, and each R¹¹ is F.

In some embodiments, $R^6$ is a

[structure: 3,3-difluoropyrrolidine attached via N-CH2-CH2 with wavy bond]

In some embodiments, at least one $R^6$ is —($C_{1-4}$ alkylene)$_p$carbocyclyl($R^{12}$)$_j$.

In some embodiments, at least one $R^6$ is —($C_{1-4}$ alkylene)$_p$carbocyclyl($R^{12}$)$_j$ and j is 0 or 1.

In some embodiments, at least one $R^6$ is —($C_{1-3}$ alkylene)$_p$carbocyclyl($R^{12}$)$_j$ and j is 0 or 1.

In some embodiments, at least one $R^6$ is —($C_{1-2}$ alkylene)$_p$carbocyclyl($R^{12}$)$_j$ and j is 0 or 1.

In some embodiments, at least one $R^6$ is —CH$_2$carbocyclyl($R^2$)$_j$.

In some embodiments, $R^6$ is a —CH$_2$carbocyclyl($R^2$)$_j$.

In some embodiments, at least one $R^6$ is —($C_{1-4}$ alkylene)$_p$aryl($R^{13}$)$_k$ and k is 0 or 1.

In some embodiments, at least one $R^6$ is —($C_{1-3}$ alkylene)$_p$aryl($R^{13}$)$_k$ and k is 0 or 1.

In some embodiments, at least one $R^6$ is —($C_{1-2}$ alkylene)$_p$aryl($R^{13}$)$_k$ and k is 0 or 1.

In some embodiments, at least one $R^6$ is —CH$_2$aryl($R^{13}$)$_k$.

In some embodiments, at least one $R^6$ is —CH$_2$phenyl($R^{13}$)$_k$.

In some embodiments, $R^6$ is a —CH$_2$phenyl($R^{13}$)$_k$.

In some embodiments, at least one $R^6$ is —NHC(=O)$R^{14}$.

In some embodiments, $R^6$ is a —NHC(=O)$R^{14}$.

In some embodiments, at least one $R^6$ is —NHC(=O)$R^{14}$ and $R^{14}$ is —($C_{1-9}$ alkyl).

In some embodiments, at least one $R^6$ is —NHC(=O)$R^{14}$ and $R^{14}$ is —($C_{1-8}$ alkyl).

In some embodiments, at least one $R^6$ is —NHC(=O)$R^{14}$ and $R^{14}$ is —($C_{1-7}$ alkyl).

In some embodiments, at least one $R^6$ is —NHC(=O)$R^{14}$ and $R^{14}$ is —($C_{1-6}$ alkyl).

In some embodiments, at least one $R^6$ is —NHC(=O)$R^{14}$ and $R^{14}$ is —($C_{1-5}$ alkyl).

In some embodiments, $R^6$ is a —NHC(=O)$R^{14}$ and $R^{14}$ is —($C_{1-5}$ alkyl).

In some embodiments, at least one $R^6$ is —NHC(=O)$R^{14}$ and $R^{14}$ is —($C_{1-4}$ alkyl).

In some embodiments, $R^6$ is a —NHC(=O)$R^{14}$ and $R^{14}$ is —($C_{1-4}$ alkyl).

In some embodiments, at least one $R^6$ is —NHC(=O)$R^{14}$ and $R^{14}$ is —($C_{1-3}$ alkyl).

In some embodiments, $R^6$ is a —NHC(=O)$R^4$ and $R^{14}$ is —($C_{1-3}$ alkyl).

In some embodiments, at least one $R^6$ is —NHC(=O)$R^{14}$ and $R^{14}$ is —($C_{1-2}$ alkyl).

In some embodiments, at least one $R^6$ is —NHC(=O)$R^{14}$ and $R^{14}$ is —($C_{2-5}$ alkyl).

In some embodiments, $R^6$ is a —NHC(=O)$R^4$ and $R^{14}$ is —($C_{2-5}$ alkyl).

In some embodiments, at least one $R^6$ is —NHC(=O)$R^{14}$ and $R^{14}$ is —($C_{3-4}$ alkyl).

In some embodiments, at least one $R^6$ is —NHC(=O)$R^{14}$ and $R^{14}$ is -aryl($R^{21}$)$_k$.

In some embodiments, at least one $R^6$ is —NHC(=O)$R^{14}$, $R^{14}$ is -phenyl($R^{21}$)$_k$, and k is 0.

In some embodiments, $R^6$ is a —NHC(=O)$R^{14}$, $R^{14}$ is -phenyl($R^{21}$)$_k$, and k is 0.

In some embodiments, at least one $R^6$ is —NHC(=O)$R^{14}$ and $R^{14}$ is —CH$_2$aryl($R^{21}$)$_k$.

In some embodiments, at least one $R^6$ is —NHC(=O)$R^{14}$, $R^{14}$ is —CH$_2$phenyl($R^{21}$)$_k$, and k is 0.

In some embodiments, $R^6$ is a —NHC(=O)$R^{14}$, $R^{14}$ is —CH$_2$phenyl($R^{21}$)$_k$, and k is 0.

In some embodiments, at least one $R^6$ is —NHC(=O)$R^4$ and $R^{14}$ is -heteroaryl($R^{20}$)$_q$.

In some embodiments, at least one $R^6$ is —NHC(=O)$R^4$ and $R^{14}$ is -carbocyclyl($R^{22}$)$_j$.

In some embodiments, at least one $R^6$ is —NHC(=O)$R^{14}$, $R^{14}$ is -carbocyclyl($R^{22}$)$_j$, and j is 0.

In some embodiments, at least one $R^6$ is —NHC(=O)$R^{14}$, $R^{14}$ is -cyclopropyl($R^{22}$)$_j$, and j is 0.

In some embodiments, $R^6$ is a —NHC(=O)$R^{14}$, $R^{14}$ is -cyclopropyl($R^{22}$)$_j$, and j is 0.

In some embodiments, at least one $R^6$ is —NHC(=O)$R^{14}$, $R^{14}$ is -cyclobutyl($R^{22}$)$_j$, and j is 0.

In some embodiments, $R^6$ is a —NHC(=O)$R^{14}$, $R^{14}$ is -cyclobutyl($R^{22}$)$_j$, and j is 0.

In some embodiments, at least one $R^6$ is —NHC(=O)$R^{14}$, $R^{14}$ is -cyclopentyl($R^{22}$)$_j$, and j is 0.

In some embodiments, $R^6$ is a —NHC(=O)$R^{14}$, $R^{14}$ is -cyclopentyl($R^{22}$)$_j$, and j is 0.

In some embodiments, at least one $R^6$ is —NHC(=O)$R^{14}$, $R^{14}$ is -cyclohexyl($R^{22}$)$_j$, and j is 0.

In some embodiments, $R^6$ is a —NHC(=O)$R^{14}$, $R^{14}$ is -cyclohexyl($R^{22}$)$_j$, and j is 0.

In some embodiments, at least one $R^6$ is —NHC(=O)$R^{14}$, $R^{14}$ is —CH$_2$carbocyclyl($R^{22}$)$_j$, and j is 0.

In some embodiments, at least one $R^6$ is —NHC(=O)$R^{14}$, $R^{14}$ is —CH$_2$cyclopropyl($R^{22}$)$_j$, and j is 0.

In some embodiments, $R^6$ is a —NHC(=O)$R^{14}$, $R^{14}$ is —CH$_2$cyclopropyl($R^{22}$)$_j$, and j is 0.

In some embodiments, at least one $R^6$ is —NR$^{15}$R$^{16}$.

In some embodiments, at least one $R^6$ is —NR$^{15}$R$^{16}$, and $R^{15}$ and $R^{16}$ are independently selected from the group consisting of H and —($C_{1-6}$ alkyl).

In some embodiments, at least one $R^6$ is —NR$^{15}$R$^{16}$, and $R^{15}$ and $R^{16}$ are independently selected from the group consisting of H and —($C_{1-5}$ alkyl).

In some embodiments, at least one $R^6$ is —NR$^{15}$R$^{16}$, and $R^{15}$ and $R^{16}$ are independently selected from the group consisting of H and —($C_{1-4}$ alkyl).

In some embodiments, at least one $R^6$ is —NR$^{15}$R$^{16}$, and $R^{15}$ and $R^{16}$ are independently selected from the group consisting of H and —($C_{1-3}$ alkyl).

In some embodiments, at least one $R^6$ is —NR$^{15}$R$^{16}$, and $R^{15}$ and $R^{16}$ are independently selected from the group consisting of H and —($C_{1-2}$ alkyl).

In some embodiments, at least one $R^6$ is —NR$^{15}$R$^{16}$, and $R^{15}$ and $R^{16}$ are independently selected from the group consisting of H and methyl.

In some embodiments, $R^6$ is a —NR$^{15}$R$^{16}$, and $R^{15}$ and $R^{16}$ are independently selected from the group consisting of H and methyl.

In some embodiments, at least one $R^6$ is —NH$_2$.

In some embodiments, $R^6$ is a —NH$_2$.

In some embodiments, at least one $R^6$ is —NHR$^{16}$ and $R^{16}$ is —($C_{1-4}$ alkyl).

In some embodiments, at least one $R^6$ is —NHR$^{16}$ and $R^{16}$ is —($C_{1-3}$ alkyl).

In some embodiments, $R^6$ is —NHR$^{16}$ and $R^{16}$ is —($C_{1-2}$ alkyl).

In some embodiments, at least one $R^6$ is —$NHR^{16}$ and $R^{16}$ is —$CH_2aryl(R^{21})_k$.

In some embodiments, $R^6$ is —$NHR^{16}$, $R^{16}$ is —$CH_2phenyl(R^{21})_k$, and k is 0.

In some embodiments, at least one $R^6$ is —$NHR^{16}$ and $R^{16}$ is —$CH_2carbocyclyl(R^{22})_j$.

In some embodiments, at least one $R^6$ is —$NHR^{16}$, $R^{16}$ is —$CH_2cyclopropyl(R^{22})_j$, and j is 0.

In some embodiments, $R^6$ is a —$NHR^{16}$, $R^{16}$ is —$CH_2cyclopropyl(R^{22})_j$, and j is 0.

In some embodiments, at least one $R^6$ is —$NHR^{16}$, $R^{16}$ is —$CH_2cyclobutyl(R^{22})_j$, and j is 0.

In some embodiments, $R^6$ is a —$NHR^{16}$, $R^{16}$ is —$CH_2cyclobutyl(R^{22})_j$, and j is 0.

In some embodiments, at least one $R^6$ is —$NHR^{16}$, $R^{16}$ is —$CH_2cyclopentyl(R^{22})_j$, and j is 0.

In some embodiments, $R^6$ is a —$NHR^{16}$, $R^{16}$ is —$CH_2cyclopentyl(R^{22})_j$, and j is 0.

In some embodiments, at least one $R^6$ is —$NHR^{16}$, $R^{16}$ is —$CH_2cyclohexyl(R^{22})_j$, and j is 0.

In some embodiments, $R^6$ is a —$NHR^{16}$, $R^{16}$ is —$CH_2cyclohexyl(R^{22})_j$, and j is 0.

In some embodiments, at least one $R^6$ is —($C_{1-6}$ alkylene)$NR^{17}R^{18}$.

In some embodiments, at least one $R^6$ is —($C_{1-5}$ alkylene)$NR^{17}R^{18}$.

In some embodiments, at least one $R^6$ is —($C_{1-4}$ alkylene)$NR^{17}R^{18}$.

In some embodiments, at least one $R^6$ is —($C_{1-3}$ alkylene)$NR^{17}R^{18}$.

In some embodiments, at least one $R^6$ is —($C_{1-2}$ alkylene)$NR^{17}R^{18}$.

In some embodiments, at least one $R^6$ is —$CH_2NR^{17}R^{18}$.

In some embodiments, $R^6$ is a —$CH_2NR^{17}R^{18}$.

In some embodiments, at least one $R^6$ is —$CH_2NR^{17}R^{18}$, and $R^{17}$ and $R^{18}$ are independently selected from the group consisting of H and —($C_{1-6}$ alkyl).

In some embodiments, at least one $R^6$ is —$CH_2NR^{17}R^{18}$, and $R^{17}$ and $R^{18}$ are independently selected from the group consisting of H and —($C_{1-5}$ alkyl).

In some embodiments, at least one $R^6$ is —$CH_2NR^{17}R^{18}$, and $R^{17}$ and $R^{18}$ are independently selected from the group consisting of H and —($C_{1-4}$ alkyl).

In some embodiments, at least one $R^6$ is —$CH_2NR^{17}R^{18}$, and $R^{17}$ and $R^{18}$ are independently selected from the group consisting of H and —($C_{1-3}$ alkyl).

In some embodiments, at least one $R^6$ is —$CH_2NR^{17}R^{18}$, and $R^{17}$ and $R^{18}$ are independently selected from the group consisting of H and —($C_{1-2}$ alkyl).

In some embodiments, at least one $R^6$ is —$CH_2NR^{17}R^{18}$, and $R^{17}$ and $R^{18}$ are independently selected from the group consisting of H and methyl.

In some embodiments, $R^6$ is a —$CH_2NR^{17}R^{18}$, $R^{17}$ and $R^{18}$ are independently selected from the group consisting of H and methyl.

In some embodiments, at least one $R^6$ is —$CH_2NH_2$.

In some embodiments, $R^6$ is a —$CH_2NH_2$.

In some embodiments, at least one $R^6$ is —$CH_2NMe_2$.

In some embodiments, $R^6$ is a —$CH_2NMe_2$.

In some embodiments, at least one $R^6$ is —$CH_2NHR^{18}$ and $R^{18}$ is —($C_{1-4}$ alkyl).

In some embodiments, at least one $R^6$ is —$CH_2NHR^{18}$ and $R^{18}$ is —($C_{1-3}$ alkyl).

In some embodiments, at least one $R^6$ is —$CH_2NHR^{18}$ and $R^{18}$ is —($C_{1-2}$ alkyl).

In some embodiments, $R^6$ is a —$CH_2NHR^{18}$ and $R^{18}$ is —($C_{1-2}$ alkyl).

In some embodiments, at least one $R^6$ is —$CH_2NHR^{18}$ and $R^{18}$ is —$CH_2aryl(R^{21})_k$.

In some embodiments, at least one $R^6$ is —$CH_2NHR^{18}$, $R^{18}$ is —$CH_2phenyl(R^{21})_k$, and k is 0.

In some embodiments, $R^6$ is a —$CH_2NHR^{18}$, $R^{18}$ is —$CH_2phenyl(R^{21})_k$, and k is 0.

In some embodiments, at least one $R^6$ is —$CH_2NHR^{18}$ and $R^{18}$ is —$CH_2carbocyclyl(R^{22})_j$.

In some embodiments, at least one $R^6$ is —$CH_2NHR^{18}$, $R^{18}$ is —$CH_2cyclopropyl(R^{22})_j$, and j is 0.

In some embodiments, $R^6$ is a —$CH_2NHR^{18}$, $R^{18}$ is —$CH_2cyclopropyl(R^{22})_j$, and j is 0.

In some embodiments, at least one $R^6$ is —$CH_2NHR^{18}$, $R^{18}$ is —$CH_2cyclobutyl(R^{22})_j$, and j is 0.

In some embodiments, $R^6$ is a —$CH_2NHR^{18}$, $R^{18}$ is —$CH_2cyclobutyl(R^{22})_j$, and j is 0.

In some embodiments, at least one $R^6$ is —$CH_2NHR^{18}$, $R^{18}$ is —$CH_2cyclopentyl(R^{22})_j$, and j is 0.

In some embodiments, $R^6$ is a —$CH_2NHR^{18}$, $R^{18}$ is —$CH_2cyclopentyl(R^{22})_j$, and j is 0.

In some embodiments, at least one $R^6$ is —$CH_2NHR^{18}$, $R^{18}$ is —$CH_2cyclohexyl(R^{22})_j$, and j is 0.

In some embodiments, $R^6$ is a —$CH_2NHR^{18}$, $R^{18}$ is —$CH_2cyclohexyl(R^{22})_j$, and j is 0.

In some embodiments, at least one $R^6$ is —$OR^{24}$.

In some embodiments, at least one $R^6$ is —OH.

In some embodiments, $R^6$ is a —OH.

In some embodiments, at least one $R^6$ is —$OR^{24}$ and $R^{24}$ is —($C_{1-3}$ alkyl).

In some embodiments, at least one $R^6$ is —$OR^{24}$ and $R^{24}$ is —($C_{1-2}$ alkyl).

In some embodiments, at least one $R^6$ is —OMe.

In some embodiments, $R^6$ is a —OMe.

In some embodiments, at least one $R^6$ is —$OR^{24}$, $R^{24}$ is -heterocyclyl($R^{23}$)$_h$, and h is 0.

In some embodiments, $R^6$ is a —$OR^{24}$, $R^{24}$ is -heterocyclyl($R^{23}$)$_h$, and h is 0.

In some embodiments, at least one $R^6$ is —$OR^{24}$, $R^{24}$ is -carbocyclyl($R^{22}$)$_j$, and j is 0.

In some embodiments, $R^6$ is a —$OR^{24}$, $R^{24}$ is -carbocyclyl($R^{22}$)$_j$, and j is 0.

In some embodiments, at least one $R^6$ is —$OR^{24}$, $R^{24}$ is —($C_{1-4}$ alkylene)heterocyclyl($R^{23}$)$_h$, and h is 0.

In some embodiments, at least one $R^6$ is —$OR^{24}$, $R^{24}$ is —($CH_2CH_2$)heterocyclyl($R^{23}$)$_h$, and h is 0.

In some embodiments, $R^6$ is a —$OR^{24}$, $R^{24}$ is —($CH_2CH_2$)heterocyclyl($R^{23}$)$_h$, and h is 0.

In some embodiments, at least one $R^6$ is —$OR^{24}$, $R^{24}$ is —($C_{1-4}$ alkylene)$NR^{25}R^{26}$ and $R^{25}$ and $R^{26}$ are independently a —($C_{1-4}$ alkyl).

In some embodiments, at least one $R^6$ is —$OR^{24}$, $R^{24}$ is —($CH_2CH_2$)$NR^{25}R^{26}$ and $R^{25}$ and $R^{26}$ are independently a —($C_{1-2}$ alkyl).

In some embodiments, at least one $R^6$ is —$OR^{24}$, and $R^{24}$ is —($CH_2CH_2$)$NMe_2$.

In some embodiments, $R^6$ is a —$OR^{24}$, and $R^{24}$ is —($CH_2CH_2$)$NMe_2$.

In some embodiments, at least one $R^6$ is —$OR^{24}$, $R^{24}$ is —($C_{1-4}$ alkylene)aryl($R^{21}$)$_k$, k is 0 or 1 and $R^{21}$ is halide.

In some embodiments, at least one $R^6$ is —$OR^{24}$, $R^{24}$ is —($CH_2CH_2$)phenyl($R^{21}$)$_k$, k is 0 or 1 and $R^{21}$ is a halide.

In some embodiments, $R^6$ is a —$OR^{24}$, $R^{24}$ is —($CH_2CH_2$)phenyl($R^{21}$)$_k$, k is 0 or 1 and $R^{21}$ is a halide.

In some embodiments, at least one $R^6$ is —$OR^{24}$, $R^{24}$ is —($CH_2$)phenyl($R^{21}$)$_k$, k is 0 or 1 and $R^{21}$ is a halide.

In some embodiments, $R^6$ is a —$OR^{24}$, $R^{24}$ is —($CH_2$)phenyl($R^{21}$)$_k$, k is 0 or 1 and $R^{21}$ is a halide.

In some embodiments, h is 0.
In some embodiments, at least one $R^7$ is a halide.
In some embodiments, at least one $R^7$ is a F.
In some embodiments, at least one $R^7$ is —($C_{1-6}$ alkyl).
In some embodiments, at least one $R^7$ is —($C_{1-5}$ alkyl).
In some embodiments, at least one $R^7$ is —($C_{1-4}$ alkyl).
In some embodiments, at least one $R^7$ is —($C_{1-3}$ alkyl).
In some embodiments, at least one $R^7$ is —($C_{1-2}$ alkyl).
In some embodiments, at least one $R^7$ is methyl.
In some embodiments, at least one $R^8$ is a halide.
In some embodiments, at least one $R^8$ is a F.
In some embodiments, at least one $R^8$ is —($C_{1-4}$ alkyl).
In some embodiments, at least one $R^8$ is —($C_{1-3}$ alkyl).
In some embodiments, at least one $R^8$ is —($C_{1-2}$ alkyl).
In some embodiments, at least one $R^8$ is methyl.
In some embodiments, $R^8$ is a methyl.
In some embodiments, at least one $R^8$ is —C(=O)($C_{1-3}$ alkyl).
In some embodiments, at least one $R^8$ is —C(=O)Me.
In some embodiments, $R^8$ is a —C(=O)Me.

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is —($C_{2-5}$ alkyl); $R^5$ is -phenyl($R^{10}$)$_k$; k is 1 or 2; and $R^{10}$ is F.

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is —($C_{2-5}$ alkyl); $R^5$ is -phenyl($R^{10}$)$_k$; k is 2; one $R^{10}$ is F and the other $R^{10}$ is —($C_{1-2}$ alkylene)$_p$NHSO$_2$$R^{19}$; p is 1; and $R^{19}$ is —($C_{1-3}$ alkyl).

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is —($C_{2-5}$ alkyl); $R^5$ is -phenyl($R^{10}$)$_k$; k is 2; one $R^{10}$ is F and the other $R^{10}$ is —NH($C_{1-6}$ alkylene)N$R^{15}$$R^{16}$; and $R^{15}$ and $R^{16}$ are independently selected from —($C_{1-3}$ alkyl).

In some embodiments, $R^1$, $R^2$, and $R^4$ are H; $R^3$ is -pyridin-3-yl($R^6$)$_q$, wherein q is 1; $R^6$ is —NHC(=O)$R^{14}$; $R^{14}$ is —($C_{2-5}$ alkyl); $R^5$ is -heteroaryl($R^8$)$_q$, wherein q is 1; $R^8$ is selected from the group consisting of halide, —($C_{1-2}$ alkyl), and —C(=O)$R^{19}$; $R^{19}$ is —($C_{1-3}$ alkyl); and the heteroaryl is selected from the group consisting of pyridine, furan, thiophene, and imidazole.

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is —($C_{2-5}$ alkyl); $R^5$ is -heterocyclyl($R^9$)$_h$; h is 1 or 2; and $R^9$ is selected from the group consisting of halide and —($C_{1-2}$ alkyl).

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is -carbocyclyl($R^{22}$)$_j$; j is 0; R is -phenyl($R^{10}$)$_k$; k is 1 or 2; $R^{10}$ is F; and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is -carbocyclyl($R^{22}$)$_j$; j is 0; $R^5$ is -phenyl($R^{10}$)$_k$; k is 2; one $R^{10}$ is F and the other $R^{10}$ is —($C_{1-2}$ alkylene)$_p$NHSO$_2$$R^{19}$; p is 1; $R^{19}$ is —($C_{1-3}$ alkyl); and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is -carbocyclyl($R^{22}$)$_j$; j is 0; $R^5$ is -phenyl($R^{10}$)$_k$; k is 2; one $R^{10}$ is F and the other $R^{10}$ is —NH($C_{1-6}$ alkylene)N$R^{15}$$R^{16}$; $R^{15}$ and $R^{16}$ are independently selected from —($C_{1-3}$ alkyl); and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$, wherein q is 1; $R^6$ is —NHC(=O)$R^{14}$; $R^{14}$ is -carbocyclyl($R^{22}$)$_j$; j is 0; R is -heteroaryl($R^8$)$_q$, wherein q is 1; $R^8$ is selected from the group consisting of halide, —($C_{1-2}$ alkyl), and —C(=O)$R^{19}$; $R^{19}$ is $C_{1-3}$ alkyl; the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is —NHC(=O)$R^{14}$; $R^{14}$ is -carbocyclyl($R^2$)$_j$; j is 0; $R^5$ is -heterocyclyl($R^9$)$_h$; h is 1 or 2; $R^9$ is selected from the group consisting of halide and —($C_{1-2}$ alkyl); and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is selected from the group consisting of —N$R^{15}$$R^{16}$ and —CH$_2$N$R^{17}$$R^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —CH$_2$phenyl($R^{21}$)$_k$, and —CH$_2$carbocyclyl($R^{22}$)$_j$, wherein k and j are 0; $R^5$ is -phenyl($R^{10}$)$_k$, wherein k is 1 or 2; $R^{10}$ is F; and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is selected from the group consisting of —N$R^{15}$$R^{16}$ and —CH$_2$N$R^{17}$$R^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —CH$_2$phenyl($R^{21}$)$_k$, and —CH$_2$carbocyclyl($R^{22}$)$_j$, wherein k and j are 0; $R^5$ is -phenyl($R^{10}$)$_k$, wherein k is 2; one $R^{10}$ is F and the other $R^{10}$ is —($C_{1-2}$ alkylene)$_p$NHSO$_2$$R^{19}$; p is 1; $R^{19}$ is —($C_{1-3}$ alkyl); and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is selected from the group consisting of —N$R^{15}$$R^{16}$ and —CH$_2$N$R^{17}$$R^{18}$, wherein $R^{15}$ and $R^{17}$ are independently selected from the group consisting of H and —($C_{1-3}$ alkyl), and $R^{16}$ and $R^{18}$ are independently selected from the group consisting of H, —($C_{1-3}$ alkyl), —CH$_2$phenyl($R^{21}$)$_k$, and —CH$_2$carbocyclyl($R^{22}$)$_j$, wherein k and j are 0; $R^5$ is -phenyl($R^{10}$)$_k$, wherein k is 2; one $R^{10}$ is F and the other $R^{10}$ is —NH($C_{1-6}$ alkylene)N$R^{15}$$R^{16}$, wherein $R^{15}$ and $R^{16}$ are independently selected from —($C_{1-3}$ alkyl); and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$, wherein q is 1; $R^6$ is selected from the group consisting of —N$R^{15}$$R^{16}$ and —CH$_2$N$R^{17}$$R^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —CH$_2$phenyl($R^{21}$)$_k$, and —CH$_2$carbocyclyl($R^{22}$)$_j$; k and j are 0; $R^5$ is -heteroaryl($R^8$)$_q$, wherein q is 1; $R^8$ is selected from the group consisting of halide, —($C_{1-2}$ alkyl), and —C(=O)$R^{19}$; $R^{19}$ is —($C_{1-3}$ alkyl); the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is selected from the group consisting of —N$R^{15}$$R^{16}$ and —CH$_2$N$R^{17}$$R^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —$CH_2$phenyl($R^{21}$)$_k$, and —$CH_2$carbocyclyl($R^{22}$)$_j$; k and j are 0; $R^5$ is -heterocyclyl($R^9$)$_h$; h is 1 or 2; each $R^9$ is independently selected from the group consisting of halide and —($C_{1-2}$ alkyl); and the carbocyclyl is selected from the group consisting of cyclopropyl, cyclobutyl, cyclopentyl, and cyclohexyl.

In some embodiments, $R^1$, $R^2$, and $R^4$ are H; $R^3$ is -pyridin-3-yl($R^6$)$_q$; q is 1; $R^6$ is —$CH_2$heterocyclyl($R^{11}$)$_h$; h is 0-2; $R^{11}$ is F; $R^5$ is -phenyl($R^{10}$)$_k$; k is 1 or 2; $R^{10}$ is F; and the heterocyclyl is selected from the group consisting of pyrrolidine and piperidine.

In some embodiments, $R^1$, $R^2$, and $R^4$ are H; $R^3$ is -pyridin-3-yl($R^6$)$_q$; q is 1; $R^6$ is —$CH_2$heterocyclyl($R^{11}$)$_h$; h is 0-2; $R^{11}$ is F; $R^5$ is -phenyl($R^{10}$)$_k$; k is 2; one $R^{10}$ is F and the other $R^{10}$ is —($C_{1-2}$ alkylene)$_p$NHSO$_2$$R^{19}$; p is 1; $R^{19}$ is —($C_{1-3}$ alkyl); and the heterocyclyl is selected from the group consisting of pyrrolidine and piperidine.

In some embodiments, $R^1$, $R^2$, and $R^4$ are H; $R^3$ is -pyridin-3-yl($R^6$)$_q$; q is 1; $R^6$ is —$CH_2$heterocyclyl($R^{11}$)$_h$; h is 0-2; $R^{11}$ is F; $R^5$ is -phenyl($R^{10}$)$_k$; k is 2; one $R^{10}$ is F and the other $R^{10}$ is —NH($C_{1-6}$ alkylene)NR$^{5S}$R$^6$; $R^{15}$ and $R^{16}$ are independently selected from —($C_{1-3}$ alkyl); and the heterocyclyl is selected from the group consisting of pyrrolidine and piperidine.

In some embodiments, $R^1$, $R^2$, and $R^4$ are H; $R^3$ is -pyridin-3-yl($R^6$)$_q$, wherein q is 1; $R^6$ is —$CH_2$heterocyclyl($R^{11}$)$_h$; h is 0-2; $R^{11}$ is F; $R^5$ is -heteroaryl($R^8$)$_q$, wherein q is 1; $R^8$ is selected from the group consisting of halide, —($C_{1-2}$ alkyl), and —C(=O)$R^{19}$; $R^{19}$ is —($C_{1-3}$ alkyl); the heteroaryl is selected from the group consisting of pyridine, furan, thiophene, and imidazole; and the heterocyclyl is selected from the group consisting of pyrrolidine and piperidine.

In some embodiments, $R^1$, $R^2$, and $R^4$ are H; $R^3$ is -pyridin-3-yl($R^6$)$_q$; q is 1; $R^6$ is —$CH_2$heterocyclyl($R^{11}$)$_h$, wherein h is 0-2; $R^{11}$ is F; $R^5$ is -heterocyclyl($R^9$)$_h$, wherein h is 1 or 2; each $R^9$ is independently selected from the group consisting of halide and —($C_{1-2}$ alkyl); and the heterocyclyl is selected from the group consisting of pyrrolidine and piperidine.

In some embodiments, $R^1$, $R^2$, and $R^4$ are H; $R^3$ is -pyrimidinyl($R^6$)$_q$; q is 0; $R^5$ is -phenyl($R^{10}$)$_k$; k is 1 or 2; and $R^{10}$ is F.

In some embodiments, $R^1$, $R^2$, and $R^4$ are H; $R^3$ is -pyrimidinyl($R^6$); q is 0; $R^5$ is -phenyl($R^{10}$)$_k$; k is 2; one $R^{10}$ is F and the other $R^{10}$ is —($C_{1-2}$ alkylene)$_p$NHSO$_2$$R^{19}$; p is 1; and $R^{19}$ is —($C_{1-3}$ alkyl).

In some embodiments, $R^1$, $R^2$, and $R^4$ are H; $R^3$ is -pyrimidinyl($R^6$)$_q$; q is 0; $R^5$ is -phenyl($R^{10}$)$_k$; k is 2; one $R^{10}$ is F and the other $R^{10}$ is —NH($C_{1-6}$ alkylene)NR$^{15}$R$^{16}$; and $R^{15}$ and $R^{16}$ are independently a —($C_{1-3}$ alkyl).

In some embodiments, $R^1$, $R^2$, and $R^4$ are H; $R^3$ is -pyrimidinyl($R^7$)$_q$, wherein q is 0; $R^5$ is -heteroaryl($R^8$)$_q$, wherein q is 1; $R^8$ is selected from the group consisting of halide, —($C_{1-2}$ alkyl), and —C(=O)$R^{19}$; $R^{19}$ is —($C_{1-3}$ alkyl); and the heteroaryl is selected from the group consisting of pyridine, furan, thiophene, and imidazole.

In some embodiments, $R^1$, $R^2$, and $R^4$ are H; $R^3$ is -pyrimidinyl($R^6$)$_q$; q is 0; $R^5$ is -heterocyclyl($R^9$)$_h$; h is 1 or 2; each $R^9$ is independently selected from the group consisting of halide and —($C_{1-2}$ alkyl).

In some embodiments, $R^2$ is F; $R^1$ and $R^4$ are H; $R^3$ is -pyridin-3-yl($R^8$)$_q$; q is 1; $R^6$ is —NHC(=O)$R^{14}$; $R^{14}$ is —($C_{2-5}$ alkyl); $R^5$ is -phenyl($R^{10}$)$_k$; k is 1 or 2; and $R^{10}$ is F.

In some embodiments, $R^2$ is F; $R^1$ and $R^4$ are H; $R^3$ is -pyridin-3-yl($R^8$)$_q$; q is 1; $R^6$ is —NHC(=O)$R^{14}$; $R^{14}$ is —($C_{2-5}$ alkyl); $R^5$ is -phenyl($R^{10}$)$_k$; k is 2; one $R^{10}$ is F and the other $R^{10}$ is —($C_{1-2}$ alkylene)$_p$NHSO$_2$$R^{19}$; p is 1; and $R^{19}$ is —($C_{1-3}$ alkyl).

In some embodiments, $R^2$ is F; $R^1$ and $R^4$ are H; $R^3$ is -pyridin-3-yl($R^8$)$_q$; q is 1; $R^6$ is —NHC(=O)$R^{14}$; $R^{14}$ is —($C_{2-5}$ alkyl); $R^5$ is -phenyl($R^{10}$)$_k$; k is 2; one $R^{10}$ is F and the other $R^{10}$ is —NH($C_{1-6}$ alkylene)NR$^{15}$R$^{16}$; and $R^{15}$ and $R^{16}$ are independently a —($C_{1-3}$ alkyl).

In some embodiments, $R^2$ is F; $R^1$ and $R^4$ are H; $R^3$ is -pyridin-3-yl($R^8$)$_q$, wherein q is 1; $R^6$ is —NHC(=O)$R^{14}$; $R^{14}$ is —($C_{2-5}$ alkyl); $R^5$ is -heteroaryl($R^8$)$_q$, wherein q is 1; $R^8$ is selected from the group consisting of halide, —($C_{1-2}$ alkyl), and —C(=O)$R^{19}$; $R^{19}$ is —($C_{1-3}$ alkyl); and the heteroaryl is selected from the group consisting of pyridine, furan, thiophene, and imidazole.

In some embodiments, $R^2$ is F; $R^1$ and $R^4$ are H; $R^3$ is -pyridin-3-yl($R^8$)$_q$; q is 1; $R^6$ is —NHC(=O)$R^4$; $R^{14}$ is —($C_{2-5}$ alkyl); $R^5$ is -heterocyclyl($R^9$)$_h$; h is 1 or 2; and each $R^9$ is independently selected from the group consisting of halide and —($C_{1-2}$ alkyl).

In some embodiments, $R^2$ is F; $R^1$ and $R^4$ are H; $R^3$ is -pyridin-3-yl($R^6$)$_q$; q is 1; $R^6$ is —NHC(=O)$R^4$; $R^{14}$ is -carbocyclyl($R^{22}$)); j is 0; $R^5$ is -phenyl($R^{10}$)$_k$; k is 1 or 2; $R^{10}$ is F; and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl($R^6$)$_q$; q is 1; $R^6$ is —NHC(=O)$R^{14}$; $R^{14}$ is -carbocyclyl($R^{22}$)$_j$; j is 0; $R^5$ is -phenyl($R^{10}$)$_k$; k is 2; one $R^{10}$ is F and the other $R^{10}$ is —($C_{1-2}$ alkylene)$_p$NHSO$_2$$R^{19}$; p is 1; $R^{19}$ is —($C_{1-3}$ alkyl); and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl($R^6$)$_q$; q is 1; $R^6$ is —NHC(=O)$R^{14}$; $R^{14}$ is -carbocyclyl($R^{22}$)$_j$; j is 0; $R^5$ is -phenyl($R^{10}$)$_k$; k is 2; one $R^{10}$ is F and the other $R^{10}$ is —NH($C_{1-6}$ alkylene)NR$^{15}$R$^{16}$; $R^{15}$ and $R^{16}$ are independently a —($C_{1-3}$ alkyl); and the carbocyclyl is selected from the group consisting of cyclopropyl, cyclobutyl, cyclobutyl, cyclopentyl, and cyclohexyl.

In some embodiments, $R^2$ is F; $R^1$ and $R^4$ are H; $R^3$ is -pyridin-3-yl($R^6$)$_q$, wherein q is 1; $R^6$ is —NHC(=O)$R^{14}$; $R^{14}$ is -carbocyclyl($R^{22}$)$_j$; j is 0; $R^5$ is -heteroaryl($R^8$)$_q$, wherein q is 1; $R^8$ is selected from the group consisting of halide, —($C_{1-2}$ alkyl), and —C(=O)$R^{19}$; $R^{19}$ is —($C_{1-3}$ alkyl); the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl($R^6$)$_q$; q is 1; $R^6$ is —NHC(=O)$R^{14}$; $R^{14}$ is -carbocyclyl($R^2$)$_j$; j is 0; $R^5$ is -heterocyclyl($R^9$)$_h$; h is 1 or 2; each $R^9$ is independently selected from the group consisting of halide and —($C_{1-2}$ alkyl); and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl($R^6$)$_q$; q is 1; $R^6$ is selected from the group consisting of —NR$^{15}$R$^{16}$ and —$CH_2$NR$^{17}$R$^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —$CH_2$phenyl($R^{21}$)$_k$, and —$CH_2$carbocyclyl($R^2$)$_j$, wherein k and j are 0; $R^5$ is -phenyl($R^{10}$)$_k$, wherein k is 1 or 2; $R^{10}$ is F; and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl$(R^6)_q$; q is 1; $R^6$ is selected from the group consisting of —$NR^{15}R^{16}$ and —$CH_2NR^{17}R^{18}$; $R^{15}$, $R^{16}$, $R^{17}$, and $R^{18}$ are independently selected from the group consisting of H, —($C_{1-3}$ alkyl), —$CH_2$phenyl$(R^{21})_k$, and —$CH_2$carbocyclyl$(R^{22})_j$, wherein k and j are 0; $R^5$ is -phenyl$(R^{10})_k$, wherein k is 2; one $R^{10}$ is F and the other $R^{10}$ is —($C_{1-2}$ alkylene)$_p$NHSO$_2R^{19}$; p is 1; $R^{19}$ is —($C_{1-3}$ alkyl); and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl$(R^6)_q$; q is 1; $R^6$ is selected from the group consisting of —$NR^{15}R^{16}$ and —$CH_2NR^{17}R^{18}$, wherein $R^{15}$ and $R^{17}$ are independently selected from the group consisting of H and —($C_{1-3}$ alkyl), and $R^{16}$ and $R^{18}$ are independently selected from the group consisting of H, —($C_{1-3}$ alkyl), —$CH_2$phenyl$(R^{21})_k$, and —$CH_2$carbocyclyl$(R^{22})$), wherein k and j are 0; $R^5$ is -phenyl$(R^{10})_k$, wherein k is 2; one $R^{10}$ is F and the other $R^{10}$ is —NH($C_{1-6}$ alkylene)$NR^{15}R^{16}$, wherein $R^{15}$ and $R^{16}$ are independently selected from —($C_{1-3}$ alkyl); and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl$(R^6)_q$, wherein q is 1; $R^6$ is selected from the group consisting of —$NR^{15}R^{16}$ and —$CH_2NR^{17}R^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —$CH_2$phenyl$(R^{21})_k$, and —$CH_2$carbocyclyl$(R^{22})$); k and j are 0; $R^5$ is -heteroaryl$(R^8)_q$, wherein q is 1; $R^8$ is selected from the group consisting of halide, —($C_{1-2}$ alkyl), and —C(=O)$R^{19}$; $R^{19}$ is —($C_{1-3}$ alkyl); the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl$(R^8)_q$; q is 1; $R^6$ is selected from the group consisting of —$NR^{15}R^{16}$ and —$CH_2NR^{17}R^{18}$; $R^{15}$ and $R^{17}$ are independently selected from the group consisting of H and —($C_{1-3}$ alkyl); $R^{16}$ and $R^{18}$ are independently selected from the group consisting of H, —($C_{1-3}$ alkyl), —$CH_2$phenyl$(R^{21})_k$, and —$CH_2$carbocyclyl$(R^{22})$); k and j are 0; $R^5$ is -heterocyclyl$(R^9)_h$; h is 1 or 2; each $R^9$ is independently selected from the group consisting of halide and $C_{1-2}$ alkyl; and the carbocyclyl is selected from the group consisting of cyclopropyl, cyclobutyl, cyclopentyl, and cyclohexyl.

In some embodiments, $R^2$ is F; $R^1$ and $R^4$ are H; $R^3$ is -pyridin-3-yl$(R^8)_q$; q is 1; $R^6$ is —$CH_2$heterocyclyl$(R^{11})_h$; h is 0-2; $R^{11}$ is F; $R^5$ is -phenyl$(R^{10})_k$; k is 1 or 2; $R^{10}$ is F; and the heterocyclyl is selected from the group consisting of pyrrolidine and piperidine.

In some embodiments, $R^2$ is F; $R^1$ and $R^4$ are H; $R^3$ is -pyridin-3-yl$(R^8)_q$; q is 1; $R^6$ is —$CH_2$heterocyclyl$(R^{11})_h$; h is 0-2; $R^{11}$ is F; $R^5$ is -phenyl$(R^{10})_k$; k is 2; one $R^{10}$ is F and the other $R^{10}$ is —($C_{1-2}$ alkylene)$_p$NHSO$_2R^{19}$; p is 1; $R^{19}$ is —($C_{1-3}$ alkyl); and the heterocyclyl is selected from the group consisting of pyrrolidine and piperidine.

In some embodiments, $R^2$ is F; $R^1$ and $R^4$ are H; $R^3$ is -pyridin-3-yl$(R^8)_q$; q is 1; $R^6$ is —$CH_2$heterocyclyl$(R^{11})_h$; h is 0-2; $R^{11}$ is F; $R^5$ is -phenyl$(R^{10})_k$; k is 2; one $R^{10}$ is F and the other $R^{10}$ is —NH($C_{1-6}$ alkylene)$NR^{15}R^{16}$; $R^{15}$ and $R^{16}$ are independently selected from —($C_{1-3}$ alkyl); and the heterocyclyl is selected from the group consisting of pyrrolidine and piperidine.

In some embodiments, $R^2$ is F; $R^1$ and $R^4$ are H; $R^3$ is -pyridin-3-yl$(R^6)_q$, wherein q is 1; $R^6$ is —$CH_2$heterocyclyl$(R^{11})_h$; h is 0-2; $R^{11}$ is F; $R^5$ is -heteroaryl$(R^8)_q$, wherein q is 1; $R^8$ is selected from the group consisting of halide, —($C_{1-2}$ alkyl), and —C(=O)$R^{19}$; $R^{19}$ is —($C_{1-3}$ alkyl); the heteroaryl is selected from the group consisting of pyridine, furan, thiophene, and imidazole; and the heterocyclyl is selected from the group consisting of pyrrolidine and piperidine.

In some embodiments, $R^2$ is F; $R^1$ and $R^4$ are H; $R^3$ is -pyridin-3-yl$(R^6)_q$; q is 1; $R^6$ is —$CH_2$heterocyclyl$(R^{11})_h$, wherein h is 0-2; $R^{11}$ is F; $R^5$ is -heterocyclyl$(R^9)_h$, wherein h is 1 or 2; $R^9$ is selected from the group consisting of halide and —($C_{1-2}$ alkyl); and the heterocyclyl is selected from the group consisting of pyrrolidine and piperidine.

In some embodiments, $R^2$ is F; $R^1$ and $R^4$ are H; $R^3$ is -pyrimidinyl$(R^6)_q$; q is 0; $R^5$ is -phenyl$(R^{10})_k$; k is 1 or 2; and $R^{10}$ is F.

In some embodiments, $R^2$ is F; $R^1$ and $R^4$ are H; $R^3$ is -pyrimidinyl$(R^6)_q$; q is 0; $R^5$ is -phenyl$(R^{10})_k$; k is 2; one $R^{10}$ is F and the other $R^{10}$ is —($C_{1-2}$ alkylene)$_p$NHSO$_2R^{19}$; p is 1; and $R^{19}$ is —($C_{1-3}$ alkyl).

In some embodiments, $R^2$ is F; $R^1$ and $R^4$ are H; $R^3$ is -pyrimidinyl$(R^6)_q$; q is 0; R is -phenyl$(R^{10})_k$; k is 2; one $R^{10}$ is F and the other $R^{10}$ is —NH($C_{1-6}$ alkylene)$NR^{15}R^{16}$; and $R^{15}$ and $R^{16}$ are independently selected from —($C_{1-3}$ alkyl).

In some embodiments, $R^2$ is F; $R^1$ and $R^4$ are H; $R^3$ is -pyrimidinyl$(R^6)_q$, wherein q is 0; $R^5$ is -heteroaryl$(R^8)_q$, wherein q is 1; $R^8$ is selected from the group consisting of halide, —($C_{1-2}$ alkyl), and —C(=O)$R^{19}$; $R^{19}$ is —($C_{1-3}$ alkyl); and the heteroaryl is selected from the group consisting of pyridine, furan, thiophene, and imidazole.

In some embodiments, $R^2$ is F; $R^1$ and $R^4$ are H; $R^3$ is -pyrimidinyl$(R^6)_q$; q is 0; R is -heterocyclyl$(R^9)_h$; h is 1 or 2; $R^9$ is selected from the group consisting of halide and —($C_{1-2}$ alkyl).

In some embodiments, $R^1$, $R^2$, and $R^4$ are H; $R^3$ is -pyrazol-4-yl$(R^6)_q$; q is 0 or 1; $R^6$ is —($C_{1-3}$ alkyl); $R^5$ is -phenyl$(R^{10})_k$; k is 1 or 2; and $R^{10}$ is F.

In some embodiments, $R^1$, $R^2$, and $R^4$ are H; $R^3$ is -imidazol-5-yl$(R^6)_q$; q is 1 or 2; each $R^6$ is independently selected from —($C_{1-3}$ alkyl); $R^5$ is -phenyl$(R^{10})_k$; k is 1 or 2; and $R^{10}$ is F.

In some embodiments, $R^1$, $R^2$, and $R^4$ are H; $R^3$ is -pyridin-3-yl$(R^6)_q$; q is 1; $R^6$ is —$OR^{24}$; $R^{24}$ is selected from the group consisting of H and —($C_{1-3}$ alkyl); $R^5$ is -phenyl$(R^{10})_k$; k is 1 or 2; and $R^{10}$ is F.

Illustrative compounds of Formula (I) are shown in Table 1.

TABLE 1

1

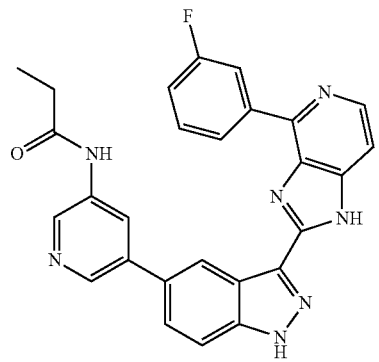 [SMILES: CCC(=O)Nc1cncc(-c2ccc3[nH]nc(-c4nc5c(-c6cccc(F)c6)nccc5[nH]4)c3c2)c1]

TABLE 1-continued
| | | | | |
|---|---|---|---|---|
| 2 | 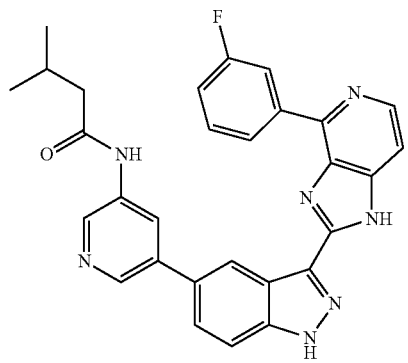 [SMILES: CC(C)CC(=O)Nc1cncc(-c2ccc3[nH]nc(-c4nc5c(-c6cccc(F)c6)nccc5[nH]4)c3c2)c1] | | 6 | 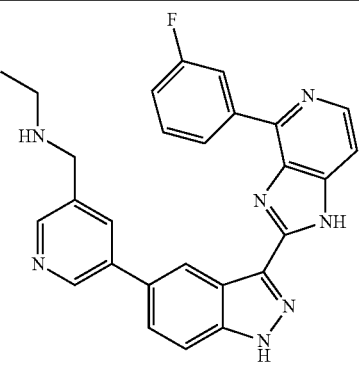 |
| 3 | 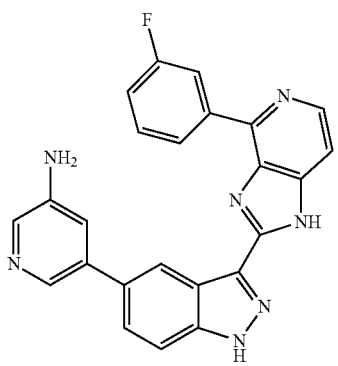 [SMILES: Nc1cncc(-c2ccc3[nH]nc(-c4nc5c(-c6cccc(F)c6)nccc5[nH]4)c3c2)c1] | | 7 | 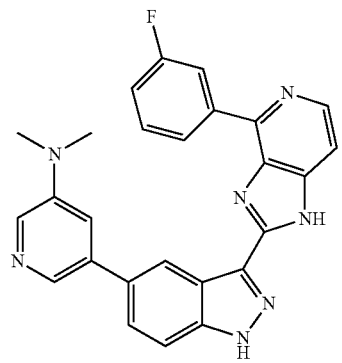 |
| 4 | 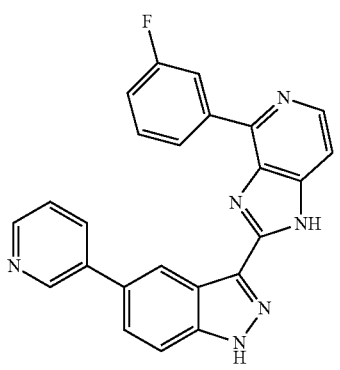 [SMILES: Fc1cccc(-c2nccc3[nH]c(-c4n[nH]c5ccc(-c6cccnc6)cc45)nc23)c1] | | 8 | 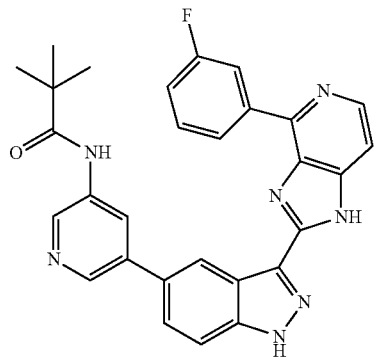 |
| 5 | 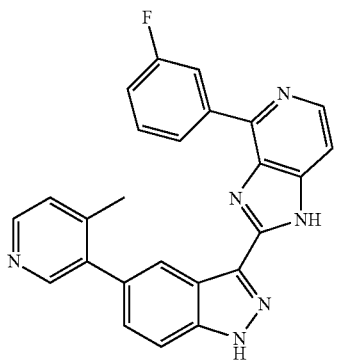 [SMILES: Cc1ccncc1-c1ccc2[nH]nc(-c3nc4c(-c5cccc(F)c5)nccc4[nH]3)c2c1] | | 9 | 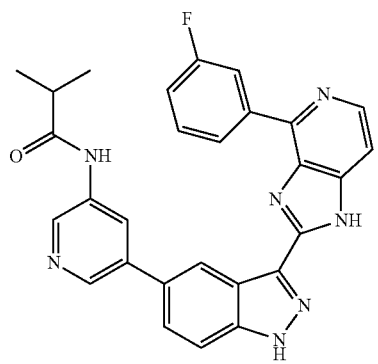 [SMILES: CC(C)C(=O)Nc1cncc(-c2ccc3[nH]nc(-c4nc5c(-c6cccc(F)c6)nccc5[nH]4)c3c2)c1] |

TABLE 1-continued
10
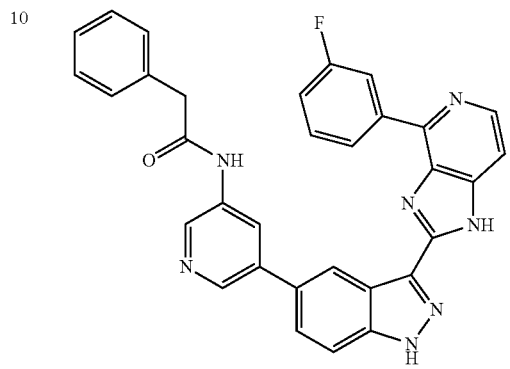
11
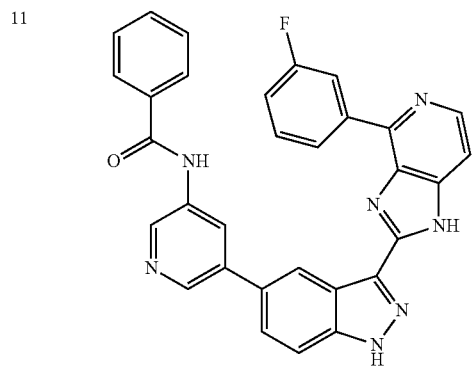
12
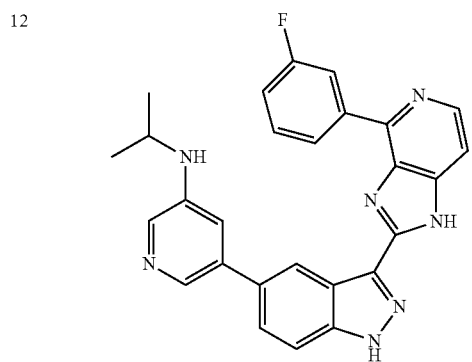
13
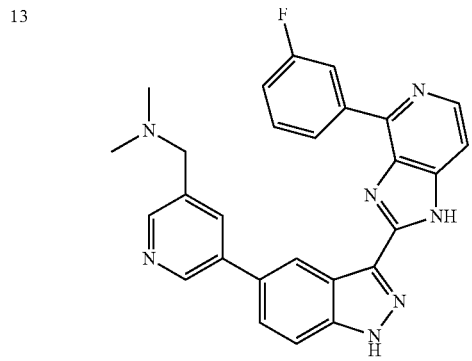
TABLE 1-continued
14

15
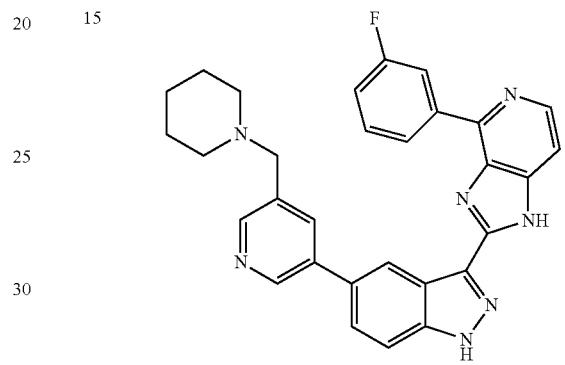
16
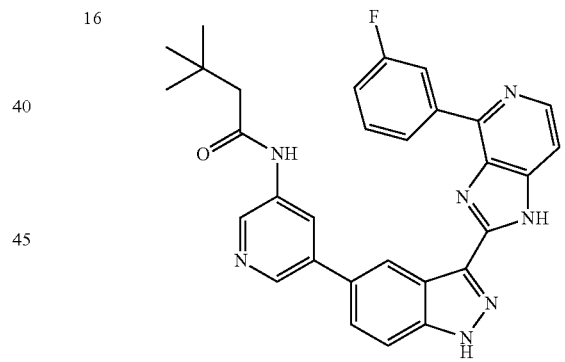
17
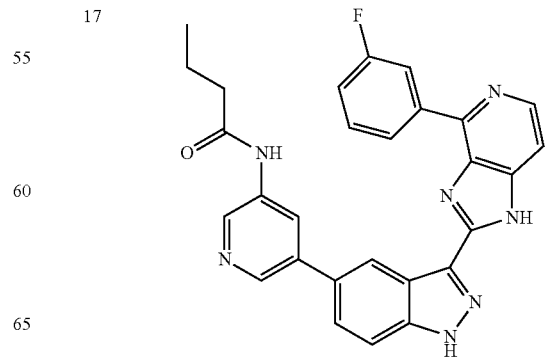

TABLE 1-continued
| 18 | 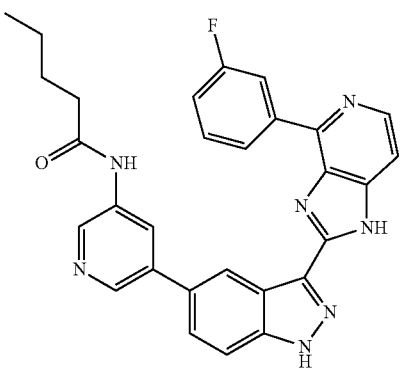 [SMILES: CCCCC(=O)Nc1cncc(-c2ccc3[nH]nc(-c4nc5c(-c6cccc(F)c6)nccc5[nH]4)c3c2)c1] |
| --- | --- |
| 19 | 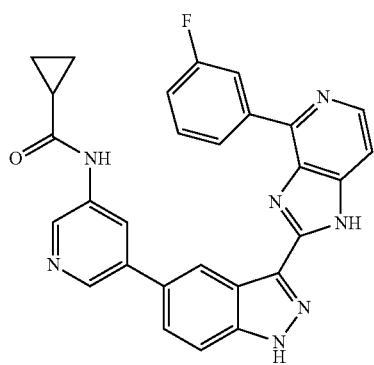 [SMILES: O=C(Nc1cncc(-c2ccc3[nH]nc(-c4nc5c(-c6cccc(F)c6)nccc5[nH]4)c3c2)c1)C1CC1] |
| 20 | 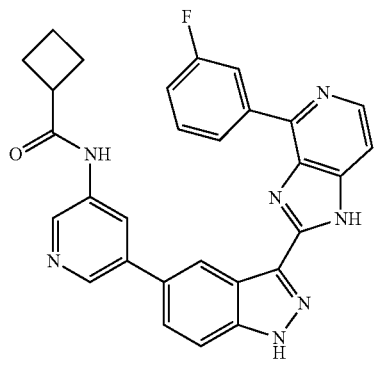 [SMILES: O=C(Nc1cncc(-c2ccc3[nH]nc(-c4nc5c(-c6cccc(F)c6)nccc5[nH]4)c3c2)c1)C1CCC1] |
| 21 | 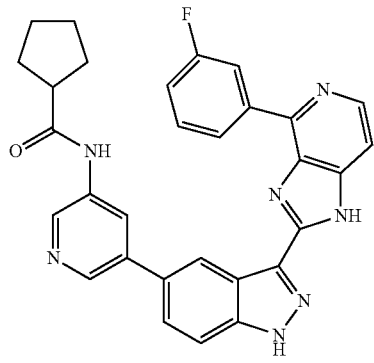 [SMILES: O=C(Nc1cncc(-c2ccc3[nH]nc(-c4nc5c(-c6cccc(F)c6)nccc5[nH]4)c3c2)c1)C1CCCC1] |
TABLE 1-continued
| 22 | 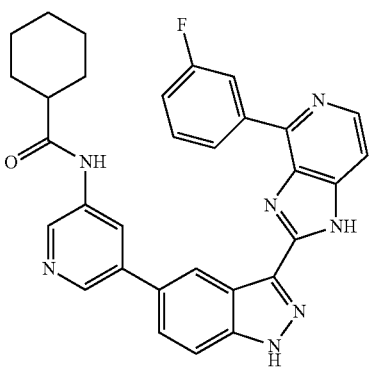 [SMILES: O=C(Nc1cncc(-c2ccc3[nH]nc(-c4nc5c(-c6cccc(F)c6)nccc5[nH]4)c3c2)c1)C1CCCCC1] |
| --- | --- |
| 23 | 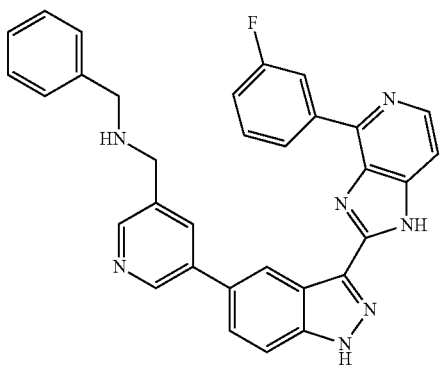 [SMILES: Fc1cccc(-c2nccc3[nH]c(-c4n[nH]c5ccc(-c6cncc(CNCc7ccccc7)c6)cc45)nc23)c1] |
| 24 | 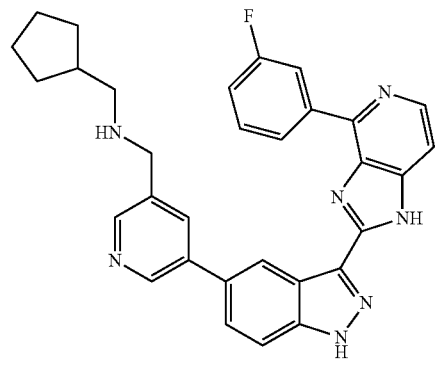 [SMILES: Fc1cccc(-c2nccc3[nH]c(-c4n[nH]c5ccc(-c6cncc(CNCC7CCCC7)c6)cc45)nc23)c1] |
| 25 | 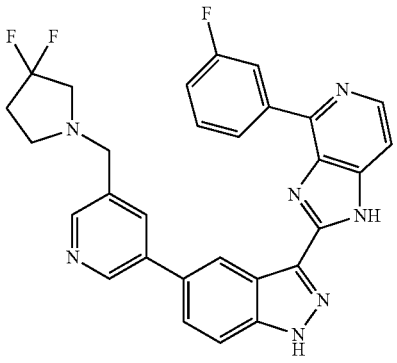 [SMILES: Fc1cccc(-c2nccc3[nH]c(-c4n[nH]c5ccc(-c6cncc(CN7CCC(F)(F)C7)c6)cc45)nc23)c1] |

TABLE 1-continued
| 26 | 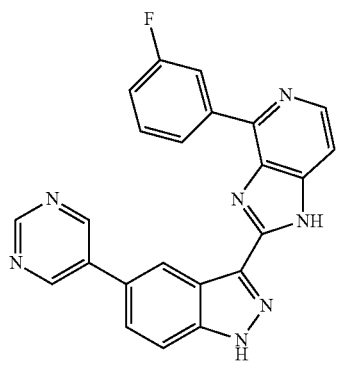 [SMILES: Fc1cccc(-c2nccc3[nH]c(-c4n[nH]c5ccc(-c6cncnc6)cc45)nc23)c1] |
| --- | --- |
| 27 | 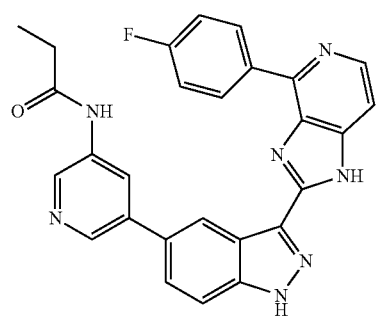 [SMILES: CCC(=O)Nc1cncc(-c2ccc3[nH]nc(-c4nc5c(-c6ccc(F)cc6)nccc5[nH]4)c3c2)c1] |
| 28 | 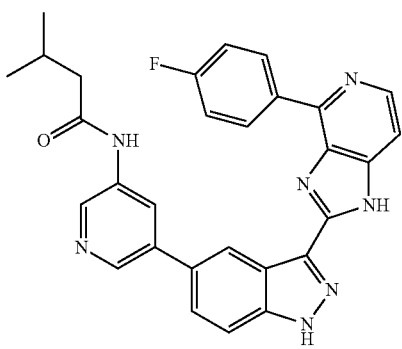 |
| 29 | 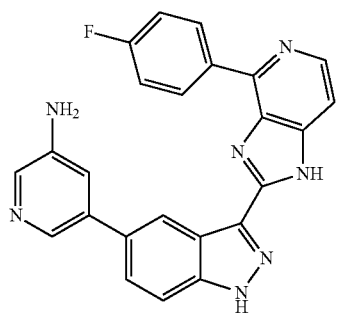 [SMILES: Nc1cncc(-c2ccc3[nH]nc(-c4nc5c(-c6ccc(F)cc6)nccc5[nH]4)c3c2)c1] |
| 30 | 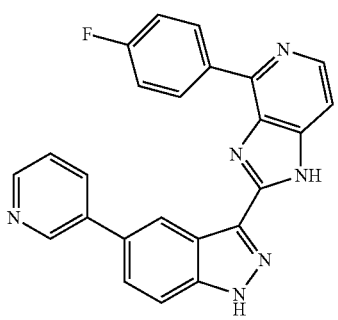 [SMILES: Fc1ccc(-c2nccc3[nH]c(-c4n[nH]c5ccc(-c6cccnc6)cc45)nc23)cc1] |
| 31 | 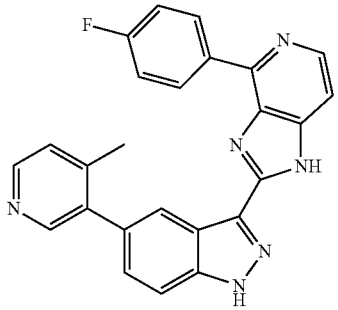 [SMILES: Cc1ccncc1-c1ccc2[nH]nc(-c3nc4c(-c5ccc(F)cc5)nccc4[nH]3)c2c1] |
| 32 | 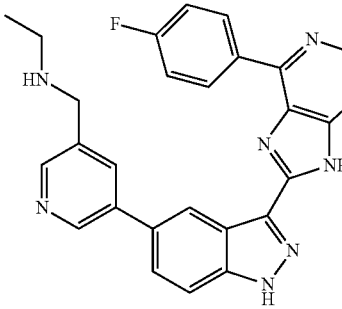 |
| 33 | 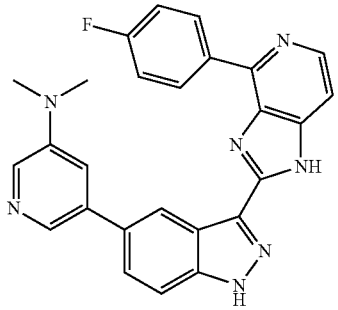 [SMILES: CN(C)c1cncc(-c2ccc3[nH]nc(-c4nc5c(-c6ccc(F)cc6)nccc5[nH]4)c3c2)c1] |
| 34 | 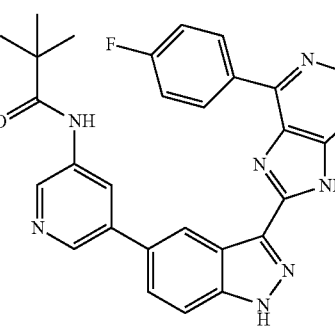 |

TABLE 1-continued
35 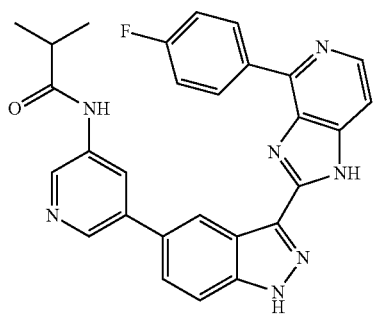 [SMILES: CC(C)C(=O)Nc1cncc(-c2ccc3[nH]nc(-c4nc5c(-c6ccc(F)cc6)nccc5[nH]4)c3c2)c1]
36 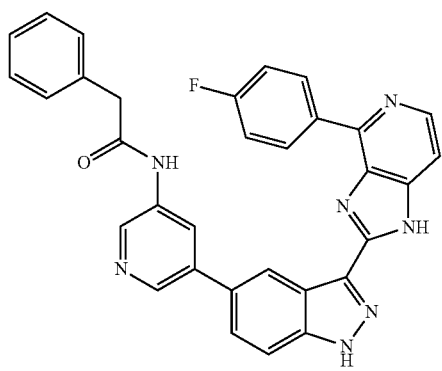 [SMILES: O=C(Cc1ccccc1)Nc1cncc(-c2ccc3[nH]nc(-c4nc5c(-c6ccc(F)cc6)nccc5[nH]4)c3c2)c1]
37 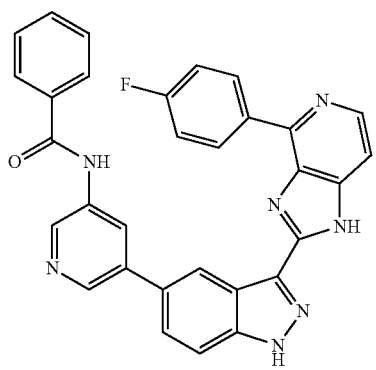 [SMILES: O=C(Nc1cncc(-c2ccc3[nH]nc(-c4nc5c(-c6ccc(F)cc6)nccc5[nH]4)c3c2)c1)c1ccccc1]
38 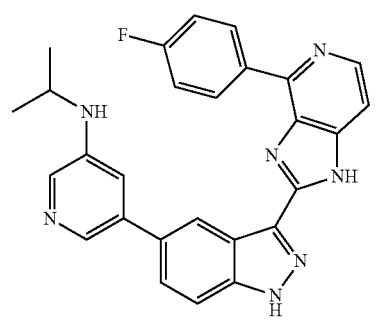 [SMILES: CC(C)Nc1cncc(-c2ccc3[nH]nc(-c4nc5c(-c6ccc(F)cc6)nccc5[nH]4)c3c2)c1]
TABLE 1-continued
39 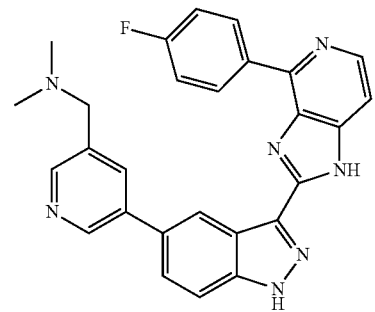 [SMILES: CN(C)Cc1cncc(-c2ccc3[nH]nc(-c4nc5c(-c6ccc(F)cc6)nccc5[nH]4)c3c2)c1]
40 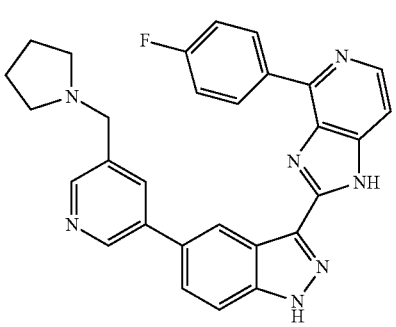 [SMILES: Fc1ccc(-c2nccc3[nH]c(-c4n[nH]c5ccc(-c6cncc(CN7CCCC7)c6)cc45)nc23)cc1]
41 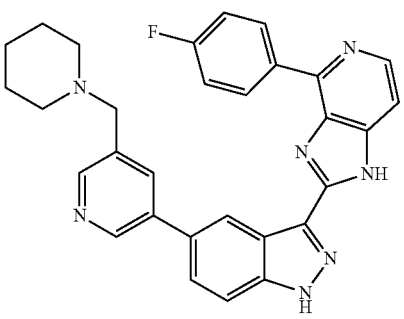
42 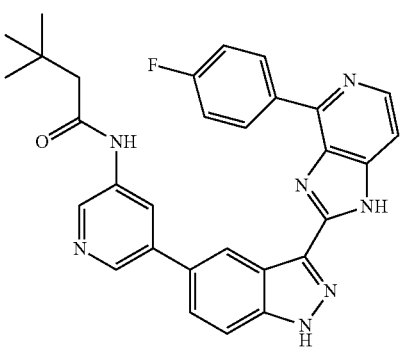 [SMILES: CC(C)(C)CC(=O)Nc1cncc(-c2ccc3[nH]nc(-c4nc5c(-c6ccc(F)cc6)nccc5[nH]4)c3c2)c1]
43 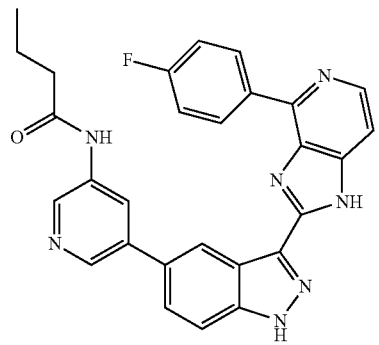 [SMILES: CCCC(=O)Nc1cncc(-c2ccc3[nH]nc(-c4nc5c(-c6ccc(F)cc6)nccc5[nH]4)c3c2)c1]

TABLE 1-continued
44 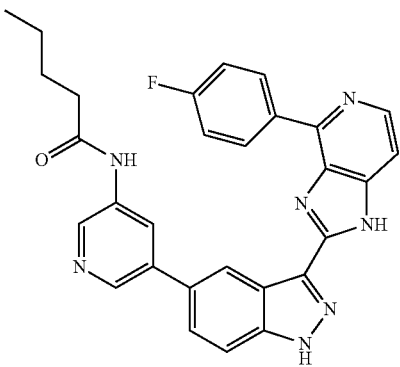 [SMILES: CCCCC(=O)Nc1cncc(-c2ccc3[nH]nc(-c4nc5c(-c6ccc(F)cc6)nccc5[nH]4)c3c2)c1]
45 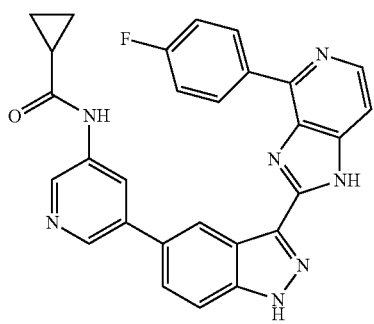 [SMILES: O=C(Nc1cncc(-c2ccc3[nH]nc(-c4nc5c(-c6ccc(F)cc6)nccc5[nH]4)c3c2)c1)C1CC1]
46 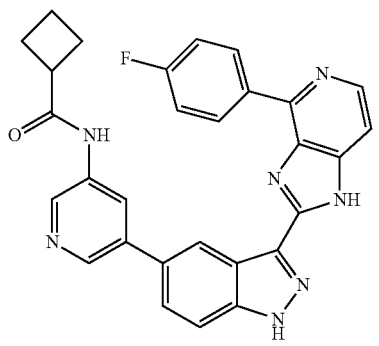 [SMILES: O=C(Nc1cncc(-c2ccc3[nH]nc(-c4nc5c(-c6ccc(F)cc6)nccc5[nH]4)c3c2)c1)C1CCC1]
47 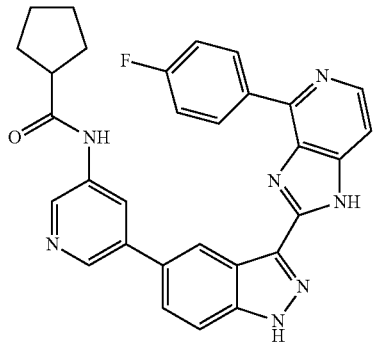 [SMILES: O=C(Nc1cncc(-c2ccc3[nH]nc(-c4nc5c(-c6ccc(F)cc6)nccc5[nH]4)c3c2)c1)C1CCCC1]
TABLE 1-continued
48 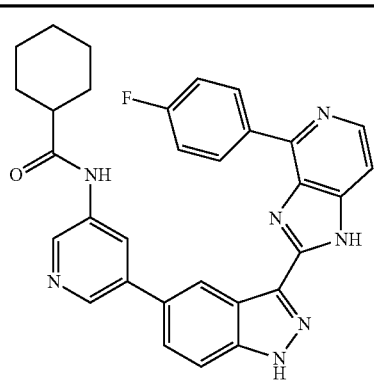
49 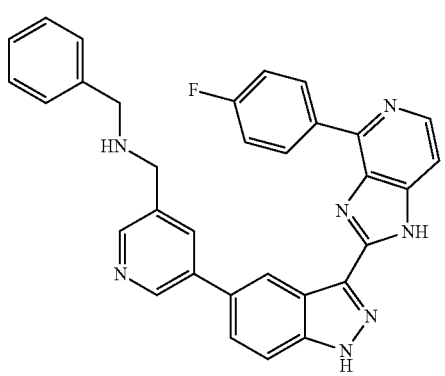 [SMILES: Fc1ccc(-c2nccc3[nH]c(-c4n[nH]c5ccc(-c6cncc(CNCc7ccccc7)c6)cc45)nc23)cc1]
50 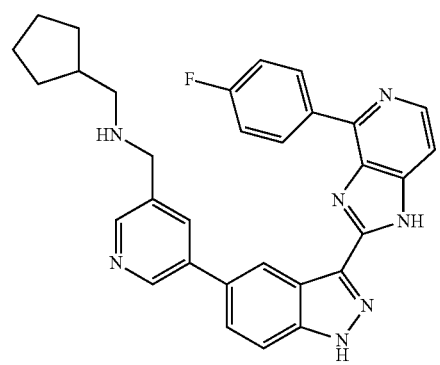 [SMILES: Fc1ccc(-c2nccc3[nH]c(-c4n[nH]c5ccc(-c6cncc(CNCC7CCCC7)c6)cc45)nc23)cc1]
51 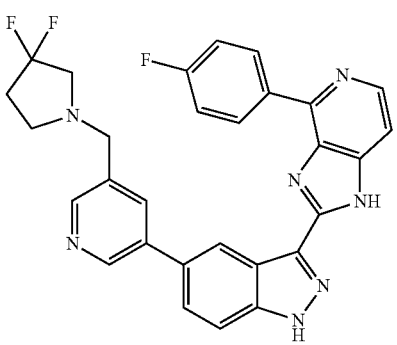 [SMILES: Fc1ccc(-c2nccc3[nH]c(-c4n[nH]c5ccc(-c6cncc(CN7CCC(F)(F)C7)c6)cc45)nc23)cc1]

TABLE 1-continued
52 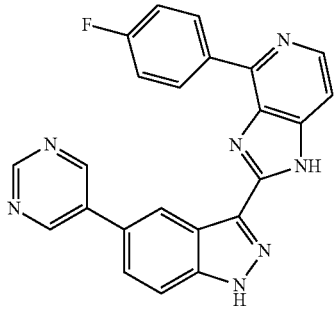
53 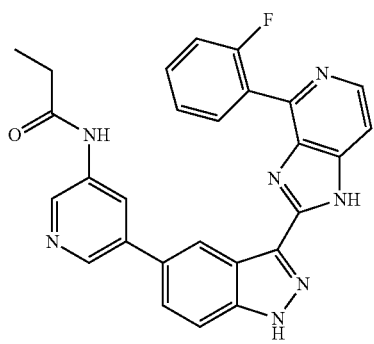 [SMILES: CCC(=O)Nc1cncc(-c2ccc3[nH]nc(-c4nc5c(-c6ccccc6F)nccc5[nH]4)c3c2)c1]
54 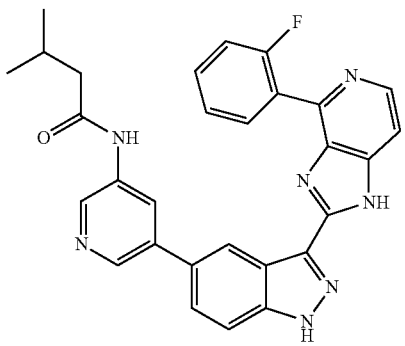 [SMILES: CC(C)CC(=O)Nc1cncc(-c2ccc3[nH]nc(-c4nc5c(-c6ccccc6F)nccc5[nH]4)c3c2)c1]
55 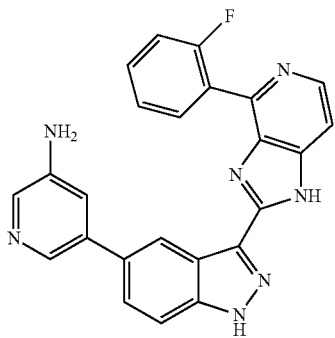 [SMILES: Nc1cncc(-c2ccc3[nH]nc(-c4nc5c(-c6ccccc6F)nccc5[nH]4)c3c2)c1]
56 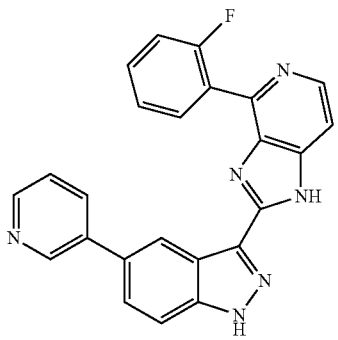
57 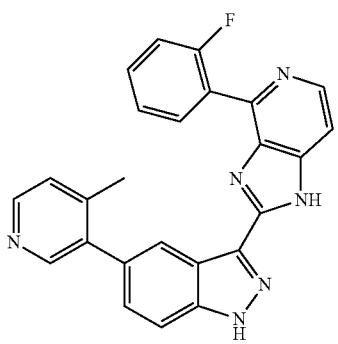 [SMILES: Cc1ccncc1-c1ccc2[nH]nc(-c3nc4c(-c5ccccc5F)nccc4[nH]3)c2c1]
58 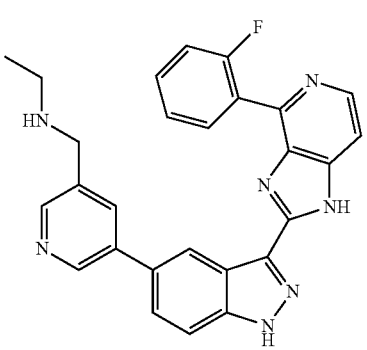 [SMILES: CCNCc1cncc(-c2ccc3[nH]nc(-c4nc5c(-c6ccccc6F)nccc5[nH]4)c3c2)c1]
59 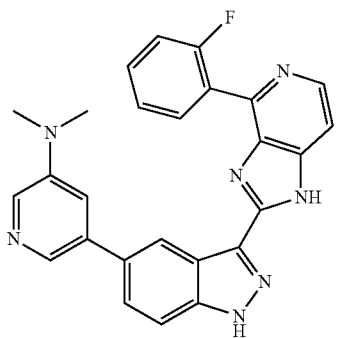 [SMILES: CN(C)c1cncc(-c2ccc3[nH]nc(-c4nc5c(-c6ccccc6F)nccc5[nH]4)c3c2)c1]

TABLE 1-continued
60
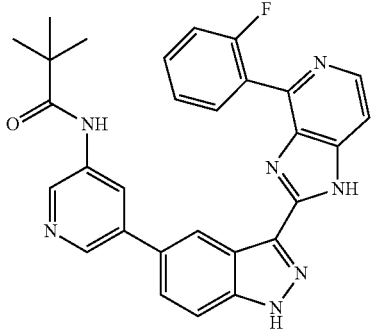 [SMILES: CC(C)(C)C(=O)Nc1cncc(-c2ccc3[nH]nc(-c4nc5c(-c6ccccc6F)nccc5[nH]4)c3c2)c1]
61
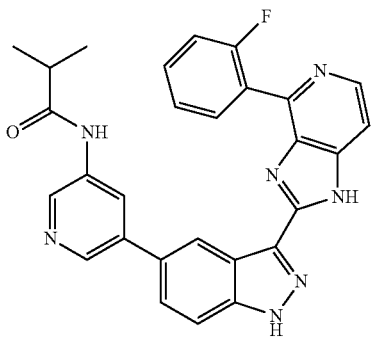 [SMILES: CC(C)C(=O)Nc1cncc(-c2ccc3[nH]nc(-c4nc5c(-c6ccccc6F)nccc5[nH]4)c3c2)c1]
62
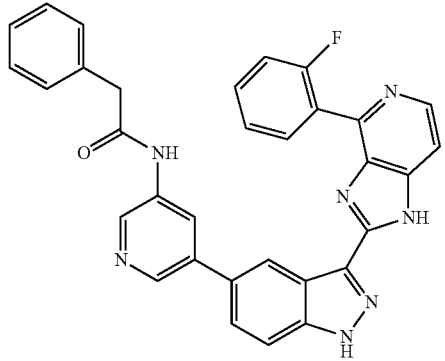 [SMILES: O=C(Cc1ccccc1)Nc1cncc(-c2ccc3[nH]nc(-c4nc5c(-c6ccccc6F)nccc5[nH]4)c3c2)c1]
63
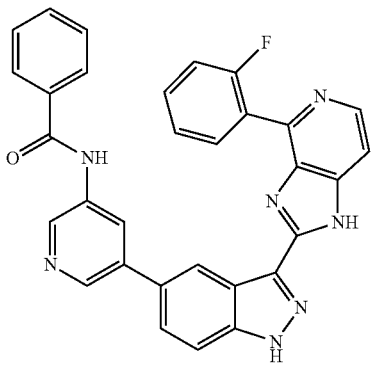 [SMILES: O=C(Nc1cncc(-c2ccc3[nH]nc(-c4nc5c(-c6ccccc6F)nccc5[nH]4)c3c2)c1)c1ccccc1]
TABLE 1-continued
64
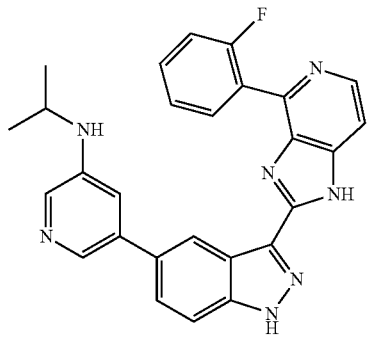 [SMILES: CC(C)Nc1cncc(-c2ccc3[nH]nc(-c4nc5c(-c6ccccc6F)nccc5[nH]4)c3c2)c1]
65
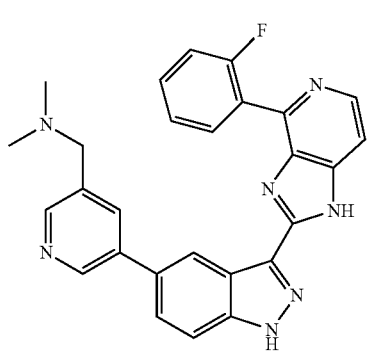 [SMILES: CN(C)Cc1cncc(-c2ccc3[nH]nc(-c4nc5c(-c6ccccc6F)nccc5[nH]4)c3c2)c1]
66
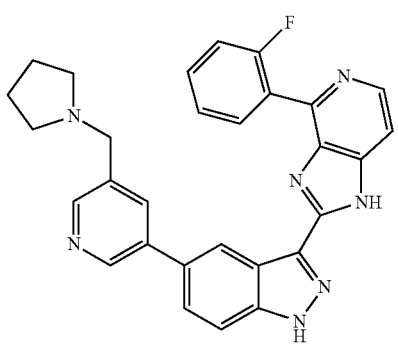 [SMILES: Fc1ccccc1-c1nccc2[nH]c(-c3n[nH]c4ccc(-c5cncc(CN6CCCC6)c5)cc34)nc12]
67
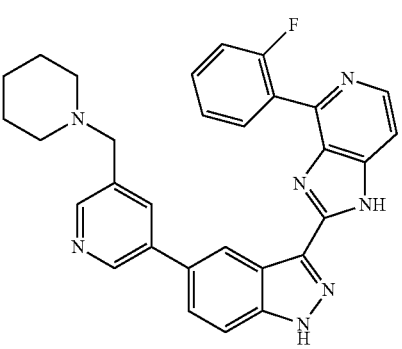 [SMILES: Fc1ccccc1-c1nccc2[nH]c(-c3n[nH]c4ccc(-c5cncc(CN6CCCCC6)c5)cc34)nc12]

TABLE 1-continued
| 68 | 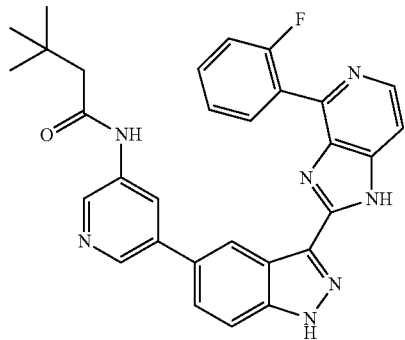 | 72 | 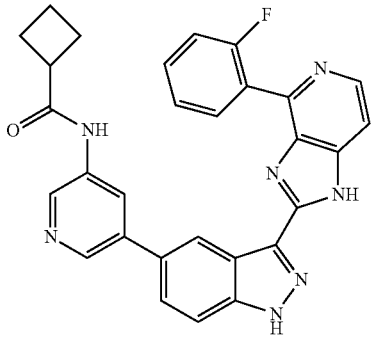 |
| 69 | 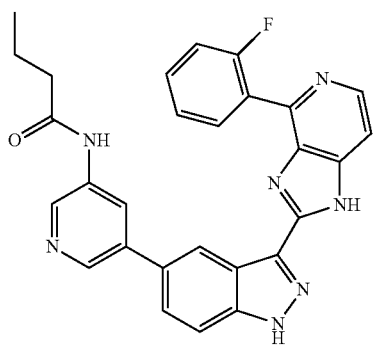 [SMILES: CCCC(=O)Nc1cncc(-c2ccc3[nH]nc(-c4nc5c(-c6ccccc6F)nccc5[nH]4)c3c2)c1] | 73 | 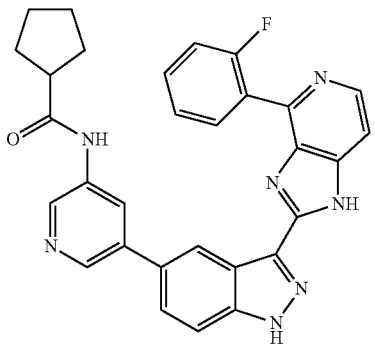 |
| 70 | 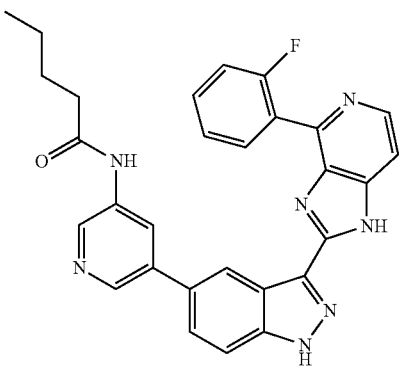 [SMILES: CCCCC(=O)Nc1cncc(-c2ccc3[nH]nc(-c4nc5c(-c6ccccc6F)nccc5[nH]4)c3c2)c1] | 74 | 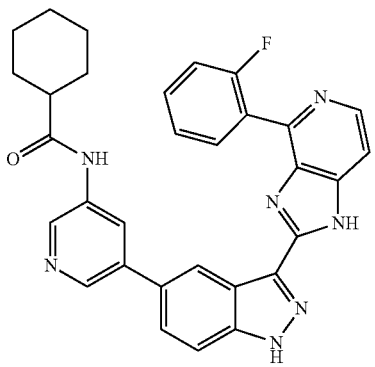 |
| 71 | 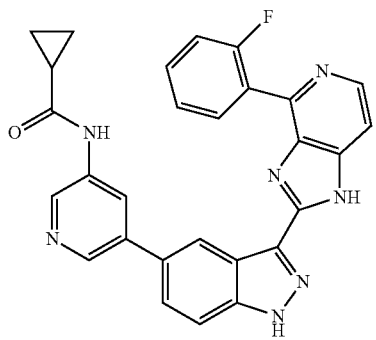 [SMILES: O=C(Nc1cncc(-c2ccc3[nH]nc(-c4nc5c(-c6ccccc6F)nccc5[nH]4)c3c2)c1)C1CC1] | 75 | 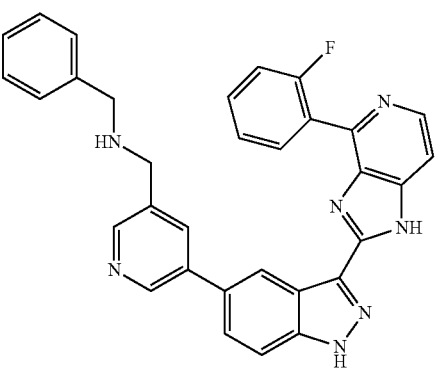 [SMILES: Fc1ccccc1-c1nccc2[nH]c(-c3n[nH]c4ccc(-c5cncc(CNCc6ccccc6)c5)cc34)nc12] |

TABLE 1-continued
| 76 | 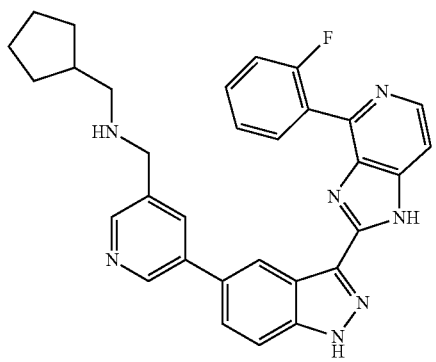 [SMILES: Fc1ccccc1-c1nccc2[nH]c(-c3n[nH]c4ccc(-c5cncc(CNCC6CCCC6)c5)cc34)nc12] |
| 77 | 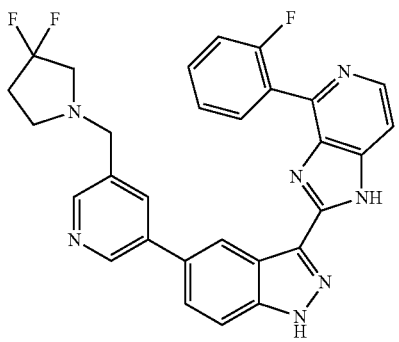 [SMILES: Fc1ccccc1-c1nccc2[nH]c(-c3n[nH]c4ccc(-c5cncc(CN6CCC(F)(F)C6)c5)cc34)nc12] |
| 78 | 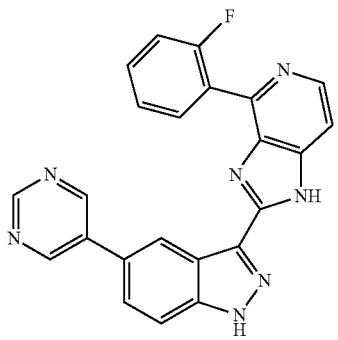 [SMILES: Fc1ccccc1-c1nccc2[nH]c(-c3n[nH]c4ccc(-c5cncnc5)cc34)nc12] |
| 79 | 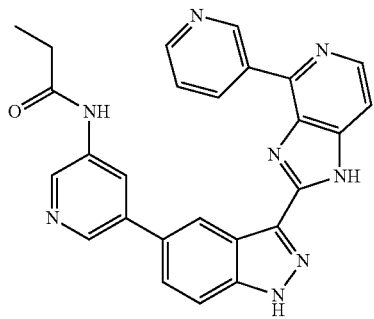 [SMILES: CCC(=O)Nc1cncc(-c2ccc3[nH]nc(-c4nc5c(-c6cccnc6)nccc5[nH]4)c3c2)c1] |
| 80 | 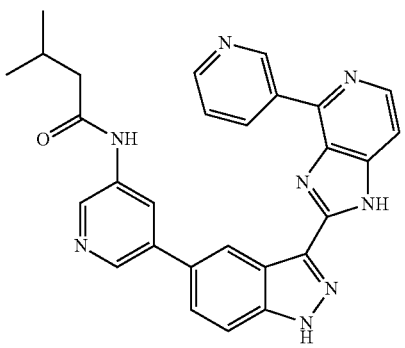 |
| 81 | 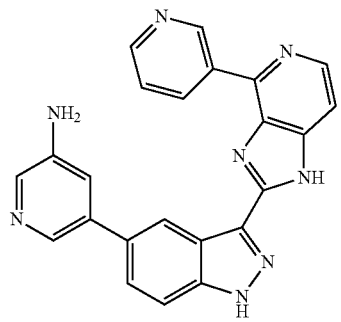 [SMILES: Nc1cncc(-c2ccc3[nH]nc(-c4nc5c(-c6cccnc6)nccc5[nH]4)c3c2)c1] |
| 82 | 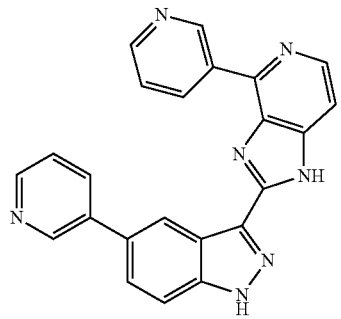 |
| 83 | 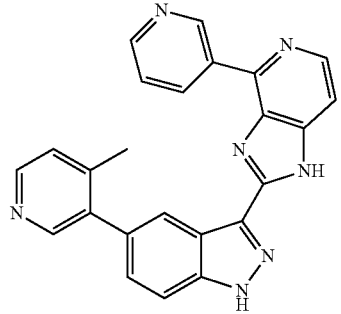 [SMILES: Cc1ccncc1-c1ccc2[nH]nc(-c3nc4c(-c5cccnc5)nccc4[nH]3)c2c1] |
| 84 | 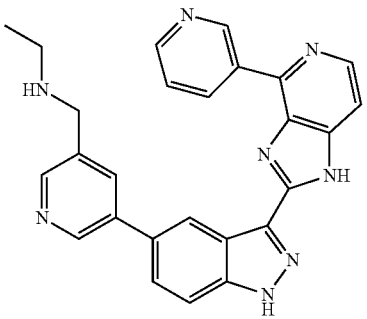 [SMILES: CCNCc1cncc(-c2ccc3[nH]nc(-c4nc5c(-c6cccnc6)nccc5[nH]4)c3c2)c1] |

TABLE 1-continued
| 85 | 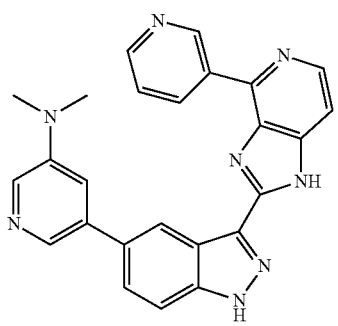 [SMILES: CN(C)c1cncc(-c2ccc3[nH]nc(-c4nc5c(-c6cccnc6)nccc5[nH]4)c3c2)c1] |
| 86 | 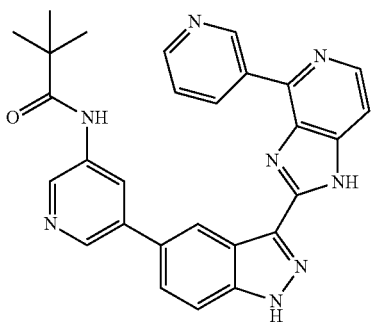 [SMILES: CC(C)(C)C(=O)Nc1cncc(-c2ccc3[nH]nc(-c4nc5c(-c6cccnc6)nccc5[nH]4)c3c2)c1] |
| 87 | 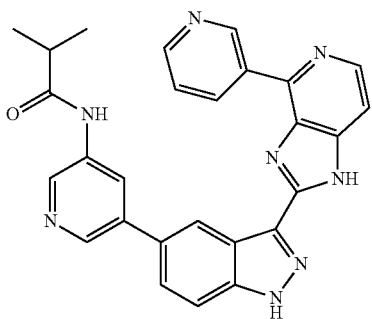 [SMILES: CC(C)C(=O)Nc1cncc(-c2ccc3[nH]nc(-c4nc5c(-c6cccnc6)nccc5[nH]4)c3c2)c1] |
| 88 | 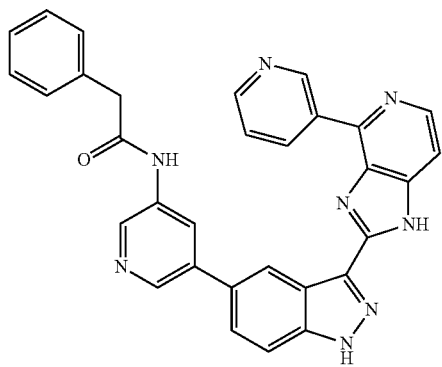 [SMILES: O=C(Cc1ccccc1)Nc1cncc(-c2ccc3[nH]nc(-c4nc5c(-c6cccnc6)nccc5[nH]4)c3c2)c1] |
TABLE 1-continued
| 89 | 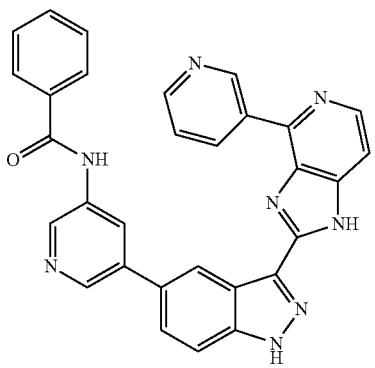 [SMILES: O=C(Nc1cncc(-c2ccc3[nH]nc(-c4nc5c(-c6cccnc6)nccc5[nH]4)c3c2)c1)c1ccccc1] |
| 90 | 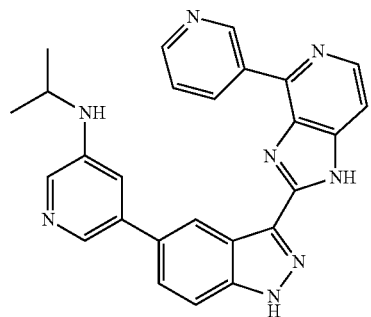 [SMILES: CC(C)Nc1cncc(-c2ccc3[nH]nc(-c4nc5c(-c6cccnc6)nccc5[nH]4)c3c2)c1] |
| 91 | 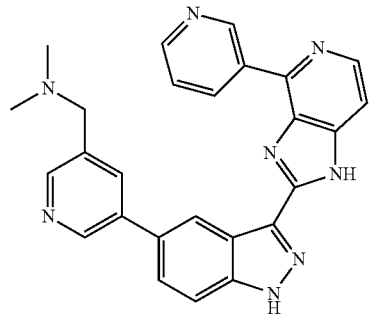 |
| 92 | 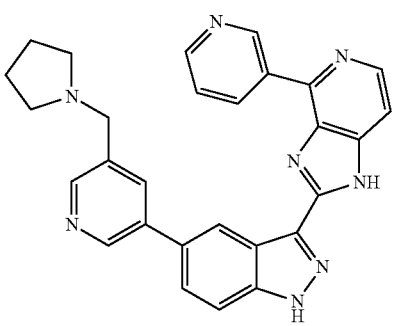 [SMILES: c1cncc(-c2nccc3[nH]c(-c4n[nH]c5ccc(-c6cncc(CN7CCCC7)c6)cc45)nc23)c1] |
| 93 | 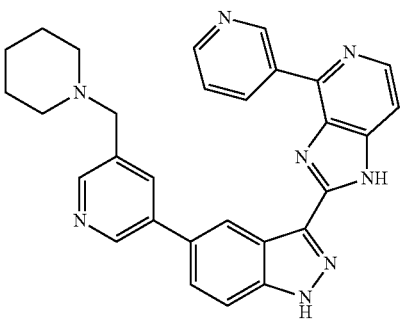 [SMILES: c1cncc(-c2nccc3[nH]c(-c4n[nH]c5ccc(-c6cncc(CN7CCCCC7)c6)cc45)nc23)c1] |

TABLE 1-continued
94
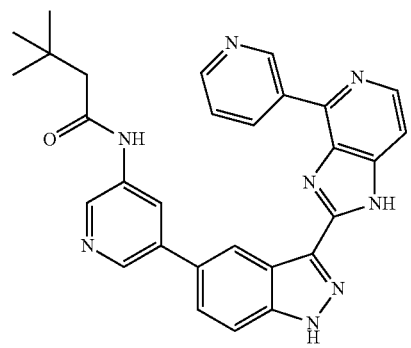
95
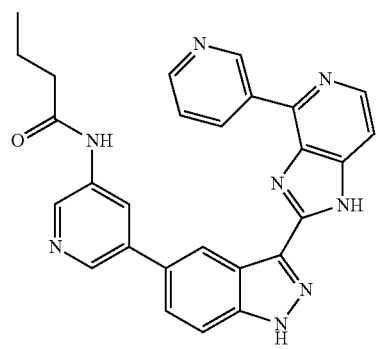 [SMILES: CCCC(=O)Nc1cncc(-c2ccc3[nH]nc(-c4nc5c(-c6cccnc6)nccc5[nH]4)c3c2)c1]
96
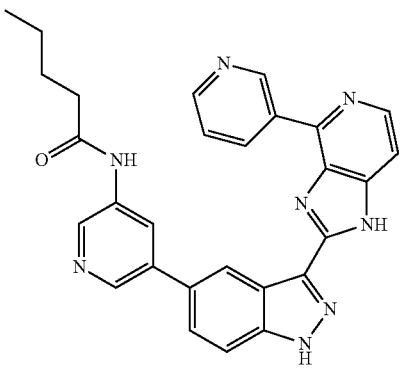 [SMILES: CCCCC(=O)Nc1cncc(-c2ccc3[nH]nc(-c4nc5c(-c6cccnc6)nccc5[nH]4)c3c2)c1]
97
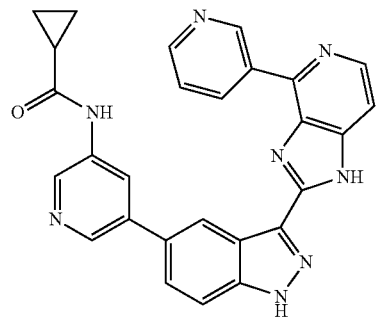 [SMILES: O=C(Nc1cncc(-c2ccc3[nH]nc(-c4nc5c(-c6cccnc6)nccc5[nH]4)c3c2)c1)C1CC1]
TABLE 1-continued
98
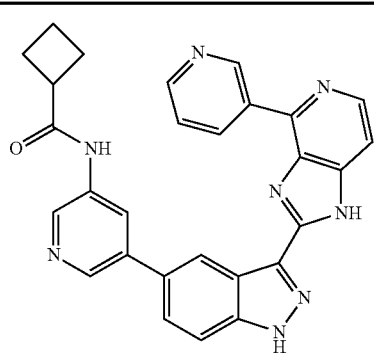
99
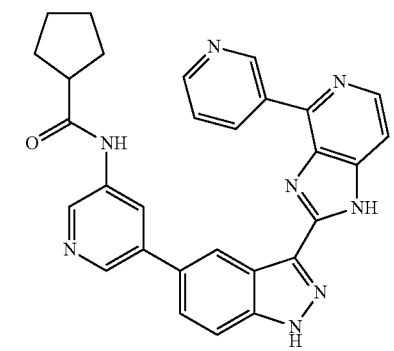 [SMILES: O=C(Nc1cncc(-c2ccc3[nH]nc(-c4nc5c(-c6cccnc6)nccc5[nH]4)c3c2)c1)C1CCCC1]
100
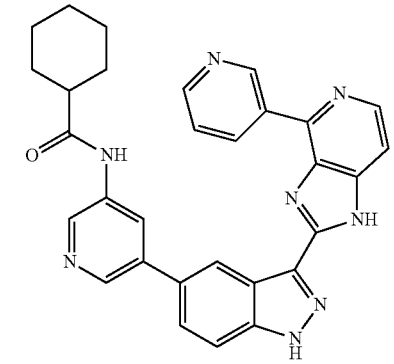 [SMILES: O=C(Nc1cncc(-c2ccc3[nH]nc(-c4nc5c(-c6cccnc6)nccc5[nH]4)c3c2)c1)C1CCCCC1]
101
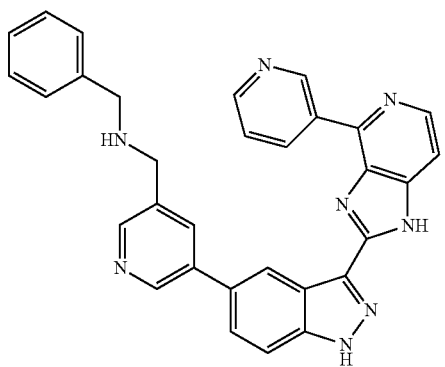 [SMILES: c1ccc(CNCc2cncc(-c3ccc4[nH]nc(-c5nc6c(-c7cccnc7)nccc6[nH]5)c4c3)c2)cc1]

TABLE 1-continued
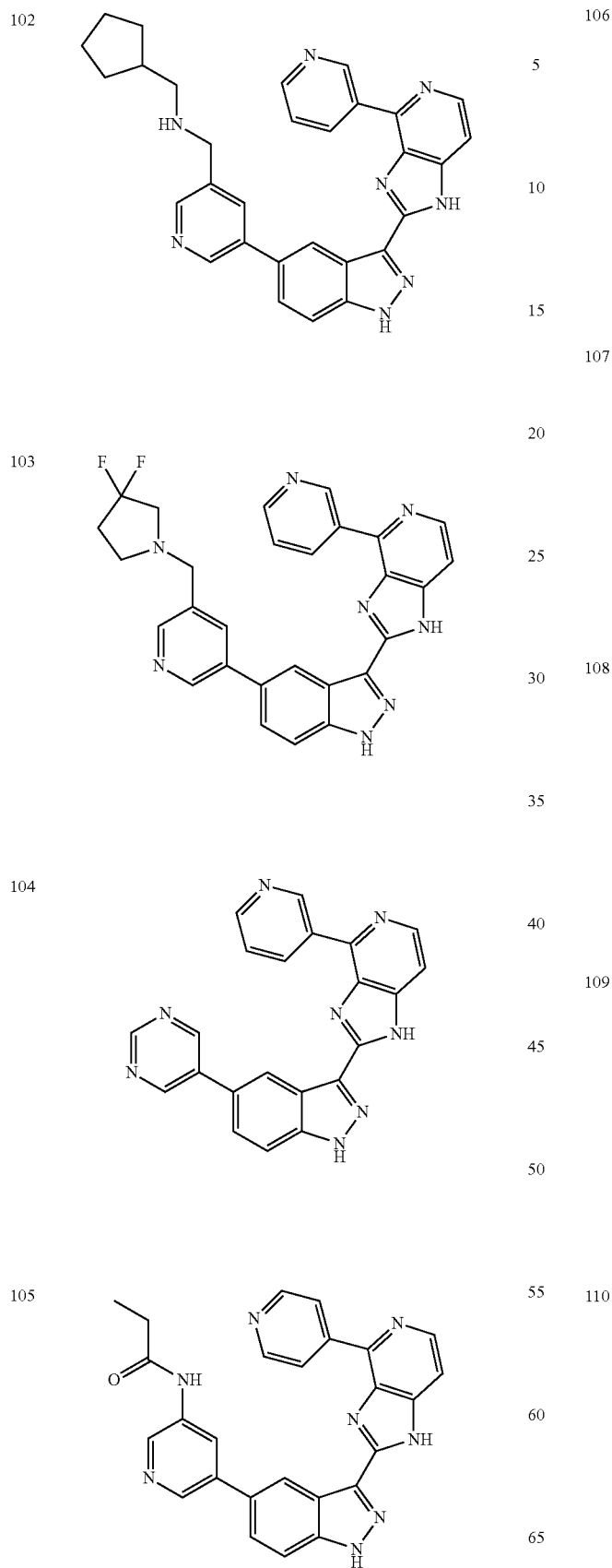
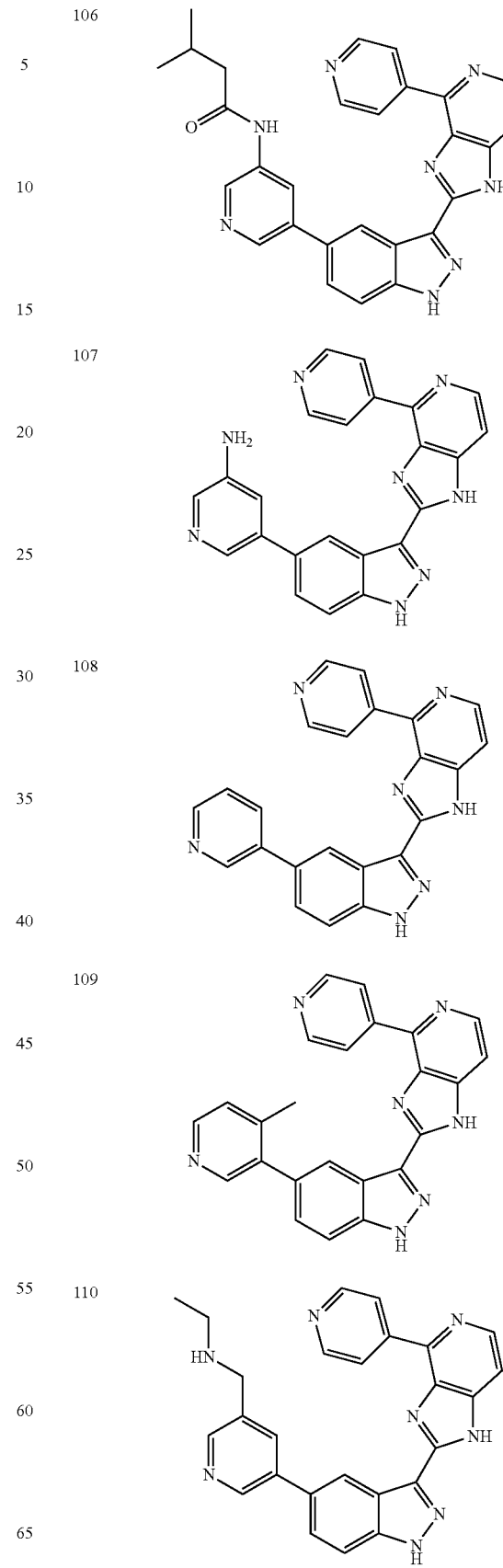

TABLE 1-continued
| | |
|---|---|
| 111 | 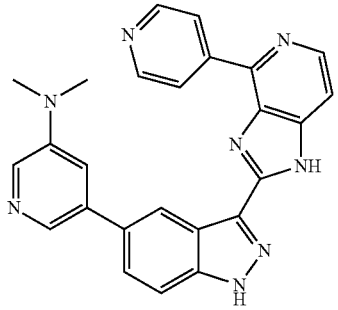 [SMILES: CN(C)c1cncc(-c2ccc3[nH]nc(-c4nc5c(-c6ccncc6)nccc5[nH]4)c3c2)c1] |
| 112 | 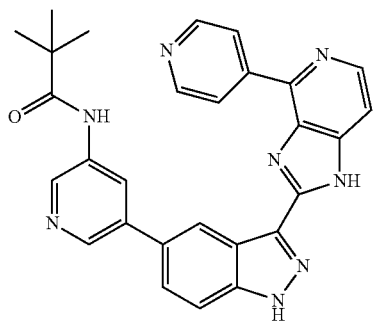 [SMILES: CC(C)(C)C(=O)Nc1cncc(-c2ccc3[nH]nc(-c4nc5c(-c6ccncc6)nccc5[nH]4)c3c2)c1] |
| 113 | 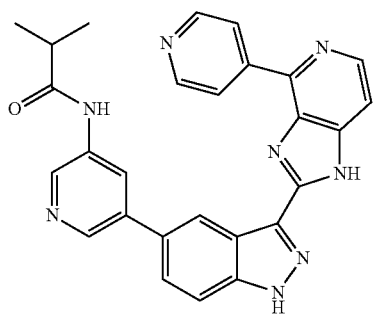 [SMILES: CC(C)C(=O)Nc1cncc(-c2ccc3[nH]nc(-c4nc5c(-c6ccncc6)nccc5[nH]4)c3c2)c1] |
| 114 | 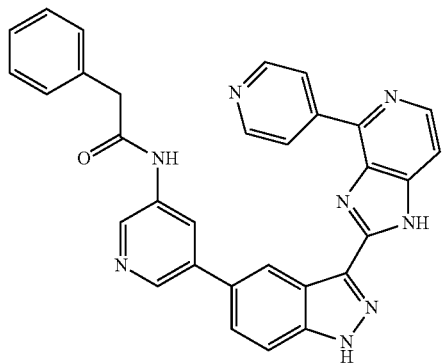 [SMILES: O=C(Cc1ccccc1)Nc1cncc(-c2ccc3[nH]nc(-c4nc5c(-c6ccncc6)nccc5[nH]4)c3c2)c1] |
| 115 | 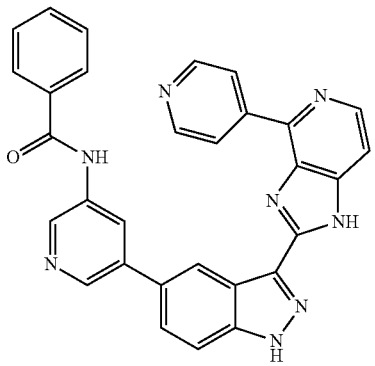 [SMILES: O=C(Nc1cncc(-c2ccc3[nH]nc(-c4nc5c(-c6ccncc6)nccc5[nH]4)c3c2)c1)c1ccccc1] |
| 116 | 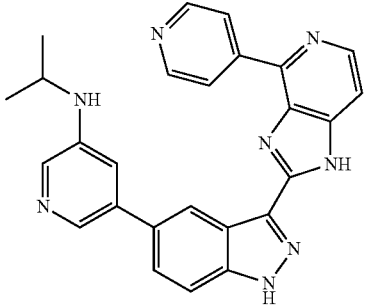 |
| 117 | 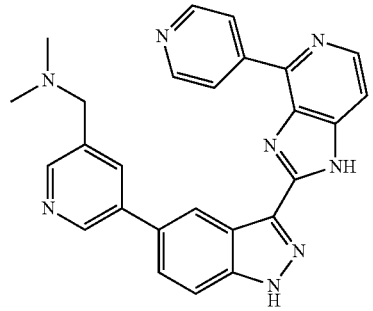 [SMILES: CN(C)Cc1cncc(-c2ccc3[nH]nc(-c4nc5c(-c6ccncc6)nccc5[nH]4)c3c2)c1] |
| 118 | 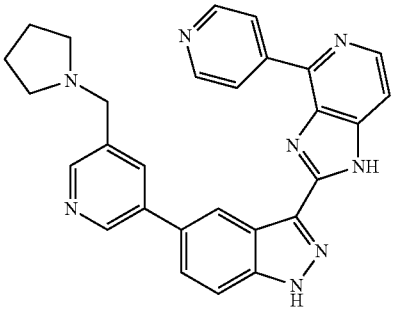 [SMILES: c1cc(-c2nccc3[nH]c(-c4n[nH]c5ccc(-c6cncc(CN7CCCC7)c6)cc45)nc23)ccn1] |
| 119 | 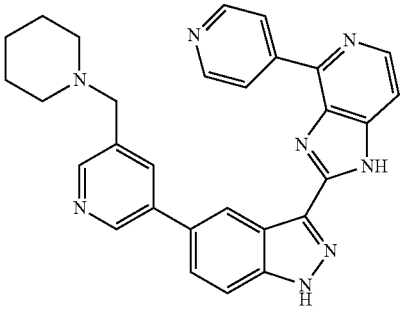 [SMILES: c1cc(-c2nccc3[nH]c(-c4n[nH]c5ccc(-c6cncc(CN7CCCCC7)c6)cc45)nc23)ccn1] |

TABLE 1-continued
| 120 | 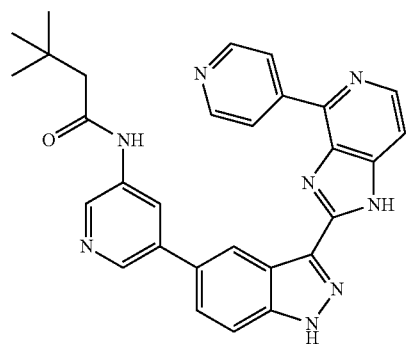 [SMILES: CC(C)(C)CC(=O)Nc1cncc(-c2ccc3[nH]nc(-c4nc5c(-c6ccncc6)nccc5[nH]4)c3c2)c1] |
| --- | --- |
| 121 | 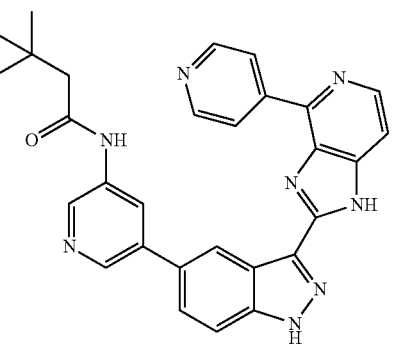 |
| 122 | 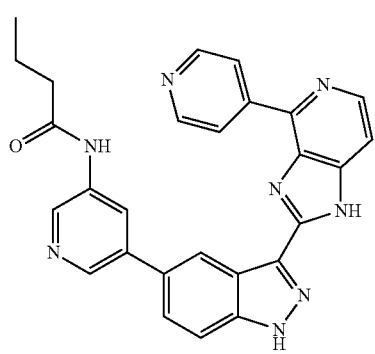 [SMILES: CCCC(=O)Nc1cncc(-c2ccc3[nH]nc(-c4nc5c(-c6ccncc6)nccc5[nH]4)c3c2)c1] |
| 123 | 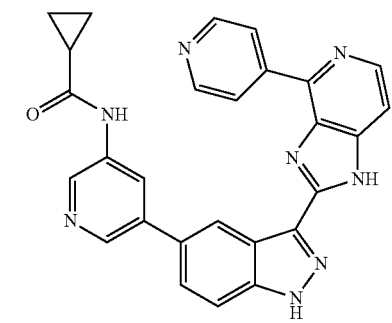 [SMILES: O=C(Nc1cncc(-c2ccc3[nH]nc(-c4nc5c(-c6ccncc6)nccc5[nH]4)c3c2)c1)C1CC1] |
TABLE 1-continued
| 124 | 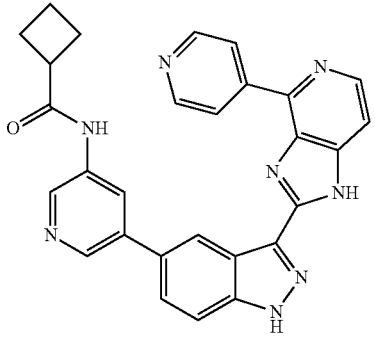 [SMILES: O=C(Nc1cncc(-c2ccc3[nH]nc(-c4nc5c(-c6ccncc6)nccc5[nH]4)c3c2)c1)C1CCC1] |
| --- | --- |
| 125 | 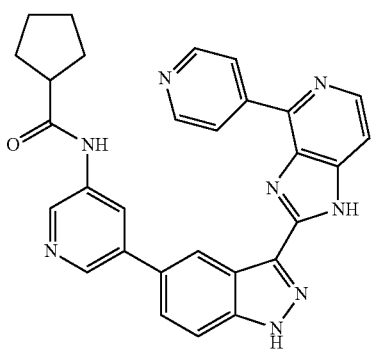 [SMILES: O=C(Nc1cncc(-c2ccc3[nH]nc(-c4nc5c(-c6ccncc6)nccc5[nH]4)c3c2)c1)C1CCCC1] |
| 126 | 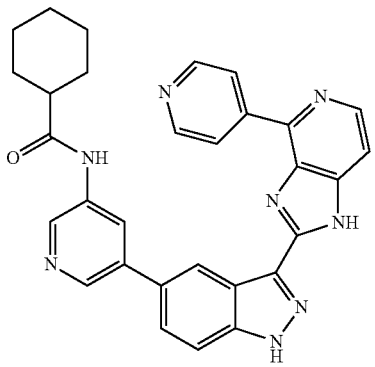 [SMILES: O=C(Nc1cncc(-c2ccc3[nH]nc(-c4nc5c(-c6ccncc6)nccc5[nH]4)c3c2)c1)C1CCCCC1] |
| 127 | 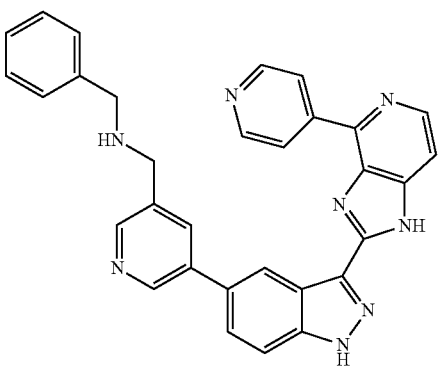 [SMILES: c1ccc(CNCc2cncc(-c3ccc4[nH]nc(-c5nc6c(-c7ccncc7)nccc6[nH]5)c4c3)c2)cc1] |

TABLE 1-continued
128 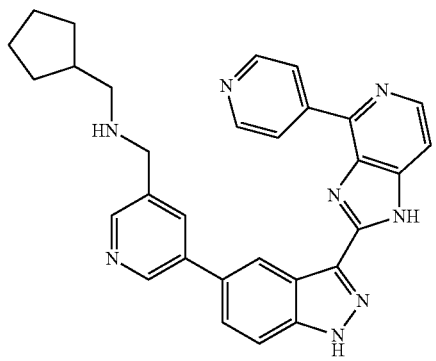 [SMILES: c1cc(-c2nccc3[nH]c(-c4n[nH]c5ccc(-c6cncc(CNCC7CCCC7)c6)cc45)nc23)ccn1]
129 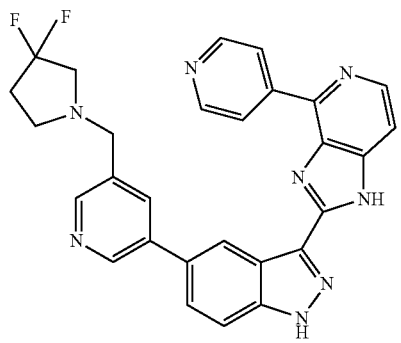
130 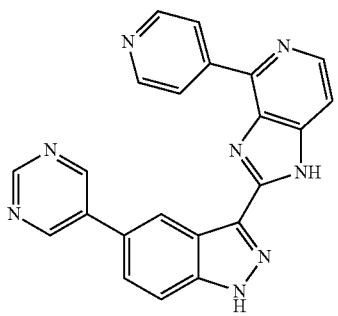 [SMILES: c1cc(-c2nccc3[nH]c(-c4n[nH]c5ccc(-c6cncnc6)cc45)nc23)ccn1]
131 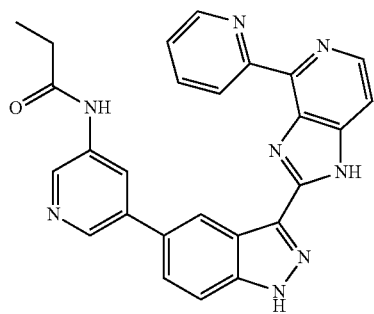 [SMILES: CCC(=O)Nc1cncc(-c2ccc3[nH]nc(-c4nc5c(-c6ccccn6)nccc5[nH]4)c3c2)c1]
TABLE 1-continued
132 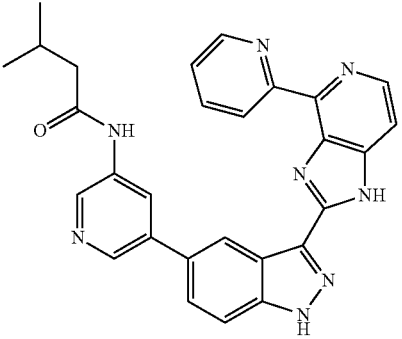 [SMILES: CC(C)CC(=O)Nc1cncc(-c2ccc3[nH]nc(-c4nc5c(-c6ccccn6)nccc5[nH]4)c3c2)c1]
133 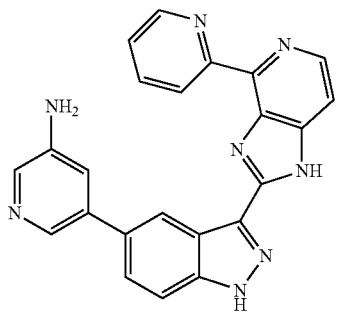
134 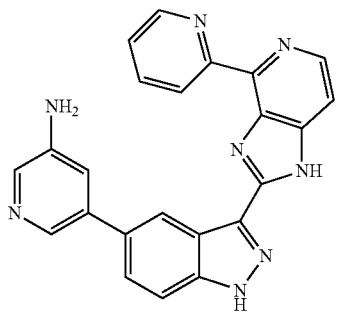
135 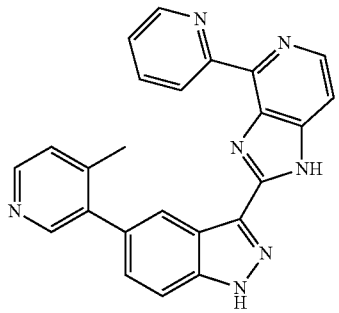 [SMILES: Cc1ccncc1-c1ccc2[nH]nc(-c3nc4c(-c5ccccn5)nccc4[nH]3)c2c1]
136 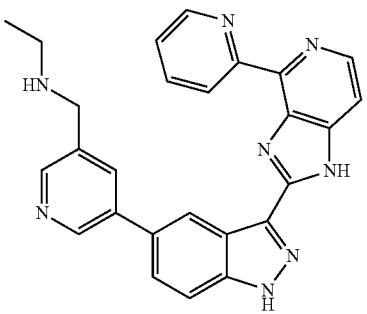 [SMILES: CCNCc1cncc(-c2ccc3[nH]nc(-c4nc5c(-c6ccccn6)nccc5[nH]4)c3c2)c1]

TABLE 1-continued
| 137 | 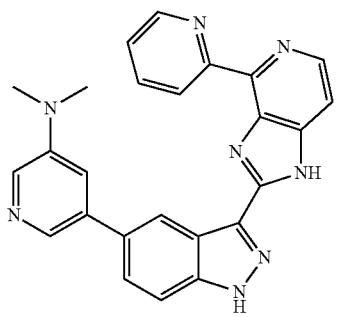 [SMILES: CN(C)c1cncc(-c2ccc3[nH]nc(-c4nc5c(-c6ccccn6)nccc5[nH]4)c3c2)c1] |
| 138 | 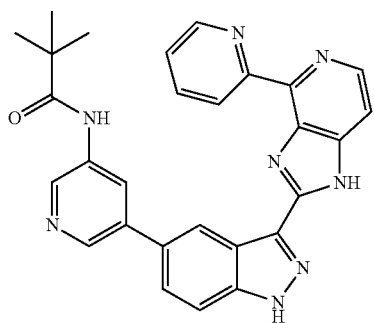 [SMILES: CC(C)(C)C(=O)Nc1cncc(-c2ccc3[nH]nc(-c4nc5c(-c6ccccn6)nccc5[nH]4)c3c2)c1] |
| 139 | 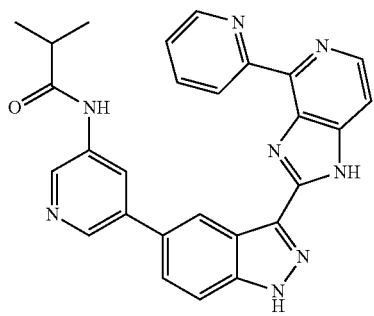 [SMILES: CC(C)C(=O)Nc1cncc(-c2ccc3[nH]nc(-c4nc5c(-c6ccccn6)nccc5[nH]4)c3c2)c1] |
| 140 | 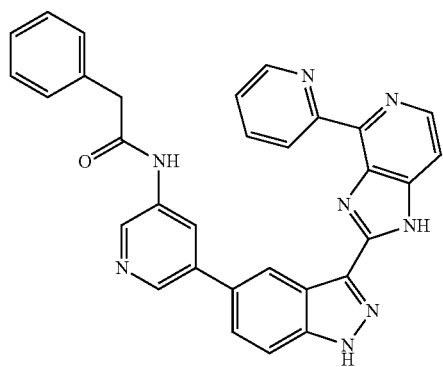 [SMILES: O=C(Cc1ccccc1)Nc1cncc(-c2ccc3[nH]nc(-c4nc5c(-c6ccccn6)nccc5[nH]4)c3c2)c1] |
TABLE 1-continued
| 141 | 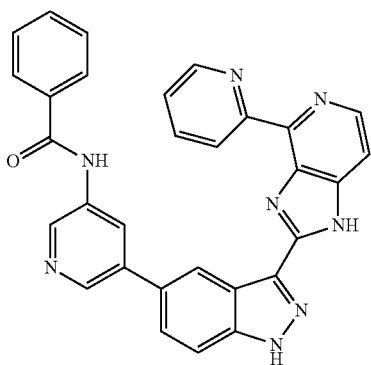 [SMILES: O=C(Nc1cncc(-c2ccc3[nH]nc(-c4nc5c(-c6ccccn6)nccc5[nH]4)c3c2)c1)c1ccccc1] |
| 142 | 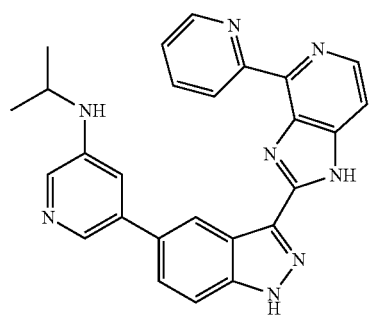 [SMILES: CC(C)Nc1cncc(-c2ccc3[nH]nc(-c4nc5c(-c6ccccn6)nccc5[nH]4)c3c2)c1] |
| 143 | 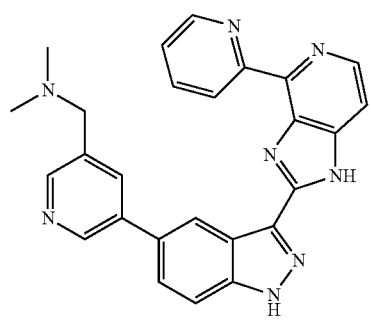 [SMILES: CN(C)Cc1cncc(-c2ccc3[nH]nc(-c4nc5c(-c6ccccn6)nccc5[nH]4)c3c2)c1] |
| 144 | 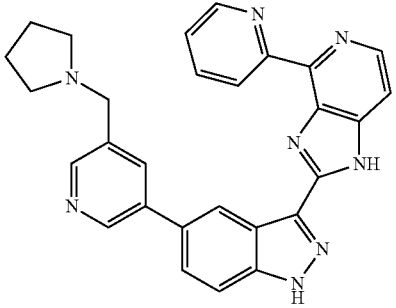 [SMILES: c1ccc(-c2nccc3[nH]c(-c4n[nH]c5ccc(-c6cncc(CN7CCCC7)c6)cc45)nc23)nc1] |
| 145 | 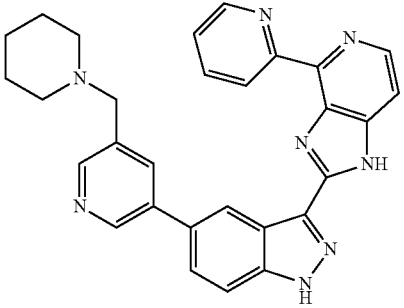 |

TABLE 1-continued
| 146 | 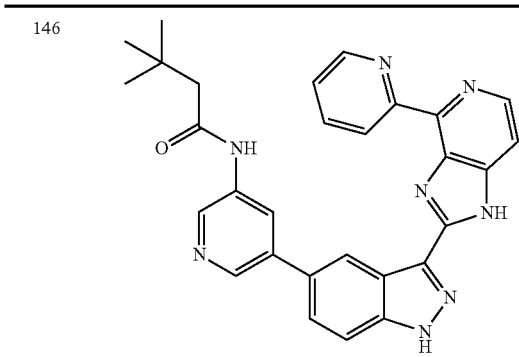 |
| --- | --- |
| 147 | |
| 148 | |
| 149 | |
TABLE 1-continued
| 150 | 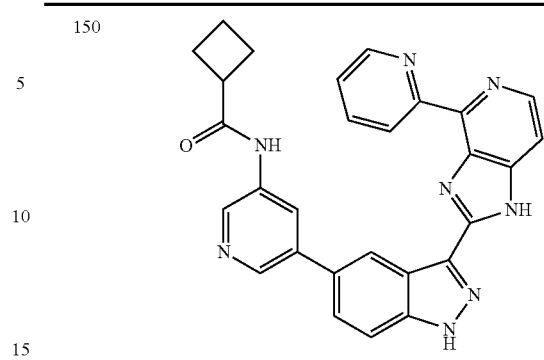 |
| --- | --- |
| 151 | |
| 152 | |
| 153 | |

TABLE 1-continued
154 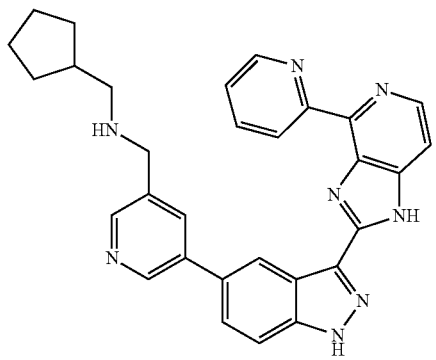 [SMILES: c1ccc(-c2nccc3[nH]c(-c4n[nH]c5ccc(-c6cncc(CNCC7CCCC7)c6)cc45)nc23)nc1]
155 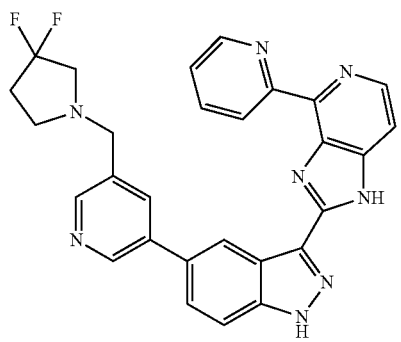 [SMILES: FC1(F)CCN(Cc2cncc(-c3ccc4[nH]nc(-c5nc6c(-c7ccccn7)nccc6[nH]5)c4c3)c2)C1]
156 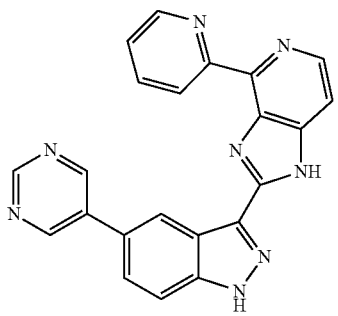 [SMILES: c1ccc(-c2nccc3[nH]c(-c4n[nH]c5ccc(-c6cncnc6)cc45)nc23)nc1]
157 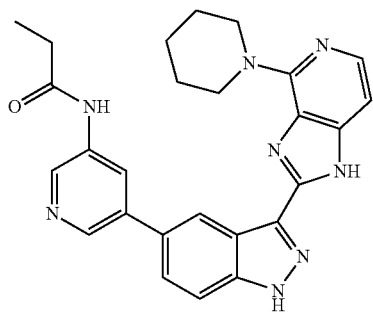 [SMILES: CCC(=O)Nc1cncc(-c2ccc3[nH]nc(-c4nc5c(N6CCCCC6)nccc5[nH]4)c3c2)c1]
TABLE 1-continued
158 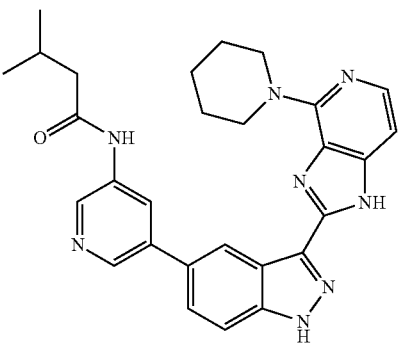 [SMILES: CC(C)CC(=O)Nc1cncc(-c2ccc3[nH]nc(-c4nc5c(N6CCCCC6)nccc5[nH]4)c3c2)c1]
159 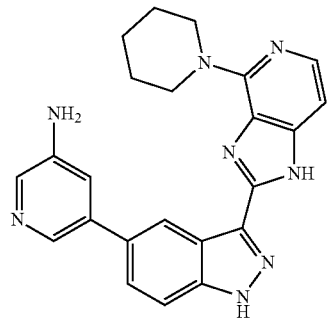 [SMILES: Nc1cncc(-c2ccc3[nH]nc(-c4nc5c(N6CCCCC6)nccc5[nH]4)c3c2)c1]
160 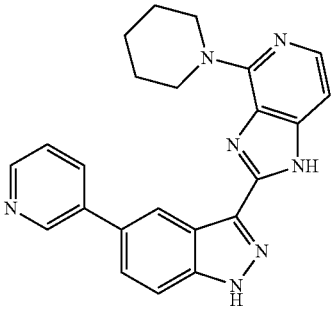
161 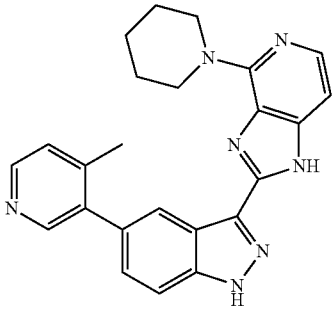 [SMILES: Cc1ccncc1-c1ccc2[nH]nc(-c3nc4c(N5CCCCC5)nccc4[nH]3)c2c1]
162 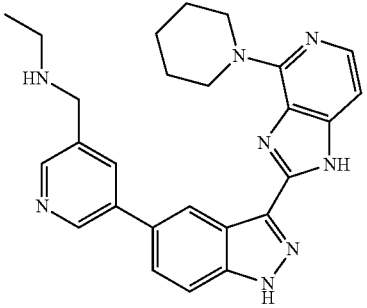 [SMILES: CCNCc1cncc(-c2ccc3[nH]nc(-c4nc5c(N6CCCCC6)nccc5[nH]4)c3c2)c1]

TABLE 1-continued
| 163 | 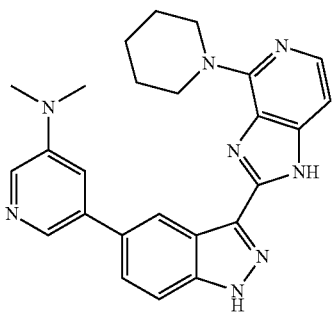 [SMILES: CN(C)c1cncc(-c2ccc3[nH]nc(-c4nc5c(N6CCCCC6)nccc5[nH]4)c3c2)c1] |
| --- | --- |
| 164 | 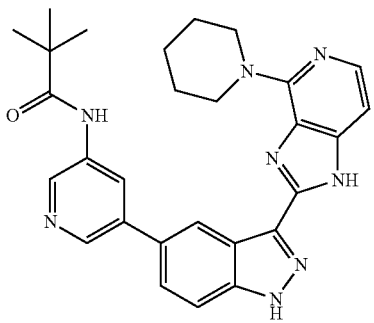 [SMILES: CC(C)(C)C(=O)Nc1cncc(-c2ccc3[nH]nc(-c4nc5c(N6CCCCC6)nccc5[nH]4)c3c2)c1] |
| 165 | 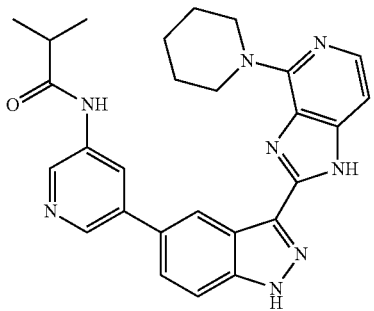 [SMILES: CC(C)C(=O)Nc1cncc(-c2ccc3[nH]nc(-c4nc5c(N6CCCCC6)nccc5[nH]4)c3c2)c1] |
| 166 | 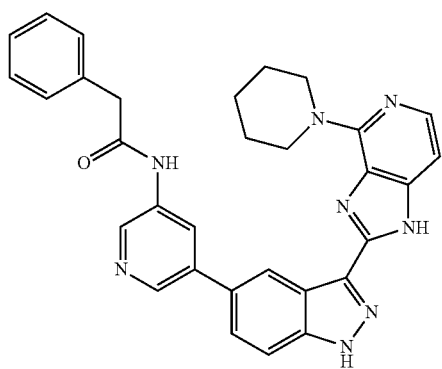 [SMILES: O=C(Cc1ccccc1)Nc1cncc(-c2ccc3[nH]nc(-c4nc5c(N6CCCCC6)nccc5[nH]4)c3c2)c1] |
| 167 | 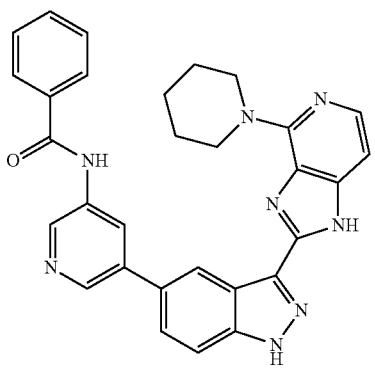 [SMILES: O=C(Nc1cncc(-c2ccc3[nH]nc(-c4nc5c(N6CCCCC6)nccc5[nH]4)c3c2)c1)c1ccccc1] |
| 168 | 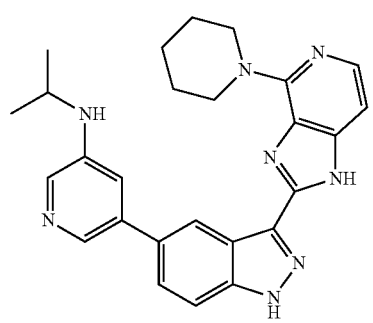 |
| 169 | 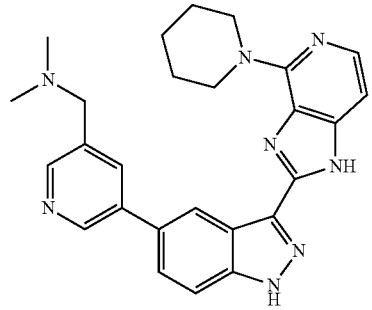 |
| 170 | 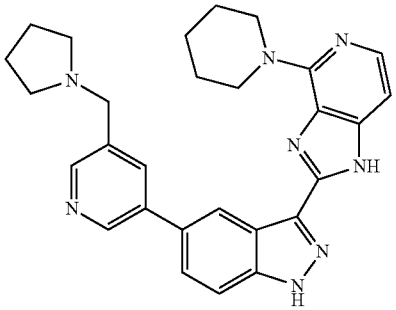 [SMILES: c1cc2[nH]c(-c3n[nH]c4ccc(-c5cncc(CN6CCCC6)c5)cc34)nc2c(N2CCCCC2)n1] |
| 171 | 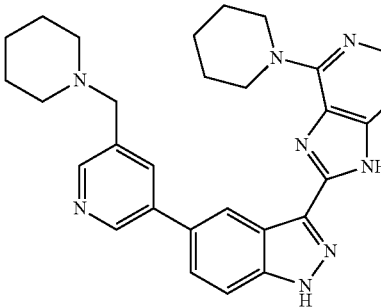 |

TABLE 1-continued
172 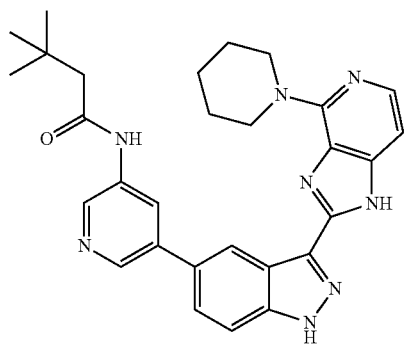 [SMILES: CC(C)(C)CC(=O)Nc1cncc(-c2ccc3[nH]nc(-c4nc5c(N6CCCCC6)nccc5[nH]4)c3c2)c1]
173 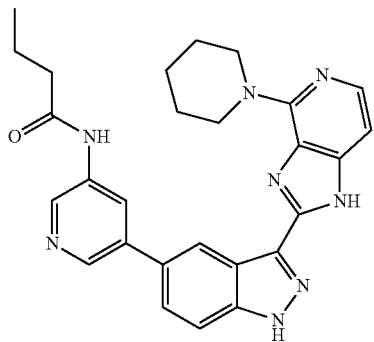 [SMILES: CCCC(=O)Nc1cncc(-c2ccc3[nH]nc(-c4nc5c(N6CCCCC6)nccc5[nH]4)c3c2)c1]
174 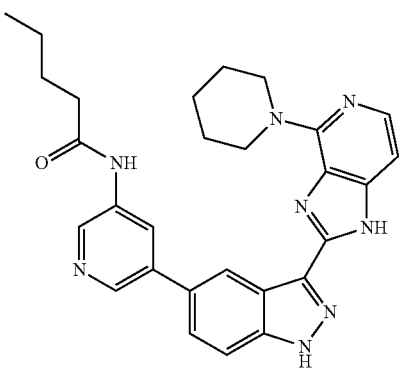
175 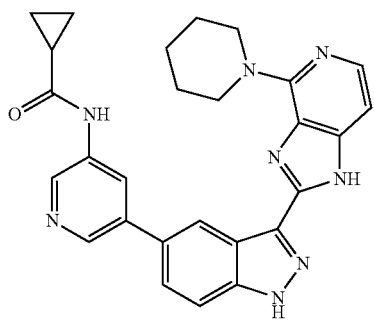 [SMILES: O=C(Nc1cncc(-c2ccc3[nH]nc(-c4nc5c(N6CCCCC6)nccc5[nH]4)c3c2)c1)C1CC1]
TABLE 1-continued
176 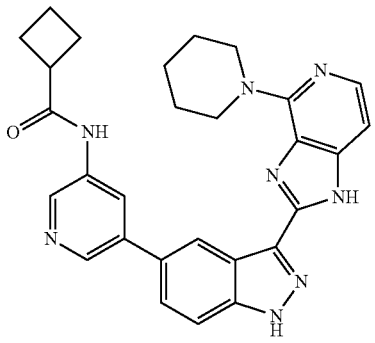 [SMILES: O=C(Nc1cncc(-c2ccc3[nH]nc(-c4nc5c(N6CCCCC6)nccc5[nH]4)c3c2)c1)C1CCC1]
177 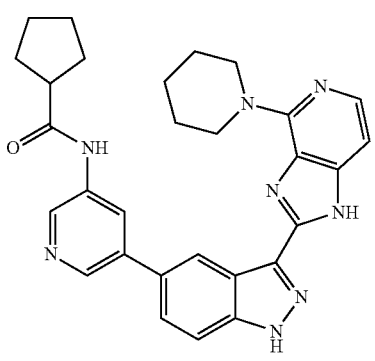 [SMILES: O=C(Nc1cncc(-c2ccc3[nH]nc(-c4nc5c(N6CCCCC6)nccc5[nH]4)c3c2)c1)C1CCCC1]
178 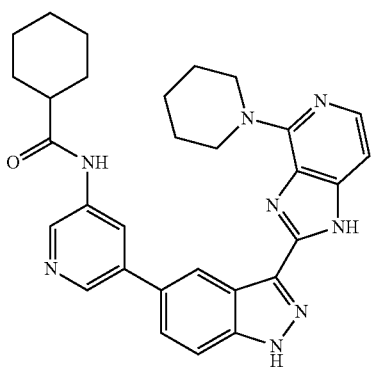 [SMILES: O=C(Nc1cncc(-c2ccc3[nH]nc(-c4nc5c(N6CCCCC6)nccc5[nH]4)c3c2)c1)C1CCCCC1]
179 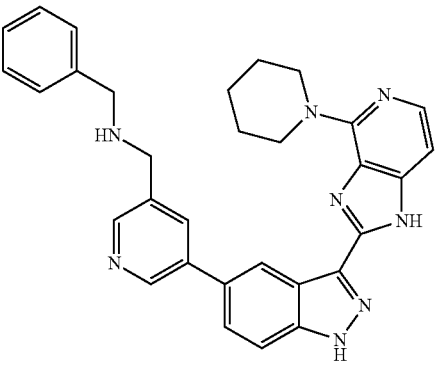 [SMILES: c1ccc(CNCc2cncc(-c3ccc4[nH]nc(-c5nc6c(N7CCCCC7)nccc6[nH]5)c4c3)c2)cc1]

TABLE 1-continued
180 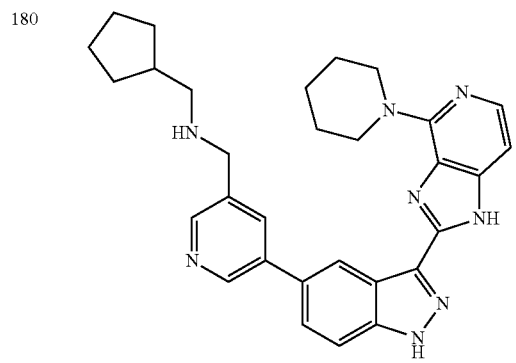
181 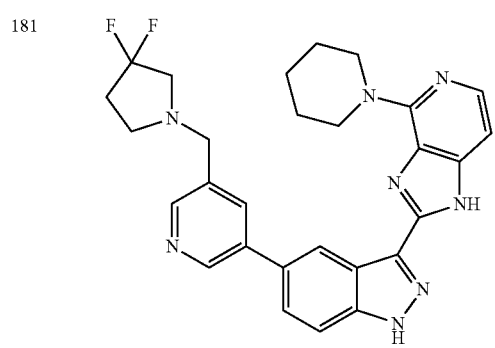
182 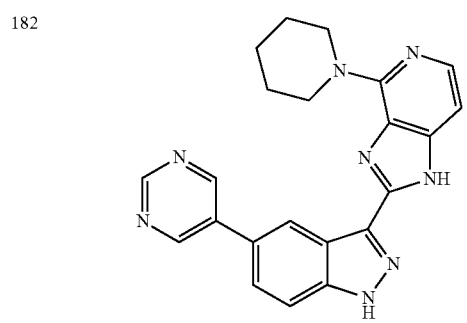
183 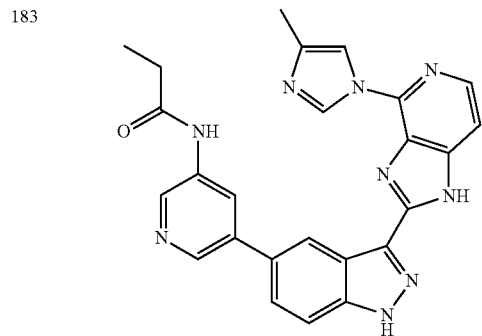
184 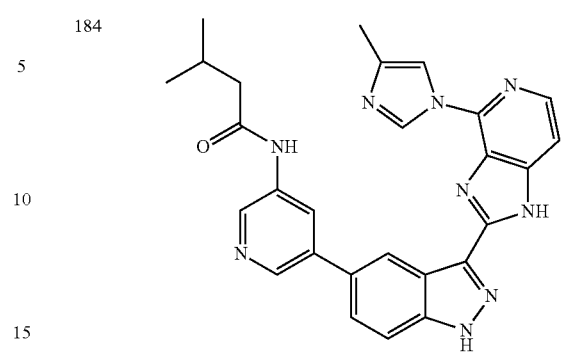
185 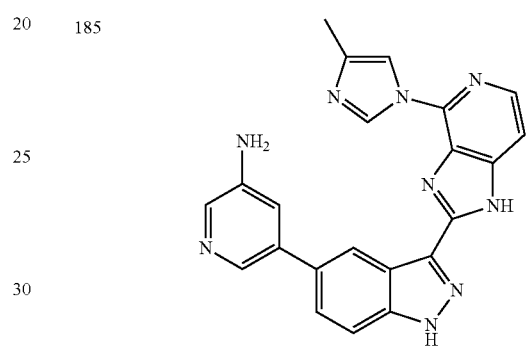
186 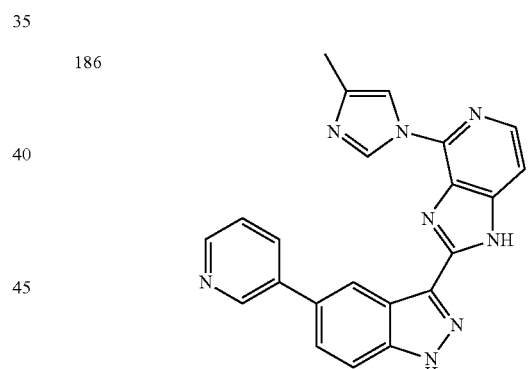
187 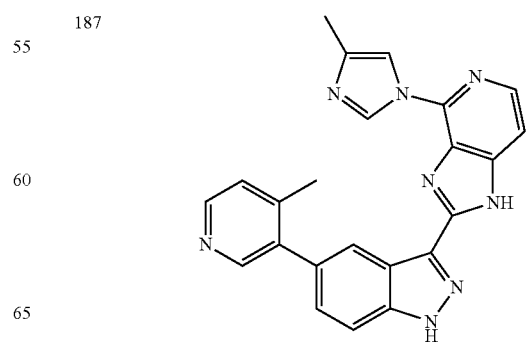

TABLE 1-continued
| 188 | 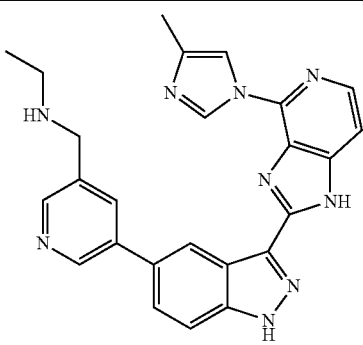 |
| --- | --- |
| 189 | 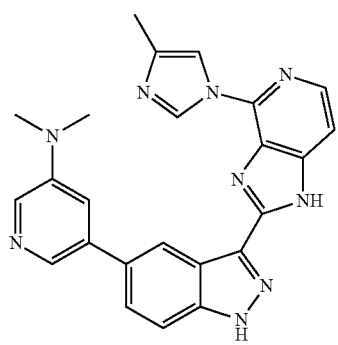 [SMILES: Cc1cn(-c2nccc3[nH]c(-c4n[nH]c5ccc(-c6cncc(N(C)C)c6)cc45)nc23)cn1] |
| 190 | 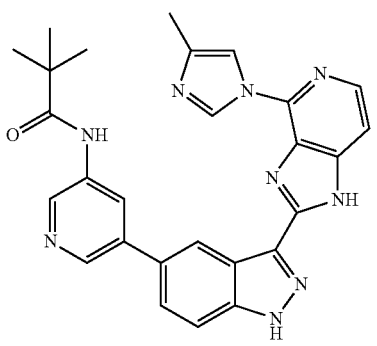 [SMILES: Cc1cn(-c2nccc3[nH]c(-c4n[nH]c5ccc(-c6cncc(NC(=O)C(C)(C)C)c6)cc45)nc23)cn1] |
| 191 | 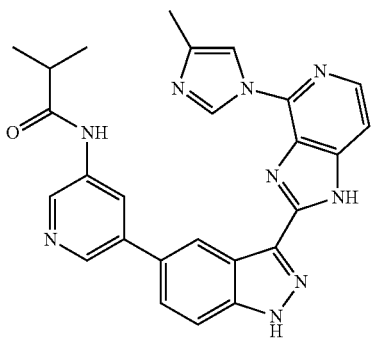 [SMILES: Cc1cn(-c2nccc3[nH]c(-c4n[nH]c5ccc(-c6cncc(NC(=O)C(C)C)c6)cc45)nc23)cn1] |
| 192 | 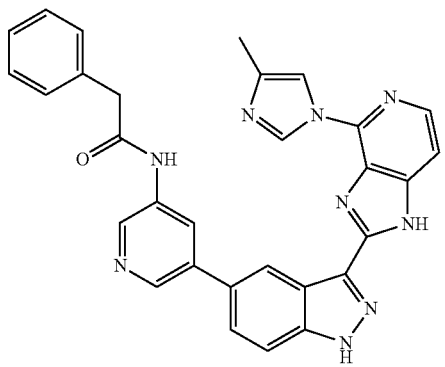 [SMILES: Cc1cn(-c2nccc3[nH]c(-c4n[nH]c5ccc(-c6cncc(NC(=O)Cc7ccccc7)c6)cc45)nc23)cn1] |
| 193 | 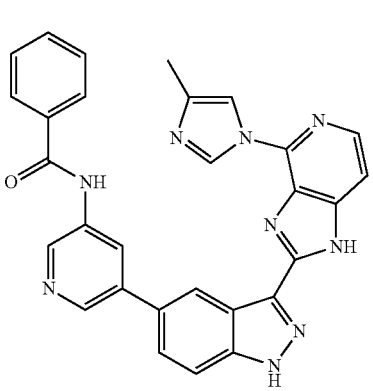 [SMILES: Cc1cn(-c2nccc3[nH]c(-c4n[nH]c5ccc(-c6cncc(NC(=O)c7ccccc7)c6)cc45)nc23)cn1] |
| 194 | |
| 195 | 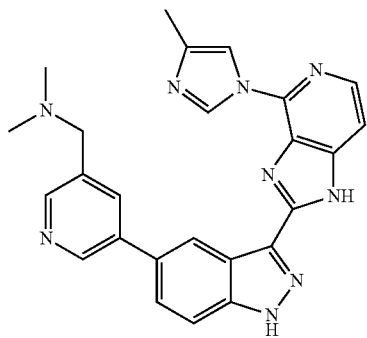 [SMILES: Cc1cn(-c2nccc3[nH]c(-c4n[nH]c5ccc(-c6cncc(CN(C)C)c6)cc45)nc23)cn1] |

TABLE 1-continued
| 196 | 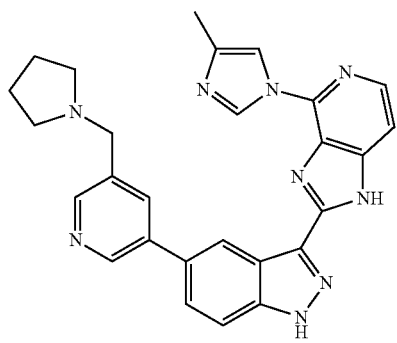 [SMILES: Cc1cn(-c2nccc3[nH]c(-c4n[nH]c5ccc(-c6cncc(CN7CCCC7)c6)cc45)nc23)cn1] |
| 197 | 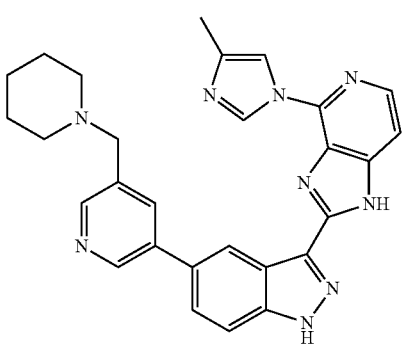 |
| 198 | 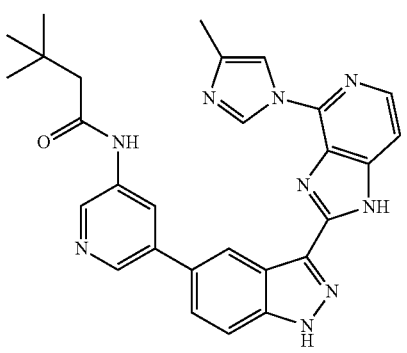 [SMILES: Cc1cn(-c2nccc3[nH]c(-c4n[nH]c5ccc(-c6cncc(NC(=O)CC(C)(C)C)c6)cc45)nc23)cn1] |
| 199 | 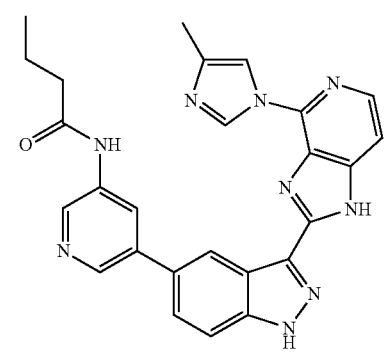 [SMILES: CCCC(=O)Nc1cncc(-c2ccc3[nH]nc(-c4nc5c(-n6cnc(C)c6)nccc5[nH]4)c3c2)c1] |
TABLE 1-continued
| 200 | 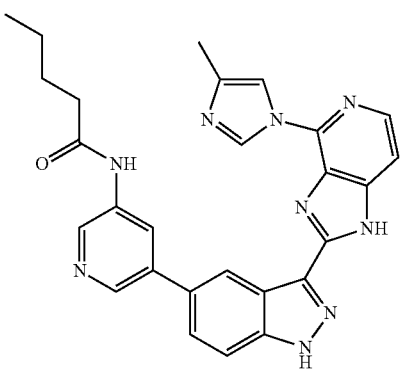 [SMILES: CCCCC(=O)Nc1cncc(-c2ccc3[nH]nc(-c4nc5c(-n6cnc(C)c6)nccc5[nH]4)c3c2)c1] |
| 201 | 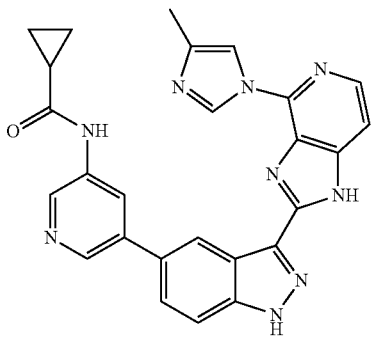 [SMILES: Cc1cn(-c2nccc3[nH]c(-c4n[nH]c5ccc(-c6cncc(NC(=O)C7CC7)c6)cc45)nc23)cn1] |
| 202 | |
| 203 | 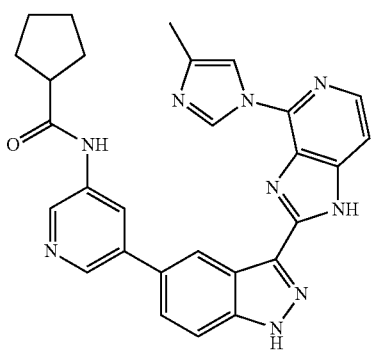 [SMILES: Cc1cn(-c2nccc3[nH]c(-c4n[nH]c5ccc(-c6cncc(NC(=O)C7CCCC7)c6)cc45)nc23)cn1] |

TABLE 1-continued
| | |
|---|---|
| 204 | 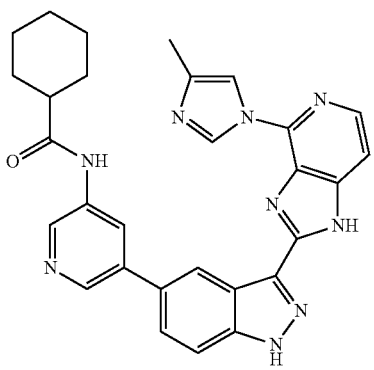 [SMILES: Cc1cn(-c2nccc3[nH]c(-c4n[nH]c5ccc(-c6cncc(NC(=O)C7CCCCC7)c6)cc45)nc23)cn1] |
| 205 | 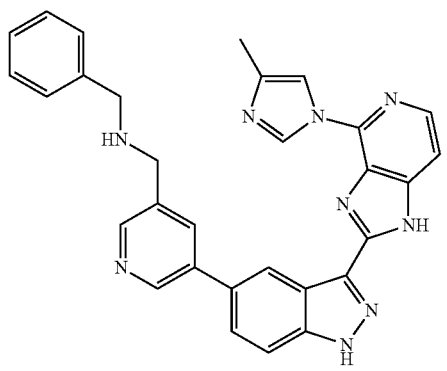 [SMILES: Cc1cn(-c2nccc3[nH]c(-c4n[nH]c5ccc(-c6cncc(CNCc7ccccc7)c6)cc45)nc23)cn1] |
| 206 | 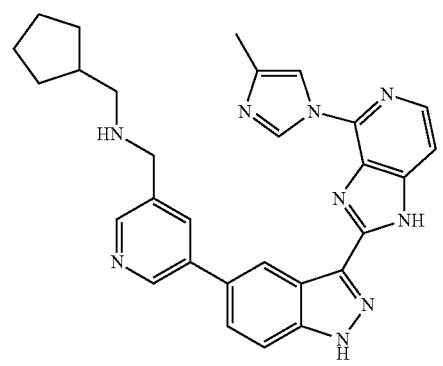 [SMILES: Cc1cn(-c2nccc3[nH]c(-c4n[nH]c5ccc(-c6cncc(CNCC7CCCC7)c6)cc45)nc23)cn1] |
| 207 | 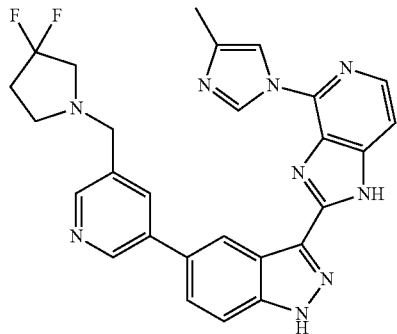 [SMILES: Cc1cn(-c2nccc3[nH]c(-c4n[nH]c5ccc(-c6cncc(CN7CCC(F)(F)C7)c6)cc45)nc23)cn1] |
TABLE 1-continued
| | |
|---|---|
| 208 | 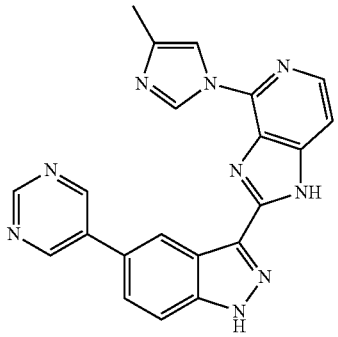 |
| 209 | 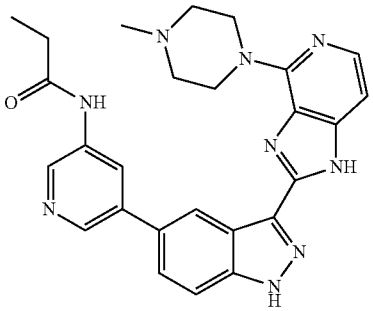 [SMILES: CCC(=O)Nc1cncc(-c2ccc3[nH]nc(-c4nc5c(N6CCN(C)CC6)nccc5[nH]4)c3c2)c1] |
| 210 | 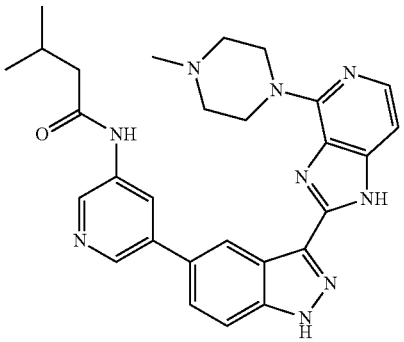 [SMILES: CC(C)CC(=O)Nc1cncc(-c2ccc3[nH]nc(-c4nc5c(N6CCN(C)CC6)nccc5[nH]4)c3c2)c1] |
| 211 | 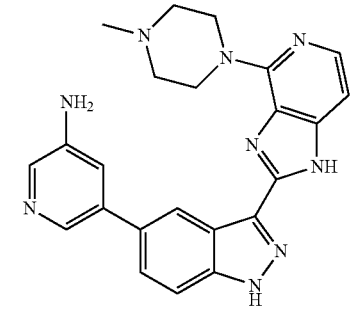 |
| 212 | 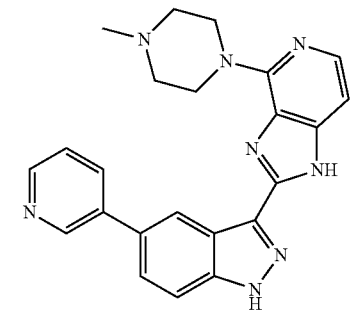 [SMILES: CN1CCN(c2nccc3[nH]c(-c4n[nH]c5ccc(-c6cccnc6)cc45)nc23)CC1] |

TABLE 1-continued
| | |
|---|---|
| 213 | 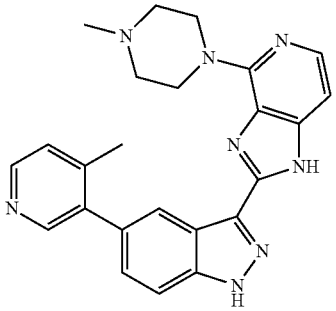 [SMILES: Cc1ccncc1-c1ccc2[nH]nc(-c3nc4c(N5CCN(C)CC5)nccc4[nH]3)c2c1] |
| 214 | 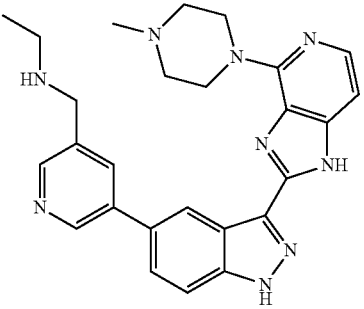 [SMILES: CCNCc1cncc(-c2ccc3[nH]nc(-c4nc5c(N6CCN(C)CC6)nccc5[nH]4)c3c2)c1] |
| 215 | 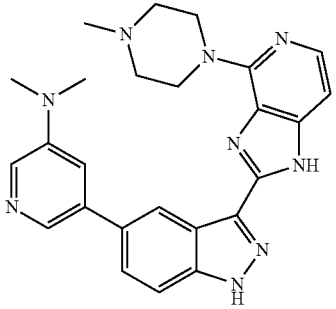 [SMILES: CN1CCN(c2nccc3[nH]c(-c4n[nH]c5ccc(-c6cncc(N(C)C)c6)cc45)nc23)CC1] |
| 216 | 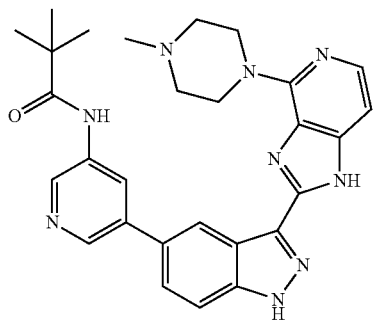 [SMILES: CN1CCN(c2nccc3[nH]c(-c4n[nH]c5ccc(-c6cncc(NC(=O)C(C)(C)C)c6)cc45)nc23)CC1] |
| 217 | 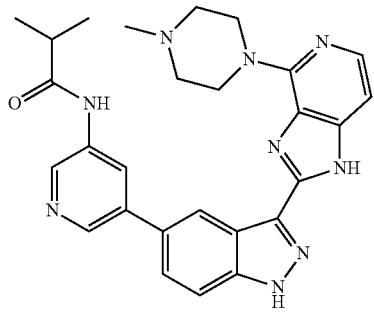 [SMILES: CC(C)C(=O)Nc1cncc(-c2ccc3[nH]nc(-c4nc5c(N6CCN(C)CC6)nccc5[nH]4)c3c2)c1] |
| 218 | 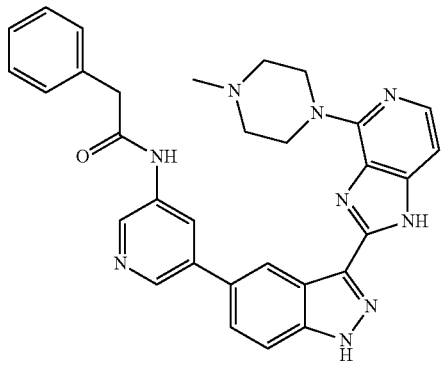 [SMILES: CN1CCN(c2nccc3[nH]c(-c4n[nH]c5ccc(-c6cncc(NC(=O)Cc7ccccc7)c6)cc45)nc23)CC1] |
| 219 | 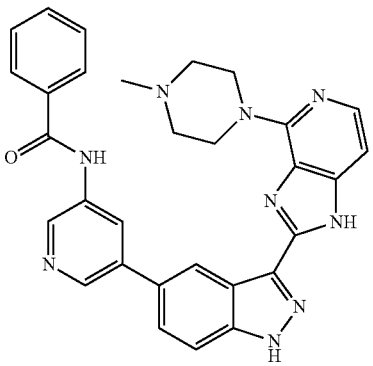 [SMILES: CN1CCN(c2nccc3[nH]c(-c4n[nH]c5ccc(-c6cncc(NC(=O)c7ccccc7)c6)cc45)nc23)CC1] |
| 220 | 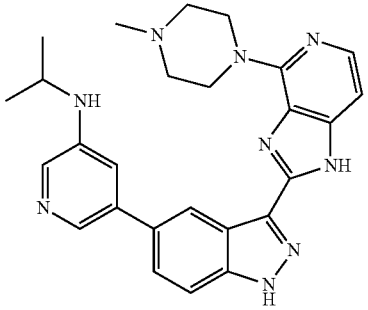 [SMILES: CC(C)Nc1cncc(-c2ccc3[nH]nc(-c4nc5c(N6CCN(C)CC6)nccc5[nH]4)c3c2)c1] |
| 221 | 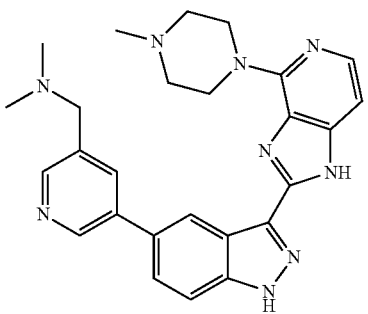 [SMILES: CN(C)Cc1cncc(-c2ccc3[nH]nc(-c4nc5c(N6CCN(C)CC6)nccc5[nH]4)c3c2)c1] |

TABLE 1-continued
| 222 | 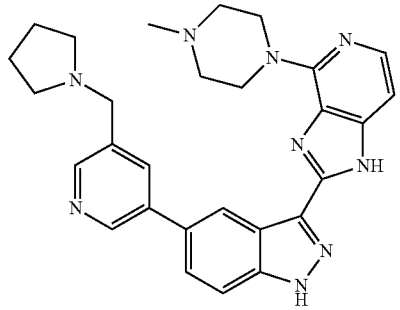 [SMILES: CN1CCN(c2nccc3[nH]c(-c4n[nH]c5ccc(-c6cncc(CN7CCCC7)c6)cc45)nc23)CC1] |
| --- | --- |
| 223 | 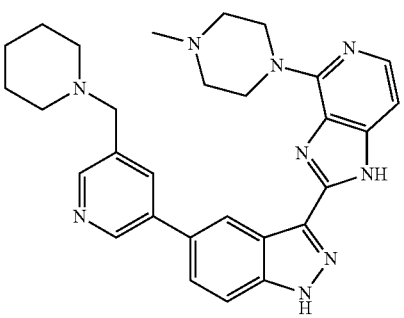 [SMILES: CN1CCN(c2nccc3[nH]c(-c4n[nH]c5ccc(-c6cncc(CN7CCCCC7)c6)cc45)nc23)CC1] |
| 224 | 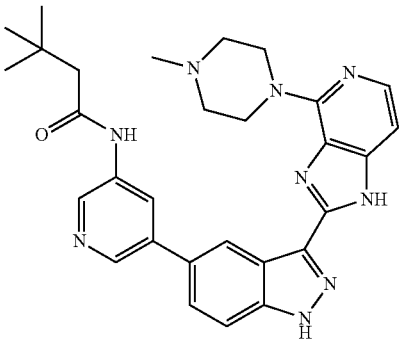 |
| 225 | 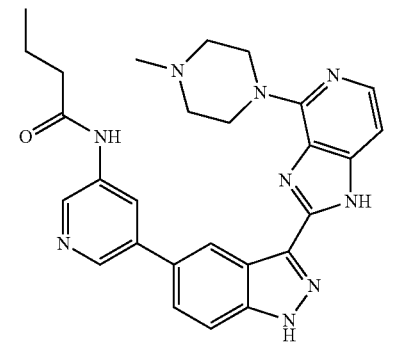 [SMILES: CCCC(=O)Nc1cncc(-c2ccc3[nH]nc(-c4nc5c(N6CCN(C)CC6)nccc5[nH]4)c3c2)c1] |
TABLE 1-continued
| 226 | 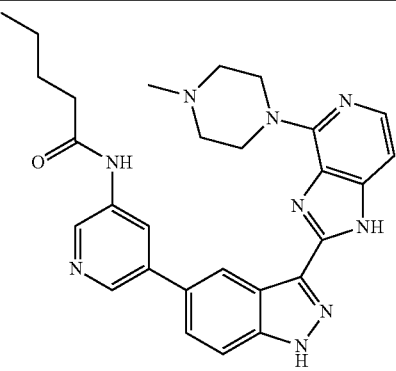 |
| --- | --- |
| 227 | 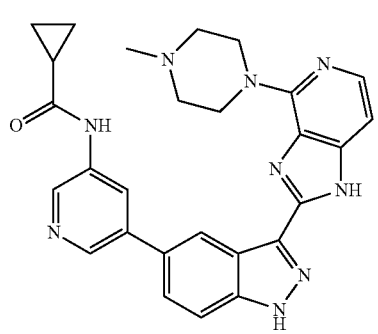 [SMILES: CN1CCN(c2nccc3[nH]c(-c4n[nH]c5ccc(-c6cncc(NC(=O)C7CC7)c6)cc45)nc23)CC1] |
| 228 | 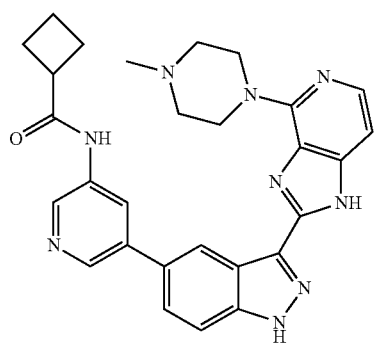 [SMILES: CN1CCN(c2nccc3[nH]c(-c4n[nH]c5ccc(-c6cncc(NC(=O)C7CCC7)c6)cc45)nc23)CC1] |
| 229 | 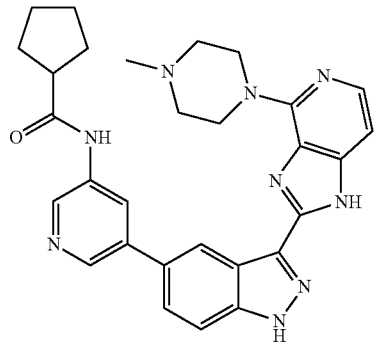 [SMILES: CN1CCN(c2nccc3[nH]c(-c4n[nH]c5ccc(-c6cncc(NC(=O)C7CCCC7)c6)cc45)nc23)CC1] |

TABLE 1-continued
| 230 | 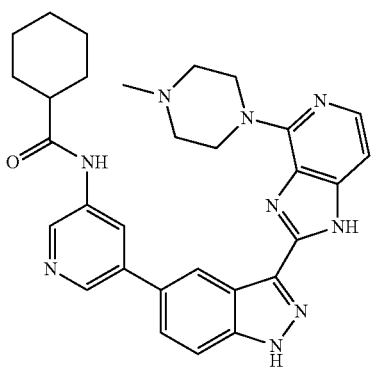 [SMILES: CN1CCN(c2nccc3[nH]c(-c4n[nH]c5ccc(-c6cncc(NC(=O)C7CCCCC7)c6)cc45)nc23)CC1] |
| --- | --- |
| 231 | 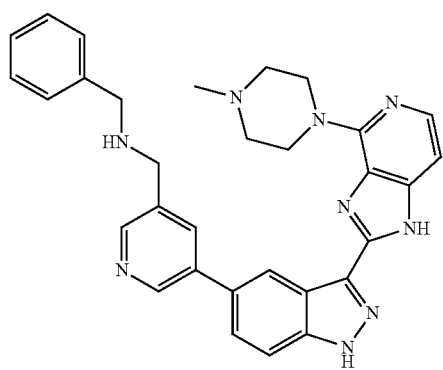 [SMILES: CN1CCN(c2nccc3[nH]c(-c4n[nH]c5ccc(-c6cncc(CNCc7ccccc7)c6)cc45)nc23)CC1] |
| 232 | 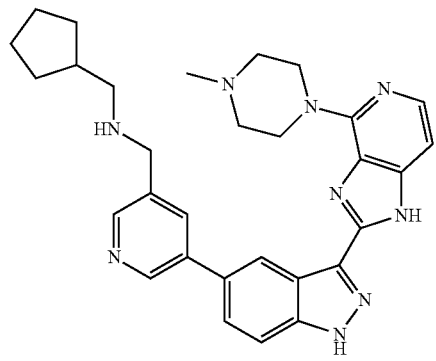 [SMILES: CN1CCN(c2nccc3[nH]c(-c4n[nH]c5ccc(-c6cncc(CNCC7CCCC7)c6)cc45)nc23)CC1] |
| 233 | 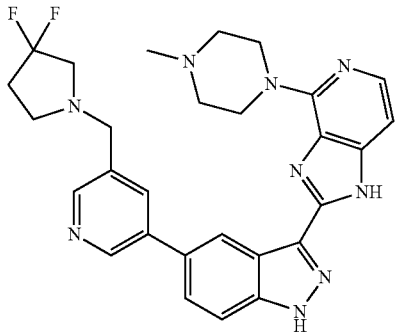 [SMILES: CN1CCN(c2nccc3[nH]c(-c4n[nH]c5ccc(-c6cncc(CN7CCC(F)(F)C7)c6)cc45)nc23)CC1] |
TABLE 1-continued
| 234 | 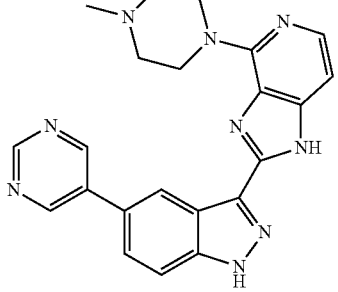 |
| --- | --- |
| 235 | 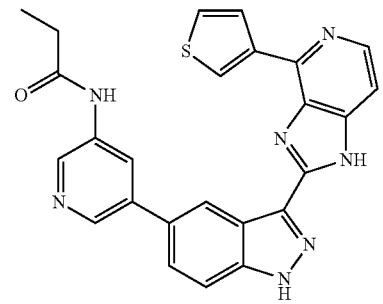 [SMILES: CCC(=O)Nc1cncc(-c2ccc3[nH]nc(-c4nc5c(-c6ccsc6)nccc5[nH]4)c3c2)c1] |
| 236 | 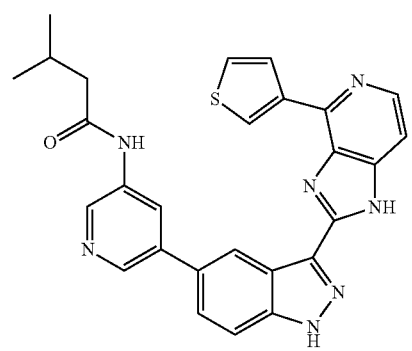 [SMILES: CC(C)CC(=O)Nc1cncc(-c2ccc3[nH]nc(-c4nc5c(-c6ccsc6)nccc5[nH]4)c3c2)c1] |
| 237 | 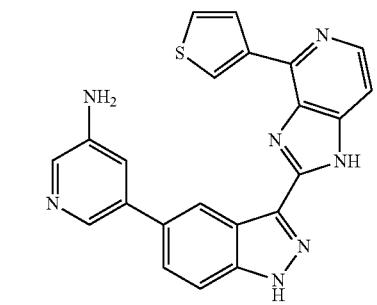 [SMILES: Nc1cncc(-c2ccc3[nH]nc(-c4nc5c(-c6ccsc6)nccc5[nH]4)c3c2)c1] |
| 238 | 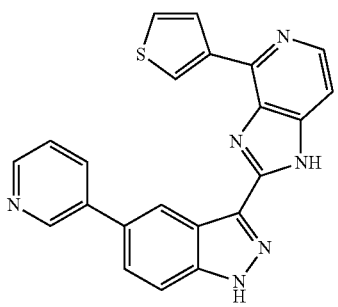 [SMILES: c1cncc(-c2ccc3[nH]nc(-c4nc5c(-c6ccsc6)nccc5[nH]4)c3c2)c1] |

TABLE 1-continued
| 239 | 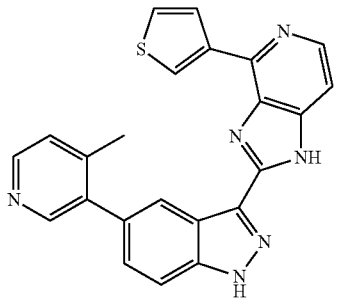 [SMILES: Cc1ccncc1-c1ccc2[nH]nc(-c3nc4c(-c5ccsc5)nccc4[nH]3)c2c1] |
| --- | --- |
| 240 | 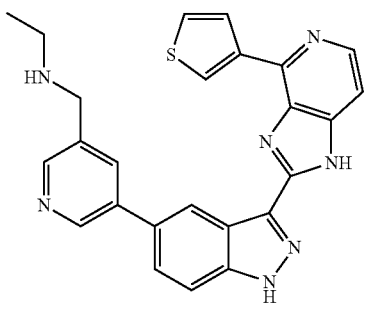 [SMILES: CCNCc1cncc(-c2ccc3[nH]nc(-c4nc5c(-c6ccsc6)nccc5[nH]4)c3c2)c1] |
| 241 | 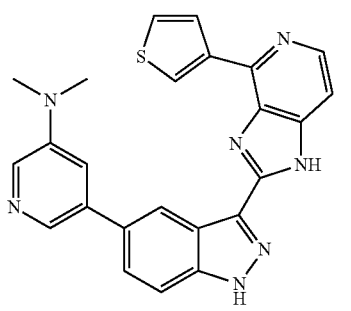 [SMILES: CN(C)c1cncc(-c2ccc3[nH]nc(-c4nc5c(-c6ccsc6)nccc5[nH]4)c3c2)c1] |
| 242 | 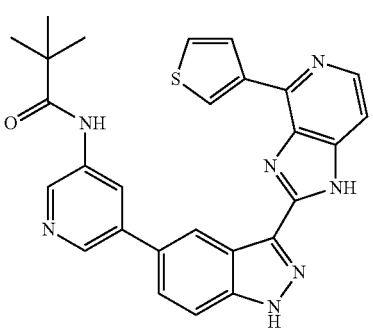 [SMILES: CC(C)(C)C(=O)Nc1cncc(-c2ccc3[nH]nc(-c4nc5c(-c6ccsc6)nccc5[nH]4)c3c2)c1] |
| 243 | 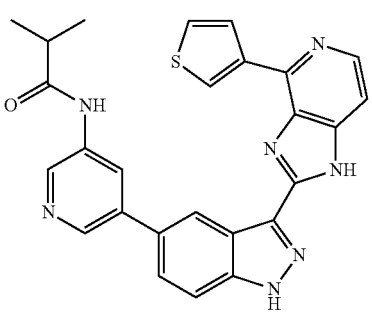 [SMILES: CC(C)C(=O)Nc1cncc(-c2ccc3[nH]nc(-c4nc5c(-c6ccsc6)nccc5[nH]4)c3c2)c1] |
| 244 | 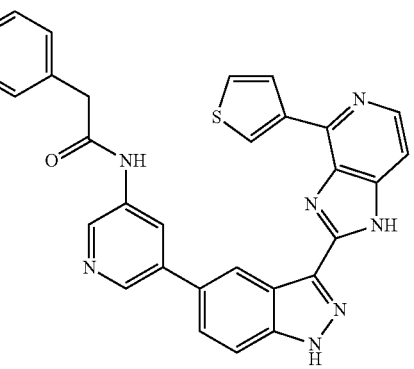 |
| 245 | 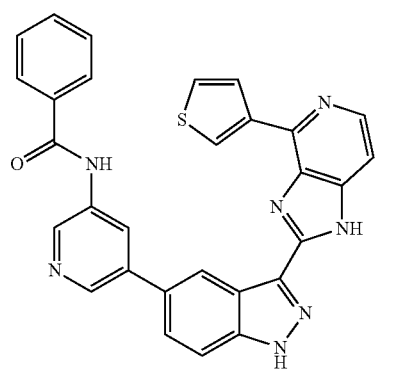 [SMILES: O=C(Nc1cncc(-c2ccc3[nH]nc(-c4nc5c(-c6ccsc6)nccc5[nH]4)c3c2)c1)c1ccccc1] |
| 246 | 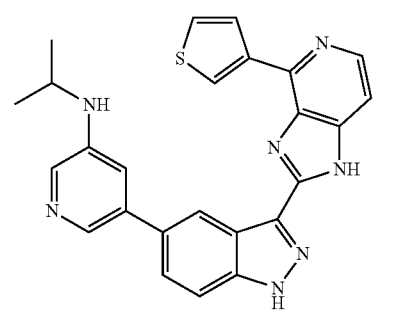 |
| 247 | 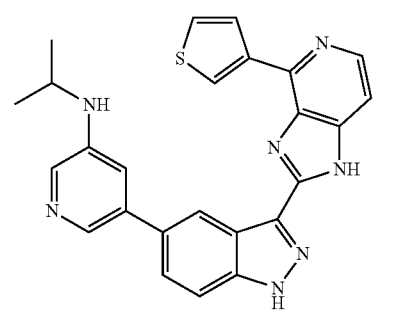 |
| 248 | 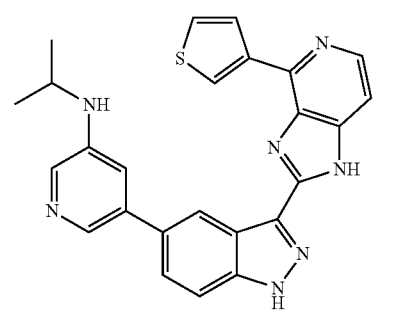 |

TABLE 1-continued
| | |
|---|---|
| 249 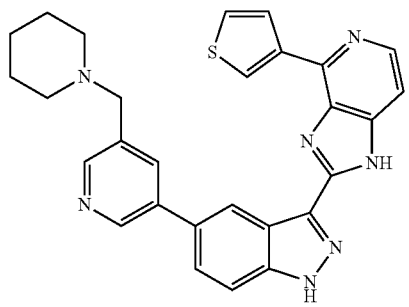 [SMILES: c1cc2[nH]c(-c3n[nH]c4ccc(-c5cncc(CN6CCCCC6)c5)cc34)nc2c(-c2ccsc2)n1] | 253 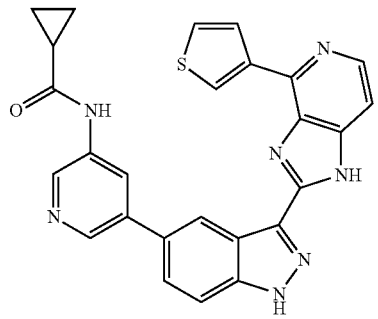 |
| 250 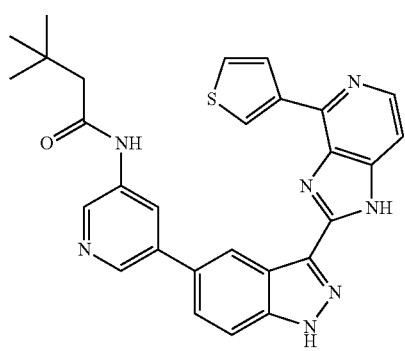 | 254 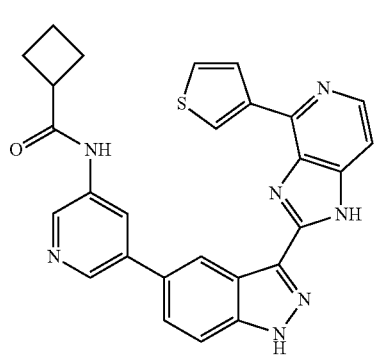 |
| 251 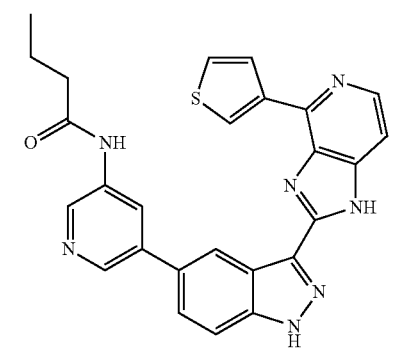 [SMILES: CCCC(=O)Nc1cncc(-c2ccc3[nH]nc(-c4nc5c(-c6ccsc6)nccc5[nH]4)c3c2)c1] | 255 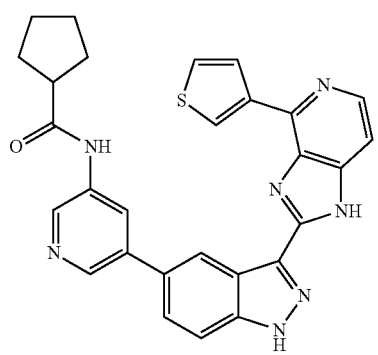 |
| 252 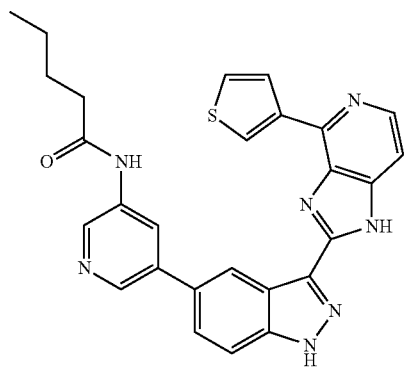 | 256 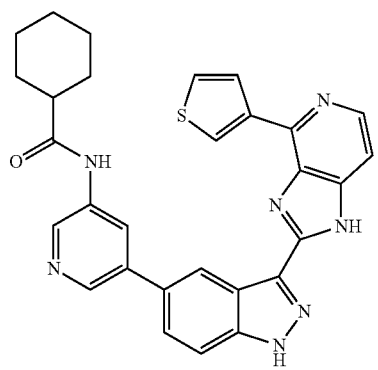 |

TABLE 1-continued
| 257 | 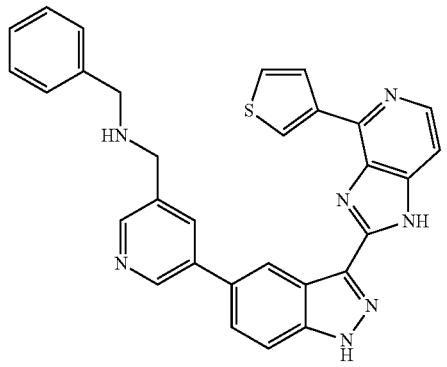 [SMILES: c1ccc(CNCc2cncc(-c3ccc4[nH]nc(-c5nc6c(-c7ccsc7)nccc6[nH]5)c4c3)c2)cc1] |
| --- | --- |
| 258 | 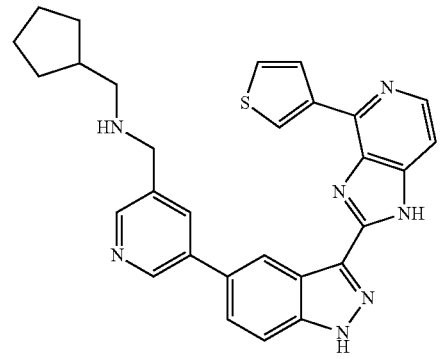 [SMILES: c1cc2[nH]c(-c3n[nH]c4ccc(-c5cncc(CNCC6CCCC6)c5)cc34)nc2c(-c2ccsc2)n1] |
| 259 | 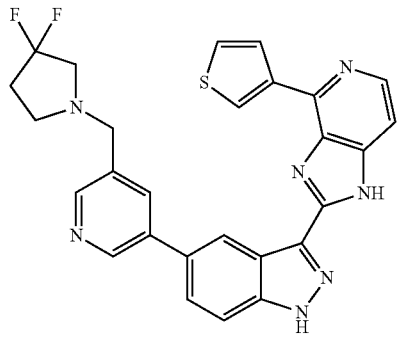 [SMILES: FC1(F)CCN(Cc2cncc(-c3ccc4[nH]nc(-c5nc6c(-c7ccsc7)nccc6[nH]5)c4c3)c2)C1] |
| 260 | 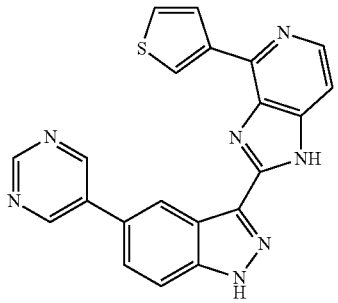 |
TABLE 1-continued
| 261 | 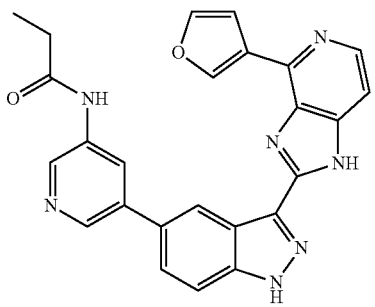 [SMILES: CCC(=O)Nc1cncc(-c2ccc3[nH]nc(-c4nc5c(-c6ccoc6)nccc5[nH]4)c3c2)c1] |
| --- | --- |
| 262 | 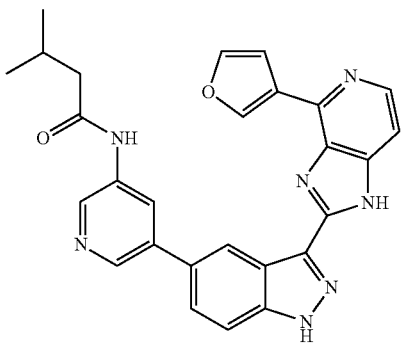 [SMILES: CC(C)CC(=O)Nc1cncc(-c2ccc3[nH]nc(-c4nc5c(-c6ccoc6)nccc5[nH]4)c3c2)c1] |
| 263 | 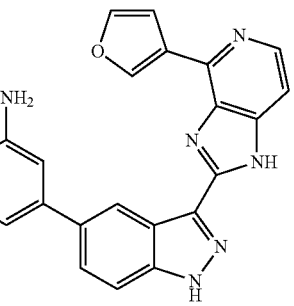 |
| 264 | 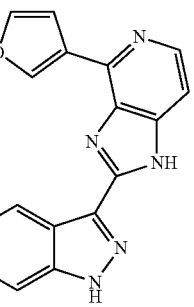 |
| 265 | 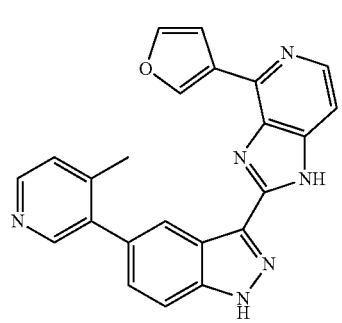 [SMILES: Cc1ccncc1-c1ccc2[nH]nc(-c3nc4c(-c5ccoc5)nccc4[nH]3)c2c1] |

TABLE 1-continued
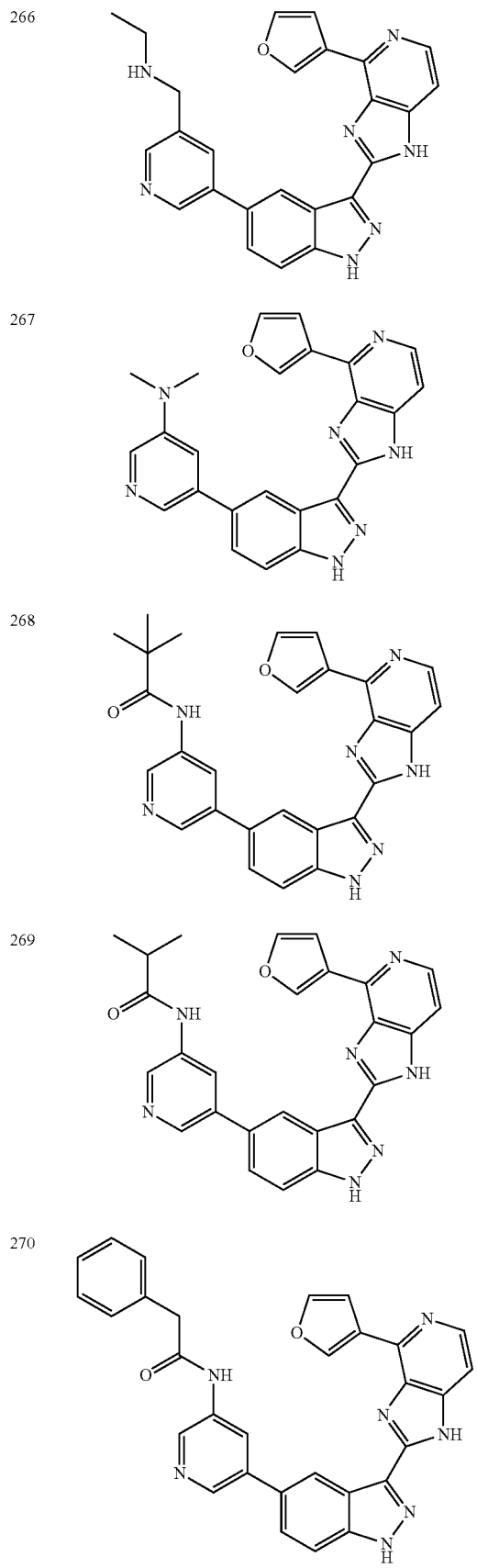
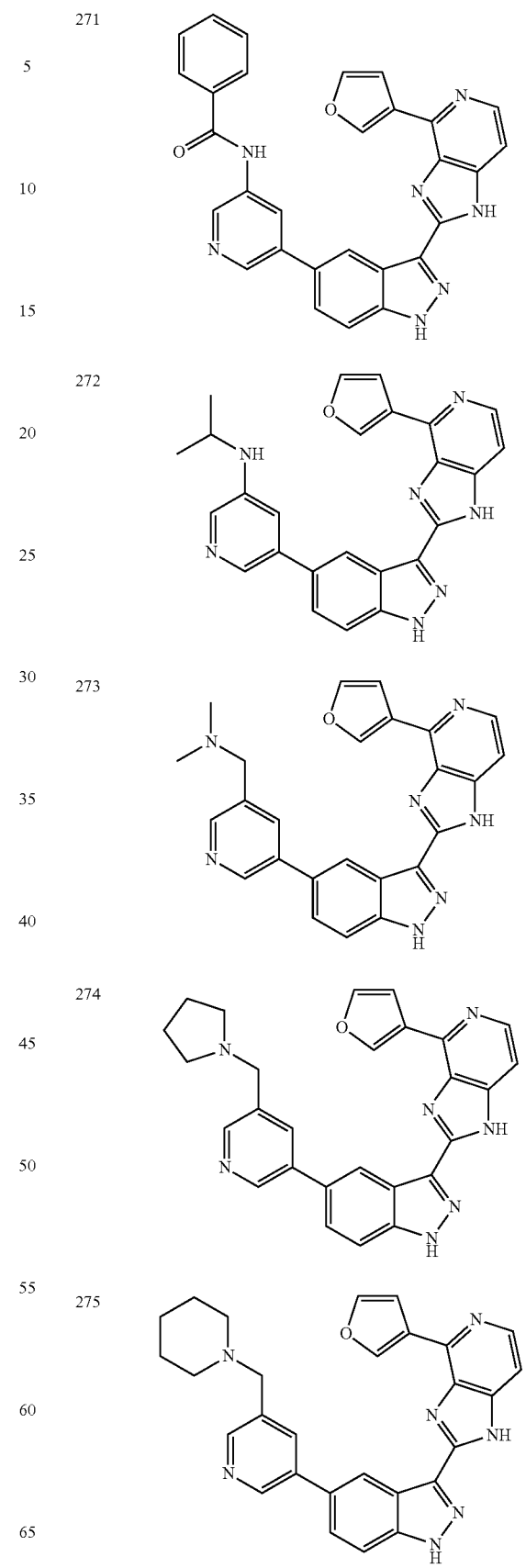

TABLE 1-continued
276 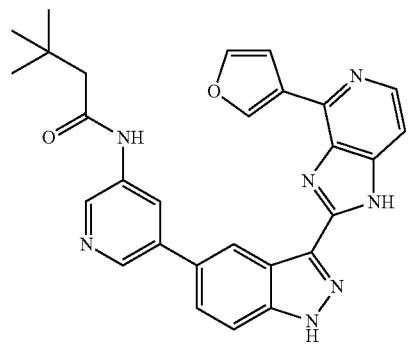
277 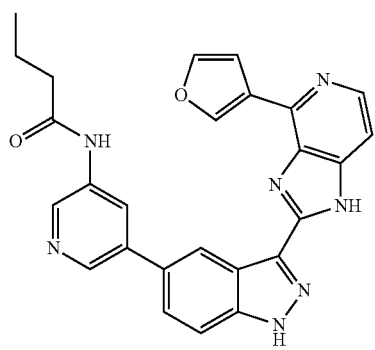 [SMILES: CCCC(=O)Nc1cncc(-c2ccc3[nH]nc(-c4nc5c(-c6ccoc6)nccc5[nH]4)c3c2)c1]
278 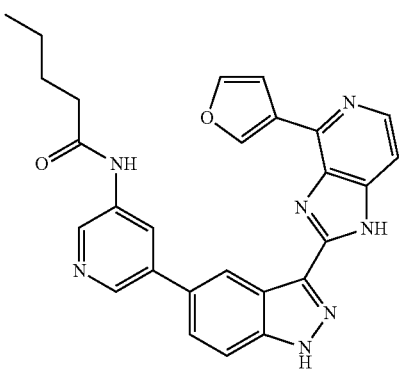
279 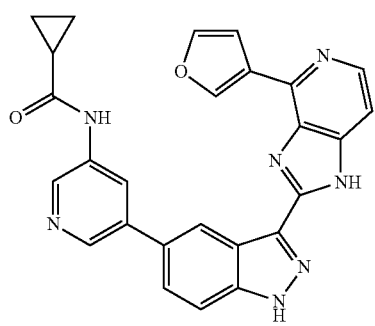 [SMILES: O=C(Nc1cncc(-c2ccc3[nH]nc(-c4nc5c(-c6ccoc6)nccc5[nH]4)c3c2)c1)C1CC1]
TABLE 1-continued
280 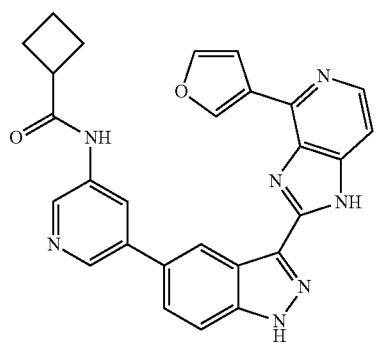 [SMILES: O=C(Nc1cncc(-c2ccc3[nH]nc(-c4nc5c(-c6ccoc6)nccc5[nH]4)c3c2)c1)C1CCC1]
281 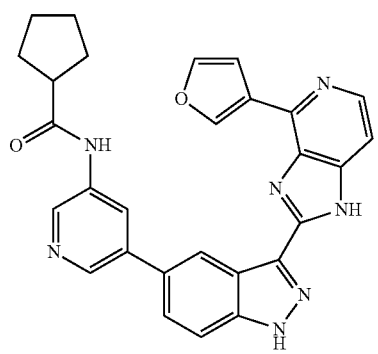 [SMILES: O=C(Nc1cncc(-c2ccc3[nH]nc(-c4nc5c(-c6ccoc6)nccc5[nH]4)c3c2)c1)C1CCCC1]
282 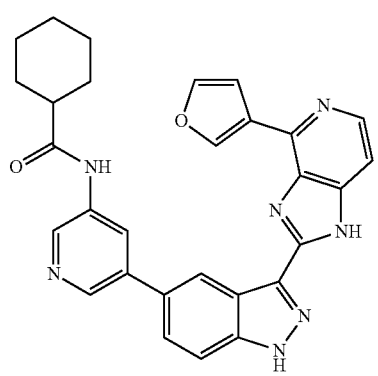 [SMILES: O=C(Nc1cncc(-c2ccc3[nH]nc(-c4nc5c(-c6ccoc6)nccc5[nH]4)c3c2)c1)C1CCCCC1]
283 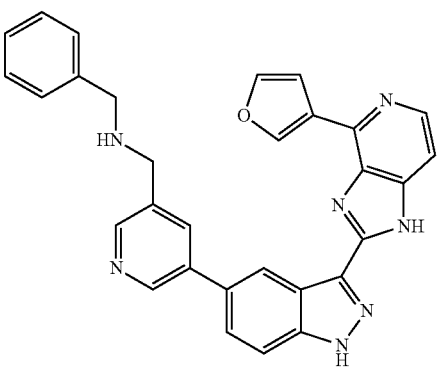 [SMILES: c1ccc(CNCc2cncc(-c3ccc4[nH]nc(-c5nc6c(-c7ccoc7)nccc6[nH]5)c4c3)c2)cc1]

TABLE 1-continued
284 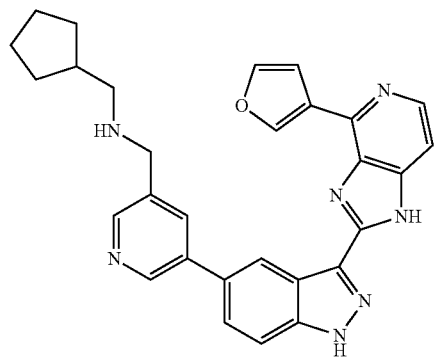 [SMILES: c1cc2[nH]c(-c3n[nH]c4ccc(-c5cncc(CNCC6CCCC6)c5)cc34)nc2c(-c2ccoc2)n1]
285 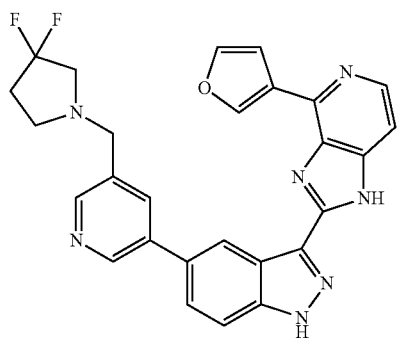 [SMILES: FC1(F)CCN(Cc2cncc(-c3ccc4[nH]nc(-c5nc6c(-c7ccoc7)nccc6[nH]5)c4c3)c2)C1]
286 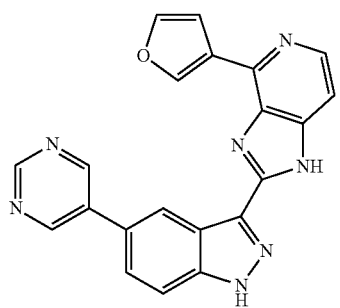 [SMILES: c1ncc(-c2ccc3[nH]nc(-c4nc5c(-c6ccoc6)nccc5[nH]4)c3c2)cn1]
287 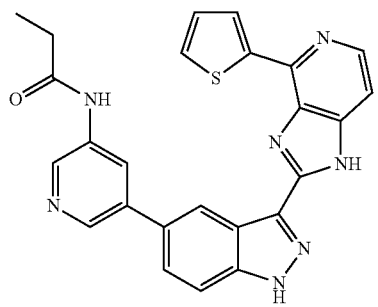 [SMILES: CCC(=O)Nc1cncc(-c2ccc3[nH]nc(-c4nc5c(-c6cccs6)nccc5[nH]4)c3c2)c1]
TABLE 1-continued
288 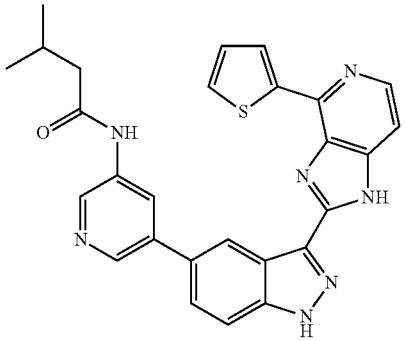 [SMILES: CC(C)CC(=O)Nc1cncc(-c2ccc3[nH]nc(-c4nc5c(-c6cccs6)nccc5[nH]4)c3c2)c1]
289 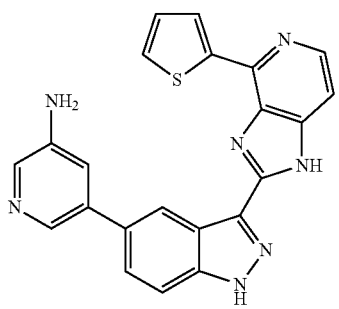 [SMILES: Nc1cncc(-c2ccc3[nH]nc(-c4nc5c(-c6cccs6)nccc5[nH]4)c3c2)c1]
290 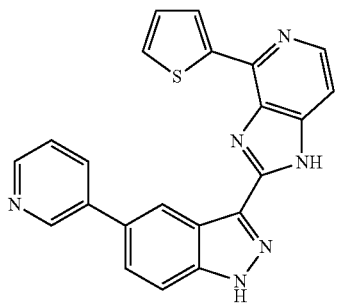 [SMILES: c1cncc(-c2ccc3[nH]nc(-c4nc5c(-c6cccs6)nccc5[nH]4)c3c2)c1]
291 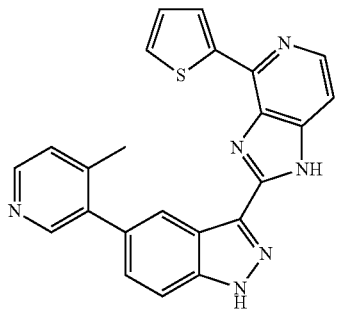
292 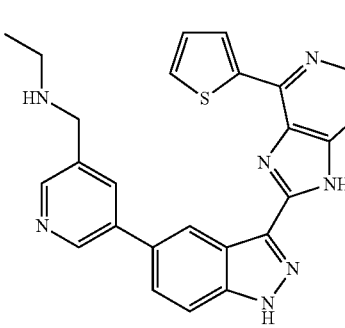

TABLE 1-continued
| | |
|---|---|
| 293 | 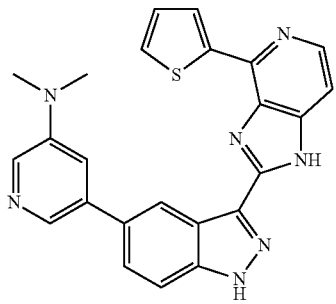 [SMILES: CN(C)c1cncc(-c2ccc3[nH]nc(-c4nc5c(-c6cccs6)nccc5[nH]4)c3c2)c1] |
| 294 | 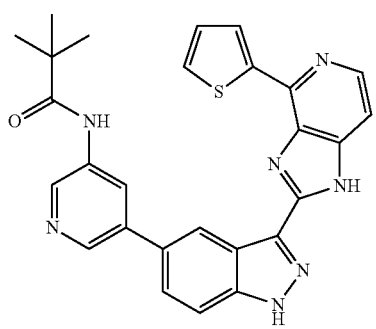 [SMILES: CC(C)(C)C(=O)Nc1cncc(-c2ccc3[nH]nc(-c4nc5c(-c6cccs6)nccc5[nH]4)c3c2)c1] |
| 295 | 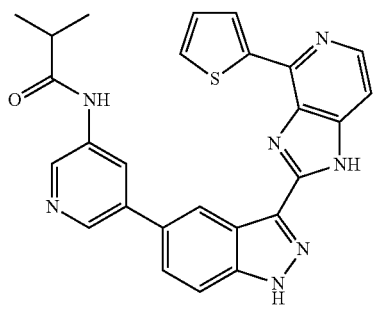 [SMILES: CC(C)C(=O)Nc1cncc(-c2ccc3[nH]nc(-c4nc5c(-c6cccs6)nccc5[nH]4)c3c2)c1] |
| 296 | 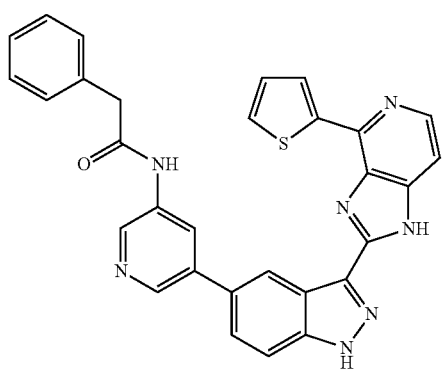 [SMILES: O=C(Cc1ccccc1)Nc1cncc(-c2ccc3[nH]nc(-c4nc5c(-c6cccs6)nccc5[nH]4)c3c2)c1] |
| 297 | 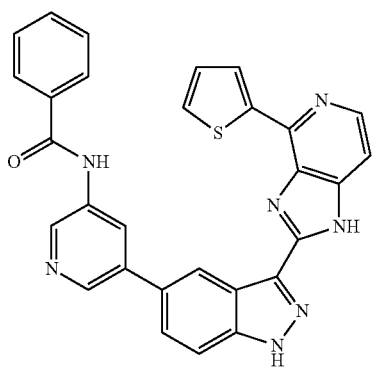 [SMILES: O=C(Nc1cncc(-c2ccc3[nH]nc(-c4nc5c(-c6cccs6)nccc5[nH]4)c3c2)c1)c1ccccc1] |
| 298 | 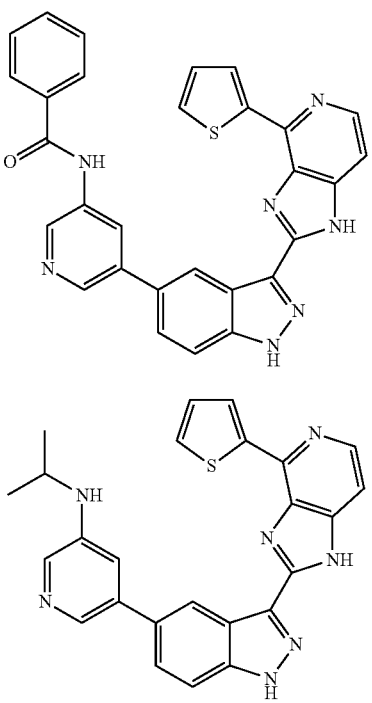 |
| 299 | |
| 300 | 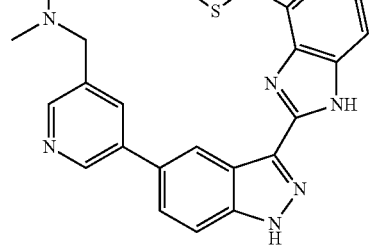 |
| 301 | 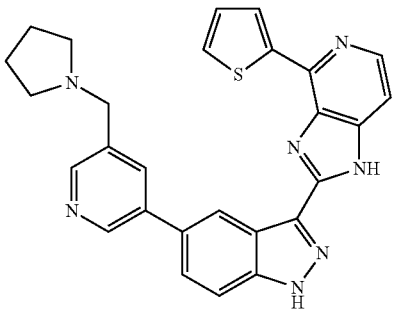 [SMILES: c1csc(-c2nccc3[nH]c(-c4n[nH]c5ccc(-c6cncc(CN7CCCC7)c6)cc45)nc23)c1] |
| | 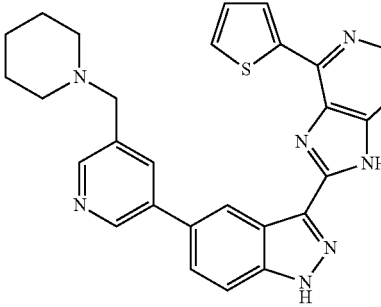 |

TABLE 1-continued
302 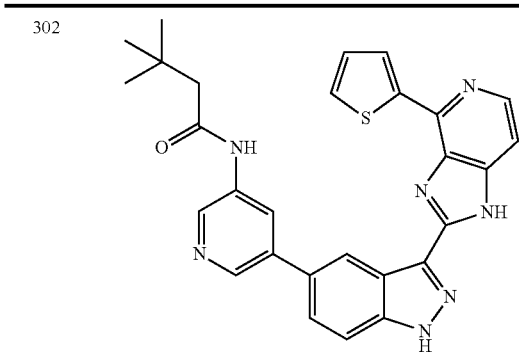
303 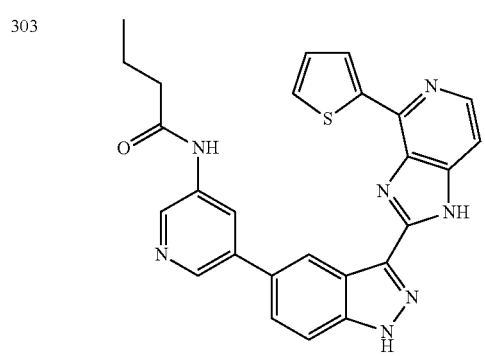
304 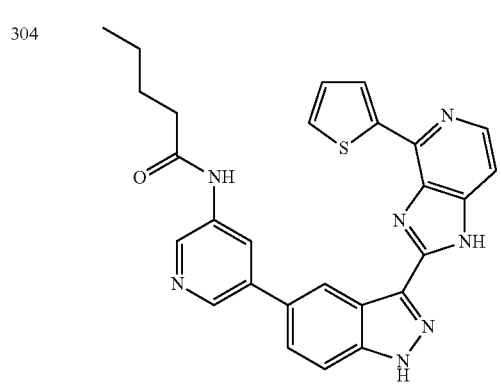
305 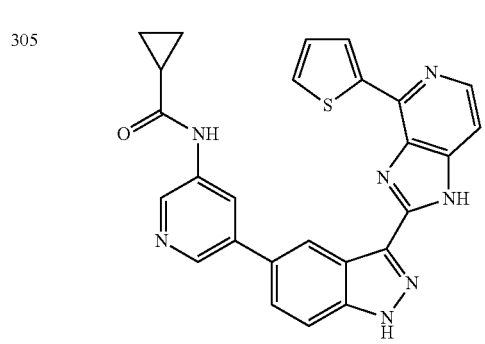
TABLE 1-continued
306 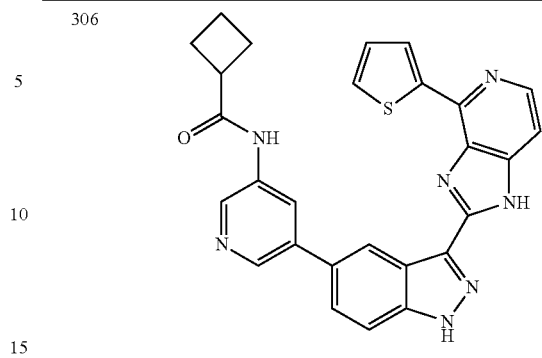
307 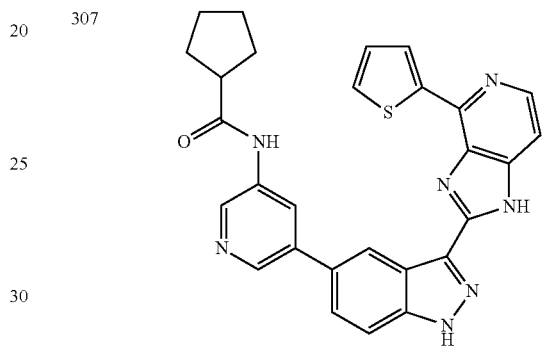
308 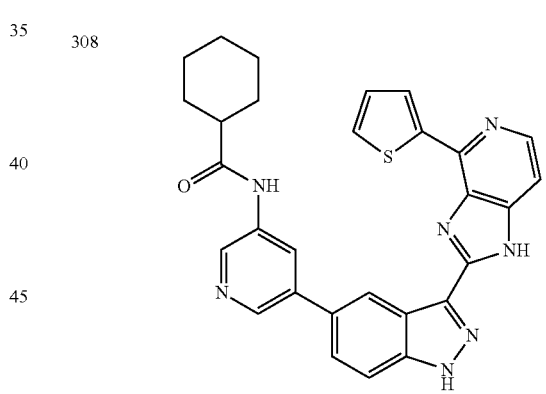
309 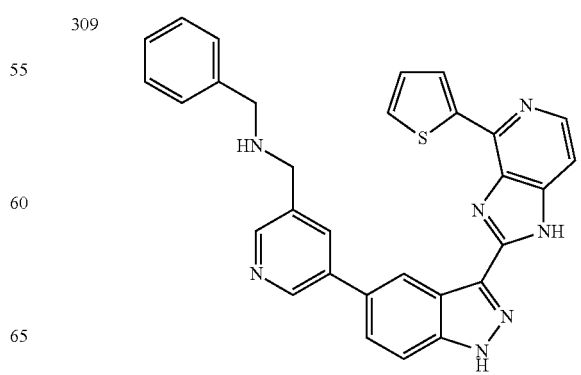

TABLE 1-continued
| | |
|---|---|
| 310 | 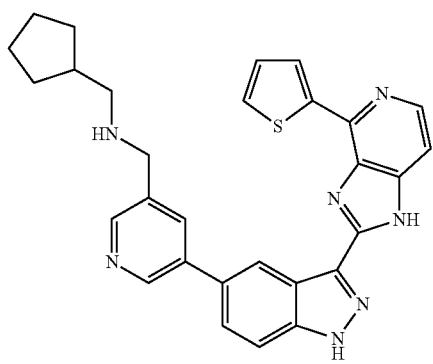 [SMILES: c1csc(-c2nccc3[nH]c(-c4n[nH]c5ccc(-c6cncc(CNCC7CCCC7)c6)cc45)nc23)c1] |
| 311 | 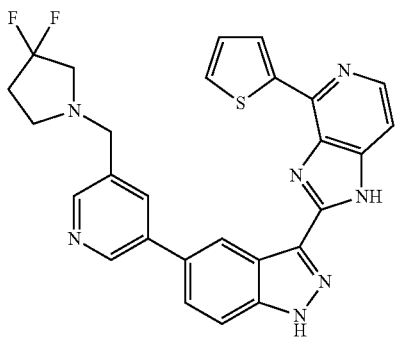 [SMILES: FC1(F)CCN(Cc2cncc(-c3ccc4[nH]nc(-c5nc6c(-c7cccs7)nccc6[nH]5)c4c3)c2)C1] |
| 312 | 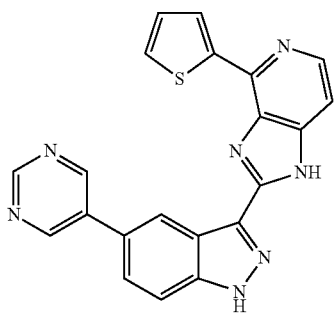 [SMILES: c1csc(-c2nccc3[nH]c(-c4n[nH]c5ccc(-c6cncnc6)cc45)nc23)c1] |
| 313 | 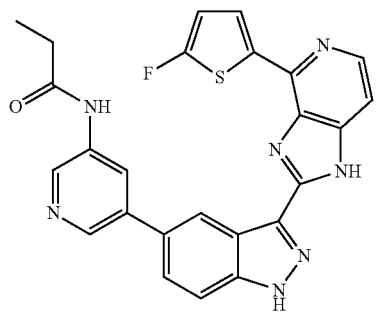 [SMILES: CCC(=O)Nc1cncc(-c2ccc3[nH]nc(-c4nc5c(-c6ccc(F)s6)nccc5[nH]4)c3c2)c1] |
| 314 | 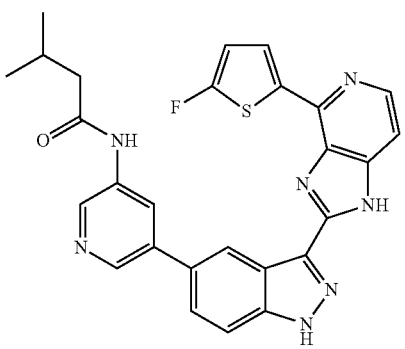 [SMILES: CC(C)CC(=O)Nc1cncc(-c2ccc3[nH]nc(-c4nc5c(-c6ccc(F)s6)nccc5[nH]4)c3c2)c1] |
| 315 | 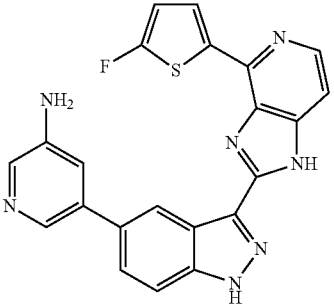 |
| 316 | 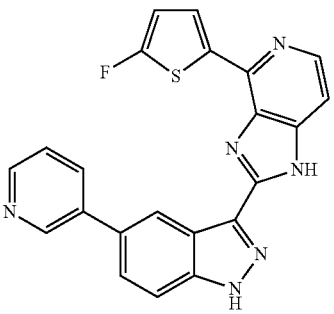 [SMILES: Fc1ccc(-c2nccc3[nH]c(-c4n[nH]c5ccc(-c6cccnc6)cc45)nc23)s1] |
| 317 | 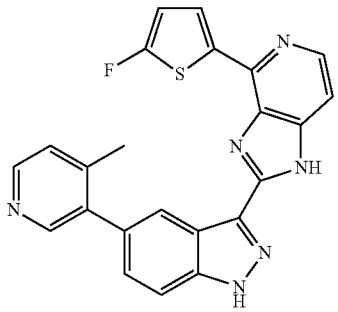 |
| 318 | 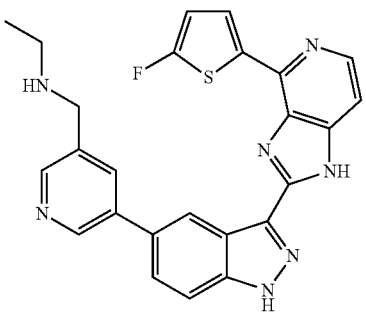 [SMILES: CCNCc1cncc(-c2ccc3[nH]nc(-c4nc5c(-c6ccc(F)s6)nccc5[nH]4)c3c2)c1] |

TABLE 1-continued
| | |
|---|---|
| 319 | 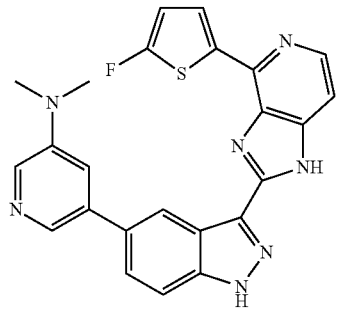 |
| 320 | 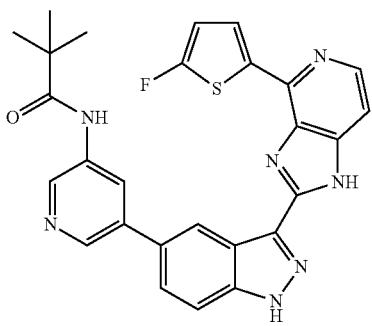 [SMILES: CC(C)(C)C(=O)Nc1cncc(-c2ccc3[nH]nc(-c4nc5c(-c6ccc(F)s6)nccc5[nH]4)c3c2)c1] |
| 321 | 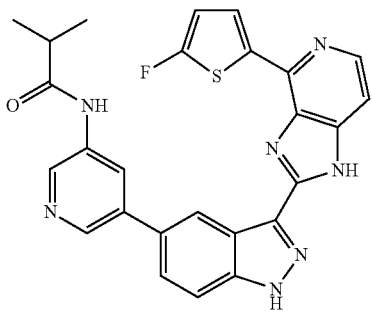 [SMILES: CC(C)C(=O)Nc1cncc(-c2ccc3[nH]nc(-c4nc5c(-c6ccc(F)s6)nccc5[nH]4)c3c2)c1] |
| 322 | 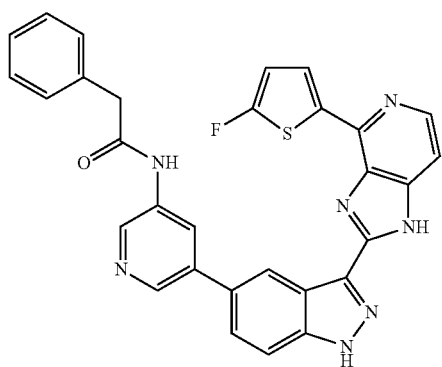 |
| 323 | 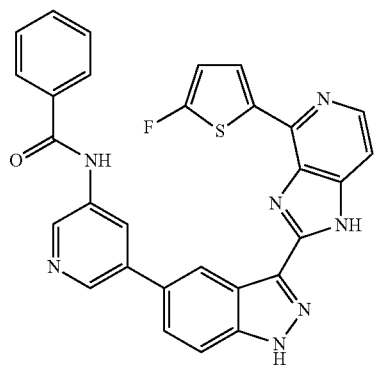 [SMILES: O=C(Nc1cncc(-c2ccc3[nH]nc(-c4nc5c(-c6ccc(F)s6)nccc5[nH]4)c3c2)c1)c1ccccc1] |
| 324 | 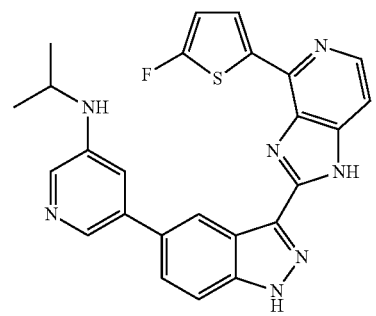 [SMILES: CC(C)Nc1cncc(-c2ccc3[nH]nc(-c4nc5c(-c6ccc(F)s6)nccc5[nH]4)c3c2)c1] |
| 325 | 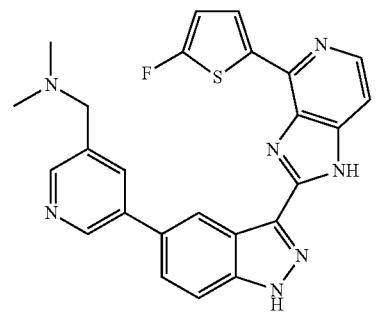 |
| 326 | 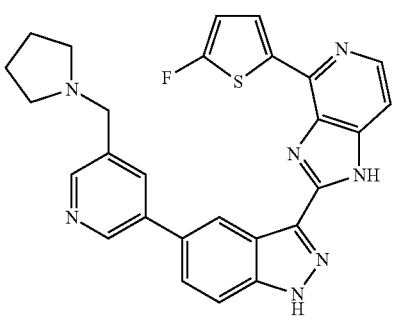 [SMILES: Fc1ccc(-c2nccc3[nH]c(-c4n[nH]c5ccc(-c6cncc(CN7CCCC7)c6)cc45)nc23)s1] |
| 327 | 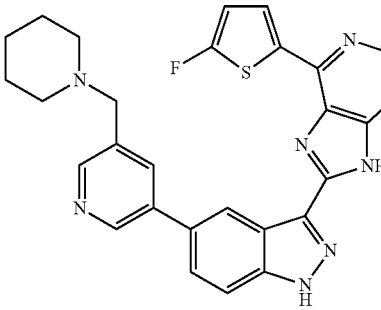 |

TABLE 1-continued
| 328 | 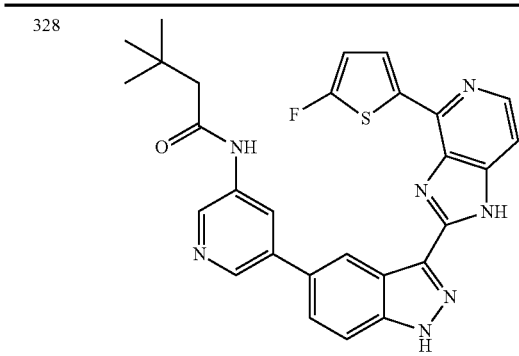 |
| --- | --- |
| 329 | 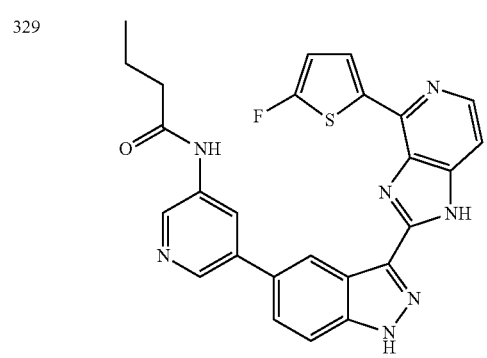 |
| 330 | 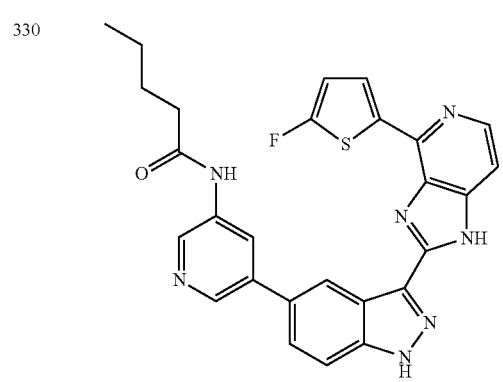 |
| 331 | 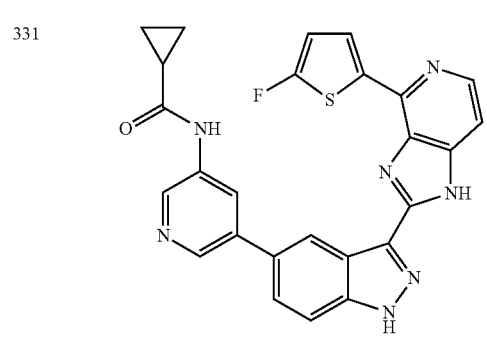 |
TABLE 1-continued
| 332 | 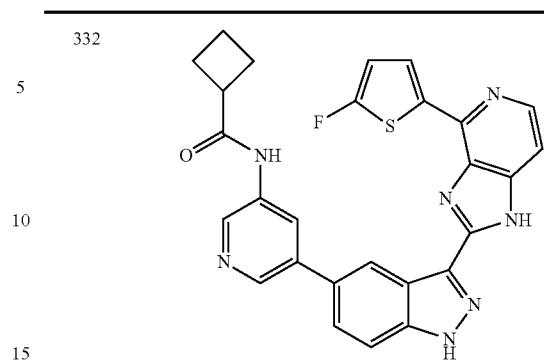 |
| --- | --- |
| 333 | 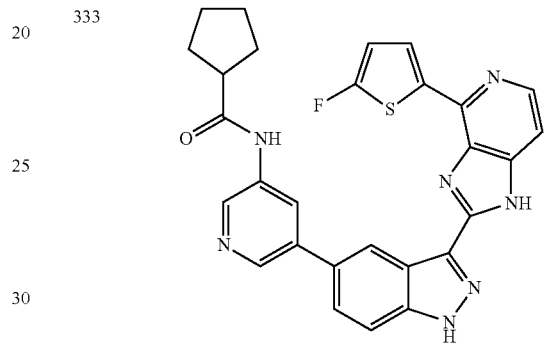 |
| 334 | 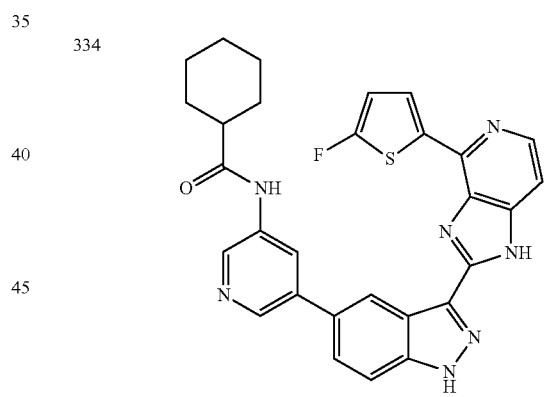 |
| 335 | 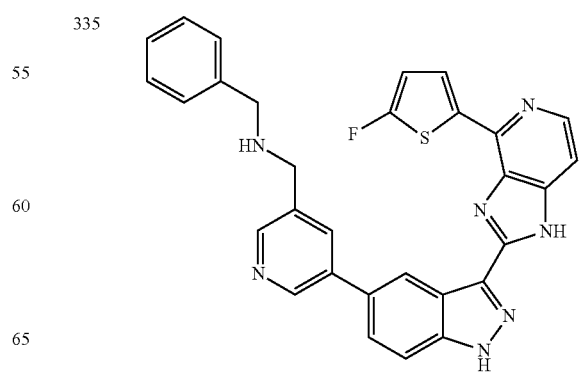 |

TABLE 1-continued
| | |
|---|---|
| 336 | 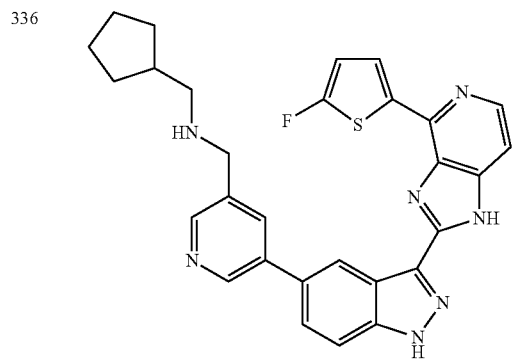 |
| 337 | 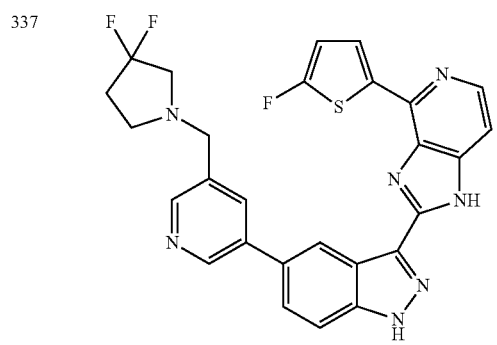 |
| 338 | 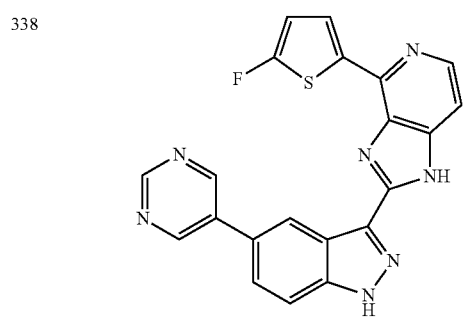 |
| 339 | 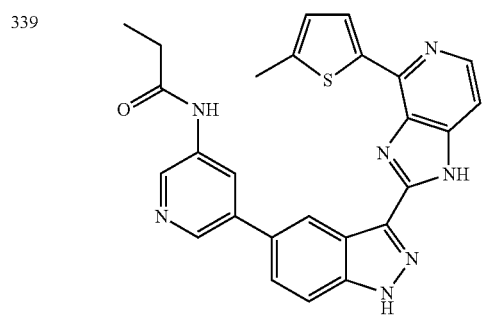 |
| 340 | 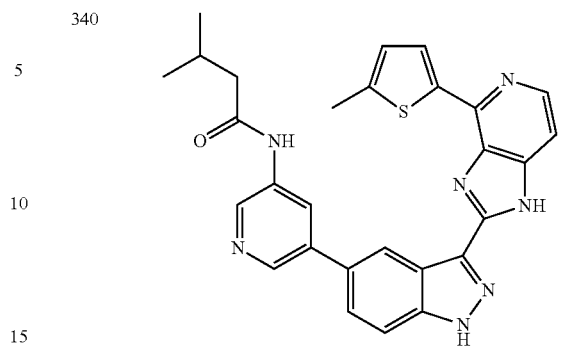 |
| 341 |  |
| 342 | 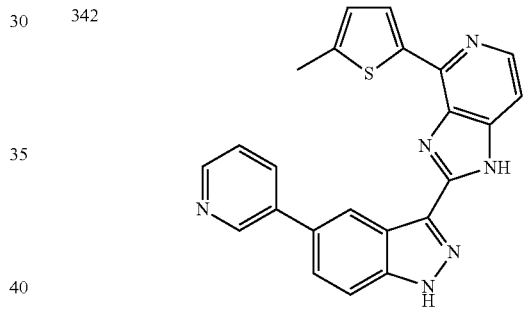 |
| 343 |  |
| 344 | 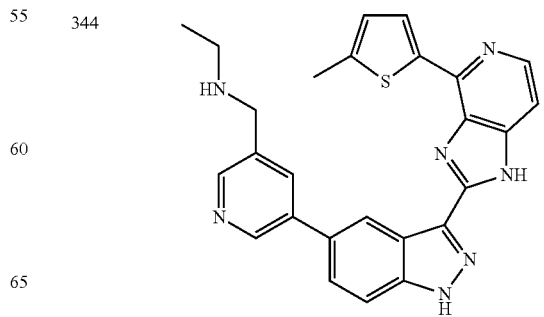 |

TABLE 1-continued
| | |
|---|---|
| 345 | 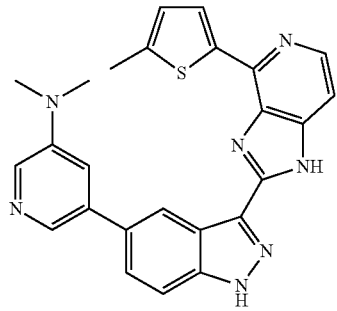 |
| 346 | 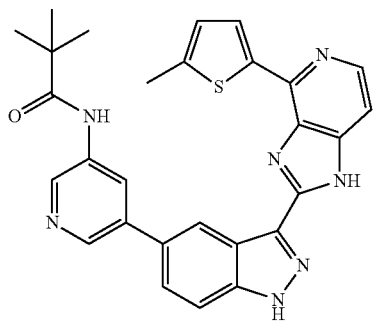 [SMILES: Cc1ccc(-c2nccc3[nH]c(-c4n[nH]c5ccc(-c6cncc(NC(=O)C(C)(C)C)c6)cc45)nc23)s1] |
| 347 | 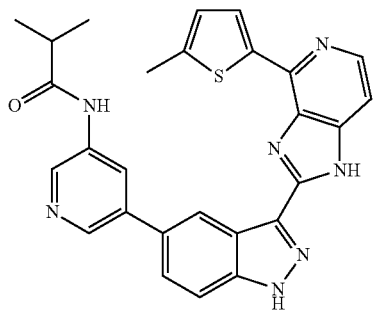 [SMILES: Cc1ccc(-c2nccc3[nH]c(-c4n[nH]c5ccc(-c6cncc(NC(=O)C(C)C)c6)cc45)nc23)s1] |
| 348 | 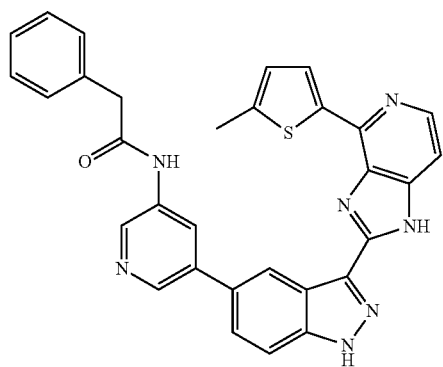 [SMILES: Cc1ccc(-c2nccc3[nH]c(-c4n[nH]c5ccc(-c6cncc(NC(=O)Cc7ccccc7)c6)cc45)nc23)s1] |
| 349 | 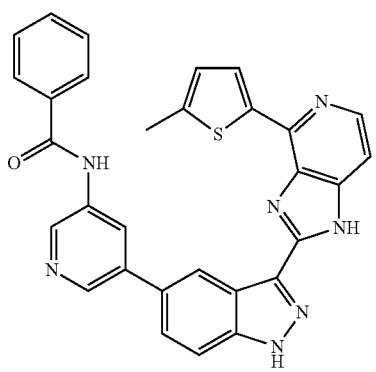 [SMILES: Cc1ccc(-c2nccc3[nH]c(-c4n[nH]c5ccc(-c6cncc(NC(=O)c7ccccc7)c6)cc45)nc23)s1] |
| 350 | 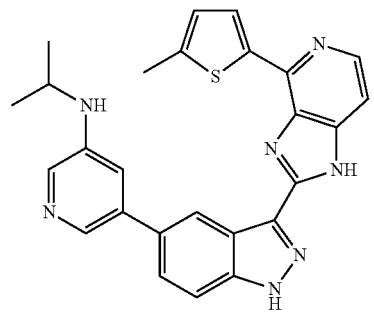 [SMILES: Cc1ccc(-c2nccc3[nH]c(-c4n[nH]c5ccc(-c6cncc(NC(C)C)c6)cc45)nc23)s1] |
| 351 | 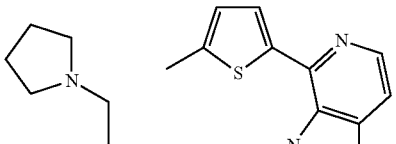 |
| 352 | 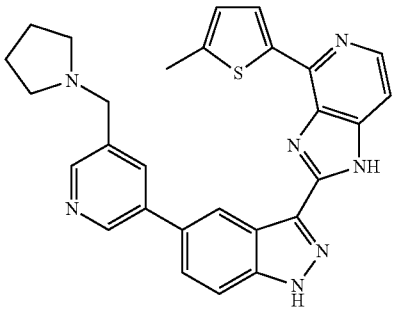 [SMILES: Cc1ccc(-c2nccc3[nH]c(-c4n[nH]c5ccc(-c6cncc(CN7CCCC7)c6)cc45)nc23)s1] |
| 353 | 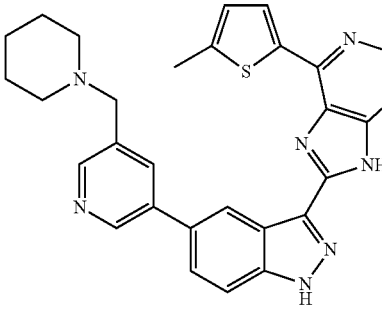 |

TABLE 1-continued
| 354 | 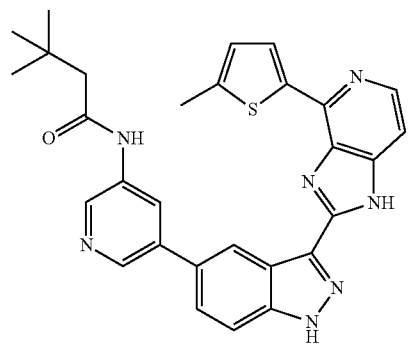 [SMILES: Cc1ccc(-c2nccc3[nH]c(-c4n[nH]c5ccc(-c6cncc(NC(=O)CC(C)(C)C)c6)cc45)nc23)s1] |
| --- | --- |
| 355 | 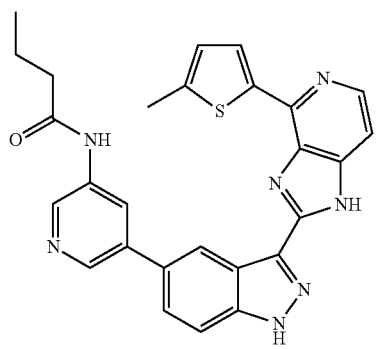 [SMILES: CCCC(=O)Nc1cncc(-c2ccc3[nH]nc(-c4nc5c(-c6ccc(C)s6)nccc5[nH]4)c3c2)c1] |
| 356 | 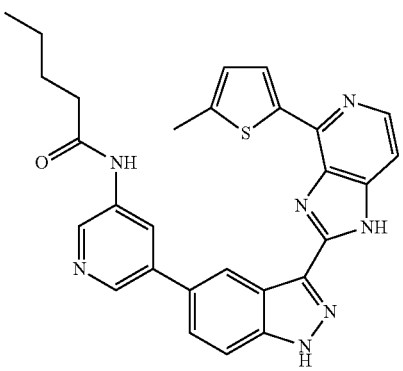 [SMILES: CCCCC(=O)Nc1cncc(-c2ccc3[nH]nc(-c4nc5c(-c6ccc(C)s6)nccc5[nH]4)c3c2)c1] |
| 357 | 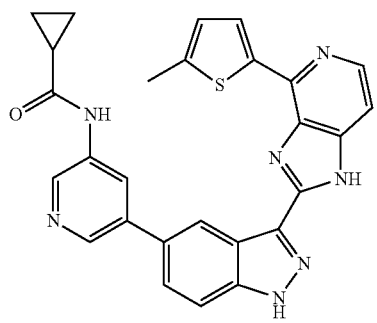 [SMILES: Cc1ccc(-c2nccc3[nH]c(-c4n[nH]c5ccc(-c6cncc(NC(=O)C7CC7)c6)cc45)nc23)s1] |
TABLE 1-continued
| 358 | 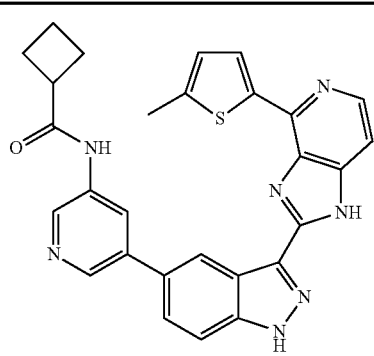 |
| --- | --- |
| 359 | 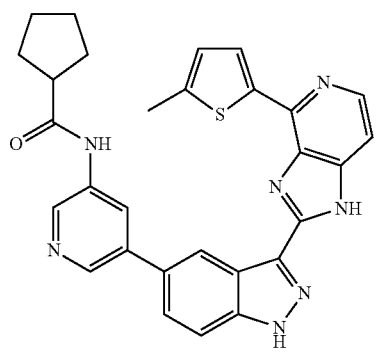 [SMILES: Cc1ccc(-c2nccc3[nH]c(-c4n[nH]c5ccc(-c6cncc(NC(=O)C7CCCC7)c6)cc45)nc23)s1] |
| 360 | 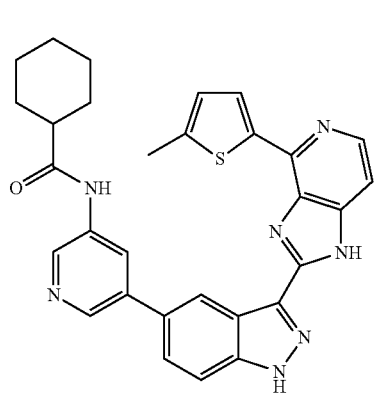 [SMILES: Cc1ccc(-c2nccc3[nH]c(-c4n[nH]c5ccc(-c6cncc(NC(=O)C7CCCCC7)c6)cc45)nc23)s1] |
| 361 | 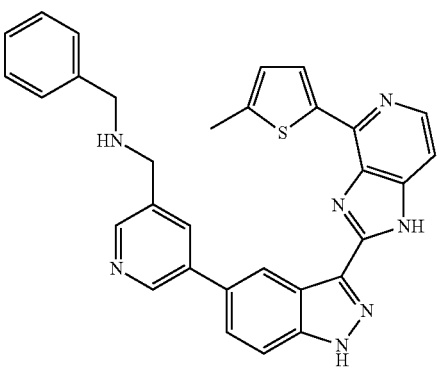 [SMILES: Cc1ccc(-c2nccc3[nH]c(-c4n[nH]c5ccc(-c6cncc(CNCc7ccccc7)c6)cc45)nc23)s1] |

TABLE 1-continued
362
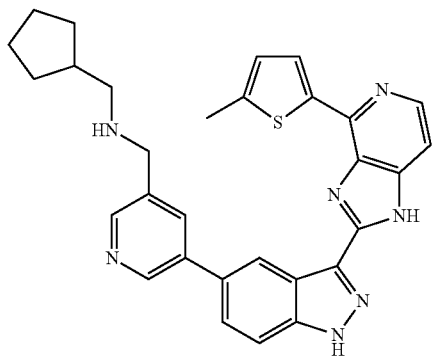 [SMILES: Cc1ccc(-c2nccc3[nH]c(-c4n[nH]c5ccc(-c6cncc(CNCC7CCCC7)c6)cc45)nc23)s1]
363
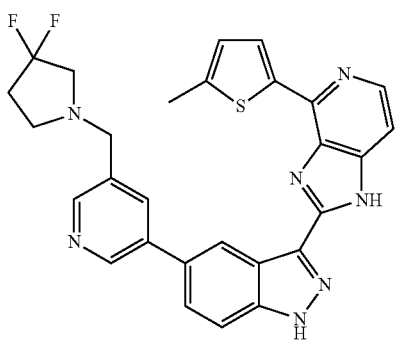 [SMILES: Cc1ccc(-c2nccc3[nH]c(-c4n[nH]c5ccc(-c6cncc(CN7CCC(F)(F)C7)c6)cc45)nc23)s1]
364
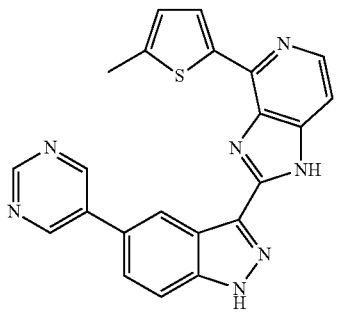
365
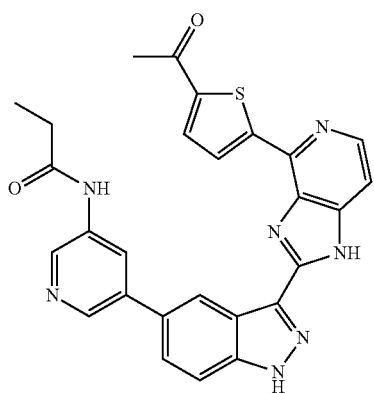 [SMILES: CCC(=O)Nc1cncc(-c2ccc3[nH]nc(-c4nc5c(-c6ccc(C(C)=O)s6)nccc5[nH]4)c3c2)c1]
TABLE 1-continued
366
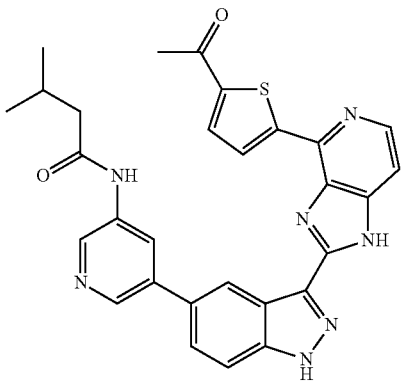 [SMILES: CC(=O)c1ccc(-c2nccc3[nH]c(-c4n[nH]c5ccc(-c6cncc(NC(=O)CC(C)C)c6)cc45)nc23)s1]
367
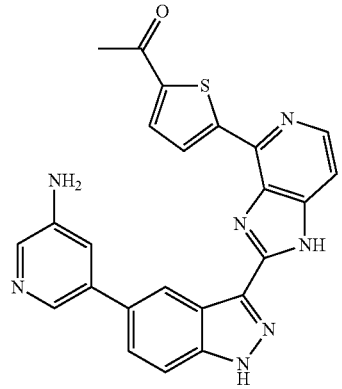 [SMILES: CC(=O)c1ccc(-c2nccc3[nH]c(-c4n[nH]c5ccc(-c6cncc(N)c6)cc45)nc23)s1]
368
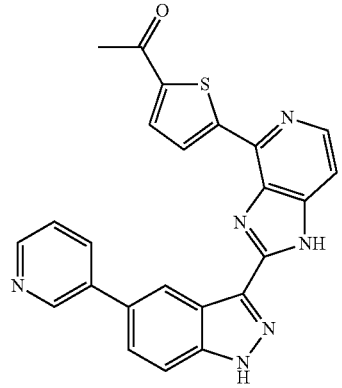 [SMILES: CC(=O)c1ccc(-c2nccc3[nH]c(-c4n[nH]c5ccc(-c6cccnc6)cc45)nc23)s1]
369
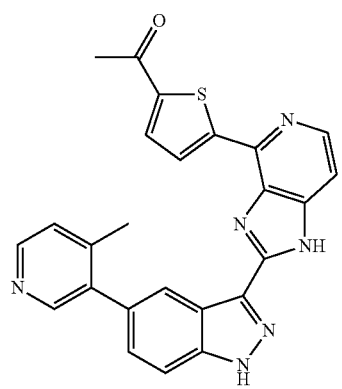 [SMILES: CC(=O)c1ccc(-c2nccc3[nH]c(-c4n[nH]c5ccc(-c6cnccc6C)cc45)nc23)s1]

TABLE 1-continued
| | |
|---|---|
| 370 | 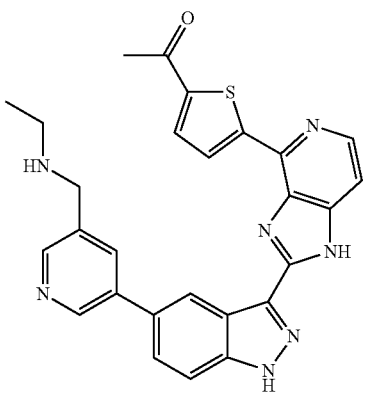 [SMILES: CCNCc1cncc(-c2ccc3[nH]nc(-c4nc5c(-c6ccc(C(C)=O)s6)nccc5[nH]4)c3c2)c1] |
| 371 | 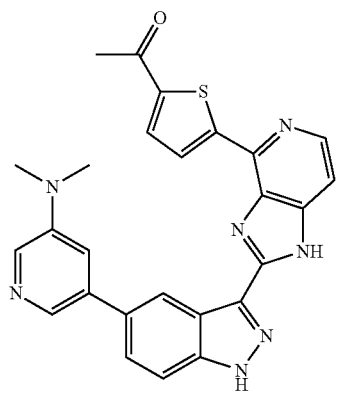 [SMILES: CC(=O)c1ccc(-c2nccc3[nH]c(-c4n[nH]c5ccc(-c6cncc(N(C)C)c6)cc45)nc23)s1] |
| 372 | 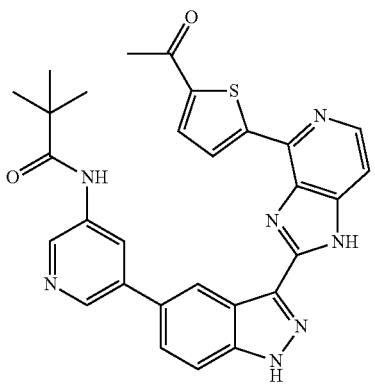 [SMILES: CC(=O)c1ccc(-c2nccc3[nH]c(-c4n[nH]c5ccc(-c6cncc(NC(=O)C(C)(C)C)c6)cc45)nc23)s1] |
| 373 | 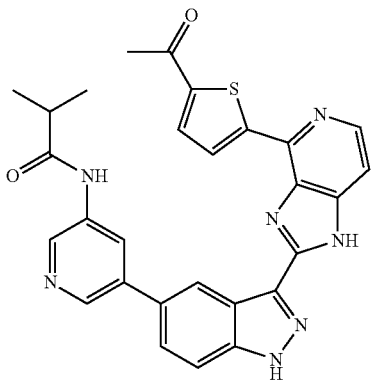 [SMILES: CC(=O)c1ccc(-c2nccc3[nH]c(-c4n[nH]c5ccc(-c6cncc(NC(=O)C(C)C)c6)cc45)nc23)s1] |
| 374 | 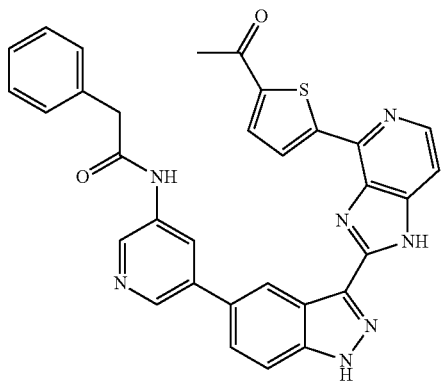 [SMILES: CC(=O)c1ccc(-c2nccc3[nH]c(-c4n[nH]c5ccc(-c6cncc(NC(=O)Cc7ccccc7)c6)cc45)nc23)s1] |
| 375 | 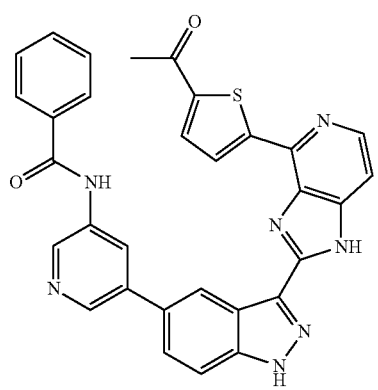 [SMILES: CC(=O)c1ccc(-c2nccc3[nH]c(-c4n[nH]c5ccc(-c6cncc(NC(=O)c7ccccc7)c6)cc45)nc23)s1] |
| 376 | 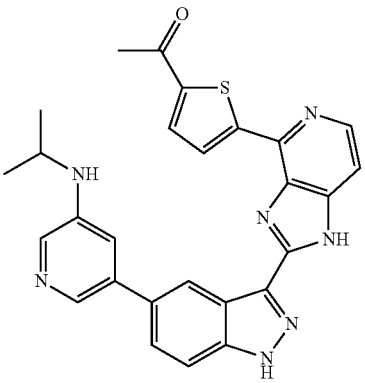 [SMILES: CC(=O)c1ccc(-c2nccc3[nH]c(-c4n[nH]c5ccc(-c6cncc(NC(C)C)c6)cc45)nc23)s1] |
| 377 | 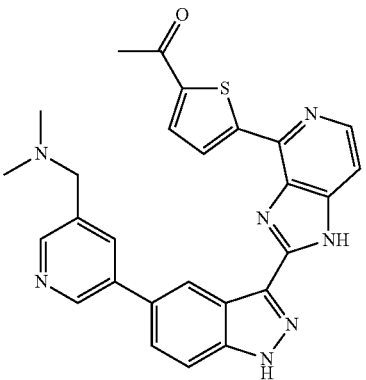 [SMILES: CC(=O)c1ccc(-c2nccc3[nH]c(-c4n[nH]c5ccc(-c6cncc(CN(C)C)c6)cc45)nc23)s1] |

TABLE 1-continued
| 378 | 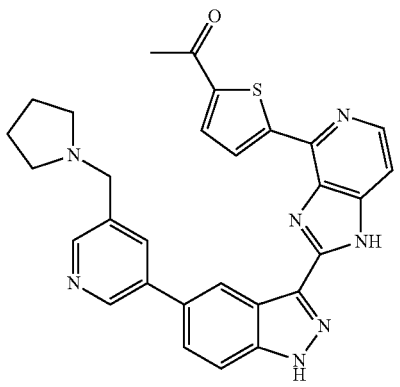 [SMILES: CC(=O)c1ccc(-c2nccc3[nH]c(-c4n[nH]c5ccc(-c6cncc(CN7CCCC7)c6)cc45)nc23)s1] | 382 | 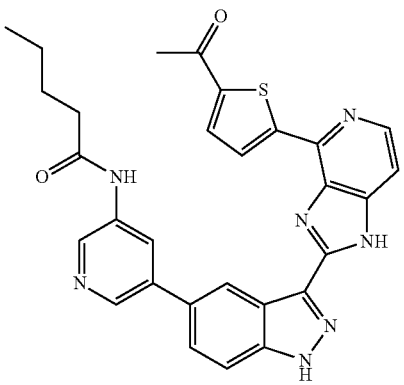 |
| 379 | 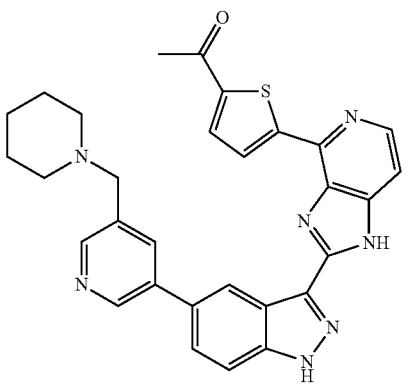 [SMILES: CC(=O)c1ccc(-c2nccc3[nH]c(-c4n[nH]c5ccc(-c6cncc(CN7CCCCC7)c6)cc45)nc23)s1] | 383 | 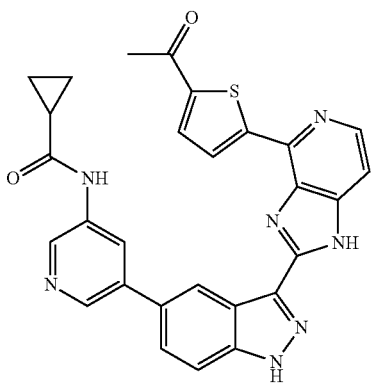 |
| 380 | 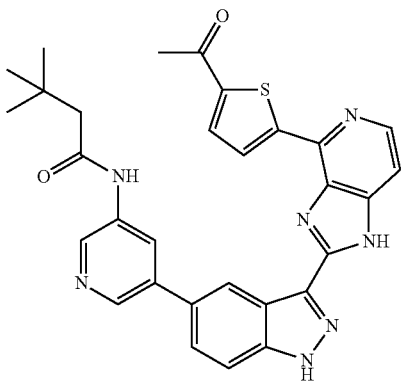 [SMILES: CC(=O)c1ccc(-c2nccc3[nH]c(-c4n[nH]c5ccc(-c6cncc(NC(=O)CC(C)(C)C)c6)cc45)nc23)s1] | 384 | 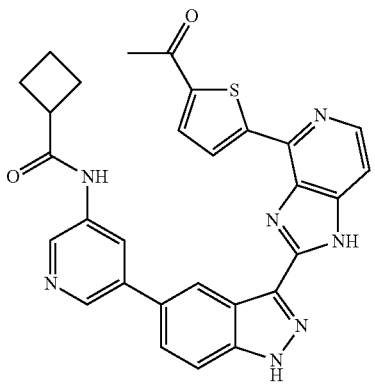 |
| 381 | 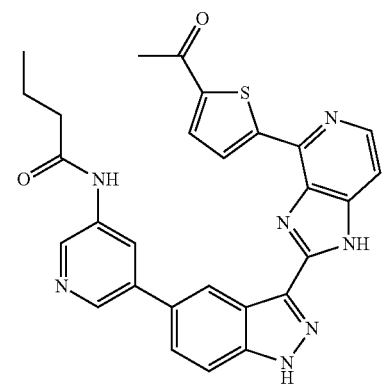 [SMILES: CCCC(=O)Nc1cncc(-c2ccc3[nH]nc(-c4nc5c(-c6ccc(C(C)=O)s6)nccc5[nH]4)c3c2)c1] | 385 | 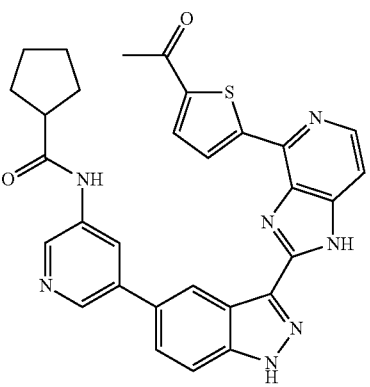 [SMILES: CC(=O)c1ccc(-c2nccc3[nH]c(-c4n[nH]c5ccc(-c6cncc(NC(=O)C7CCCC7)c6)cc45)nc23)s1] |

TABLE 1-continued
| 386 | 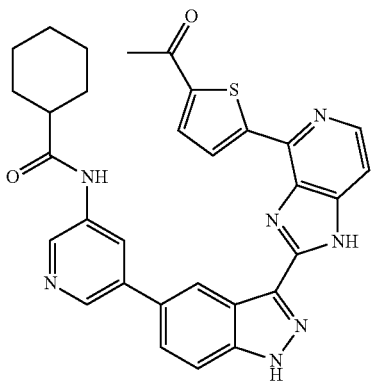 [SMILES: CC(=O)c1ccc(-c2nccc3[nH]c(-c4n[nH]c5ccc(-c6cncc(NC(=O)C7CCCCC7)c6)cc45)nc23)s1] |
| --- | --- |
| 387 | 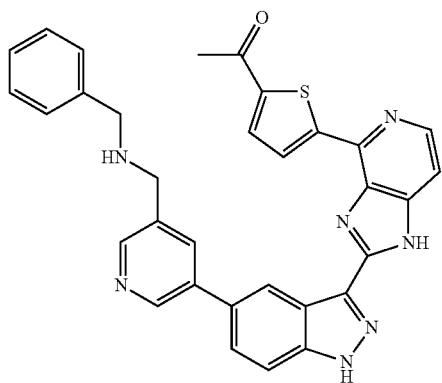 [SMILES: CC(=O)c1ccc(-c2nccc3[nH]c(-c4n[nH]c5ccc(-c6cncc(CNCc7ccccc7)c6)cc45)nc23)s1] |
| 388 | 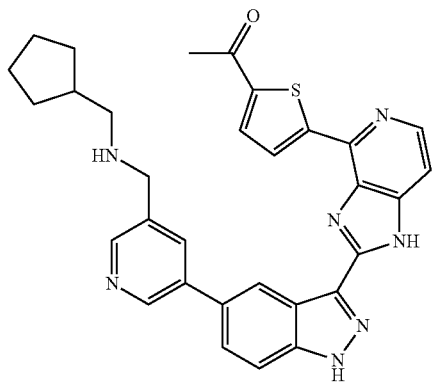 [SMILES: CC(=O)c1ccc(-c2nccc3[nH]c(-c4n[nH]c5ccc(-c6cncc(CNCC7CCCC7)c6)cc45)nc23)s1] |
| 389 | 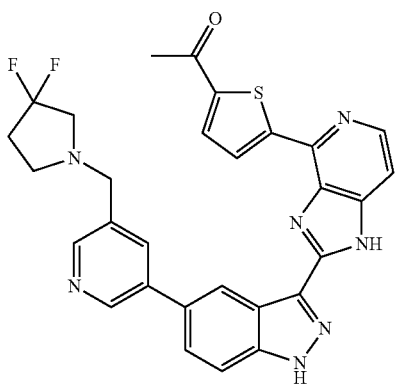 [SMILES: CC(=O)c1ccc(-c2nccc3[nH]c(-c4n[nH]c5ccc(-c6cncc(CN7CCC(F)(F)C7)c6)cc45)nc23)s1] |
TABLE 1-continued
| 390 | 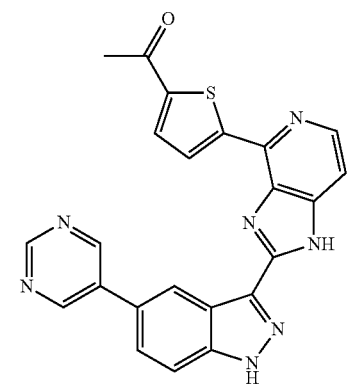 [SMILES: CC(=O)c1ccc(-c2nccc3[nH]c(-c4n[nH]c5ccc(-c6cncnc6)cc45)nc23)s1] |
| --- | --- |
| 391 | 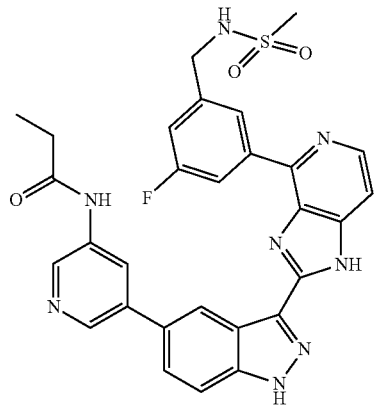 [SMILES: CCC(=O)Nc1cncc(-c2ccc3[nH]nc(-c4nc5c(-c6cc(F)cc(CNS(C)(=O)=O)c6)nccc5[nH]4)c3c2)c1] |
| 392 | 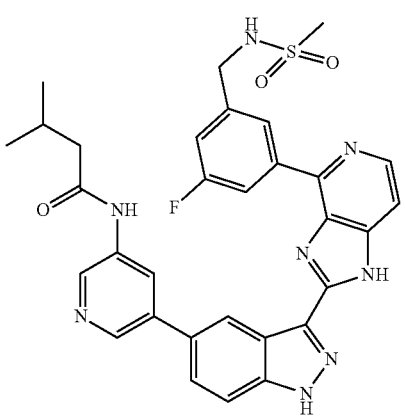 [SMILES: CC(C)CC(=O)Nc1cncc(-c2ccc3[nH]nc(-c4nc5c(-c6cc(F)cc(CNS(C)(=O)=O)c6)nccc5[nH]4)c3c2)c1] |
| 393 | 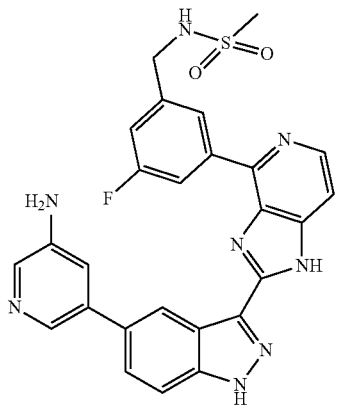 [SMILES: CS(=O)(=O)NCc1cc(F)cc(-c2nccc3[nH]c(-c4n[nH]c5ccc(-c6cncc(N)c6)cc45)nc23)c1] |

TABLE 1-continued
| 394 | 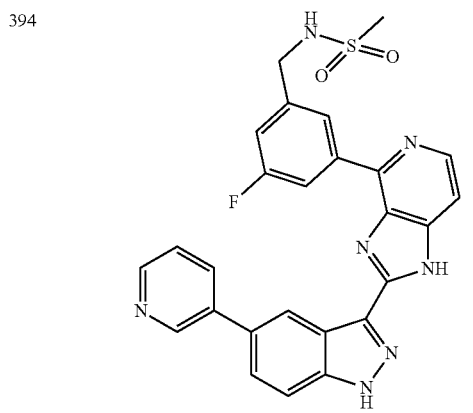 |
| --- | --- |
| 395 | 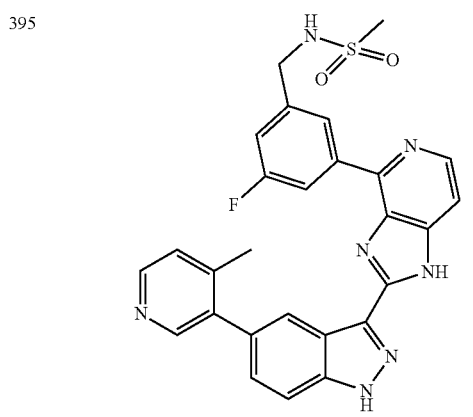 |
| 396 | 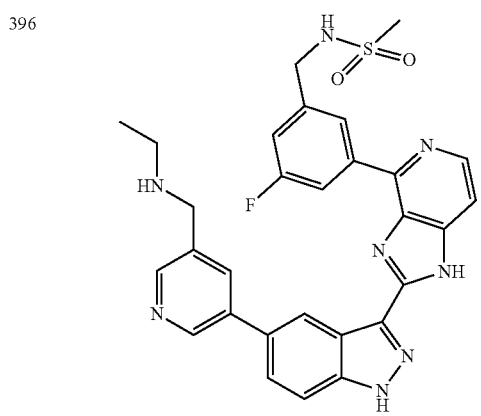 |
| 397 | 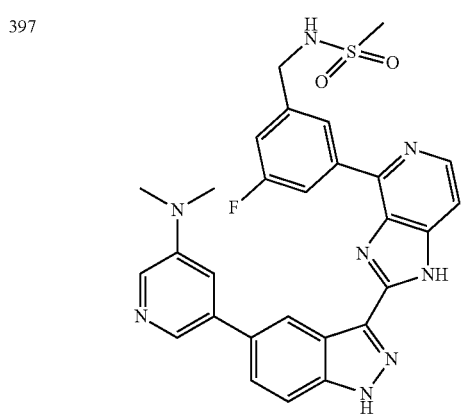 |
TABLE 1-continued
| 398 | 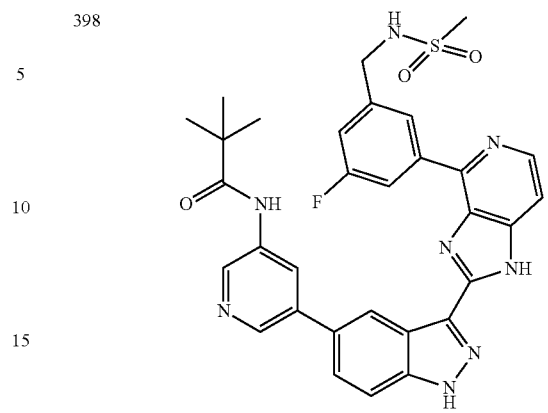 |
| --- | --- |
| 399 | 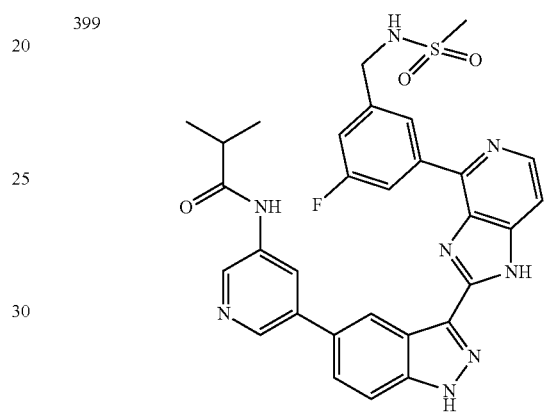 |
| 400 | 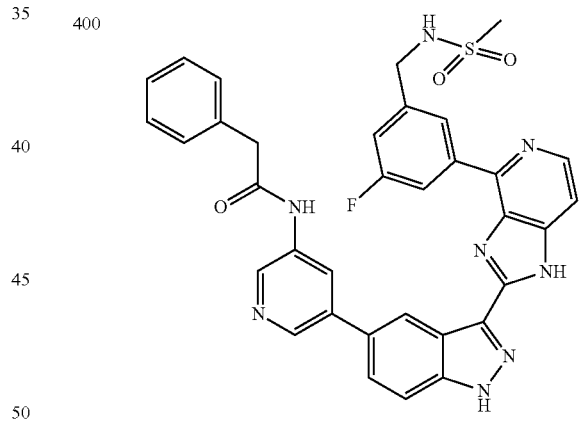 |
| 401 | 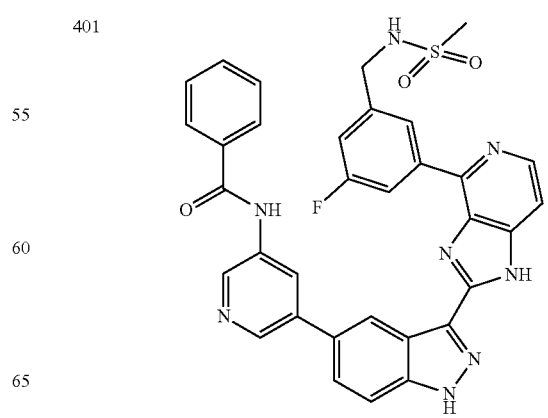 |

TABLE 1-continued
402 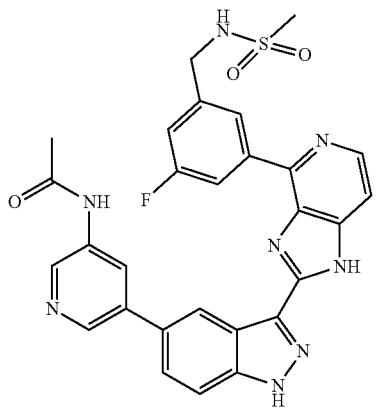 [SMILES: CC(=O)Nc1cncc(-c2ccc3[nH]nc(-c4nc5c(-c6cc(F)cc(CNS(C)(=O)=O)c6)nccc5[nH]4)c3c2)c1]
403 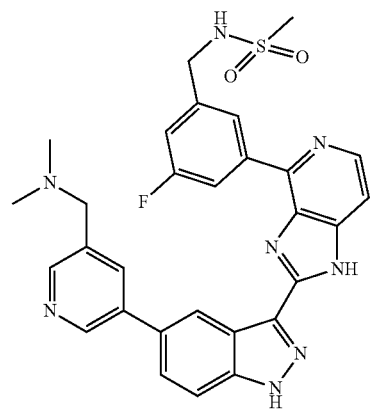 [SMILES: CN(C)Cc1cncc(-c2ccc3[nH]nc(-c4nc5c(-c6cc(F)cc(CNS(C)(=O)=O)c6)nccc5[nH]4)c3c2)c1]
404 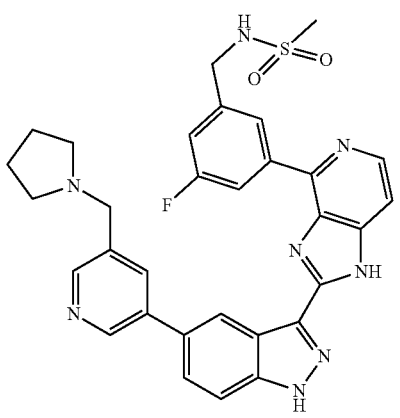 [SMILES: CS(=O)(=O)NCc1cc(F)cc(-c2nccc3[nH]c(-c4n[nH]c5ccc(-c6cncc(CN7CCCC7)c6)cc45)nc23)c1]
405 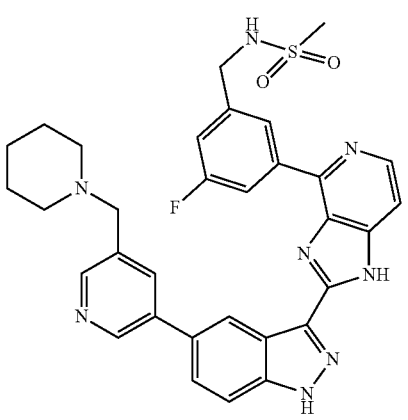 [SMILES: CS(=O)(=O)NCc1cc(F)cc(-c2nccc3[nH]c(-c4n[nH]c5ccc(-c6cncc(CN7CCCCC7)c6)cc45)nc23)c1]
406 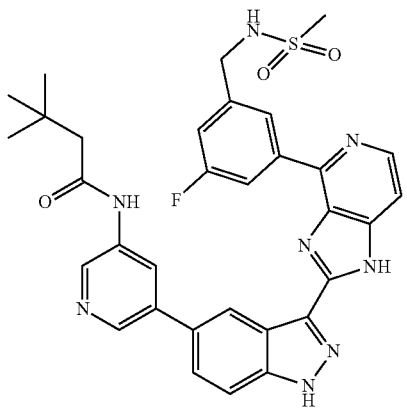 [SMILES: CC(C)(C)CC(=O)Nc1cncc(-c2ccc3[nH]nc(-c4nc5c(-c6cc(F)cc(CNS(C)(=O)=O)c6)nccc5[nH]4)c3c2)c1]
407 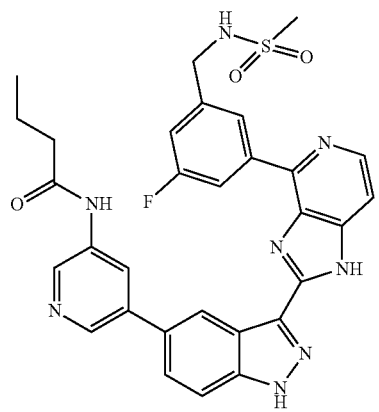 [SMILES: CCCC(=O)Nc1cncc(-c2ccc3[nH]nc(-c4nc5c(-c6cc(F)cc(CNS(C)(=O)=O)c6)nccc5[nH]4)c3c2)c1]
408 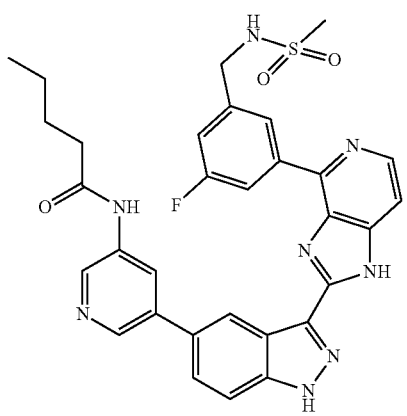 [SMILES: CCCCC(=O)Nc1cncc(-c2ccc3[nH]nc(-c4nc5c(-c6cc(F)cc(CNS(C)(=O)=O)c6)nccc5[nH]4)c3c2)c1]
409 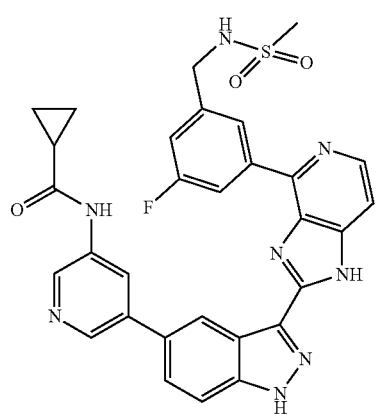 [SMILES: CS(=O)(=O)NCc1cc(F)cc(-c2nccc3[nH]c(-c4n[nH]c5ccc(-c6cncc(NC(=O)C7CC7)c6)cc45)nc23)c1]

TABLE 1-continued
| | |
|---|---|
| 410 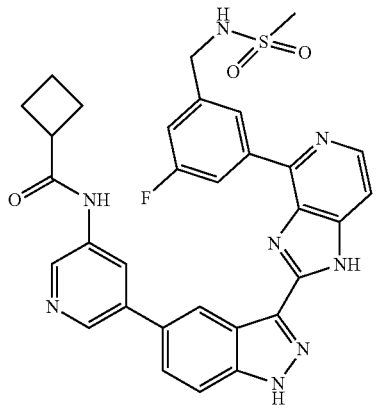 [SMILES: CS(=O)(=O)NCc1cc(F)cc(-c2nccc3[nH]c(-c4n[nH]c5ccc(-c6cncc(NC(=O)C7CCC7)c6)cc45)nc23)c1] | 414 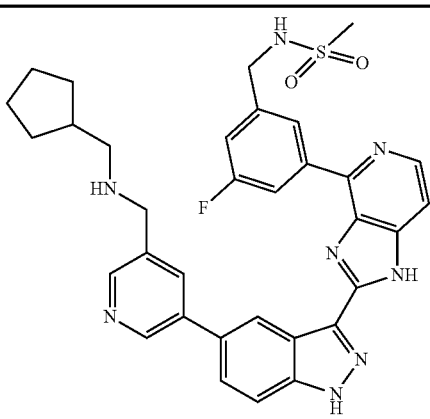 |
| 411 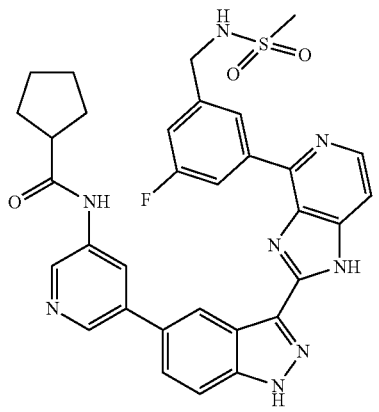 [SMILES: CS(=O)(=O)NCc1cc(F)cc(-c2nccc3[nH]c(-c4n[nH]c5ccc(-c6cncc(NC(=O)C7CCCC7)c6)cc45)nc23)c1] | 415 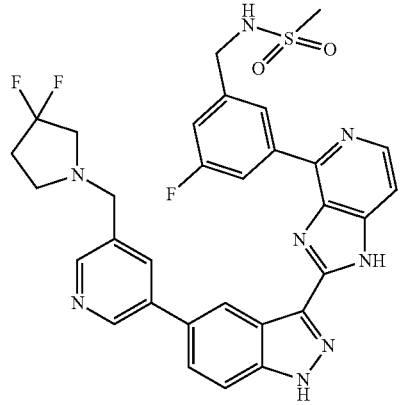 |
| 412 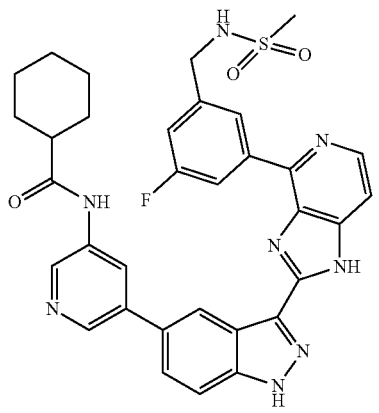 [SMILES: CS(=O)(=O)NCc1cc(F)cc(-c2nccc3[nH]c(-c4n[nH]c5ccc(-c6cncc(NC(=O)C7CCCCC7)c6)cc45)nc23)c1] | 416 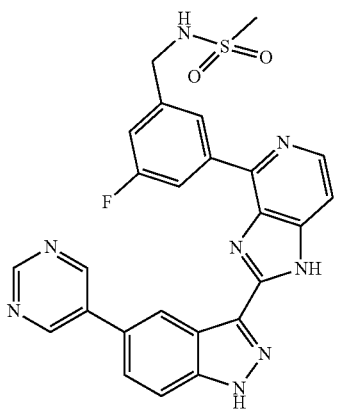 |
| 413 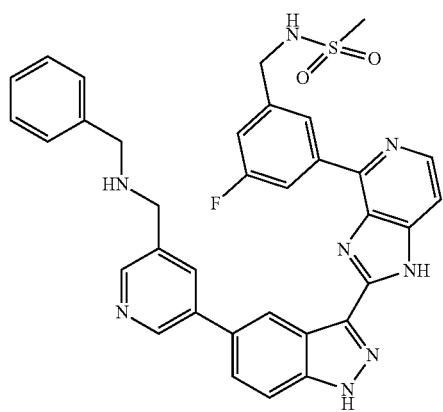 [SMILES: CS(=O)(=O)NCc1cc(F)cc(-c2nccc3[nH]c(-c4n[nH]c5ccc(-c6cncc(CNCc7ccccc7)c6)cc45)nc23)c1] | 417 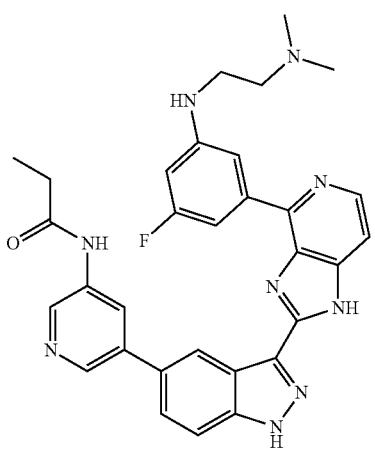 [SMILES: CCC(=O)Nc1cncc(-c2ccc3[nH]nc(-c4nc5c(-c6cc(F)cc(NCCN(C)C)c6)nccc5[nH]4)c3c2)c1] |

TABLE 1-continued
418
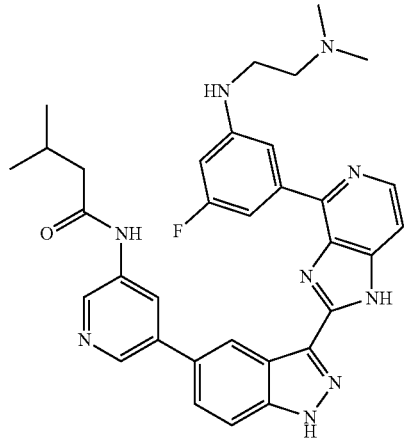 [SMILES: CC(C)CC(=O)Nc1cncc(-c2ccc3[nH]nc(-c4nc5c(-c6cc(F)cc(NCCN(C)C)c6)nccc5[nH]4)c3c2)c1]
419
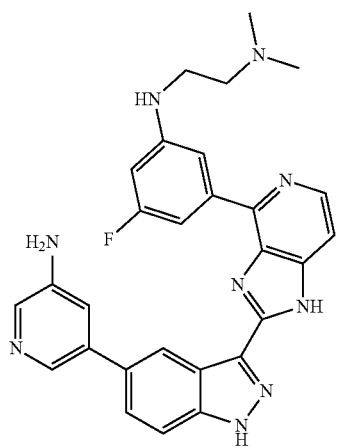 [SMILES: CN(C)CCNc1cc(F)cc(-c2nccc3[nH]c(-c4n[nH]c5ccc(-c6cncc(N)c6)cc45)nc23)c1]
420
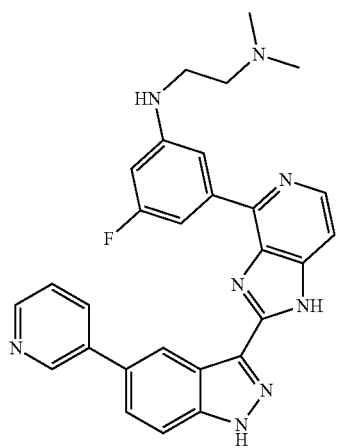
TABLE 1-continued
421
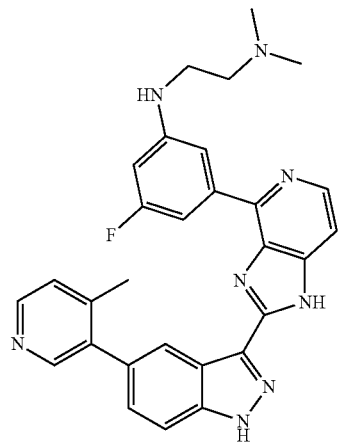 [SMILES: Cc1ccncc1-c1ccc2[nH]nc(-c3nc4c(-c5cc(F)cc(NCCN(C)C)c5)nccc4[nH]3)c2c1]
422
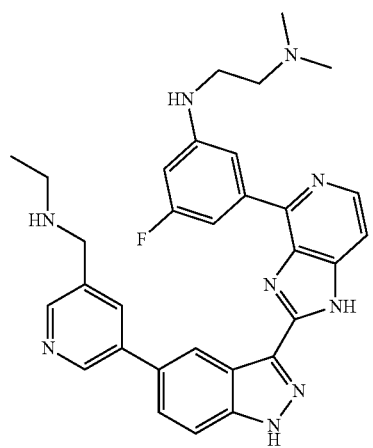 [SMILES: CCNCc1cncc(-c2ccc3[nH]nc(-c4nc5c(-c6cc(F)cc(NCCN(C)C)c6)nccc5[nH]4)c3c2)c1]
423
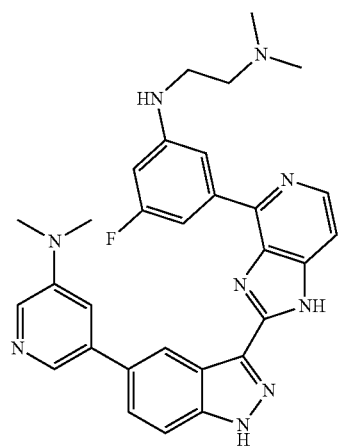 [SMILES: CN(C)CCNc1cc(F)cc(-c2nccc3[nH]c(-c4n[nH]c5ccc(-c6cncc(N(C)C)c6)cc45)nc23)c1]

TABLE 1-continued
424
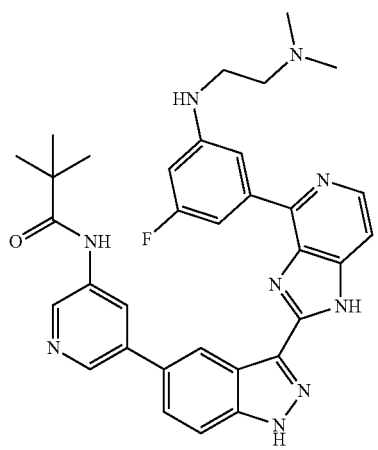 [SMILES: CN(C)CCNc1cc(F)cc(-c2nccc3[nH]c(-c4n[nH]c5ccc(-c6cncc(NC(=O)C(C)(C)C)c6)cc45)nc23)c1]
425
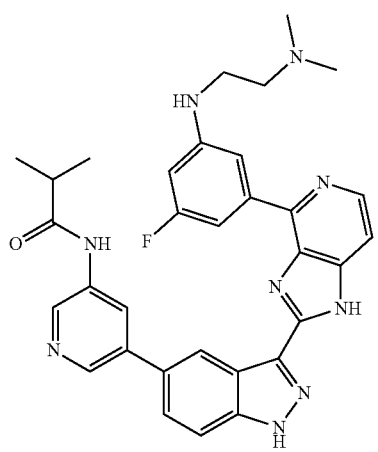 [SMILES: CC(C)C(=O)Nc1cncc(-c2ccc3[nH]nc(-c4nc5c(-c6cc(F)cc(NCCN(C)C)c6)nccc5[nH]4)c3c2)c1]
426
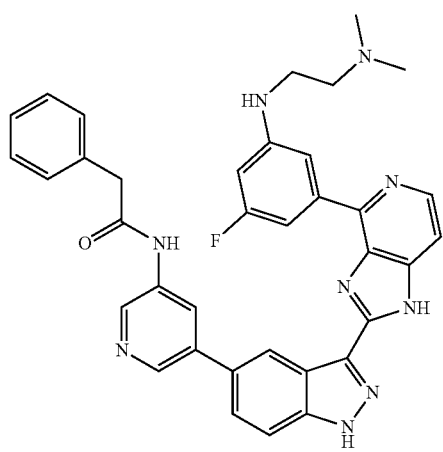 [SMILES: CN(C)CCNc1cc(F)cc(-c2nccc3[nH]c(-c4n[nH]c5ccc(-c6cncc(NC(=O)Cc7ccccc7)c6)cc45)nc23)c1]
TABLE 1-continued
427
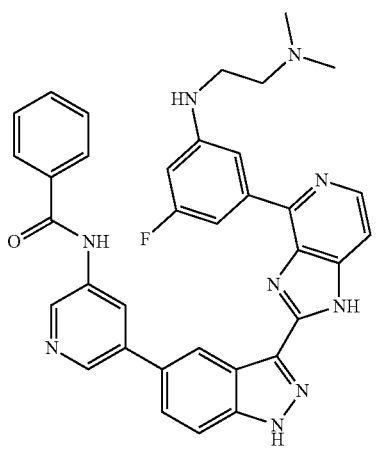 [SMILES: CN(C)CCNc1cc(F)cc(-c2nccc3[nH]c(-c4n[nH]c5ccc(-c6cncc(NC(=O)c7ccccc7)c6)cc45)nc23)c1]
428
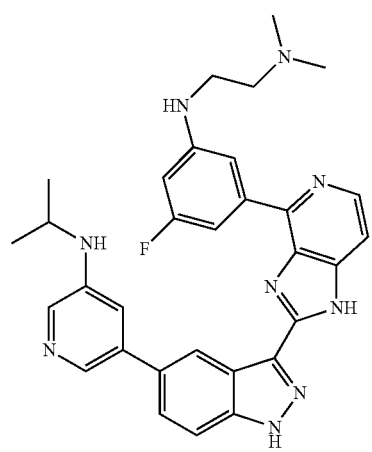 [SMILES: CC(C)Nc1cncc(-c2ccc3[nH]nc(-c4nc5c(-c6cc(F)cc(NCCN(C)C)c6)nccc5[nH]4)c3c2)c1]
429
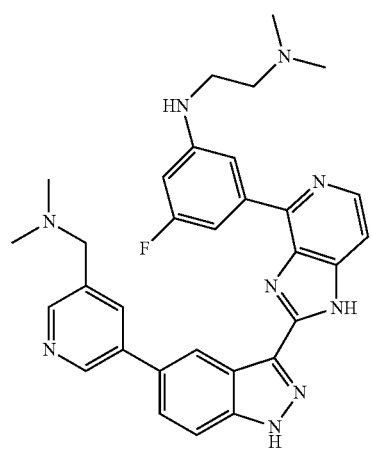 [SMILES: CN(C)CCNc1cc(F)cc(-c2nccc3[nH]c(-c4n[nH]c5ccc(-c6cncc(CN(C)C)c6)cc45)nc23)c1]

TABLE 1-continued
430
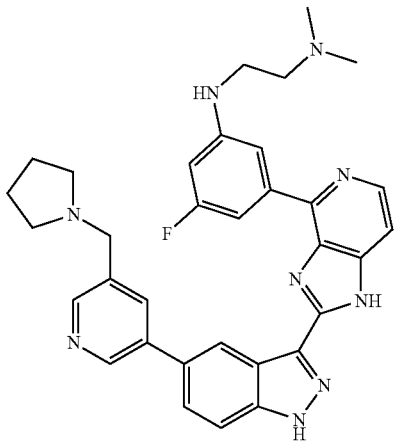 [SMILES: CN(C)CCNc1cc(F)cc(-c2nccc3[nH]c(-c4n[nH]c5ccc(-c6cncc(CN7CCCC7)c6)cc45)nc23)c1]
431
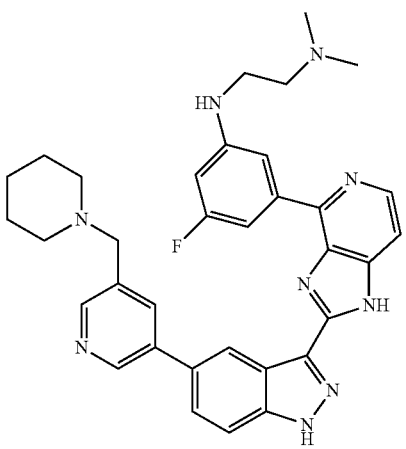 [SMILES: CN(C)CCNc1cc(F)cc(-c2nccc3[nH]c(-c4n[nH]c5ccc(-c6cncc(CN7CCCCC7)c6)cc45)nc23)c1]
432
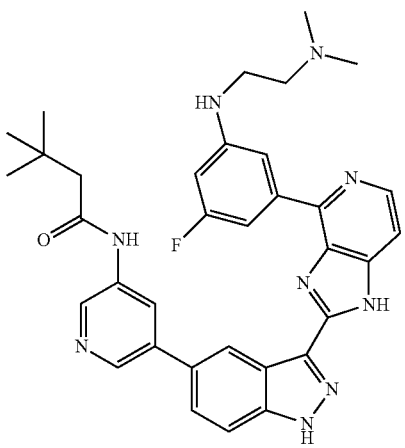 [SMILES: CN(C)CCNc1cc(F)cc(-c2nccc3[nH]c(-c4n[nH]c5ccc(-c6cncc(NC(=O)CC(C)(C)C)c6)cc45)nc23)c1]
433
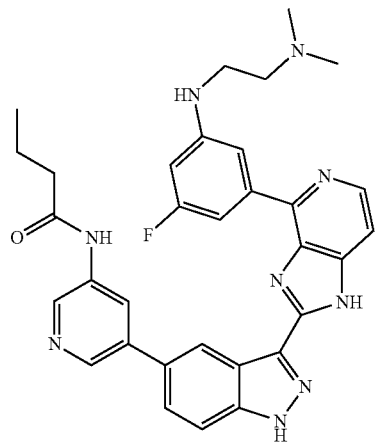 [SMILES: CCCC(=O)Nc1cncc(-c2ccc3[nH]nc(-c4nc5c(-c6cc(F)cc(NCCN(C)C)c6)nccc5[nH]4)c3c2)c1]
434
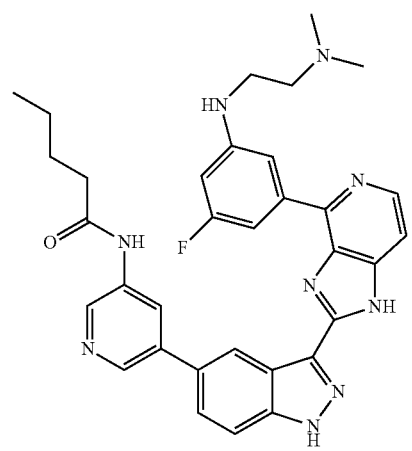 [SMILES: CCCCC(=O)Nc1cncc(-c2ccc3[nH]nc(-c4nc5c(-c6cc(F)cc(NCCN(C)C)c6)nccc5[nH]4)c3c2)c1]
435
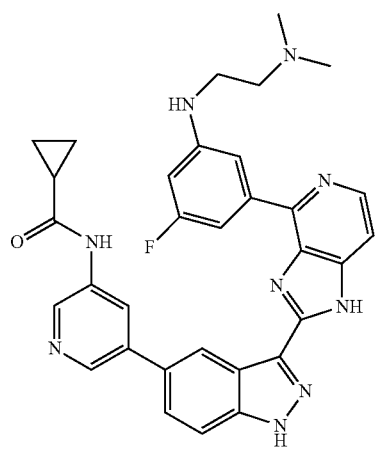 [SMILES: CN(C)CCNc1cc(F)cc(-c2nccc3[nH]c(-c4n[nH]c5ccc(-c6cncc(NC(=O)C7CC7)c6)cc45)nc23)c1]

TABLE 1-continued
436
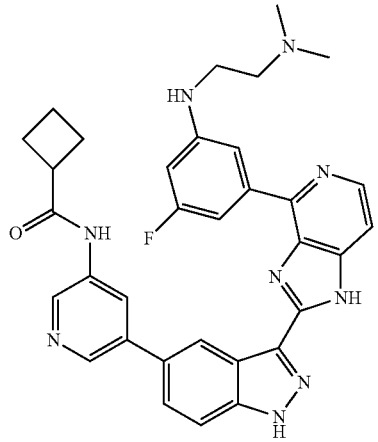 [SMILES: CN(C)CCNc1cc(F)cc(-c2nccc3[nH]c(-c4n[nH]c5ccc(-c6cncc(NC(=O)C7CCC7)c6)cc45)nc23)c1]
437
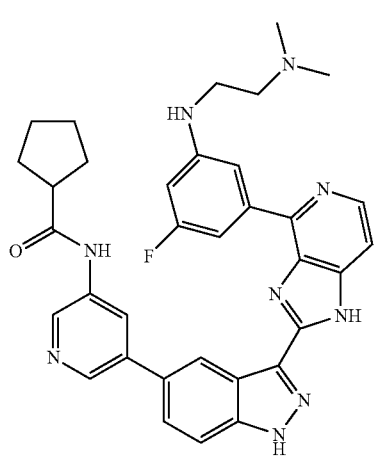 [SMILES: CN(C)CCNc1cc(F)cc(-c2nccc3[nH]c(-c4n[nH]c5ccc(-c6cncc(NC(=O)C7CCCC7)c6)cc45)nc23)c1]
438
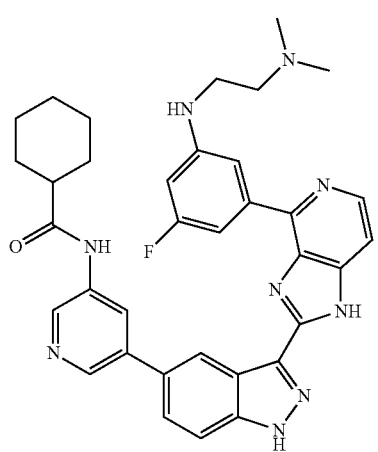 [SMILES: CN(C)CCNc1cc(F)cc(-c2nccc3[nH]c(-c4n[nH]c5ccc(-c6cncc(NC(=O)C7CCCCC7)c6)cc45)nc23)c1]
TABLE 1-continued
439
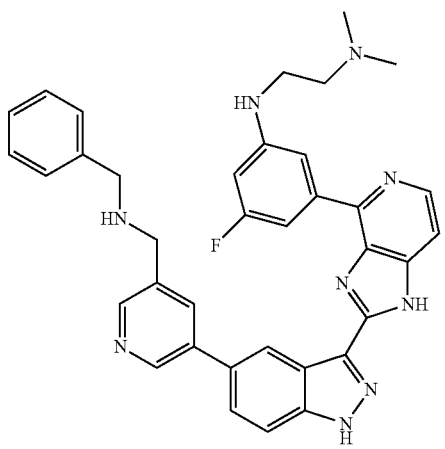 [SMILES: CN(C)CCNc1cc(F)cc(-c2nccc3[nH]c(-c4n[nH]c5ccc(-c6cncc(CNCc7ccccc7)c6)cc45)nc23)c1]
440
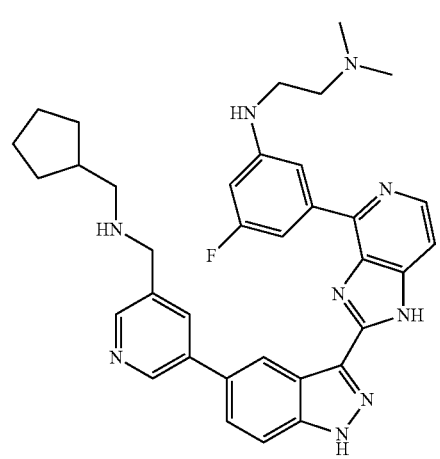 [SMILES: CN(C)CCNc1cc(F)cc(-c2nccc3[nH]c(-c4n[nH]c5ccc(-c6cncc(CNCC7CCCC7)c6)cc45)nc23)c1]
441
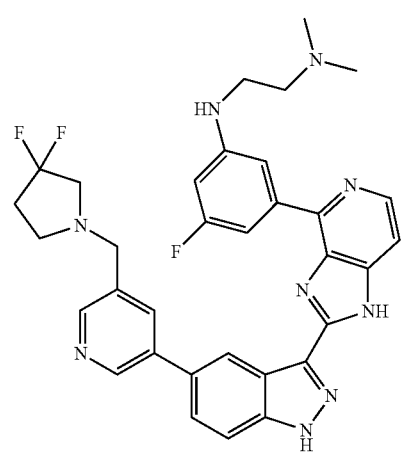 [SMILES: CN(C)CCNc1cc(F)cc(-c2nccc3[nH]c(-c4n[nH]c5ccc(-c6cncc(CN7CCC(F)(F)C7)c6)cc45)nc23)c1]

TABLE 1-continued
442 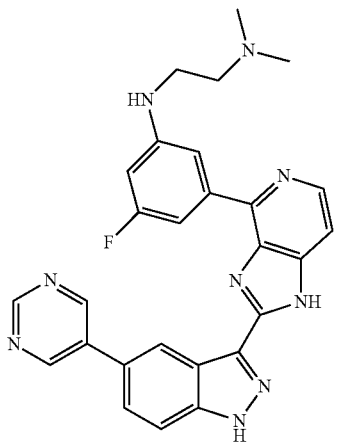 [SMILES: CN(C)CCNc1cc(F)cc(-c2nccc3[nH]c(-c4n[nH]c5ccc(-c6cncnc6)cc45)nc23)c1]
443 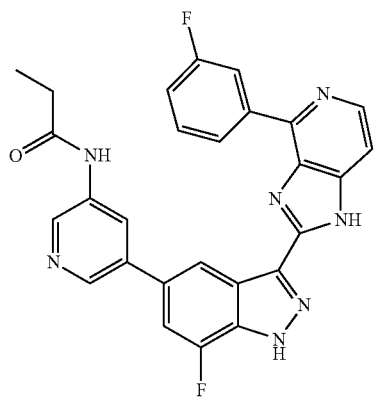 [SMILES: CCC(=O)Nc1cncc(-c2cc(F)c3[nH]nc(-c4nc5c(-c6cccc(F)c6)nccc5[nH]4)c3c2)c1]
444 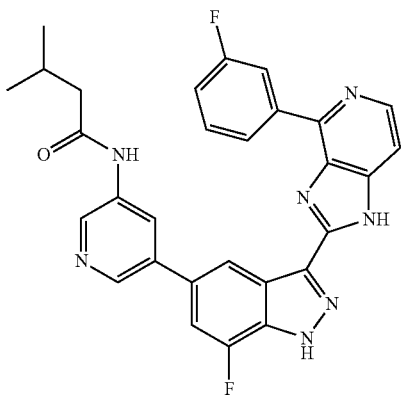
445 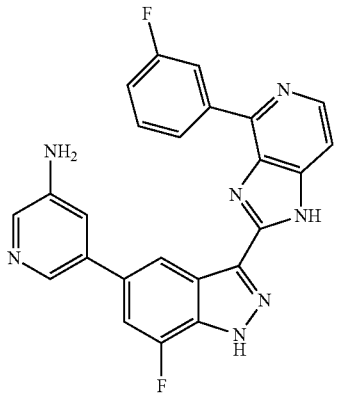 [SMILES: Nc1cncc(-c2cc(F)c3[nH]nc(-c4nc5c(-c6cccc(F)c6)nccc5[nH]4)c3c2)c1]
TABLE 1-continued
446 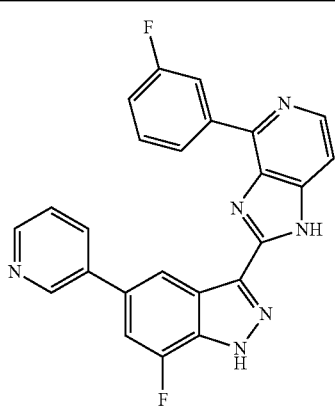
447 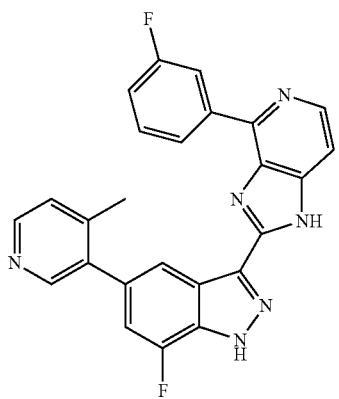 [SMILES: Cc1ccncc1-c1cc(F)c2[nH]nc(-c3nc4c(-c5cccc(F)c5)nccc4[nH]3)c2c1]
448 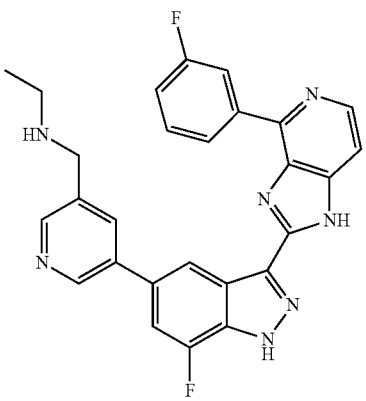 [SMILES: CCNCc1cncc(-c2cc(F)c3[nH]nc(-c4nc5c(-c6cccc(F)c6)nccc5[nH]4)c3c2)c1]
449 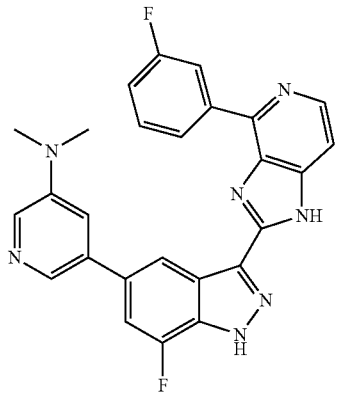 [SMILES: CN(C)c1cncc(-c2cc(F)c3[nH]nc(-c4nc5c(-c6cccc(F)c6)nccc5[nH]4)c3c2)c1]

TABLE 1-continued
| 450 | 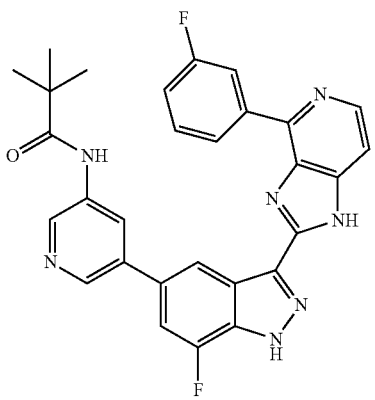 [SMILES: CC(C)(C)C(=O)Nc1cncc(-c2cc(F)c3[nH]nc(-c4nc5c(-c6cccc(F)c6)nccc5[nH]4)c3c2)c1] |
| --- | --- |
| 451 | 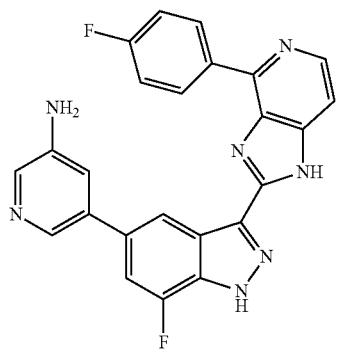 [SMILES: Nc1cncc(-c2cc(F)c3[nH]nc(-c4nc5c(-c6ccc(F)cc6)nccc5[nH]4)c3c2)c1] |
| 452 | 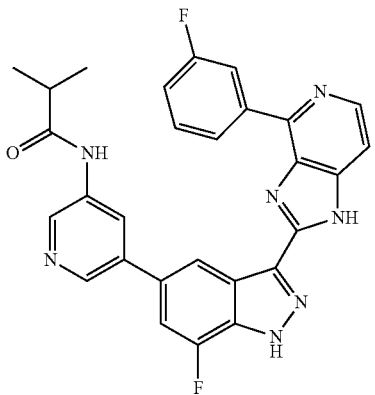 [SMILES: CC(C)C(=O)Nc1cncc(-c2cc(F)c3[nH]nc(-c4nc5c(-c6cccc(F)c6)nccc5[nH]4)c3c2)c1] |
| 453 | 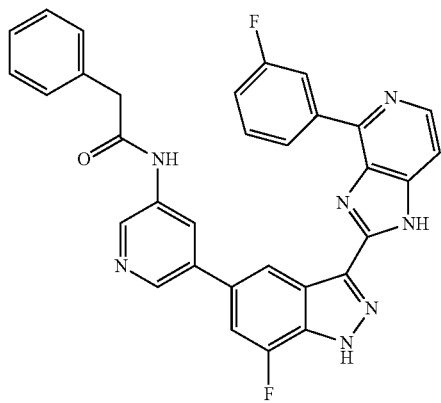 [SMILES: O=C(Cc1ccccc1)Nc1cncc(-c2cc(F)c3[nH]nc(-c4nc5c(-c6cccc(F)c6)nccc5[nH]4)c3c2)c1] |
TABLE 1-continued
| 454 | 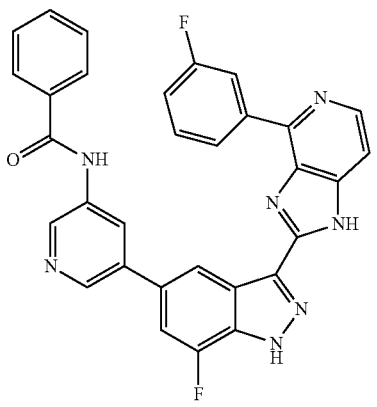 [SMILES: O=C(Nc1cncc(-c2cc(F)c3[nH]nc(-c4nc5c(-c6cccc(F)c6)nccc5[nH]4)c3c2)c1)c1ccccc1] |
| --- | --- |
| 455 | 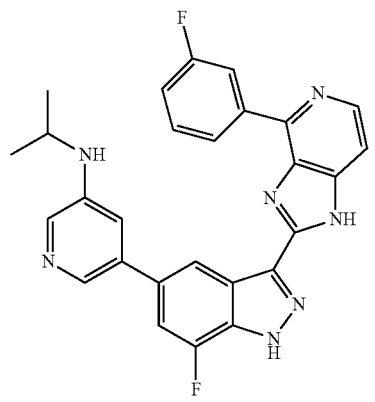 |
| 456 | 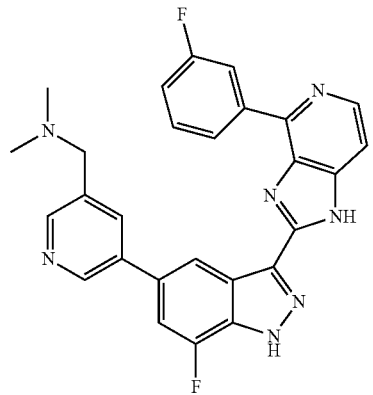 [SMILES: CN(C)Cc1cncc(-c2cc(F)c3[nH]nc(-c4nc5c(-c6cccc(F)c6)nccc5[nH]4)c3c2)c1] |
| 457 | 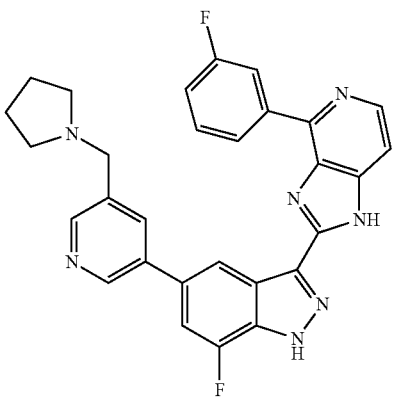 [SMILES: Fc1cccc(-c2nccc3[nH]c(-c4n[nH]c5c(F)cc(-c6cncc(CN7CCCC7)c6)cc45)nc23)c1] |

TABLE 1-continued
| 458 | 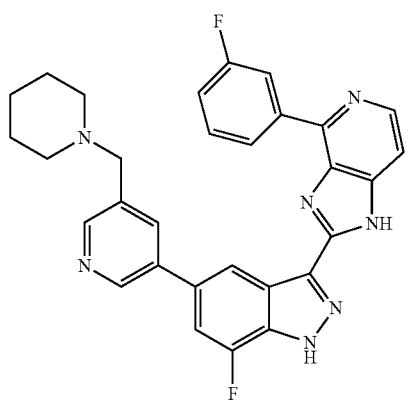 [SMILES: Fc1cccc(-c2nccc3[nH]c(-c4n[nH]c5c(F)cc(-c6cncc(CN7CCCCC7)c6)cc45)nc23)c1] | 462 | 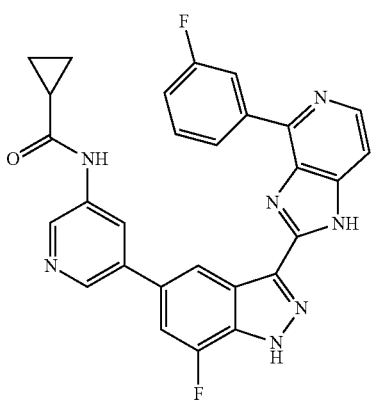 |
| 459 | 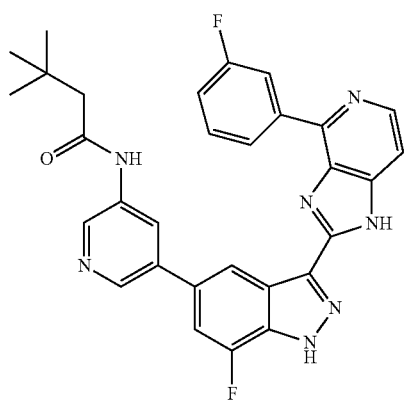 [SMILES: CC(C)(C)CC(=O)Nc1cncc(-c2cc(F)c3[nH]nc(-c4nc5c(-c6cccc(F)c6)nccc5[nH]4)c3c2)c1] | 463 | 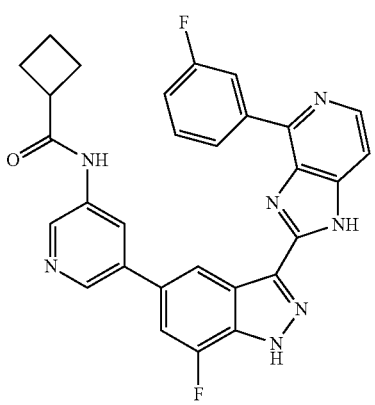 |
| 460 | 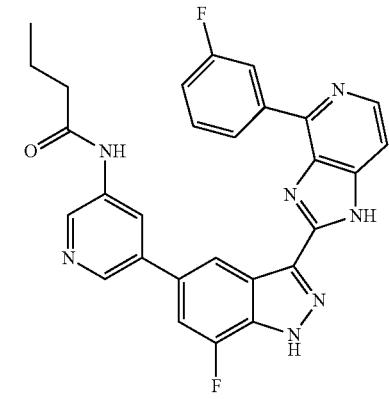 [SMILES: CCCC(=O)Nc1cncc(-c2cc(F)c3[nH]nc(-c4nc5c(-c6cccc(F)c6)nccc5[nH]4)c3c2)c1] | 464 | 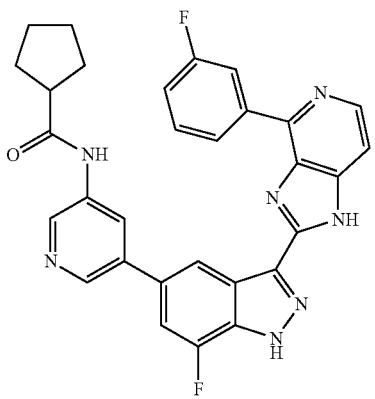 |
| 461 | 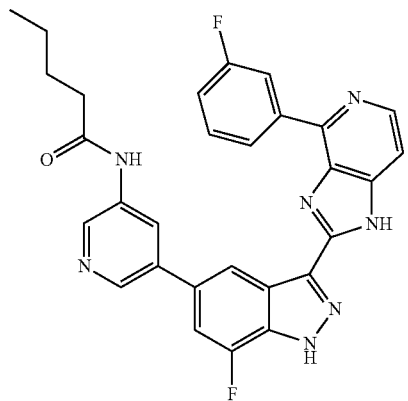 [SMILES: CCCCC(=O)Nc1cncc(-c2cc(F)c3[nH]nc(-c4nc5c(-c6cccc(F)c6)nccc5[nH]4)c3c2)c1] | 465 | 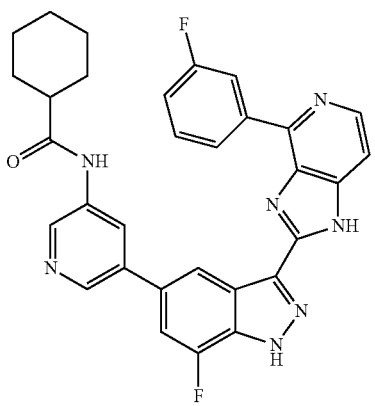 [SMILES: O=C(Nc1cncc(-c2cc(F)c3[nH]nc(-c4nc5c(-c6cccc(F)c6)nccc5[nH]4)c3c2)c1)C1CCCCC1] |

TABLE 1-continued
| | | | | |
|---|---|---|---|---|
| 466 | 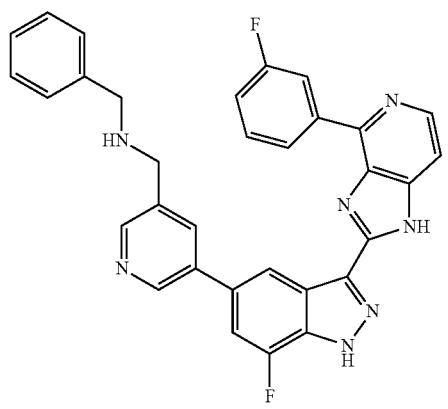 [SMILES: Fc1cccc(-c2nccc3[nH]c(-c4n[nH]c5c(F)cc(-c6cncc(CNCc7ccccc7)c6)cc45)nc23)c1] | | 470 | 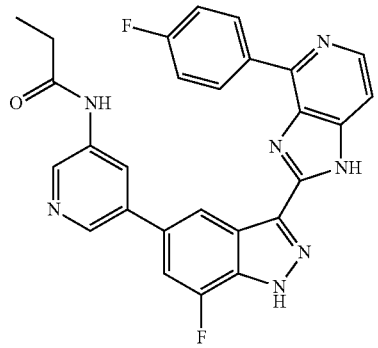 |
| 467 | 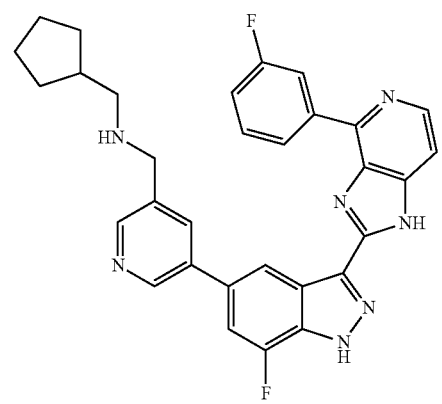 [SMILES: Fc1cccc(-c2nccc3[nH]c(-c4n[nH]c5c(F)cc(-c6cncc(CNCC7CCCC7)c6)cc45)nc23)c1] | | 471 | 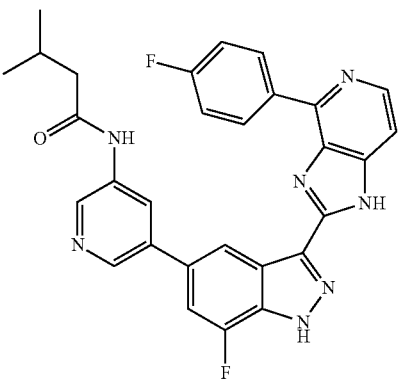 |
| 468 | 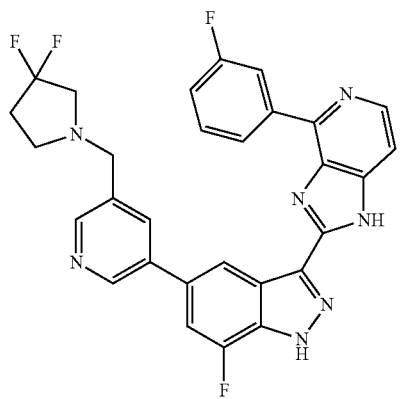 [SMILES: Fc1cccc(-c2nccc3[nH]c(-c4n[nH]c5c(F)cc(-c6cncc(CN7CCC(F)(F)C7)c6)cc45)nc23)c1] | | 472 | 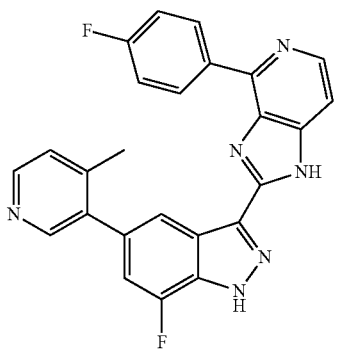 |
| 469 | 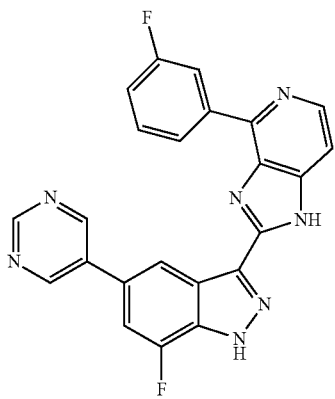 [SMILES: Fc1cccc(-c2nccc3[nH]c(-c4n[nH]c5c(F)cc(-c6cncnc6)cc45)nc23)c1] | | 473 | 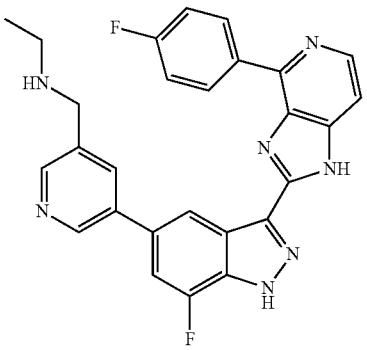 [SMILES: CCNCc1cncc(-c2cc(F)c3[nH]nc(-c4nc5c(-c6ccc(F)cc6)nccc5[nH]4)c3c2)c1] |

TABLE 1-continued
| | |
|---|---|
| 474 | 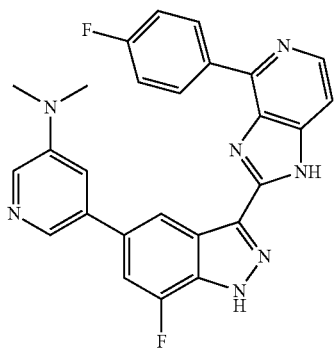 [SMILES: CN(C)c1cncc(-c2cc(F)c3[nH]nc(-c4nc5c(-c6ccc(F)cc6)nccc5[nH]4)c3c2)c1] |
| 475 | 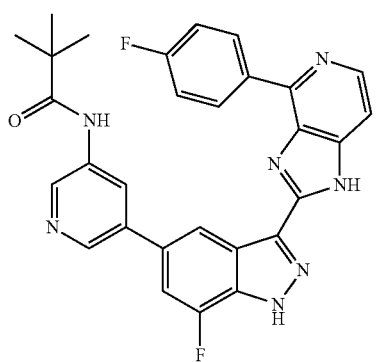 [SMILES: CC(C)(C)C(=O)Nc1cncc(-c2cc(F)c3[nH]nc(-c4nc5c(-c6ccc(F)cc6)nccc5[nH]4)c3c2)c1] |
| 476 | 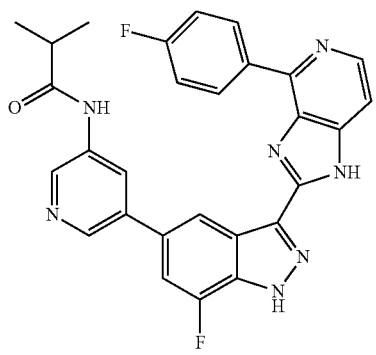 [SMILES: CC(C)C(=O)Nc1cncc(-c2cc(F)c3[nH]nc(-c4nc5c(-c6ccc(F)cc6)nccc5[nH]4)c3c2)c1] |
| 477 | 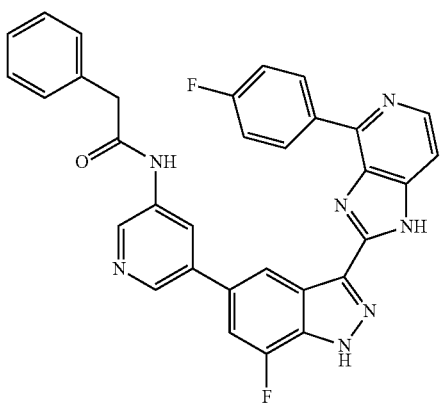 [SMILES: O=C(Cc1ccccc1)Nc1cncc(-c2cc(F)c3[nH]nc(-c4nc5c(-c6ccc(F)cc6)nccc5[nH]4)c3c2)c1] |
| 478 | 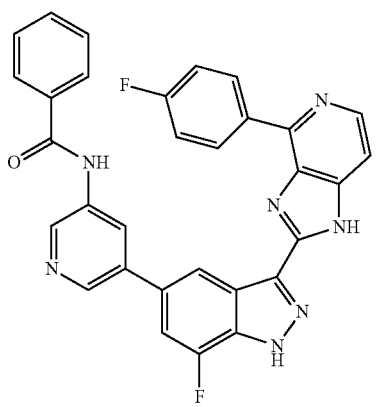 [SMILES: O=C(Nc1cncc(-c2cc(F)c3[nH]nc(-c4nc5c(-c6ccc(F)cc6)nccc5[nH]4)c3c2)c1)c1ccccc1] |
| 479 | 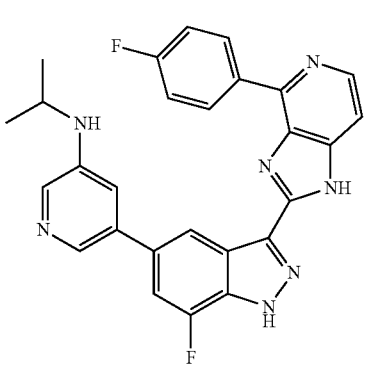 |
| 480 | 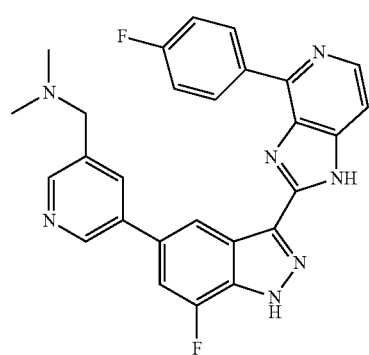 [SMILES: CN(C)Cc1cncc(-c2cc(F)c3[nH]nc(-c4nc5c(-c6ccc(F)cc6)nccc5[nH]4)c3c2)c1] |
| 481 | 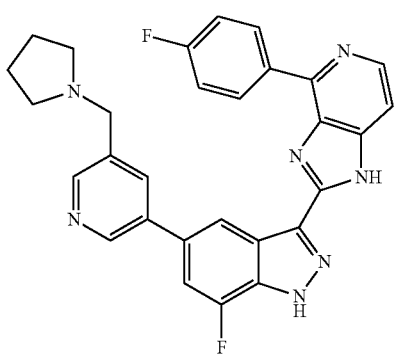 [SMILES: Fc1ccc(-c2nccc3[nH]c(-c4n[nH]c5c(F)cc(-c6cncc(CN7CCCC7)c6)cc45)nc23)cc1] |

TABLE 1-continued
482 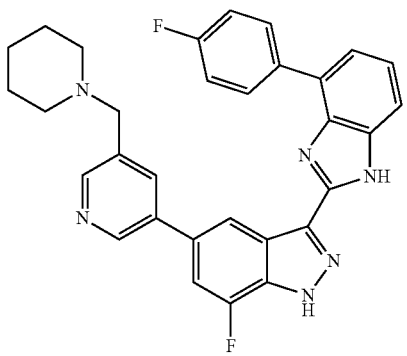 [SMILES: Fc1ccc(-c2cccc3[nH]c(-c4n[nH]c5c(F)cc(-c6cncc(CN7CCCCC7)c6)cc45)nc23)cc1]
483 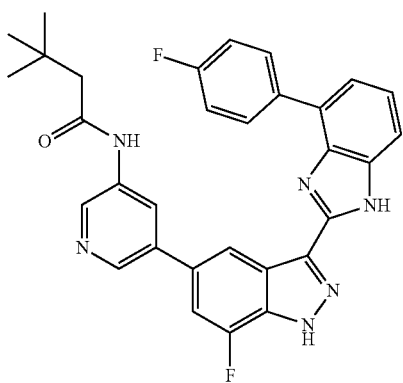 [SMILES: CC(C)(C)CC(=O)Nc1cncc(-c2cc(F)c3[nH]nc(-c4nc5c(-c6ccc(F)cc6)cccc5[nH]4)c3c2)c1]
484 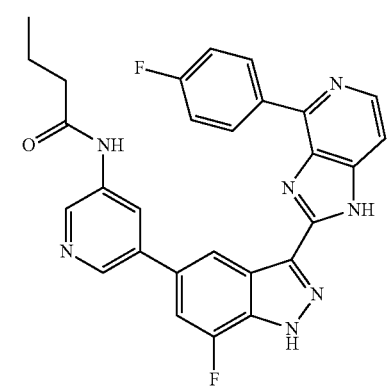 [SMILES: CCCC(=O)Nc1cncc(-c2cc(F)c3[nH]nc(-c4nc5c(-c6ccc(F)cc6)nccc5[nH]4)c3c2)c1]
485 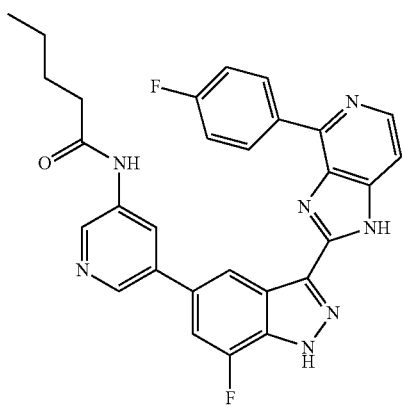
486 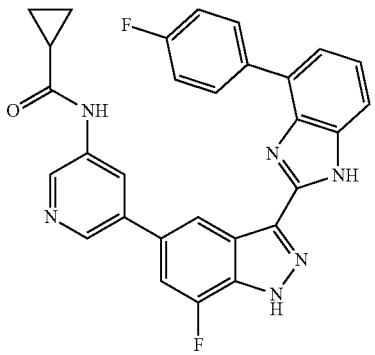 [SMILES: O=C(Nc1cncc(-c2cc(F)c3[nH]nc(-c4nc5c(-c6ccc(F)cc6)cccc5[nH]4)c3c2)c1)C1CC1]
487 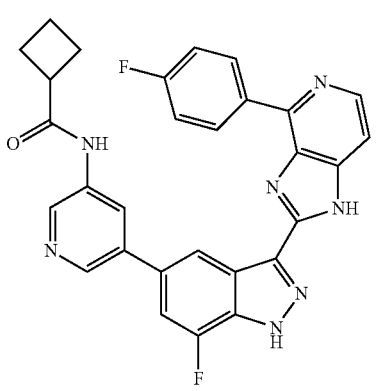 [SMILES: O=C(Nc1cncc(-c2cc(F)c3[nH]nc(-c4nc5c(-c6ccc(F)cc6)nccc5[nH]4)c3c2)c1)C1CCC1]
488 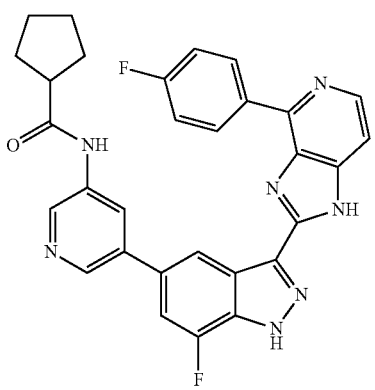 [SMILES: O=C(Nc1cncc(-c2cc(F)c3[nH]nc(-c4nc5c(-c6ccc(F)cc6)nccc5[nH]4)c3c2)c1)C1CCCC1]
489 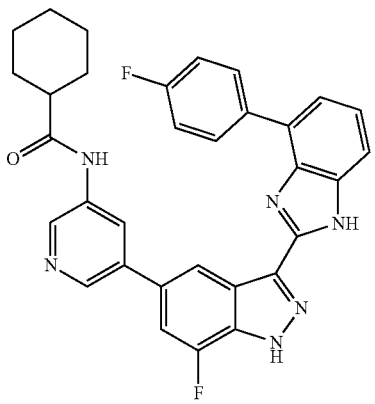 [SMILES: O=C(Nc1cncc(-c2cc(F)c3[nH]nc(-c4nc5c(-c6ccc(F)cc6)cccc5[nH]4)c3c2)c1)C1CCCCC1]

TABLE 1-continued
490 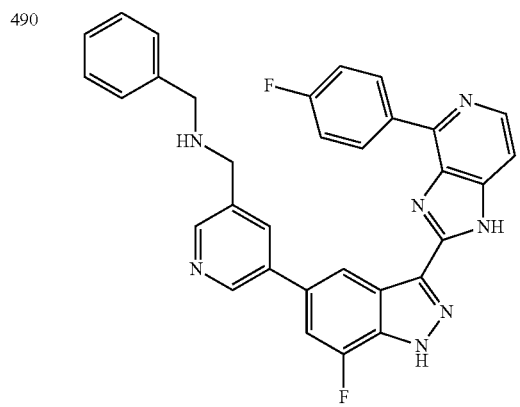
491 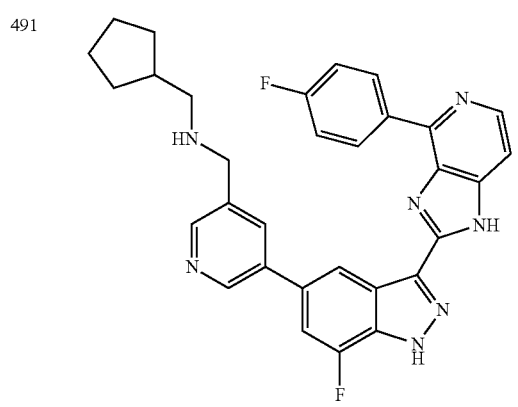
492 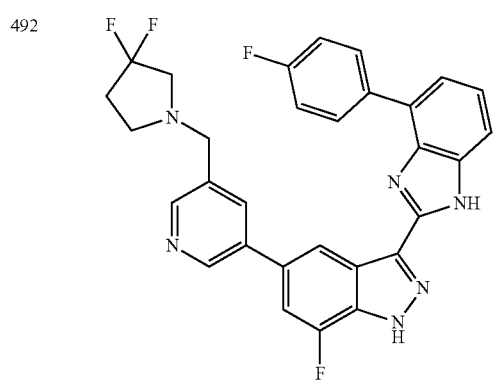
493 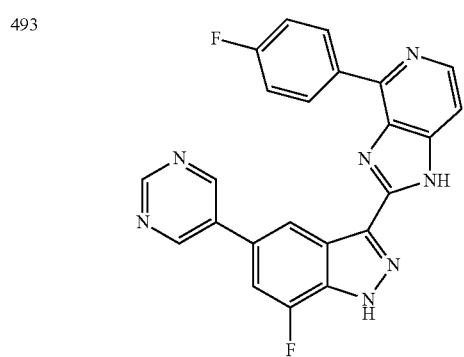
TABLE 1-continued
494 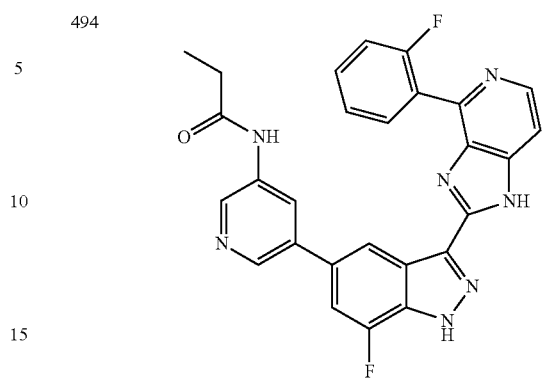
495 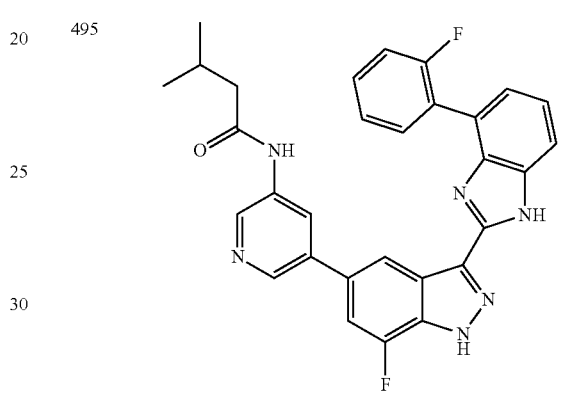
496 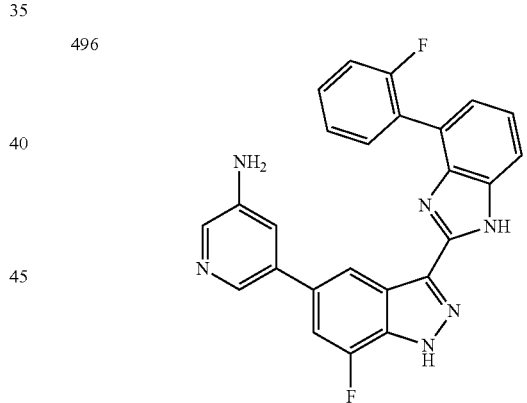
497 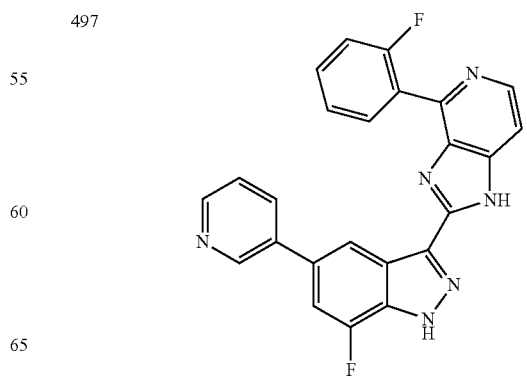

TABLE 1-continued
498
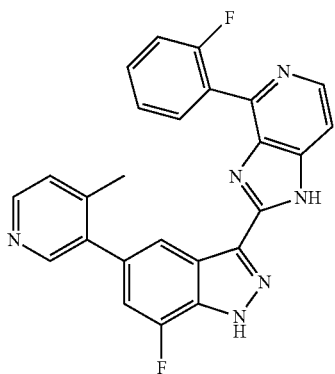 [SMILES: Cc1ccncc1-c1cc(F)c2[nH]nc(-c3nc4c(-c5ccccc5F)nccc4[nH]3)c2c1]
499
500
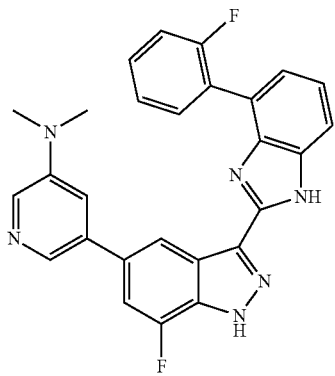 [SMILES: CN(C)c1cncc(-c2cc(F)c3[nH]nc(-c4nc5c(-c6ccccc6F)cccc5[nH]4)c3c2)c1]
501
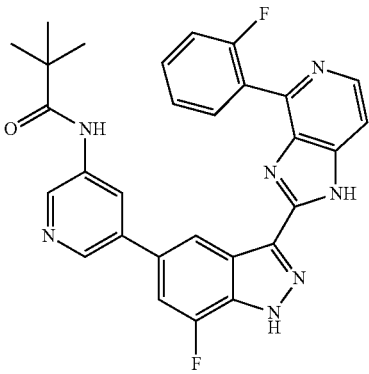 [SMILES: CC(C)(C)C(=O)Nc1cncc(-c2cc(F)c3[nH]nc(-c4nc5c(-c6ccccc6F)nccc5[nH]4)c3c2)c1]
TABLE 1-continued
502
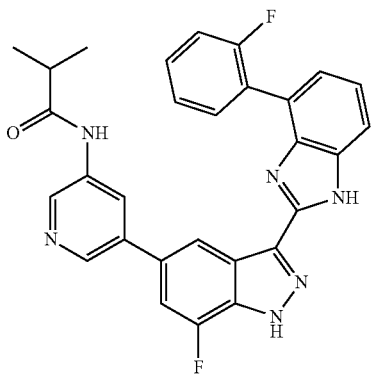 [SMILES: CC(C)C(=O)Nc1cncc(-c2cc(F)c3[nH]nc(-c4nc5c(-c6ccccc6F)cccc5[nH]4)c3c2)c1]
503
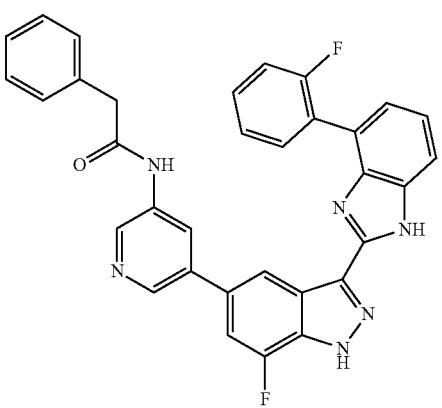 [SMILES: O=C(Cc1ccccc1)Nc1cncc(-c2cc(F)c3[nH]nc(-c4nc5c(-c6ccccc6F)cccc5[nH]4)c3c2)c1]
504
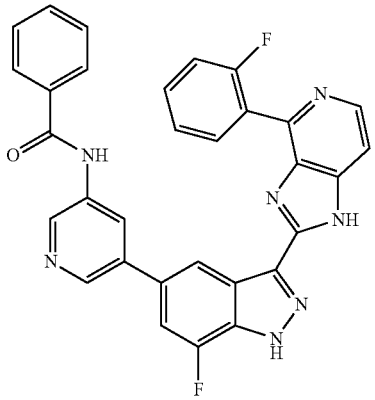 [SMILES: O=C(Nc1cncc(-c2cc(F)c3[nH]nc(-c4nc5c(-c6ccccc6F)nccc5[nH]4)c3c2)c1)c1ccccc1]
505
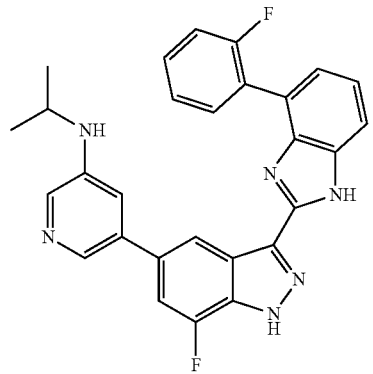 [SMILES: CC(C)Nc1cncc(-c2cc(F)c3[nH]nc(-c4nc5c(-c6ccccc6F)cccc5[nH]4)c3c2)c1]

TABLE 1-continued
506 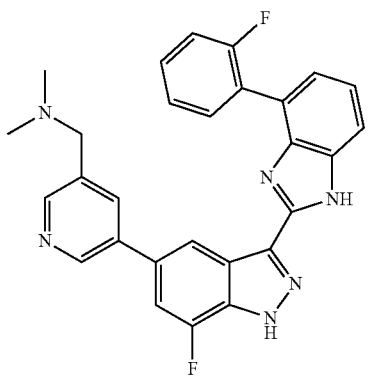 [SMILES: CN(C)Cc1cncc(-c2cc(F)c3[nH]nc(-c4nc5c(-c6ccccc6F)cccc5[nH]4)c3c2)c1]
507 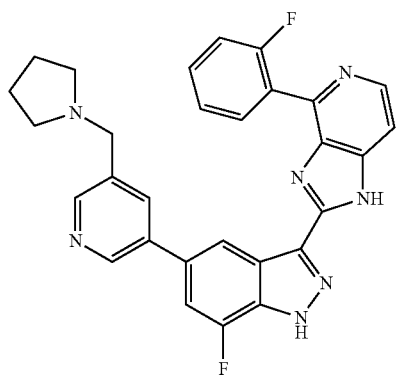 [SMILES: Fc1ccccc1-c1nccc2[nH]c(-c3n[nH]c4c(F)cc(-c5cncc(CN6CCCC6)c5)cc34)nc12]
508 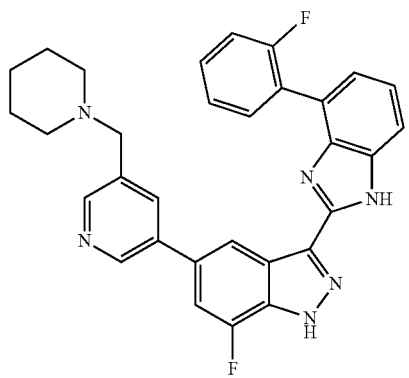 [SMILES: Fc1ccccc1-c1cccc2[nH]c(-c3n[nH]c4c(F)cc(-c5cncc(CN6CCCCC6)c5)cc34)nc12]
509 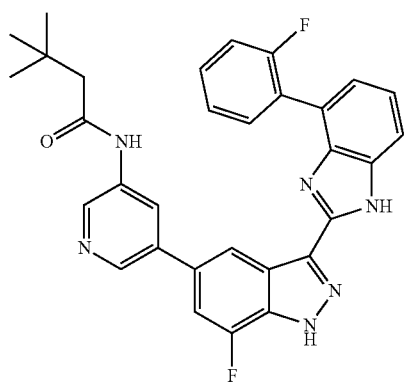
TABLE 1-continued
510 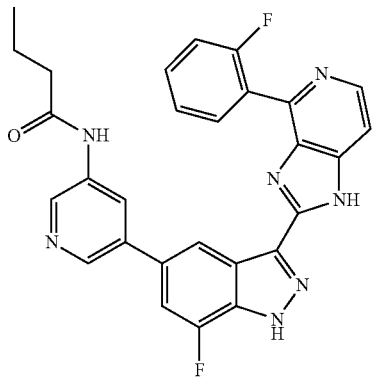 [SMILES: CCCC(=O)Nc1cncc(-c2cc(F)c3[nH]nc(-c4nc5c(-c6ccccc6F)nccc5[nH]4)c3c2)c1]
511 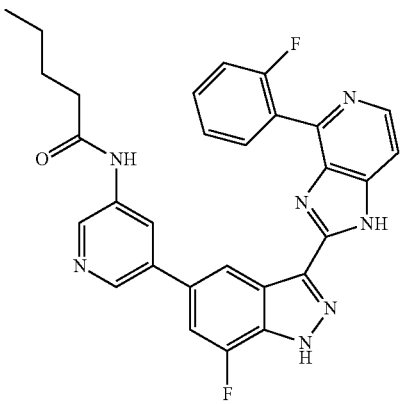 [SMILES: CCCCC(=O)Nc1cncc(-c2cc(F)c3[nH]nc(-c4nc5c(-c6ccccc6F)nccc5[nH]4)c3c2)c1]
512 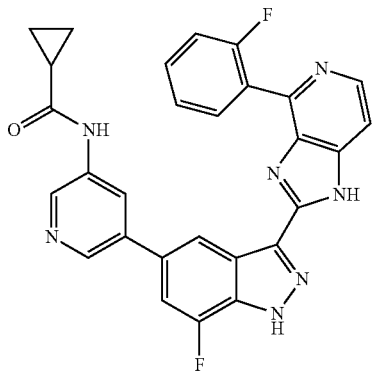 [SMILES: O=C(Nc1cncc(-c2cc(F)c3[nH]nc(-c4nc5c(-c6ccccc6F)nccc5[nH]4)c3c2)c1)C1CC1]
513 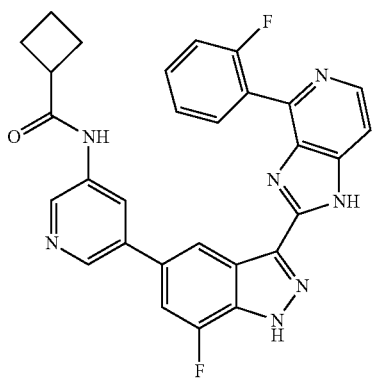 [SMILES: O=C(Nc1cncc(-c2cc(F)c3[nH]nc(-c4nc5c(-c6ccccc6F)nccc5[nH]4)c3c2)c1)C1CCC1]

TABLE 1-continued
| | |
|---|---|
| 514 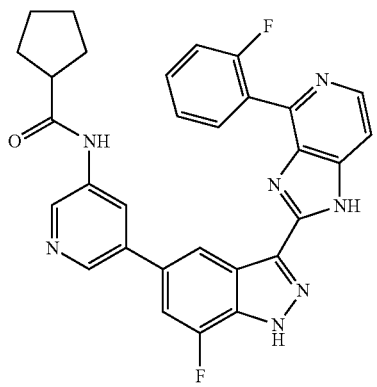 [SMILES: O=C(Nc1cncc(-c2cc(F)c3[nH]nc(-c4nc5c(-c6ccccc6F)nccc5[nH]4)c3c2)c1)C1CCCC1] | 518 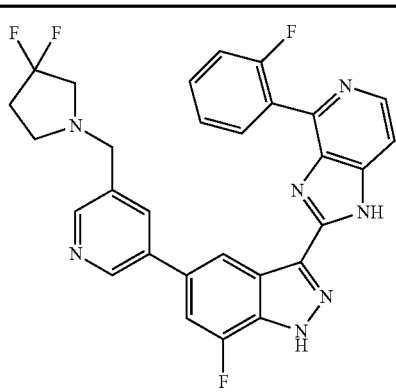 |
| 515 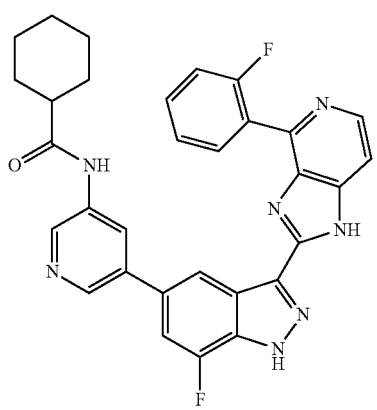 [SMILES: O=C(Nc1cncc(-c2cc(F)c3[nH]nc(-c4nc5c(-c6ccccc6F)nccc5[nH]4)c3c2)c1)C1CCCCC1] | 519 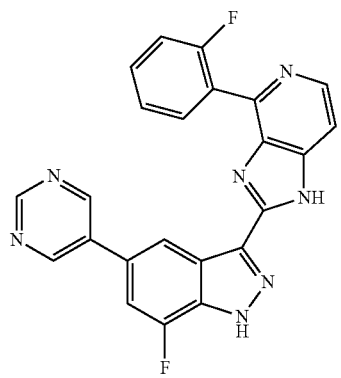 |
| 516 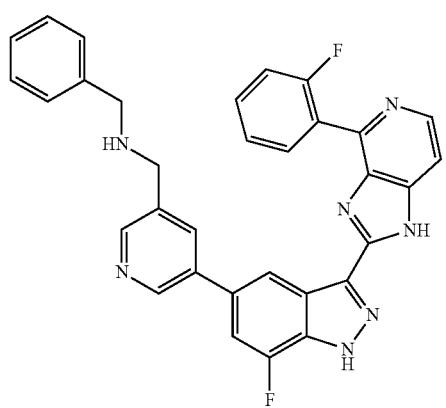 [SMILES: Fc1ccccc1-c1nccc2[nH]c(-c3n[nH]c4c(F)cc(-c5cncc(CNCc6ccccc6)c5)cc34)nc12] | 520 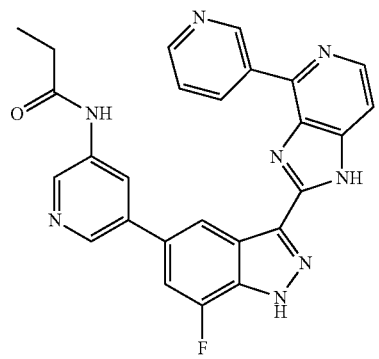 |
| 517 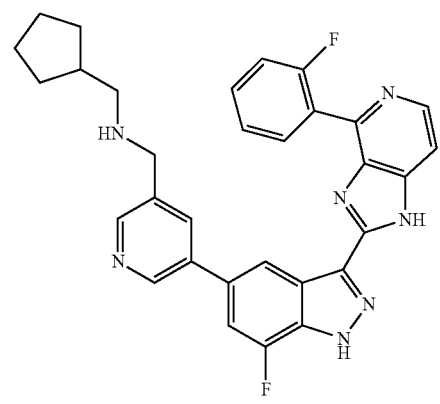 [SMILES: Fc1ccccc1-c1nccc2[nH]c(-c3n[nH]c4c(F)cc(-c5cncc(CNCC6CCCC6)c5)cc34)nc12] | 521 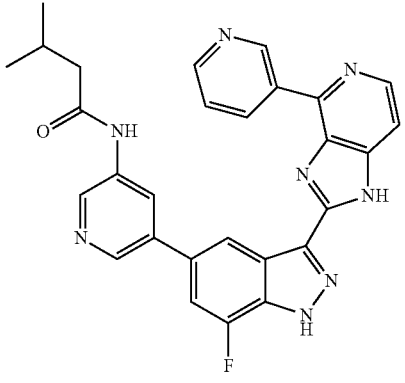 [SMILES: CC(C)CC(=O)Nc1cncc(-c2cc(F)c3[nH]nc(-c4nc5c(-c6cccnc6)nccc5[nH]4)c3c2)c1] |

TABLE 1-continued
| | |
|---|---|
| 522 | 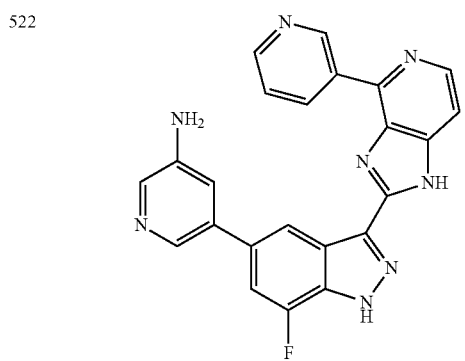 |
| 523 | 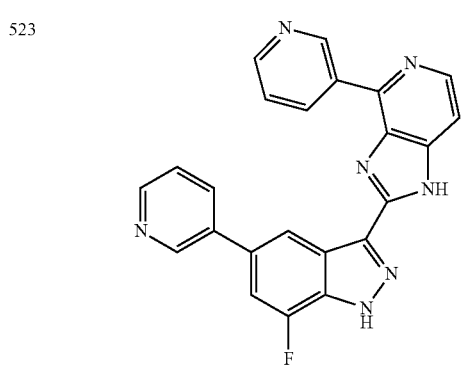 |
| 524 | 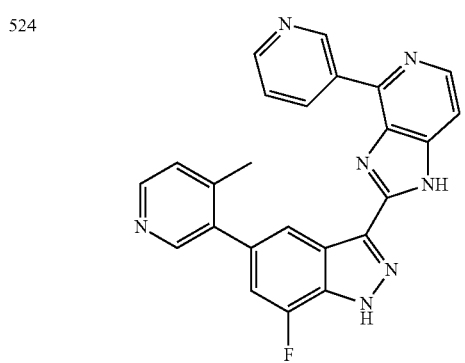 |
| 525 | 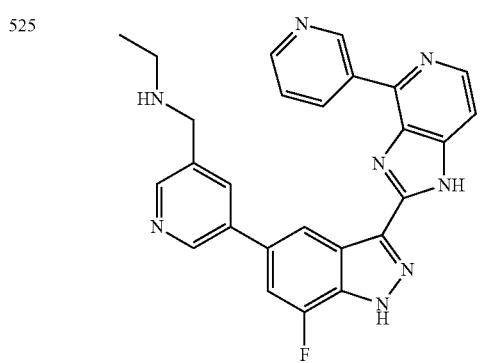 |
| 526 | 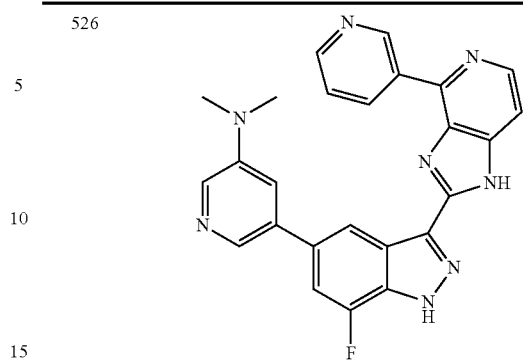 |
| 527 | 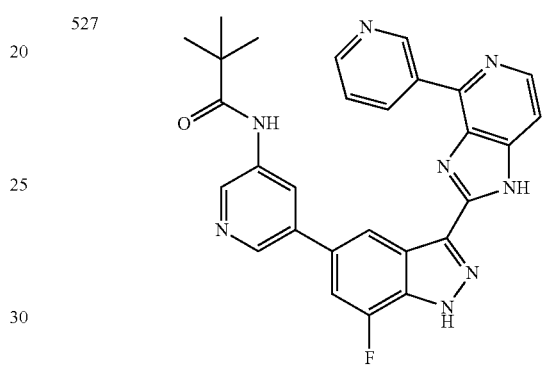 |
| 528 | 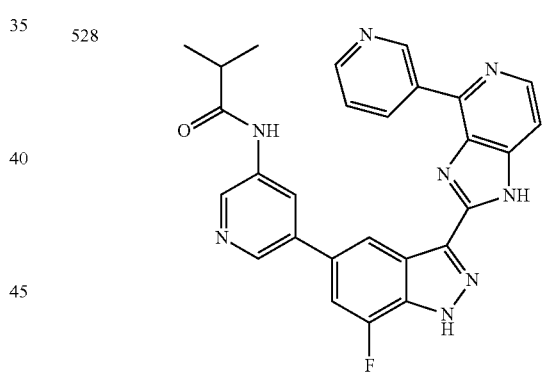 |
| 529 | 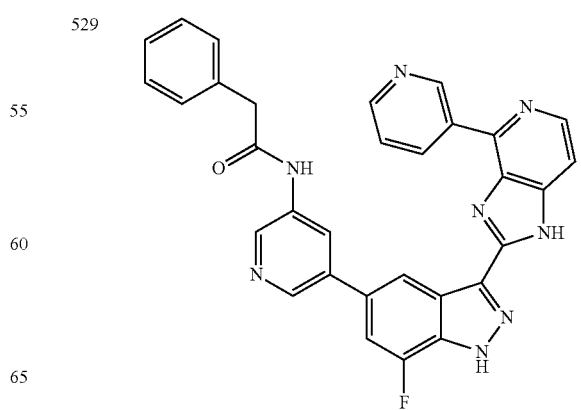 |

TABLE 1-continued
530 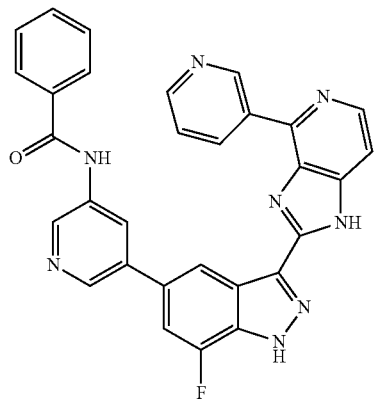 [SMILES: O=C(Nc1cncc(-c2cc(F)c3[nH]nc(-c4nc5c(-c6cccnc6)nccc5[nH]4)c3c2)c1)c1ccccc1]
531 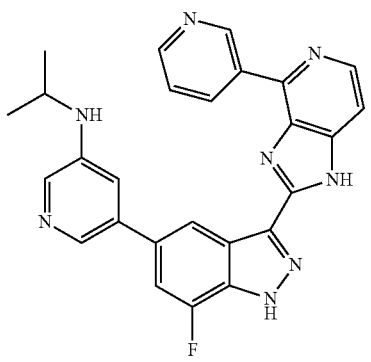 [SMILES: CC(C)Nc1cncc(-c2cc(F)c3[nH]nc(-c4nc5c(-c6cccnc6)nccc5[nH]4)c3c2)c1]
532 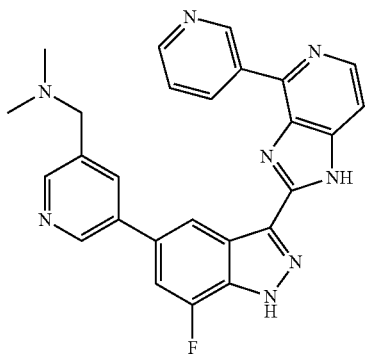 [SMILES: CN(C)Cc1cncc(-c2cc(F)c3[nH]nc(-c4nc5c(-c6cccnc6)nccc5[nH]4)c3c2)c1]
533 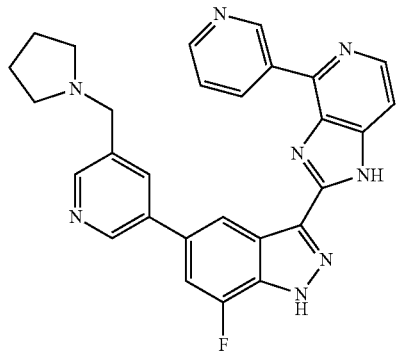 [SMILES: Fc1cc(-c2cncc(CN3CCCC3)c2)cc2c(-c3nc4c(-c5cccnc5)nccc4[nH]3)n[nH]c12]
TABLE 1-continued
534 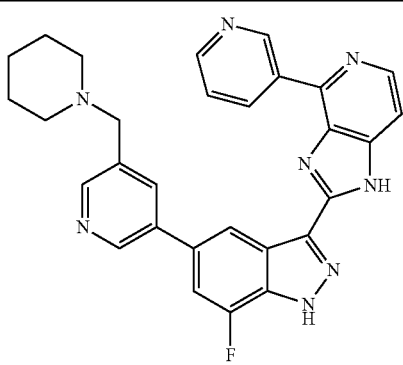
535 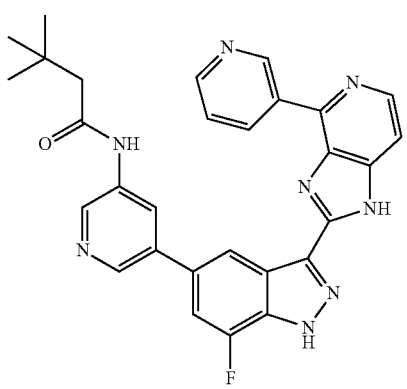 [SMILES: CC(C)(C)CC(=O)Nc1cncc(-c2cc(F)c3[nH]nc(-c4nc5c(-c6cccnc6)nccc5[nH]4)c3c2)c1]
536 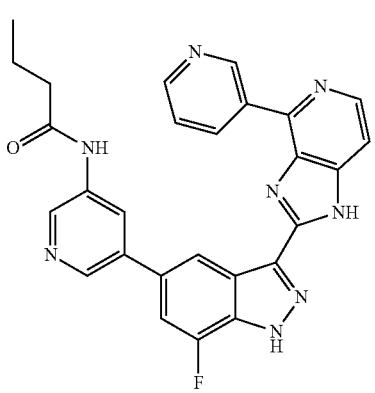 [SMILES: CCCC(=O)Nc1cncc(-c2cc(F)c3[nH]nc(-c4nc5c(-c6cccnc6)nccc5[nH]4)c3c2)c1]
537 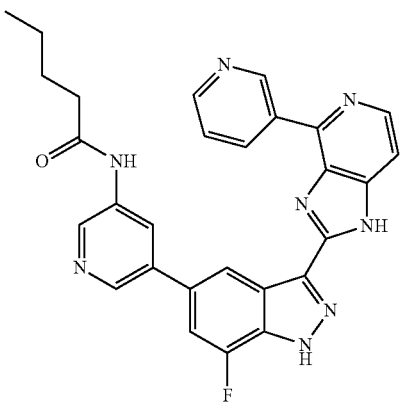 [SMILES: CCCCC(=O)Nc1cncc(-c2cc(F)c3[nH]nc(-c4nc5c(-c6cccnc6)nccc5[nH]4)c3c2)c1]

TABLE 1-continued
538 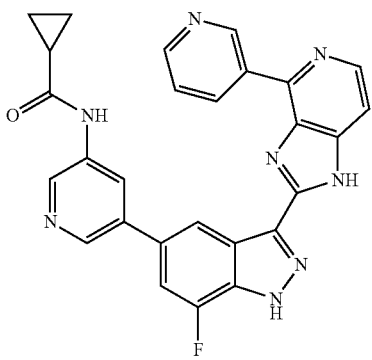 [SMILES: O=C(Nc1cncc(-c2cc(F)c3[nH]nc(-c4nc5c(-c6cccnc6)nccc5[nH]4)c3c2)c1)C1CC1]
539 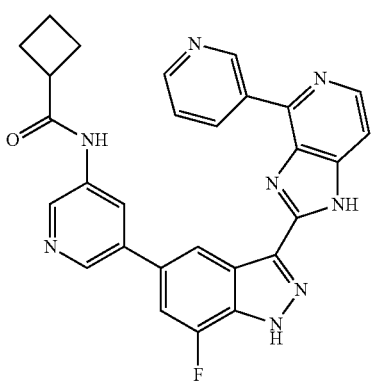 [SMILES: O=C(Nc1cncc(-c2cc(F)c3[nH]nc(-c4nc5c(-c6cccnc6)nccc5[nH]4)c3c2)c1)C1CCC1]
540 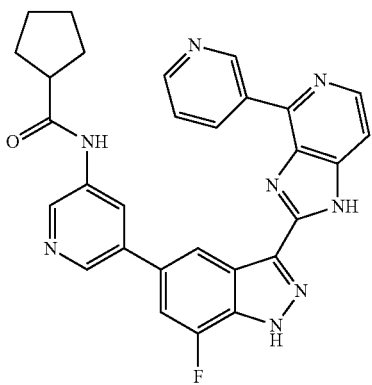 [SMILES: O=C(Nc1cncc(-c2cc(F)c3[nH]nc(-c4nc5c(-c6cccnc6)nccc5[nH]4)c3c2)c1)C1CCCC1]
541 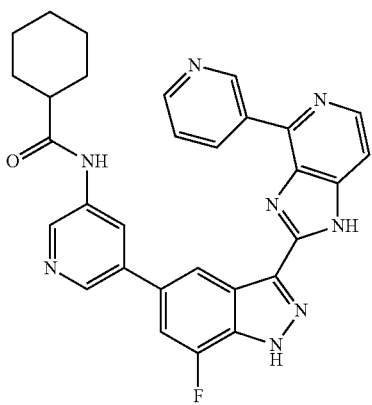 [SMILES: O=C(Nc1cncc(-c2cc(F)c3[nH]nc(-c4nc5c(-c6cccnc6)nccc5[nH]4)c3c2)c1)C1CCCCC1]
542 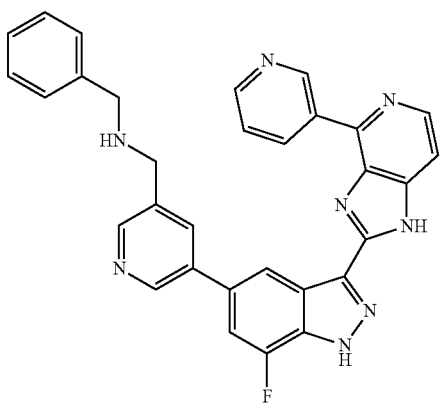 [SMILES: Fc1cc(-c2cncc(CNCc3ccccc3)c2)cc2c(-c3nc4c(-c5cccnc5)nccc4[nH]3)n[nH]c12]
543 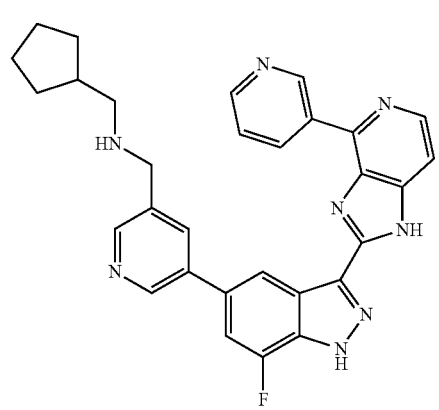 [SMILES: Fc1cc(-c2cncc(CNCC3CCCC3)c2)cc2c(-c3nc4c(-c5cccnc5)nccc4[nH]3)n[nH]c12]
544 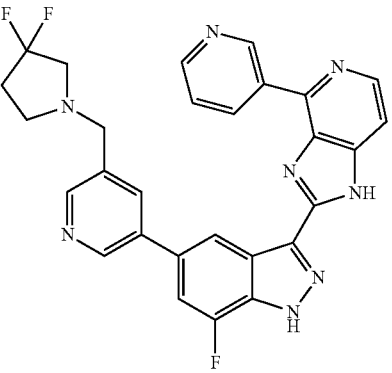 [SMILES: Fc1cc(-c2cncc(CN3CCC(F)(F)C3)c2)cc2c(-c3nc4c(-c5cccnc5)nccc4[nH]3)n[nH]c12]
545 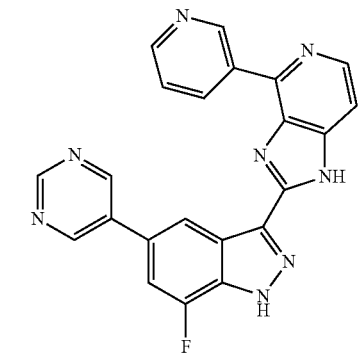

TABLE 1-continued
| | |
|---|---|
| 546 | 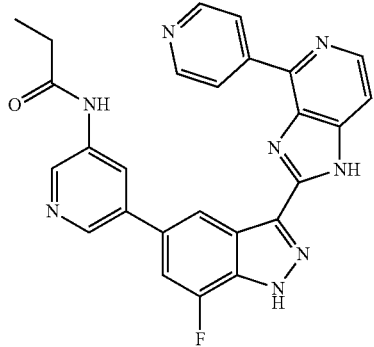 [SMILES: CCC(=O)Nc1cncc(-c2cc(F)c3[nH]nc(-c4nc5c(-c6ccncc6)nccc5[nH]4)c3c2)c1] |
| 547 | 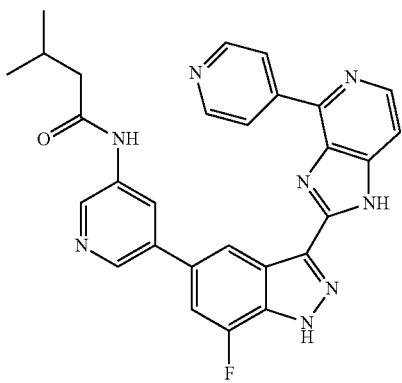 [SMILES: CC(C)CC(=O)Nc1cncc(-c2cc(F)c3[nH]nc(-c4nc5c(-c6ccncc6)nccc5[nH]4)c3c2)c1] |
| 548 | 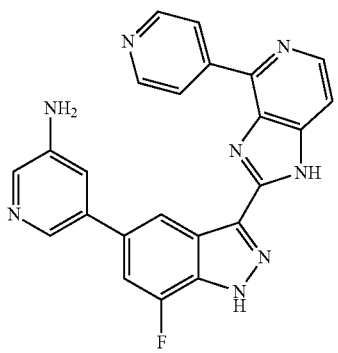 [SMILES: Nc1cncc(-c2cc(F)c3[nH]nc(-c4nc5c(-c6ccncc6)nccc5[nH]4)c3c2)c1] |
| 549 | 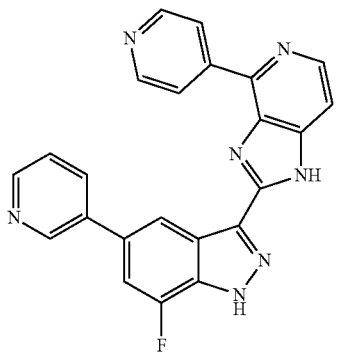 [SMILES: Fc1cc(-c2cccnc2)cc2c(-c3nc4c(-c5ccncc5)nccc4[nH]3)n[nH]c12] |
| 550 | 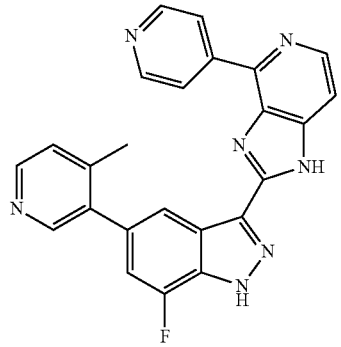 [SMILES: Cc1ccncc1-c1cc(F)c2[nH]nc(-c3nc4c(-c5ccncc5)nccc4[nH]3)c2c1] |
| 551 | 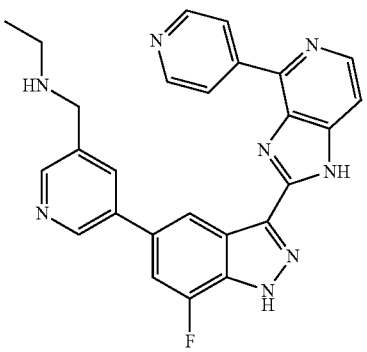 [SMILES: CCNCc1cncc(-c2cc(F)c3[nH]nc(-c4nc5c(-c6ccncc6)nccc5[nH]4)c3c2)c1] |
| 552 | 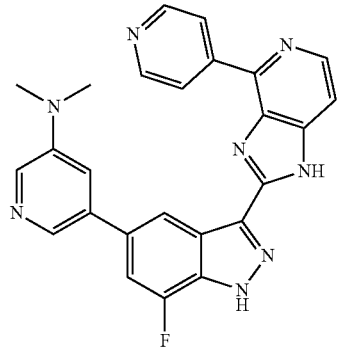 [SMILES: CN(C)c1cncc(-c2cc(F)c3[nH]nc(-c4nc5c(-c6ccncc6)nccc5[nH]4)c3c2)c1] |
| 553 | 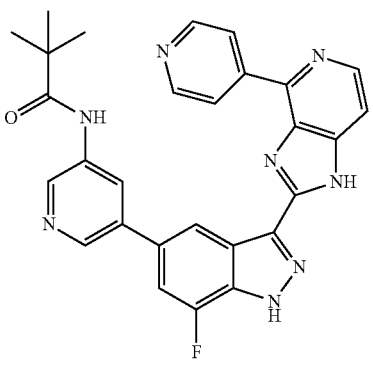 [SMILES: CC(C)(C)C(=O)Nc1cncc(-c2cc(F)c3[nH]nc(-c4nc5c(-c6ccncc6)nccc5[nH]4)c3c2)c1] |

TABLE 1-continued
554 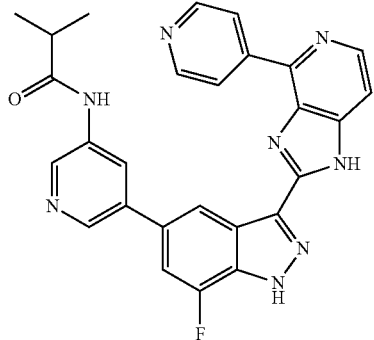 [SMILES: CC(C)C(=O)Nc1cncc(-c2cc(F)c3[nH]nc(-c4nc5c(-c6ccncc6)nccc5[nH]4)c3c2)c1]
555 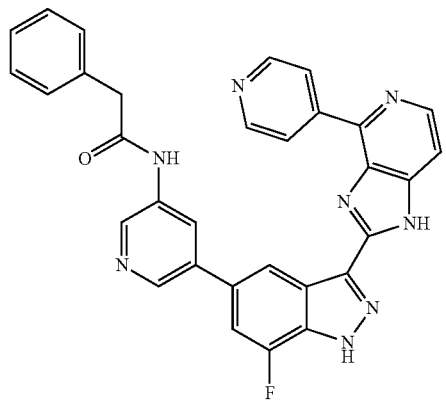 [SMILES: O=C(Cc1ccccc1)Nc1cncc(-c2cc(F)c3[nH]nc(-c4nc5c(-c6ccncc6)nccc5[nH]4)c3c2)c1]
556 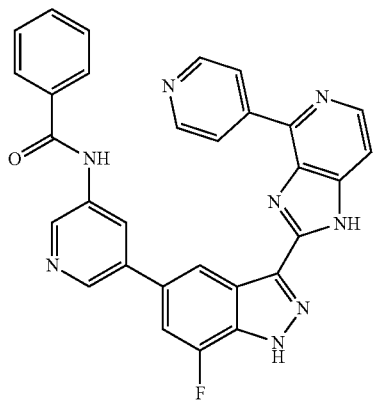 [SMILES: O=C(Nc1cncc(-c2cc(F)c3[nH]nc(-c4nc5c(-c6ccncc6)nccc5[nH]4)c3c2)c1)c1ccccc1]
557 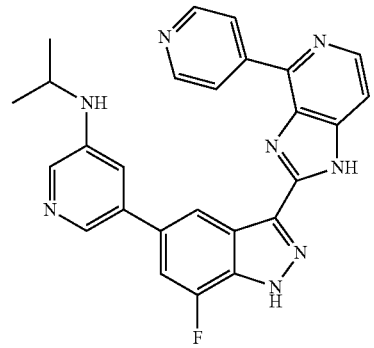 [SMILES: CC(C)Nc1cncc(-c2cc(F)c3[nH]nc(-c4nc5c(-c6ccncc6)nccc5[nH]4)c3c2)c1]
TABLE 1-continued
558 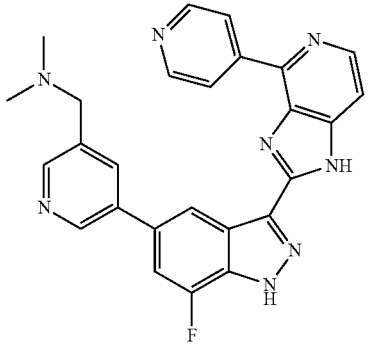
559 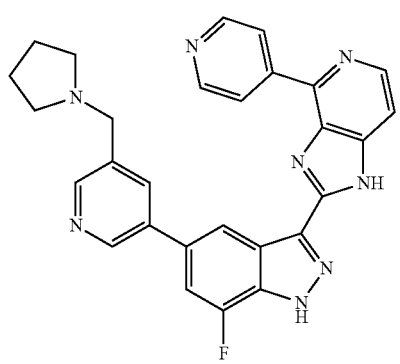 [SMILES: Fc1cc(-c2cncc(CN3CCCC3)c2)cc2c(-c3nc4c(-c5ccncc5)nccc4[nH]3)n[nH]c12]
560 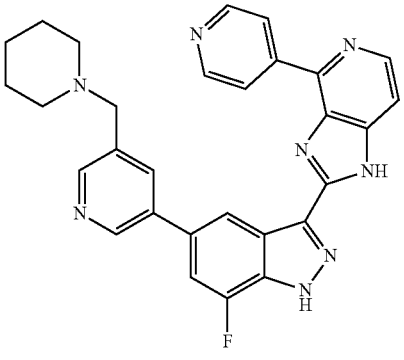 [SMILES: Fc1cc(-c2cncc(CN3CCCCC3)c2)cc2c(-c3nc4c(-c5ccncc5)nccc4[nH]3)n[nH]c12]
561 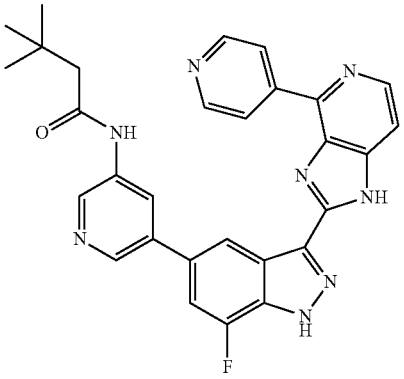 [SMILES: CC(C)(C)CC(=O)Nc1cncc(-c2cc(F)c3[nH]nc(-c4nc5c(-c6ccncc6)nccc5[nH]4)c3c2)c1]

TABLE 1-continued
562 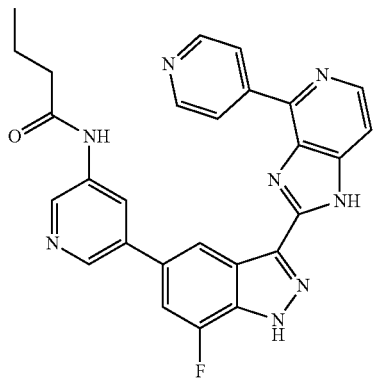 [SMILES: CCCC(=O)Nc1cncc(-c2cc(F)c3[nH]nc(-c4nc5c(-c6ccncc6)nccc5[nH]4)c3c2)c1]
563 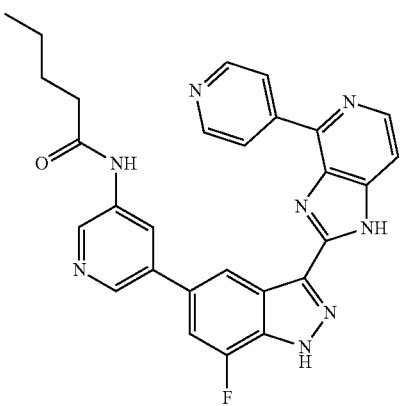 [SMILES: CCCCC(=O)Nc1cncc(-c2cc(F)c3[nH]nc(-c4nc5c(-c6ccncc6)nccc5[nH]4)c3c2)c1]
564 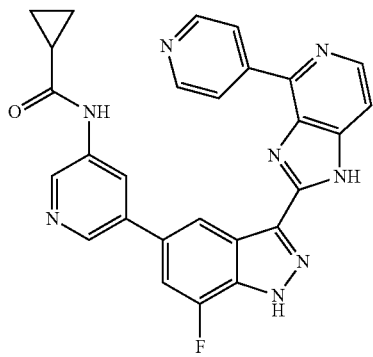 [SMILES: O=C(Nc1cncc(-c2cc(F)c3[nH]nc(-c4nc5c(-c6ccncc6)nccc5[nH]4)c3c2)c1)C1CC1]
565 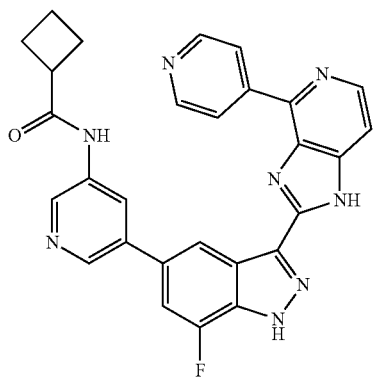 [SMILES: O=C(Nc1cncc(-c2cc(F)c3[nH]nc(-c4nc5c(-c6ccncc6)nccc5[nH]4)c3c2)c1)C1CCC1]
TABLE 1-continued
566 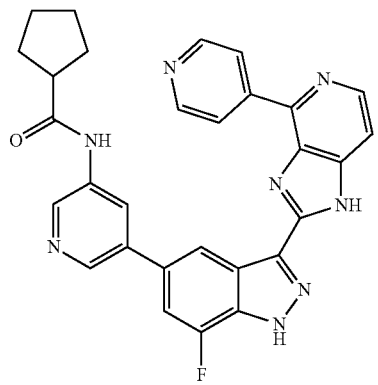 [SMILES: O=C(Nc1cncc(-c2cc(F)c3[nH]nc(-c4nc5c(-c6ccncc6)nccc5[nH]4)c3c2)c1)C1CCCC1]
567 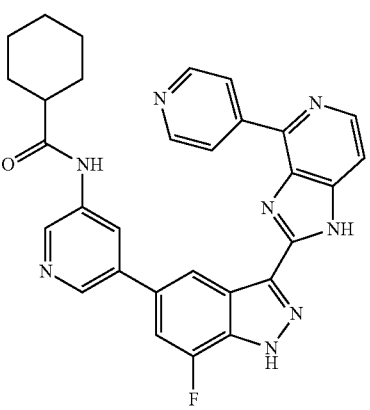 [SMILES: O=C(Nc1cncc(-c2cc(F)c3[nH]nc(-c4nc5c(-c6ccncc6)nccc5[nH]4)c3c2)c1)C1CCCCC1]
568 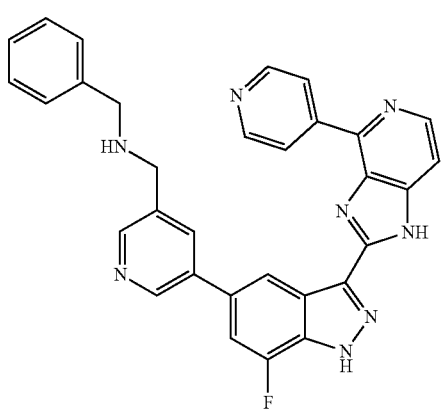 [SMILES: Fc1cc(-c2cncc(CNCc3ccccc3)c2)cc2c(-c3nc4c(-c5ccncc5)nccc4[nH]3)n[nH]c12]
569 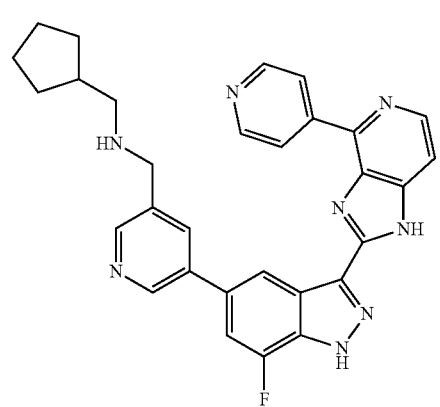 [SMILES: Fc1cc(-c2cncc(CNCC3CCCC3)c2)cc2c(-c3nc4c(-c5ccncc5)nccc4[nH]3)n[nH]c12]

TABLE 1-continued
| | |
|---|---|
| 570 | 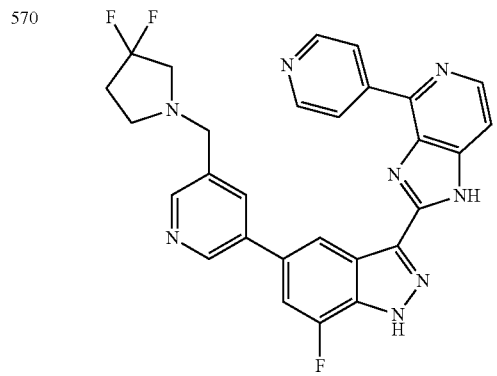 |
| 571 | 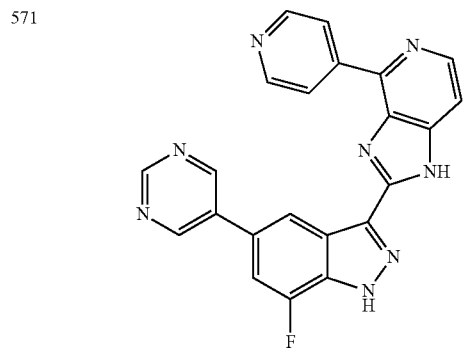 |
| 572 | 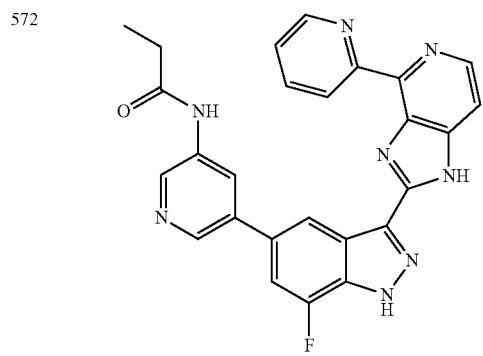 |
| 573 | 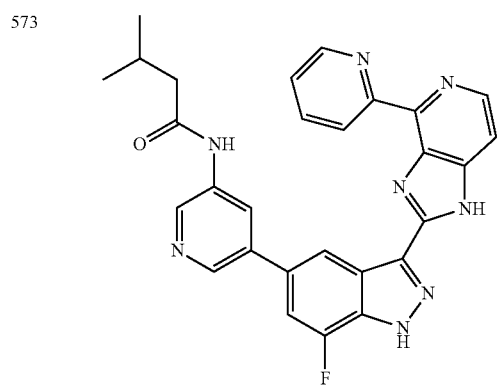 |
| 574 | 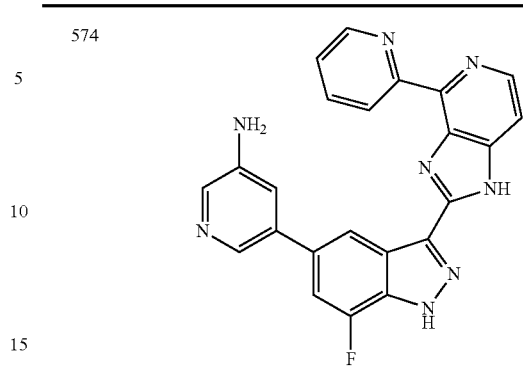 |
| 575 | 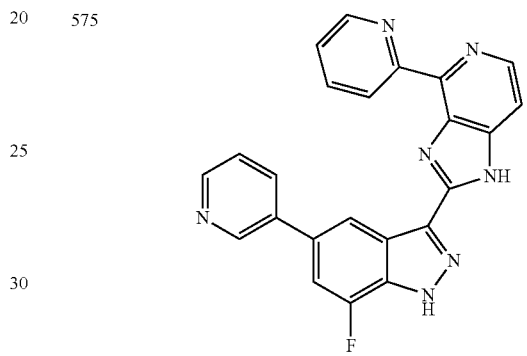 |
| 576 | 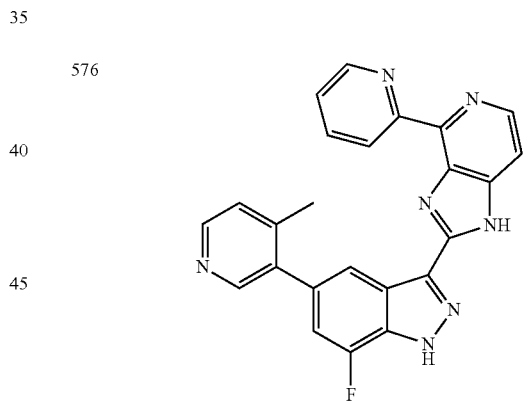 |
| 577 | 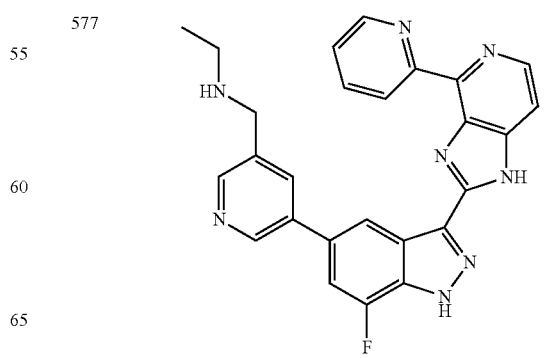 |

TABLE 1-continued
578 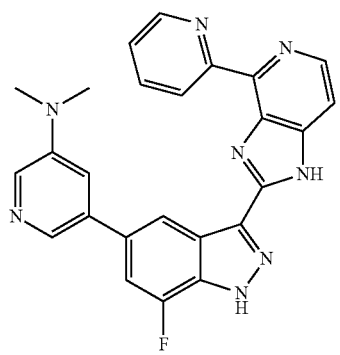 [SMILES: CN(C)c1cncc(-c2cc(F)c3[nH]nc(-c4nc5c(-c6ccccn6)nccc5[nH]4)c3c2)c1]
579 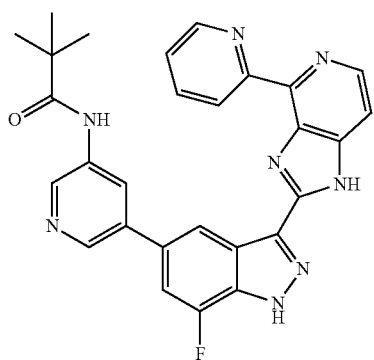 [SMILES: CC(C)(C)C(=O)Nc1cncc(-c2cc(F)c3[nH]nc(-c4nc5c(-c6ccccn6)nccc5[nH]4)c3c2)c1]
580 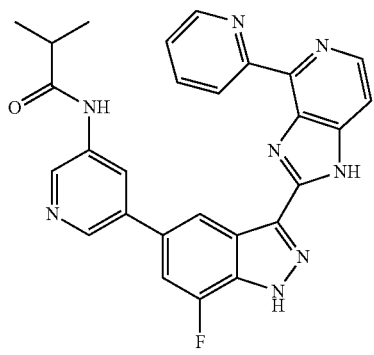 [SMILES: CC(C)C(=O)Nc1cncc(-c2cc(F)c3[nH]nc(-c4nc5c(-c6ccccn6)nccc5[nH]4)c3c2)c1]
581 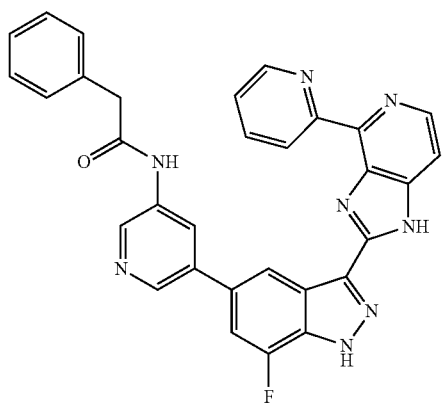 [SMILES: O=C(Cc1ccccc1)Nc1cncc(-c2cc(F)c3[nH]nc(-c4nc5c(-c6ccccn6)nccc5[nH]4)c3c2)c1]
TABLE 1-continued
582 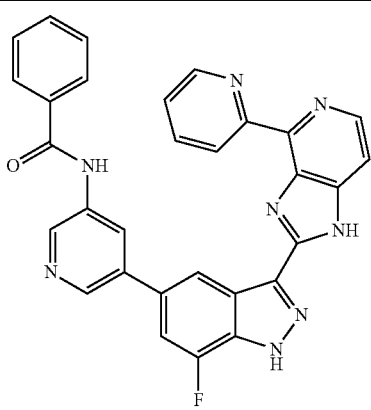
583 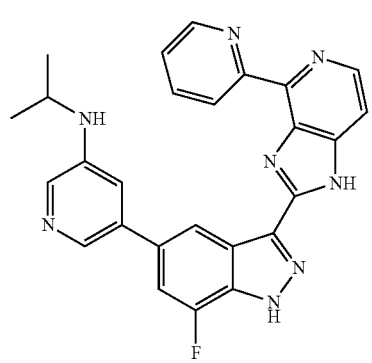
584 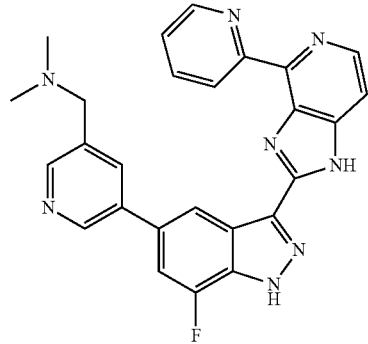 [SMILES: CN(C)Cc1cncc(-c2cc(F)c3[nH]nc(-c4nc5c(-c6ccccn6)nccc5[nH]4)c3c2)c1]
585 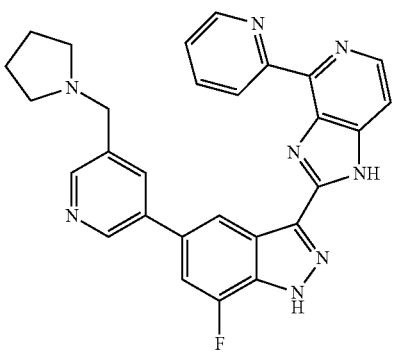 [SMILES: Fc1cc(-c2cncc(CN3CCCC3)c2)cc2c(-c3nc4c(-c5ccccn5)nccc4[nH]3)n[nH]c12]

TABLE 1-continued
| 586 | 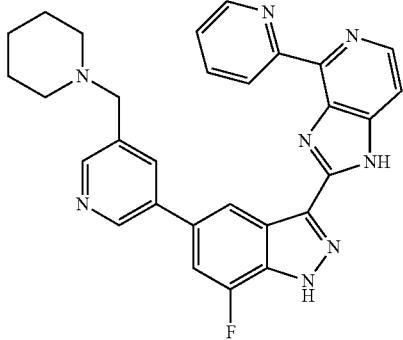 [SMILES: Fc1cc(-c2cncc(CN3CCCCC3)c2)cc2c(-c3nc4c(-c5ccccn5)nccc4[nH]3)n[nH]c12] | 590 | 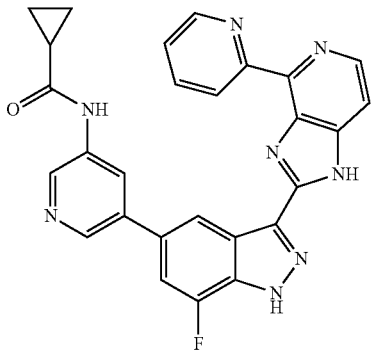 |
| 587 | 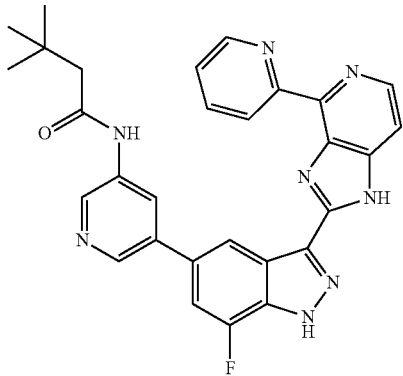 [SMILES: CC(C)(C)CC(=O)Nc1cncc(-c2cc(F)c3[nH]nc(-c4nc5c(-c6ccccn6)nccc5[nH]4)c3c2)c1] | 591 | 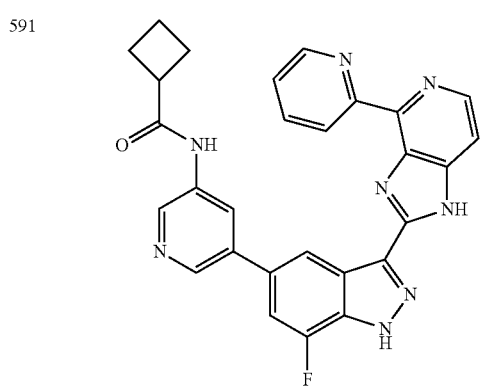 |
| 588 | 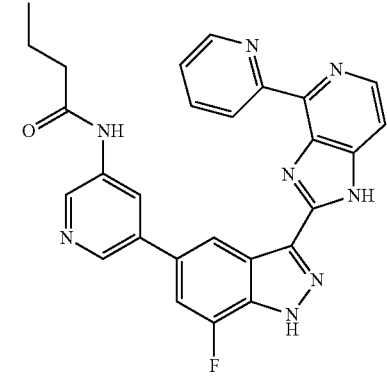 [SMILES: CCCC(=O)Nc1cncc(-c2cc(F)c3[nH]nc(-c4nc5c(-c6ccccn6)nccc5[nH]4)c3c2)c1] | 592 | 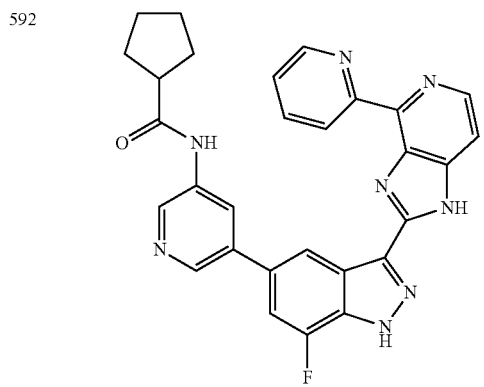 |
| 589 | 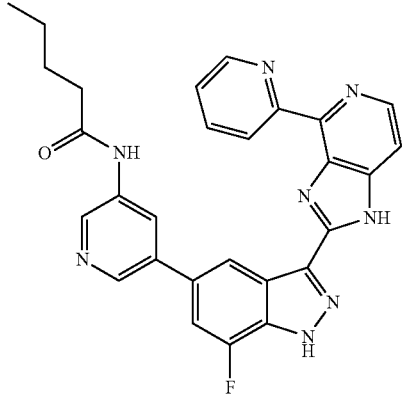 [SMILES: CCCCC(=O)Nc1cncc(-c2cc(F)c3[nH]nc(-c4nc5c(-c6ccccn6)nccc5[nH]4)c3c2)c1] | 593 | 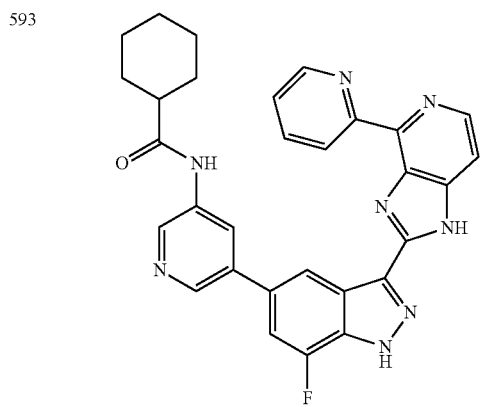 |

TABLE 1-continued
594 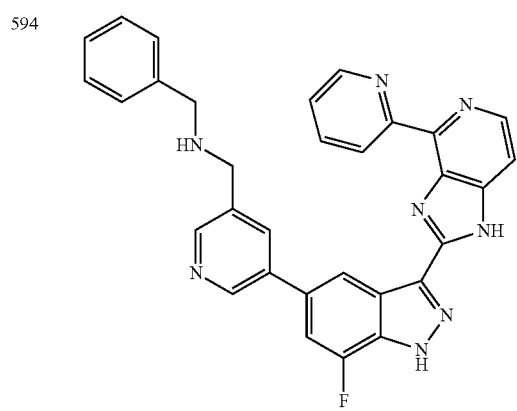
595 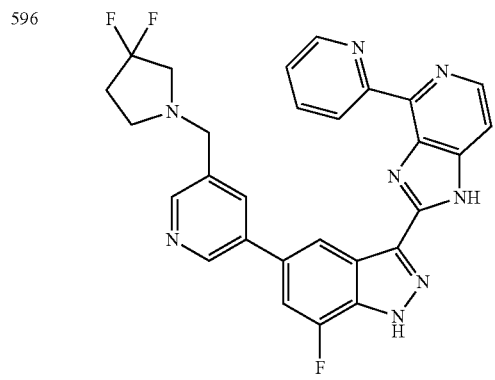
596 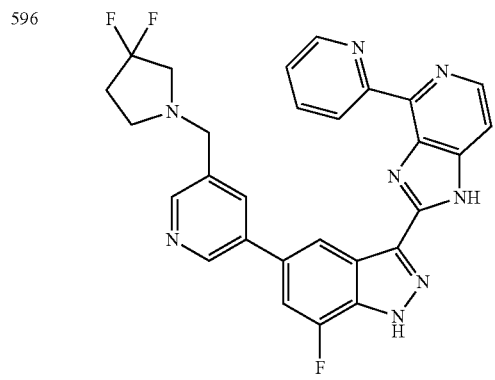
597 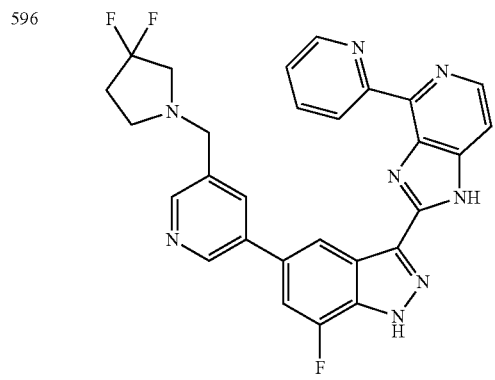
TABLE 1-continued
598 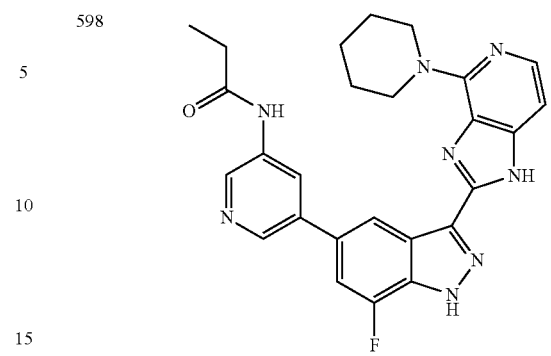
599 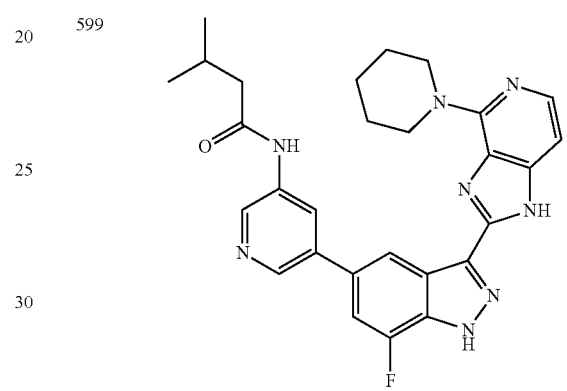
600 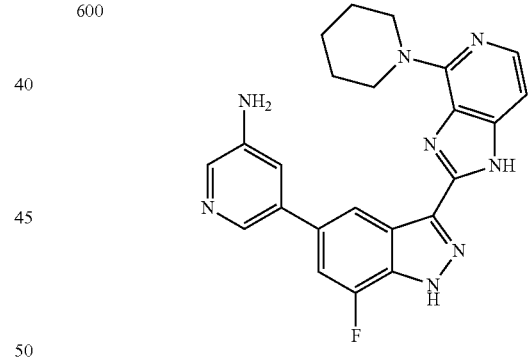
601 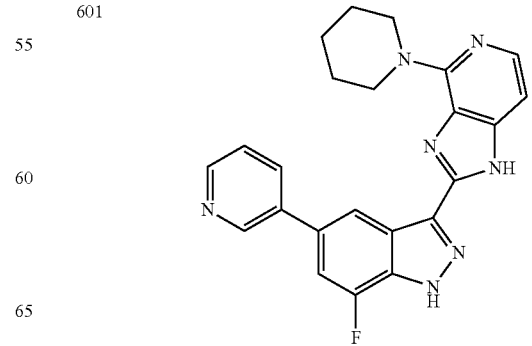

TABLE 1-continued
602 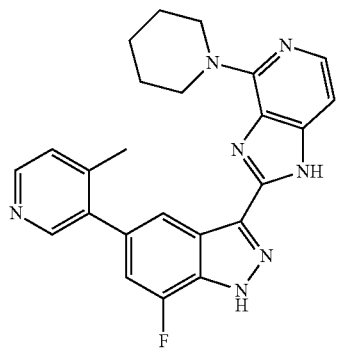 [SMILES: Cc1ccncc1-c1cc(F)c2[nH]nc(-c3nc4c(N5CCCCC5)nccc4[nH]3)c2c1]
603 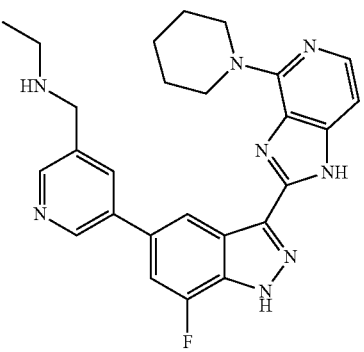 [SMILES: CCNCc1cncc(-c2cc(F)c3[nH]nc(-c4nc5c(N6CCCCC6)nccc5[nH]4)c3c2)c1]
604 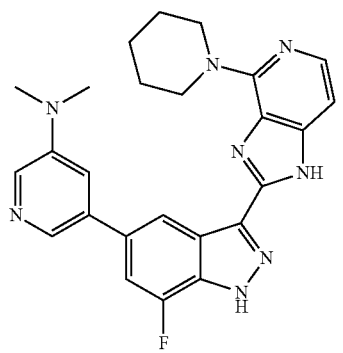 [SMILES: CN(C)c1cncc(-c2cc(F)c3[nH]nc(-c4nc5c(N6CCCCC6)nccc5[nH]4)c3c2)c1]
605 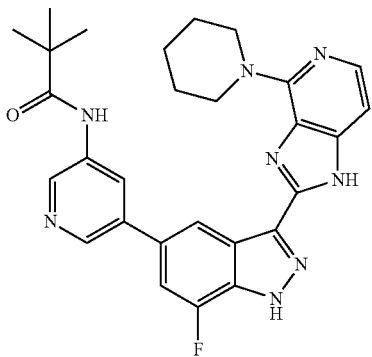 [SMILES: CC(C)(C)C(=O)Nc1cncc(-c2cc(F)c3[nH]nc(-c4nc5c(N6CCCCC6)nccc5[nH]4)c3c2)c1]
606 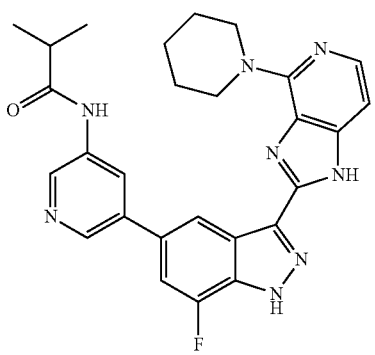 [SMILES: CC(C)C(=O)Nc1cncc(-c2cc(F)c3[nH]nc(-c4nc5c(N6CCCCC6)nccc5[nH]4)c3c2)c1]
607 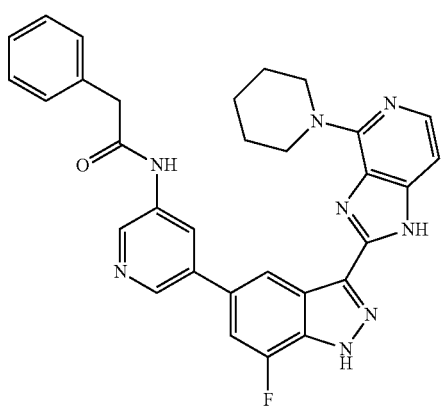 [SMILES: O=C(Cc1ccccc1)Nc1cncc(-c2cc(F)c3[nH]nc(-c4nc5c(N6CCCCC6)nccc5[nH]4)c3c2)c1]
608 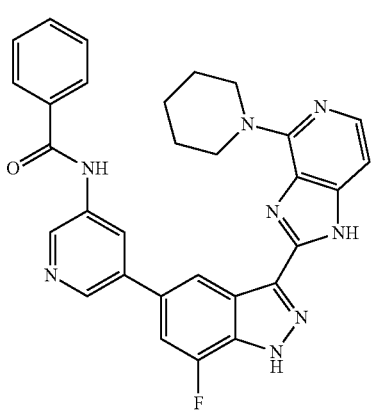 [SMILES: O=C(Nc1cncc(-c2cc(F)c3[nH]nc(-c4nc5c(N6CCCCC6)nccc5[nH]4)c3c2)c1)c1ccccc1]
609 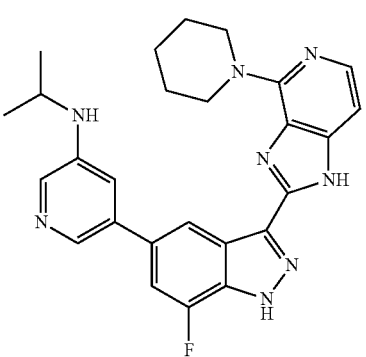 [SMILES: CC(C)Nc1cncc(-c2cc(F)c3[nH]nc(-c4nc5c(N6CCCCC6)nccc5[nH]4)c3c2)c1]

TABLE 1-continued
610 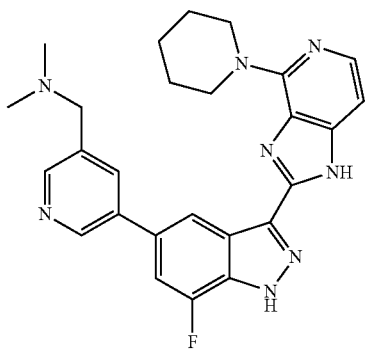 [SMILES: CN(C)Cc1cncc(-c2cc(F)c3[nH]nc(-c4nc5c(N6CCCCC6)nccc5[nH]4)c3c2)c1]
611 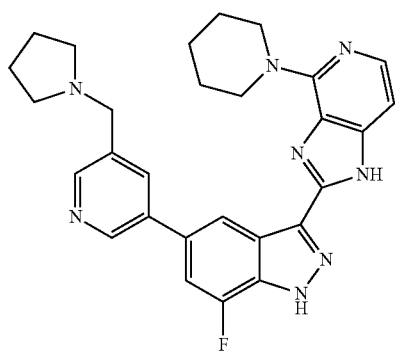 [SMILES: Fc1cc(-c2cncc(CN3CCCC3)c2)cc2c(-c3nc4c(N5CCCCC5)nccc4[nH]3)n[nH]c12]
612 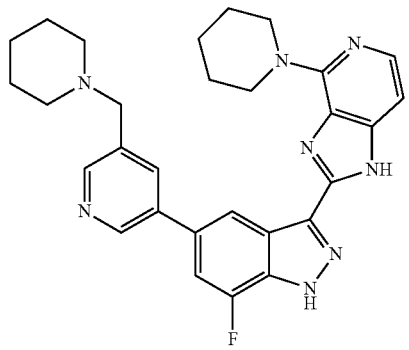 [SMILES: Fc1cc(-c2cncc(CN3CCCCC3)c2)cc2c(-c3nc4c(N5CCCCC5)nccc4[nH]3)n[nH]c12]
613 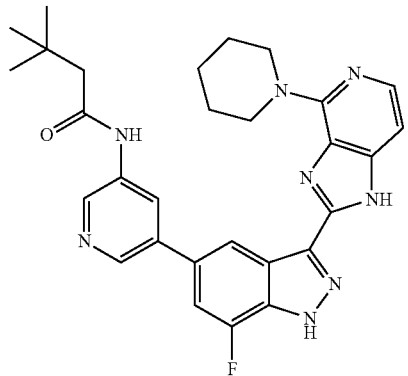 [SMILES: CC(C)(C)CC(=O)Nc1cncc(-c2cc(F)c3[nH]nc(-c4nc5c(N6CCCCC6)nccc5[nH]4)c3c2)c1]
TABLE 1-continued
614 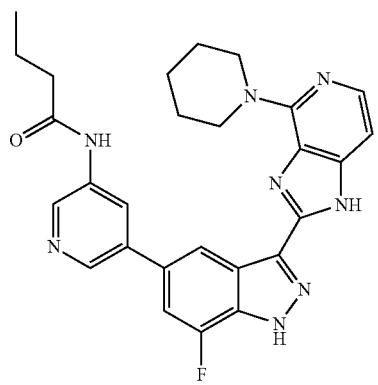 [SMILES: CCCC(=O)Nc1cncc(-c2cc(F)c3[nH]nc(-c4nc5c(N6CCCCC6)nccc5[nH]4)c3c2)c1]
615 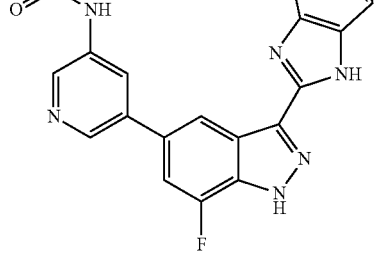
616 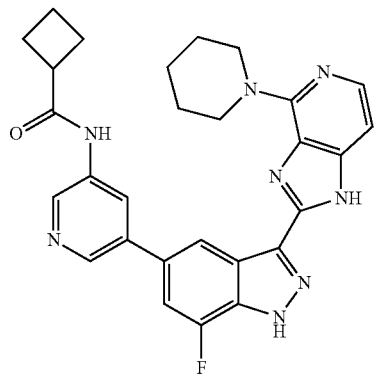 [SMILES: O=C(Nc1cncc(-c2cc(F)c3[nH]nc(-c4nc5c(N6CCCCC6)nccc5[nH]4)c3c2)c1)C1CCC1]
617

TABLE 1-continued
618 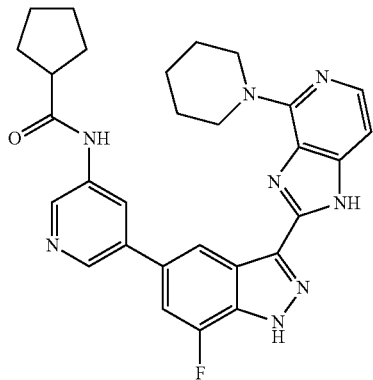 [SMILES: O=C(Nc1cncc(-c2cc(F)c3[nH]nc(-c4nc5c(N6CCCCC6)nccc5[nH]4)c3c2)c1)C1CCCC1]
619 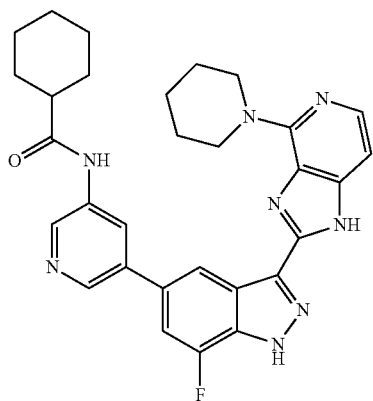 [SMILES: O=C(Nc1cncc(-c2cc(F)c3[nH]nc(-c4nc5c(N6CCCCC6)nccc5[nH]4)c3c2)c1)C1CCCCC1]
620 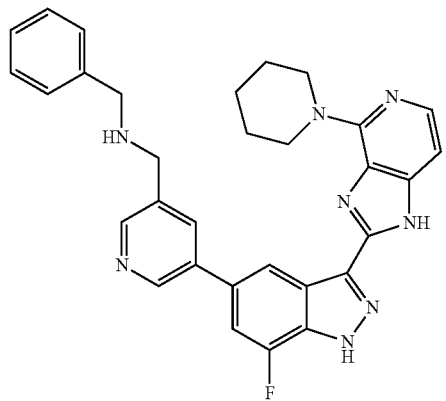 [SMILES: Fc1cc(-c2cncc(CNCc3ccccc3)c2)cc2c(-c3nc4c(N5CCCCC5)nccc4[nH]3)n[nH]c12]
621 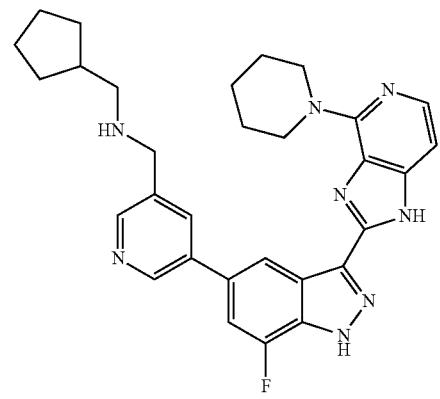 [SMILES: Fc1cc(-c2cncc(CNCC3CCCC3)c2)cc2c(-c3nc4c(N5CCCCC5)nccc4[nH]3)n[nH]c12]
TABLE 1-continued
622 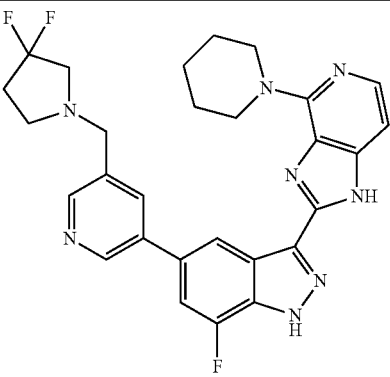
623 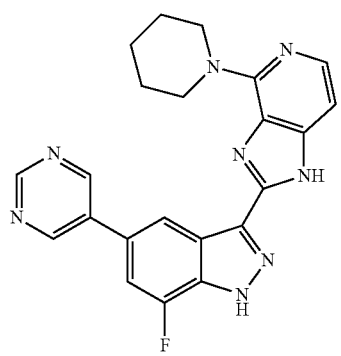
624 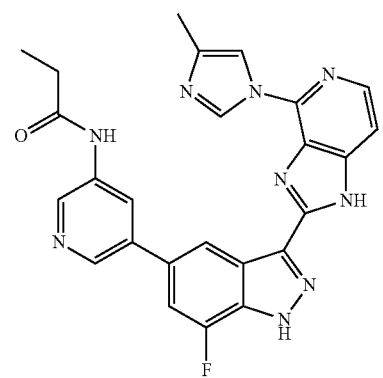 [SMILES: CCC(=O)Nc1cncc(-c2cc(F)c3[nH]nc(-c4nc5c(-n6cnc(C)c6)nccc5[nH]4)c3c2)c1]
625 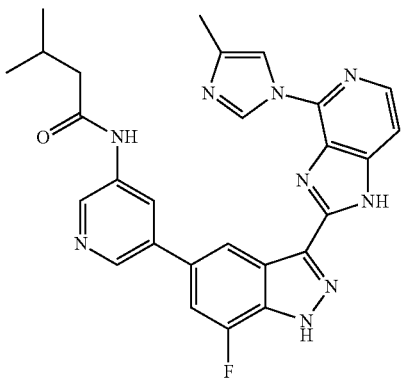 [SMILES: Cc1cn(-c2nccc3[nH]c(-c4n[nH]c5c(F)cc(-c6cncc(NC(=O)CC(C)C)c6)cc45)nc23)cn1]

TABLE 1-continued
626
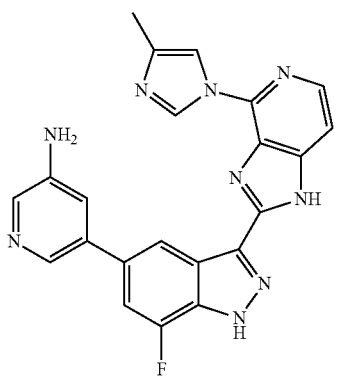 [SMILES: Cc1cn(-c2nccc3[nH]c(-c4n[nH]c5c(F)cc(-c6cncc(N)c6)cc45)nc23)cn1]
627
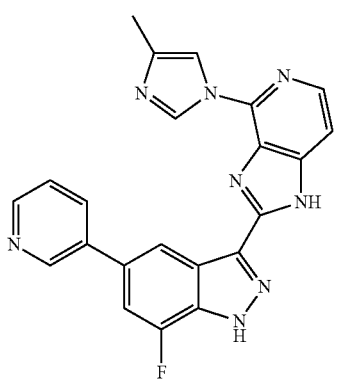 [SMILES: Cc1cn(-c2nccc3[nH]c(-c4n[nH]c5c(F)cc(-c6cccnc6)cc45)nc23)cn1]
628
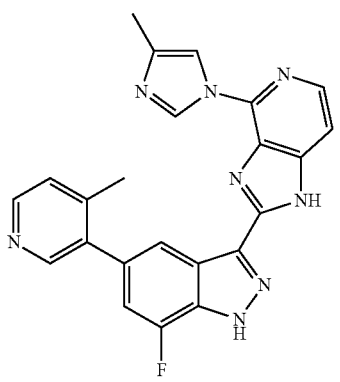 [SMILES: Cc1cn(-c2nccc3[nH]c(-c4n[nH]c5c(F)cc(-c6cnccc6C)cc45)nc23)cn1]
629
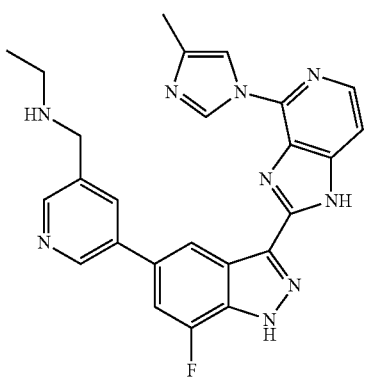 [SMILES: CCNCc1cncc(-c2cc(F)c3[nH]nc(-c4nc5c(-n6cnc(C)c6)nccc5[nH]4)c3c2)c1]
TABLE 1-continued
630
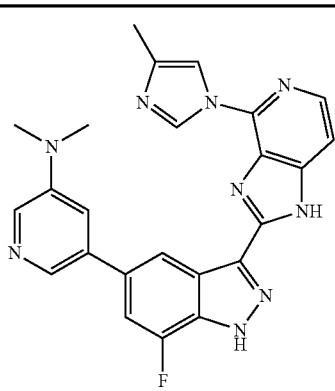
631
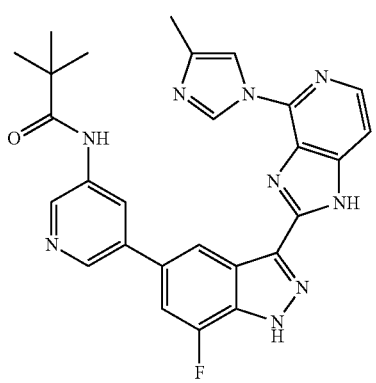 [SMILES: Cc1cn(-c2nccc3[nH]c(-c4n[nH]c5c(F)cc(-c6cncc(NC(=O)C(C)(C)C)c6)cc45)nc23)cn1]
632
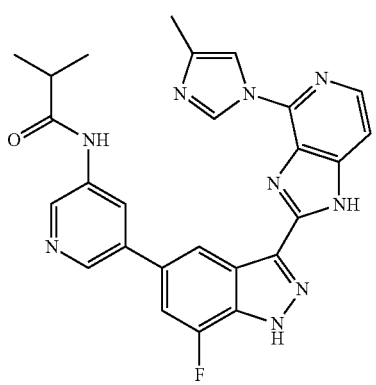 [SMILES: Cc1cn(-c2nccc3[nH]c(-c4n[nH]c5c(F)cc(-c6cncc(NC(=O)C(C)C)c6)cc45)nc23)cn1]
633
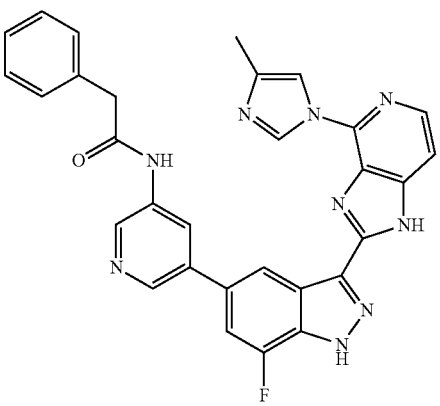 [SMILES: Cc1cn(-c2nccc3[nH]c(-c4n[nH]c5c(F)cc(-c6cncc(NC(=O)Cc7ccccc7)c6)cc45)nc23)cn1]

TABLE 1-continued
634 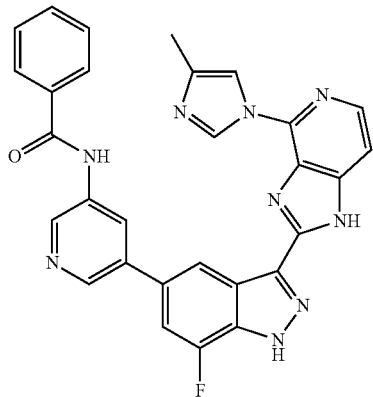 [SMILES: Cc1cn(-c2nccc3[nH]c(-c4n[nH]c5c(F)cc(-c6cncc(NC(=O)c7ccccc7)c6)cc45)nc23)cn1]
635 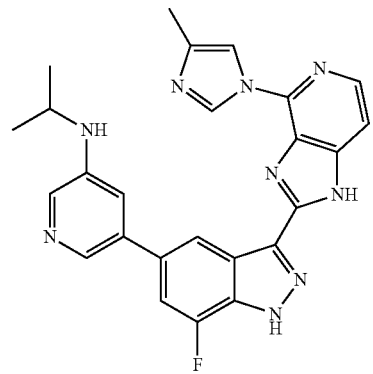 [SMILES: Cc1cn(-c2nccc3[nH]c(-c4n[nH]c5c(F)cc(-c6cncc(NC(C)C)c6)cc45)nc23)cn1]
636 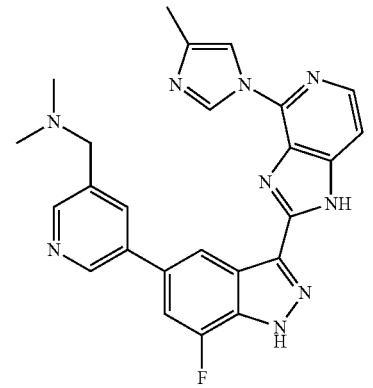 [SMILES: Cc1cn(-c2nccc3[nH]c(-c4n[nH]c5c(F)cc(-c6cncc(CN(C)C)c6)cc45)nc23)cn1]
637 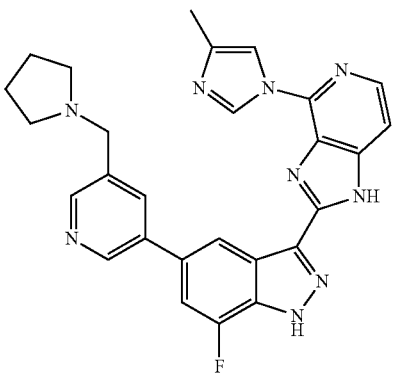 [SMILES: Cc1cn(-c2nccc3[nH]c(-c4n[nH]c5c(F)cc(-c6cncc(CN7CCCC7)c6)cc45)nc23)cn1]
TABLE 1-continued
638 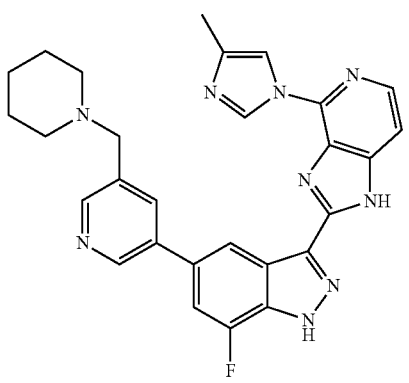 [SMILES: Cc1cn(-c2nccc3[nH]c(-c4n[nH]c5c(F)cc(-c6cncc(CN7CCCCC7)c6)cc45)nc23)cn1]
639 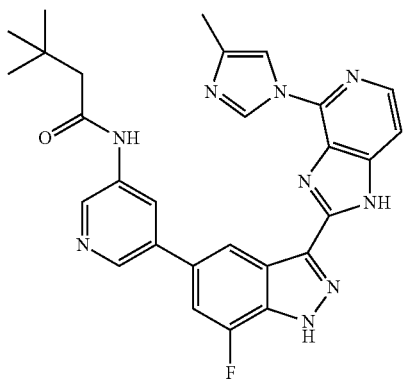 [SMILES: Cc1cn(-c2nccc3[nH]c(-c4n[nH]c5c(F)cc(-c6cncc(NC(=O)CC(C)(C)C)c6)cc45)nc23)cn1]
640 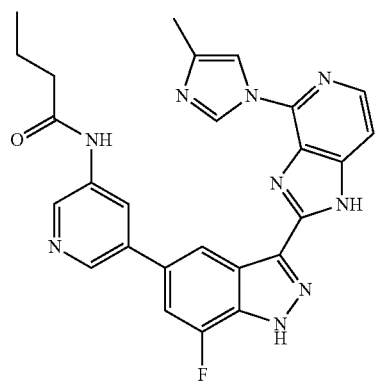 [SMILES: CCCC(=O)Nc1cncc(-c2cc(F)c3[nH]nc(-c4nc5c(-n6cnc(C)c6)nccc5[nH]4)c3c2)c1]
641 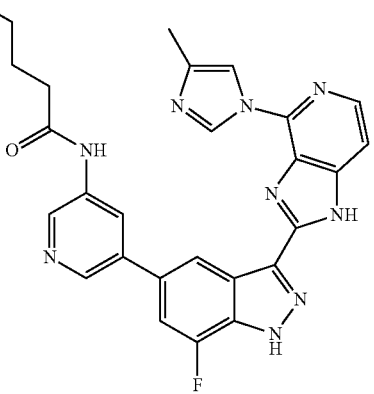

TABLE 1-continued
642 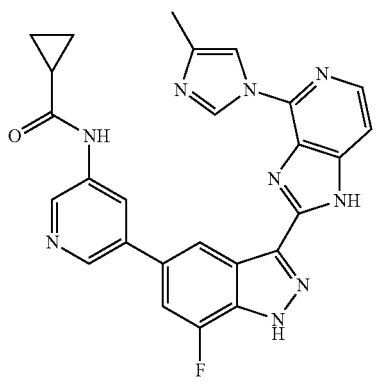 [SMILES: Cc1cn(-c2nccc3[nH]c(-c4n[nH]c5c(F)cc(-c6cncc(NC(=O)C7CC7)c6)cc45)nc23)cn1]
643 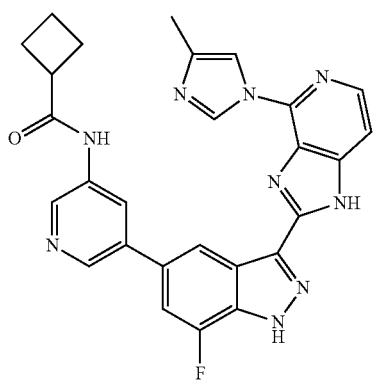 [SMILES: Cc1cn(-c2nccc3[nH]c(-c4n[nH]c5c(F)cc(-c6cncc(NC(=O)C7CCC7)c6)cc45)nc23)cn1]
644 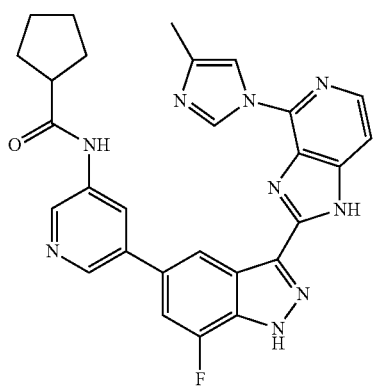 [SMILES: Cc1cn(-c2nccc3[nH]c(-c4n[nH]c5c(F)cc(-c6cncc(NC(=O)C7CCCC7)c6)cc45)nc23)cn1]
645 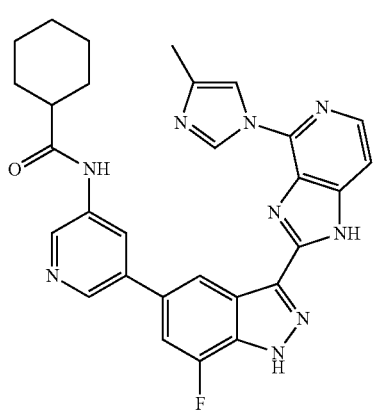 [SMILES: Cc1cn(-c2nccc3[nH]c(-c4n[nH]c5c(F)cc(-c6cncc(NC(=O)C7CCCCC7)c6)cc45)nc23)cn1]
TABLE 1-continued
646 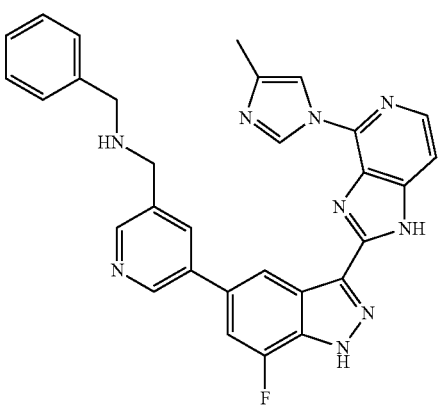 [SMILES: Cc1cn(-c2nccc3[nH]c(-c4n[nH]c5c(F)cc(-c6cncc(CNCc7ccccc7)c6)cc45)nc23)cn1]
647 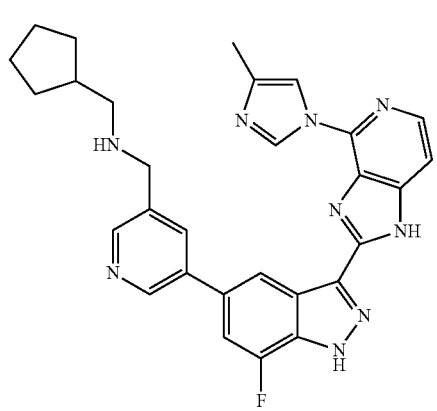 [SMILES: Cc1cn(-c2nccc3[nH]c(-c4n[nH]c5c(F)cc(-c6cncc(CNCC7CCCC7)c6)cc45)nc23)cn1]
648 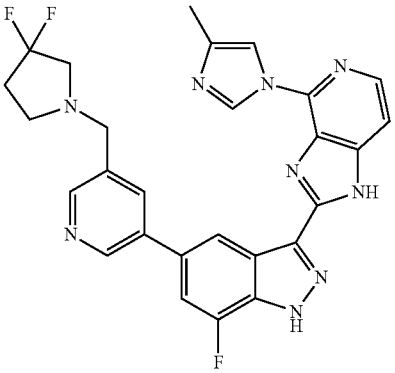 [SMILES: Cc1cn(-c2nccc3[nH]c(-c4n[nH]c5c(F)cc(-c6cncc(CN7CCC(F)(F)C7)c6)cc45)nc23)cn1]
649 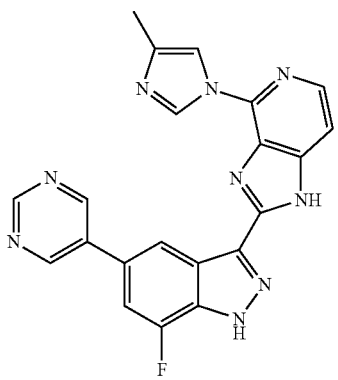 [SMILES: Cc1cn(-c2nccc3[nH]c(-c4n[nH]c5c(F)cc(-c6cncnc6)cc45)nc23)cn1]

TABLE 1-continued
650 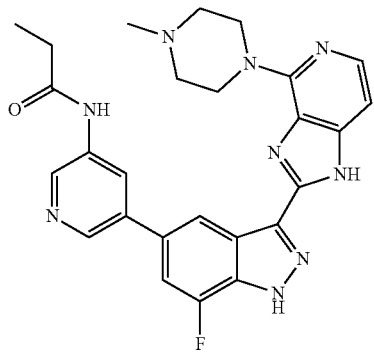 [SMILES: CCC(=O)Nc1cncc(-c2cc(F)c3[nH]nc(-c4nc5c(N6CCN(C)CC6)nccc5[nH]4)c3c2)c1]
651 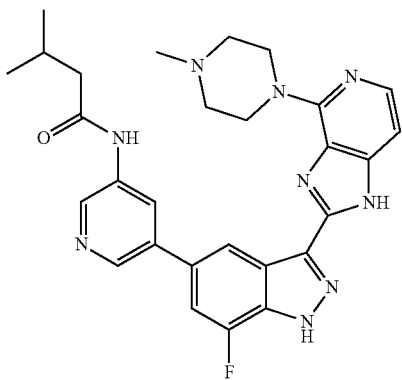 [SMILES: CC(C)CC(=O)Nc1cncc(-c2cc(F)c3[nH]nc(-c4nc5c(N6CCN(C)CC6)nccc5[nH]4)c3c2)c1]
652 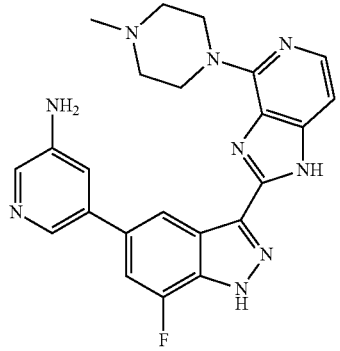 [SMILES: CN1CCN(c2nccc3[nH]c(-c4n[nH]c5c(F)cc(-c6cncc(N)c6)cc45)nc23)CC1]
653 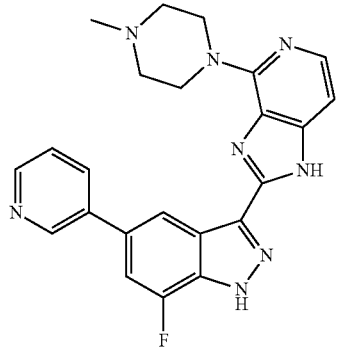 [SMILES: CN1CCN(c2nccc3[nH]c(-c4n[nH]c5c(F)cc(-c6cccnc6)cc45)nc23)CC1]
TABLE 1-continued
654 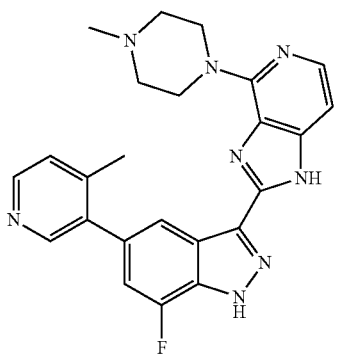 [SMILES: Cc1ccncc1-c1cc(F)c2[nH]nc(-c3nc4c(N5CCN(C)CC5)nccc4[nH]3)c2c1]
655 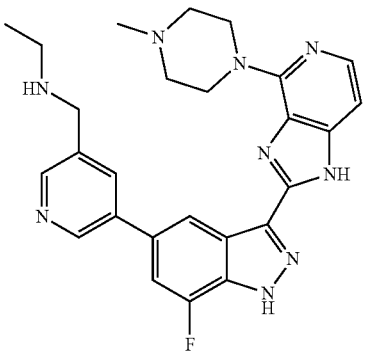 [SMILES: CCNCc1cncc(-c2cc(F)c3[nH]nc(-c4nc5c(N6CCN(C)CC6)nccc5[nH]4)c3c2)c1]
656 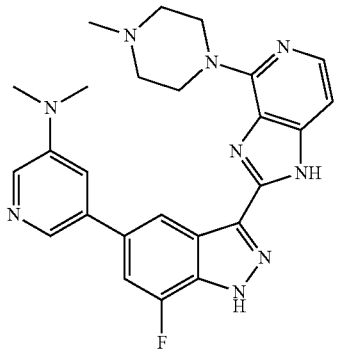 [SMILES: CN1CCN(c2nccc3[nH]c(-c4n[nH]c5c(F)cc(-c6cncc(N(C)C)c6)cc45)nc23)CC1]
657 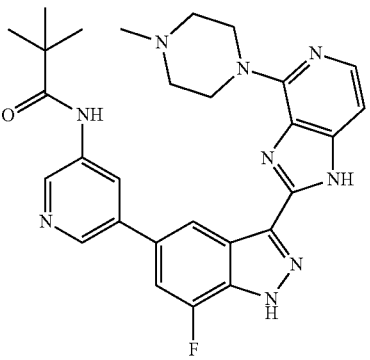 [SMILES: CN1CCN(c2nccc3[nH]c(-c4n[nH]c5c(F)cc(-c6cncc(NC(=O)C(C)(C)C)c6)cc45)nc23)CC1]

TABLE 1-continued
658 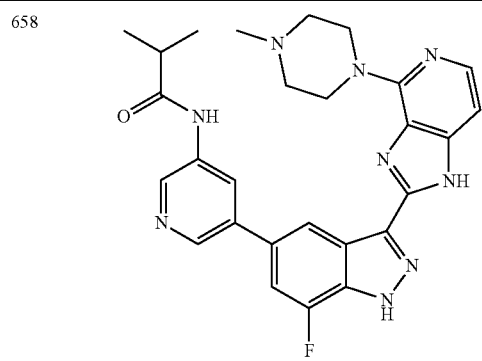
659 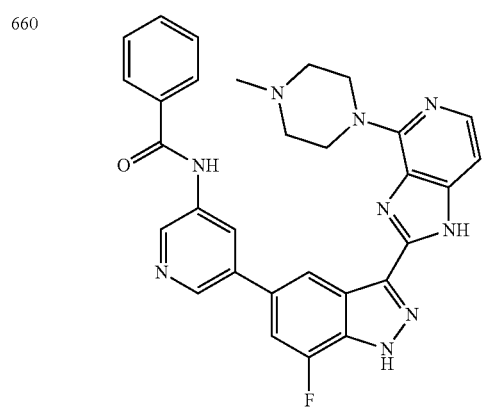
660
661
662 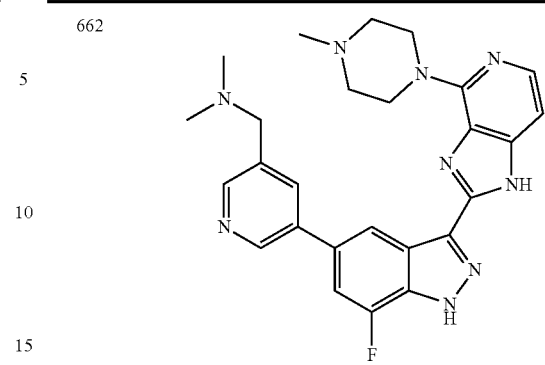
663 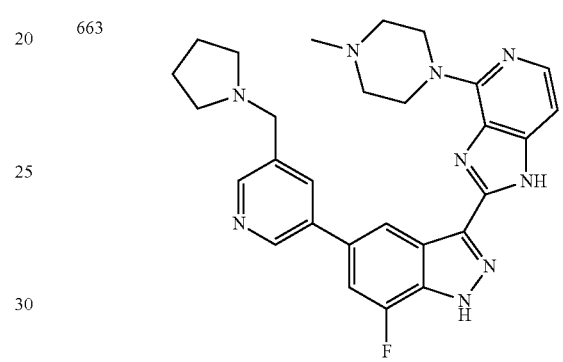
664 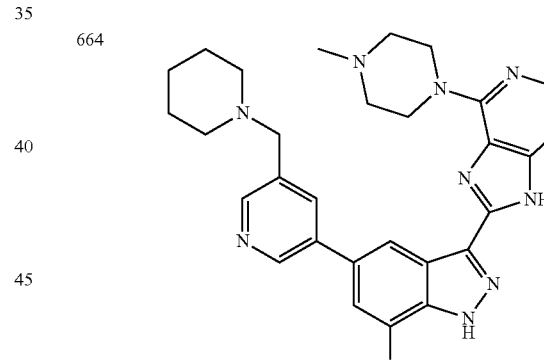
665 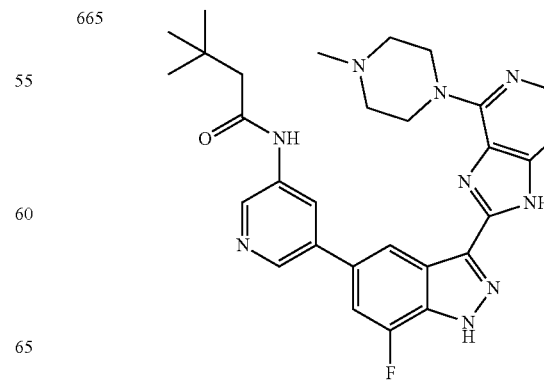

TABLE 1-continued
666 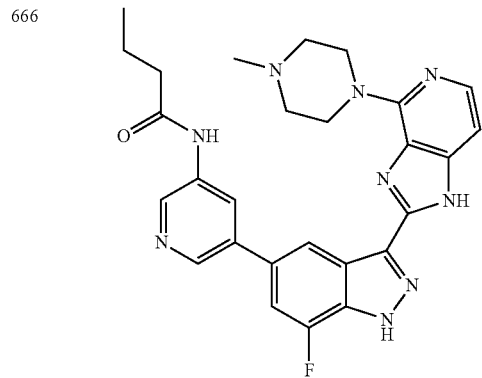
667 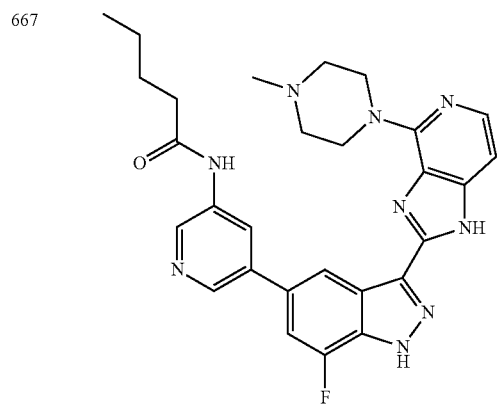
668 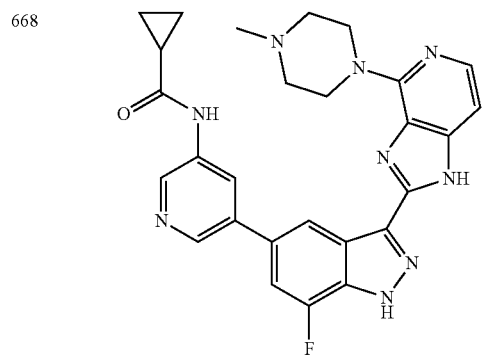
669 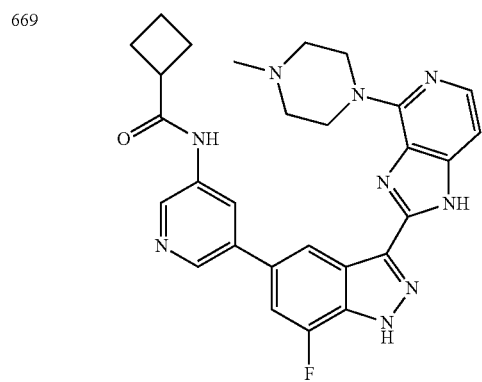
TABLE 1-continued
670 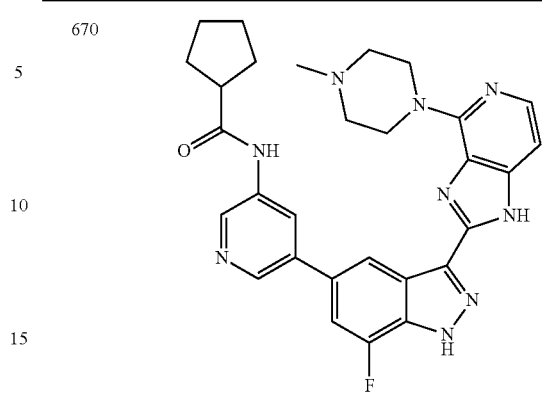
671 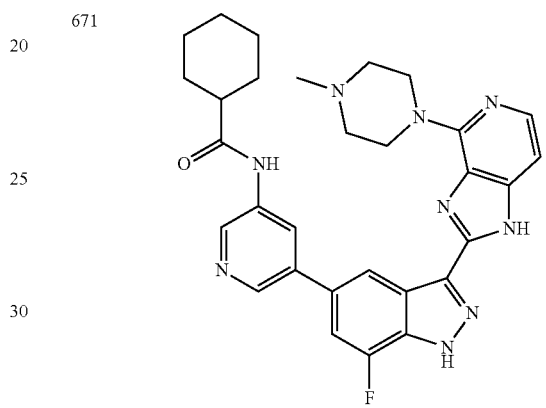
672 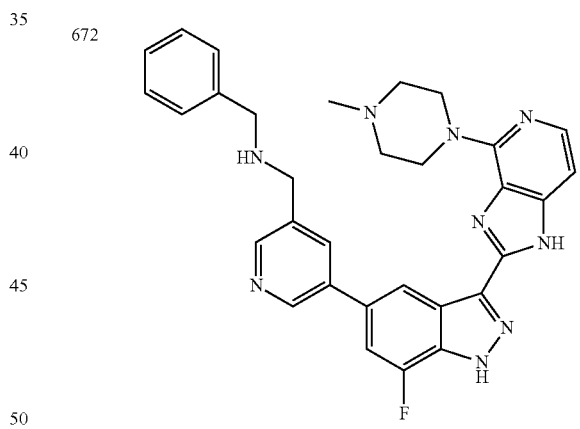
673 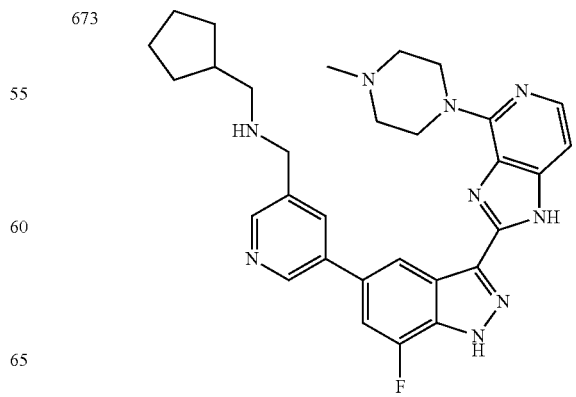

TABLE 1-continued
| 674 | 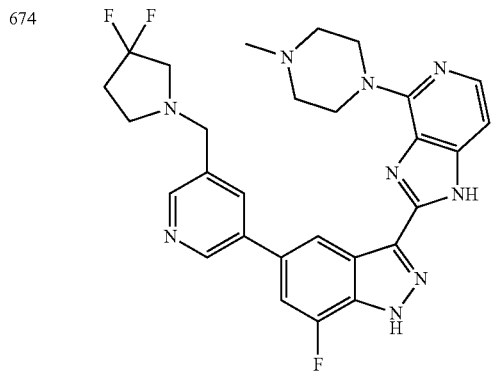 | 678 | 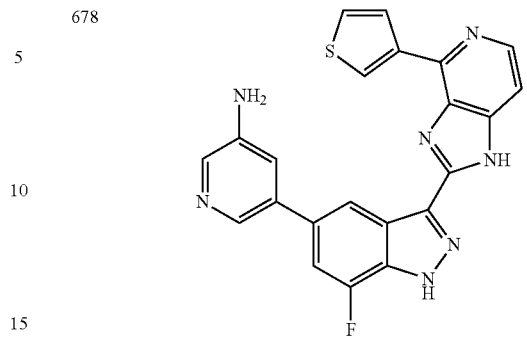 |
| 675 | 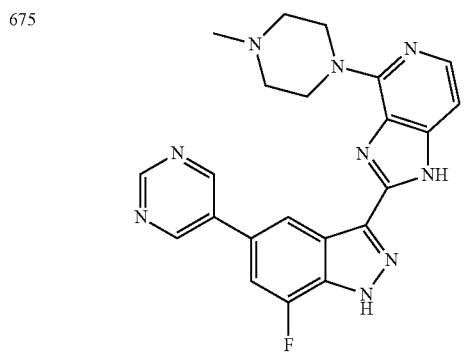 | 679 | 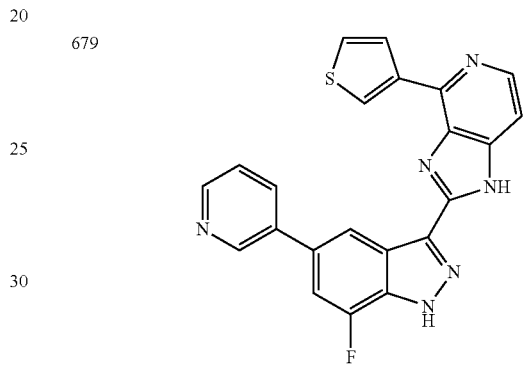 |
| 676 | 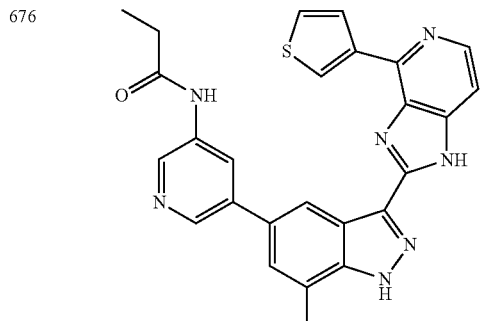 | 680 | 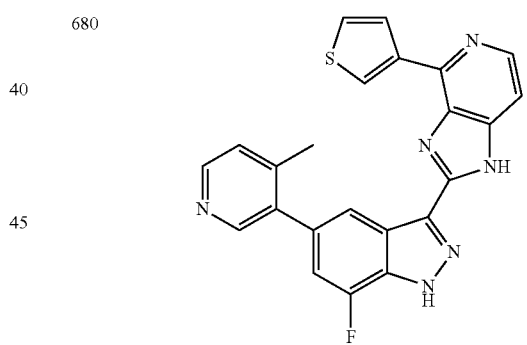 |
| 677 | 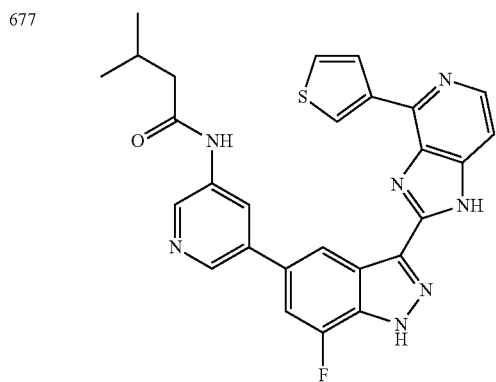 | 681 | 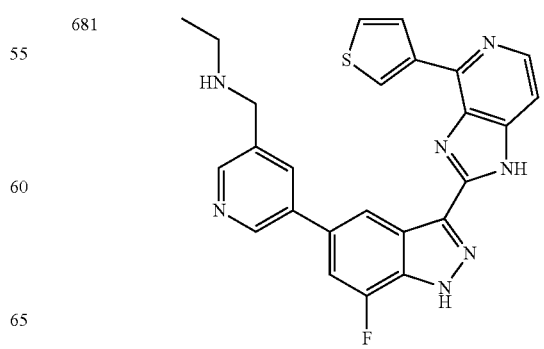 |

TABLE 1-continued
682 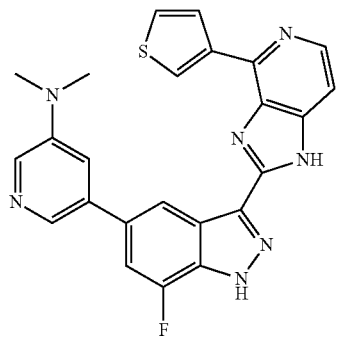
683 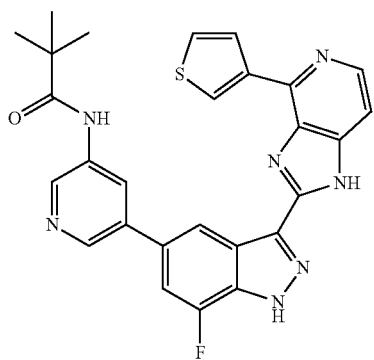 [SMILES: CC(C)(C)C(=O)Nc1cncc(-c2cc(F)c3[nH]nc(-c4nc5c(-c6ccsc6)nccc5[nH]4)c3c2)c1]
684 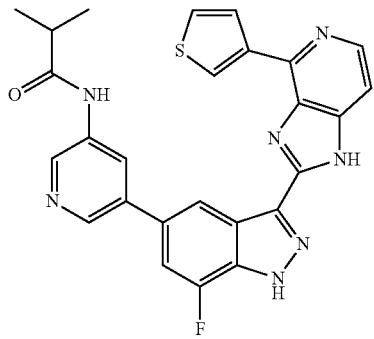 [SMILES: CC(C)C(=O)Nc1cncc(-c2cc(F)c3[nH]nc(-c4nc5c(-c6ccsc6)nccc5[nH]4)c3c2)c1]
685 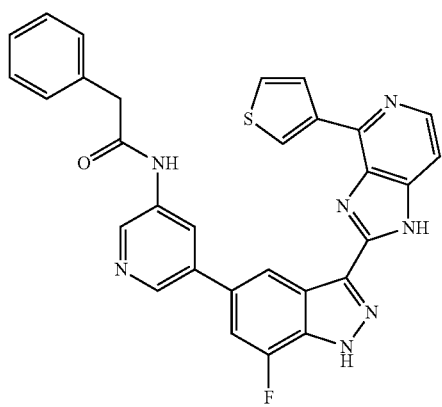
TABLE 1-continued
686 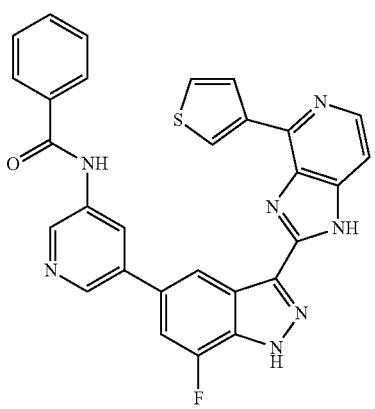
687 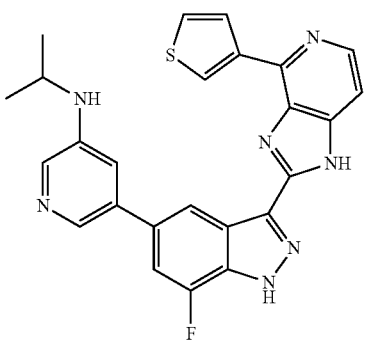
688 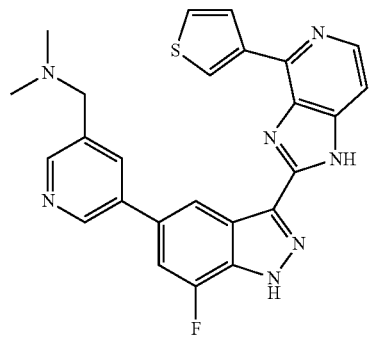
689 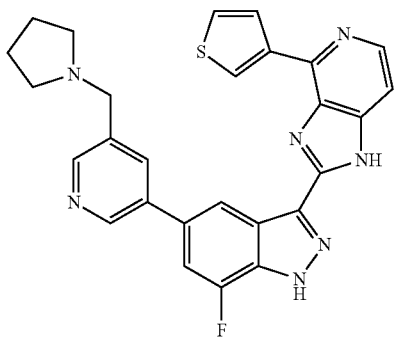 [SMILES: Fc1cc(-c2cncc(CN3CCCC3)c2)cc2c(-c3nc4c(-c5ccsc5)nccc4[nH]3)n[nH]c12]

TABLE 1-continued
690 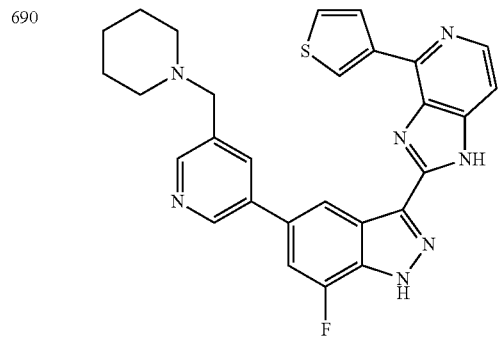
691 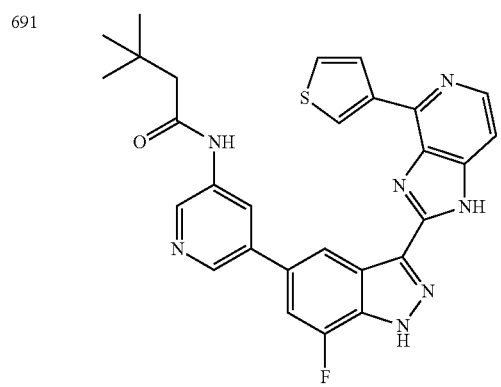
692 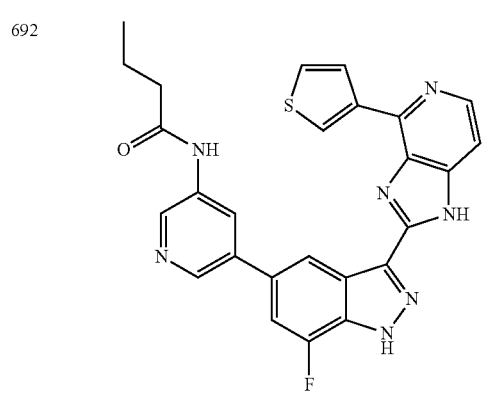
693 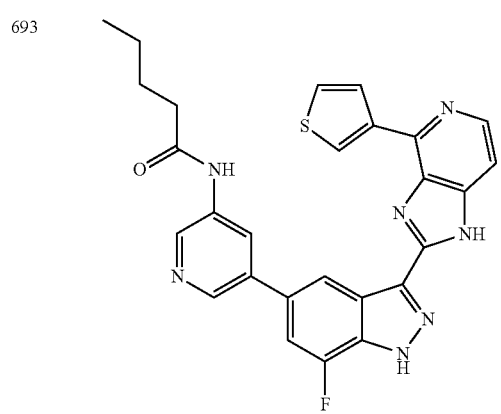
TABLE 1-continued
694 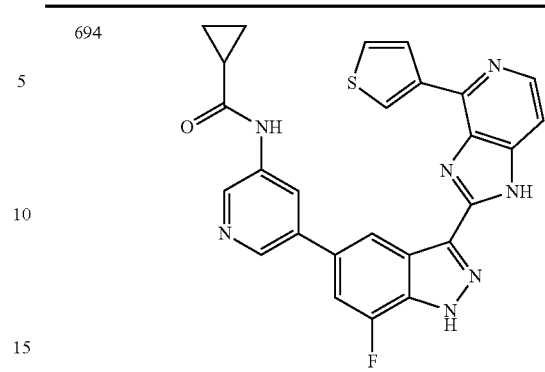
695 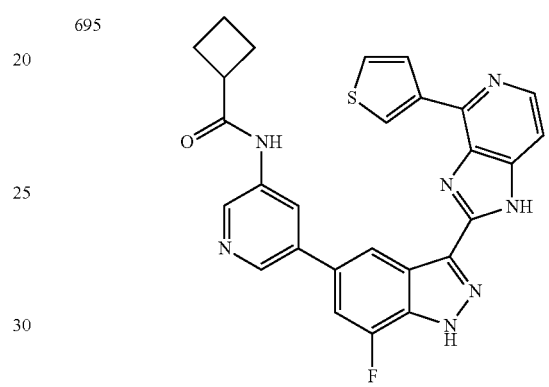
696 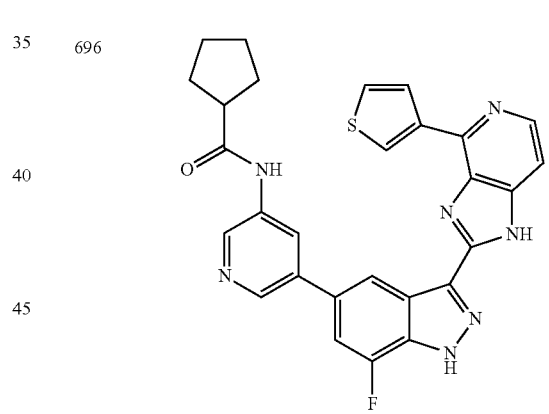
697 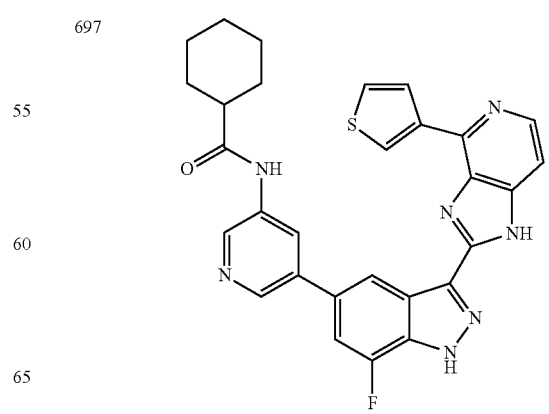

TABLE 1-continued
698 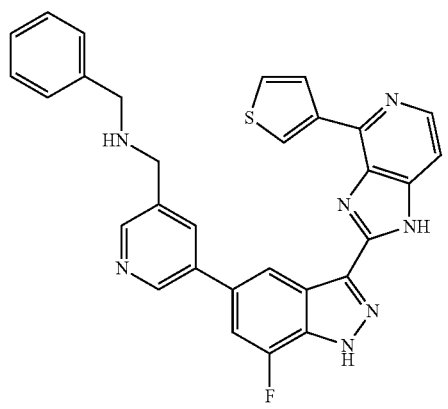 [SMILES: Fc1cc(-c2cncc(CNCc3ccccc3)c2)cc2c(-c3nc4c(-c5ccsc5)nccc4[nH]3)n[nH]c12]
699 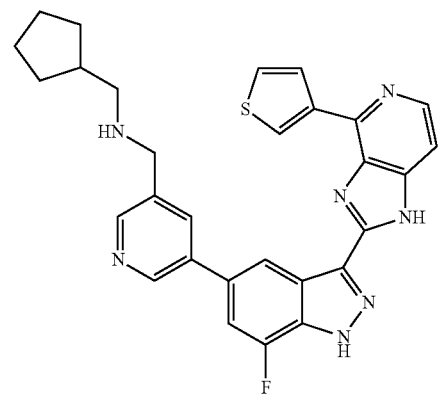 [SMILES: Fc1cc(-c2cncc(CNCC3CCCC3)c2)cc2c(-c3nc4c(-c5ccsc5)nccc4[nH]3)n[nH]c12]
700 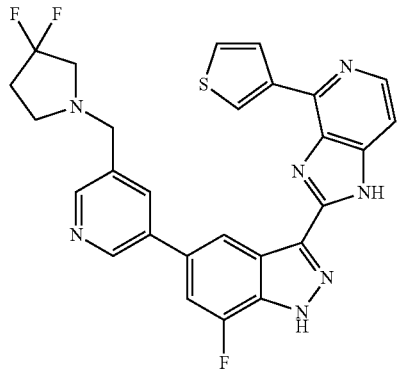
701 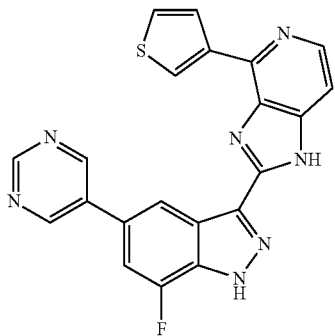
TABLE 1-continued
702 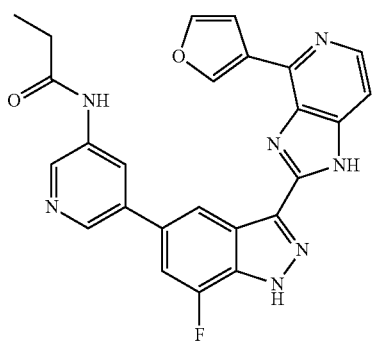 [SMILES: CCC(=O)Nc1cncc(-c2cc(F)c3[nH]nc(-c4nc5c(-c6ccoc6)nccc5[nH]4)c3c2)c1]
703 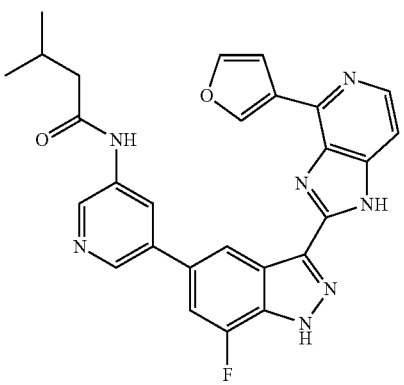
704 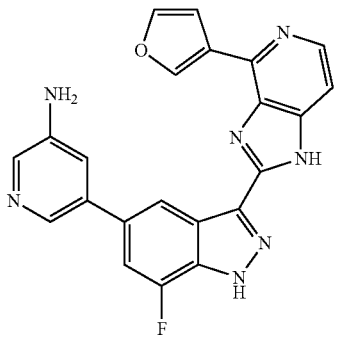 [SMILES: Nc1cncc(-c2cc(F)c3[nH]nc(-c4nc5c(-c6ccoc6)nccc5[nH]4)c3c2)c1]
705 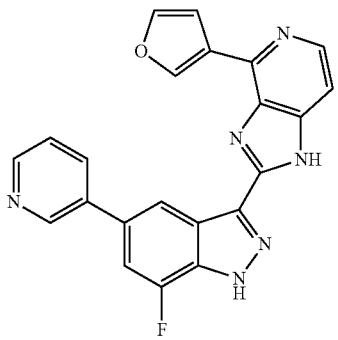 [SMILES: Fc1cc(-c2cccnc2)cc2c(-c3nc4c(-c5ccoc5)nccc4[nH]3)n[nH]c12]

TABLE 1-continued
706 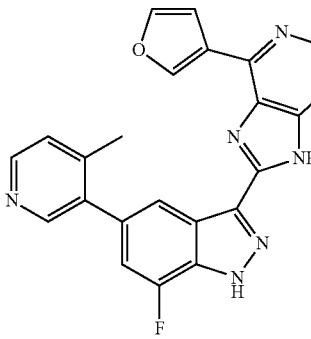
707 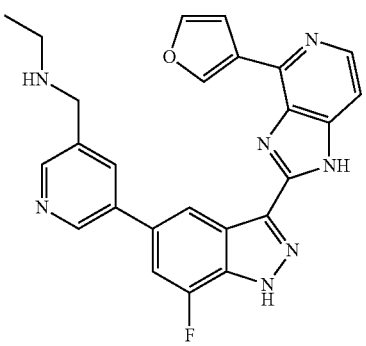
708 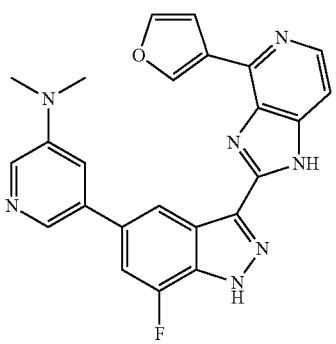
709 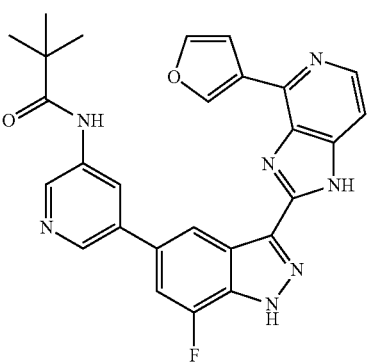 [SMILES: CC(C)(C)C(=O)Nc1cncc(-c2cc(F)c3[nH]nc(-c4nc5c(-c6ccoc6)nccc5[nH]4)c3c2)c1]
710 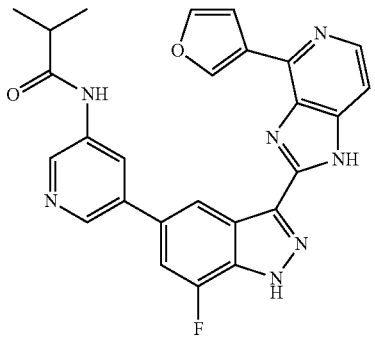 [SMILES: CC(C)C(=O)Nc1cncc(-c2cc(F)c3[nH]nc(-c4nc5c(-c6ccoc6)nccc5[nH]4)c3c2)c1]
711 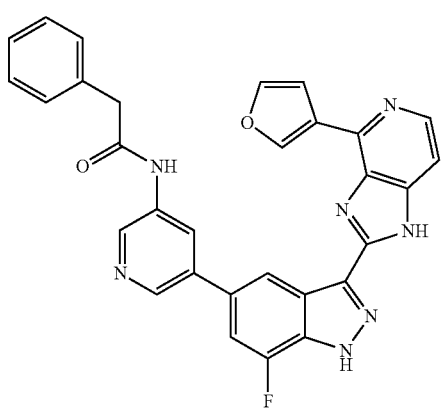 [SMILES: O=C(Cc1ccccc1)Nc1cncc(-c2cc(F)c3[nH]nc(-c4nc5c(-c6ccoc6)nccc5[nH]4)c3c2)c1]
712 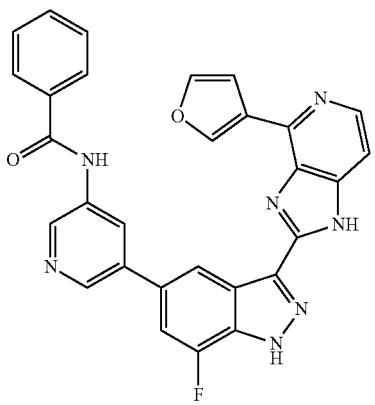 [SMILES: O=C(Nc1cncc(-c2cc(F)c3[nH]nc(-c4nc5c(-c6ccoc6)nccc5[nH]4)c3c2)c1)c1ccccc1]
713 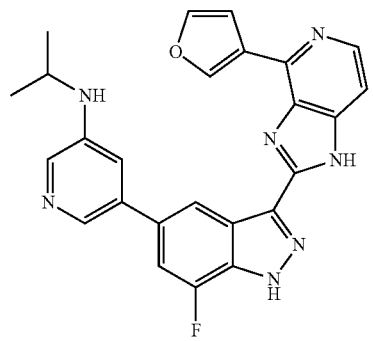 [SMILES: CC(C)Nc1cncc(-c2cc(F)c3[nH]nc(-c4nc5c(-c6ccoc6)nccc5[nH]4)c3c2)c1]

TABLE 1-continued
| 714 | 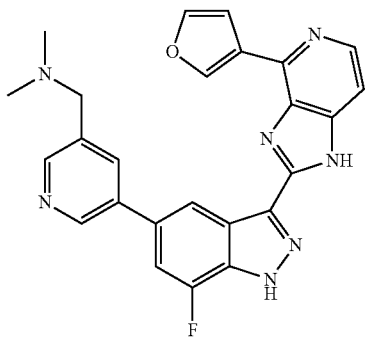 [SMILES: CN(C)Cc1cncc(-c2cc(F)c3[nH]nc(-c4nc5c(-c6ccoc6)nccc5[nH]4)c3c2)c1] |
| --- | --- |
| 715 | 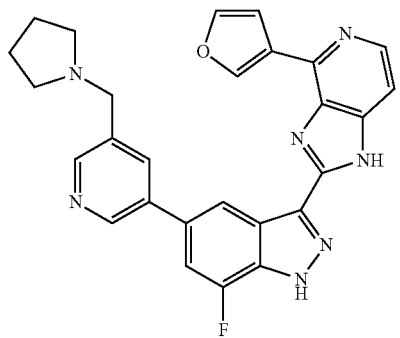 [SMILES: Fc1cc(-c2cncc(CN3CCCC3)c2)cc2c(-c3nc4c(-c5ccoc5)nccc4[nH]3)n[nH]c12] |
| 716 | 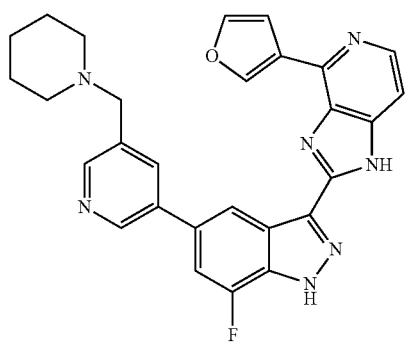 |
| 717 | 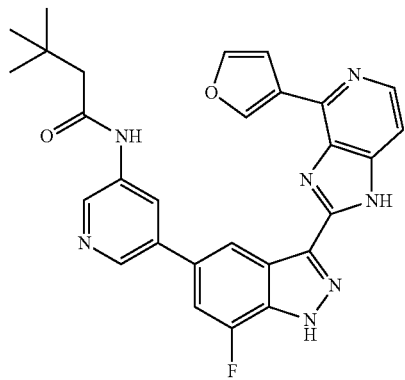 |
TABLE 1-continued
| 718 | 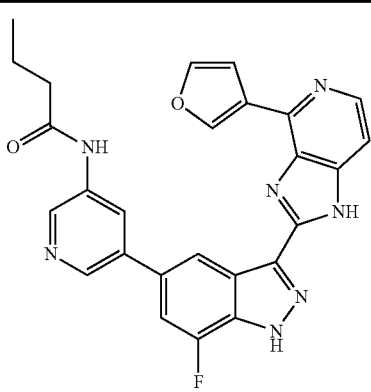 |
| --- | --- |
| 719 | 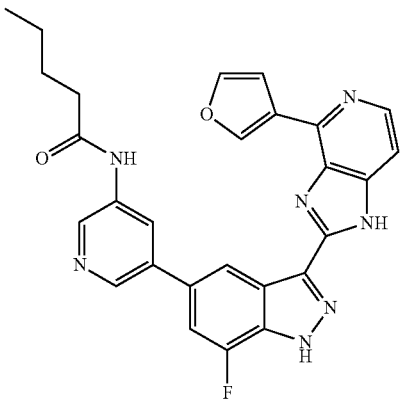 [SMILES: CCCCC(=O)Nc1cncc(-c2cc(F)c3[nH]nc(-c4nc5c(-c6ccoc6)nccc5[nH]4)c3c2)c1] |
| 720 | 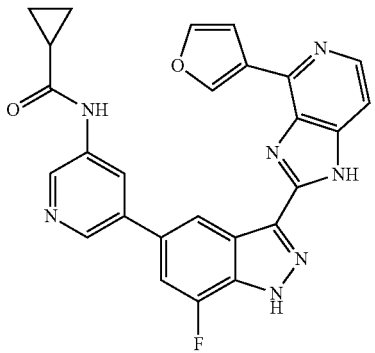 [SMILES: O=C(Nc1cncc(-c2cc(F)c3[nH]nc(-c4nc5c(-c6ccoc6)nccc5[nH]4)c3c2)c1)C1CC1] |
| 721 | 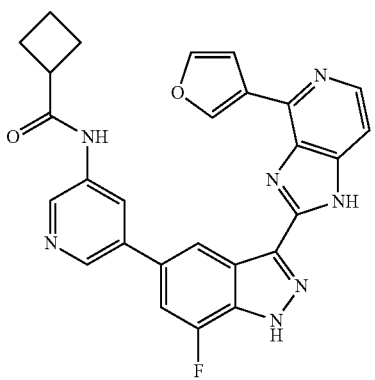 |

TABLE 1-continued
722 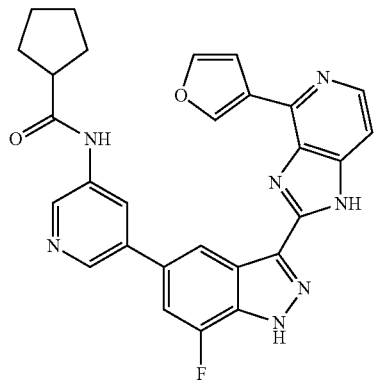 [SMILES: O=C(Nc1cncc(-c2cc(F)c3[nH]nc(-c4nc5c(-c6ccoc6)nccc5[nH]4)c3c2)c1)C1CCCC1]
723 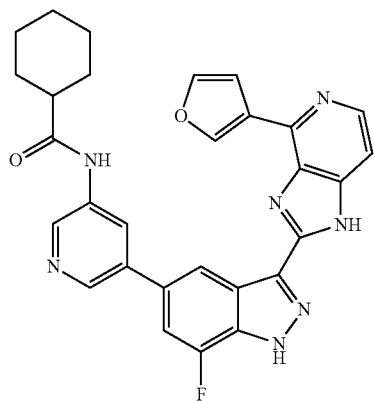 [SMILES: O=C(Nc1cncc(-c2cc(F)c3[nH]nc(-c4nc5c(-c6ccoc6)nccc5[nH]4)c3c2)c1)C1CCCCC1]
724 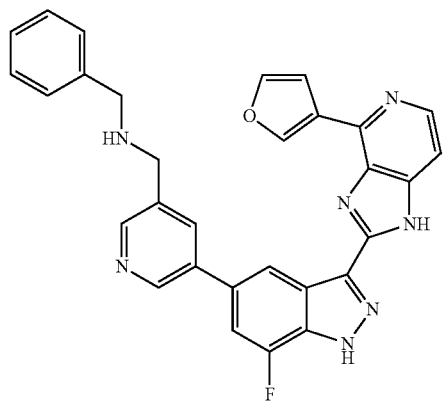 [SMILES: Fc1cc(-c2cncc(CNCc3ccccc3)c2)cc2c(-c3nc4c(-c5ccoc5)nccc4[nH]3)n[nH]c12]
725 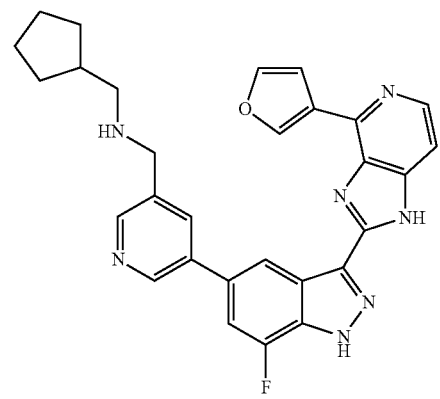 [SMILES: Fc1cc(-c2cncc(CNCC3CCCC3)c2)cc2c(-c3nc4c(-c5ccoc5)nccc4[nH]3)n[nH]c12]
TABLE 1-continued
726 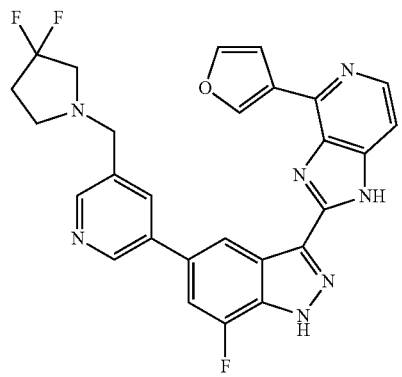 [SMILES: Fc1cc(-c2cncc(CN3CCC(F)(F)C3)c2)cc2c(-c3nc4c(-c5ccoc5)nccc4[nH]3)n[nH]c12]
727 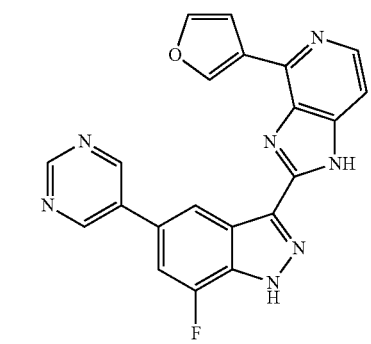 [SMILES: Fc1cc(-c2cncnc2)cc2c(-c3nc4c(-c5ccoc5)nccc4[nH]3)n[nH]c12]
728 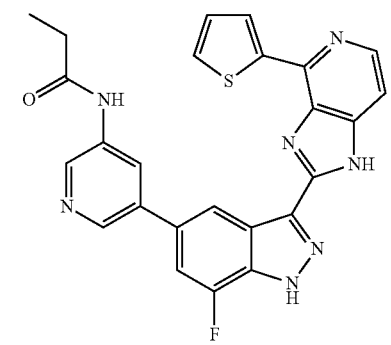 [SMILES: CCC(=O)Nc1cncc(-c2cc(F)c3[nH]nc(-c4nc5c(-c6cccs6)nccc5[nH]4)c3c2)c1]
729 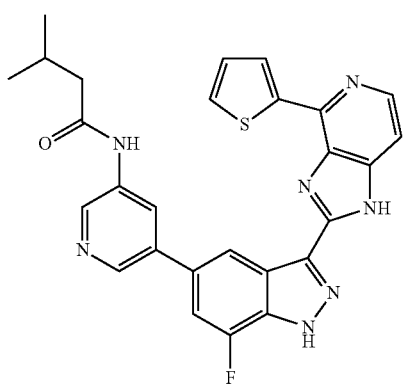 [SMILES: CC(C)CC(=O)Nc1cncc(-c2cc(F)c3[nH]nc(-c4nc5c(-c6cccs6)nccc5[nH]4)c3c2)c1]

TABLE 1-continued
| 730 | 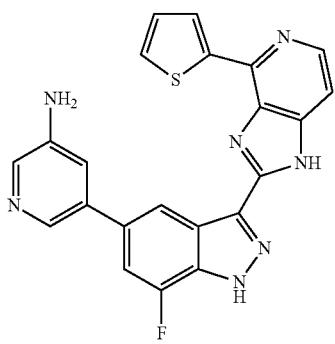 [SMILES: Nc1cncc(-c2cc(F)c3[nH]nc(-c4nc5c(-c6cccs6)nccc5[nH]4)c3c2)c1] |
| --- | --- |
| 731 | 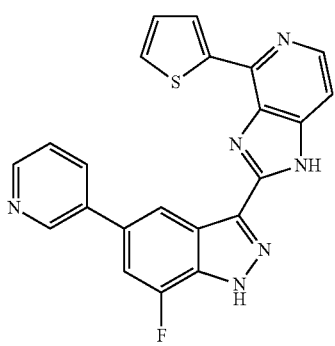 [SMILES: Fc1cc(-c2cccnc2)cc2c(-c3nc4c(-c5cccs5)nccc4[nH]3)n[nH]c12] |
| 732 | 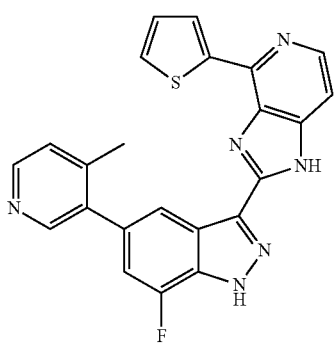 [SMILES: Cc1ccncc1-c1cc(F)c2[nH]nc(-c3nc4c(-c5cccs5)nccc4[nH]3)c2c1] |
| 733 | 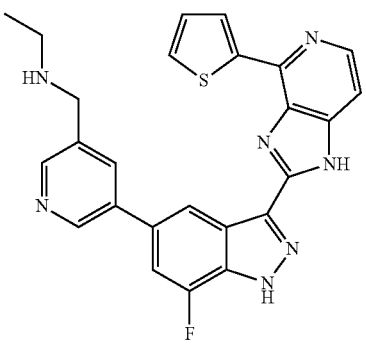 [SMILES: CCNCc1cncc(-c2cc(F)c3[nH]nc(-c4nc5c(-c6cccs6)nccc5[nH]4)c3c2)c1] |
TABLE 1-continued
| 734 | 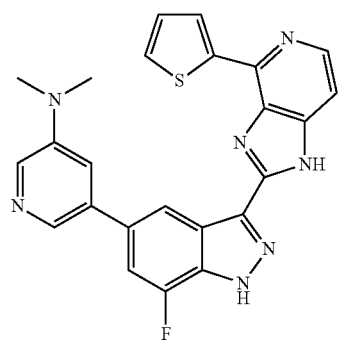 |
| --- | --- |
| 735 | 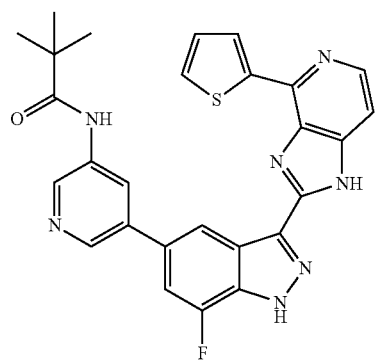 [SMILES: CC(C)(C)C(=O)Nc1cncc(-c2cc(F)c3[nH]nc(-c4nc5c(-c6cccs6)nccc5[nH]4)c3c2)c1] |
| 736 | 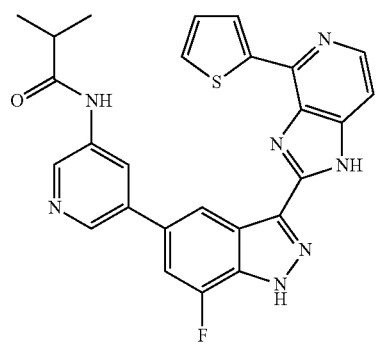 [SMILES: CC(C)C(=O)Nc1cncc(-c2cc(F)c3[nH]nc(-c4nc5c(-c6cccs6)nccc5[nH]4)c3c2)c1] |
| 737 | 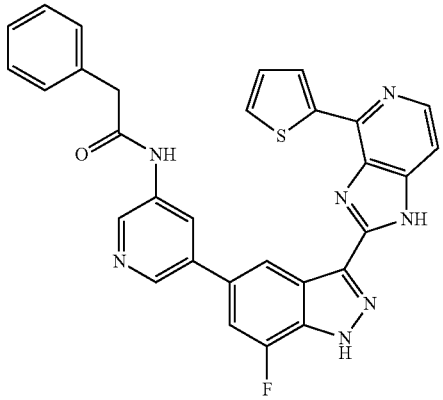 [SMILES: O=C(Cc1ccccc1)Nc1cncc(-c2cc(F)c3[nH]nc(-c4nc5c(-c6cccs6)nccc5[nH]4)c3c2)c1] |

| | |
|---|---|
| 738 | 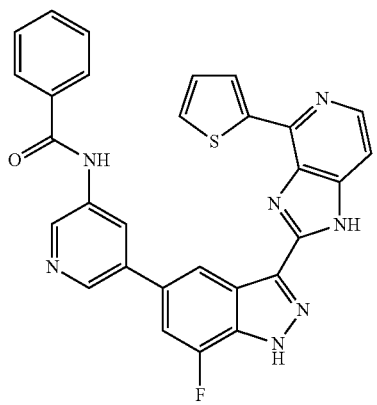 [SMILES: O=C(Nc1cncc(-c2cc(F)c3[nH]nc(-c4nc5c(-c6cccs6)nccc5[nH]4)c3c2)c1)c1ccccc1] |
| 739 | 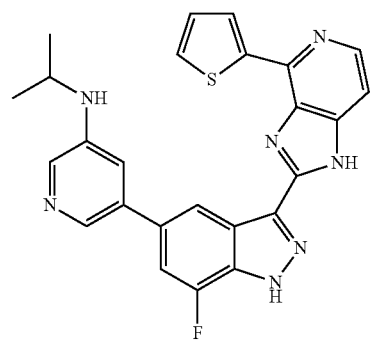 [SMILES: CC(C)Nc1cncc(-c2cc(F)c3[nH]nc(-c4nc5c(-c6cccs6)nccc5[nH]4)c3c2)c1] |
| 740 | 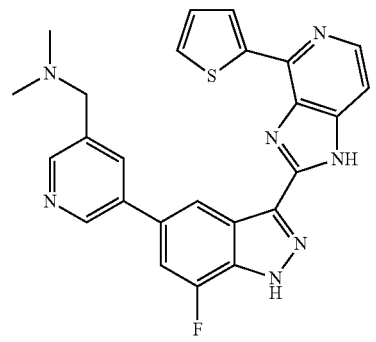 [SMILES: CN(C)Cc1cncc(-c2cc(F)c3[nH]nc(-c4nc5c(-c6cccs6)nccc5[nH]4)c3c2)c1] |
| 741 | 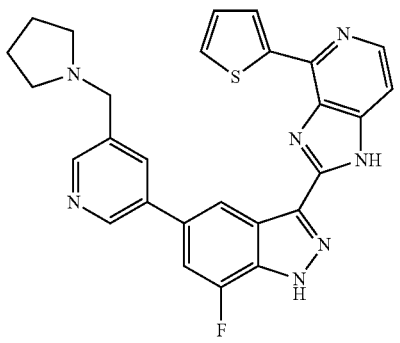 [SMILES: Fc1cc(-c2cncc(CN3CCCC3)c2)cc2c(-c3nc4c(-c5cccs5)nccc4[nH]3)n[nH]c12] |
| 742 | 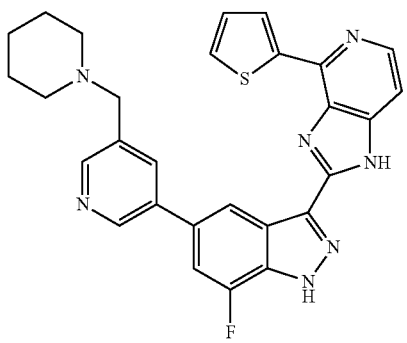 [SMILES: Fc1cc(-c2cncc(CN3CCCCC3)c2)cc2c(-c3nc4c(-c5cccs5)nccc4[nH]3)n[nH]c12] |
| 743 | 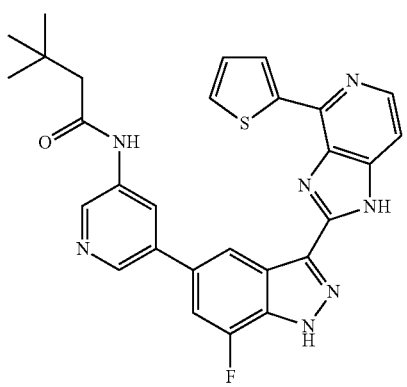 [SMILES: CC(C)(C)CC(=O)Nc1cncc(-c2cc(F)c3[nH]nc(-c4nc5c(-c6cccs6)nccc5[nH]4)c3c2)c1] |
| 744 | 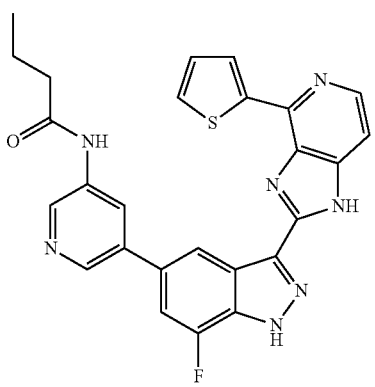 [SMILES: CCCC(=O)Nc1cncc(-c2cc(F)c3[nH]nc(-c4nc5c(-c6cccs6)nccc5[nH]4)c3c2)c1] |
| 745 | 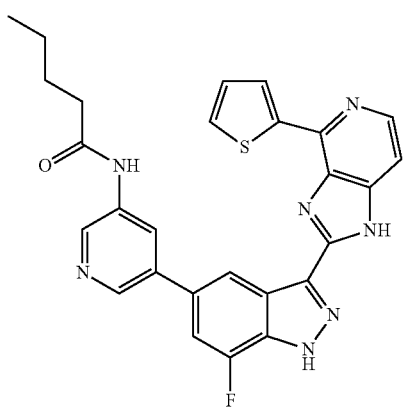 [SMILES: CCCCC(=O)Nc1cncc(-c2cc(F)c3[nH]nc(-c4nc5c(-c6cccs6)nccc5[nH]4)c3c2)c1] |

TABLE 1-continued
| 746 | 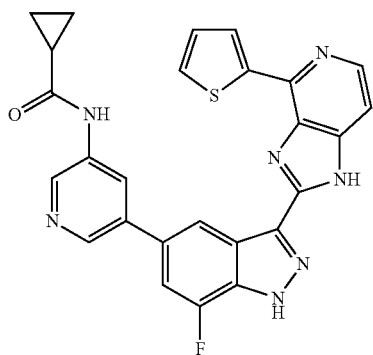 [SMILES: O=C(Nc1cncc(-c2cc(F)c3[nH]nc(-c4nc5c(-c6cccs6)nccc5[nH]4)c3c2)c1)C1CC1] |
| 747 | 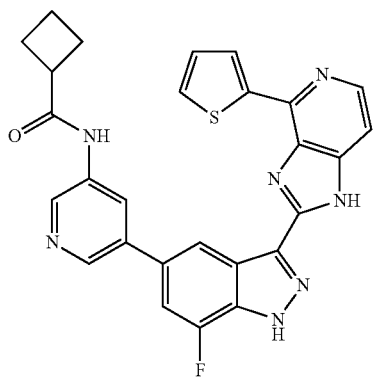 [SMILES: O=C(Nc1cncc(-c2cc(F)c3[nH]nc(-c4nc5c(-c6cccs6)nccc5[nH]4)c3c2)c1)C1CCC1] |
| 748 | 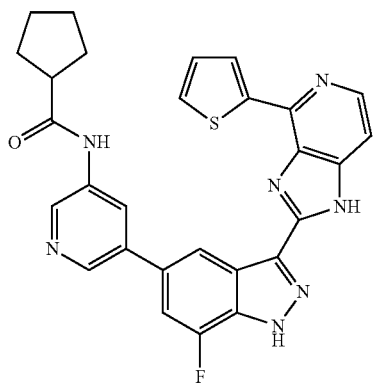 [SMILES: O=C(Nc1cncc(-c2cc(F)c3[nH]nc(-c4nc5c(-c6cccs6)nccc5[nH]4)c3c2)c1)C1CCCC1] |
| 749 | 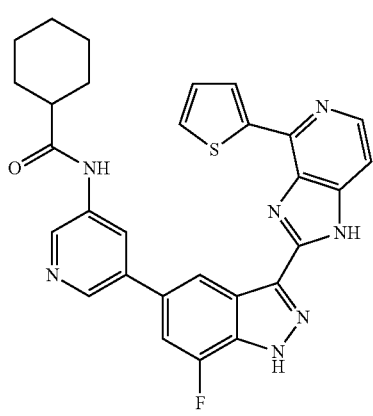 [SMILES: O=C(Nc1cncc(-c2cc(F)c3[nH]nc(-c4nc5c(-c6cccs6)nccc5[nH]4)c3c2)c1)C1CCCCC1] |
| 750 | 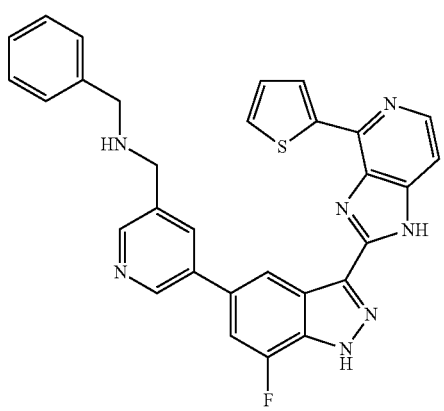 [SMILES: Fc1cc(-c2cncc(CNCc3ccccc3)c2)cc2c(-c3nc4c(-c5cccs5)nccc4[nH]3)n[nH]c12] |
| 751 | 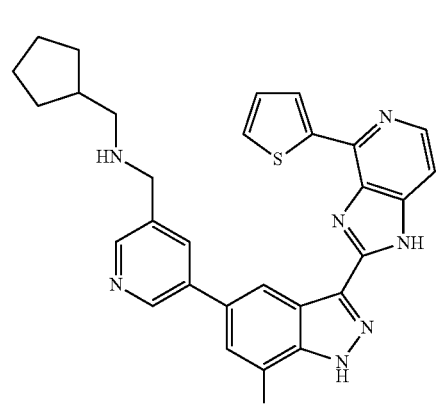 |
| 752 | 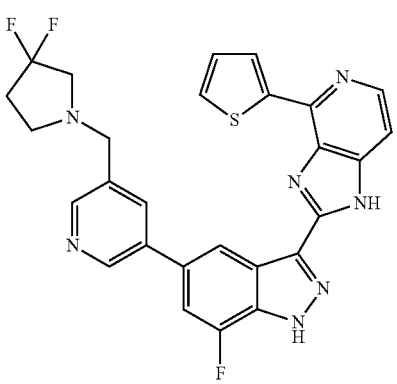 [SMILES: Fc1cc(-c2cncc(CN3CCC(F)(F)C3)c2)cc2c(-c3nc4c(-c5cccs5)nccc4[nH]3)n[nH]c12] |
| 753 | 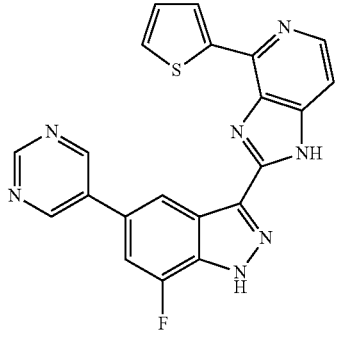 [SMILES: Fc1cc(-c2cncnc2)cc2c(-c3nc4c(-c5cccs5)nccc4[nH]3)n[nH]c12] |

TABLE 1-continued
754 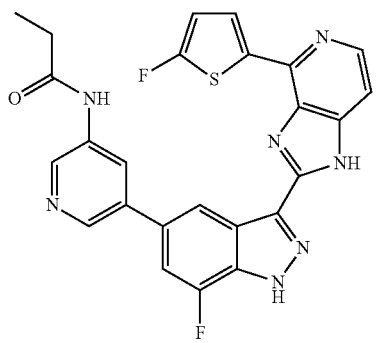 [SMILES: CCC(=O)Nc1cncc(-c2cc(F)c3[nH]nc(-c4nc5c(-c6ccc(F)s6)nccc5[nH]4)c3c2)c1]
755 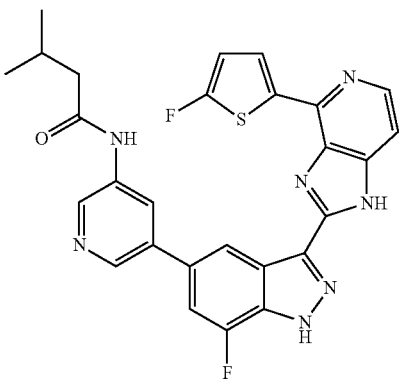
756 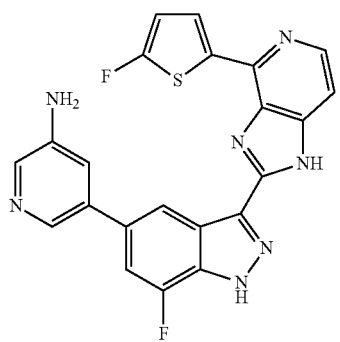 [SMILES: Nc1cncc(-c2cc(F)c3[nH]nc(-c4nc5c(-c6ccc(F)s6)nccc5[nH]4)c3c2)c1]
757 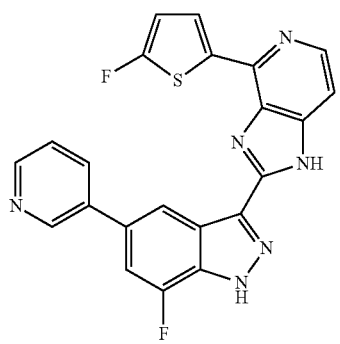 [SMILES: Fc1ccc(-c2nccc3[nH]c(-c4n[nH]c5c(F)cc(-c6cccnc6)cc45)nc23)s1]
TABLE 1-continued
758 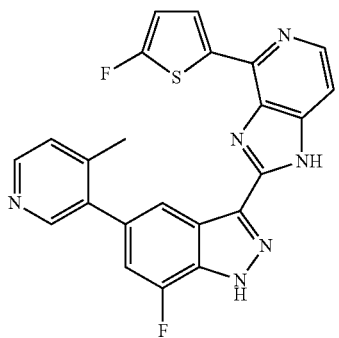 [SMILES: Cc1ccncc1-c1cc(F)c2[nH]nc(-c3nc4c(-c5ccc(F)s5)nccc4[nH]3)c2c1]
759 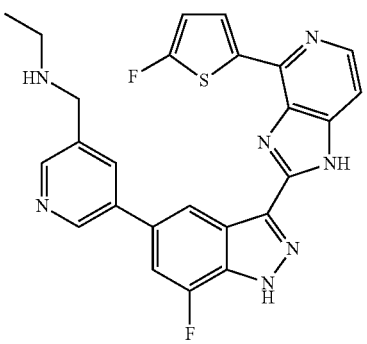
760 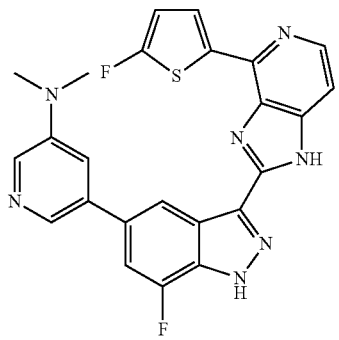
761 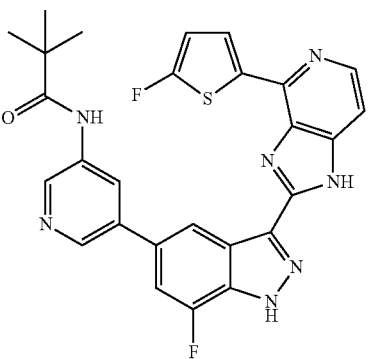 [SMILES: CC(C)(C)C(=O)Nc1cncc(-c2cc(F)c3[nH]nc(-c4nc5c(-c6ccc(F)s6)nccc5[nH]4)c3c2)c1]

TABLE 1-continued
| 762 | 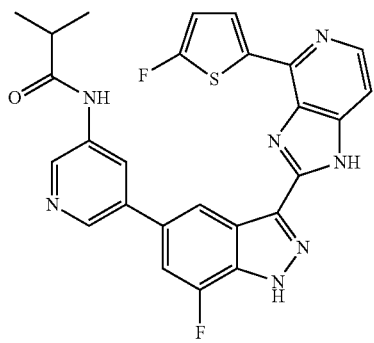 |
| 763 | 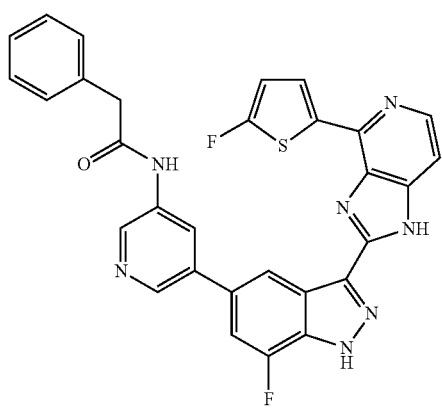 [SMILES: O=C(Cc1ccccc1)Nc1cncc(-c2cc(F)c3[nH]nc(-c4nc5c(-c6ccc(F)s6)nccc5[nH]4)c3c2)c1] |
| 764 | 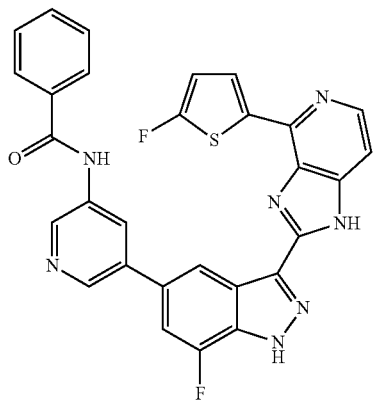 |
| 765 | 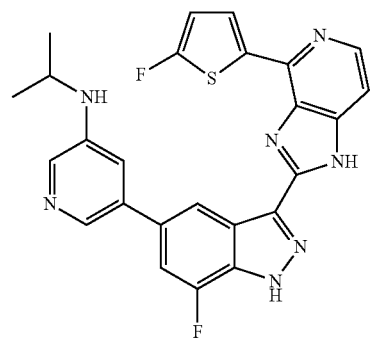 [SMILES: CC(C)Nc1cncc(-c2cc(F)c3[nH]nc(-c4nc5c(-c6ccc(F)s6)nccc5[nH]4)c3c2)c1] |
TABLE 1-continued
| 766 | 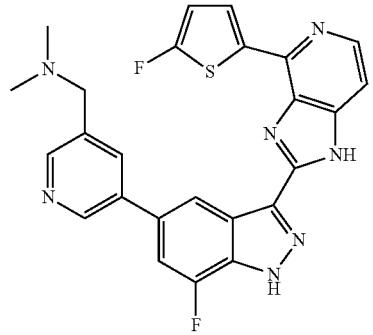 [SMILES: CN(C)Cc1cncc(-c2cc(F)c3[nH]nc(-c4nc5c(-c6ccc(F)s6)nccc5[nH]4)c3c2)c1] |
| 767 | 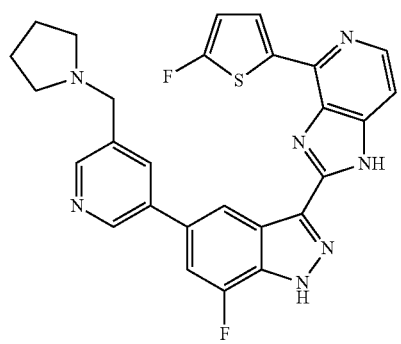 [SMILES: Fc1ccc(-c2nccc3[nH]c(-c4n[nH]c5c(F)cc(-c6cncc(CN7CCCC7)c6)cc45)nc23)s1] |
| 768 | |
| 769 | 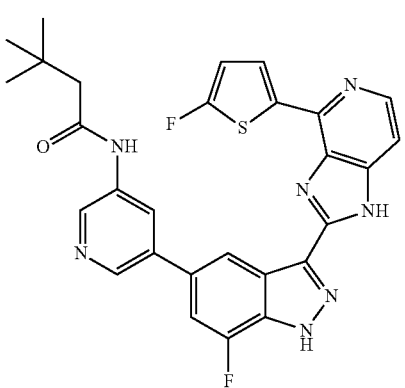 |

TABLE 1-continued
770 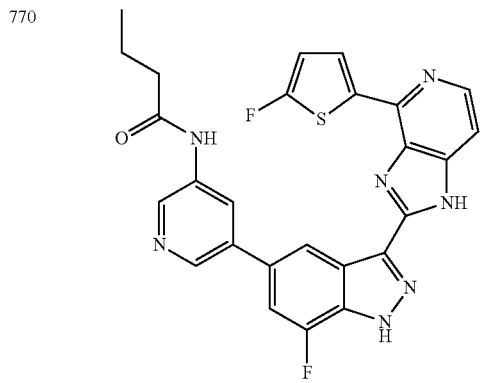
771 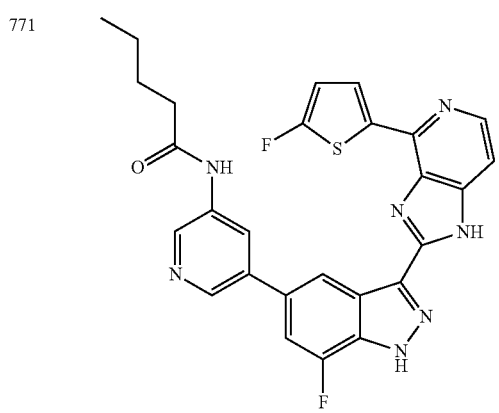
772 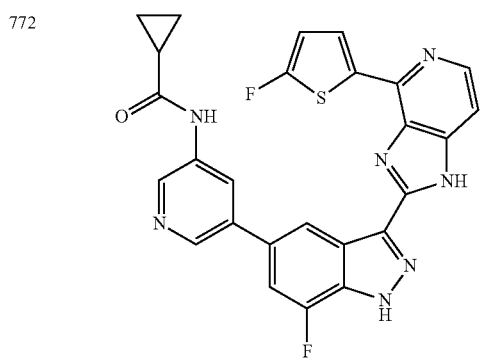
773 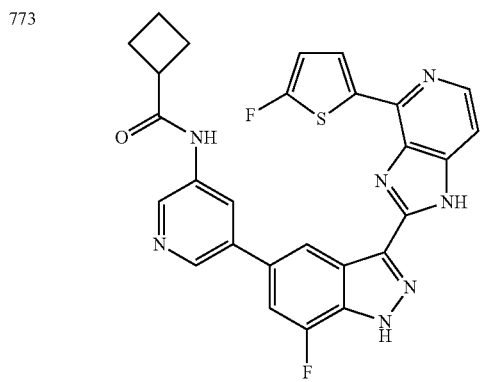
774 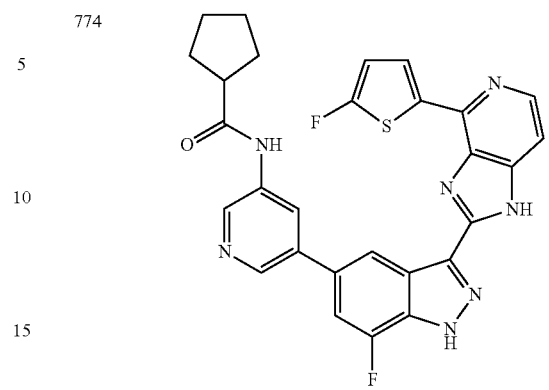
775 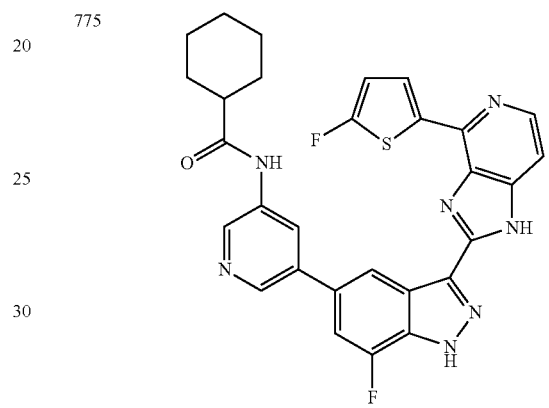
776 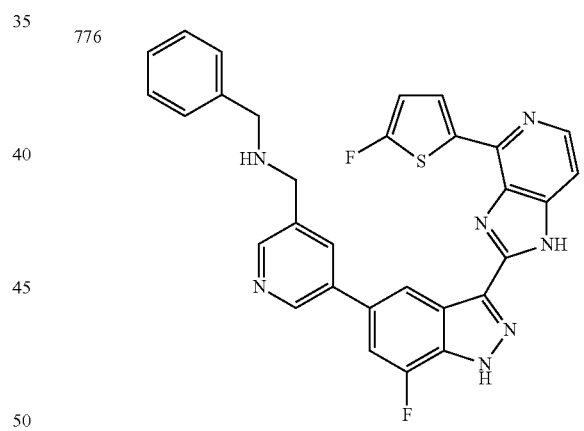
777 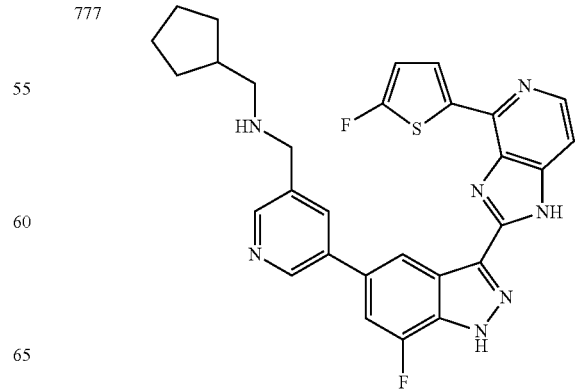

TABLE 1-continued
| | |
|---|---|
| 778 | 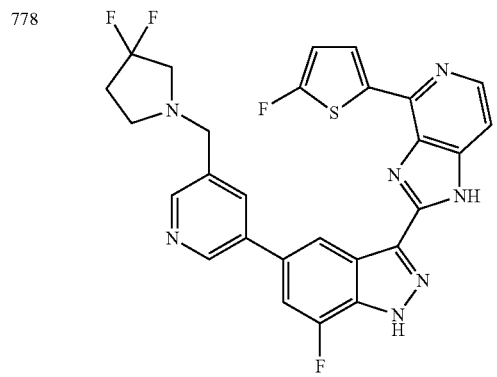 |
| 779 | 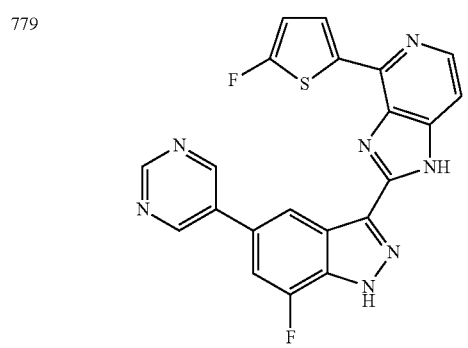 |
| 780 | 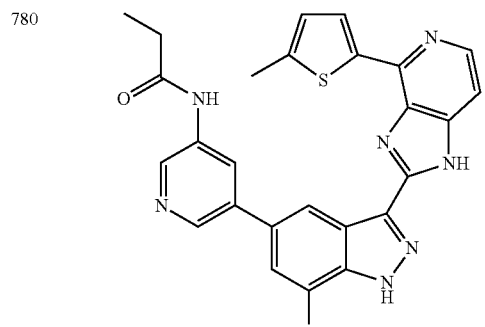 |
| 781 | 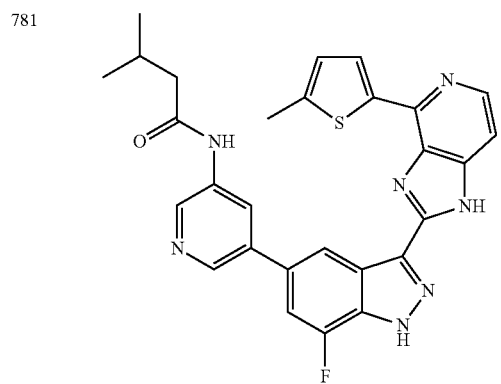 |
| 782 | 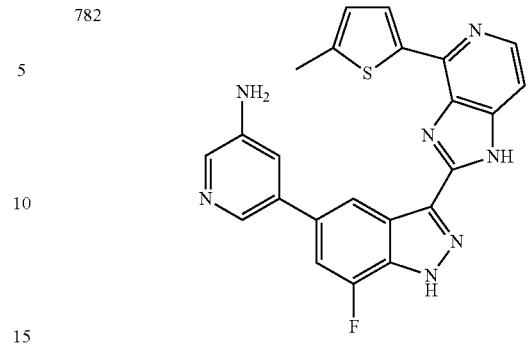 |
| 783 | 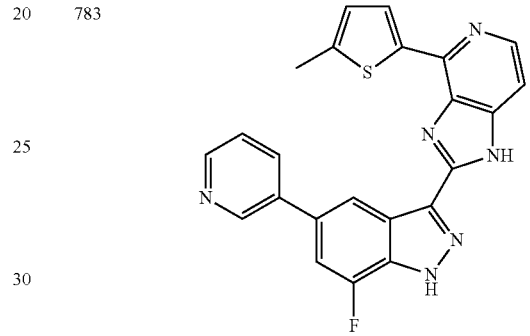 |
| 784 | 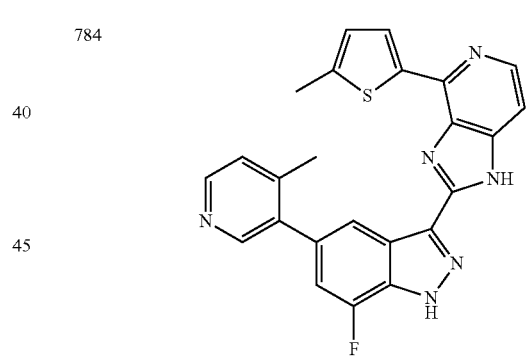 |
| 785 | 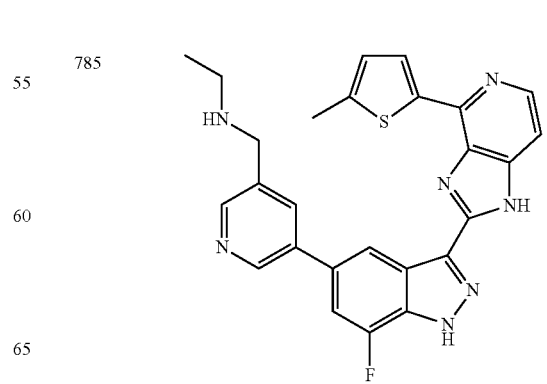 |

US 9,828,372 B2
TABLE 1-continued
786 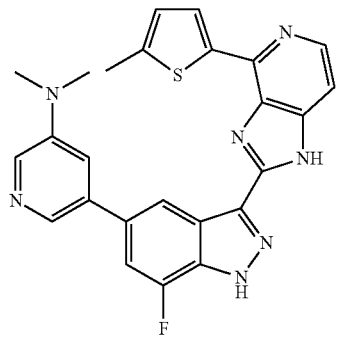
787 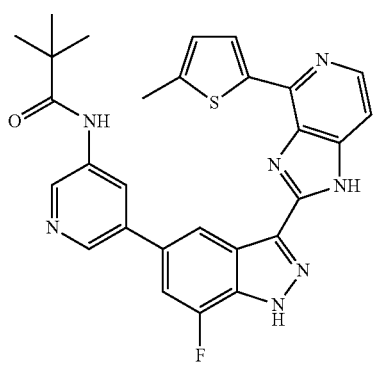 [SMILES: Cc1ccc(-c2nccc3[nH]c(-c4n[nH]c5c(F)cc(-c6cncc(NC(=O)C(C)(C)C)c6)cc45)nc23)s1]
788 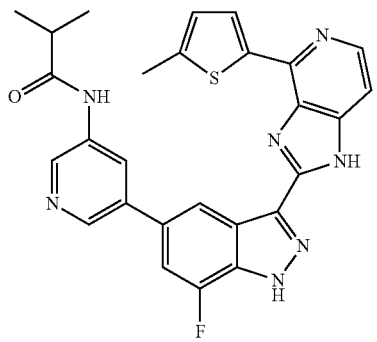 [SMILES: Cc1ccc(-c2nccc3[nH]c(-c4n[nH]c5c(F)cc(-c6cncc(NC(=O)C(C)C)c6)cc45)nc23)s1]
789 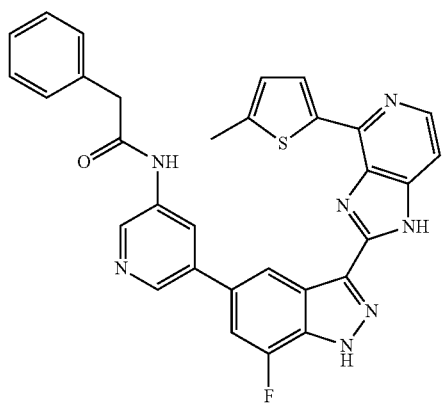
TABLE 1-continued
790 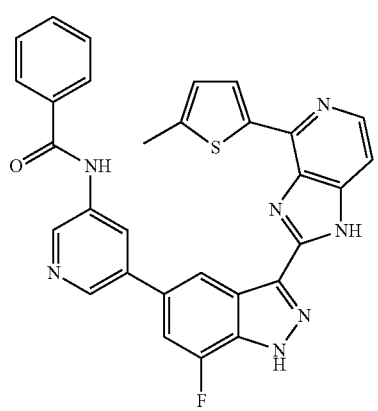 [SMILES: Cc1ccc(-c2nccc3[nH]c(-c4n[nH]c5c(F)cc(-c6cncc(NC(=O)c7ccccc7)c6)cc45)nc23)s1]
791 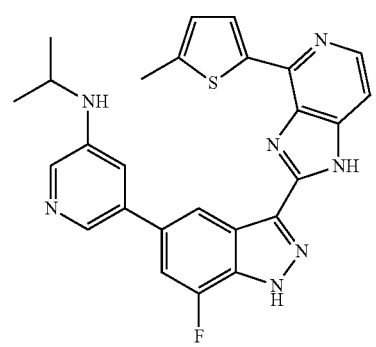
792 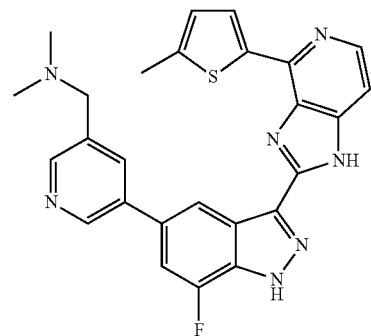 [SMILES: Cc1ccc(-c2nccc3[nH]c(-c4n[nH]c5c(F)cc(-c6cncc(CN(C)C)c6)cc45)nc23)s1]
793 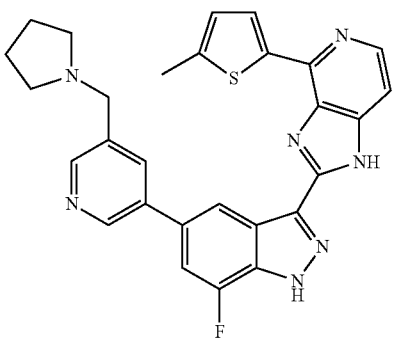 [SMILES: Cc1ccc(-c2nccc3[nH]c(-c4n[nH]c5c(F)cc(-c6cncc(CN7CCCC7)c6)cc45)nc23)s1]

TABLE 1-continued
794 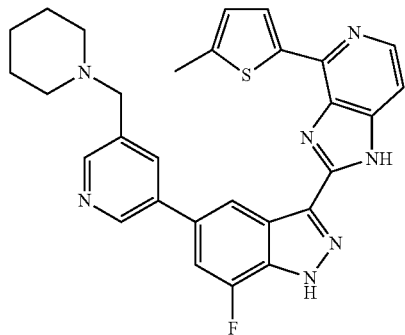
795 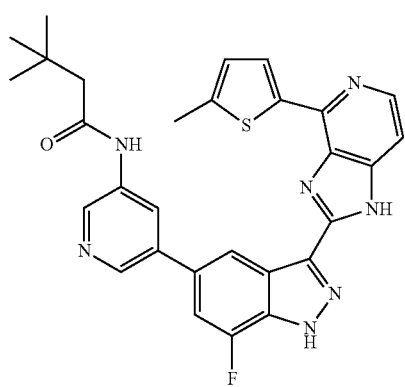 [SMILES: Cc1ccc(-c2nccc3[nH]c(-c4n[nH]c5c(F)cc(-c6cncc(NC(=O)CC(C)(C)C)c6)cc45)nc23)s1]
796 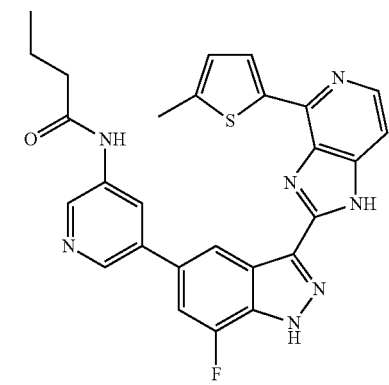 [SMILES: CCCC(=O)Nc1cncc(-c2cc(F)c3[nH]nc(-c4nc5c(-c6ccc(C)s6)nccc5[nH]4)c3c2)c1]
797 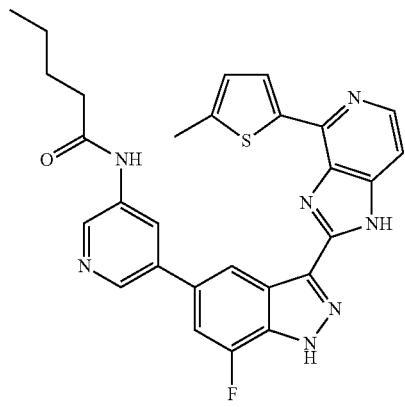
798 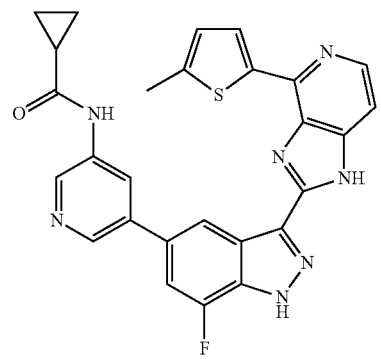 [SMILES: Cc1ccc(-c2nccc3[nH]c(-c4n[nH]c5c(F)cc(-c6cncc(NC(=O)C7CC7)c6)cc45)nc23)s1]
799 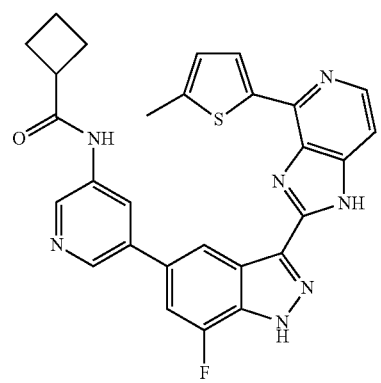 [SMILES: Cc1ccc(-c2nccc3[nH]c(-c4n[nH]c5c(F)cc(-c6cncc(NC(=O)C7CCC7)c6)cc45)nc23)s1]
800 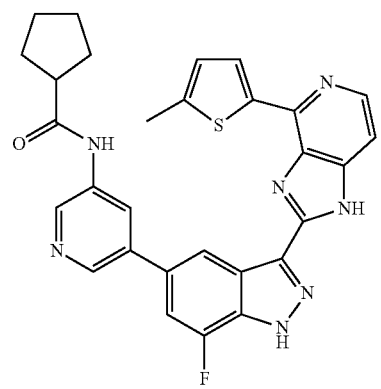 [SMILES: Cc1ccc(-c2nccc3[nH]c(-c4n[nH]c5c(F)cc(-c6cncc(NC(=O)C7CCCC7)c6)cc45)nc23)s1]
801 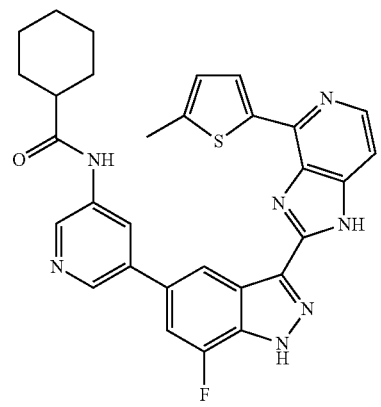 [SMILES: Cc1ccc(-c2nccc3[nH]c(-c4n[nH]c5c(F)cc(-c6cncc(NC(=O)C7CCCCC7)c6)cc45)nc23)s1]

TABLE 1-continued
802 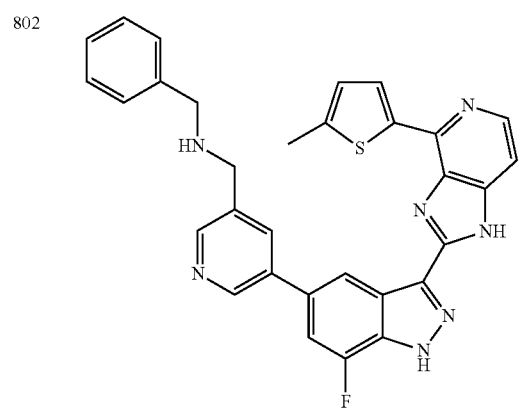
803 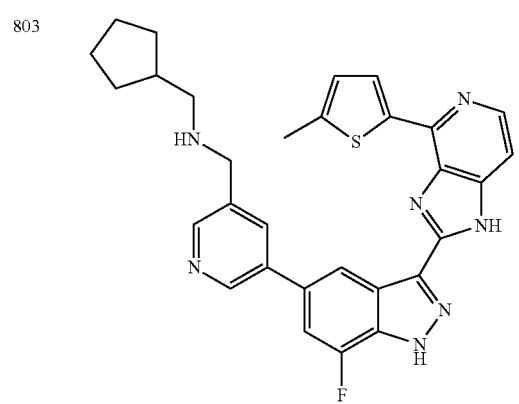
804 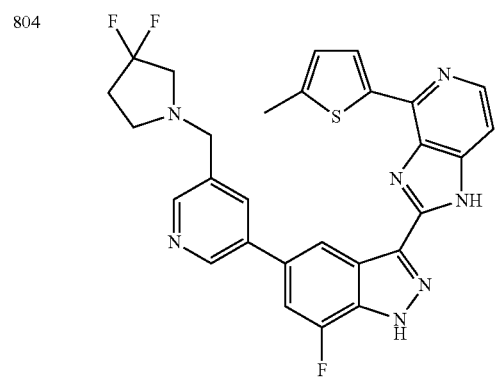
805 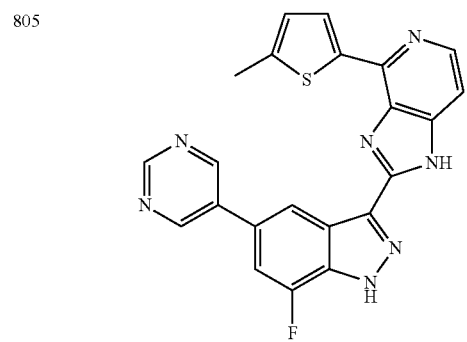
TABLE 1-continued
806 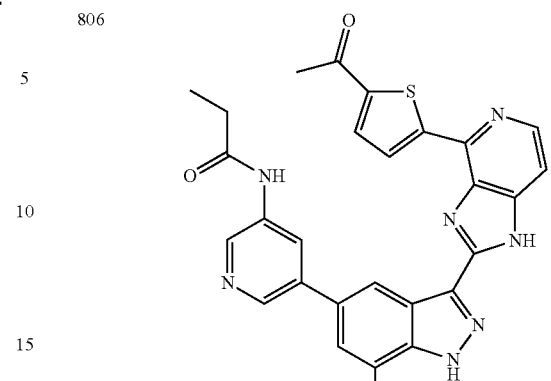
807 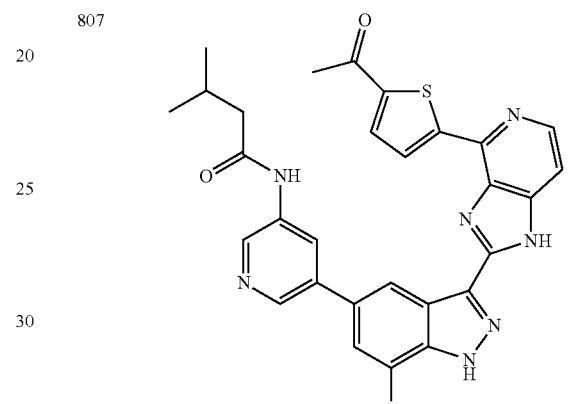
808 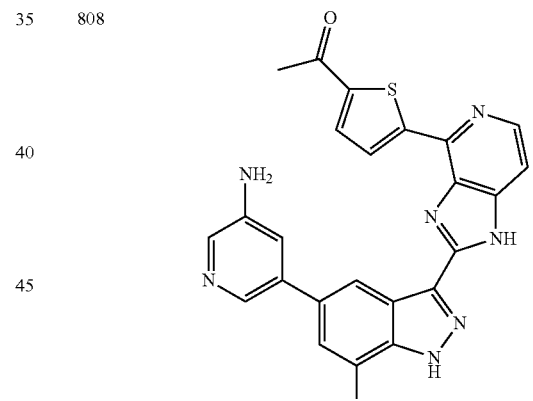
809 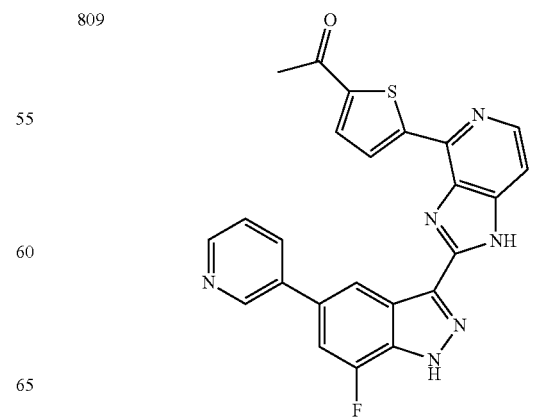

TABLE 1-continued
| 810 | 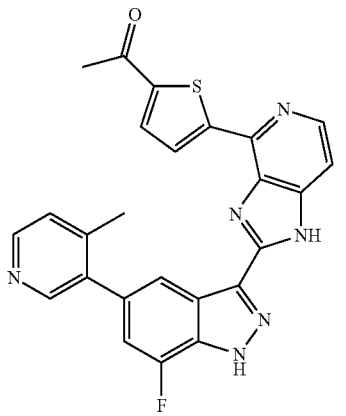 [SMILES: CC(=O)c1ccc(-c2nccc3[nH]c(-c4n[nH]c5c(F)cc(-c6cnccc6C)cc45)nc23)s1] |
| 811 | 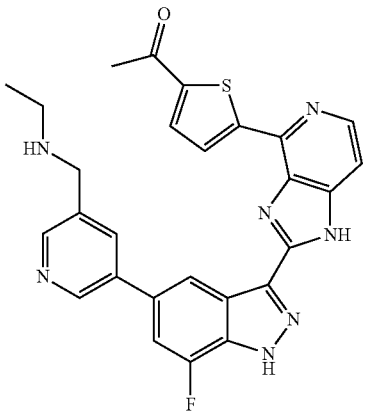 [SMILES: CCNCc1cncc(-c2cc(F)c3[nH]nc(-c4nc5c(-c6ccc(C(C)=O)s6)nccc5[nH]4)c3c2)c1] |
| 812 | 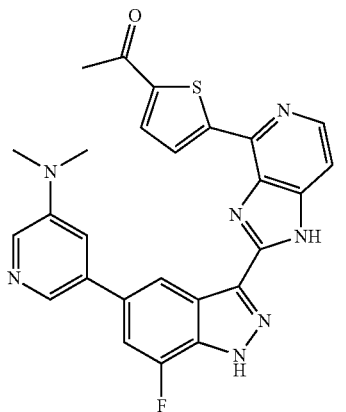 [SMILES: CC(=O)c1ccc(-c2nccc3[nH]c(-c4n[nH]c5c(F)cc(-c6cncc(N(C)C)c6)cc45)nc23)s1] |
| 813 | 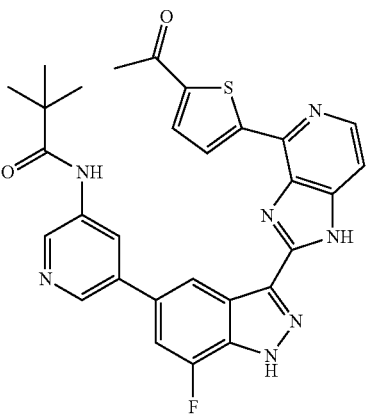 [SMILES: CC(=O)c1ccc(-c2nccc3[nH]c(-c4n[nH]c5c(F)cc(-c6cncc(NC(=O)C(C)(C)C)c6)cc45)nc23)s1] |
| 814 | 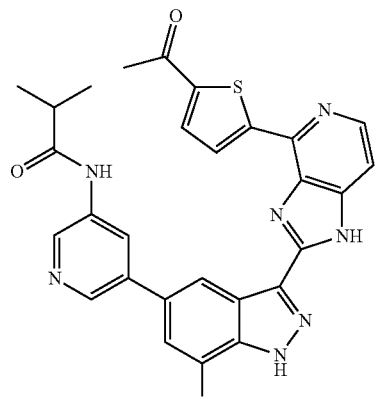 |
| 815 | 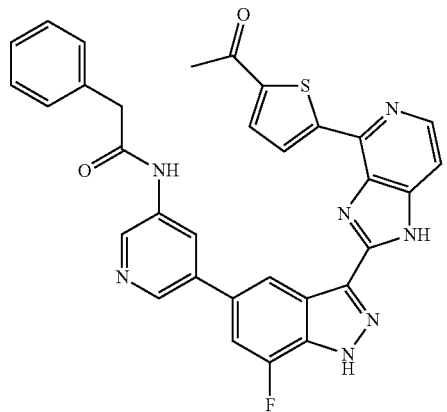 [SMILES: CC(=O)c1ccc(-c2nccc3[nH]c(-c4n[nH]c5c(F)cc(-c6cncc(NC(=O)Cc7ccccc7)c6)cc45)nc23)s1] |
| 816 | 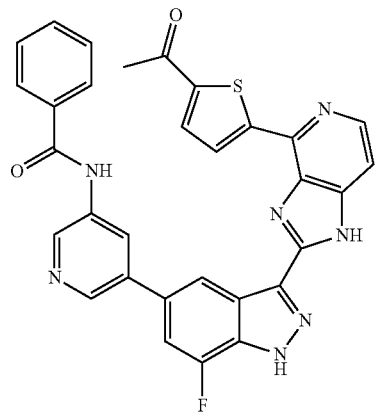 [SMILES: CC(=O)c1ccc(-c2nccc3[nH]c(-c4n[nH]c5c(F)cc(-c6cncc(NC(=O)c7ccccc7)c6)cc45)nc23)s1] |
| 817 | 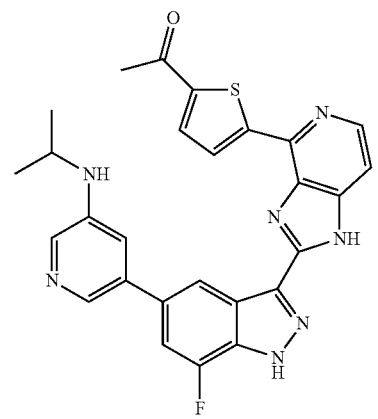 [SMILES: CC(=O)c1ccc(-c2nccc3[nH]c(-c4n[nH]c5c(F)cc(-c6cncc(NC(C)C)c6)cc45)nc23)s1] |

TABLE 1-continued
| 818 | 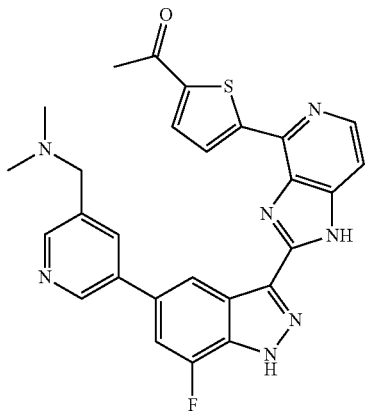 [SMILES: CC(=O)c1ccc(-c2nccc3[nH]c(-c4n[nH]c5c(F)cc(-c6cncc(CN(C)C)c6)cc45)nc23)s1] |
| 819 | 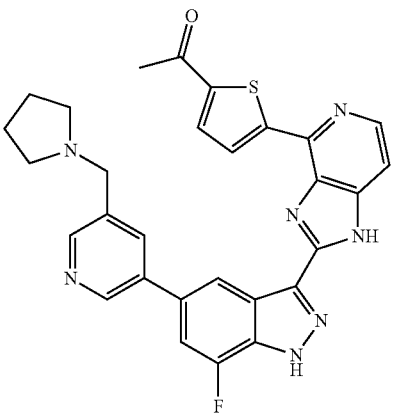 [SMILES: CC(=O)c1ccc(-c2nccc3[nH]c(-c4n[nH]c5c(F)cc(-c6cncc(CN7CCCC7)c6)cc45)nc23)s1] |
| 820 | 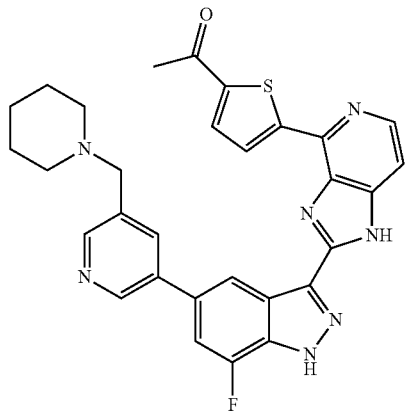 [SMILES: CC(=O)c1ccc(-c2nccc3[nH]c(-c4n[nH]c5c(F)cc(-c6cncc(CN7CCCCC7)c6)cc45)nc23)s1] |
| 821 | 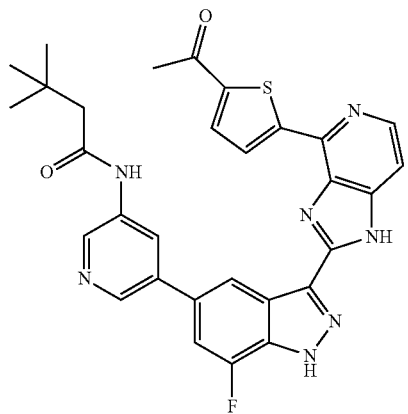 [SMILES: CC(=O)c1ccc(-c2nccc3[nH]c(-c4n[nH]c5c(F)cc(-c6cncc(NC(=O)CC(C)(C)C)c6)cc45)nc23)s1] |
TABLE 1-continued
| 822 | 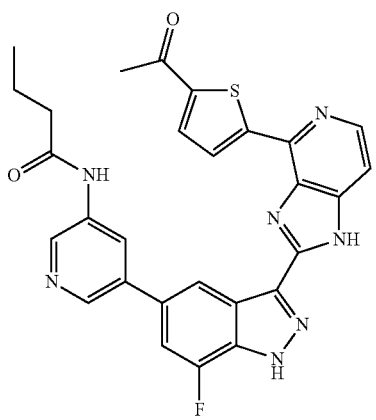 [SMILES: CCCC(=O)Nc1cncc(-c2cc(F)c3[nH]nc(-c4nc5c(-c6ccc(C(C)=O)s6)nccc5[nH]4)c3c2)c1] |
| 823 | 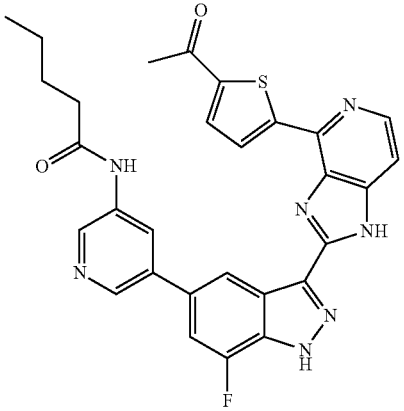 [SMILES: CCCCC(=O)Nc1cncc(-c2cc(F)c3[nH]nc(-c4nc5c(-c6ccc(C(C)=O)s6)nccc5[nH]4)c3c2)c1] |
| 824 | 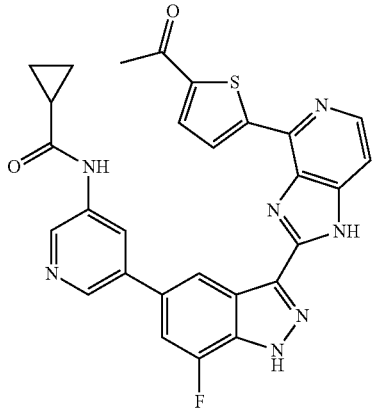 [SMILES: CC(=O)c1ccc(-c2nccc3[nH]c(-c4n[nH]c5c(F)cc(-c6cncc(NC(=O)C7CC7)c6)cc45)nc23)s1] |
| 825 | 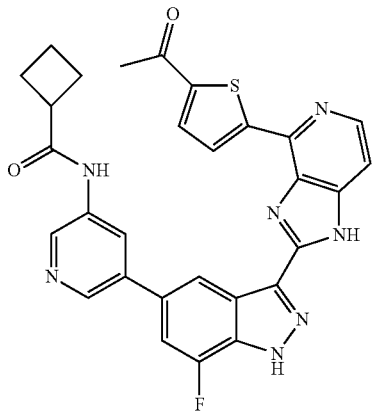 [SMILES: CC(=O)c1ccc(-c2nccc3[nH]c(-c4n[nH]c5c(F)cc(-c6cncc(NC(=O)C7CCC7)c6)cc45)nc23)s1] |

TABLE 1-continued
| 826 | 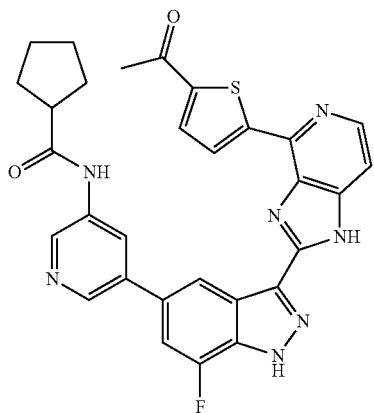 [SMILES: CC(=O)c1ccc(-c2nccc3[nH]c(-c4n[nH]c5c(F)cc(-c6cncc(NC(=O)C7CCCC7)c6)cc45)nc23)s1] | 830 | 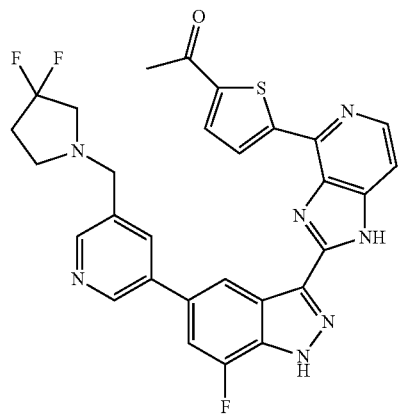 |
| 827 | 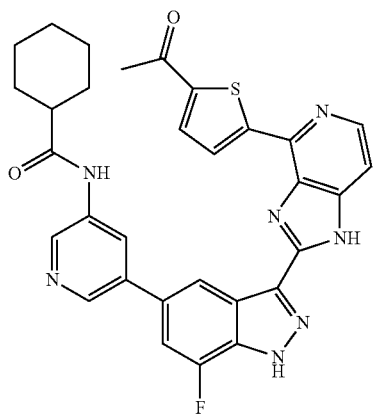 [SMILES: CC(=O)c1ccc(-c2nccc3[nH]c(-c4n[nH]c5c(F)cc(-c6cncc(NC(=O)C7CCCCC7)c6)cc45)nc23)s1] | 831 | 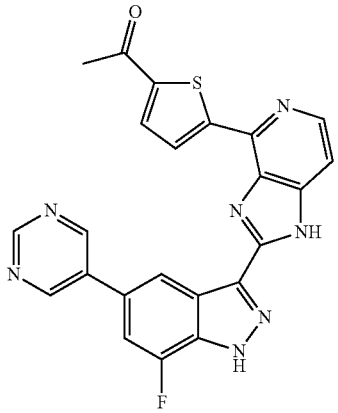 |
| 828 | 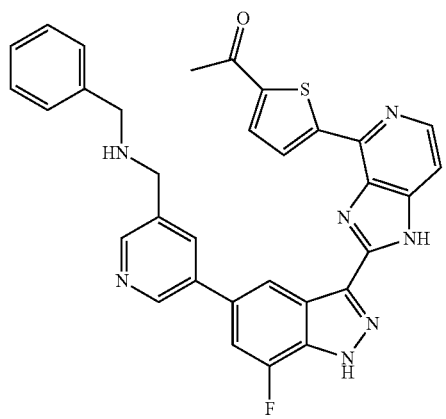 [SMILES: CC(=O)c1ccc(-c2nccc3[nH]c(-c4n[nH]c5c(F)cc(-c6cncc(CNCc7ccccc7)c6)cc45)nc23)s1] | 832 | 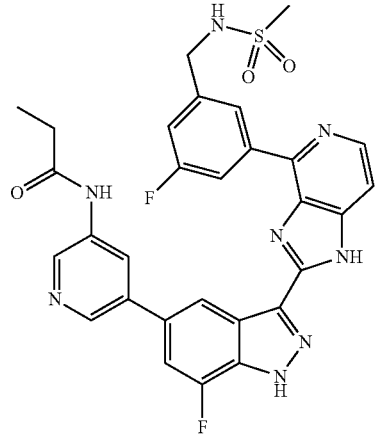 |
| 829 | 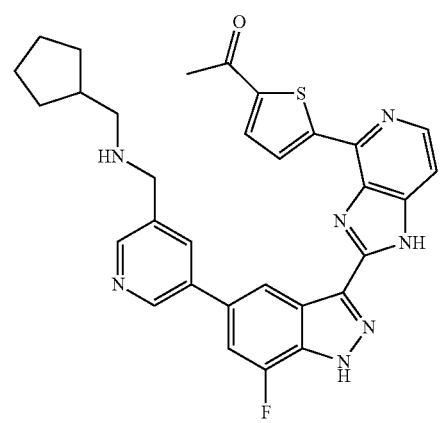 [SMILES: CC(=O)c1ccc(-c2nccc3[nH]c(-c4n[nH]c5c(F)cc(-c6cncc(CNCC7CCCC7)c6)cc45)nc23)s1] | 833 | 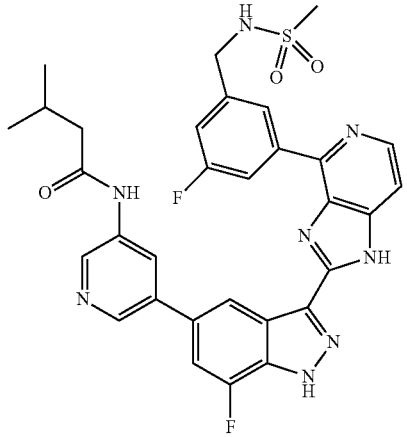 [SMILES: CC(C)CC(=O)Nc1cncc(-c2cc(F)c3[nH]nc(-c4nc5c(-c6cc(F)cc(CNS(C)(=O)=O)c6)nccc5[nH]4)c3c2)c1] |

235
TABLE 1-continued
834 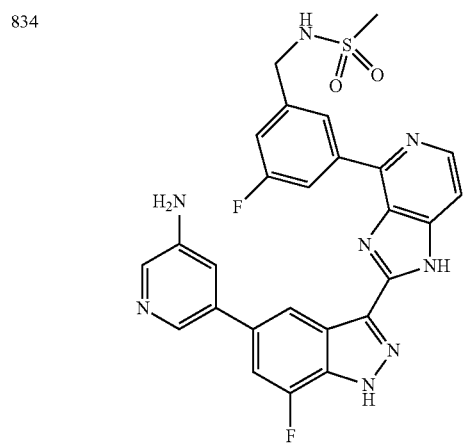
835
836
236
TABLE 1-continued
837 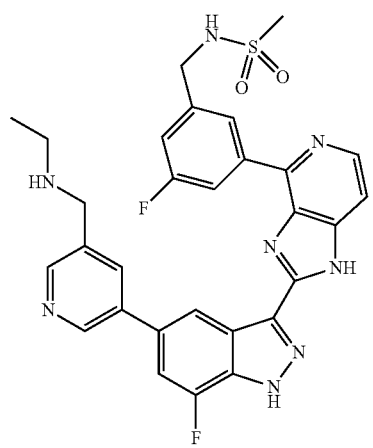 [SMILES: CCNCc1cncc(-c2cc(F)c3[nH]nc(-c4nc5c(-c6cc(F)cc(CNS(C)(=O)=O)c6)nccc5[nH]4)c3c2)c1]
838
839 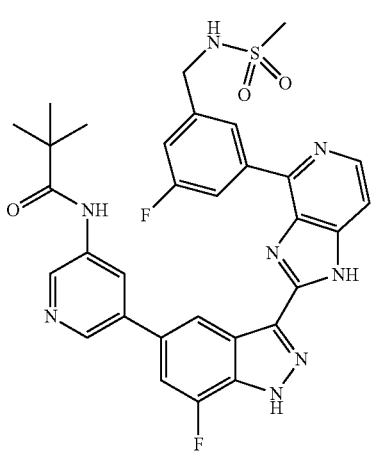 [SMILES: CC(C)(C)C(=O)Nc1cncc(-c2cc(F)c3[nH]nc(-c4nc5c(-c6cc(F)cc(CNS(C)(=O)=O)c6)nccc5[nH]4)c3c2)c1]

TABLE 1-continued
840
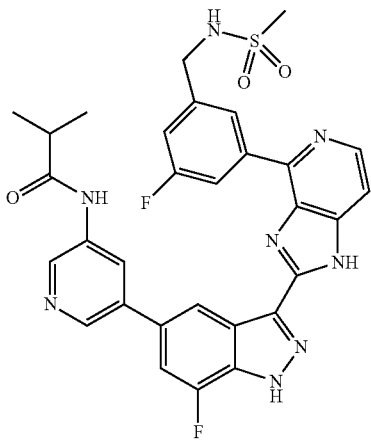 [SMILES: CC(C)C(=O)Nc1cncc(-c2cc(F)c3[nH]nc(-c4nc5c(-c6cc(F)cc(CNS(C)(=O)=O)c6)nccc5[nH]4)c3c2)c1]
841
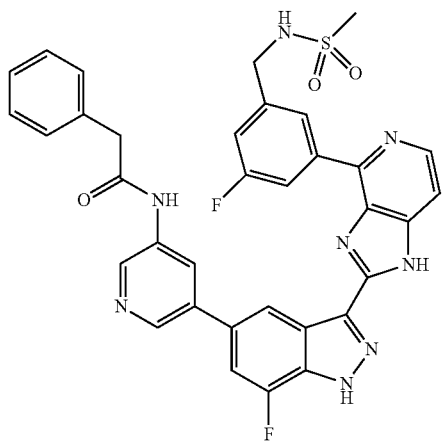 [SMILES: CS(=O)(=O)NCc1cc(F)cc(-c2nccc3[nH]c(-c4n[nH]c5c(F)cc(-c6cncc(NC(=O)Cc7ccccc7)c6)cc45)nc23)c1]
842
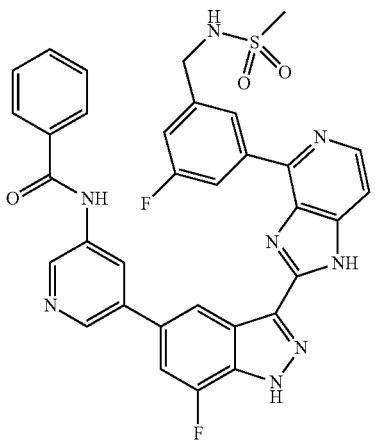 [SMILES: CS(=O)(=O)NCc1cc(F)cc(-c2nccc3[nH]c(-c4n[nH]c5c(F)cc(-c6cncc(NC(=O)c7ccccc7)c6)cc45)nc23)c1]
843
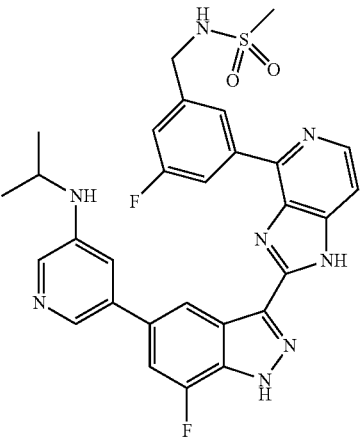 [SMILES: CC(C)Nc1cncc(-c2cc(F)c3[nH]nc(-c4nc5c(-c6cc(F)cc(CNS(C)(=O)=O)c6)nccc5[nH]4)c3c2)c1]
844
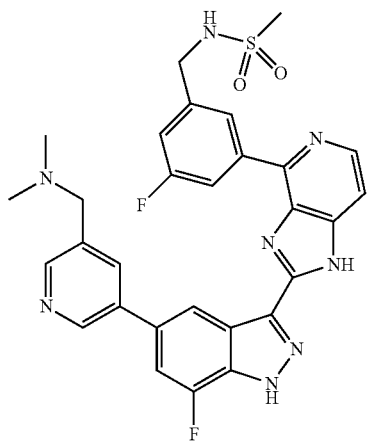 [SMILES: CN(C)Cc1cncc(-c2cc(F)c3[nH]nc(-c4nc5c(-c6cc(F)cc(CNS(C)(=O)=O)c6)nccc5[nH]4)c3c2)c1]
845
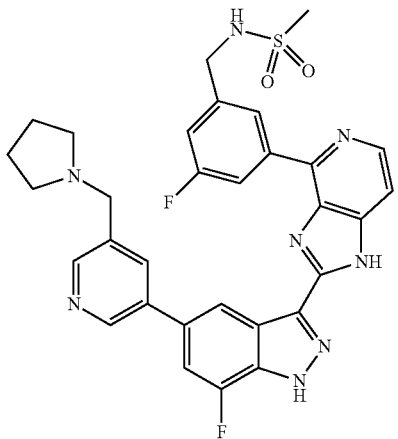 [SMILES: CS(=O)(=O)NCc1cc(F)cc(-c2nccc3[nH]c(-c4n[nH]c5c(F)cc(-c6cncc(CN7CCCC7)c6)cc45)nc23)c1]

TABLE 1-continued
846 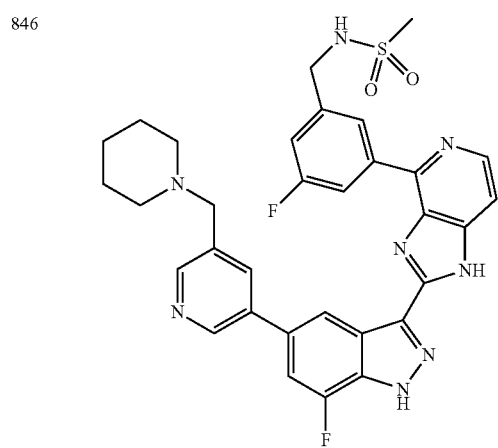
849 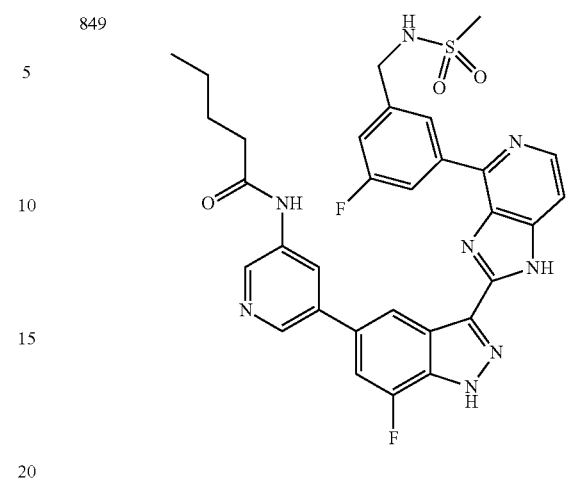
847 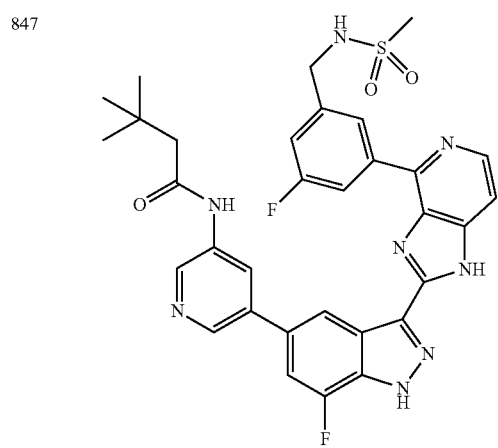
850 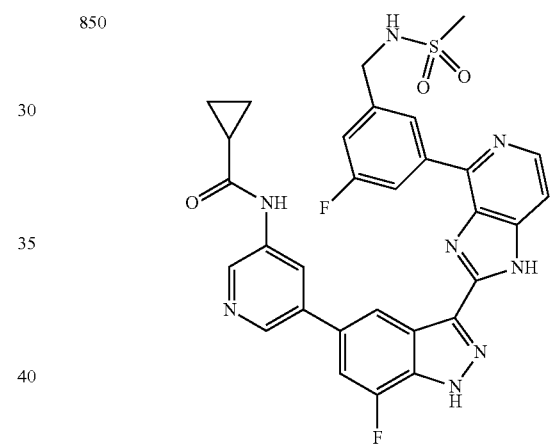
848 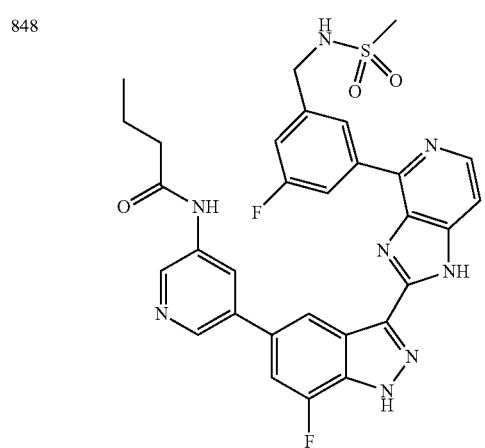
851 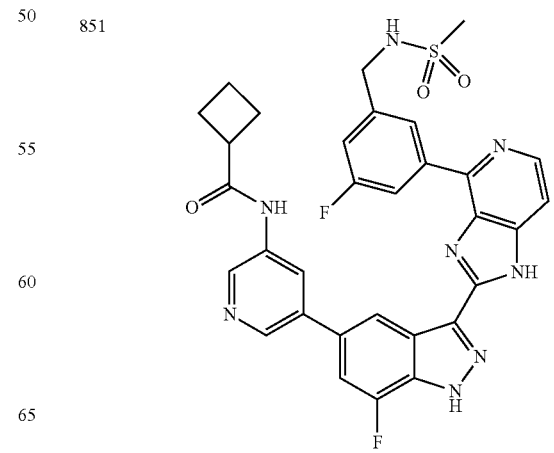

TABLE 1-continued
852 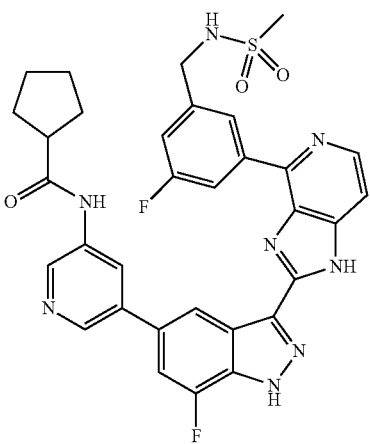 [SMILES: CS(=O)(=O)NCc1cc(F)cc(-c2nccc3[nH]c(-c4n[nH]c5c(F)cc(-c6cncc(NC(=O)C7CCCC7)c6)cc45)nc23)c1]
853 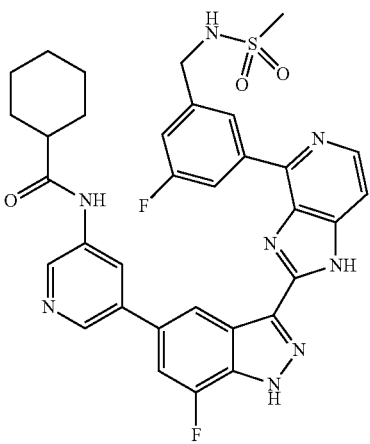 [SMILES: CS(=O)(=O)NCc1cc(F)cc(-c2nccc3[nH]c(-c4n[nH]c5c(F)cc(-c6cncc(NC(=O)C7CCCCC7)c6)cc45)nc23)c1]
854 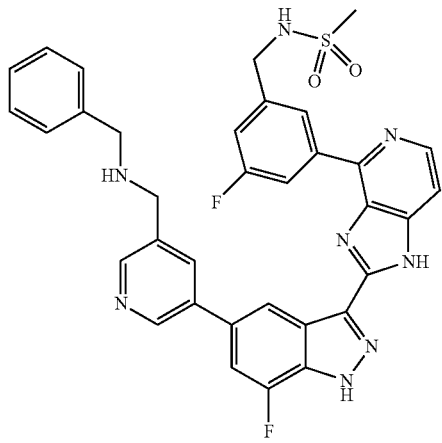 [SMILES: CS(=O)(=O)NCc1cc(F)cc(-c2nccc3[nH]c(-c4n[nH]c5c(F)cc(-c6cncc(CNCc7ccccc7)c6)cc45)nc23)c1]
TABLE 1-continued
855 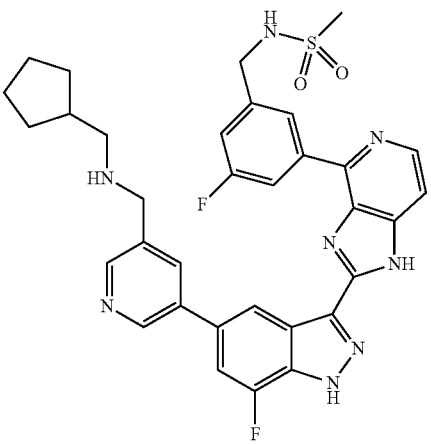 [SMILES: CS(=O)(=O)NCc1cc(F)cc(-c2nccc3[nH]c(-c4n[nH]c5c(F)cc(-c6cncc(CNCC7CCCC7)c6)cc45)nc23)c1]
856 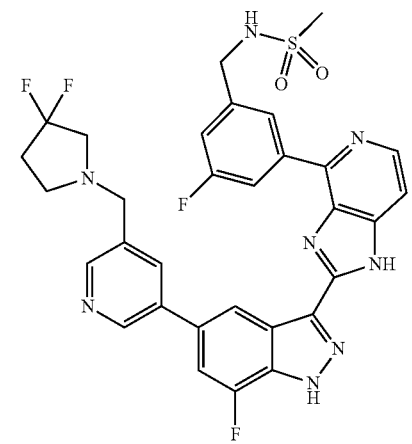 [SMILES: CS(=O)(=O)NCc1cc(F)cc(-c2nccc3[nH]c(-c4n[nH]c5c(F)cc(-c6cncc(CN7CCC(F)(F)C7)c6)cc45)nc23)c1]
857 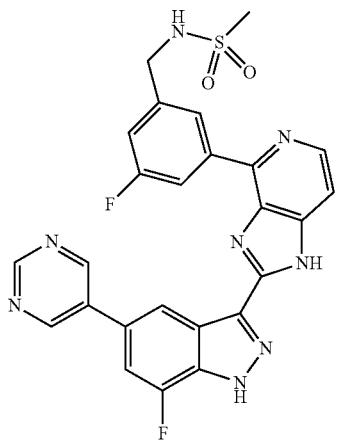

TABLE 1-continued
858
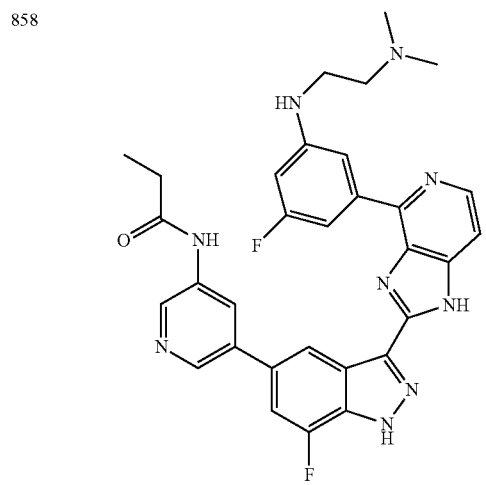
859
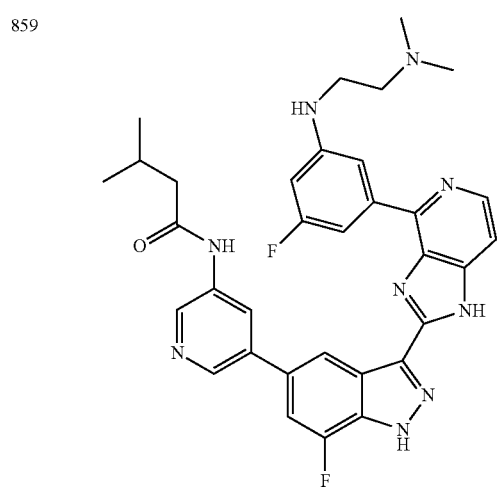
860
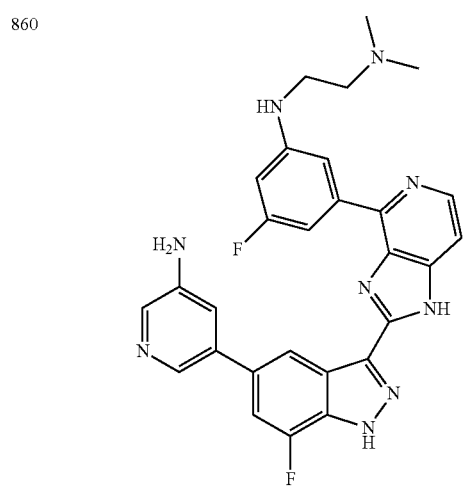
861
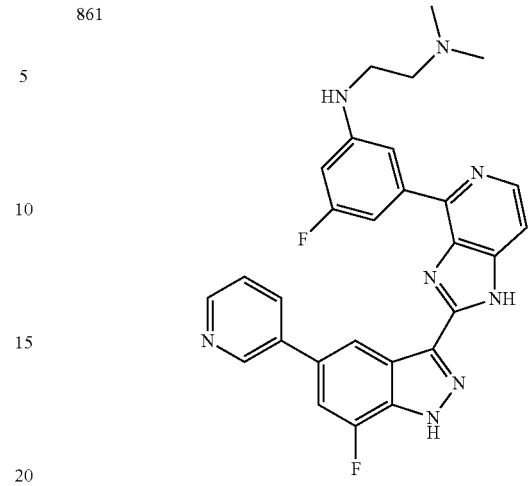
862
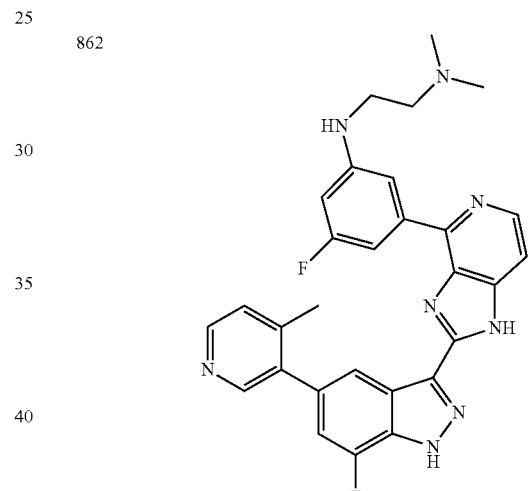
863
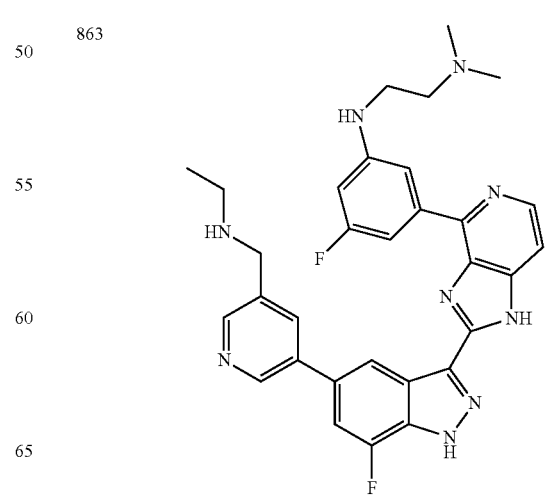

TABLE 1-continued
| | |
|---|---|
| 864 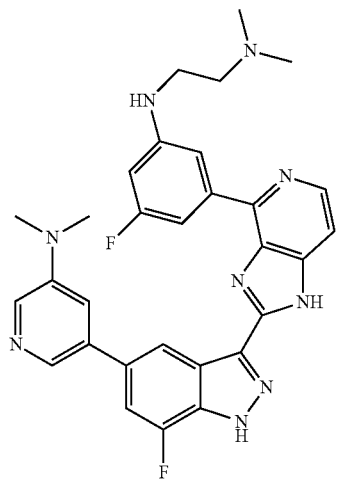 [SMILES: CN(C)CCNc1cc(F)cc(-c2nccc3[nH]c(-c4n[nH]c5c(F)cc(-c6cncc(N(C)C)c6)cc45)nc23)c1] | 867 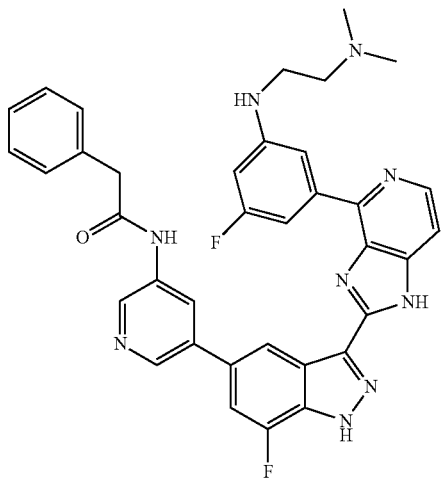 |
| 865 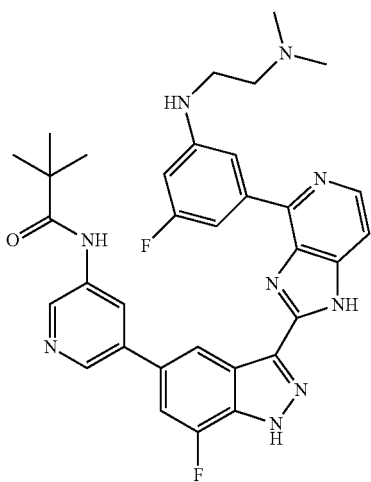 [SMILES: CN(C)CCNc1cc(F)cc(-c2nccc3[nH]c(-c4n[nH]c5c(F)cc(-c6cncc(NC(=O)C(C)(C)C)c6)cc45)nc23)c1] | 868 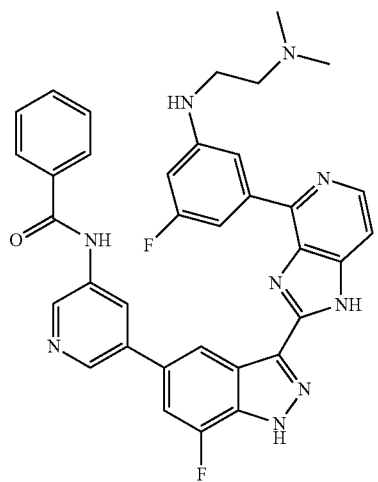 |
| 866 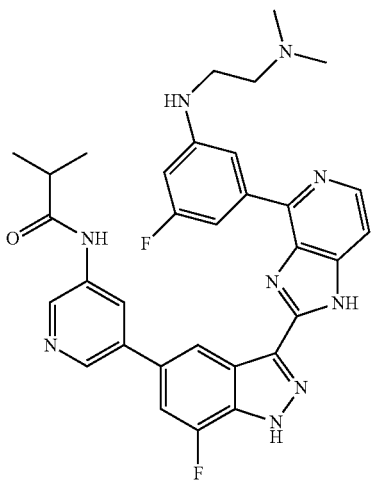 [SMILES: CC(C)C(=O)Nc1cncc(-c2cc(F)c3[nH]nc(-c4nc5c(-c6cc(F)cc(NCCN(C)C)c6)nccc5[nH]4)c3c2)c1] | 869 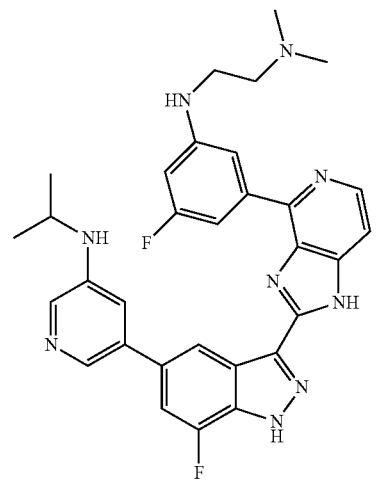 [SMILES: CC(C)Nc1cncc(-c2cc(F)c3[nH]nc(-c4nc5c(-c6cc(F)cc(NCCN(C)C)c6)nccc5[nH]4)c3c2)c1] |

TABLE 1-continued
870
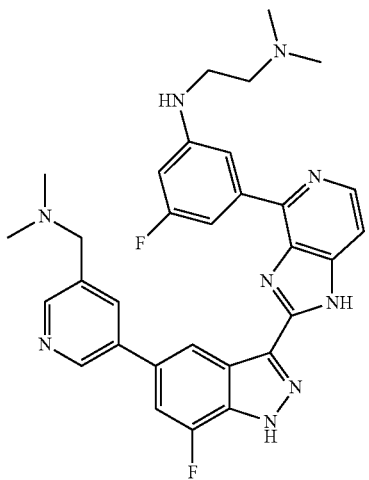 [SMILES: CN(C)CCNc1cc(F)cc(-c2nccc3[nH]c(-c4n[nH]c5c(F)cc(-c6cncc(CN(C)C)c6)cc45)nc23)c1]
871
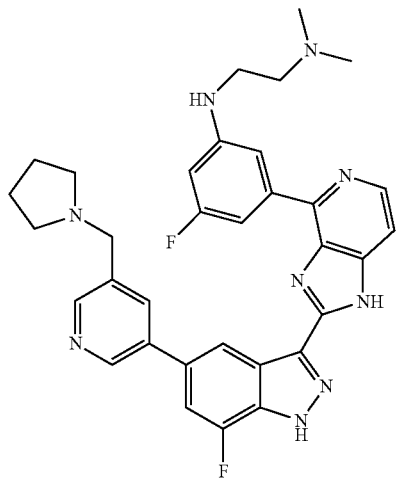 [SMILES: CN(C)CCNc1cc(F)cc(-c2nccc3[nH]c(-c4n[nH]c5c(F)cc(-c6cncc(CN7CCCC7)c6)cc45)nc23)c1]
872
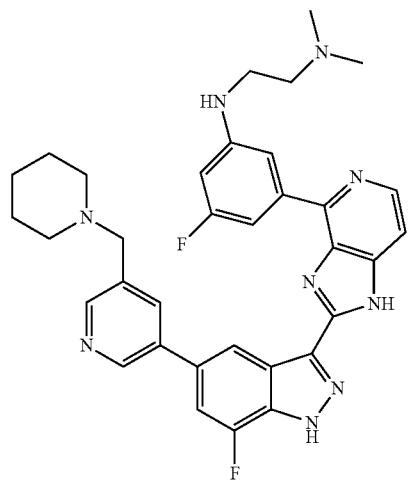 [SMILES: CN(C)CCNc1cc(F)cc(-c2nccc3[nH]c(-c4n[nH]c5c(F)cc(-c6cncc(CN7CCCCC7)c6)cc45)nc23)c1]
TABLE 1-continued
873
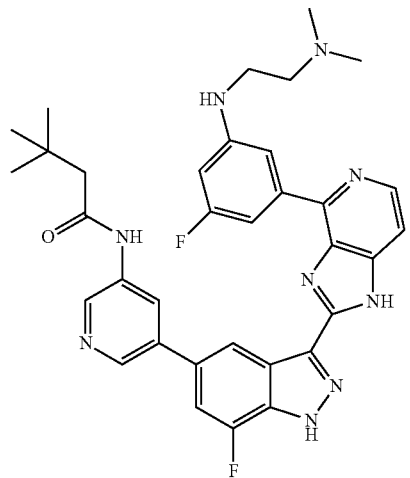 [SMILES: CN(C)CCNc1cc(F)cc(-c2nccc3[nH]c(-c4n[nH]c5c(F)cc(-c6cncc(NC(=O)CC(C)(C)C)c6)cc45)nc23)c1]
874
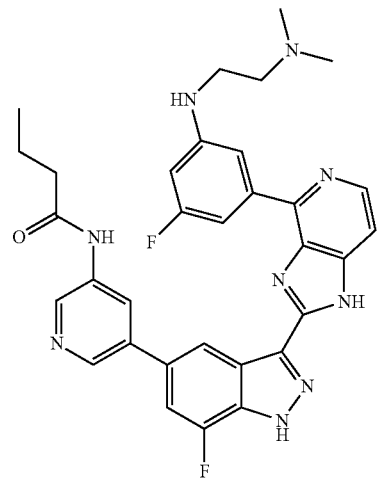 [SMILES: CCCC(=O)Nc1cncc(-c2cc(F)c3[nH]nc(-c4nc5c(-c6cc(F)cc(NCCN(C)C)c6)nccc5[nH]4)c3c2)c1]
875
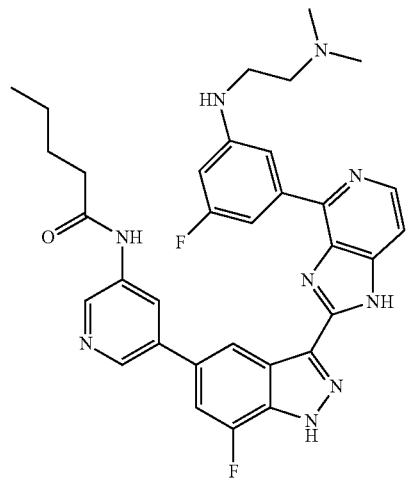 [SMILES: CCCCC(=O)Nc1cncc(-c2cc(F)c3[nH]nc(-c4nc5c(-c6cc(F)cc(NCCN(C)C)c6)nccc5[nH]4)c3c2)c1]

TABLE 1-continued
876
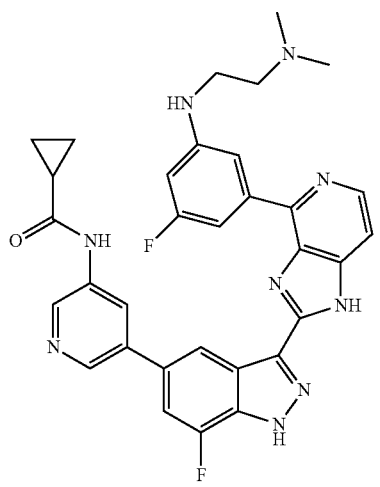 [SMILES: CN(C)CCNc1cc(F)cc(-c2nccc3[nH]c(-c4n[nH]c5c(F)cc(-c6cncc(NC(=O)C7CC7)c6)cc45)nc23)c1]
877
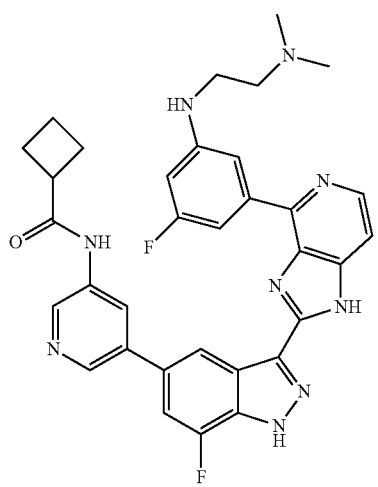 [SMILES: CN(C)CCNc1cc(F)cc(-c2nccc3[nH]c(-c4n[nH]c5c(F)cc(-c6cncc(NC(=O)C7CCC7)c6)cc45)nc23)c1]
878
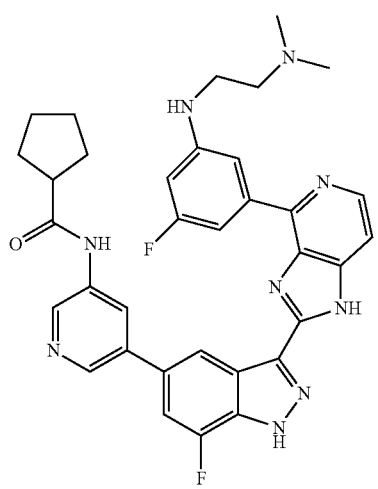 [SMILES: CN(C)CCNc1cc(F)cc(-c2nccc3[nH]c(-c4n[nH]c5c(F)cc(-c6cncc(NC(=O)C7CCCC7)c6)cc45)nc23)c1]
TABLE 1-continued
879
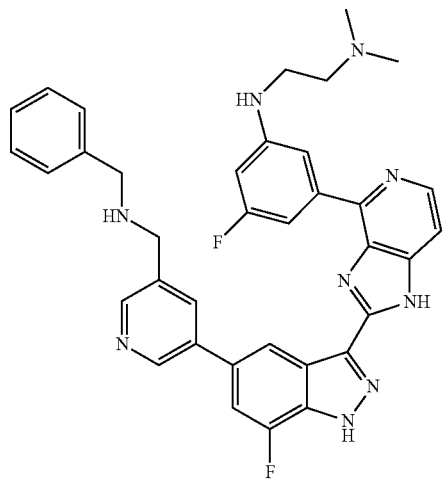 [SMILES: CN(C)CCNc1cc(F)cc(-c2nccc3[nH]c(-c4n[nH]c5c(F)cc(-c6cncc(CNCc7ccccc7)c6)cc45)nc23)c1]
880
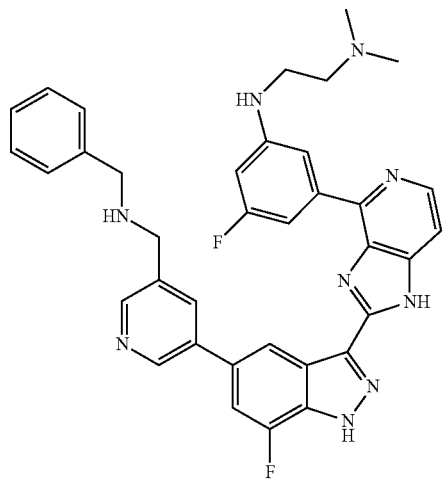 [SMILES: CN(C)CCNc1cc(F)cc(-c2nccc3[nH]c(-c4n[nH]c5c(F)cc(-c6cncc(CNCc7ccccc7)c6)cc45)nc23)c1]
881
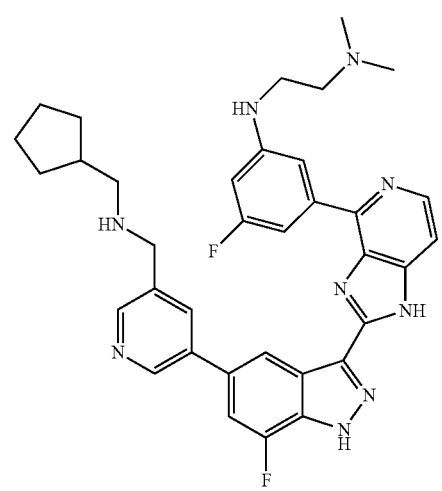 [SMILES: CN(C)CCNc1cc(F)cc(-c2nccc3[nH]c(-c4n[nH]c5c(F)cc(-c6cncc(CNCC7CCCC7)c6)cc45)nc23)c1]

TABLE 1-continued
882
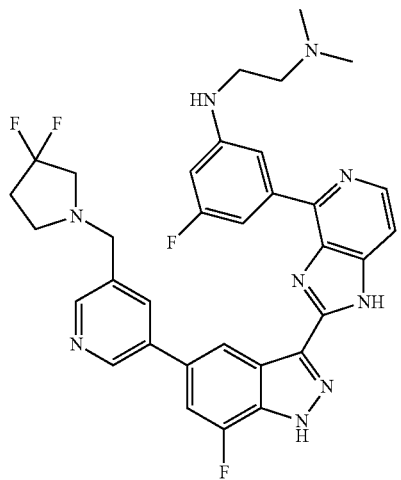 [SMILES: CN(C)CCNc1cc(F)cc(-c2nccc3[nH]c(-c4n[nH]c5c(F)cc(-c6cncc(CN7CCC(F)(F)C7)c6)cc45)nc23)c1]
883
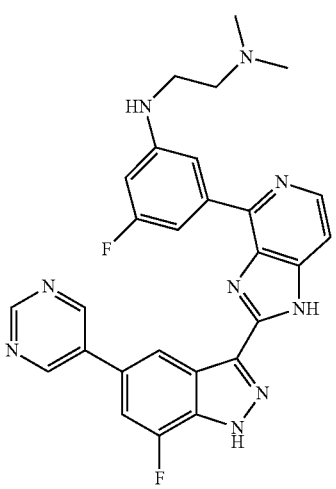 [SMILES: CN(C)CCNc1cc(F)cc(-c2nccc3[nH]c(-c4n[nH]c5c(F)cc(-c6cncnc6)cc45)nc23)c1]
884
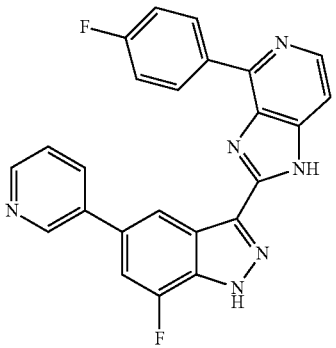 [SMILES: Fc1ccc(-c2nccc3[nH]c(-c4n[nH]c5c(F)cc(-c6cccnc6)cc45)nc23)cc1]
885
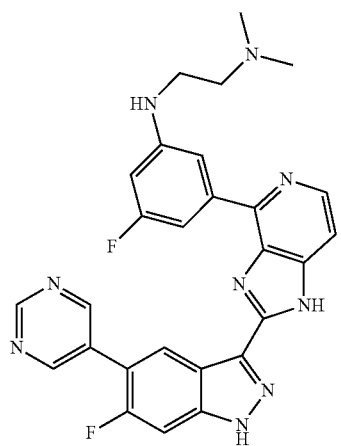 [SMILES: CN(C)CCNc1cc(F)cc(-c2nccc3[nH]c(-c4n[nH]c5cc(F)c(-c6cncnc6)cc45)nc23)c1]
886
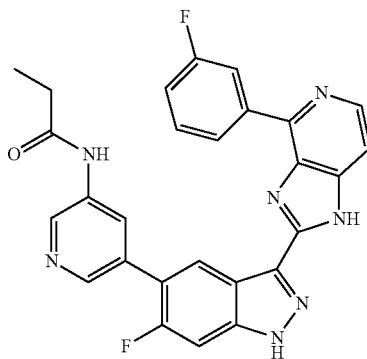
887
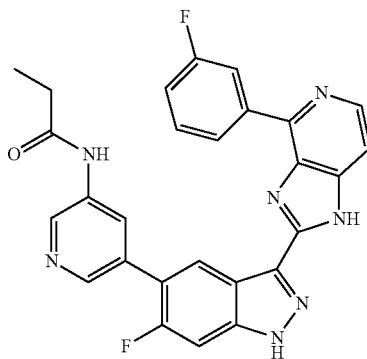
888
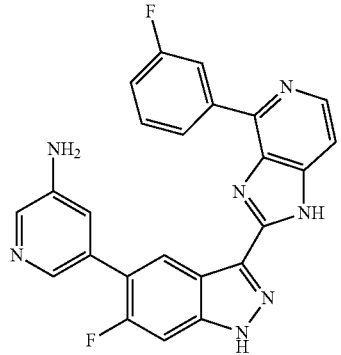 [SMILES: Nc1cncc(-c2cc3c(-c4nc5c(-c6cccc(F)c6)nccc5[nH]4)n[nH]c3cc2F)c1]

TABLE 1-continued
889 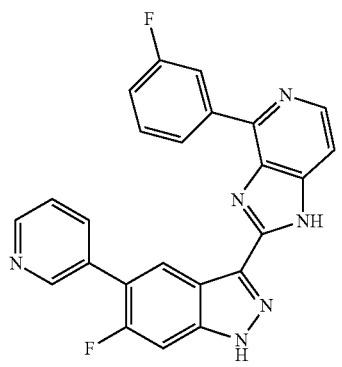 [SMILES: Fc1cccc(-c2nccc3[nH]c(-c4n[nH]c5cc(F)c(-c6cccnc6)cc45)nc23)c1]
890 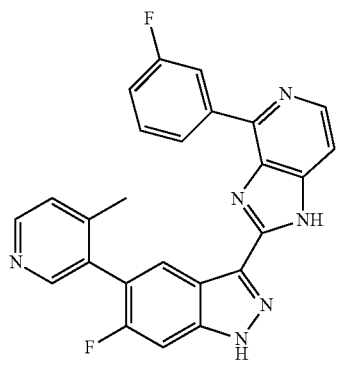 [SMILES: Cc1ccncc1-c1cc2c(-c3nc4c(-c5cccc(F)c5)nccc4[nH]3)n[nH]c2cc1F]
891 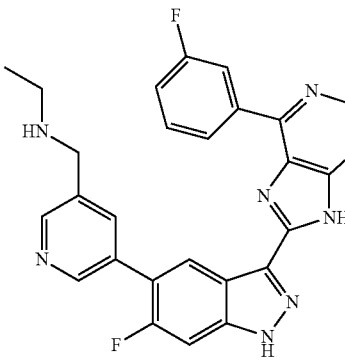
892 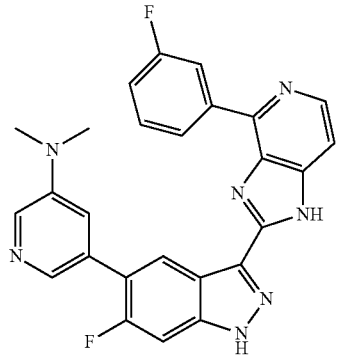 [SMILES: CN(C)c1cncc(-c2cc3c(-c4nc5c(-c6cccc(F)c6)nccc5[nH]4)n[nH]c3cc2F)c1]
TABLE 1-continued
893 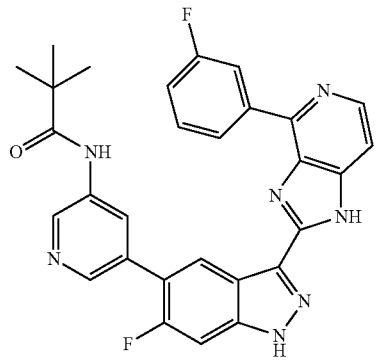 [SMILES: CC(C)(C)C(=O)Nc1cncc(-c2cc3c(-c4nc5c(-c6cccc(F)c6)nccc5[nH]4)n[nH]c3cc2F)c1]
894 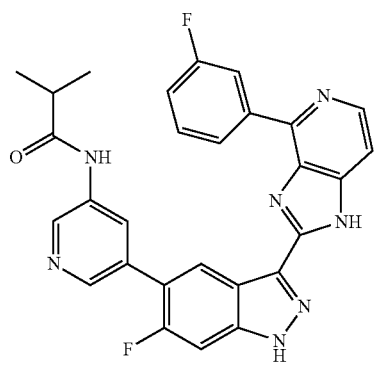 [SMILES: CC(C)C(=O)Nc1cncc(-c2cc3c(-c4nc5c(-c6cccc(F)c6)nccc5[nH]4)n[nH]c3cc2F)c1]
895 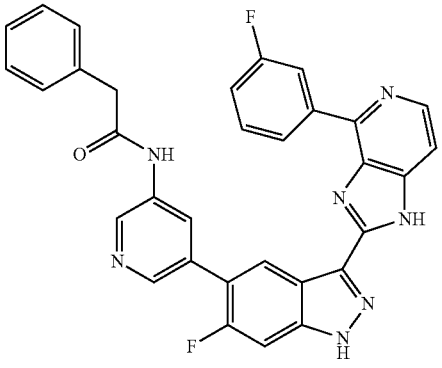 [SMILES: O=C(Cc1ccccc1)Nc1cncc(-c2cc3c(-c4nc5c(-c6cccc(F)c6)nccc5[nH]4)n[nH]c3cc2F)c1]
896 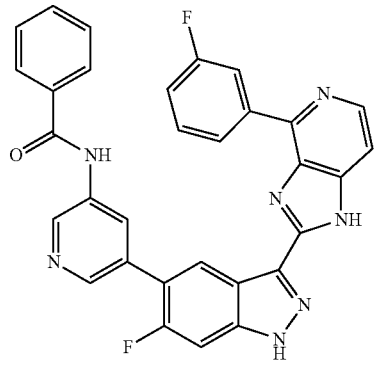 [SMILES: O=C(Nc1cncc(-c2cc3c(-c4nc5c(-c6cccc(F)c6)nccc5[nH]4)n[nH]c3cc2F)c1)c1ccccc1]

TABLE 1-continued
| 897 | 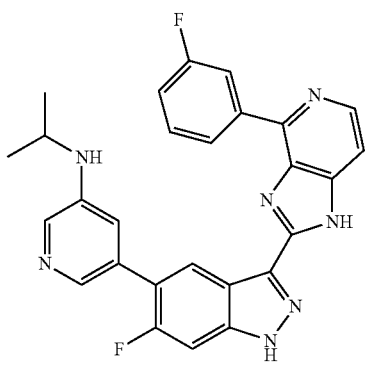 [SMILES: CC(C)Nc1cncc(-c2cc3c(-c4nc5c(-c6cccc(F)c6)nccc5[nH]4)n[nH]c3cc2F)c1] |
| --- | --- |
| 898 | 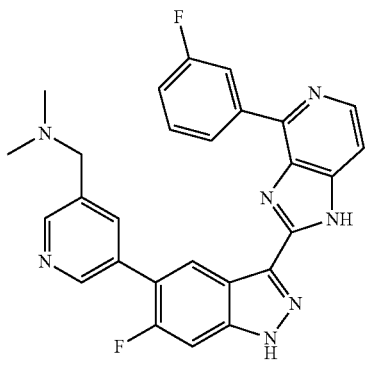 [SMILES: CN(C)Cc1cncc(-c2cc3c(-c4nc5c(-c6cccc(F)c6)nccc5[nH]4)n[nH]c3cc2F)c1] |
| 899 | 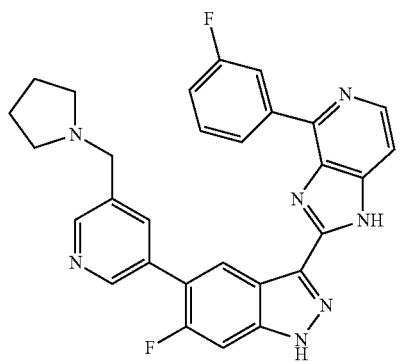 [SMILES: Fc1cccc(-c2nccc3[nH]c(-c4n[nH]c5cc(F)c(-c6cncc(CN7CCCC7)c6)cc45)nc23)c1] |
| 900 | 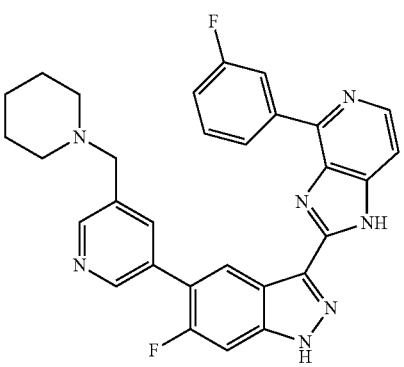 [SMILES: Fc1cccc(-c2nccc3[nH]c(-c4n[nH]c5cc(F)c(-c6cncc(CN7CCCCC7)c6)cc45)nc23)c1] |
TABLE 1-continued
| 901 | 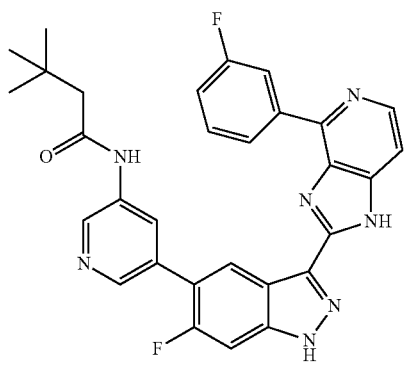 [SMILES: CC(C)(C)CC(=O)Nc1cncc(-c2cc3c(-c4nc5c(-c6cccc(F)c6)nccc5[nH]4)n[nH]c3cc2F)c1] |
| --- | --- |
| 902 | 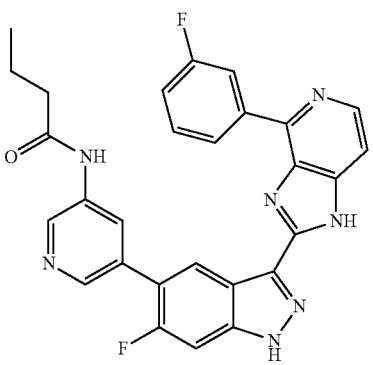 [SMILES: CCCC(=O)Nc1cncc(-c2cc3c(-c4nc5c(-c6cccc(F)c6)nccc5[nH]4)n[nH]c3cc2F)c1] |
| 903 | 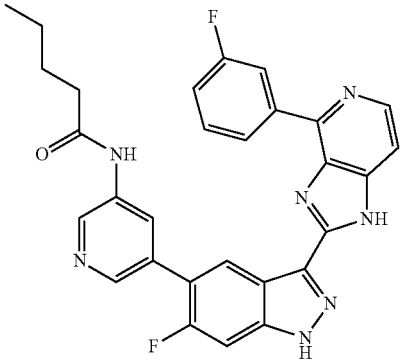 [SMILES: CCCCC(=O)Nc1cncc(-c2cc3c(-c4nc5c(-c6cccc(F)c6)nccc5[nH]4)n[nH]c3cc2F)c1] |
| 904 | 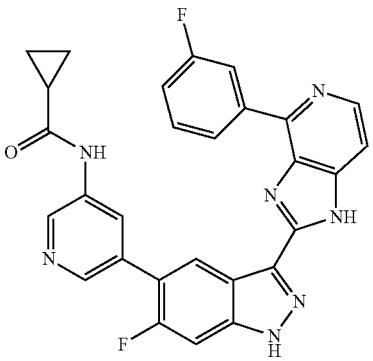 [SMILES: O=C(Nc1cncc(-c2cc3c(-c4nc5c(-c6cccc(F)c6)nccc5[nH]4)n[nH]c3cc2F)c1)C1CC1] |

TABLE 1-continued
905 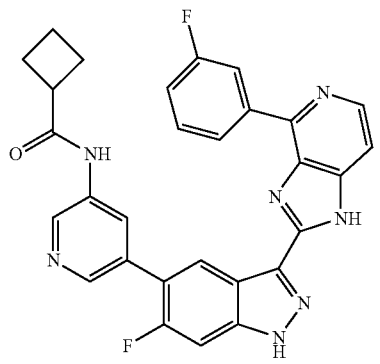 [SMILES: O=C(Nc1cncc(-c2cc3c(-c4nc5c(-c6cccc(F)c6)nccc5[nH]4)n[nH]c3cc2F)c1)C1CCC1]
906 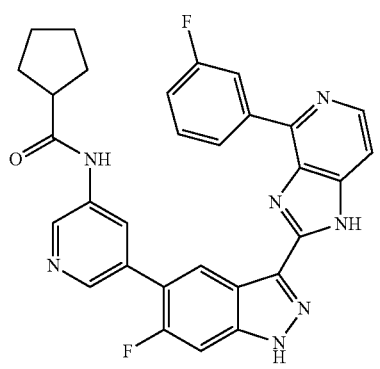 [SMILES: O=C(Nc1cncc(-c2cc3c(-c4nc5c(-c6cccc(F)c6)nccc5[nH]4)n[nH]c3cc2F)c1)C1CCCC1]
907 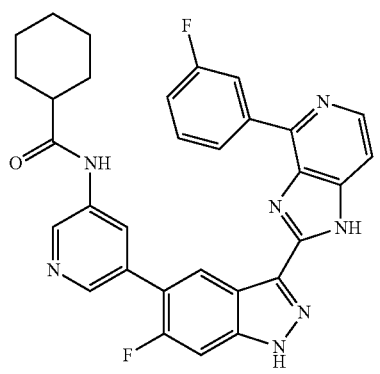 [SMILES: O=C(Nc1cncc(-c2cc3c(-c4nc5c(-c6cccc(F)c6)nccc5[nH]4)n[nH]c3cc2F)c1)C1CCCCC1]
908 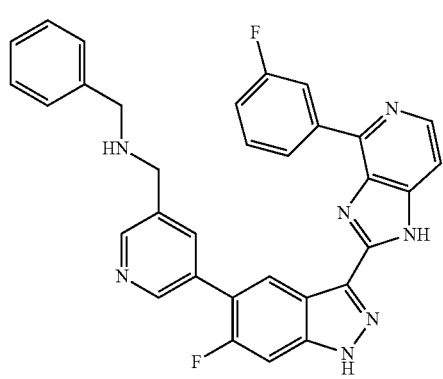 [SMILES: Fc1cccc(-c2nccc3[nH]c(-c4n[nH]c5cc(F)c(-c6cncc(CNCc7ccccc7)c6)cc45)nc23)c1]
TABLE 1-continued
909 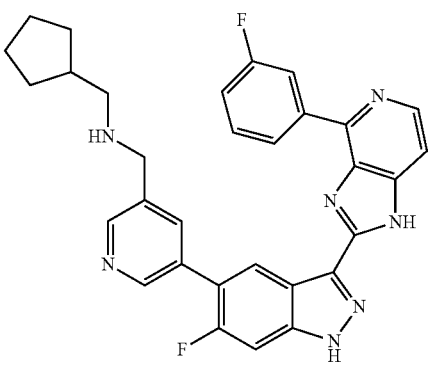 [SMILES: Fc1cccc(-c2nccc3[nH]c(-c4n[nH]c5cc(F)c(-c6cncc(CNCC7CCCC7)c6)cc45)nc23)c1]
910 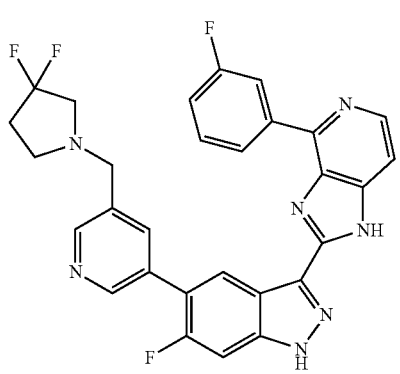 [SMILES: Fc1cccc(-c2nccc3[nH]c(-c4n[nH]c5cc(F)c(-c6cncc(CN7CCC(F)(F)C7)c6)cc45)nc23)c1]
911 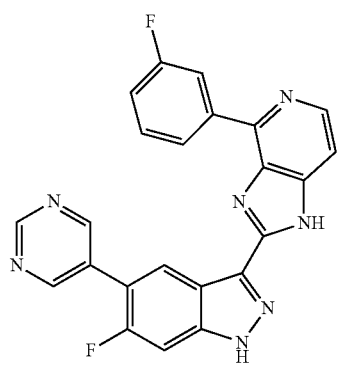
912 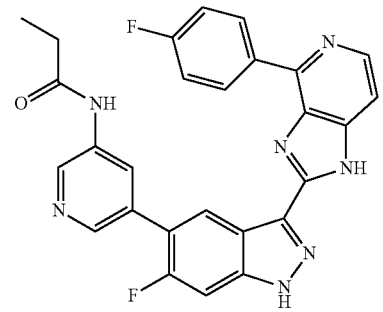 [SMILES: CCC(=O)Nc1cncc(-c2cc3c(-c4nc5c(-c6ccc(F)cc6)nccc5[nH]4)n[nH]c3cc2F)c1]

TABLE 1-continued
913 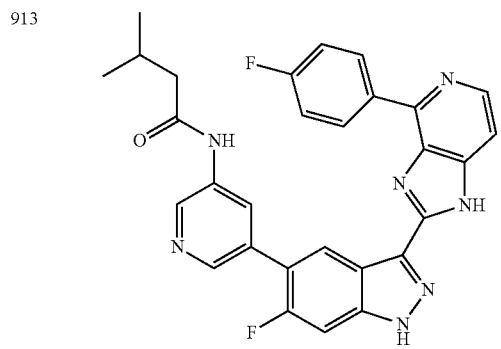
914 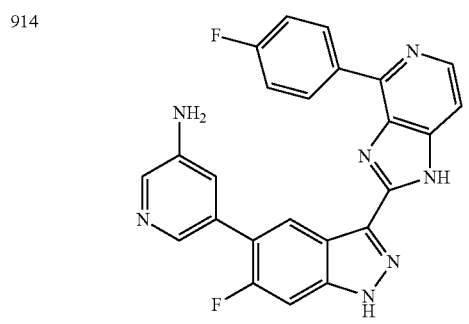
915 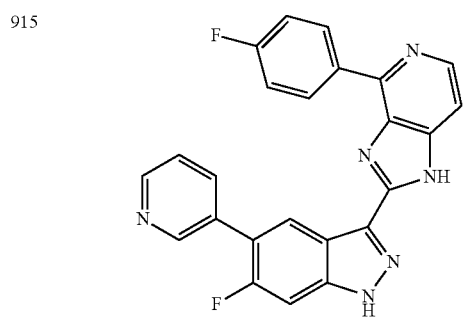
916 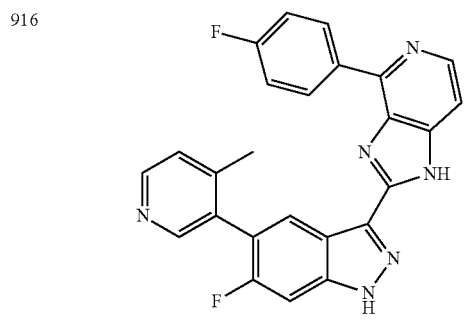
917 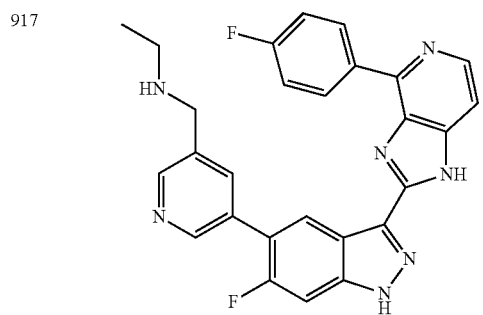
TABLE 1-continued
918 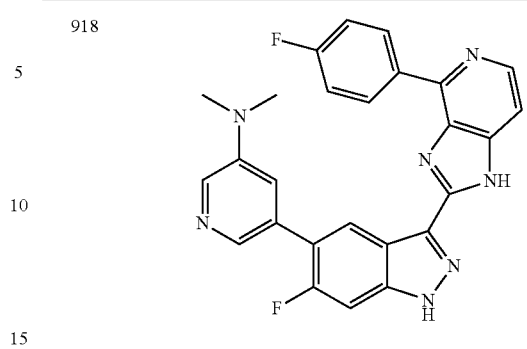
919 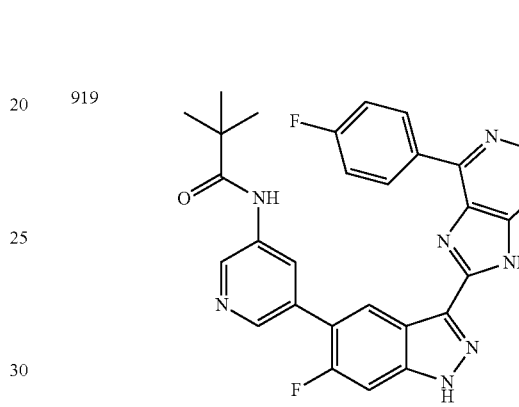
920 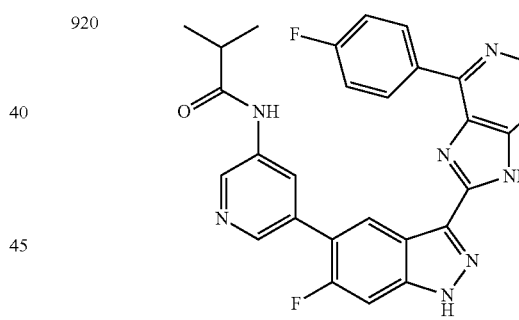
921 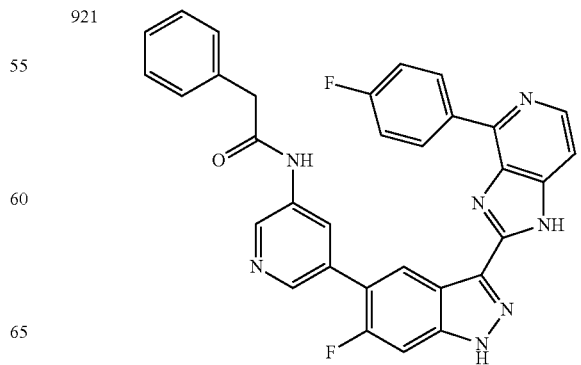

TABLE 1-continued
922 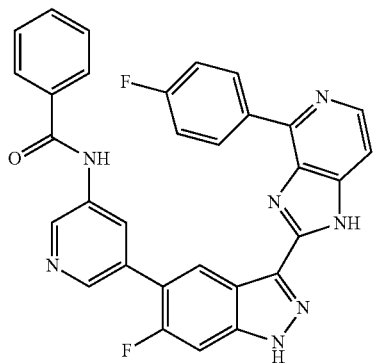 [SMILES: O=C(Nc1cncc(-c2cc3c(-c4nc5c(-c6ccc(F)cc6)nccc5[nH]4)n[nH]c3cc2F)c1)c1ccccc1]
923 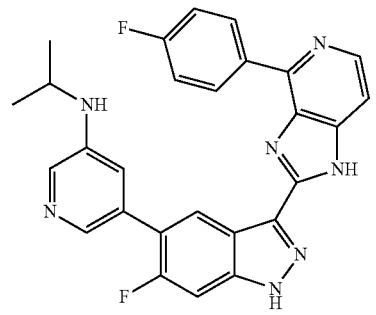 [SMILES: CC(C)Nc1cncc(-c2cc3c(-c4nc5c(-c6ccc(F)cc6)nccc5[nH]4)n[nH]c3cc2F)c1]
924 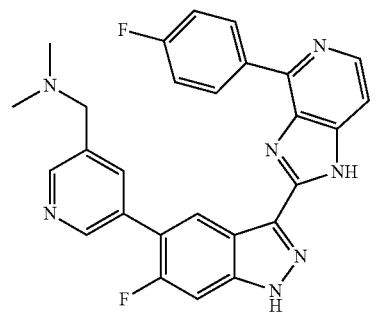 [SMILES: CN(C)Cc1cncc(-c2cc3c(-c4nc5c(-c6ccc(F)cc6)nccc5[nH]4)n[nH]c3cc2F)c1]
925 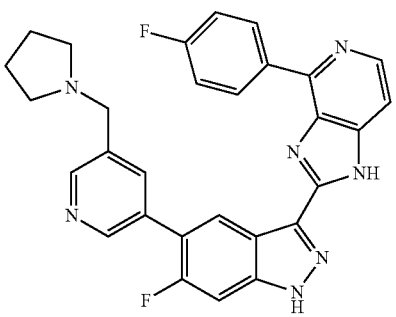 [SMILES: Fc1ccc(-c2nccc3[nH]c(-c4n[nH]c5cc(F)c(-c6cncc(CN7CCCC7)c6)cc45)nc23)cc1]
926 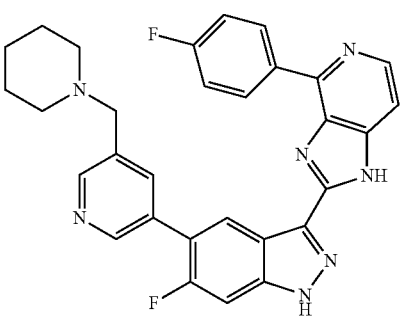 [SMILES: Fc1ccc(-c2nccc3[nH]c(-c4n[nH]c5cc(F)c(-c6cncc(CN7CCCCC7)c6)cc45)nc23)cc1]
TABLE 1-continued
927 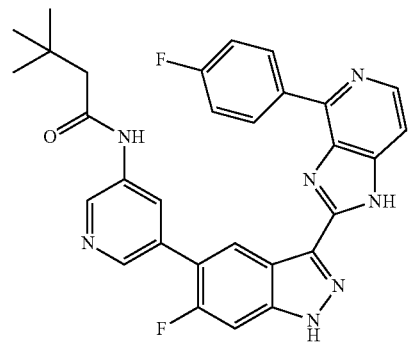 [SMILES: CC(C)(C)CC(=O)Nc1cncc(-c2cc3c(-c4nc5c(-c6ccc(F)cc6)nccc5[nH]4)n[nH]c3cc2F)c1]
928 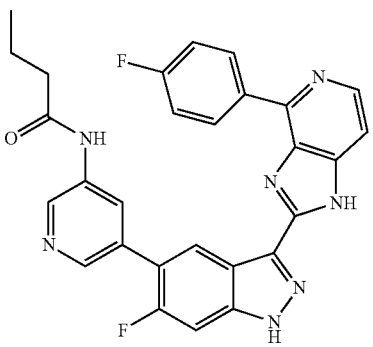 [SMILES: CCCC(=O)Nc1cncc(-c2cc3c(-c4nc5c(-c6ccc(F)cc6)nccc5[nH]4)n[nH]c3cc2F)c1]
929 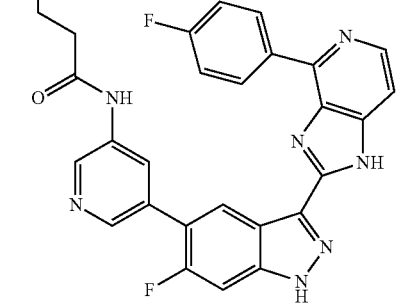
930 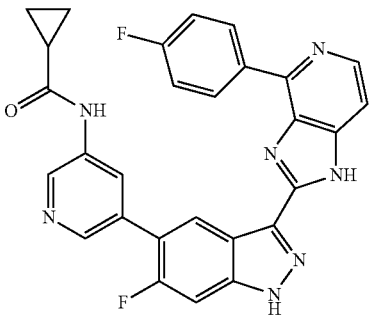 [SMILES: O=C(Nc1cncc(-c2cc3c(-c4nc5c(-c6ccc(F)cc6)nccc5[nH]4)n[nH]c3cc2F)c1)C1CC1]

TABLE 1-continued
931 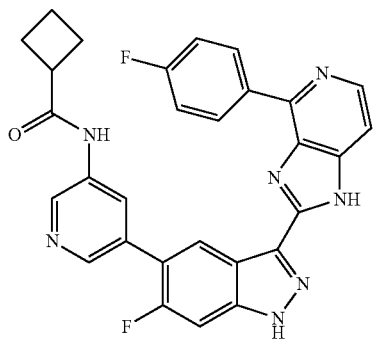 [SMILES: O=C(Nc1cncc(-c2cc3c(-c4nc5c(-c6ccc(F)cc6)nccc5[nH]4)n[nH]c3cc2F)c1)C1CCC1]
932 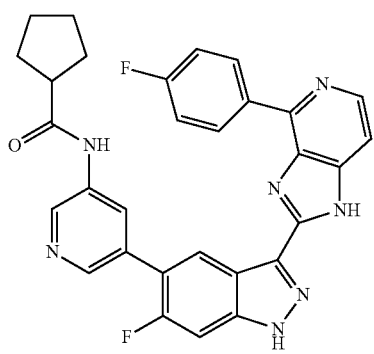 [SMILES: O=C(Nc1cncc(-c2cc3c(-c4nc5c(-c6ccc(F)cc6)nccc5[nH]4)n[nH]c3cc2F)c1)C1CCCC1]
933 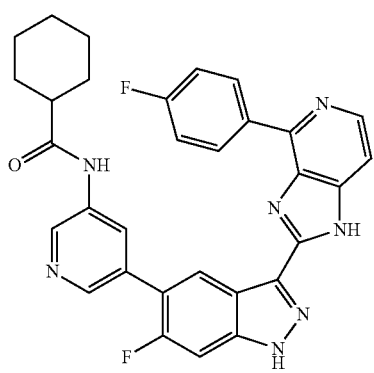 [SMILES: O=C(Nc1cncc(-c2cc3c(-c4nc5c(-c6ccc(F)cc6)nccc5[nH]4)n[nH]c3cc2F)c1)C1CCCCC1]
934 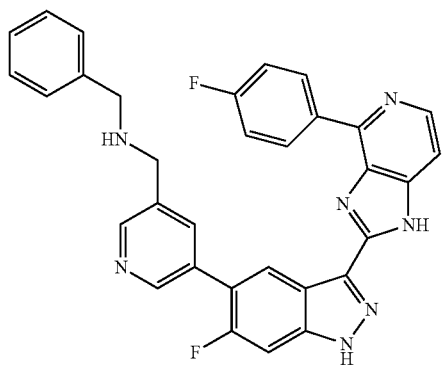 [SMILES: Fc1ccc(-c2nccc3[nH]c(-c4n[nH]c5cc(F)c(-c6cncc(CNCc7ccccc7)c6)cc45)nc23)cc1]
TABLE 1-continued
935 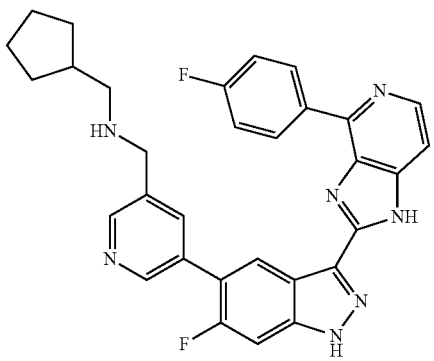
936 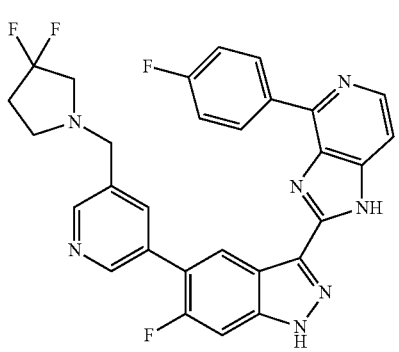 [SMILES: Fc1ccc(-c2nccc3[nH]c(-c4n[nH]c5cc(F)c(-c6cncc(CN7CCC(F)(F)C7)c6)cc45)nc23)cc1]
937 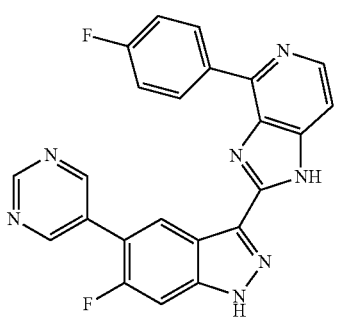
938 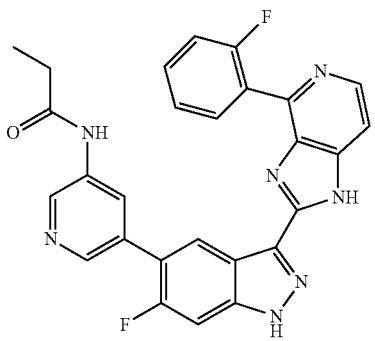 [SMILES: CCC(=O)Nc1cncc(-c2cc3c(-c4nc5c(-c6ccccc6F)nccc5[nH]4)n[nH]c3cc2F)c1]

TABLE 1-continued
939 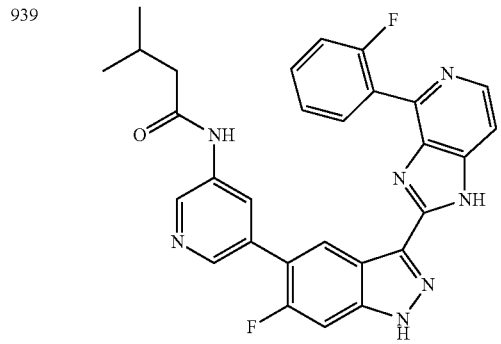
940 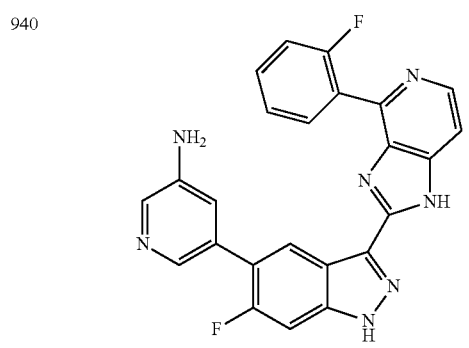
941 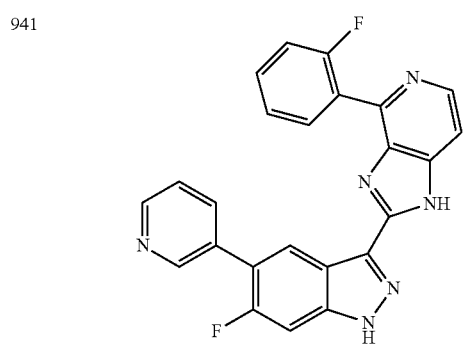
942 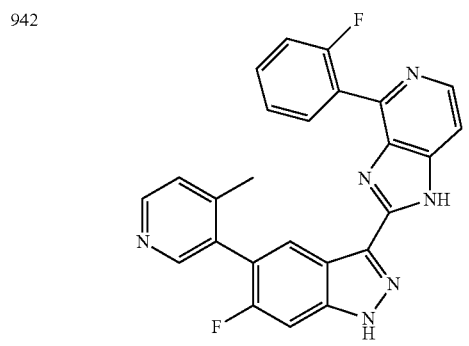
TABLE 1-continued
943 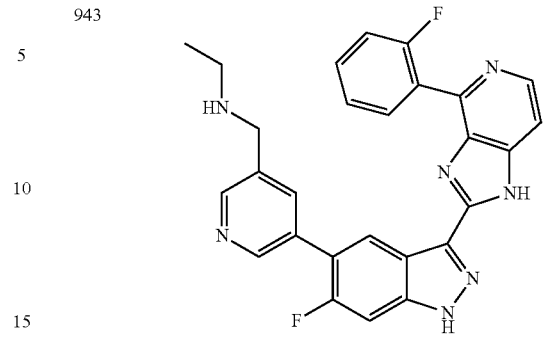
944 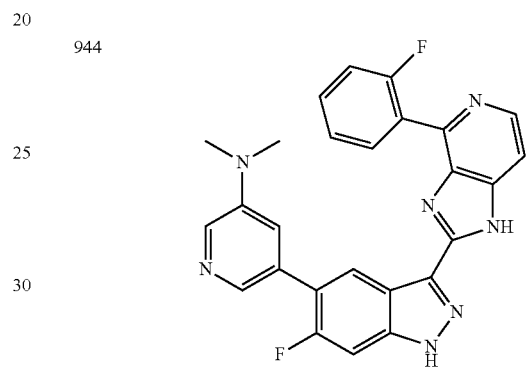
945 
946 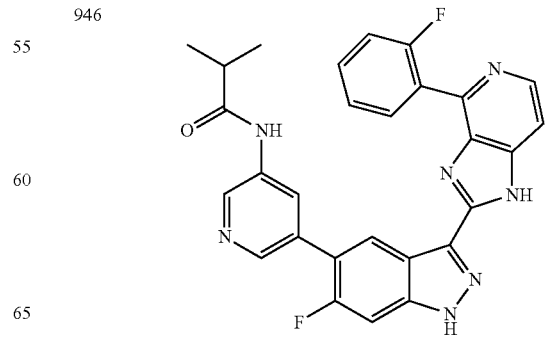

TABLE 1-continued
947 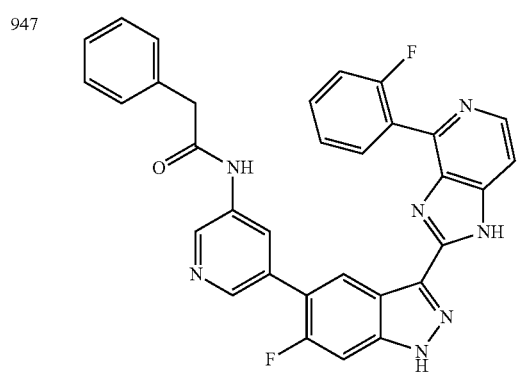
948 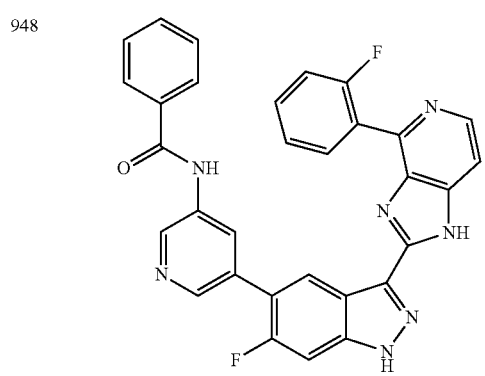
949 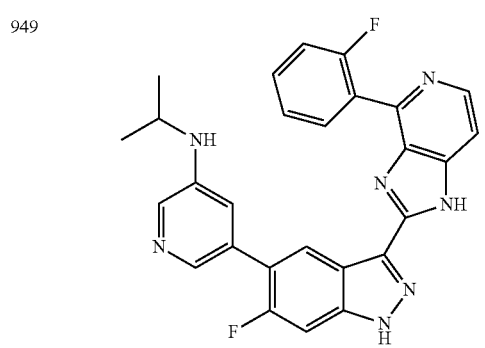
950 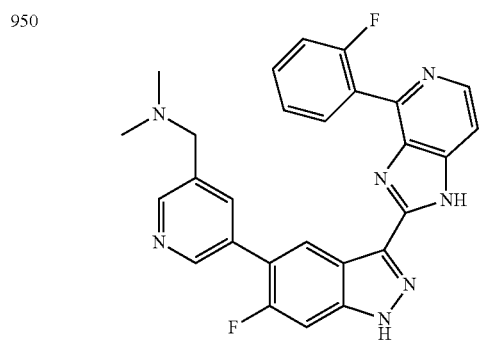
TABLE 1-continued
951 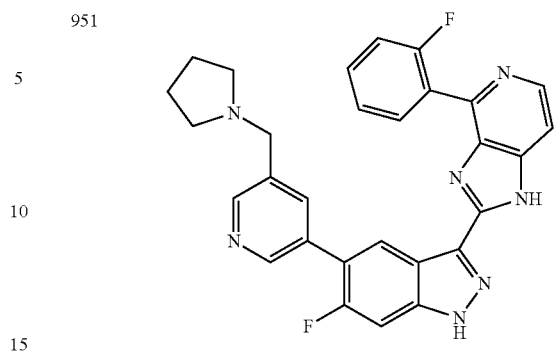
952 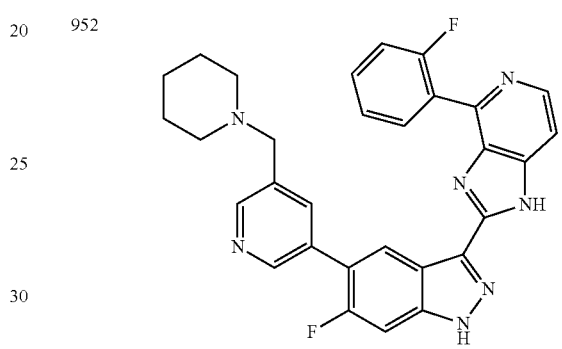
953 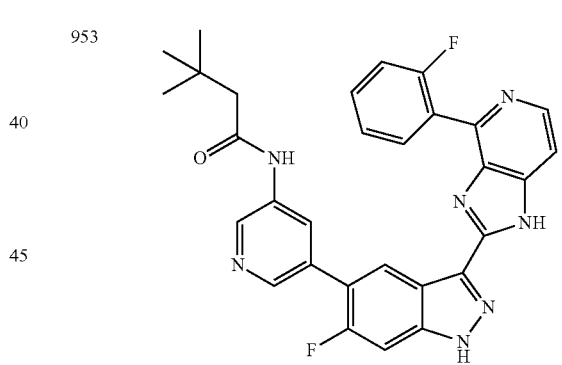
954 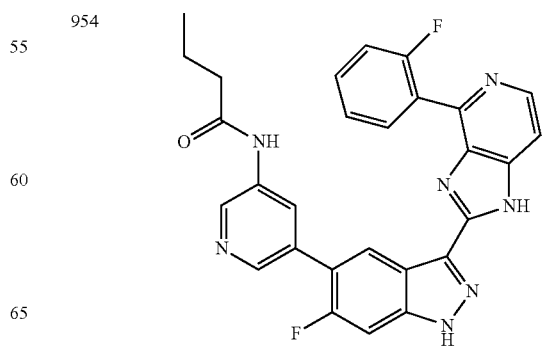

TABLE 1-continued
| | |
|---|---|
| 955 | 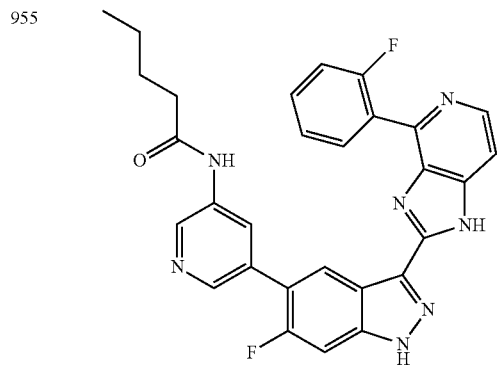 |
| 956 | 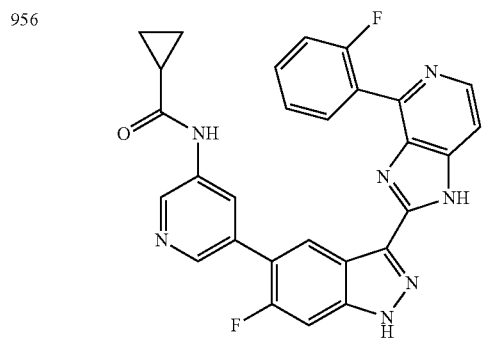 |
| 957 | 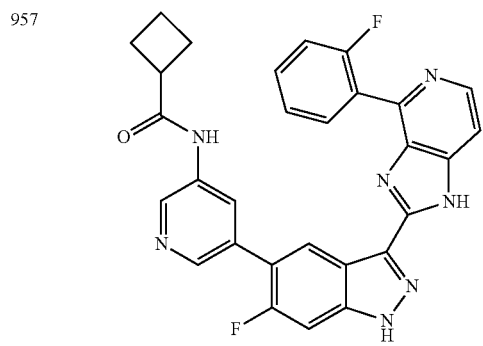 |
| 958 | 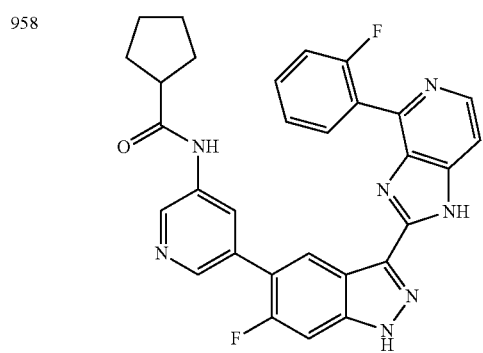 |
| 959 | 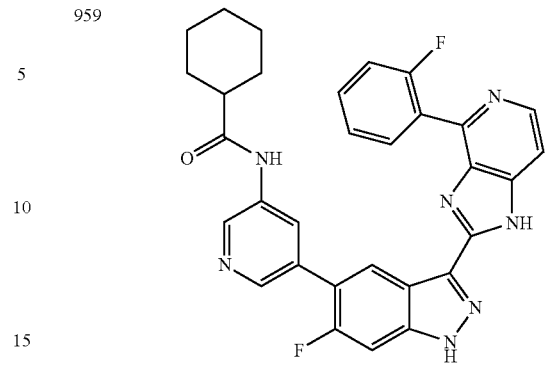 |
| 960 | 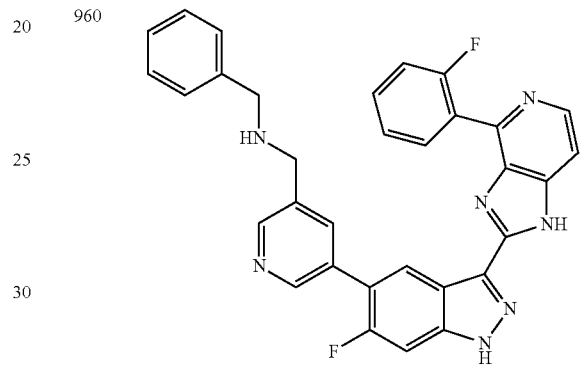 |
| 961 | 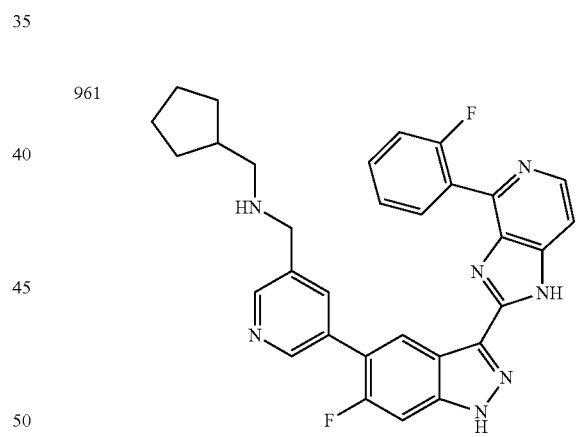 |
| 962 | 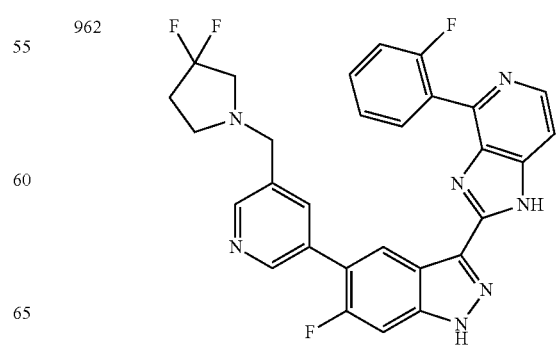 |

TABLE 1-continued
| | |
|---|---|
| 963 | 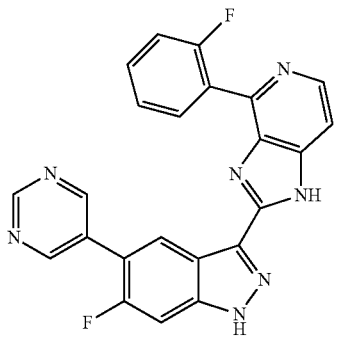 [SMILES: Fc1cc2[nH]nc(-c3nc4c(-c5ccccc5F)nccc4[nH]3)c2cc1-c1cncnc1] |
| 964 | 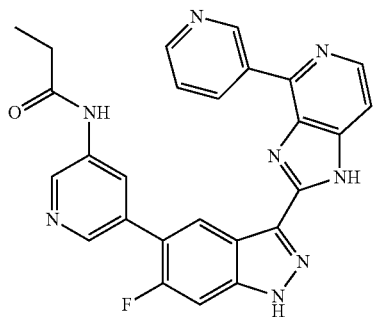 [SMILES: CCC(=O)Nc1cncc(-c2cc3c(-c4nc5c(-c6cccnc6)nccc5[nH]4)n[nH]c3cc2F)c1] |
| 965 | 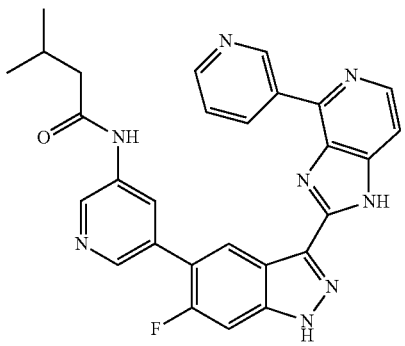 [SMILES: CC(C)CC(=O)Nc1cncc(-c2cc3c(-c4nc5c(-c6cccnc6)nccc5[nH]4)n[nH]c3cc2F)c1] |
| 966 | 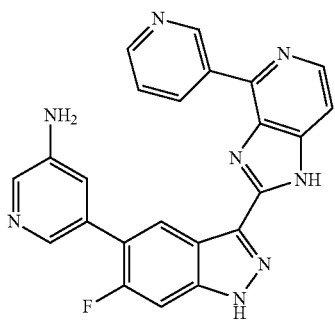 [SMILES: Nc1cncc(-c2cc3c(-c4nc5c(-c6cccnc6)nccc5[nH]4)n[nH]c3cc2F)c1] |
| 967 | 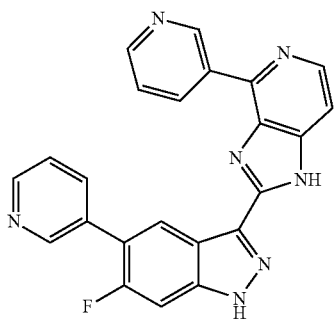 [SMILES: Fc1cc2[nH]nc(-c3nc4c(-c5cccnc5)nccc4[nH]3)c2cc1-c1cccnc1] |
| 968 | 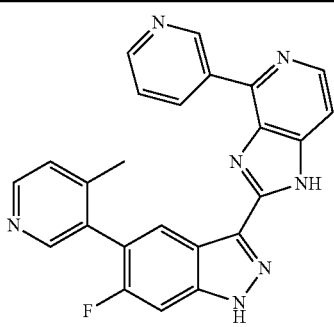 |
| 969 | 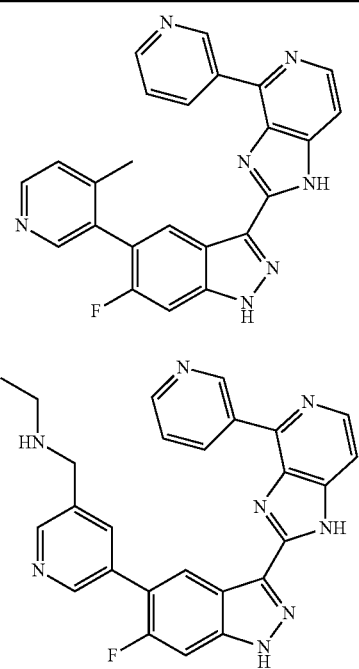 |
| 970 | 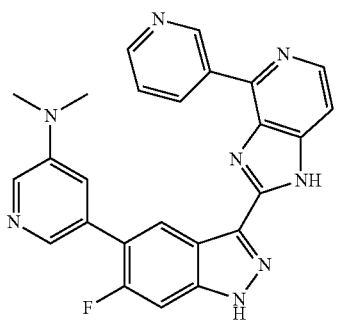 [SMILES: CN(C)c1cncc(-c2cc3c(-c4nc5c(-c6cccnc6)nccc5[nH]4)n[nH]c3cc2F)c1] |
| 971 | 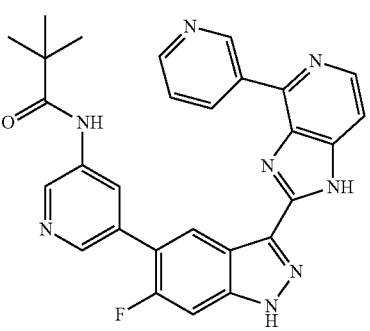 [SMILES: CC(C)(C)C(=O)Nc1cncc(-c2cc3c(-c4nc5c(-c6cccnc6)nccc5[nH]4)n[nH]c3cc2F)c1] |
| 972 | 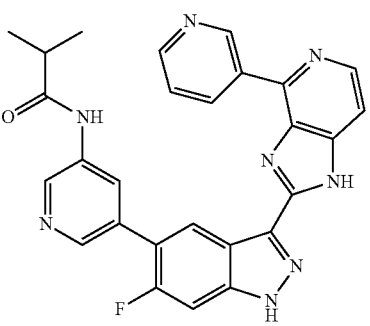 [SMILES: CC(C)C(=O)Nc1cncc(-c2cc3c(-c4nc5c(-c6cccnc6)nccc5[nH]4)n[nH]c3cc2F)c1] |

TABLE 1-continued
973 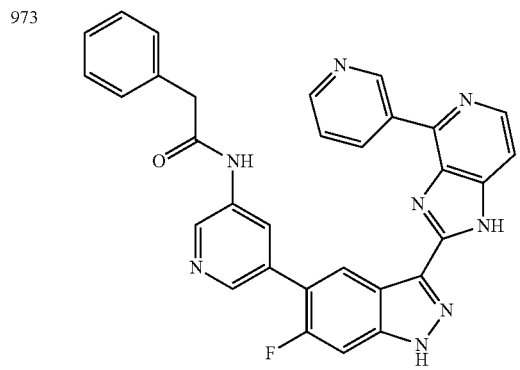
974 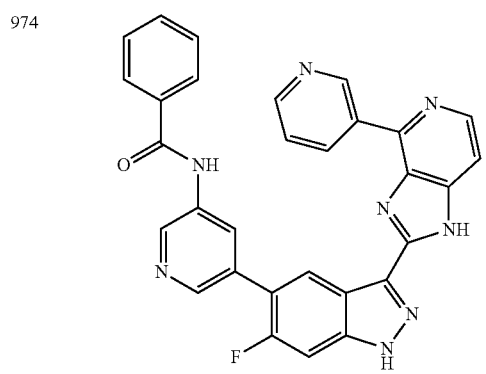
975 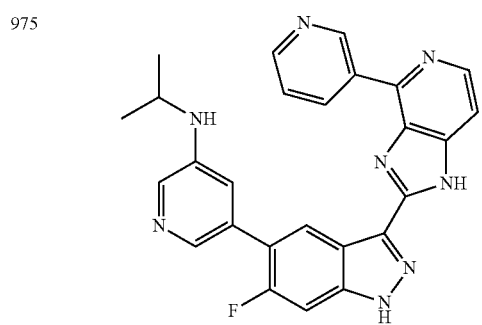
976 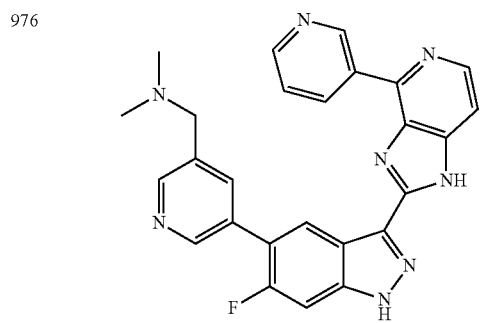
TABLE 1-continued
977 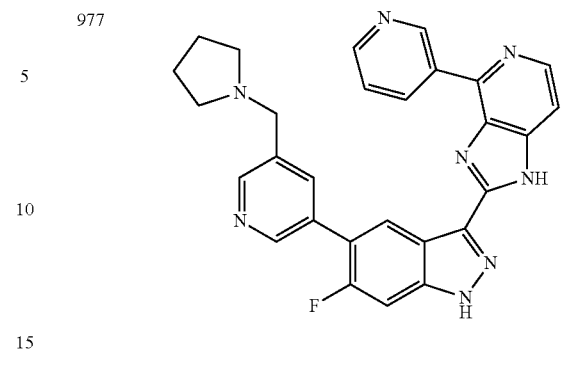
978 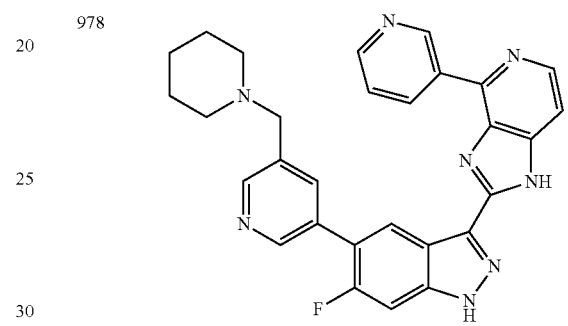
979 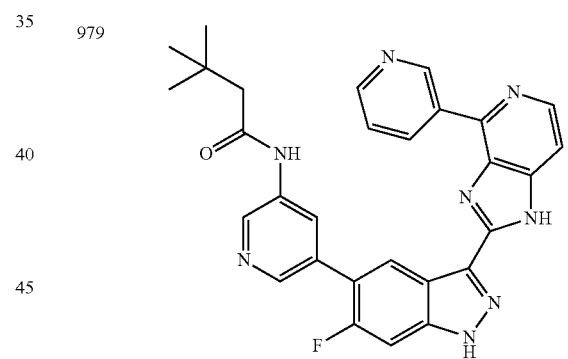
980 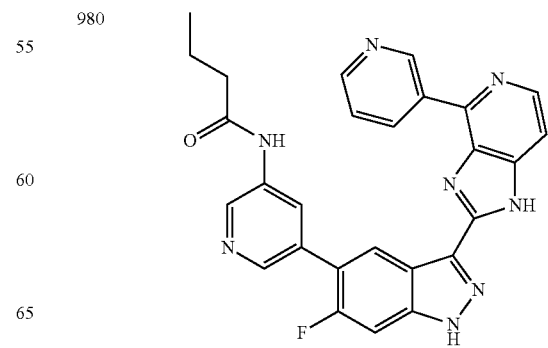

TABLE 1-continued
| 981 | 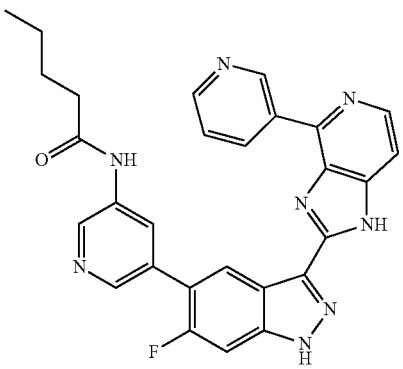 |
|---|---|
| 982 | 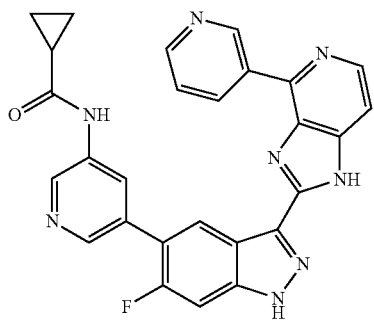 [SMILES: O=C(Nc1cncc(-c2cc3c(-c4nc5c(-c6cccnc6)nccc5[nH]4)n[nH]c3cc2F)c1)C1CC1] |
| 983 | 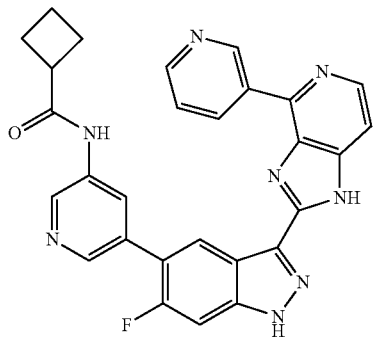 [SMILES: O=C(Nc1cncc(-c2cc3c(-c4nc5c(-c6cccnc6)nccc5[nH]4)n[nH]c3cc2F)c1)C1CCC1] |
| 984 | 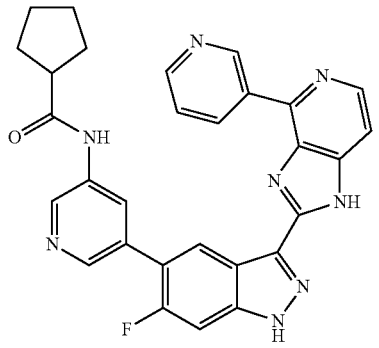 [SMILES: O=C(Nc1cncc(-c2cc3c(-c4nc5c(-c6cccnc6)nccc5[nH]4)n[nH]c3cc2F)c1)C1CCCC1] |
TABLE 1-continued
| 985 | 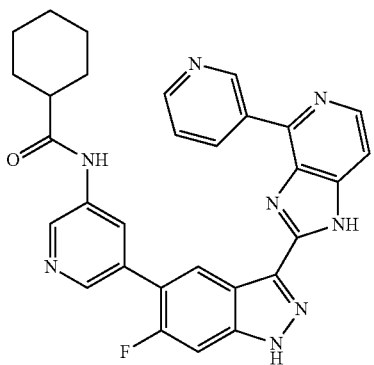 [SMILES: O=C(Nc1cncc(-c2cc3c(-c4nc5c(-c6cccnc6)nccc5[nH]4)n[nH]c3cc2F)c1)C1CCCCC1] |
|---|---|
| 986 | 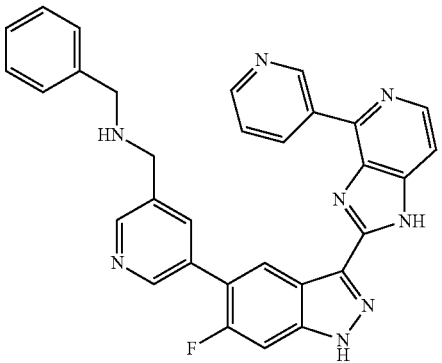 [SMILES: Fc1cc2[nH]nc(-c3nc4c(-c5cccnc5)nccc4[nH]3)c2cc1-c1cncc(CNCc2ccccc2)c1] |
| 987 | 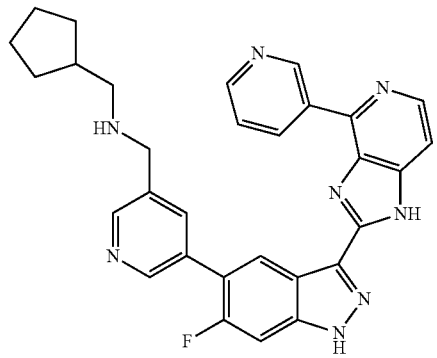 [SMILES: Fc1cc2[nH]nc(-c3nc4c(-c5cccnc5)nccc4[nH]3)c2cc1-c1cncc(CNCC2CCCC2)c1] |
| 988 | 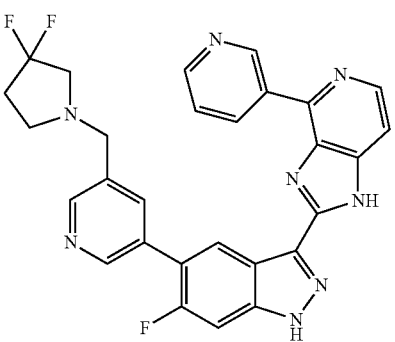 [SMILES: Fc1cc2[nH]nc(-c3nc4c(-c5cccnc5)nccc4[nH]3)c2cc1-c1cncc(CN2CCC(F)(F)C2)c1] |

TABLE 1-continued
989 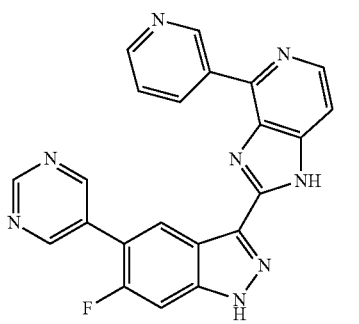 [SMILES: Fc1cc2[nH]nc(-c3nc4c(-c5cccnc5)nccc4[nH]3)c2cc1-c1cncnc1]
990 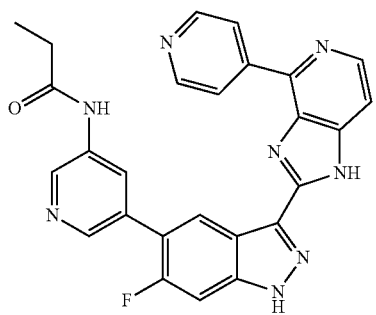 [SMILES: CCC(=O)Nc1cncc(-c2cc3c(-c4nc5c(-c6ccncc6)nccc5[nH]4)n[nH]c3cc2F)c1]
991 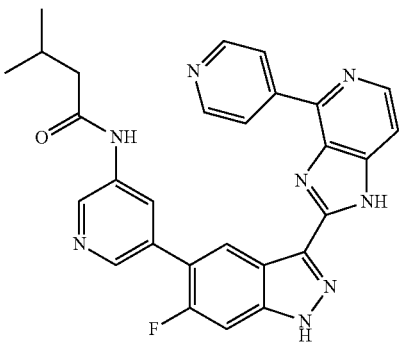
992 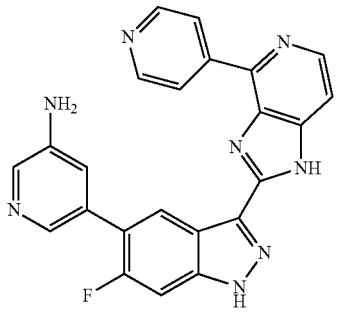 [SMILES: Nc1cncc(-c2cc3c(-c4nc5c(-c6ccncc6)nccc5[nH]4)n[nH]c3cc2F)c1]
993 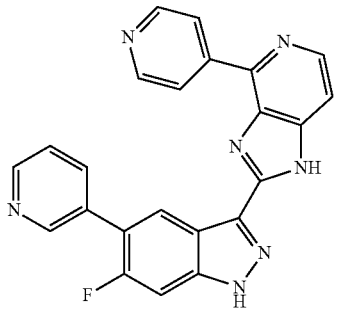 [SMILES: Fc1cc2[nH]nc(-c3nc4c(-c5ccncc5)nccc4[nH]3)c2cc1-c1cccnc1]
994 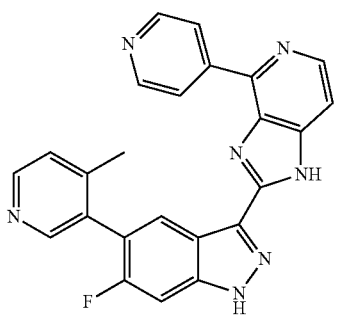 [SMILES: Cc1ccncc1-c1cc2c(-c3nc4c(-c5ccncc5)nccc4[nH]3)n[nH]c2cc1F]
995 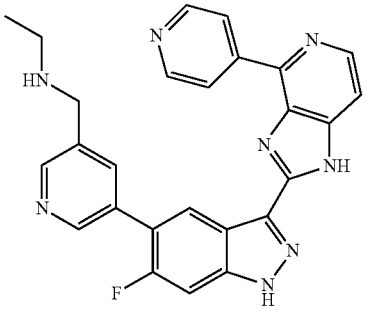
996 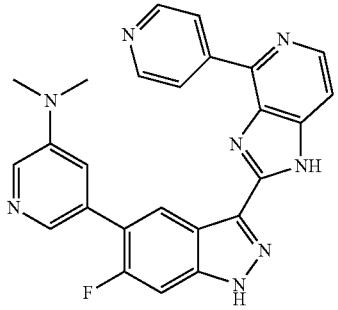 [SMILES: CN(C)c1cncc(-c2cc3c(-c4nc5c(-c6ccncc6)nccc5[nH]4)n[nH]c3cc2F)c1]
997 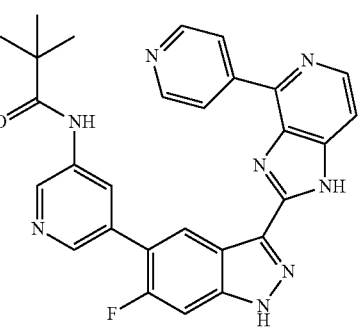
998 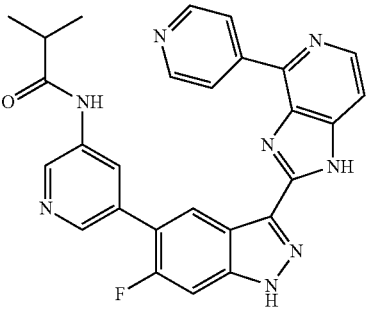 [SMILES: CC(C)C(=O)Nc1cncc(-c2cc3c(-c4nc5c(-c6ccncc6)nccc5[nH]4)n[nH]c3cc2F)c1]

TABLE 1-continued
999 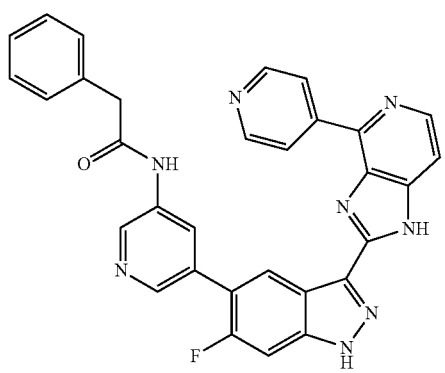 [SMILES: O=C(Cc1ccccc1)Nc1cncc(-c2cc3c(-c4nc5c(-c6ccncc6)nccc5[nH]4)n[nH]c3cc2F)c1]
1000 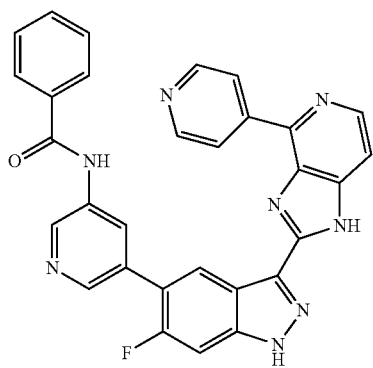 [SMILES: O=C(Nc1cncc(-c2cc3c(-c4nc5c(-c6ccncc6)nccc5[nH]4)n[nH]c3cc2F)c1)c1ccccc1]
1001 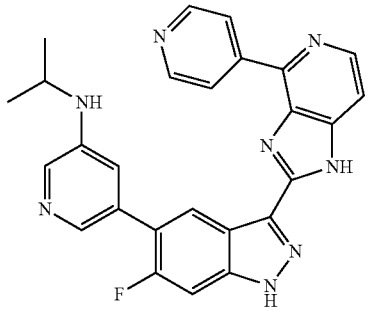 [SMILES: CC(C)Nc1cncc(-c2cc3c(-c4nc5c(-c6ccncc6)nccc5[nH]4)n[nH]c3cc2F)c1]
1002 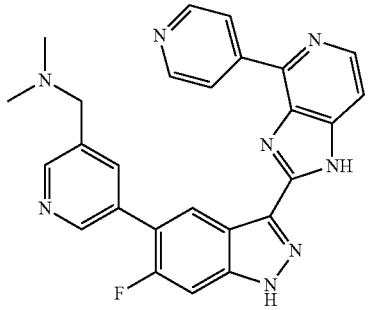 [SMILES: CN(C)Cc1cncc(-c2cc3c(-c4nc5c(-c6ccncc6)nccc5[nH]4)n[nH]c3cc2F)c1]
1003 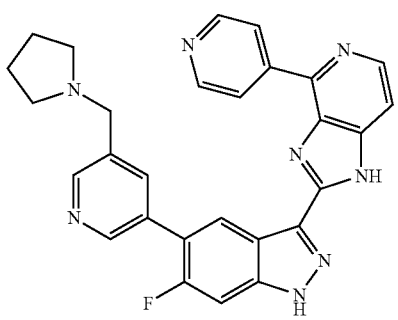 [SMILES: Fc1cc2[nH]nc(-c3nc4c(-c5ccncc5)nccc4[nH]3)c2cc1-c1cncc(CN2CCCC2)c1]
1004 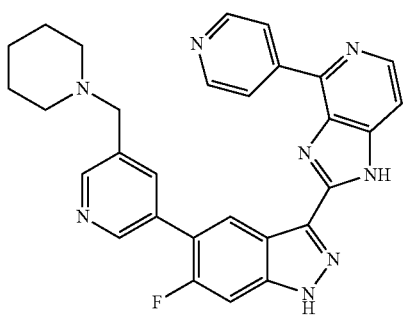 [SMILES: Fc1cc2[nH]nc(-c3nc4c(-c5ccncc5)nccc4[nH]3)c2cc1-c1cncc(CN2CCCCC2)c1]
1005 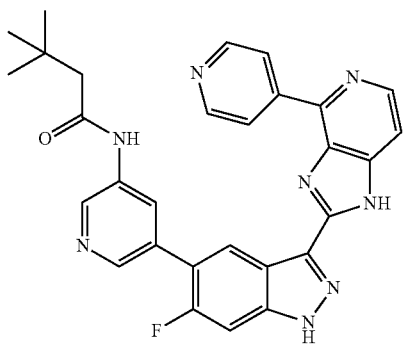 [SMILES: CC(C)(C)CC(=O)Nc1cncc(-c2cc3c(-c4nc5c(-c6ccncc6)nccc5[nH]4)n[nH]c3cc2F)c1]
1006 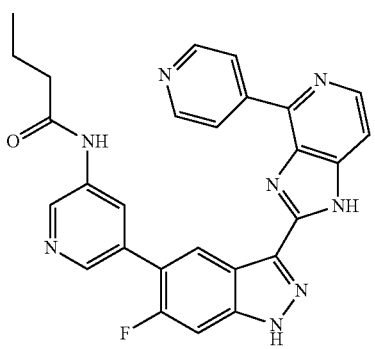 [SMILES: CCCC(=O)Nc1cncc(-c2cc3c(-c4nc5c(-c6ccncc6)nccc5[nH]4)n[nH]c3cc2F)c1]

TABLE 1-continued
1007 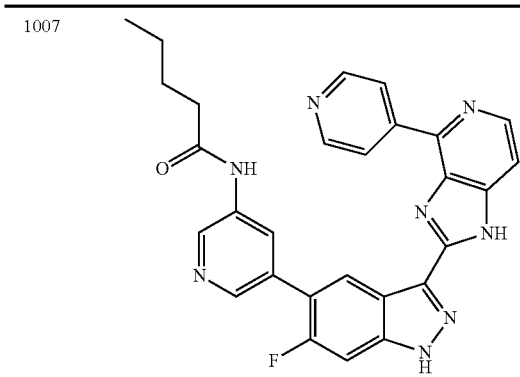
1008 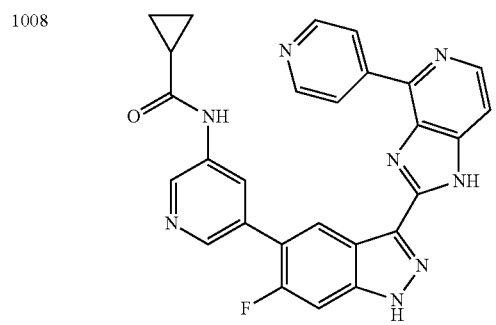
1009 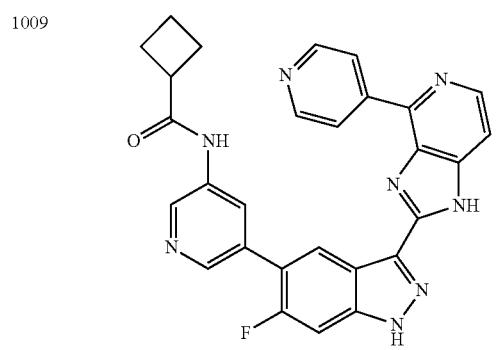
1010 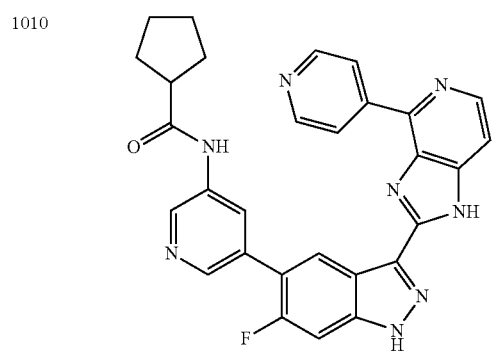
TABLE 1-continued
1011 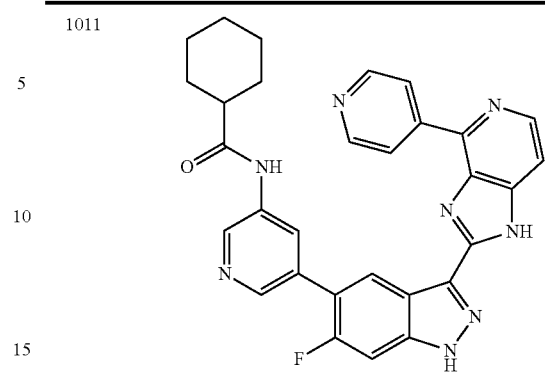
1012 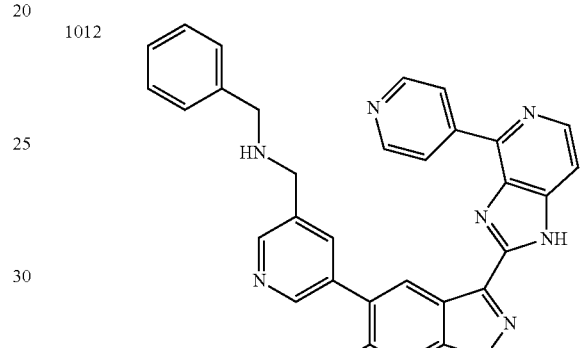
1013 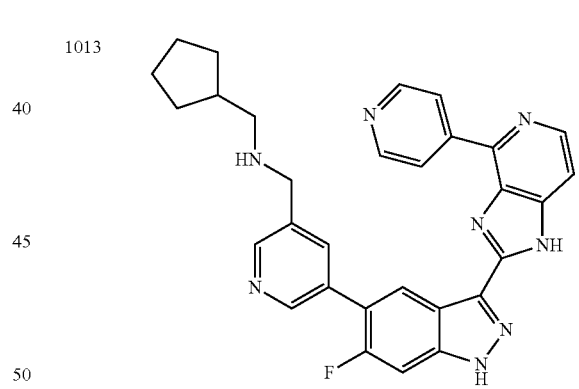
1014 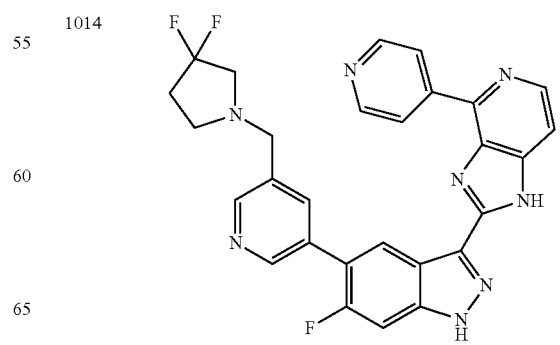

TABLE 1-continued
| | |
|---|---|
| 1015 | 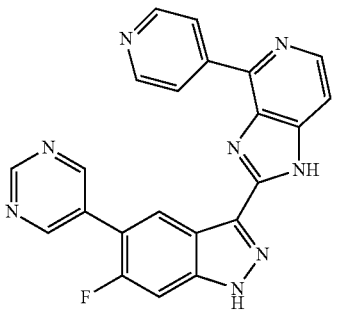 [SMILES: Fc1cc2[nH]nc(-c3nc4c(-c5ccncc5)nccc4[nH]3)c2cc1-c1cncnc1] |
| 1016 | 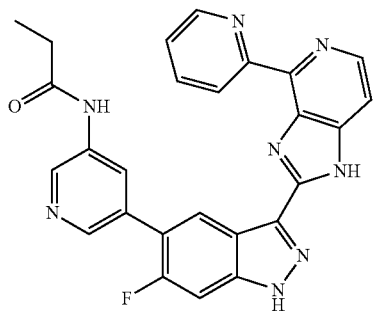 [SMILES: CCC(=O)Nc1cncc(-c2cc3c(-c4nc5c(-c6ccccn6)nccc5[nH]4)n[nH]c3cc2F)c1] |
| 1017 | 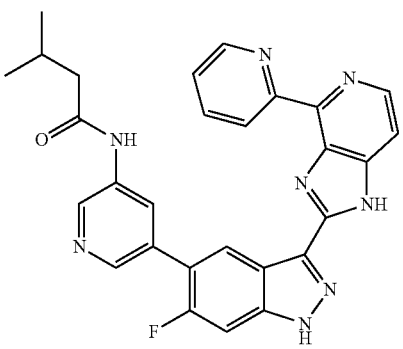 |
| 1018 | 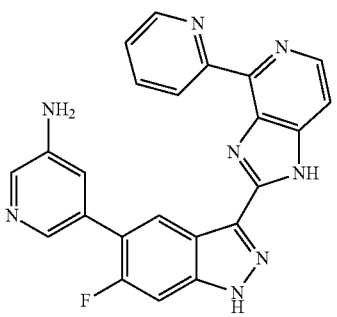 [SMILES: Nc1cncc(-c2cc3c(-c4nc5c(-c6ccccn6)nccc5[nH]4)n[nH]c3cc2F)c1] |
| 1019 | 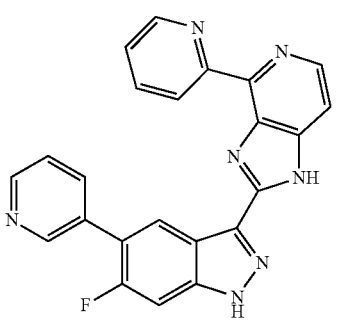 |
| 1020 | 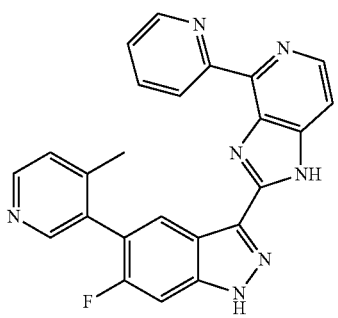 |
| 1021 | 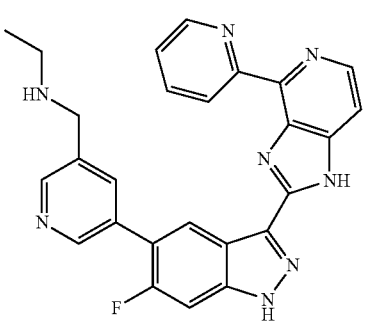 [SMILES: CCNCc1cncc(-c2cc3c(-c4nc5c(-c6ccccn6)nccc5[nH]4)n[nH]c3cc2F)c1] |
| 1022 | 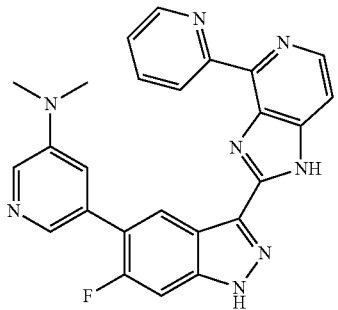 [SMILES: CN(C)c1cncc(-c2cc3c(-c4nc5c(-c6ccccn6)nccc5[nH]4)n[nH]c3cc2F)c1] |
| 1023 | 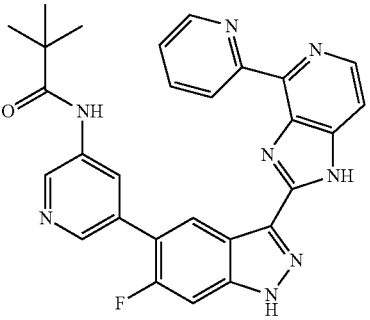 [SMILES: CC(C)(C)C(=O)Nc1cncc(-c2cc3c(-c4nc5c(-c6ccccn6)nccc5[nH]4)n[nH]c3cc2F)c1] |
| 1024 | 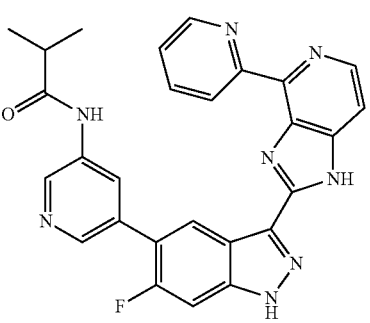 [SMILES: CC(C)C(=O)Nc1cncc(-c2cc3c(-c4nc5c(-c6ccccn6)nccc5[nH]4)n[nH]c3cc2F)c1] |

TABLE 1-continued
1025 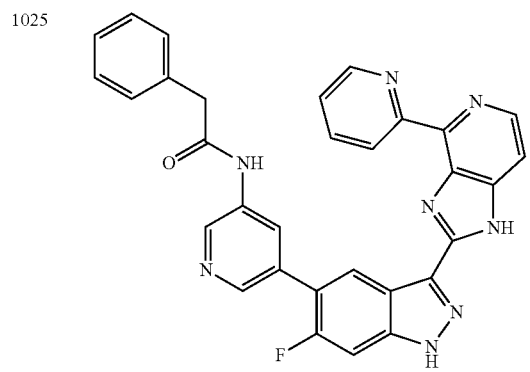
1026 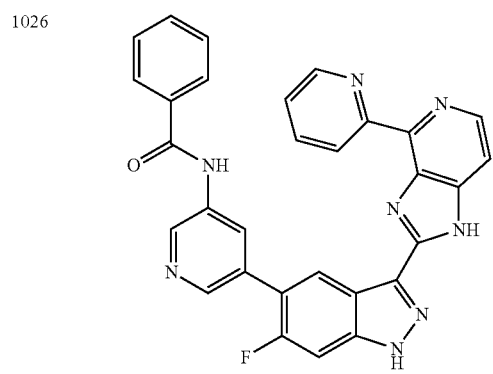
1027 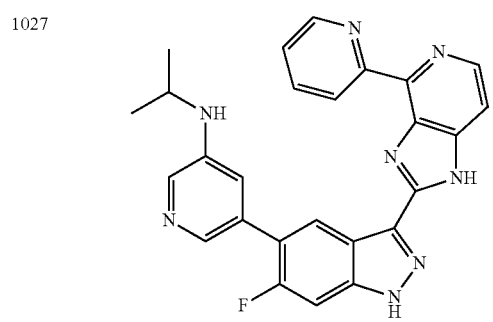
1028 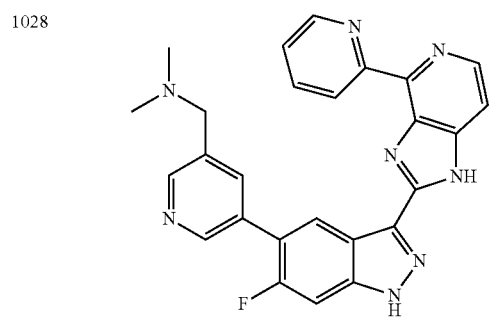
TABLE 1-continued
1029 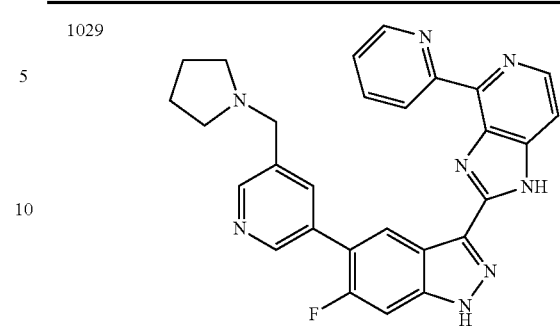
1030 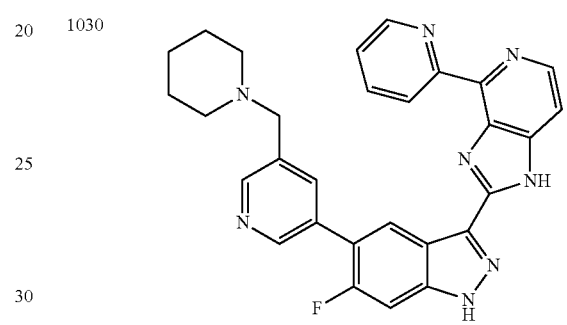
1031 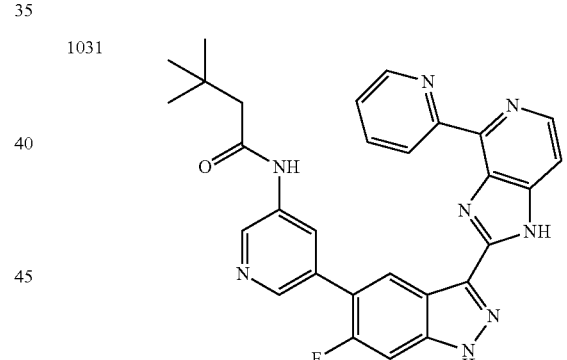
1032 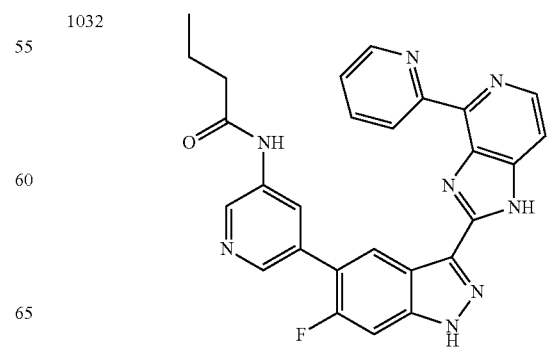

TABLE 1-continued
| 1033 | 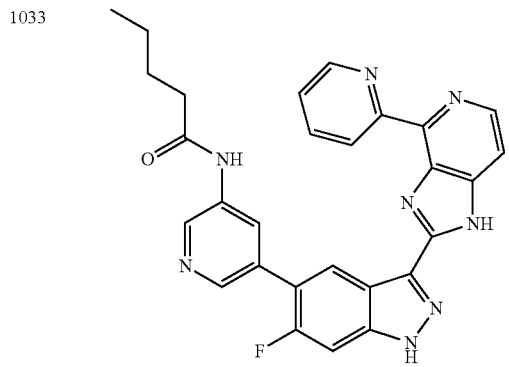 | 1037 | 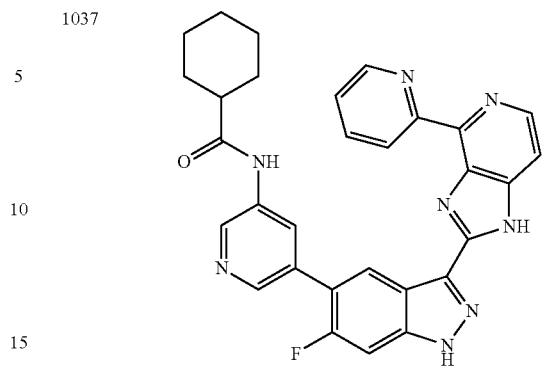 |
| 1034 | 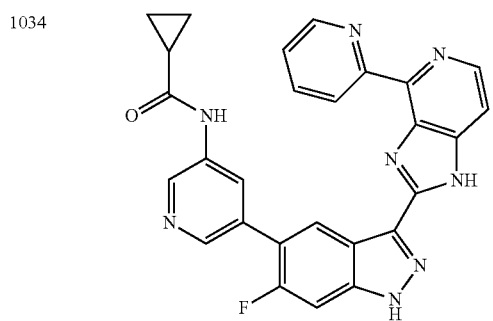 | 1038 | 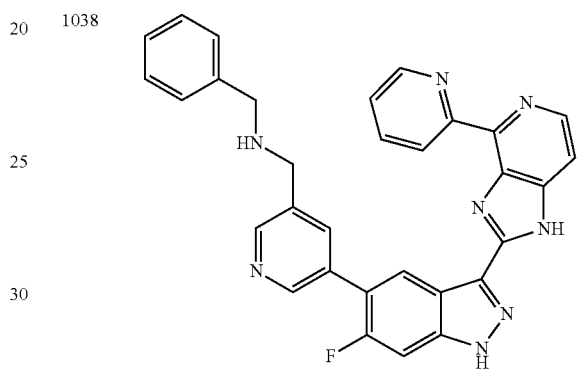 |
| 1035 | 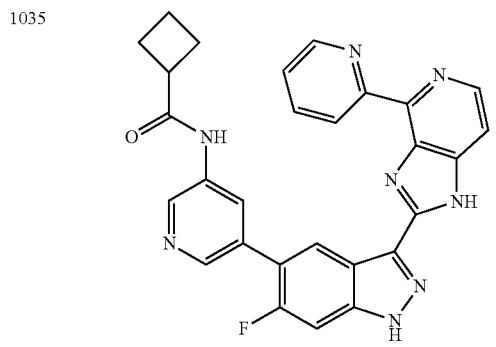 | 1039 | 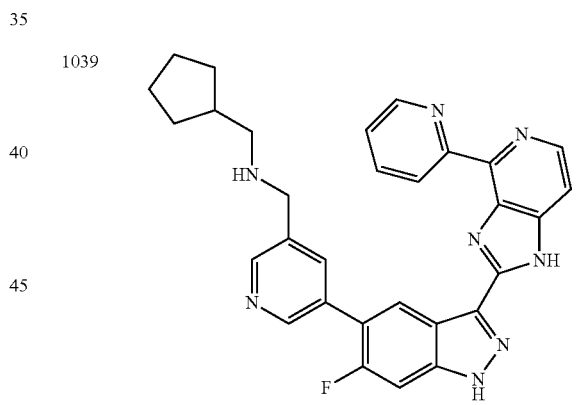 |
| 1036 | 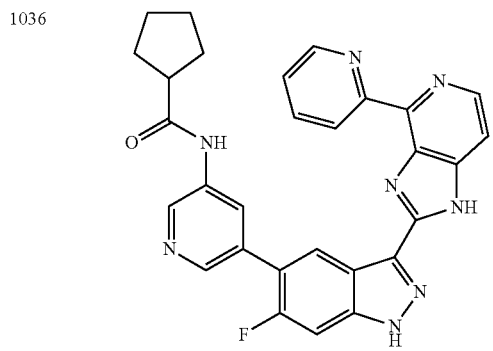 | 1040 | 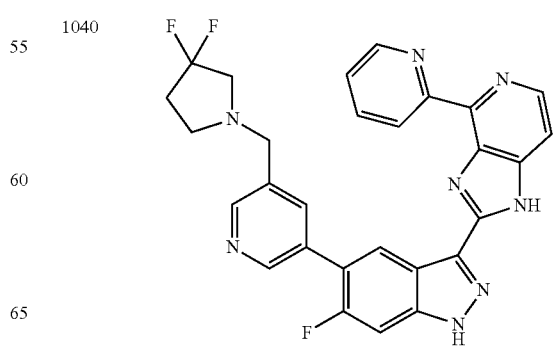 |

TABLE 1-continued
1041 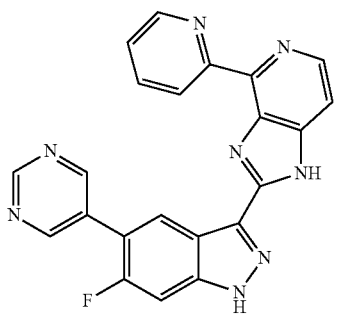 [SMILES: Fc1cc2[nH]nc(-c3nc4c(-c5ccccn5)nccc4[nH]3)c2cc1-c1cncnc1]
1042 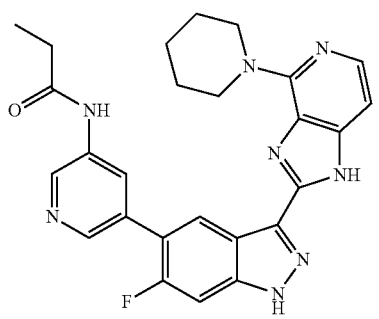 [SMILES: CCC(=O)Nc1cncc(-c2cc3c(-c4nc5c(N6CCCCC6)nccc5[nH]4)n[nH]c3cc2F)c1]
1043 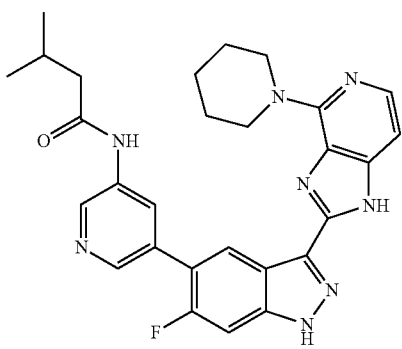 [SMILES: CC(C)CC(=O)Nc1cncc(-c2cc3c(-c4nc5c(N6CCCCC6)nccc5[nH]4)n[nH]c3cc2F)c1]
1044 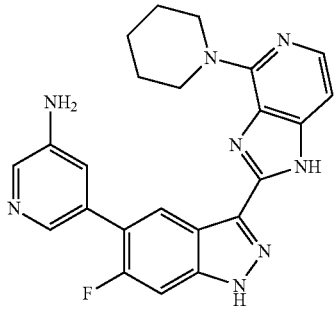 [SMILES: Nc1cncc(-c2cc3c(-c4nc5c(N6CCCCC6)nccc5[nH]4)n[nH]c3cc2F)c1]
1045 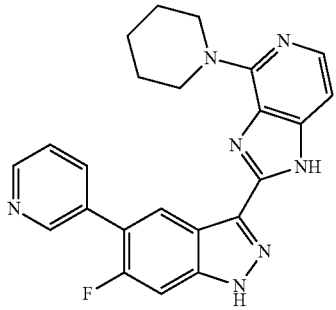 [SMILES: Fc1cc2[nH]nc(-c3nc4c(N5CCCCC5)nccc4[nH]3)c2cc1-c1cccnc1]
1046 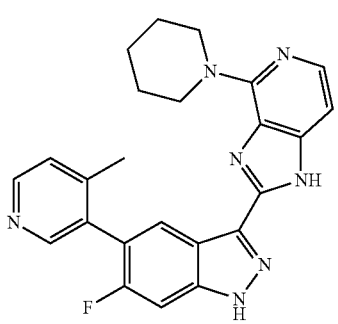
1047 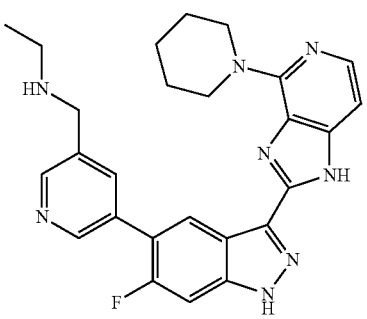
1048 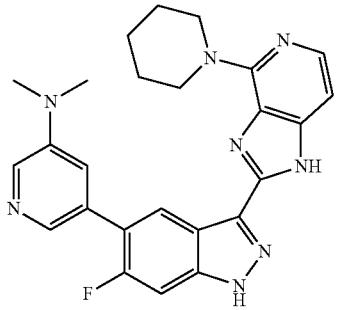 [SMILES: CN(C)c1cncc(-c2cc3c(-c4nc5c(N6CCCCC6)nccc5[nH]4)n[nH]c3cc2F)c1]
1049 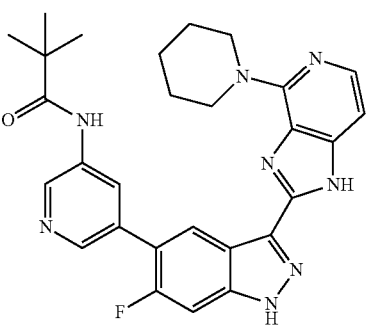 [SMILES: CC(C)(C)C(=O)Nc1cncc(-c2cc3c(-c4nc5c(N6CCCCC6)nccc5[nH]4)n[nH]c3cc2F)c1]
1050 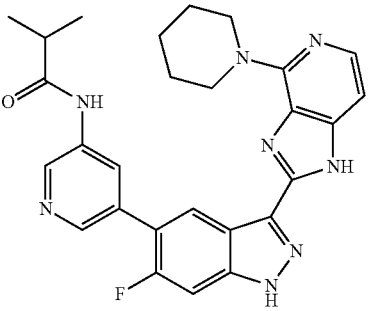 [SMILES: CC(C)C(=O)Nc1cncc(-c2cc3c(-c4nc5c(N6CCCCC6)nccc5[nH]4)n[nH]c3cc2F)c1]

TABLE 1-continued
1051 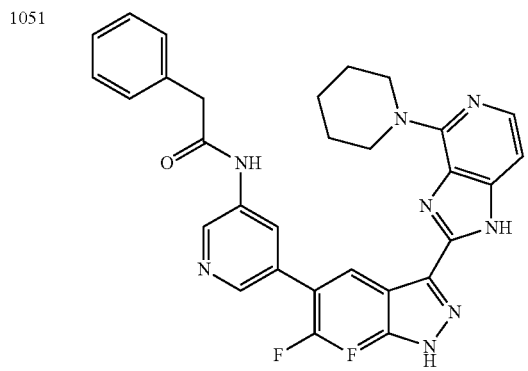
1052 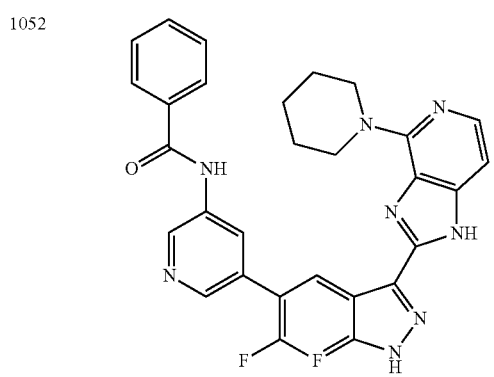
1053 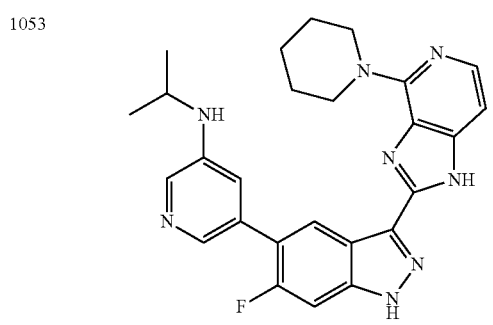
1054 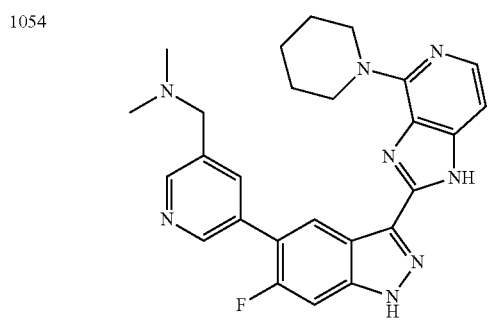
TABLE 1-continued
1055 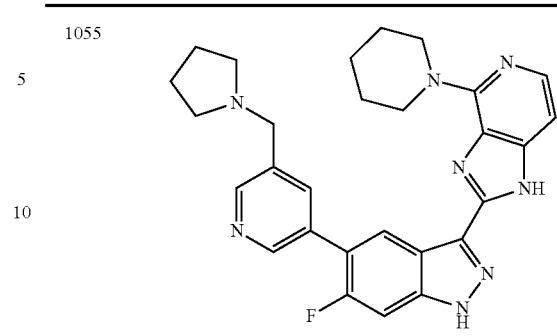
1056 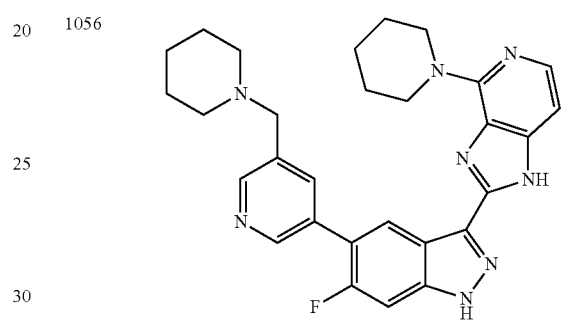
1057 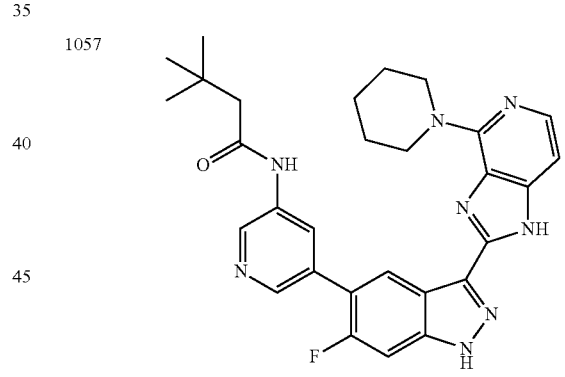
1058 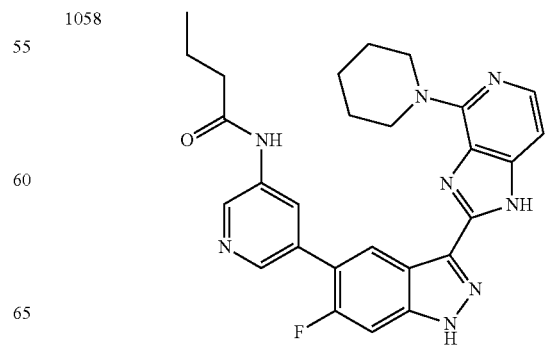

| | |
|---|---|
| 1059 | 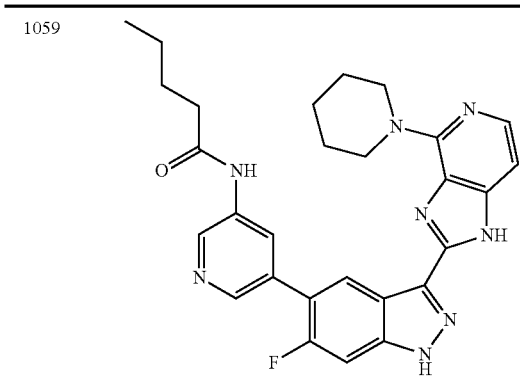 |
| 1060 | 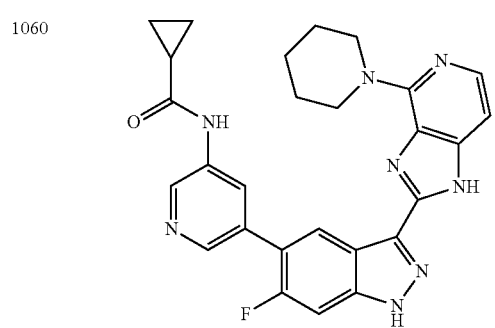 |
| 1061 | 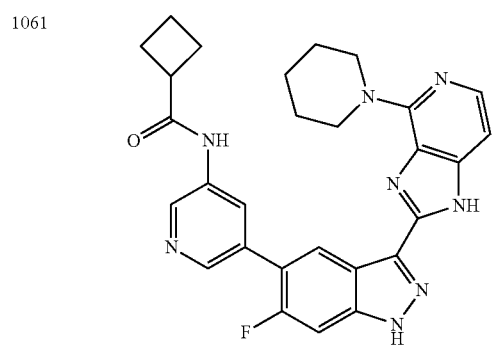 |
| 1062 | 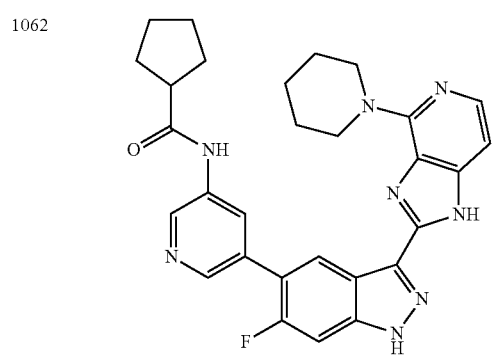 |
| 1063 | 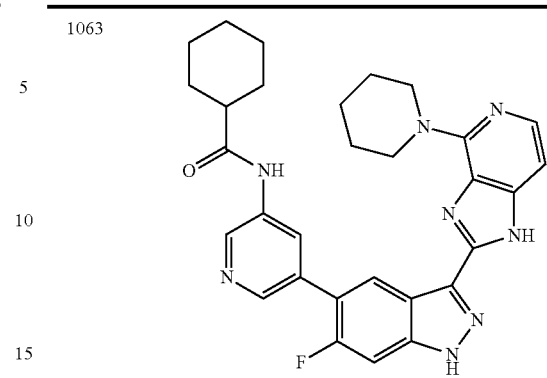 |
| 1064 | 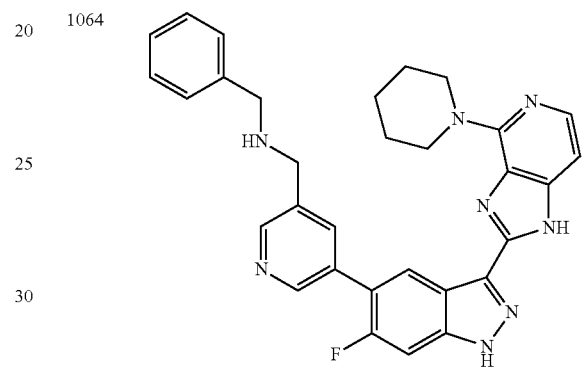 |
| 1065 | 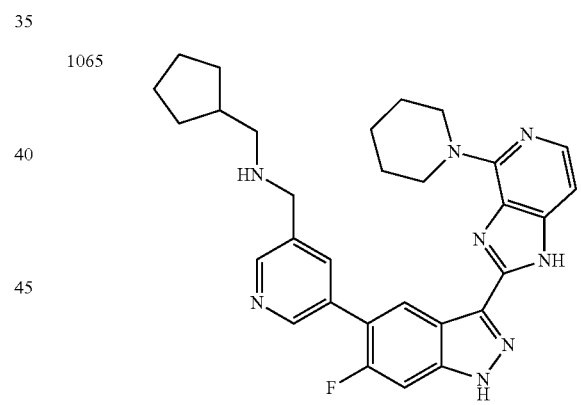 |
| 1066 | 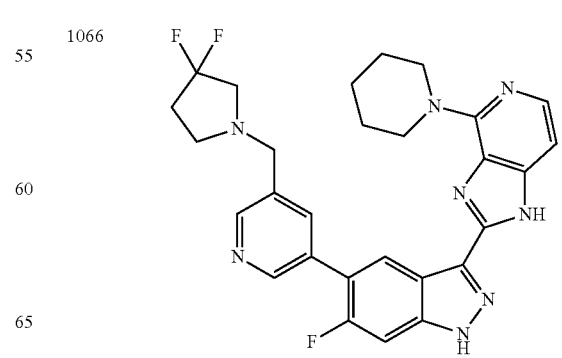 |

TABLE 1-continued
1067
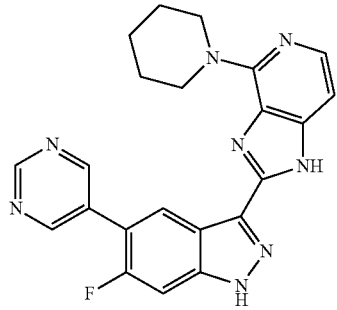 [SMILES: Fc1cc2[nH]nc(-c3nc4c(N5CCCCC5)nccc4[nH]3)c2cc1-c1cncnc1]
1068
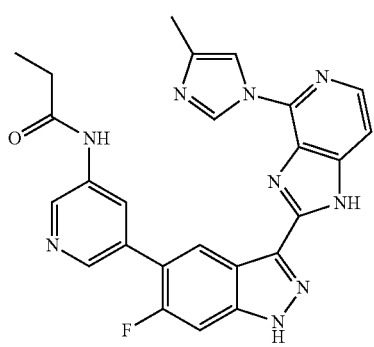 [SMILES: CCC(=O)Nc1cncc(-c2cc3c(-c4nc5c(-n6cnc(C)c6)nccc5[nH]4)n[nH]c3cc2F)c1]
1069
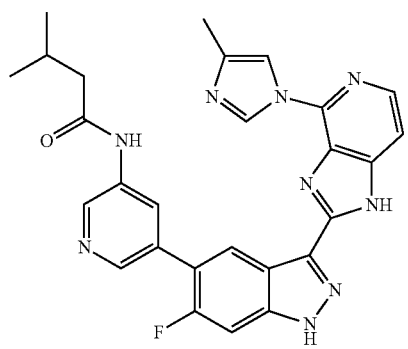 [SMILES: Cc1cn(-c2nccc3[nH]c(-c4n[nH]c5cc(F)c(-c6cncc(NC(=O)CC(C)C)c6)cc45)nc23)cn1]
1070
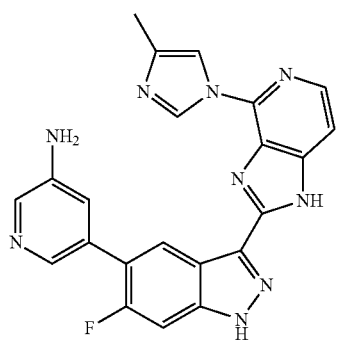 [SMILES: Cc1cn(-c2nccc3[nH]c(-c4n[nH]c5cc(F)c(-c6cncc(N)c6)cc45)nc23)cn1]
TABLE 1-continued
1071
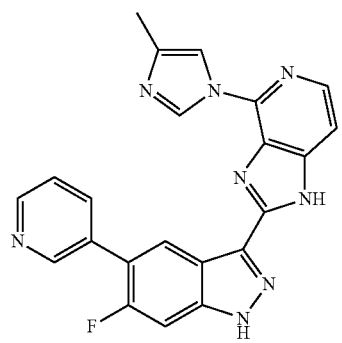
1072
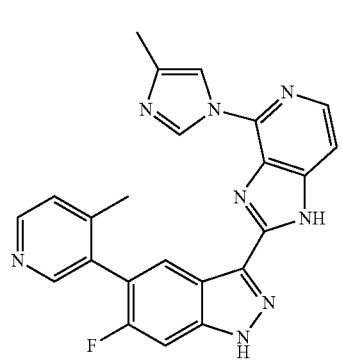 [SMILES: Cc1cn(-c2nccc3[nH]c(-c4n[nH]c5cc(F)c(-c6cnccc6C)cc45)nc23)cn1]
1073
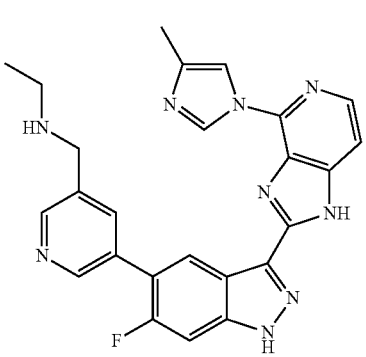
1074
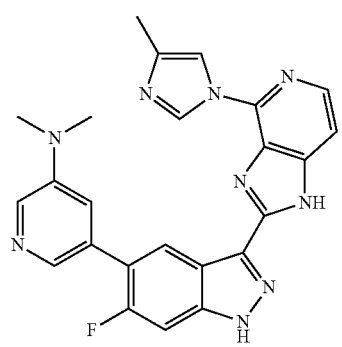 [SMILES: Cc1cn(-c2nccc3[nH]c(-c4n[nH]c5cc(F)c(-c6cncc(N(C)C)c6)cc45)nc23)cn1]

TABLE 1-continued
1075 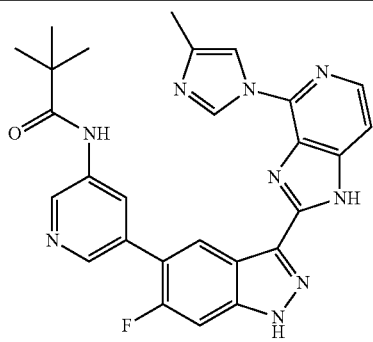
1076 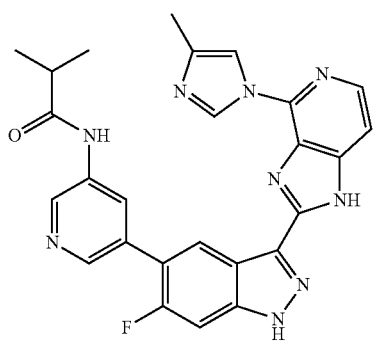 [SMILES: Cc1cn(-c2nccc3[nH]c(-c4n[nH]c5cc(F)c(-c6cncc(NC(=O)C(C)C)c6)cc45)nc23)cn1]
1077 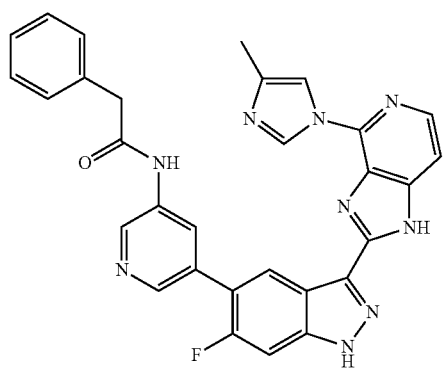 [SMILES: Cc1cn(-c2nccc3[nH]c(-c4n[nH]c5cc(F)c(-c6cncc(NC(=O)Cc7ccccc7)c6)cc45)nc23)cn1]
1078 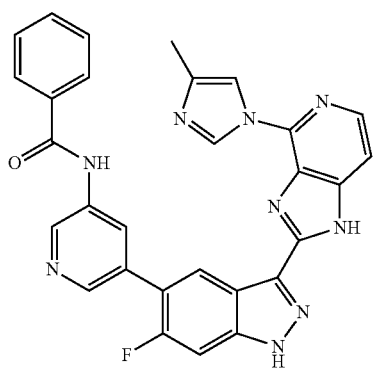 [SMILES: Cc1cn(-c2nccc3[nH]c(-c4n[nH]c5cc(F)c(-c6cncc(NC(=O)c7ccccc7)c6)cc45)nc23)cn1]
1079 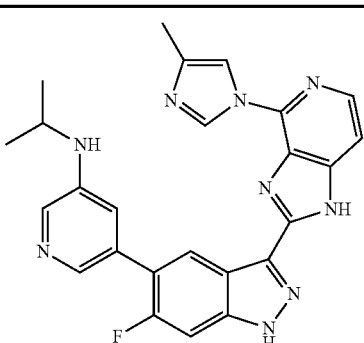
1080 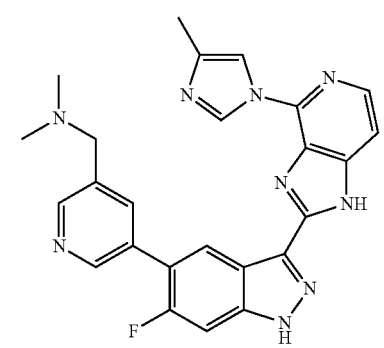
1081 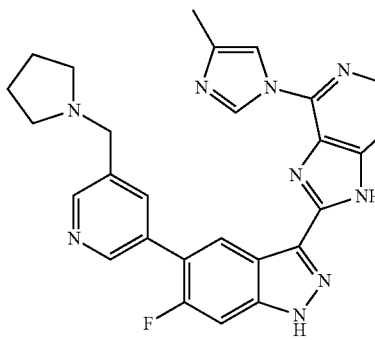
1082 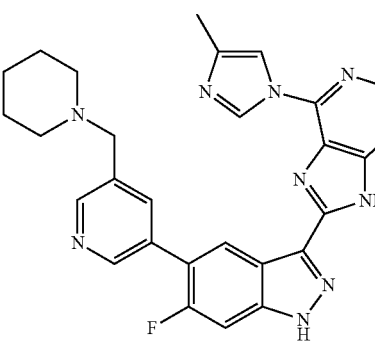

TABLE 1-continued
1083 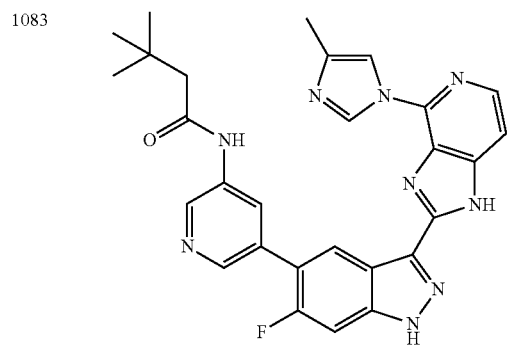
1084 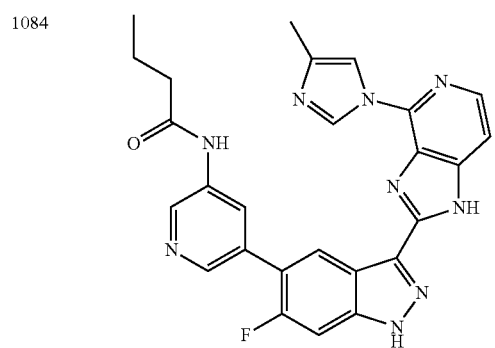
1085 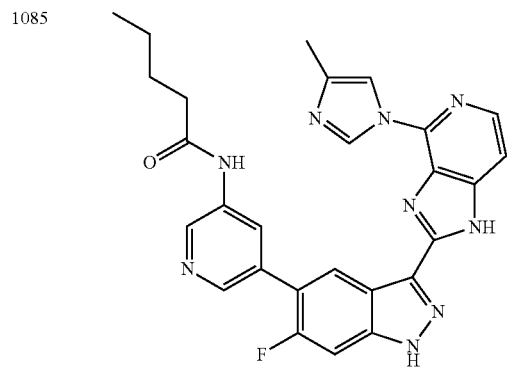
1086 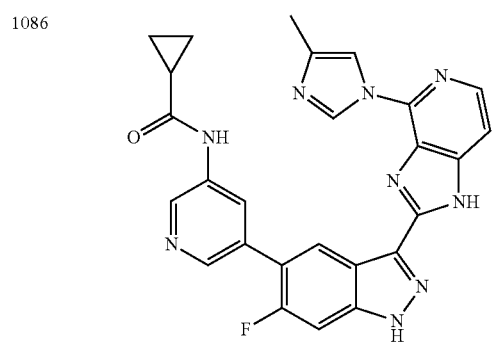
TABLE 1-continued
1087 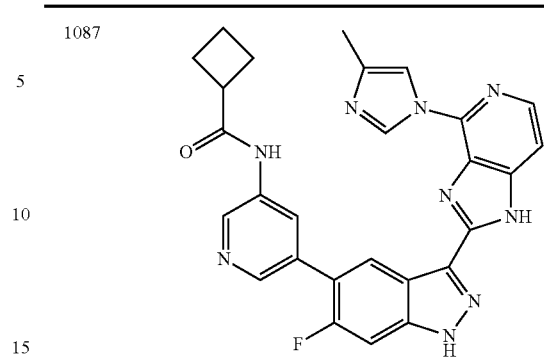
1088 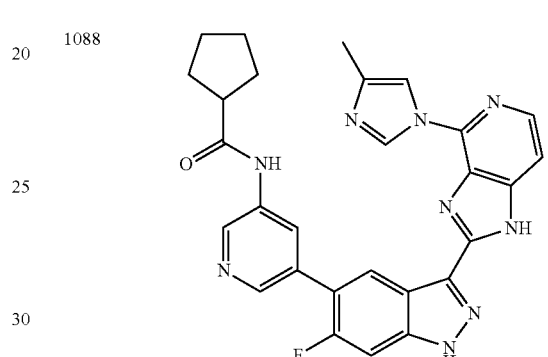
1089 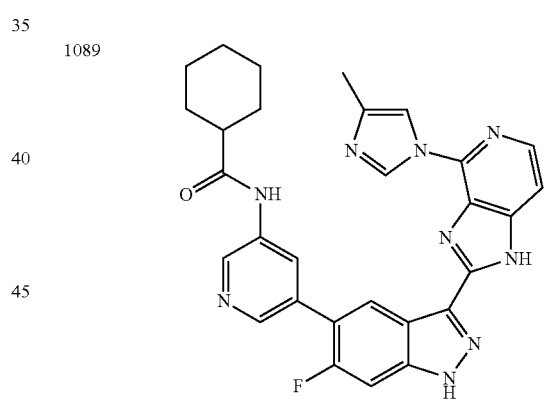
1090 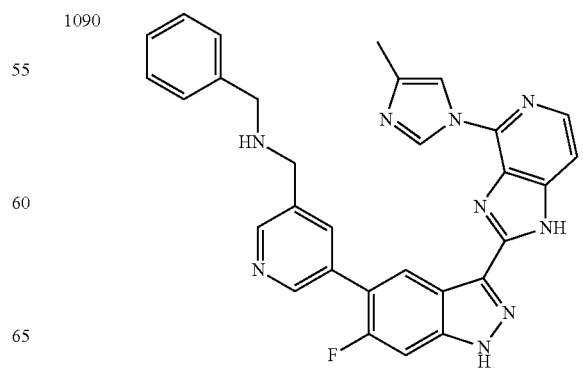

TABLE 1-continued
1091 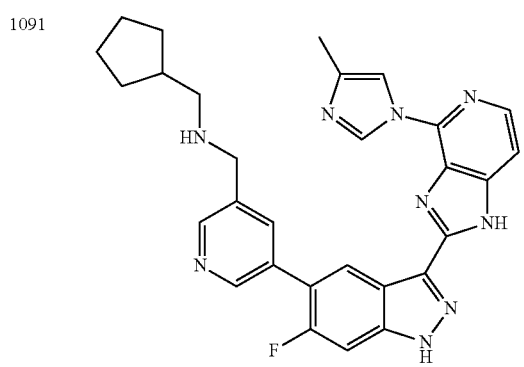
1092 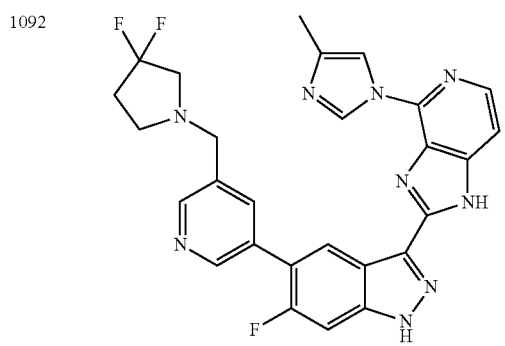
1093 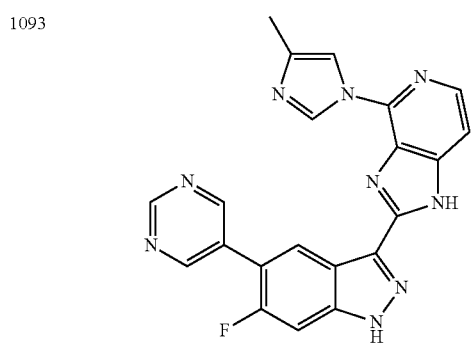
1094 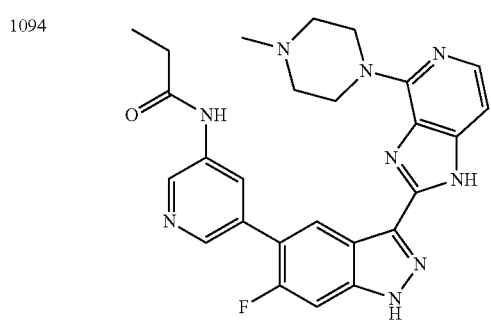
TABLE 1-continued
1095 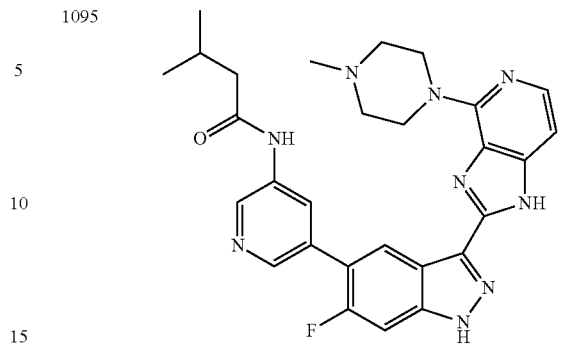
1096 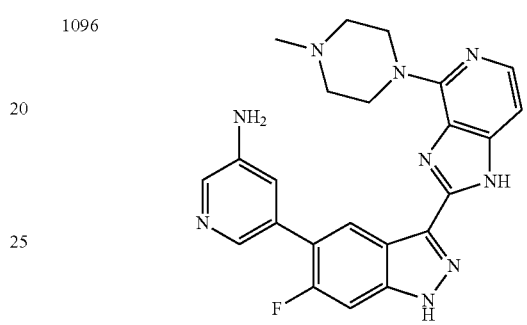
1097 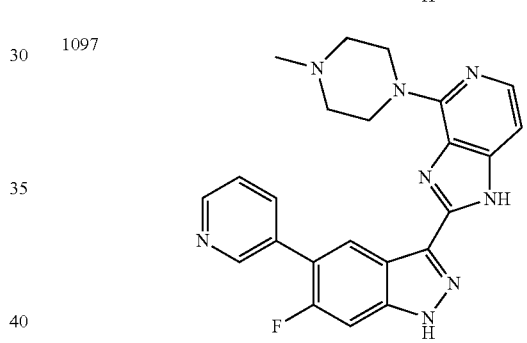
1098 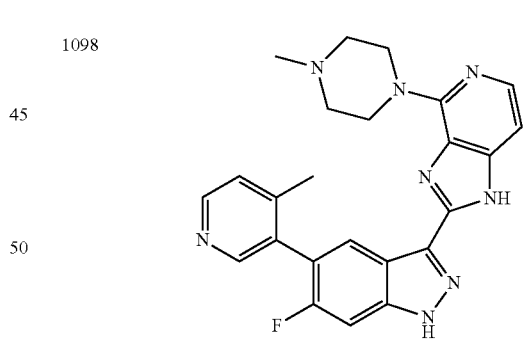
1099 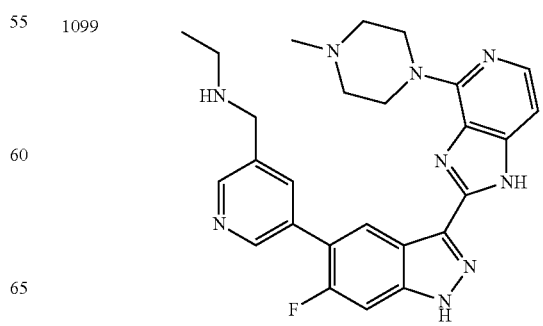

TABLE 1-continued
| | |
|---|---|
| 1100 | 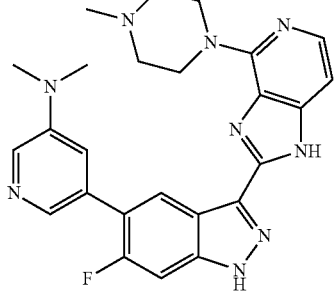 |
| 1101 | 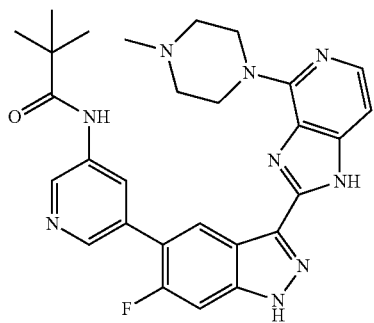 [SMILES: CN1CCN(c2nccc3[nH]c(-c4n[nH]c5cc(F)c(-c6cncc(NC(=O)C(C)(C)C)c6)cc45)nc23)CC1] |
| 1102 | 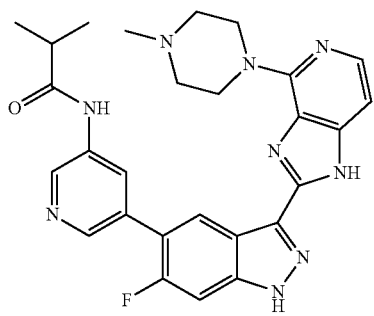 [SMILES: CC(C)C(=O)Nc1cncc(-c2cc3c(-c4nc5c(N6CCN(C)CC6)nccc5[nH]4)n[nH]c3cc2F)c1] |
| 1103 | 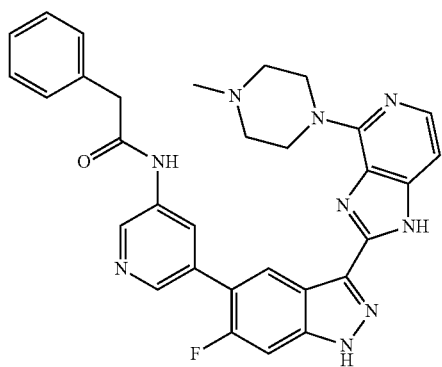 [SMILES: CN1CCN(c2nccc3[nH]c(-c4n[nH]c5cc(F)c(-c6cncc(NC(=O)Cc7ccccc7)c6)cc45)nc23)CC1] |
| 1104 | 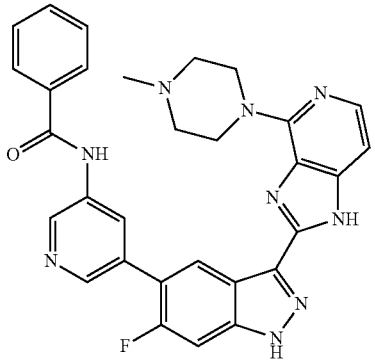 [SMILES: CN1CCN(c2nccc3[nH]c(-c4n[nH]c5cc(F)c(-c6cncc(NC(=O)c7ccccc7)c6)cc45)nc23)CC1] |
| 1105 | 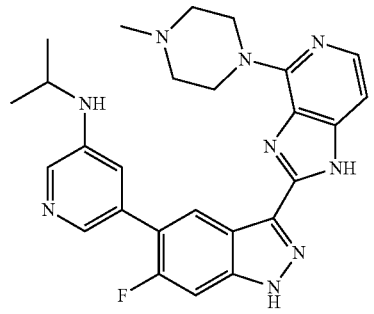 [SMILES: CC(C)Nc1cncc(-c2cc3c(-c4nc5c(N6CCN(C)CC6)nccc5[nH]4)n[nH]c3cc2F)c1] |
| 1106 | 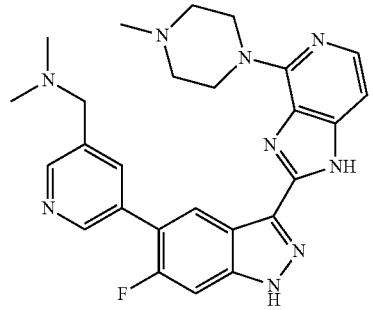 |
| 1107 | 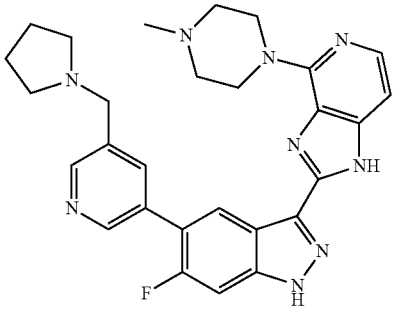 [SMILES: CN1CCN(c2nccc3[nH]c(-c4n[nH]c5cc(F)c(-c6cncc(CN7CCCC7)c6)cc45)nc23)CC1] |
| 1108 | |

TABLE 1-continued
| 1109 | 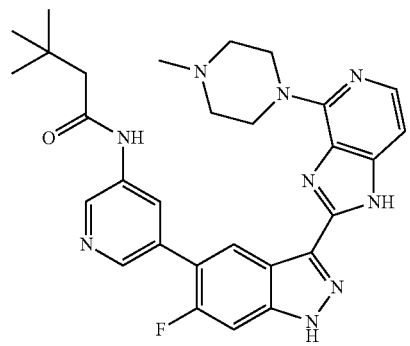 [SMILES: CN1CCN(c2nccc3[nH]c(-c4n[nH]c5cc(F)c(-c6cncc(NC(=O)CC(C)(C)C)c6)cc45)nc23)CC1] | 1113 | 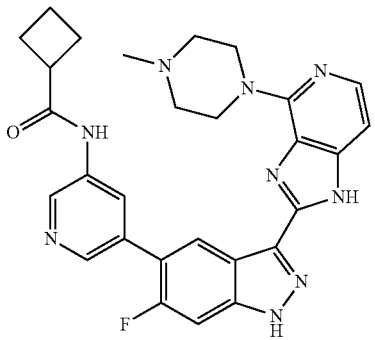 |
| 1110 | 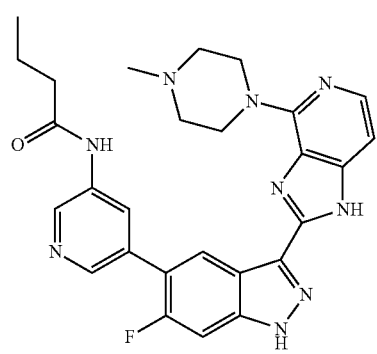 [SMILES: CCCC(=O)Nc1cncc(-c2cc3c(-c4nc5c(N6CCN(C)CC6)nccc5[nH]4)n[nH]c3cc2F)c1] | 1114 | 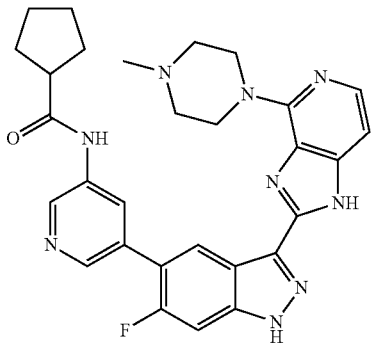 |
| 1111 | 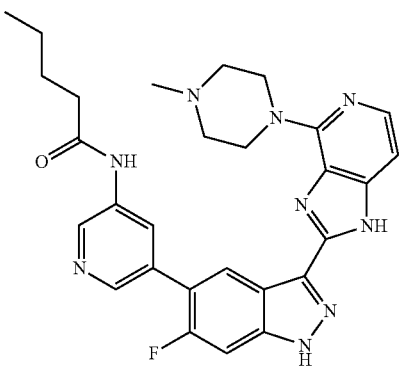 [SMILES: CCCCC(=O)Nc1cncc(-c2cc3c(-c4nc5c(N6CCN(C)CC6)nccc5[nH]4)n[nH]c3cc2F)c1] | 1115 | 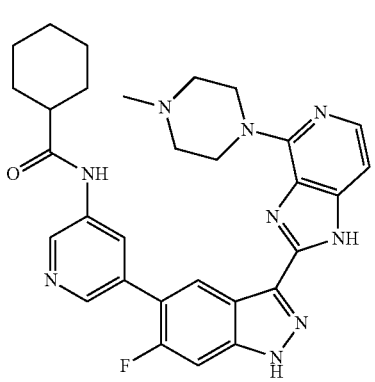 |
| 1112 | 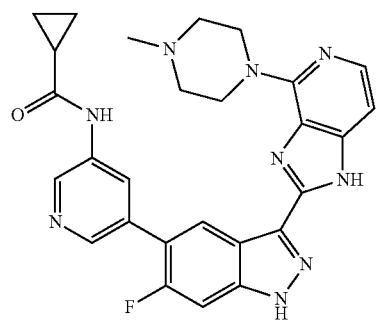 [SMILES: CN1CCN(c2nccc3[nH]c(-c4n[nH]c5cc(F)c(-c6cncc(NC(=O)C7CC7)c6)cc45)nc23)CC1] | 1116 | 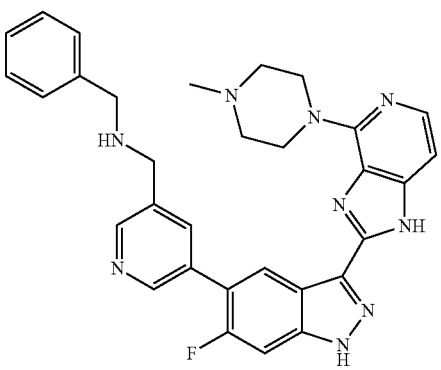 [SMILES: CN1CCN(c2nccc3[nH]c(-c4n[nH]c5cc(F)c(-c6cncc(CNCc7ccccc7)c6)cc45)nc23)CC1] |

TABLE 1-continued
| | |
|---|---|
| 1117 | 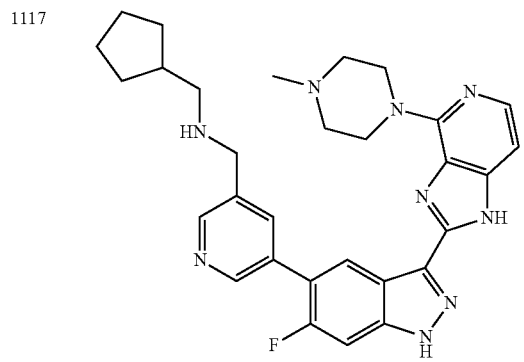 |
| 1118 | 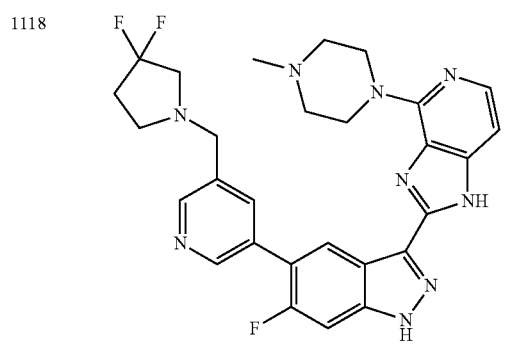 |
| 1119 | 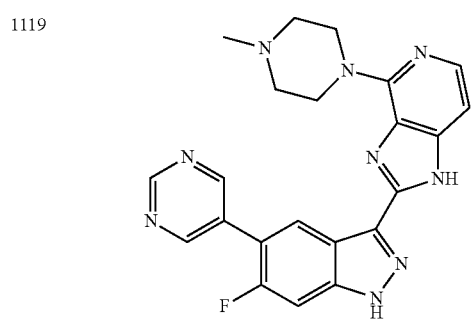 |
| 1120 | 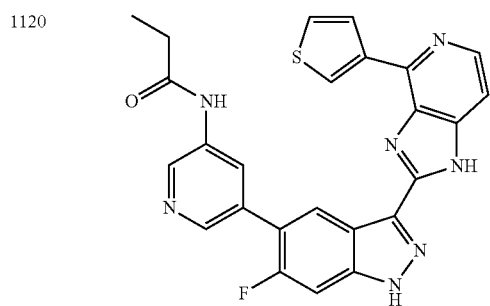 |
| 1121 | 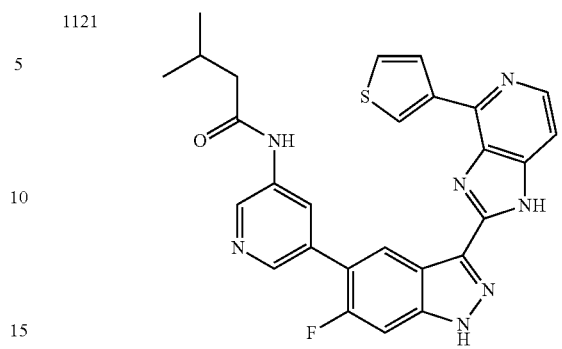 |
| 1122 | 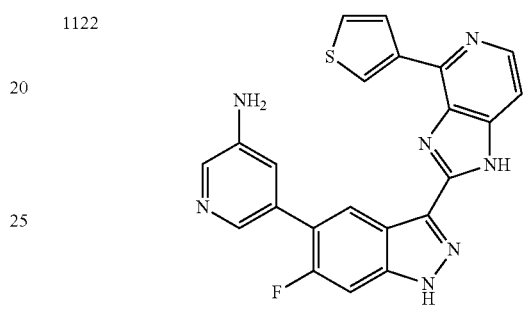 |
| 1123 | 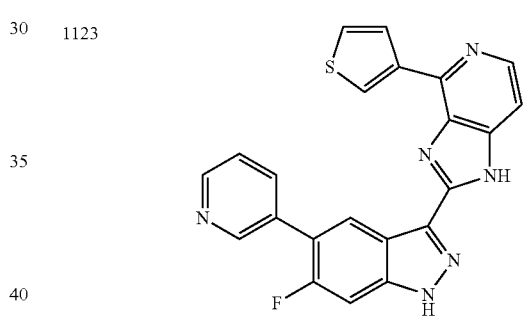 |
| 1124 | 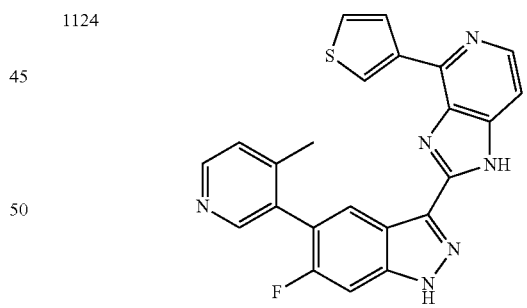 |
| 1125 | 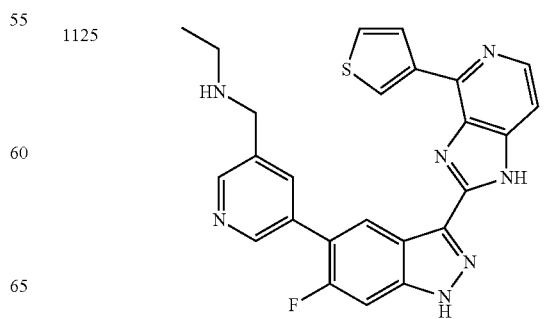 |

TABLE 1-continued
1126 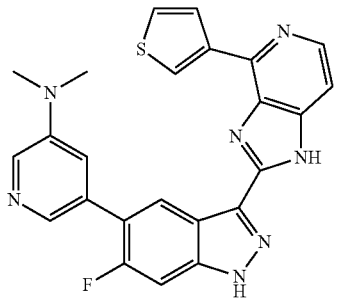 [SMILES: CN(C)c1cncc(-c2cc3c(-c4nc5c(-c6ccsc6)nccc5[nH]4)n[nH]c3cc2F)c1]
1127 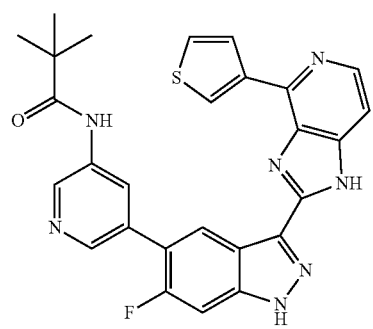 [SMILES: CC(C)(C)C(=O)Nc1cncc(-c2cc3c(-c4nc5c(-c6ccsc6)nccc5[nH]4)n[nH]c3cc2F)c1]
1128 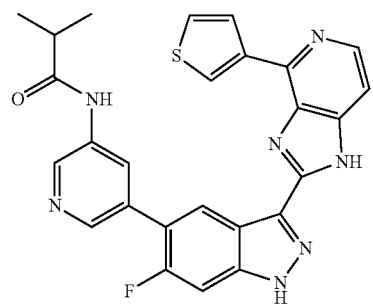
1129 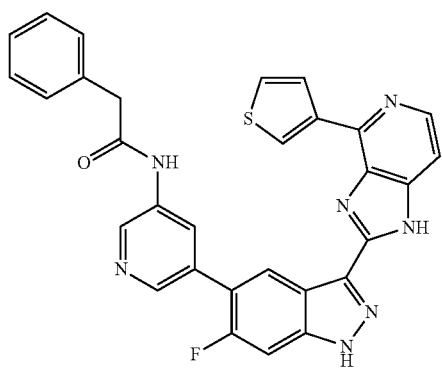 [SMILES: O=C(Cc1ccccc1)Nc1cncc(-c2cc3c(-c4nc5c(-c6ccsc6)nccc5[nH]4)n[nH]c3cc2F)c1]
TABLE 1-continued
1130 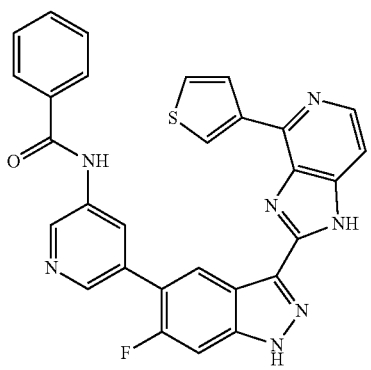
1131 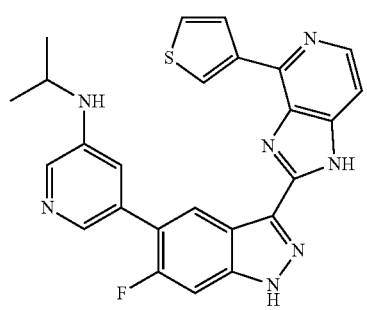 [SMILES: CC(C)Nc1cncc(-c2cc3c(-c4nc5c(-c6ccsc6)nccc5[nH]4)n[nH]c3cc2F)c1]
1132 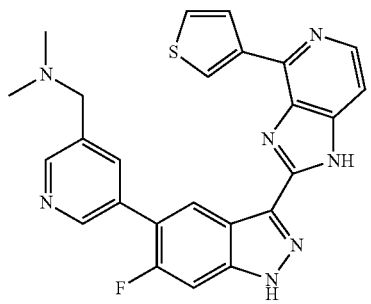 [SMILES: CN(C)Cc1cncc(-c2cc3c(-c4nc5c(-c6ccsc6)nccc5[nH]4)n[nH]c3cc2F)c1]
1133 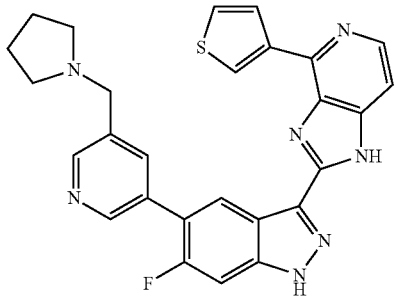 [SMILES: Fc1cc2[nH]nc(-c3nc4c(-c5ccsc5)nccc4[nH]3)c2cc1-c1cncc(CN2CCCC2)c1]
1134 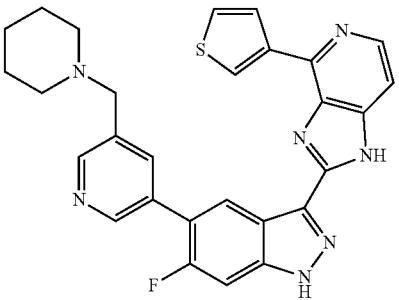 [SMILES: Fc1cc2[nH]nc(-c3nc4c(-c5ccsc5)nccc4[nH]3)c2cc1-c1cncc(CN2CCCCC2)c1]

TABLE 1-continued
1135 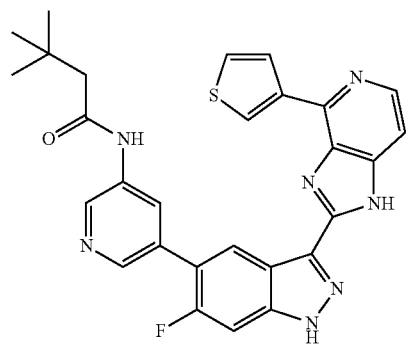
1136 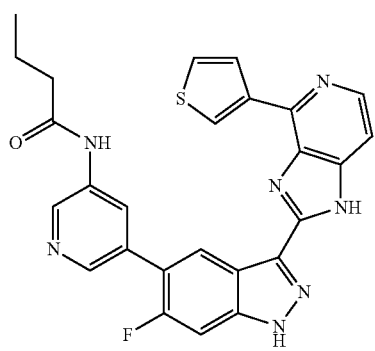 [SMILES: CCCC(=O)Nc1cncc(-c2cc3c(-c4nc5c(-c6ccsc6)nccc5[nH]4)n[nH]c3cc2F)c1]
1137 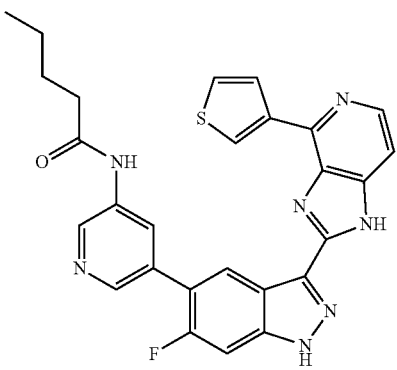 [SMILES: CCCCC(=O)Nc1cncc(-c2cc3c(-c4nc5c(-c6ccsc6)nccc5[nH]4)n[nH]c3cc2F)c1]
1138 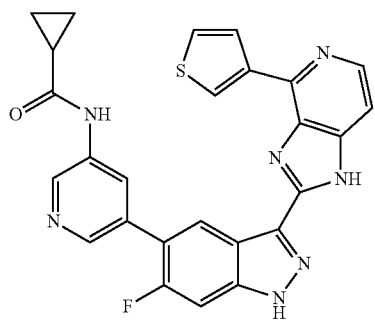 [SMILES: O=C(Nc1cncc(-c2cc3c(-c4nc5c(-c6ccsc6)nccc5[nH]4)n[nH]c3cc2F)c1)C1CC1]
TABLE 1-continued
1139 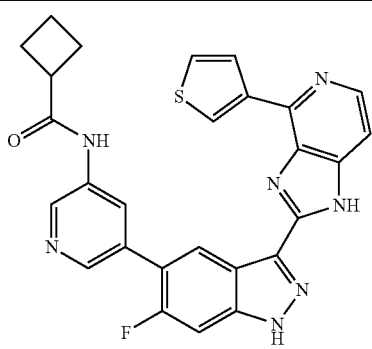
1140 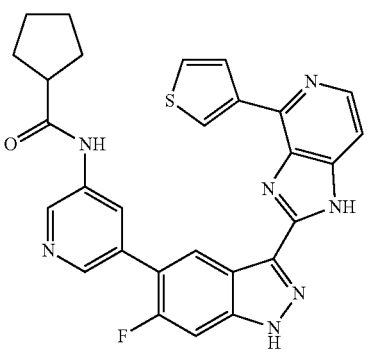 [SMILES: O=C(Nc1cncc(-c2cc3c(-c4nc5c(-c6ccsc6)nccc5[nH]4)n[nH]c3cc2F)c1)C1CCCC1]
1141 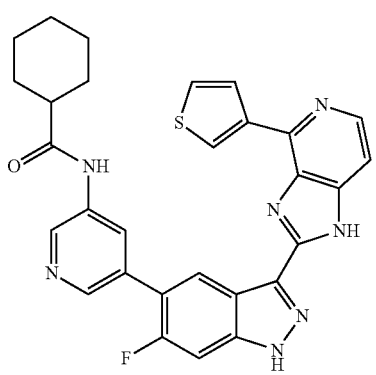 [SMILES: O=C(Nc1cncc(-c2cc3c(-c4nc5c(-c6ccsc6)nccc5[nH]4)n[nH]c3cc2F)c1)C1CCCCC1]
1142 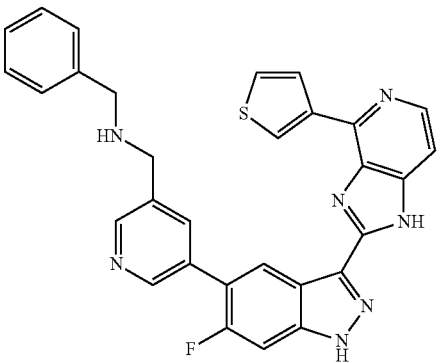 [SMILES: Fc1cc2[nH]nc(-c3nc4c(-c5ccsc5)nccc4[nH]3)c2cc1-c1cncc(CNCc2ccccc2)c1]

TABLE 1-continued
| 1143 | 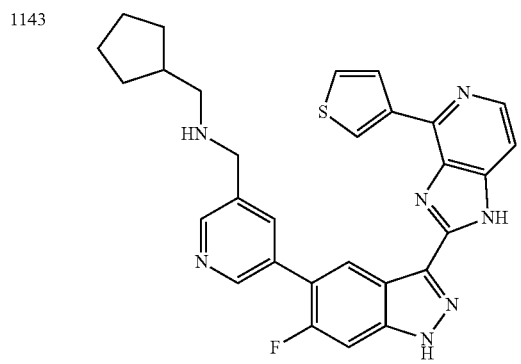 |
| 1144 | 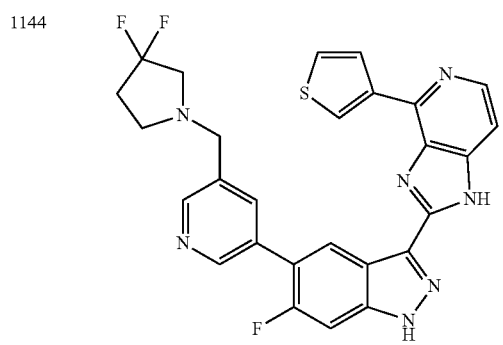 |
| 1145 | 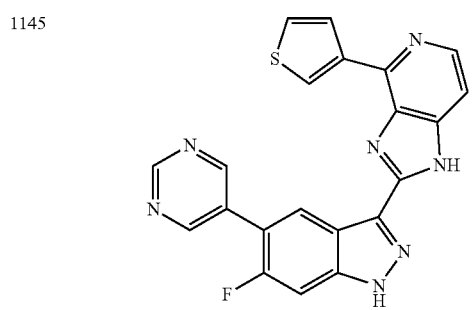 |
| 1146 | 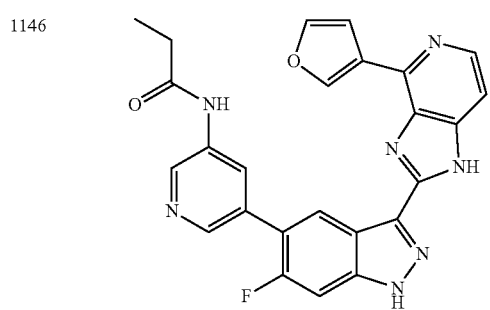 |
TABLE 1-continued
| 1147 | 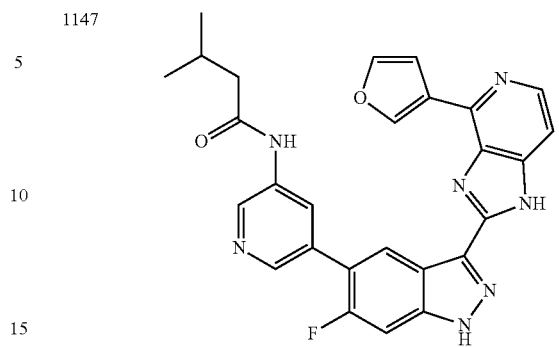 |
| 1148 | 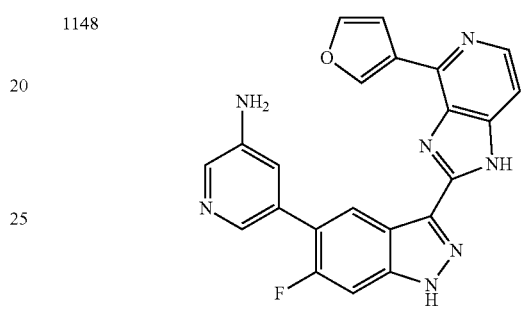 |
| 1149 | 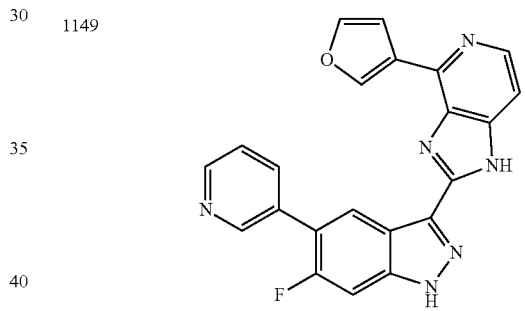 |
| 1150 | 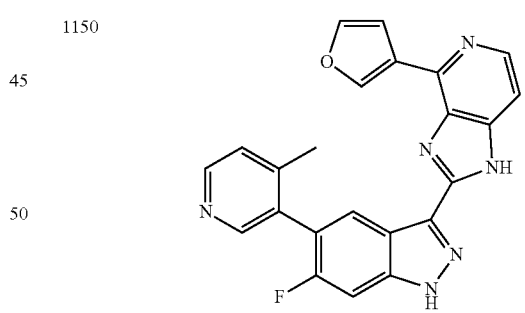 |
| 1151 | 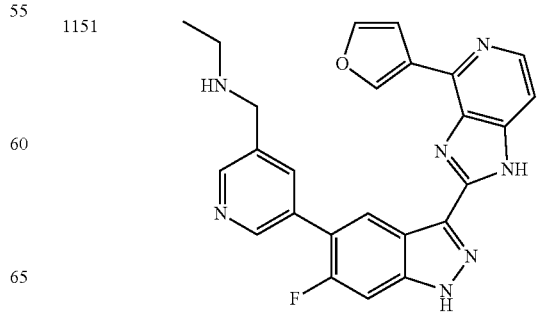 |

TABLE 1-continued
| 1152 | 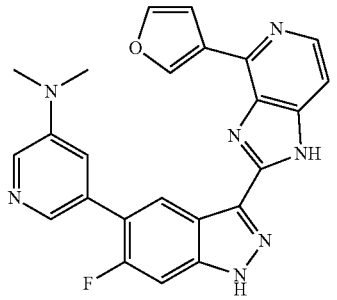 [SMILES: CN(C)c1cncc(-c2cc3c(-c4nc5c(-c6ccoc6)nccc5[nH]4)n[nH]c3cc2F)c1] |
| --- | --- |
| 1153 | 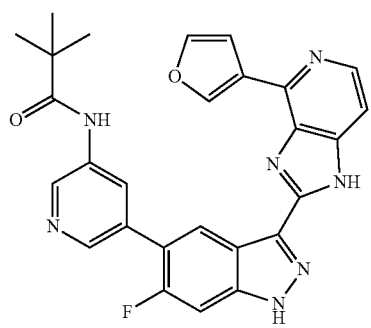 [SMILES: CC(C)(C)C(=O)Nc1cncc(-c2cc3c(-c4nc5c(-c6ccoc6)nccc5[nH]4)n[nH]c3cc2F)c1] |
| 1154 | 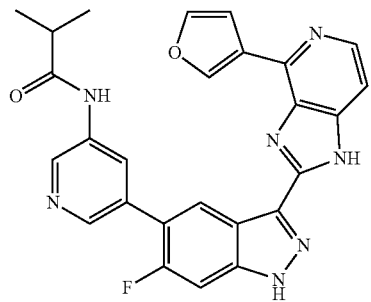 |
| 1155 | 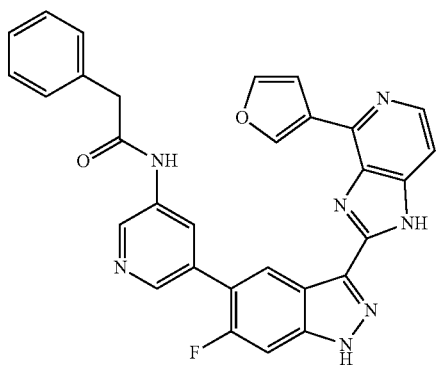 [SMILES: O=C(Cc1ccccc1)Nc1cncc(-c2cc3c(-c4nc5c(-c6ccoc6)nccc5[nH]4)n[nH]c3cc2F)c1] |
TABLE 1-continued
| 1156 | 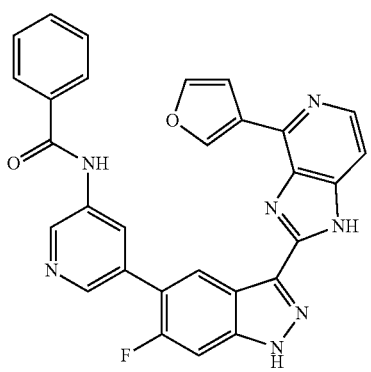 |
| --- | --- |
| 1157 | 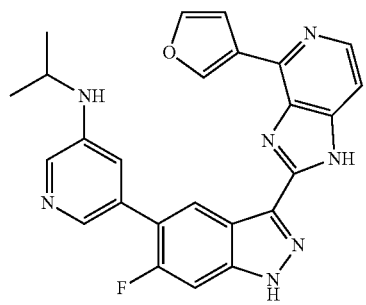 |
| 1158 | 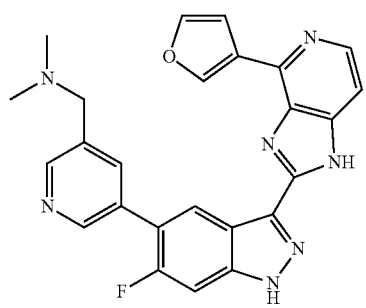 [SMILES: CN(C)Cc1cncc(-c2cc3c(-c4nc5c(-c6ccoc6)nccc5[nH]4)n[nH]c3cc2F)c1] |
| 1159 | 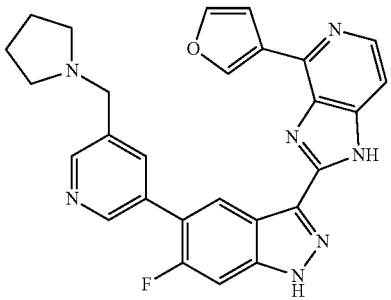 [SMILES: Fc1cc2[nH]nc(-c3nc4c(-c5ccoc5)nccc4[nH]3)c2cc1-c1cncc(CN2CCCC2)c1] |
| 1160 | 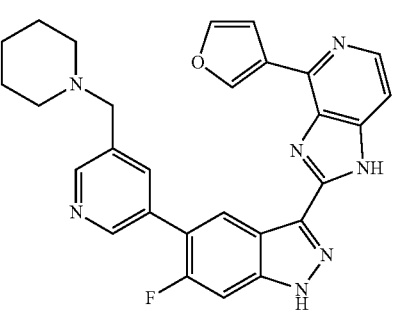 [SMILES: Fc1cc2[nH]nc(-c3nc4c(-c5ccoc5)nccc4[nH]3)c2cc1-c1cncc(CN2CCCCC2)c1] |

TABLE 1-continued
| 1161 | 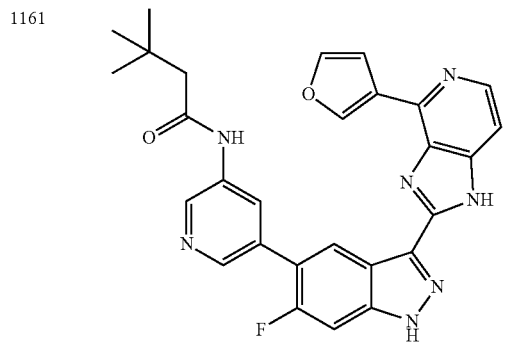 |
| --- | --- |
| 1162 | 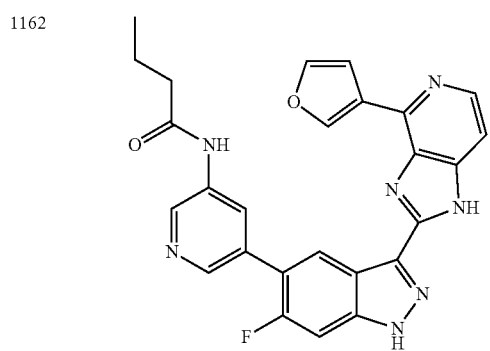 |
| 1163 | 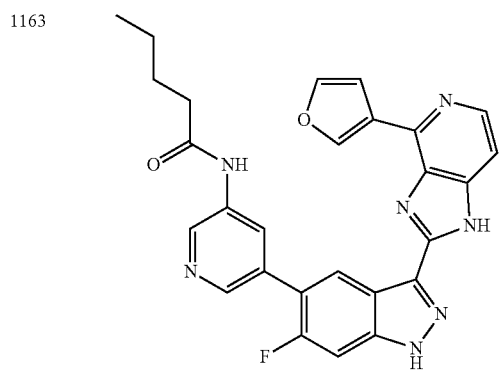 |
| 1164 | 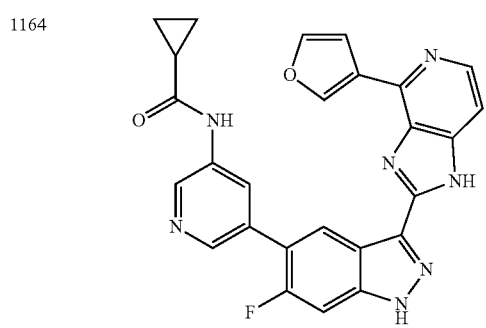 |
| 1165 | 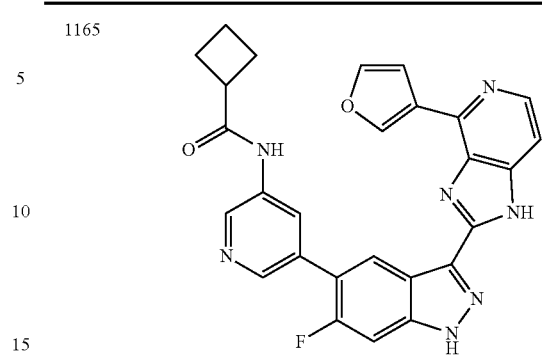 |
| 1166 | 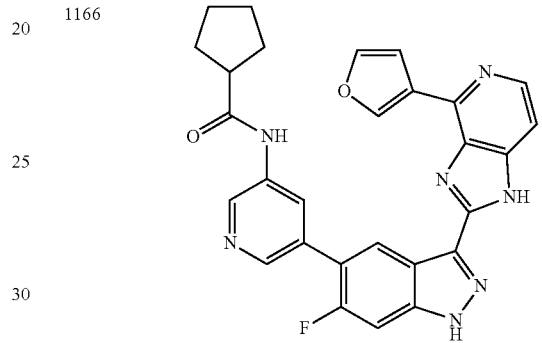 |
| 1167 | 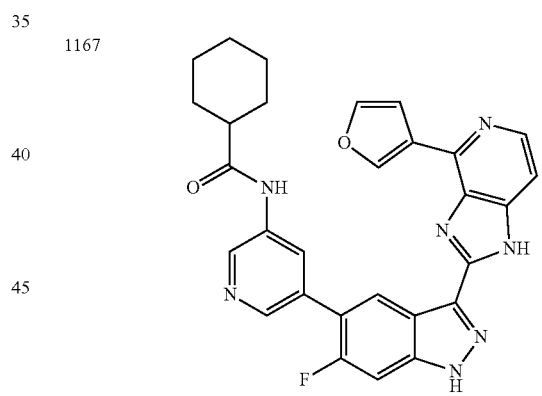 |
| 1168 | 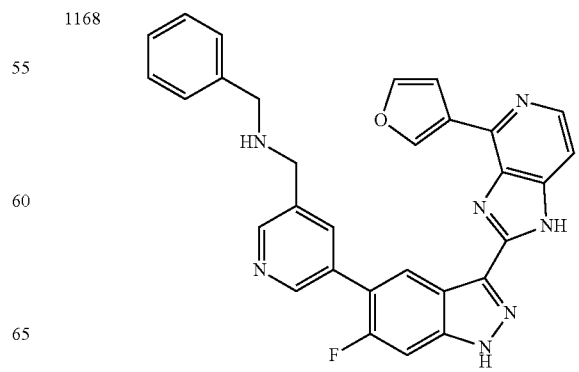 |

TABLE 1-continued
| 1169 | 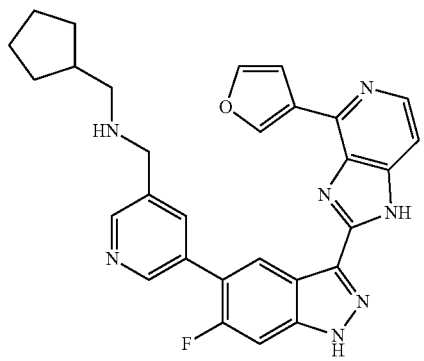 [SMILES: Fc1cc2[nH]nc(-c3nc4c(-c5ccoc5)nccc4[nH]3)c2cc1-c1cncc(CNCC2CCCC2)c1] |
| 1170 | 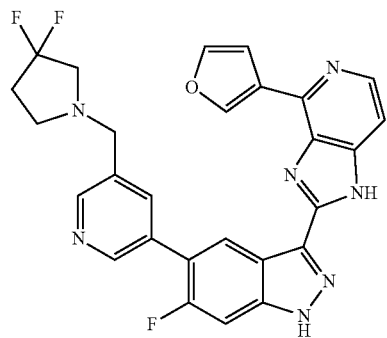 [SMILES: Fc1cc2[nH]nc(-c3nc4c(-c5ccoc5)nccc4[nH]3)c2cc1-c1cncc(CN2CCC(F)(F)C2)c1] |
| 1171 | 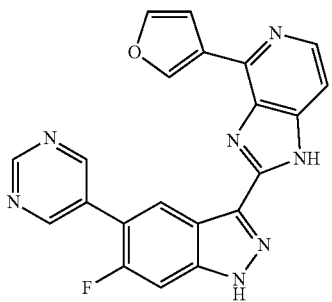 [SMILES: Fc1cc2[nH]nc(-c3nc4c(-c5ccoc5)nccc4[nH]3)c2cc1-c1cncnc1] |
| 1172 | 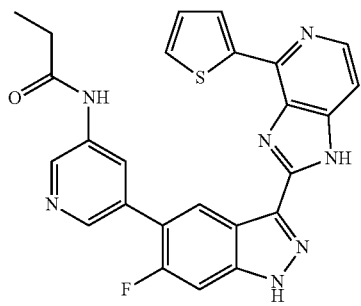 [SMILES: CCC(=O)Nc1cncc(-c2cc3c(-c4nc5c(-c6cccs6)nccc5[nH]4)n[nH]c3cc2F)c1] |
TABLE 1-continued
| 1173 | 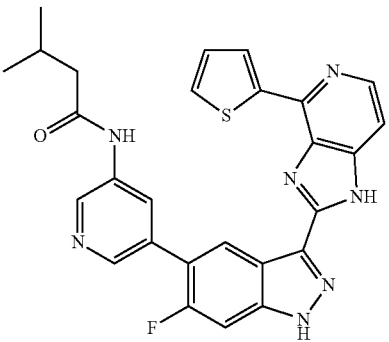 [SMILES: CC(C)CC(=O)Nc1cncc(-c2cc3c(-c4nc5c(-c6cccs6)nccc5[nH]4)n[nH]c3cc2F)c1] |
| 1174 | 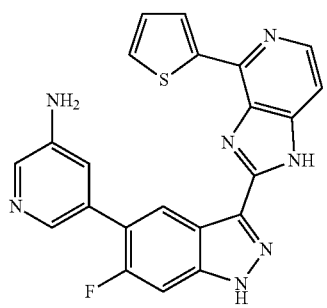 [SMILES: Nc1cncc(-c2cc3c(-c4nc5c(-c6cccs6)nccc5[nH]4)n[nH]c3cc2F)c1] |
| 1175 | 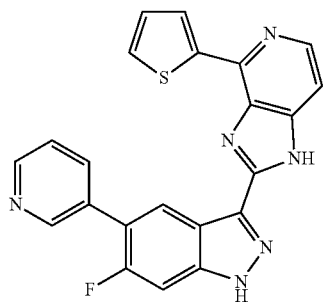 [SMILES: Fc1cc2[nH]nc(-c3nc4c(-c5cccs5)nccc4[nH]3)c2cc1-c1cccnc1] |
| 1176 | 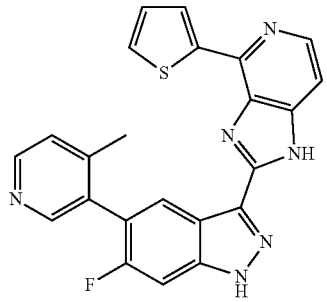 [SMILES: Cc1ccncc1-c1cc2c(-c3nc4c(-c5cccs5)nccc4[nH]3)n[nH]c2cc1F] |
| 1177 | 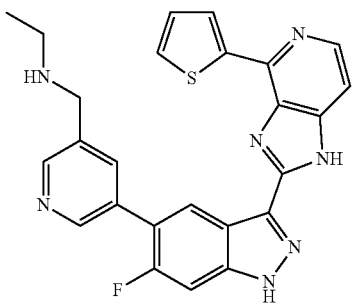 [SMILES: CCNCc1cncc(-c2cc3c(-c4nc5c(-c6cccs6)nccc5[nH]4)n[nH]c3cc2F)c1] |

TABLE 1-continued
1178 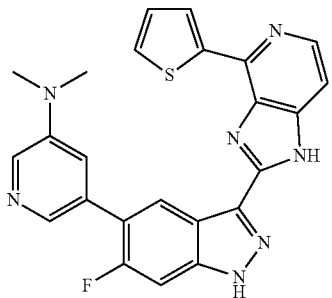 [SMILES: CN(C)c1cncc(-c2cc3c(-c4nc5c(-c6cccs6)nccc5[nH]4)n[nH]c3cc2F)c1]
1179 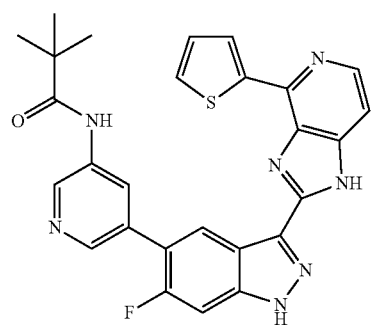 [SMILES: CC(C)(C)C(=O)Nc1cncc(-c2cc3c(-c4nc5c(-c6cccs6)nccc5[nH]4)n[nH]c3cc2F)c1]
1180 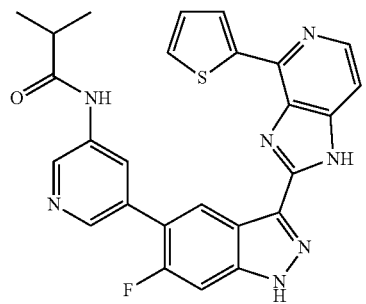 [SMILES: CC(C)C(=O)Nc1cncc(-c2cc3c(-c4nc5c(-c6cccs6)nccc5[nH]4)n[nH]c3cc2F)c1]
1181 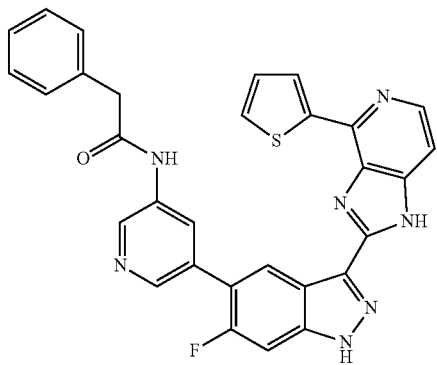 [SMILES: O=C(Cc1ccccc1)Nc1cncc(-c2cc3c(-c4nc5c(-c6cccs6)nccc5[nH]4)n[nH]c3cc2F)c1]
1182 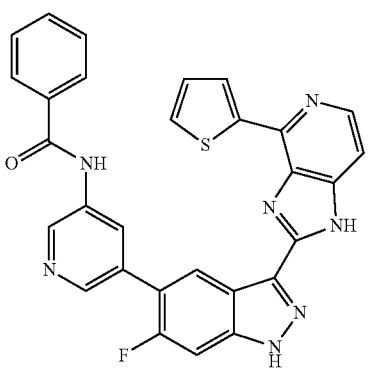 [SMILES: O=C(Nc1cncc(-c2cc3c(-c4nc5c(-c6cccs6)nccc5[nH]4)n[nH]c3cc2F)c1)c1ccccc1]
1183 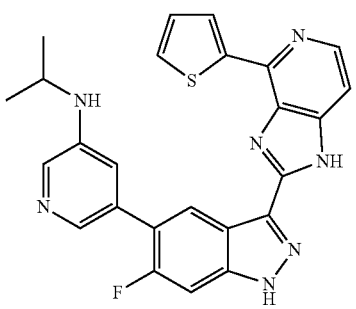 [SMILES: CC(C)Nc1cncc(-c2cc3c(-c4nc5c(-c6cccs6)nccc5[nH]4)n[nH]c3cc2F)c1]
1184 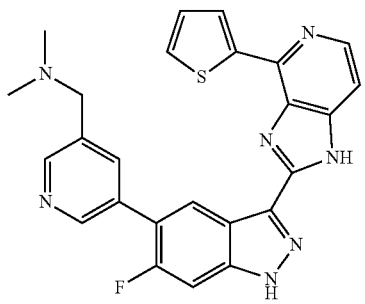 [SMILES: CN(C)Cc1cncc(-c2cc3c(-c4nc5c(-c6cccs6)nccc5[nH]4)n[nH]c3cc2F)c1]
1185 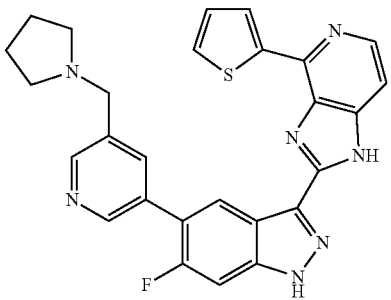 [SMILES: Fc1cc2[nH]nc(-c3nc4c(-c5cccs5)nccc4[nH]3)c2cc1-c1cncc(CN2CCCC2)c1]
1186 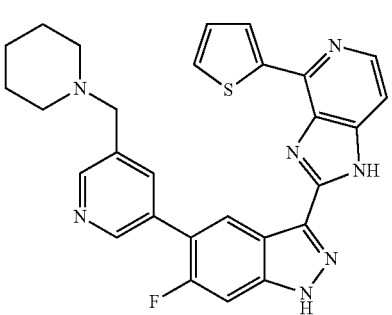 [SMILES: Fc1cc2[nH]nc(-c3nc4c(-c5cccs5)nccc4[nH]3)c2cc1-c1cncc(CN2CCCCC2)c1]

TABLE 1-continued
| 1187 | 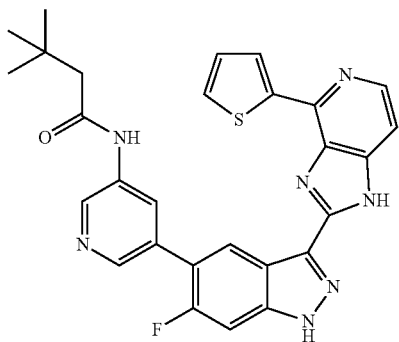 [SMILES: CC(C)(C)CC(=O)Nc1cncc(-c2cc3c(-c4nc5c(-c6cccs6)nccc5[nH]4)n[nH]c3cc2F)c1] |
| --- | --- |
| 1188 | 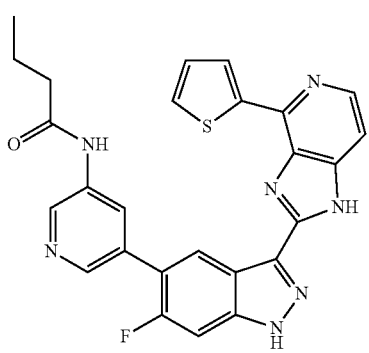 [SMILES: CCCC(=O)Nc1cncc(-c2cc3c(-c4nc5c(-c6cccs6)nccc5[nH]4)n[nH]c3cc2F)c1] |
| 1189 | 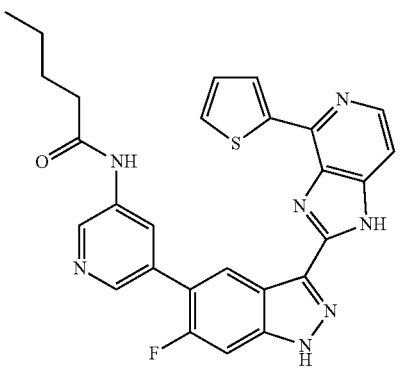 [SMILES: CCCCC(=O)Nc1cncc(-c2cc3c(-c4nc5c(-c6cccs6)nccc5[nH]4)n[nH]c3cc2F)c1] |
| 1190 | 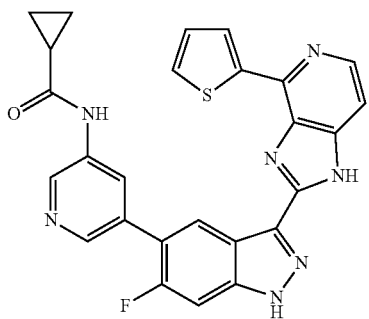 [SMILES: O=C(Nc1cncc(-c2cc3c(-c4nc5c(-c6cccs6)nccc5[nH]4)n[nH]c3cc2F)c1)C1CC1] |
| 1191 | 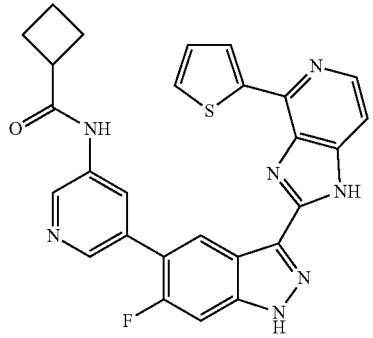 [SMILES: O=C(Nc1cncc(-c2cc3c(-c4nc5c(-c6cccs6)nccc5[nH]4)n[nH]c3cc2F)c1)C1CCC1] |
| 1192 | 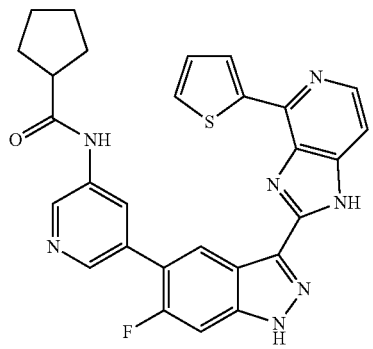 [SMILES: O=C(Nc1cncc(-c2cc3c(-c4nc5c(-c6cccs6)nccc5[nH]4)n[nH]c3cc2F)c1)C1CCCC1] |
| 1193 | 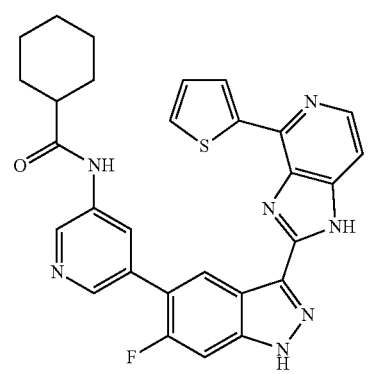 [SMILES: O=C(Nc1cncc(-c2cc3c(-c4nc5c(-c6cccs6)nccc5[nH]4)n[nH]c3cc2F)c1)C1CCCCC1] |
| 1194 | 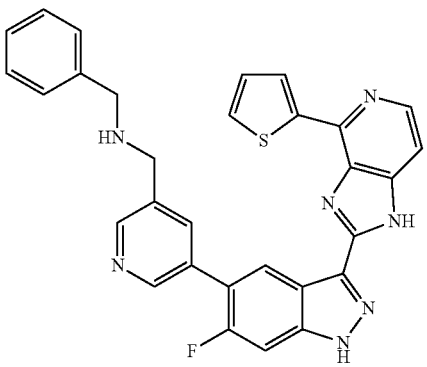 [SMILES: Fc1cc2[nH]nc(-c3nc4c(-c5cccs5)nccc4[nH]3)c2cc1-c1cncc(CNCc2ccccc2)c1] |

TABLE 1-continued
| 1195 | 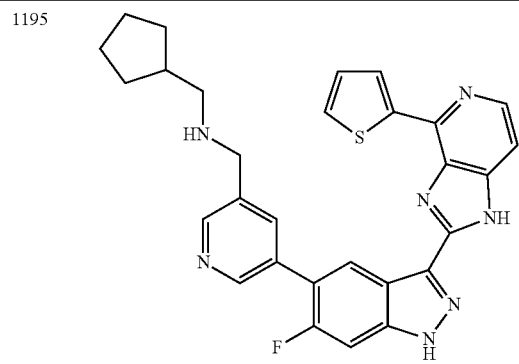 |
| 1196 | 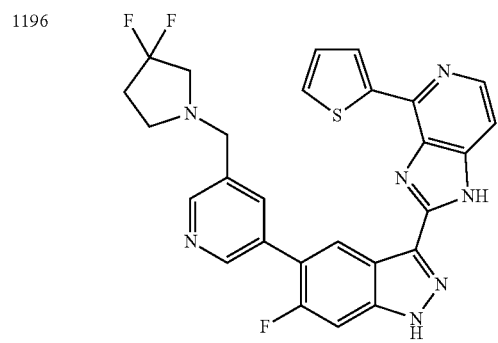 |
| 1197 | 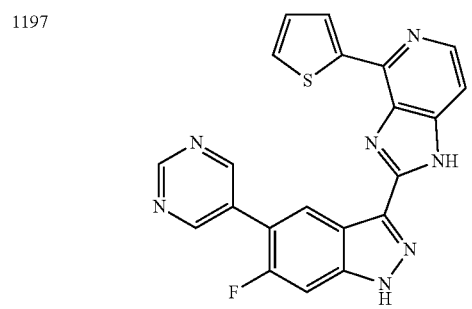 |
| 1198 | 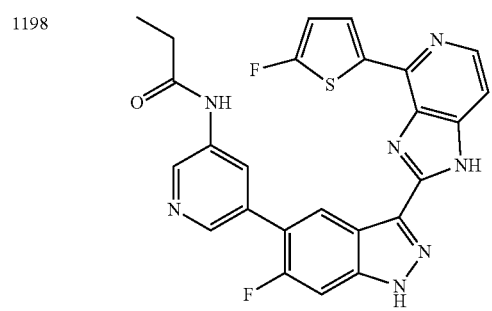 |
| 1199 | 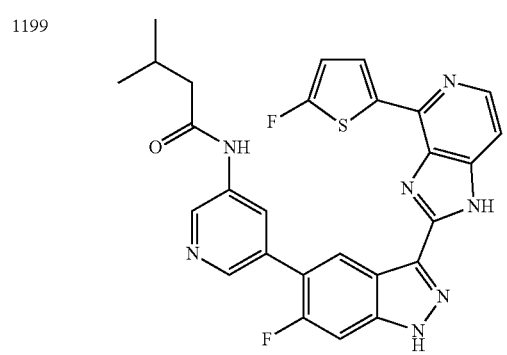 |
| 1200 | 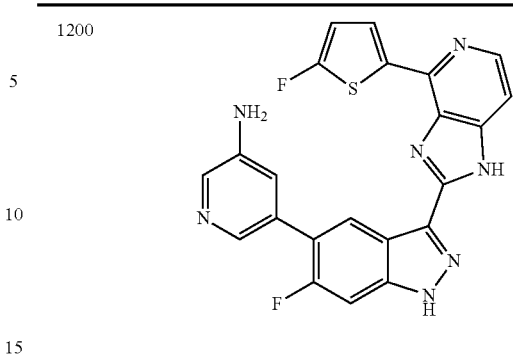 |
| 1201 | 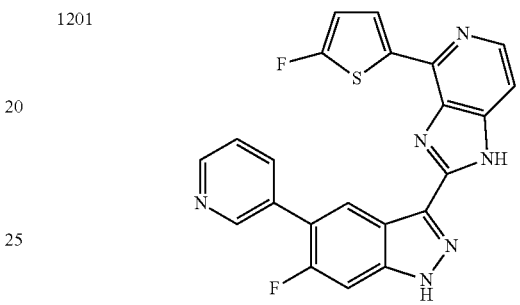 |
| 1202 | 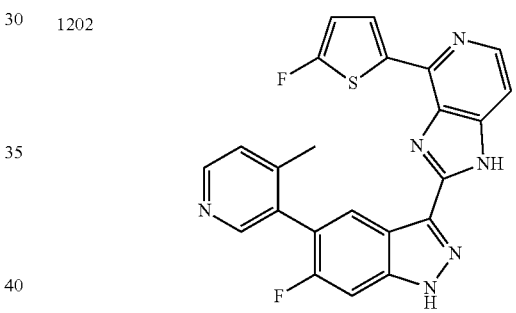 |
| 1203 | 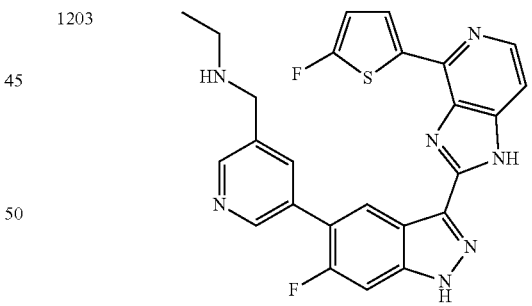 |
| 1204 | 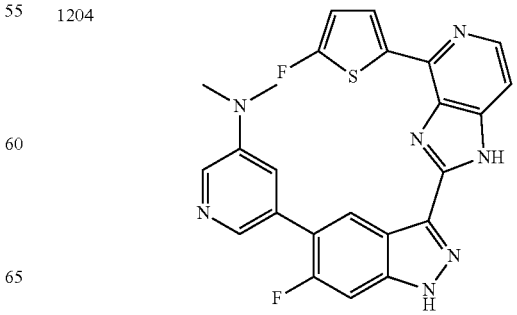 |

TABLE 1-continued
| 1205 | 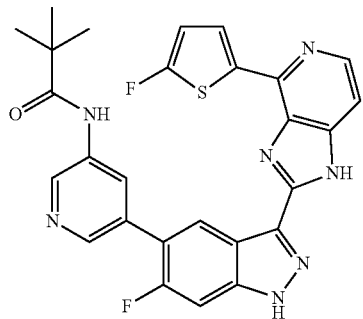 [SMILES: CC(C)(C)C(=O)Nc1cncc(-c2cc3c(-c4nc5c(-c6ccc(F)s6)nccc5[nH]4)n[nH]c3cc2F)c1] |
| 1206 | 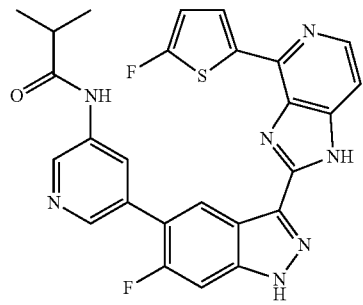 |
| 1207 | 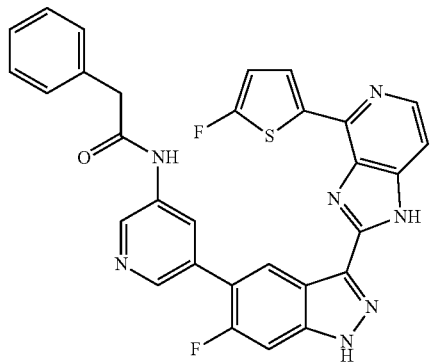 [SMILES: O=C(Cc1ccccc1)Nc1cncc(-c2cc3c(-c4nc5c(-c6ccc(F)s6)nccc5[nH]4)n[nH]c3cc2F)c1] |
| 1208 | 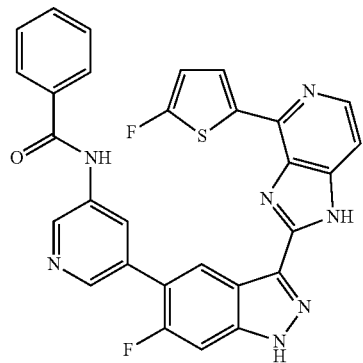 [SMILES: O=C(Nc1cncc(-c2cc3c(-c4nc5c(-c6ccc(F)s6)nccc5[nH]4)n[nH]c3cc2F)c1)c1ccccc1] |
TABLE 1-continued
| 1209 | 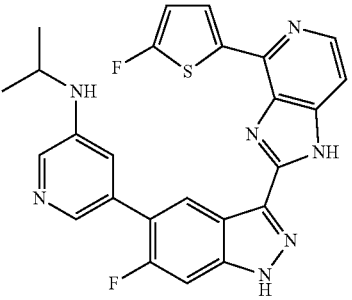 [SMILES: CC(C)Nc1cncc(-c2cc3c(-c4nc5c(-c6ccc(F)s6)nccc5[nH]4)n[nH]c3cc2F)c1] |
| 1210 | 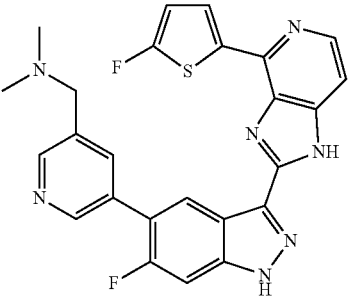 [SMILES: CN(C)Cc1cncc(-c2cc3c(-c4nc5c(-c6ccc(F)s6)nccc5[nH]4)n[nH]c3cc2F)c1] |
| 1211 | 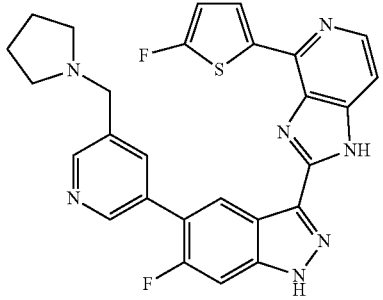 [SMILES: Fc1ccc(-c2nccc3[nH]c(-c4n[nH]c5cc(F)c(-c6cncc(CN7CCCC7)c6)cc45)nc23)s1] |
| 1212 | 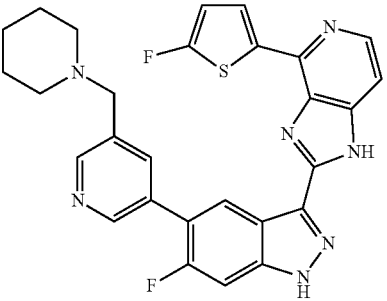 [SMILES: Fc1ccc(-c2nccc3[nH]c(-c4n[nH]c5cc(F)c(-c6cncc(CN7CCCCC7)c6)cc45)nc23)s1] |
| 1213 | 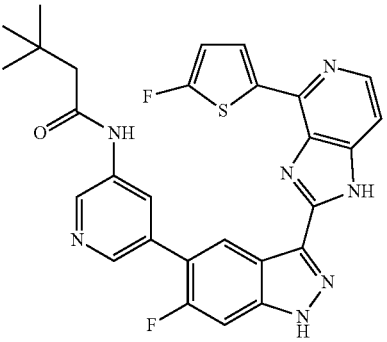 [SMILES: CC(C)(C)CC(=O)Nc1cncc(-c2cc3c(-c4nc5c(-c6ccc(F)s6)nccc5[nH]4)n[nH]c3cc2F)c1] |

TABLE 1-continued
| 1214 | 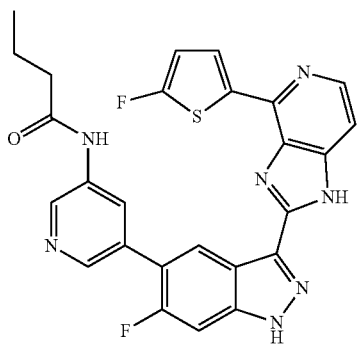 [SMILES: CCCC(=O)Nc1cncc(-c2cc3c(-c4nc5c(-c6ccc(F)s6)nccc5[nH]4)n[nH]c3cc2F)c1] |
| --- | --- |
| 1215 | 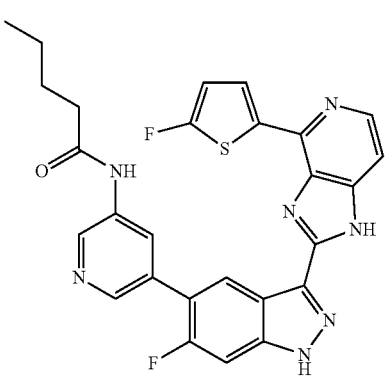 [SMILES: CCCCC(=O)Nc1cncc(-c2cc3c(-c4nc5c(-c6ccc(F)s6)nccc5[nH]4)n[nH]c3cc2F)c1] |
| 1216 | 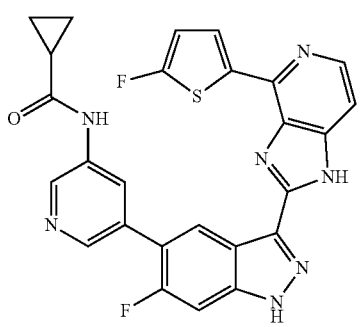 [SMILES: O=C(Nc1cncc(-c2cc3c(-c4nc5c(-c6ccc(F)s6)nccc5[nH]4)n[nH]c3cc2F)c1)C1CC1] |
| 1217 | 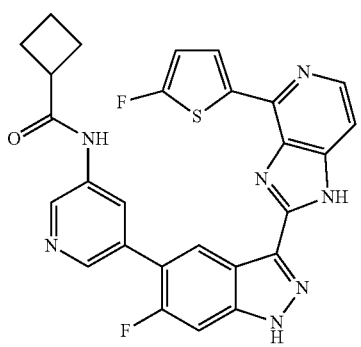 [SMILES: O=C(Nc1cncc(-c2cc3c(-c4nc5c(-c6ccc(F)s6)nccc5[nH]4)n[nH]c3cc2F)c1)C1CCC1] |
TABLE 1-continued
| 1218 | 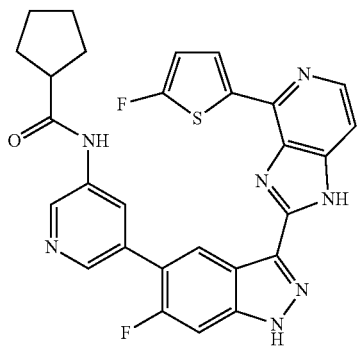 [SMILES: O=C(Nc1cncc(-c2cc3c(-c4nc5c(-c6ccc(F)s6)nccc5[nH]4)n[nH]c3cc2F)c1)C1CCCC1] |
| --- | --- |
| 1219 | 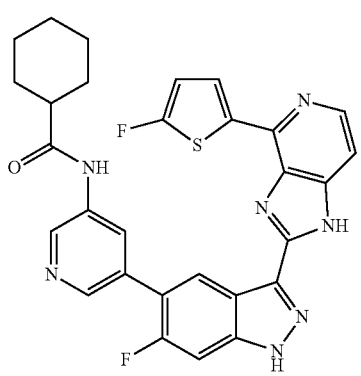 [SMILES: O=C(Nc1cncc(-c2cc3c(-c4nc5c(-c6ccc(F)s6)nccc5[nH]4)n[nH]c3cc2F)c1)C1CCCCC1] |
| 1220 | 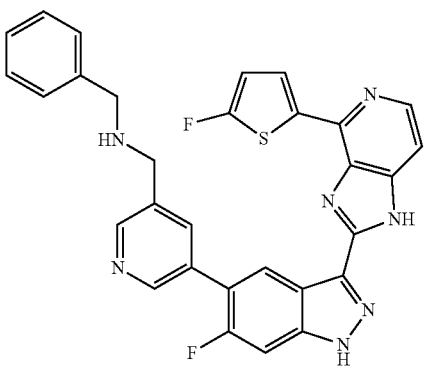 [SMILES: Fc1ccc(-c2nccc3[nH]c(-c4n[nH]c5cc(F)c(-c6cncc(CNCc7ccccc7)c6)cc45)nc23)s1] |
| 1221 | 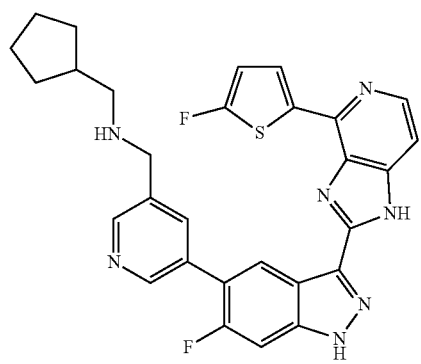 [SMILES: Fc1ccc(-c2nccc3[nH]c(-c4n[nH]c5cc(F)c(-c6cncc(CNCC7CCCC7)c6)cc45)nc23)s1] |

US 9,828,372 B2
331
TABLE 1-continued
332
TABLE 1-continued
1222 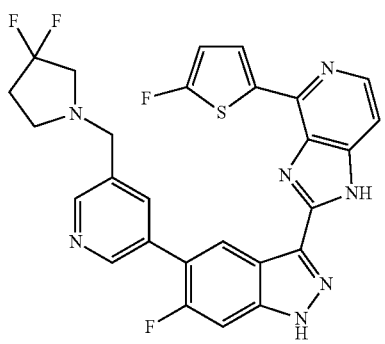 [SMILES: Fc1ccc(-c2nccc3[nH]c(-c4n[nH]c5cc(F)c(-c6cncc(CN7CCC(F)(F)C7)c6)cc45)nc23)s1]
1227 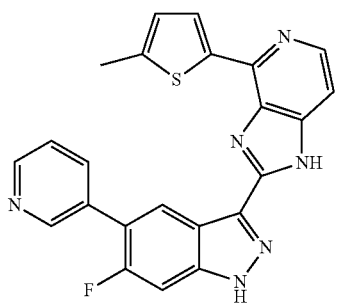
1223 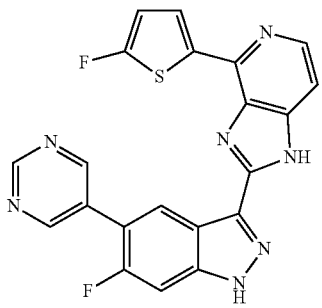 [SMILES: Fc1ccc(-c2nccc3[nH]c(-c4n[nH]c5cc(F)c(-c6cncnc6)cc45)nc23)s1]
1228 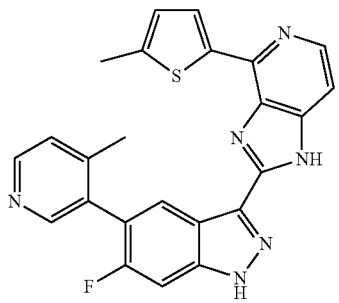
1224 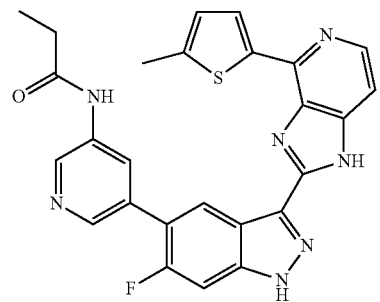 [SMILES: CCC(=O)Nc1cncc(-c2cc3c(-c4nc5c(-c6ccc(C)s6)nccc5[nH]4)n[nH]c3cc2F)c1]
1229 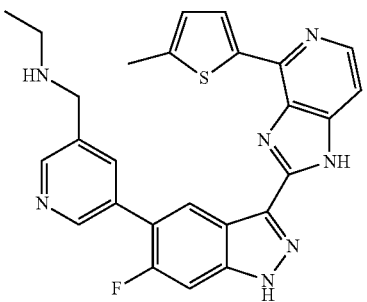
1225 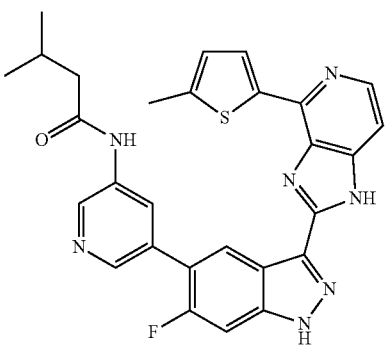 [SMILES: Cc1ccc(-c2nccc3[nH]c(-c4n[nH]c5cc(F)c(-c6cncc(NC(=O)CC(C)C)c6)cc45)nc23)s1]
1230 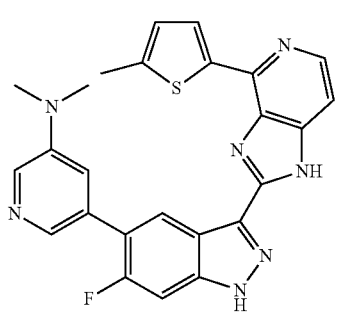
1226 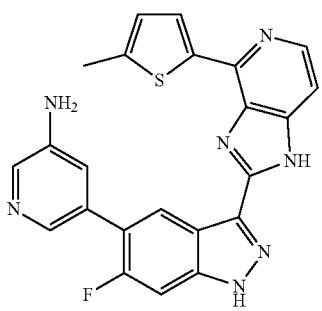 [SMILES: Cc1ccc(-c2nccc3[nH]c(-c4n[nH]c5cc(F)c(-c6cncc(N)c6)cc45)nc23)s1]
1231 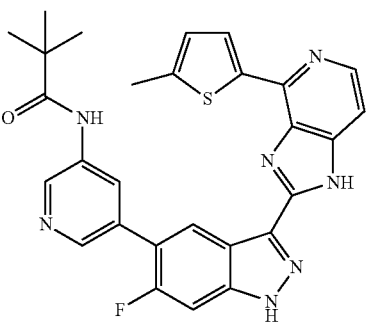 [SMILES: Cc1ccc(-c2nccc3[nH]c(-c4n[nH]c5cc(F)c(-c6cncc(NC(=O)C(C)(C)C)c6)cc45)nc23)s1]

TABLE 1-continued
| 1232 | 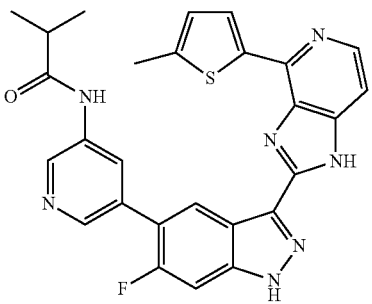 [SMILES: Cc1ccc(-c2nccc3[nH]c(-c4n[nH]c5cc(F)c(-c6cncc(NC(=O)C(C)C)c6)cc45)nc23)s1] |
| --- | --- |
| 1233 | 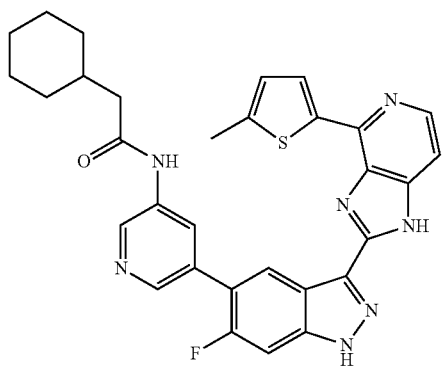 [SMILES: Cc1ccc(-c2nccc3[nH]c(-c4n[nH]c5cc(F)c(-c6cncc(NC(=O)CC7CCCCC7)c6)cc45)nc23)s1] |
| 1234 | 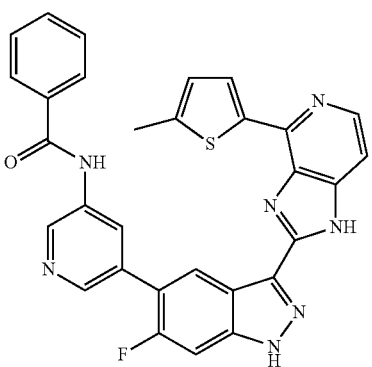 [SMILES: Cc1ccc(-c2nccc3[nH]c(-c4n[nH]c5cc(F)c(-c6cncc(NC(=O)c7ccccc7)c6)cc45)nc23)s1] |
| 1235 | 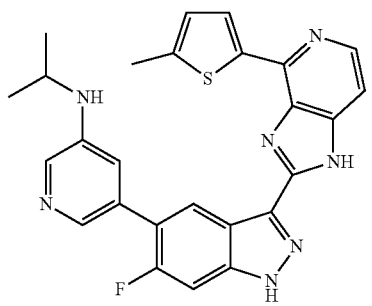 [SMILES: Cc1ccc(-c2nccc3[nH]c(-c4n[nH]c5cc(F)c(-c6cncc(NC(C)C)c6)cc45)nc23)s1] |
| 1236 | 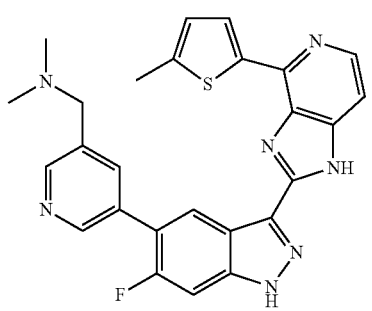 [SMILES: Cc1ccc(-c2nccc3[nH]c(-c4n[nH]c5cc(F)c(-c6cncc(CN(C)C)c6)cc45)nc23)s1] |
TABLE 1-continued
| 1237 | 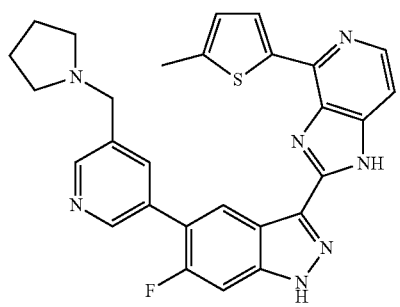 [SMILES: Cc1ccc(-c2nccc3[nH]c(-c4n[nH]c5cc(F)c(-c6cncc(CN7CCCC7)c6)cc45)nc23)s1] |
| --- | --- |
| 1238 | 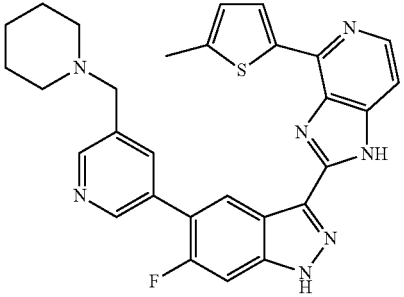 [SMILES: Cc1ccc(-c2nccc3[nH]c(-c4n[nH]c5cc(F)c(-c6cncc(CN7CCCCC7)c6)cc45)nc23)s1] |
| 1239 | 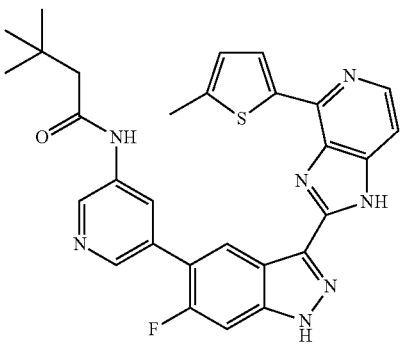 [SMILES: Cc1ccc(-c2nccc3[nH]c(-c4n[nH]c5cc(F)c(-c6cncc(NC(=O)CC(C)(C)C)c6)cc45)nc23)s1] |
| 1240 | 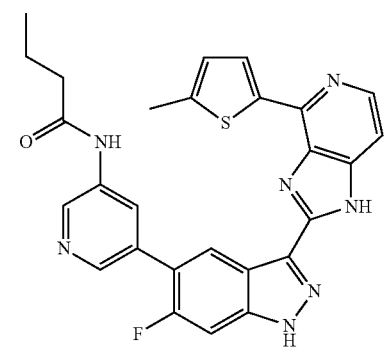 [SMILES: CCCC(=O)Nc1cncc(-c2cc3c(-c4nc5c(-c6ccc(C)s6)nccc5[nH]4)n[nH]c3cc2F)c1] |

TABLE 1-continued
| 1241 | 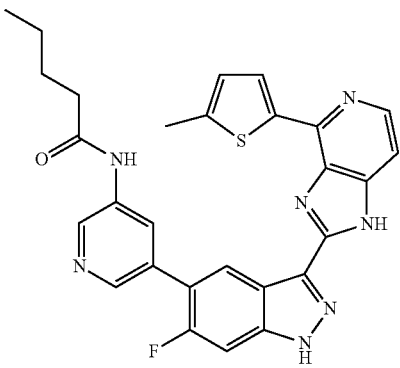 [SMILES: CCCCC(=O)Nc1cncc(-c2cc3c(-c4nc5c(-c6ccc(C)s6)nccc5[nH]4)n[nH]c3cc2F)c1] |
| --- | --- |
| 1242 | 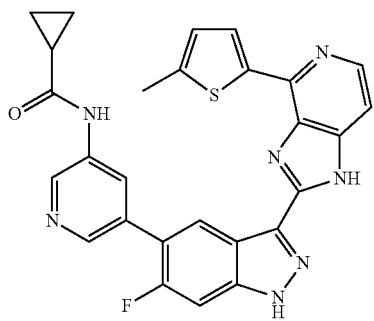 [SMILES: Cc1ccc(-c2nccc3[nH]c(-c4n[nH]c5cc(F)c(-c6cncc(NC(=O)C7CC7)c6)cc45)nc23)s1] |
| 1243 | 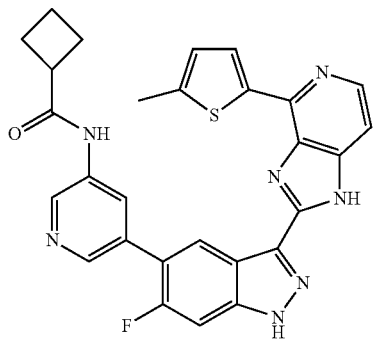 [SMILES: Cc1ccc(-c2nccc3[nH]c(-c4n[nH]c5cc(F)c(-c6cncc(NC(=O)C7CCC7)c6)cc45)nc23)s1] |
| 1244 | 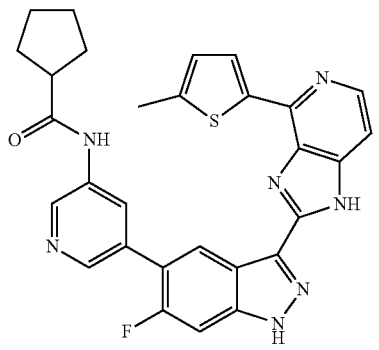 [SMILES: Cc1ccc(-c2nccc3[nH]c(-c4n[nH]c5cc(F)c(-c6cncc(NC(=O)C7CCCC7)c6)cc45)nc23)s1] |
| 1245 | 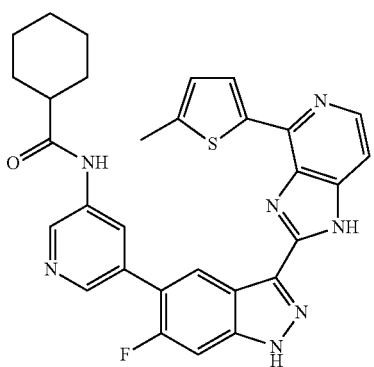 [SMILES: Cc1ccc(-c2nccc3[nH]c(-c4n[nH]c5cc(F)c(-c6cncc(NC(=O)C7CCCCC7)c6)cc45)nc23)s1] |
| 1246 | 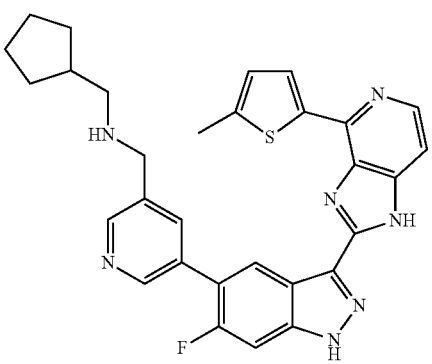 [SMILES: Cc1ccc(-c2nccc3[nH]c(-c4n[nH]c5cc(F)c(-c6cncc(CNCC7CCCC7)c6)cc45)nc23)s1] |
| 1247 | 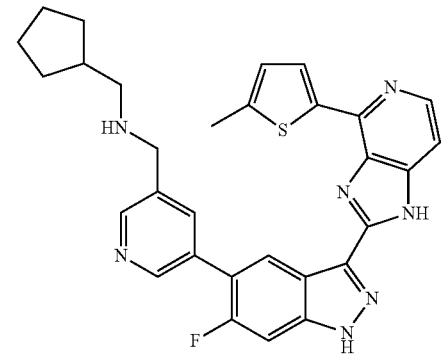 [SMILES: Cc1ccc(-c2nccc3[nH]c(-c4n[nH]c5cc(F)c(-c6cncc(CNCC7CCCC7)c6)cc45)nc23)s1] |
| 1248 | 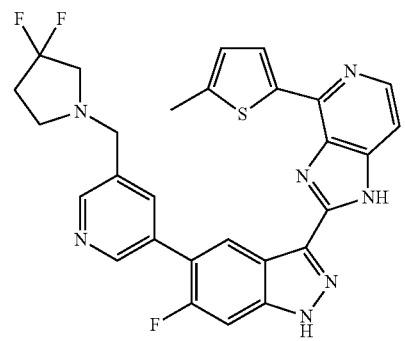 [SMILES: Cc1ccc(-c2nccc3[nH]c(-c4n[nH]c5cc(F)c(-c6cncc(CN7CCC(F)(F)C7)c6)cc45)nc23)s1] |

TABLE 1-continued
1249 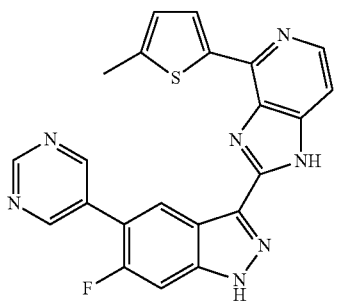 [SMILES: Cc1ccc(-c2nccc3[nH]c(-c4n[nH]c5cc(F)c(-c6cncnc6)cc45)nc23)s1]
1250 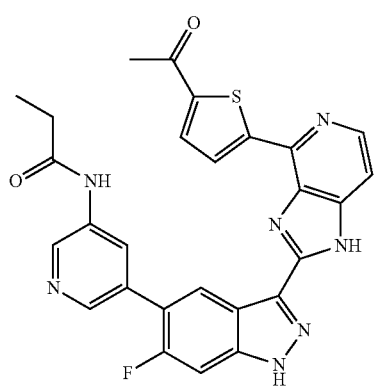 [SMILES: CCC(=O)Nc1cncc(-c2cc3c(-c4nc5c(-c6ccc(C(C)=O)s6)nccc5[nH]4)n[nH]c3cc2F)c1]
1251 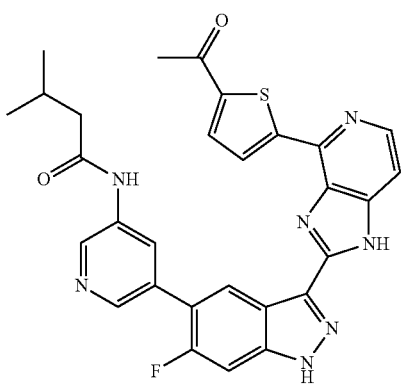 [SMILES: CC(=O)c1ccc(-c2nccc3[nH]c(-c4n[nH]c5cc(F)c(-c6cncc(NC(=O)CC(C)C)c6)cc45)nc23)s1]
1252 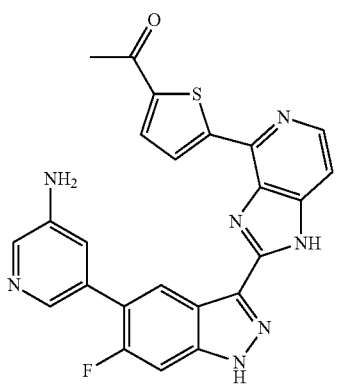 [SMILES: CC(=O)c1ccc(-c2nccc3[nH]c(-c4n[nH]c5cc(F)c(-c6cncc(N)c6)cc45)nc23)s1]
TABLE 1-continued
1253 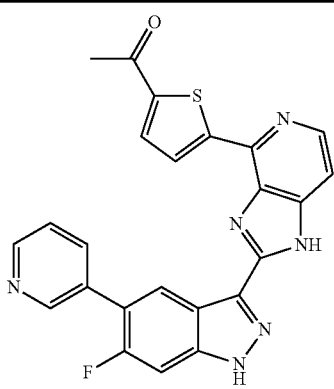
1254 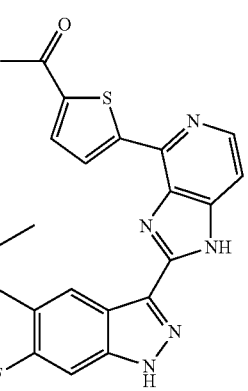
1255 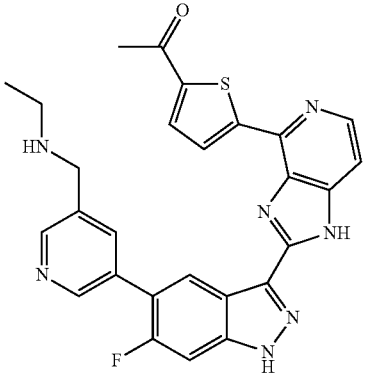 [SMILES: CCNCc1cncc(-c2cc3c(-c4nc5c(-c6ccc(C(C)=O)s6)nccc5[nH]4)n[nH]c3cc2F)c1]
1256 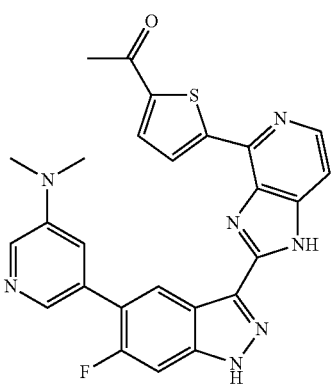 [SMILES: CC(=O)c1ccc(-c2nccc3[nH]c(-c4n[nH]c5cc(F)c(-c6cncc(N(C)C)c6)cc45)nc23)s1]

TABLE 1-continued
| | |
|---|---|
| 1257 | 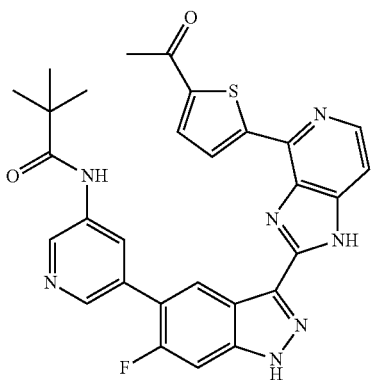 [SMILES: CC(=O)c1ccc(-c2nccc3[nH]c(-c4n[nH]c5cc(F)c(-c6cncc(NC(=O)C(C)(C)C)c6)cc45)nc23)s1] |
| 1258 | 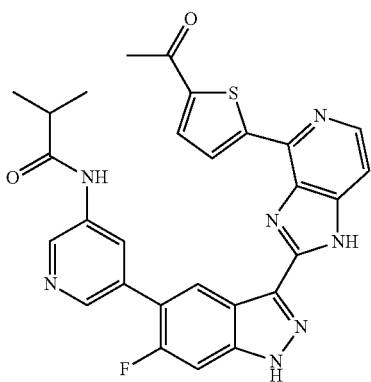 [SMILES: CC(=O)c1ccc(-c2nccc3[nH]c(-c4n[nH]c5cc(F)c(-c6cncc(NC(=O)C(C)C)c6)cc45)nc23)s1] |
| 1259 | 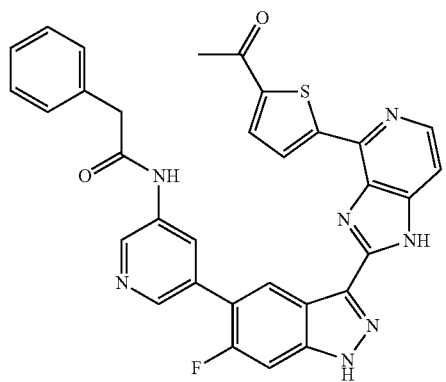 [SMILES: CC(=O)c1ccc(-c2nccc3[nH]c(-c4n[nH]c5cc(F)c(-c6cncc(NC(=O)Cc7ccccc7)c6)cc45)nc23)s1] |
| 1260 | 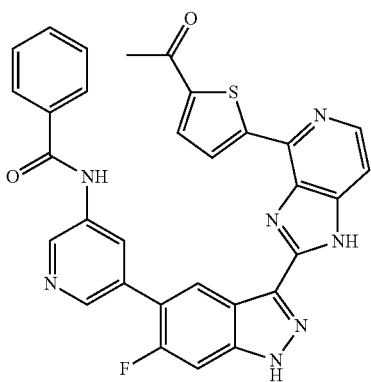 [SMILES: CC(=O)c1ccc(-c2nccc3[nH]c(-c4n[nH]c5cc(F)c(-c6cncc(NC(=O)c7ccccc7)c6)cc45)nc23)s1] |
| 1261 | 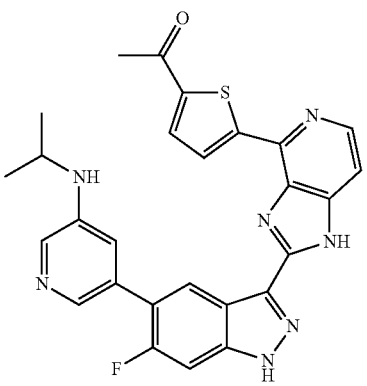 [SMILES: CC(=O)c1ccc(-c2nccc3[nH]c(-c4n[nH]c5cc(F)c(-c6cncc(NC(C)C)c6)cc45)nc23)s1] |
| 1262 | 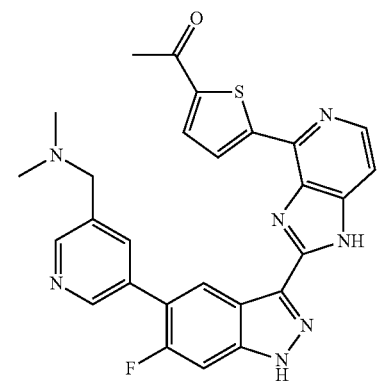 [SMILES: CC(=O)c1ccc(-c2nccc3[nH]c(-c4n[nH]c5cc(F)c(-c6cncc(CN(C)C)c6)cc45)nc23)s1] |
| 1263 | 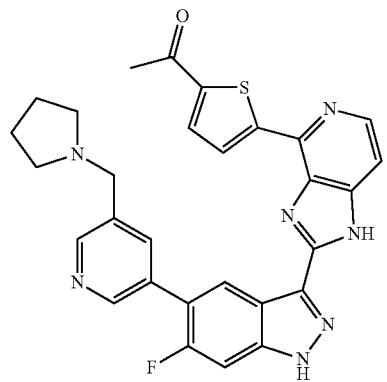 [SMILES: CC(=O)c1ccc(-c2nccc3[nH]c(-c4n[nH]c5cc(F)c(-c6cncc(CN7CCCC7)c6)cc45)nc23)s1] |
| 1264 | 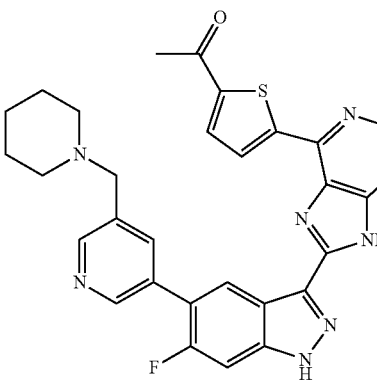 |

TABLE 1-continued
1265 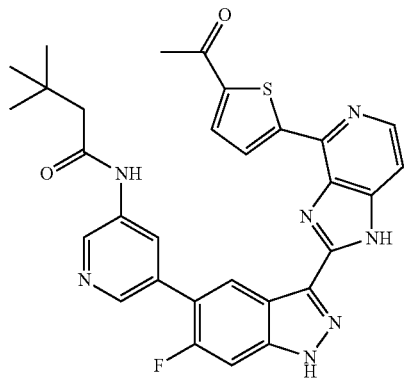 [SMILES: CC(=O)c1ccc(-c2nccc3[nH]c(-c4n[nH]c5cc(F)c(-c6cncc(NC(=O)CC(C)(C)C)c6)cc45)nc23)s1]
1266 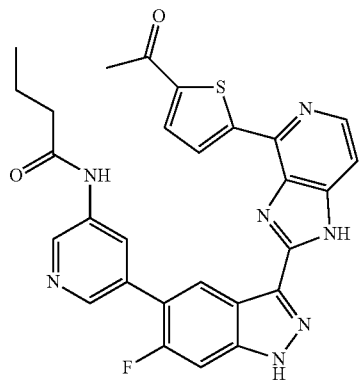 [SMILES: CCCC(=O)Nc1cncc(-c2cc3c(-c4nc5c(-c6ccc(C(C)=O)s6)nccc5[nH]4)n[nH]c3cc2F)c1]
1267 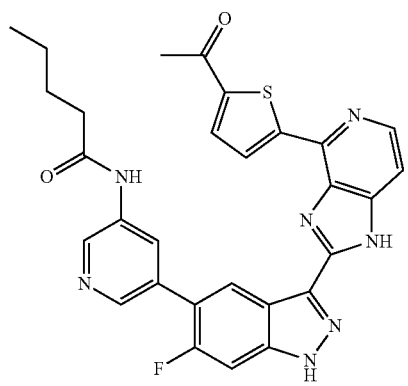 [SMILES: CCCCC(=O)Nc1cncc(-c2cc3c(-c4nc5c(-c6ccc(C(C)=O)s6)nccc5[nH]4)n[nH]c3cc2F)c1]
1268 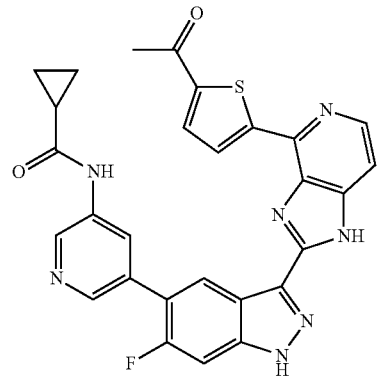 [SMILES: CC(=O)c1ccc(-c2nccc3[nH]c(-c4n[nH]c5cc(F)c(-c6cncc(NC(=O)C7CC7)c6)cc45)nc23)s1]
1269 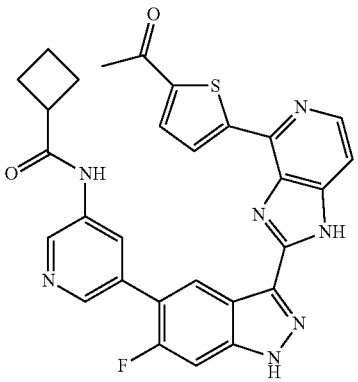 [SMILES: CC(=O)c1ccc(-c2nccc3[nH]c(-c4n[nH]c5cc(F)c(-c6cncc(NC(=O)C7CCC7)c6)cc45)nc23)s1]
1270 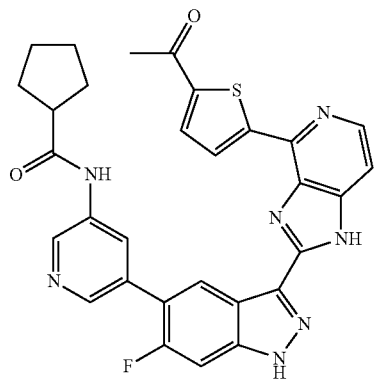 [SMILES: CC(=O)c1ccc(-c2nccc3[nH]c(-c4n[nH]c5cc(F)c(-c6cncc(NC(=O)C7CCCC7)c6)cc45)nc23)s1]
1271 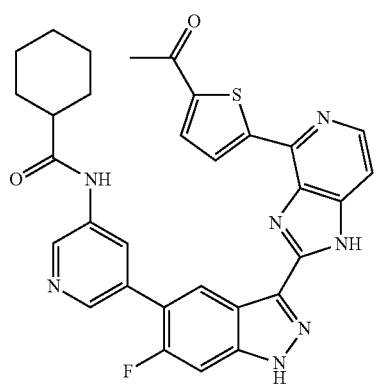 [SMILES: CC(=O)c1ccc(-c2nccc3[nH]c(-c4n[nH]c5cc(F)c(-c6cncc(NC(=O)C7CCCCC7)c6)cc45)nc23)s1]
1272 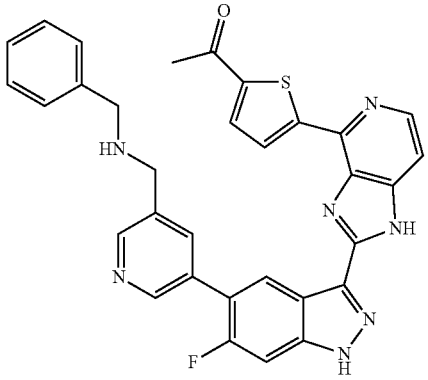 [SMILES: CC(=O)c1ccc(-c2nccc3[nH]c(-c4n[nH]c5cc(F)c(-c6cncc(CNCc7ccccc7)c6)cc45)nc23)s1]

TABLE 1-continued
1273 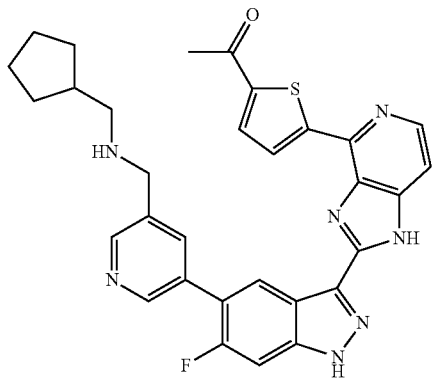 [SMILES: CC(=O)c1ccc(-c2nccc3[nH]c(-c4n[nH]c5cc(F)c(-c6cncc(CNCC7CCCC7)c6)cc45)nc23)s1]
1274 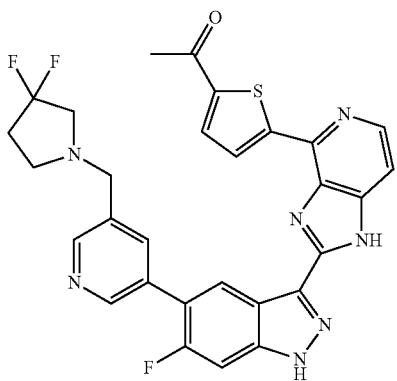 [SMILES: CC(=O)c1ccc(-c2nccc3[nH]c(-c4n[nH]c5cc(F)c(-c6cncc(CN7CCC(F)(F)C7)c6)cc45)nc23)s1]
1275 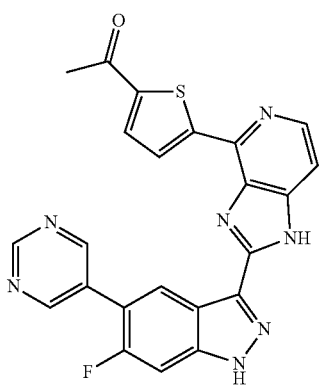 [SMILES: CC(=O)c1ccc(-c2nccc3[nH]c(-c4n[nH]c5cc(F)c(-c6cncnc6)cc45)nc23)s1]
1276 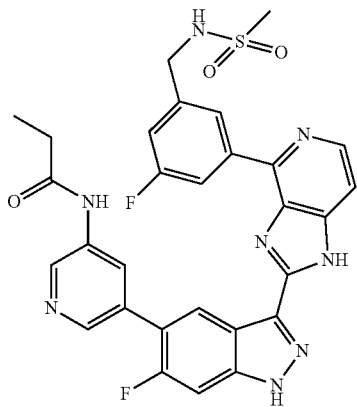 [SMILES: CCC(=O)Nc1cncc(-c2cc3c(-c4nc5c(-c6cc(F)cc(CNS(C)(=O)=O)c6)nccc5[nH]4)n[nH]c3cc2F)c1]
1277 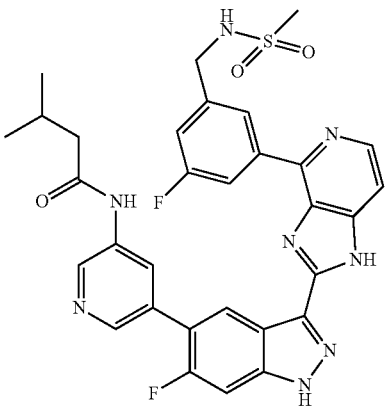 [SMILES: CC(C)CC(=O)Nc1cncc(-c2cc3c(-c4nc5c(-c6cc(F)cc(CNS(C)(=O)=O)c6)nccc5[nH]4)n[nH]c3cc2F)c1]
1278 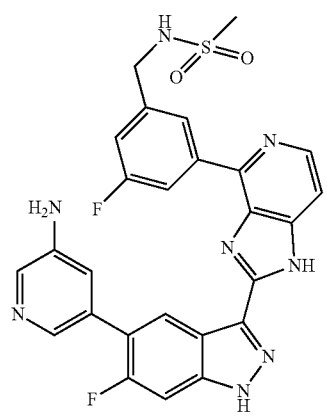 [SMILES: CS(=O)(=O)NCc1cc(F)cc(-c2nccc3[nH]c(-c4n[nH]c5cc(F)c(-c6cncc(N)c6)cc45)nc23)c1]
1279 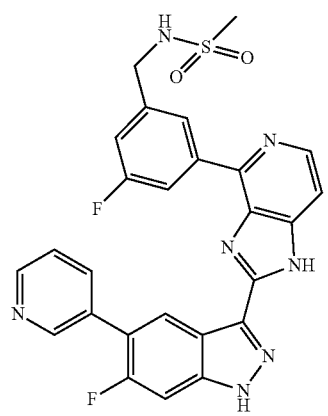 [SMILES: CS(=O)(=O)NCc1cc(F)cc(-c2nccc3[nH]c(-c4n[nH]c5cc(F)c(-c6cccnc6)cc45)nc23)c1]
1280 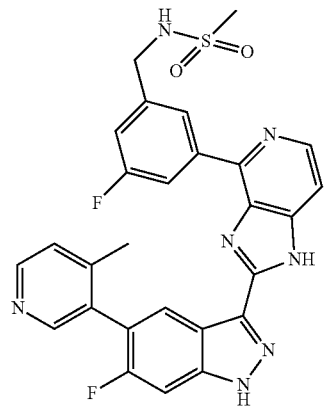 [SMILES: Cc1ccncc1-c1cc2c(-c3nc4c(-c5cc(F)cc(CNS(C)(=O)=O)c5)nccc4[nH]3)n[nH]c2cc1F]

TABLE 1-continued
| 1281 | 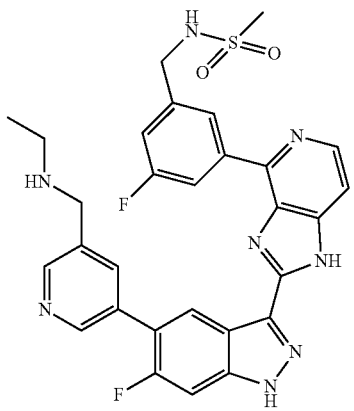 [SMILES: CCNCc1cncc(-c2cc3c(-c4nc5c(-c6cc(F)cc(CNS(C)(=O)=O)c6)nccc5[nH]4)n[nH]c3cc2F)c1] |
| --- | --- |
| 1282 | 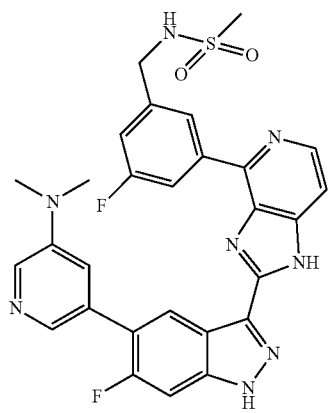 [SMILES: CN(C)c1cncc(-c2cc3c(-c4nc5c(-c6cc(F)cc(CNS(C)(=O)=O)c6)nccc5[nH]4)n[nH]c3cc2F)c1] |
| 1283 | 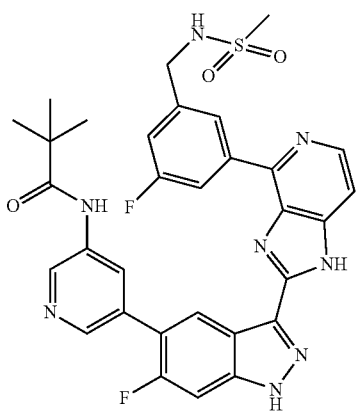 [SMILES: CC(C)(C)C(=O)Nc1cncc(-c2cc3c(-c4nc5c(-c6cc(F)cc(CNS(C)(=O)=O)c6)nccc5[nH]4)n[nH]c3cc2F)c1] |
| 1284 | 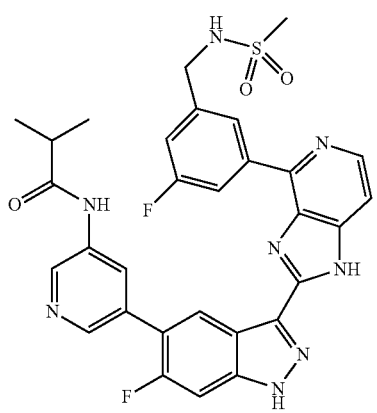 [SMILES: CC(C)C(=O)Nc1cncc(-c2cc3c(-c4nc5c(-c6cc(F)cc(CNS(C)(=O)=O)c6)nccc5[nH]4)n[nH]c3cc2F)c1] |
TABLE 1-continued
| 1285 | 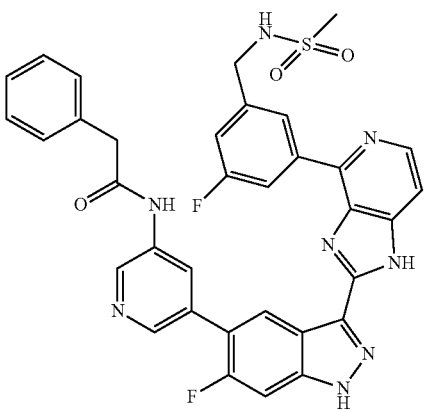 [SMILES: CS(=O)(=O)NCc1cc(F)cc(-c2nccc3[nH]c(-c4n[nH]c5cc(F)c(-c6cncc(NC(=O)Cc7ccccc7)c6)cc45)nc23)c1] |
| --- | --- |
| 1286 | 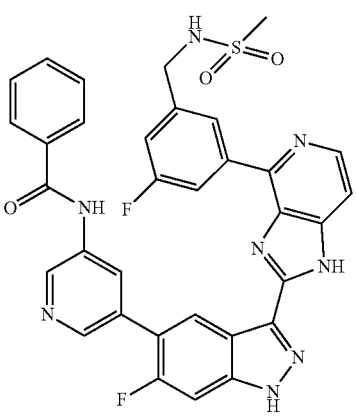 [SMILES: CS(=O)(=O)NCc1cc(F)cc(-c2nccc3[nH]c(-c4n[nH]c5cc(F)c(-c6cncc(NC(=O)c7ccccc7)c6)cc45)nc23)c1] |
| 1287 | 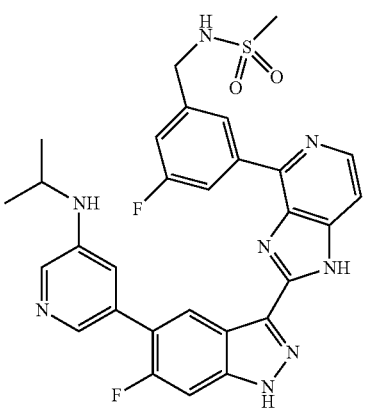 |
| 1288 | 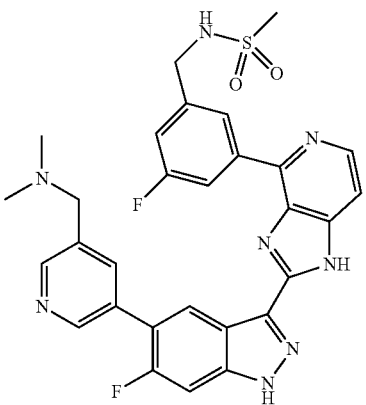 [SMILES: CN(C)Cc1cncc(-c2cc3c(-c4nc5c(-c6cc(F)cc(CNS(C)(=O)=O)c6)nccc5[nH]4)n[nH]c3cc2F)c1] |

TABLE 1-continued
1289 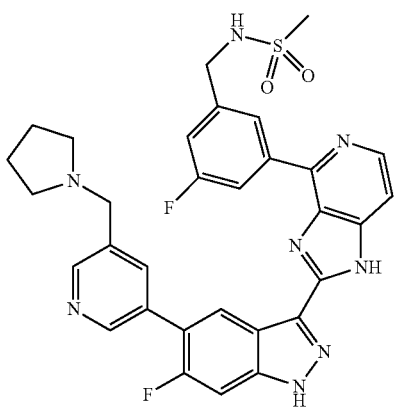 [SMILES: CS(=O)(=O)NCc1cc(F)cc(-c2nccc3[nH]c(-c4n[nH]c5cc(F)c(-c6cncc(CN7CCCC7)c6)cc45)nc23)c1]
1290 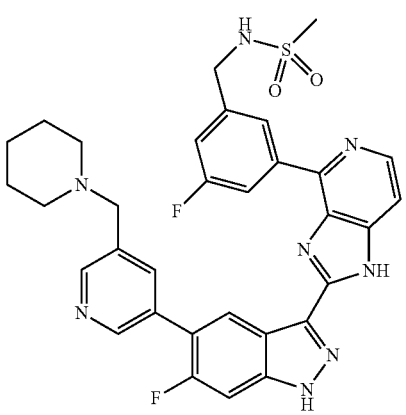 [SMILES: CS(=O)(=O)NCc1cc(F)cc(-c2nccc3[nH]c(-c4n[nH]c5cc(F)c(-c6cncc(CN7CCCCC7)c6)cc45)nc23)c1]
1291 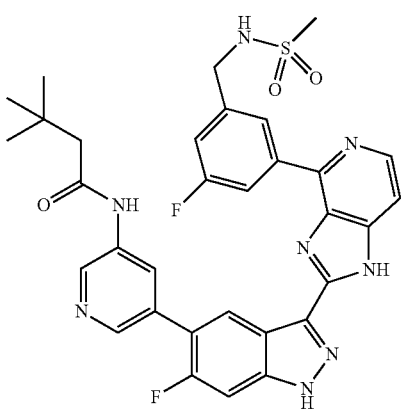 [SMILES: CC(C)(C)CC(=O)Nc1cncc(-c2cc3c(-c4nc5c(-c6cc(F)cc(CNS(C)(=O)=O)c6)nccc5[nH]4)n[nH]c3cc2F)c1]
1292 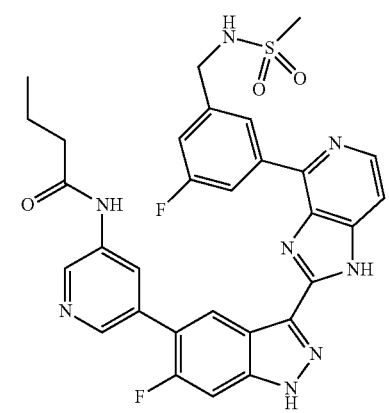 [SMILES: CCCC(=O)Nc1cncc(-c2cc3c(-c4nc5c(-c6cc(F)cc(CNS(C)(=O)=O)c6)nccc5[nH]4)n[nH]c3cc2F)c1]
TABLE 1-continued
1293 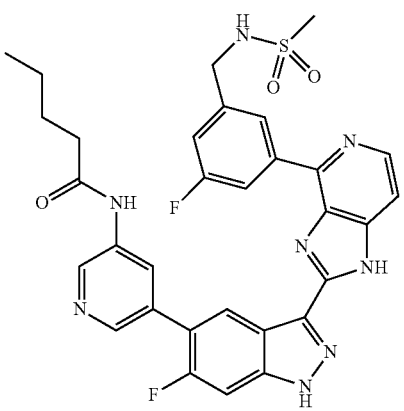 [SMILES: CCCCC(=O)Nc1cncc(-c2cc3c(-c4nc5c(-c6cc(F)cc(CNS(C)(=O)=O)c6)nccc5[nH]4)n[nH]c3cc2F)c1]
1294 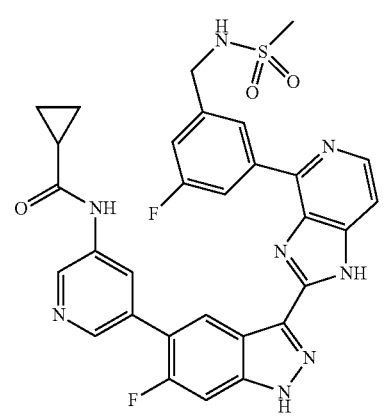 [SMILES: CS(=O)(=O)NCc1cc(F)cc(-c2nccc3[nH]c(-c4n[nH]c5cc(F)c(-c6cncc(NC(=O)C7CC7)c6)cc45)nc23)c1]
1295 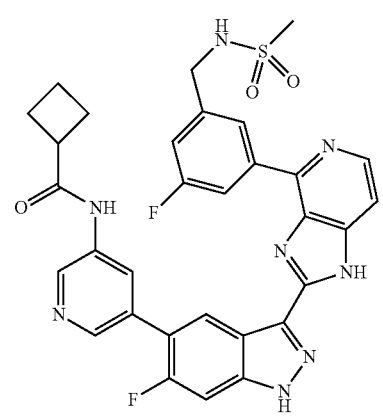 [SMILES: CS(=O)(=O)NCc1cc(F)cc(-c2nccc3[nH]c(-c4n[nH]c5cc(F)c(-c6cncc(NC(=O)C7CCC7)c6)cc45)nc23)c1]
1296 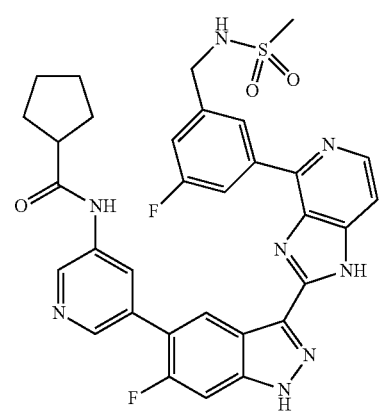 [SMILES: CS(=O)(=O)NCc1cc(F)cc(-c2nccc3[nH]c(-c4n[nH]c5cc(F)c(-c6cncc(NC(=O)C7CCCC7)c6)cc45)nc23)c1]

TABLE 1-continued
1297 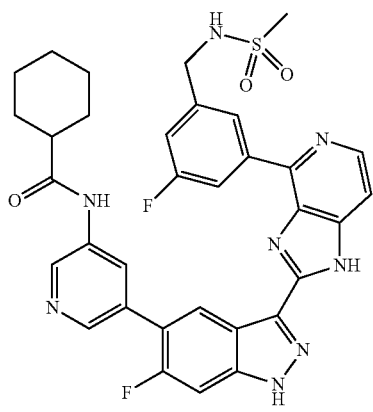 [SMILES: CS(=O)(=O)NCc1cc(F)cc(-c2nccc3[nH]c(-c4n[nH]c5cc(F)c(-c6cncc(NC(=O)C7CCCCC7)c6)cc45)nc23)c1]
1298 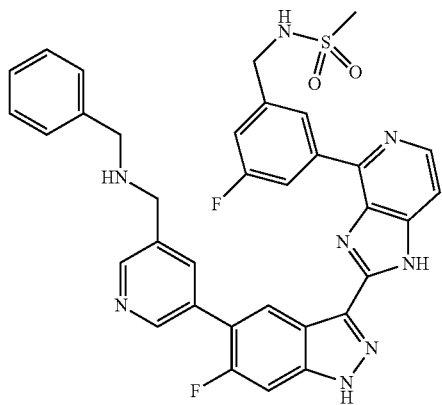 [SMILES: CS(=O)(=O)NCc1cc(F)cc(-c2nccc3[nH]c(-c4n[nH]c5cc(F)c(-c6cncc(CNCc7ccccc7)c6)cc45)nc23)c1]
1299 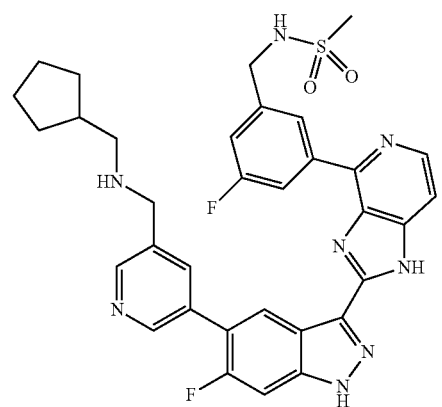 [SMILES: CS(=O)(=O)NCc1cc(F)cc(-c2nccc3[nH]c(-c4n[nH]c5cc(F)c(-c6cncc(CNCC7CCCC7)c6)cc45)nc23)c1]
1300 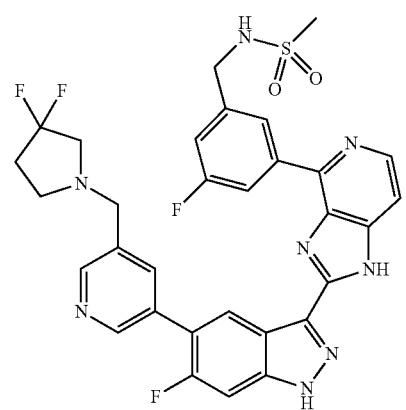 [SMILES: CS(=O)(=O)NCc1cc(F)cc(-c2nccc3[nH]c(-c4n[nH]c5cc(F)c(-c6cncc(CN7CCC(F)(F)C7)c6)cc45)nc23)c1]
TABLE 1-continued
1301 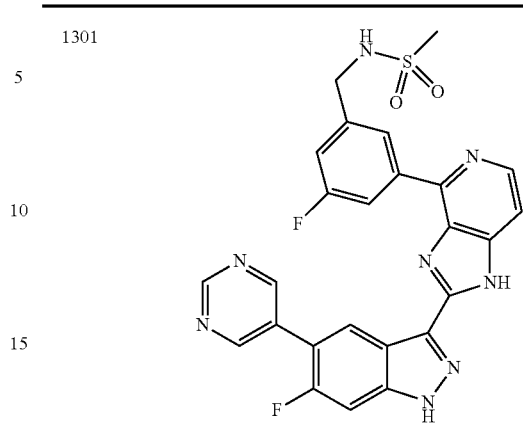
1302 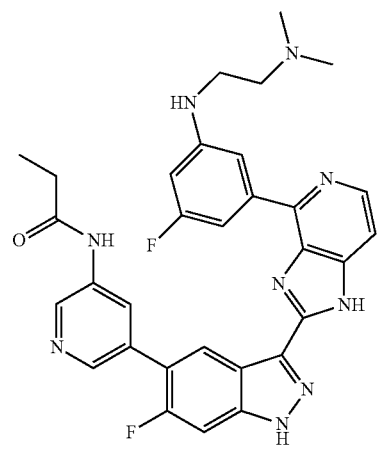 [SMILES: CCC(=O)Nc1cncc(-c2cc3c(-c4nc5c(-c6cc(F)cc(NCCN(C)C)c6)nccc5[nH]4)n[nH]c3cc2F)c1]
1303 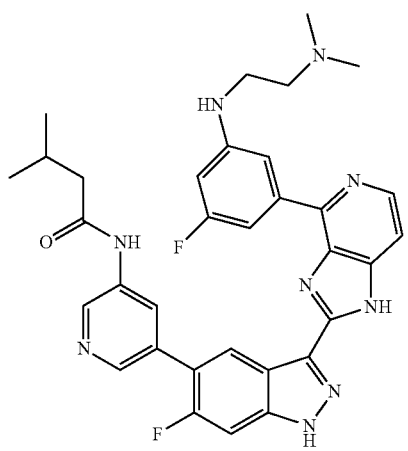 [SMILES: CC(C)CC(=O)Nc1cncc(-c2cc3c(-c4nc5c(-c6cc(F)cc(NCCN(C)C)c6)nccc5[nH]4)n[nH]c3cc2F)c1]

TABLE 1-continued
1304
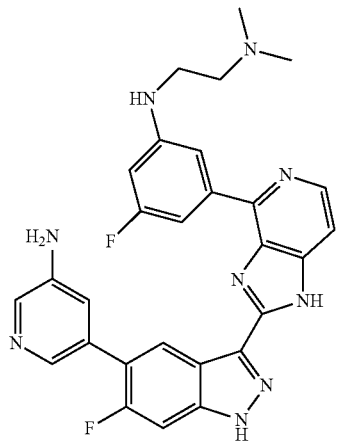 [SMILES: CN(C)CCNc1cc(F)cc(-c2nccc3[nH]c(-c4n[nH]c5cc(F)c(-c6cncc(N)c6)cc45)nc23)c1]
1307
1305
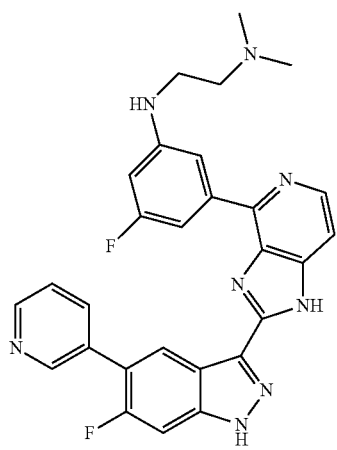 [SMILES: CN(C)CCNc1cc(F)cc(-c2nccc3[nH]c(-c4n[nH]c5cc(F)c(-c6cccnc6)cc45)nc23)c1]
1308
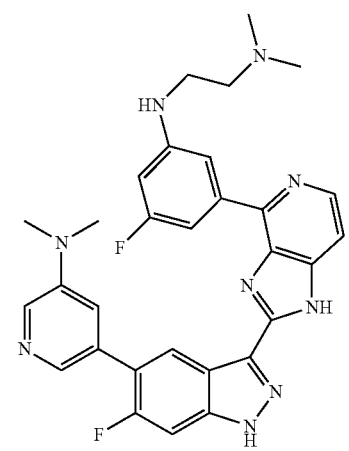
1306
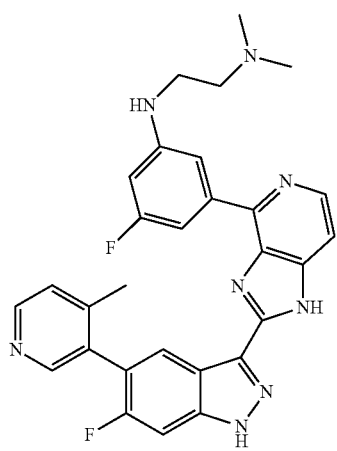 [SMILES: Cc1ccncc1-c1cc2c(-c3nc4c(-c5cc(F)cc(NCCN(C)C)c5)nccc4[nH]3)n[nH]c2cc1F]
1309
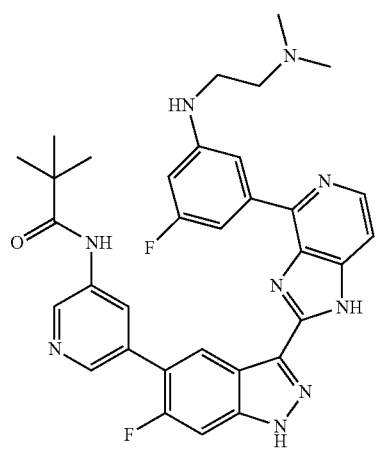 [SMILES: CN(C)CCNc1cc(F)cc(-c2nccc3[nH]c(-c4n[nH]c5cc(F)c(-c6cncc(NC(=O)C(C)(C)C)c6)cc45)nc23)c1]

TABLE 1-continued
1310
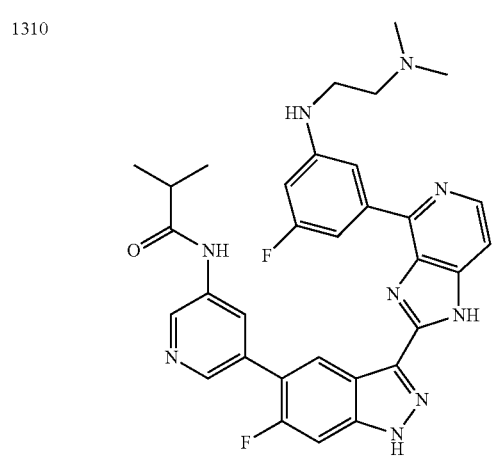
1311
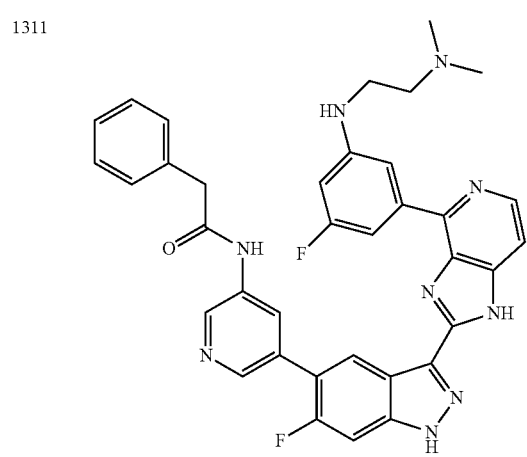
1312
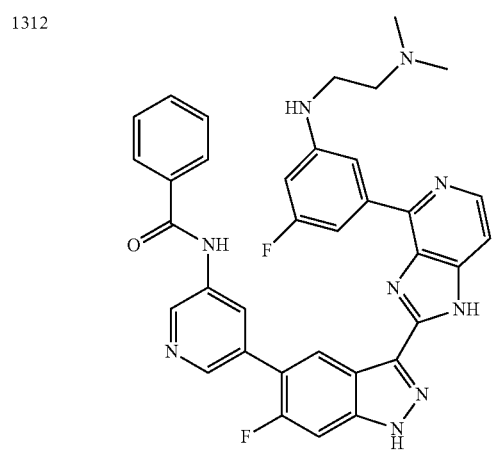
1313
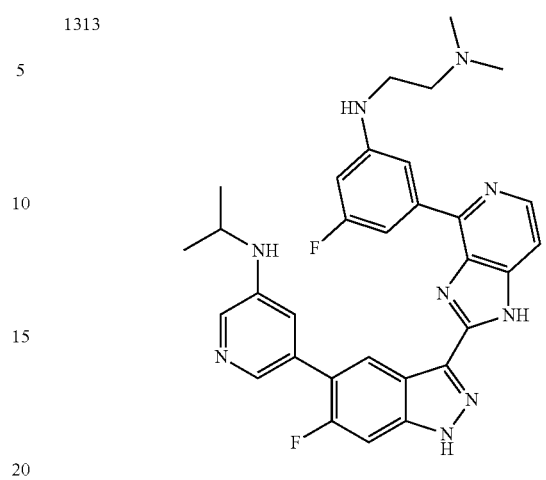
1314
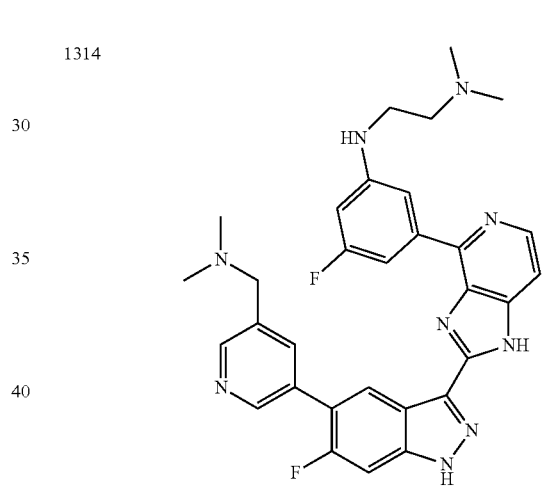
1315
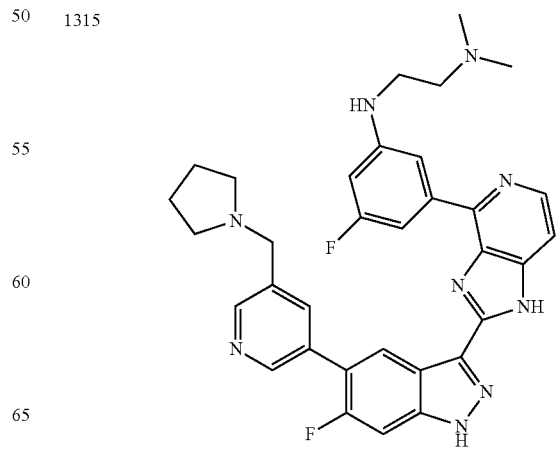

TABLE 1-continued
1316
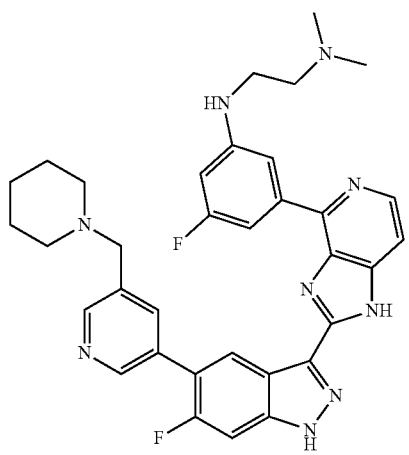 [SMILES: CN(C)CCNc1cc(F)cc(-c2nccc3[nH]c(-c4n[nH]c5cc(F)c(-c6cncc(CN7CCCCC7)c6)cc45)nc23)c1]
1319
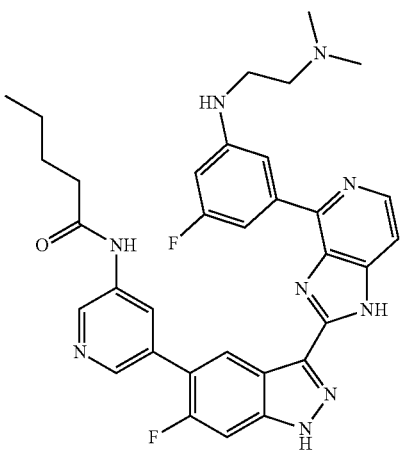
1317
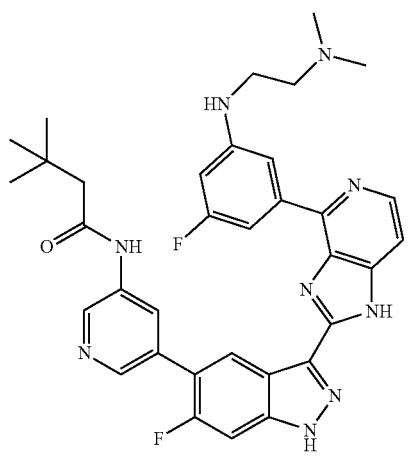 [SMILES: CN(C)CCNc1cc(F)cc(-c2nccc3[nH]c(-c4n[nH]c5cc(F)c(-c6cncc(NC(=O)CC(C)(C)C)c6)cc45)nc23)c1]
1320
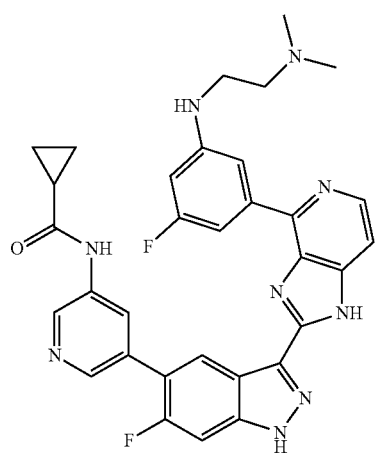
1318
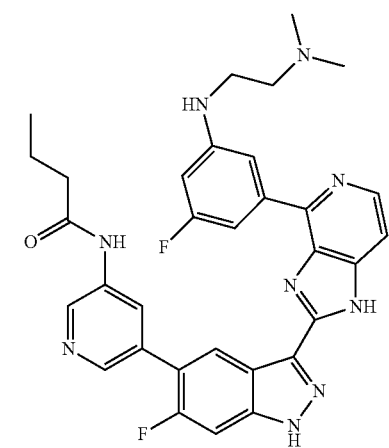 [SMILES: CCCC(=O)Nc1cncc(-c2cc3c(-c4nc5c(-c6cc(F)cc(NCCN(C)C)c6)nccc5[nH]4)n[nH]c3cc2F)c1]
1321
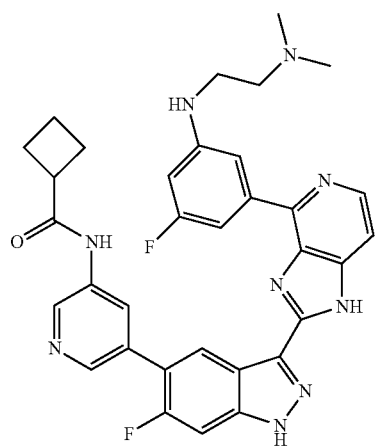 [SMILES: CN(C)CCNc1cc(F)cc(-c2nccc3[nH]c(-c4n[nH]c5cc(F)c(-c6cncc(NC(=O)C7CCC7)c6)cc45)nc23)c1]

TABLE 1-continued
1322
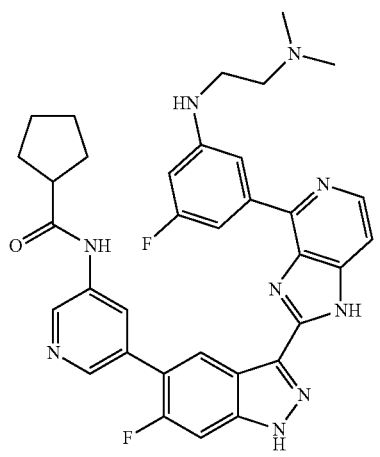 [SMILES: CN(C)CCNc1cc(F)cc(-c2nccc3[nH]c(-c4n[nH]c5cc(F)c(-c6cncc(NC(=O)C7CCCC7)c6)cc45)nc23)c1]
1323
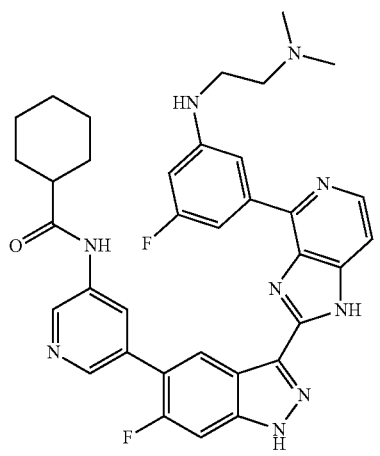 [SMILES: CN(C)CCNc1cc(F)cc(-c2nccc3[nH]c(-c4n[nH]c5cc(F)c(-c6cncc(NC(=O)C7CCCCC7)c6)cc45)nc23)c1]
1324
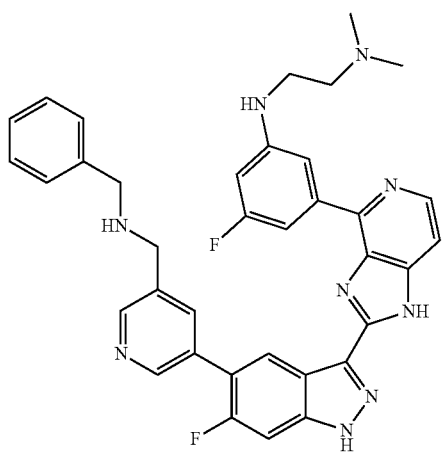 [SMILES: CN(C)CCNc1cc(F)cc(-c2nccc3[nH]c(-c4n[nH]c5cc(F)c(-c6cncc(CNCc7ccccc7)c6)cc45)nc23)c1]
TABLE 1-continued
1325
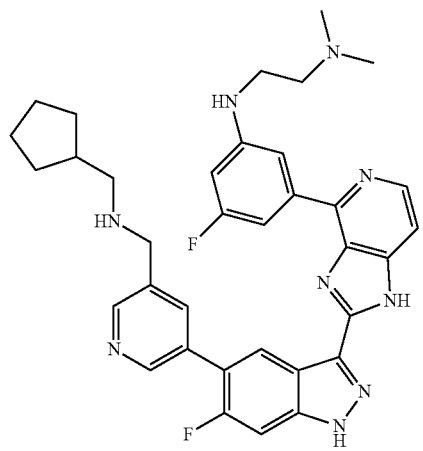 [SMILES: CN(C)CCNc1cc(F)cc(-c2nccc3[nH]c(-c4n[nH]c5cc(F)c(-c6cncc(CNCC7CCCC7)c6)cc45)nc23)c1]
1326
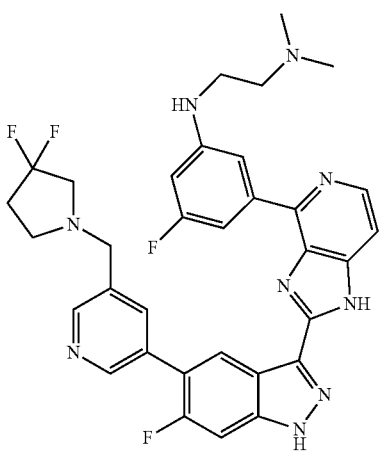 [SMILES: CN(C)CCNc1cc(F)cc(-c2nccc3[nH]c(-c4n[nH]c5cc(F)c(-c6cncc(CN7CCC(F)(F)C7)c6)cc45)nc23)c1]
1327
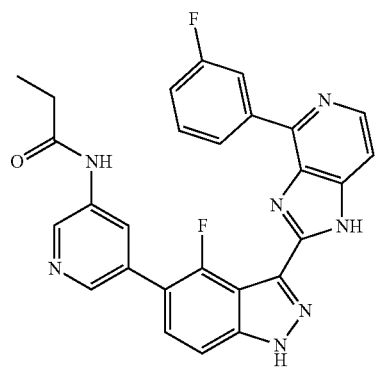 [SMILES: CCC(=O)Nc1cncc(-c2ccc3[nH]nc(-c4nc5c(-c6cccc(F)c6)nccc5[nH]4)c3c2F)c1]
1328
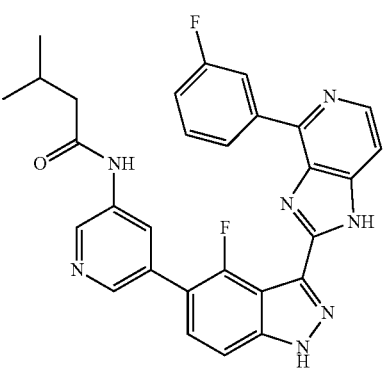 [SMILES: CC(C)CC(=O)Nc1cncc(-c2ccc3[nH]nc(-c4nc5c(-c6cccc(F)c6)nccc5[nH]4)c3c2F)c1]

TABLE 1-continued
1329 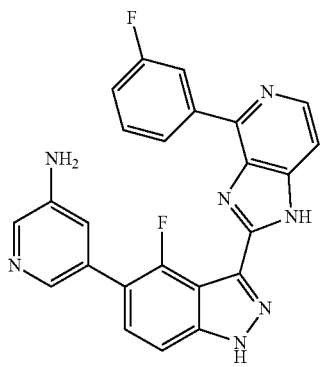 [SMILES: Nc1cncc(-c2ccc3[nH]nc(-c4nc5c(-c6cccc(F)c6)nccc5[nH]4)c3c2F)c1]
1330 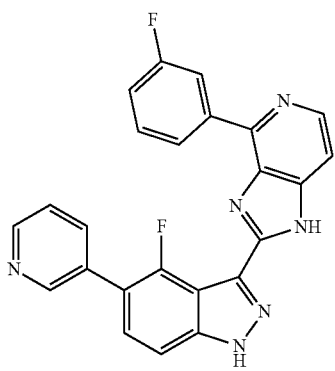 [SMILES: Fc1cccc(-c2nccc3[nH]c(-c4n[nH]c5ccc(-c6cccnc6)c(F)c45)nc23)c1]
1331 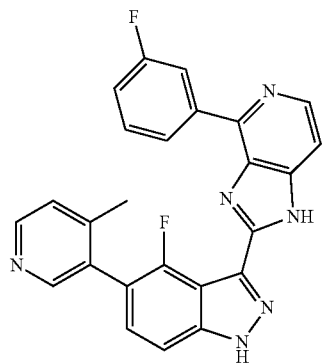 [SMILES: Cc1ccncc1-c1ccc2[nH]nc(-c3nc4c(-c5cccc(F)c5)nccc4[nH]3)c2c1F]
1332 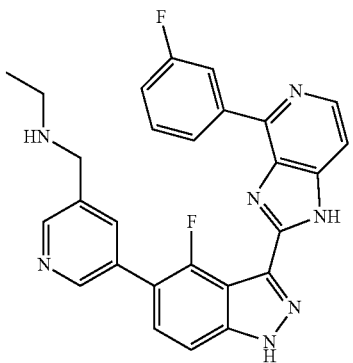 [SMILES: CCNCc1cncc(-c2ccc3[nH]nc(-c4nc5c(-c6cccc(F)c6)nccc5[nH]4)c3c2F)c1]
TABLE 1-continued
1333 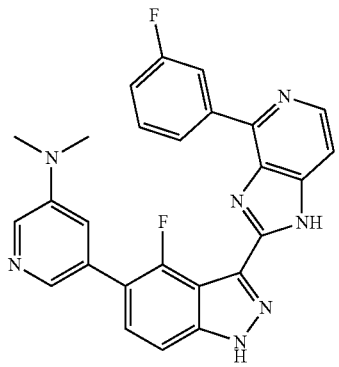 [SMILES: CN(C)c1cncc(-c2ccc3[nH]nc(-c4nc5c(-c6cccc(F)c6)nccc5[nH]4)c3c2F)c1]
1334 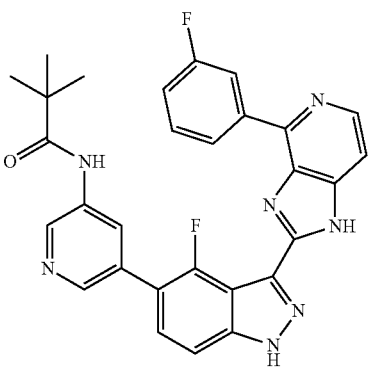 [SMILES: CC(C)(C)C(=O)Nc1cncc(-c2ccc3[nH]nc(-c4nc5c(-c6cccc(F)c6)nccc5[nH]4)c3c2F)c1]
1335 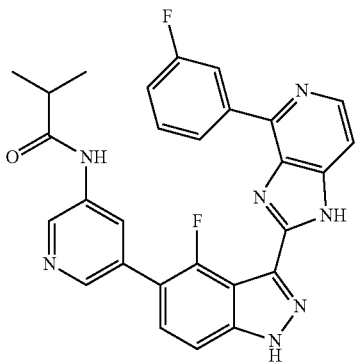 [SMILES: CC(C)C(=O)Nc1cncc(-c2ccc3[nH]nc(-c4nc5c(-c6cccc(F)c6)nccc5[nH]4)c3c2F)c1]
1336 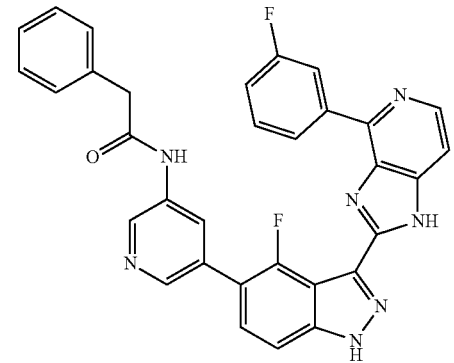 [SMILES: O=C(Cc1ccccc1)Nc1cncc(-c2ccc3[nH]nc(-c4nc5c(-c6cccc(F)c6)nccc5[nH]4)c3c2F)c1]

TABLE 1-continued
| 1337 | 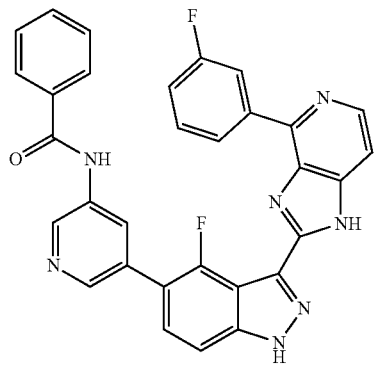 [SMILES: O=C(Nc1cncc(-c2ccc3[nH]nc(-c4nc5c(-c6cccc(F)c6)nccc5[nH]4)c3c2F)c1)c1ccccc1] |
| 1338 | 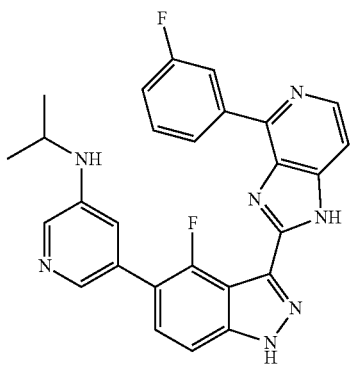 [SMILES: CC(C)Nc1cncc(-c2ccc3[nH]nc(-c4nc5c(-c6cccc(F)c6)nccc5[nH]4)c3c2F)c1] |
| 1339 | 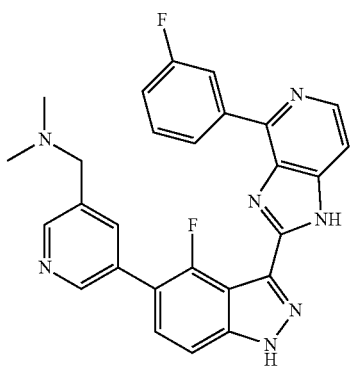 [SMILES: CN(C)Cc1cncc(-c2ccc3[nH]nc(-c4nc5c(-c6cccc(F)c6)nccc5[nH]4)c3c2F)c1] |
| 1340 | 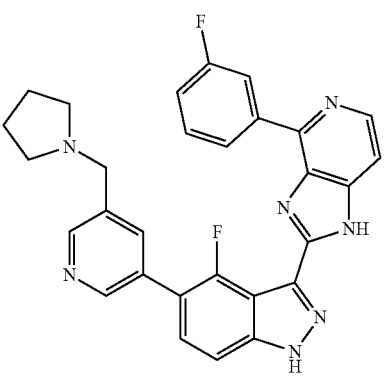 [SMILES: Fc1cccc(-c2nccc3[nH]c(-c4n[nH]c5ccc(-c6cncc(CN7CCCC7)c6)c(F)c45)nc23)c1] |
TABLE 1-continued
| 1341 | 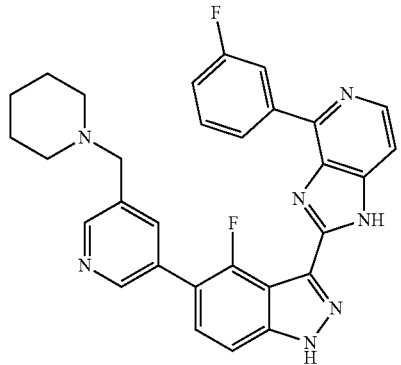 [SMILES: Fc1cccc(-c2nccc3[nH]c(-c4n[nH]c5ccc(-c6cncc(CN7CCCCC7)c6)c(F)c45)nc23)c1] |
| 1342 | 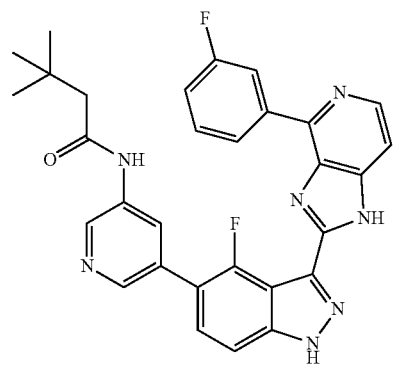 [SMILES: CC(C)(C)CC(=O)Nc1cncc(-c2ccc3[nH]nc(-c4nc5c(-c6cccc(F)c6)nccc5[nH]4)c3c2F)c1] |
| 1343 | 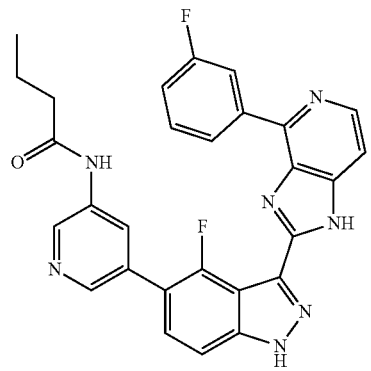 [SMILES: CCCC(=O)Nc1cncc(-c2ccc3[nH]nc(-c4nc5c(-c6cccc(F)c6)nccc5[nH]4)c3c2F)c1] |
| 1344 | 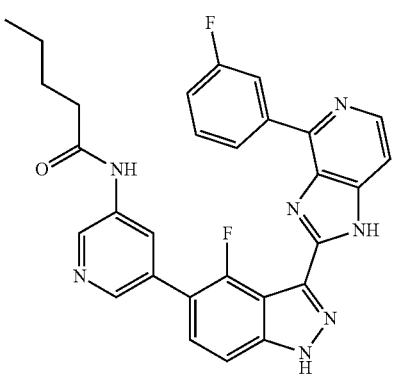 [SMILES: CCCCC(=O)Nc1cncc(-c2ccc3[nH]nc(-c4nc5c(-c6cccc(F)c6)nccc5[nH]4)c3c2F)c1] |

TABLE 1-continued
| 1345 | 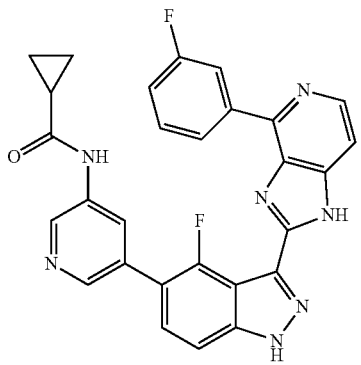 [SMILES: O=C(Nc1cncc(-c2ccc3[nH]nc(-c4nc5c(-c6cccc(F)c6)nccc5[nH]4)c3c2F)c1)C1CC1] | 1349 | 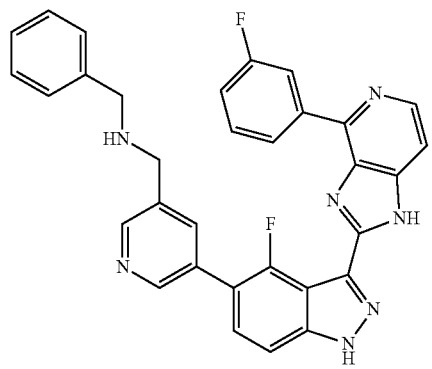 |
|---|---|---|---|
| 1346 | 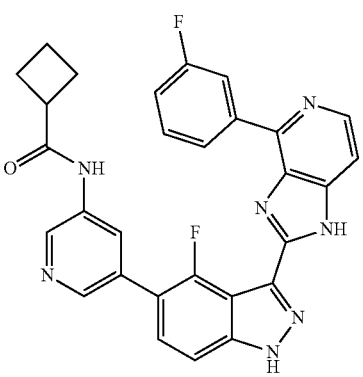 [SMILES: O=C(Nc1cncc(-c2ccc3[nH]nc(-c4nc5c(-c6cccc(F)c6)nccc5[nH]4)c3c2F)c1)C1CCC1] | 1350 | 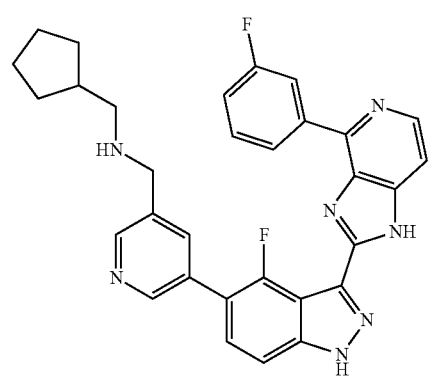 |
| 1347 | 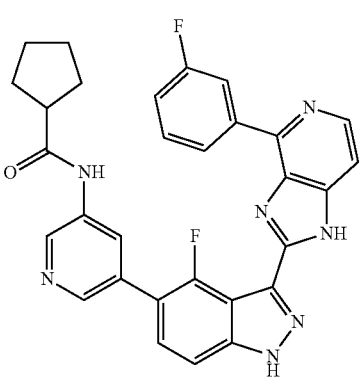 [SMILES: O=C(Nc1cncc(-c2ccc3[nH]nc(-c4nc5c(-c6cccc(F)c6)nccc5[nH]4)c3c2F)c1)C1CCCC1] | 1351 | 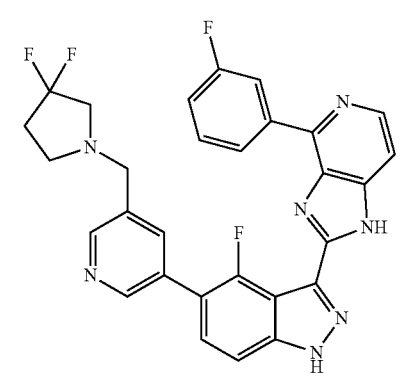 |
| 1348 | 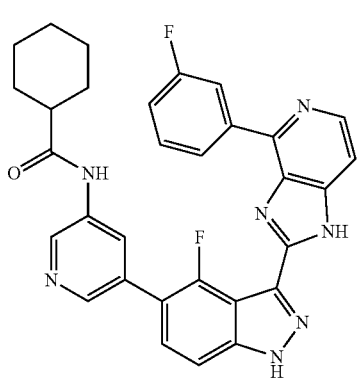 [SMILES: O=C(Nc1cncc(-c2ccc3[nH]nc(-c4nc5c(-c6cccc(F)c6)nccc5[nH]4)c3c2F)c1)C1CCCCC1] | 1352 | 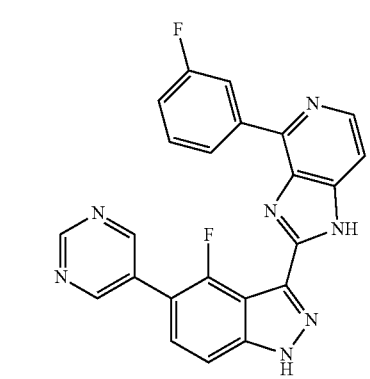 [SMILES: Fc1cccc(-c2nccc3[nH]c(-c4n[nH]c5ccc(-c6cncnc6)c(F)c45)nc23)c1] |

TABLE 1-continued
| 1353 | 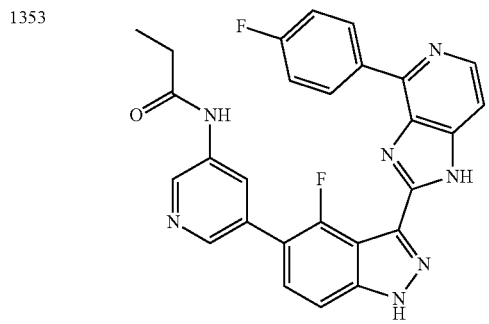 |
| --- | --- |
| 1354 | 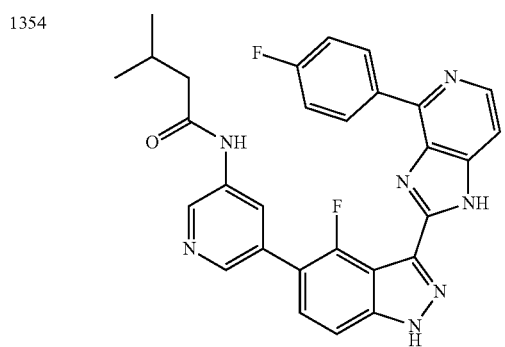 |
| 1355 | 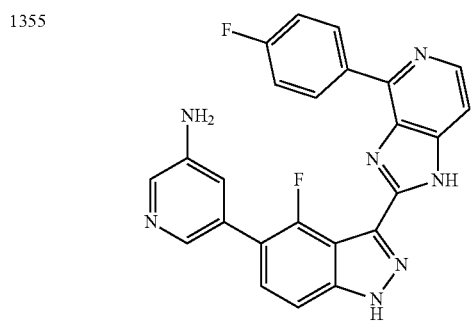 |
| 1356 | 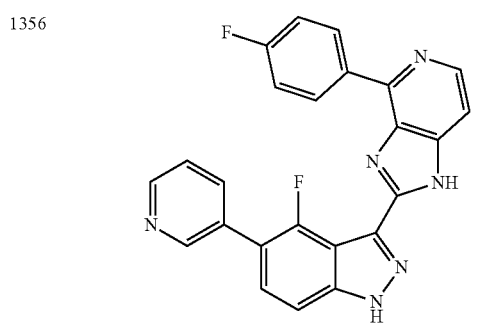 |
| 1357 | 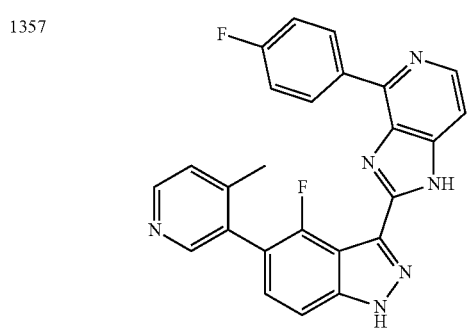 |
| 1358 | 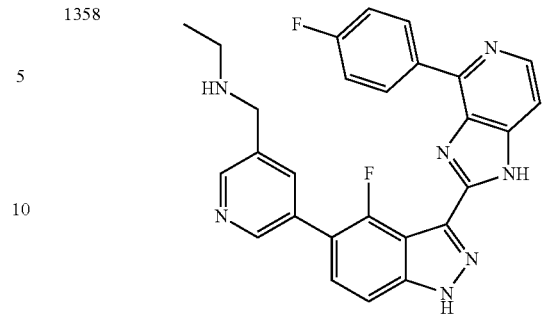 |
| 1359 | 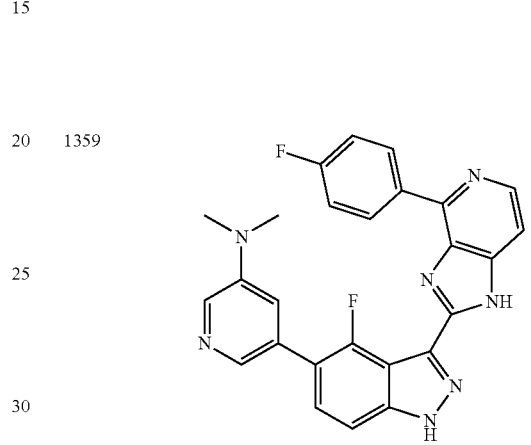 |
| 1360 | 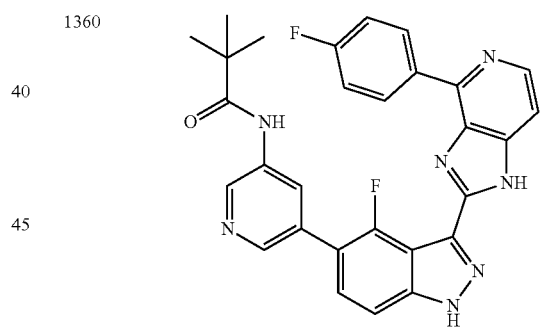 |
| 1361 | 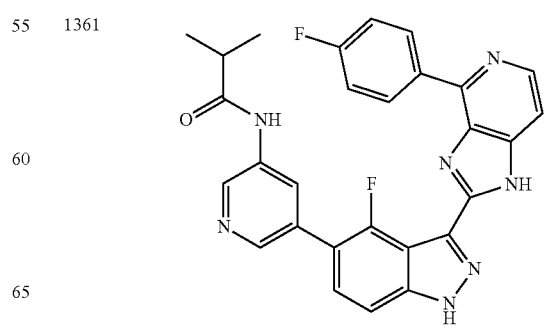 |

TABLE 1-continued
1362 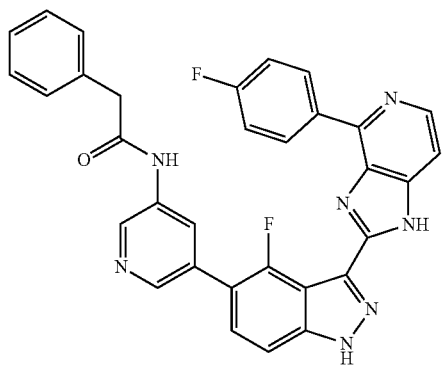 [SMILES: O=C(Cc1ccccc1)Nc1cncc(-c2ccc3[nH]nc(-c4nc5c(-c6ccc(F)cc6)nccc5[nH]4)c3c2F)c1]
1363 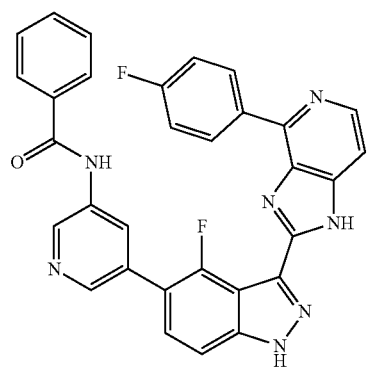 [SMILES: O=C(Nc1cncc(-c2ccc3[nH]nc(-c4nc5c(-c6ccc(F)cc6)nccc5[nH]4)c3c2F)c1)c1ccccc1]
1364 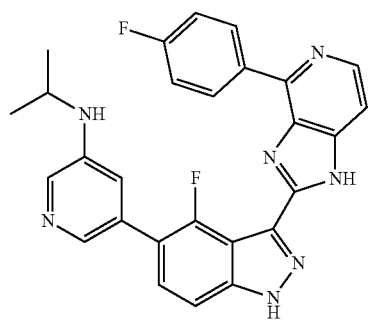 [SMILES: CC(C)Nc1cncc(-c2ccc3[nH]nc(-c4nc5c(-c6ccc(F)cc6)nccc5[nH]4)c3c2F)c1]
1365 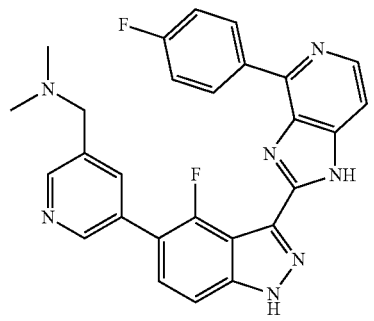 [SMILES: CN(C)Cc1cncc(-c2ccc3[nH]nc(-c4nc5c(-c6ccc(F)cc6)nccc5[nH]4)c3c2F)c1]
TABLE 1-continued
1366 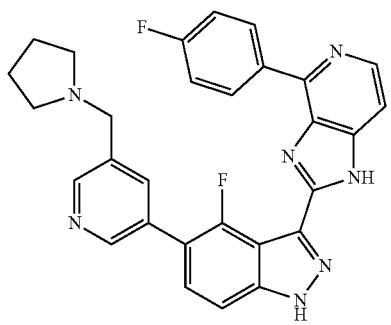 [SMILES: Fc1ccc(-c2nccc3[nH]c(-c4n[nH]c5ccc(-c6cncc(CN7CCCC7)c6)c(F)c45)nc23)cc1]
1367 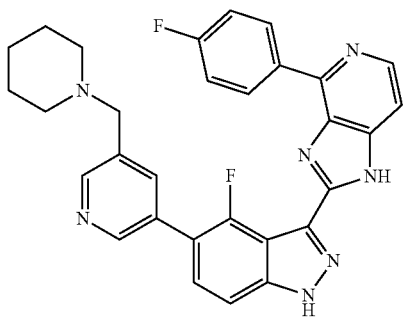 [SMILES: Fc1ccc(-c2nccc3[nH]c(-c4n[nH]c5ccc(-c6cncc(CN7CCCCC7)c6)c(F)c45)nc23)cc1]
1368 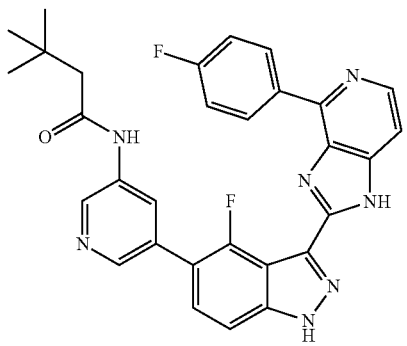 [SMILES: CC(C)(C)CC(=O)Nc1cncc(-c2ccc3[nH]nc(-c4nc5c(-c6ccc(F)cc6)nccc5[nH]4)c3c2F)c1]
1369 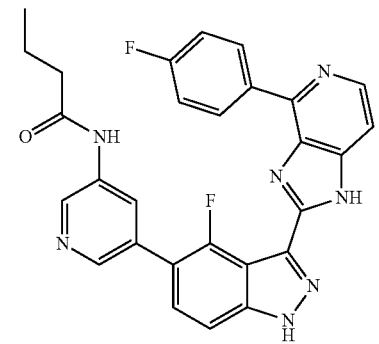 [SMILES: CCCC(=O)Nc1cncc(-c2ccc3[nH]nc(-c4nc5c(-c6ccc(F)cc6)nccc5[nH]4)c3c2F)c1]

TABLE 1-continued
1370 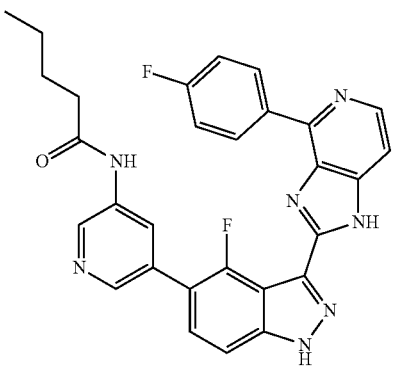 [SMILES: CCCCC(=O)Nc1cncc(-c2ccc3[nH]nc(-c4nc5c(-c6ccc(F)cc6)nccc5[nH]4)c3c2F)c1]
1371 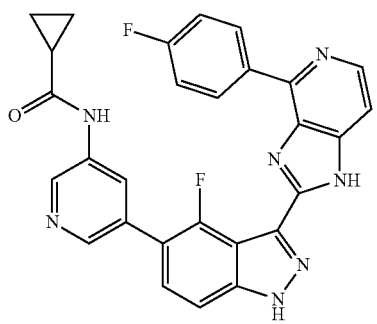 [SMILES: O=C(Nc1cncc(-c2ccc3[nH]nc(-c4nc5c(-c6ccc(F)cc6)nccc5[nH]4)c3c2F)c1)C1CC1]
1372 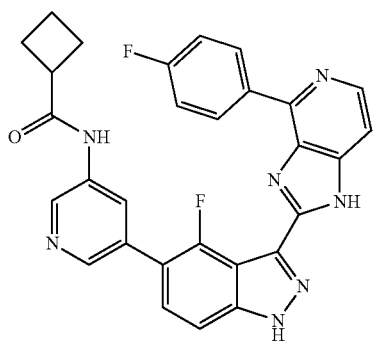 [SMILES: O=C(Nc1cncc(-c2ccc3[nH]nc(-c4nc5c(-c6ccc(F)cc6)nccc5[nH]4)c3c2F)c1)C1CCC1]
1373 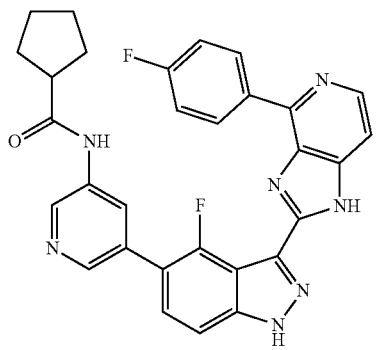 [SMILES: O=C(Nc1cncc(-c2ccc3[nH]nc(-c4nc5c(-c6ccc(F)cc6)nccc5[nH]4)c3c2F)c1)C1CCCC1]
TABLE 1-continued
1374 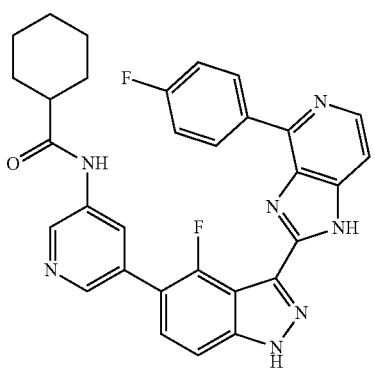 [SMILES: O=C(Nc1cncc(-c2ccc3[nH]nc(-c4nc5c(-c6ccc(F)cc6)nccc5[nH]4)c3c2F)c1)C1CCCCC1]
1375 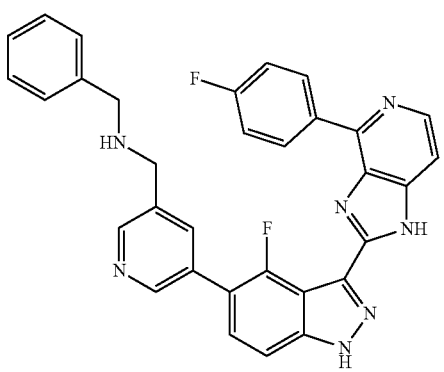 [SMILES: Fc1ccc(-c2nccc3[nH]c(-c4n[nH]c5ccc(-c6cncc(CNCc7ccccc7)c6)c(F)c45)nc23)cc1]
1376 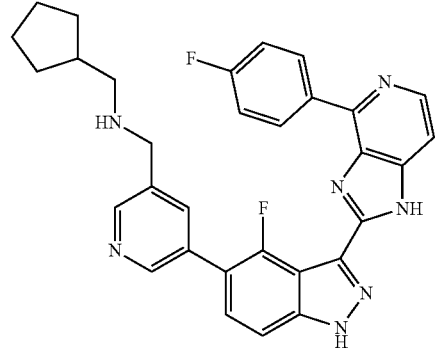 [SMILES: Fc1ccc(-c2nccc3[nH]c(-c4n[nH]c5ccc(-c6cncc(CNCC7CCCC7)c6)c(F)c45)nc23)cc1]
1377 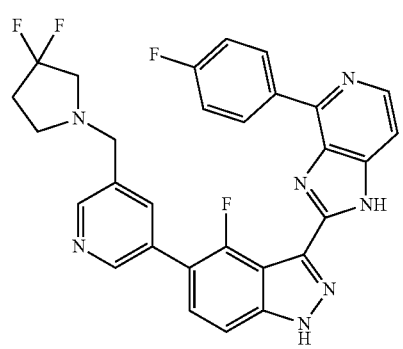 [SMILES: Fc1ccc(-c2nccc3[nH]c(-c4n[nH]c5ccc(-c6cncc(CN7CCC(F)(F)C7)c6)c(F)c45)nc23)cc1]

TABLE 1-continued
| 1378 | 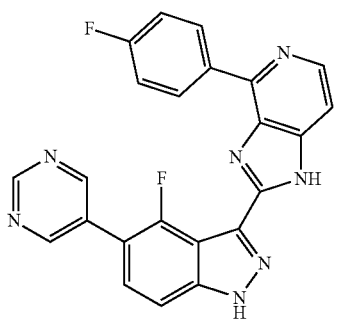 |
| 1379 | 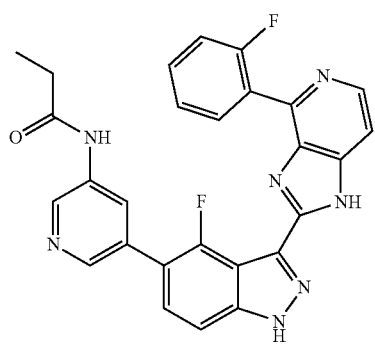 [SMILES: CCC(=O)Nc1cncc(-c2ccc3[nH]nc(-c4nc5c(-c6ccccc6F)nccc5[nH]4)c3c2F)c1] |
| 1380 | 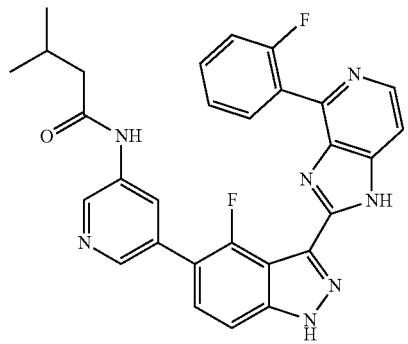 |
| 1381 | 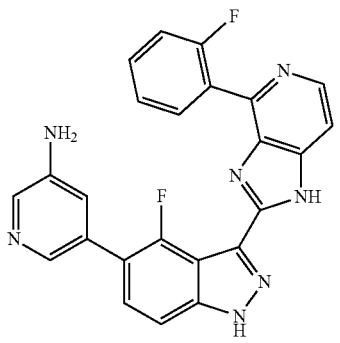 [SMILES: Nc1cncc(-c2ccc3[nH]nc(-c4nc5c(-c6ccccc6F)nccc5[nH]4)c3c2F)c1] |
TABLE 1-continued
| 1382 | 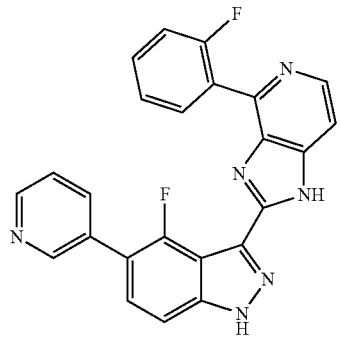 [SMILES: Fc1ccccc1-c1nccc2[nH]c(-c3n[nH]c4ccc(-c5cccnc5)c(F)c34)nc12] |
| 1383 | 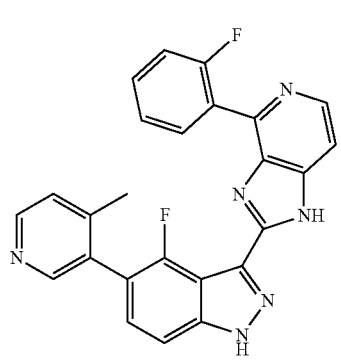 [SMILES: Cc1ccncc1-c1ccc2[nH]nc(-c3nc4c(-c5ccccc5F)nccc4[nH]3)c2c1F] |
| 1384 | 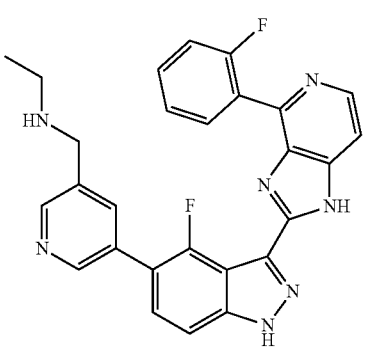 [SMILES: CCNCc1cncc(-c2ccc3[nH]nc(-c4nc5c(-c6ccccc6F)nccc5[nH]4)c3c2F)c1] |
| 1385 | 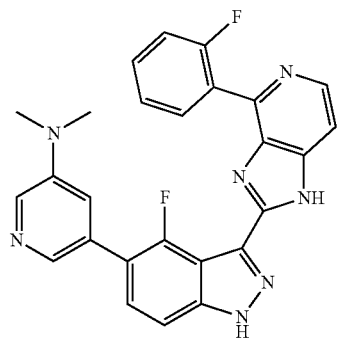 [SMILES: CN(C)c1cncc(-c2ccc3[nH]nc(-c4nc5c(-c6ccccc6F)nccc5[nH]4)c3c2F)c1] |

TABLE 1-continued
1386 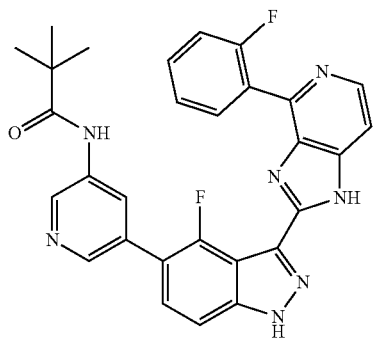 [SMILES: CC(C)(C)C(=O)Nc1cncc(-c2ccc3[nH]nc(-c4nc5c(-c6ccccc6F)nccc5[nH]4)c3c2F)c1]
1387 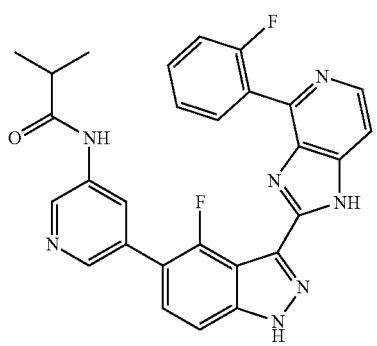 [SMILES: CC(C)C(=O)Nc1cncc(-c2ccc3[nH]nc(-c4nc5c(-c6ccccc6F)nccc5[nH]4)c3c2F)c1]
1388 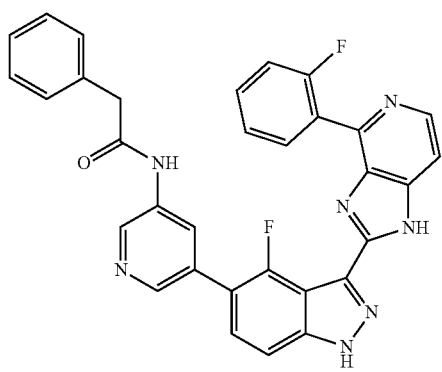 [SMILES: O=C(Cc1ccccc1)Nc1cncc(-c2ccc3[nH]nc(-c4nc5c(-c6ccccc6F)nccc5[nH]4)c3c2F)c1]
1389 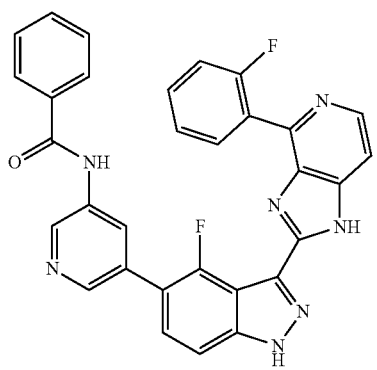 [SMILES: O=C(Nc1cncc(-c2ccc3[nH]nc(-c4nc5c(-c6ccccc6F)nccc5[nH]4)c3c2F)c1)c1ccccc1]
TABLE 1-continued
1390 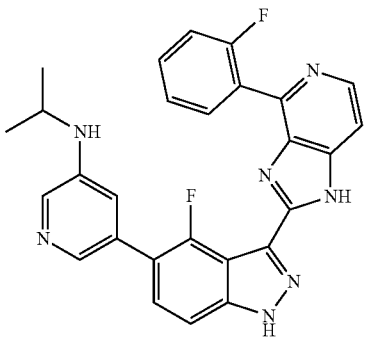 [SMILES: CC(C)Nc1cncc(-c2ccc3[nH]nc(-c4nc5c(-c6ccccc6F)nccc5[nH]4)c3c2F)c1]
1391 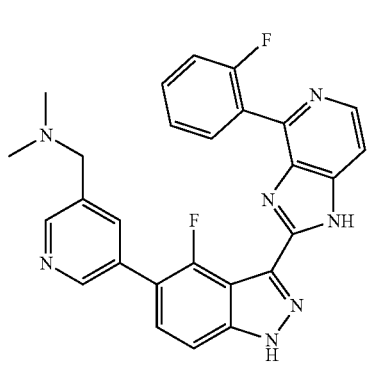 [SMILES: CN(C)Cc1cncc(-c2ccc3[nH]nc(-c4nc5c(-c6ccccc6F)nccc5[nH]4)c3c2F)c1]
1392 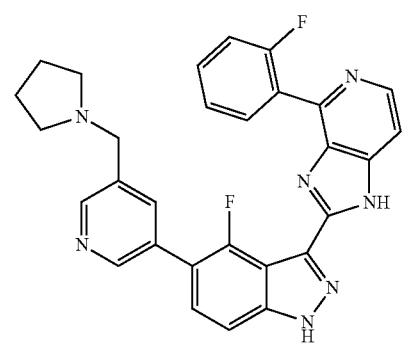 [SMILES: Fc1ccccc1-c1nccc2[nH]c(-c3n[nH]c4ccc(-c5cncc(CN6CCCC6)c5)c(F)c34)nc12]
1393 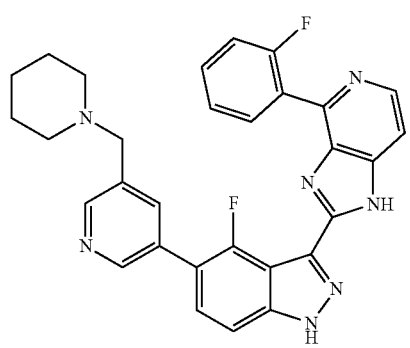 [SMILES: Fc1ccccc1-c1nccc2[nH]c(-c3n[nH]c4ccc(-c5cncc(CN6CCCCC6)c5)c(F)c34)nc12]

TABLE 1-continued
| 1394 | 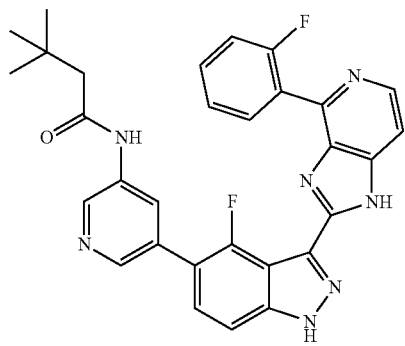 [SMILES: CC(C)(C)CC(=O)Nc1cncc(-c2ccc3[nH]nc(-c4nc5c(-c6ccccc6F)nccc5[nH]4)c3c2F)c1] | 1398 | 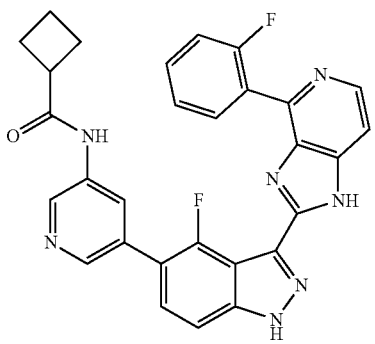 |
| --- | --- | --- | --- |
| 1395 | 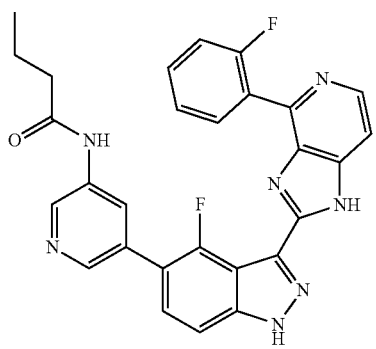 [SMILES: CCCC(=O)Nc1cncc(-c2ccc3[nH]nc(-c4nc5c(-c6ccccc6F)nccc5[nH]4)c3c2F)c1] | 1399 | 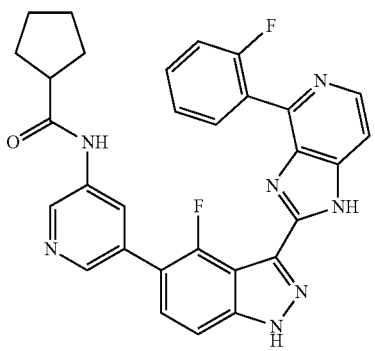 |
| 1396 | 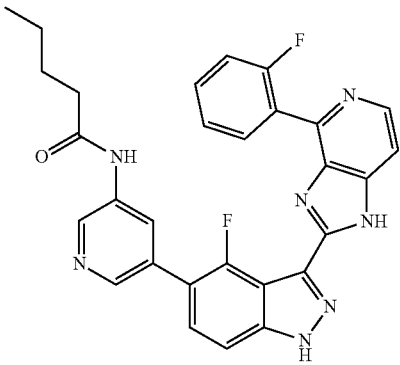 [SMILES: CCCCC(=O)Nc1cncc(-c2ccc3[nH]nc(-c4nc5c(-c6ccccc6F)nccc5[nH]4)c3c2F)c1] | 1400 | 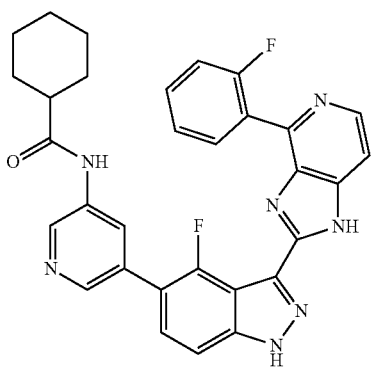 |
| 1397 | 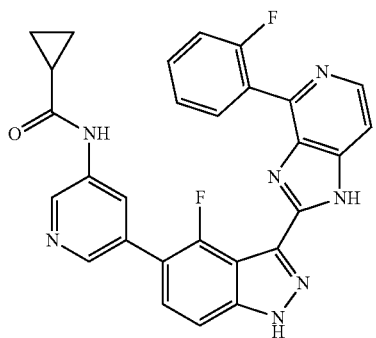 [SMILES: O=C(Nc1cncc(-c2ccc3[nH]nc(-c4nc5c(-c6ccccc6F)nccc5[nH]4)c3c2F)c1)C1CC1] | 1401 | 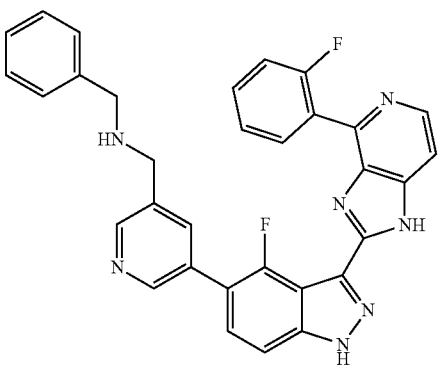 [SMILES: Fc1ccccc1-c1nccc2[nH]c(-c3n[nH]c4ccc(-c5cncc(CNCc6ccccc6)c5)c(F)c34)nc12] |

TABLE 1-continued
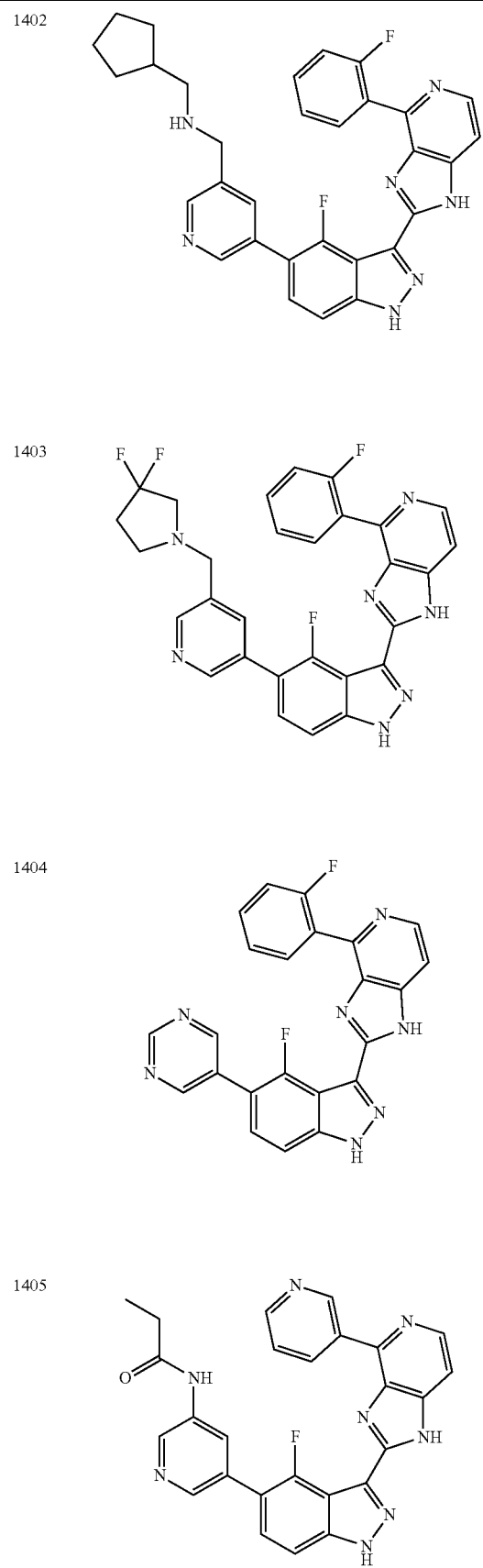
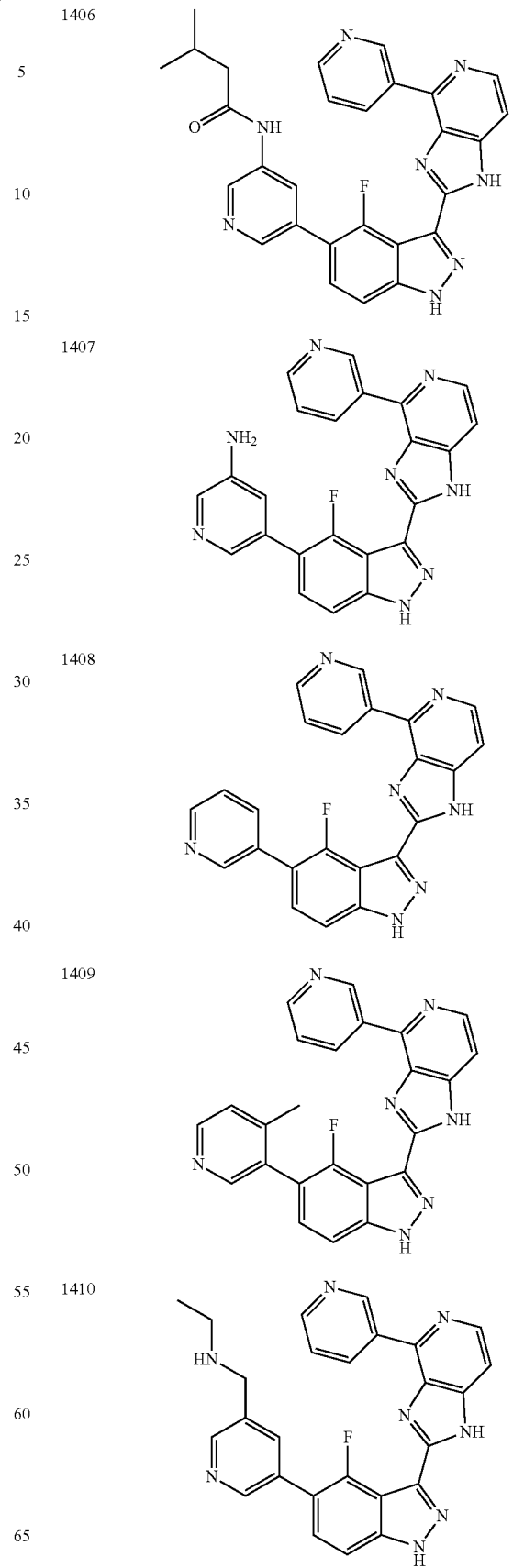

| | | | |
|---|---|---|---|
| 1411 | 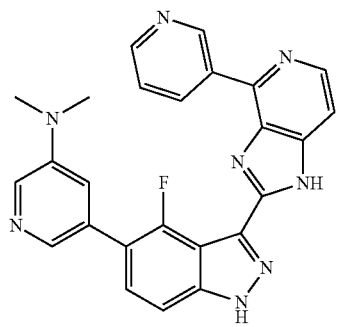 [SMILES: CN(C)c1cncc(-c2ccc3[nH]nc(-c4nc5c(-c6cccnc6)nccc5[nH]4)c3c2F)c1] | 1415 | 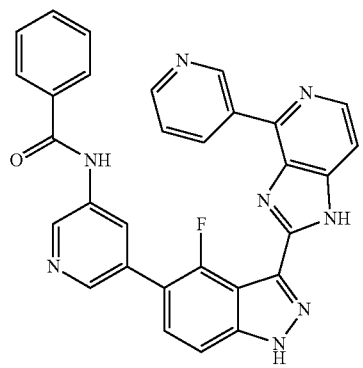 |
| 1412 | 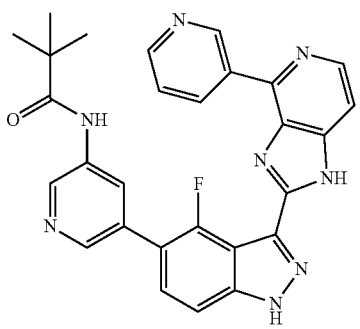 [SMILES: CC(C)(C)C(=O)Nc1cncc(-c2ccc3[nH]nc(-c4nc5c(-c6cccnc6)nccc5[nH]4)c3c2F)c1] | 1416 | 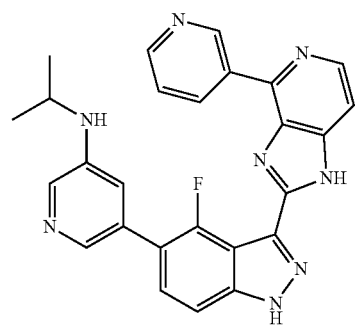 |
| 1413 | 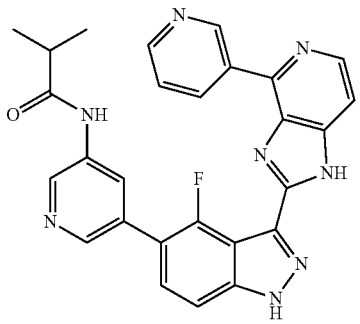 [SMILES: CC(C)C(=O)Nc1cncc(-c2ccc3[nH]nc(-c4nc5c(-c6cccnc6)nccc5[nH]4)c3c2F)c1] | 1417 | 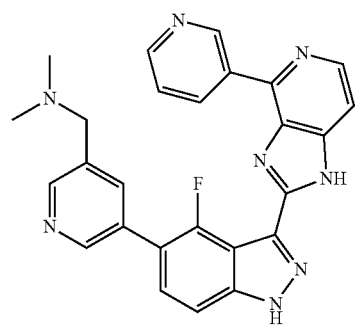 |
| 1414 | 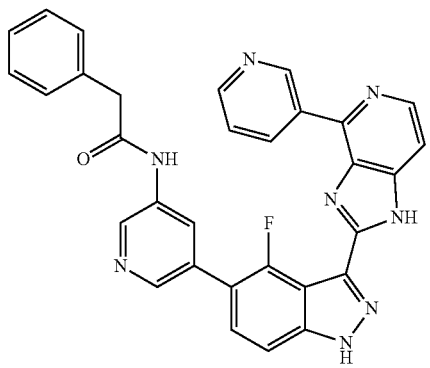 [SMILES: O=C(Cc1ccccc1)Nc1cncc(-c2ccc3[nH]nc(-c4nc5c(-c6cccnc6)nccc5[nH]4)c3c2F)c1] | 1418 | 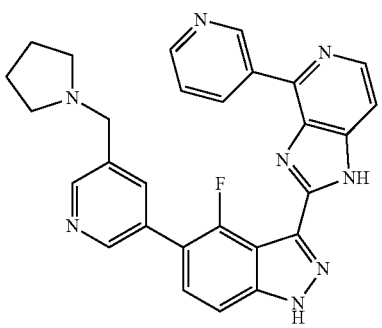 [SMILES: Fc1c(-c2cncc(CN3CCCC3)c2)ccc2[nH]nc(-c3nc4c(-c5cccnc5)nccc4[nH]3)c12] |

TABLE 1-continued
1419 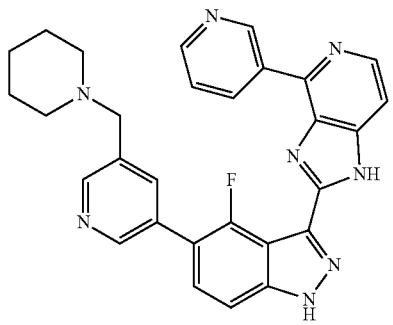 [SMILES: Fc1c(-c2cncc(CN3CCCCC3)c2)ccc2[nH]nc(-c3nc4c(-c5cccnc5)nccc4[nH]3)c12]
1420 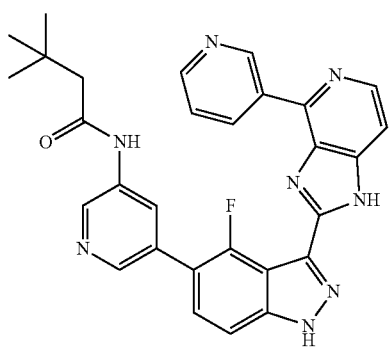 [SMILES: CC(C)(C)CC(=O)Nc1cncc(-c2ccc3[nH]nc(-c4nc5c(-c6cccnc6)nccc5[nH]4)c3c2F)c1]
1421 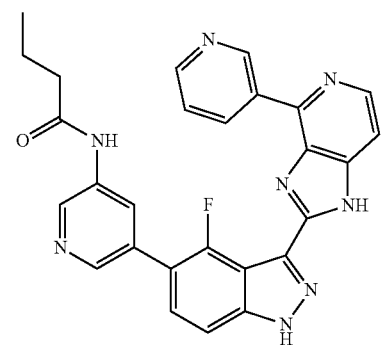 [SMILES: CCCC(=O)Nc1cncc(-c2ccc3[nH]nc(-c4nc5c(-c6cccnc6)nccc5[nH]4)c3c2F)c1]
1422 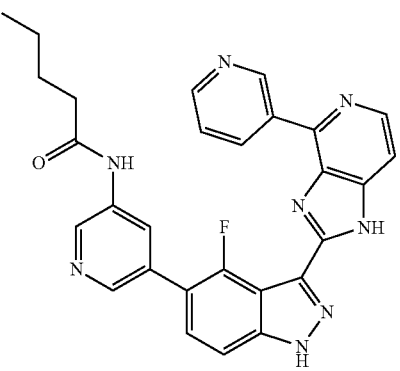 [SMILES: CCCCC(=O)Nc1cncc(-c2ccc3[nH]nc(-c4nc5c(-c6cccnc6)nccc5[nH]4)c3c2F)c1]
1423 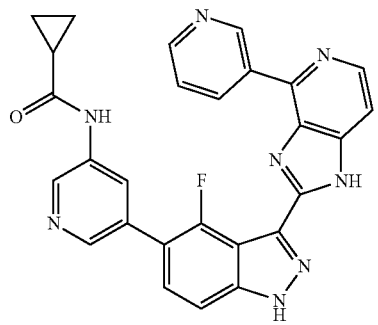 [SMILES: O=C(Nc1cncc(-c2ccc3[nH]nc(-c4nc5c(-c6cccnc6)nccc5[nH]4)c3c2F)c1)C1CC1]
1424 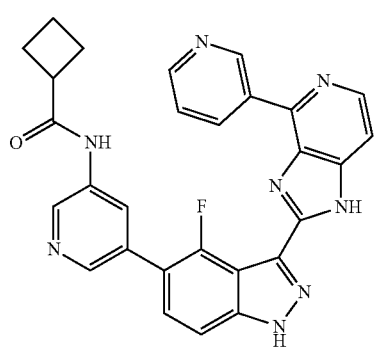 [SMILES: O=C(Nc1cncc(-c2ccc3[nH]nc(-c4nc5c(-c6cccnc6)nccc5[nH]4)c3c2F)c1)C1CCC1]
1425 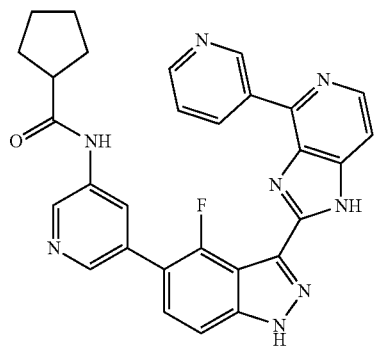 [SMILES: O=C(Nc1cncc(-c2ccc3[nH]nc(-c4nc5c(-c6cccnc6)nccc5[nH]4)c3c2F)c1)C1CCCC1]
1426 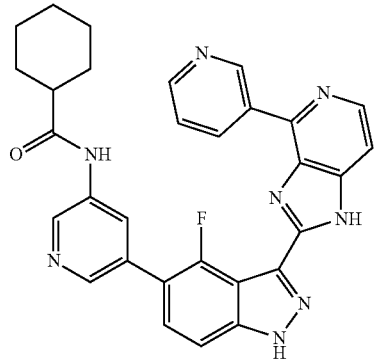 [SMILES: O=C(Nc1cncc(-c2ccc3[nH]nc(-c4nc5c(-c6cccnc6)nccc5[nH]4)c3c2F)c1)C1CCCCC1]

TABLE 1-continued
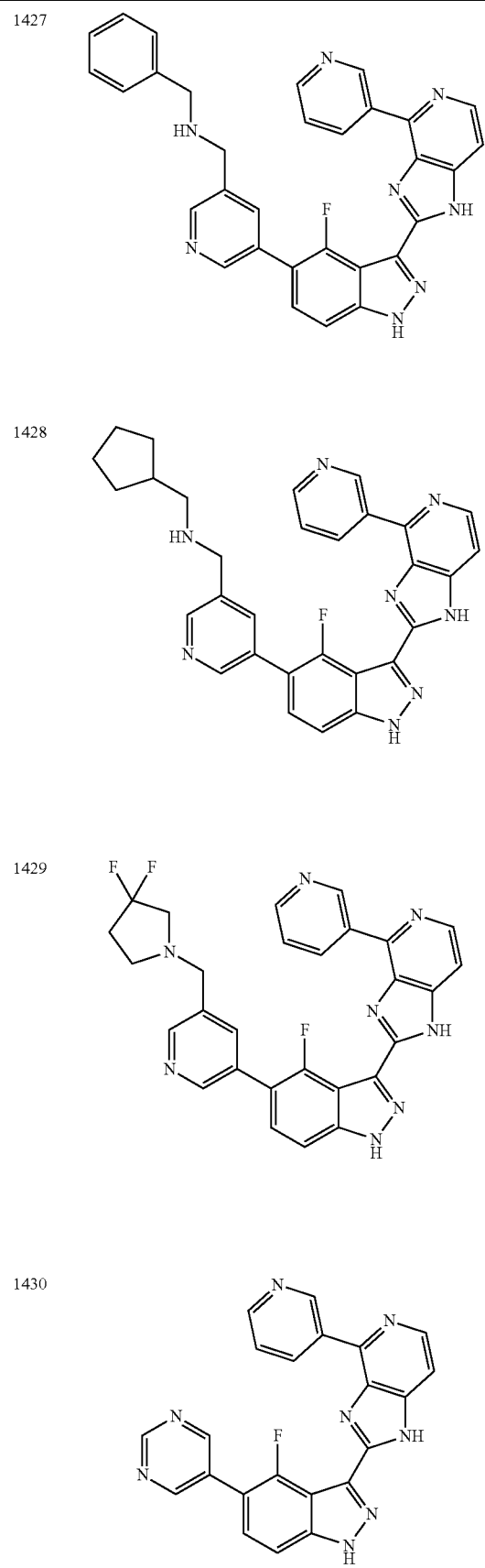
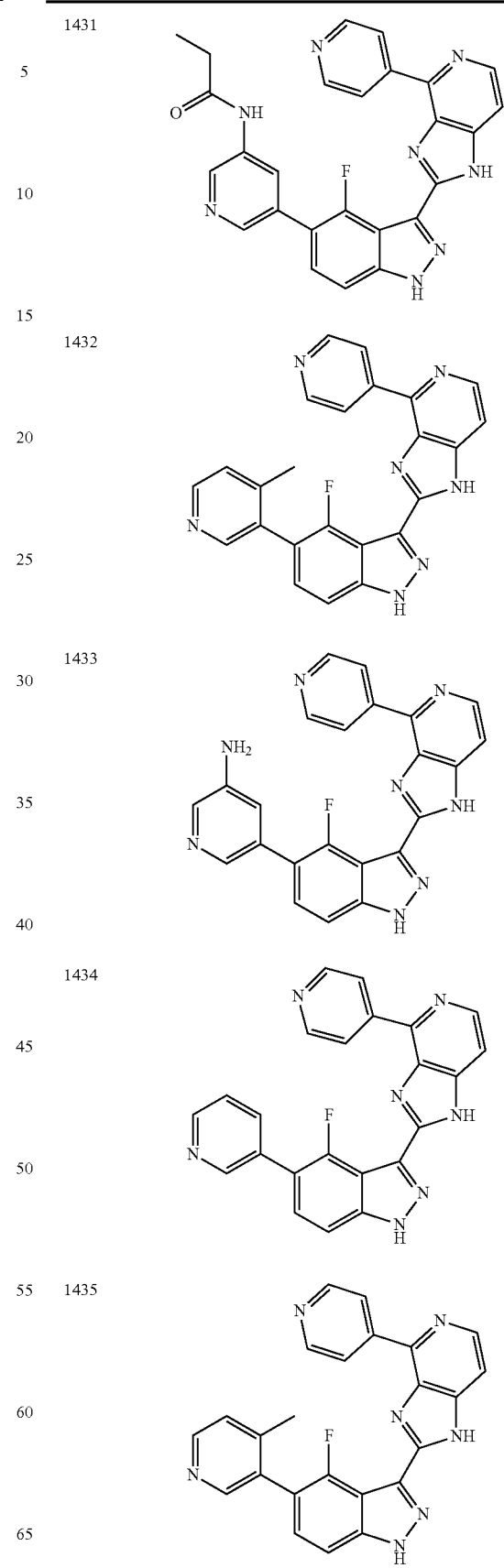

TABLE 1-continued
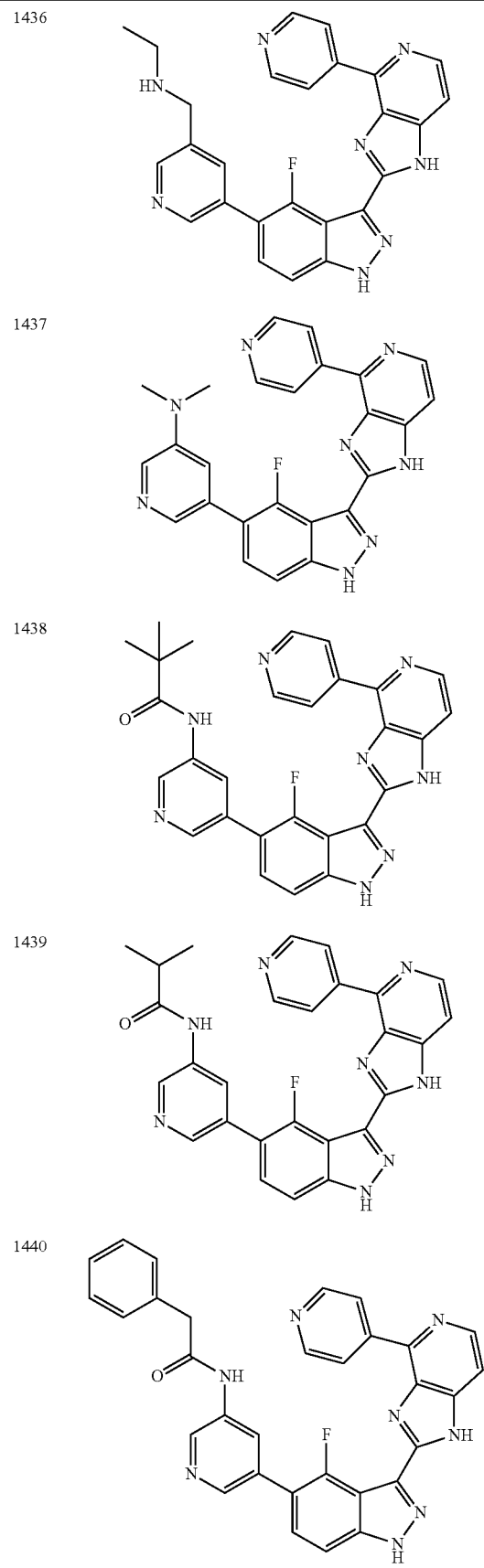
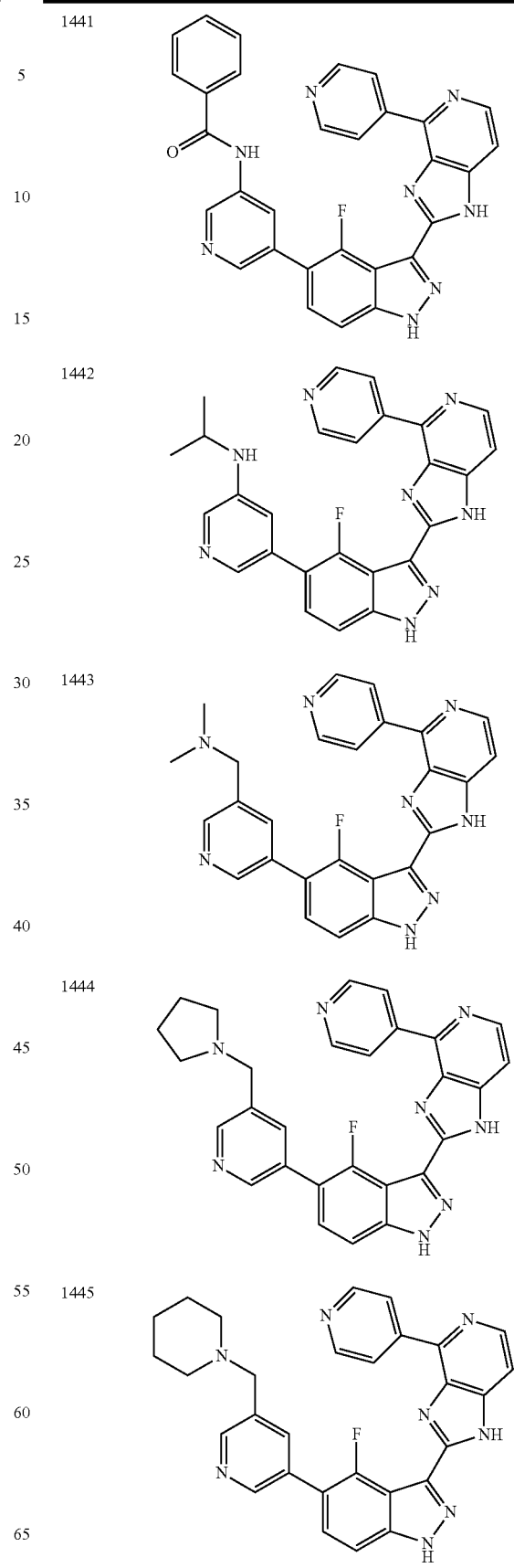

TABLE 1-continued
| | |
|---|---|
| 1446 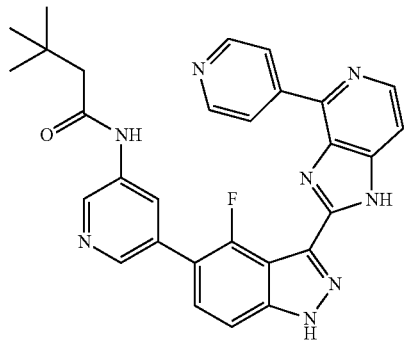 [SMILES: CC(C)(C)CC(=O)Nc1cncc(-c2ccc3[nH]nc(-c4nc5c(-c6ccncc6)nccc5[nH]4)c3c2F)c1] | 1450 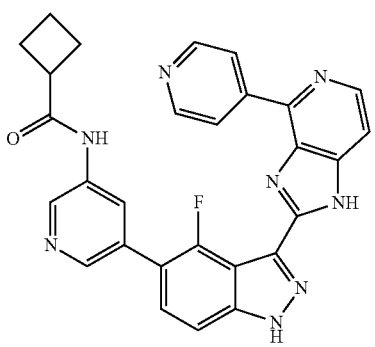 |
| 1447 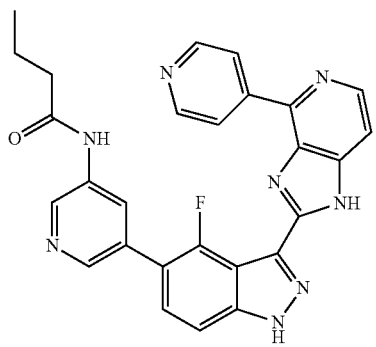 [SMILES: CCCC(=O)Nc1cncc(-c2ccc3[nH]nc(-c4nc5c(-c6ccncc6)nccc5[nH]4)c3c2F)c1] | 1451 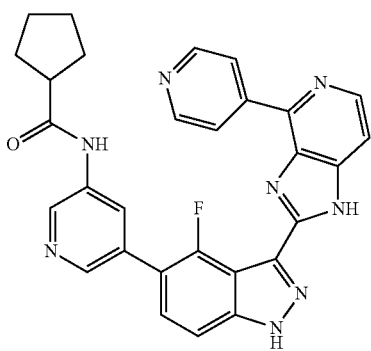 [SMILES: O=C(Nc1cncc(-c2ccc3[nH]nc(-c4nc5c(-c6ccncc6)nccc5[nH]4)c3c2F)c1)C1CCCC1] |
| 1448 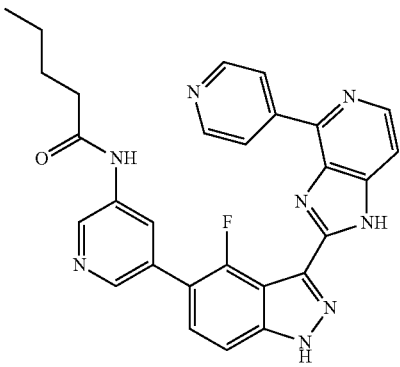 | 1452 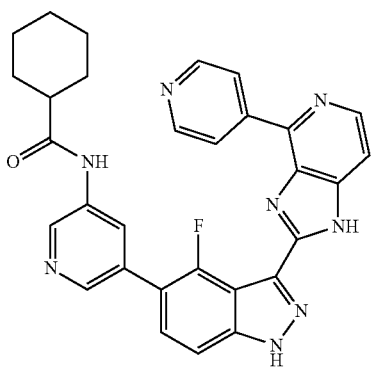 [SMILES: O=C(Nc1cncc(-c2ccc3[nH]nc(-c4nc5c(-c6ccncc6)nccc5[nH]4)c3c2F)c1)C1CCCCC1] |
| 1449 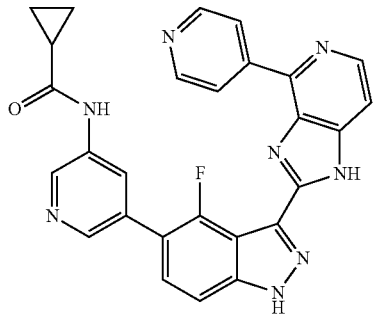 | 1453 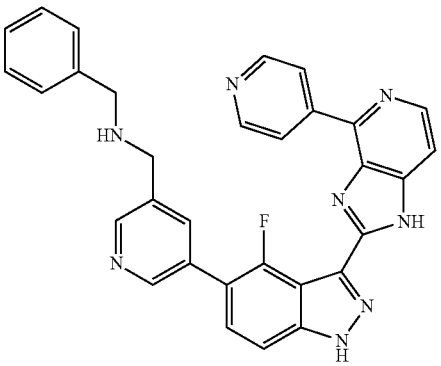 [SMILES: Fc1c(-c2cncc(CNCc3ccccc3)c2)ccc2[nH]nc(-c3nc4c(-c5ccncc5)nccc4[nH]3)c12] |

TABLE 1-continued
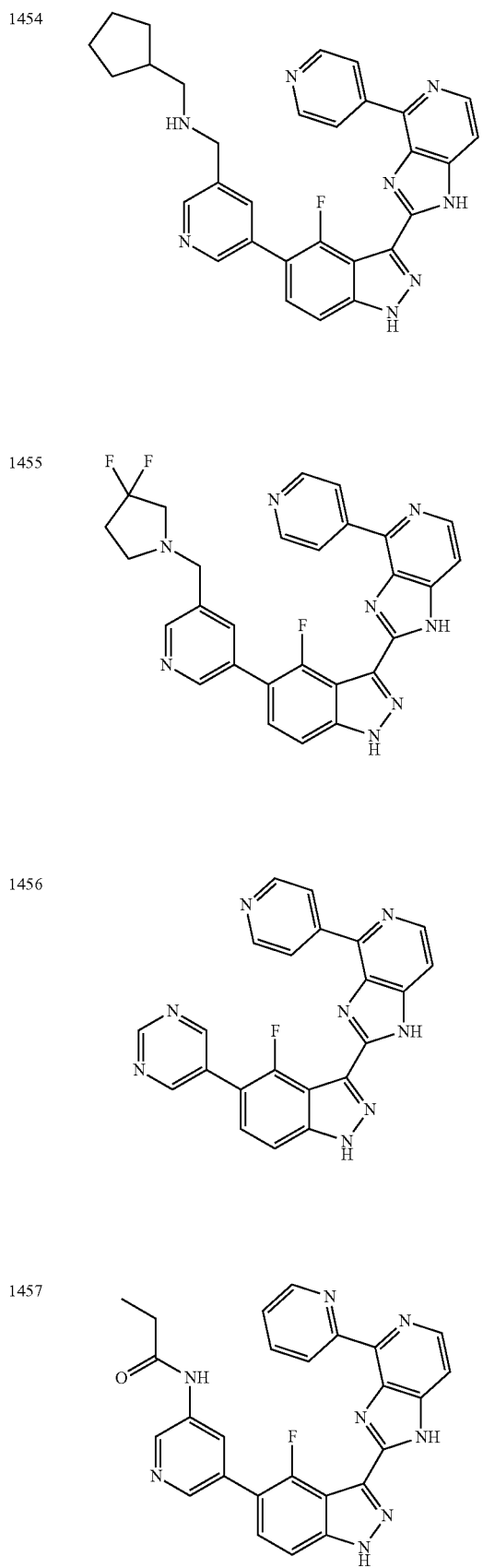
TABLE 1-continued
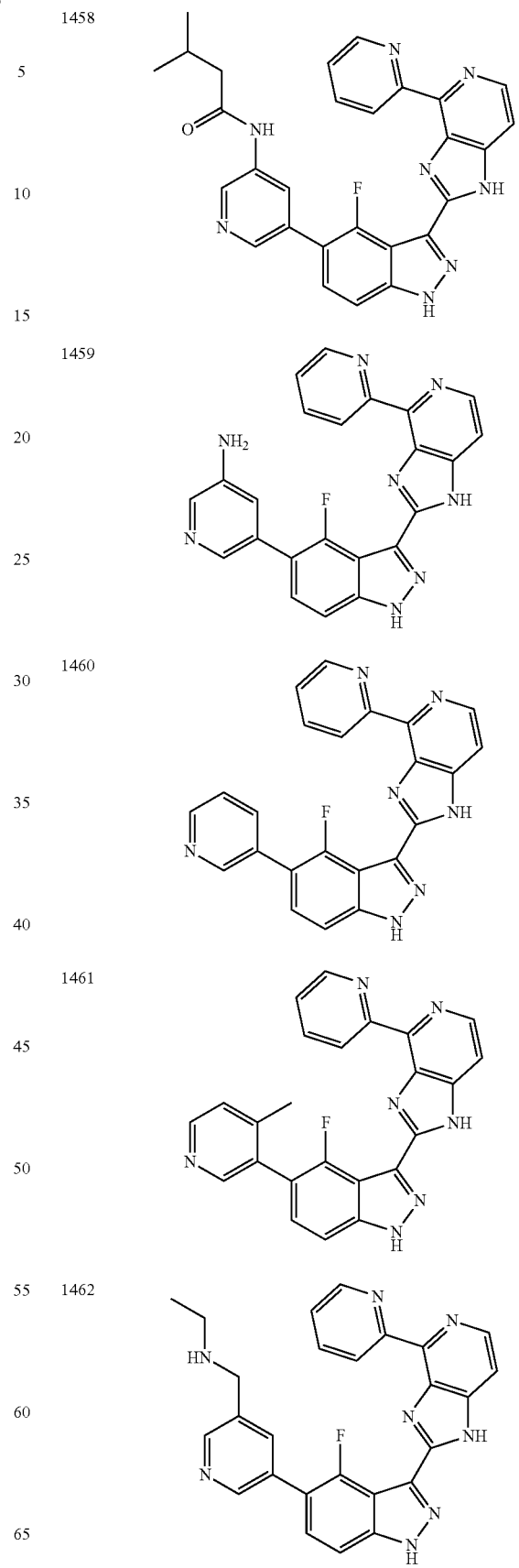

TABLE 1-continued
| | |
|---|---|
| 1463 | 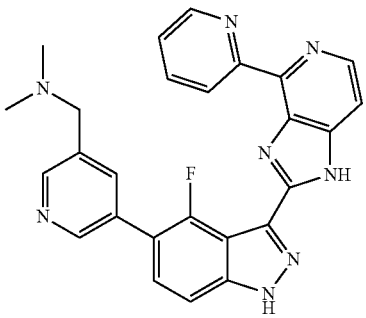 [SMILES: CN(C)Cc1cncc(-c2ccc3[nH]nc(-c4nc5c(-c6ccccn6)nccc5[nH]4)c3c2F)c1] |
| 1464 | 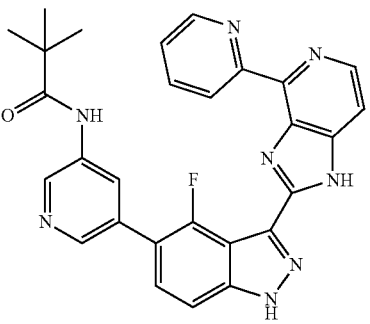 [SMILES: CC(C)(C)C(=O)Nc1cncc(-c2ccc3[nH]nc(-c4nc5c(-c6ccccn6)nccc5[nH]4)c3c2F)c1] |
| 1465 | 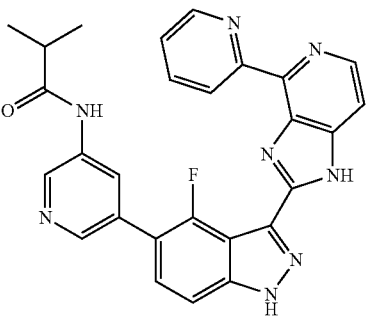 [SMILES: CC(C)C(=O)Nc1cncc(-c2ccc3[nH]nc(-c4nc5c(-c6ccccn6)nccc5[nH]4)c3c2F)c1] |
| 1466 | 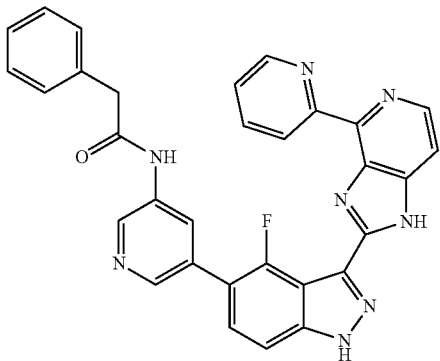 [SMILES: O=C(Cc1ccccc1)Nc1cncc(-c2ccc3[nH]nc(-c4nc5c(-c6ccccn6)nccc5[nH]4)c3c2F)c1] |
TABLE 1-continued
| | |
|---|---|
| 1467 | 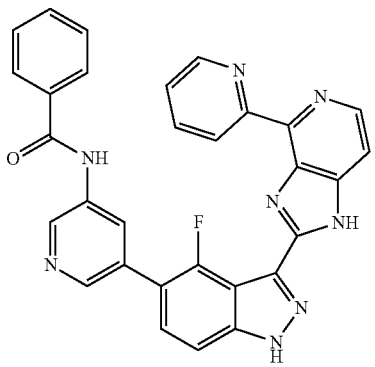 [SMILES: O=C(Nc1cncc(-c2ccc3[nH]nc(-c4nc5c(-c6ccccn6)nccc5[nH]4)c3c2F)c1)c1ccccc1] |
| 1468 | 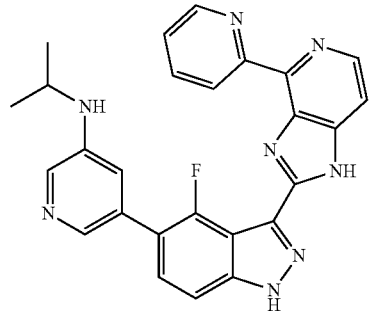 [SMILES: CC(C)Nc1cncc(-c2ccc3[nH]nc(-c4nc5c(-c6ccccn6)nccc5[nH]4)c3c2F)c1] |
| 1469 | 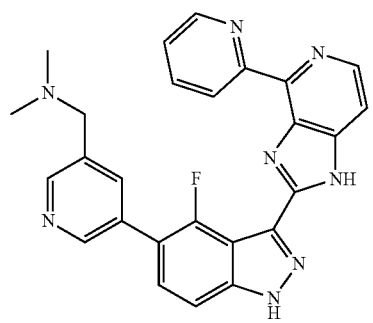 [SMILES: CN(C)Cc1cncc(-c2ccc3[nH]nc(-c4nc5c(-c6ccccn6)nccc5[nH]4)c3c2F)c1] |
| 1470 | 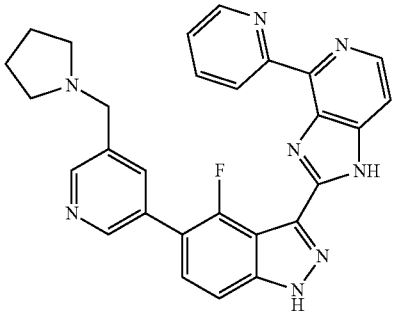 [SMILES: Fc1c(-c2cncc(CN3CCCC3)c2)ccc2[nH]nc(-c3nc4c(-c5ccccn5)nccc4[nH]3)c12] |
| 1471 | 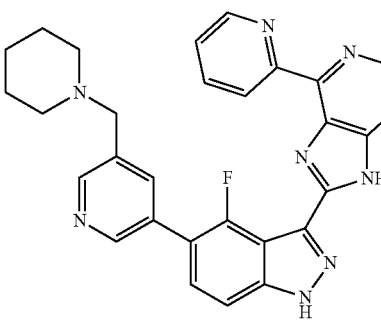 |

TABLE 1-continued
1472 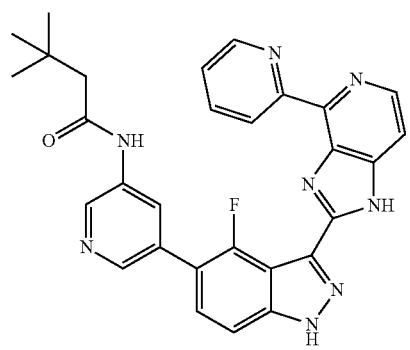
1473 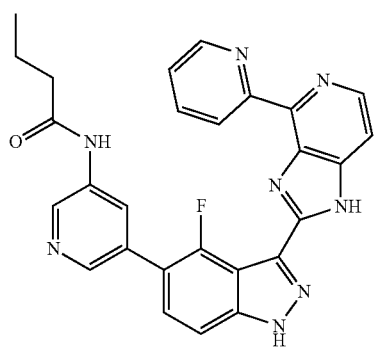 [SMILES: CCCC(=O)Nc1cncc(-c2ccc3[nH]nc(-c4nc5c(-c6ccccn6)nccc5[nH]4)c3c2F)c1]
1474 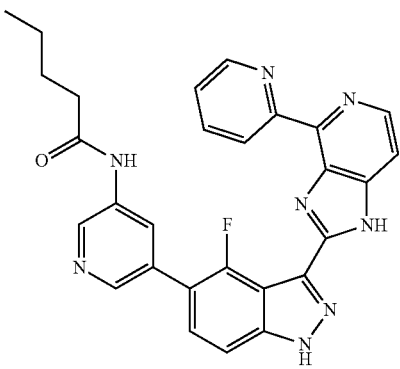
1475 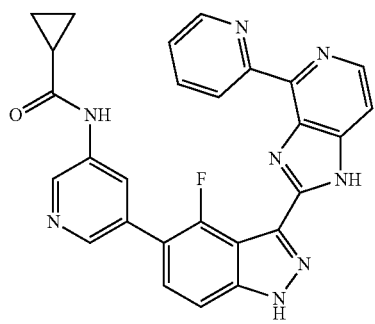 [SMILES: O=C(Nc1cncc(-c2ccc3[nH]nc(-c4nc5c(-c6ccccn6)nccc5[nH]4)c3c2F)c1)C1CC1]
TABLE 1-continued
1476 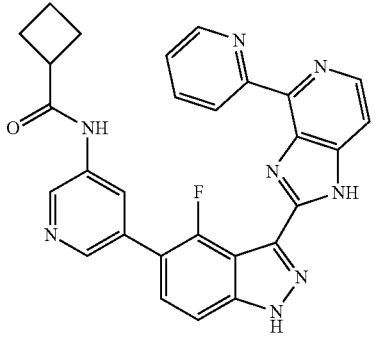 [SMILES: O=C(Nc1cncc(-c2ccc3[nH]nc(-c4nc5c(-c6ccccn6)nccc5[nH]4)c3c2F)c1)C1CCC1]
1477 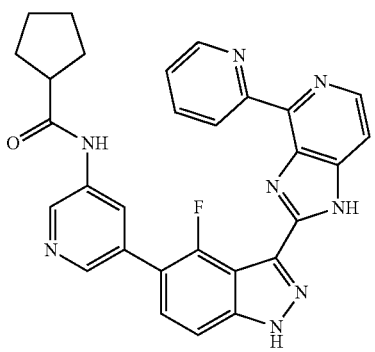 [SMILES: O=C(Nc1cncc(-c2ccc3[nH]nc(-c4nc5c(-c6ccccn6)nccc5[nH]4)c3c2F)c1)C1CCCC1]
1478 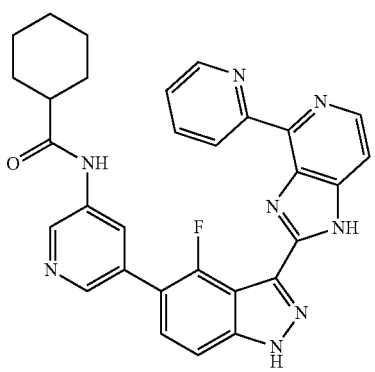 [SMILES: O=C(Nc1cncc(-c2ccc3[nH]nc(-c4nc5c(-c6ccccn6)nccc5[nH]4)c3c2F)c1)C1CCCCC1]
1479 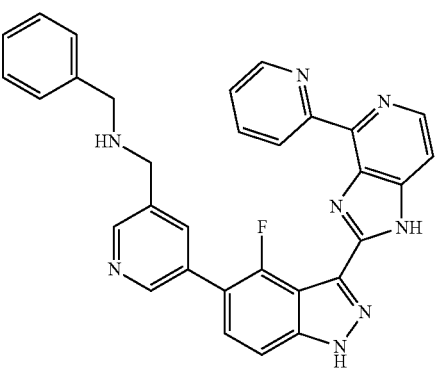 [SMILES: Fc1c(-c2cncc(CNCc3ccccc3)c2)ccc2[nH]nc(-c3nc4c(-c5ccccn5)nccc4[nH]3)c12]

TABLE 1-continued
1480 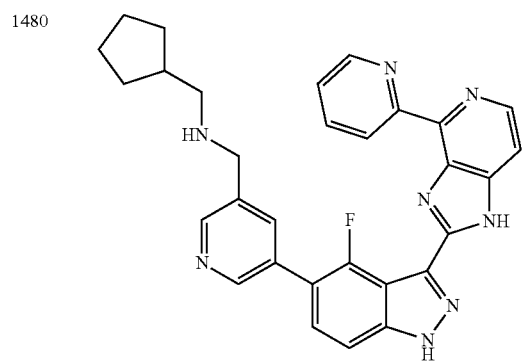
1481 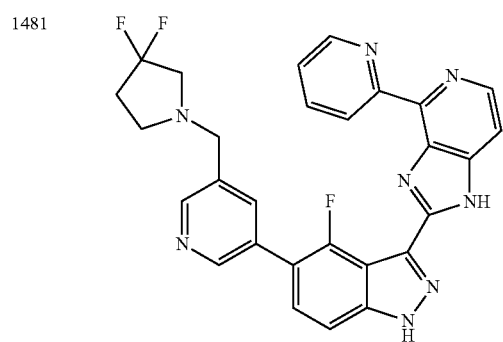
1482 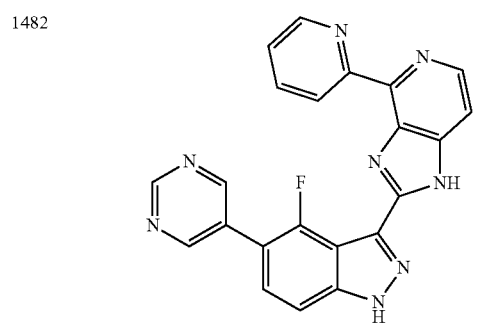
1483 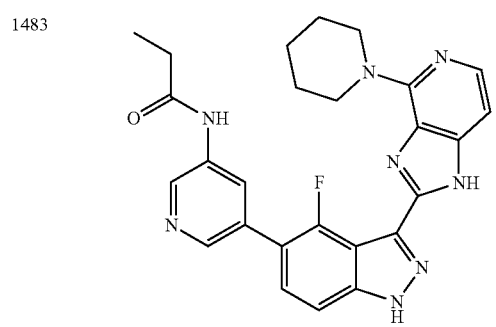
TABLE 1-continued
1484 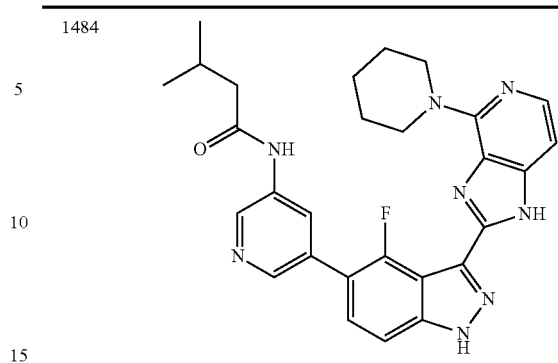
1485 
1486 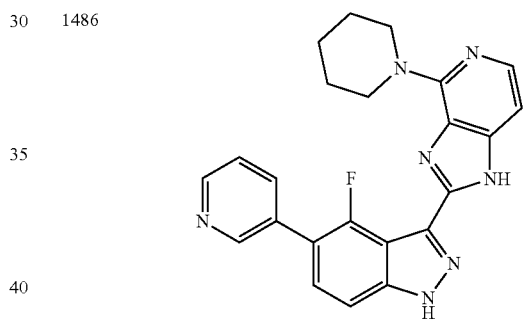
1487 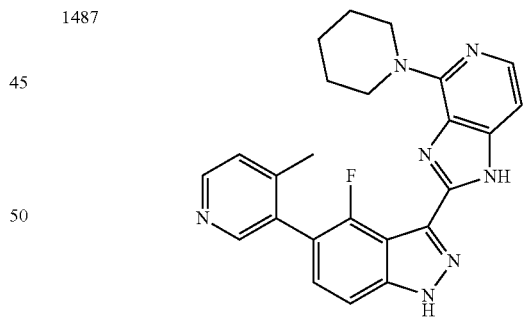
1488 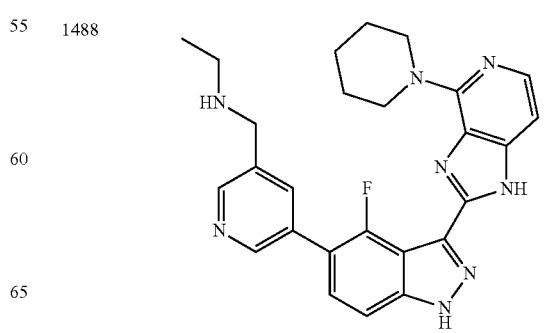

TABLE 1-continued
| 1489 | 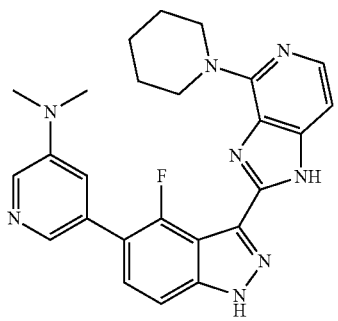 [SMILES: CN(C)c1cncc(-c2ccc3[nH]nc(-c4nc5c(N6CCCCC6)nccc5[nH]4)c3c2F)c1] |
| 1490 | 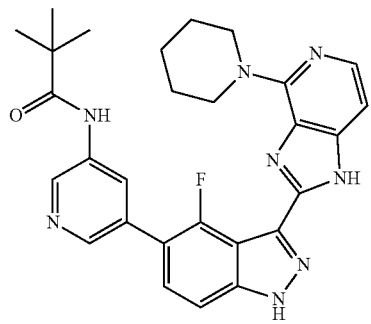 [SMILES: CC(C)(C)C(=O)Nc1cncc(-c2ccc3[nH]nc(-c4nc5c(N6CCCCC6)nccc5[nH]4)c3c2F)c1] |
| 1491 | 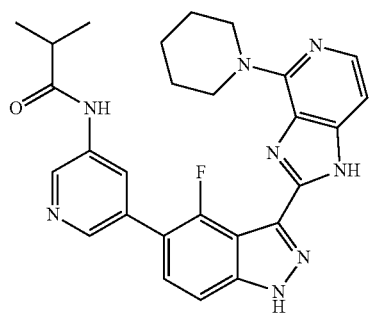 [SMILES: CC(C)C(=O)Nc1cncc(-c2ccc3[nH]nc(-c4nc5c(N6CCCCC6)nccc5[nH]4)c3c2F)c1] |
| 1492 | 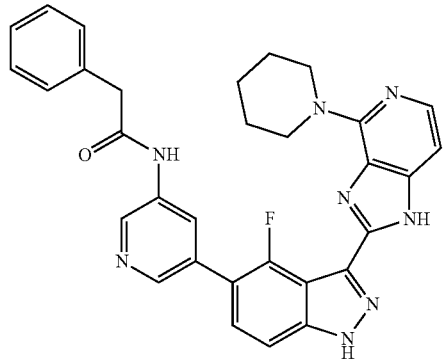 [SMILES: O=C(Cc1ccccc1)Nc1cncc(-c2ccc3[nH]nc(-c4nc5c(N6CCCCC6)nccc5[nH]4)c3c2F)c1] |
TABLE 1-continued
| 1493 | 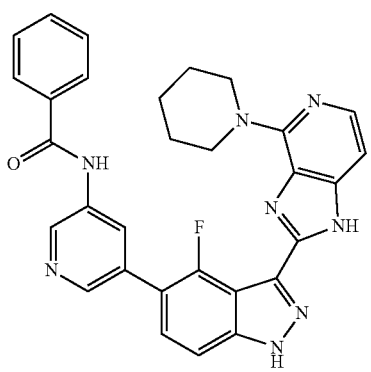 [SMILES: O=C(Nc1cncc(-c2ccc3[nH]nc(-c4nc5c(N6CCCCC6)nccc5[nH]4)c3c2F)c1)c1ccccc1] |
| 1494 | 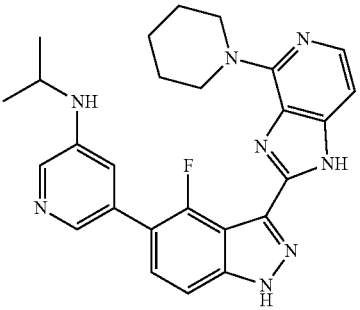 [SMILES: CC(C)Nc1cncc(-c2ccc3[nH]nc(-c4nc5c(N6CCCCC6)nccc5[nH]4)c3c2F)c1] |
| 1495 | 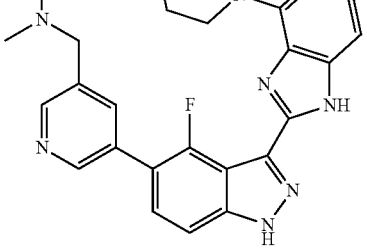 |
| 1496 | 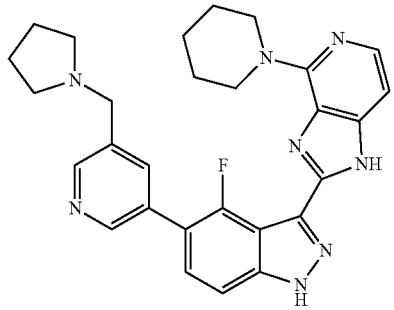 [SMILES: Fc1c(-c2cncc(CN3CCCC3)c2)ccc2[nH]nc(-c3nc4c(N5CCCCC5)nccc4[nH]3)c12] |
| 1497 | 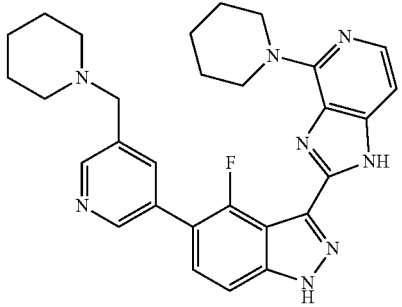 [SMILES: Fc1c(-c2cncc(CN3CCCCC3)c2)ccc2[nH]nc(-c3nc4c(N5CCCCC5)nccc4[nH]3)c12] |

TABLE 1-continued
1498 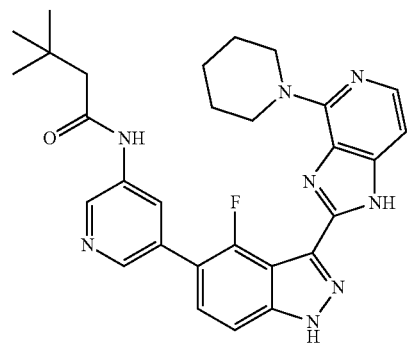 [SMILES: CC(C)(C)CC(=O)Nc1cncc(-c2ccc3[nH]nc(-c4nc5c(N6CCCCC6)nccc5[nH]4)c3c2F)c1]
1499 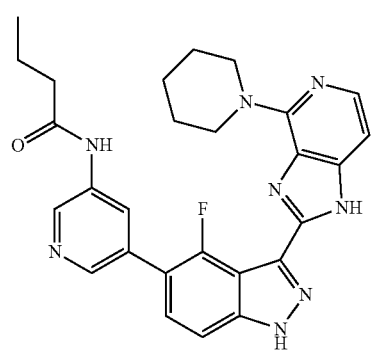 [SMILES: CCCC(=O)Nc1cncc(-c2ccc3[nH]nc(-c4nc5c(N6CCCCC6)nccc5[nH]4)c3c2F)c1]
1500 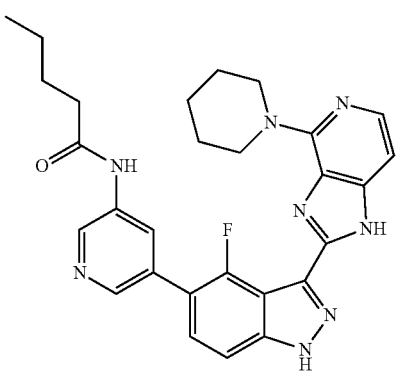 [SMILES: CCCCC(=O)Nc1cncc(-c2ccc3[nH]nc(-c4nc5c(N6CCCCC6)nccc5[nH]4)c3c2F)c1]
1501 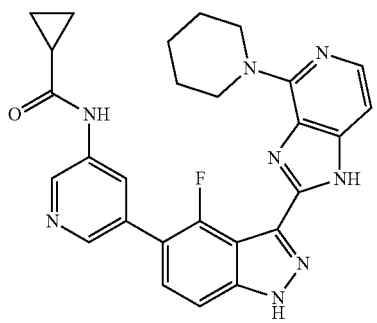 [SMILES: O=C(Nc1cncc(-c2ccc3[nH]nc(-c4nc5c(N6CCCCC6)nccc5[nH]4)c3c2F)c1)C1CC1]
TABLE 1-continued
1502 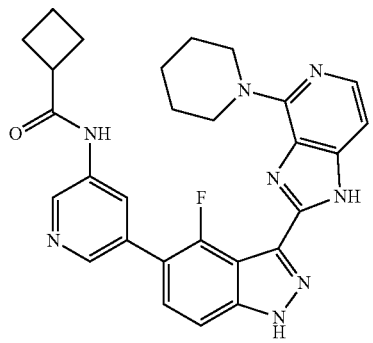 [SMILES: O=C(Nc1cncc(-c2ccc3[nH]nc(-c4nc5c(N6CCCCC6)nccc5[nH]4)c3c2F)c1)C1CCC1]
1503 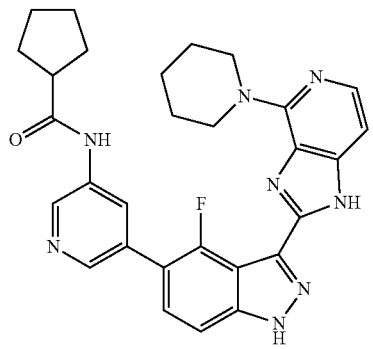 [SMILES: O=C(Nc1cncc(-c2ccc3[nH]nc(-c4nc5c(N6CCCCC6)nccc5[nH]4)c3c2F)c1)C1CCCC1]
1504 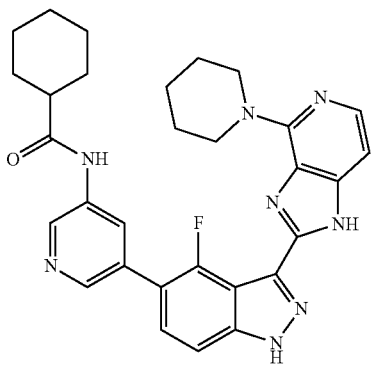 [SMILES: O=C(Nc1cncc(-c2ccc3[nH]nc(-c4nc5c(N6CCCCC6)nccc5[nH]4)c3c2F)c1)C1CCCCC1]
1505 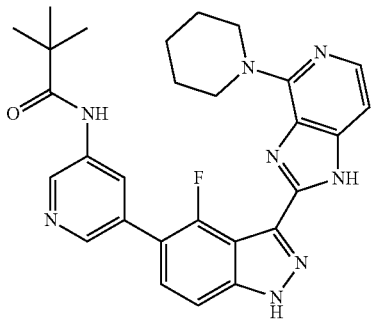 [SMILES: CC(C)(C)C(=O)Nc1cncc(-c2ccc3[nH]nc(-c4nc5c(N6CCCCC6)nccc5[nH]4)c3c2F)c1]

TABLE 1-continued
1506 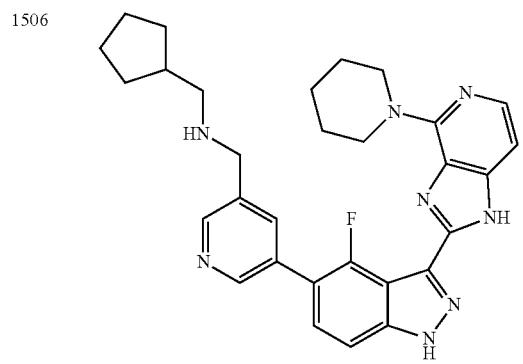
1507 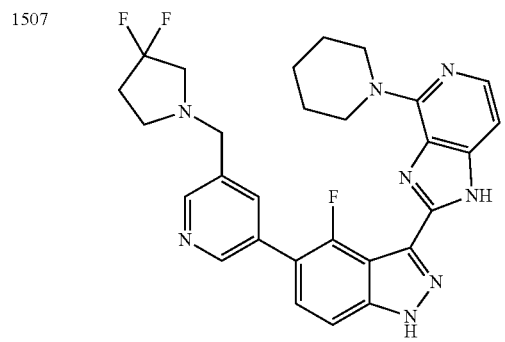
1508 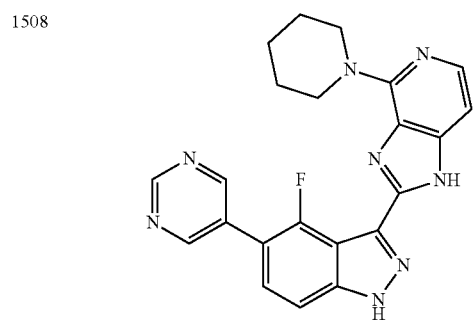
1509 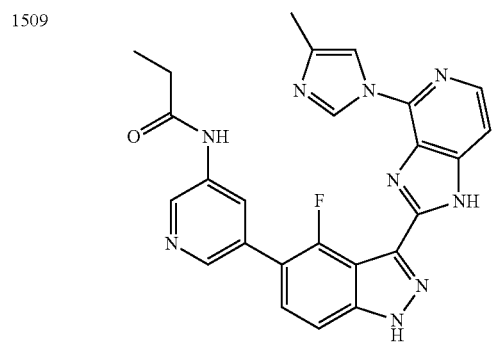
TABLE 1-continued
1510 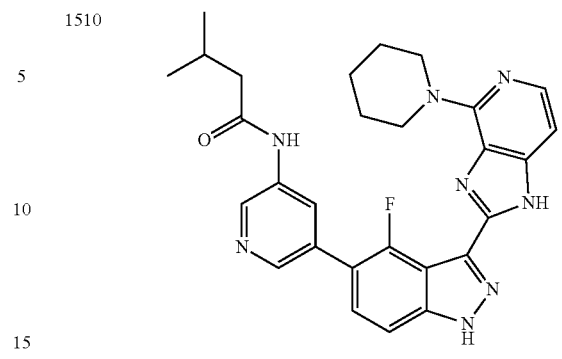
1511 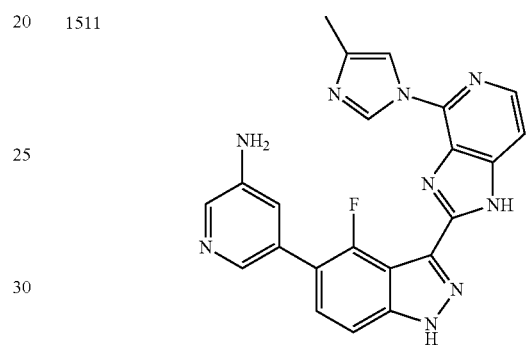
1512 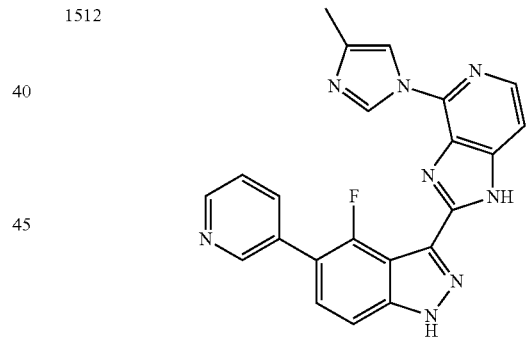
1513 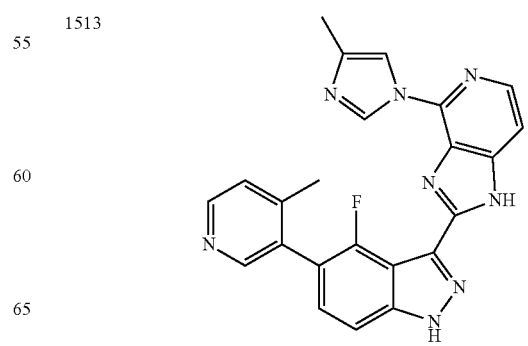

TABLE 1-continued
1514 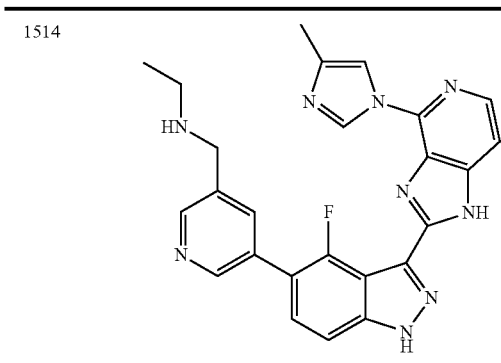
1515 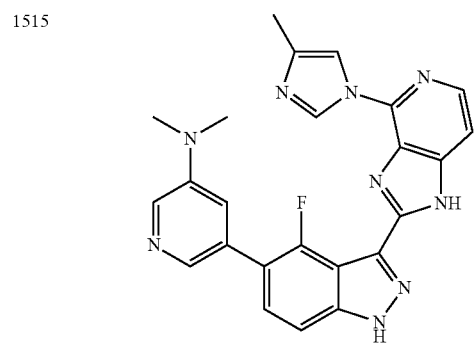
1516 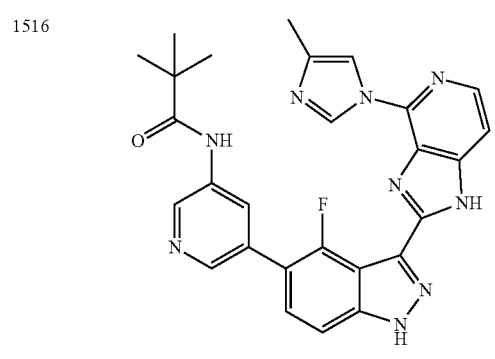
1517 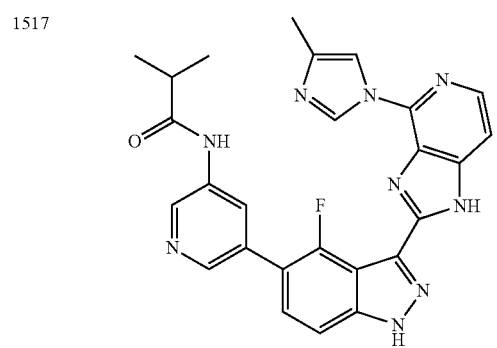
1518 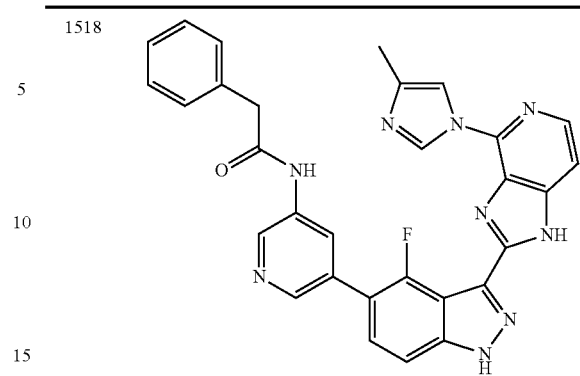
1519 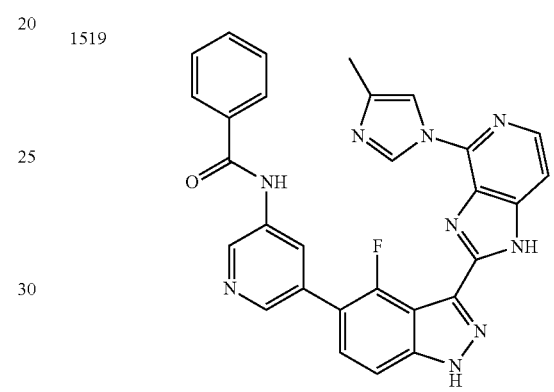
1520 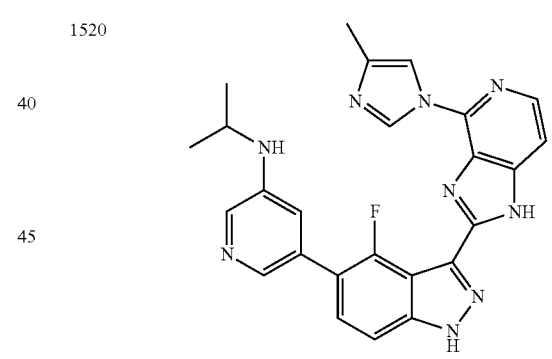
1521 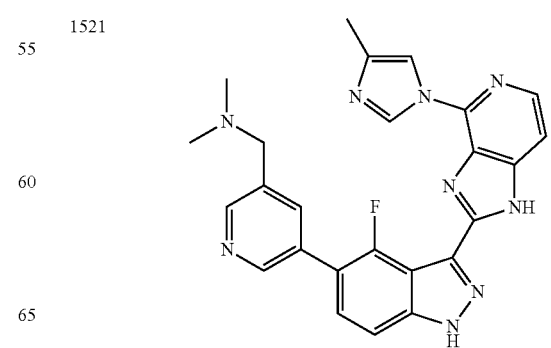

TABLE 1-continued
1522 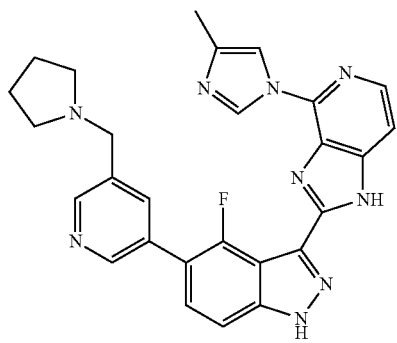 [SMILES: Cc1cn(-c2nccc3[nH]c(-c4n[nH]c5ccc(-c6cncc(CN7CCCC7)c6)c(F)c45)nc23)cn1]
1523 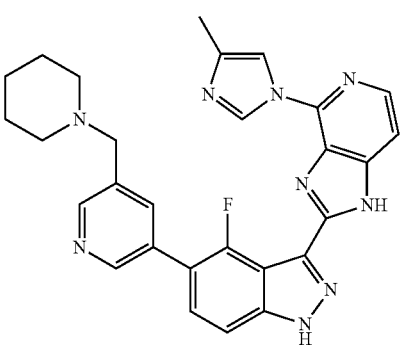 [SMILES: Cc1cn(-c2nccc3[nH]c(-c4n[nH]c5ccc(-c6cncc(CN7CCCCC7)c6)c(F)c45)nc23)cn1]
1524 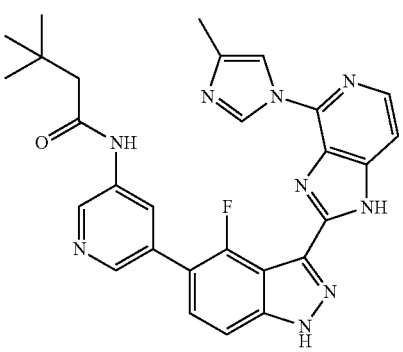 [SMILES: Cc1cn(-c2nccc3[nH]c(-c4n[nH]c5ccc(-c6cncc(NC(=O)CC(C)(C)C)c6)c(F)c45)nc23)cn1]
1525 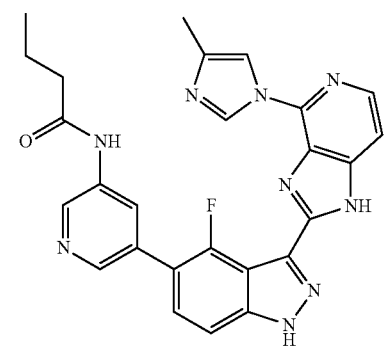 [SMILES: CCCC(=O)Nc1cncc(-c2ccc3[nH]nc(-c4nc5c(-n6cnc(C)c6)nccc5[nH]4)c3c2F)c1]
1526 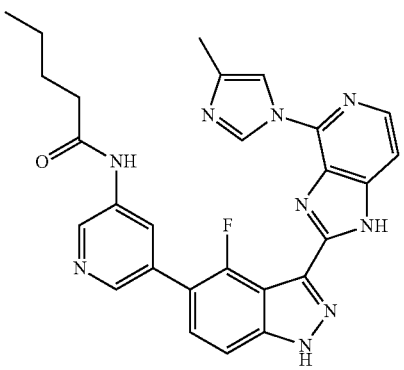 [SMILES: CCCCC(=O)Nc1cncc(-c2ccc3[nH]nc(-c4nc5c(-n6cnc(C)c6)nccc5[nH]4)c3c2F)c1]
1527 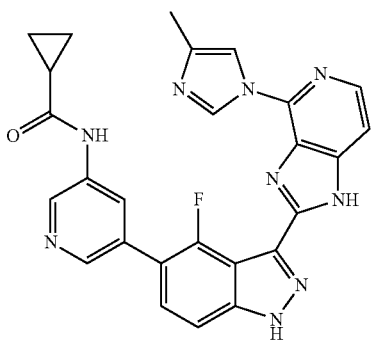 [SMILES: Cc1cn(-c2nccc3[nH]c(-c4n[nH]c5ccc(-c6cncc(NC(=O)C7CC7)c6)c(F)c45)nc23)cn1]
1528
1529 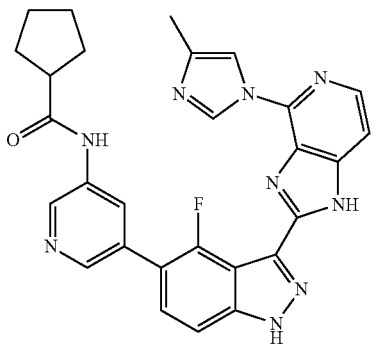 [SMILES: Cc1cn(-c2nccc3[nH]c(-c4n[nH]c5ccc(-c6cncc(NC(=O)C7CCCC7)c6)c(F)c45)nc23)cn1]

TABLE 1-continued
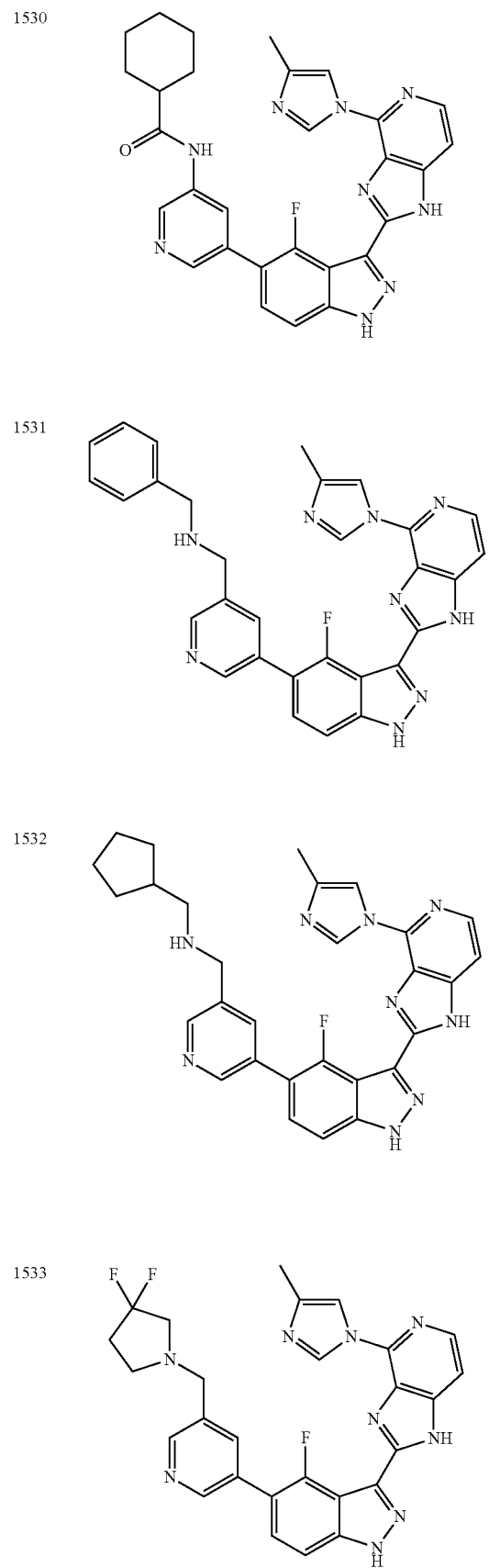
TABLE 1-continued
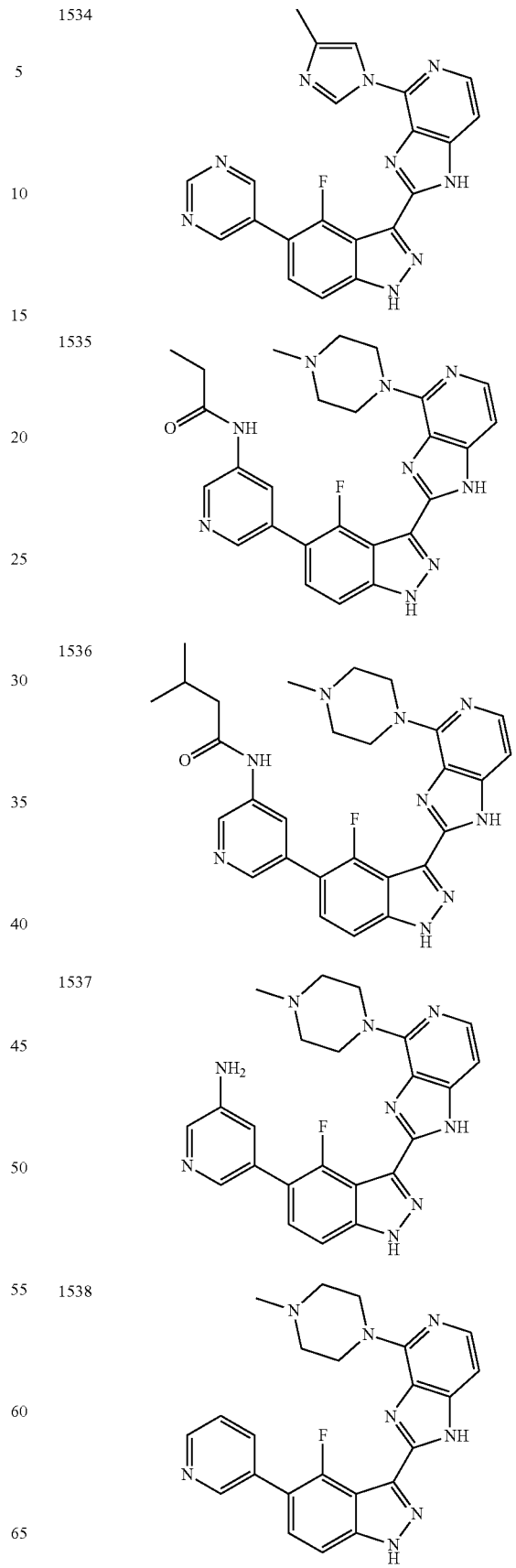

TABLE 1-continued
1539 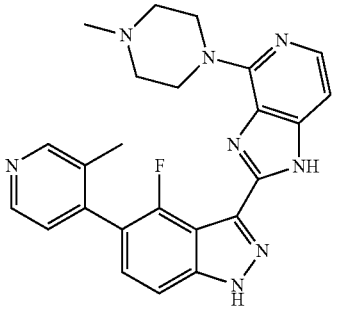 [SMILES: Cc1cnccc1-c1ccc2[nH]nc(-c3nc4c(N5CCN(C)CC5)nccc4[nH]3)c2c1F]
1540 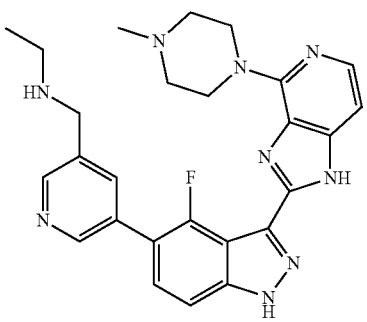 [SMILES: CCNCc1cncc(-c2ccc3[nH]nc(-c4nc5c(N6CCN(C)CC6)nccc5[nH]4)c3c2F)c1]
1541 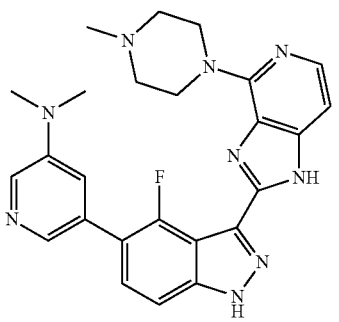 [SMILES: CN1CCN(c2nccc3[nH]c(-c4n[nH]c5ccc(-c6cncc(N(C)C)c6)c(F)c45)nc23)CC1]
1542 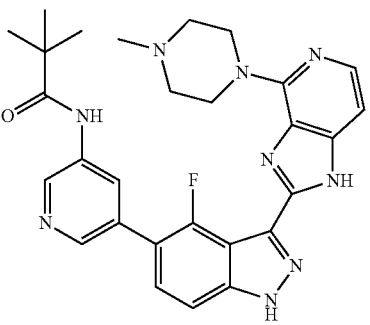 [SMILES: CN1CCN(c2nccc3[nH]c(-c4n[nH]c5ccc(-c6cncc(NC(=O)C(C)(C)C)c6)c(F)c45)nc23)CC1]
1543 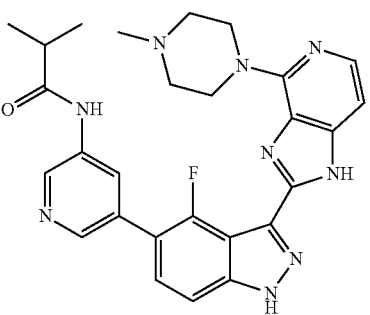 [SMILES: CC(C)C(=O)Nc1cncc(-c2ccc3[nH]nc(-c4nc5c(N6CCN(C)CC6)nccc5[nH]4)c3c2F)c1]
1544 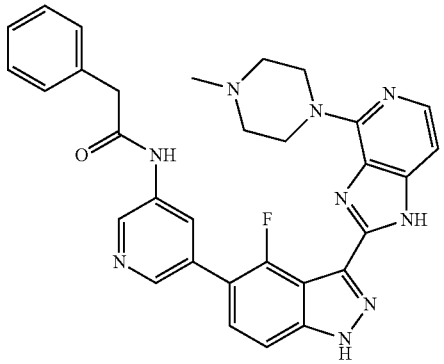 [SMILES: CN1CCN(c2nccc3[nH]c(-c4n[nH]c5ccc(-c6cncc(NC(=O)Cc7ccccc7)c6)c(F)c45)nc23)CC1]
1545 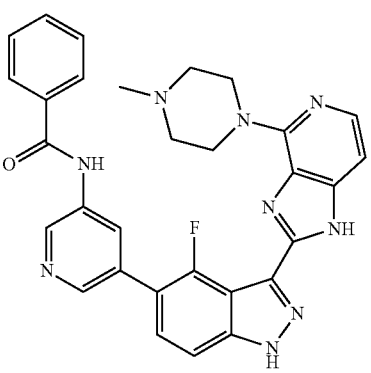 [SMILES: CN1CCN(c2nccc3[nH]c(-c4n[nH]c5ccc(-c6cncc(NC(=O)c7ccccc7)c6)c(F)c45)nc23)CC1]
1546 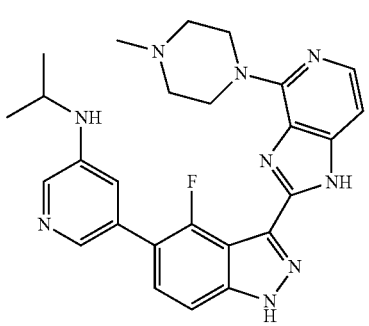 [SMILES: CC(C)Nc1cncc(-c2ccc3[nH]nc(-c4nc5c(N6CCN(C)CC6)nccc5[nH]4)c3c2F)c1]
1547 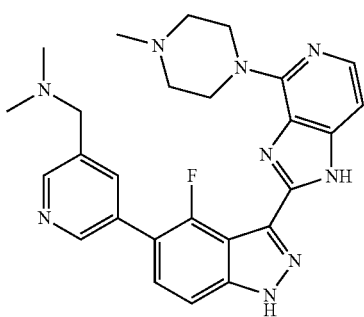

TABLE 1-continued
| 1548 | 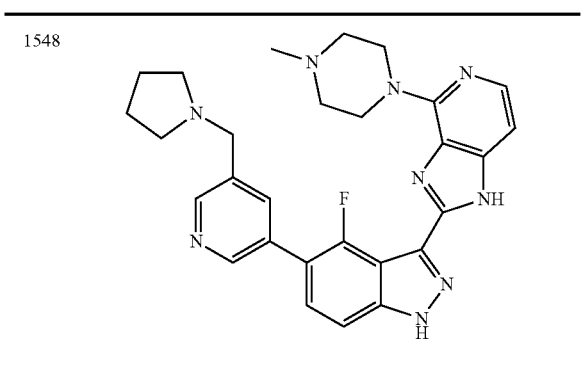 |
| --- | --- |
| 1549 | 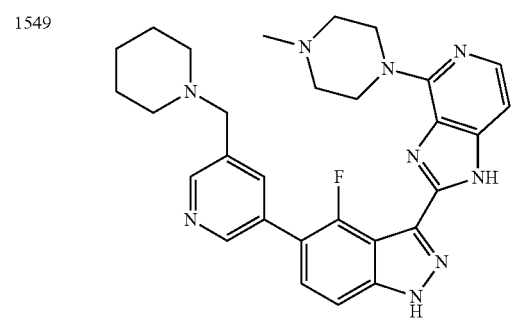 |
| 1550 | 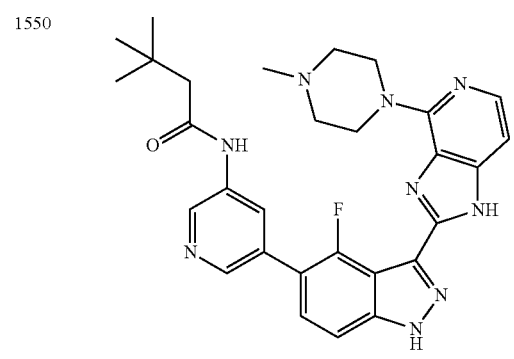 |
| 1551 | 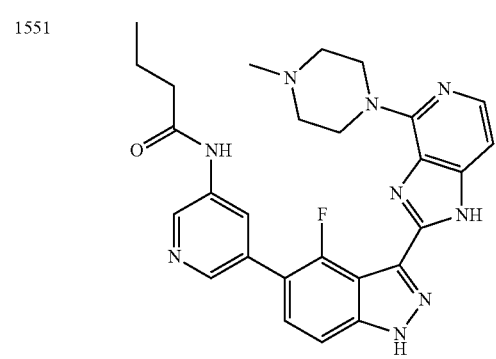 |
TABLE 1-continued
| 1552 | 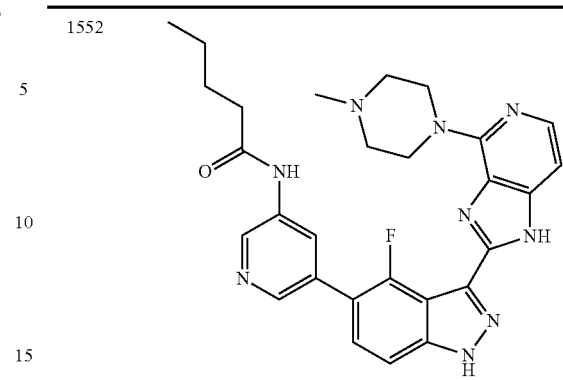 |
| --- | --- |
| 1553 | 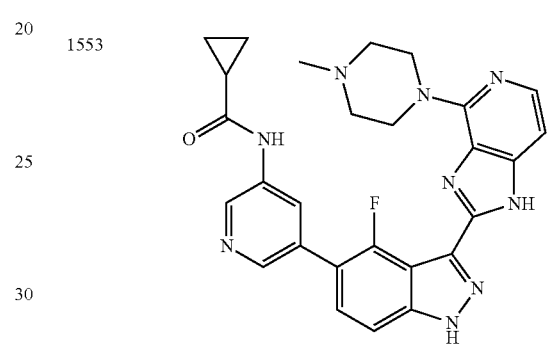 |
| 1554 | 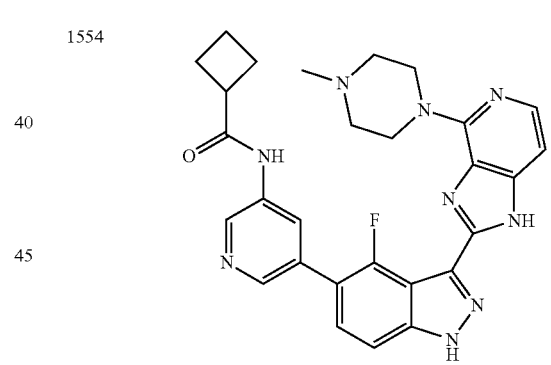 |
| 1555 | 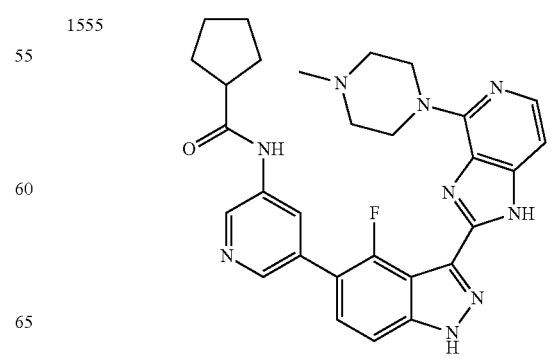 |

TABLE 1-continued
1556 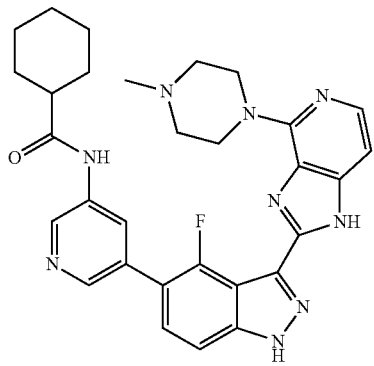 [SMILES: CN1CCN(c2nccc3[nH]c(-c4n[nH]c5ccc(-c6cncc(NC(=O)C7CCCCC7)c6)c(F)c45)nc23)CC1]
1557 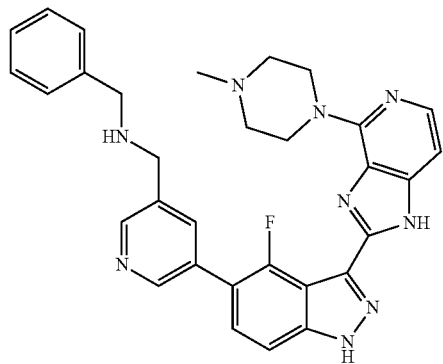 [SMILES: CN1CCN(c2nccc3[nH]c(-c4n[nH]c5ccc(-c6cncc(CNCc7ccccc7)c6)c(F)c45)nc23)CC1]
1558 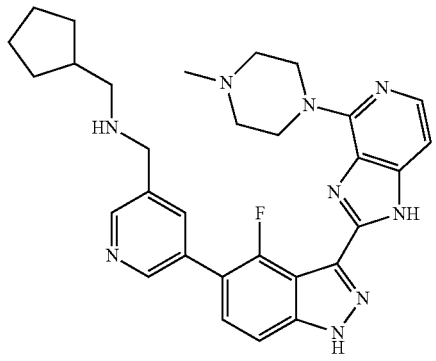 [SMILES: CN1CCN(c2nccc3[nH]c(-c4n[nH]c5ccc(-c6cncc(CNCC7CCCC7)c6)c(F)c45)nc23)CC1]
1559 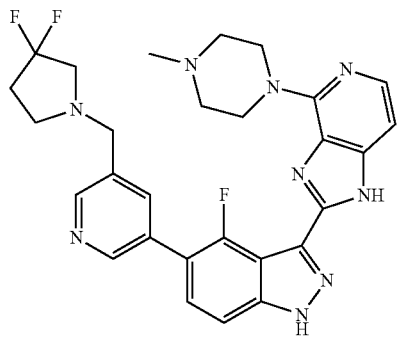 [SMILES: CN1CCN(c2nccc3[nH]c(-c4n[nH]c5ccc(-c6cncc(CN7CCC(F)(F)C7)c6)c(F)c45)nc23)CC1]
TABLE 1-continued
1560 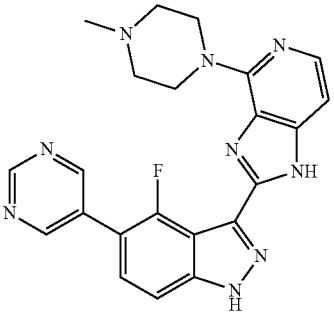
1561 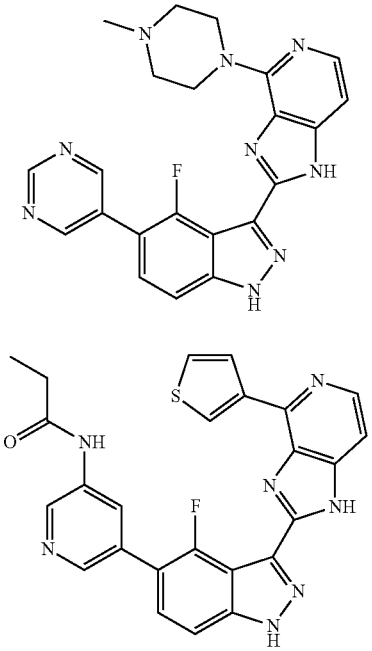
1562
1563 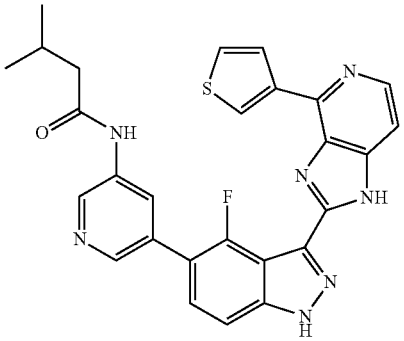 [SMILES: CC(C)CC(=O)Nc1cncc(-c2ccc3[nH]nc(-c4nc5c(-c6ccsc6)nccc5[nH]4)c3c2F)c1]
1564 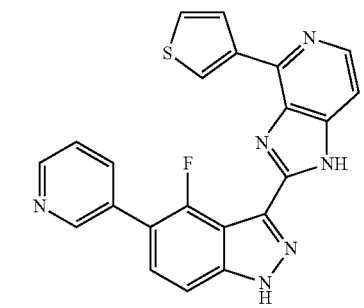 [SMILES: Fc1c(-c2cccnc2)ccc2[nH]nc(-c3nc4c(-c5ccsc5)nccc4[nH]3)c12]

TABLE 1-continued
| 1565 | 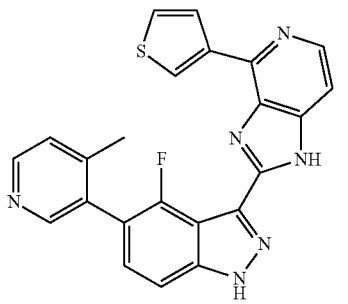 |
| --- | --- |
| 1566 | 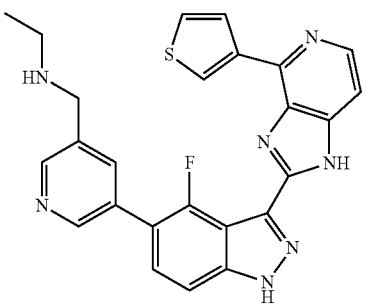 |
| 1567 | 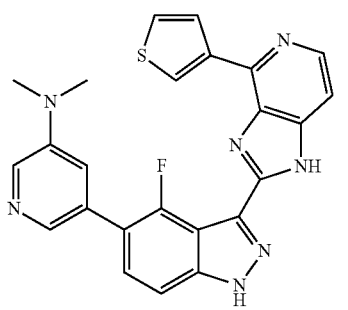 [SMILES: CN(C)c1cncc(-c2ccc3[nH]nc(-c4nc5c(-c6ccsc6)nccc5[nH]4)c3c2F)c1] |
| 1568 | 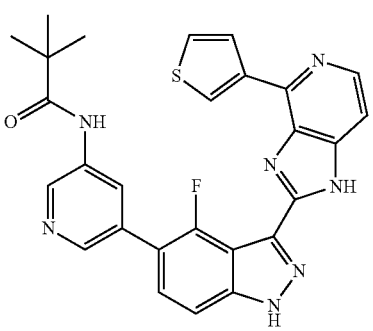 [SMILES: CC(C)(C)C(=O)Nc1cncc(-c2ccc3[nH]nc(-c4nc5c(-c6ccsc6)nccc5[nH]4)c3c2F)c1] |
| 1569 | 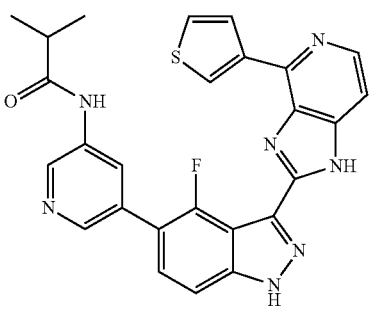 [SMILES: CC(C)C(=O)Nc1cncc(-c2ccc3[nH]nc(-c4nc5c(-c6ccsc6)nccc5[nH]4)c3c2F)c1] |
| 1570 | 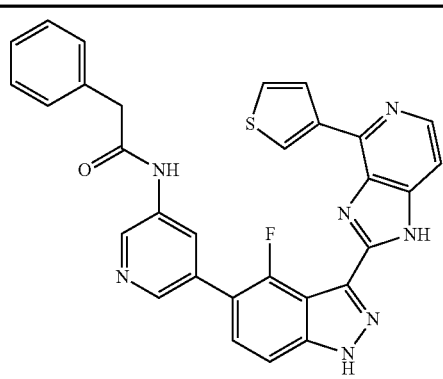 |
| 1571 | 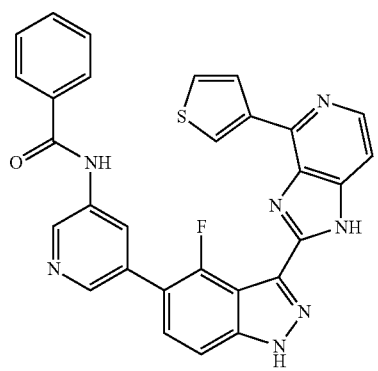 [SMILES: O=C(Nc1cncc(-c2ccc3[nH]nc(-c4nc5c(-c6ccsc6)nccc5[nH]4)c3c2F)c1)c1ccccc1] |
| 1572 | 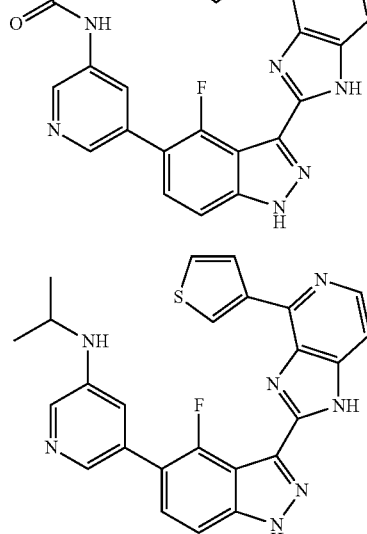 |
| 1573 | 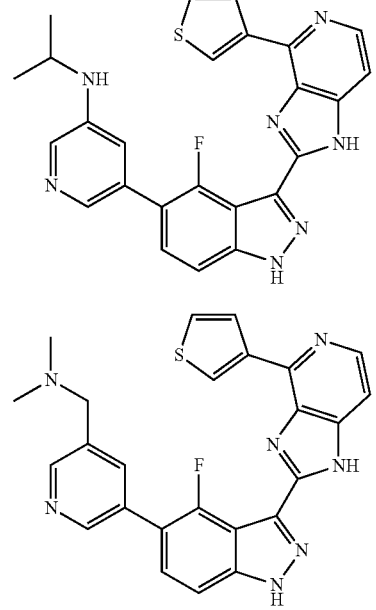 |
| 1574 | 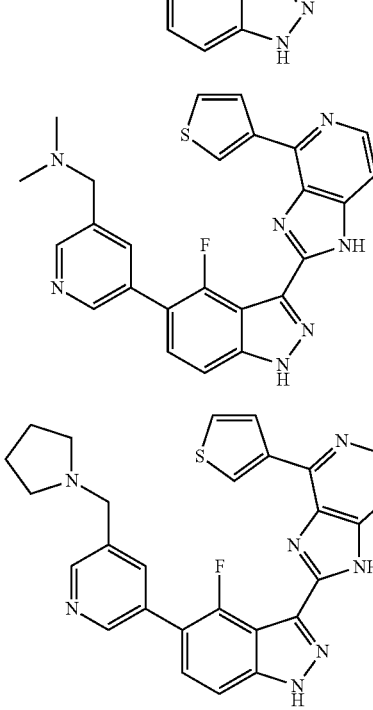 |

TABLE 1-continued
| 1575 | 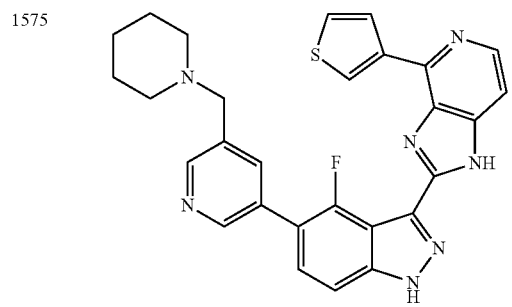 | 1579 | 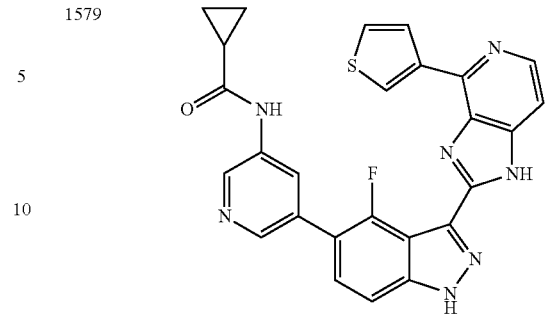 |
| 1576 | 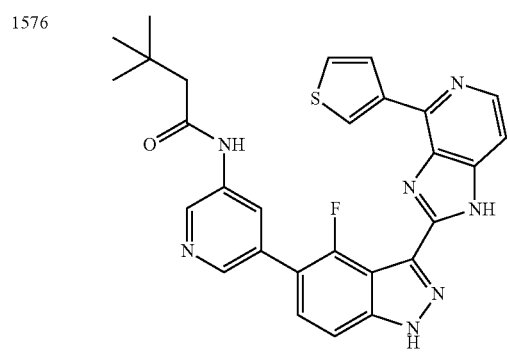 | 1580 | 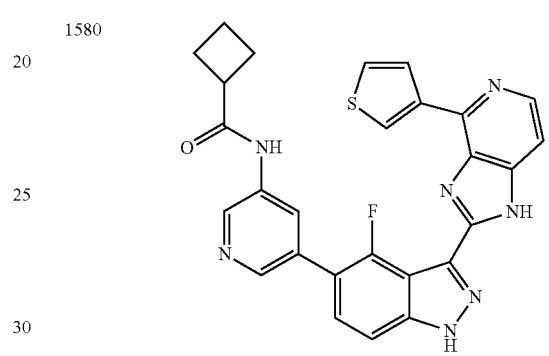 |
| 1577 | 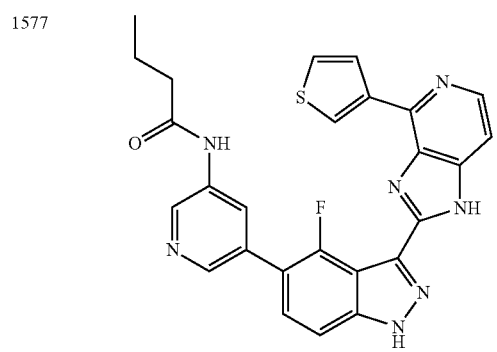 | 1581 | 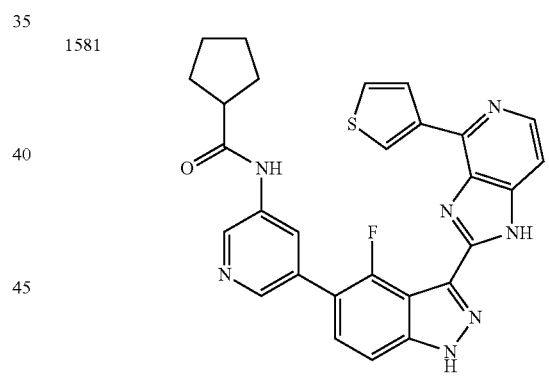 |
| 1578 | 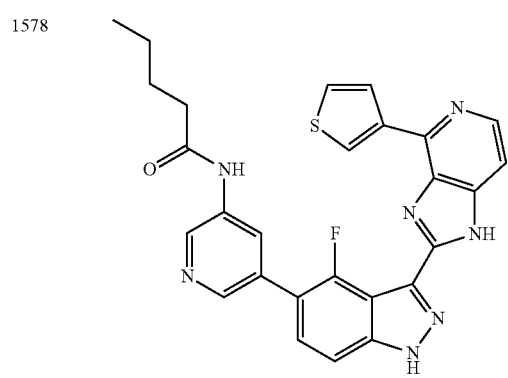 | 1582 | 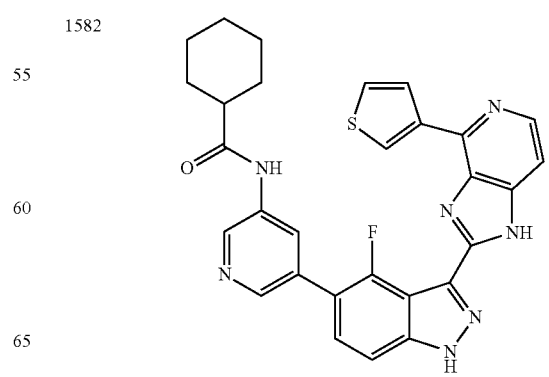 |

TABLE 1-continued
1583 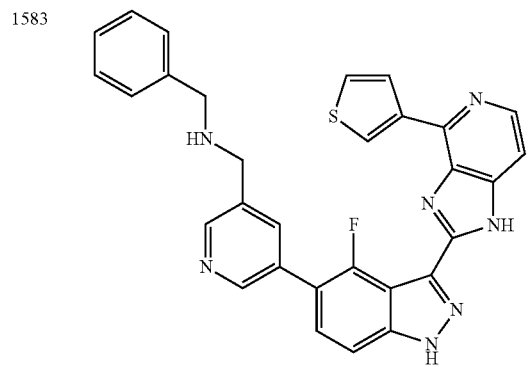
1584 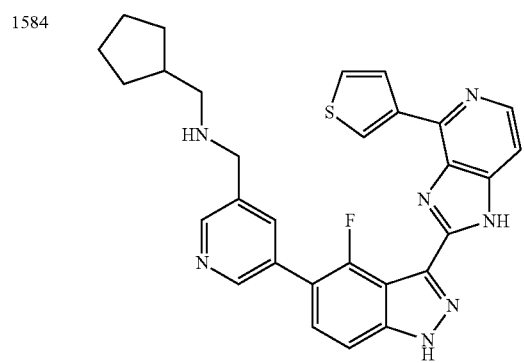
1585 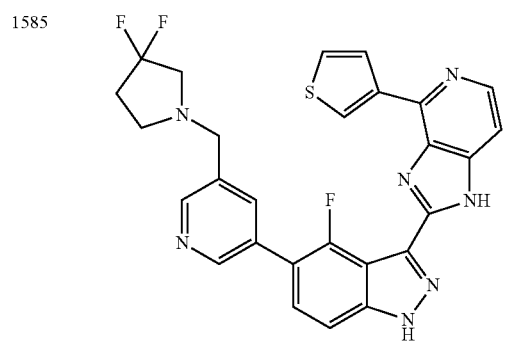
1586 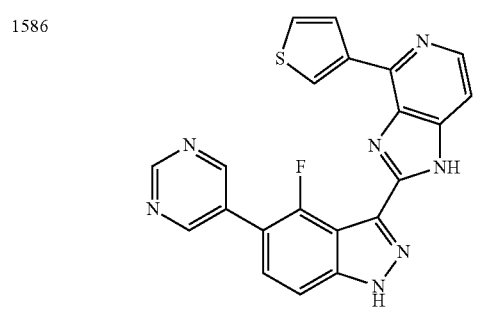
TABLE 1-continued
1587 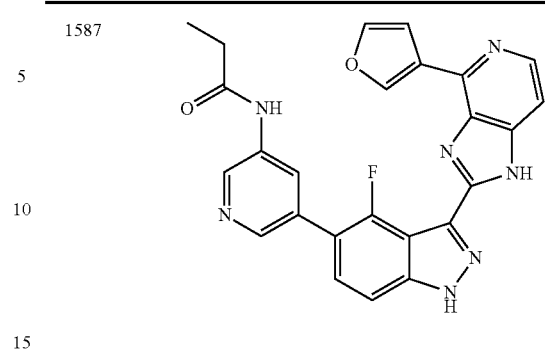
1588 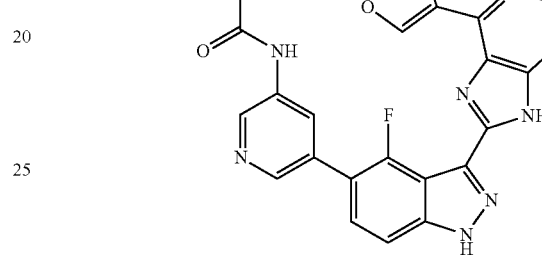
1589 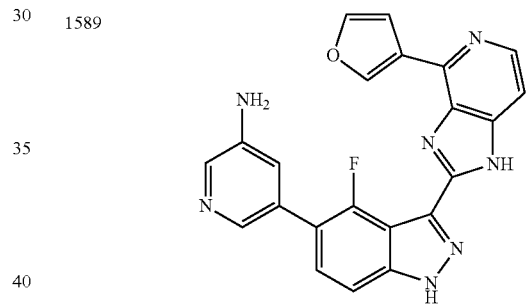
1590 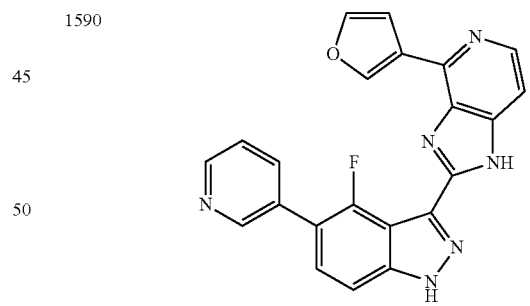
1591 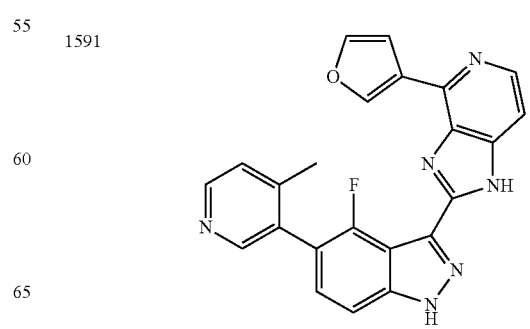

TABLE 1-continued
| | |
|---|---|
| 1592 | 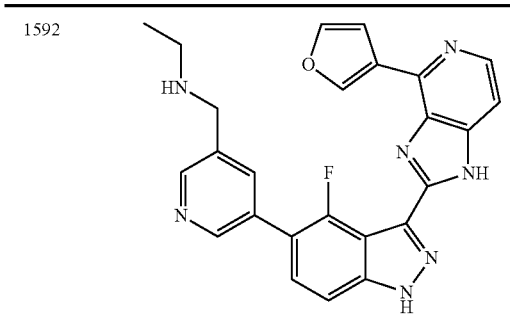 |
| 1593 | 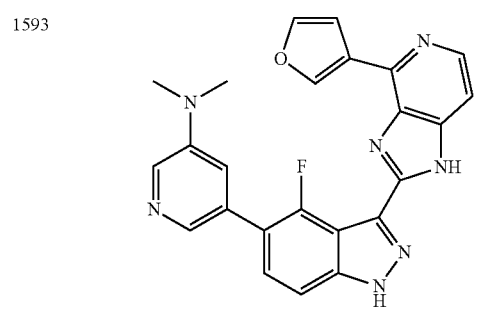 |
| 1594 | 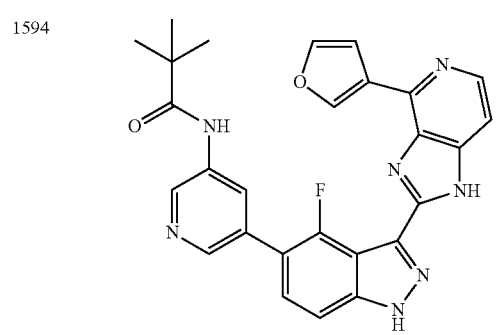 |
| 1595 | 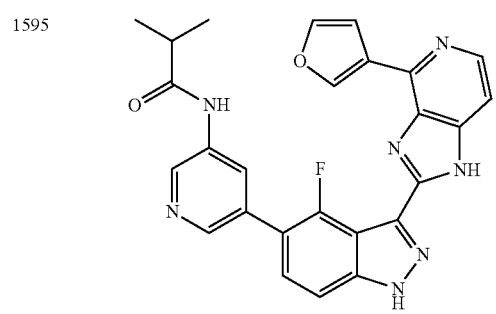 |
| 1596 | 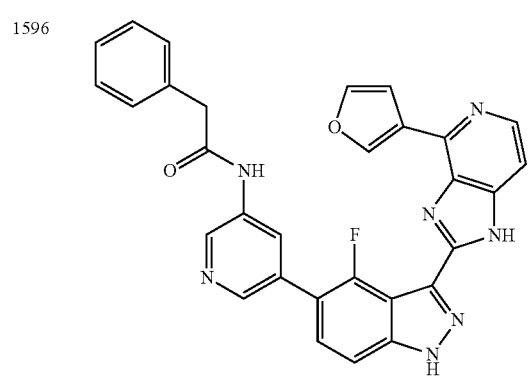 |
TABLE 1-continued
| | |
|---|---|
| 1597 | 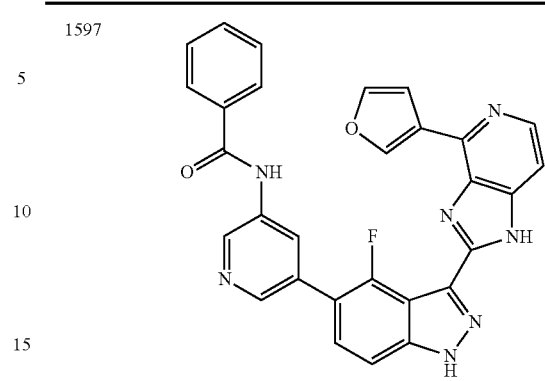 |
| 1598 | 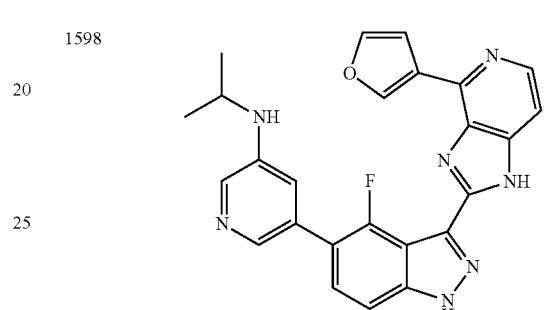 |
| 1599 | 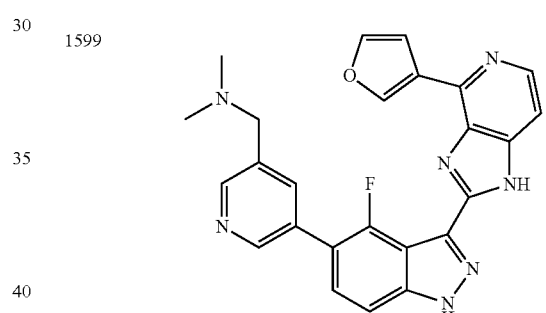 |
| 1600 | 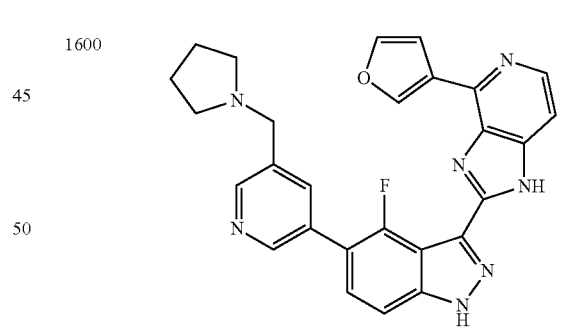 |
| 1601 | 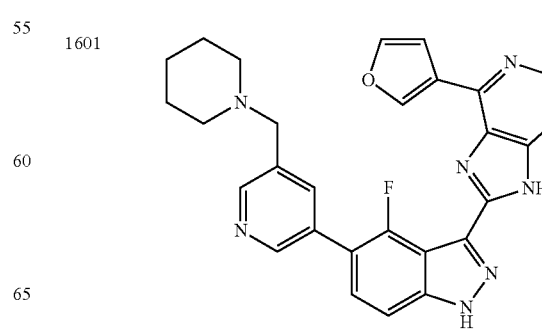 |

423
TABLE 1-continued
1602
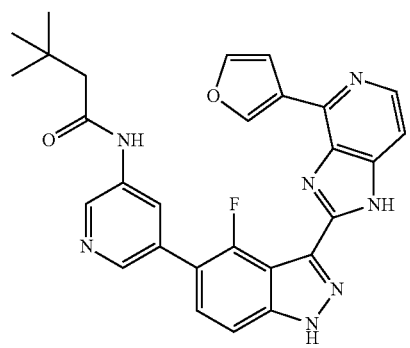 [SMILES: CC(C)CC(=O)Nc1cncc(-c2ccc3[nH]nc(-c4nc5c(-c6ccoc6)nccc5[nH]4)c3c2F)c1]
1603
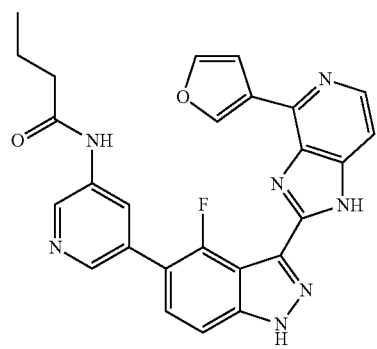 [SMILES: CCCC(=O)Nc1cncc(-c2ccc3[nH]nc(-c4nc5c(-c6ccoc6)nccc5[nH]4)c3c2F)c1]
1604
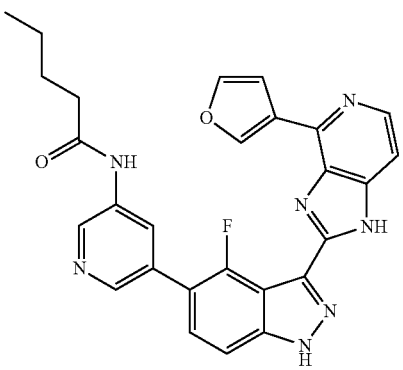
1605
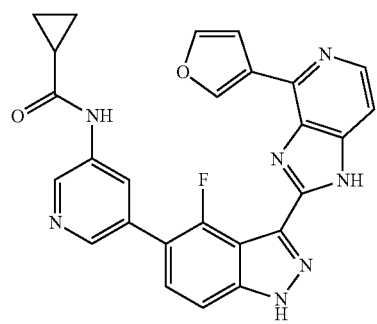 [SMILES: O=C(Nc1cncc(-c2ccc3[nH]nc(-c4nc5c(-c6ccoc6)nccc5[nH]4)c3c2F)c1)C1CC1]
424
TABLE 1-continued
1606
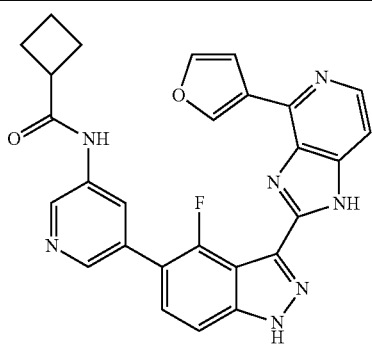
1607
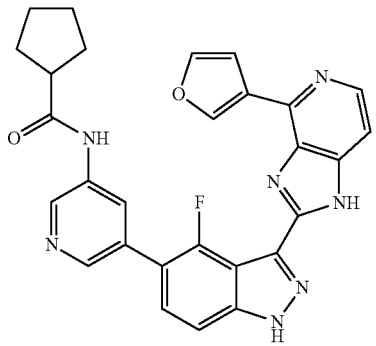
1608
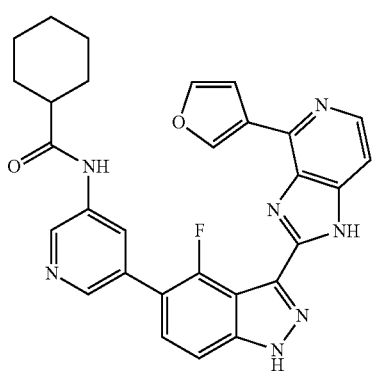 [SMILES: O=C(Nc1cncc(-c2ccc3[nH]nc(-c4nc5c(-c6ccoc6)nccc5[nH]4)c3c2F)c1)C1CCCCC1]
1609
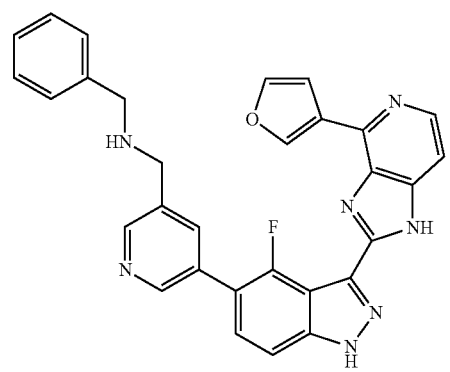 [SMILES: Fc1c(-c2cncc(CNCc3ccccc3)c2)ccc2[nH]nc(-c3nc4c(-c5ccoc5)nccc4[nH]3)c12]

TABLE 1-continued
| | |
|---|---|
| 1610 | 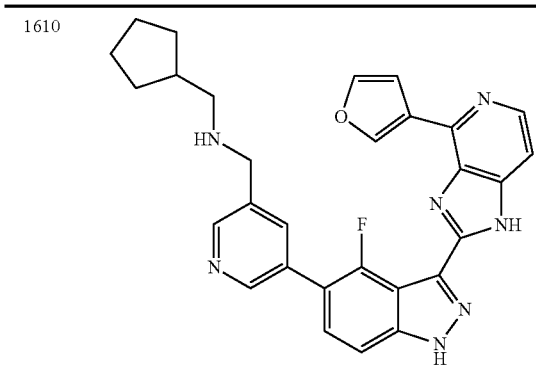 |
| 1611 | 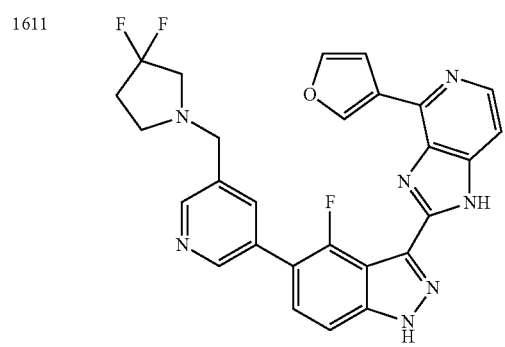 |
| 1612 | 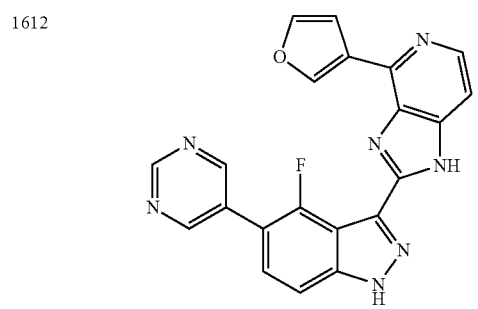 |
| 1613 | 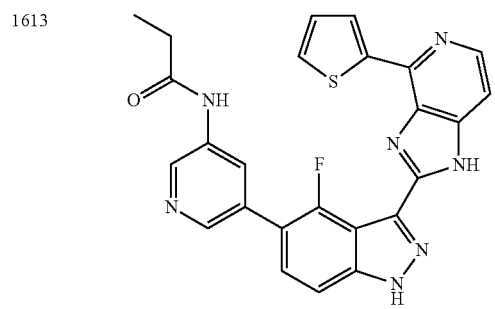 |
| 1614 | 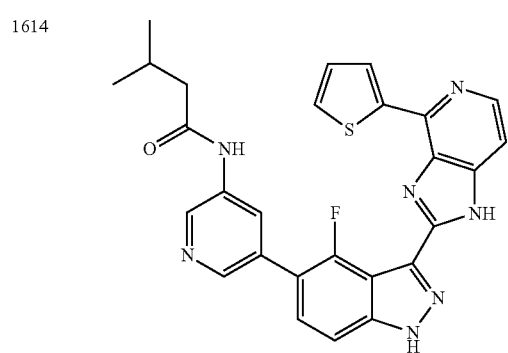 |
TABLE 1-continued
| | |
|---|---|
| 1615 | 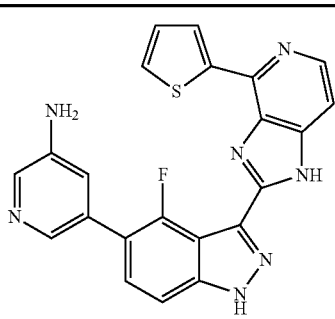 |
| 1616 | 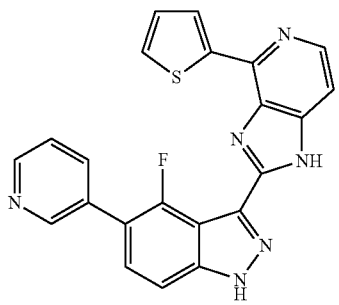 |
| 1617 | 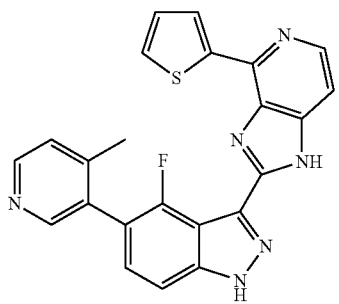 [SMILES: Cc1ccncc1-c1ccc2[nH]nc(-c3nc4c(-c5cccs5)nccc4[nH]3)c2c1F] |
| 1618 | 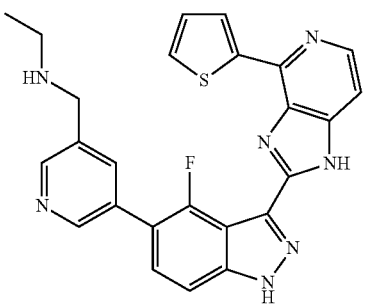 [SMILES: CCNCc1cncc(-c2ccc3[nH]nc(-c4nc5c(-c6cccs6)nccc5[nH]4)c3c2F)c1] |
| 1619 | 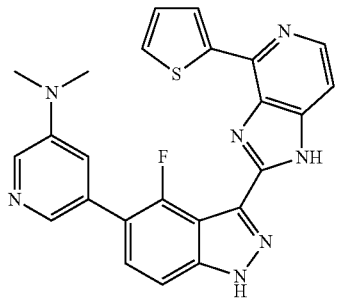 [SMILES: CN(C)c1cncc(-c2ccc3[nH]nc(-c4nc5c(-c6ccc(F)s6)nccc5[nH]4)c3c2F)c1] |

TABLE 1-continued
1620
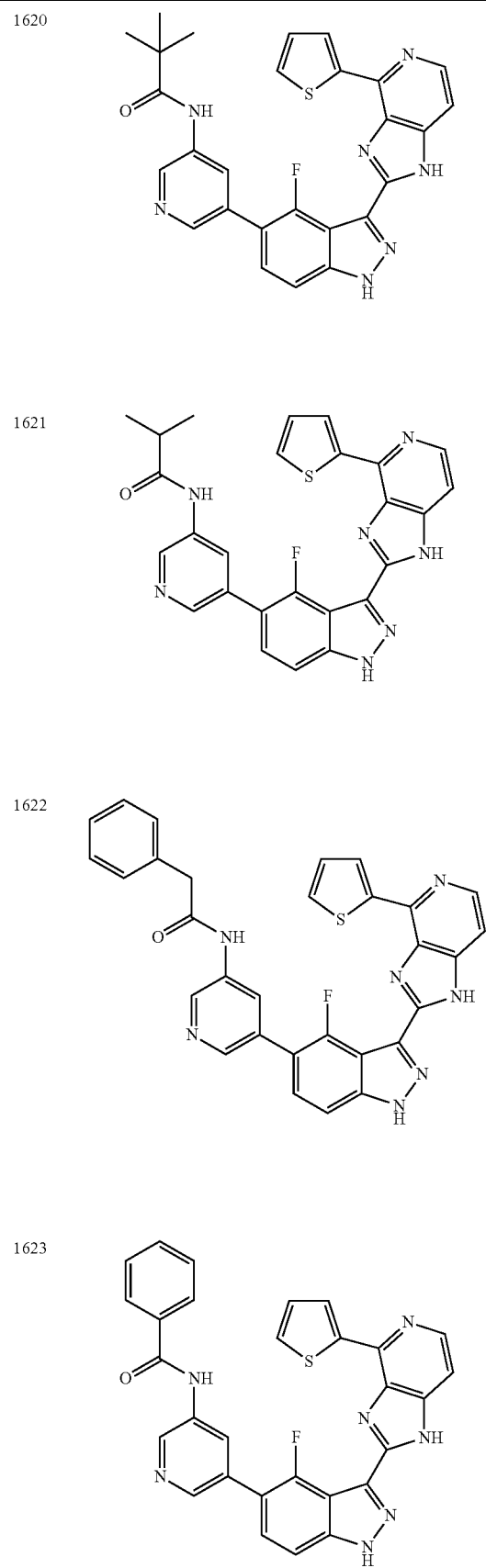
1621
1622
1623
TABLE 1-continued
1624
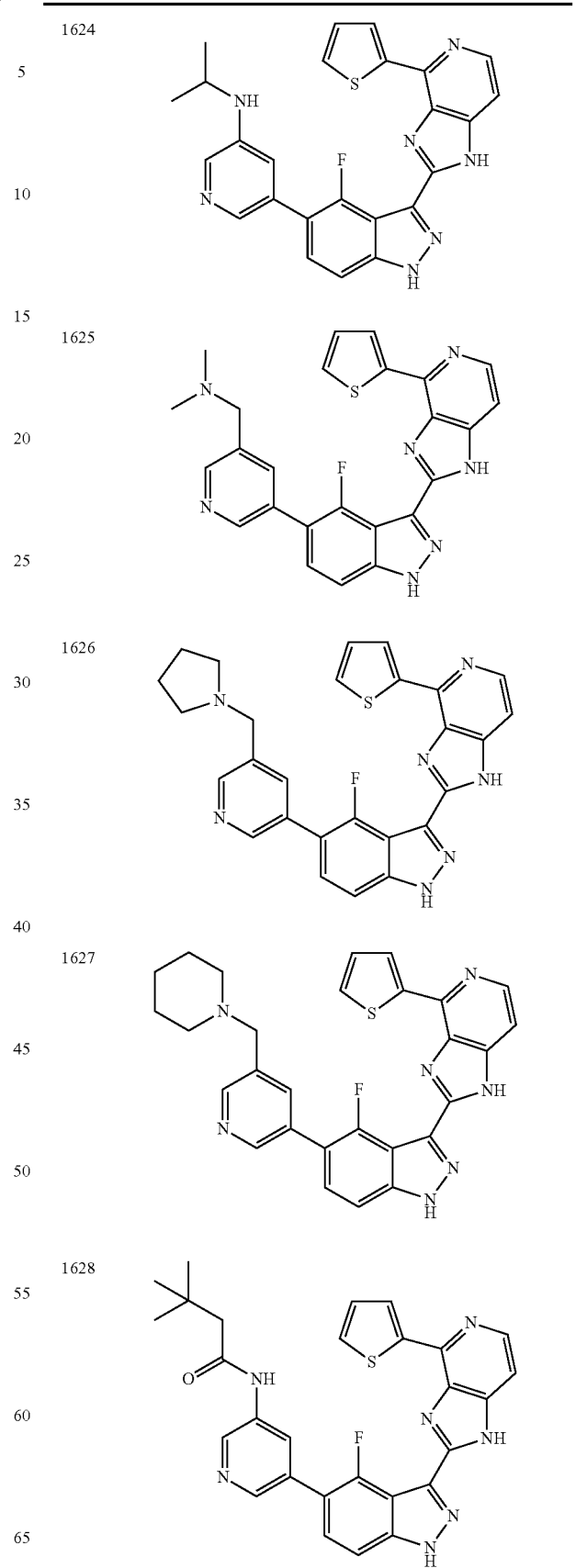
1625
1626
1627
1628

TABLE 1-continued
1629 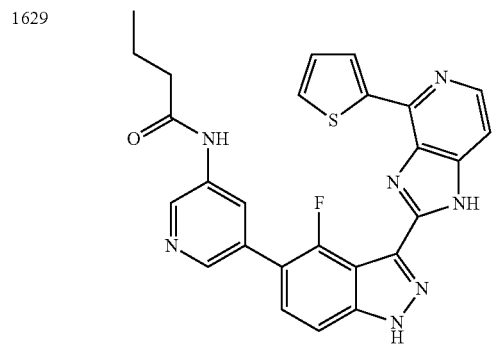
1630 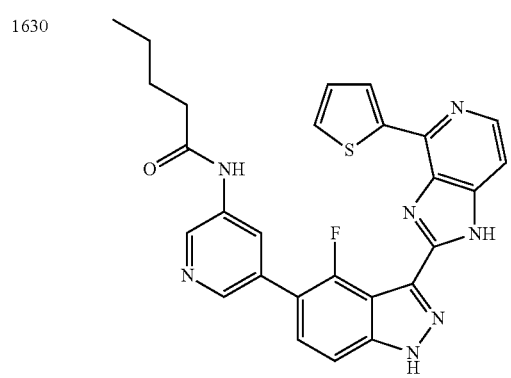
1631 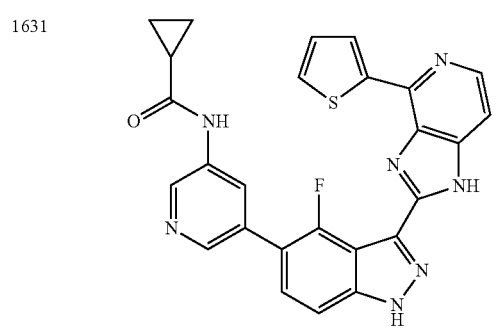
1632 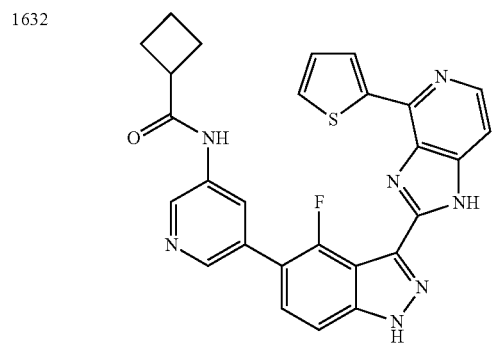
1633 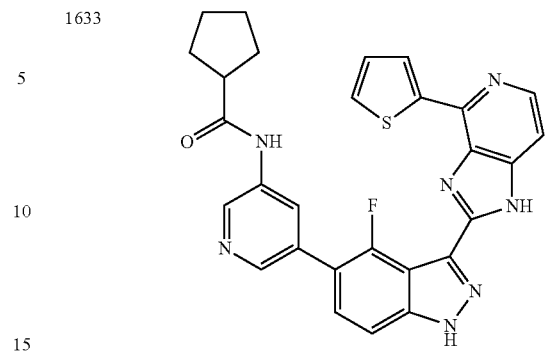
1634 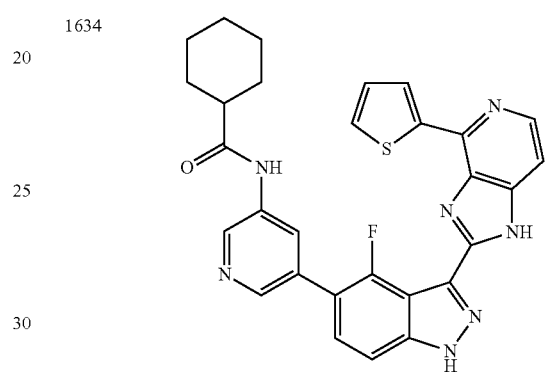
1635 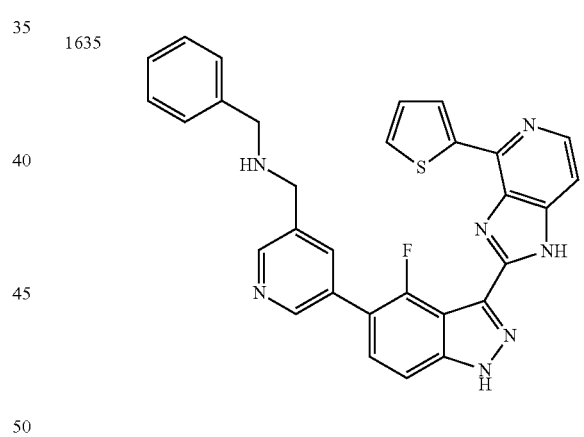
1636 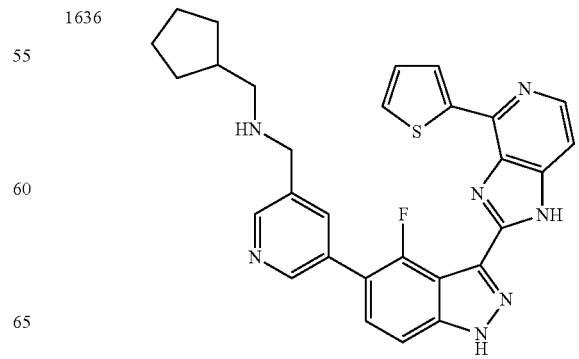

431
TABLE 1-continued
1637 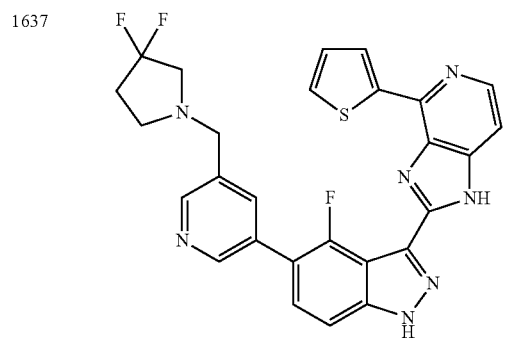
1638 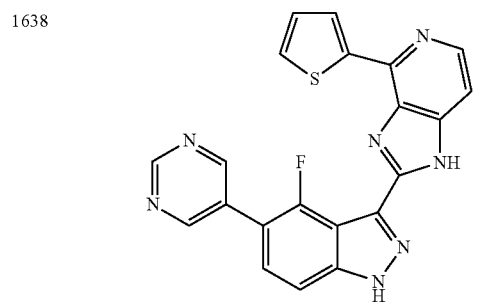
1639 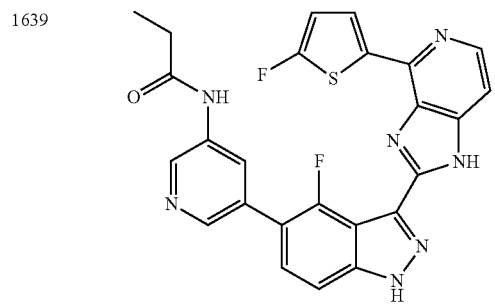
1640 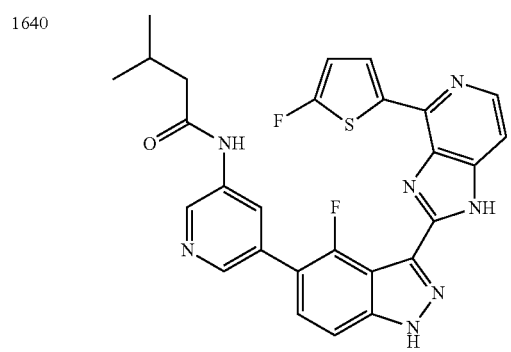
1641 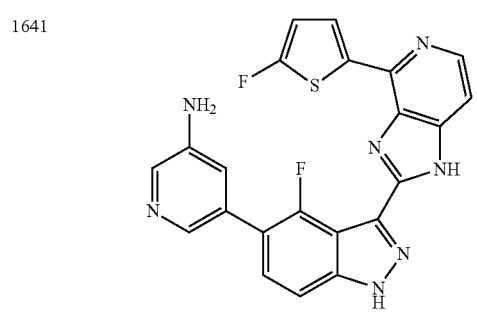
432
TABLE 1-continued
1642 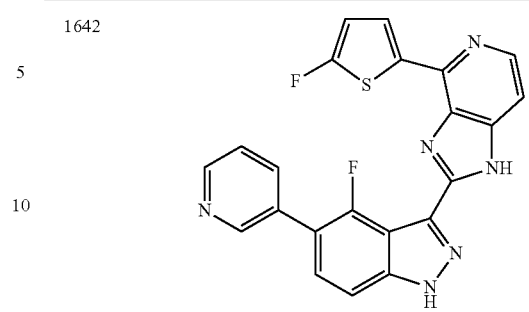
1643 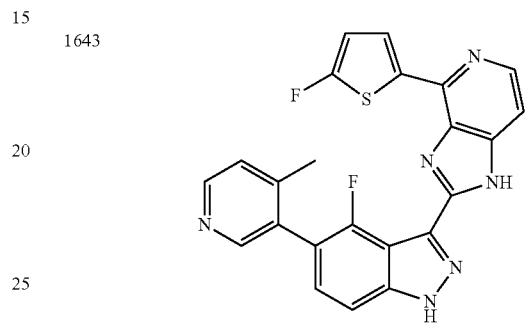
1644 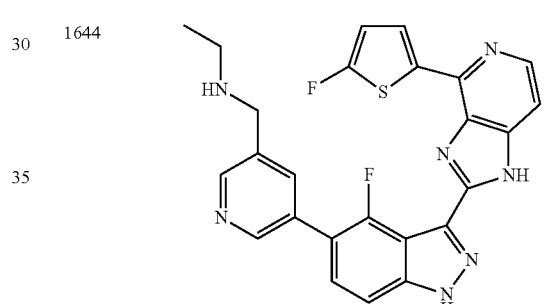
1645 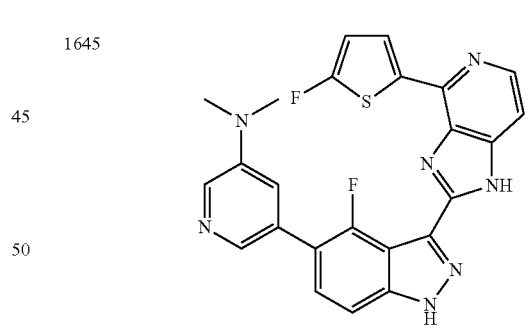
1646 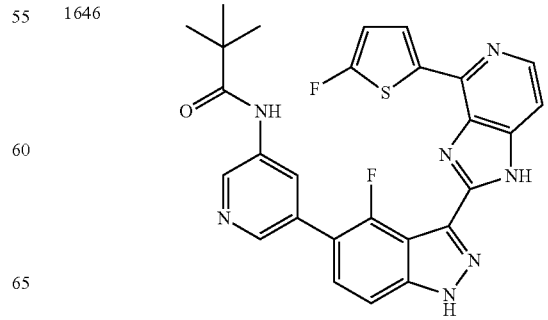

TABLE 1-continued
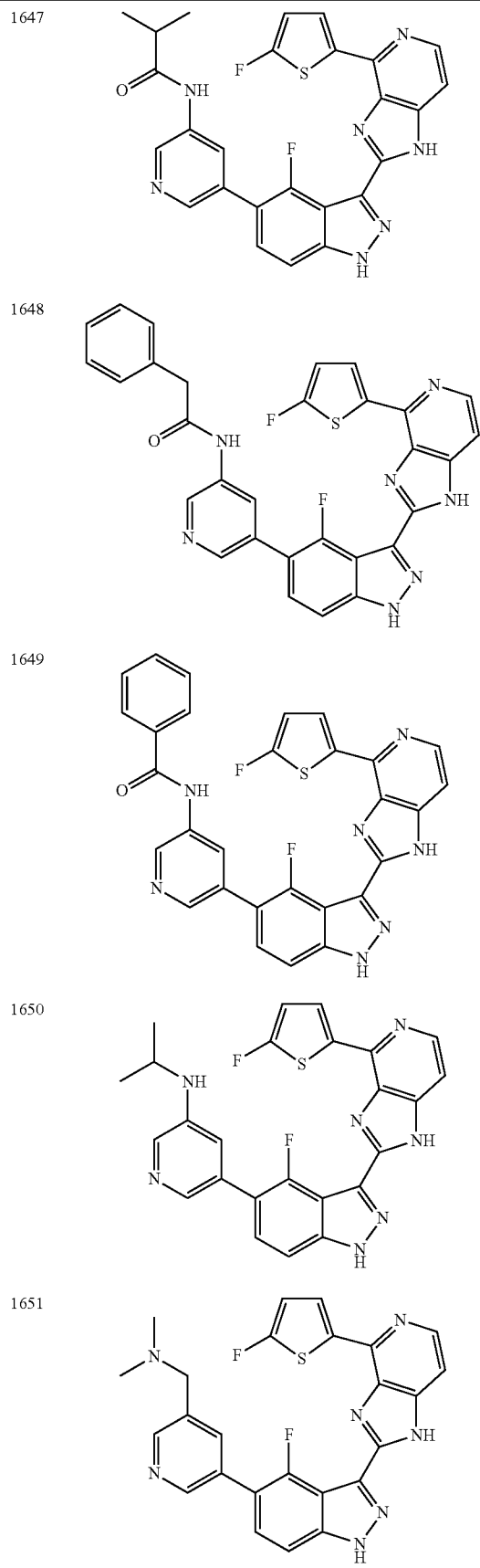
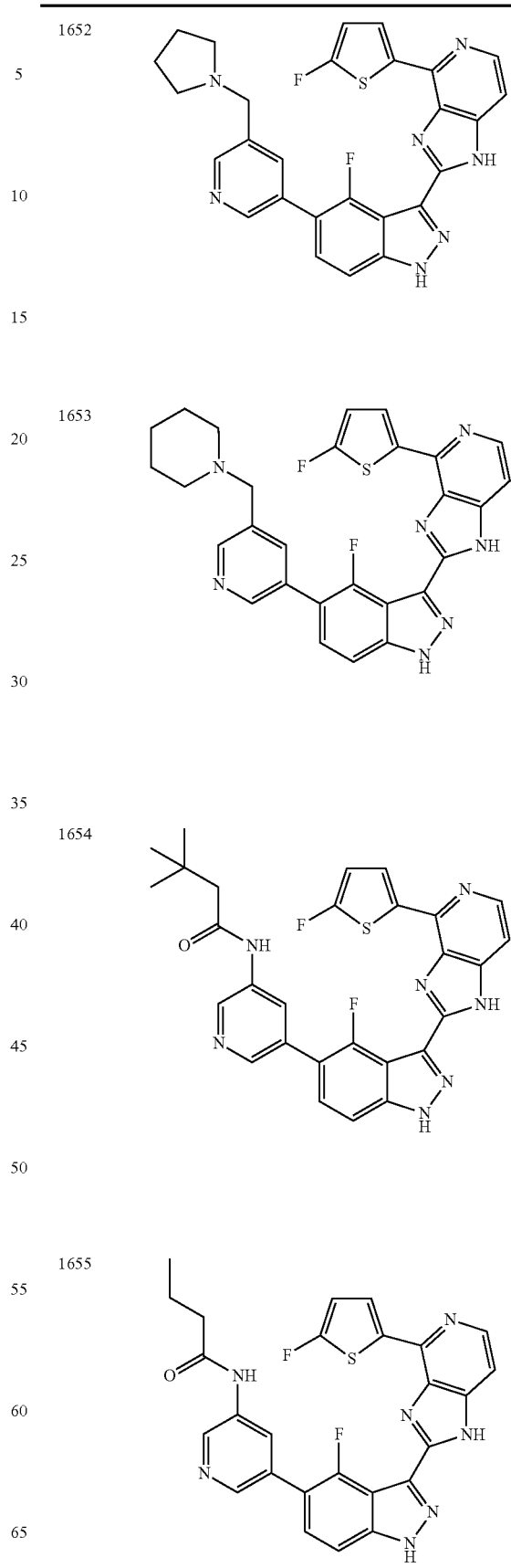

TABLE 1-continued
| | |
|---|---|
| 1656 | 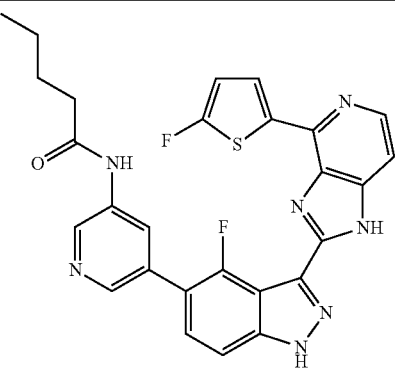 |
| 1657 | 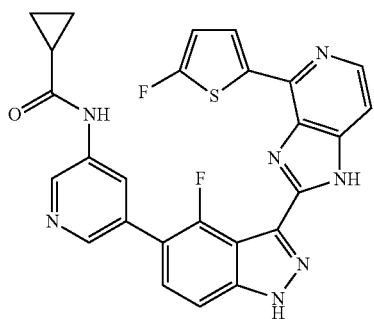 [SMILES: O=C(Nc1cncc(-c2ccc3[nH]nc(-c4nc5c(-c6ccc(F)s6)nccc5[nH]4)c3c2F)c1)C1CC1] |
| 1658 | 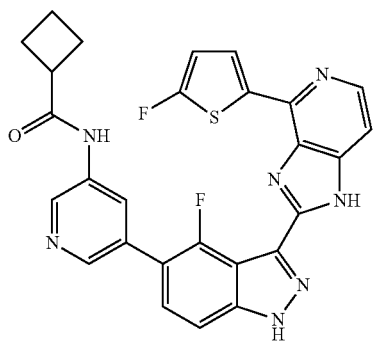 [SMILES: O=C(Nc1cncc(-c2ccc3[nH]nc(-c4nc5c(-c6ccc(F)s6)nccc5[nH]4)c3c2F)c1)C1CCC1] |
| 1659 | 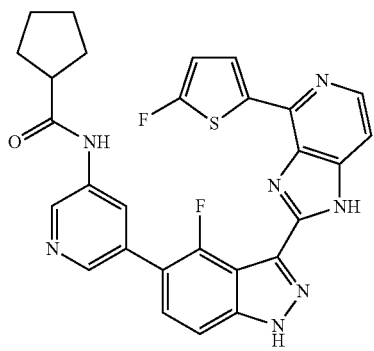 [SMILES: O=C(Nc1cncc(-c2ccc3[nH]nc(-c4nc5c(-c6ccc(F)s6)nccc5[nH]4)c3c2F)c1)C1CCCC1] |
| 1660 | 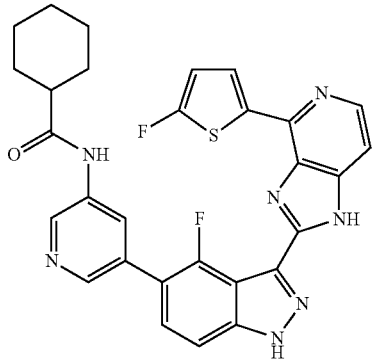 |
| 1661 | 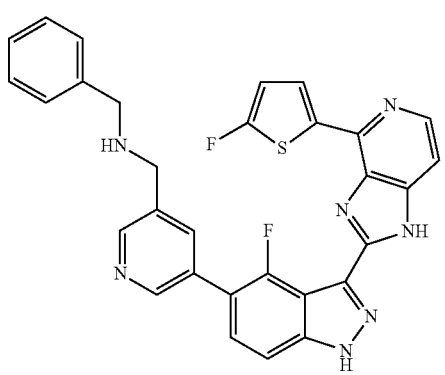 |
| 1662 | 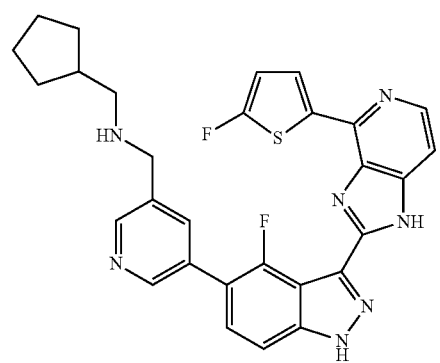 [SMILES: Fc1ccc(-c2nccc3[nH]c(-c4n[nH]c5ccc(-c6cncc(CNCC7CCCC7)c6)c(F)c45)nc23)s1] |
| 1663 | 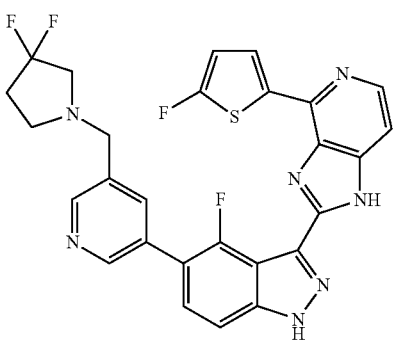 [SMILES: Fc1ccc(-c2nccc3[nH]c(-c4n[nH]c5ccc(-c6cncc(CN7CCC(F)(F)C7)c6)c(F)c45)nc23)s1] |

TABLE 1-continued
| | |
|---|---|
| 1664 | 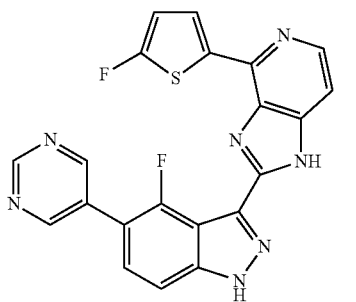 [SMILES: Fc1ccc(-c2nccc3[nH]c(-c4n[nH]c5ccc(-c6cncnc6)c(F)c45)nc23)s1] |
| 1665 | 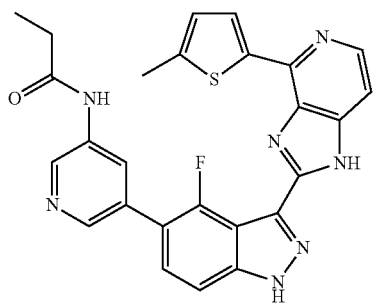 [SMILES: CCC(=O)Nc1cncc(-c2ccc3[nH]nc(-c4nc5c(-c6ccc(C)s6)nccc5[nH]4)c3c2F)c1] |
| 1666 | 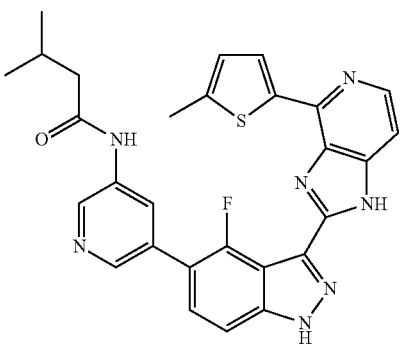 [SMILES: Cc1ccc(-c2nccc3[nH]c(-c4n[nH]c5ccc(-c6cncc(NC(=O)CC(C)C)c6)c(F)c45)nc23)s1] |
| 1667 | 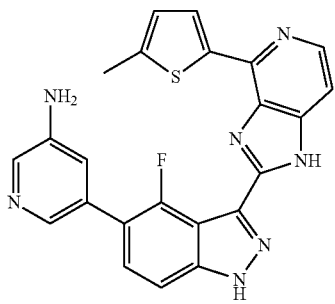 |
| 1668 | 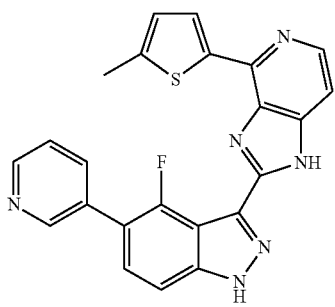 |
| 1669 | 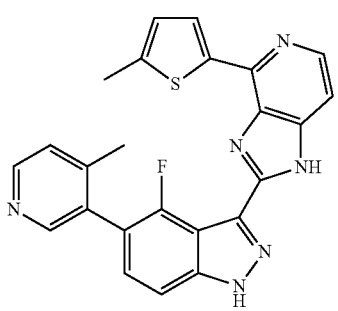 [SMILES: Cc1ccc(-c2nccc3[nH]c(-c4n[nH]c5ccc(-c6cnccc6C)c(F)c45)nc23)s1] |
| 1670 | 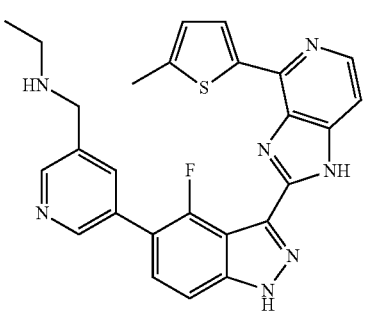 [SMILES: CCNCc1cncc(-c2ccc3[nH]nc(-c4nc5c(-c6ccc(C)s6)nccc5[nH]4)c3c2F)c1] |
| 1671 | 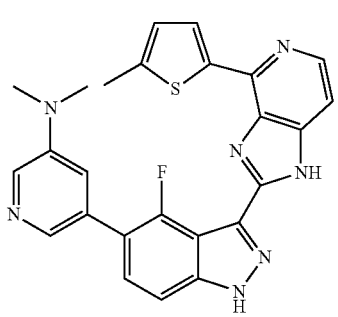 |
| 1672 | 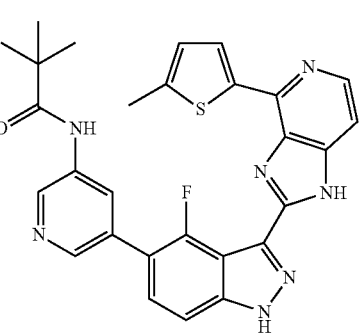 |
| 1673 | 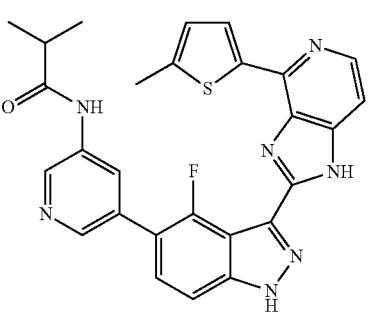 [SMILES: Cc1ccc(-c2nccc3[nH]c(-c4n[nH]c5ccc(-c6cncc(NC(=O)C(C)C)c6)c(F)c45)nc23)s1] |

TABLE 1-continued
1674 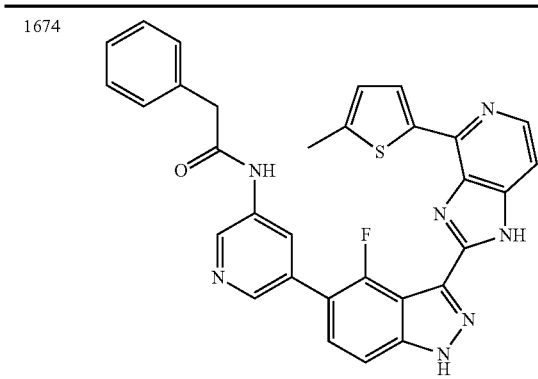
1675 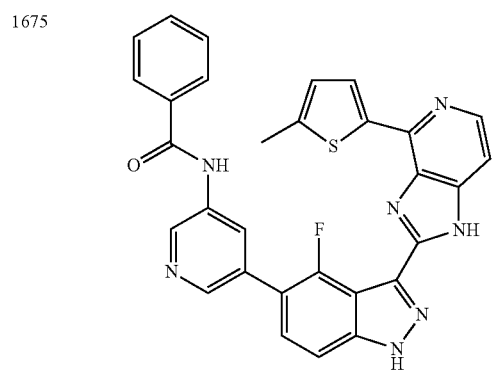
1676 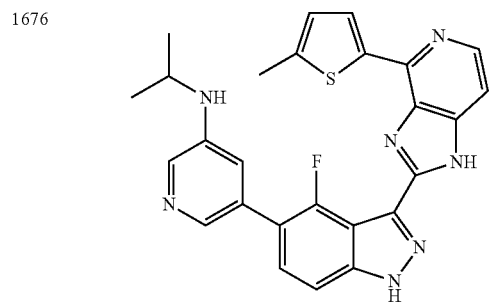
1677 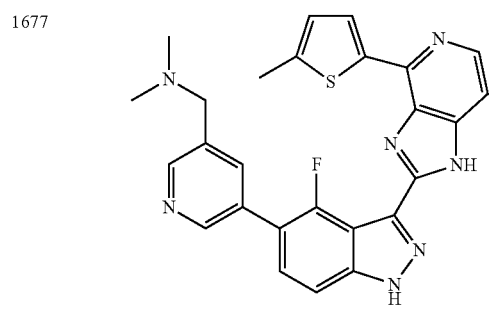
1678 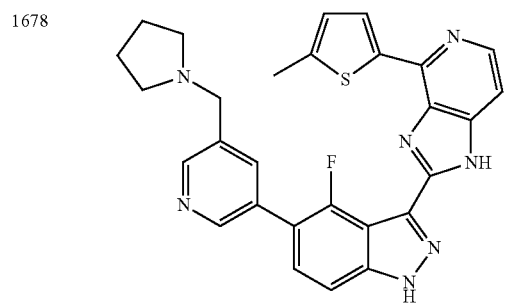
TABLE 1-continued
1679 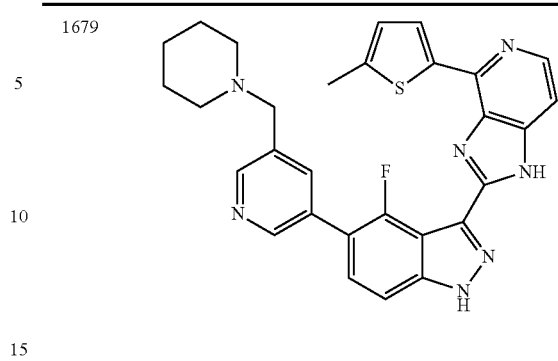
1680 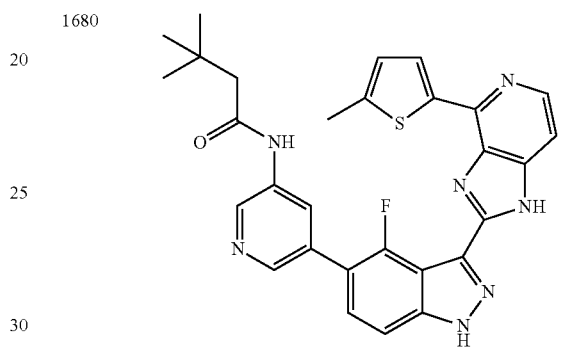
1681 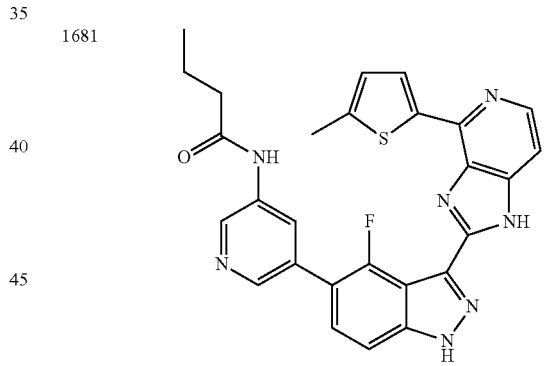
1682 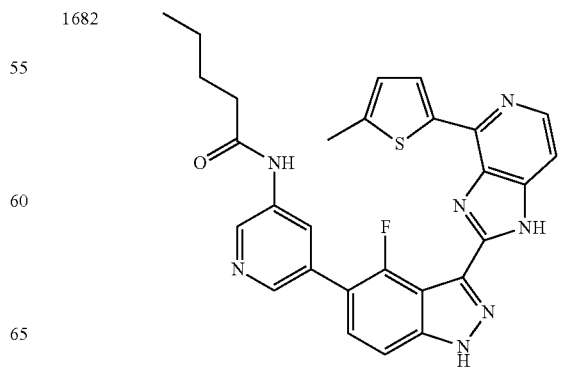

TABLE 1-continued
| | |
|---|---|
| 1683 | 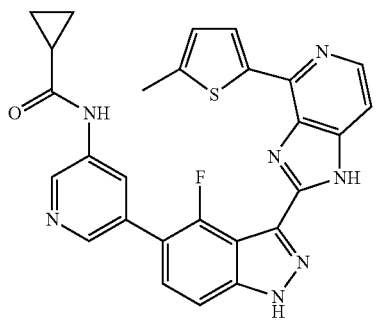 [SMILES: Cc1ccc(-c2nccc3[nH]c(-c4n[nH]c5ccc(-c6cncc(NC(=O)C7CC7)c6)c(F)c45)nc23)s1] |
| 1684 | 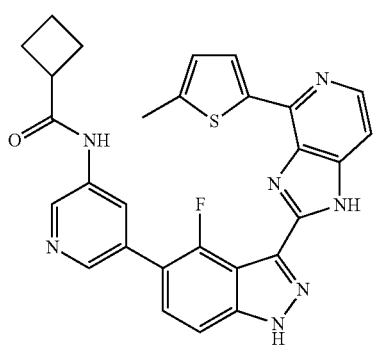 [SMILES: Cc1ccc(-c2nccc3[nH]c(-c4n[nH]c5ccc(-c6cncc(NC(=O)C7CCC7)c6)c(F)c45)nc23)s1] |
| 1685 | 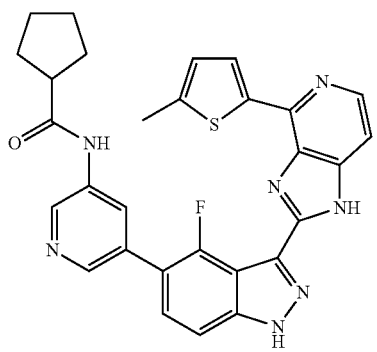 [SMILES: Cc1ccc(-c2nccc3[nH]c(-c4n[nH]c5ccc(-c6cncc(NC(=O)C7CCCC7)c6)c(F)c45)nc23)s1] |
| 1686 | 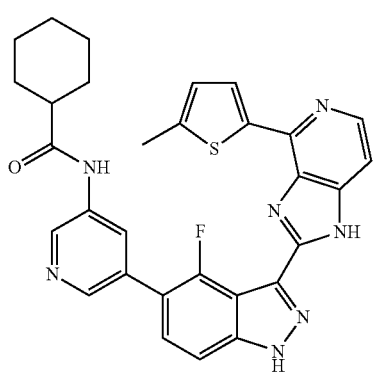 [SMILES: Cc1ccc(-c2nccc3[nH]c(-c4n[nH]c5ccc(-c6cncc(NC(=O)C7CCCCC7)c6)c(F)c45)nc23)s1] |
| 1687 | 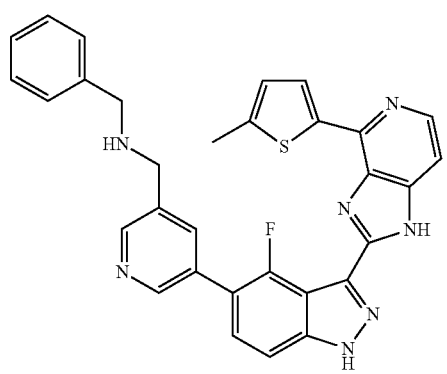 [SMILES: Cc1ccc(-c2nccc3[nH]c(-c4n[nH]c5ccc(-c6cncc(CNCc7ccccc7)c6)c(F)c45)nc23)s1] |
| 1688 | 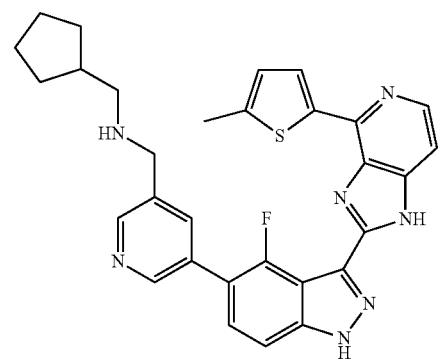 [SMILES: Cc1ccc(-c2nccc3[nH]c(-c4n[nH]c5ccc(-c6cncc(CNCC7CCCC7)c6)c(F)c45)nc23)s1] |
| 1689 | 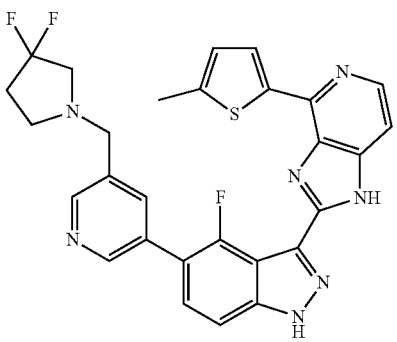 [SMILES: Cc1ccc(-c2nccc3[nH]c(-c4n[nH]c5ccc(-c6cncc(CN7CCC(F)(F)C7)c6)c(F)c45)nc23)s1] |
| 1690 | 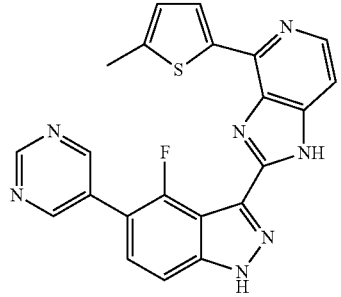 |

TABLE 1-continued
1691 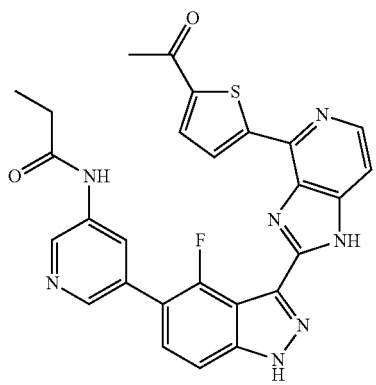 [SMILES: CCC(=O)Nc1cncc(-c2ccc3[nH]nc(-c4nc5c(-c6ccc(C(C)=O)s6)nccc5[nH]4)c3c2F)c1]
1692 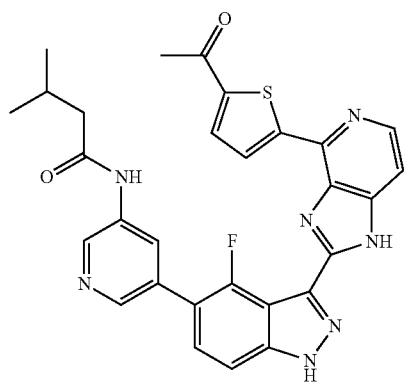 [SMILES: CC(=O)c1ccc(-c2nccc3[nH]c(-c4n[nH]c5ccc(-c6cncc(NC(=O)CC(C)C)c6)c(F)c45)nc23)s1]
1693 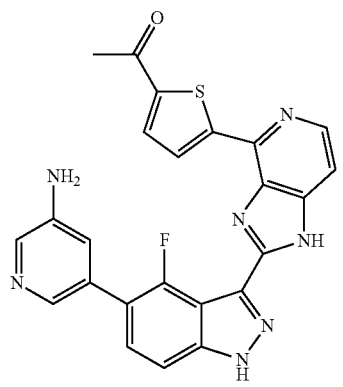 [SMILES: CC(=O)c1ccc(-c2nccc3[nH]c(-c4n[nH]c5ccc(-c6cncc(N)c6)c(F)c45)nc23)s1]
1694 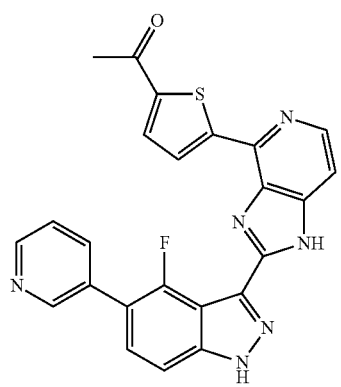 [SMILES: CC(=O)c1ccc(-c2nccc3[nH]c(-c4n[nH]c5ccc(-c6cccnc6)c(F)c45)nc23)s1]
1695 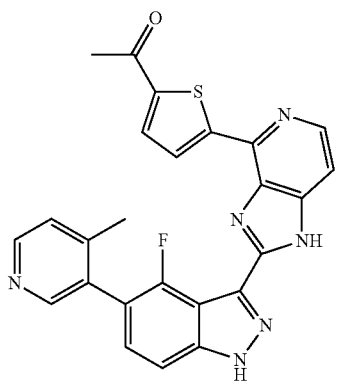 [SMILES: CC(=O)c1ccc(-c2nccc3[nH]c(-c4n[nH]c5ccc(-c6cnccc6C)c(F)c45)nc23)s1]
1696 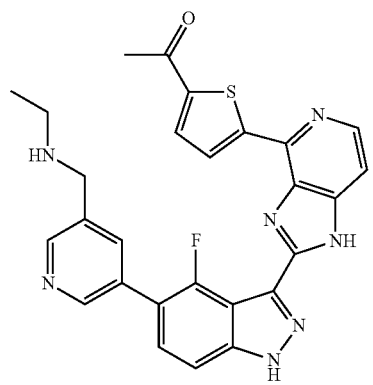 [SMILES: CCNCc1cncc(-c2ccc3[nH]nc(-c4nc5c(-c6ccc(C(C)=O)s6)nccc5[nH]4)c3c2F)c1]
1697 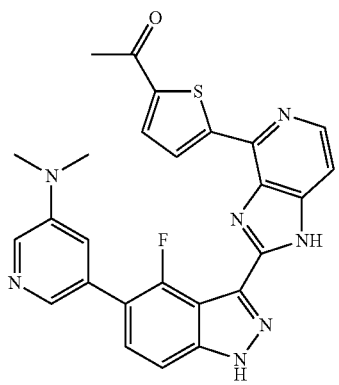 [SMILES: CC(=O)c1ccc(-c2nccc3[nH]c(-c4n[nH]c5ccc(-c6cncc(N(C)C)c6)c(F)c45)nc23)s1]
1698 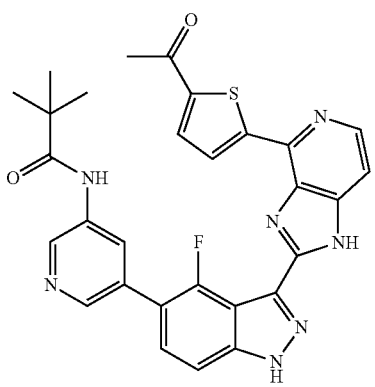 [SMILES: CC(=O)c1ccc(-c2nccc3[nH]c(-c4n[nH]c5ccc(-c6cncc(NC(=O)C(C)(C)C)c6)c(F)c45)nc23)s1]

TABLE 1-continued
1699 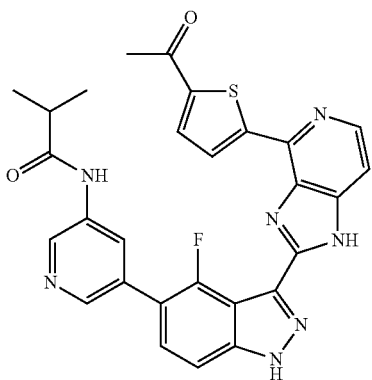 [SMILES: CC(=O)c1ccc(-c2nccc3[nH]c(-c4n[nH]c5ccc(-c6cncc(NC(=O)C(C)C)c6)c(F)c45)nc23)s1]
1700 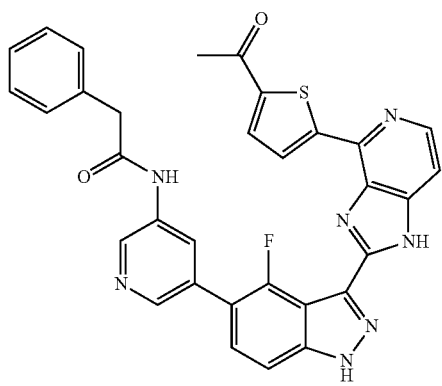 [SMILES: CC(=O)c1ccc(-c2nccc3[nH]c(-c4n[nH]c5ccc(-c6cncc(NC(=O)Cc7ccccc7)c6)c(F)c45)nc23)s1]
1701 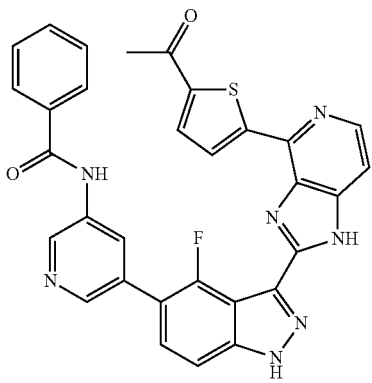 [SMILES: CC(=O)c1ccc(-c2nccc3[nH]c(-c4n[nH]c5ccc(-c6cncc(NC(=O)c7ccccc7)c6)c(F)c45)nc23)s1]
1702 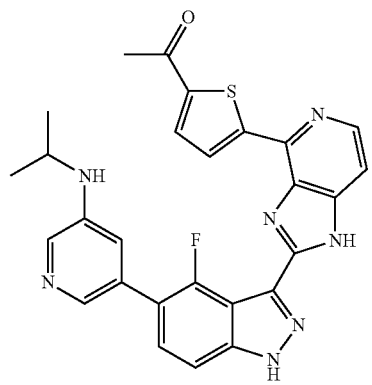 [SMILES: CC(=O)c1ccc(-c2nccc3[nH]c(-c4n[nH]c5ccc(-c6cncc(NC(C)C)c6)c(F)c45)nc23)s1]
1703 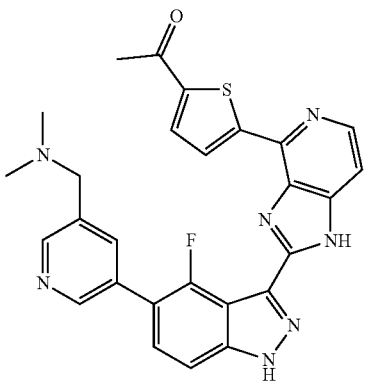 [SMILES: CC(=O)c1ccc(-c2nccc3[nH]c(-c4n[nH]c5ccc(-c6cncc(CN(C)C)c6)c(F)c45)nc23)s1]
1704 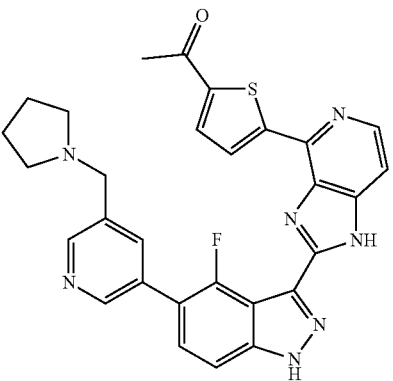 [SMILES: CC(=O)c1ccc(-c2nccc3[nH]c(-c4n[nH]c5ccc(-c6cncc(CN7CCCC7)c6)c(F)c45)nc23)s1]
1705 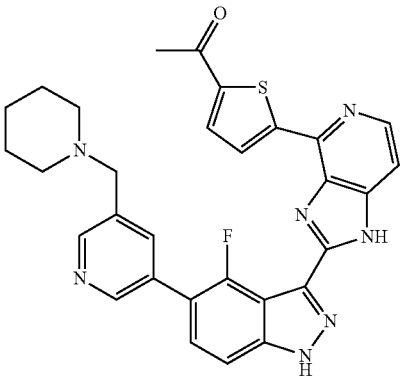 [SMILES: CC(=O)c1ccc(-c2nccc3[nH]c(-c4n[nH]c5ccc(-c6cncc(CN7CCCCC7)c6)c(F)c45)nc23)s1]
1706 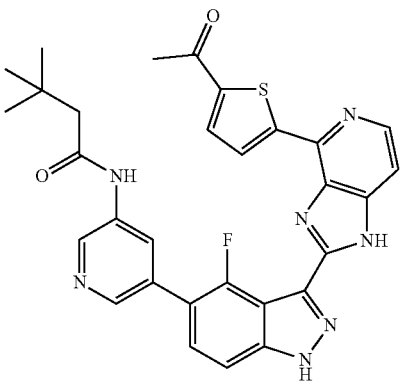 [SMILES: CC(=O)c1ccc(-c2nccc3[nH]c(-c4n[nH]c5ccc(-c6cncc(NC(=O)CC(C)(C)C)c6)c(F)c45)nc23)s1]

TABLE 1-continued
1707 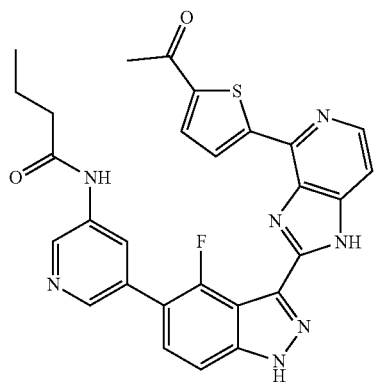 [SMILES: CCCC(=O)Nc1cncc(-c2ccc3[nH]nc(-c4nc5c(-c6ccc(C(C)=O)s6)nccc5[nH]4)c3c2F)c1]
1708 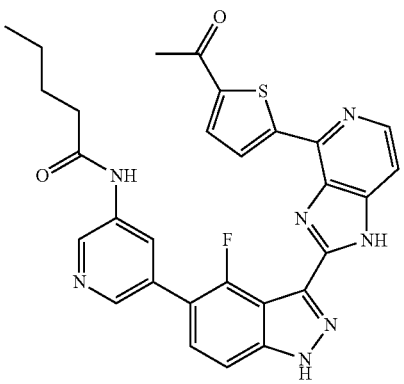 [SMILES: CCCCC(=O)Nc1cncc(-c2ccc3[nH]nc(-c4nc5c(-c6ccc(C(C)=O)s6)nccc5[nH]4)c3c2F)c1]
1709 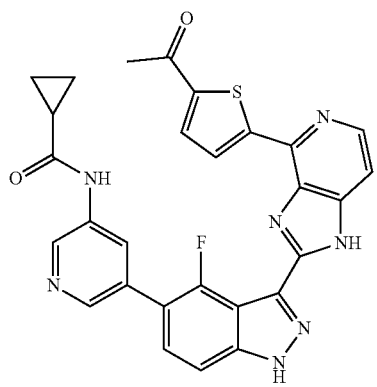 [SMILES: CC(=O)c1ccc(-c2nccc3[nH]c(-c4n[nH]c5ccc(-c6cncc(NC(=O)C7CC7)c6)c(F)c45)nc23)s1]
1710 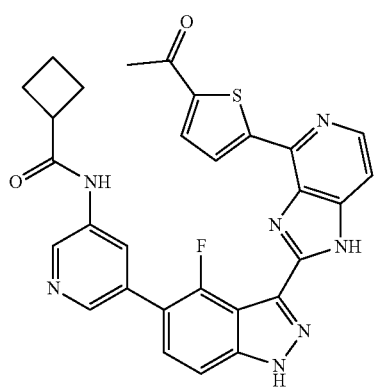 [SMILES: CC(=O)c1ccc(-c2nccc3[nH]c(-c4n[nH]c5ccc(-c6cncc(NC(=O)C7CCC7)c6)c(F)c45)nc23)s1]
TABLE 1-continued
1711 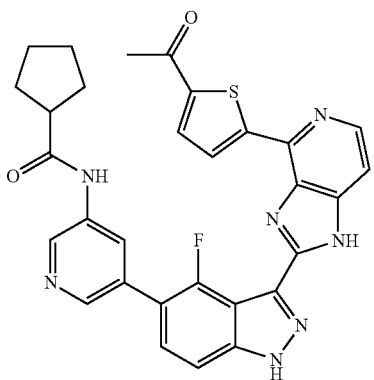 [SMILES: CC(=O)c1ccc(-c2nccc3[nH]c(-c4n[nH]c5ccc(-c6cncc(NC(=O)C7CCCC7)c6)c(F)c45)nc23)s1]
1712 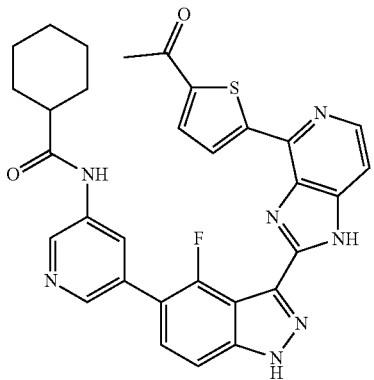 [SMILES: CC(=O)c1ccc(-c2nccc3[nH]c(-c4n[nH]c5ccc(-c6cncc(NC(=O)C7CCCCC7)c6)c(F)c45)nc23)s1]
1713 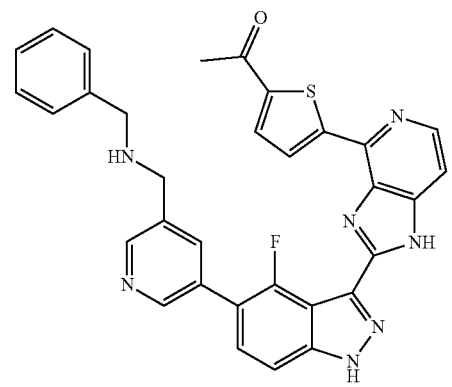 [SMILES: CC(=O)c1ccc(-c2nccc3[nH]c(-c4n[nH]c5ccc(-c6cncc(CNCc7ccccc7)c6)c(F)c45)nc23)s1]
1714 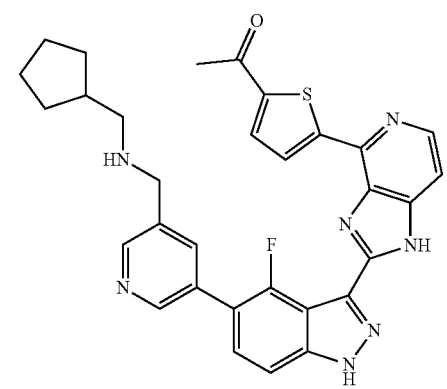 [SMILES: CC(=O)c1ccc(-c2nccc3[nH]c(-c4n[nH]c5ccc(-c6cncc(CNCC7CCCC7)c6)c(F)c45)nc23)s1]

TABLE 1-continued
1715 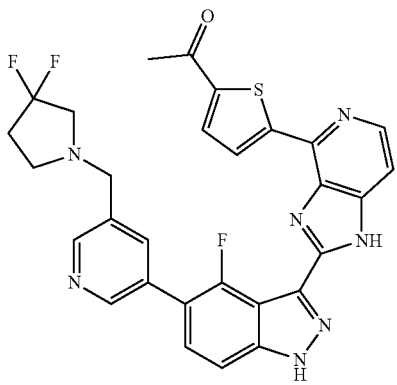 [SMILES: CC(=O)c1ccc(-c2nccc3[nH]c(-c4n[nH]c5ccc(-c6cncc(CN7CCC(F)(F)C7)c6)c(F)c45)nc23)s1]
1716 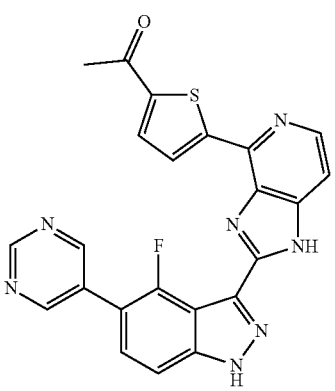 [SMILES: CC(=O)c1ccc(-c2nccc3[nH]c(-c4n[nH]c5ccc(-c6cncnc6)c(F)c45)nc23)s1]
1717 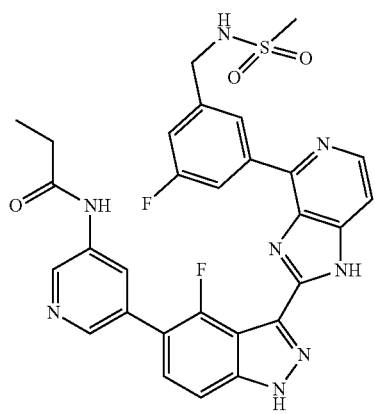 [SMILES: CCC(=O)Nc1cncc(-c2ccc3[nH]nc(-c4nc5c(-c6cc(F)cc(CNS(C)(=O)=O)c6)nccc5[nH]4)c3c2F)c1]
1718 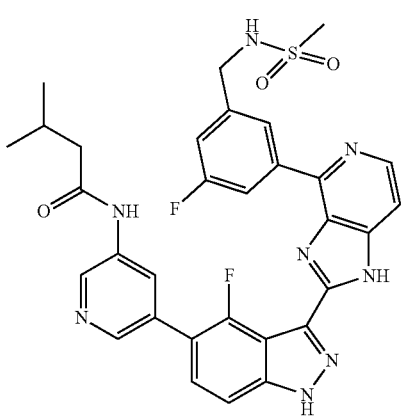 [SMILES: CC(C)CC(=O)Nc1cncc(-c2ccc3[nH]nc(-c4nc5c(-c6cc(F)cc(CNS(C)(=O)=O)c6)nccc5[nH]4)c3c2F)c1]
1719 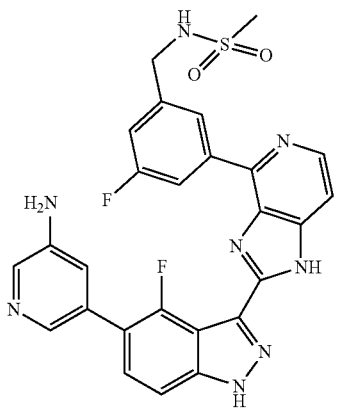 [SMILES: CS(=O)(=O)NCc1cc(F)cc(-c2nccc3[nH]c(-c4n[nH]c5ccc(-c6cncc(N)c6)c(F)c45)nc23)c1]
1720 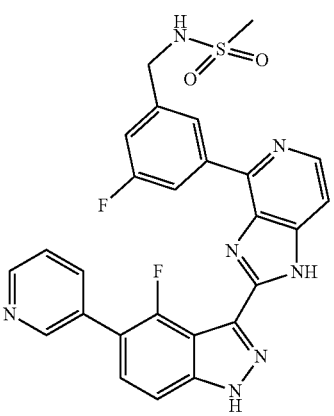 [SMILES: CS(=O)(=O)NCc1cc(F)cc(-c2nccc3[nH]c(-c4n[nH]c5ccc(-c6cccnc6)c(F)c45)nc23)c1]
1721 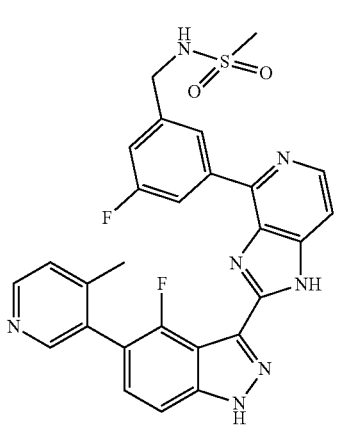 [SMILES: Cc1ccncc1-c1ccc2[nH]nc(-c3nc4c(-c5cc(F)cc(CNS(C)(=O)=O)c5)nccc4[nH]3)c2c1F]
1722 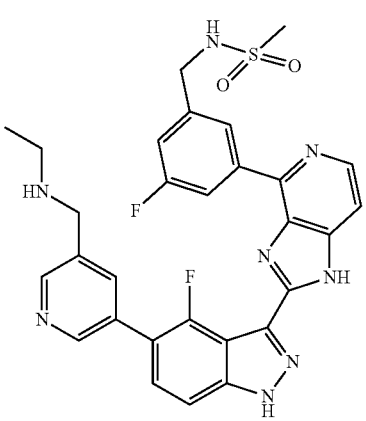 [SMILES: CCNCc1cncc(-c2ccc3[nH]nc(-c4nc5c(-c6cc(F)cc(CNS(C)(=O)=O)c6)nccc5[nH]4)c3c2F)c1]

TABLE 1-continued
| 1723 | 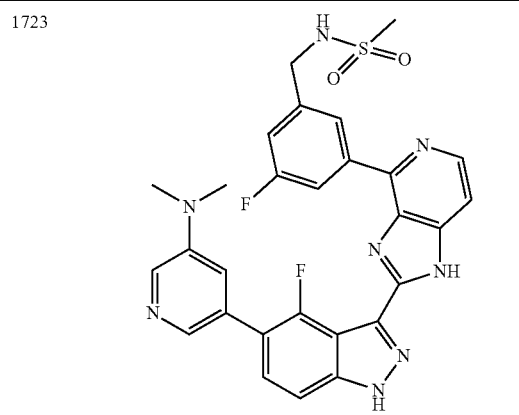 |
| --- | --- |
| 1724 | 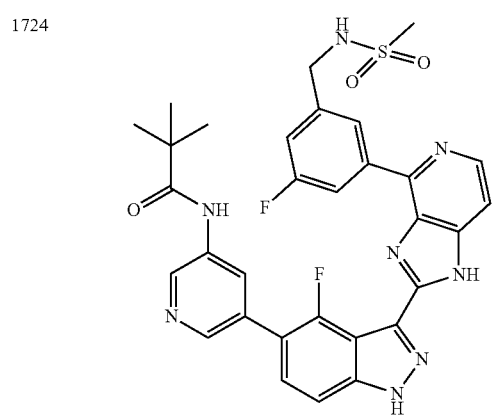 |
| 1725 | 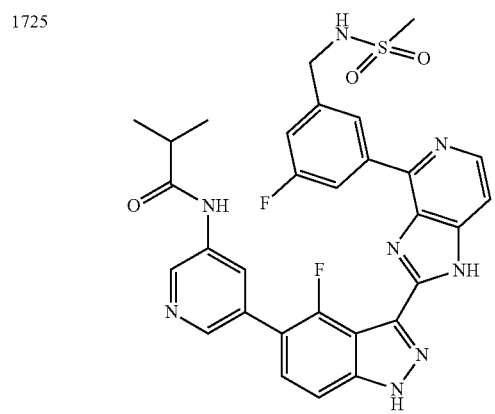 |
| 1726 | 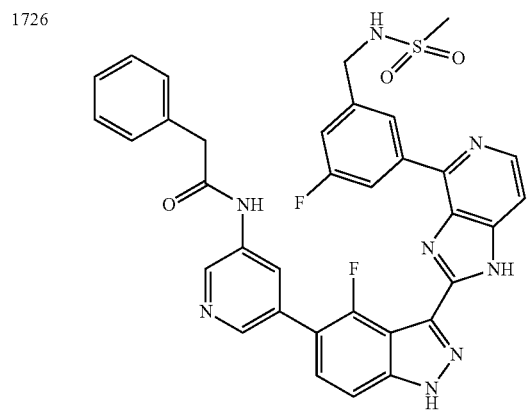 |
TABLE 1-continued
| 1727 | 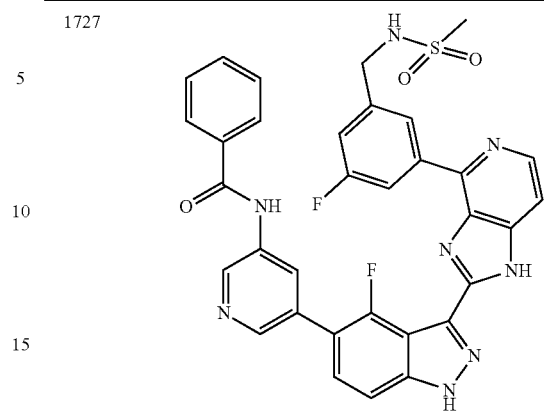 |
| --- | --- |
| 1728 | 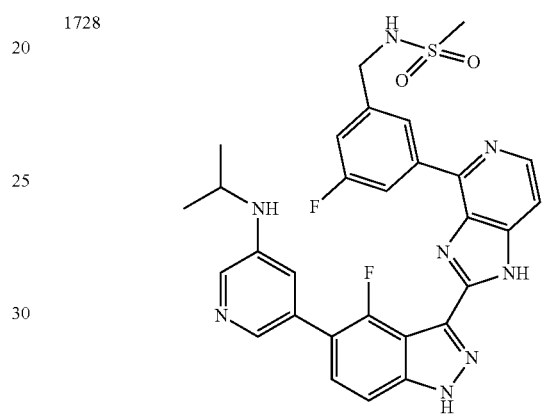 |
| 1729 | 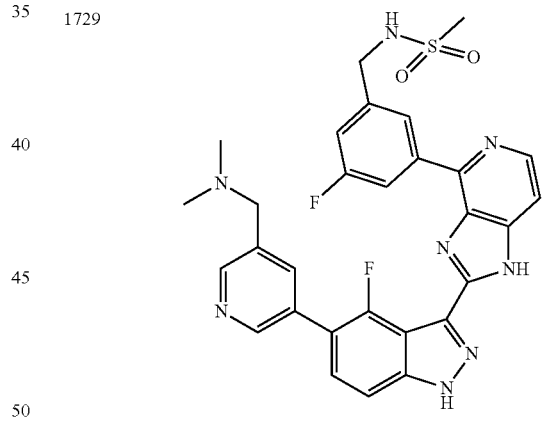 |
| 1730 | 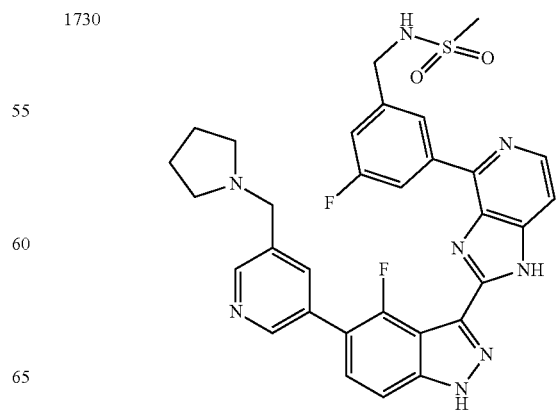 |

TABLE 1-continued
1731 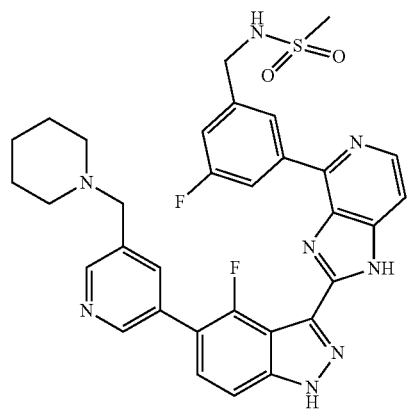 [SMILES: CS(=O)(=O)NCc1cc(F)cc(-c2nccc3[nH]c(-c4n[nH]c5ccc(-c6cncc(CN7CCCCC7)c6)c(F)c45)nc23)c1]
1732 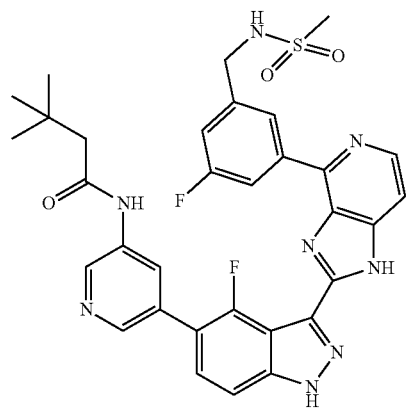 [SMILES: CC(C)(C)CC(=O)Nc1cncc(-c2ccc3[nH]nc(-c4nc5c(-c6cc(F)cc(CNS(C)(=O)=O)c6)nccc5[nH]4)c3c2F)c1]
1733 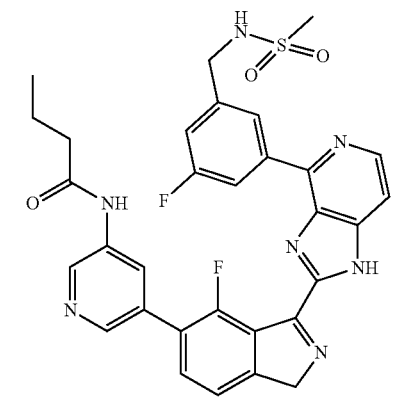 [SMILES: CCCC(=O)Nc1cncc(-c2ccc3c(c2F)C(c2nc4c(-c5cc(F)cc(CNS(C)(=O)=O)c5)nccc4[nH]2)=NC3)c1]
1734 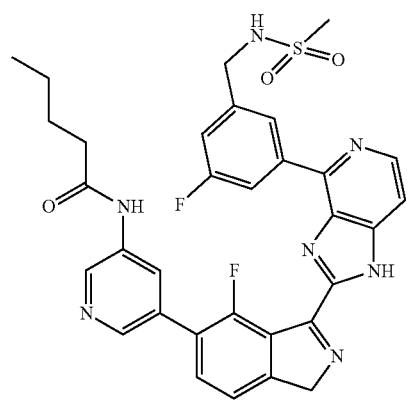 [SMILES: CCCCC(=O)Nc1cncc(-c2ccc3c(c2F)C(c2nc4c(-c5cc(F)cc(CNS(C)(=O)=O)c5)nccc4[nH]2)=NC3)c1]
1735 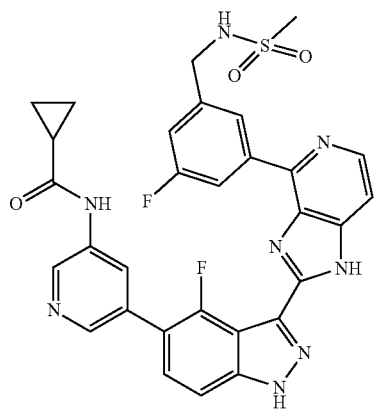 [SMILES: CS(=O)(=O)NCc1cc(F)cc(-c2nccc3[nH]c(-c4n[nH]c5ccc(-c6cncc(NC(=O)C7CC7)c6)c(F)c45)nc23)c1]
1736 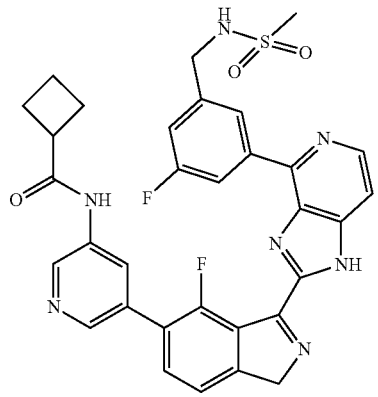 [SMILES: CS(=O)(=O)NCc1cc(F)cc(-c2nccc3[nH]c(C4=NCc5ccc(-c6cncc(NC(=O)C7CCC7)c6)c(F)c54)nc23)c1]
1737 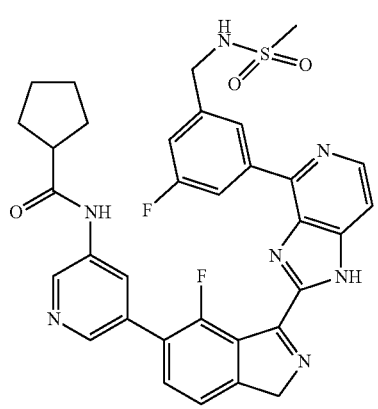 [SMILES: CS(=O)(=O)NCc1cc(F)cc(-c2nccc3[nH]c(C4=NCc5ccc(-c6cncc(NC(=O)C7CCCC7)c6)c(F)c54)nc23)c1]
1738 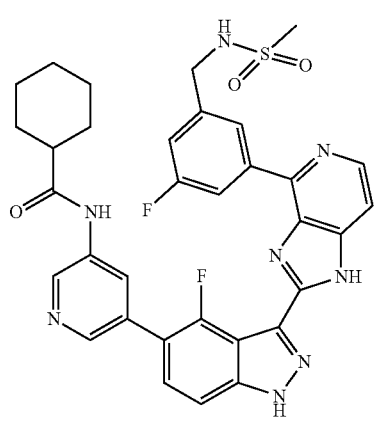 [SMILES: CS(=O)(=O)NCc1cc(F)cc(-c2nccc3[nH]c(-c4n[nH]c5ccc(-c6cncc(NC(=O)C7CCCCC7)c6)c(F)c45)nc23)c1]

TABLE 1-continued
1739
1740
1741
1742
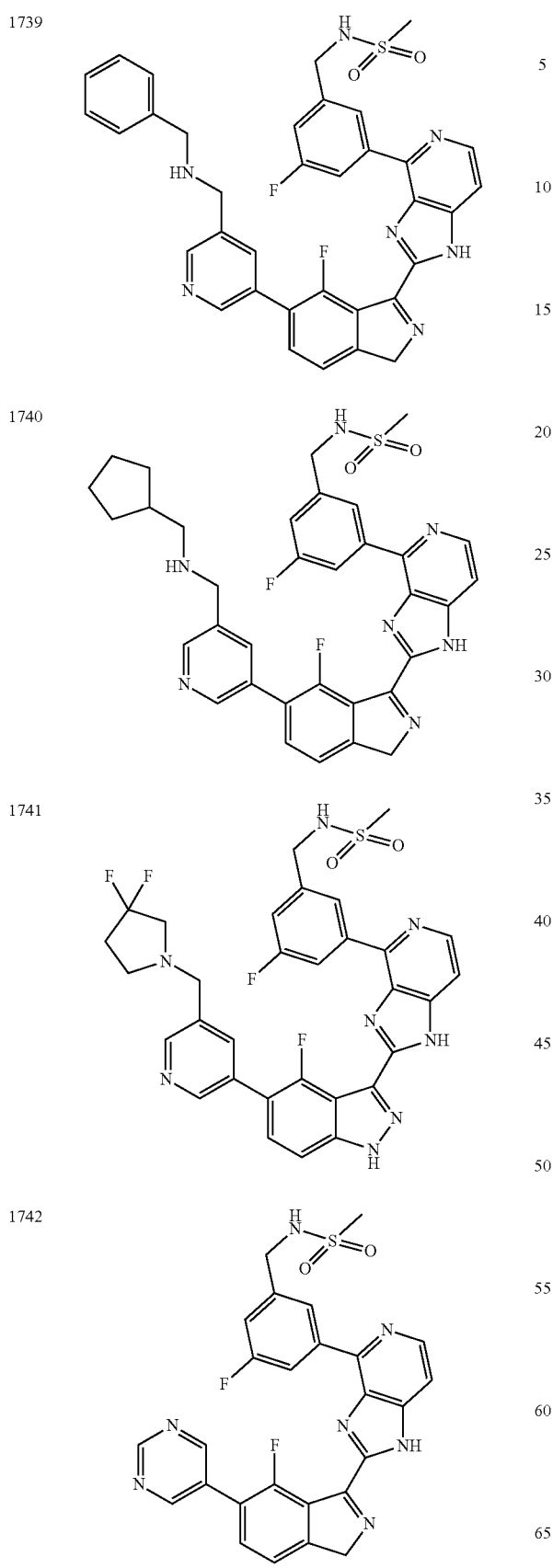
1743
1744
1745
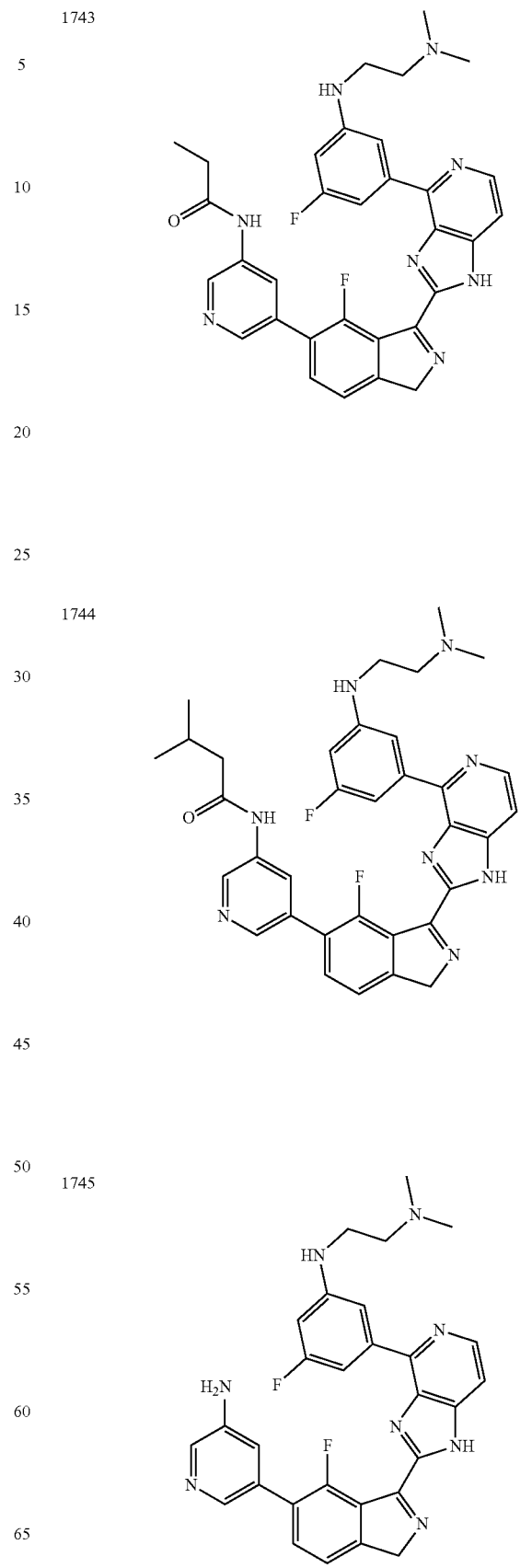

457
TABLE 1-continued
1746
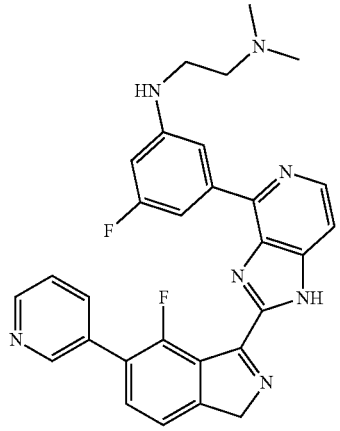 [SMILES: CN(C)CCNc1cc(F)cc(-c2nccc3[nH]c(C4=NCc5ccc(-c6cccnc6)c(F)c54)nc23)c1]
1747
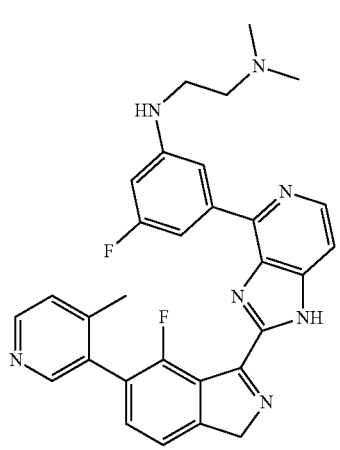 [SMILES: Cc1ccncc1-c1ccc2c(c1F)C(c1nc3c(-c4cc(F)cc(NCCN(C)C)c4)nccc3[nH]1)=NC2]
1748
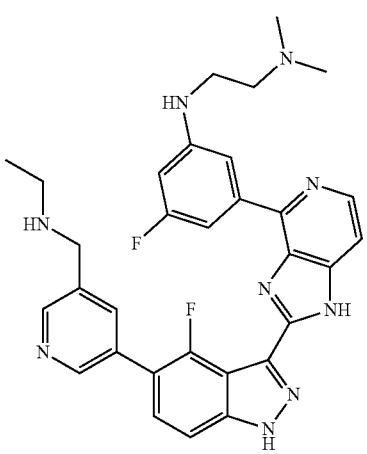 [SMILES: CCNCc1cncc(-c2ccc3[nH]nc(-c4nc5c(-c6cc(F)cc(NCCN(C)C)c6)nccc5[nH]4)c3c2F)c1]
458
TABLE 1-continued
1749
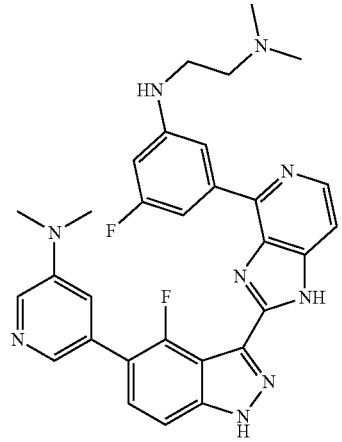 [SMILES: CN(C)CCNc1cc(F)cc(-c2nccc3[nH]c(-c4n[nH]c5ccc(-c6cncc(N(C)C)c6)c(F)c45)nc23)c1]
1750
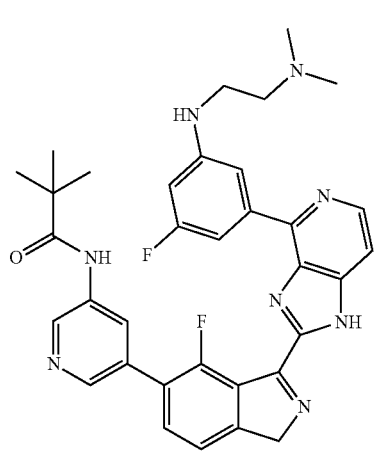 [SMILES: CN(C)CCNc1cc(F)cc(-c2nccc3[nH]c(C4=NCc5ccc(-c6cncc(NC(=O)C(C)(C)C)c6)c(F)c54)nc23)c1]
1751
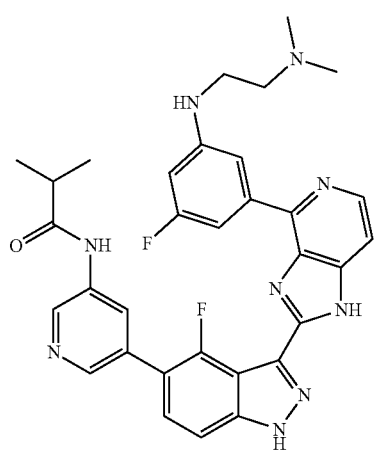 [SMILES: CC(C)C(=O)Nc1cncc(-c2ccc3[nH]nc(-c4nc5c(-c6cc(F)cc(NCCN(C)C)c6)nccc5[nH]4)c3c2F)c1]

TABLE 1-continued
1752
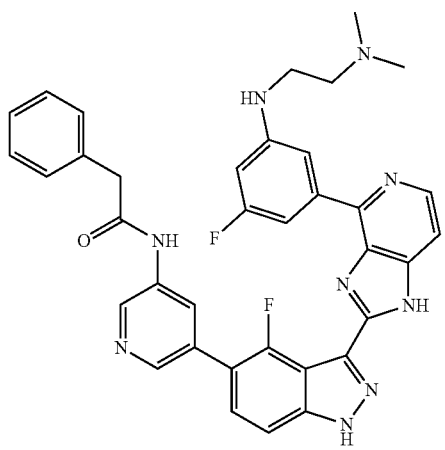 [SMILES: CN(C)CCNc1cc(F)cc(-c2nccc3[nH]c(-c4n[nH]c5ccc(-c6cncc(NC(=O)Cc7ccccc7)c6)c(F)c45)nc23)c1]
1753
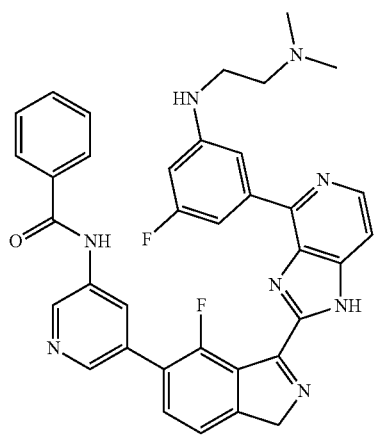 [SMILES: CN(C)CCNc1cc(F)cc(-c2nccc3[nH]c(C4=NCc5ccc(-c6cncc(NC(=O)c7ccccc7)c6)c(F)c54)nc23)c1]
1754
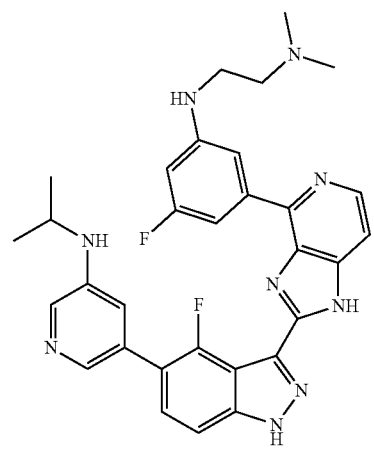
TABLE 1-continued
1755
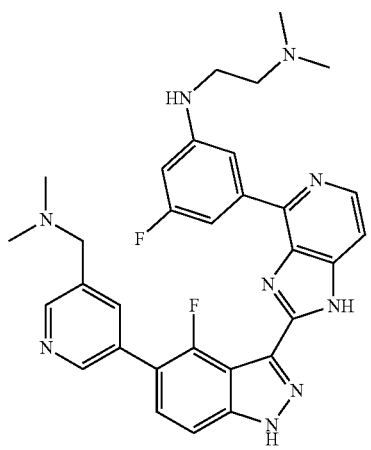 [SMILES: CN(C)CCNc1cc(F)cc(-c2nccc3[nH]c(-c4n[nH]c5ccc(-c6cncc(CN(C)C)c6)c(F)c45)nc23)c1]
1756
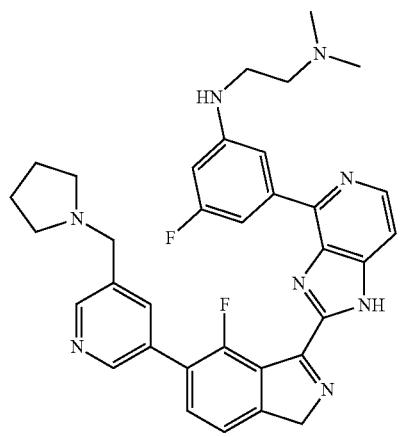 [SMILES: CN(C)CCNc1cc(F)cc(-c2nccc3[nH]c(C4=NCc5ccc(-c6cncc(CN7CCCC7)c6)c(F)c54)nc23)c1]
1757
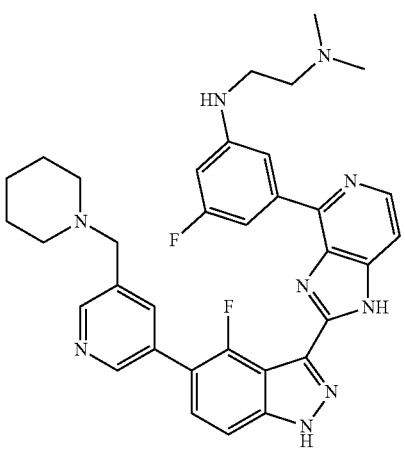 [SMILES: CN(C)CCNc1cc(F)cc(-c2nccc3[nH]c(-c4n[nH]c5ccc(-c6cncc(CN7CCCCC7)c6)c(F)c45)nc23)c1]

TABLE 1-continued
1758
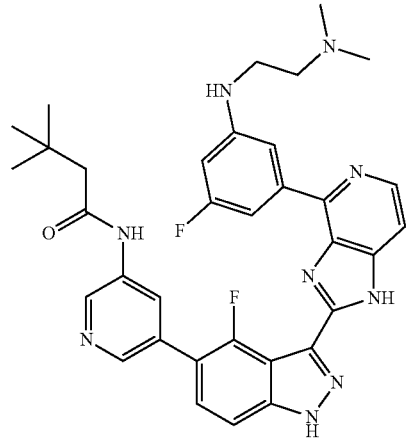
1759
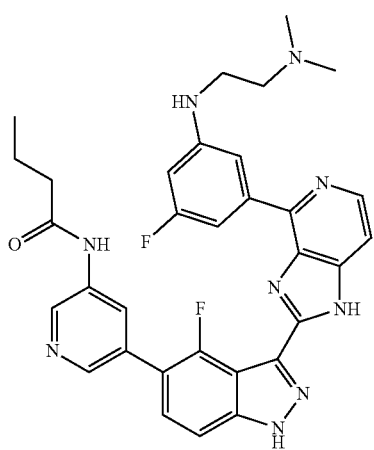 [SMILES: CCCC(=O)Nc1cncc(-c2ccc3[nH]nc(-c4nc5c(-c6cc(F)cc(NCCN(C)C)c6)nccc5[nH]4)c3c2F)c1]
1760
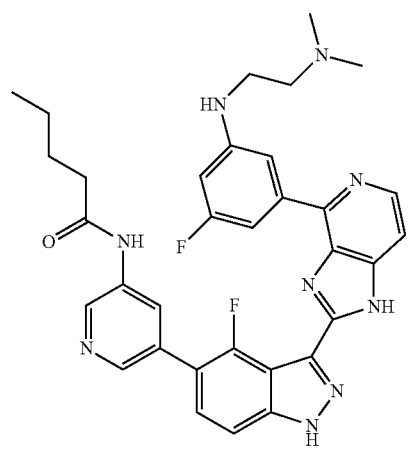 [SMILES: CCCCC(=O)Nc1cncc(-c2ccc3[nH]nc(-c4nc5c(-c6cc(F)cc(NCCN(C)C)c6)nccc5[nH]4)c3c2F)c1]
TABLE 1-continued
1761
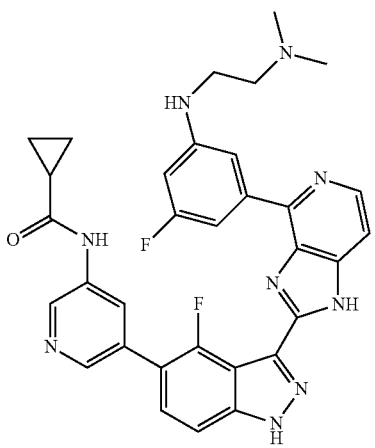 [SMILES: CN(C)CCNc1cc(F)cc(-c2nccc3[nH]c(-c4n[nH]c5ccc(-c6cncc(NC(=O)C7CC7)c6)c(F)c45)nc23)c1]
1762
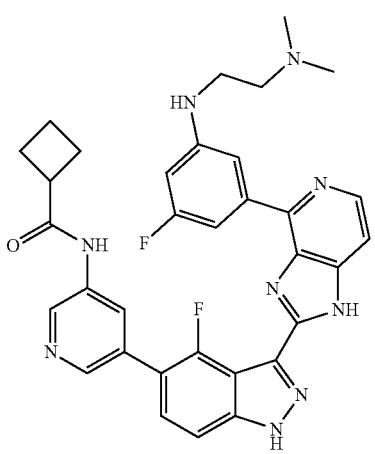 [SMILES: CN(C)CCNc1cc(F)cc(-c2nccc3[nH]c(-c4n[nH]c5ccc(-c6cncc(NC(=O)C7CCC7)c6)c(F)c45)nc23)c1]
1763
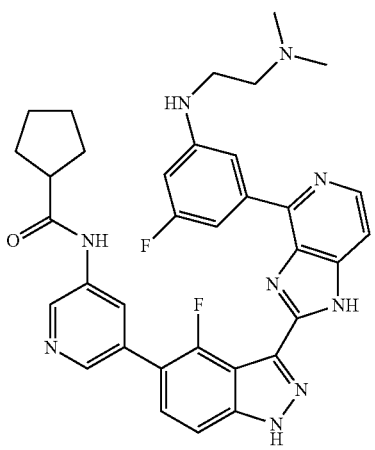 [SMILES: CN(C)CCNc1cc(F)cc(-c2nccc3[nH]c(-c4n[nH]c5ccc(-c6cncc(NC(=O)C7CCCC7)c6)c(F)c45)nc23)c1]

TABLE 1-continued
1764
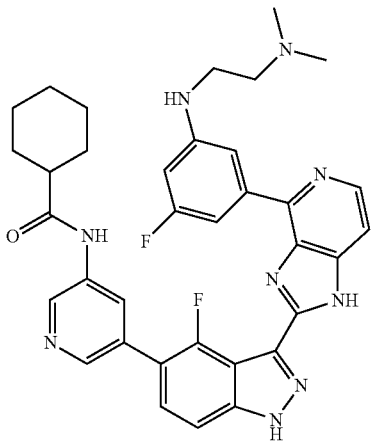 [SMILES: CN(C)CCNc1cc(F)cc(-c2nccc3[nH]c(-c4n[nH]c5ccc(-c6cncc(NC(=O)C7CCCCC7)c6)c(F)c45)nc23)c1]
1765
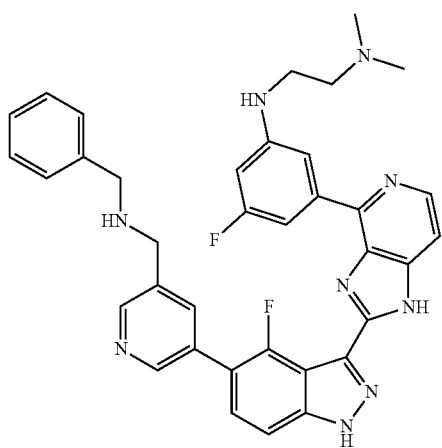 [SMILES: CN(C)CCNc1cc(F)cc(-c2nccc3[nH]c(-c4n[nH]c5ccc(-c6cncc(CNCc7ccccc7)c6)c(F)c45)nc23)c1]
1766
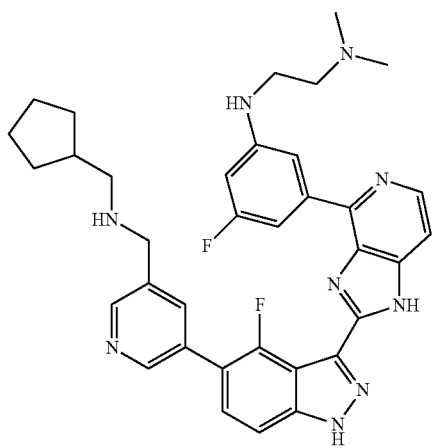 [SMILES: CN(C)CCNc1cc(F)cc(-c2nccc3[nH]c(-c4n[nH]c5ccc(-c6cncc(CNCC7CCCC7)c6)c(F)c45)nc23)c1]
TABLE 1-continued
1767
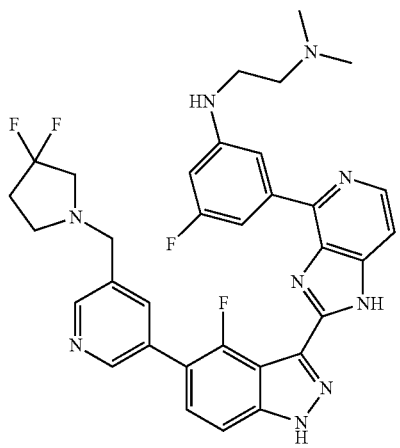 [SMILES: CN(C)CCNc1cc(F)cc(-c2nccc3[nH]c(-c4n[nH]c5ccc(-c6cncc(CN7CCC(F)(F)C7)c6)c(F)c45)nc23)c1]
1768
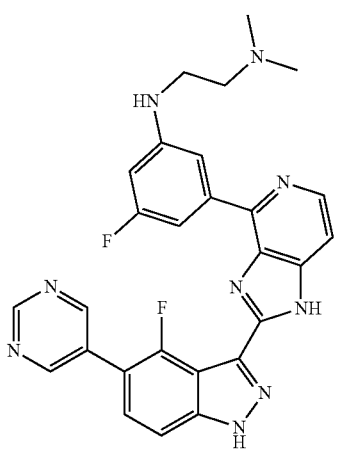 [SMILES: CN(C)CCNc1cc(F)cc(-c2nccc3[nH]c(-c4n[nH]c5ccc(-c6cncnc6)c(F)c45)nc23)c1]
1769
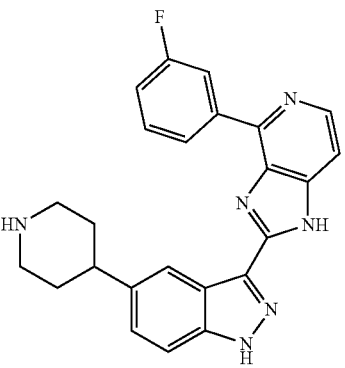 [SMILES: Fc1cccc(-c2nccc3[nH]c(-c4n[nH]c5ccc(C6CCNCC6)cc45)nc23)c1]
1770
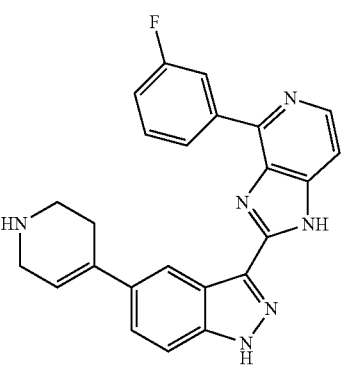 [SMILES: Fc1cccc(-c2nccc3[nH]c(-c4n[nH]c5ccc(C6=CCNCC6)cc45)nc23)c1]

TABLE 1-continued
1771 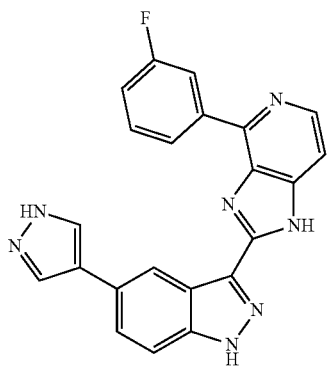 [SMILES: Fc1cccc(-c2nccc3[nH]c(-c4n[nH]c5ccc(-c6cn[nH]c6)cc45)nc23)c1]
1772 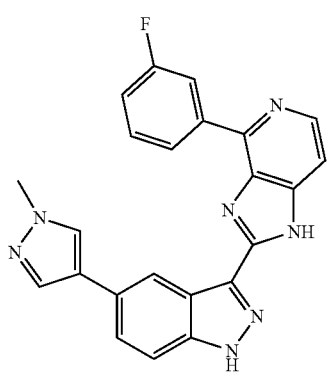 [SMILES: Cn1cc(-c2ccc3[nH]nc(-c4nc5c(-c6cccc(F)c6)nccc5[nH]4)c3c2)cn1]
1773 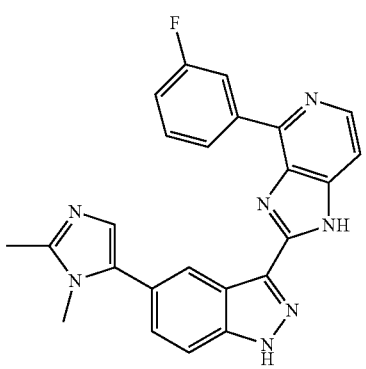 [SMILES: Cc1ncc(-c2ccc3[nH]nc(-c4nc5c(-c6cccc(F)c6)nccc5[nH]4)c3c2)n1C]
1774 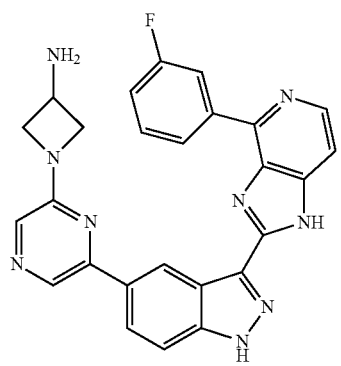 [SMILES: NC1CN(c2cncc(-c3ccc4[nH]nc(-c5nc6c(-c7cccc(F)c7)nccc6[nH]5)c4c3)n2)C1]
1775 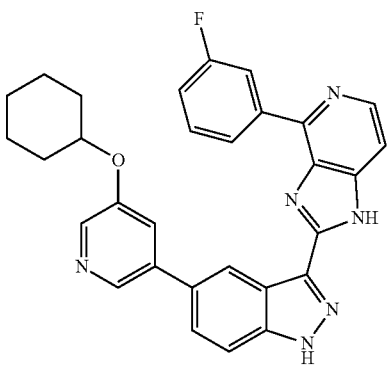 [SMILES: Fc1cccc(-c2nccc3[nH]c(-c4n[nH]c5ccc(-c6cncc(OC7CCCCC7)c6)cc45)nc23)c1]
1776 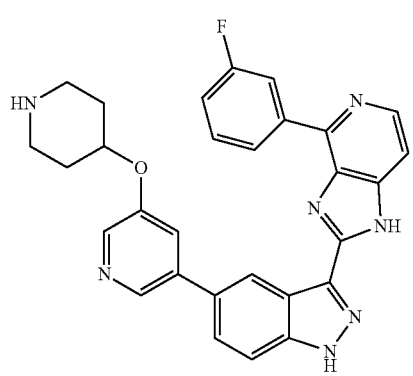 [SMILES: Fc1cccc(-c2nccc3[nH]c(-c4n[nH]c5ccc(-c6cncc(OC7CCNCC7)c6)cc45)nc23)c1]
1777 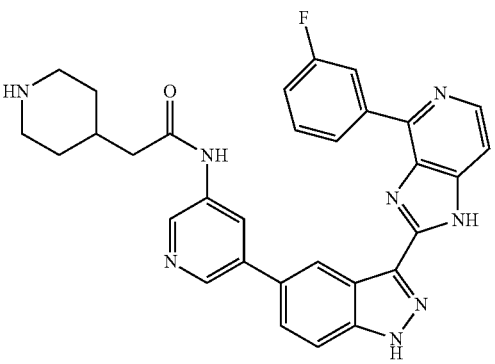 [SMILES: O=C(CC1CCNCC1)Nc1cncc(-c2ccc3[nH]nc(-c4nc5c(-c6cccc(F)c6)nccc5[nH]4)c3c2)c1]
1778 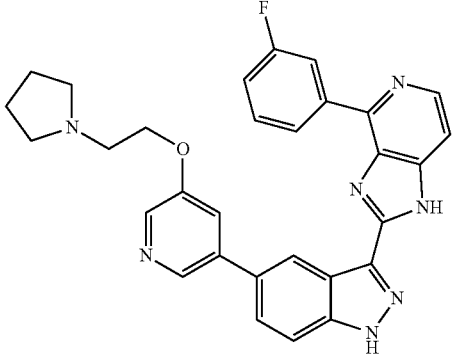 [SMILES: Fc1cccc(-c2nccc3[nH]c(-c4n[nH]c5ccc(-c6cncc(OCCN7CCCC7)c6)cc45)nc23)c1]

TABLE 1-continued
1779 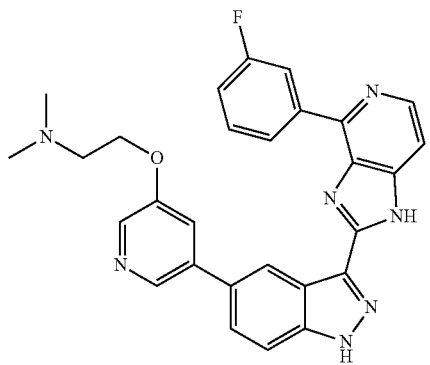 [SMILES: CN(C)CCOc1cncc(-c2ccc3[nH]nc(-c4nc5c(-c6cccc(F)c6)nccc5[nH]4)c3c2)c1]
1780 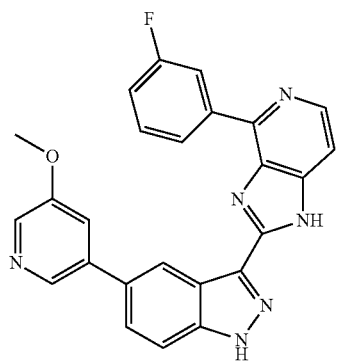 [SMILES: COc1cncc(-c2ccc3[nH]nc(-c4nc5c(-c6cccc(F)c6)nccc5[nH]4)c3c2)c1]
1781 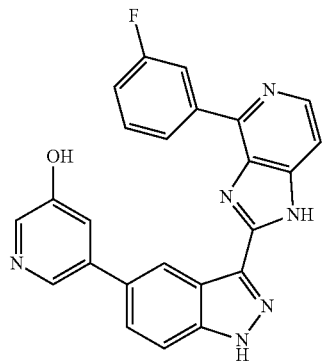 [SMILES: Oc1cncc(-c2ccc3[nH]nc(-c4nc5c(-c6cccc(F)c6)nccc5[nH]4)c3c2)c1]
1782 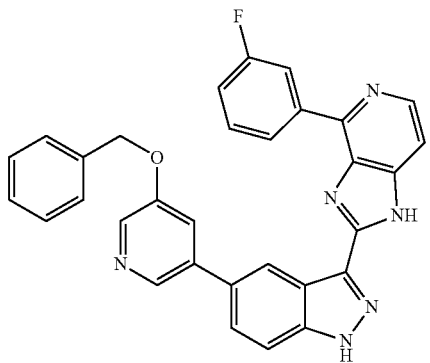 [SMILES: Fc1cccc(-c2nccc3[nH]c(-c4n[nH]c5ccc(-c6cncc(OCc7ccccc7)c6)cc45)nc23)c1]
TABLE 1-continued
1783 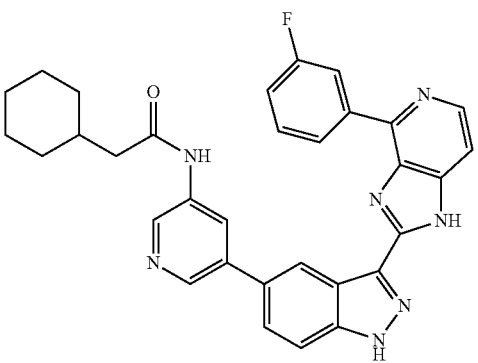 [SMILES: O=C(CC1CCCCC1)Nc1cncc(-c2ccc3[nH]nc(-c4nc5c(-c6cccc(F)c6)nccc5[nH]4)c3c2)c1]
1784 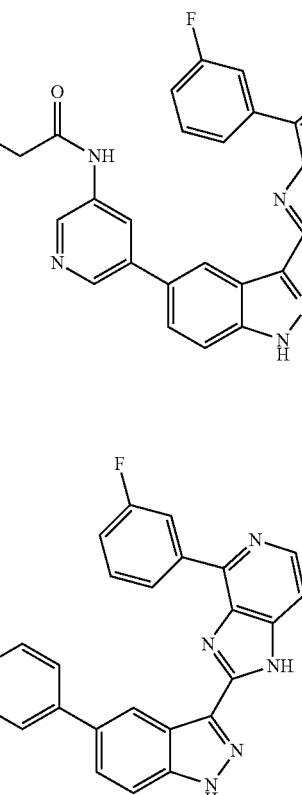
1785 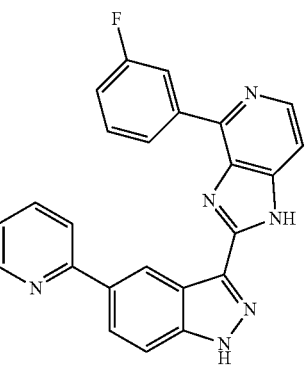 [SMILES: Fc1cccc(-c2nccc3[nH]c(-c4n[nH]c5ccc(-c6ccccn6)cc45)nc23)c1]
1786 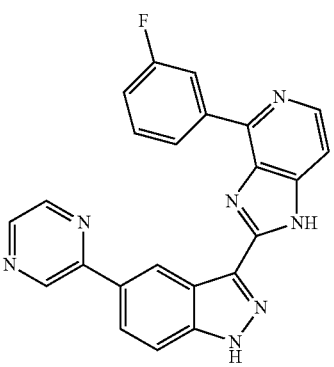 [SMILES: Fc1cccc(-c2nccc3[nH]c(-c4n[nH]c5ccc(-c6cnccn6)cc45)nc23)c1]

TABLE 1-continued
1787 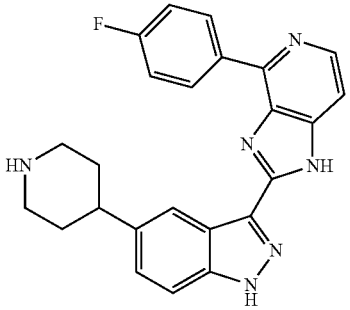 [SMILES: Fc1ccc(-c2nccc3[nH]c(-c4n[nH]c5ccc(C6CCNCC6)cc45)nc23)cc1]
1788 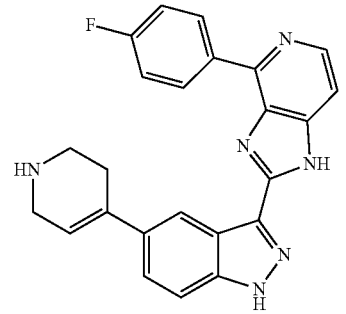 [SMILES: Fc1ccc(-c2nccc3[nH]c(-c4n[nH]c5ccc(C6=CCNCC6)cc45)nc23)cc1]
1789 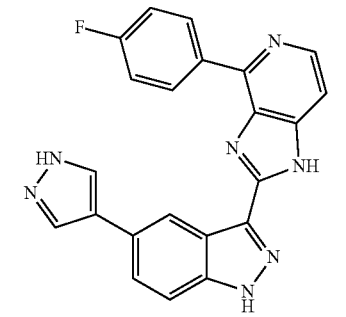 [SMILES: Fc1ccc(-c2nccc3[nH]c(-c4n[nH]c5ccc(-c6cn[nH]c6)cc45)nc23)cc1]
1790 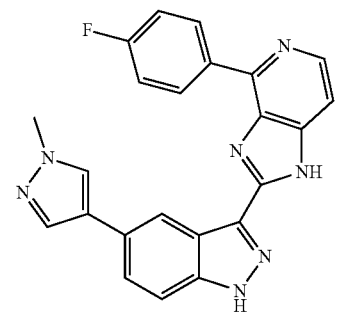 [SMILES: Cn1cc(-c2ccc3[nH]nc(-c4nc5c(-c6ccc(F)cc6)nccc5[nH]4)c3c2)cn1]
1791 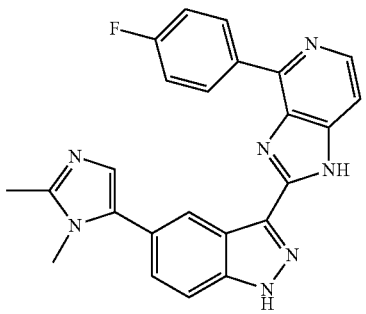 [SMILES: Cc1ncc(-c2ccc3[nH]nc(-c4nc5c(-c6ccc(F)cc6)nccc5[nH]4)c3c2)n1C]
TABLE 1-continued
1792 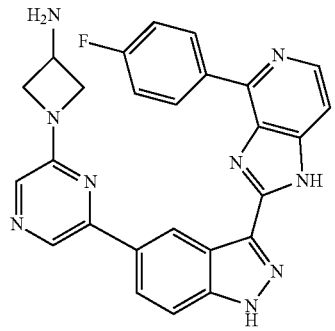 [SMILES: NC1CN(c2cncc(-c3ccc4[nH]nc(-c5nc6c(-c7ccc(F)cc7)nccc6[nH]5)c4c3)n2)C1]
1793 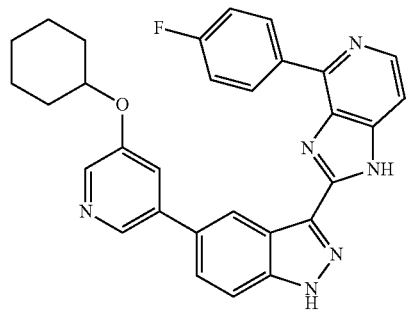 [SMILES: Fc1ccc(-c2nccc3[nH]c(-c4n[nH]c5ccc(-c6cncc(OC7CCCCC7)c6)cc45)nc23)cc1]
1794 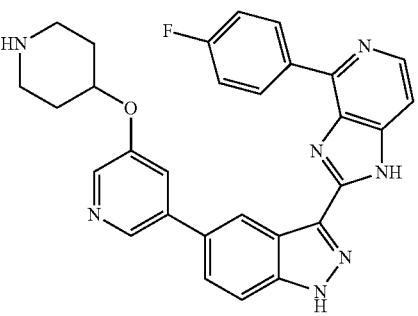 [SMILES: Fc1ccc(-c2nccc3[nH]c(-c4n[nH]c5ccc(-c6cncc(OC7CCNCC7)c6)cc45)nc23)cc1]
1795 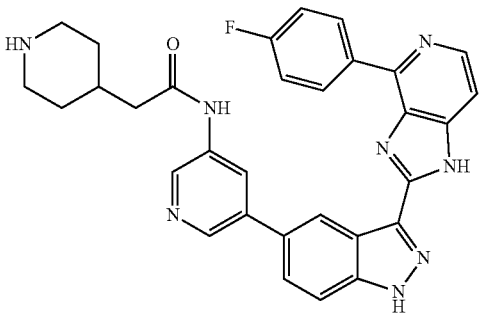 [SMILES: O=C(CC1CCNCC1)Nc1cncc(-c2ccc3[nH]nc(-c4nc5c(-c6ccc(F)cc6)nccc5[nH]4)c3c2)c1]
1796 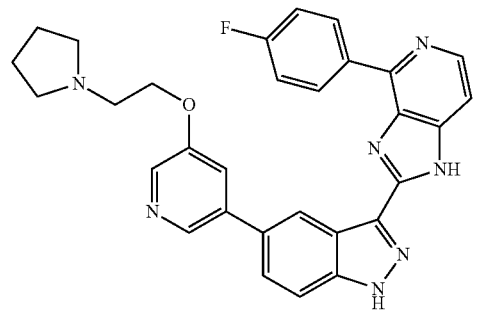 [SMILES: Fc1ccc(-c2nccc3[nH]c(-c4n[nH]c5ccc(-c6cncc(OCCN7CCCC7)c6)cc45)nc23)cc1]

TABLE 1-continued
1797 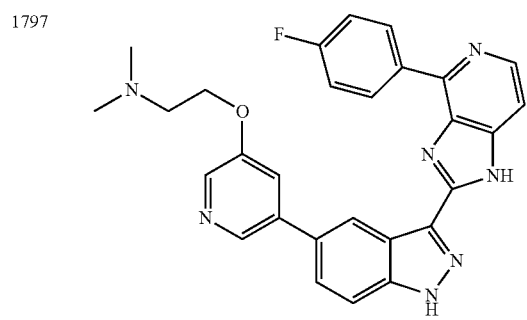
1798 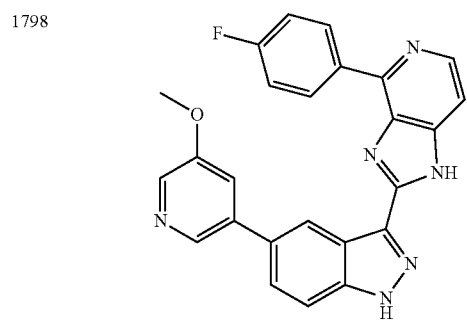
1799 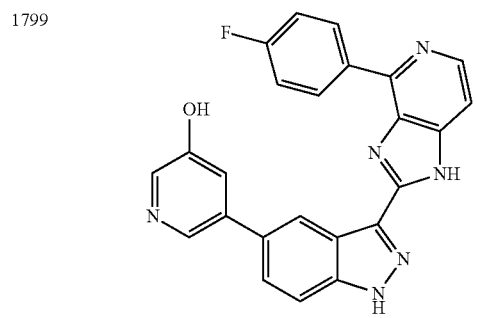
1800 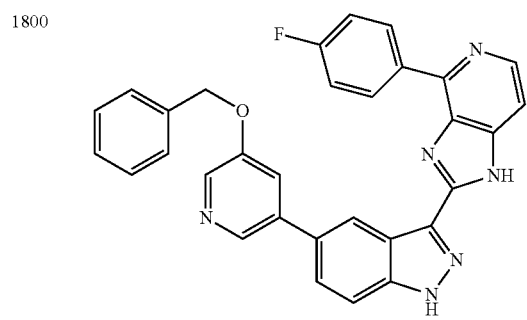
1801 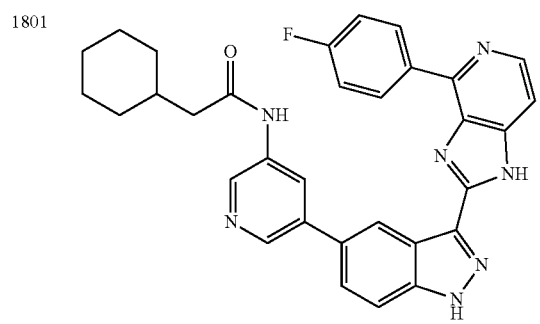
TABLE 1-continued
1802 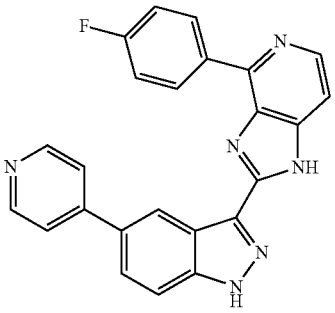 [SMILES: Fc1ccc(-c2nccc3[nH]c(-c4n[nH]c5ccc(-c6ccncc6)cc45)nc23)cc1]
1803 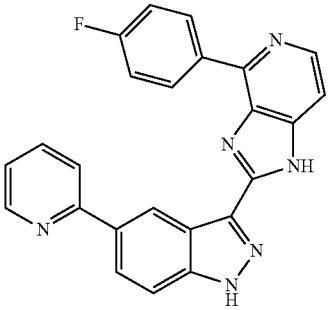 [SMILES: Fc1ccc(-c2nccc3[nH]c(-c4n[nH]c5ccc(-c6ccccn6)cc45)nc23)cc1]
1804 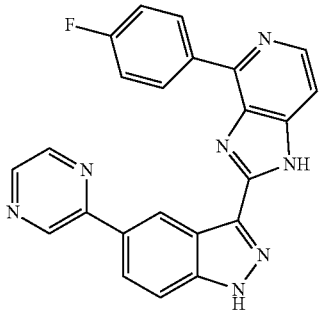 [SMILES: Fc1ccc(-c2nccc3[nH]c(-c4n[nH]c5ccc(-c6cnccn6)cc45)nc23)cc1]
1805 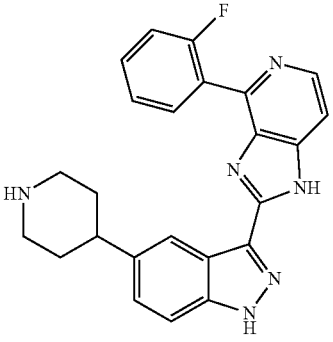 [SMILES: Fc1ccccc1-c1nccc2[nH]c(-c3n[nH]c4ccc(C5CCNCC5)cc34)nc12]
1806 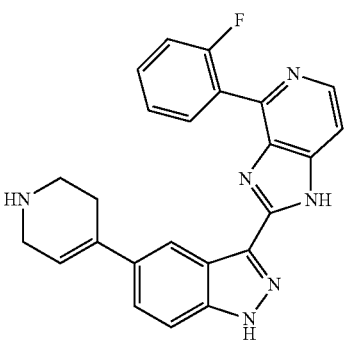 [SMILES: Fc1ccccc1-c1nccc2[nH]c(-c3n[nH]c4ccc(C5=CCNCC5)cc34)nc12]

TABLE 1-continued
| 1807 | 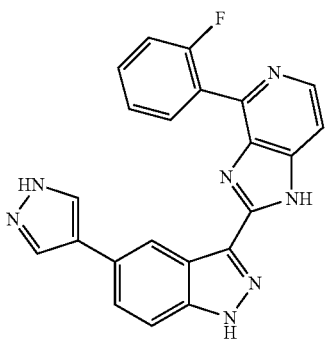 [SMILES: Fc1ccccc1-c1nccc2[nH]c(-c3n[nH]c4ccc(-c5cn[nH]c5)cc34)nc12] |
| 1808 | 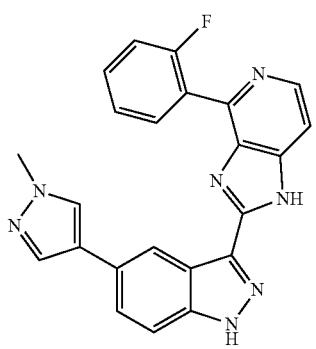 [SMILES: Cn1cc(-c2ccc3[nH]nc(-c4nc5c(-c6ccccc6F)nccc5[nH]4)c3c2)cn1] |
| 1809 | 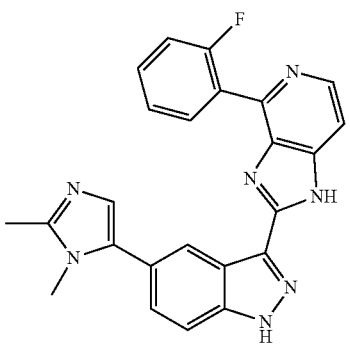 [SMILES: Cc1ncc(-c2ccc3[nH]nc(-c4nc5c(-c6ccccc6F)nccc5[nH]4)c3c2)n1C] |
| 1810 | 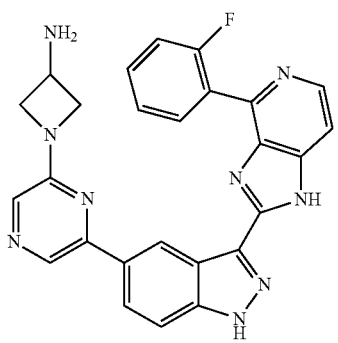 [SMILES: NC1CN(c2cncc(-c3ccc4[nH]nc(-c5nc6c(-c7ccccc7F)nccc6[nH]5)c4c3)n2)C1] |
| 1811 | 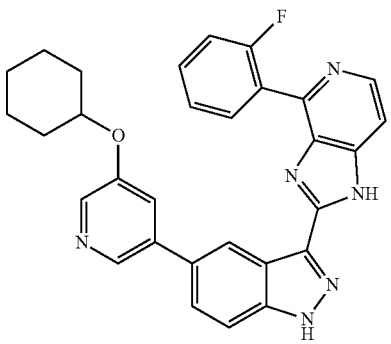 [SMILES: Fc1ccccc1-c1nccc2[nH]c(-c3n[nH]c4ccc(-c5cncc(OC6CCCCC6)c5)cc34)nc12] |
| 1812 | 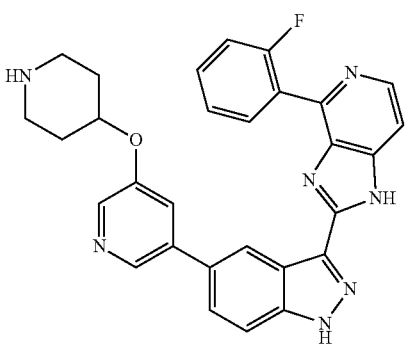 [SMILES: Fc1ccccc1-c1nccc2[nH]c(-c3n[nH]c4ccc(-c5cncc(OC6CCNCC6)c5)cc34)nc12] |
| 1813 | 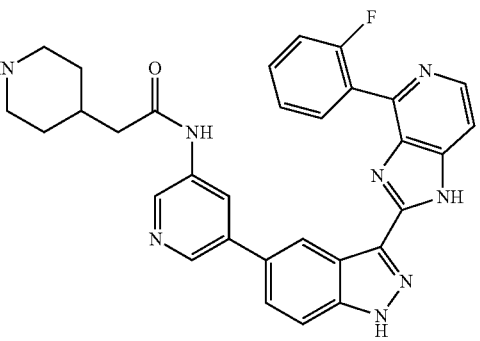 |
| 1814 | 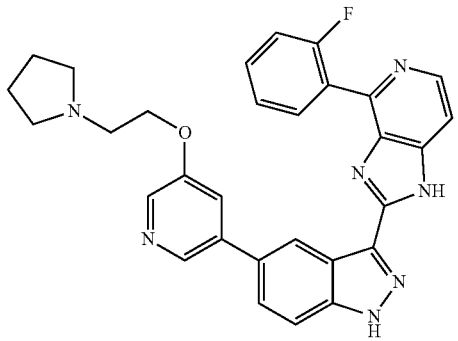 [SMILES: Fc1ccccc1-c1nccc2[nH]c(-c3n[nH]c4ccc(-c5cncc(OCCN6CCCC6)c5)cc34)nc12] |

TABLE 1-continued
1815 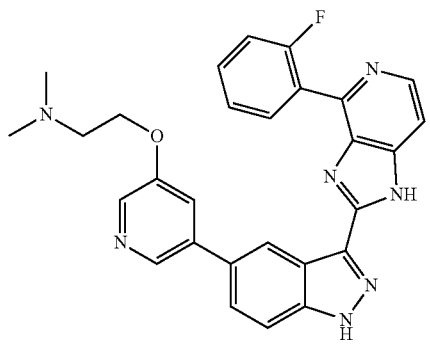 [SMILES: CN(C)CCOc1cncc(-c2ccc3[nH]nc(-c4nc5c(-c6ccccc6F)nccc5[nH]4)c3c2)c1]
1816 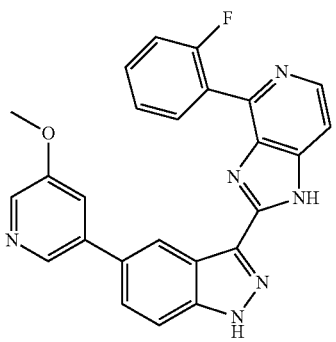 [SMILES: COc1cncc(-c2ccc3[nH]nc(-c4nc5c(-c6ccccc6F)nccc5[nH]4)c3c2)c1]
1817 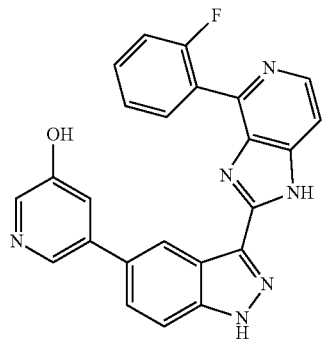 [SMILES: Oc1cncc(-c2ccc3[nH]nc(-c4nc5c(-c6ccccc6F)nccc5[nH]4)c3c2)c1]
1818 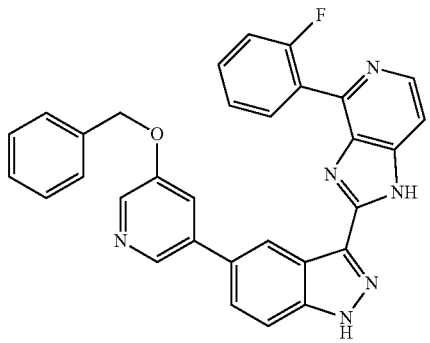 [SMILES: Fc1ccccc1-c1nccc2[nH]c(-c3n[nH]c4ccc(-c5cncc(OCc6ccccc6)c5)cc34)nc12]
1819 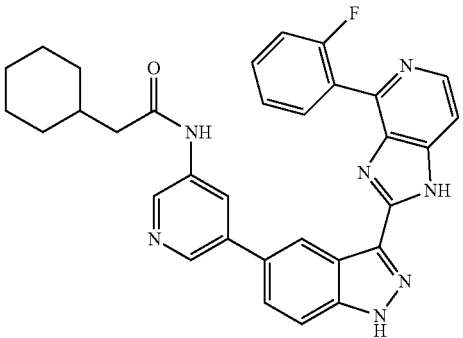 [SMILES: O=C(CC1CCCCC1)Nc1cncc(-c2ccc3[nH]nc(-c4nc5c(-c6ccccc6F)nccc5[nH]4)c3c2)c1]
1820 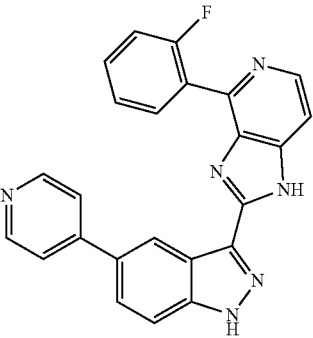 [SMILES: Fc1ccccc1-c1nccc2[nH]c(-c3n[nH]c4ccc(-c5ccncc5)cc34)nc12]
1821 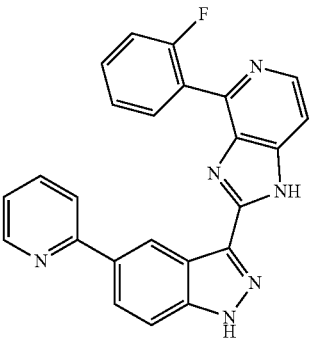 [SMILES: Fc1ccccc1-c1nccc2[nH]c(-c3n[nH]c4ccc(-c5ccccn5)cc34)nc12]
1822 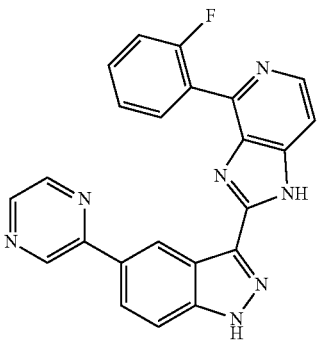 [SMILES: Fc1ccccc1-c1nccc2[nH]c(-c3n[nH]c4ccc(-c5cnccn5)cc34)nc12]

TABLE 1-continued
| 1823 | 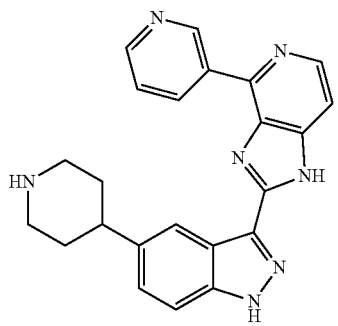 | 1828 | 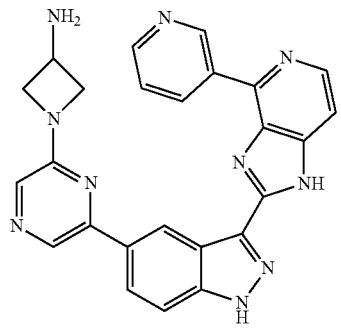 |
| 1824 | 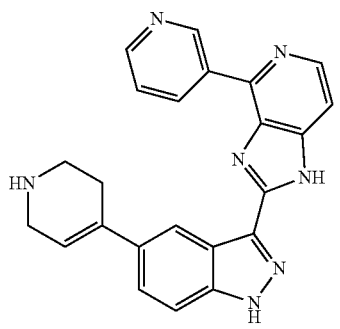 [SMILES: C1=C(c2ccc3[nH]nc(-c4nc5c(-c6cccnc6)nccc5[nH]4)c3c2)CCNC1] | 1829 | 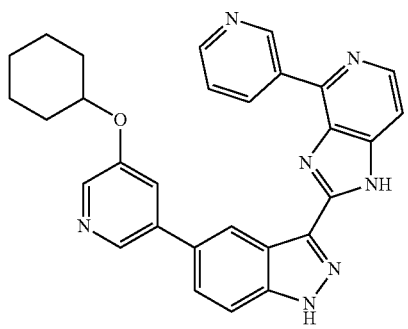 |
| 1825 | 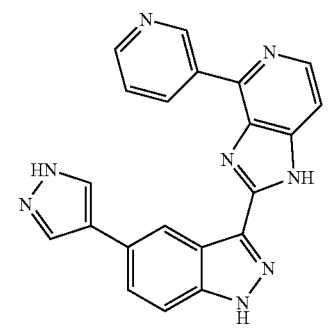 [SMILES: c1cncc(-c2nccc3[nH]c(-c4n[nH]c5ccc(-c6cn[nH]c6)cc45)nc23)c1] | 1830 | 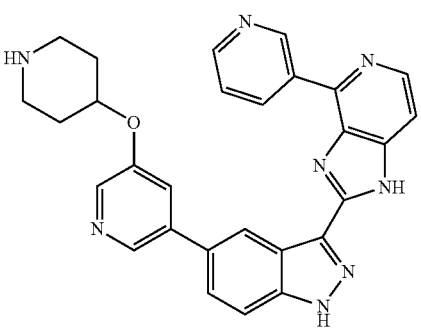 |
| 1826 | 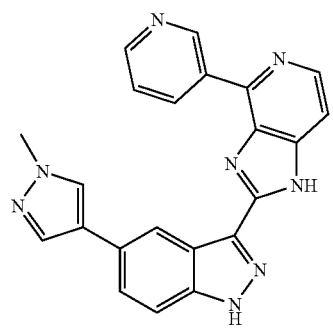 [SMILES: Cn1cc(-c2ccc3[nH]nc(-c4nc5c(-c6cccnc6)nccc5[nH]4)c3c2)cn1] | 1831 | 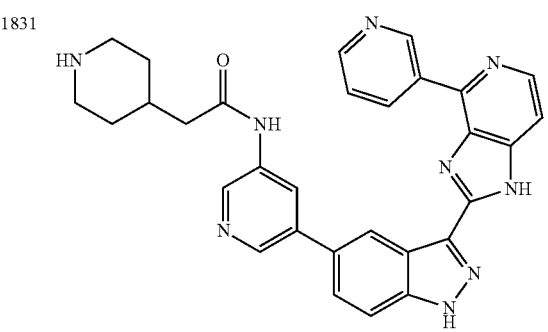 |
| 1827 | 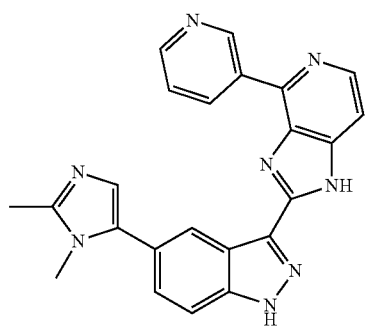 [SMILES: Cc1ncc(-c2ccc3[nH]nc(-c4nc5c(-c6cccnc6)nccc5[nH]4)c3c2)n1C] | 1832 | 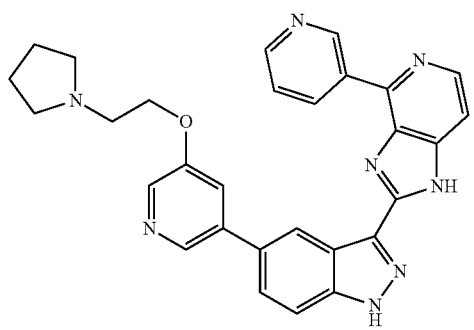 [SMILES: c1cncc(-c2nccc3[nH]c(-c4n[nH]c5ccc(-c6cncc(OCCN7CCCC7)c6)cc45)nc23)c1] |

TABLE 1-continued
| | |
|---|---|
| 1833 | 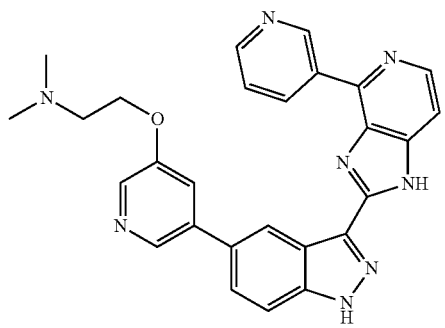 [SMILES: CN(C)CCOc1cncc(-c2ccc3[nH]nc(-c4nc5c(-c6cccnc6)nccc5[nH]4)c3c2)c1] |
| 1834 | 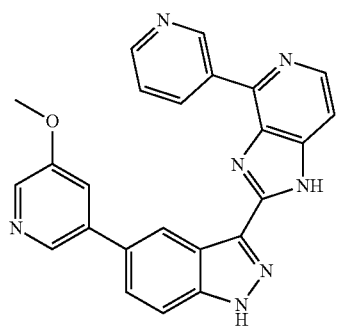 [SMILES: COc1cncc(-c2ccc3[nH]nc(-c4nc5c(-c6cccnc6)nccc5[nH]4)c3c2)c1] |
| 1835 | 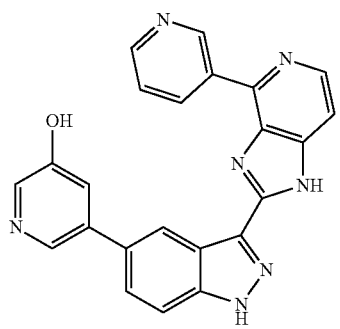 [SMILES: Oc1cncc(-c2ccc3[nH]nc(-c4nc5c(-c6cccnc6)nccc5[nH]4)c3c2)c1] |
| 1836 | 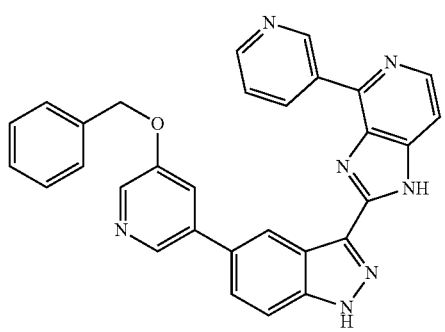 [SMILES: c1ccc(COc2cncc(-c3ccc4[nH]nc(-c5nc6c(-c7cccnc7)nccc6[nH]5)c4c3)c2)cc1] |
| 1837 | 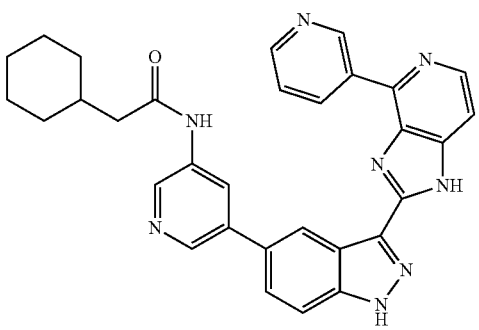 [SMILES: O=C(CC1CCCCC1)Nc1cncc(-c2ccc3[nH]nc(-c4nc5c(-c6cccnc6)nccc5[nH]4)c3c2)c1] |
TABLE 1-continued
| | |
|---|---|
| 1838 | 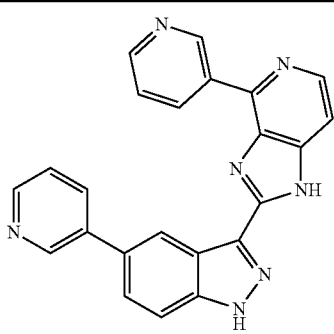 |
| 1839 | 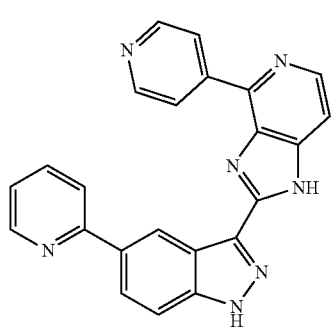 [SMILES: c1ccc(-c2ccc3[nH]nc(-c4nc5c(-c6ccncc6)nccc5[nH]4)c3c2)nc1] |
| 1840 | 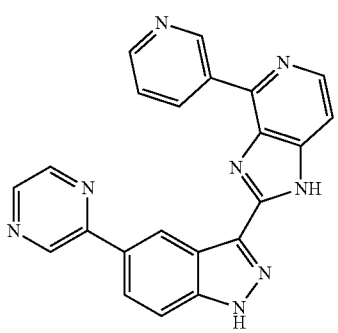 [SMILES: c1cncc(-c2nccc3[nH]c(-c4n[nH]c5ccc(-c6cnccn6)cc45)nc23)c1] |
| 1841 | 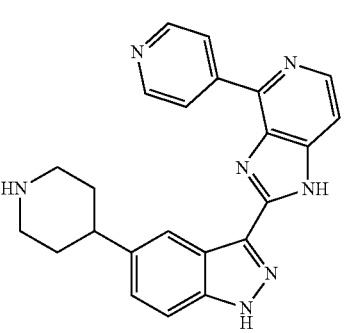 [SMILES: c1cc(-c2nccc3[nH]c(-c4n[nH]c5ccc(C6CCNCC6)cc45)nc23)ccn1] |
| 1842 | 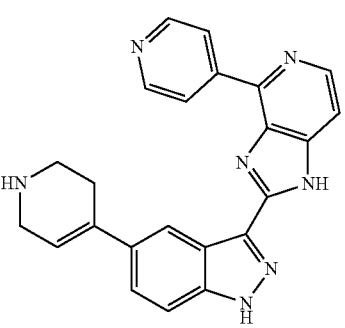 [SMILES: C1=C(c2ccc3[nH]nc(-c4nc5c(-c6ccncc6)nccc5[nH]4)c3c2)CCNC1] |

TABLE 1-continued
| | |
|---|---|
| 1843 | 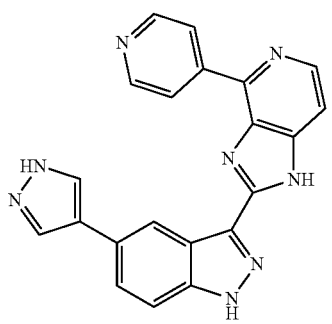 [SMILES: c1cc(-c2nccc3[nH]c(-c4n[nH]c5ccc(-c6cn[nH]c6)cc45)nc23)ccn1] |
| 1844 | 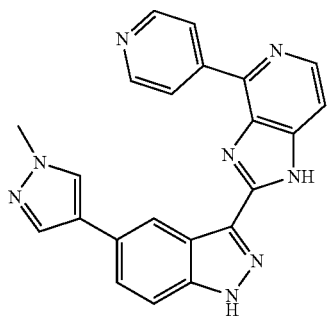 [SMILES: Cn1cc(-c2ccc3[nH]nc(-c4nc5c(-c6ccncc6)nccc5[nH]4)c3c2)cn1] |
| 1845 | 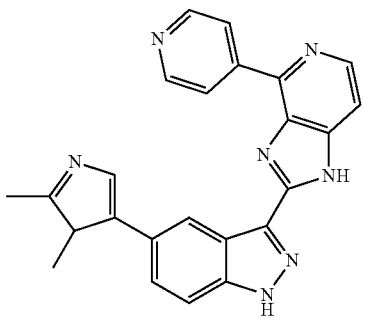 [SMILES: CC1=NC=C(c2ccc3[nH]nc(-c4nc5c(-c6ccncc6)nccc5[nH]4)c3c2)C1C] |
| 1846 | 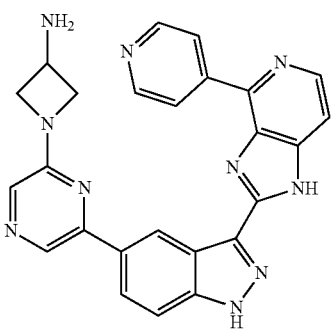 [SMILES: NC1CN(c2cncc(-c3ccc4[nH]nc(-c5nc6c(-c7ccncc7)nccc6[nH]5)c4c3)n2)C1] |
| 1847 | 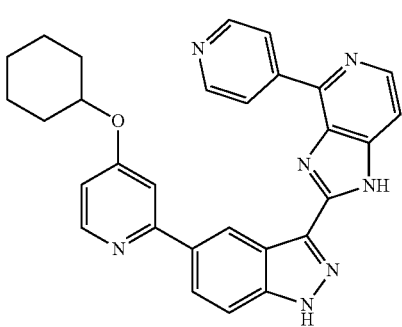 [SMILES: c1cc(-c2nccc3[nH]c(-c4n[nH]c5ccc(-c6cc(OC7CCCCC7)ccn6)cc45)nc23)ccn1] |
TABLE 1-continued
| | |
|---|---|
| 1848 | 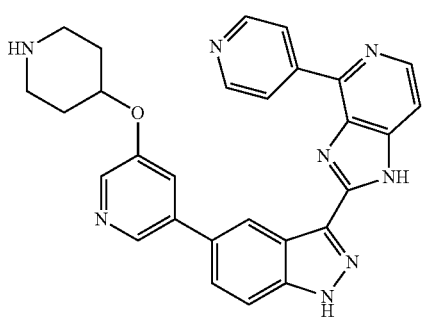 |
| 1849 | 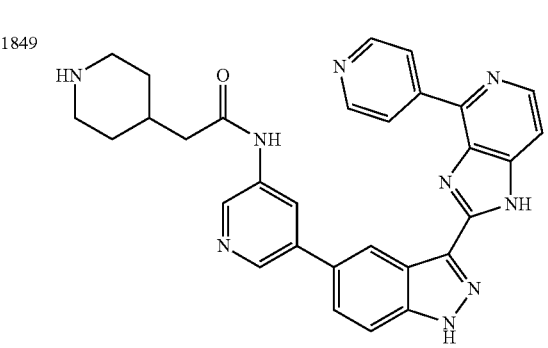 |
| 1850 | 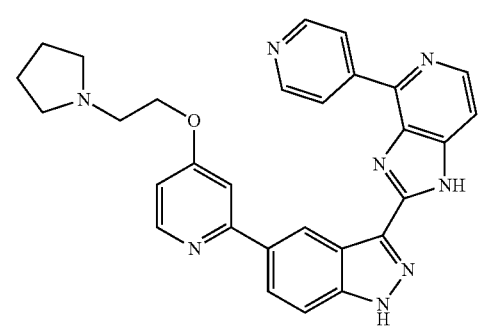 [SMILES: c1cc(-c2nccc3[nH]c(-c4n[nH]c5ccc(-c6cc(OCCN7CCCC7)ccn6)cc45)nc23)ccn1] |
| 1851 | 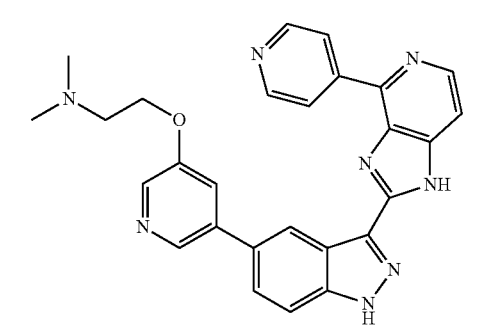 [SMILES: CN(C)CCOc1cncc(-c2ccc3[nH]nc(-c4nc5c(-c6ccncc6)nccc5[nH]4)c3c2)c1] |
| 1852 | 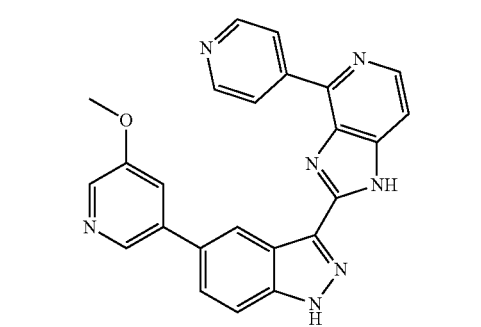 [SMILES: COc1cncc(-c2ccc3[nH]nc(-c4nc5c(-c6ccncc6)nccc5[nH]4)c3c2)c1] |

TABLE 1-continued
| | |
|---|---|
| 1853 | 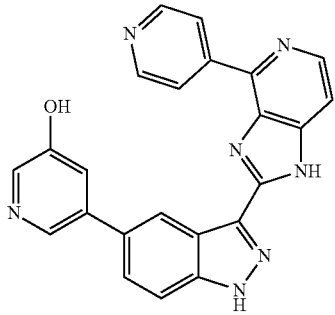 [SMILES: Oc1cncc(-c2ccc3[nH]nc(-c4nc5c(-c6ccncc6)nccc5[nH]4)c3c2)c1] |
| 1854 | 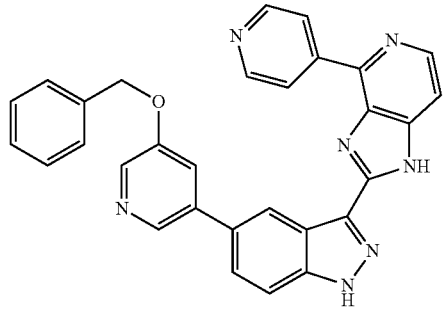 |
| 1855 | 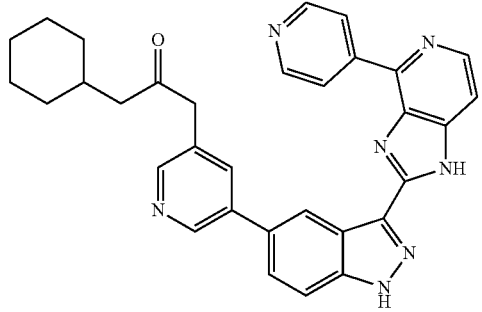 [SMILES: O=C(Cc1cncc(-c2ccc3[nH]nc(-c4nc5c(-c6ccncc6)nccc5[nH]4)c3c2)c1)CC1CCCCC1] |
| 1856 | 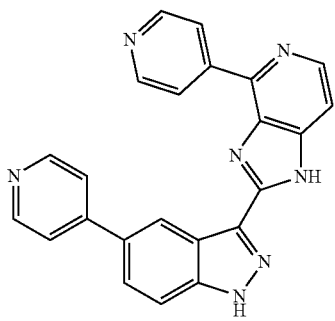 [SMILES: c1cc(-c2ccc3[nH]nc(-c4nc5c(-c6ccncc6)nccc5[nH]4)c3c2)ccn1] |
| 1857 | 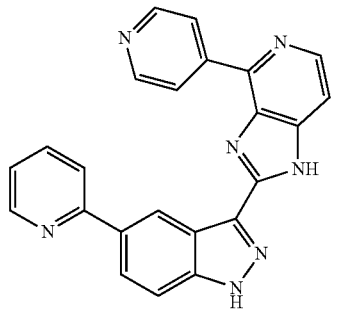 [SMILES: c1ccc(-c2ccc3[nH]nc(-c4nc5c(-c6ccncc6)nccc5[nH]4)c3c2)nc1] |
| 1858 | 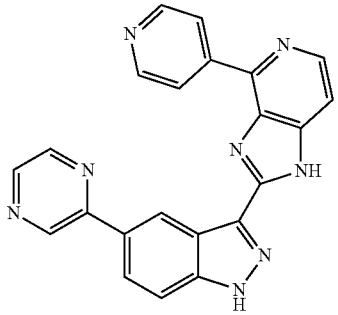 |
| 1859 | 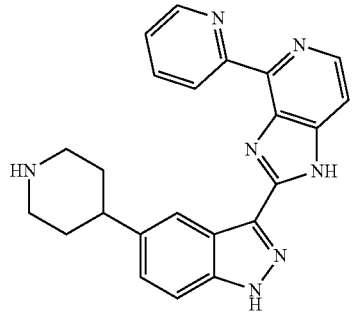 [SMILES: c1ccc(-c2nccc3[nH]c(-c4n[nH]c5ccc(C6CCNCC6)cc45)nc23)nc1] |
| 1860 | 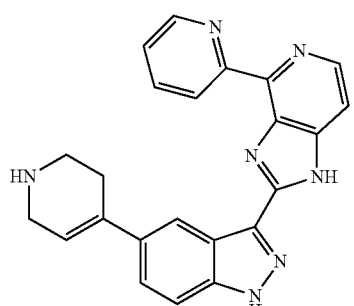 |
| 1861 | 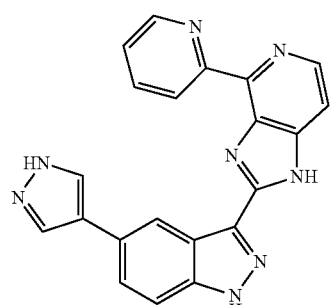 |
| 1862 | 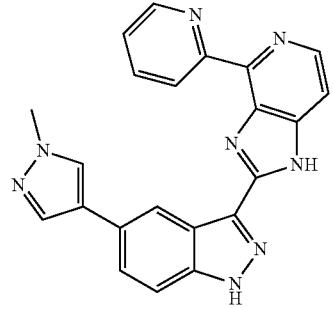 [SMILES: Cn1cc(-c2ccc3[nH]nc(-c4nc5c(-c6ccccn6)nccc5[nH]4)c3c2)cn1] |

TABLE 1-continued
1863 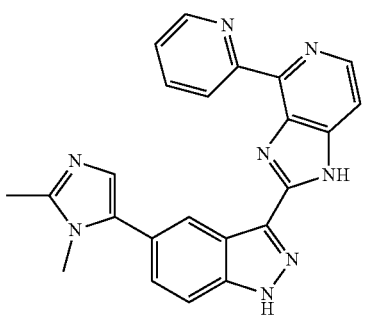 [SMILES: Cc1ncc(-c2ccc3[nH]nc(-c4nc5c(-c6ccccn6)nccc5[nH]4)c3c2)n1C]
1864 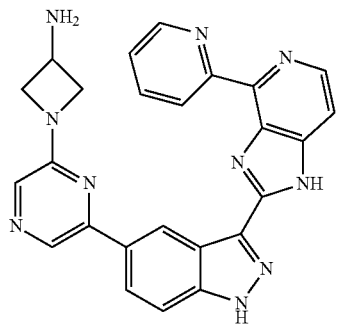 [SMILES: NC1CN(c2cncc(-c3ccc4[nH]nc(-c5nc6c(-c7ccccn7)nccc6[nH]5)c4c3)n2)C1]
1865 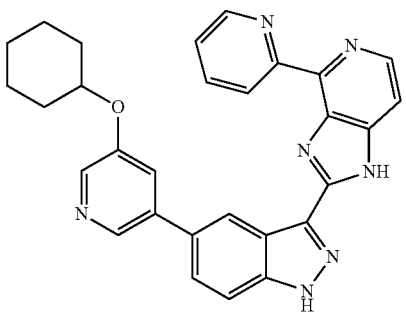 [SMILES: c1ccc(-c2nccc3[nH]c(-c4n[nH]c5ccc(-c6cncc(OC7CCCCC7)c6)cc45)nc23)nc1]
1866 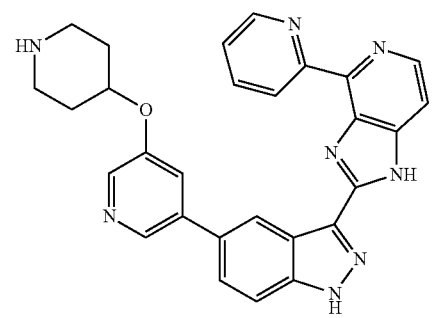 [SMILES: c1ccc(-c2nccc3[nH]c(-c4n[nH]c5ccc(-c6cncc(OC7CCNCC7)c6)cc45)nc23)nc1]
1867 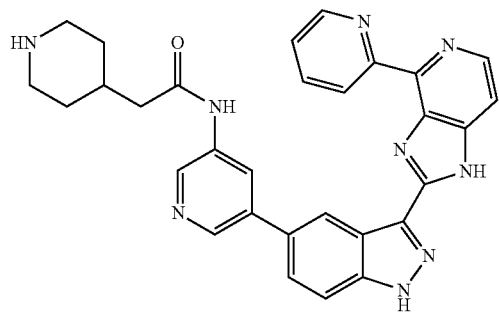 [SMILES: O=C(CC1CCNCC1)Nc1cncc(-c2ccc3[nH]nc(-c4nc5c(-c6ccccn6)nccc5[nH]4)c3c2)c1]
TABLE 1-continued
1868 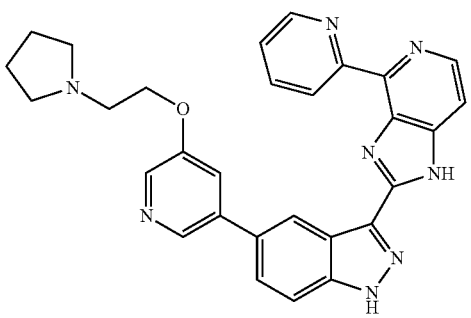 [SMILES: c1ccc(-c2nccc3[nH]c(-c4n[nH]c5ccc(-c6cncc(OCCN7CCCC7)c6)cc45)nc23)nc1]
1869 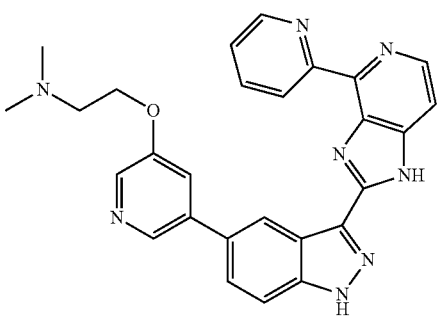 [SMILES: CN(C)CCOc1cncc(-c2ccc3[nH]nc(-c4nc5c(-c6ccccn6)nccc5[nH]4)c3c2)c1]
1870 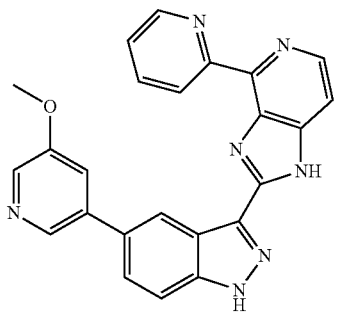 [SMILES: COc1cncc(-c2ccc3[nH]nc(-c4nc5c(-c6ccccn6)nccc5[nH]4)c3c2)c1]
1871 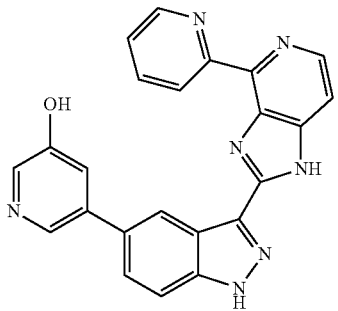 [SMILES: Oc1cncc(-c2ccc3[nH]nc(-c4nc5c(-c6ccccn6)nccc5[nH]4)c3c2)c1]
1872 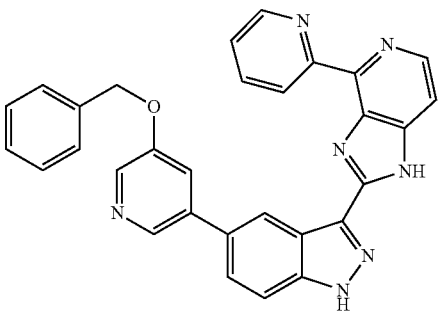 [SMILES: c1ccc(COc2cncc(-c3ccc4[nH]nc(-c5nc6c(-c7ccccn7)nccc6[nH]5)c4c3)c2)cc1]

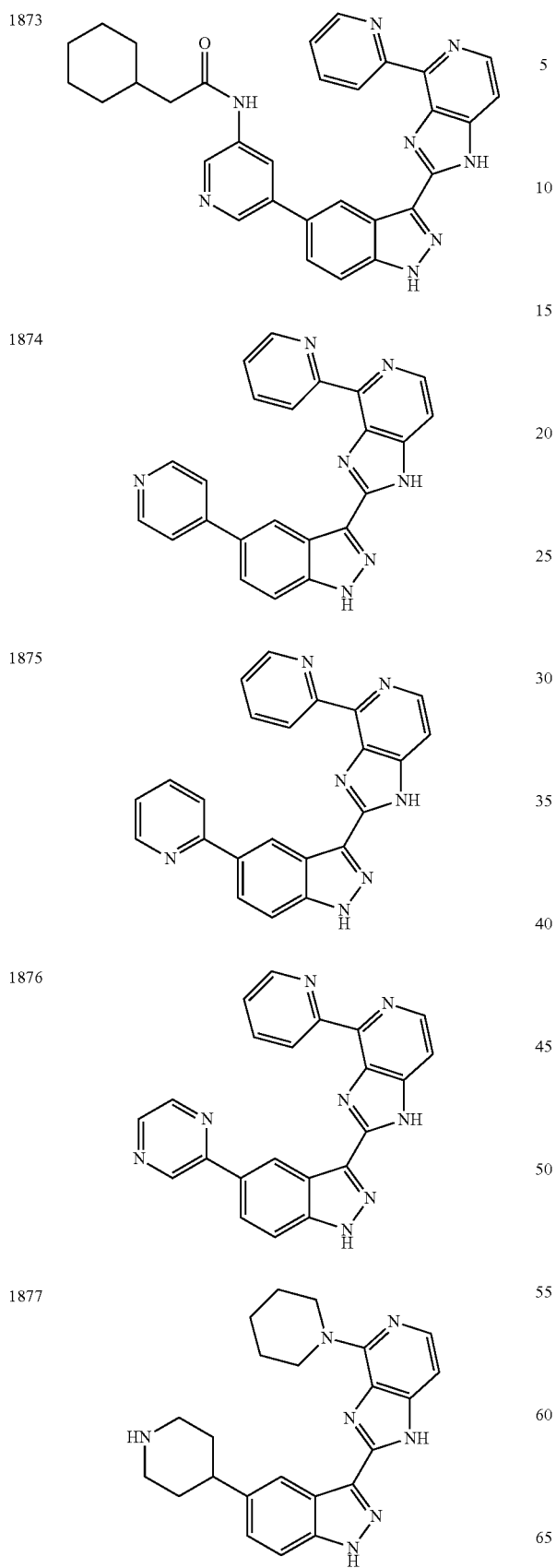

TABLE 1-continued
| 1883 | 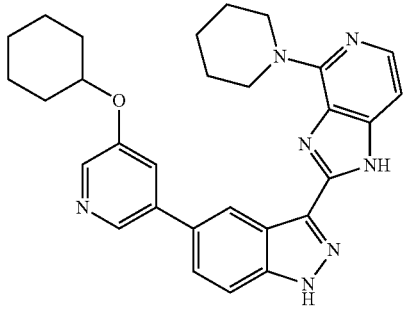 [SMILES: c1cc2[nH]c(-c3n[nH]c4ccc(-c5cncc(OC6CCCCC6)c5)cc34)nc2c(N2CCCCC2)n1] |
| --- | --- |
| 1884 | 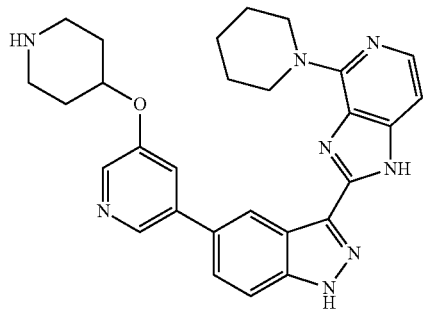 [SMILES: c1cc2[nH]c(-c3n[nH]c4ccc(-c5cncc(OC6CCNCC6)c5)cc34)nc2c(N2CCCCC2)n1] |
| 1885 | 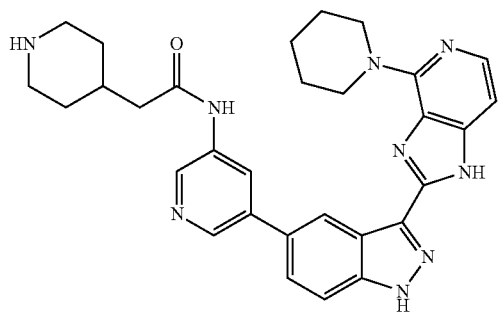 [SMILES: O=C(CC1CCNCC1)Nc1cncc(-c2ccc3[nH]nc(-c4nc5c(N6CCCCC6)nccc5[nH]4)c3c2)c1] |
| 1886 | 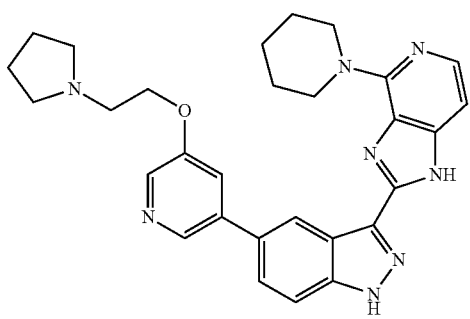 [SMILES: c1cc2[nH]c(-c3n[nH]c4ccc(-c5cncc(OCCN6CCCC6)c5)cc34)nc2c(N2CCCCC2)n1] |
| 1887 | 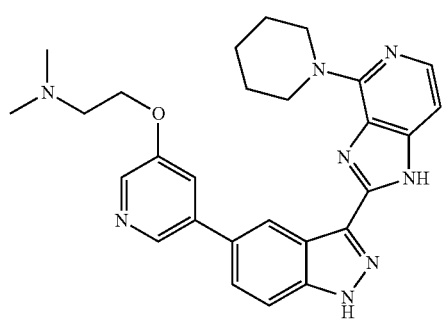 [SMILES: CN(C)CCOc1cncc(-c2ccc3[nH]nc(-c4nc5c(N6CCCCC6)nccc5[nH]4)c3c2)c1] |
TABLE 1-continued
| 1888 | 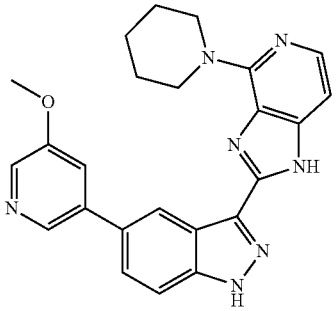 [SMILES: COc1cncc(-c2ccc3[nH]nc(-c4nc5c(N6CCCCC6)nccc5[nH]4)c3c2)c1] |
| --- | --- |
| 1889 | 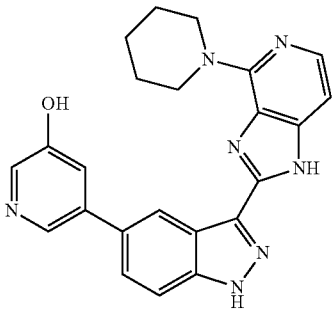 |
| 1890 | 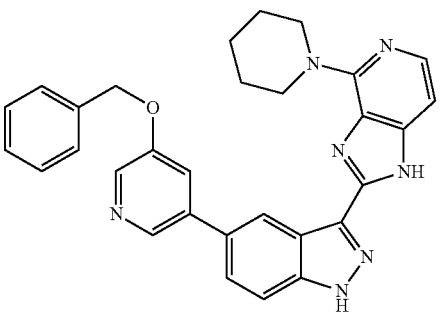 [SMILES: c1ccc(COc2cncc(-c3ccc4[nH]nc(-c5nc6c(N7CCCCC7)nccc6[nH]5)c4c3)c2)cc1] |
| 1891 | 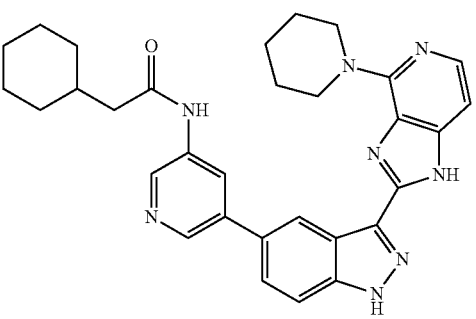 [SMILES: O=C(CC1CCCCC1)Nc1cncc(-c2ccc3[nH]nc(-c4nc5c(N6CCCCC6)nccc5[nH]4)c3c2)c1] |
| 1892 | 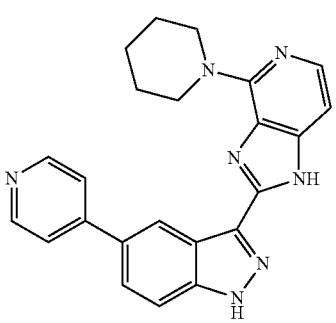 [SMILES: c1cc(-c2ccc3[nH]nc(-c4nc5c(N6CCCCC6)nccc5[nH]4)c3c2)ccn1] |

TABLE 1-continued
| | |
|---|---|
| 1893 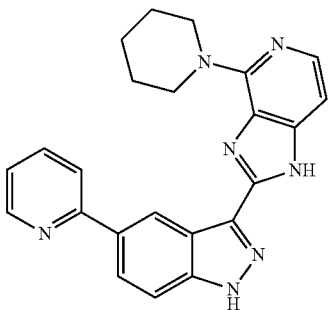 [SMILES: c1ccc(-c2ccc3[nH]nc(-c4nc5c(N6CCCCC6)nccc5[nH]4)c3c2)nc1] | 1898 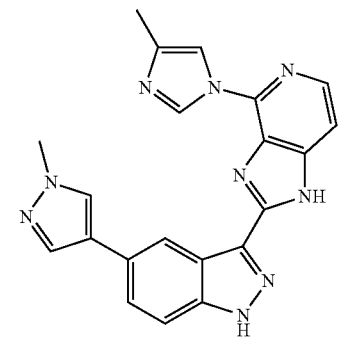 |
| 1894 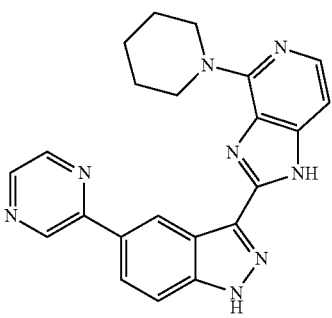 [SMILES: c1cnc(-c2ccc3[nH]nc(-c4nc5c(N6CCCCC6)nccc5[nH]4)c3c2)cn1] | 1899 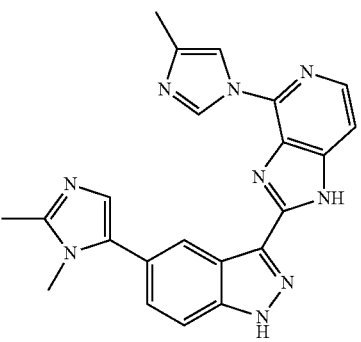 |
| 1895 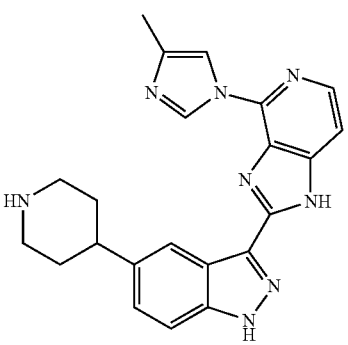 [SMILES: Cc1cn(-c2nccc3[nH]c(-c4n[nH]c5ccc(C6CCNCC6)cc45)nc23)cn1] | 1900 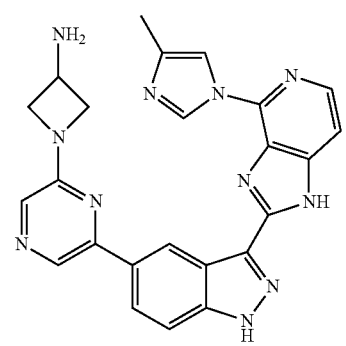 |
| 1896 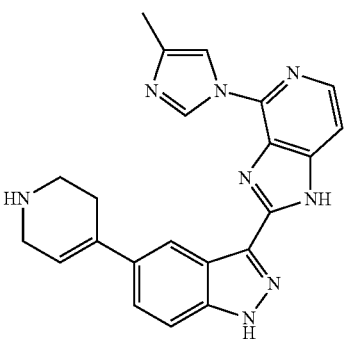 [SMILES: Cc1cn(-c2nccc3[nH]c(-c4n[nH]c5ccc(C6=CCNCC6)cc45)nc23)cn1] | 1901 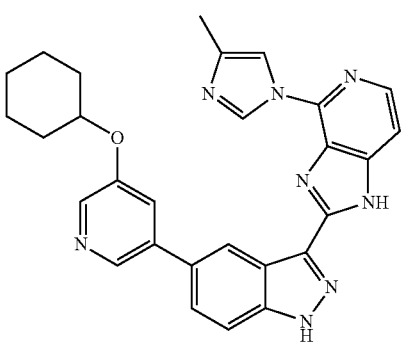 |
| 1897 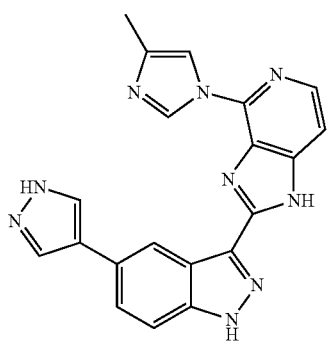 [SMILES: Cc1cn(-c2nccc3[nH]c(-c4n[nH]c5ccc(-c6cn[nH]c6)cc45)nc23)cn1] | |

TABLE 1-continued
1902 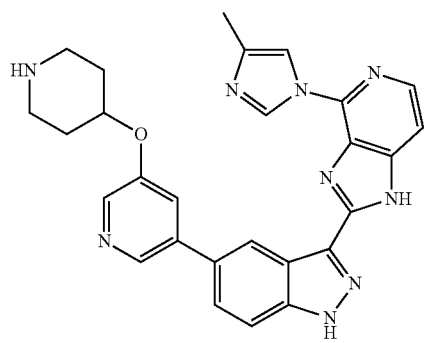 [SMILES: Cc1cn(-c2nccc3[nH]c(-c4n[nH]c5ccc(-c6cncc(OC7CCNCC7)c6)cc45)nc23)cn1]
1903 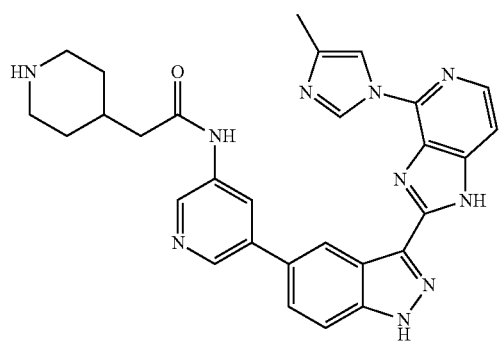 [SMILES: Cc1cn(-c2nccc3[nH]c(-c4n[nH]c5ccc(-c6cncc(NC(=O)CC7CCNCC7)c6)cc45)nc23)cn1]
1904 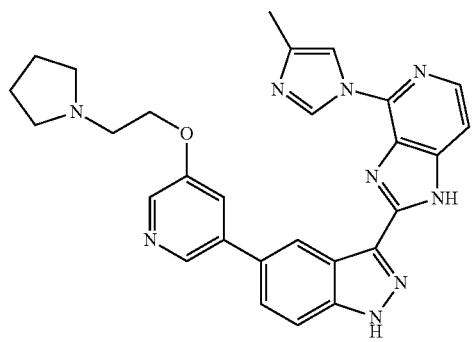 [SMILES: Cc1cn(-c2nccc3[nH]c(-c4n[nH]c5ccc(-c6cncc(OCCN7CCCC7)c6)cc45)nc23)cn1]
1905 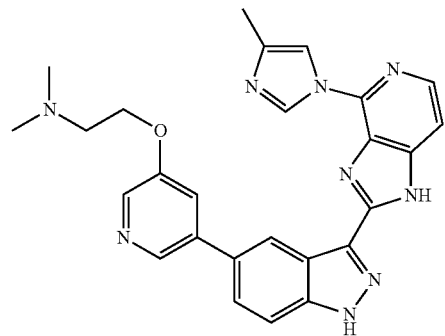 [SMILES: Cc1cn(-c2nccc3[nH]c(-c4n[nH]c5ccc(-c6cncc(OCCN(C)C)c6)cc45)nc23)cn1]
TABLE 1-continued
1906 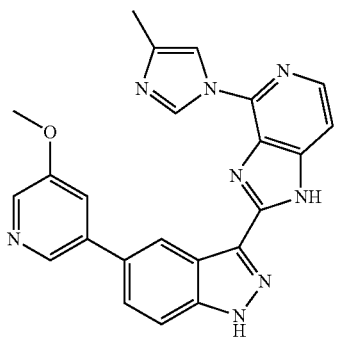 [SMILES: COc1cncc(-c2ccc3[nH]nc(-c4nc5c(-n6cnc(C)c6)nccc5[nH]4)c3c2)c1]
1907
1908
1909 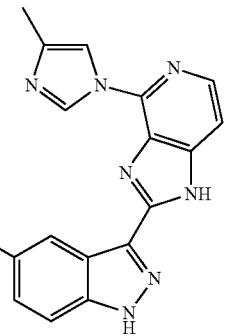

TABLE 1-continued
1910 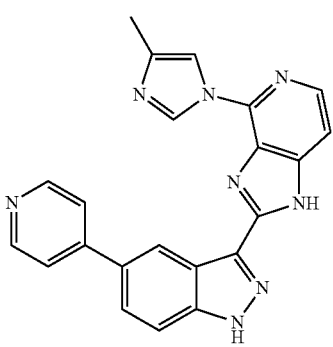
1911 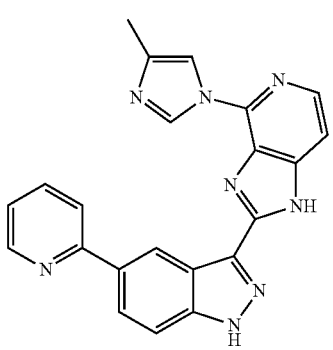 [SMILES: Cc1cn(-c2nccc3[nH]c(-c4n[nH]c5ccc(-c6ccccn6)cc45)nc23)cn1]
1912 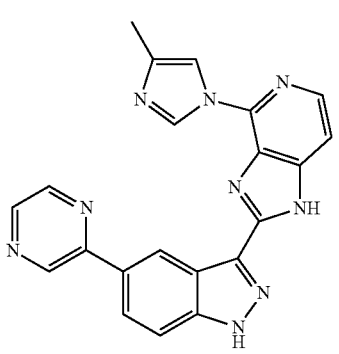
1913 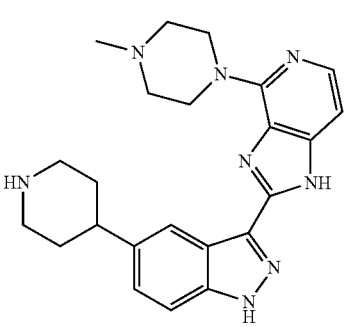 [SMILES: CN1CCN(c2nccc3[nH]c(-c4n[nH]c5ccc(C6=CCNCC6)cc45)nc23)CC1]
TABLE 1-continued
1914 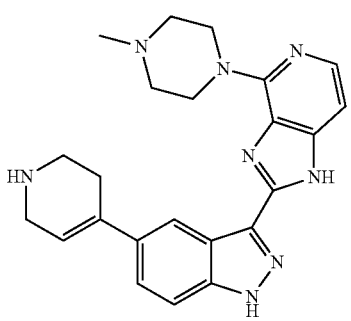
1915 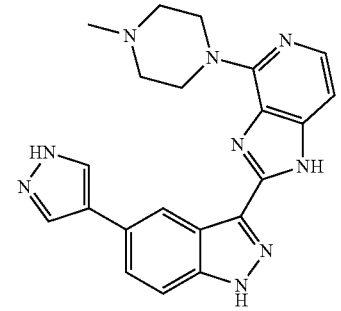 [SMILES: CN1CCN(c2nccc3[nH]c(-c4n[nH]c5ccc(-c6cn[nH]c6)cc45)nc23)CC1]
1916 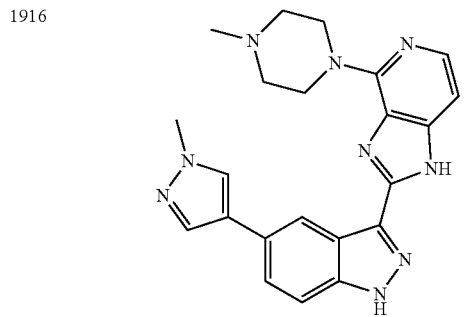
1917 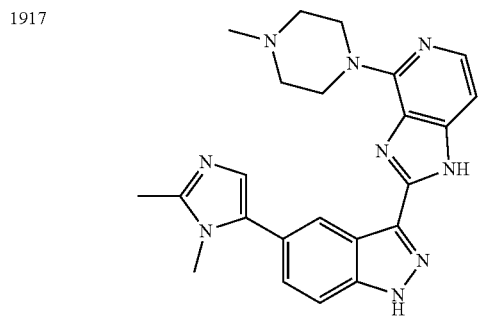
1918 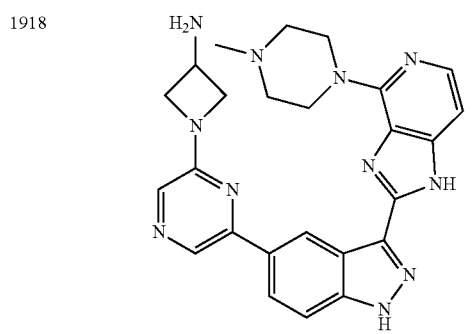

TABLE 1-continued
| | |
|---|---|
| 1919 | 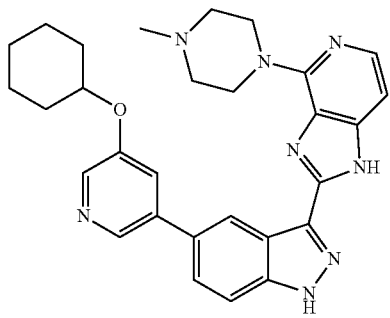 [SMILES: CN1CCN(c2nccc3[nH]c(-c4n[nH]c5ccc(-c6cncc(OC7CCCCC7)c6)cc45)nc23)CC1] |
| 1920 | 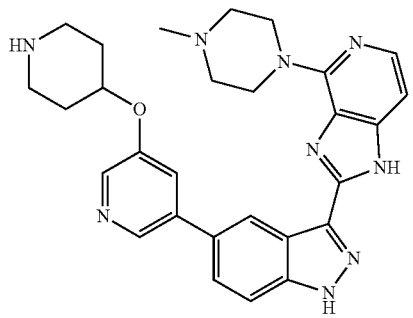 [SMILES: CN1CCN(c2nccc3[nH]c(-c4n[nH]c5ccc(-c6cncc(OC7CCNCC7)c6)cc45)nc23)CC1] |
| 1921 | 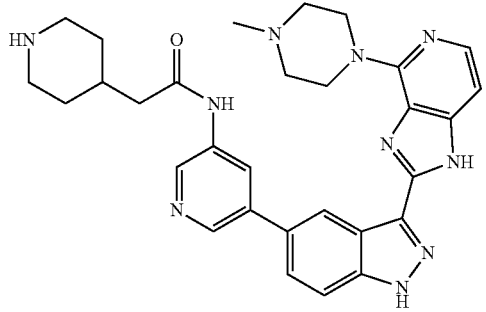 [SMILES: CN1CCN(c2nccc3[nH]c(-c4n[nH]c5ccc(-c6cncc(NC(=O)CC7CCNCC7)c6)cc45)nc23)CC1] |
| 1922 | 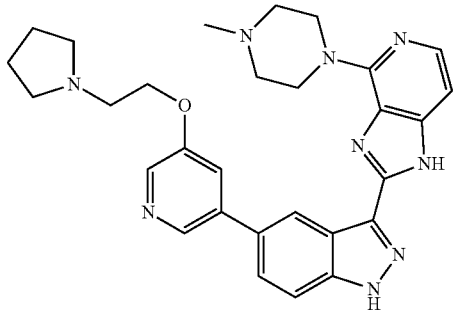 [SMILES: CN1CCN(c2nccc3[nH]c(-c4n[nH]c5ccc(-c6cncc(OCCN7CCCC7)c6)cc45)nc23)CC1] |
| 1923 | 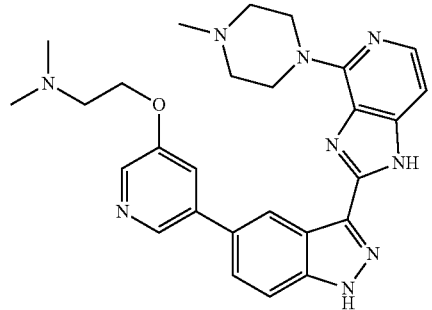 [SMILES: CN(C)CCOc1cncc(-c2ccc3[nH]nc(-c4nc5c(N6CCN(C)CC6)nccc5[nH]4)c3c2)c1] |
TABLE 1-continued
| | |
|---|---|
| 1924 | 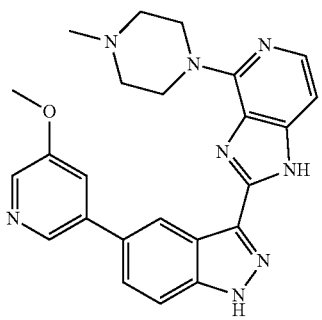 [SMILES: COc1cncc(-c2ccc3[nH]nc(-c4nc5c(N6CCN(C)CC6)nccc5[nH]4)c3c2)c1] |
| 1925 | 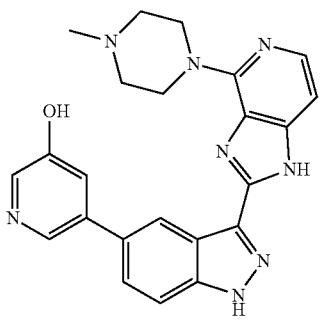 [SMILES: CN1CCN(c2nccc3[nH]c(-c4n[nH]c5ccc(-c6cncc(O)c6)cc45)nc23)CC1] |
| 1926 | 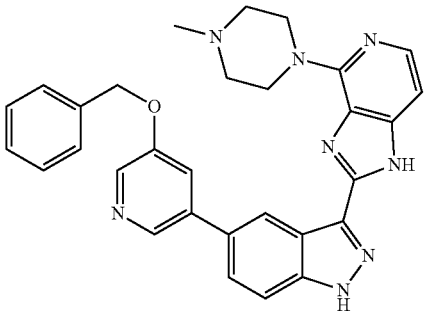 [SMILES: CN1CCN(c2nccc3[nH]c(-c4n[nH]c5ccc(-c6cncc(OCc7ccccc7)c6)cc45)nc23)CC1] |
| 1927 | 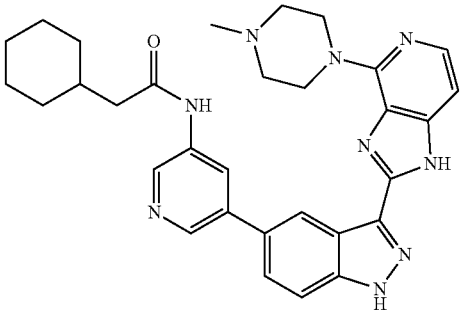 [SMILES: CN1CCN(c2nccc3[nH]c(-c4n[nH]c5ccc(-c6cncc(NC(=O)CC7CCCCC7)c6)cc45)nc23)CC1] |
| 1928 | 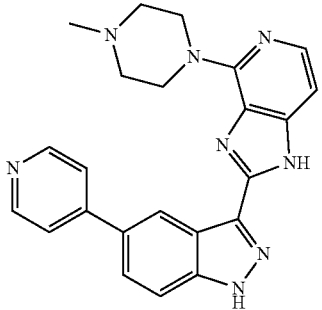 [SMILES: CN1CCN(c2nccc3[nH]c(-c4n[nH]c5ccc(-c6ccncc6)cc45)nc23)CC1] |

TABLE 1-continued
| 1929 | 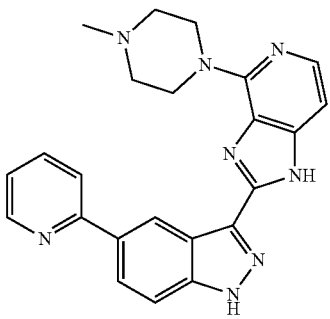 [SMILES: CN1CCN(c2nccc3[nH]c(-c4n[nH]c5ccc(-c6ccccn6)cc45)nc23)CC1] |
| 1930 | 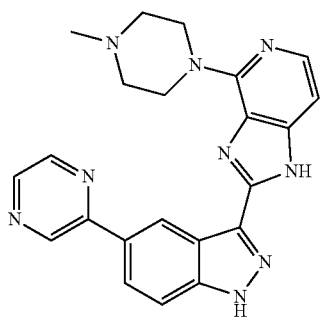 [SMILES: CN1CCN(c2nccc3[nH]c(-c4n[nH]c5ccc(-c6cnccn6)cc45)nc23)CC1] |
| 1931 | 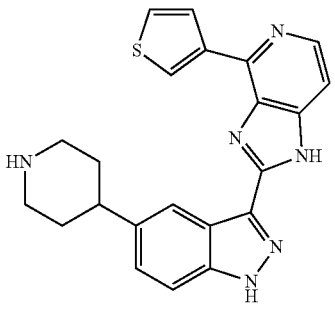 [SMILES: c1cc2[nH]c(-c3n[nH]c4ccc(C5CCNCC5)cc34)nc2c(-c2ccsc2)n1] |
| 1932 | 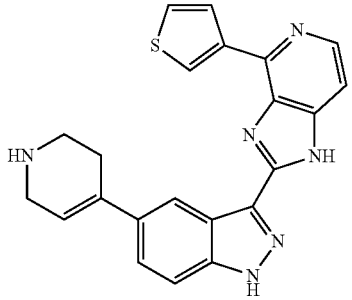 [SMILES: C1=C(c2ccc3[nH]nc(-c4nc5c(-c6ccsc6)nccc5[nH]4)c3c2)CCNC1] |
| 1933 | 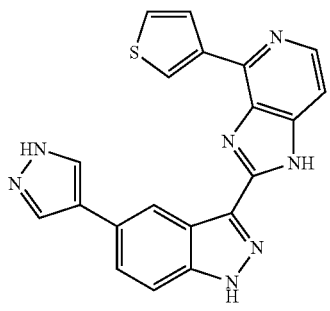 [SMILES: c1cc2[nH]c(-c3n[nH]c4ccc(-c5cn[nH]c5)cc34)nc2c(-c2ccsc2)n1] |
| 1934 | 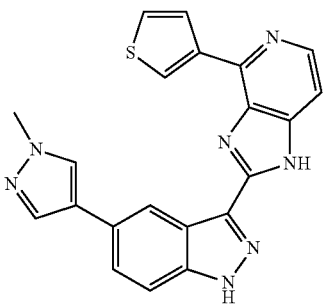 [SMILES: Cn1cc(-c2ccc3[nH]nc(-c4nc5c(-c6ccsc6)nccc5[nH]4)c3c2)cn1] |
| 1935 | 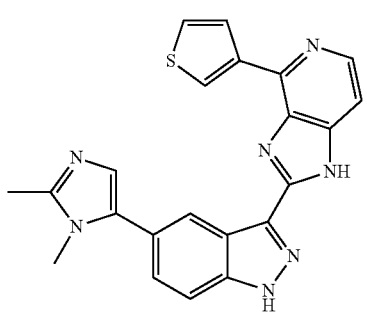 [SMILES: Cc1ncc(-c2ccc3[nH]nc(-c4nc5c(-c6ccsc6)nccc5[nH]4)c3c2)n1C] |
| 1936 | 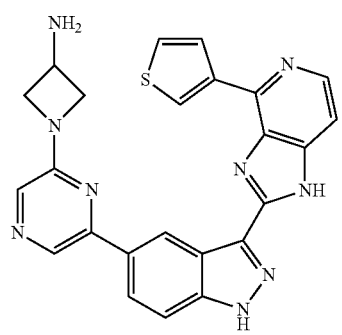 [SMILES: NC1CN(c2cncc(-c3ccc4[nH]nc(-c5nc6c(-c7ccsc7)nccc6[nH]5)c4c3)n2)C1] |
| 1937 | 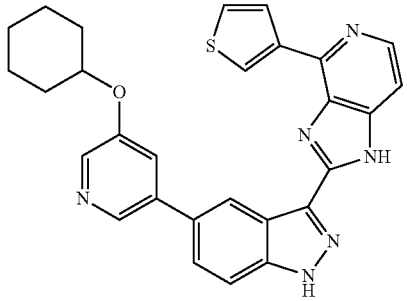 [SMILES: c1cc2[nH]c(-c3n[nH]c4ccc(-c5cncc(OC6CCCCC6)c5)cc34)nc2c(-c2ccsc2)n1] |
| 1938 | 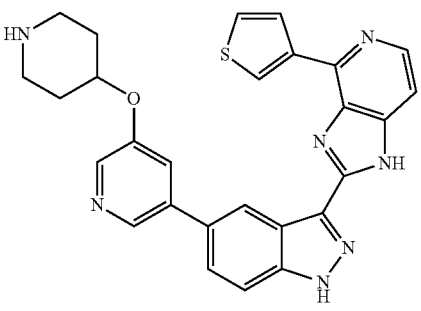 [SMILES: c1cc2[nH]c(-c3n[nH]c4ccc(-c5cncc(OC6CCNCC6)c5)cc34)nc2c(-c2ccsc2)n1] |

501
TABLE 1-continued
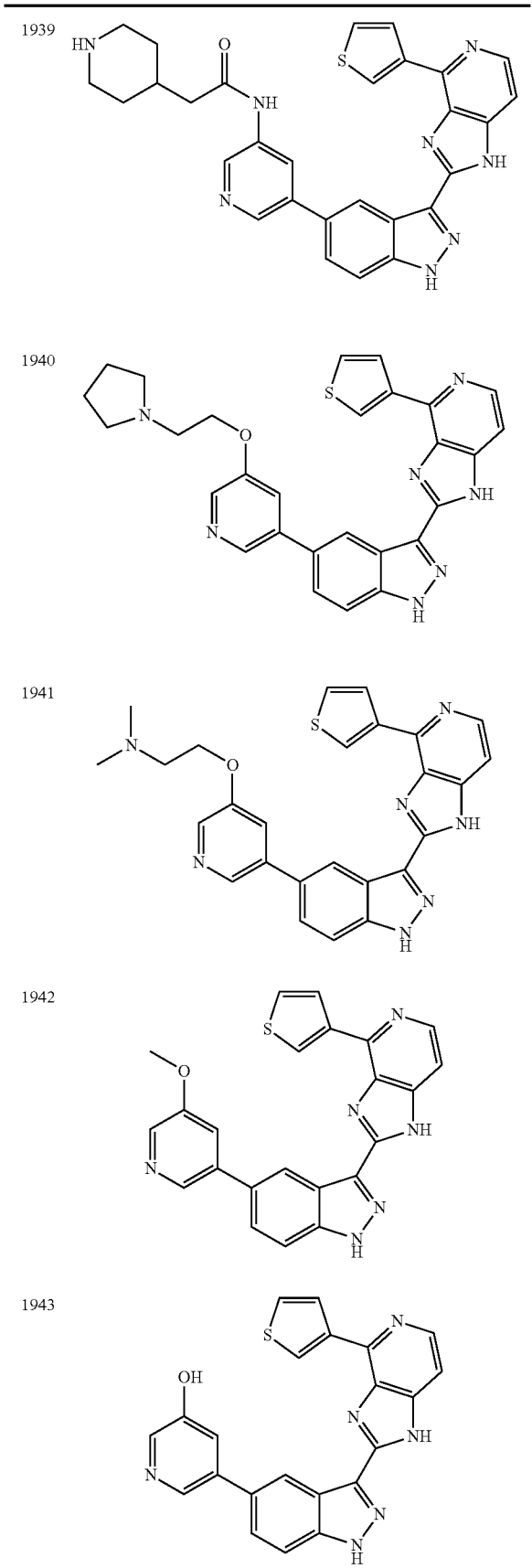
502
TABLE 1-continued
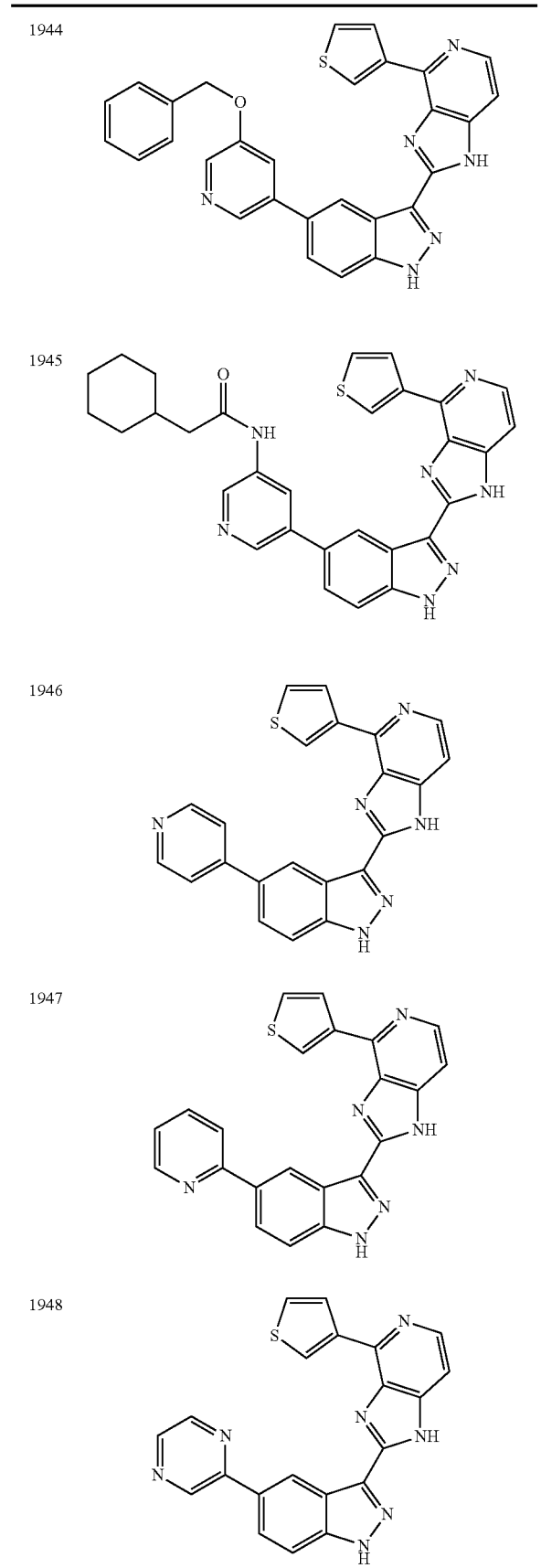

503
TABLE 1-continued
| 1949 | 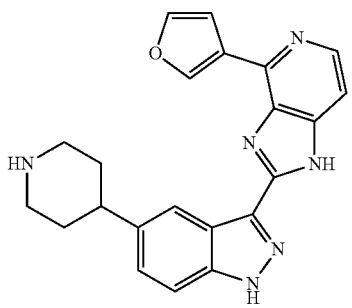 [SMILES: c1cc2[nH]c(-c3n[nH]c4ccc(C5CCNCC5)cc34)nc2c(-c2ccoc2)n1] |
| --- | --- |
| 1950 | 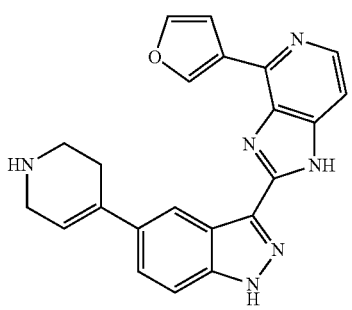 [SMILES: C1=C(c2ccc3[nH]nc(-c4nc5c(-c6ccoc6)nccc5[nH]4)c3c2)CCNC1] |
| 1951 | 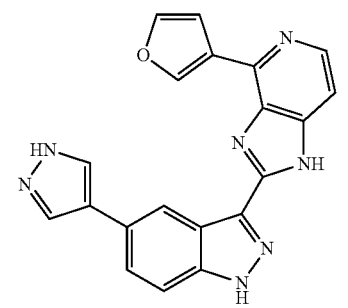 |
| 1952 | 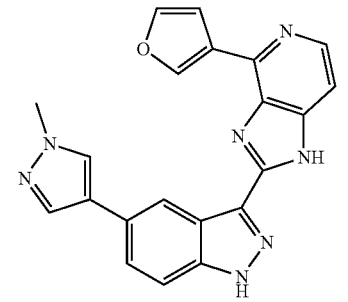 [SMILES: Cn1cc(-c2ccc3[nH]nc(-c4nc5c(-c6ccoc6)nccc5[nH]4)c3c2)cn1] |
| 1953 | 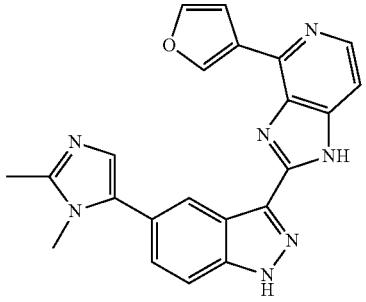 [SMILES: Cc1ncc(-c2ccc3[nH]nc(-c4nc5c(-c6ccoc6)nccc5[nH]4)c3c2)n1C] |
504
TABLE 1-continued
| 1954 | 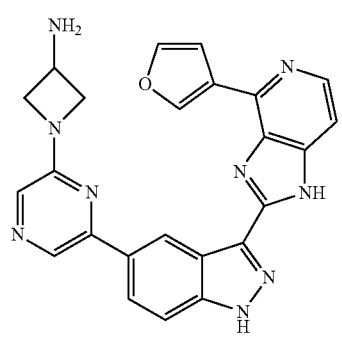 [SMILES: NC1CN(c2cncc(-c3ccc4[nH]nc(-c5nc6c(-c7ccoc7)nccc6[nH]5)c4c3)n2)C1] |
| --- | --- |
| 1955 | 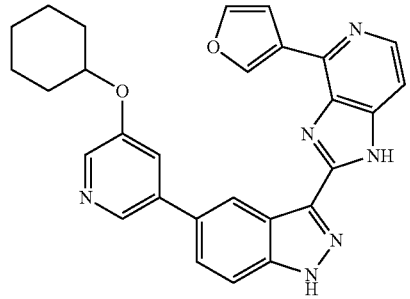 [SMILES: c1cc2[nH]c(-c3n[nH]c4ccc(-c5cncc(OC6CCCCC6)c5)cc34)nc2c(-c2ccoc2)n1] |
| 1956 | 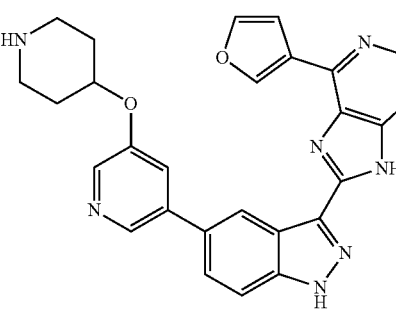 |
| 1957 | 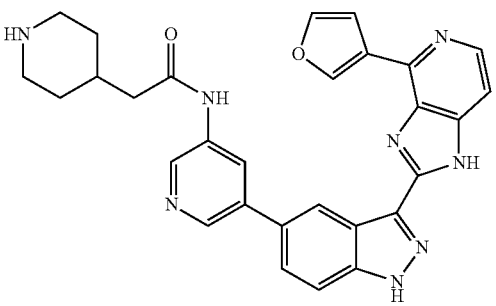 |
| 1958 | 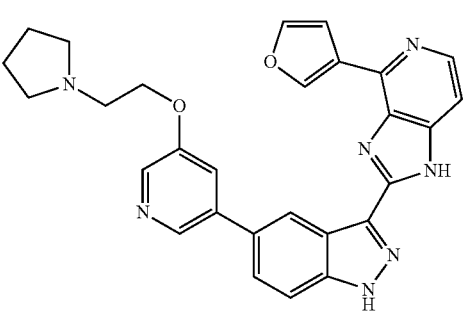 [SMILES: c1cc2[nH]c(-c3n[nH]c4ccc(-c5cncc(OCCN6CCCC6)c5)cc34)nc2c(-c2ccoc2)n1] |

TABLE 1-continued
1959
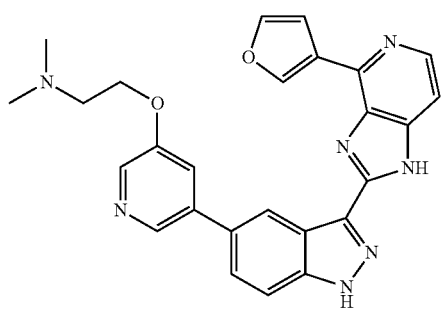 [SMILES: CN(C)CCOc1cncc(-c2ccc3[nH]nc(-c4nc5c(-c6ccoc6)nccc5[nH]4)c3c2)c1]
1960
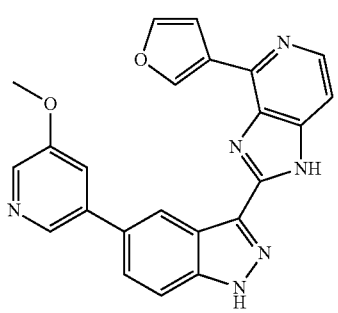 [SMILES: COc1cncc(-c2ccc3[nH]nc(-c4nc5c(-c6ccoc6)nccc5[nH]4)c3c2)c1]
1961
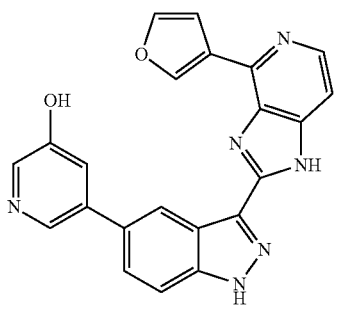
1962
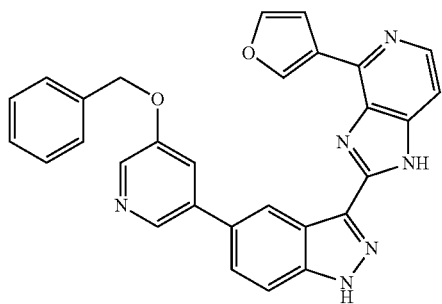 [SMILES: c1ccc(COc2cncc(-c3ccc4[nH]nc(-c5nc6c(-c7ccoc7)nccc6[nH]5)c4c3)c2)cc1]
1963
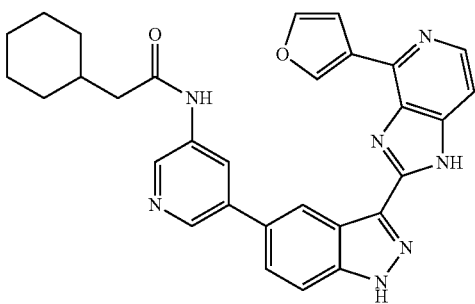 [SMILES: O=C(CC1CCCCC1)Nc1cncc(-c2ccc3[nH]nc(-c4nc5c(-c6ccoc6)nccc5[nH]4)c3c2)c1]
TABLE 1-continued
1964
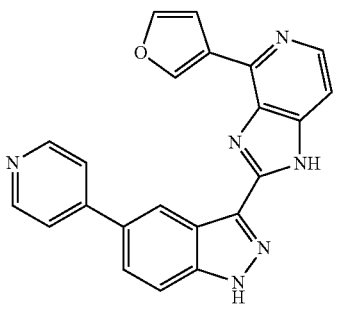
1965
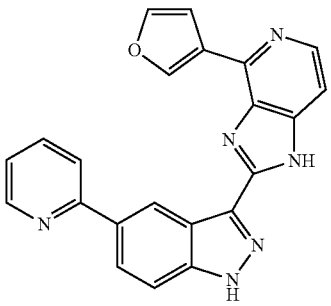 [SMILES: c1ccc(-c2ccc3[nH]nc(-c4nc5c(-c6ccoc6)nccc5[nH]4)c3c2)nc1]
1966
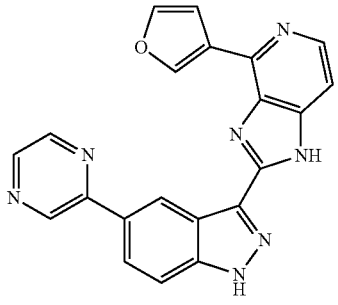
1967
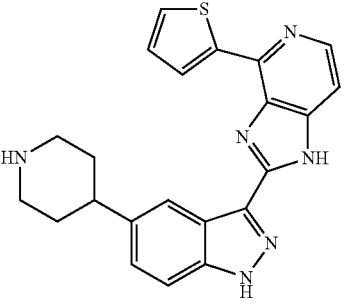 [SMILES: c1csc(-c2nccc3[nH]c(-c4n[nH]c5ccc(C6CCNCC6)cc45)nc23)c1]
1968
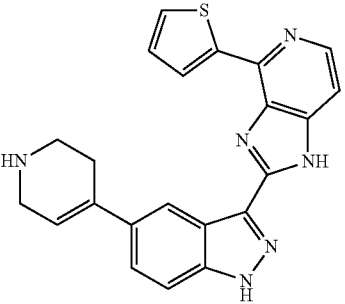 [SMILES: C1=C(c2ccc3[nH]nc(-c4nc5c(-c6cccs6)nccc5[nH]4)c3c2)CCNC1]

TABLE 1-continued
| | |
|---|---|
| 1969 | 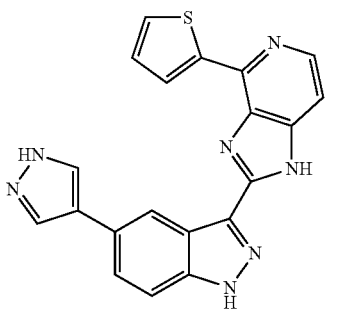 [SMILES: c1csc(-c2nccc3[nH]c(-c4n[nH]c5ccc(-c6cn[nH]c6)cc45)nc23)c1] |
| 1970 | 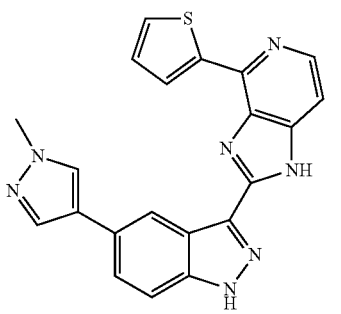 [SMILES: Cn1cc(-c2ccc3[nH]nc(-c4nc5c(-c6cccs6)nccc5[nH]4)c3c2)cn1] |
| 1971 | 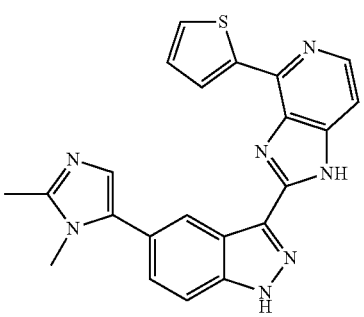 [SMILES: Cc1ncc(-c2ccc3[nH]nc(-c4nc5c(-c6cccs6)nccc5[nH]4)c3c2)n1C] |
| 1972 | 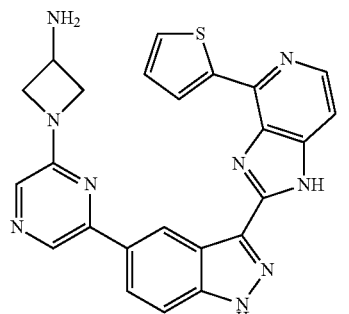 |
| 1973 | 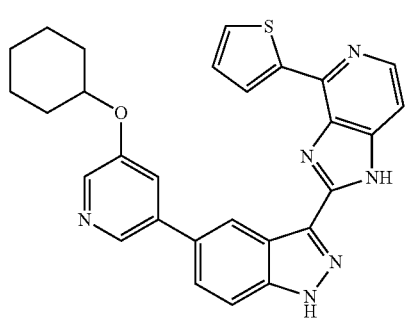 [SMILES: c1csc(-c2nccc3[nH]c(-c4n[nH]c5ccc(-c6cncc(OC7CCCCC7)c6)cc45)nc23)c1] |
TABLE 1-continued
| | |
|---|---|
| 1974 | 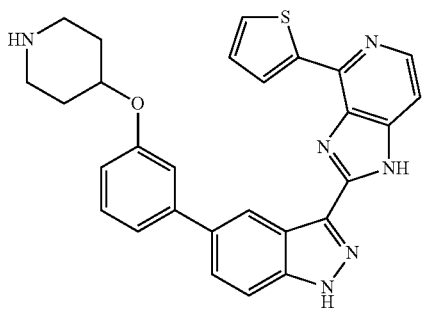 [SMILES: c1cc(OC2CCNCC2)cc(-c2ccc3[nH]nc(-c4nc5c(-c6cccs6)nccc5[nH]4)c3c2)c1] |
| 1975 | 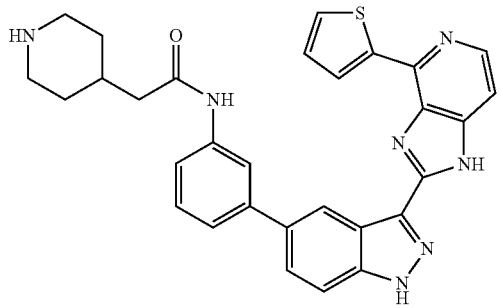 [SMILES: O=C(CC1CCNCC1)Nc1cccc(-c2ccc3[nH]nc(-c4nc5c(-c6cccs6)nccc5[nH]4)c3c2)c1] |
| 1976 | 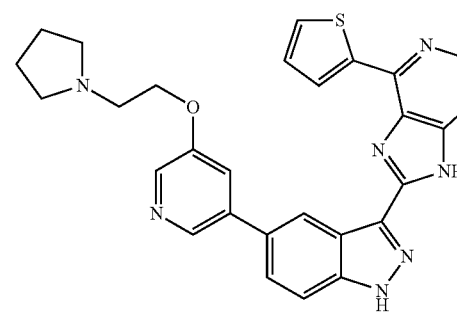 |
| 1977 | 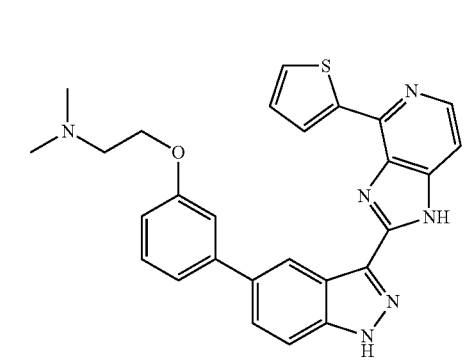 [SMILES: CN(C)CCOc1cccc(-c2ccc3[nH]nc(-c4nc5c(-c6cccs6)nccc5[nH]4)c3c2)c1] |
| 1978 | 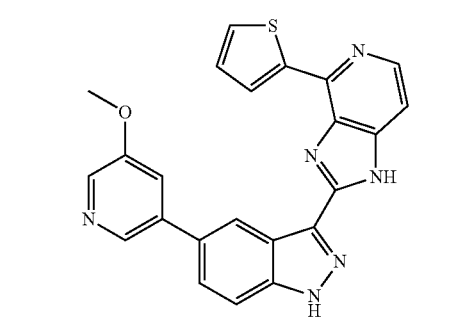 [SMILES: COc1cncc(-c2ccc3[nH]nc(-c4nc5c(-c6cccs6)nccc5[nH]4)c3c2)c1] |

TABLE 1-continued
| 1979 | 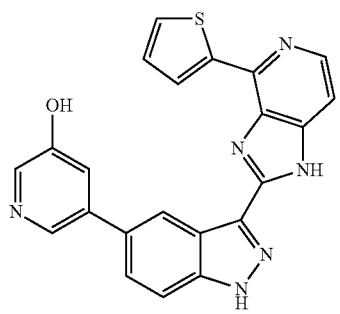 [SMILES: Oc1cncc(-c2ccc3[nH]nc(-c4nc5c(-c6cccs6)nccc5[nH]4)c3c2)c1] |
| --- | --- |
| 1980 | 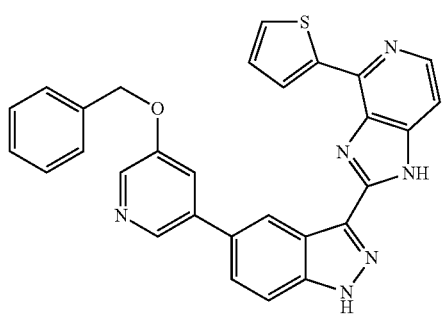 [SMILES: c1ccc(COc2cncc(-c3ccc4[nH]nc(-c5nc6c(-c7cccs7)nccc6[nH]5)c4c3)c2)cc1] |
| 1981 | 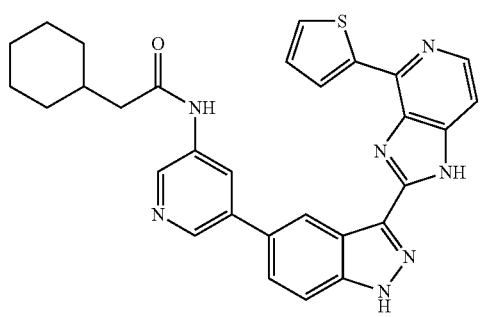 [SMILES: O=C(CC1CCCCC1)Nc1cncc(-c2ccc3[nH]nc(-c4nc5c(-c6cccs6)nccc5[nH]4)c3c2)c1] |
| 1982 | 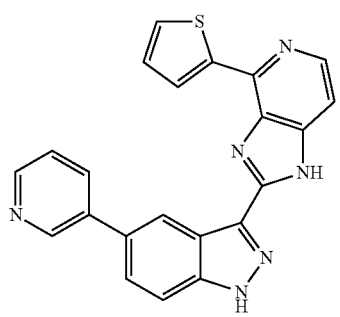 [SMILES: c1cncc(-c2ccc3[nH]nc(-c4nc5c(-c6cccs6)nccc5[nH]4)c3c2)c1] |
| 1983 | 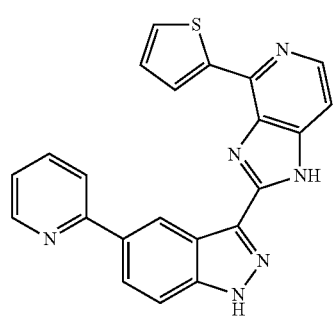 [SMILES: c1ccc(-c2ccc3[nH]nc(-c4nc5c(-c6cccs6)nccc5[nH]4)c3c2)nc1] |
TABLE 1-continued
| 1984 | 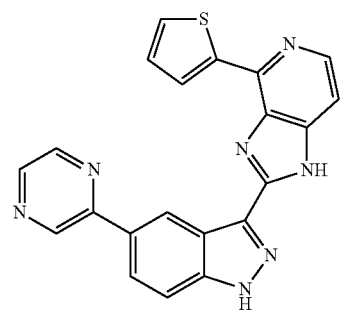 [SMILES: c1csc(-c2nccc3[nH]c(-c4n[nH]c5ccc(-c6cnccn6)cc45)nc23)c1] |
| --- | --- |
| 1985 | 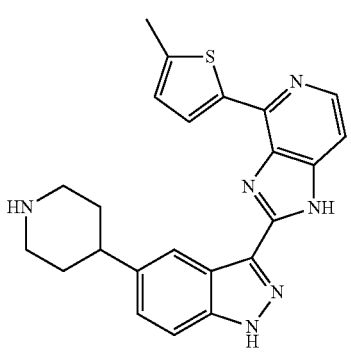 [SMILES: Cc1ccc(-c2nccc3[nH]c(-c4n[nH]c5ccc(C6CCNCC6)cc45)nc23)s1] |
| 1986 | 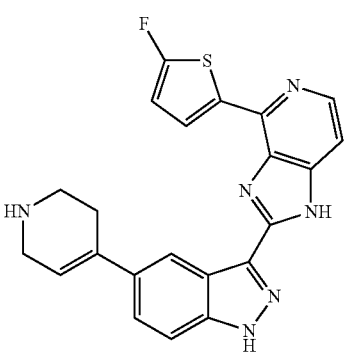 [SMILES: Fc1ccc(-c2nccc3[nH]c(-c4n[nH]c5ccc(C6=CCNCC6)cc45)nc23)s1] |
| 1987 | 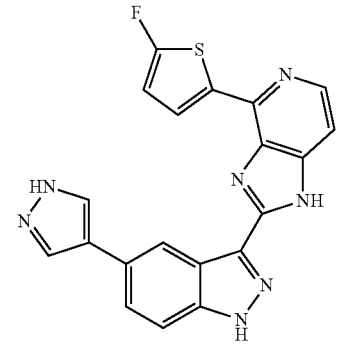 [SMILES: Fc1ccc(-c2nccc3[nH]c(-c4n[nH]c5ccc(-c6cn[nH]c6)cc45)nc23)s1] |

511
TABLE 1-continued
1988
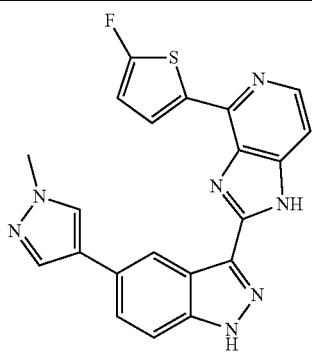
1989
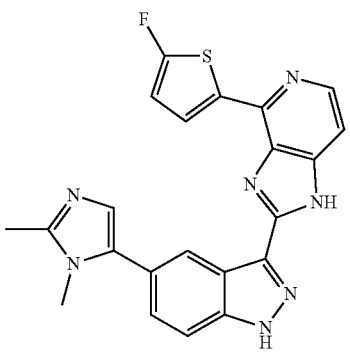 [SMILES: Cc1ncc(-c2ccc3[nH]nc(-c4nc5c(-c6ccc(F)s6)nccc5[nH]4)c3c2)n1C]
1990
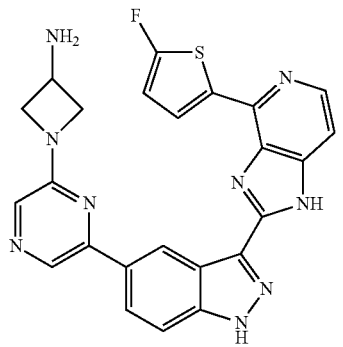 [SMILES: NC1CN(c2cncc(-c3ccc4[nH]nc(-c5nc6c(-c7ccc(F)s7)nccc6[nH]5)c4c3)n2)C1]
1991
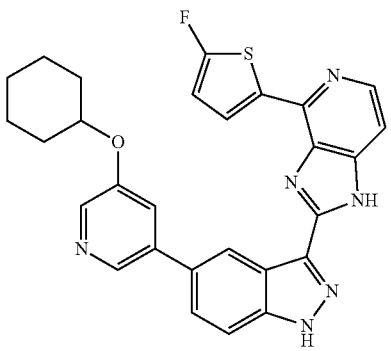 [SMILES: Fc1ccc(-c2nccc3[nH]c(-c4n[nH]c5ccc(-c6cncc(OC7CCCCC7)c6)cc45)nc23)s1]
512
TABLE 1-continued
1992
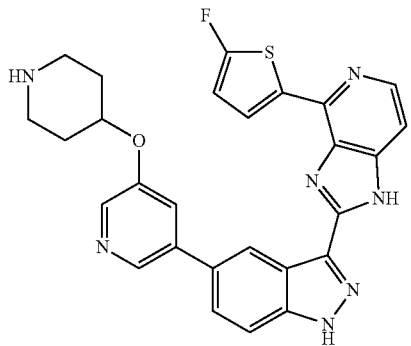 [SMILES: Fc1ccc(-c2nccc3[nH]c(-c4n[nH]c5ccc(-c6cncc(OC7CCNCC7)c6)cc45)nc23)s1]
1993
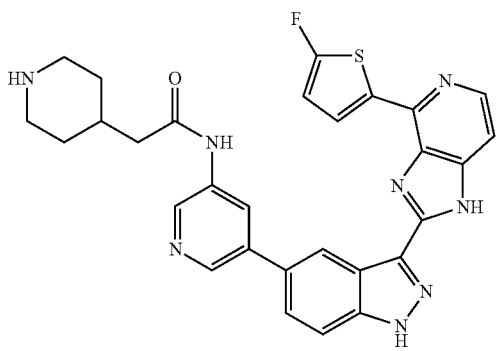 [SMILES: O=C(CC1CCNCC1)Nc1cncc(-c2ccc3[nH]nc(-c4nc5c(-c6ccc(F)s6)nccc5[nH]4)c3c2)c1]
1994
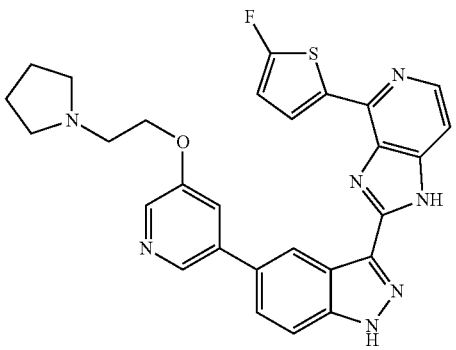 [SMILES: Fc1ccc(-c2nccc3[nH]c(-c4n[nH]c5ccc(-c6cncc(OCCN7CCCC7)c6)cc45)nc23)s1]
1995
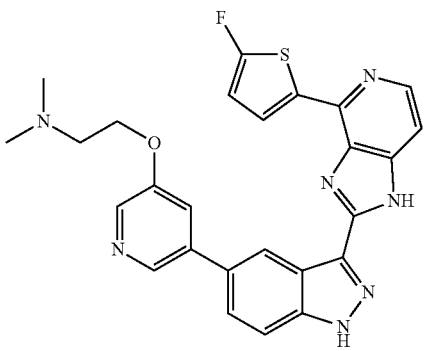 [SMILES: CN(C)CCOc1cncc(-c2ccc3[nH]nc(-c4nc5c(-c6ccc(F)s6)nccc5[nH]4)c3c2)c1]

TABLE 1-continued
| 1996 | 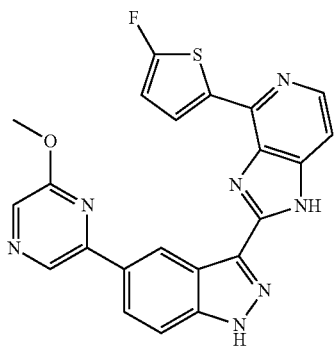 [SMILES: COc1cncc(-c2ccc3[nH]nc(-c4nc5c(-c6ccc(F)s6)nccc5[nH]4)c3c2)n1] |
| --- | --- |
| 1997 | 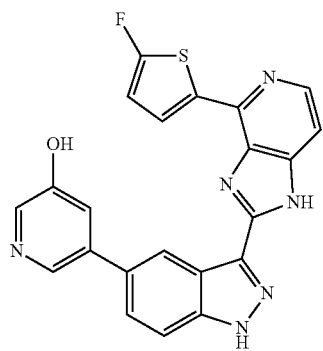 [SMILES: Oc1cncc(-c2ccc3[nH]nc(-c4nc5c(-c6ccc(F)s6)nccc5[nH]4)c3c2)c1] |
| 1998 | 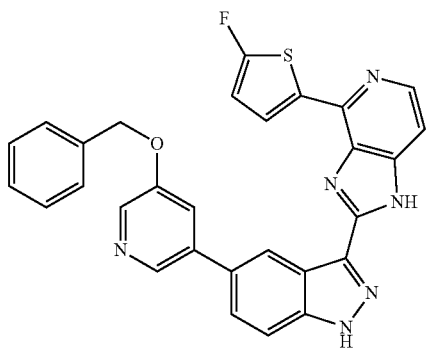 [SMILES: Fc1ccc(-c2nccc3[nH]c(-c4n[nH]c5ccc(-c6cncc(OCc7ccccc7)c6)cc45)nc23)s1] |
| 1999 | 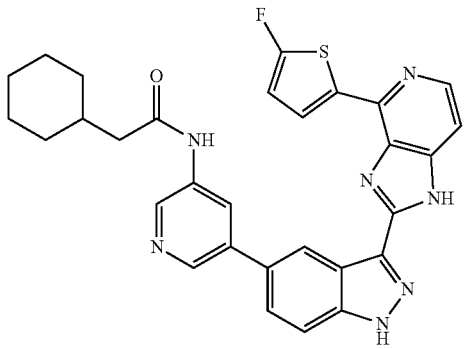 [SMILES: O=C(CC1CCCCC1)Nc1cncc(-c2ccc3[nH]nc(-c4nc5c(-c6ccc(F)s6)nccc5[nH]4)c3c2)c1] |
TABLE 1-continued
| 2000 | 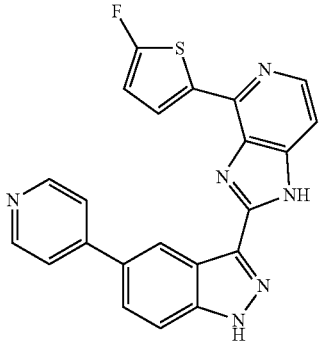 [SMILES: Fc1ccc(-c2nccc3[nH]c(-c4n[nH]c5ccc(-c6ccncc6)cc45)nc23)s1] |
| --- | --- |
| 2001 | 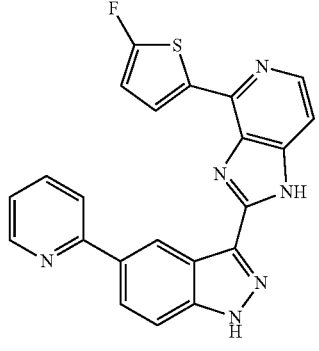 [SMILES: Fc1ccc(-c2nccc3[nH]c(-c4n[nH]c5ccc(-c6ccccn6)cc45)nc23)s1] |
| 2002 | 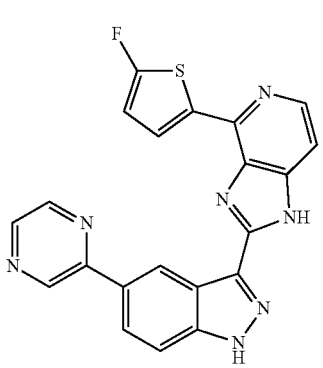 [SMILES: Fc1ccc(-c2nccc3[nH]c(-c4n[nH]c5ccc(-c6cnccn6)cc45)nc23)s1] |
| 2003 | 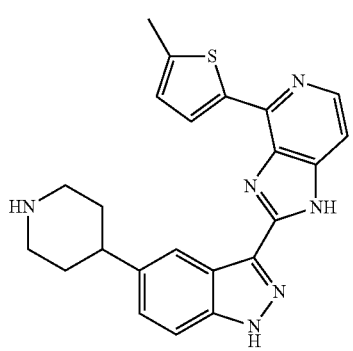 [SMILES: Cc1ccc(-c2nccc3[nH]c(-c4n[nH]c5ccc(C6CCNCC6)cc45)nc23)s1] |

TABLE 1-continued
2004 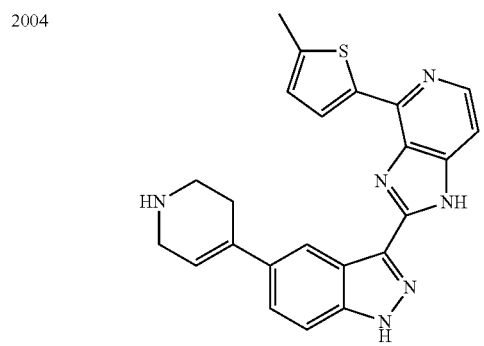
2005 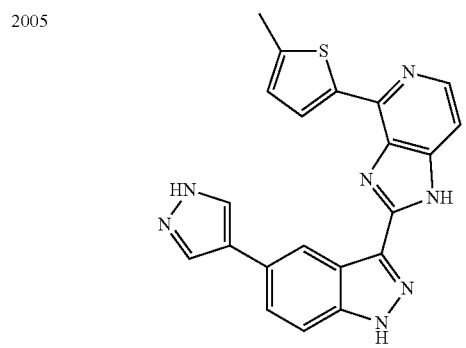
2006 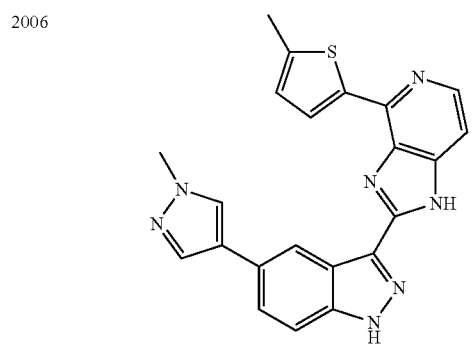
2007 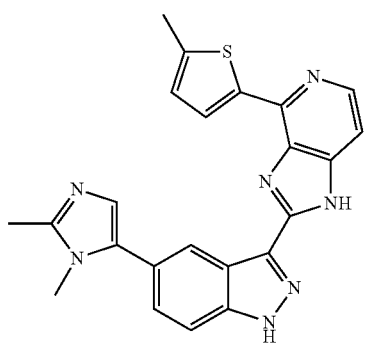 [SMILES: Cc1ccc(-c2nccc3[nH]c(-c4n[nH]c5ccc(-c6cnc(C)n6C)cc45)nc23)s1]
TABLE 1-continued
2008 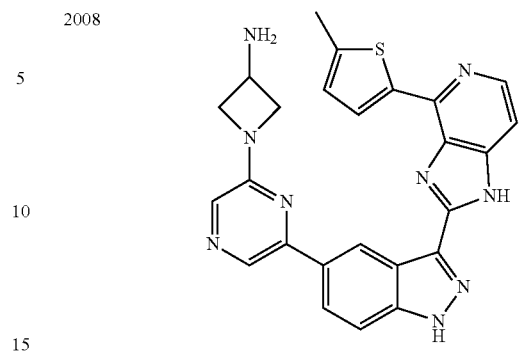
2009 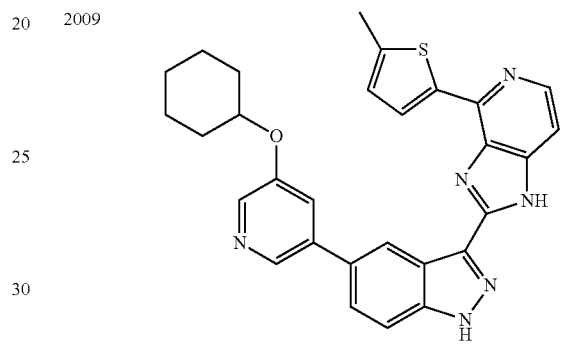
2010 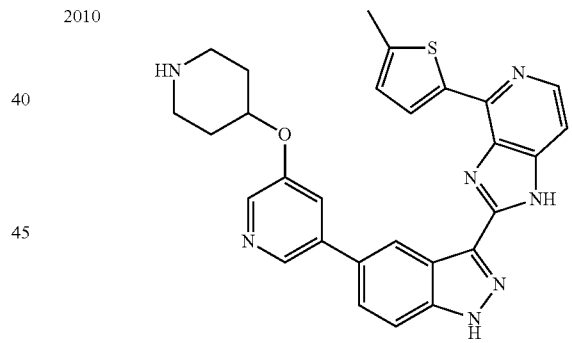
2011 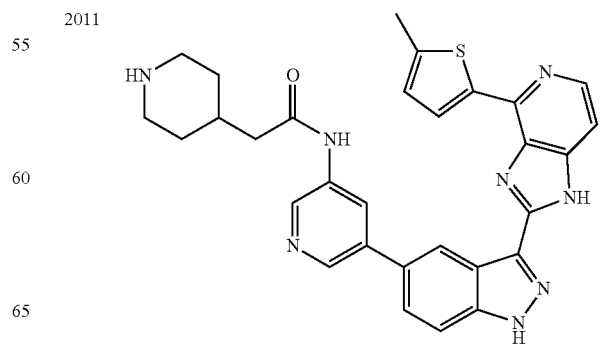

TABLE 1-continued
2012
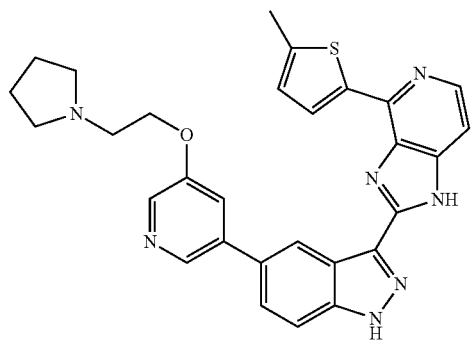 [SMILES: Cc1ccc(-c2nccc3[nH]c(-c4n[nH]c5ccc(-c6cncc(OCCN7CCCC7)c6)cc45)nc23)s1]
2013
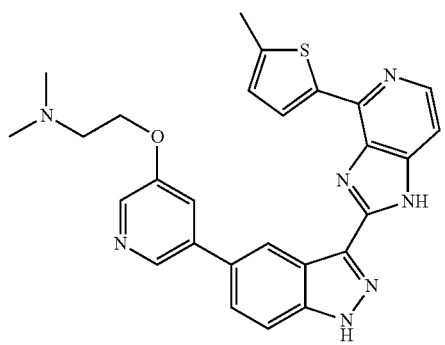 [SMILES: Cc1ccc(-c2nccc3[nH]c(-c4n[nH]c5ccc(-c6cncc(OCCN(C)C)c6)cc45)nc23)s1]
2014
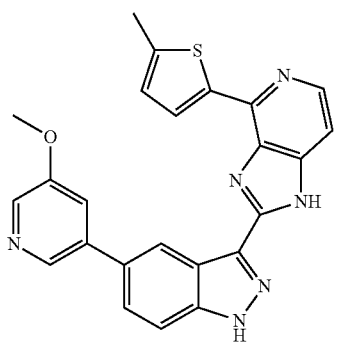 [SMILES: COc1cncc(-c2ccc3[nH]nc(-c4nc5c(-c6ccc(C)s6)nccc5[nH]4)c3c2)c1]
2015
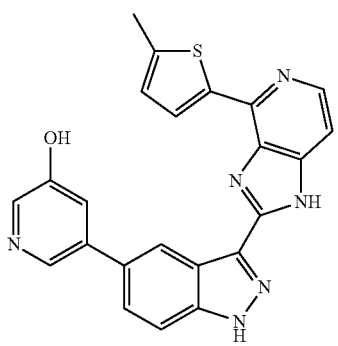 [SMILES: Cc1ccc(-c2nccc3[nH]c(-c4n[nH]c5ccc(-c6cncc(O)c6)cc45)nc23)s1]
TABLE 1-continued
2016
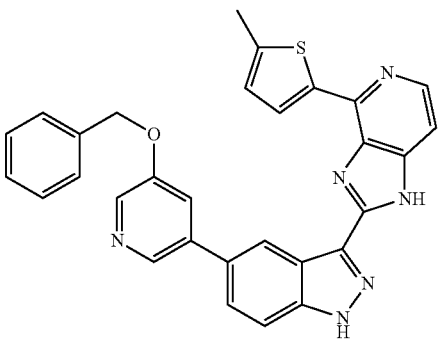 [SMILES: Cc1ccc(-c2nccc3[nH]c(-c4n[nH]c5ccc(-c6cncc(OCc7ccccc7)c6)cc45)nc23)s1]
2017
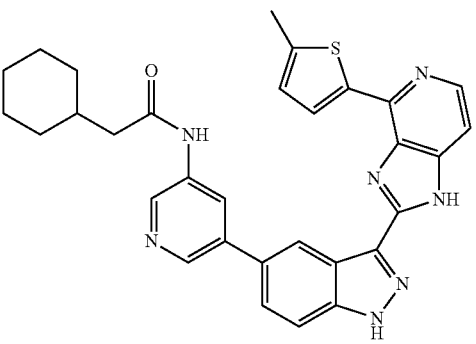 [SMILES: Cc1ccc(-c2nccc3[nH]c(-c4n[nH]c5ccc(-c6cncc(NC(=O)CC7CCCCC7)c6)cc45)nc23)s1]
2018
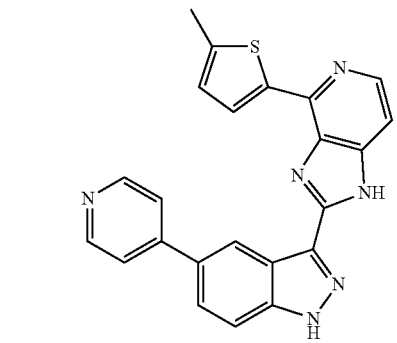 [SMILES: Cc1ccc(-c2nccc3[nH]c(-c4n[nH]c5ccc(-c6ccncc6)cc45)nc23)s1]
2019
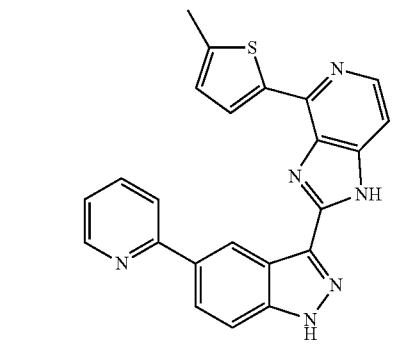 [SMILES: Cc1ccc(-c2nccc3[nH]c(-c4n[nH]c5ccc(-c6ccccn6)cc45)nc23)s1]

519
TABLE 1-continued
2020 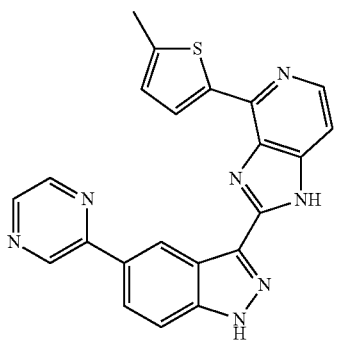 [SMILES: Cc1ccc(-c2nccc3[nH]c(-c4n[nH]c5ccc(-c6cnccn6)cc45)nc23)s1]
2021 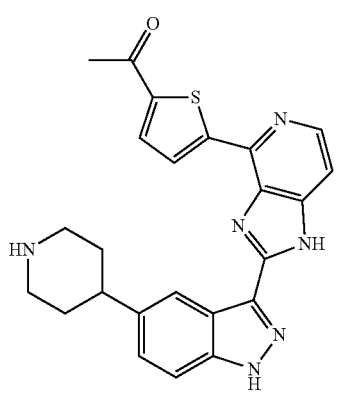 [SMILES: CC(=O)c1ccc(-c2nccc3[nH]c(-c4n[nH]c5ccc(C6CCNCC6)cc45)nc23)s1]
2022 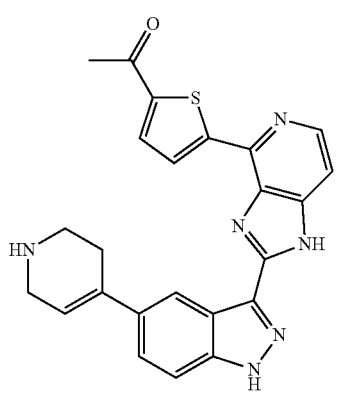 [SMILES: CC(=O)c1ccc(-c2nccc3[nH]c(-c4n[nH]c5ccc(C6=CCNCC6)cc45)nc23)s1]
2023 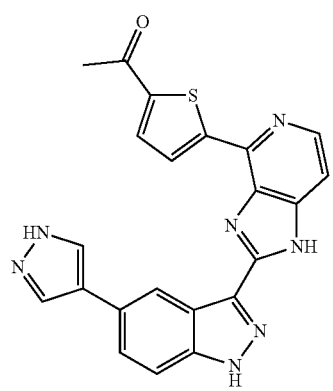 [SMILES: CC(=O)c1ccc(-c2nccc3[nH]c(-c4n[nH]c5ccc(-c6cn[nH]c6)cc45)nc23)s1]
520
TABLE 1-continued
2024 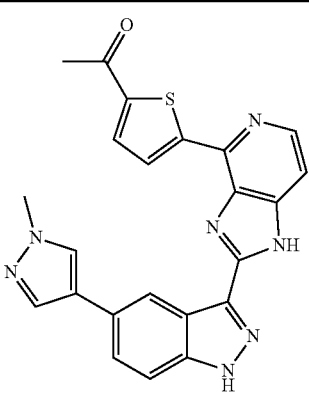
2025 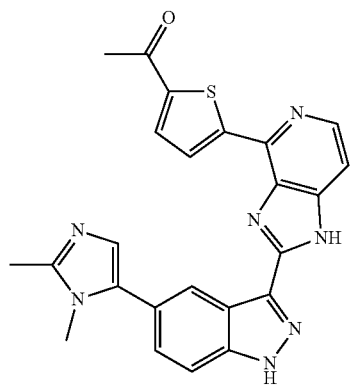 [SMILES: CC(=O)c1ccc(-c2nccc3[nH]c(-c4n[nH]c5ccc(-c6cnc(C)n6C)cc45)nc23)s1]
2026 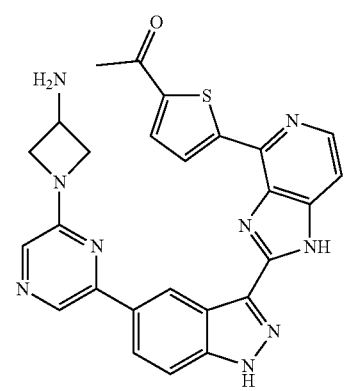 [SMILES: CC(=O)c1ccc(-c2nccc3[nH]c(-c4n[nH]c5ccc(-c6cncc(N7CC(N)C7)n6)cc45)nc23)s1]
2027 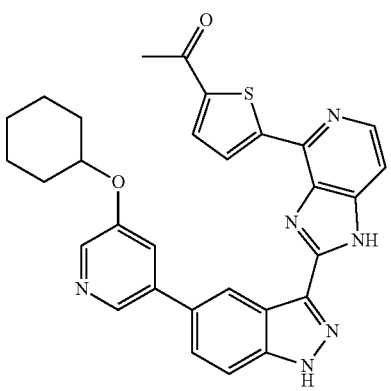 [SMILES: CC(=O)c1ccc(-c2nccc3[nH]c(-c4n[nH]c5ccc(-c6cncc(OC7CCCCC7)c6)cc45)nc23)s1]

TABLE 1-continued
2028 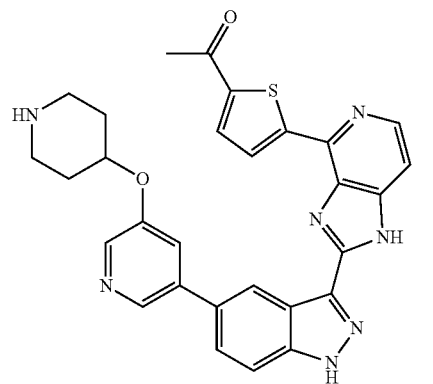 [SMILES: CC(=O)c1ccc(-c2nccc3[nH]c(-c4n[nH]c5ccc(-c6cncc(OC7CCNCC7)c6)cc45)nc23)s1]
2029 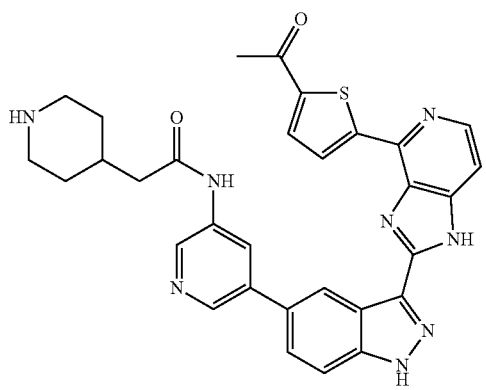 [SMILES: CC(=O)c1ccc(-c2nccc3[nH]c(-c4n[nH]c5ccc(-c6cncc(NC(=O)CC7CCNCC7)c6)cc45)nc23)s1]
2030 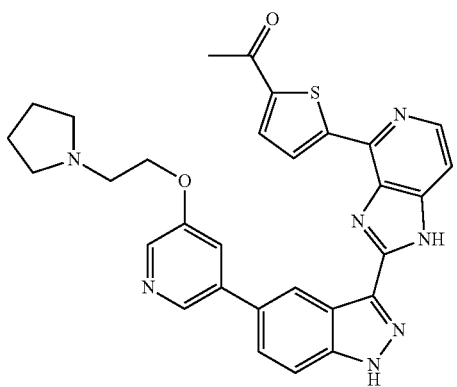 [SMILES: CC(=O)c1ccc(-c2nccc3[nH]c(-c4n[nH]c5ccc(-c6cncc(OCCN7CCCC7)c6)cc45)nc23)s1]
2031 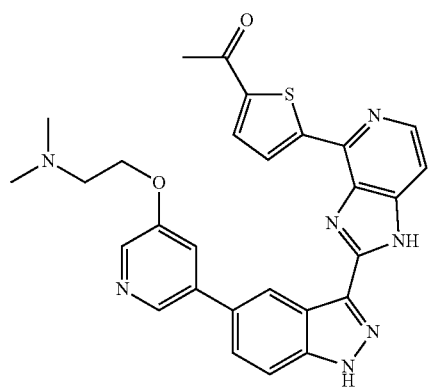 [SMILES: CC(=O)c1ccc(-c2nccc3[nH]c(-c4n[nH]c5ccc(-c6cncc(OCCN(C)C)c6)cc45)nc23)s1]
TABLE 1-continued
2032 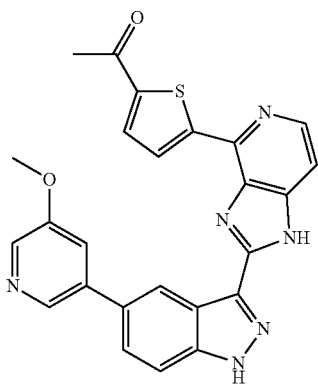 [SMILES: COc1cncc(-c2ccc3[nH]nc(-c4nc5c(-c6ccc(C(C)=O)s6)nccc5[nH]4)c3c2)c1]
2033 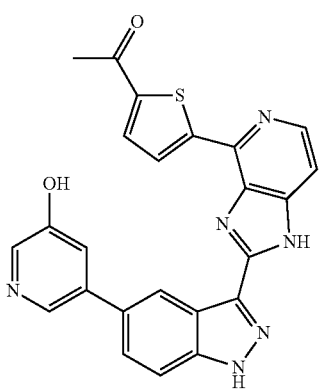 [SMILES: CC(=O)c1ccc(-c2nccc3[nH]c(-c4n[nH]c5ccc(-c6cncc(O)c6)cc45)nc23)s1]
2034 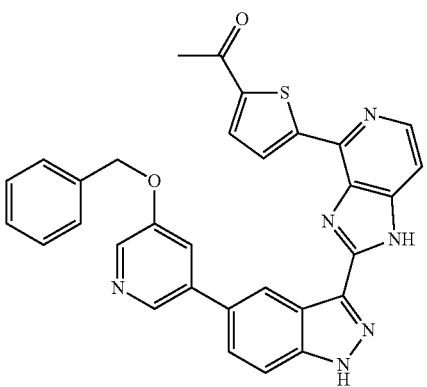 [SMILES: CC(=O)c1ccc(-c2nccc3[nH]c(-c4n[nH]c5ccc(-c6cncc(OCc7ccccc7)c6)cc45)nc23)s1]
2035 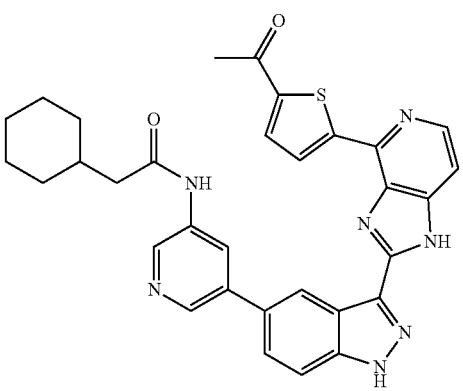 [SMILES: CC(=O)c1ccc(-c2nccc3[nH]c(-c4n[nH]c5ccc(-c6cncc(NC(=O)CC7CCCCC7)c6)cc45)nc23)s1]

TABLE 1-continued
| 2036 | 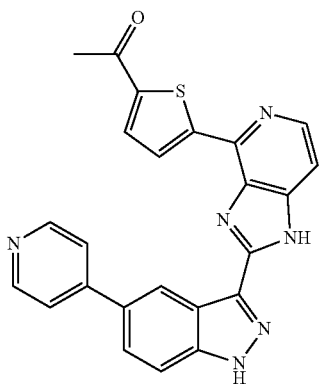 [SMILES: CC(=O)c1ccc(-c2nccc3[nH]c(-c4n[nH]c5ccc(-c6ccncc6)cc45)nc23)s1] | 2040 | 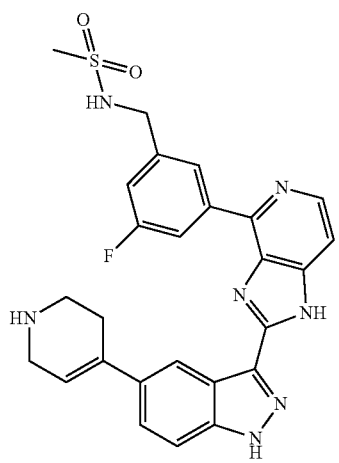 |
| 2037 | 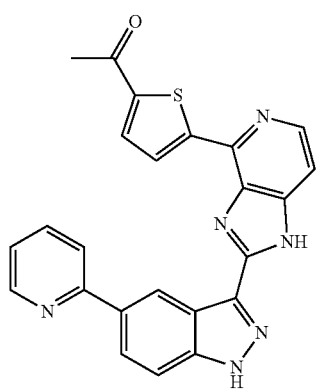 [SMILES: CC(=O)c1ccc(-c2nccc3[nH]c(-c4n[nH]c5ccc(-c6ccccn6)cc45)nc23)s1] | | |
| 2038 | 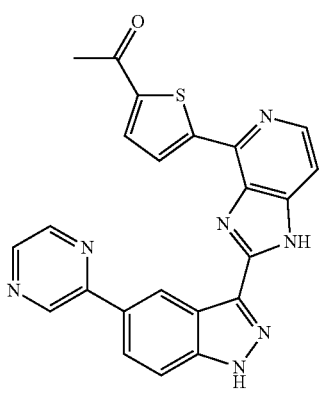 [SMILES: CC(=O)c1ccc(-c2nccc3[nH]c(-c4n[nH]c5ccc(-c6cnccn6)cc45)nc23)s1] | 2041 | 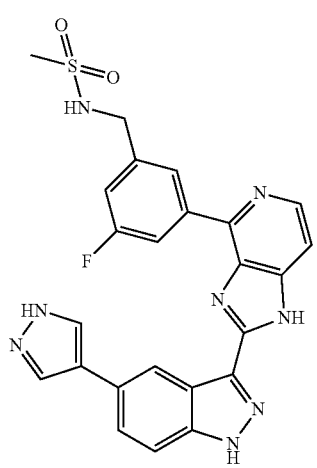 |
| 2039 | 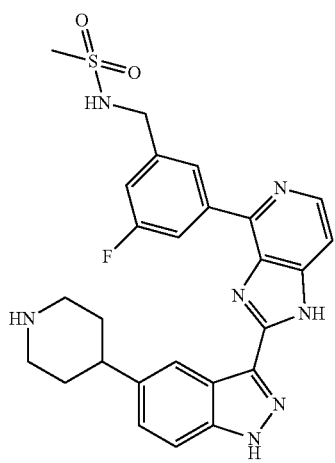 [SMILES: CS(=O)(=O)NCc1cc(F)cc(-c2nccc3[nH]c(-c4n[nH]c5ccc(C6CCNCC6)cc45)nc23)c1] | 2042 | 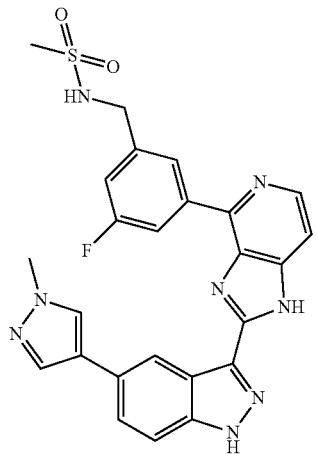 [SMILES: Cn1cc(-c2ccc3[nH]nc(-c4nc5c(-c6cc(F)cc(CNS(C)(=O)=O)c6)nccc5[nH]4)c3c2)cn1] |

TABLE 1-continued
2043 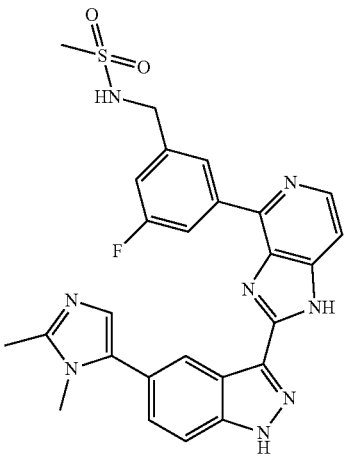 [SMILES: Cc1ncc(-c2ccc3[nH]nc(-c4nc5c(-c6cc(F)cc(CNS(C)(=O)=O)c6)nccc5[nH]4)c3c2)n1C]
2044 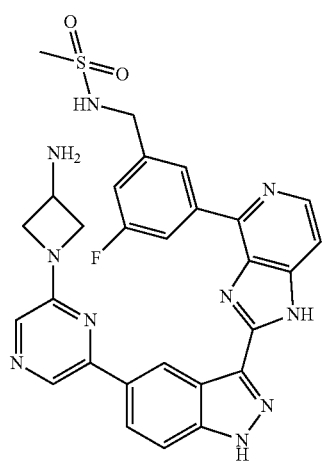 [SMILES: CS(=O)(=O)NCc1cc(F)cc(-c2nccc3[nH]c(-c4n[nH]c5ccc(-c6cncc(N7CC(N)C7)n6)cc45)nc23)c1]
2045 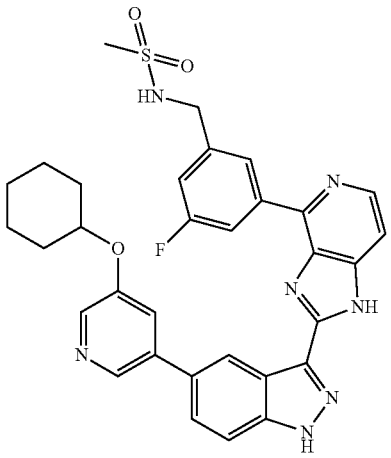 [SMILES: CS(=O)(=O)NCc1cc(F)cc(-c2nccc3[nH]c(-c4n[nH]c5ccc(-c6cncc(OC7CCCCC7)c6)cc45)nc23)c1]
TABLE 1-continued
2046 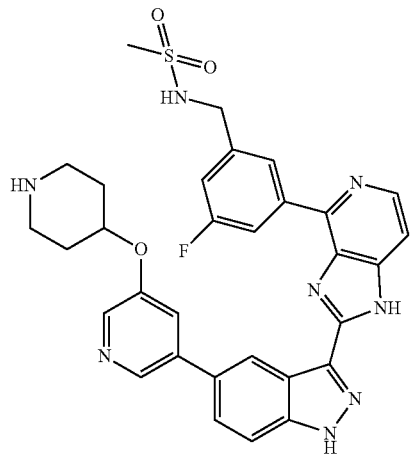 [SMILES: CS(=O)(=O)NCc1cc(F)cc(-c2nccc3[nH]c(-c4n[nH]c5ccc(-c6cncc(OC7CCNCC7)c6)cc45)nc23)c1]
2047 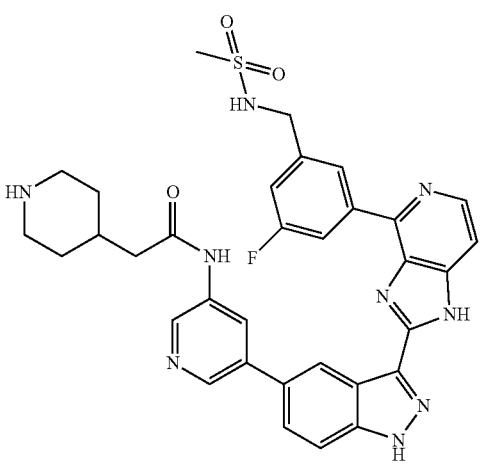 [SMILES: CS(=O)(=O)NCc1cc(F)cc(-c2nccc3[nH]c(-c4n[nH]c5ccc(-c6cncc(NC(=O)CC7CCNCC7)c6)cc45)nc23)c1]
2048 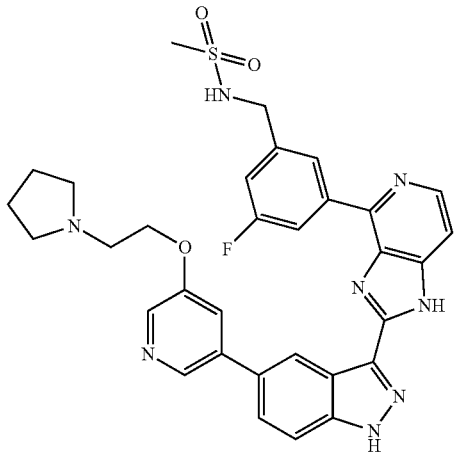 [SMILES: CS(=O)(=O)NCc1cc(F)cc(-c2nccc3[nH]c(-c4n[nH]c5ccc(-c6cncc(OCCN7CCCC7)c6)cc45)nc23)c1]

TABLE 1-continued
2049
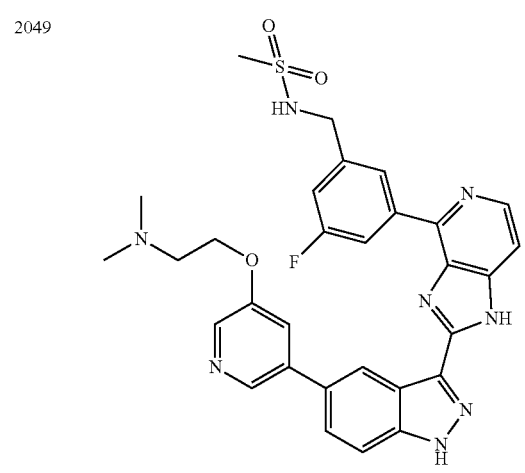
2050
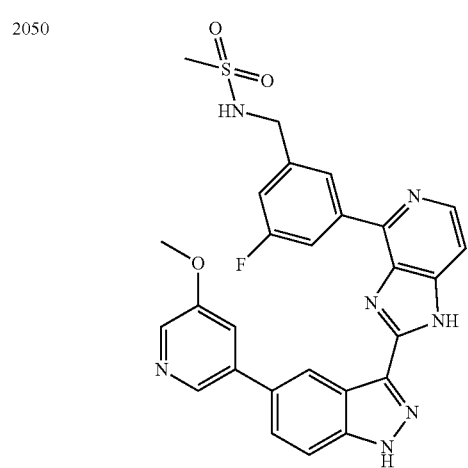
2051
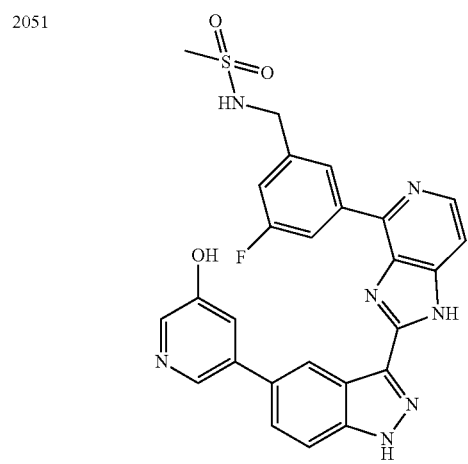
2052
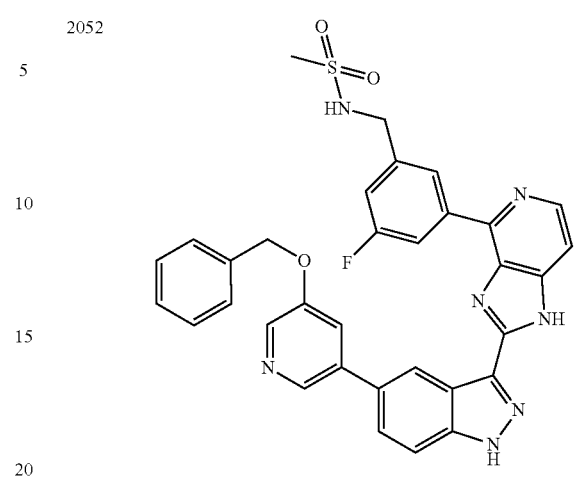
2053
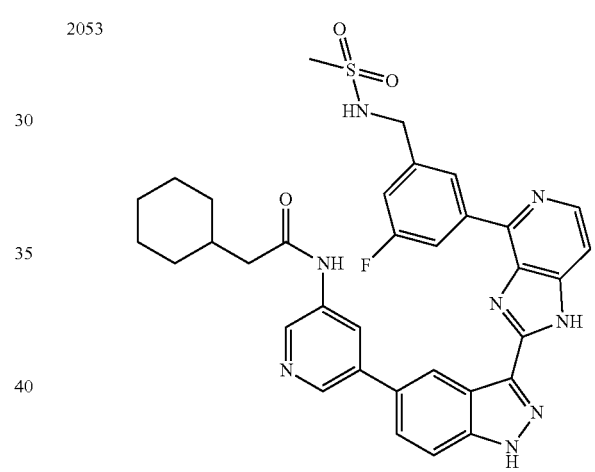
2054
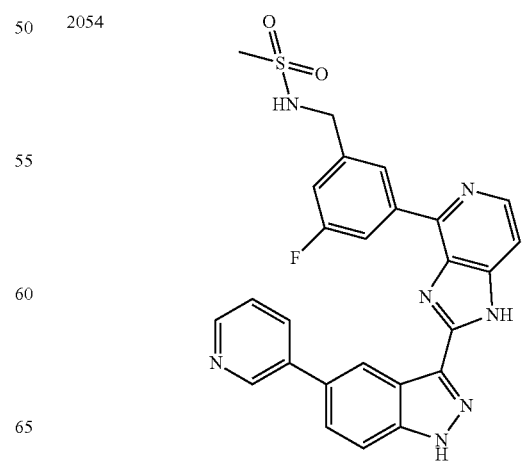

TABLE 1-continued
2055 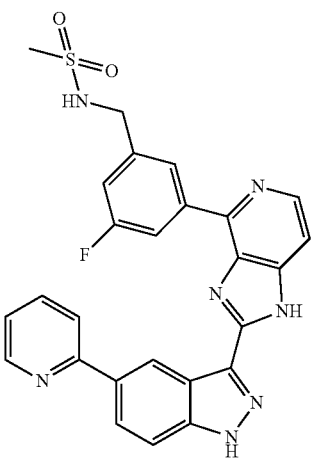 [SMILES: CS(=O)(=O)NCc1cc(F)cc(-c2nccc3[nH]c(-c4n[nH]c5ccc(-c6ccccn6)cc45)nc23)c1]
2056 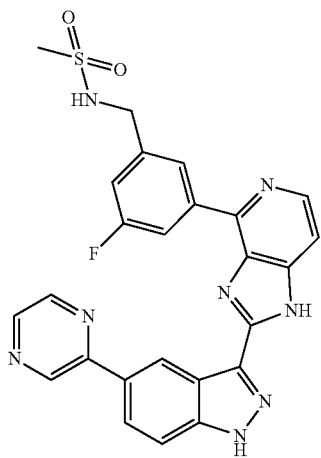 [SMILES: CS(=O)(=O)NCc1cc(F)cc(-c2nccc3[nH]c(-c4n[nH]c5ccc(-c6cnccn6)cc45)nc23)c1]
2057 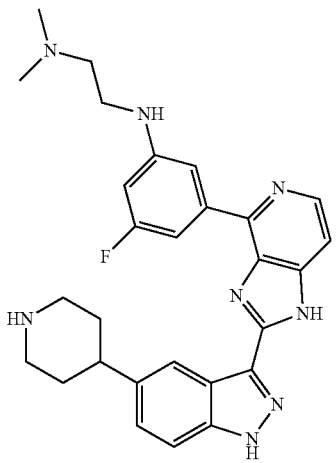 [SMILES: CN(C)CCNc1cc(F)cc(-c2nccc3[nH]c(-c4n[nH]c5ccc(C6CCNCC6)cc45)nc23)c1]
TABLE 1-continued
2058 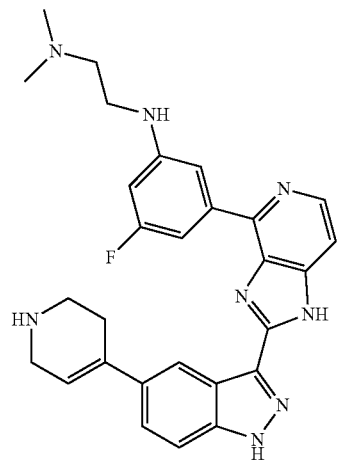 [SMILES: CN(C)CCNc1cc(F)cc(-c2nccc3[nH]c(-c4n[nH]c5ccc(C6=CCNCC6)cc45)nc23)c1]
2059 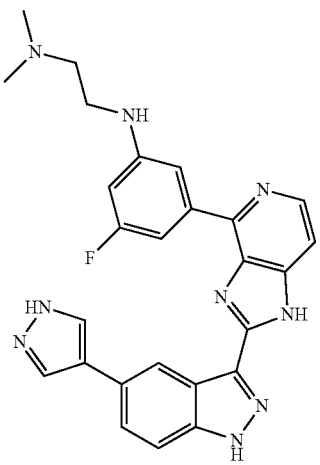 [SMILES: CN(C)CCNc1cc(F)cc(-c2nccc3[nH]c(-c4n[nH]c5ccc(-c6cn[nH]c6)cc45)nc23)c1]
2060 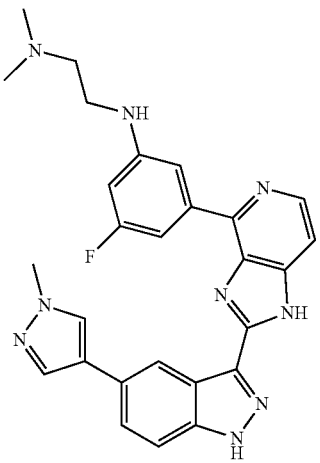

TABLE 1-continued
2061
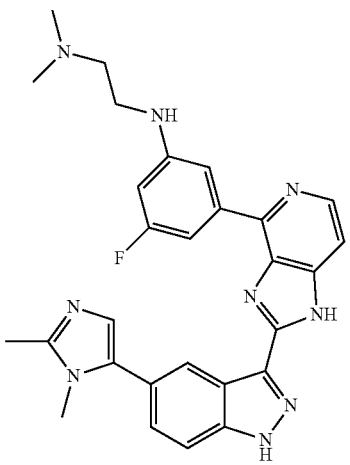 [SMILES: Cc1ncc(-c2ccc3[nH]nc(-c4nc5c(-c6cc(F)cc(NCCN(C)C)c6)nccc5[nH]4)c3c2)n1C]
2062
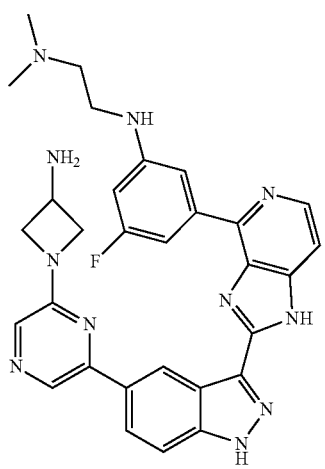 [SMILES: CN(C)CCNc1cc(F)cc(-c2nccc3[nH]c(-c4n[nH]c5ccc(-c6cncc(N7CC(N)C7)n6)cc45)nc23)c1]
2063
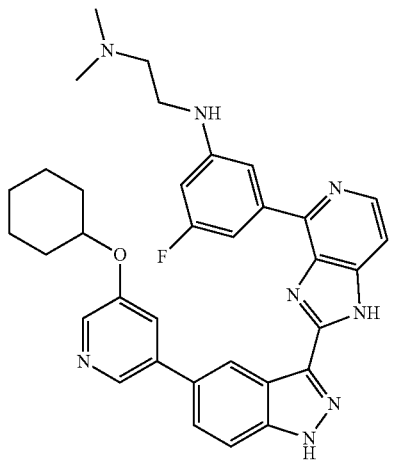 [SMILES: CN(C)CCNc1cc(F)cc(-c2nccc3[nH]c(-c4n[nH]c5ccc(-c6cncc(OC7CCCCC7)c6)cc45)nc23)c1]
TABLE 1-continued
2064
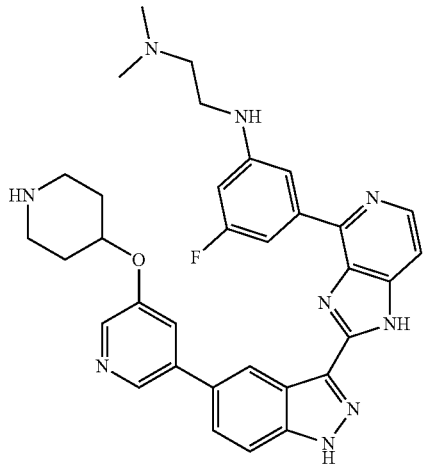 [SMILES: CN(C)CCNc1cc(F)cc(-c2nccc3[nH]c(-c4n[nH]c5ccc(-c6cncc(OC7CCNCC7)c6)cc45)nc23)c1]
2065
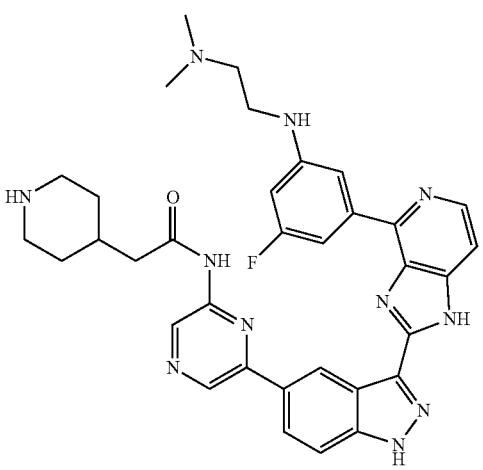 [SMILES: CN(C)CCNc1cc(F)cc(-c2nccc3[nH]c(-c4n[nH]c5ccc(-c6cncc(NC(=O)CC7CCNCC7)n6)cc45)nc23)c1]
2066
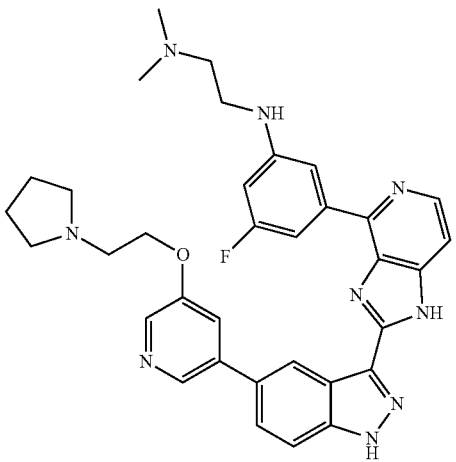 [SMILES: CN(C)CCNc1cc(F)cc(-c2nccc3[nH]c(-c4n[nH]c5ccc(-c6cncc(OCCN7CCCC7)c6)cc45)nc23)c1]

TABLE 1-continued
2067 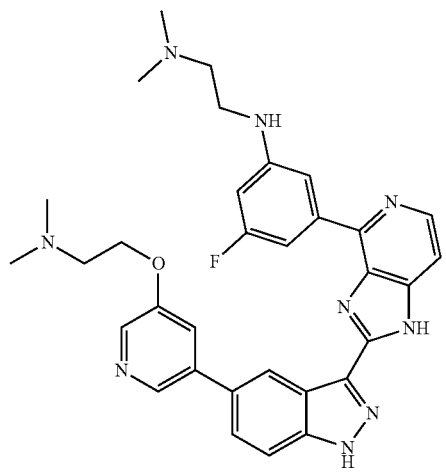 [SMILES: CN(C)CCNc1cc(F)cc(-c2nccc3[nH]c(-c4n[nH]c5ccc(-c6cncc(OCCN(C)C)c6)cc45)nc23)c1]
2068 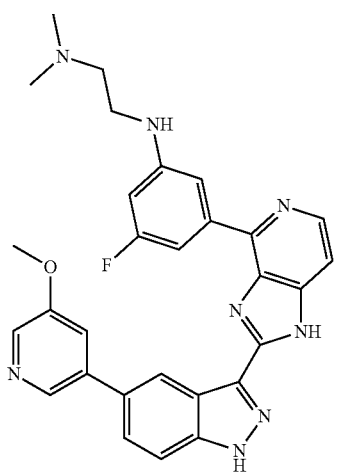 [SMILES: COc1cncc(-c2ccc3[nH]nc(-c4nc5c(-c6cc(F)cc(NCCN(C)C)c6)nccc5[nH]4)c3c2)c1]
2069 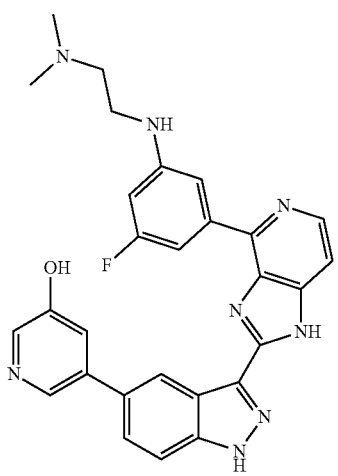 [SMILES: CN(C)CCNc1cc(F)cc(-c2nccc3[nH]c(-c4n[nH]c5ccc(-c6cncc(O)c6)cc45)nc23)c1]
2070 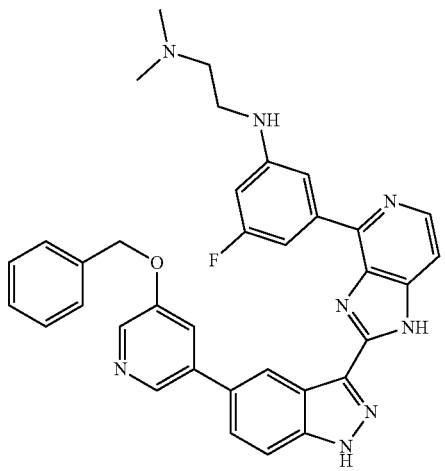 [SMILES: CN(C)CCNc1cc(F)cc(-c2nccc3[nH]c(-c4n[nH]c5ccc(-c6cncc(OCc7ccccc7)c6)cc45)nc23)c1]
2071 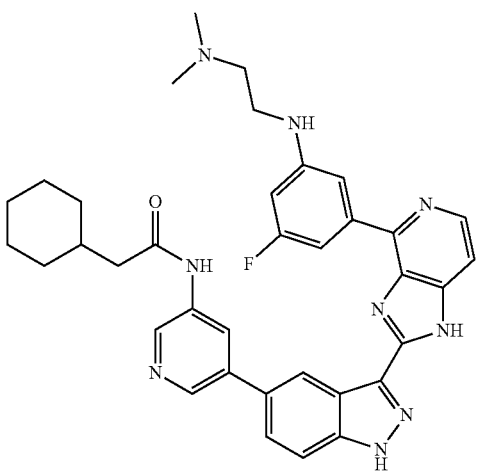 [SMILES: CN(C)CCNc1cc(F)cc(-c2nccc3[nH]c(-c4n[nH]c5ccc(-c6cncc(NC(=O)CC7CCCCC7)c6)cc45)nc23)c1]
2072 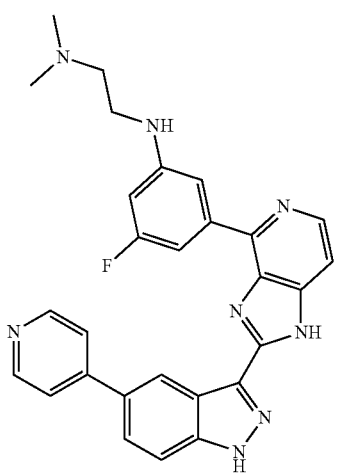 [SMILES: CN(C)CCNc1cc(F)cc(-c2nccc3[nH]c(-c4n[nH]c5ccc(-c6ccncc6)cc45)nc23)c1]

TABLE 1-continued
2073
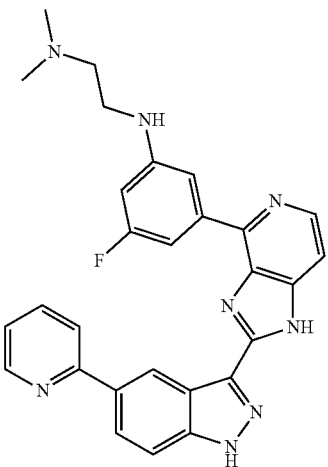 [SMILES: CN(C)CCNc1cc(F)cc(-c2nccc3[nH]c(-c4n[nH]c5ccc(-c6ccccn6)cc45)nc23)c1]
2074
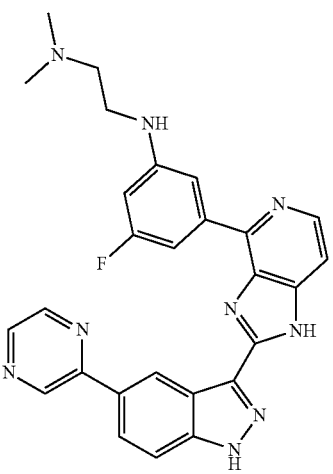 [SMILES: CN(C)CCNc1cc(F)cc(-c2nccc3[nH]c(-c4n[nH]c5ccc(-c6cnccn6)cc45)nc23)c1]
2075
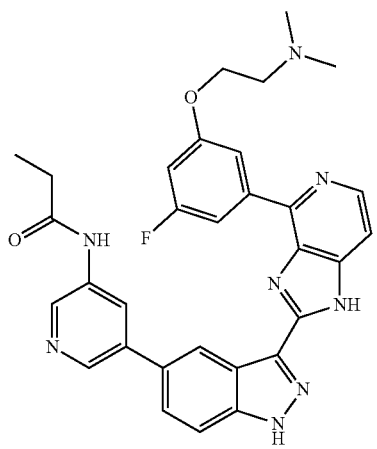 [SMILES: CCC(=O)Nc1cncc(-c2ccc3[nH]nc(-c4nc5c(-c6cc(F)cc(OCCN(C)C)c6)nccc5[nH]4)c3c2)c1]
2076
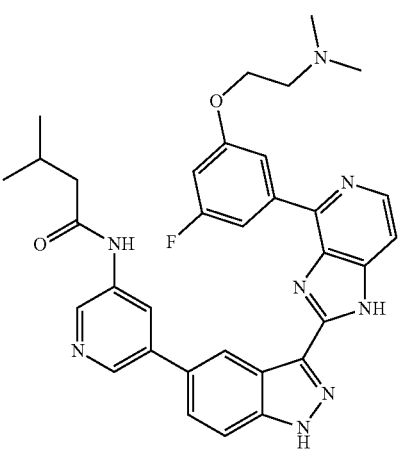 [SMILES: CC(C)CC(=O)Nc1cncc(-c2ccc3[nH]nc(-c4nc5c(-c6cc(F)cc(OCCN(C)C)c6)nccc5[nH]4)c3c2)c1]
2077
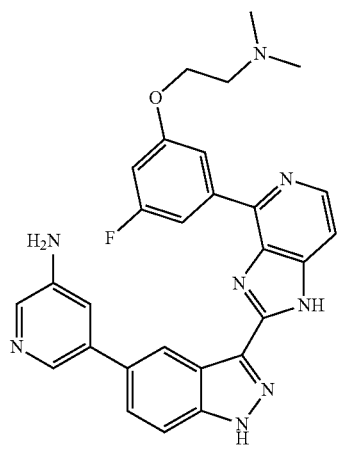 [SMILES: CN(C)CCOc1cc(F)cc(-c2nccc3[nH]c(-c4n[nH]c5ccc(-c6cncc(N)c6)cc45)nc23)c1]
2078
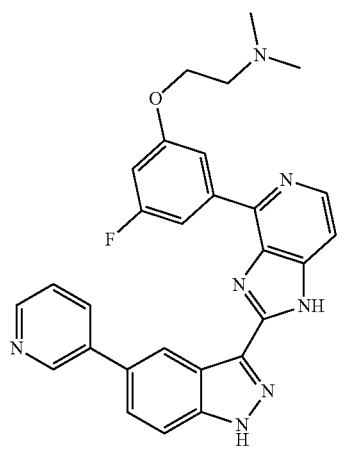 [SMILES: CN(C)CCOc1cc(F)cc(-c2nccc3[nH]c(-c4n[nH]c5ccc(-c6cccnc6)cc45)nc23)c1]

TABLE 1-continued
2079
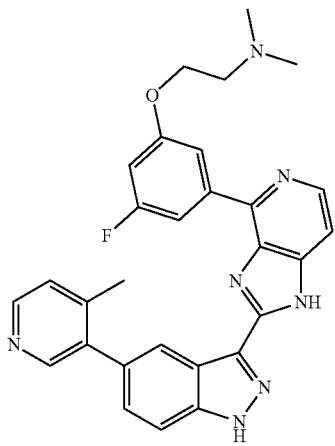 [SMILES: Cc1ccncc1-c1ccc2[nH]nc(-c3nc4c(-c5cc(F)cc(OCCN(C)C)c5)nccc4[nH]3)c2c1]
2082
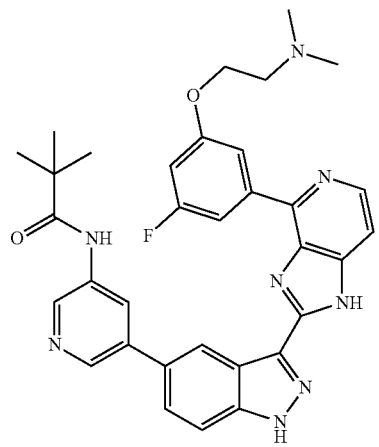 [SMILES: CN(C)CCOc1cc(F)cc(-c2nccc3[nH]c(-c4n[nH]c5ccc(-c6cncc(NC(=O)C(C)(C)C)c6)cc45)nc23)c1]
2080
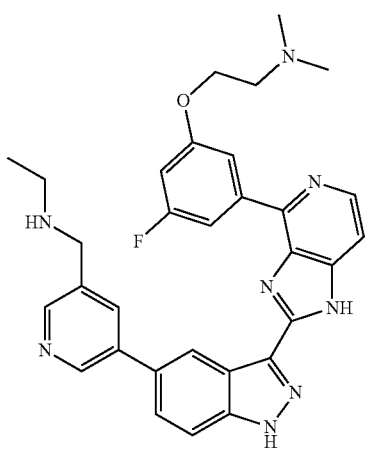
2083
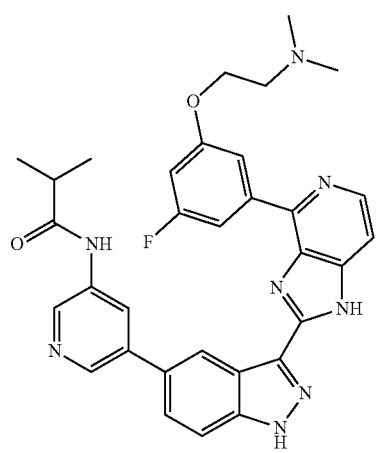 [SMILES: CC(C)C(=O)Nc1cncc(-c2ccc3[nH]nc(-c4nc5c(-c6cc(F)cc(OCCN(C)C)c6)nccc5[nH]4)c3c2)c1]
2081
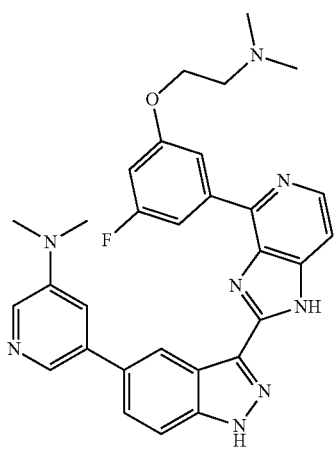
2084
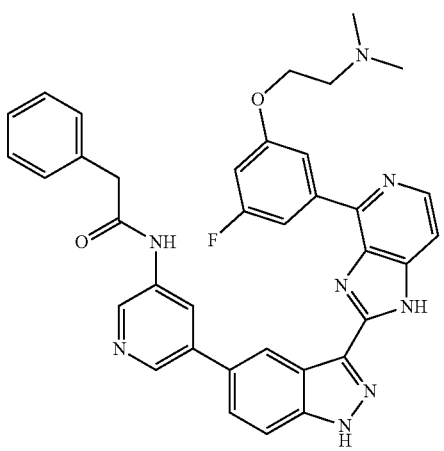 [SMILES: CN(C)CCOc1cc(F)cc(-c2nccc3[nH]c(-c4n[nH]c5ccc(-c6cncc(NC(=O)Cc7ccccc7)c6)cc45)nc23)c1]

TABLE 1-continued
2085
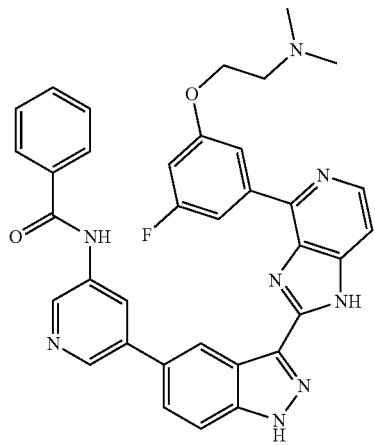 [SMILES: CN(C)CCOc1cc(F)cc(-c2nccc3[nH]c(-c4n[nH]c5ccc(-c6cncc(NC(=O)c7ccccc7)c6)cc45)nc23)c1]
2086
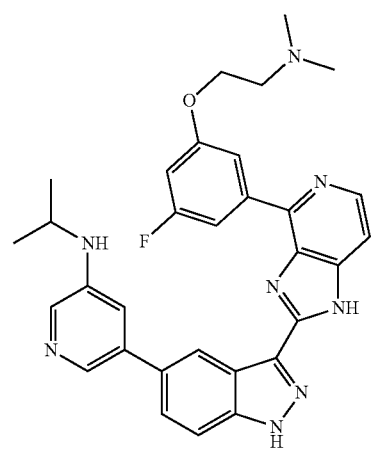 [SMILES: CC(C)Nc1cncc(-c2ccc3[nH]nc(-c4nc5c(-c6cc(F)cc(OCCN(C)C)c6)nccc5[nH]4)c3c2)c1]
2087
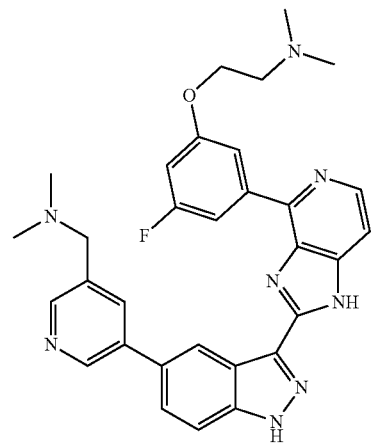 [SMILES: CN(C)CCOc1cc(F)cc(-c2nccc3[nH]c(-c4n[nH]c5ccc(-c6cncc(CN(C)C)c6)cc45)nc23)c1]
2088
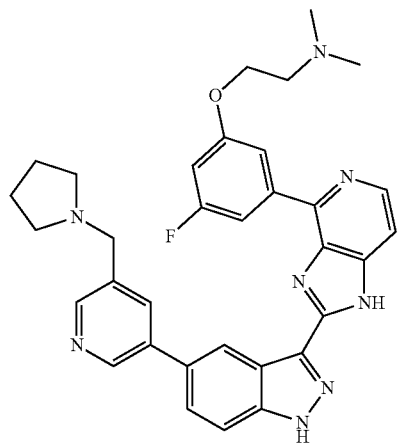 [SMILES: CN(C)CCOc1cc(F)cc(-c2nccc3[nH]c(-c4n[nH]c5ccc(-c6cncc(CN7CCCC7)c6)cc45)nc23)c1]
2089
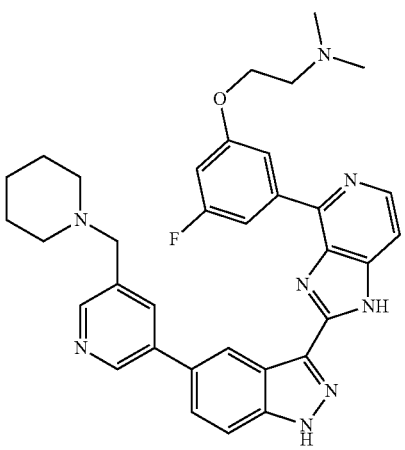 [SMILES: CN(C)CCOc1cc(F)cc(-c2nccc3[nH]c(-c4n[nH]c5ccc(-c6cncc(CN7CCCCC7)c6)cc45)nc23)c1]
2090
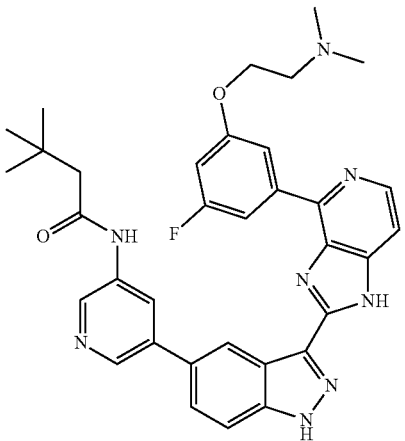 [SMILES: CN(C)CCOc1cc(F)cc(-c2nccc3[nH]c(-c4n[nH]c5ccc(-c6cncc(NC(=O)CC(C)(C)C)c6)cc45)nc23)c1]

TABLE 1-continued
2091
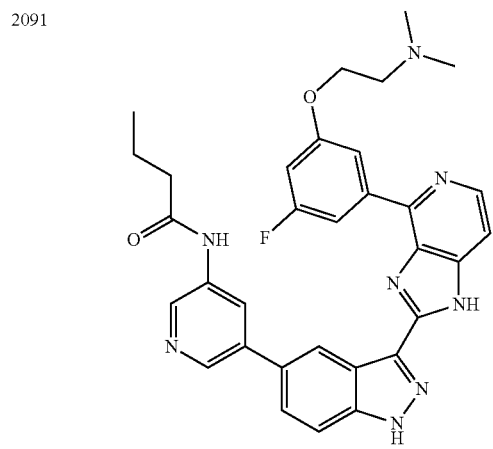
2092
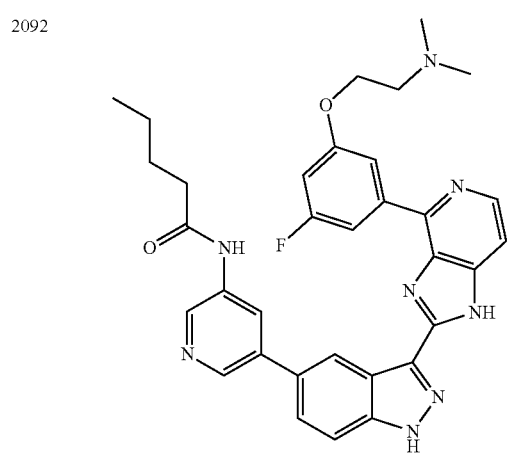
2093
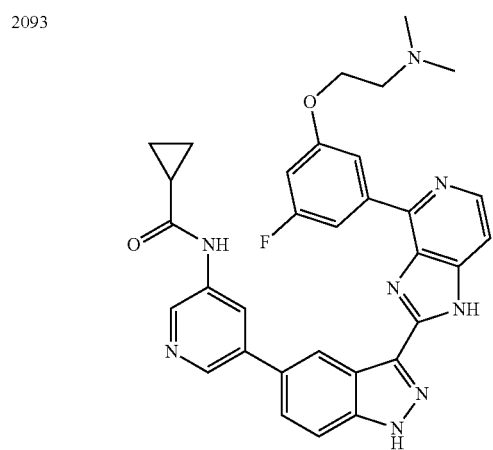
TABLE 1-continued
2094
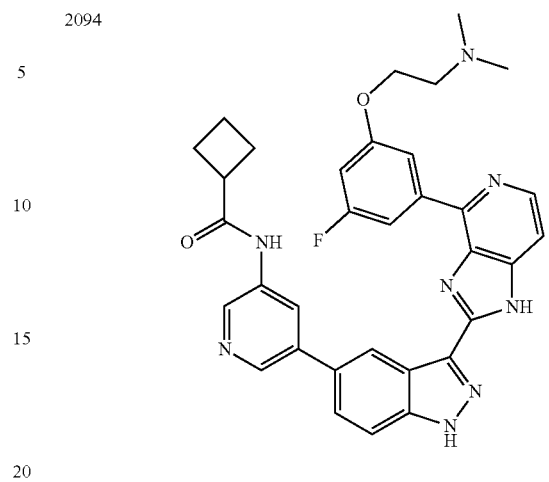
2095
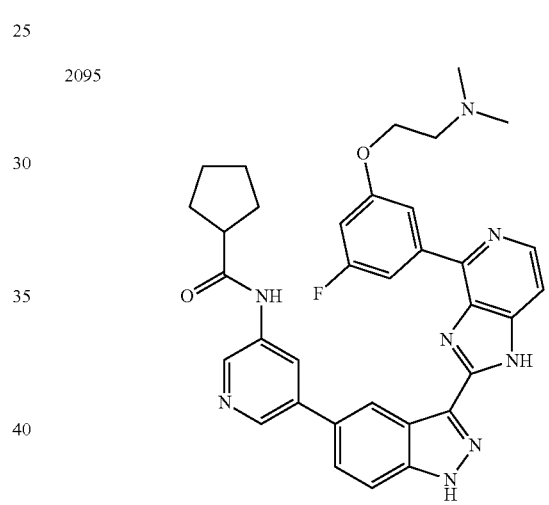
2096
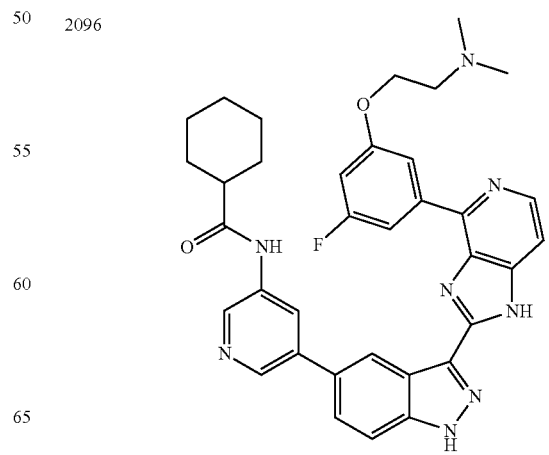

TABLE 1-continued
| 2097 | 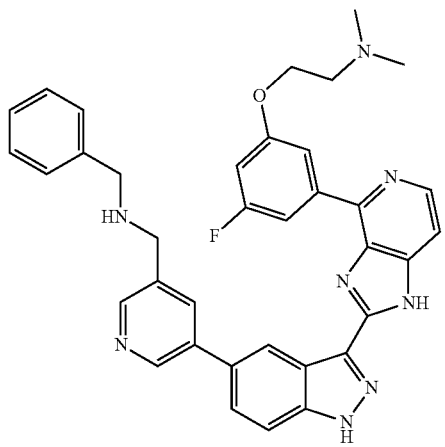 [SMILES: CN(C)CCOc1cc(F)cc(-c2nccc3[nH]c(-c4n[nH]c5ccc(-c6cncc(CNCc7ccccc7)c6)cc45)nc23)c1] |
| --- | --- |
| 2098 | 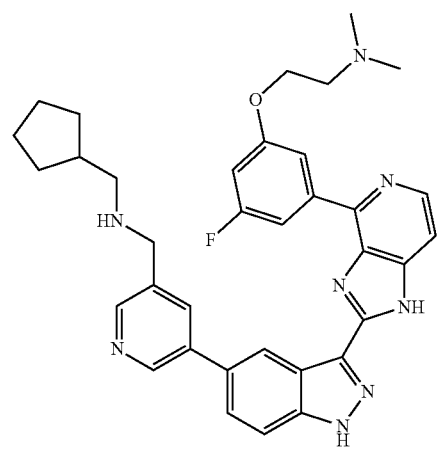 [SMILES: CN(C)CCOc1cc(F)cc(-c2nccc3[nH]c(-c4n[nH]c5ccc(-c6cncc(CNCC7CCCC7)c6)cc45)nc23)c1] |
| 2099 | 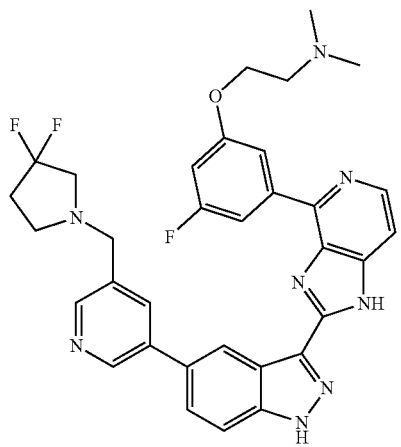 [SMILES: CN(C)CCOc1cc(F)cc(-c2nccc3[nH]c(-c4n[nH]c5ccc(-c6cncc(CN7CCC(F)(F)C7)c6)cc45)nc23)c1] |
TABLE 1-continued
| 2100 | 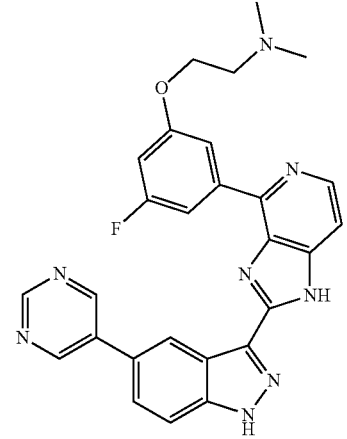 |
| --- | --- |
| 2101 | 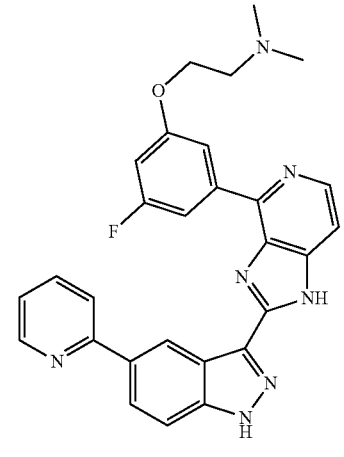 [SMILES: CN(C)CCOc1cc(F)cc(-c2nccc3[nH]c(-c4n[nH]c5ccc(-c6ccccn6)cc45)nc23)c1] |
| 2102 | 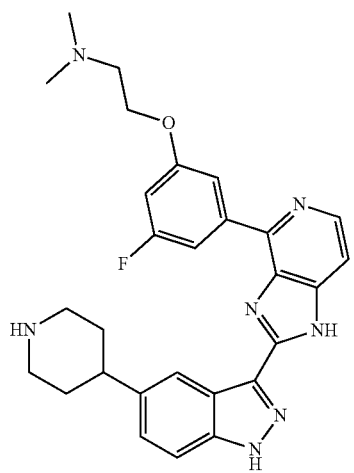 [SMILES: CN(C)CCOc1cc(F)cc(-c2nccc3[nH]c(-c4n[nH]c5ccc(C6CCNCC6)cc45)nc23)c1] |

TABLE 1-continued
2103 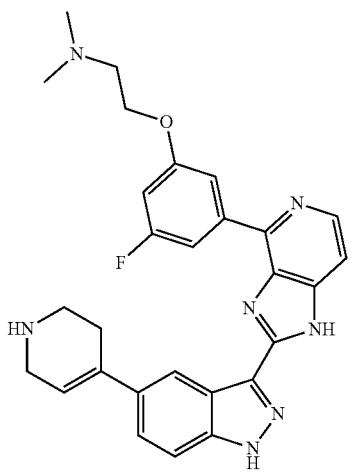 [SMILES: CN(C)CCOc1cc(F)cc(-c2nccc3[nH]c(-c4n[nH]c5ccc(C6=CCNCC6)cc45)nc23)c1]
2104 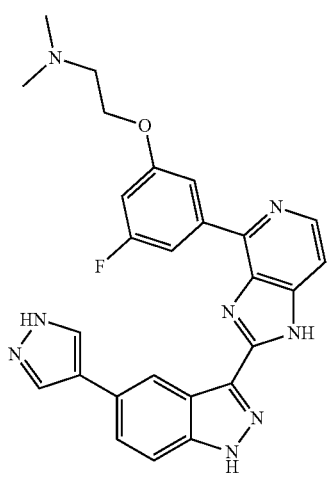 [SMILES: CN(C)CCOc1cc(F)cc(-c2nccc3[nH]c(-c4n[nH]c5ccc(-c6cn[nH]c6)cc45)nc23)c1]
2105 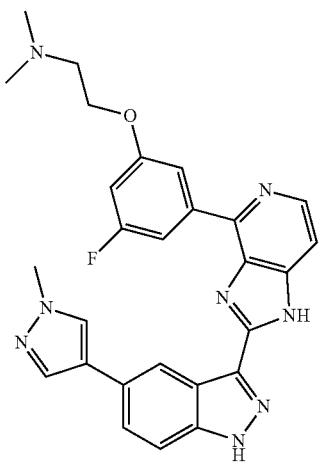 [SMILES: CN(C)CCOc1cc(F)cc(-c2nccc3[nH]c(-c4n[nH]c5ccc(-c6cnn(C)c6)cc45)nc23)c1]
2106 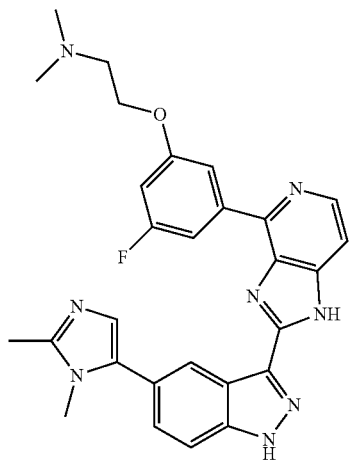 [SMILES: Cc1ncc(-c2ccc3[nH]nc(-c4nc5c(-c6cc(F)cc(OCCN(C)C)c6)nccc5[nH]4)c3c2)n1C]
2107 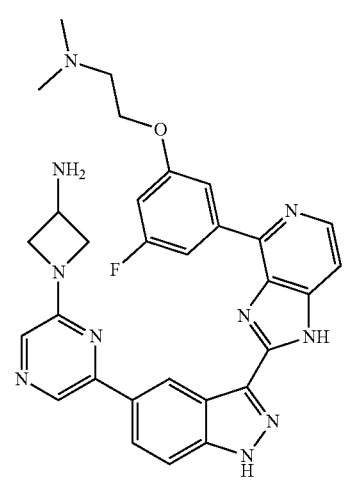 [SMILES: CN(C)CCOc1cc(F)cc(-c2nccc3[nH]c(-c4n[nH]c5ccc(-c6cncc(N7CC(N)C7)n6)cc45)nc23)c1]
2108 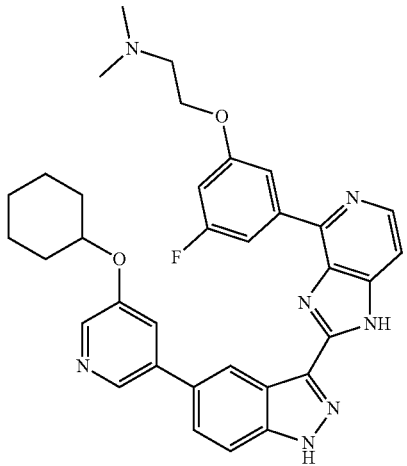 [SMILES: CN(C)CCOc1cc(F)cc(-c2nccc3[nH]c(-c4n[nH]c5ccc(-c6cncc(OC7CCCCC7)c6)cc45)nc23)c1]

TABLE 1-continued
2109
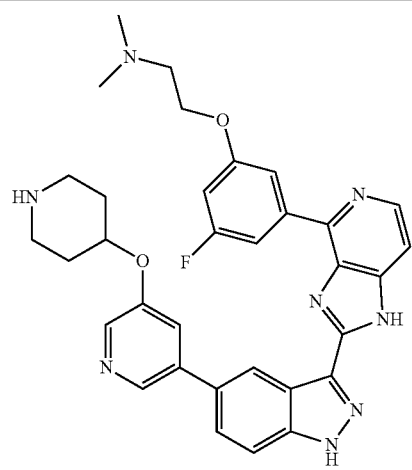 [SMILES: CN(C)CCOc1cc(F)cc(-c2nccc3[nH]c(-c4n[nH]c5ccc(-c6cncc(OC7CCNCC7)c6)cc45)nc23)c1]
2110
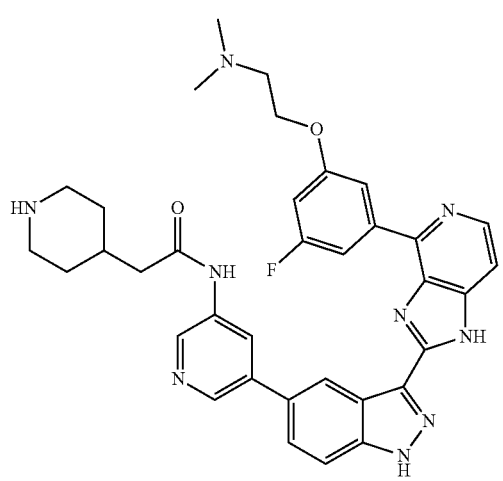 [SMILES: CN(C)CCOc1cc(F)cc(-c2nccc3[nH]c(-c4n[nH]c5ccc(-c6cncc(NC(=O)CC7CCNCC7)c6)cc45)nc23)c1]
2111
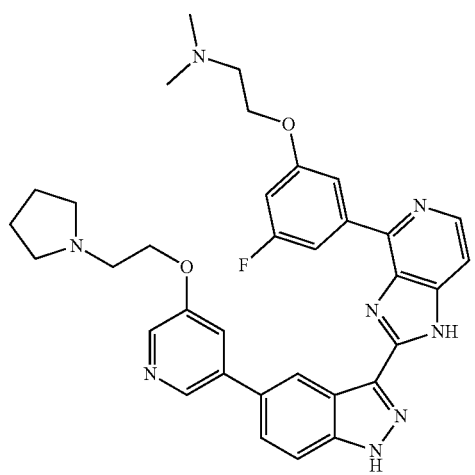 [SMILES: CN(C)CCOc1cc(F)cc(-c2nccc3[nH]c(-c4n[nH]c5ccc(-c6cncc(OCCN7CCCC7)c6)cc45)nc23)c1]
TABLE 1-continued
2112
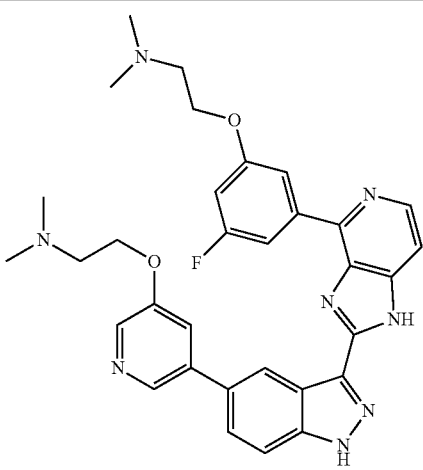 [SMILES: CN(C)CCOc1cncc(-c2ccc3[nH]nc(-c4nc5c(-c6cc(F)cc(OCCN(C)C)c6)nccc5[nH]4)c3c2)c1]
2113
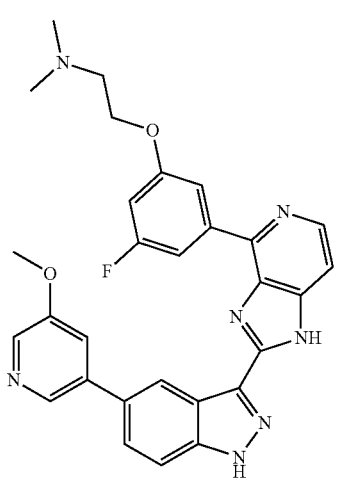 [SMILES: COc1cncc(-c2ccc3[nH]nc(-c4nc5c(-c6cc(F)cc(OCCN(C)C)c6)nccc5[nH]4)c3c2)c1]
2114
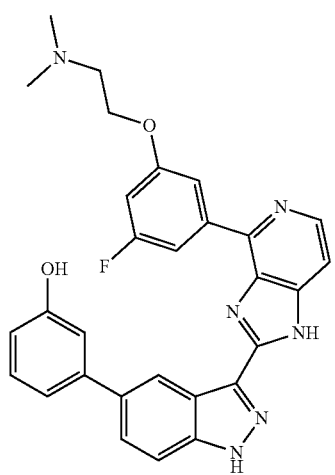 [SMILES: CN(C)CCOc1cc(F)cc(-c2nccc3[nH]c(-c4n[nH]c5ccc(-c6cccc(O)c6)cc45)nc23)c1]

TABLE 1-continued
2115
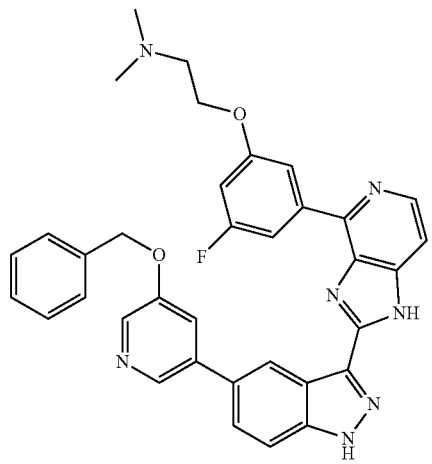 [SMILES: CN(C)CCOc1cc(F)cc(-c2nccc3[nH]c(-c4n[nH]c5ccc(-c6cncc(OCc7ccccc7)c6)cc45)nc23)c1]
2116
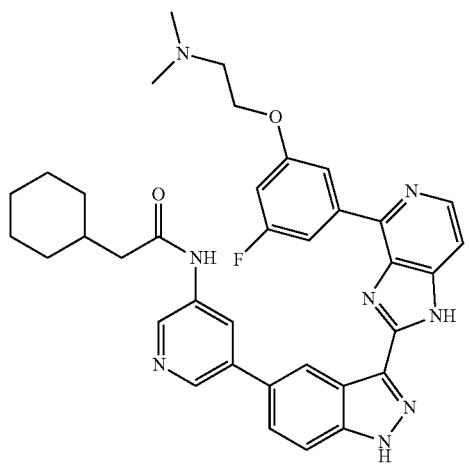 [SMILES: CN(C)CCOc1cc(F)cc(-c2nccc3[nH]c(-c4n[nH]c5ccc(-c6cncc(NC(=O)CC7CCCCC7)c6)cc45)nc23)c1]
2117
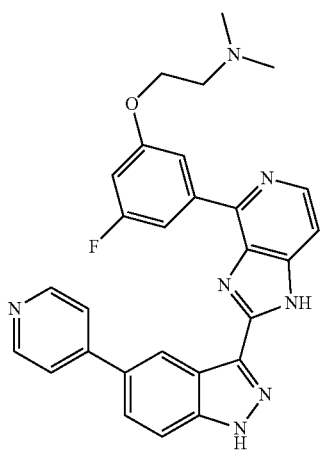 [SMILES: CN(C)CCOc1cc(F)cc(-c2nccc3[nH]c(-c4n[nH]c5ccc(-c6ccncc6)cc45)nc23)c1]
TABLE 1-continued
2118
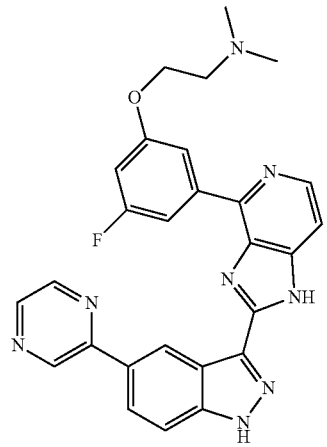 [SMILES: CN(C)CCOc1cc(F)cc(-c2nccc3[nH]c(-c4n[nH]c5ccc(-c6cnccn6)cc45)nc23)c1]
2119
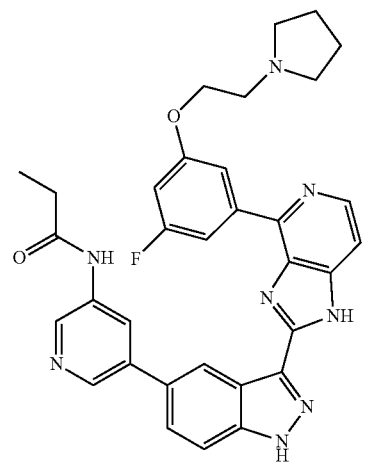 [SMILES: CCC(=O)Nc1cncc(-c2ccc3[nH]nc(-c4nc5c(-c6cc(F)cc(OCCN7CCCC7)c6)nccc5[nH]4)c3c2)c1]
2120
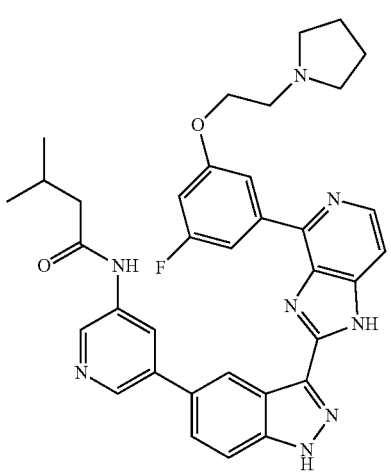 [SMILES: CC(C)CC(=O)Nc1cncc(-c2ccc3[nH]nc(-c4nc5c(-c6cc(F)cc(OCCN7CCCC7)c6)nccc5[nH]4)c3c2)c1]

TABLE 1-continued
2121
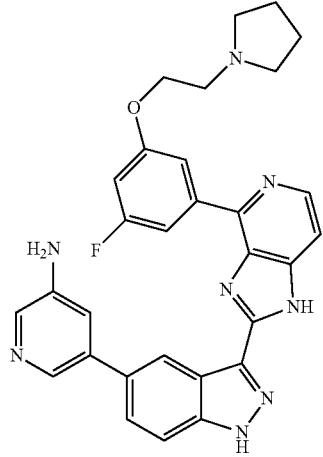 [SMILES: Nc1cncc(-c2ccc3[nH]nc(-c4nc5c(-c6cc(F)cc(OCCN7CCCC7)c6)nccc5[nH]4)c3c2)c1]
2122
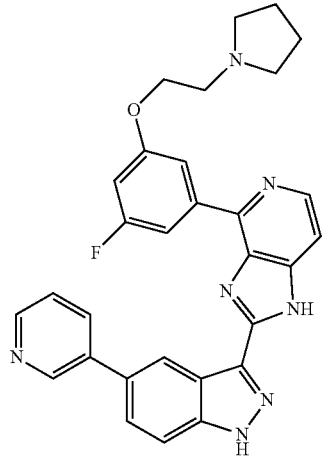 [SMILES: Fc1cc(OCCN2CCCC2)cc(-c2nccc3[nH]c(-c4n[nH]c5ccc(-c6cccnc6)cc45)nc23)c1]
2123
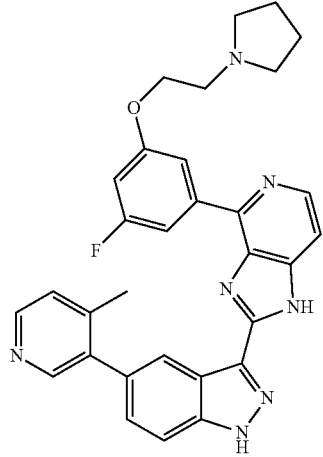 [SMILES: Cc1ccncc1-c1ccc2[nH]nc(-c3nc4c(-c5cc(F)cc(OCCN6CCCC6)c5)nccc4[nH]3)c2c1]
TABLE 1-continued
2124
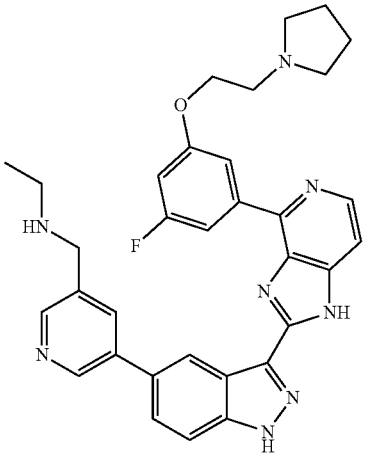
2125
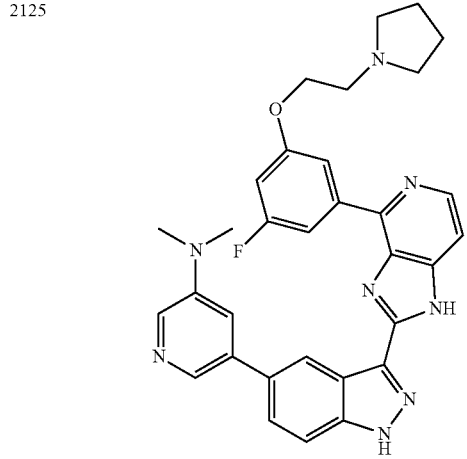
2126
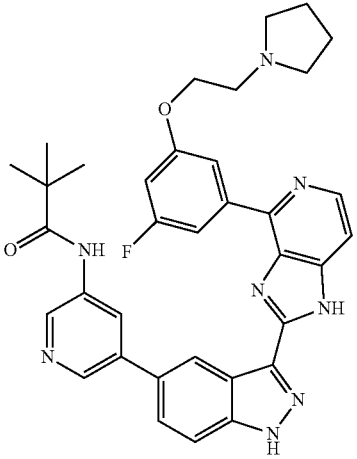 [SMILES: CC(C)(C)C(=O)Nc1cncc(-c2ccc3[nH]nc(-c4nc5c(-c6cc(F)cc(OCCN7CCCC7)c6)nccc5[nH]4)c3c2)c1]

TABLE 1-continued
2127
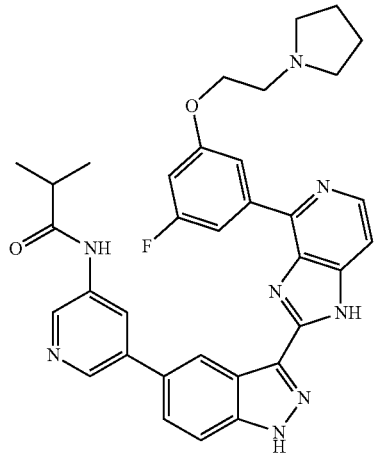 [SMILES: CC(C)C(=O)Nc1cncc(-c2ccc3[nH]nc(-c4nc5c(-c6cc(F)cc(OCCN7CCCC7)c6)nccc5[nH]4)c3c2)c1]
2130
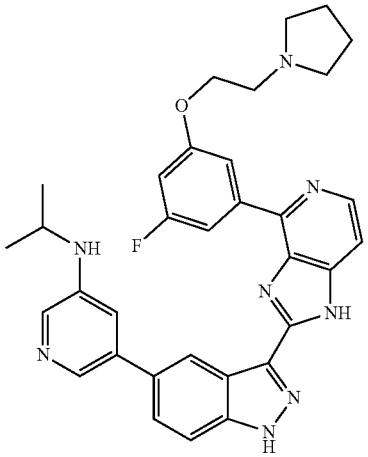
2128
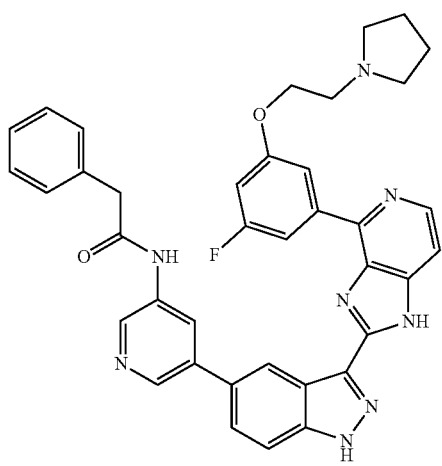 [SMILES: O=C(Cc1ccccc1)Nc1cncc(-c2ccc3[nH]nc(-c4nc5c(-c6cc(F)cc(OCCN7CCCC7)c6)nccc5[nH]4)c3c2)c1]
2131
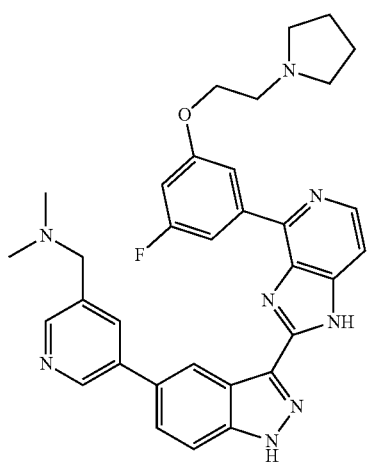
2129
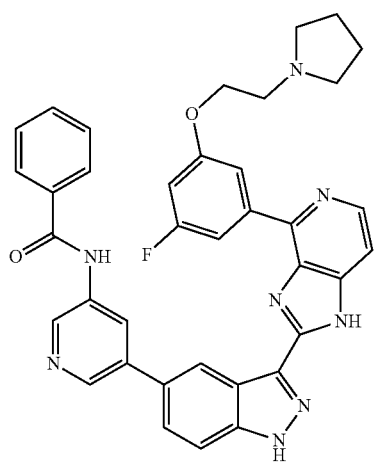 [SMILES: O=C(Nc1cncc(-c2ccc3[nH]nc(-c4nc5c(-c6cc(F)cc(OCCN7CCCC7)c6)nccc5[nH]4)c3c2)c1)c1ccccc1]
2132
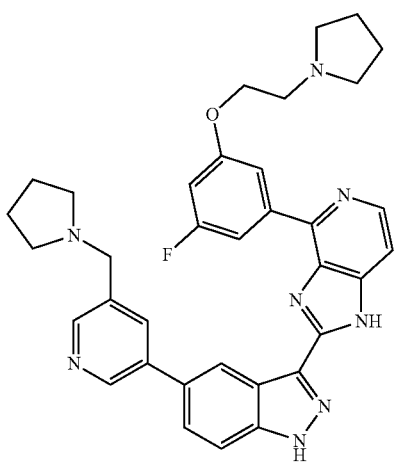 [SMILES: Fc1cc(OCCN2CCCC2)cc(-c2nccc3[nH]c(-c4n[nH]c5ccc(-c6cncc(CN7CCCC7)c6)cc45)nc23)c1]

TABLE 1-continued
2133
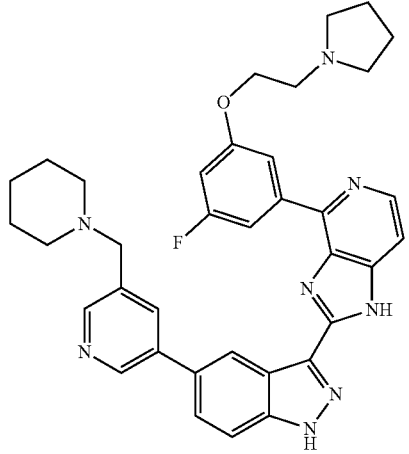 [SMILES: Fc1cc(OCCN2CCCC2)cc(-c2nccc3[nH]c(-c4n[nH]c5ccc(-c6cncc(CN7CCCCC7)c6)cc45)nc23)c1]
2134
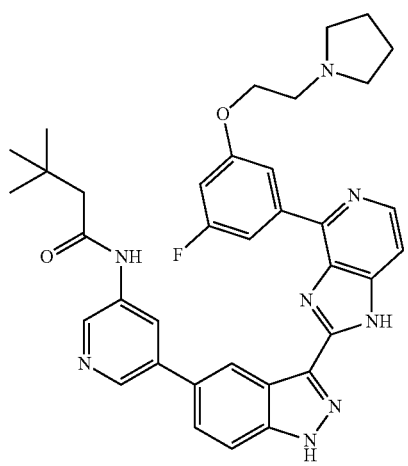 [SMILES: CC(C)(C)CC(=O)Nc1cncc(-c2ccc3[nH]nc(-c4nc5c(-c6cc(F)cc(OCCN7CCCC7)c6)nccc5[nH]4)c3c2)c1]
2135
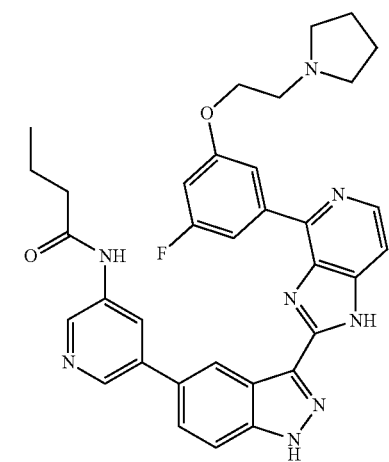 [SMILES: CCCC(=O)Nc1cncc(-c2ccc3[nH]nc(-c4nc5c(-c6cc(F)cc(OCCN7CCCC7)c6)nccc5[nH]4)c3c2)c1]
TABLE 1-continued
2136
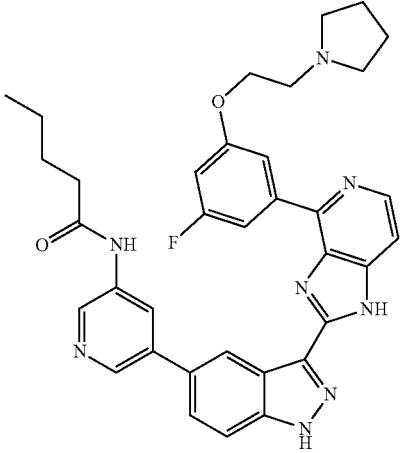 [SMILES: CCCCC(=O)Nc1cncc(-c2ccc3[nH]nc(-c4nc5c(-c6cc(F)cc(OCCN7CCCC7)c6)nccc5[nH]4)c3c2)c1]
2137
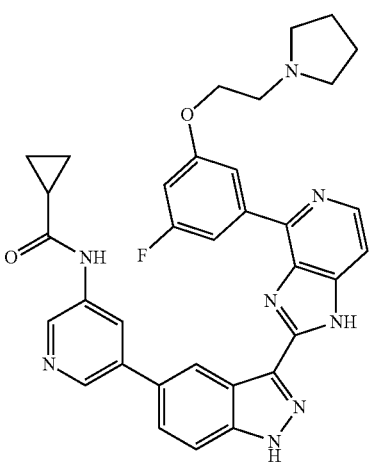 [SMILES: O=C(Nc1cncc(-c2ccc3[nH]nc(-c4nc5c(-c6cc(F)cc(OCCN7CCCC7)c6)nccc5[nH]4)c3c2)c1)C1CC1]
2138
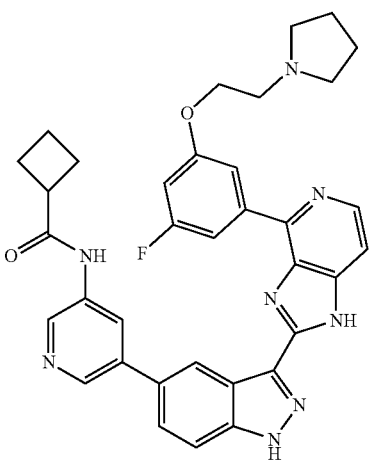 [SMILES: O=C(Nc1cncc(-c2ccc3[nH]nc(-c4nc5c(-c6cc(F)cc(OCCN7CCCC7)c6)nccc5[nH]4)c3c2)c1)C1CCC1]

TABLE 1-continued
2139
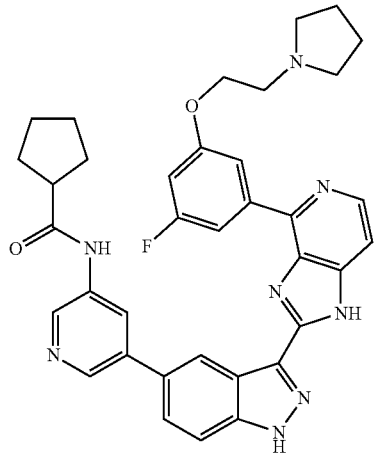 [SMILES: O=C(Nc1cncc(-c2ccc3[nH]nc(-c4nc5c(-c6cc(F)cc(OCCN7CCCC7)c6)nccc5[nH]4)c3c2)c1)C1CCCC1]
2142
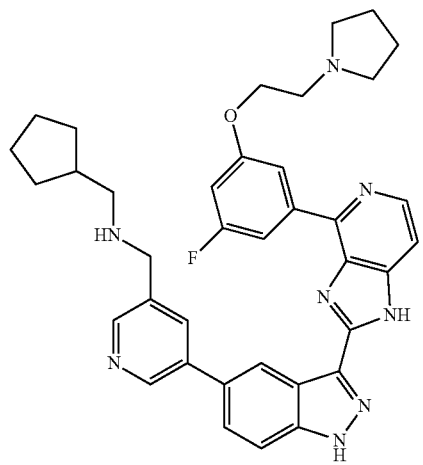
2140
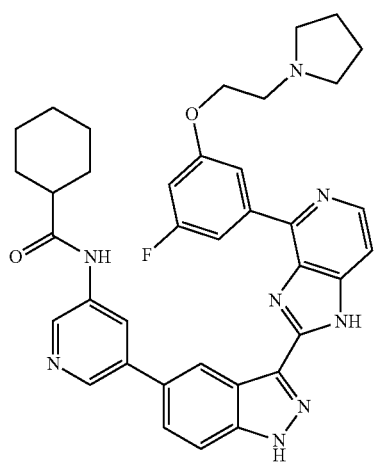 [SMILES: O=C(Nc1cncc(-c2ccc3[nH]nc(-c4nc5c(-c6cc(F)cc(OCCN7CCCC7)c6)nccc5[nH]4)c3c2)c1)C1CCCCC1]
2143
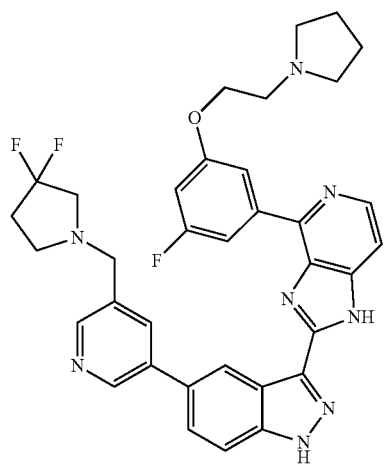
2141
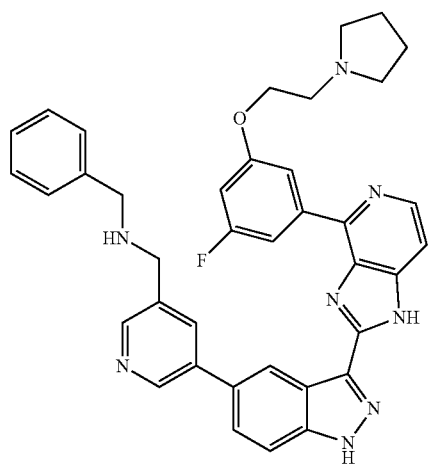 [SMILES: Fc1cc(OCCN2CCCC2)cc(-c2nccc3[nH]c(-c4n[nH]c5ccc(-c6cncc(CNCc7ccccc7)c6)cc45)nc23)c1]
2144
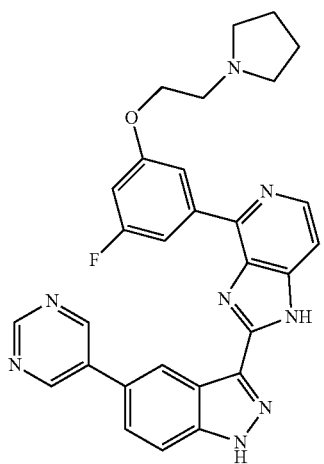 [SMILES: Fc1cc(OCCN2CCCC2)cc(-c2nccc3[nH]c(-c4n[nH]c5ccc(-c6cncnc6)cc45)nc23)c1]

TABLE 1-continued
| | |
|---|---|
| 2145 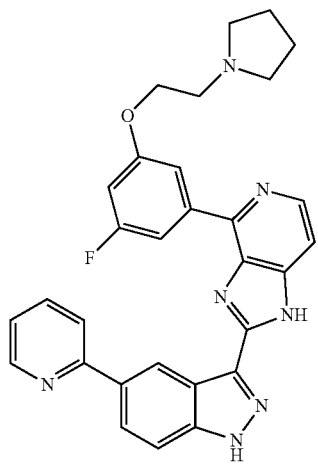 [SMILES: Fc1cc(OCCN2CCCC2)cc(-c2nccc3[nH]c(-c4n[nH]c5ccc(-c6ccccn6)cc45)nc23)c1] | 2148 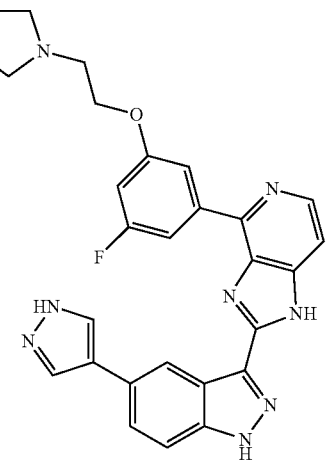 |
| 2146 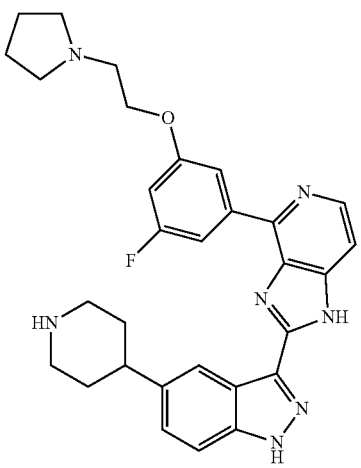 [SMILES: Fc1cc(OCCN2CCCC2)cc(-c2nccc3[nH]c(-c4n[nH]c5ccc(C6CCNCC6)cc45)nc23)c1] | 2149 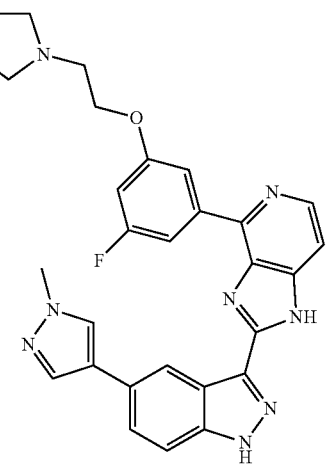 |
| 2147 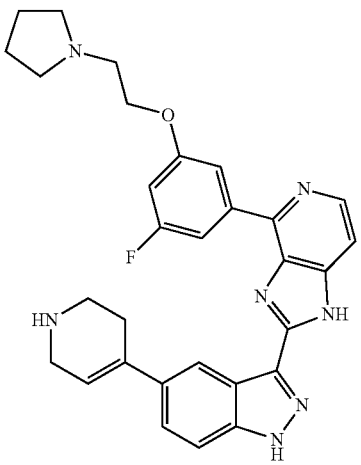 [SMILES: Fc1cc(OCCN2CCCC2)cc(-c2nccc3[nH]c(-c4n[nH]c5ccc(C6=CCNCC6)cc45)nc23)c1] | 2150 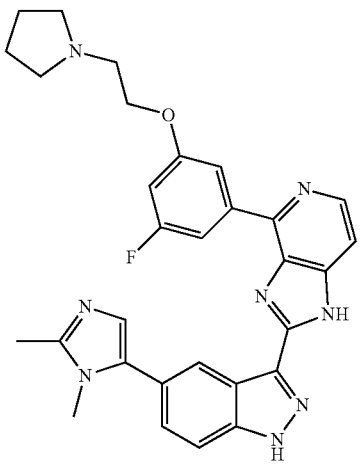 [SMILES: Cc1ncc(-c2ccc3[nH]nc(-c4nc5c(-c6cc(F)cc(OCCN7CCCC7)c6)nccc5[nH]4)c3c2)n1C] |

TABLE 1-continued
2151
2152
2153
2154
2155
2156
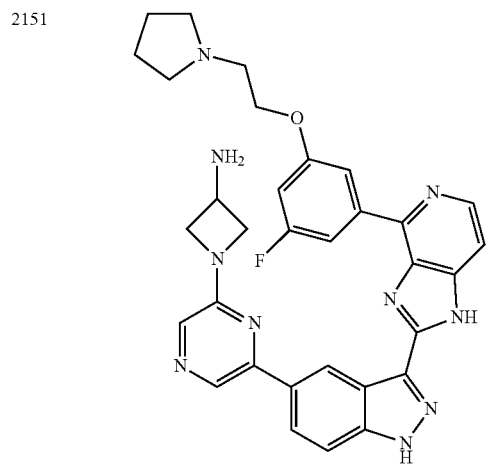
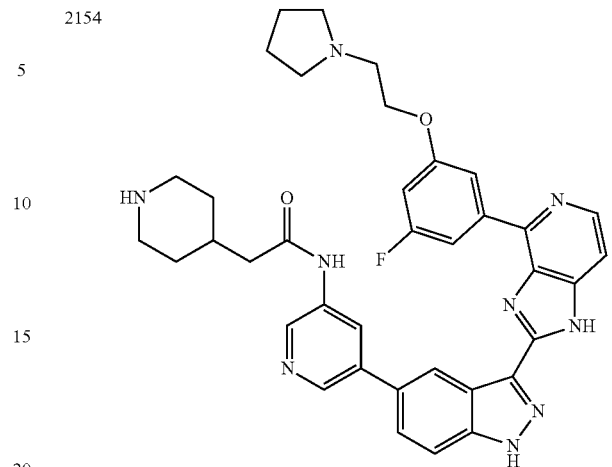

TABLE 1-continued
2157
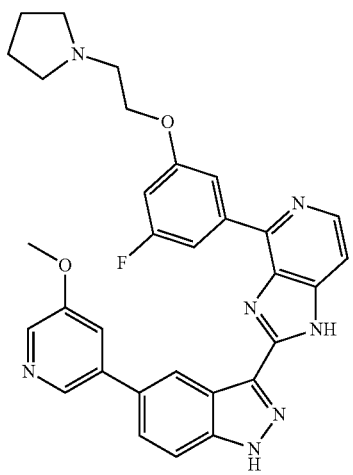 [SMILES: COc1cncc(-c2ccc3[nH]nc(-c4nc5c(-c6cc(F)cc(OCCN7CCCC7)c6)nccc5[nH]4)c3c2)c1]
2160
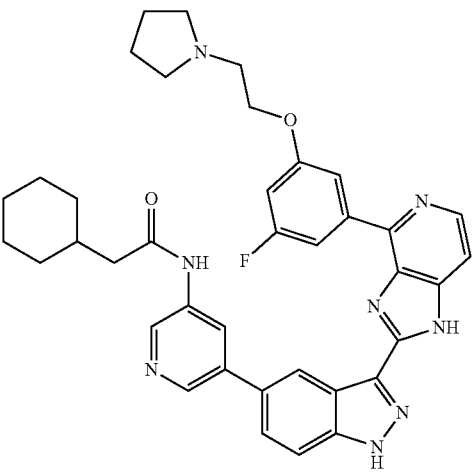
2158
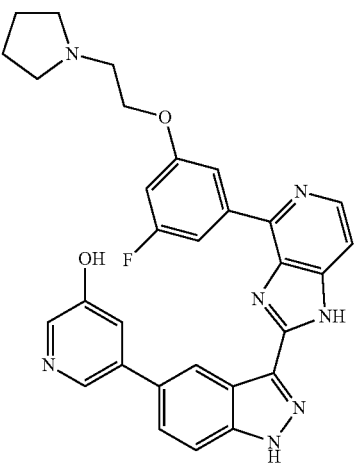 [SMILES: Oc1cncc(-c2ccc3[nH]nc(-c4nc5c(-c6cc(F)cc(OCCN7CCCC7)c6)nccc5[nH]4)c3c2)c1]
2161
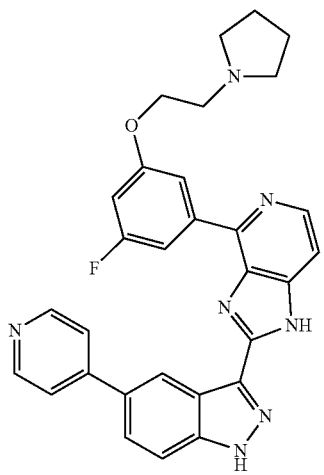
2159
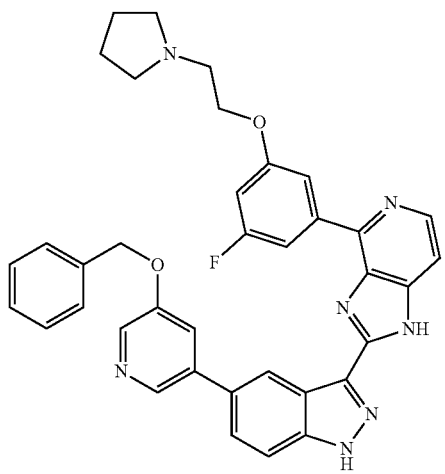 [SMILES: Fc1cc(OCCN2CCCC2)cc(-c2nccc3[nH]c(-c4n[nH]c5ccc(-c6cncc(OCc7ccccc7)c6)cc45)nc23)c1]
2162
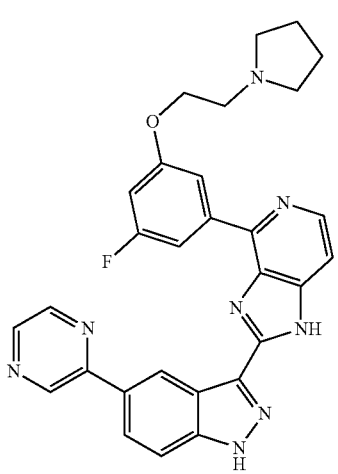 [SMILES: Fc1cc(OCCN2CCCC2)cc(-c2nccc3[nH]c(-c4n[nH]c5ccc(-c6cnccn6)cc45)nc23)c1]

TABLE 1-continued
2163 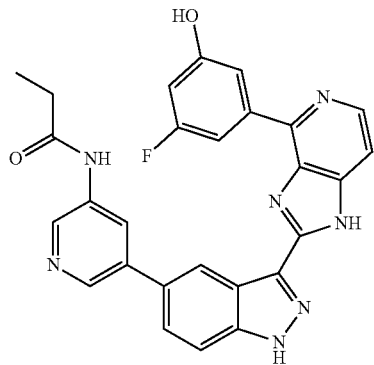 [SMILES: CCC(=O)Nc1cncc(-c2ccc3[nH]nc(-c4nc5c(-c6cc(O)cc(F)c6)nccc5[nH]4)c3c2)c1]
2164 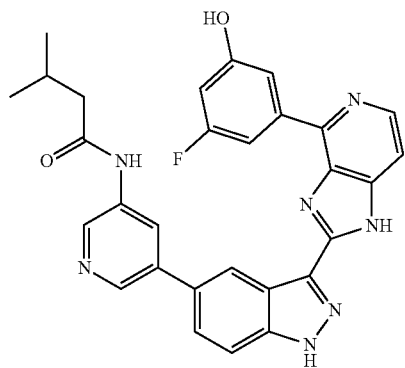 [SMILES: CC(C)CC(=O)Nc1cncc(-c2ccc3[nH]nc(-c4nc5c(-c6cc(O)cc(F)c6)nccc5[nH]4)c3c2)c1]
2165 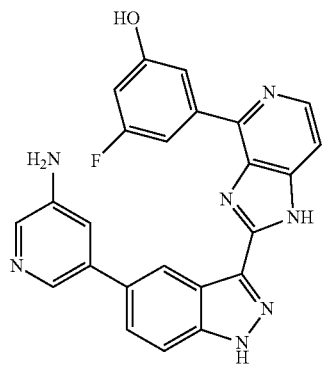 [SMILES: Nc1cncc(-c2ccc3[nH]nc(-c4nc5c(-c6cc(O)cc(F)c6)nccc5[nH]4)c3c2)c1]
2166 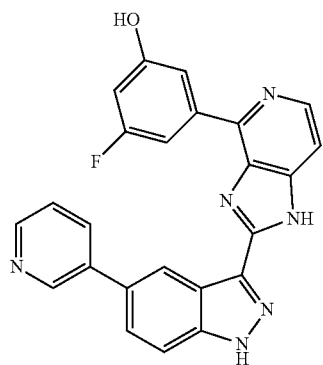 [SMILES: Oc1cc(F)cc(-c2nccc3[nH]c(-c4n[nH]c5ccc(-c6cccnc6)cc45)nc23)c1]
2167 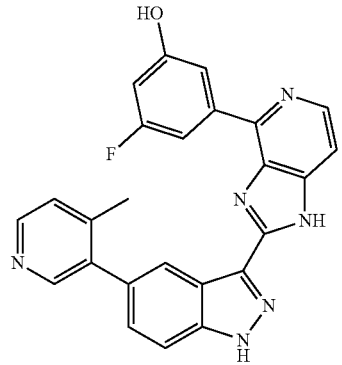 [SMILES: Cc1ccncc1-c1ccc2[nH]nc(-c3nc4c(-c5cc(O)cc(F)c5)nccc4[nH]3)c2c1]
2168 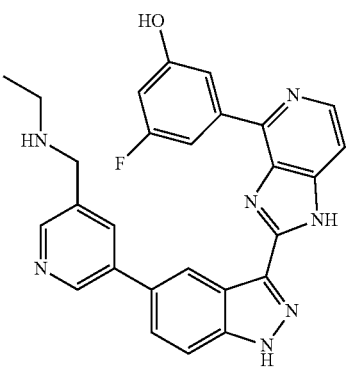 [SMILES: CCNCc1cncc(-c2ccc3[nH]nc(-c4nc5c(-c6cc(O)cc(F)c6)nccc5[nH]4)c3c2)c1]
2169 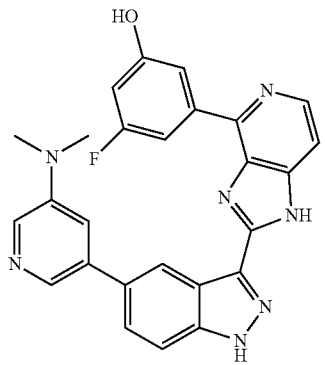 [SMILES: CN(C)c1cncc(-c2ccc3[nH]nc(-c4nc5c(-c6cc(O)cc(F)c6)nccc5[nH]4)c3c2)c1]
2170 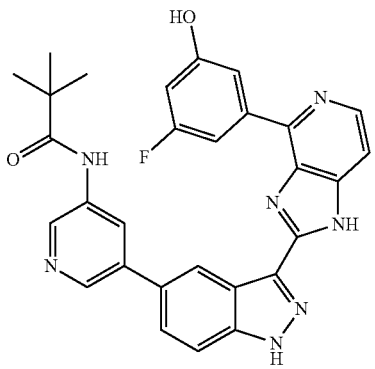 [SMILES: CC(C)(C)C(=O)Nc1cncc(-c2ccc3[nH]nc(-c4nc5c(-c6cc(O)cc(F)c6)nccc5[nH]4)c3c2)c1]

TABLE 1-continued
2171 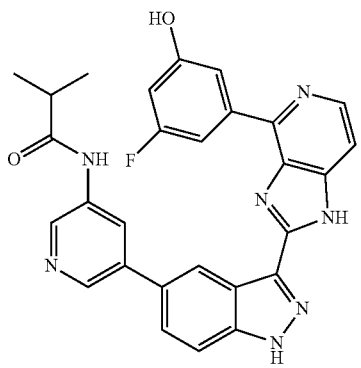 [SMILES: CC(C)C(=O)Nc1cncc(-c2ccc3[nH]nc(-c4nc5c(-c6cc(O)cc(F)c6)nccc5[nH]4)c3c2)c1]
2172 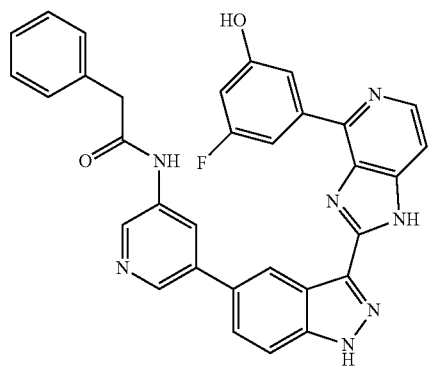 [SMILES: O=C(Cc1ccccc1)Nc1cncc(-c2ccc3[nH]nc(-c4nc5c(-c6cc(O)cc(F)c6)nccc5[nH]4)c3c2)c1]
2173 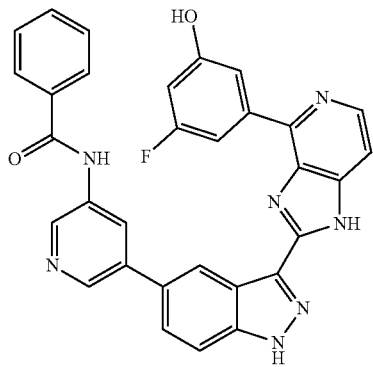 [SMILES: O=C(Nc1cncc(-c2ccc3[nH]nc(-c4nc5c(-c6cc(O)cc(F)c6)nccc5[nH]4)c3c2)c1)c1ccccc1]
2174 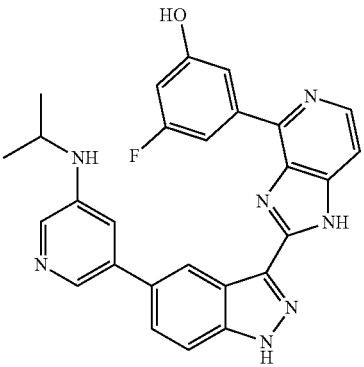 [SMILES: CC(C)Nc1cncc(-c2ccc3[nH]nc(-c4nc5c(-c6cc(O)cc(F)c6)nccc5[nH]4)c3c2)c1]
TABLE 1-continued
2175 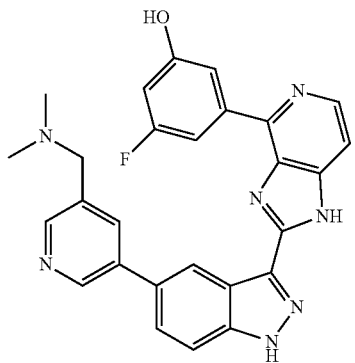 [SMILES: CN(C)Cc1cncc(-c2ccc3[nH]nc(-c4nc5c(-c6cc(O)cc(F)c6)nccc5[nH]4)c3c2)c1]
2176 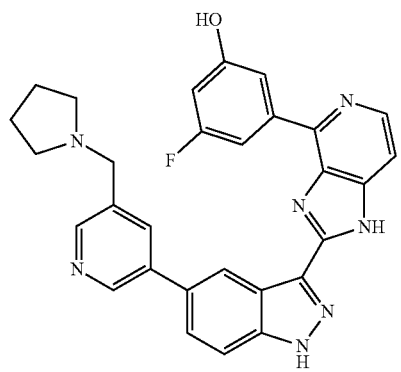 [SMILES: Oc1cc(F)cc(-c2nccc3[nH]c(-c4n[nH]c5ccc(-c6cncc(CN7CCCC7)c6)cc45)nc23)c1]
2177 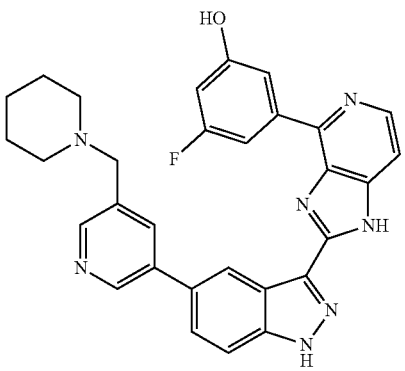 [SMILES: Oc1cc(F)cc(-c2nccc3[nH]c(-c4n[nH]c5ccc(-c6cncc(CN7CCCCC7)c6)cc45)nc23)c1]
2178 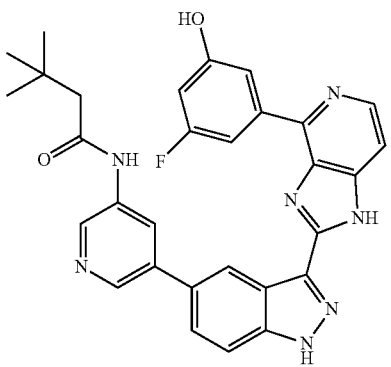 [SMILES: CC(C)(C)CC(=O)Nc1cncc(-c2ccc3[nH]nc(-c4nc5c(-c6cc(O)cc(F)c6)nccc5[nH]4)c3c2)c1]

TABLE 1-continued
| 2179 | 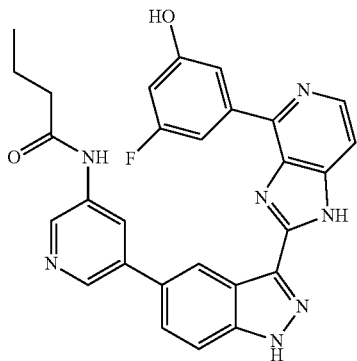 [SMILES: CCCC(=O)Nc1cncc(-c2ccc3[nH]nc(-c4nc5c(-c6cc(O)cc(F)c6)nccc5[nH]4)c3c2)c1] | 2183 | 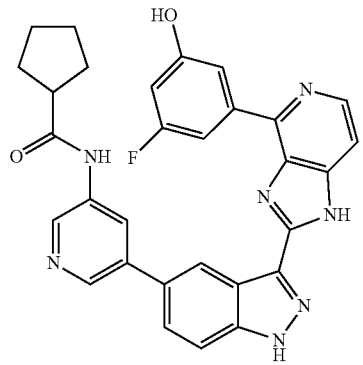 |
| 2180 | 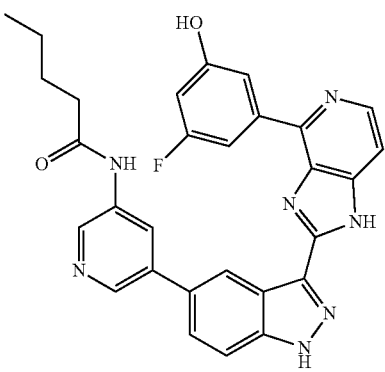 [SMILES: CCCCC(=O)Nc1cncc(-c2ccc3[nH]nc(-c4nc5c(-c6cc(O)cc(F)c6)nccc5[nH]4)c3c2)c1] | 2184 | 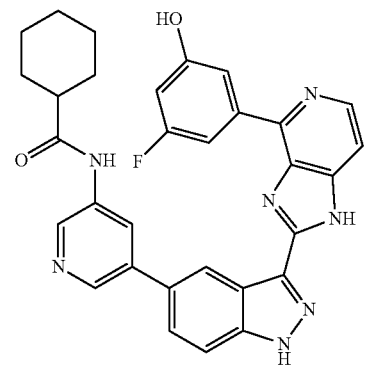 |
| 2181 | 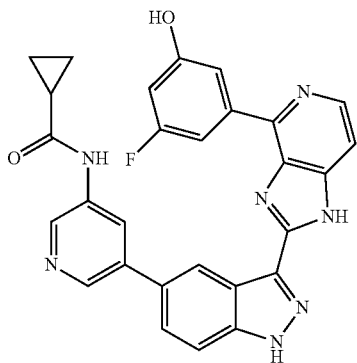 [SMILES: O=C(Nc1cncc(-c2ccc3[nH]nc(-c4nc5c(-c6cc(O)cc(F)c6)nccc5[nH]4)c3c2)c1)C1CC1] | 2185 | 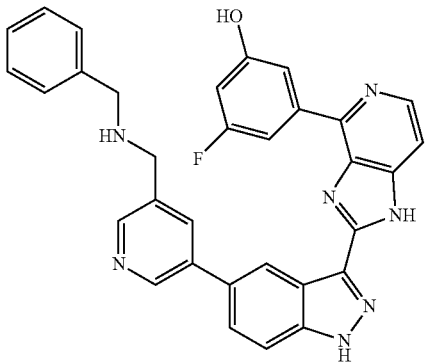 |
| 2182 | 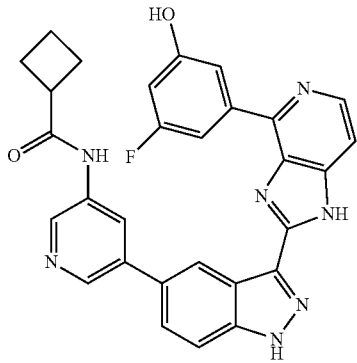 [SMILES: O=C(Nc1cncc(-c2ccc3[nH]nc(-c4nc5c(-c6cc(O)cc(F)c6)nccc5[nH]4)c3c2)c1)C1CCC1] | 2186 | 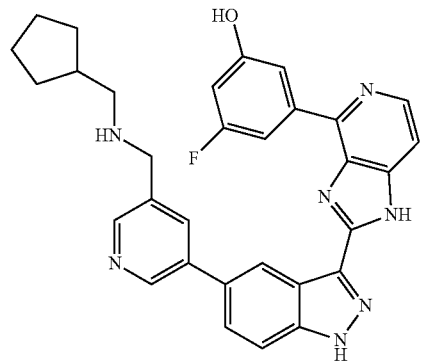 [SMILES: Oc1cc(F)cc(-c2nccc3[nH]c(-c4n[nH]c5ccc(-c6cncc(CNCC7CCCC7)c6)cc45)nc23)c1] |

TABLE 1-continued
| 2187 | 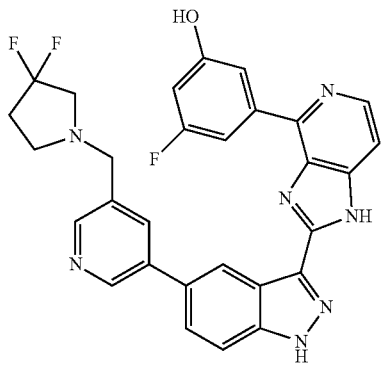 [SMILES: Oc1cc(F)cc(-c2nccc3[nH]c(-c4n[nH]c5ccc(-c6cncc(CN7CCC(F)(F)C7)c6)cc45)nc23)c1] |
| --- | --- |
| 2188 | 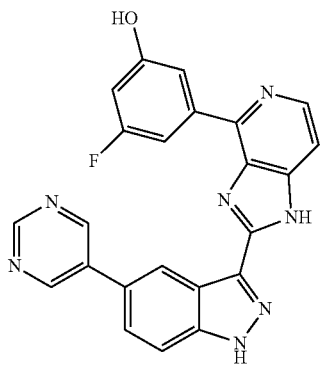 [SMILES: Oc1cc(F)cc(-c2nccc3[nH]c(-c4n[nH]c5ccc(-c6cncnc6)cc45)nc23)c1] |
| 2189 | 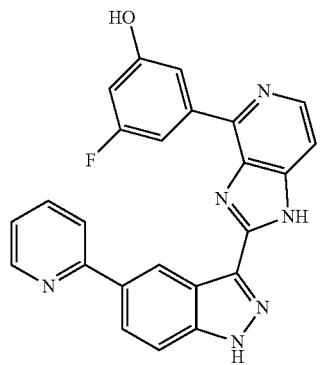 |
| 2190 | 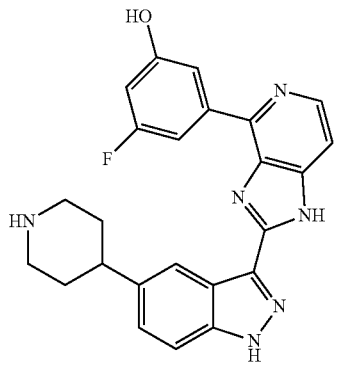 [SMILES: Oc1cc(F)cc(-c2nccc3[nH]c(-c4n[nH]c5ccc(C6CCNCC6)cc45)nc23)c1] |
TABLE 1-continued
| 2191 | 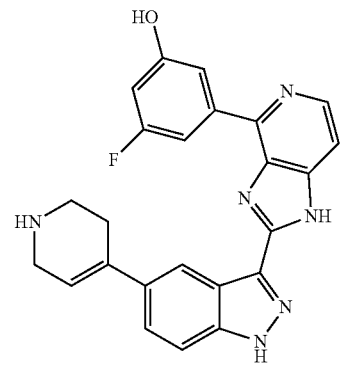 [SMILES: Oc1cc(F)cc(-c2nccc3[nH]c(-c4n[nH]c5ccc(C6=CCNCC6)cc45)nc23)c1] |
| --- | --- |
| 2192 | 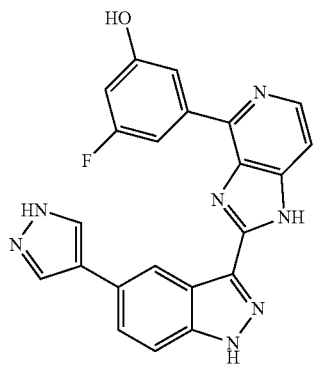 [SMILES: Oc1cc(F)cc(-c2nccc3[nH]c(-c4n[nH]c5ccc(-c6cn[nH]c6)cc45)nc23)c1] |
| 2193 | 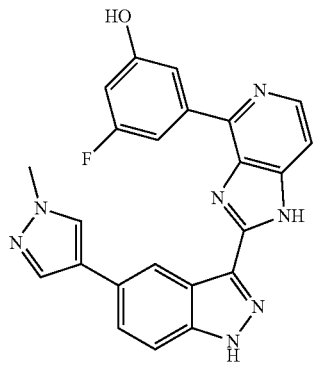 [SMILES: Cn1cc(-c2ccc3[nH]nc(-c4nc5c(-c6cc(O)cc(F)c6)nccc5[nH]4)c3c2)cn1] |
| 2194 | 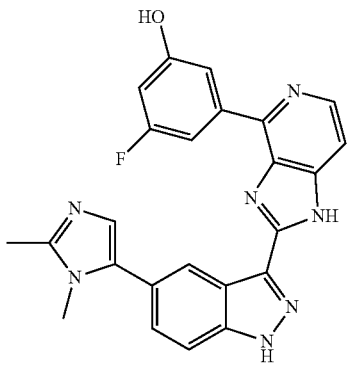 [SMILES: Cc1ncc(-c2ccc3[nH]nc(-c4nc5c(-c6cc(O)cc(F)c6)nccc5[nH]4)c3c2)n1C] |

TABLE 1-continued
2195 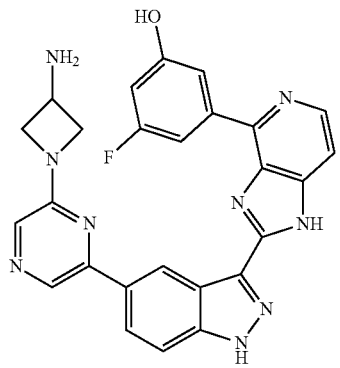 [SMILES: NC1CN(c2cncc(-c3ccc4[nH]nc(-c5nc6c(-c7cc(O)cc(F)c7)nccc6[nH]5)c4c3)n2)C1]
2196 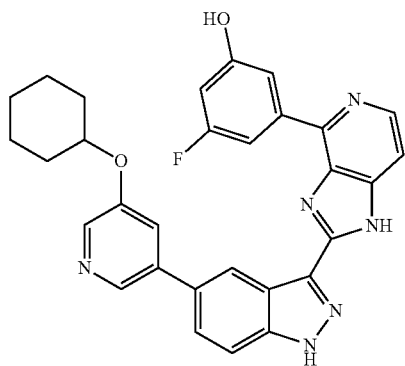 [SMILES: Oc1cc(F)cc(-c2nccc3[nH]c(-c4n[nH]c5ccc(-c6cncc(OC7CCCCC7)c6)cc45)nc23)c1]
2197 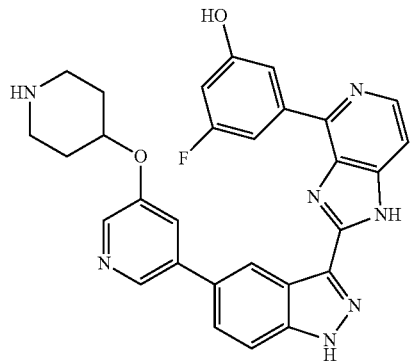 [SMILES: Oc1cc(F)cc(-c2nccc3[nH]c(-c4n[nH]c5ccc(-c6cncc(OC7CCNCC7)c6)cc45)nc23)c1]
2198 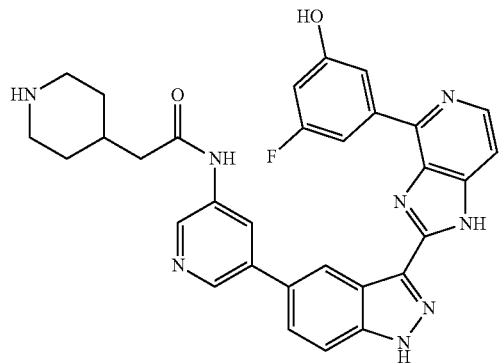 [SMILES: O=C(CC1CCNCC1)Nc1cncc(-c2ccc3[nH]nc(-c4nc5c(-c6cc(O)cc(F)c6)nccc5[nH]4)c3c2)c1]
TABLE 1-continued
2199 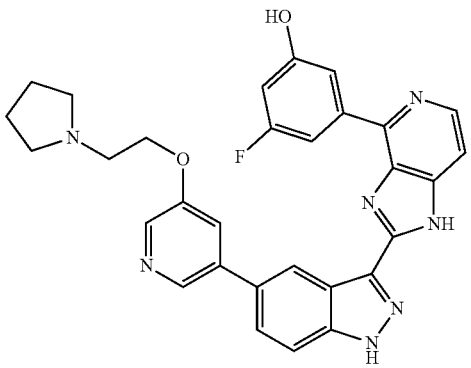 [SMILES: Oc1cc(F)cc(-c2nccc3[nH]c(-c4n[nH]c5ccc(-c6cncc(OCCN7CCCC7)c6)cc45)nc23)c1]
2200 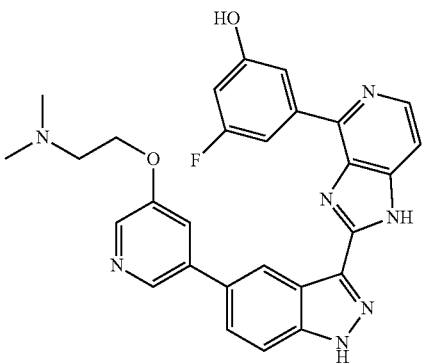 [SMILES: CN(C)CCOc1cncc(-c2ccc3[nH]nc(-c4nc5c(-c6cc(O)cc(F)c6)nccc5[nH]4)c3c2)c1]
2201 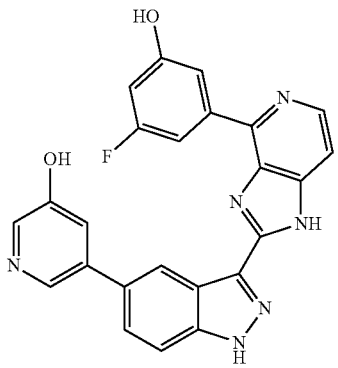 [SMILES: Oc1cncc(-c2ccc3[nH]nc(-c4nc5c(-c6cc(O)cc(F)c6)nccc5[nH]4)c3c2)c1]
2202

TABLE 1-continued
| 2203 | 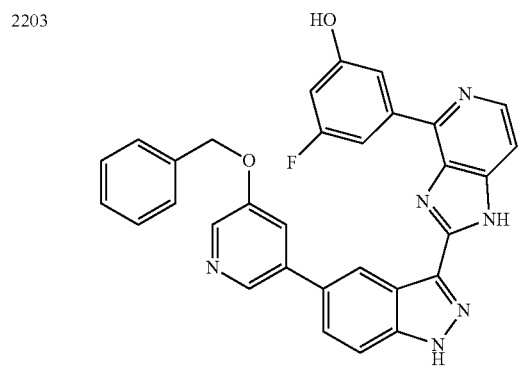 | 2207 | 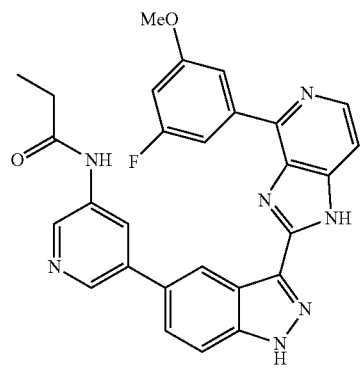 |
| 2204 | 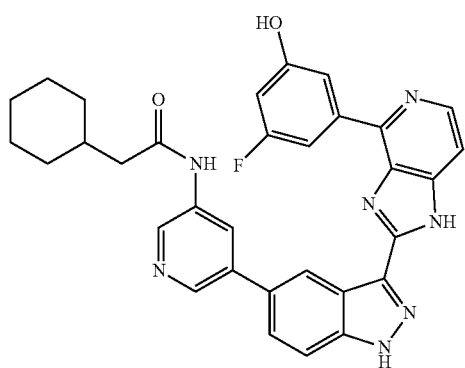 [SMILES: O=C(CC1CCCCC1)Nc1cncc(-c2ccc3[nH]nc(-c4nc5c(-c6cc(O)cc(F)c6)nccc5[nH]4)c3c2)c1] | 2208 | |
| 2205 | 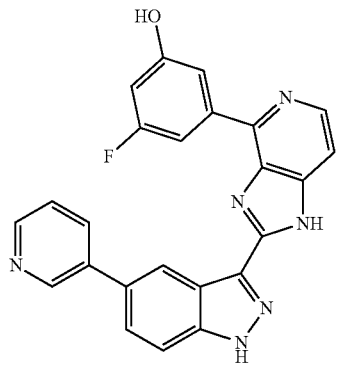 [SMILES: Oc1cc(F)cc(-c2nccc3[nH]c(-c4n[nH]c5ccc(-c6cccnc6)cc45)nc23)c1] | 2209 | |
| 2206 | 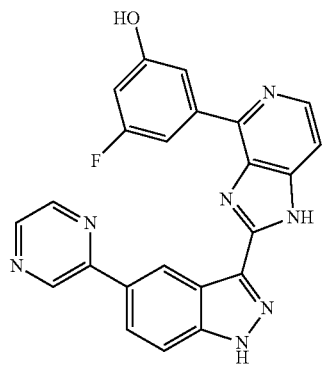 [SMILES: Oc1cc(F)cc(-c2nccc3[nH]c(-c4n[nH]c5ccc(-c6cnccn6)cc45)nc23)c1] | 2210 | |

TABLE 1-continued
| | |
|---|---|
| 2211 | 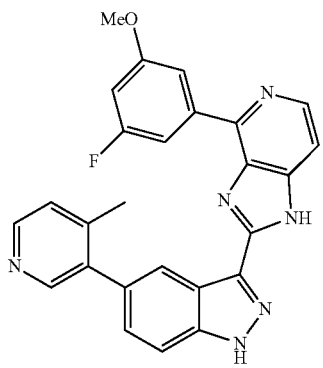 [SMILES: COc1cc(F)cc(-c2nccc3[nH]c(-c4n[nH]c5ccc(-c6cnccc6C)cc45)nc23)c1] |
| 2212 | 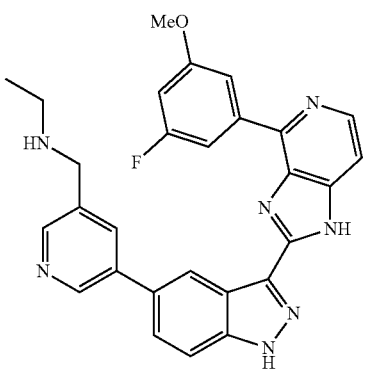 [SMILES: CCNCc1cncc(-c2ccc3[nH]nc(-c4nc5c(-c6cc(F)cc(OC)c6)nccc5[nH]4)c3c2)c1] |
| 2213 | 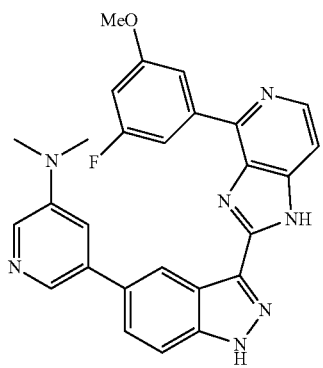 [SMILES: COc1cc(F)cc(-c2nccc3[nH]c(-c4n[nH]c5ccc(-c6cncc(N(C)C)c6)cc45)nc23)c1] |
| 2214 | 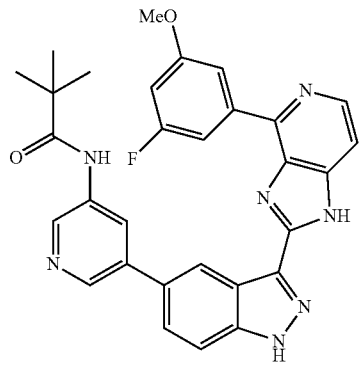 [SMILES: COc1cc(F)cc(-c2nccc3[nH]c(-c4n[nH]c5ccc(-c6cncc(NC(=O)C(C)(C)C)c6)cc45)nc23)c1] |
| 2215 | 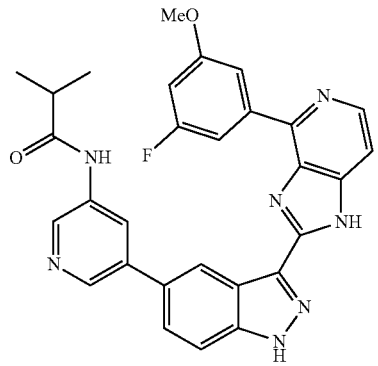 [SMILES: COc1cc(F)cc(-c2nccc3[nH]c(-c4n[nH]c5ccc(-c6cncc(NC(=O)C(C)C)c6)cc45)nc23)c1] |
| 2216 | 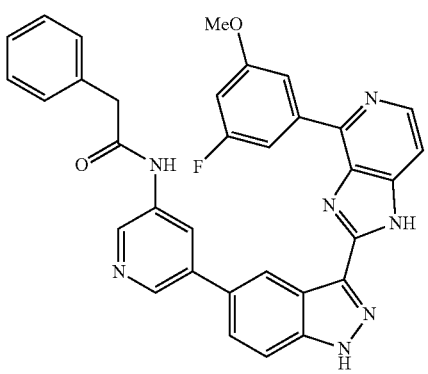 [SMILES: COc1cc(F)cc(-c2nccc3[nH]c(-c4n[nH]c5ccc(-c6cncc(NC(=O)Cc7ccccc7)c6)cc45)nc23)c1] |
| 2217 | 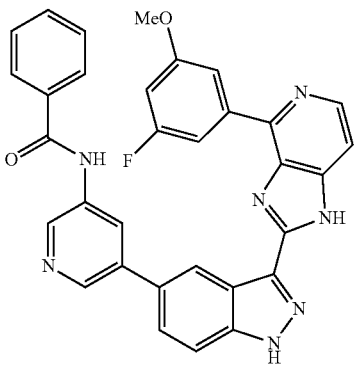 [SMILES: COc1cc(F)cc(-c2nccc3[nH]c(-c4n[nH]c5ccc(-c6cncc(NC(=O)c7ccccc7)c6)cc45)nc23)c1] |
| 2218 | 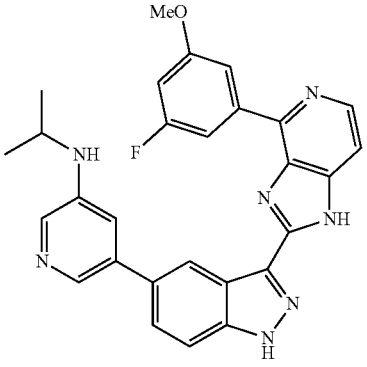 [SMILES: COc1cc(F)cc(-c2nccc3[nH]c(-c4n[nH]c5ccc(-c6cncc(NC(C)C)c6)cc45)nc23)c1] |

TABLE 1-continued
| 2219 | 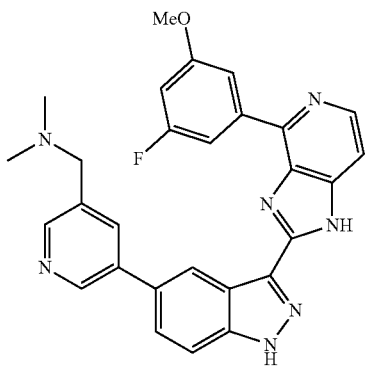 [SMILES: COc1cc(F)cc(-c2nccc3[nH]c(-c4n[nH]c5ccc(-c6cncc(CN(C)C)c6)cc45)nc23)c1] | 2223 | 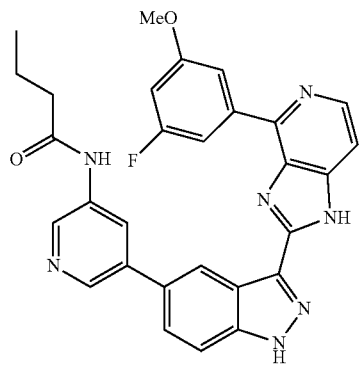 |
| --- | --- | --- | --- |
| 2220 | 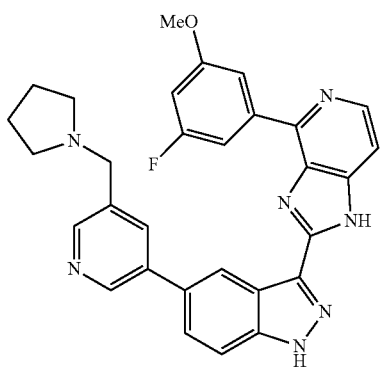 [SMILES: COc1cc(F)cc(-c2nccc3[nH]c(-c4n[nH]c5ccc(-c6cncc(CN7CCCC7)c6)cc45)nc23)c1] | 2224 | 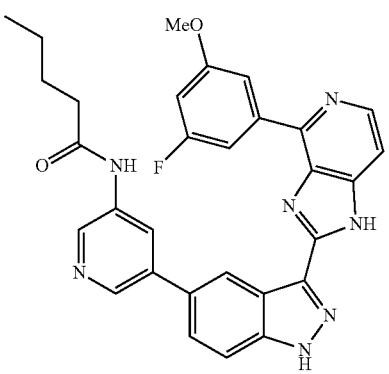 |
| 2221 | 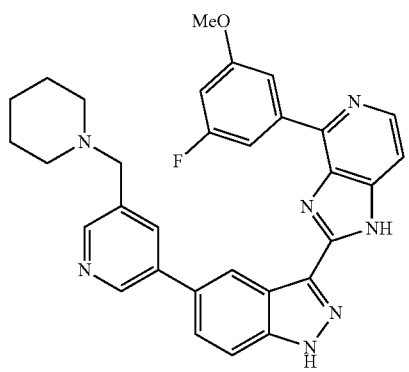 [SMILES: COc1cc(F)cc(-c2nccc3[nH]c(-c4n[nH]c5ccc(-c6cncc(CN7CCCCC7)c6)cc45)nc23)c1] | 2225 | 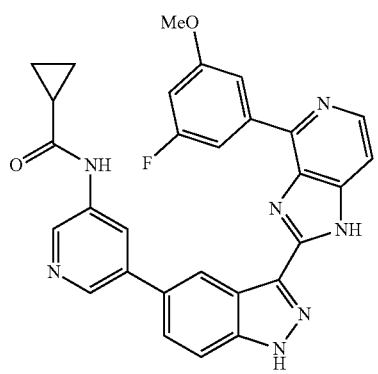 |
| 2222 | 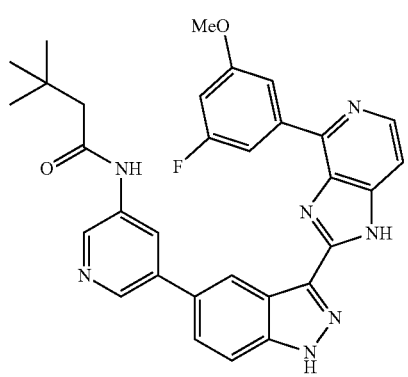 [SMILES: COc1cc(F)cc(-c2nccc3[nH]c(-c4n[nH]c5ccc(-c6cncc(NC(=O)CC(C)(C)C)c6)cc45)nc23)c1] | 2226 | 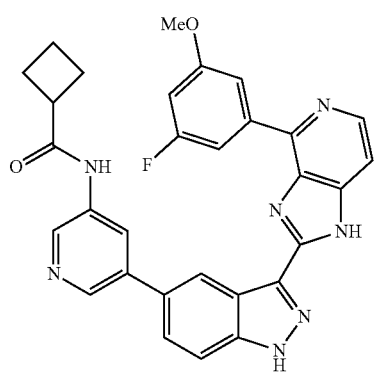 [SMILES: COc1cc(F)cc(-c2nccc3[nH]c(-c4n[nH]c5ccc(-c6cncc(NC(=O)C7CCC7)c6)cc45)nc23)c1] |

TABLE 1-continued
| | |
|---|---|
| 2227 | 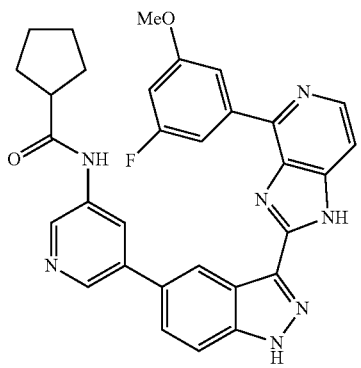 [SMILES: COc1cc(F)cc(-c2nccc3[nH]c(-c4n[nH]c5ccc(-c6cncc(NC(=O)C7CCCC7)c6)cc45)nc23)c1] |
| 2228 | 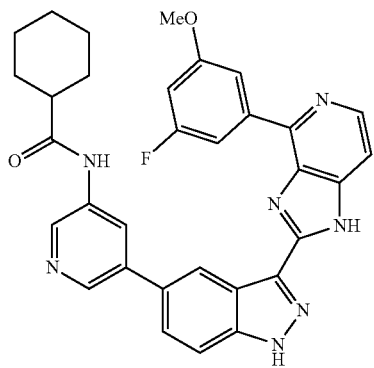 [SMILES: COc1cc(F)cc(-c2nccc3[nH]c(-c4n[nH]c5ccc(-c6cncc(NC(=O)C7CCCCC7)c6)cc45)nc23)c1] |
| 2229 | 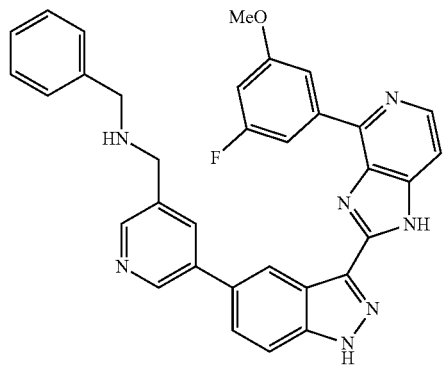 [SMILES: COc1cc(F)cc(-c2nccc3[nH]c(-c4n[nH]c5ccc(-c6cncc(CNCc7ccccc7)c6)cc45)nc23)c1] |
| 2230 | 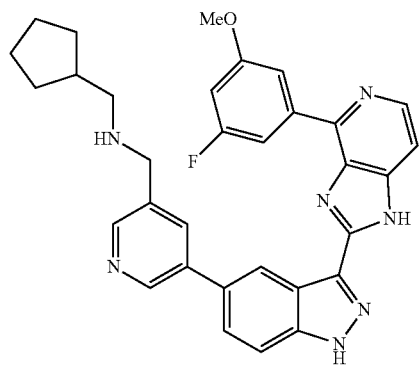 |
| 2231 | 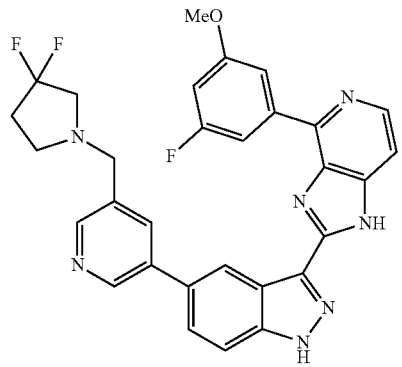 [SMILES: COc1cc(F)cc(-c2nccc3[nH]c(-c4n[nH]c5ccc(-c6cncc(CN7CCC(F)(F)C7)c6)cc45)nc23)c1] |
| 2232 | 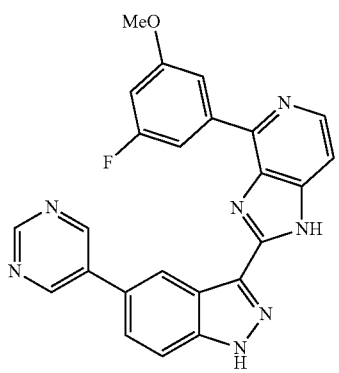 [SMILES: COc1cc(F)cc(-c2nccc3[nH]c(-c4n[nH]c5ccc(-c6cncnc6)cc45)nc23)c1] |
| 2233 | 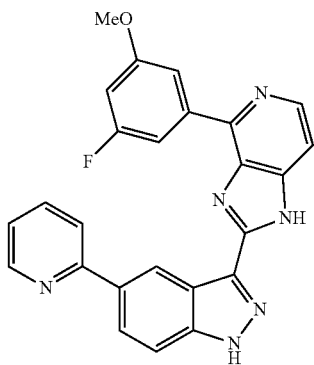 [SMILES: COc1cc(F)cc(-c2nccc3[nH]c(-c4n[nH]c5ccc(-c6ccccn6)cc45)nc23)c1] |
| 2234 | 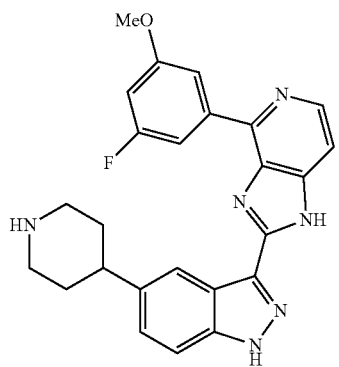 [SMILES: COc1cc(F)cc(-c2nccc3[nH]c(-c4n[nH]c5ccc(C6CCNCC6)cc45)nc23)c1] |

TABLE 1-continued
| 2235 | 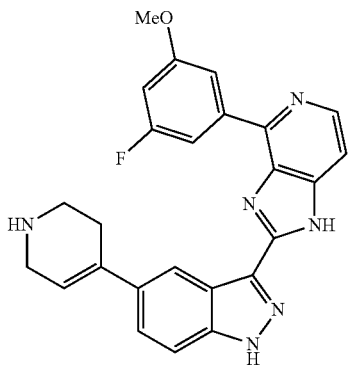 [SMILES: COc1cc(F)cc(-c2nccc3[nH]c(-c4n[nH]c5ccc(C6=CCNCC6)cc45)nc23)c1] | 2239 | 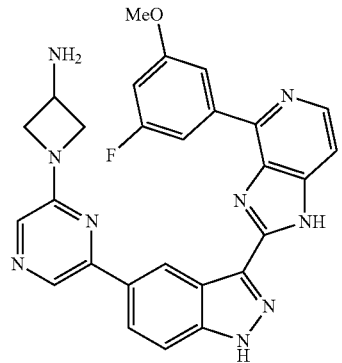 |
| 2236 | 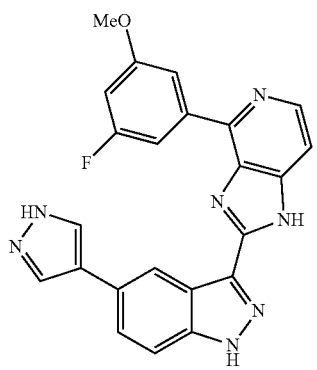 [SMILES: COc1cc(F)cc(-c2nccc3[nH]c(-c4n[nH]c5ccc(-c6cn[nH]c6)cc45)nc23)c1] | 2240 | 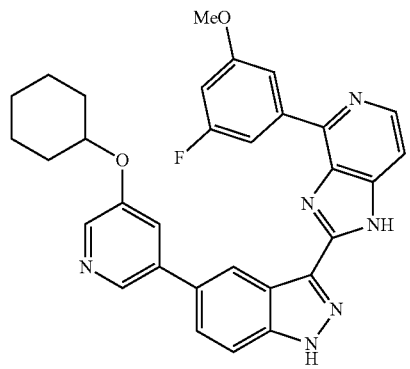 |
| 2237 | 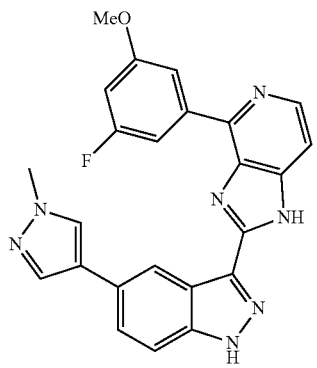 [SMILES: COc1cc(F)cc(-c2nccc3[nH]c(-c4n[nH]c5ccc(-c6cnn(C)c6)cc45)nc23)c1] | 2241 | 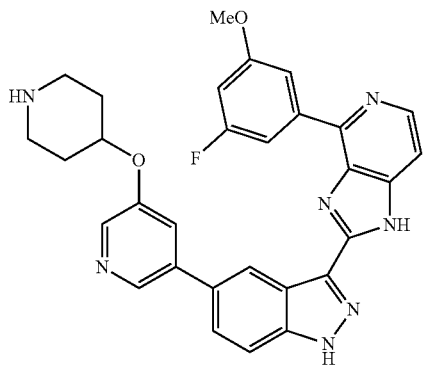 |
| 2238 | 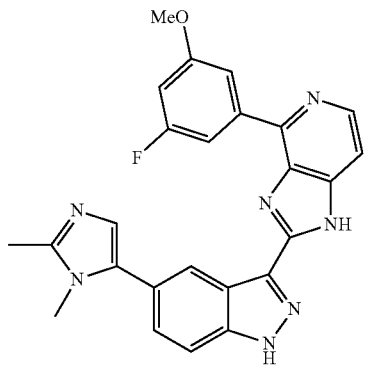 [SMILES: COc1cc(F)cc(-c2nccc3[nH]c(-c4n[nH]c5ccc(-c6cnc(C)n6C)cc45)nc23)c1] | 2242 | 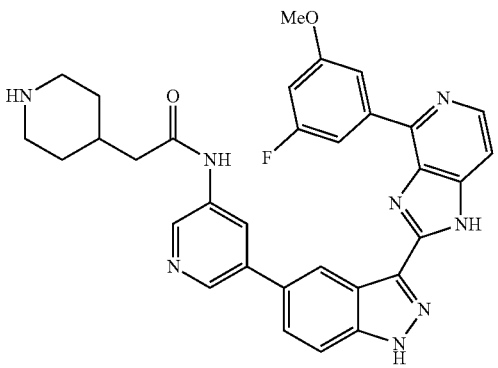 [SMILES: COc1cc(F)cc(-c2nccc3[nH]c(-c4n[nH]c5ccc(-c6cncc(NC(=O)CC7CCNCC7)c6)cc45)nc23)c1] |

TABLE 1-continued
| 2243 | 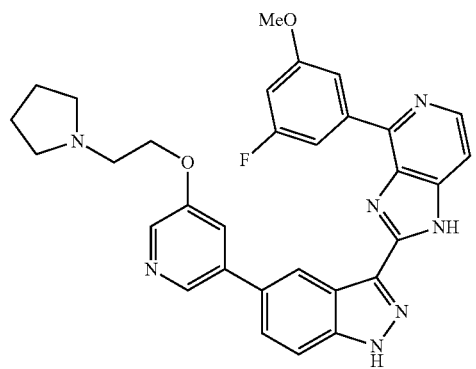 [SMILES: COc1cc(F)cc(-c2nccc3[nH]c(-c4n[nH]c5ccc(-c6cncc(OCCN7CCCC7)c6)cc45)nc23)c1] |
| --- | --- |
| 2244 | 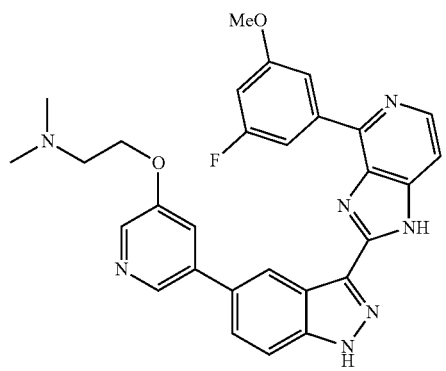 [SMILES: COc1cc(F)cc(-c2nccc3[nH]c(-c4n[nH]c5ccc(-c6cncc(OCCN(C)C)c6)cc45)nc23)c1] |
| 2245 | 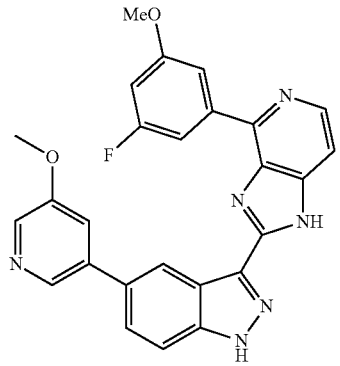 [SMILES: COc1cncc(-c2ccc3[nH]nc(-c4nc5c(-c6cc(F)cc(OC)c6)nccc5[nH]4)c3c2)c1] |
| 2246 | 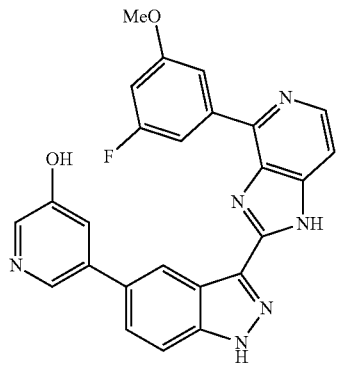 [SMILES: COc1cc(F)cc(-c2nccc3[nH]c(-c4n[nH]c5ccc(-c6cncc(O)c6)cc45)nc23)c1] |
| 2247 | 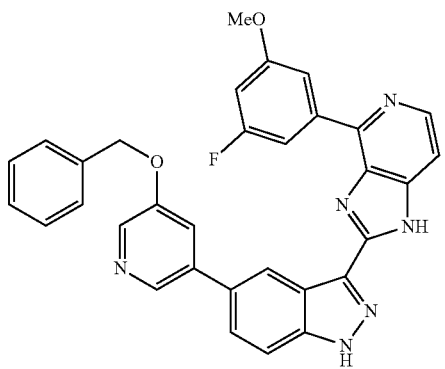 [SMILES: COc1cc(F)cc(-c2nccc3[nH]c(-c4n[nH]c5ccc(-c6cncc(OCc7ccccc7)c6)cc45)nc23)c1] |
| 2248 | 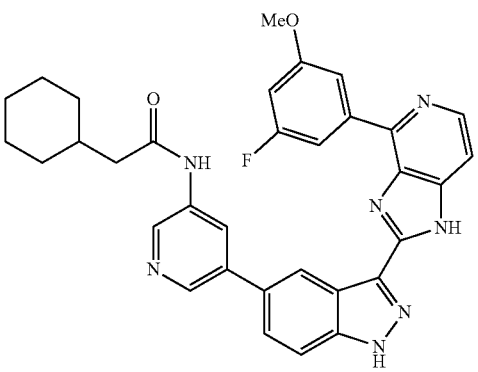 [SMILES: COc1cc(F)cc(-c2nccc3[nH]c(-c4n[nH]c5ccc(-c6cncc(NC(=O)CC7CCCCC7)c6)cc45)nc23)c1] |
| 2249 | 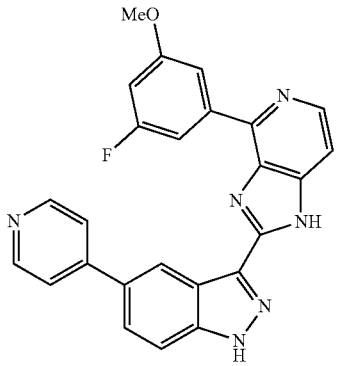 |
| 2250 | 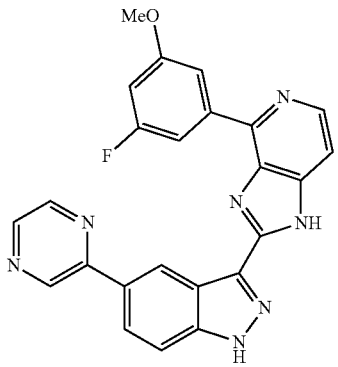 |

TABLE 1-continued
2251
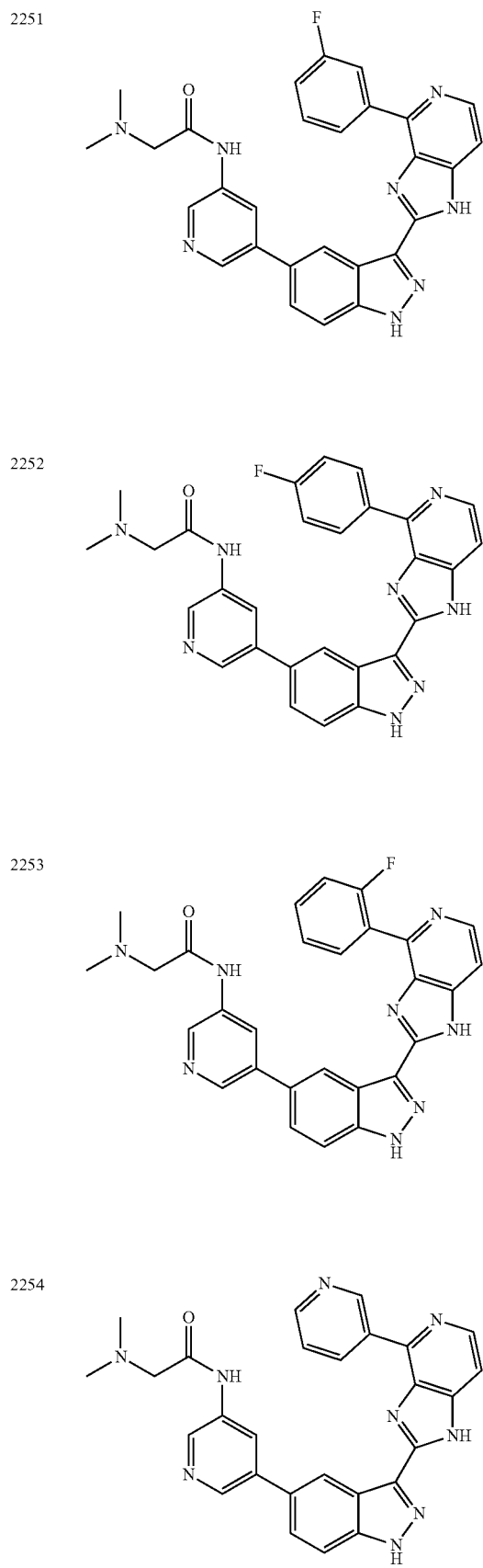
2252
2253
2254
TABLE 1-continued
2255
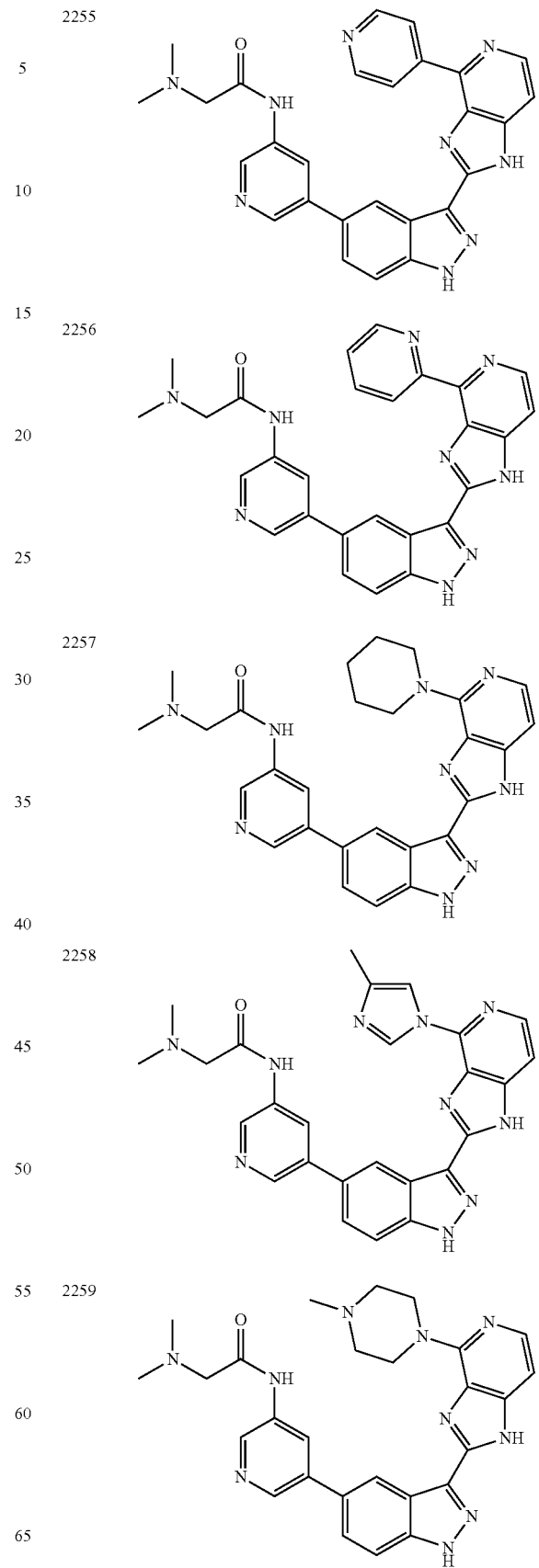
2256
2257
2258
2259

TABLE 1-continued
| | |
|---|---|
| 2260 | 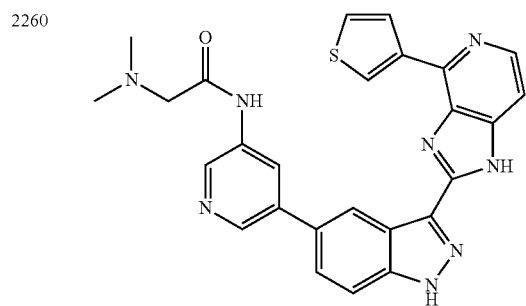 |
| 2261 | 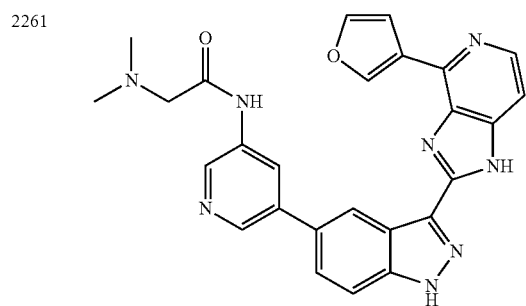 |
| 2262 | 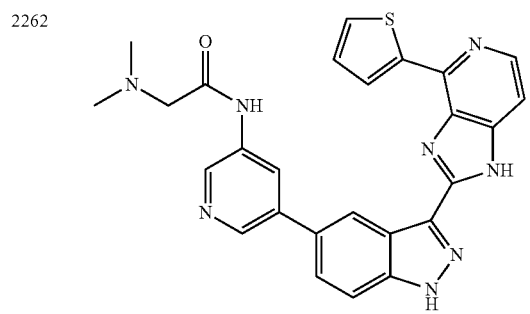 |
| 2263 | 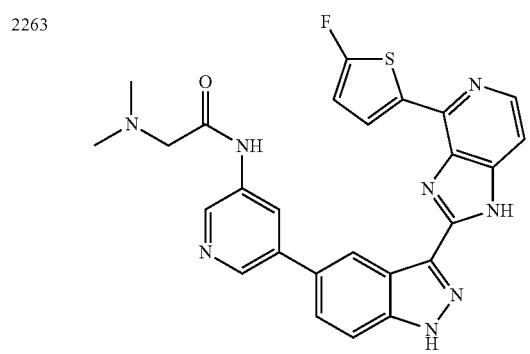 |
| 2264 | 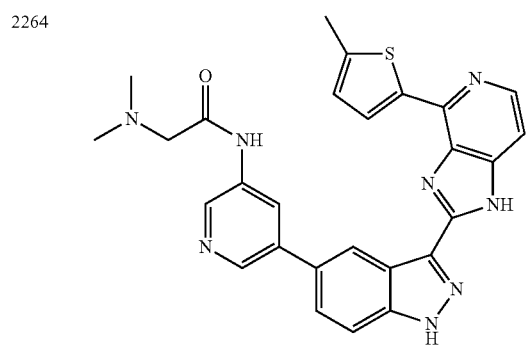 |
TABLE 1-continued
| | |
|---|---|
| 2265 | 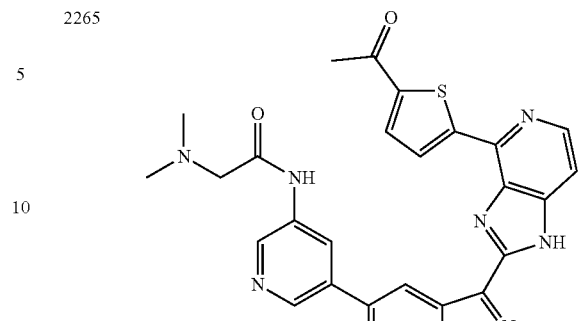 |
| 2266 | 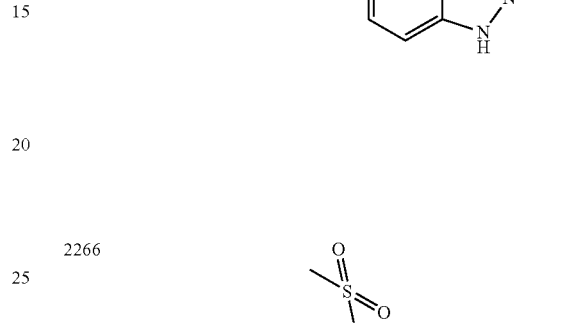 |
| | 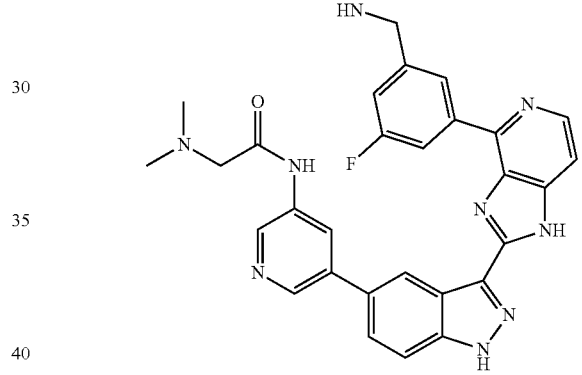 |
| 2267 | 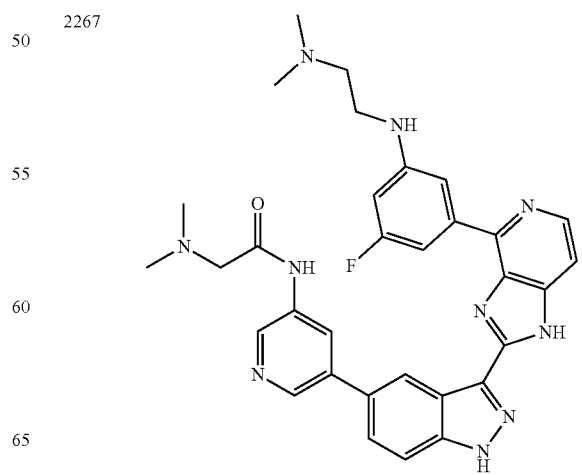 |

TABLE 1-continued
| 2268 | 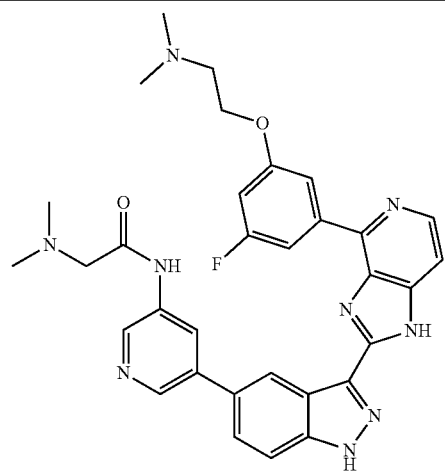 |
| --- | --- |
| 2269 | 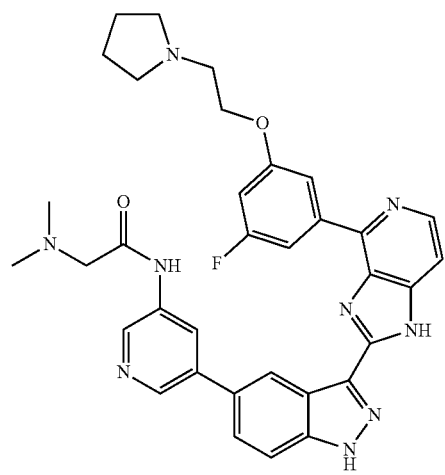 [SMILES: CN(C)CC(=O)Nc1cncc(-c2ccc3[nH]nc(-c4nc5c(-c6cc(F)cc(OCCN7CCCC7)c6)nccc5[nH]4)c3c2)c1] |
| 2270 | 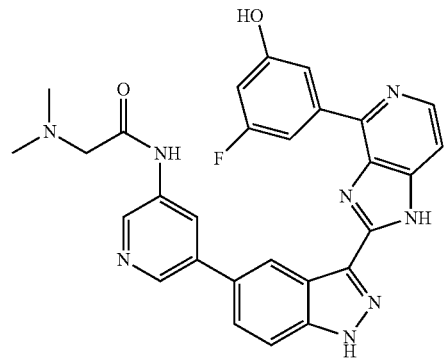 [SMILES: CN(C)CC(=O)Nc1cncc(-c2ccc3[nH]nc(-c4nc5c(-c6cc(O)cc(F)c6)nccc5[nH]4)c3c2)c1] |
| 2271 | 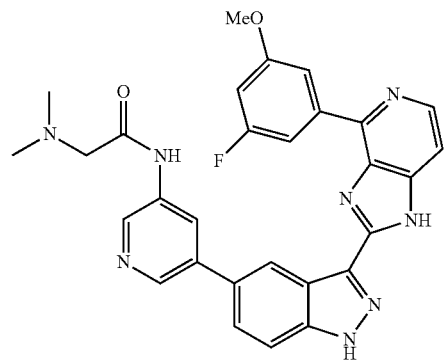 [SMILES: COc1cc(F)cc(-c2nccc3[nH]c(-c4n[nH]c5ccc(-c6cncc(NC(=O)CN(C)C)c6)cc45)nc23)c1] |
TABLE 1-continued
| 2272 | 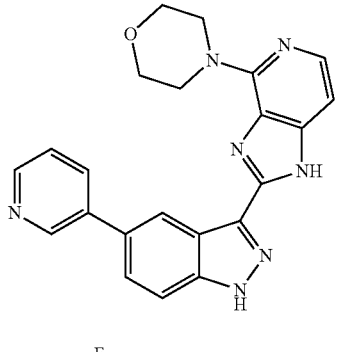 |
| --- | --- |
| 2273 | 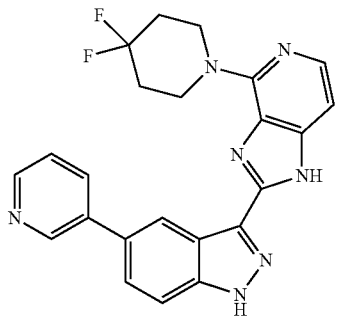 [SMILES: FC1(F)CCN(c2nccc3[nH]c(-c4n[nH]c5ccc(-c6cccnc6)cc45)nc23)CC1] |
| 2274 | 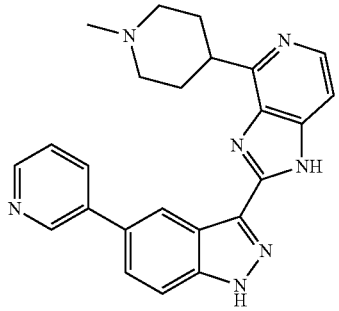 |
| 2275 | 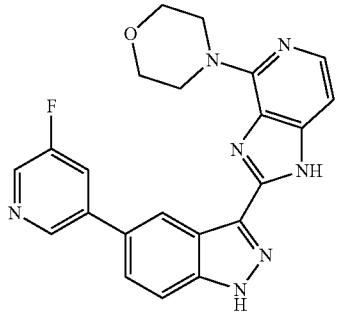 [SMILES: Fc1cncc(-c2ccc3[nH]nc(-c4nc5c(N6CCOCC6)nccc5[nH]4)c3c2)c1] |
| 2276 | 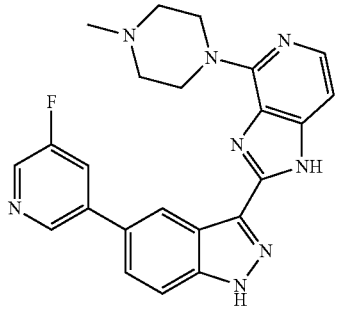 [SMILES: CN1CCN(c2nccc3[nH]c(-c4n[nH]c5ccc(-c6cncc(F)c6)cc45)nc23)CC1] |

TABLE 1-continued
| | | | | |
|---|---|---|---|---|
| 2277 | 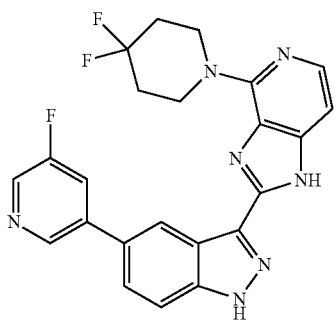 [SMILES: Fc1cncc(-c2ccc3[nH]nc(-c4nc5c(N6CCC(F)(F)CC6)nccc5[nH]4)c3c2)c1] | | 2282 | 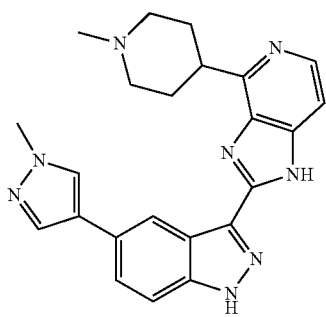 |
| 2278 | 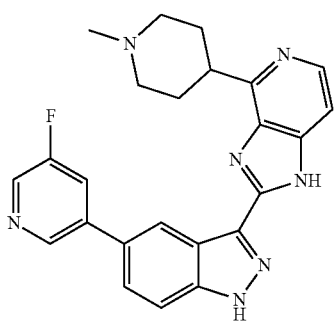 [SMILES: CN1CCC(c2nccc3[nH]c(-c4n[nH]c5ccc(-c6cncc(F)c6)cc45)nc23)CC1] | | 2283 | 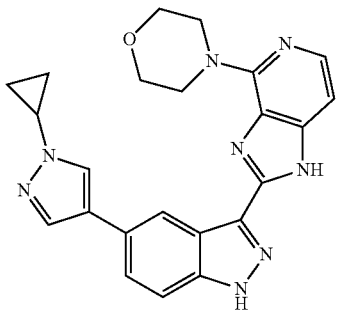 |
| 2279 | 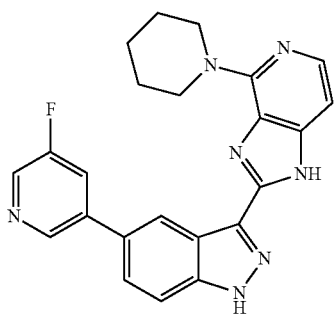 [SMILES: Fc1cncc(-c2ccc3[nH]nc(-c4nc5c(N6CCCCC6)nccc5[nH]4)c3c2)c1] | | 2284 | 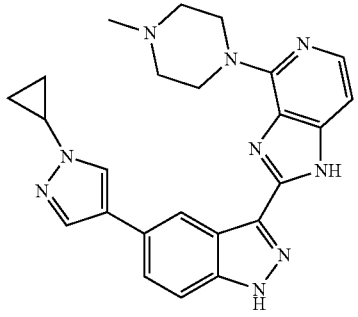 |
| 2280 | 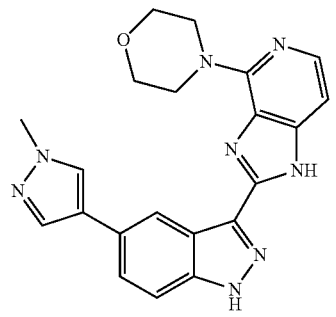 [SMILES: Cn1cc(-c2ccc3[nH]nc(-c4nc5c(N6CCOCC6)nccc5[nH]4)c3c2)cn1] | | 2285 | 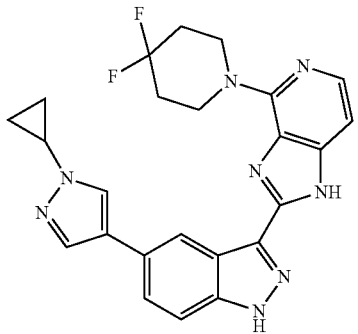 |
| 2281 | 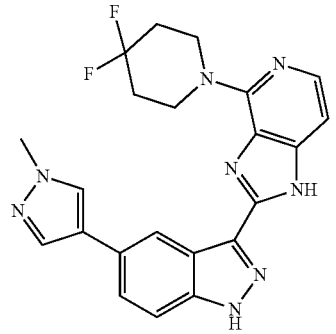 [SMILES: Cn1cc(-c2ccc3[nH]nc(-c4nc5c(N6CCC(F)(F)CC6)nccc5[nH]4)c3c2)cn1] | | 2286 | 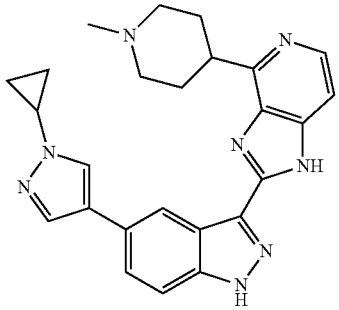 [SMILES: CN1CCC(c2nccc3[nH]c(-c4n[nH]c5ccc(-c6cnn(C7CC7)c6)cc45)nc23)CC1] |

TABLE 1-continued

| | |
|---|---|
| 2287 | 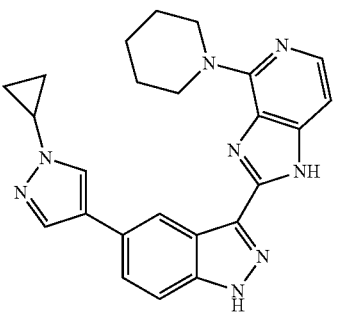 [SMILES: c1cc2[nH]c(-c3n[nH]c4ccc(-c5cnn(C6CC6)c5)cc34)nc2c(N2CCCCC2)n1] |
| 2288 | 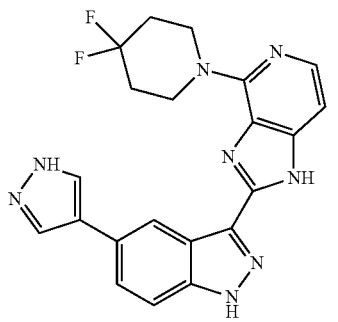 [SMILES: FC1(F)CCN(c2nccc3[nH]c(-c4n[nH]c5ccc(-c6cn[nH]c6)cc45)nc23)CC1] |
| 2289 | 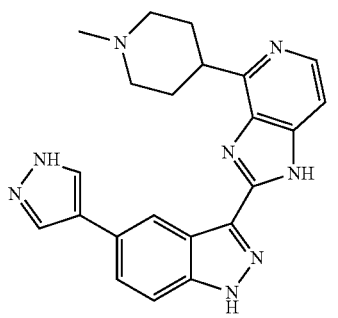 [SMILES: CN1CCC(c2nccc3[nH]c(-c4n[nH]c5ccc(-c6cn[nH]c6)cc45)nc23)CC1] |
| 2290 | 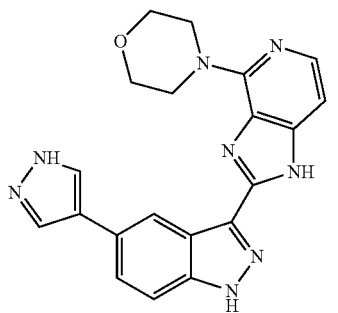 [SMILES: c1cc2[nH]c(-c3n[nH]c4ccc(-c5cn[nH]c5)cc34)nc2c(N2CCOCC2)n1] |

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and other known agents are colorectal cancer, ovarian cancer, retinitis pigmentosa, macular degeneration, diabetic retinopathy, idiopathic pulmonary fibrosis/pulmonary fibrosis, and osteoarthritis.

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formula (I) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formula (I) can be used to treat idiopathic pulmonary fibrosis/pulmonary fibrosis in combination with any of the following methods: oxygen therapy, pulmonary rehabilitation and surgery.

In some embodiments, a compound of Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formula (I) and one or more of the following drugs: UF-021 (Ocuseva™), vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intramenin-geally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, $22^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 µm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG) and other eye diseases or syndromes associated with defects and/or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG) and other eye diseases or syndromes associated with defects and/or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, non-limiting examples of eye diseases which can be treated with the compounds and compositions provided herein include age-related macular degeneration (AMD or ARMD), rod cone dystrophy, retinitis pigmentosa (RP), acute idiopathic blind spot enlargement (AIBSE), acute zonal occult outer retinopathy (AZOOR), acute macular neuroretinopathy (AMN), multiple evanescent white dot syndrome (MEWDS), multifocal choroiditis, opticneuropathy. Further causes of photoreceptor damage that can be treated with the compounds and compositions provided herein include retinal detachment, vascular disturbance, eye tumors or extreme light damage.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG) and other eye diseases or syndromes associated with defects and/or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, de Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barre syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to claim 1, or a pharmaceutically acceptable salt thereof.

In some embodiments, the pharmaceutical composition comprises a therapeutically effective amount of a compound of Formula (I), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendonitis.

In some embodiments, the disorder or disease is damage to a tendon requiring tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the method inhibits one or more proteins in the Wnt pathway, the method comprises contacting a cell with an effective amount of a compound of Formula (I).

In some embodiments, the cell is a human cell.

In some embodiments, the human cell is a cancerous cell.

In some embodiments, the cancerous cell is a colon cancer cell.

In some embodiments, the contacting is in vitro.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$ or $G_1$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a Xenopus secondary axis bioassay (Leyns, L. et al. *Cell* (1997), 88(6), 747-756).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry*: Reactions, Mechanisms, and Structure $7^{th}$ Ed., John Wiley & Sons (2013), Carey and Sundberg, *Advanced Organic Chemistry* $5^{th}$ Ed., Springer (2007), *Comprehensive Organic Transformations: A Guide to Functional Group Transformations,* 2nd Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis,* 4th Ed., John Wiley & Sons (2007), incorporated herein by reference in its entirety.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
BH$_3$-Me$_2$S=borane dimethyl sulfide complex
(Boc)$_2$O=di-tert-butyl dicarbonate
brine=saturated aqueous sodium chloride
CDCl$_3$=deuterated chloroform
CD$_3$OD=deuterated methanol
DCAD=di-(4-chlorobenzyl)azodicarboxylate
DCE=dichloroethane
DCM=dichloromethane
DEAD=diethyl azodicarboxylate
DHP=dihydropyran
DMAP=4-dimethylaminopyridine
DMF=N,N-dimethylformamide
DMSO-d$_6$=deuterated dimethylsulfoxide
ESIMS=electron spray mass spectrometry
Et=ethyl
EtOAc=ethyl acetate
EtOH=ethanol
HCl=hydrochloric acid
HOAc=acetic acid
K$_2$CO$_3$=potassium carbonate
KOAc=potassium acetate
LC/MS=liquid chromatography-mass spectrometry
Me=methyl
MeOH=methanol
MgSO$_4$=magnesium sulfate
MsCl=methanesulfonyl chloride or mesyl chloride
MW=microwave
NaBH$_4$=sodium borohydride
NaBH(OAc)$_3$=sodium triacetoxyborohydride
NaCNBH$_3$=sodium cyanoborohydride
NaHCO$_3$=sodium bicarbonate
NaOH=sodium hydroxide
Na$_2$S$_2$O$_5$=sodium metabisulfite or sodium pyrosulfite
NBS=N-bromosuccinimide
NH$_4$OH=ammonium hydroxide
NMR=nuclear magnetic resonance
ON=overnight
Pd/C=palladium(0) on carbon
Pd(dppf)Cl$_2$=1,1'-bis(diphenylphosphino)ferrocene]palladium(II) chloride
Pd(PPh$_3$)$_4$=tetrakis(triphenylphosphine)palladium(0)
Pd(PPh$_3$)$_2$Cl$_2$=bis(triphenylphosphine)palladium(II) dichloride
PE=petroleum ether
Pin$_2$B$_2$=bis(pinacolato)diboron
PPh$_3$=triphenylphosphine
PPTS=pyridinium p-toluenesulfonate
r.t=room temperature
SEM-Cl=2-(trimethylsilyl)ethoxymethyl chloride
TBME=methyl tert-butyl ether
TEA=triethylamine
TFA=trifluoroacetic acid
THF=tetrahydrofuran
THP=tetrahydropyran
TLC=thin layer chromatography
p-TsOH=p-toluenesulfonic acid The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedure

Compounds of Formula (I) of the present invention can be prepared as depicted in Scheme 1.

Scheme 1

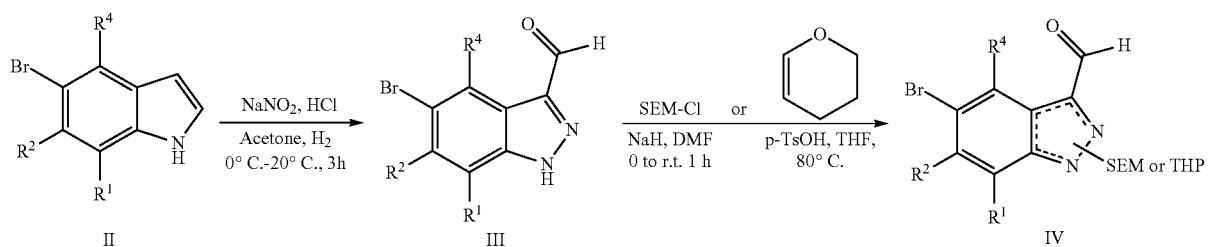

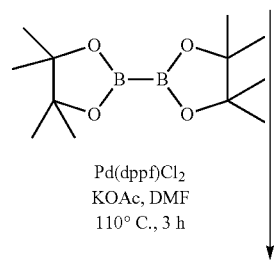

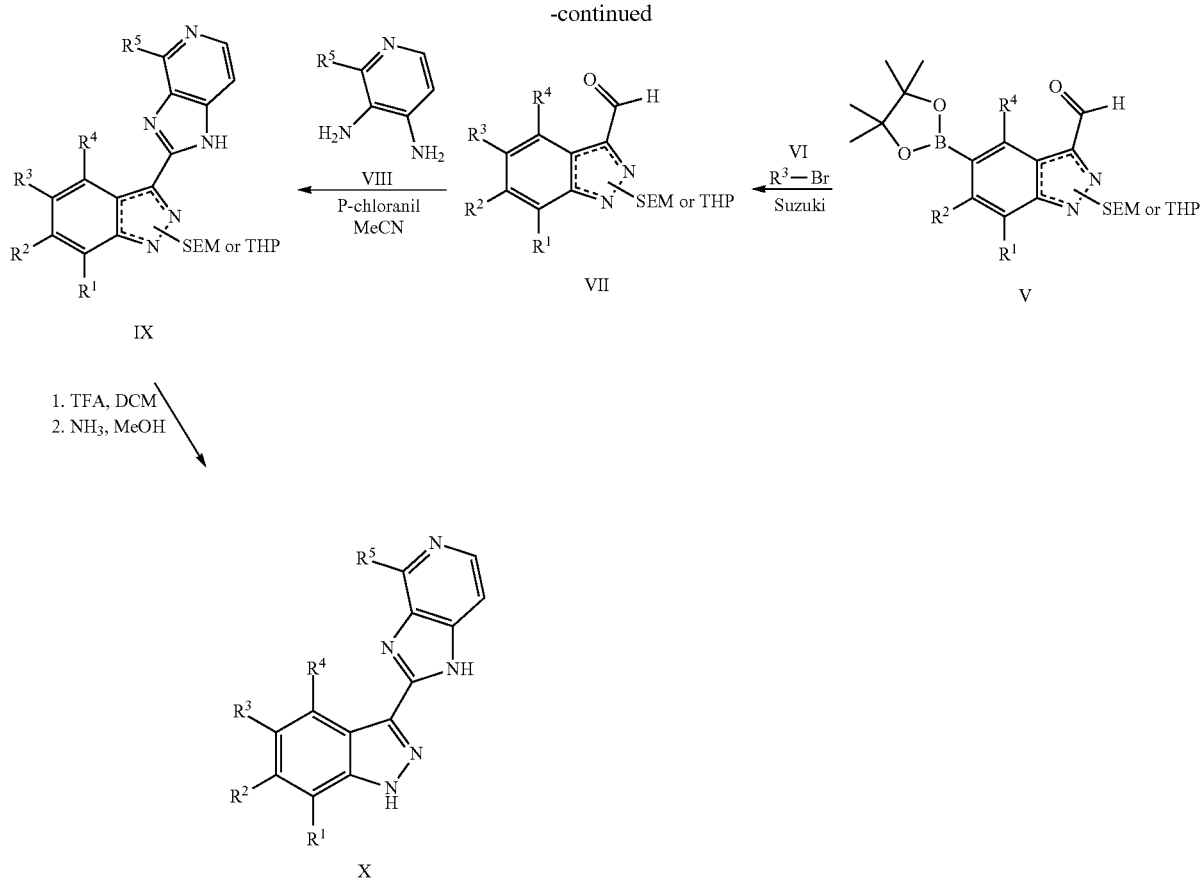

Scheme 1 describes an alternative method for preparation of indazole derivatives (X) by first formylating 5-bromo-1H-indole (II) to produce 5-bromo-1H-indazole-3-carbaldehyde (III) followed by protection with either SEM-Cl or DHP to give the protected aldehyde (IV). Aldehyde (IV) is then reacted with bis(pinacolato)diboron to form the borate ester (V). Suzuki coupling with various bromides (VI) yields indazole derivatives (VII). Aldehyde (VII) is reacted with various 1,2-diamines (VIII) to produce (IX). Final deprotection of the pyrazole nitrogen yields the desired indazole derivatives (X).

Illustrative Compound Examples

Preparation of SEM protected intermediate (XII) is depicted below in Scheme 2.

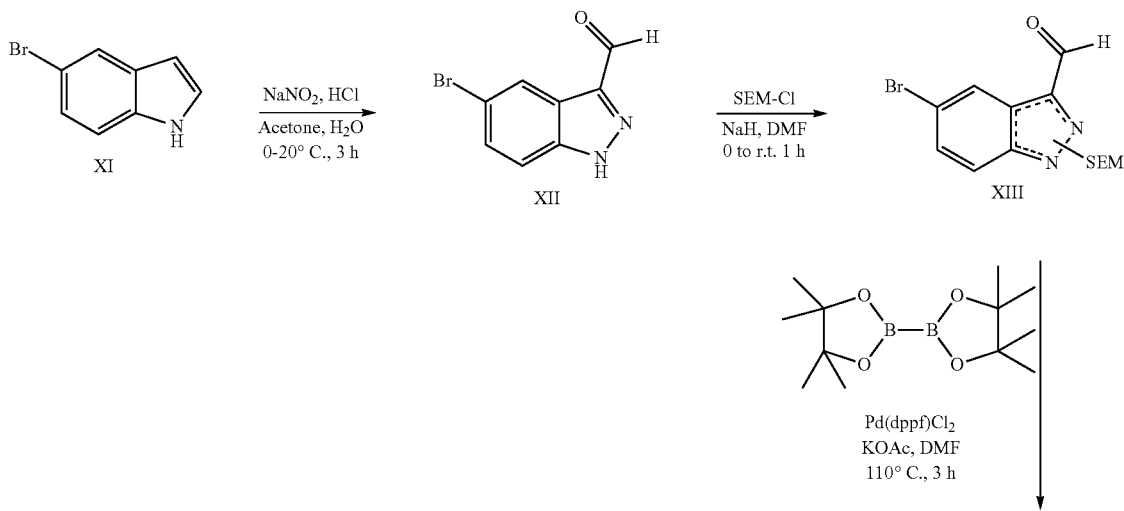

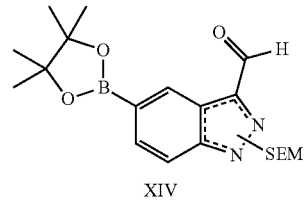

XIV

Step 1

A solution of NaNO$_2$ (110.4 g, 1.6 mol, 8 eq) in water (200 mL) was added dropwise to a solution of 5-bromoindole (XI) (39.2 g, 0.2 mol, 1 eq) in acetone (1000 mL) stirred at −10→0° C., while adding NaNO$_2$ the solution temperature was maintained below 20° C. An aqueous 2N HCl solution (480 mL) was added slowly to the solution with vigorously stirring while keeping the internal temperature between 0 and 20° C. The solution was further stirred at 20° C. for 3 h after the addition. The solution was concentrated under reduced pressure to remove acetone while keeping the temperature below 35° C. The solid was collected by filtration and transferred to a flask. Cold (−10° C.) DCM (200 mL) was added and stirred for 30 min at −5° C., the solids were filtered and dried under vacuum at 40° C. to get 5-bromo-1H-indazole-3-carbaldehyde (XII) (34.0 g, 151 mmol, 76% yield) as a brown solid. ESIMS found for C$_8$H$_5$BrN$_2$O m/z 225 (M+H).

Step 2

To a suspension of NaH (6.6 g, 166 mmol, 1.10 eq) in DMF (500 mL) was added a solution of 5-bromo-1H-indazole-3-carbaldehyde (XII) (34.0 g, 151 mmol, 1.0 eq) in DMF (50 mL) dropwise at 0° C. over a period of 30 min. The mixture was stirred at room temperature for 2 h, then SEM-Cl (26.4 g, 159 mmol, 1.08 eq) was added dropwise and the mixture was stirred at room temperature for another 3 h. Then the mixture was poured into an ice-water mixture (1000 mL) and extracted with EtOAc (300 mL×3), the organic phases were combined, dried over Na$_2$SO$_4$, filtered and concentrated in vacuo, the resultant residue was purified by flash chromatography on silica gel (PE:EtOAc=20:1→10:1) to afford 5-bromo-1-((2-(trimethylsilyl)ethoxy)methyl)-1H-indazole-3-carbaldehyde (XIII) as a mixture of regioisomers (53.0 g, 151 mmol, 100% yield) as a yellow oil. ESIMS found for C$_{14}$H$_{19}$BrN$_2$O$_2$Si m/z 355 (M+H).

Step 3

To a solution of the mixed 5-bromo-1-((2-(trimethylsilyl)ethoxy)methyl)-1H-indazole-3-carbaldehyde (XIII) (53.0 g, 151 mmol, 1.0 eq), bis(pinacolato)diboron (38.0 g, 150 mmol, 1.0 eq) and KOAc (44.0 g, 450 mmol, 3.0 eq) in DMF (1000 mL) was added Pd(dppf)Cl$_2$ (7.7 g, 10.5 mmol, 0.07 eq). The mixture was stirred at 90° C. under nitrogen for 10 h. The mixture was filtered; the filtrate was poured onto water (1000 mL) and extracted with EtOAc (500 mL×3). The combined organic phases were dried, filtered and concentrated in vacuo. The resultant residue was purified by flash chromatography on silica gel (PE:EtOAc=10:1→1:1) to give the 5-(4,4,5,5-tetramethyl-1,3,2-dioxaborolan-2-yl)-1-((2-(trimethylsilyl)ethoxy)methyl)-1H-indazole-3-carbaldehyde (XIV) as a mixture of regioisomers (42.9 g, 106 mmol, 71% yield) as a yellow oil. ESIMS found for C$_{20}$H$_{31}$BN$_2$O$_4$Si m/z 403 (M+H).

Preparation of THP protected intermediate (XIII) is depicted below in Scheme 3.

Scheme 3

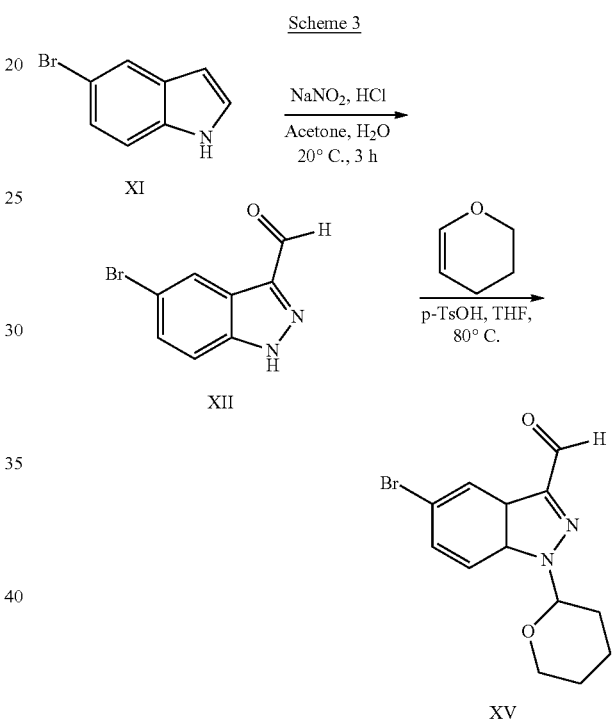

Step 1

Procedure can be found in Scheme 2, Step 1.

Step 2

A mixture of 5-bromo-1H-indazole-3-carbaldehyde (XII) (29.9 g, 133 mmol), 3,4-dihydro-2H-pyran (27.4 mL, 300 mmol) and PPTS (352 mg, 1.4 mmol) in DCM was heated to reflux for 5 hours. The solution was poured into a saturated NaHCO$_3$ solution, the layers were separated, and the aqueous layer was extracted with DCM. The combined organic layers were washed with 5% aqueous citric acid and brine, dried over MgSO$_4$, and concentrated. The crude product was purified on a silica gel column (100% EtOAc→3:97 MeOH:DCM) to provide 5-bromo-1-(tetrahydro-2H-pyran-2-yl)-3a,7a-dihydro-1H-indazole-3-carbaldehyde (XV) was isolated as a white solid (16.4 g, 52.7 mmol, 39.6% yield). $^1$H NMR (DMSO-d$_6$, 500 MHz) δ ppm 1.57-1.65 (m, 2H), 1.72-1.83 (m, 1H), 2.02-2.11 (m, 2H), 2.33-2.44 (m 1H), 3.76-3.83 (m, 1H), 3.84-3.93 (m, 1H), 6.08 (dd, J=2.5 Hz, 9 Hz, 1H), 7.72 (dd, J=1.5 Hz, J=8.5 Hz, 1H), 7.92 (d, J=9 Hz, 1H), 8.28 (d, J=2 Hz, 1H), 10.17 (s, 1H); ESIMS found C$_{13}$H$_{15}$BrN$_2$O$_2$ m/z 311.0 (M+H).

Preparation of 6-fluoro-substituted indazole intermediate (XXII) is depicted below in Scheme 4.

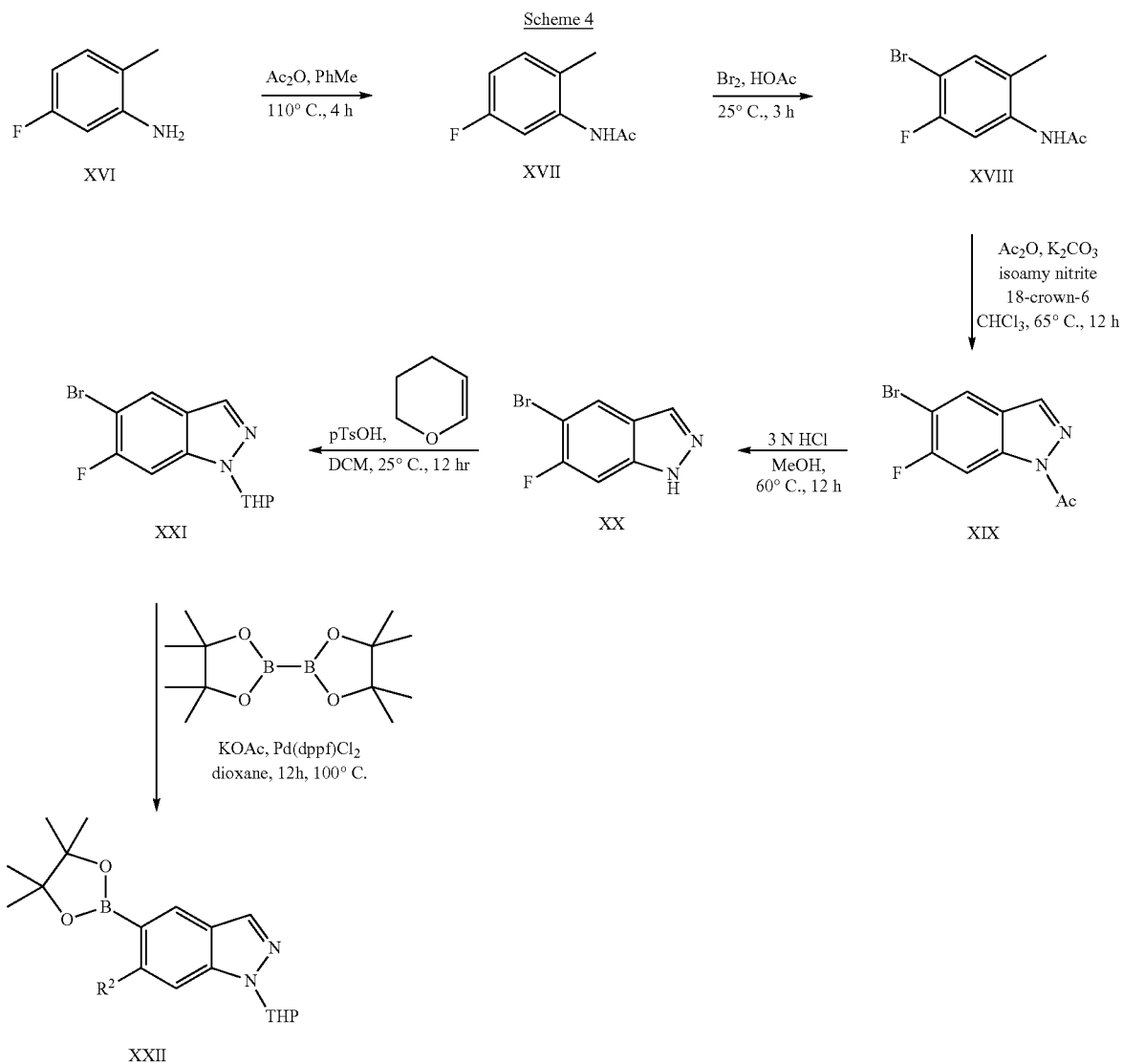

Step 1

A solution of 5-fluoro-2-methylaniline (XVI) (100 g, 799 mmol, 1.0 eq) and Ac₂O (89 g, 879 mmol, 1.1 eq) in toluene (4.0 L) was stirred at 110° C. for 4 h. TLC (PE:EtOAc=2:1) showed (XVI) was consumed. The reaction mixture was cooled to 25° C. The precipitated solid was filtered, washed with petro ether. The solid was dried in vacuo to give N-(5-fluoro-2-methylphenyl)acetamide (XVII) as a white solid (120 g, 717.8 mmol, 89.8% yield), which was used in step 2 without further purification. ESIMS found $C_9H_{10}FNO$ m/z 168.1 (M+1).

Step 2

To a solution of N-(5-fluoro-2-methylphenyl)acetamide (XVII) (120 g, 717 mmol, 1.0 eq) in HOAc (3 L) was added a solution of Br₂ (140 g, 876 mmol, 1.2 eq) in HOAc (1 L) dropwise. The mixture was stirred at 25° C. for 3 h. LC/MS showed compound 2 was (XVII) completely consumed. The reaction mixture was quenched with water (8 L). The solid was filtered, washed with water and petroleum ether. The solid was dried in vacuo to give N-(4-bromo-5-fluoro-2-methylphenyl)acetamide (XVIII) as a white solid (155 g, 629.9 mmol, 87.8% yield). ¹H NMR (CDCl₃, 400 MHz) δ ppm 2.20 (s, 6H), 7.07 (brs, 1H), 7.32 (d, J=7.2 Hz, 1H), 7.85 (d, J 10.8 Hz, 1H); ESIMS found $C_9H_9BrFNO$ m/z 247.2 (M+1).

Step 3

A solution of N-(4-bromo-5-fluoro-2-methylphenyl)acetamide (XVIII) (155 g, 629.9 mmol, 1.0 eq), Ac₂O (192 g, 1.8 mol, 3.0 eq), KOAc (123 g, 1.26 mol, 2.0 eq), 18-CROWN-6 (8.3 g, 31 mmol, 0.05 eq) and isoamyl nitrite (147 g, 1.2 mol, 2.0 eq) in CHCl₃ (7.0 L) was stirred at 65° C. for 12 h. TLC (PE:EtOAc=5:1, Rf=0.2) showed (XVIII) was consumed completely. The solvent was removed under reduced pressure. The residue was extracted with EtOAc (1.5 L) and water (1.5 L). The organic layer was dried over anhydrous Na₂SO₄, concentrated under reduced pressure to give 1-(5-bromo-6-fluoro-1H-indazol-1-yl)ethan-1-one (XIX) as a white solid (170 g, crude, quantitative yield), which was used in step 4 without further purification. ESIMS found $C_9H_6BrFN_2O$ m/z 258.1 (M+1).

Step 4

A solution of 1-(5-bromo-6-fluoro-1H-indazol-1-yl)ethan-1-one (XIX) (170 g, 629.9 mmol, 1.0 eq) in 3 N HCl (6.6 mol, 10 eq) and MeOH (900 mL) was stirred at 60° C. for 12 h. TLC (PE:EtOAc=5:1, Rf=0.8) showed (XIX) was consumed completely. The reaction mixture was cooled to room temperature and basified with 1N aq. NaOH to pH=10. The precipitated solid was filtered and dried in vacuo to afford 5-bromo-6-fluoro-1H-indazole (XX) as a yellow solid (100 g, 465.1 mmol, 73.8% yield). ESIMS found $C_7H_4BrFN_2$ m/z 215.1 (M+1).

Step 5

To solution of a mixture of 5-bromo-6-fluoro-1H-indazole (XX) (90 g, 418 mmol, 1.0 eq) and 3,4-dihydro-2H-pyran (70 g, 837 mmol, 2.0 eq) in DCM (2.0 L) was added p-TsOH (3.6 g, 20 mmol, 0.05 eq) at 25° C. The resulting mixture was stirred at 25° C. for 12 h. TLC (PE:EtOAc=5:1, Rf=0.7) showed (XX) was completely consumed. To the reaction mixture was added saturated aqueous NaHCO$_3$ (4 L). The organic layer was separated, dried over Na$_2$SO$_4$, concentrated in vacuo to give a residue, which was further purified by silica gel column (EtOAc:PE=20:1) to give 5-bromo-6-fluoro-1-(tetrahydro-2H-pyran-2-yl)-1H-indazole (XXI) as a brown oil (120 g, 401.1 mmol, 96.0% yield), which was used in step 6 without further purification. ESIMS found $C_{12}H_{12}BrFN_2O$ m/z 299.2 (M+1).

Step 6

A solution of 5-bromo-6-fluoro-1-(tetrahydro-2H-pyran-2-yl)-1H-indazole (XXI) (30 g, 100 mmol, 1.0 eq), 4,4,5,5-tetramethyl-2-(4,4,5,5-tetramethyl-1,3,2-dioxaborolan-2-yl)-1,3,2-dioxaborolane (25 g, 100 mmol, 1.0 eq), Pd(dppf)Cl$_2$ (3.6 g, 5.0 mmol, 0.05 eq), KOAc (19.6 g, 200 mmol, 2.0 eq) in dioxane (550 mL) was stirred at 100° C. for 12 h under N$_2$. LC/MS showed (XXI) was completely consumed. The reaction mixture was concentrated and then extracted with EtOAc (300 mL) and water (100 mL). The mixture was filtered and separated. The organic layer was dried over anhydrous Na$_2$SO$_4$, concentrated to give crude product, which was further purified by silica gel column (EtOAc:PE=20/1) to give 6-fluoro-1-(tetrahydro-2H-pyran-2-yl)-5-(4,4,5,5-tetramethyl-1,3,2-dioxaborolan-2-yl)-1H-indazole (XXII) as a green solid (13 g, 37.5 mmol, 37.4% yield). $^1$H NMR (CDCl$_3$, 400 MHz) δ ppm 1.37 (s, 12H), 1.73-1.43 (m, 3H), 2.58-2.50 (m, 1H), 3.79-3.73 (m, 1H), 4.06-4.04 (m, 1H), 5.66-5.63 (m, 1H), 7.28-7.21 (m, 1H), 8.00 (s, 1H), 8.19 (d, J=5.6 Hz, 1H); ESIMS found $C_{18}H_{24}BFN_2O_3$ m/z 347.2 (M+1).

Preparation of 7-fluoro-substituted indazole intermediate (XXVIII) is depicted below in Scheme 5.

Scheme 5

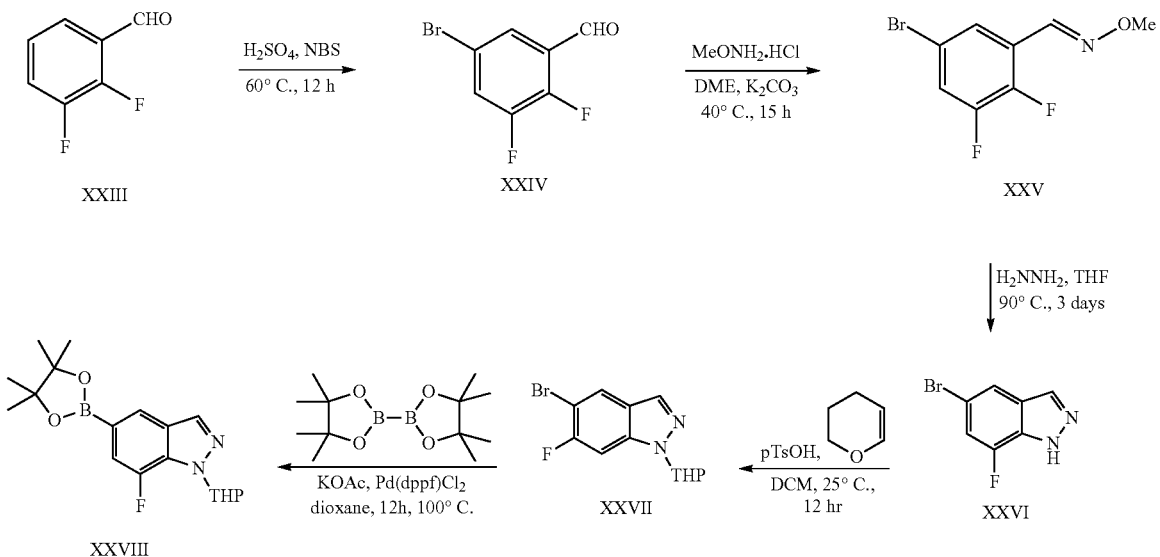

Step 1

To a stirred solution of 2,3-difluorobenzaldehyde (XXIII) (75.0 g, 528 mmol, 1.0 eq) in H$_2$SO$_4$ (565 mL) was added NBS (113 g, 633 mmol, 1.2 eq) in portions at 60° C. The resulting mixture was stirred at 60° C. for 12 hr. LC/MS showed the reaction was completed. The reaction mixture was poured into ice water and petroleum ether (500 mL) and stirred for 10 min, the organic layer was separated and concentrated under vacuum to give crude product. The residue was purified column chromatography silica gel (100% petroleum ether) to give 5-bromo-2,3-difluorobenzaldehyde (XXIV) (120 g, 543.0 mmol, quantitative yield). ESIMS found $C_7H_3BrF_2O$ m/z 221.1 (M+1).

Step 2

To a solution of 5-bromo-2,3-difluorobenzaldehyde (XXIV) (115 g, 520 mmol, 1.0 eq), MeONH$_2$ HCl (47.8 g, 572 mmol, 1.1 eq) and K$_2$CO$_3$ (86.3 g, 624 mmol, 1.20 eq) was in DME (1.30 L) was heated to 40° C. for 15 h. TLC (petroleum ether) showed (XXIV) was consumed. The reaction was filtered and the filtrate was concentrated under vacuum to give crude product. The residue was purified by column chromatography on silica gel (100% petroleum ether) to give (E)-5-bromo-2,3-difluorobenzaldehyde O-methyl oxime (XXV) (74 g, 56.9% yield). $^1$H NMR (CDCl$_3$, 400 MHz) δ ppm 4.04 (s, 3H), 7.37-7.32 (m, 1H), 7.77 (s, 1H), 8.23 (s, 1H); ESIMS found $C_8H_6BrF_2NO$ m/z 250.2 (M+1).

Step 3

A solution of (E)-5-bromo-2,3-difluorobenzaldehyde O-methyl oxime (XXV) (150 g, 600 mmol, 1.0 eq), NH$_2$NH$_2$—H$_2$O (600 mL) in dry THF (600 mL) was heated to 90° C. for 84 h. LC/MS showed the reaction was completed. The solvent was evaporated and the resulting mixture was diluted with EtOAc, washed with water, dried over Na₂SO₄ and concentrated under vacuum to give crude product. The residue was purified by column chromatography on silica gel (PE:EtOAc=10:1) to give 5-bromo-7-fluoro-1H-indazole (XXVI) as a white solid (78 g, 362.7 mmol, 60.5% yield). ¹H NMR (DMSO-d₆, 400 MHz) δ ppm 7.44 (d, J=9.6 Hz, 1H), 7.87 (d, J=1.6 Hz, 1H), 8.17 (s, 1H), 13.90 (s, 1H); ESIMS found C₇H₄BrFN₂ m/z 215 (M+1).

Step 4

Preparation of 5-bromo-7-fluoro-1-(tetrahydro-2H-pyran-2-yl)-1H-indazole (XXVII) was performed following the procedure listed in Scheme 4, Step 5. Light yellow solid (98 g, 327.6 mmol, 93.9% yield). ¹H NMR (CDCl₃, 400 MHz) δ ppm 1.78-1.62 (m, 3H), 2.17-2.09 (m, 2H), 2.63-2.58 (m, 1H), 3.76 (t, J=11.6 Hz, 1H), 4.05 (d, J=9.6 Hz, 1H), 5.85 (d, J=9.6 Hz, 1H), 7.22 (d, J=12.0 Hz, 1H), 7.65 (s, 1H), 8.00 (s, 1H); ESIMS found C₁₂H₁₂BrFN₂O m/z 299.2 (M+1).

Step 5

Preparation of 7-fluoro-1-(tetrahydro-2H-pyran-2-yl)-5-(4,4,5,5-tetramethyl-1,3,2-dioxaborolan-2-yl)-1H-indazole (XXVIII) was performed following the procedure listed in Scheme 4, Step 6. White solid (45 g, 130.0 mmol, 86.7% yield). ESIMS found C₁₈H₂₄BFN₂O₃ m/z 347.1 (M+1).

Preparation of 4-fluoro-substituted indazole intermediate (XXXIII) is depicted below in Scheme 6.

washed with PE (1 L), the solid was filtered, washed again with PE (500 mL) and dried under vacuum to give 4-bromo-3-fluoro-2-methylaniline (XXX) as a white solid (163.0 g, 798.9 mmol, 66.7% yield). ESIMS found C₇H₇BrFN m/z 204.1 (M+1).

Step 2

To a stirred solution of 4-bromo-3-fluoro-2-methylaniline (XXX) (40 g, 196 mmol, 1.0 eq) in HOAc (1.2 L) was added NaNO₂ (16 g, 235 mmol, 1.2 eq) in portions at 10° C., the resulting mixture was stirred at 25° C. for 4 h. LC/MS showed the reaction was completed. Upon completion, aqueous NaOH (50%) was added to the reaction mixture until pH 7-8, then the mixture was extracted with EtOAc (1.6 L), the organic layer was dried over Na₂SO₄, filtered; filtrate was concentrated under vacuum to give crude 5-bromo-4-fluoro-1H-indazole (XXXI) (40 g, 186.0 mmol, 94.9% yield), which was used in step 3 without further purification. ¹H NMR (CDCl₃, 400 MHz) δ ppm 7.47-7.42 (m, 1H), 7.56-7.53 (m, 1H), 8.23 (s, 1H); ESIMS found C₇H₄BrFN₂ m/z 215 (M+1).

Step 3

Preparation of 5-bromo-4-fluoro-1-(tetrahydro-2H-pyran-2-yl)-1H-indazole (XXXII) was performed following the procedure listed in Scheme 4, Step 5. Brown oil (9.9 g, 33.1 mmol, 71.9% yield). ¹H NMR (CDCl₃, 400 MHz) δ ppm 1.75-1.67 (m, 3H), 2.10-1.76 (m, 2H), 2.52-2.14 (m, 1H), 3.76-3.71 (m, 1H), 4.01-3.97 (m, 1H), 5.70-5.69 (m, 1H),

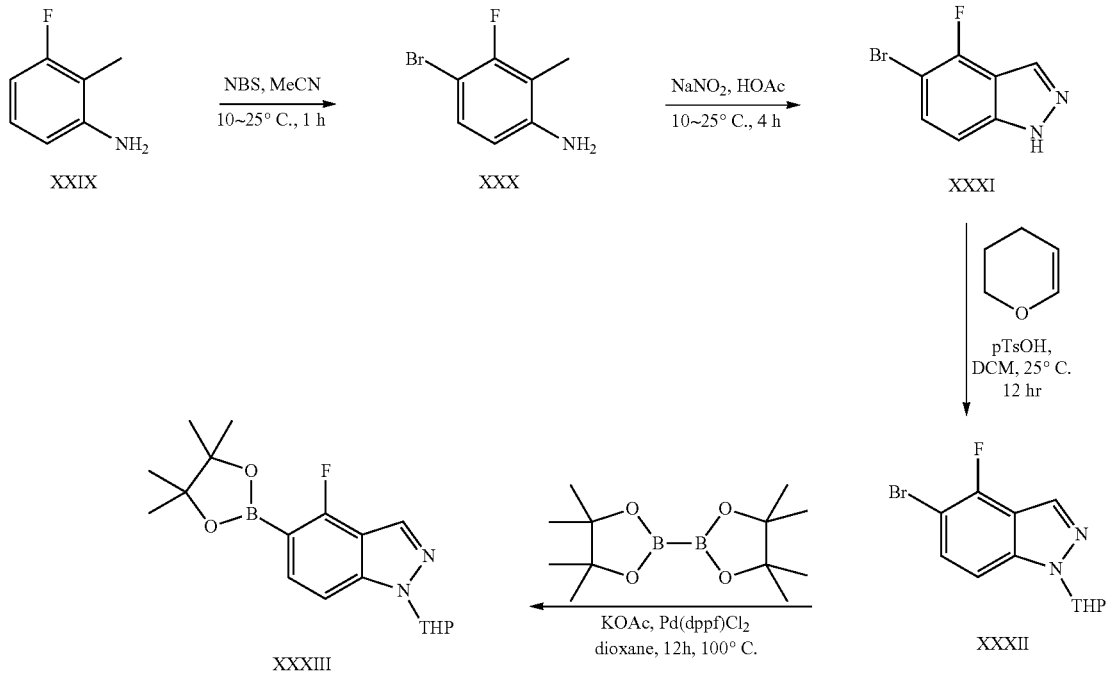

Scheme 6

Step 1

To a stirred solution of 3-fluoro-2-methylaniline (XXIX) (50 g, 399 mmol, 1.0 eq) in CH₃CN (1.2 L) was added NBS (78 g, 439 mmol, 1.1 eq) in portions at 10° C., the resulting mixture was stirred at 25° C. for 1 h. LC/MS showed the reaction was completed. Saturated Na₂S₂O₃ (1.2 L) was then added slowly to the reaction mixture at 10° C., extracted with EtOAc (2 L) and the organic layer was concentrated under vacuum to give crude product. The residue was 7.30-7.26 (m, 1H), 7.47-7.45 (m, 1H), 8.06 (s, 1H); ESIMS found C₁₂H₁₂BrFN₂O m/z 299 (M+1).

Step 4

Preparation of 4-fluoro-1-(tetrahydro-2H-pyran-2-yl)-5-(4,4,5,5-tetramethyl-1,3,2-dioxaborolan-2-yl)-1H-indazole (XXXIII) was performed following the procedure listed in Scheme 4, Step 6. Red oil (25 g, 72.2 mmol, 72.2% yield). ¹H NMR (CD₃OD, 400 MHz) δ ppm 1.72 (s, 12H), 2.12-1.74 (m, 5H), 2.52-2.16 (m, 1H), 3.85-3.80 (m, 1H), 4.12-

4.00 (m, 1H), 5.84-5.81 (m, 1H), 7.48 (d, J=8.0 Hz, 1H), 7.71-7.67 (m, 1H), 8.15 (s, 1H); ESIMS found $C_{18}H_{24}BFN_2O_3$ m/z 347 (M+1).

Preparation of intermediate N-(5-bromopyridin-3-yl)pivalamide (XXXVI) is depicted below in Scheme 7.

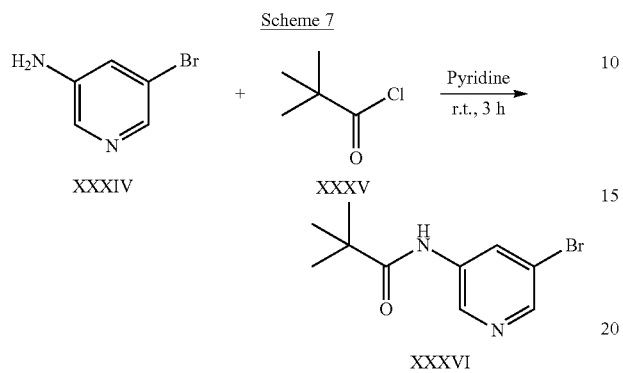

Step 1

To a solution of 3-amino-5-bromo pyridine (XXXIV) (1.0 g, 5.78 mmol) in dry pyridine (10 mL) was added pivaloyl chloride (XXXV) (769 mg, 6.38 mmol). The reaction mixture was stirred at room temperature for 3 h. The reaction was poured into an ice water/saturated aqueous NaHCO₃ mixture and stirred for 30 min. The precipitate was filtered, washed with cold water and dried at room temperature to yield N-(5-bromopyridin-3-yl)pivalamide (XXXVI) as an off-white solid (1.082 g, 4.22 mmol, 73.1% yield). $^1$H NMR (DMSO-$d_6$, 500 MHz) δ ppm 1.23 (s, 9H), 8.37 (d, J=2 Hz, 1H), 8.39 (t, J=2 Hz, 1H), 8.80 (d, J=2 Hz, 1H), 9.58 (brs, 1H); ESIMS found $C_{10}H_{13}BrN_2O$ m/z 258.9 ($Br^{81}$M+H).

The following intermediates were prepared in accordance with the procedure described in the above Scheme 7.

N-(5-Bromopyridin-3-yl)isobutyramide (XXXVII): Off-white solid, (71% yield). $^1$H NMR (CDC₃) δ ppm 8.55-8.35 (m, 3H), 7.32 (s, 1H), 2.59-2.48 (m, 1H), 1.28-1.27 (d, 6H); ESIMS found $C_9H_{11}BrN_2O$ m/z 242.9 ($Br^{79}$M+H).

N-(5-Bromopyridin-3-yl)propionamide (XXXVIII): Off white solid (92% yield). $^1$H NMR (DMSO-$d_6$) δ ppm 1.09 (t, J=7.54 Hz, 3H), 2.36 (q, J=7.54 Hz, 2H), 8.36 (m, 2H), 8.65 (d, J=2.07 Hz, 1H), 10.26 (s, 1H); ESIMS found $C_8H_9BrN_2O$ m/z 231.1 ($Br^{81}$M+H).

N-(5-Bromopyridin-3-yl)butyramide (XXXIX): Yellow solid (2.1 g, 8.64 mmol, 88.8% yield). $^1$H NMR (CD₃OD, 400 MHz) δ ppm 1.02 (t, J=7.2 Hz, 3H), 1.74 (sxt, J=7.2 Hz, 2H), 2.40 (t, J=7.2 Hz, 2H), 8.35 (d, J=2 Hz, 1H), 8.46 (t, J=2 Hz, 1H), 8.63 (d, J=2 Hz, 1H); ESIMS found $C_9H_{11}BrN_2O$ m/z 243.1 ($Br^{79}$M+H).

N-(5-Bromopyridin-3-yl)pentanamide (XL): Yellow solid (2.0 g, 7.78 mmol, 85.3% yield). $^1$H NMR (CD₃OD, 400 MHz) δ ppm 0.98 (t, J=7.4 Hz, 3H), 1.43 (sxt, J=7.4 Hz, 2H), 1.70 (quin, J=7.4 Hz, 2H), 2.43 (t, J=7.6 Hz, 2H), 8.35 (s, 1H), 8.45 (d, J=2 Hz, 1H), 8.64 (d, J=2 Hz, 1H); ESIMS found $C_{10}H_{13}BrN_2O$ m/z 256.9 ($Br^{79}$M+H).

N-(5-Bromopyridin-3-yl)-3-methylbutanamide (XLI): Off white solid, (67% yield), $^1$H NMR (CDCl₃, 500 MHz) δ ppm 8.55-8.42 (m, 3H), 7.62 (s, 1H), 2.31-2.18 (m, 3H), 1.02-1.01 (d, J=6 Hz, 6H); ESIMS found $C_{10}H_{13}BrN_2O$ m/z 258.9 ($Br^{81}$M+H).

N-(5-Bromopyridin-3-yl)-3,3-dimethylbutanamide (XLII): Yellow solid (1.7 g, 6.27 mmol, 78.6% yield). $^1$H NMR (CD₃OD, 400 MHz) δ ppm 1.10 (s, 9H), 2.29 (s, 2H), 8.36 (d, J=1.6 Hz, 1H), 8.46 (d, J=2.0 Hz, 1H), 8.64 (d, J=2.0 Hz, 1H); ESIMS found $C_{11}H_{15}BrN_2O$ m/z 273.1 (($Br^{s8}$M+H).

N-(5-Bromopyridin-3-yl)-2-phenylacetamide (XLIII): White solid (2.5 g, 8.59 mmol, 77.9% yield). $^1$H NMR (CDCl₃, 400 MHz) δ ppm 3.76 (s, 2H), 7.26-7.45 (m, 5H), 7.57 (brs, 1H), 8.33 (s, 1H), 8.37 (s, 2H); ESIMS found $C_{13}H_{11}BrN_2O$ m/z 292.8 ($Br^{81}$M+H).

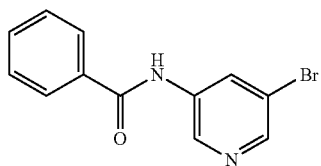

N-(5-Bromopyridin-3-yl)benzamide (XLIV): White solid (2.7 g, 9.74 mmol, 60% yield). $^1$H NMR (CDCl$_3$, 400 MHz) δ ppm 7.40-7.52 (m, 2H), 7.52-7.62 (m, 1H), 7.86 (d, J=7.2 Hz, 2H), 8.39 (d, J=1.6 Hz, 1H), 8.46 (s, 1H), 8.55 (d, J=1.6 Hz, 1H), 8.57 (d, J=2.0 Hz, 1H); ESIMS found C$_{12}$H$_9$BrN$_2$O m/z 278.8 (Br$^{81}$M+H).

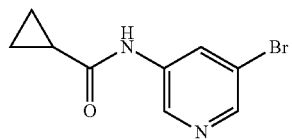

N-(5-Bromopyridin-3-yl)cyclopropanecarboxamide (XLV): Off-white solid, (83% yield), $^1$H NMR (CDCl$_3$, 500 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for C$_9$H$_9$BrN$_2$O m/z 240.9 (Br$^{79}$M+H).

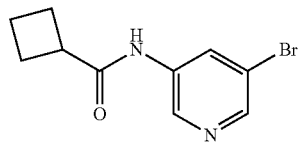

N-(5-Bromopyridin-3-yl)cyclobutanecarboxamide (XLVI): Yellow solid (2.1 g, 6.27 mmol, 86.6% yield). $^1$H NMR (CD$_3$OD, 400 MHz) δ ppm 1.80-1.99 (m, 1H), 1.99-2.15 (m, 1H), 2.16-2.30 (m, 2H), 2.30-2.45 (m, 2H), 3.25-3.35 (m, 1H), 8.34 (d, J=2.0 Hz, 1H), 8.47 (s, 1H), 8.64 (d, J=2.0 Hz, 1H); ESIMS found C$_{10}$H$_{11}$BrN$_2$O m/z 257.1 (Br$^{81}$M+H).

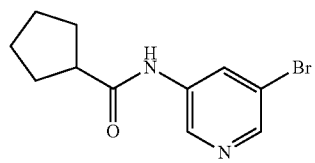

N-(5-Bromopyridin-3-yl)cyclopentanecarboxamide (XLVII): Yellow solid (1.9 g, 7.06 mmol, 80.2% yield). $^1$H NMR (CD$_3$OD, 400 MHz) δ ppm 1.57-1.74 (m, 2H), 1.74-1.91 (m, 4H), 1.91-2.07 (m, 2H), 2.77-2.92 (m, 1H), 8.34 (d, J=1.6 Hz, 1H), 8.45 (s, 1H), 8.65 (d, J=2.0 Hz, 1H); ESIMS found C$_{10}$H$_{13}$BrN$_2$O m/z 271.1 (Br$^{81}$M+H).

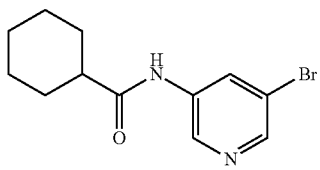

N-(5-bromopyridin-3-yl)cyclohexanecarboxamide (XLVIII): Yellow solid (2.0 g, 7.06 mmol, 84.3% yield). $^1$H NMR (CD$_3$OD, 400 MHz) δ ppm 1.19-1.46 (m, 3H), 1.46-1.63 (m, 2H), 1.74 (d, J=11.6 Hz, 1H), 1.88 (t, J=14.0 Hz, 4H), 2.40 (tt, J=11.6 Hz, J=3.6 Hz, 1H), 8.34 (d, J=2.0 Hz, 1H), 8.44 (t, J=2.0 Hz, 1H), 8.64 (d, J=2.0 Hz, 1H); ESIMS found C$_{12}$H$_{15}$BrN$_2$O m/z 285.1 (Br$^{81}$M+H).

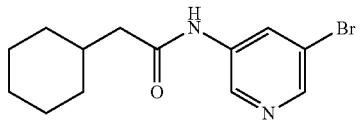

N-(5-bromopyridin-3-yl)-2-cyclohexylacetamide (XLIX): Yellow solid (261 mg, 0.878 mmol, 84.4% yield). ESIMS found C$_{13}$H$_{17}$BrN$_2$O m/z 297.1 (Br$^{81}$M+H).

Preparation of intermediate 5-bromo-N,N-dimethylpyridin-3-amine (LI) is depicted below in Scheme 8.

Scheme 8

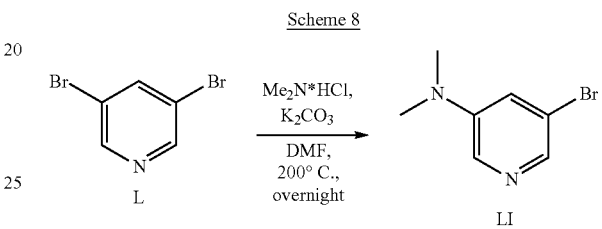

Step 1

To a solution of 3,5-dibromopyridine (L) (2.37 g, 10.0 mmol) in dry DMF (20.0 mL) was added K$_2$CO$_3$ (4.5 g, 33 mmol) and dimethylamino hydrochloride (1.79 g, 22 mmol). The mixture was heated overnight at 200° C. in a sealed tube. The solution was cooled to room temperature and excess DMF was removed under vacuum. The residue was partitioned between EtOAc and water. The organic phase was separated. The aqueous phase was washed with EtOAc and the combined organic phases were dried over MgSO$_4$, and concentrated to afford 5-bromo-N,N-dimethylpyridin-3-amine (LI) as an off-white solid (1.78 g, 8.85 mmol, 88% yield). $^1$H NMR (DMSO-d$_6$, 500 MHz) δ ppm 2.94 (s, 6H), 7.25 (t, J=2 Hz, 1H), 7.91 (d, J=2 Hz, 1H), 8.07 (d, J=2 Hz, 1H); ESIMS found C$_7$H$_9$BrN$_2$ m/z 201.1 (M+H).

Preparation of intermediate 5-bromo-N-isopropylpyridin-3-amine (LII) is depicted below in Scheme 9.

Scheme 9

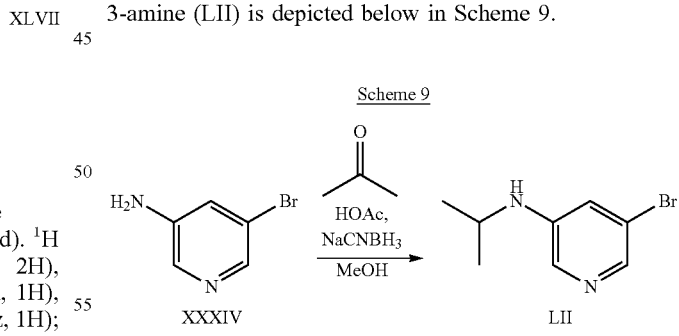

Steps 1

To a solution of 5-bromopyridin-3-amine (XXXIV) (535 mg, 3.09 mmol) in MeOH (62 mL) was added acetone (296 μL, 4.02 mL). The pH was adjusted to 4 using HOAc and stirred for 30 min. NaCNBH$_3$ (272 mg, 4.33 mmol) was added and stirred at room temperature overnight. The MeOH was removed under vacuum and the residue was partitioned between EtOAc and saturated aqueous NaHCO$_3$. The organic layer was dried over MgSO$_4$ and evaporated under vacuum. The crude product was purified on a silica gel column (100% hexane→90:10 hexane:EtOAc) to produce 5-bromo-N-isopropylpyridin-3-amine (LII) as an oil which slowly solidified into an off-white solid (309 mg, 1.44 mmol, 47% yield). $^1$H NMR (DMSO-d$_6$, 500 MHz) δ ppm 1.12 (d, J=6.3 Hz, 6H), 3.55-3.59 (m, 1H), 6.03 (d, J=7.9 Hz, 1H), 7.05-7.06 (m, 1H), 7.75 (d, J=2 Hz, 1H), 7.90 (d, J=2 Hz, 1H); ESIMS found C$_8$H$_{11}$BrN$_2$ m/z 215.1 (M+H).

Preparation of intermediate 1-(5-bromopyridin-3-yl)-N,N-dimethylmethanamine (LIV) is depicted below in Scheme 10.

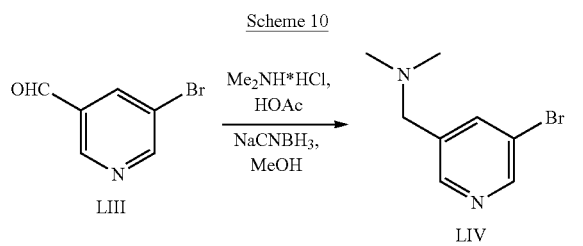

Steps 1

Preparation of 1-(5-bromopyridin-3-yl)-N,N-dimethylmethanamine (LIV) was performed following the procedure listed in Scheme 9, Step 1. Brown oil (1.20 g, 5.59 mmol, 45% yield). $^1$H NMR (DMSO-d$_6$, 500 MHz) δ ppm 2.15 (s, 6H), 3.43 (s, 2H), 7.94 (s, 1H), 8.47 (d, J=1.1 Hz, 1H), 8.59 (d, J=2.2 Hz, 1H); ESIMS found C$_8$H$_{11}$BrN$_2$ m/z 215 (M$^{Br79}$+H) and 217 (M$^{Br81}$+H).

Preparation of intermediate 3-bromo-5-((3,3-difluoropyrrolidin-1-yl)methyl)pyridine (LV) is depicted below in Scheme 11.

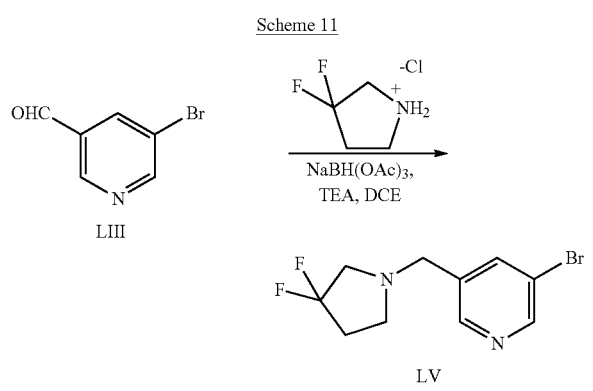

Steps 1

To a mixture of 5-bromopyridine-3-carbaldehyde (LIII) (6.00 g, 32.26 mmol, 1.0 eq), 3,3-difluoropyrrolidine (5.56 g, 38.71 mmol, 1.20 eq) and TEA (5.39 mL, 38.71 mmol, 1.2 Eq) in DCE (200 mL) was stirred at room temperature for 30 min, then added sodium triacetoxyborohydride (10.25 g, 48.38 mmol, 1.50 eq) in one portion at room temperature under N$_2$. The mixture was stirred at room temperature for 6 hours. TLC showed the reaction was complete. The reaction was quenched with 1N NaOH (100 mL), extracted with DCE (100 mL×2). The combined organic layers were washed with brine (100 mL), dried and concentrated. The residue was purified by silica gel chromatography (column height: 50 mm, diameter: 50 mm, 300-400 mesh silica gel, DCM/MeOH=30/1→20/1) to give 3-bromo-5-((3,3-difluoropyrrolidin-1-yl)methyl) pyridine (LV): Yellow oil (8.00 g, 28.9 mmol, 89.5% yield). $^1$H NMR (CDCl$_3$, 400 MHz) δ ppm 2.30 (spt, J=7.2 Hz. 2H), 2.75 (t, J=6.8 Hz, 2H), 2.91 (t, J=13.2 Hz, 2H), 7.85 (s, 1H), 8.45 (s, 1H), 8.59 (d, J=2 Hz, 1H); ESIMS found for C$_{10}$H$_{11}$BrF$_2$N$_2$ m/z 277.0 (M+H).

The following intermediates were prepared in accordance with the procedure described in the above Scheme 10 or Scheme 11.

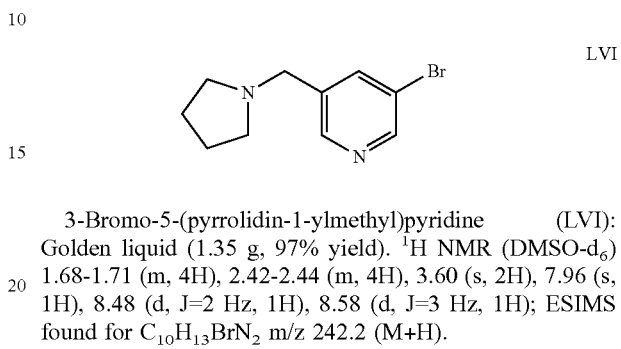

3-Bromo-5-(pyrrolidin-1-ylmethyl)pyridine (LVI): Golden liquid (1.35 g, 97% yield). $^1$H NMR (DMSO-d$_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for C$_{10}$H$_{13}$BrN$_2$ m/z 242.2 (M+H).

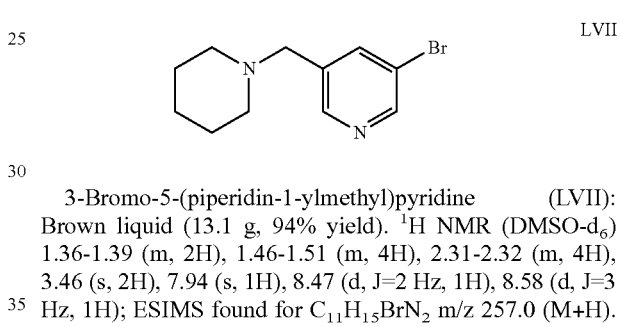

3-Bromo-5-(piperidin-1-ylmethyl)pyridine (LVII): Brown liquid (13.1 g, 94% yield). $^1$H NMR (DMSO-d$_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for C$_{11}$H$_{15}$BrN$_2$ m/z 257.0 (M+H).

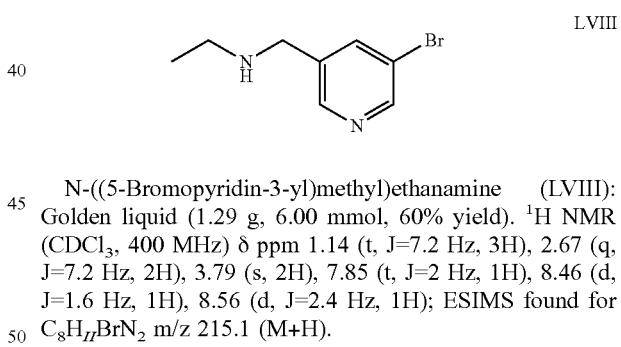

N-((5-Bromopyridin-3-yl)methyl)ethanamine (LVIII): Golden liquid (1.29 g, 6.00 mmol, 60% yield). $^1$H NMR (CDCl$_3$, 400 MHz) δ ppm 1.14 (t, J=7.2 Hz, 3H), 2.67 (q, J=7.2 Hz, 2H), 3.79 (s, 2H), 7.85 (t, J=2 Hz, 1H), 8.46 (d, J=1.6 Hz, 1H), 8.56 (d, J=2.4 Hz, 1H); ESIMS found for C$_8$H$_{11}$BrN$_2$ m/z 215.1 (M+H).

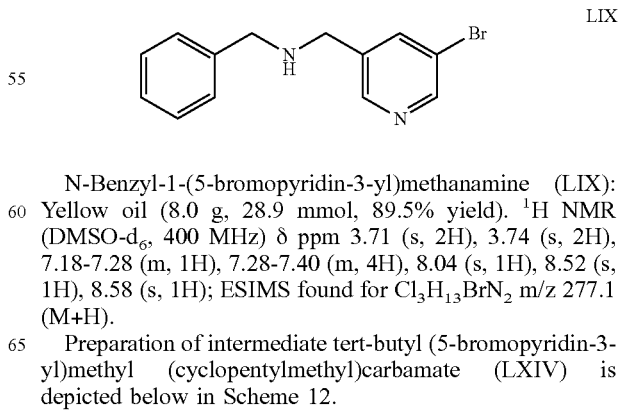

N-Benzyl-1-(5-bromopyridin-3-yl)methanamine (LIX): Yellow oil (8.0 g, 28.9 mmol, 89.5% yield). $^1$H NMR (DMSO-d$_6$, 400 MHz) δ ppm 3.71 (s, 2H), 3.74 (s, 2H), 7.18-7.28 (m, 1H), 7.28-7.40 (m, 4H), 8.04 (s, 1H), 8.52 (s, 1H), 8.58 (s, 1H); ESIMS found for C$_{13}$H$_{13}$BrN$_2$ m/z 277.1 (M+H).

Preparation of intermediate tert-butyl (5-bromopyridin-3-yl)methyl (cyclopentylmethyl)carbamate (LXIV) is depicted below in Scheme 12.

Scheme 12

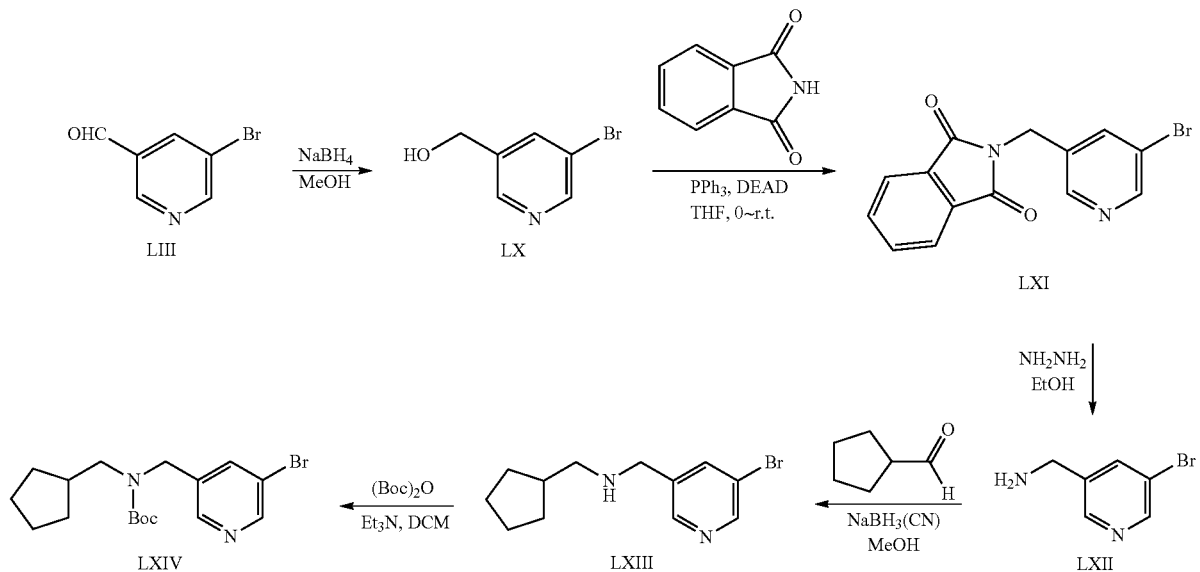

Step 1

To a solution of 5-bromonicotinaldehyde (LIII) (2.0 g, 10.8 mmol, 1 eq) in MeOH (20 mL) was added NaBH₄ (2.4 g, 64.9 mmol, 6 eq) and the reaction mixture was stirred at room temperature for 3 h. The mixture was concentrated in vacuo and the residue was diluted in water (15 mL), the aqueous phase was extracted with DCM (10 mL×3). The combined organic layers were dried over MgSO₄, filtered and concentrated in vacuo to afford (5-bromopyridin-3-yl) methanol (LX) (1.8 g, 9.57 mmol, 90.0% yield) as a colorless oil. $^1$H NMR (CDCl₃, 500 MHz) δ ppm 4.73 (s, 2H), 7.90 (s, 1H), 8.47 (s, 1H), 8.57 (s, 1H). ESIMS found for C₆H₆BrNO m/z 188.0 (M+H).

Step 2

To a stirred solution of (5-bromopyridin-3-yl)methanol (LX) (1.60 g, 8.5 mmol, 1 eq), phthalimide (1.24 g, 8.5 mmol, 1 eq) and PPh₃ (3.33 g, 12.75 mmol, 1.5 eq) in anhydrous THF (15 mL) was added DEAD (2.21 g, 12.75 mmol, 1.5 eq) dropwise at 0° C. under N₂. Then the reaction mixture was stirred at room temperature for 6 h. The mixture was washed with saturated NaHCO₃ solution (15 mL), water (15 mL) and brine (15 mL) subsequently. The organic layers were dried over MgSO₄, concentrated under reduced pressure, the resultant residue was purified by flash chromatography on silica gel (PE:EtOAc=4:1) to give 2-((5-bromopyridin-3-yl)methyl)isoindoline-1,3-dione (LXI) (2.5 g, 7.88 mmol, 82.3% yield) as a white solid. ESIMS found for C₁₄H₉BrN₂O₂ m/z 317.1 (M+H).

Step 3

A solution of 2-((5-bromopyridin-3-yl)methyl)isoindoline-1,3-dione (LXI) (1.9 g, 6.0 mmol, 1 eq) and hydrazine hydrate (2.0 g, 40 mmol, 6 eq) in EtOH (20 mL) was heated at 70° C. for 3 h. The mixture was filtered through a Celite® pad and the filtrate was concentrated in vacuo, the crude product was dissolved in 1N HCl solution (15 mL) and concentrated to dryness, then it was washed with acetone (10 mL×3), the precipitate was collected by filtration, dried in vacuo to give (5-bromopyridin-3-yl)methanamine (LXII) (1.3 g, 6.95 mmol, 97.7% yield) as a white solid. $^1$H NMR (D₂O, 500 MHz) δ ppm 4.34 (s, 2H), 8.56 (s, 1H), 8.75 (d, J=1.2 Hz, 1H), 8.91 (d, J=1.6 Hz, 1H). ESIMS found for C₆H₇BrN₂ m/z 187.0 (M+H).

Step 4

A solution of (5-bromopyridin-3-yl)methanamine (LXII) (1.30 g, 5.8 mmol, 1.0 eq), cyclopentanecarbaldehyde (0.57 g, 5.8 mmol, 1.0 eq) and TEA (0.60 g, 5.8 mmol, 1.0 eq) in MeOH (15 mL) was stirred at room temperature for 2 h. Then NaBH₃CN (1.98 g, 34.6 mmol, 6.0 eq) was added and the mixture was stirred at the same temperature for another 3 h. The solvent was removed under reduced pressure and the residue was diluted in water (20 mL) and extracted with DCM (10 mL×3), combined organic layers were dried over MgSO₄ and concentrated in vacuo to give 1-(5-bromopyridin-3-yl)-N-(cyclopentylmethyl)methanamine (LXIII) (1.23 g, 4.57 mmol, 79.3% yield) as a yellow oil. $^1$H NMR (CDCl₃, 400 MHz) δ ppm 1.07-1.23 (m, 2H), 1.47-1.67 (m, 4H), 1.70-1.84 (m, 2H), 2.02 (spt, J=7.6 Hz. 1H), 2.53 (d, J=7.2 Hz, 2H), 3.80 (s, 2H), 7.86 (s, 1H), 8.47 (s, 1H), 8.56 (d, J=2.0 Hz, 1H); ESIMS found for C₁₂H₁₇BrN₂ m/z 269.1 (M+H).

Step 5

To a solution of 1-(5-bromopyridin-3-yl)-N-(cyclopentylmethyl) methanamine (LXIII) (1.00 g, 3.7 mmol, 1 eq) and TEA (0.93 g, 9.2 mmol, 2.5 eq) in DCM (20 mL) was added portionwise (Boc)₂O (0.85 g, 4.0 mmol, 1.1 eq) at 0° C., the reaction mixture was stirred at room temperature for 1 h. The mixture was washed with water (10 mL), brine (10 mL), the organic layer was separated, dried over MgSO₄ and concentrated in vacuo to give tert-butyl (5-bromopyridin-3-yl) methyl (cyclopentylmethyl)carbamate (LXIV) (1.25 g, 3.38 mmol, 91.9% yield) as a white solid. ESIMS found for C₁₇H₂₅BrN₂O₂ m/z 369.1 (M+H).

Preparation of intermediate 3-bromo-5-(cyclohexyloxy) pyridine (LXVII) is depicted below in Scheme 13.

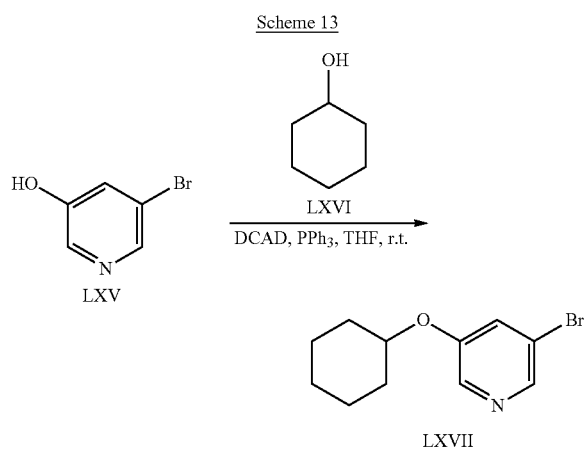

Step 1

To a solution of 5-bromopyridin-3-ol (LXV) (523 mg, 3.01 mmol) in THF (30 mL) cooled to 0° C. were added triphenylphosphine (867 mg, 3.31 mmol) and cyclohexanol (LXVI) (331 mg, 3.31 mmol) followed by (E)-bis(4-chlorobenzyl) diazene-1,2-dicarboxylate (1.21 g, 3.31 mmol), added portionwise. The reaction mixture was then stirred at 25° C. overnight. The reaction was worked-up with a EtOAc-NaHCO$_3$ extraction and the solid filtered off. The solvent was removed and the residue was purified by Isco (20% EtOAc-Hexanes) to give 3-bromo-5-(cyclohexyloxy) pyridine (LXVII) (209 mg, 0.82 mmol, 27.2% yield) as a yellow oil. $^1$H NMR (DMSO-d$_6$, 500 MHz) δ ppm 1.21-1.31 (m, 1H) 1.34-1.48 (m, 4H) 1.49-1.57 (m, 1H) 1.70 (br dd, J=9.74, 4.25 Hz, 2H) 1.88-1.96 (m, 2H) 2.50 (dt, J=3.70, 1.72 Hz, 5H) 4.46-4.54 (m, 1H) 7.72 (t, J=2.20 Hz, 1H) 8.24 (d, J=1.92 Hz, 1H) 8.27 (d, J=2.47 Hz, 1H).

The following intermediate was prepared in accordance with the procedure described in the above Scheme 13.

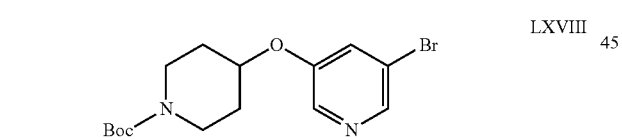

tert-Butyl 4-((5-bromopyridin-3-yl)oxy)piperidine-1-carboxylate (LXVIII): Yellow oil (244 mg, 0.683 mmol, 23.2% yield). ESIMS found for C$_{15}$H$_{21}$BrN$_2$O$_3$ m/z 358.3 (M+H).

Preparation of intermediate 3-(benzyloxy)-5-bromopyridine (LXX) is depicted below in Scheme 14.

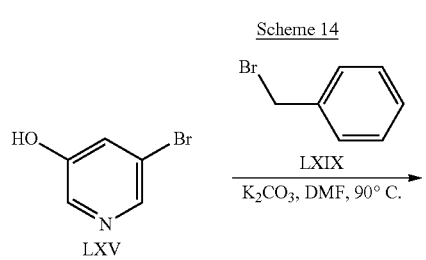

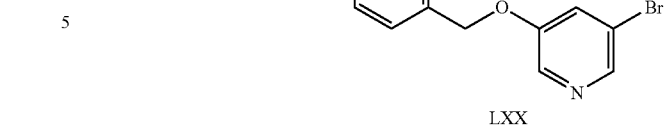

Step 1

To a solution of 5-bromopyridin-3-ol (LXV) (174 mg, 1.0 mmol) in DMF (3 mL) was added potassium carbonate (415 mg, 3.0 mmol). The slurry was heated at 90° C. for 1 hour and then cooled to 25° C. The (bromomethyl)benzene (LXIX) (171 mg, 1.0 mmol) was added and the mixture was stirred at 25° C. overnight. The reaction was worked-up using a saturated sodium bicarbonate and ethyl acetate extraction. The product was purified by ISCO column eluted with 40-100% EtOAc-Hexanes. The 3-(benzyloxy)-5-bromopyridine (LXX) (105 mg, 0.398 mmol, 39.8% yield) was obtained as yellow oil. MS: 266.1. ESIMS found for C$_{12}$H$_{10}$BrNO m/z 266.1 (M+H).

The following intermediates were prepared in accordance with the procedure described in the above Scheme 14.

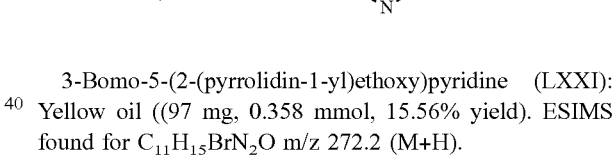

3-Bomo-5-(2-(pyrrolidin-1-yl)ethoxy)pyridine (LXXI): Yellow oil ((97 mg, 0.358 mmol, 15.56% yield). ESIMS found for C$_{11}$H$_{15}$BrN$_2$O m/z 272.2 (M+H).

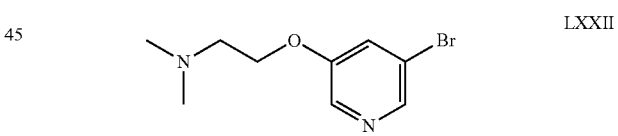

2-((5-bromopyridin-3-yl)oxy)-N,N-dimethylethan-1-amine (LXXII): Yellow oil (97 mg, 0.396 mmol, 28.9% yield). ESIMS found for C$_9$H$_{13}$BrN$_2$O m/z 245.1 (M+H).

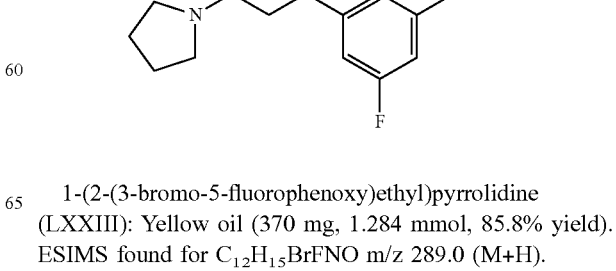

1-(2-(3-bromo-5-fluorophenoxy)ethyl)pyrrolidine (LXXIII): Yellow oil (370 mg, 1.284 mmol, 85.8% yield). ESIMS found for C$_{12}$H$_{15}$BrFNO m/z 289.0 (M+H).

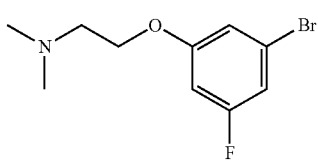

2-(3-bromo-5-fluorophenoxy)-N,N-dimethylethan-1-amine (LXXIV): Yellow oil (364 mg, 1.389 mmol, 50.2% yield). ESIMS found for $C_{10}H_{13}BrFNO$ m/z 263.9 (M+H).

Preparation of intermediate tert-butyl 4-(2-((5-bromopyridin-3-yl)amino)-2-oxoethyl)piperidine-1-carboxylate (LXXVI) is depicted below in Scheme 15.

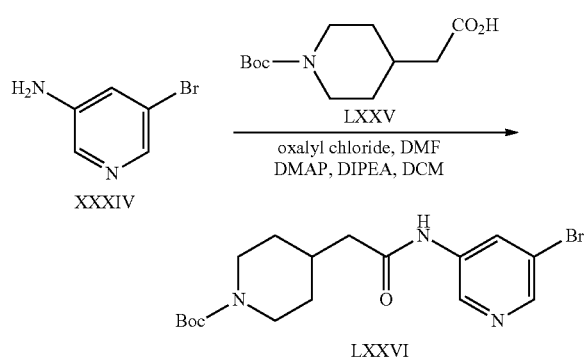

Step 1

To a solution of 2-(1-(tert-butoxycarbonyl)piperidin-4-yl)acetic acid (LXXV) (3.4 g, 13.97 mmol) in DCM (10 mL) was added DMF (1 mL). The solution was cooled in ice-water to 0° C. Oxalyl chloride (1.835 mL, 20.96 mmol) was then added dropwise. The mixture was stirred for one hour at 25° C. The organic volatile was then removed under vacuum. The residue was dissolved in DCM (10 mL). DMAP (0.171 g, 1.397 mmol) and 5-bromopyridin-3-amine (XXXIV) (2.418 g, 13.97 mmol) were added to the solution and cooled to 0° C. DIEA (4.88 ml, 27.9 mmol) was then added dropwise and the mixture was stirred for 2 hours at 25° C. The reaction was worked-up with DCM and saturated NaHCO3. The product was purified by ISCO eluted with 0-100% EtOAc-Hexanes. The tert-butyl 4-(2-((5-bromopyridin-3-yl)amino)-2-oxoethyl)piperidine-1-carboxylate (LXXVI) (2.82 g, 7.08 mmol, 50.7% yield) was obtained as yellow oil. ESIMS found for $C_{17}H_{24}BrN_3O_3$ m/z 343.1 (M-56).

The following intermediate was prepared in accordance with the procedure described in the above Scheme 15.

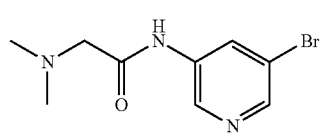

N-(5-Bromopyridin-3-yl)-2-(dimethylamino)acetamide (LXXVII): Yellow oil (528 mg, 2.05 mmol, 19.0% yield). ESIMS found for $C_9H_{12}BrN_3O$ m/z 259.3 (M+H).

Preparation of tert-butyl (1-(6-chloropyrazin-2-yl)azetidin-3-yl)carbamate (LXXX) is depicted below in Scheme 16.

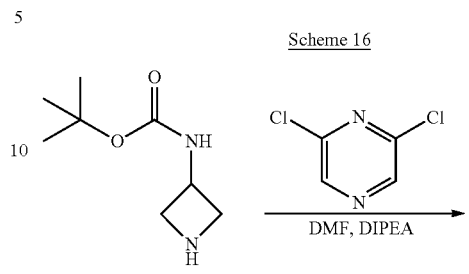

Step 1

To a solution of tert-butyl azetidin-3-ylcarbamate hydrochloride (LXXVIII) (2 g, 9.58 mmol) in dry DMF (19.2 mL) was added DIPEA (8.37 ml, 47.9 mmol). To this mixture was added 2,6-dichloropyrazine (LXXIX) (1.428 g, 9.58 mmol) and the reaction was stirred at 95° C. for 3 hours. The reaction was quenched with water (20 mL) and extracted with EtOAc. The organic layer was dried over anhydrous $Na_2SO_4$, filtered and concentrated. The residue was purified by silica gel column chromatography (40 g) (100% hexanes→hexanes:EtOAc 1:1) to yield tert-butyl (1-(6-chloropyrazin-2-yl)azetidin-3-yl)carbamate (LXXX) (2.2882 g, 8.04 mmol, 84% yield) as a white solid. ESIMS found for $C_{12}H_{17}ClN_4O_2$ m/z 285.1 (M+H).

Preparation of intermediate 2-(3-fluorophenyl)pyridine-3,4-diamine (LXXXIV) is depicted below in Scheme 17.

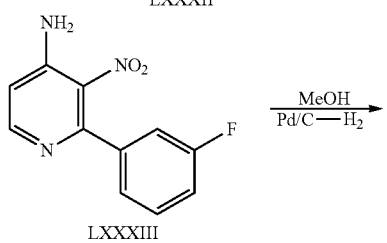

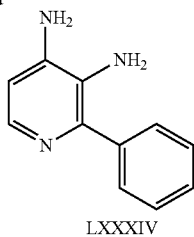

LXXXIV

Step 1

A solution of 2-chloro-3-nitropyridin-4-amine (LXXXI) (2.0 g, 11.5 mmol, 1.0 eq), (3-fluorophenyl)boronic acid (LXXXII) (1.93 g, 13.8 mmol, 1.2 eq), Pd(PPh$_3$)$_4$ (0.40 g, 0.34 mmol, 0.03 eq), Na$_2$CO$_3$ (2.44 g, 23.05 mmol, 2.0 eq) in a mixed solvent of toluene (20 mL), H$_2$O (10 mL) and EtOH (4 mL) was stirred at 75° C. for 15 h under nitrogen atmosphere. Then the reaction mixture was washed with brine (30 mL) and dried over anhydrous Na$_2$SO$_4$, filtered and concentrated in vacuo, the resultant residue was purified by chromatography on silica gel (PE:EtOAc=1:1) to afford 2-(3-fluorophenyl)-3-nitropyridin-4-amine (LXXXIII) (1.91 g, 8.2 mmol, 71.2% yield) as a yellow solid. ESIMS found for C$_{11}$H$_8$FN$_3$O$_2$ m/z 234.2 (M+H).

Step 2

To a solution of 2-(3-fluorophenyl)-3-nitropyridin-4-amine (LXXXIII) (1.91 g, 8.19 mmol, 1.0 eq) in MeOH (100 mL) was added Pd/C (0.8 g) under nitrogen atmosphere. The mixture was stirred under 50 psi of H$_2$ for 6 h at room temperature. The mixture was then filtered and concentrated in vacuo to afford 2-(3-fluorophenyl)pyridine-3,4-diamine (LXXXIV) as a black solid (1.52 g, 7.48 mmol, 91.3% yield). $^1$H NMR (DMSO-d$_6$, 400 MHz) δ ppm 4.30 (s, 2H), 5.55 (s, 2H), 6.44 (d, J=4.8 Hz, 1H), 7.07-7.19 (m, 1H), 7.33 (dd, J=4.4 Hz, J=2 Hz, 1H), 7.38-7.49 (m, 2H), 7.57 (d, J=4.8 Hz, 1H); ESIMS found C$_{11}$H$_{10}$FN$_3$ m/z 204.0 (M+H).

The following intermediates were prepared in accordance with the procedure described in the above Scheme 17.

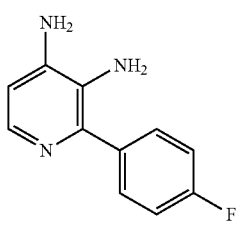

LXXXV 2-(4-Fluorophenyl)pyridine-3,4-diamine (LXXXV): White Solid (1.56 g, 7.67 mmol, 92.0% yield). $^1$H NMR (CDCl$_3$, 400 MHz) 3.38 (brs, 2H), 4.02 (brs, 2H), 6.57 (d, J=4.8 Hz, 1H), 7.15 (t, J=4.8 Hz, 2H), 7.59 (dd, J=8.4 Hz, J=5.6 Hz, 2H), 7.94 (d, J=5.2 Hz, 1H); ESIMS found for C$_{11}$H$_{10}$FN$_3$ m/z 204.0 (M+H).

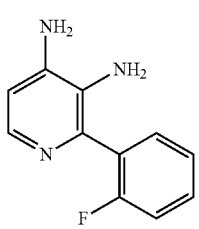

LXXXVI 2-(2-Fluorophenyl)pyridine-3,4-diamine (LXXXVI): Yellow Solid (1.45 g, 7.14 mmol, 89.2% yield). $^1$H NMR (CDCl$_3$, 400 MHz) 3.23 (brs, 2H), 4.12 (brs, 2H), 6.62 (d, J=4.89 Hz, 1H), 7.19 (t, J=9.03 Hz, 1H), 7.24-7.33 (m, 1H), 7.42 (d, J=6.02 Hz, 1H), 7.45-7.61 (m, 1H), 8.00 (d, J=4.89 Hz, 1H); ESIMS found for C$_{11}$H$_{10}$FN$_3$ m/z 204.0 (M+H).

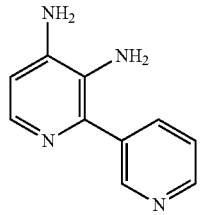

LXXXVII

[2,3'-Bipyridine]-3,4-diamine (LXXXVII): Black Solid (1.19 g, 6.39 mmol, 86.4% yield). ESIMS found for C$_{10}$H$_{10}$N$_4$ m/z 187.1 (M+H).

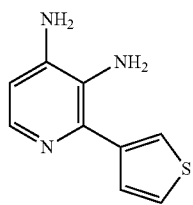

LXXXVIII 2-(Thiophen-3-yl)pyridine-3,4-diamine (LXXXVIII): Yellow oil (1.12 g, 5.86 mmol, 96.7% yield). $^1$H NMR (CDCl$_3$, 400 MHz) 3.53 (brs, 2H), 3.99 (brs, 2H), 6.55 (d, J=5.14 Hz, 1H), 7.40-7.49 (m, 2H), 7.56-7.62 (m, 1H), 7.93 (d, J=5.14 Hz, 1H); ESIMS found for C$_9$H$_9$N$_3$S m/z 192.0 (M+H).

LXXXIX 2-(Furan-3-yl)pyridine-3,4-diamine (LXXXIX): Yellow oil (1.32 g, 7.53 mmol, 95.2% yield). ESIMS found for C$_9$H$_9$N$_3$O m/z 176.0 (M+H).

XC 2-(Thiophen-2-yl)pyridine-3,4-diamine (XC): Yellow oil (1.04 g, 5.44 mmol, 98.3% yield). $^1$H NMR (CDCl$_3$, 400

MHz) 3.22 (brs, 2H), 4.11 (brs, 2H), 6.61 (d, J=4.8 Hz, 1H), 7.18 (t, J=9.0 Hz, 1H), 7.50 (d, J=6.8 Hz, 1H), 7.44-7.58 (m, 1H), 7.99 (d, J=4.8 Hz, 1H); ESIMS found for $C_9H_9N_3S$ m/z 192.0 (M+H).

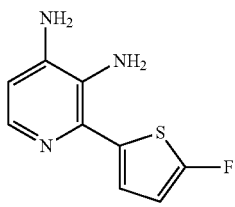

XCI 2-(5-Fluorothiophen-2-yl)pyridine-3,4-diamine (XCI): Yellow oil (1.2 g, 5.74 mmol, 91.5% yield). ESIMS found for $C_9H_8FN_3S$ m/z 210.1 (M+H).

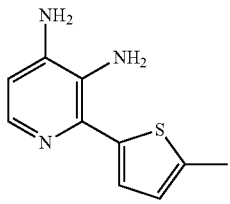

XCII 2-(5-Methylthiophen-2-yl)pyridine-3,4-diamine (XCII): Yellow oil (1.20 g, 5.85 mmol, 86.0% yield). $^1$H NMR (CD$_3$OD, 400 MHz) 2.55 (s, 3H), 6.62 (d, J=6 Hz, 1H), 6.87 (d, J=1.2 Hz, 1H), 7.23 (d, J=3.2 Hz, 1H), 7.63 (d, J=5.6 Hz, 1H); ESIMS found for $C_{10}H_{11}N_3S$ m/z 206.0 (M+H).

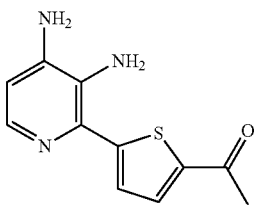

XCIII 1-(5-(3,4-Diaminopyridin-2-yl)thiophen-2-yl)ethan-1-one (XCIII): Yellow oil (1.20 g, 5.85 mmol, 86.0% yield). $^1$H NMR (DMSO-d$_6$, 400 MHz) 2.52 (s, 3H), 4.84 (s, 2H), 5.83 (s, 2H), 6.46 (d, J=4.8 Hz, 1H), 7.57 (d, J=4.8 Hz, 1H), 7.66 (d, J=4 Hz, 1H), 7.88 (d, J=4 Hz, 1H); ESIMS found for $C_{11}H_{11}N_3OS$ m/z 234.0 (M+H).

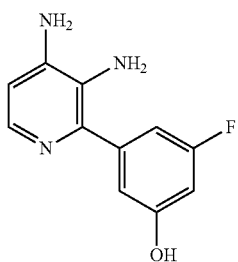

XCIV 3-(3,4-Diaminopyridin-2-yl)-5-fluorophenol (XCIV): White solid (320 mg, 1.46 mmol, 84.6% yield). ESIMS found for $C_{11}H_{10}FN_3O$ m/z 220.1 (M+H).

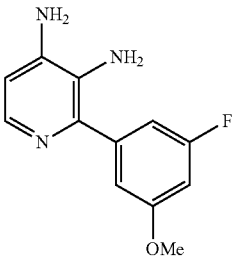

XCV 2-(3-Fluoro-5-methoxyphenyl)pyridine-3,4-diamine (XCV): White solid (501 mg, 2.148 mmol, 93.1% yield). ESIMS found for $C_{12}H_{12}FN_3O$ m/z 234.1 (M+H).

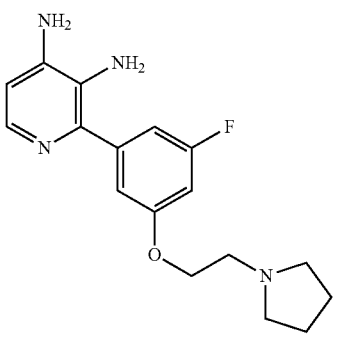

XCVI 2-(3-Fluoro-5-(2-(pyrrolidin-1-yl)ethoxy)phenyl)pyridine-3,4-diamine (XCVI): Black oil (167 mg, 0.528 mmol, 80.9% yield). ESIMS found for $C_{17}H_{21}FN_4O$ m/z 317.1 (M+H).

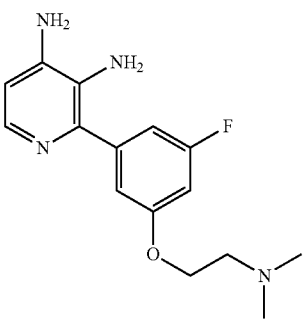

XCVII 2-(3-(2-(Dimethylamino)ethoxy)-5-fluorophenyl)pyridine-3,4-diamine (XCVII): Black oil (88 mg, 0.303 mmol, 20.83% yield). $^1$H NMR (DMSO-d$_6$, 400 MHz); ESIMS found for $C_{15}H_{19}FN_4O$ m/z 291.1 (M+H).

Preparation of intermediate [2,4'-bipyridine]-3,4-diamine (C) is depicted below in Scheme 18.

Scheme 18

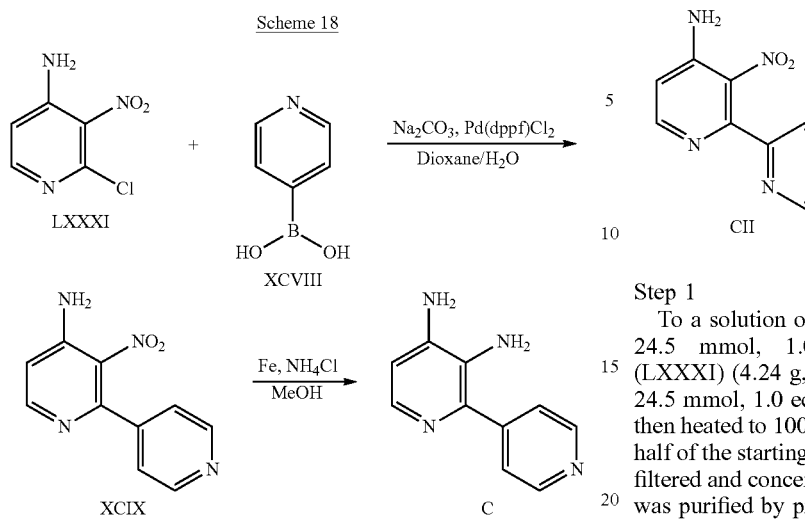

Step 1

To a solution of pyridin-4-ylboronic acid (XCVIII) (2.00 g, 16.3 mmol), 2-chloro-3-nitropyridin-4-amine (LXXXI) (2.35 g, 13.6 mmol), Na$_2$CO$_3$ (5.03 g, 47.5 mmol) and Pd(dppf)Cl$_2$ (502.87 mg, 677.92 µmol) in dioxane (40 mL) and H$_2$O (8 mL) was de-gassed and then heated to 80° C. overnight under N$_2$. TLC (100% EtOAc) showed the starting material was consumed completely. The reaction mixture was poured into H$_2$O (300 mL). The mixture was extracted with EtOAc (3×250 mL). The organic phase was washed with brine (300 mL), dried over anhydrous MgSO$_4$, concentrated in vacuum to give a residue, which was purified by silica gel column chromatography (DCM/MeOH=20/1) to afford 3-nitro-[2,4'-bipyridin]-4-amine (XCIX) (1.60 g, 7.4 mmol, 54.6% yield) as yellow solid. ESIMS found for C$_{10}$H$_8$N$_4$O$_2$ m/z 217.1 (M+H).

Step 2

To a solution of 3-nitro-[2,4'-bipyridin]-4-amine (XCIX) (1.60 g, 7.4 mmol) in MeOH (30 mL), was added Fe (1.65 g, 29.6 mmol) and NH$_4$Cl (3.10 g, 59.2 mmol) in one portion at rt. The mixture was stirred at rt. for 10 min. Then heated to 80° C. and stirred for 16 hours. TLC showed the reaction was completed. The mixture was cooled to rt. and concentrated in reduced pressure at 60° C. The combined organic phase was washed with saturated brine (100 mL×2), dried over anhydrous Na$_2$SO$_4$, filtered and concentrated in vacuo. The to give crude [2,4'-bipyridine]-3,4-diamine (C) (1.20 g, 6.44 mmol, 87.1% yield) as a yellow solid. $^1$H NMR (DMSO-d$_6$, 400 MHz) 4.52 (s, 2H), 5.69 (s, 2H), 6.50 (d, J=4.8 Hz, 1H), 7.62 (d, J=6 Hz, 2H), 7.63 (d, J=4.8 Hz, 1H), 8.61 (d, J=6 Hz, 2H); ESIMS found for C$_{10}$H$_{10}$N$_4$ m/z 187.0 (M+H).

Preparation of intermediate [2,2'-bipyridine]-3,4-diamine (CIII) is depicted below in Scheme 19.

Scheme 19

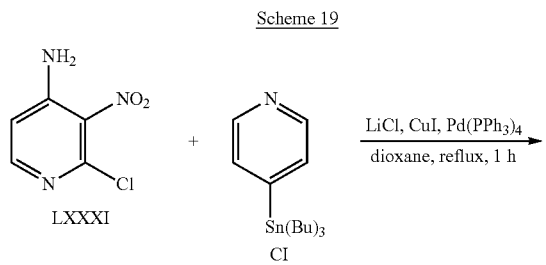

Step 1

To a solution of 2-(tributylstannyl)pyridine (CI) (9.00 g, 24.5 mmol, 1.0 eq), 2-chloro-3-nitropyridin-4-amine (LXXXI) (4.24 g, 24.5 mmol, 1.0 eq), Pd(PPh$_3$)$_4$ (28.25 g, 24.5 mmol, 1.0 eq) in dioxane (40 mL) was de-gassed and then heated to 100° C. for 1 h under N$_2$. LC/MS showed that half of the starting material was consumed. The mixture was filtered and concentrated in vacuum to give a residue, which was purified by prep-HPLC (Base) to afford the 3-nitro-[2,2'-bipyridin]-4-amine (CII) (0.70 g, 3.24 mmol, 13.2% yield) as a light yellow oil. ESIMS found for C$_{10}$H$_8$N$_4$O$_2$ m/z 217.1 (M+H).

Step 2

To a solution of 3-nitro-[2,2'-bipyridin]-4-amine (CII) (700 mg, 3.24 mmol, 1.0 eq) in MeOH (15 mL) was added Pd/C (200 mg, 3.24 mmol, 1.0 eq). The mixture was stirred at 25° C. for 4 h. LC/MS showed that the starting material was completely consumed. The mixture was filtered and concentrated to give [2,2'-bipyridine]-3,4-diamine (CIII) (450.0 mg, 2.42 mmol, 74.6% yield) as a light brown solid. $^1$H NMR (DMSO-d$_6$, 400 MHz) 5.73 (brs, 2H), 6.52 (d, J=4.8 Hz, 1H), 6.76 (brs, 2H), 7.31 (dt, J=5.6 Hz, J=1.2 Hz, 1H), 7.52-7.58 (m, 1H), 7.82 (dt, J=8 Hz, J=1.2 Hz, 1H), 8.44 (d, J=8 Hz, 1H), 8.60 (d, J=6 Hz, 1H); ESIMS found for C$_{10}$H$_{10}$N$_4$ m/z 187.1 (M+H).

Preparation of intermediate 2-(piperidin-1-yl)pyridine-3,4-diamine (CV) is depicted below in Scheme 20.

Scheme 20

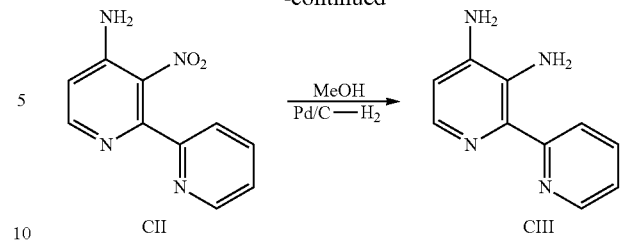

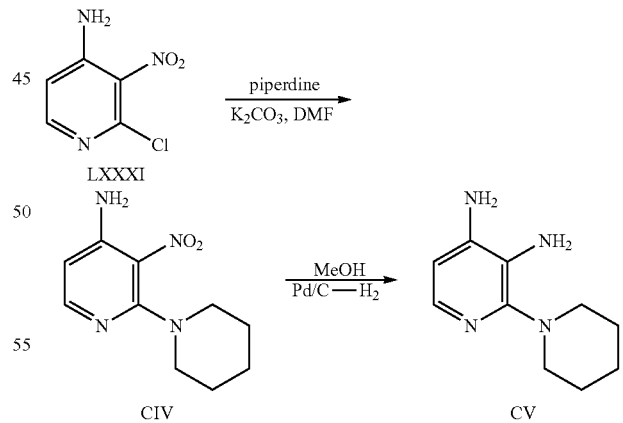

Step 1

To a solution of 2-chloro-3-nitropyridin-4-amine (LXXXI) (4.00 g, 23.5 mmol, 1.0 eq) and piperidine (5.89 g, 69.1 mmol, 3.0 eq) in DMF (60 mL) was added K$_2$CO$_3$ (9.56 g, 69.1 mmol, 3.0 eq) in one portion and the mixture was stirred at 120° C. under nitrogen overnight. The reaction mixture was diluted with EtOAc (30 mL) and washed with aqueous saturated NaHCO$_3$ solution (80 mL). The organic phases were dried over Na$_2$SO$_4$ and concentrated in vacuo, the resultant residue was purified by silica gel column chromatography (PE:EtOAc=5:1→1:1) to give 3-nitro-2-(piperidin-1-yl)pyridin-4-amine (CIV) (3.87 g, 5.42 mmol, 75.6% yield) as a black oil. ESIMS found for C$_{10}$H$_{14}$N$_4$O$_2$ m/z 223.1 (M+H).

Step 2

A mixture of 3-nitro-2-(piperidin-1-yl)pyridin-4-amine (CIV) (3.87 g, 5.42 mmol, 1.0 eq) and Pd/C (0.80 g) in MeOH (20 mL) was stirred at room temperature under 50 psi H$_2$ overnight. After the starting material was consumed completely, the mixture was filtered through a Celite pad and the filtrate was concentrated in vacuo to give the 2-(piperidin-1-yl)pyridine-3,4-diamine (CV) (2.63 g, 13.7 mmol, 78.5% yield) as a black solid. ESIMS found C$_{10}$H$_{16}$N$_4$ m/z 193.0 (M+H).

The following intermediates were prepared in accordance with the procedure described in the above Scheme 20.

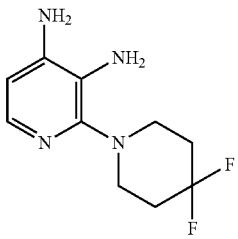

CVI 2-(4,4-Difluoropiperidin-1-yl)pyridine-3,4-diamine (CVI): Black Solid (1.9 g, 8.32 mol, 97.7% yield). ESIMS found for C$_{10}$H$_{14}$F$_2$N$_4$ m/z 229.1 (M+H).

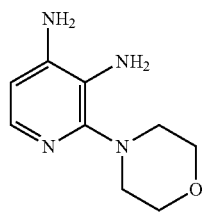

CVII

2-Morpholinopyridine-3,4-diamine (CVII): Black Solid (1.4 g, 7.21 mol, 89.8% yield). ESIMS found for C$_9$H$_{14}$N$_4$O m/z 195.1 (M+H).

Preparation of intermediate 2-(4-methyl-1H-imidazol-1-yl)pyridine-3,4-diamine (CXI) is depicted below in Scheme 21.

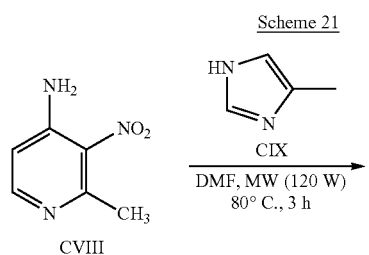

Scheme 21

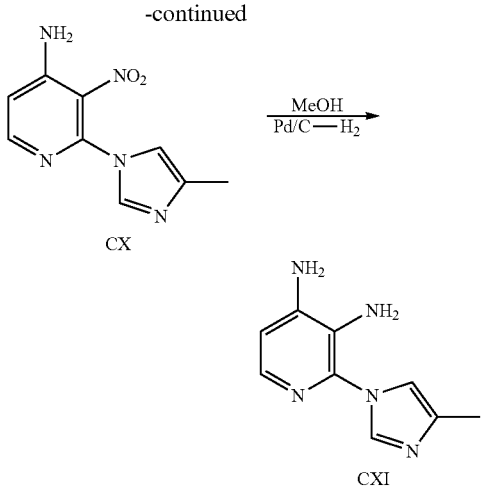

CX

CXI

Step 1

A solution of 2-methyl-3-nitropyridin-4-amine (CVIII) (1.00 g, 5.76 mmol, 1.0 eq), 4-methyl-1H-imidazole (CIX) (0.94 g, 11.5 mmol, 2.0 eq) in DMF (10 mL) was stirred at 80° C. for 3 h under microwave irradiation. The reaction was then quenched by water (15 mL). The mixture was extracted with EtOAc (20 mL×3), the organic layer were combined, washed with brine (20 mL), dried over anhydrous Na$_2$SO$_4$, filtered and concentrated in vacuo, the resultant residue was purified by chromatography on silica gel (PE:EtOAc=5:1→3:1) to afford 2-(4-methyl-1H-imidazol-1-yl)-3-nitropyridin-4-amine (CX) (700 mg, 3.19 mmol, 56.1% yield) as a yellow solid. $^1$H NMR (DMSO-d$_6$, 400 MHz) δ ppm 2.13 (s, 3H), 6.88 (d, J=6 Hz, 1H), 7.03 (s, 1H), 7.54 (brs, 2H), 7.82 (s, 1H), 8.01 (d, J=5.6 Hz, 1H); ESIMS found for C$_9$H$_9$N$_5$O$_2$ m/z 220.1 (M+H).

Step 2

To a solution of 2-(4-methyl-1H-imidazol-1-yl)-3-nitropyridin-4-amine (CX) (700 mg, 3.19 mmol, 1.0 eq) in MeOH (20 mL) was added Pd/C (0.3 g) under a nitrogen atmosphere. The mixture was stirred under 50 psi of H$_2$ for 12 h at room temperature. The mixture was the filtered and concentrated in vacuo to afford 2-(4-methyl-1H-imidazol-1-yl)pyridine-3,4-diamine (CXI) (500 mg, 2.64 mmol, 82.7% yield) as a white solid. $^1$H NMR (DMSO-d$_6$, 400 MHz) 2.17 (s, 3H), 4.36 (brs, 2H), 5.86 (brs, 2H), 6.51 (d, J=5.2 Hz, 1H), 7.14 (s, 1H), 7.43 (d, J=5.2 Hz, 1H), 7.77 (s, 1H); ESIMS found C$_9$H$_{11}$N$_5$ m/z 190.1 (M+H).

Preparation of intermediate 2-(4-methylpiperazin-1-yl)pyridine-3,4-diamine (CXIV) is depicted below in Scheme 22.

Scheme 22

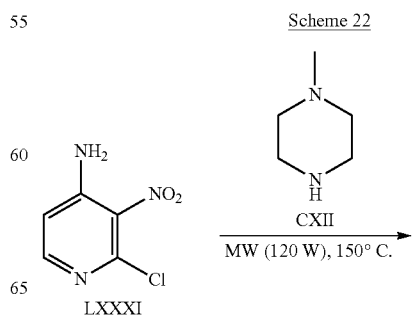

LXXXI

-continued

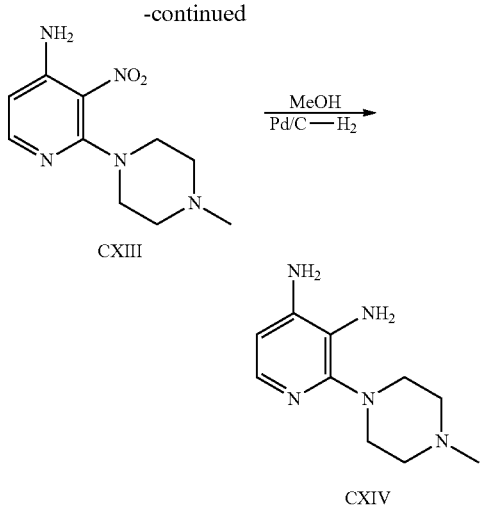

CXIII

CXIV

Step 1
A mixture of 1-methylpiperazine (CXII) (20 mL) and 2-chloro-3-nitropyridin-4-amine (LXXXI) (4.0 g, 23.1 mmol, 1.0 eq) was stirred at 50° C. for 1 h under microwave irradiation. The reaction mixture was diluted with water (100 mL) and filtered, the cake was washed with water (30 mL×3), dried in vacuo to give 2-(4-methylpiperazin-1-yl)-3-nitropyridin-4-amine (CXIII) (4.0 g, 16.9 mmol, 73.2% yield) as a yellow solid. ESIMS found for $C_{10}H_{15}N_5O_2$ m/z 238.1 (M+H).

Step 2
A mixture of 2-(4-methylpiperazin-1-yl)-3-nitropyridin-4-amine (CXIII) (4.0 g, 16.9 mmol, 1.0 eq) and Pd/C (0.5 g) in MeOH (200 mL) was stirred under 50 psi of $H_2$ at room temperature overnight. The reaction was monitored by TLC. The mixture was filtered and the filtrate was concentrated in vacuo to give 2-(4-methylpiperazin-1-yl)pyridine-3,4-diamine (CXIV) (3.13 g, 89.6% yield) as a black solid. $^1$H NMR (DMSO-$d_6$, 400 MHz) 2.74 (s, 4H), 3.12 (s, 3H), 3.44 (brs, 4H), 5.19 (brs, 4H), 6.60 (d, J=6.4 Hz, 2H); ESIMS found $C_{10}H_{17}N_5$ m/z 208.1 (M+H).

Preparation of intermediate N-(3-(3,4-diaminopyridin-2-yl)-5-fluorobenzyl)methanesulfonamide (CXX) is depicted below in Scheme 23.

Scheme 23

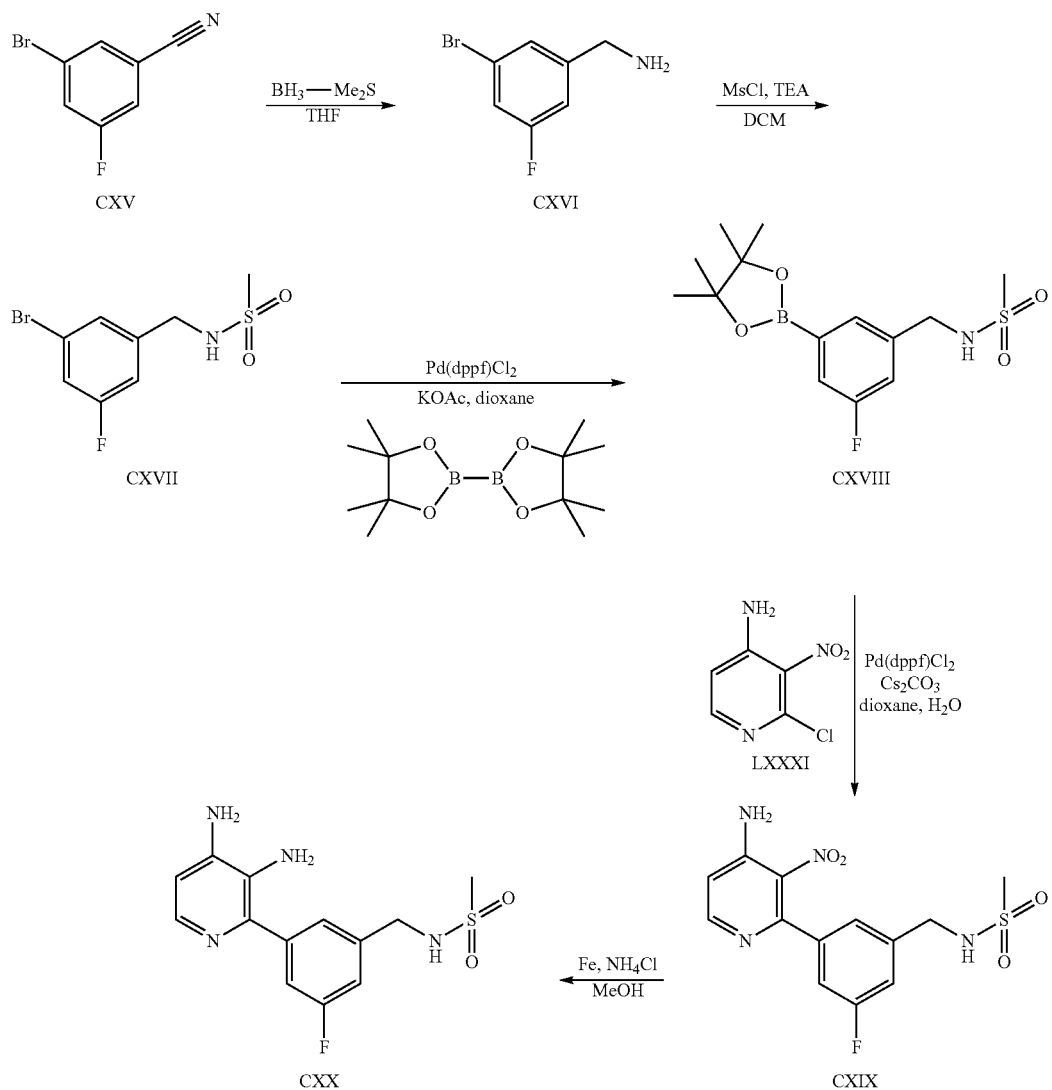

Step 1

A solution of 3-bromo-5-fluorobenzonitrile (CXV) (44.0 g, 220.0 mmol, 1.0 eq) was dissolved in THF (30 mL). $BH_3$-$Me_2S$ (33.43 g, 440.0 mmol, 2.0 eq) was added to the solution at 20° C. Then it was stirred at 80° C. for 2 h, HCl (6 N, 100 mL) was added to the mixture slowly at 20° C. The mixture was stirred at 80° C. for 1 h, then it was washed with EtOAc (300 ml). The water phase was basified with 50% aqueous NaOH and it was extracted with EtOAc (300 mL×3). The combined organic layers were dried over anhydrous $Na_2SO_4$ and concentrated in vacuo to produce (3-bromo-5-fluoro-phenyl)methanamine (CXVI) (24.0 g, 117.62 mmol, 53.5% yield). $^1H$ NMR ($CDCl_3$, 300 MHz) 3.86 (s, 2H), 7.01 (d, J=8 Hz, 1H), 7.12 (d, J=8 Hz, 1H), 7.28 (s, 1H); ESIMS found $C_7H_7BrFN$ m/z 203.9 ($Br^{79}$M+H).

Step 2

A solution of (3-bromo-5-fluoro-phenyl)methanamine (CXVI) (23.0 g, 112.7 mmol, 1.0 eq) was dissolved in DCM (15 mL), TEA (34.22 g, 338.2 mmol, 3.0 eq) was added to the mixture. Then MsCl (13.44 g, 117.3 mmol, 1.04 eq) was added slowly to the solution at 0° C. It was stirred at 0-30° C. for 2 h. The reaction was washed with water and extracted with EtOAc. The combined organic layers were dried over anhydrous $Na_2SO_4$ and concentrated to give N-(3-bromo-5-fluorobenzyl)methanesulfonamide (CXVII) (34.0 g, 102.44 mmol, 90.9% yield, 85% purity) as an oil. $^1H$ NMR ($CDCl_3$, 300 MHz) 2.88 (s, 3H), 4.24 (d, J=4.5 Hz, 2H), 6.99 (d, J=9 Hz, 1H), 7.13 (dt, J=8.1 Hz, J=2 Hz, 1H), 7.25 (s, 1H); ESIMS found $C_8H_9BrFNO_2S$ m/z 282.0 ($Br^{79}$M+H).

Step 3

A solution of N-(3-bromo-5-fluorobenzyl)methanesulfonamide (CXVII) (34.0 g, 102.4 mmol, 1.0 eq) and 4,4,5,5-tetramethyl-2-(4,4,5,5-tetramethyl-1,3,2-dioxaborolan-2-yl)-1,3,2-dioxaborolane (52.02 g, 204.9 mmol, 2.0 eq), KOAc (20.11 g, 204.9 mmol, 2.0 eq) was dissolved in dioxane (20 mL). Then Pd(dppf)$Cl_2$ (7.60 g, 10.2 mmol, 0.1 eq) was added to the mixture. It was stirred at 90° C. for 2 h. Then the solvent was removed to get the residue which was purified by silica gel column (PE:EtOAc=10:1→100% EtOAc) to get N-(3-fluoro-5-(4,4,5,5-tetramethyl-1,3,2-dioxaborolan-2-yl)benzyl)methanesulfonamide (CXVIII) (30.0 g, crude). $^1H$ NMR ($CDCl_3$, 400 MHz) 1.37 (s, 12H), 2.92 (s, 3H), 4.34 (d, J=6.3 Hz, 2H), 7.19 (dt, J=9.3 Hz, J=2.1 Hz, 1H), 7.44 (dd, J=8.7 Hz, J=2.4 Hz, 1H), 7.54 (s, 1H); ESIMS found $C_{14}H_{21}BFNO_4S$ m/z 330.1 (M+H).

Step 4

A solution of N-(3-fluoro-5-(4,4,5,5-tetramethyl-1,3,2-dioxaborolan-2-yl) benzyl)methanesulfonamide (CXVIII) (5.00 g, 15.19 mmol, 1.0 eq) and 2-chloro-3-nitropyridin-4-amine (LXXXI) (2.64 g, 15.19 mmol, 1.0 eq), $Cs_2CO_3$ (9.90 g, 30.4 mmol, 2.0 eq) was dissolved in dioxane (40 mL) and water (8 mL). Then Pd(dppf)$Cl_2$ (1.13 g, 1.52 mmol, 0.1 eq) was added to the mixture. The mixture was stirred at 100° C. for 10 h under $N_2$. The solvent was removed to get the residue which was purified by silica column to get N-(3-(4-amino-3-nitropyridin-2-yl)-5-fluorobenzyl)methanesulfonamide (CXIX) (3.00 g, 8.81 mmol, 58.0% yield) as an oil. ESIMS found $C_{13}H_{13}FN_4O_4S$ m/z 341.1 (M+H).

Step 5

A solution of N-[[3-(4-amino-3-nitro-2-pyridyl)-5-fluoro-phenyl]methyl]methanesulfonamide (CXIX) (3.00 g, 8.8 mmol, 1.0 eq), Fe (2.46 g, 44.1 mmol, 5.0 eq) and $NH_4Cl$ (2.36 g, 44.1 mmol, 5.0 eq) was dissolved in MeOH (35 mL). The mixture was stirred at 80° C. for 2 h. After filtration, the filtrate was concentrated to get N-(3-(3,4-diaminopyridin-2-yl)-5-fluorobenzyl)methanesulfonamide (CXX) (2.20 g, 7.09 mmol, 80.5% yield) as black solid. $^1H$ NMR ($CDCl_3$, 400 MHz) 2.96 (s, 3H), 4.28 (d, J=6 Hz, 2H), 5.33 (brs, 2H), 6.81 (d, J=6.5 Hz, 1H), 7.38-7.40 (m, 2H), 7.75 (d, J=6.5 Hz, 1H); ESIMS found $Cl_3H_{15}FN_4O_2S$ m/z 311.1 (M+H).

Preparation of intermediate 5-(3-((2-(dimethylamino)ethyl)amino)-5-fluorophenyl)pyridine-3,4-diamine (CXXVI) is depicted below in Scheme 24.

Scheme 24

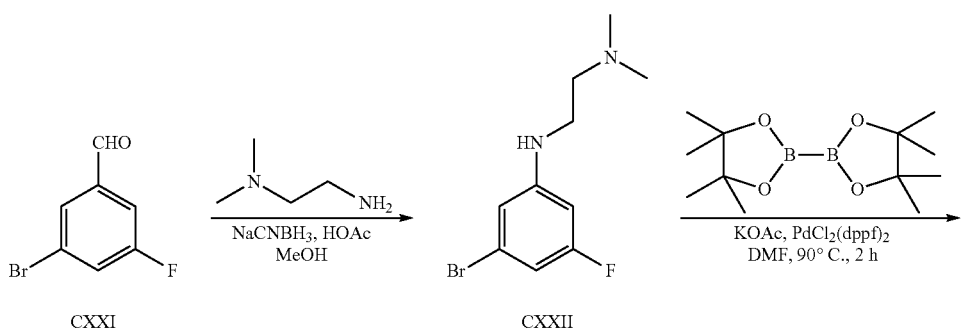

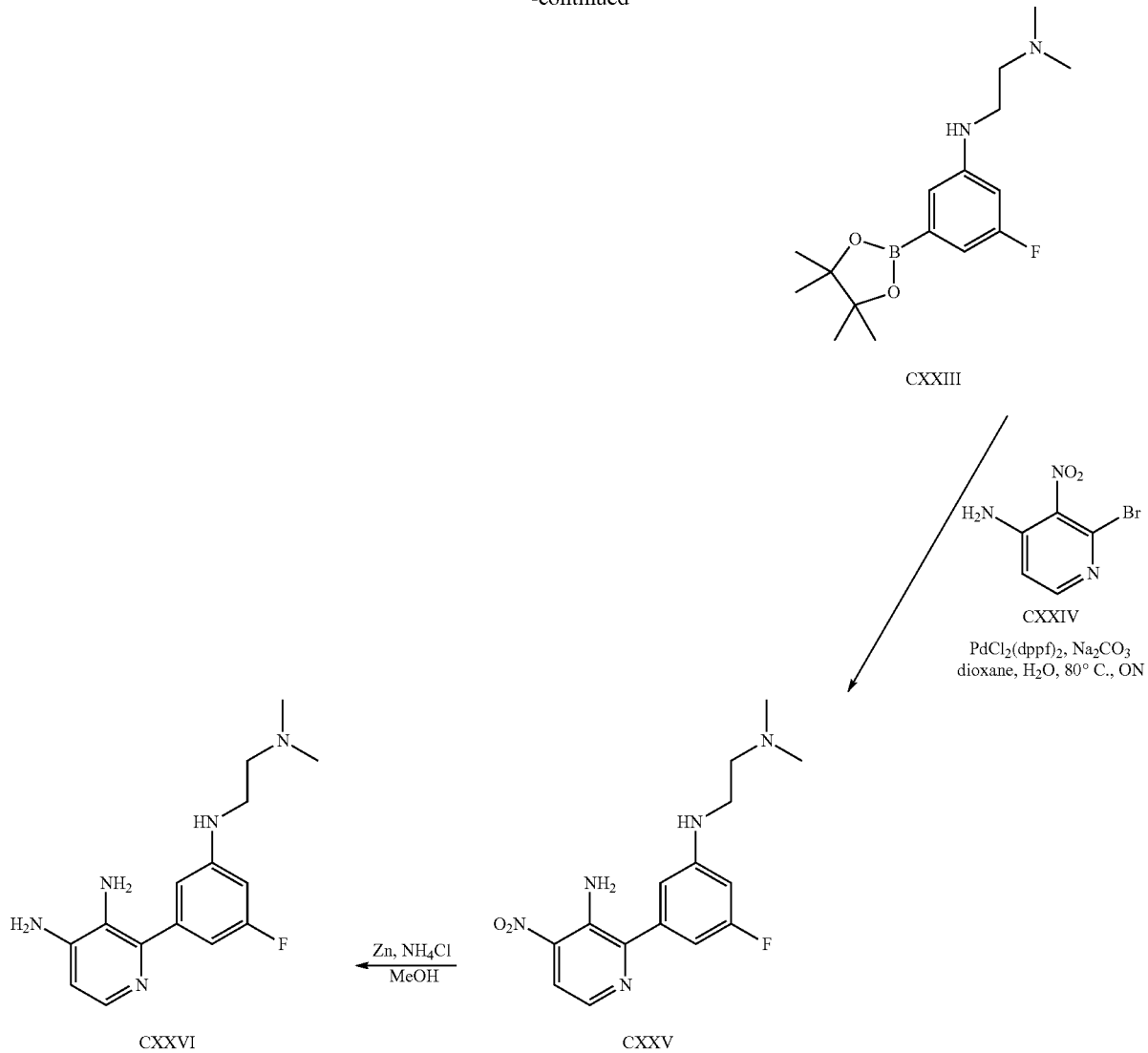

Step 1

A solution of 3-bromo-5-fluorobenzaldehyde (CXXI) (20.0 g, 98.2 mmol, 1.0 eq) in MeOH (1.8 L) was added $N^1,N^1$-dimethylethane-1,2-diamine (21.5 mL, 196.4 mmol, 2.0 eq). The pH was adjusted to 6 using HOAc and stirred for 1 h. $NaCNBH_3$ (8.6 g, 137.5 mmol, 1.4 eq) was added and stirred at room temperature overnight. The MeOH was removed under vacuum and the residue was partitioned between $CHCl_3$ and saturated aqueous $NaHCO_3$. The organic layer was dried over $MgSO_4$ and evaporated under vacuum. The crude product was purified on a silica gel column (100% $CHCl_3 \rightarrow$ 3:97 MeOH[7N $NH_3$]:$CHCl_3$) to produce $N^1$-(3-bromo-5-fluorophenyl)-$N^2,N^2$-dimethylethane-1,2-diamine (CXXII) as a yellow oil (13.0 g, 49.9 mmol, 51% yield). $^1$H NMR (DMSO-$d_6$, 500 MHz) δ ppm 1.28 (s, 6H), 2.39 (t, J=4 Hz, 2H), 3.07 (q, J=6 Hz, 2H), 6.10 (t, J=5 Hz, 1H), 6.38 (td, J=12 Hz, J=2 Hz, 1H), 6.51 (td, J=8.6 Hz, J=2 Hz, 1H), 6.61 (t, J=2 Hz, 1H); ESIMS found $C_{10}H_{14}BrFN_2$ m/z 261.0 (M+H).

Step 2

A solution of $N^1$-(3-bromo-5-fluorophenyl)-$N^2,N^2$-dimethylethane-1,2-diamine (CXXII) (13.0 g, 49.9 mmol, 1.0 eq), bis(pinacolato)diboron (12.6 g, 59.9 mmol, 1.2 eq), KOAc (12.1 g, 124.3 mmol, 2.5 eq) and dioxane (600 mL) was purged with argon. Pd(dppf)$Cl_2$ (2.0 g, 2.47 mmol, 0.05 eq) was added to the reaction and purged again with argon. The solution was heated at 90° C. for 2 h. Once TLC showed the disappearance of (CXXII), the solution was cooled to room temperature and then concentrated under reduced pressure to produce crude $N^1$-(3-fluoro-5-(4,4,5,5-tetramethyl-1,3,2-dioxaborolan-2-yl)phenyl)-$N^2,N^2$-dimethylethane-1,2-diamine (CXXIII) (7.4 g, 24.0 mmol, 48.2% yield).

Step 3

To a solution of $N^1$-(3-fluoro-5-(4,4,5,5-tetramethyl-1,3,2-dioxaborolan-2-yl)phenyl)-$N^2,N^2$-dimethylethane-1,2-diamine (CXXIII) (2.00 g, 6.49 mmol, 1.2 eq), 2-bromo-3-nitropyridin-4-amine (CXXIV) (1.18 g, 5.41 mmol, 1.0 eq), $Na_2CO_3$ (1.15 g, 10.82 mmol, 2.0 eq) and Pd(dppf)$Cl_2$ (395.73 mg, 540.83 μmol, 0.1 eq) in dioxane (40 mL) and $H_2O$ (8 mL) was de-gassed and then heated to 80° C. overnight under $N_2$. TLC (PE:EtOAc=1:1) showed the starting material was consumed completely. The reaction mixture was poured into $H_2O$ (300 mL). The mixture was extracted with EtOAc (3×250 mL). The organic phase was washed with saturated brine (300 mL), dried over anhydrous MgSO$_4$, concentrated in vacuum to give a residue, which was purified by silica gel column chromatography (PE/EtOAc=5/1) to afford N$^1$-(3-(4-amino-3-nitropyridin-2-yl)-5-fluorophenyl)-N$^2$,N$^2$-dimethylethane-1,2-diamine (CXXV) (1.50 g, 4.70 mmol, 86.9% yield) as a solid. ESIMS found for C$_{15}$H$_{18}$FN$_5$O$_2$ m/z 320.1 (M+H).

Step 4

To a solution of N$^1$-(3-(4-amino-3-nitropyridin-2-yl)-5-fluorophenyl)-N$^2$,N$^2$-dimethylethane-1,2-diamine (CXXV) (1.50 g, 4.70 mmol, 1.0 eq) in MeOH (30 mL) was added Zn (1.54 g, 23.50 mmol, 5.0 eq) and NH$_4$Cl (754.21 mg, 14.10 mmol, 3.0 eq) in one portion at room temperature. The mixture was stirred at room temperature for 10 min. TLC showed the reaction was completed. The mixture was filtered and concentrated in vacuum to afford 5-(3-((2-(dimethylamino)ethyl)amino)-5-fluorophenyl)pyridine-3,4-diamine (CXXVI) (1.2 g, 4.15 mmol, 4.15 mmol, 88.2% yield) as a yellow oil. $^1$H NMR (CD$_3$OD, 300 MHz) 2.44 (s, 6H), 2.78 (t, J=5.25 Hz, 2H), 3.24-3.34 (m, 2H), 6.40-6.51 (m, 2H), 6.53 (d, J=1.5 Hz, 1H), 6.71 (d, J=6.3 Hz, 1H), 7.58 (d, J=6.6 Hz, 1H); ESIMS found for C$_{15}$H$_{20}$FN$_5$ m/z 290.1 (M+H).

Example 1

Preparation of N-(5-(3-(4-(4-fluorophenyl)-1H-imidazo[4,5-c]pyridin-2-yl)-1H-indazol-5-yl)pyridin-3-yl)pivalamide (34) is depicted below in Scheme 25.

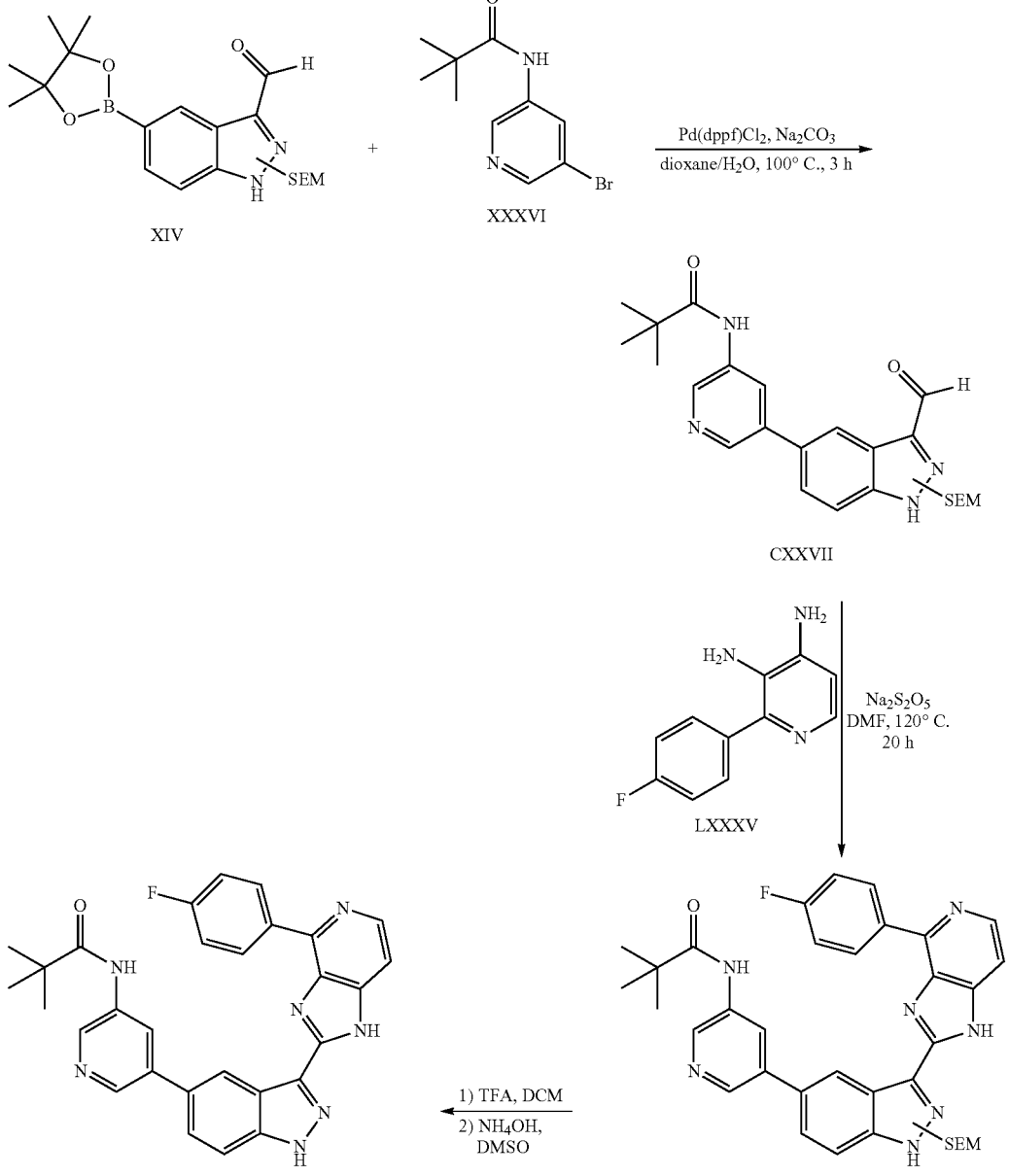

Step 1

To a solution of N-(5-bromopyridin-3-yl)pivalamide (XXXVI) (800 mg, 3.11 mmol, 1.0 eq) and 5-(4,4,5,5-tetramethyl-1,3,2-dioxaborolan-2-yl)-1-(2-trimethylsilylethoxymethyl)indazole-3-carbaldehyde (XIV) (1.56 g, 3.73 mmol, 1.2 eq), Pd(dppf)Cl$_2$ (228 mg, 0.31 mmol, 0.10 eq) and Na$_2$CO$_3$ (659 mg, 6.22 mmol, 2.0 eq) in dioxane (34 mL) and H$_2$O (5.5 mL) was de-gassed and then heated to 100° C. for 3 h under N$_2$. TLC (100% EtOAc) showed the starting material was consumed completely. The reaction mixture was concentrated in vacuum to give a residue, which was pre-purified by silica gel column chromatography (PE:EtOAc=10:1→1:1) to afford pure N-(5-(3-formyl-1-((2-(trimethylsilyl)ethoxy)methyl)-1H-indazol-5-yl)pyridin-3-yl)pivalamide (CXXVII) as a red brown solid (1.25 mg, 2.76 mmol, 88.8% yield). $^1$H NMR (CDCl$_3$, 400 MHz) δ ppm −0.03 (s, 9H), 0.94 (t, J=8 Hz, 2H), 1.40 (s, 9H), 3.63 (t, J=8 Hz, 2H), 5.88 (s, 2H), 7.58 (s, 1H), 7.86-7.91 (m, 2H), 8.47 (d, J=2.4 Hz, 1H), 8.53 (s, 1H), 8.67 (dd, J=5.6 Hz, J=2.4 Hz, 2H), 10.31 (s, 1H); ESIMS found for C$_{24}$H$_{32}$N$_4$O$_3$Si m/z 453.1 (M+H).

Step 2-3

A solution of N-(5-(3-formyl-1-((2-(trimethylsilyl)ethoxy)methyl)-1H-indazol-5-yl)pyridin-3-yl)pivalamide (CXXVII) (100.0 mg, 0.22 mmol, 1.0 eq), 2-(4-fluorophenyl)pyridine-3,4-diamine (LXXXV) (45 mg, 0.22 mmol, 1.0 eq) and Na$_2$S$_2$O$_5$ (49 mg, 0.26 mmol, 1.20 eq) in DMF (2 mL) was stirred at 120° C. for 20 h. LC/MS showed the starting material was consumed. Water (5 mL) was then added dropwise to the mixture and stirred at room temperature for 10 min, the mixture was filtered, then the filtrate was washed by H$_2$O (2 mL×3), dried over anhydrous MgSO$_4$, and evaporated under vacuum to give crude N-(5-(3-(4-(4-fluorophenyl)-1H-imidazo[4,5-c]pyridin-2-yl)-1-((2-(trimethylsilyl)ethoxy)methyl)-1H-indazol-5-yl)pyridin-3-yl)pivalamide (CXXVIII). CXXVIII was dissolved in dry DCM (5 mL) before adding triethylsilane (84 μL, 0.52 mmol) and TFA (2.5 mL). The reaction was stirred at room temperature for 2 h under N$_2$. The solvent was evaporated under reduced pressure; the residue was taken up water (10 mL), and basified with 5N NH$_4$OH. The precipitates were filtered, washed by cold water and dried under vacuum at room temperature. The crude product was suspended in DCM (10 mL), sonicated briefly and then heated to boiling for 5 min. The solution was cooled to room temperature and the solids were filtered, washed with DCM and dried under vacuum at room temperature to produce N-(5-(3-(4-(4-fluorophenyl)-1H-imidazo[4,5-c]pyridin-2-yl)-1H-indazol-5-yl)pyridin-3-yl)pivalamie (34) as a yellow solid (41.0 mg, 0.08 mmol, 36.4% yield). $^1$H NMR (DMSO-d$_6$, 400 MHz) δ ppm 1.31 (s, 9H), 7.38 (t, J=8.23 Hz, 2H), 7.51 (d, J=5.27 Hz, 1H), 7.82-7.92 (m, 2H), 8.16 (s, 1H), 8.43 (d, J=5.52 Hz, 1H), 8.65-8.74 (m, 2H), 8.88 (s, 1H), 8.90 (d, J=2.26 Hz, 1H), 9.06 (dd, J=8.80 Hz, J=6.04 Hz, 2H), 9.65 (s, 1H), 13.68 (brs, 1H), 13.99 (brs, 1H); ESIMS found for C$_{29}$H$_{24}$FN$_7$O m/z 506.3 (M+1).

The following compounds were prepared in accordance with the procedure described in the above Example 1.

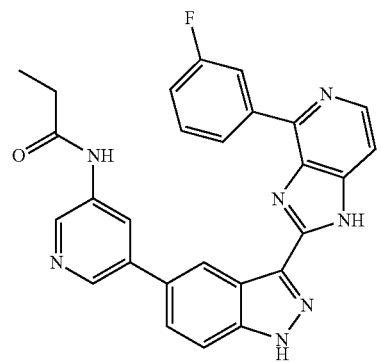

N-(5-(3-(4-(3-Fluorophenyl)-1H-imidazo[4,5-c]pyridin-2-yl)-1H-indazol-5-yl)pyridin-3-yl)propionamide 1.

White solid (18.9 mg, 0.04 mmol). $^1$H NMR (DMSO-d$_6$, 400 MHz) δ ppm 1.14 (t, J=7.53 Hz, 3H), 2.46 (q, J=7.52 Hz, 4H), 7.34-7.46 (m, 1H), 7.63-7.79 (m, 2H), 7.82-7.92 (m, 2H), 8.52 (d, J=6.02 Hz, 1H), 8.60 (d, J=0.76 Hz, 1H), 8.67-8.75 (m, 2H), 8.76-8.77 (m, 1H), 8.79 (s, 1H), 8.86 (s, 1H), 10.40 (brs, 1H), 14.21 (brs, 1H), 14.27 (brs, 1H); ESIMS found for C$_{27}$H$_{20}$FN$_7$O m/z 478.1 (M+1).

N-(5-(3-(4-(3-Fluorophenyl)-1H-imidazo[4,5-c]pyridin-2-yl)-1H-indazol-5-yl)pyridin-3-yl)-3-methylbutanamide 2.

Beige solid (34.0 mg, 0.07 mmol). $^1$H NMR (DMSO-d$_6$, 500 MHz) δ ppm 0.98 (d, J=7 Hz, 6H), 2.13 (non, J=7 Hz, 1H), 2.29 (d, J=7 Hz, 2H), 7.27 (td, J=2 Hz, J=8 Hz, 1H), 7.55 (d, J=5.5 Hz, 1H), 7.61 (q, J=8 Hz, 1H), 7.84 (dd, J=1.5 Hz, J=8.5 Hz, 1H), 7.87 (d, J=9 Hz, 1H), 8.46 (d, J=5.5 Hz, 1H), 8.54 (t, J=2 Hz, 1H), 8.71 (d, J=1.5 Hz, 1H), 8.78 (d, J=2 Hz, 1H), 8.83 (d, J=4.5 Hz, 1H), 8.85 (s, 1H), 8.91 (s, 1H), 10.24 (s, 1H), 13.72 (brs, 1H), 13.99 (brs, 1H); ESIMS found for C$_{29}$H$_{24}$FN$_7$O m/z 506.0 (M+1).

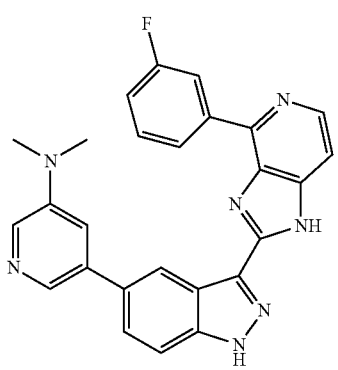

5-(3-(4-(3-Fluorophenyl)-1H-imidazo[4,5-c]pyridin-2-yl)-1H-indazol-5-yl)-N,N-dimethylpyridin-3-amine 7.

White solid (8.1 mg, 0.02 mmol). $^1$H NMR (DMSO-d$_6$, 400 MHz) δ ppm 3.04 (s, 6H), 7.32 (dd, J=8.28 Hz, J=2.0 Hz, 1H), 7.36 (t, J=2.01 Hz, 1H), 7.53-7.61 (m, 2H), 7.80-7.91 (m, 3H), 8.18 (d, J=2.76 Hz, 1H), 8.20 (s, 1H), 8.33 (d, J=1.76 Hz, 1H), 8.46 (d, J=5.27 Hz, 1H), 8.77-8.86 (m, 2H), 8.88 (s, 1H), 13.72 (brs, 1H), 13.98 (brs, 1H); ESIMS found for C$_{26}$H$_{20}$FN$_7$ m/z 450.1 (M+1).

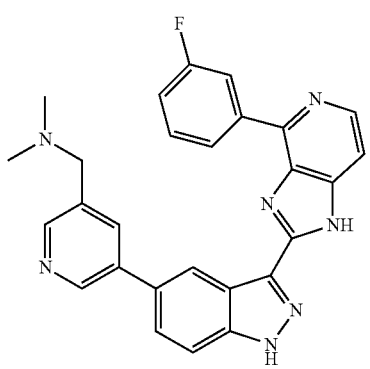

1-(5-(3-(4-(3-Fluorophenyl)-1H-imidazo[4,5-c]pyridin-2-yl)-1H-indazol-5-yl)pyridin-3-yl)-N,N-dimethylmethanamine 13.

White solid (31.7 mg, 0.07 mmol). $^1$H NMR (DMSO-d$_6$, 400 MHz) δ ppm 2.21-2.40 (m, 6H), 3.69 (s, 2H), 7.34 (td, J=8.16, 3.01 Hz, 1H), 7.55 (d, J=5.27 Hz, 1H), 7.59-7.69 (m, 1H), 7.81-7.97 (m, 2H), 8.08-8.20 (m, 2H), 8.46 (d, J=5.27 Hz, 1H), 8.57 (d, J=1.76 Hz, 1H), 8.76-8.90 (m, 2H), 8.93 (s, 1H), 8.98 (d, J=2.01 Hz, 1H), 13.73 (brs, 1H), 14.00 (s, 1H); ESIMS found for C$_{27}$H$_{22}$FN$_7$ m/z 464.3 (M+1).

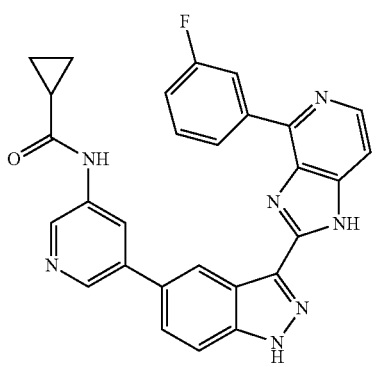

N-(5-(3-(4-(3-Fluorophenyl)-1H-imidazo[4,5-c]pyridin-2-yl)-1H-indazol-5-yl)pyridin-3-yl)cyclopropanecarboxamide 19.

White solid (20.7 mg, 0.04 mmol). $^1$H NMR (DMSO-d$_6$, 400 MHz) δ ppm 0.80-0.95 (m, 4H), 1.81-1.93 (m, 1H), 7.29 (dt, J=8.28 Hz, J=2.00 Hz, 1H), 7.51-7.67 (m, 2H), 7.86 (s, 2H), 8.26 (s, 1H), 8.46 (d, J=5.52 Hz, 1H), 8.56 (d, J=1.76 Hz, 1H), 8.71 (d, J=3.69 Hz, 1H), 8.74 (d, J=5.81 Hz, 1H), 8.77-8.88 (m, 2H), 8.91 (s, 1H), 10.60 (s, 1H), 13.75 (brs, 1H), 14.04 (brs, 1H); ESIMS found for C$_{28}$H$_{20}$FN$_7$O m/z 490.2 (M+1).

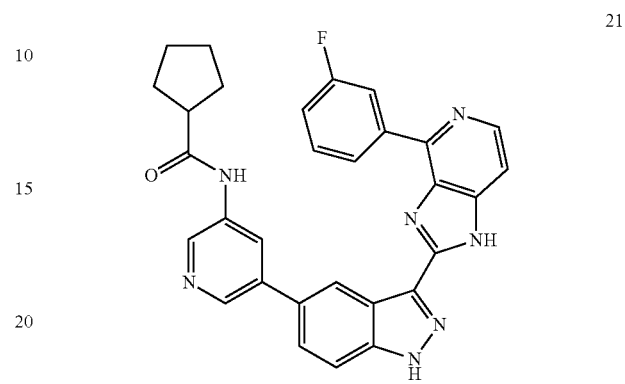

N-(5-(3-(4-(3-Fluorophenyl)-1H-imidazo[4,5-c]pyridin-2-yl)-1H-indazol-5-yl)pyridin-3-yl)cyclopentanecarboxamide 21.

White solid (27.6 mg, 0.05 mmol). $^1$H NMR (DMSO-d$_6$, 400 MHz) δ ppm 1.54-1.64 (m, 2H), 1.64-1.73 (m, 2H), 1.74-1.86 (m, 2H), 1.88-2.02 (m, 2H), 2.97 (quin, J=7.80 Hz, 1H), 7.49 (td, J=8.34, 2.13 Hz, 1H), 7.76-7.84 (m, 1H), 7.85-7.92 (m, 2H), 7.95 (d, J=6.27 Hz, 1H), 8.55 (d, J=6.28 Hz, 1H), 8.52-8.63 (m, 2H), 8.73 (s, 1H), 8.87 (s, 1H), 8.89 (s, 1H), 9.10 (d, J=1.76 Hz, 1H), 11.06 (s, 1H), 14.47 (brs, 1H), 14.86 (brs, 1H); ESIMS found for C$_{30}$H$_{24}$FN$_7$O m/z 518.2 (M+1).

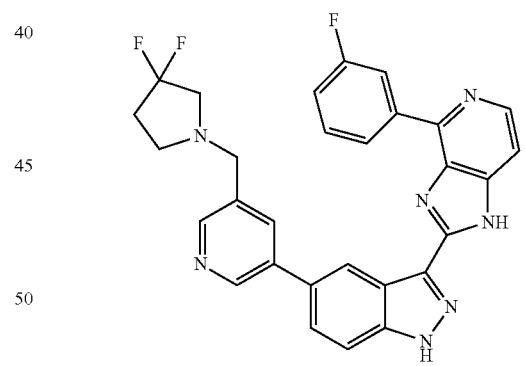

2-(5-(5-((3,3-Difluoropyrrolidin-1-yl)methyl)pyridin-3-yl)-1H-indazol-3-yl)-4-(3-fluorophenyl)-1H-imidazo[4,5-c]pyridine 25.

White solid (91.7 mg, 0.17 mmol). $^1$H NMR (DMSO-d$_6$, 400 MHz) δ ppm 2.18-2.31 (m, 2H), 2.77 (t, J=6.90 Hz, 2H), 2.96 (t, J=13.28 Hz, 2H), 3.81 (s, 2H), 7.34 (td, J=8.41, 2.26 Hz, 1H), 7.56 (d, J=5.27 Hz, 1H), 7.57-7.67 (m, 1H), 7.86 (d, J=8.80 Hz, 1H), 7.92 (dd, J=8.76 Hz, J=1.76 Hz, 1H), 8.10 (t, J=2.01 Hz, 1H), 8.17-8.21 (m, 1H), 8.46 (d, J=5.27 Hz, 1H), 8.58 (d, J=2.01 Hz, 1H), 8.75-8.83 (m, 1H), 8.89 (d, J=11.80 Hz, 1H), 8.93 (s, 1H), 8.97 (d, J=2.26 Hz, 1H), 13.74 (brs, 1H), 14.01 (brs, 1H); ESIMS found for C$_{29}$H$_{22}$F$_3$N$_7$ m/z 526.3 (M+1).

28

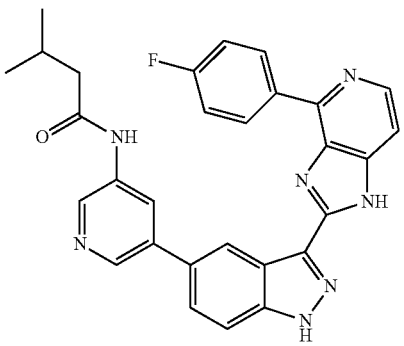

N-(5-(3-(4-(4-Fluorophenyl)-1H-imidazo[4,5-c]pyridin-2-yl)-1H-indazol-5-yl)pyridin-3-yl)-3-methylbutanamide 28.

White solid (37.8 mg, 0.07 mmol). $^1$H NMR (DMSO-d$_6$, 400 MHz) δ ppm 0.98 (d, J=6.53 Hz, 6H), 2.17 (non, J=13.43, 6.84 Hz, 1H), 2.32 (d, J=7.03 Hz, 3H), 7.39 (t, J=8.29 Hz, 2H), 7.51 (d, J=5.27 Hz, 1H), 7.86 (s, 2H), 8.25 (s, 1H), 8.43 (d, J=5.27 Hz, 1H), 8.66 (s, 1H), 8.72 (dd, J=8.16, 2.13 Hz, 2H), 8.87 (s, 1H), 9.04 (dd, J=7.91, 6.40 Hz, 2H), 10.35 (s, 1H), 13.69 (brs, 1H), 14.02 (brs, 1H); ESIMS found for C$_{29}$H$_{24}$FN$_7$O m/z 506.3 (M+1).

38

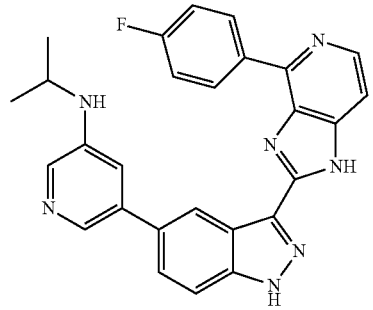

5-(3-(4-(4-Fluorophenyl)-1H-imidazo[4,5-c]pyridin-2-yl)-1H-indazol-5-yl)-N-isopropylpyridin-3-amine 38.

White solid (40.6 mg, 0.09 mmol). $^1$H NMR (DMSO-d$_6$, 400 MHz) δ ppm 1.23 (d, J=6.27 Hz, 6H), 3.79-3.90 (m, 1H), 6.89 (brs, 1H), 7.48 (t, J=8.78 Hz, 2H), 7.68 (d, J=5.77 Hz, 1H), 7.80 (brs, 1H), 7.89 (s, 2H), 8.10 (d, J=2.26 Hz, 1H), 8.37 (d, J=0.75 Hz, 1H), 8.48 (d, J=5.77 Hz, 1H), 8.84 (s, 1H), 8.88-8.97 (m, 2H), 14.14 (brs, 1H), 14.27 (s, 1H); ESIMS found for C$_{27}$H$_{22}$FN$_7$ m/z 464.3 (M+1).

40

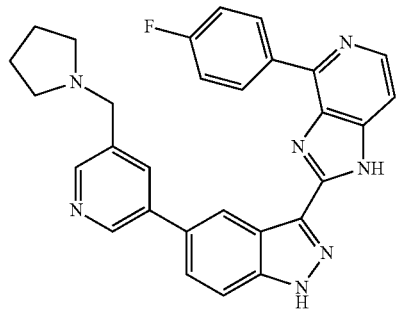

4-(4-Fluorophenyl)-2-(5-(5-(pyrrolidin-1-ylmethyl)pyridin-3-yl)-1H-indazol-3-yl)-1H-imidazo[4,5-c]pyridine 40.

White solid (16.1 mg, 0.03 mmol). $^1$H NMR (DMSO-d$_6$, 400 MHz) δ ppm 1.67-1.77 (m, 4H), 2.53-2.58 (m, 4H), 3.79 (s, 2H), 7.40 (t, J=8.22 Hz, 2H), 7.51 (d, J=5.27 Hz, 1H), 7.84 (d, J=8.78 Hz, 1H), 7.94 (dd, J=8.76, J=1.52 Hz, 1H), 8.12-8.15 (m, 1H), 8.20 (s, 2H), 8.43 (d, J=5.27 Hz, 1H), 8.57 (d, J=1.76 Hz, 1H), 8.94 (s, 1H), 8.96 (d, J=2.01 Hz, 1H), 8.98-9.06 (m, 2H), 13.70 (brs, 1H), 14.00 (brs, 1H); ESIMS found for C$_{29}$H$_{24}$FN$_7$ m/z 490.3 (M+1).

46

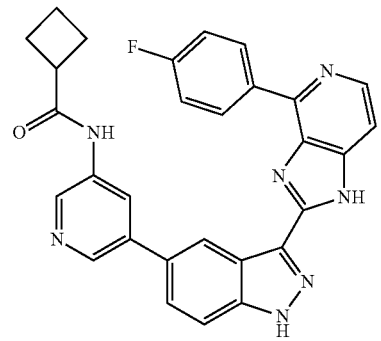

N-(5-(3-(4-(4-Fluorophenyl)-1H-imidazo[4,5-c]pyridin-2-yl)-1H-indazol-5-yl)pyridin-3-yl)cyclobutanecarboxamide 46.

White solid (14.1 mg, 0.03 mmol). $^1$H NMR (DMSO-d$_6$, 400 MHz) δ ppm 1.79-1.90 (m, 2H), 1.92-2.06 (m, 2H), 2.13-2.23 (m, 3H), 2.25-2.38 (m, 3H), 4.57 (s, 1H), 7.41 (t, J=8.91 Hz, 2H), 7.51 (d, J=5.52 Hz, 1H), 7.86 (s, 2H), 8.43 (d, J=5.27 Hz, 1H), 8.69 (s, 1H), 8.72 (s, 2H), 8.88 (s, 1H), 9.05 (dd, J=9.28 Hz, J=6.00 Hz, 2H), 10.24 (s, 1H), 13.70 (brs, 1H), 14.03 (brs, 1H); ESIMS found for C$_{29}$H$_{22}$FN$_7$O m/z 504.2 (M+1).

52

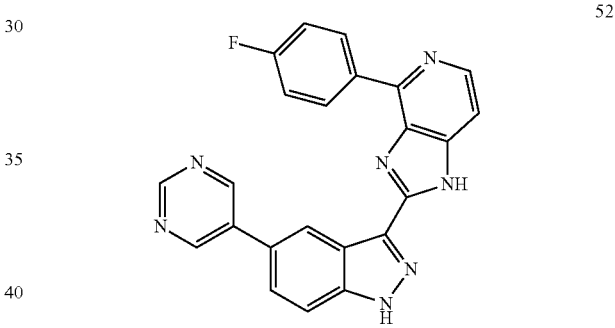

4-(4-Fluorophenyl)-2-(5-(pyrimidin-5-yl)-1H-indazol-3-yl)-1H-imidazo[4,5-c]pyridine 52.

White solid (17.1 mg, 0.04 mmol). $^1$H NMR (DMSO-d$_6$, 400 MHz) δ ppm 7.40 (t, J=8.66 Hz, 2H), 7.54-7.66 (m, 1H), 7.88 (d, J=9.03 Hz, 1H), 7.99 (d, J=9.03 Hz, 1H), 8.45 (d, J=5.52 Hz, 1H), 8.97 (brs, 3H), 9.29 (d, J=11.04 Hz, 3H), 13.88 (brs, 1H) 14.06 (s, 1H); ESIMS found for C$_{23}$H$_{14}$FN$_7$ m/z 408.1 (M+1).

55

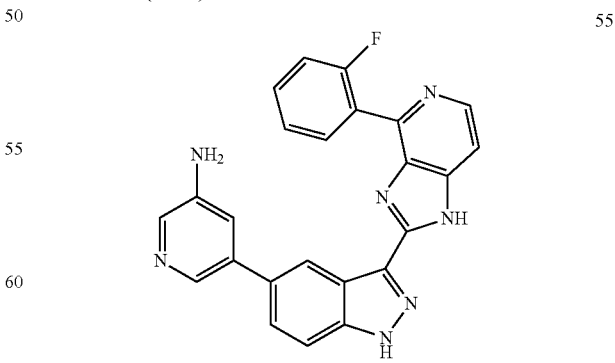

5-(3-(4-(2-Fluorophenyl)-1H-imidazo[4,5-c]pyridin-2-yl)-1H-indazol-5-yl)pyridin-3-amine 55.

White solid (20.3 mg, 0.05 mmol). $^1$H NMR (DMSO-d$_6$, 400 MHz) δ ppm 7.63-7.74 (m, 2H), 7.78-7.89 (m, 2H), 7.91-8.02 (m, 2H), 8.09 (d, J=2.26 Hz, 1H), 8.11-8.16 (m, 1H), 8.18-8.29 (m, 1H), 8.35 (s, 1H), 8.63-8.76 (m, 2H), 14.57 (brs, 1H), 15.04 (brs 1H); ESIMS found for $C_{24}H_{16}FN_7$ m/z 422.1 (M+1).

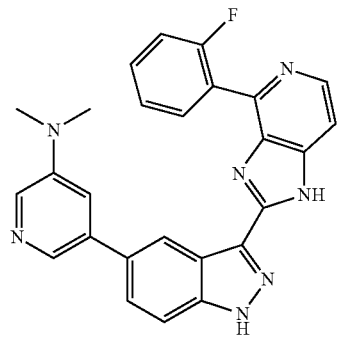

5-(3-(4-(2-Fluorophenyl)-1H-imidazo[4,5-c]pyridin-2-yl)-1H-indazol-5-yl)-N,N-dimethylpyridin-3-amine 59.

White solid (14.3 mg, 0.03 mmol). $^1$H NMR (DMSO-d$_6$, 400 MHz) δ ppm 3.12 (s, 6H), 7.46-7.59 (m, 2H), 7.67-7.78 (m, 2H), 7.84-7.89 (m, 1H), 7.92 (d, J=5.27 Hz, 1H), 7.96 (dd, J=8.78, 1.25 Hz, 1H), 8.03-8.15 (m, 1H), 8.20 (d, J=2.51 Hz, 1H), 8.35 (s, 1H), 8.58 (d, J=6.02 Hz, 1H), 8.72 (s, 1H), 14.38 (s, 1H); ESIMS found for $C_{26}H_{20}FN_7$ m/z 450.1 (M+1).

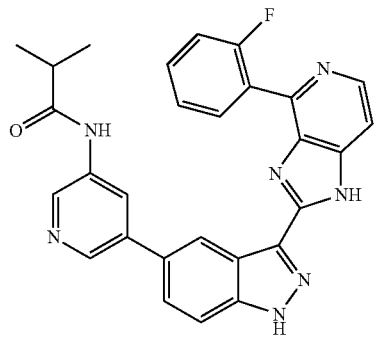

N-(5-(3-(4-(2-Fluorophenyl)-1H-imidazo[4,5-c]pyridin-2-yl)-1H-indazol-5-yl)pyridin-3-yl)isobutyramide 61.

White solid (11.8 mg, 0.02 mmol). $^1$H NMR (CD$_3$OD, 400 MHz) δ ppm 1.27 (d, J=6.78 Hz, 6H), 2.73 (spt, J=6.87 Hz, 1H), 7.34-7.46 (m, 2H), 7.54-7.64 (m, 1H), 7.72-7.77 (m, 1H), 7.77-7.84 (m, 2H), 7.91-8.00 (m, 1H), 8.27-8.34 (m, 1H), 8.44 (d, J=5.77 Hz, 1H), 8.49 (t, J=2.13 Hz, 1H), 8.64 (d, J=1.51 Hz, 1H), 8.77 (d, J=2.26 Hz, 1H), 8.79 (s, 1H); ESIMS found for $C_{28}H_{22}FN_7O$ m/z 492.2 (M+1).

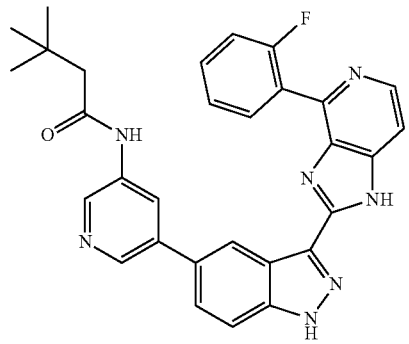

N-(5-(3-(4-(2-Fluorophenyl)-1H-imidazo[4,5-c]pyridin-2-yl)-1H-indazol-5-yl)pyridin-3-yl)-3,3-dimethylbutanamide 68.

White solid (43.9 mg, 0.08 mmol). $^1$H NMR (DMSO-d$_6$, 400 MHz) δ ppm 1.05-1.11 (m, 9H), 2.29 (s, 2H), 7.31-7.42 (m, 2H), 7.47-7.60 (m, 2H), 7.74-7.86 (m, 2H), 8.02 (t, J=7.28 Hz, 1H), 8.18 (s, 1H), 8.45 (d, J=5.52 Hz, 2H), 8.59 (s, 1H), 8.73 (s, 2H), 10.20 (s, 1H), 13.61 (brs, 1H), 13.94 (brs, 1H); ESIMS found for $C_{30}H_{26}FN_7O$ m/z 520.3 (M+1).

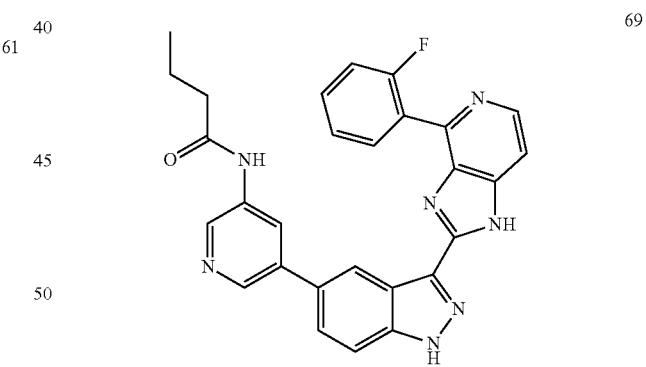

N-(5-(3-(4-(2-Fluorophenyl)-1H-imidazo[4,5-c]pyridin-2-yl)-1H-indazol-5-yl)pyridin-3-yl)butyramide 69.

White solid (15.8 mg, 0.03 mmol). $^1$H NMR (DMSO-d$_6$, 400 MHz) δ ppm 0.97 (t, J=7.28 Hz, 3H), 1.68 (sxt, J=7.18 Hz, 2H), 2.42 (t, J=7.15 Hz, 2H), 7.48 (t, J=7.53 Hz, 2H), 7.61-7.70 (m, 1H), 7.77-7.83 (m, 1H), 7.84-7.91 (m, 2H), 8.13 (brs, 1H), 8.51 (brs, 1H), 8.56 (d, J=5.77 Hz, 1H), 8.60 (brs, 1H), 8.68 (s, 1H), 8.79 (brs, 1H), 10.51 (brs, 1H), 14.30 (brs, 2H); ESIMS found for $C_{28}H_{22}FN_7O$ m/z 492.1 (M+1).

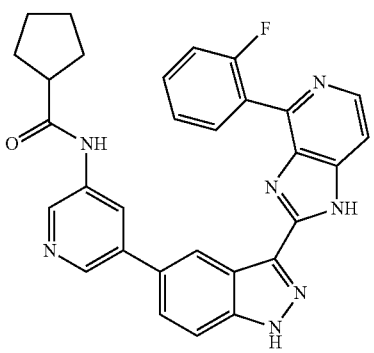

N-(5-(3-(4-(2-Fluorophenyl)-1H-imidazo[4,5-c]pyridin-2-yl)-1H-indazol-5-yl)pyridin-3-yl)cyclopentanecarboxamide 73.

White solid (43.8 mg, 0.09 mmol). $^1$H NMR (DMSO-d$_6$, 400 MHz) δ ppm 1.52-1.85 (m, 6H), 1.87-2.03 (m, 2H), 2.82-2.95 (m, 1H), 7.33-7.43 (m, 2H), 7.47-7.63 (m, 2H), 7.74-7.91 (m, 2H), 7.98-8.08 (m, 1H), 8.17 (s, 1H), 8.39-8.53 (m, 2H), 8.56-8.66 (m, 1H), 8.70-8.82 (m, 2H), 10.23-10.31 (m, 1H), 13.61 (brs, 1H), 13.94 (brs, 1H); ESIMS found for $C_{30}H_{24}FN_7O$ m/z 518.3 (M+1).

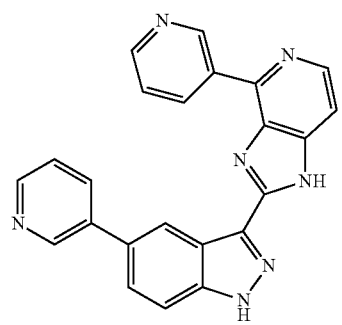

4-(Pyridin-3-yl)-2-(5-(pyridin-3-yl)-1H-indazol-3-yl)-1H-imidazo[4,5-c]pyridine 82.

White solid (16.8 mg, 0.04 mmol). $^1$H NMR (DMSO-d$_6$, 400 MHz) δ ppm 7.54-7.65 (m, 3H), 7.82-7.95 (m, 2H), 8.22 (d, J=8.28 Hz, 1H), 8.49 (d, J=5.27 Hz, 1H), 8.65 (d, J=4.52 Hz, 1H), 8.70 (d, J=4.02 Hz, 1H), 8.92 (s, 1H), 9.05 (s, 1H), 9.23 (d, J=8.28 Hz, 1H), 10.03 (brs, 1H), 13.78 (brs, 1H), 14.00 (s, 1H); ESIMS found for $C_{23}H_{15}N_7$ m/z 390.0 (M+1).

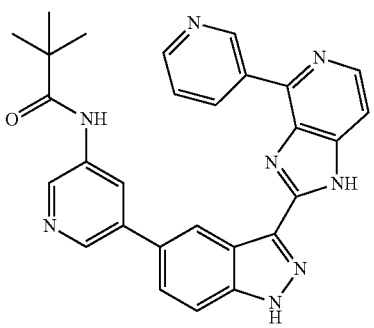

N-(5-(3-(4-(Pyridin-3-yl)-1H-imidazo[4,5-c]pyridin-2-yl)-1H-indazol-5-yl)pyridin-3-yl)pivalamide 86.

White solid (16.4 mg, 0.03 mmol). $^1$H NMR (DMSO-d$_6$, 400 MHz) δ ppm 1.27-1.38 (m, 9H), 7.90 (d, J=5.52 Hz, 1H), 7.95 (s, 2H), 8.11 (td, J=6.34, 1.38 Hz, 1H), 8.61 (d, J=5.77 Hz, 1H), 8.86 (s, 1H), 8.94 (d, J=4.77 Hz, 1H), 9.07 (s, 1H), 9.18 (brs, 1H), 9.34 (s, 1H), 9.50 (brs, 1H), 9.99 (brs, 1H), 10.48 (s, 1H), 14.47 (brs, 1H); ESIMS found for $C_{28}H_{24}N_8O$ m/z 489.2 (M+1).

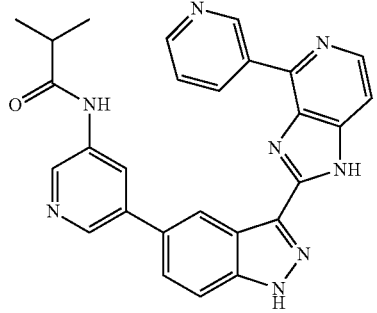

N-(5-(3-(4-(Pyridin-3-yl)-1H-imidazo[4,5-c]pyridin-2-yl)-1H-indazol-5-yl)pyridin-3-yl)isobutyramide 87.

White solid (24.7 mg, 0.05 mmol). $^1$H NMR (DMSO-d$_6$, 400 MHz) δ ppm 1.19 (d, J=6.78 Hz, 6H), 2.78 (spt, J=6.76 Hz, 1H), 7.88-7.96 (m, 3H), 8.08 (dd, J=7.78, 5.52 Hz, 1H), 8.62 (d, J=6.02 Hz, 1H), 8.83 (s, 1H), 8.88 (s, 1H), 8.94 (dd, J=5.14, 1.38 Hz, 1H), 8.97 (d, J=1.76 Hz, 1H), 9.11 (d, J=2.01 Hz, 1H), 9.38-9.54 (m, 1H), 9.88-9.98 (m, 1H), 10.97 (s, 1H), 14.41 (s, 1H), 14.54 (brs, 1H); ESIMS found for $C_{27}H_{22}N_8O$ m/z 475.3 (M+1).

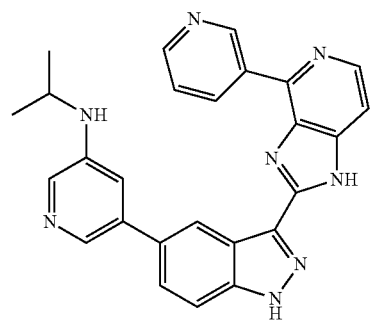

N-Isopropyl-5-(3-(4-(pyridin-3-yl)-1H-imidazo[4,5-c]pyridin-2-yl)-1H-indazol-5-yl)pyridin-3-amine 90.

White solid (36.5 mg, 0.08 mmol). $^1$H NMR (DMSO-d$_6$, 400 MHz) δ ppm 1.22 (d, J=6.27 Hz, 6H), 3.81-391 (m, 1H), 7.65 (d, J=5.27 Hz, 1H), 7.68-7.82 (m, 2H), 7.88 (s, 2H), 8.10 (d, J=1.72 1H), 8.36 (s, 1H), 8.51 (d, J=5.52 Hz, 1H), 8.72 (d, J=4.52 Hz, 1H), 8.87 (s, 1H), 9.23 (d, J=6.78 Hz, 1H), 10.01 (brs, 1H), 14.00 (brs, 1H), 14.30 (s, 1H); ESIMS found for $C_{26}H_{22}N_8$ m/z 447.3 (M+1).

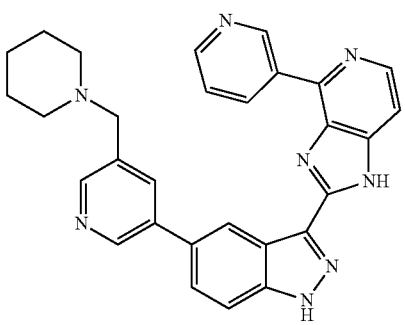

2-(5-(5-(Piperidin-1-ylmethyl)pyridin-3-yl)-1H-indazol-3-yl)-4-(pyridin-3-yl)-1H-imidazo[4,5-c]pyridine 93.

White solid (11.1 mg, 0.02 mmol). $^1$H NMR (DMSO-d$_6$, 400 MHz) δ ppm 1.33-1.44 (m, 2H), 1.44-1.57 (m, 4H), 2.37-2.46 (m, 4H), 3.65 (s, 2H), 7.55-7.65 (m, 2H), 7.85 (d, J=8.78 Hz, 1H), 7.93 (dd, J=8.76 Hz, J=1.52 Hz, 1H), 8.06-8.12 (m, 1H), 8.27 (s, 1H), 8.46-8.52 (m, 1H), 8.54 (d, J=1.76 Hz, 1H), 8.68 (dd, J=4.77, 1.51 Hz, 1H), 8.89-8.99 (m, 2H), 9.13-9.23 (m, 1H), 10.07 (d, J=1.25 Hz, 1H); ESIMS found for $C_{29}H_{26}N_8$ m/z 487.1 (M+1).

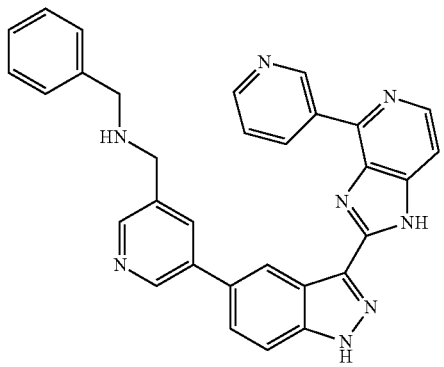

N-Benzyl-1-(5-(3-(4-(pyridin-3-yl)-1H-imidazo[4,5-c]pyridin-2-yl)-1H-indazol-5-yl)pyridin-3-yl)methanamine 101.

White solid (29.1 mg, 0.06 mmol). $^1$H NMR (DMSO-$d_6$, 400 MHz) δ ppm 4.31 (s, 2H), 4.50 (s, 2H), 7.38-7.49 (m, 2H), 7.61 (dd, J=7.65, 1.88 Hz, 2H), 7.85-7.99 (m, 2H), 8.04 (dd, J=8.78, 1.76 Hz, 2H), 8.63 (d, J=6.02 Hz, 1H), 8.79-9.06 (m, 3H), 9.24 (d, J=1.51 Hz, 1H), 9.33-9.47 (brs, 1H), 10.04 (brs Hz, 2H), 14.43 (brs, 1H); ESIMS found for $C_{31}H_{24}N_8$ m/z 509.3 (M+1).

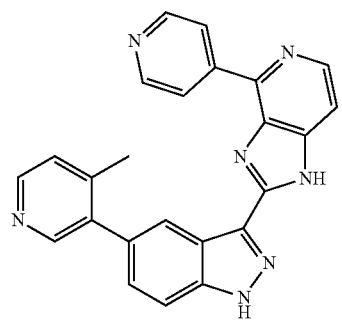

2-(5-(4-Methylpyridin-3-yl)-1H-indazol-3-yl)-4-(pyridin-4-yl)-1H-imidazo [4,5-c]pyridine 109.

White solid (11.7 mg, 0.03 mmol). $^1$H NMR (DMSO-$d_6$, 400 MHz) δ ppm 2.44 (s, 3H), 7.43 (d, J=5.02 Hz, 1H), 7.58 (dd, J=8.28, 1.00 Hz, 1H), 7.63 (d, J=5.27 Hz, 1H), 7.82 (d, J=8.53 Hz, 1H), 8.50 (dd, J=5.02, 3.51 Hz, 2H), 8.57 (s, 1H), 8.64 (s, 1H), 8.66 (s, 1H), 8.67 (s, 1H), 8.76 (d, J=5.27 Hz, 2H); ESIMS found for $C_{24}H_{17}N_7$ m/z 404.0 (M+1).

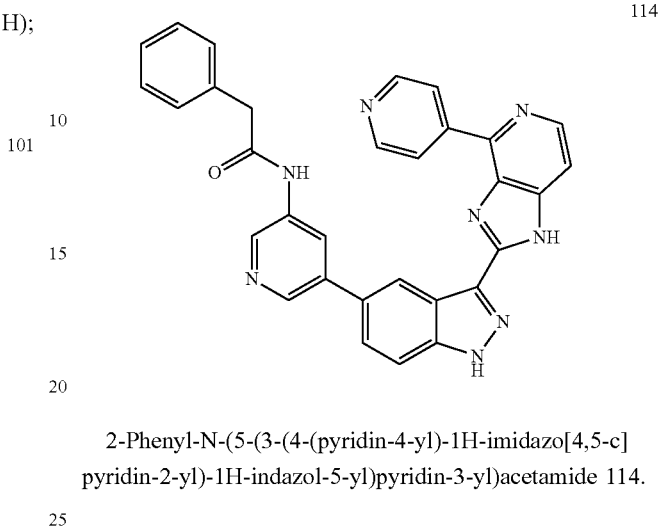

2-Phenyl-N-(5-(3-(4-(pyridin-4-yl)-1H-imidazo[4,5-c]pyridin-2-yl)-1H-indazol-5-yl)pyridin-3-yl)acetamide 114.

White solid (27.7 mg, 0.05 mmol). $^1$H NMR (DMSO-$d_6$, 400 MHz) δ ppm 3.76-3.84 (m, 2H), 7.09-7.18 (m, 1H), 7.22-7.29 (m, 1H), 7.33 (t, J=7.53 Hz, 2H), 7.37-7.44 (m, 2H), 7.63 (d, J=5.52 Hz, 1H), 7.86 (s, 2H), 8.52 (d, J=5.27 Hz, 1H), 8.62 (s, 1H), 8.75 (d, J=1.00 Hz, 1H), 8.81 (brs, 2H), 8.87 (d, J=6.02 Hz, 2H), 8.92 (s, 1H), 10.81 (s, 1H), 13.84 (brs, 1H), 14.12 (s, 1H); ESIMS found for $C_{31}H_{22}N_8O$ m/z 523.2 (M+1).

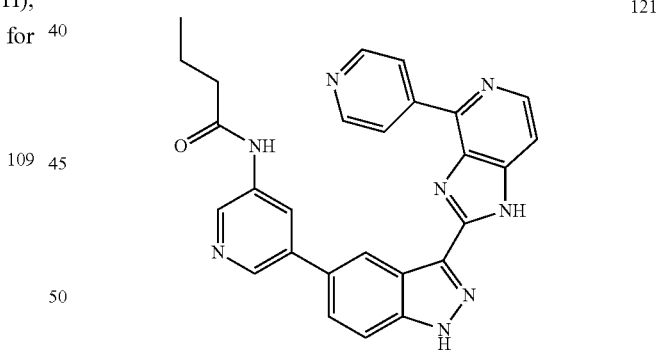

N-(5-(3-(4-(Pyridin-4-yl)-1H-imidazo[4,5-c]pyridin-2-yl)-1H-indazol-5-yl)pyridin-3-yl)butyramide 121.

White solid (14.8 mg, 0.03 mmol). $^1$H NMR (DMSO-$d_6$, 400 MHz) δ 0.97 (t, J=7.28 Hz, 3H), 1.629 (sxt, J=7.04 Hz, 2H), 2.43 (t, J=7.28 Hz, 2H), 7.65 (d, J=5.52 Hz, 1H), 7.88 (s, 2H), 8.53 (d, J=5.28 Hz, 1H), 8.70 (d, J=1.76 Hz, 1H), 8.73 (s, 1H), 8.81 (d, J=5.77 Hz, 1H), 8.91 (brs, 3H), 10.41 (brs, 1H), 13.88 (brs, 1H), 14.10 (brs, 1H); ESIMS found for $C_{27}H_{22}N_8O$ m/z 475.2 (M+1).

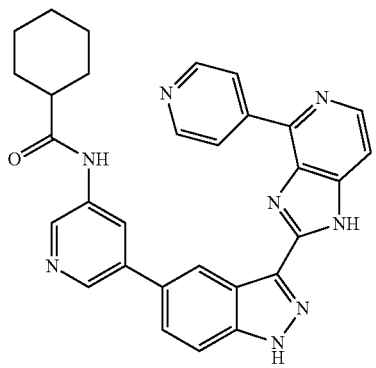

126

N-(5-(3-(4-(Pyridin-4-yl)-1H-imidazo[4,5-c]pyridin-2-yl)-1H-indazol-5-yl)pyridin-3-yl)cyclohexanecarboxamide 126.

White solid (15.8 mg, 0.03 mmol). $^1$H NMR (DMSO-d$_6$, 400 MHz) δ ppm 1.17-1.39 (m, 3H), 1.40-1.58 (m, 2H), 1.63-1.72 (m, 1H), 1.72-1.84 (m, 2H), 1.86-2.01 (m, 2H), 7.63 (d, J=5.52 Hz, 1H), 7.87 (s, 2H), 8.51 (d, J=5.52 Hz, 1H), 8.62-8.76 (m, 3H), 8.76-8.81 (m, 2H), 8.83-8.90 (m, 2H), 8.91 (s, 1H), 10.36 (s, 1H); ESIMS found for C$_{30}$H$_{26}$N$_8$O m/z 515.3 (M+1).

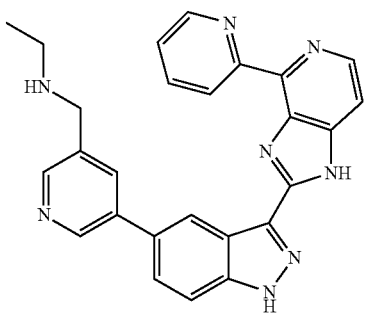

136

N-((5-(3-(4-(Pyridin-2-yl)-1H-imidazo[4,5-c]pyridin-2-yl)-1H-indazol-5-yl)pyridin-3-yl)methyl)ethanamine 136.

White solid (13.2 mg, 0.03 mmol). $^1$H NMR (DMSO-d$_6$, 400 MHz) δ ppm 1.31 (t, J=7.15 Hz, 3H), 2.97-3.15 (m, 2H), 4.32 (brs, 2H), 7.67-7.83 (m, 1H), 7.89 (d, J=8.52 Hz, 1H), 7.93-8.12 (m, 2H), 8.26 (t, J=4.52 Hz, 1H), 8.55 (d, J=6.27 Hz, 1H), 8.66 (brs, 1H), 8.81 (d, J=5.02 Hz, 2H), 8.97 (d, J=4.02 Hz, 1H), 9.07 (brs, 1H), 9.44-9.66 (m, 1H), 9.71-9.98 (m, 2H), 14.57 (brs, 1H), 15.04 (brs, 1H); ESIMS found for C$_{26}$H$_{22}$N$_8$ m/z 447.2 (M+1).

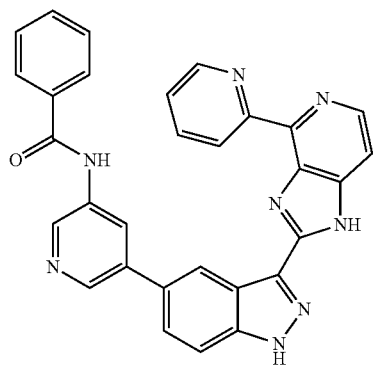

141

N-(5-(3-(4-(Pyridin-2-yl)-1H-imidazo[4,5-c]pyridin-2-yl)-1H-indazol-5-yl)pyridin-3-yl)benzamide 141.

White solid (12.9 mg, 0.03 mmol). $^1$H NMR (DMSO-d$_6$, 400 MHz) δ ppm 7.53-7.67 (m, 3H), 7.71 (t, J=7.52 Hz, 1H), 7.92-8.02 (m, 2H), 8.04 (d, J=6.27 Hz, 1H), 8.14 (d, J=7.28 Hz, 2H), 8.34 (dt, J=7.78 Hz, J=1.48 Hz, 1H), 8.57 (d, J=6.27 Hz, 1H), 8.89 (s, 1H), 8.95 (d, J=4.77 Hz, 1H), 9.01 (s, 1H), 9.17 (d, J=10.79 Hz, 2H), 9.61 (d, J=8.03 Hz, 1H), 11.18 (s, 1H), 14.57 (s, 1H), 15.05 (brs, 1H); ESIMS found for C$_{30}$H$_{20}$N$_8$O m/z 509.1 (M+1).

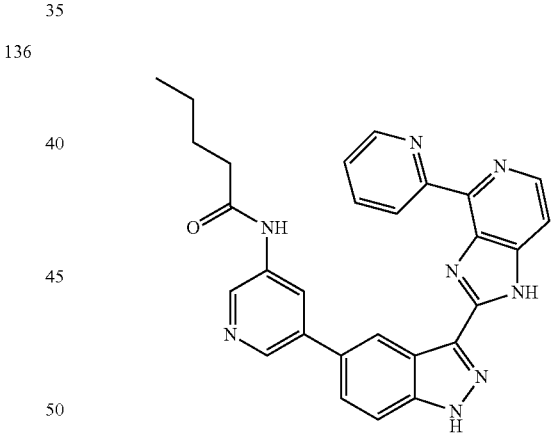

148

N-(5-(3-(4-(Pyridin-2-yl)-1H-imidazo[4,5-c]pyridin-2-yl)-1H-indazol-5-yl)pyridin-3-yl)pentanamide 148.

White solid (15.7 mg, 0.03 mmol). $^1$H NMR (DMSO-d$_6$, 300 MHz) δ 0.96 (t, J=7.53 Hz, 3H), 1.36-1.49 (m, 2H), 1.60-1.76 (m, 2H), 2.34-2.46 (m, 2H), 7.48-7.60 (m, 1H), 7.75-7.93 (m, 2H), 8.01-8.12 (m, 1H), 8.36-8.45 (m, 1H), 8.52 (d, J=4.90 Hz, 1H), 8.64 (brs, 1H), 8.71-8.82 (m, 1H), 8.81-8.89 (m, 1H), 8.90-8.98 (m, 1H), 10.01-10.13 (m, 1H); ESIMS found for C$_{28}$H$_{24}$N$_8$O m/z 489.1 (M+1).

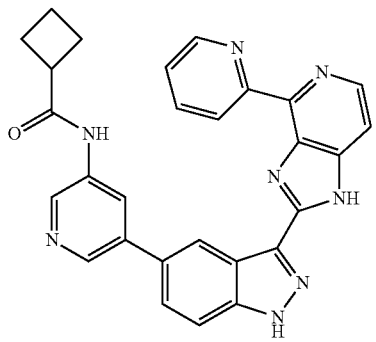

N-(5-(3-(4-(Pyridin-2-yl)-1H-imidazo[4,5-c]pyridin-2-yl)-1H-indazol-5-yl) pyridin-3-yl)cyclobutanecarboxamide 150.

White solid (17.8 mg, 0.04 mmol). $^1$H NMR (DMSO-$d_6$, 400 MHz) δ ppm 1.80-1.92 (m, 1H), 1.95-2.08 (m, 1H), 2.16-2.36 (m, 4H), 3.36-3.46 (m, 1H), 7.69-7.77 (m, 1H), 7.90 (s, 2H), 8.02 (d, J=6.27 Hz, 1H), 8.36 (t, J=7.53 Hz, 1H), 8.55 (d, J=6.27 Hz, 1H), 8.75 (s, 1H), 8.77 (s, 1H), 8.83 (s, 1H), 8.87 (brs, 1H), 8.96 (d, J=4.27 Hz, 1H), 9.56 (brs, 1H), 10.65 (brs, 1H), 14.53 (s, 1H), 15.00 (brs, 1H); ESIMS found for $C_{28}H_{22}N_8O$ m/z 487.2 (M+1).

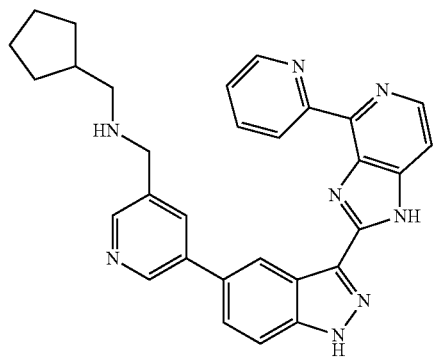

1-Cyclopentyl-N-((5-(3-(4-(pyridin-2-yl)-1H-imidazo[4,5-c]pyridin-2-yl)-1H-indazol-5-yl)pyridin-3-yl)methyl)methanamine 154.

White solid (21.5 mg, 0.04 mmol). $^1$H NMR (DMSO-$d_6$, 400 MHz) δ ppm 1.19-1.37 (m, 2H), 1.41-1.68 (m, 4H), 1.73-1.92 (m, 2H), 2.23-2.37 (m, 1H), 2.92-3.05 (m, 2H), 4.29-4.49 (m, 2H), 7.84 (dd, J=7.28 Hz, J=4.76 Hz, 1H), 7.96-8.03 (m, 1H), 8.03-8.13 (m, 2H), 8.40 (t, J=8.02 Hz, 1H), 8.62 (d, J=6.52 Hz, 1H), 8.84-8.99 (m, 2H), 9.03 (d, J=4.02 Hz, 1H), 9.25 (s, 1H), 9.57 (brs, 2H), 9.67 (d, J=7.52 Hz, 1H), 14.59 (brs, 1H), 15.09 (brs, 1H); ESIMS found for $C_{30}H_{28}N_8$ m/z 501.2 (M+1).

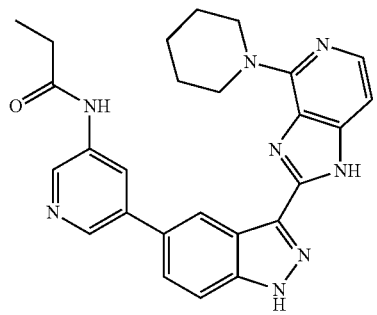

N-(5-(3-(4-(Piperidin-1-yl)-1H-imidazo[4,5-c]pyridin-2-yl)-1H-indazol-5-yl)pyridin-3-yl)propionamide 157.

White solid (28.8 mg, 0.06 mmol). $^1$H NMR (DMSO-$d_6$, 400 MHz) δ ppm 1.14 (t, J=7.53 Hz, 3H), 1.56-1.75 (m, 6H), 2.41 (q, J=7.53 Hz, 2H), 4.19 (brs, 4H), 6.80 (d, J=5.52 Hz, 1H), 7.76-7.86 (m, 2H), 8.17 (s, 1H), 8.55-8.60 (m, 1H), 8.63 (dd, J=4.14, 2.13 Hz, 2H), 8.75 (s, 1H), 10.25 (s, 1H), 13.20 (brs, 1H) 13.75 (brs, 1H); ESIMS found for $C_{26}H_{26}N_8O$ m/z 467.2 (M+1).

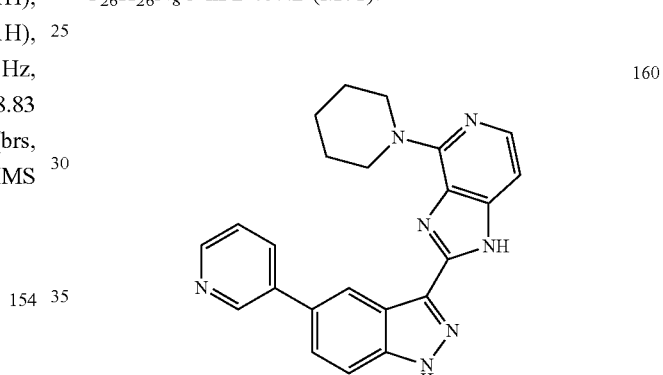

4-(Piperidin-1-yl)-2-(5-(pyridin-3-yl)-1H-indazol-3-yl)-1H-imidazo[4,5-c]pyridine 160.

Orange-yellow solid (72.9 mg, 0.184 mmol, 77.0% yield). $^1$H NMR (DMSO-$d_6$, 500 MHz) δ ppm 1.70 (br s, 6H), 4.20 (br d, J=5.21 Hz, 4H), 6.81 (d, J=5.49 Hz, 1H), 7.55 (dd, J=7.82, 4.80 Hz, 1H), 7.76-7.83 (m, 2H), 7.84-7.90 (m, 1H), 8.10-8.16 (m, 1H), 8.60 (dd, J=4.67, 1.37 Hz, 1H), 8.79 (s, 1H), 8.96 (d, J=2.20 Hz, 1H), 13.19 (s, 1H), 13.71 (s, 1H); ESIMS found for $C_{23}H_{21}N_7$ m/z 396.2 (M+1).

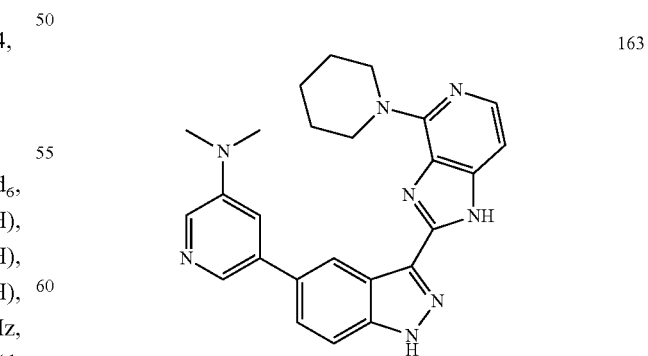

N,N-Dimethyl-5-(3-(4-(piperidin-1-yl)-1H-imidazo[4,5-c]pyridin-2-yl)-1H-indazol-5-yl)pyridin-3-amine 163.

White solid (17.1 mg, 0.04 mmol). $^1$H NMR (DMSO-$d_6$, 400 MHz) δ ppm 1.69 (s, 6H), 3.03 (s, 6H), 3.49-3.71 (m, 4H), 4.15-4.33 (m, 4H), 6.80-6.90 (m, 1H), 7.32 (t, J=2.26 Hz, 1H), 7.78 (t, J=5.76 Hz, 2H), 7.84 (dd, J=8.56 Hz, J=1.28 Hz, 1H), 8.13 (d, J=2.76 Hz, 1H), 8.23 (d, J=1.25 Hz, 1H), 8.70 (s, 1H), 13.36 (brs, 1H), 13.79 (brs, 1H); ESIMS found for $C_{25}H_{26}N_8$ m/z 439.1 (M+1).

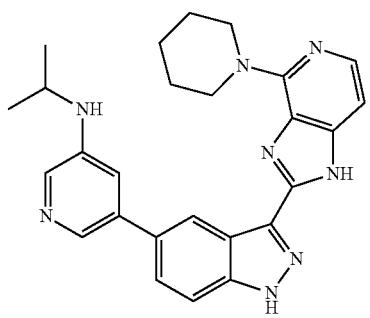

168

N-Isopropyl-5-(3-(4-(piperidin-1-yl)-1H-imidazo[4,5-c]pyridin-2-yl)-1H-indazol-5-yl)pyridin-3-amine 168.

White solid (13.6 mg, 0.03 mmol). $^1$H NMR (DMSO-$d_6$, 400 MHz) δ ppm 1.22 (d, J=6.27 Hz, 6H), 1.69-1.90 (m, 6H), 3.77-3.91 (m, 1H), 4.35 (brs, 4H), 6.92 (brs, 1H), 7.13 (d, J=6.78 Hz, 1H), 7.73 (d, J=6.78 Hz, 1H), 7.76 (brs, 1H), 7.87 (s, 2H), 8.07 (brs, 1H), 8.27 (s, 1H), 8.62 (s, 1H), 14.20 (s, 1H), 14.36 (s, 1H); ESIMS found for $C_{26}H_{28}N_8$ m/z 453.2 (M+1).

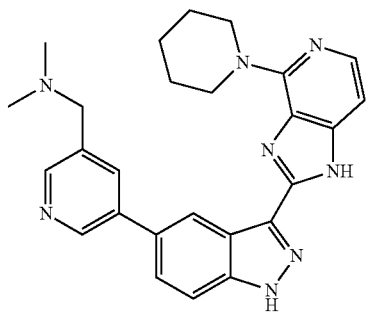

169

N,N-Dimethyl-1-(5-(3-(4-(piperidin-1-yl)-1H-imidazo[4,5-c]pyridin-2-yl)-1H-indazol-5-yl)pyridin-3-yl)methanamine 169.

White solid (25.8 mg, 0.06 mmol). $^1$H NMR (DMSO-$d_6$, 400 MHz) δ ppm 1.71 (brs, 6H), 2.25 (s, 6H), 3.57 (s, 2H), 4.20 (brs, 4H), 6.81 (d, J=5.52 Hz, 1H), 7.76-7.83 (m, 2H), 7.89 (dd, J=8.8 Hz, J=1.52 Hz, 1H), 8.05 (s, 1H), 8.14 (s, 2H), 8.50 (d, J=1.51 Hz, 1H), 8.78 (s, 1H), 8.89 (d, J=2.26 Hz, 1H), 13.21 (brs, 1H), 13.74 (brs, 1H); ESIMS found for $C_{26}H_{28}N_8$ m/z 453.3 (M+1).

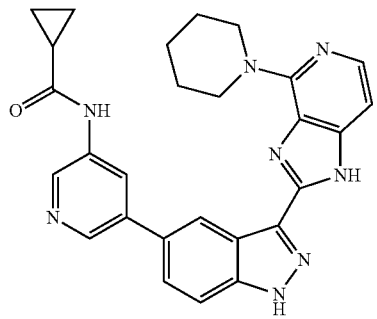

175

N-(5-(3-(4-(Piperidin-1-yl)-1H-imidazo[4,5-c]pyridin-2-yl)-1H-indazol-5-yl)pyridin-3-yl)cyclopropanecarboxamide 175.

White solid (30.4 mg, 0.06 mmol). $^1$H NMR (DMSO-$d_6$, 400 MHz) δ ppm 0.88 (d, J=6.02 Hz, 4H), 1.67 (brs, 6H), 1.85 (q, J=6.28 Hz, 1H), 4.18 (brs, 4H), 6.80 (d, J=5.52 Hz, 1H), 7.76-7.84 (m, 2H), 8.17 (s, 1H), 8.58-8.66 (m, 3H), 8.75 (s, 1H), 10.58 (s, 1H), 13.74 (brs, 1H); ESIMS found for $C_{27}H_{26}N_8O$ m/z 479.3 (M+1).

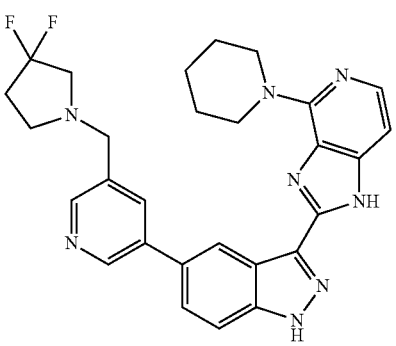

181

2-(5-(5-((3,3-Difluoropyrrolidin-1-yl)methyl)pyridin-3-yl)-1H-indazol-3-yl)-4-(piperidin-1-yl)-1H-imidazo[4,5-c]pyridine 181.

White solid (46.6 mg, 0.09 mmol). $^1$H NMR (DMSO-$d_6$, 400 MHz) δ ppm 1.70 (brs, 6H), 2.21-2.37 (m, 3H), 2.76 (t, J=6.78 Hz, 2H), 2.94 (t, J=13.30 Hz, 2H), 3.76 (s, 2H), 4.20 (brs, 4H), 6.81 (d, J=5.52 Hz, 1H), 7.75-7.83 (m, 2H), 7.88 (dd, J=8.78, 1.76 Hz, 1H), 8.05 (t, J=2.01 Hz, 1H), 8.18 (s, 1H), 8.53 (d, J=1.76 Hz, 1H), 8.78 (s, 1H), 8.89 (d, J=2.26 Hz, 1H), 13.21 (brs, 1H), 13.75 (brs, 1H); ESIMS found for $C_{28}H_{28}F_2N_8$ m/z 515.3 (M+1).

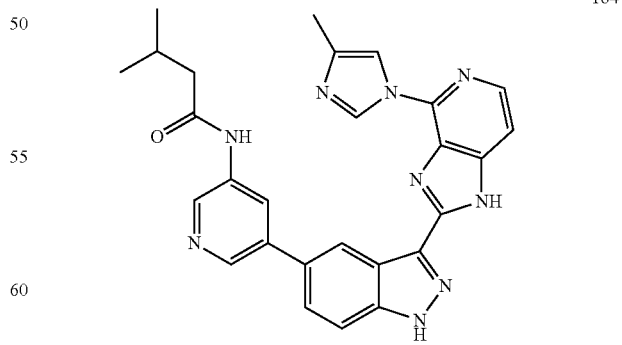

184

3-Methyl-N-(5-(3-(4-(4-methyl-1H-imidazol-1-yl)-1H-imidazo[4,5-c]pyridin-2-yl)-1H-indazol-5-yl)pyridin-3-yl)butanamide 184.

White solid (10.2 mg, 0.02 mmol). $^1$H NMR (DMSO-$d_6$, 400 MHz) δ ppm 0.97 (d, J=6.53 Hz, 6H), 2.07-2.19 (m, 1H), 2.33 (d, J=7.04 Hz, 2H), 2.44 (s, 3H), 7.73 (d, J=5.52 Hz, 1H), 7.82-7.97 (m, 2H), 8.35 (d, J=5.28 Hz, 1H), 8.68 (d, J=6.78 Hz, 2H), 8.83 (s, 1H), 8.87 (brs, 1H), 8.96 (brs, 1H), 10.19 (s, 1H), 10.78 (brs, 1H), 14.27 (brs, 1H), 14.32 (brs, 1H); ESIMS found for $C_{27}H_{25}N_9O$ m/z 492.1 (M+1).

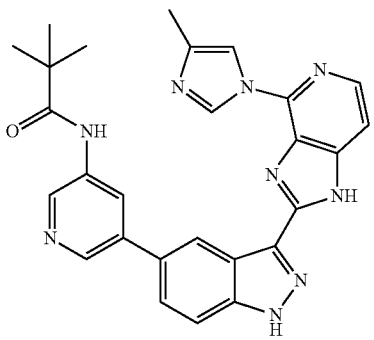

190

N-(5-(3-(4-(4-Methyl-1H-imidazol-1-yl)-1H-imidazo-[4,5-c]pyrimidin-2-yl)-1H-indazol-5-yl)pyridin-3-yl)pivalamide 190.

White solid (11.2 mg, 0.02 mmol). $^1$H NMR (DMSO-d$_6$, 400 MHz) δ ppm 1.31 (s, 9H), 2.44 (s, 3H), 7.74 (d, J=5.27 Hz, 1H), 7.86-7.96 (m, 2H), 8.35 (d, J=5.27 Hz, 1H), 8.71 (s, 1H), 8.88 (s, 1H), 8.94-9.03 (m, 2H), 9.19 (s, 1H), 10.19-10.32 (m, 2H), 14.30 (brs, 1H), 14.38 (s, 1H); ESIMS found for $C_{27}H_{25}N_9O$ m/z 492.2 (M+1).

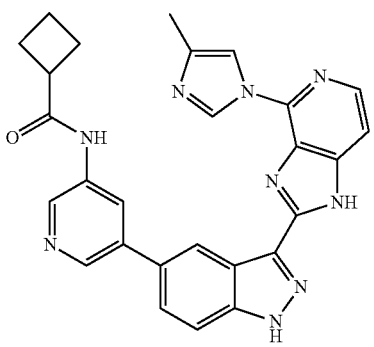

202

N-(5-(3-(4-(4-Methyl-1H-imidazol-1-yl)-1H-imidazo[4,5-c]pyrimidin-2-yl)-1H-indazol-5-yl)pyridin-3-yl)cyclobutanecarboxamide 202.

White solid (10.2 mg, 0.02 mmol) $^1$H NMR (DMSO-d$_6$ 400 MHz) δ ppm 1.73-1.91 (m, 1H), 1.92-2.08 (m, 1H), 2.09-2.36 (m, 5H), 2.44 (s, 3H) 7.74 (d, J=5.02 Hz, 1H), 7.82-8.01 (m, 2H) 8.36 (d, J=5.76 Hz, 1H), 8.73 (brs, 2H), 8.86 (s, 1H), 8.92 (d, J=1.0 Hz, 1H), 8.99 (s, 1H), 10.23 (s, 1H), 10.60 (brs, 1H), 14.29 (brs, 1H), ESIMS found for $C_{27}H_{23}N_9O$ m/z 490.3 (M+1).

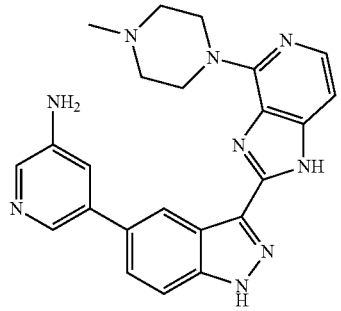

211

5-(3-(4-(4-Methylpiperazin-1-yl)-1H-imidazo[4,5-c]pyridin-2-yl)-1H-indazol-5-yl)pyridin-3-amine 211.

White solid (7.7 mg, 0.02 mmol). $^1$H NMR (DMSO-d$_6$, 400 MHz) δ ppm 2.84 (s, 3H), 3.49-3.68 (m, 4H), 5.25-5.55 (m, 2H), 5.86-6.21 (m, 2H), 7.04 (d, J=6.33 Hz, 1H), 7.56 (brs, 1H), 7.72-7.86 (m, 2H), 7.90 (d, J=5.77 Hz, 1H), 8.01 (d, J=2.51 Hz, 1H), 8.26 (s, 1H), 8.66 (s, 1H), 13.58 (brs, 1H) 13.96 (s, 1H); ESIMS found for $C_{23}H_{23}N_9$ m/z 426.1 (M+1).

212

4-(4-Methylpiperazin-1-yl)-2-(5-(pyridin-3-yl)-1H-indazol-3-yl)-1H-imidazo[4,5-c]pyridine 212.

White solid (35.5 mg, 0.086 mmol, 87.8% yield). $^1$H NMR (DMSO-d$_6$, 500 MHz) δ ppm 2.26 (s, 3H), 2.51-2.55 (m, 4H), 4.19 (br s, 4H), 6.86 (d, J=5.49 Hz, 1H), 7.56 (dd, J=7.96, 4.67 Hz, 1H), 7.79 (d, J=8.51 Hz, 1H), 7.82 (d, J=5.49 Hz, 1H), 7.87 (dd, J=8.64, 1.78 Hz, 1H), 8.14 (dt, J=7.96, 1.92 Hz, 1H), 8.61 (dd, J=4.80, 1.51 Hz, 1H), 8.76 (d, J=0.10 Hz, 1H), 8.97 (d, J=1.92 Hz, 1H), 13.26 (s, 1H), 13.70 (s, 1H); ESIMS found for $C_{23}H_{22}N_8$ m/z 411.2 (M+1).

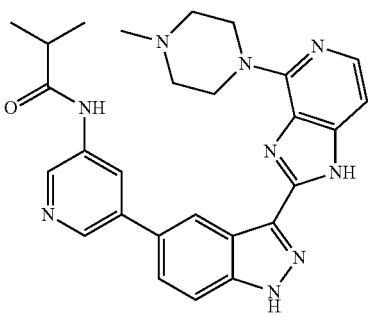

217

N-(5-(3-(4-(4-Methylpiperazin-1-yl)-1H-imidazo[4,5-c] pyridin-2-yl)-1H-indazol-5-yl)pyridin-3-yl)isobutyramide 217.

White solid (18.8 mg, 0.04 mmol). $^1$H NMR (CD$_3$OD, 400 MHz) δ ppm 1.27 (d, J=6.78 Hz, 6H), 2.73 (spt, J=6.81

Hz, 1H), 2.84 (s, 3H), 3.32-3.37 (m, 4H), 4.30-4.59 (m, 4H), 7.07 (d, J=5.77 Hz, 1H), 7.70-7.79 (m, 2H), 7.86 (d, J=5.77 Hz, 1H), 8.33-8.51 (m, 1H), 8.55-8.64 (m, 2H), 8.66 (d, J=2.01 Hz, 1H), 8.68 (s, 1H); ESIMS found for C$_{27}$H$_{29}$N$_9$O m/z 496.2 (M+1).

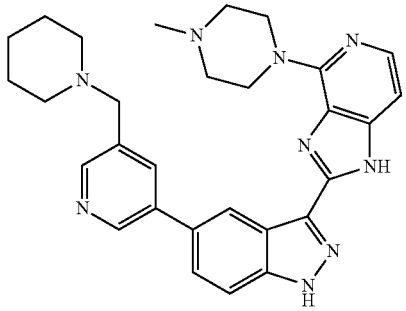

223

4-(4-Methylpiperazin-1-yl)-2-(5-(5-(piperidin-1-ylmethyl)pyridin-3-yl)-1H-indazol-3-yl)-1H-imidazo[4,5-c]pyridine 223.

White solid (11.2 mg, 0.02 mmol). $^1$H NMR (DMSO-d$_6$, 400 MHz) δ ppm 1.31-1.49 (m, 1H), 1.66-1.76 (m, 1H), 1.76-1.91 (m, 3H), 2.85 (s, 3H), 2.91-3.06 (m, 2H), 3.64-3.73 (m, 2H), 3.90-4.09 (m, 2H), 4.47 (brs, 2H), 5.34-5.54 (m, 2H), 5.51-5.54 (m, 1H), 7.26 (d, J=6.27 Hz, 1H), 7.81-7.93 (m, 2H), 7.99 (dd, J=8.78, 1.51 Hz, 1H), 8.63-8.76 (m, 2H), 8.77-8.86 (m, 1H), 9.12 (s, 1H), 11.20 (brs, 1H), 11.60 (brs, 1H), 14.25 (brs, 1H), 14.41 (brs, 1H); ESIMS found for C$_{29}$H$_{33}$N$_9$ m/z 508.2 (M+1).

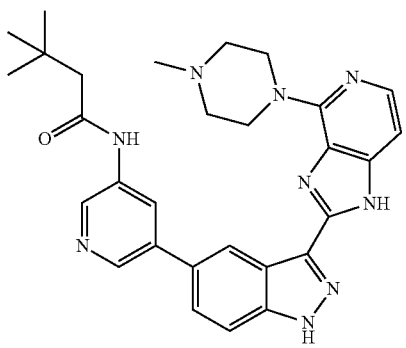

224

3,3-Dimethyl-N-(5-(3-(4-(4-methylpiperazin-1-yl)-1H-imidazo[4,5-c]pyridin-2-yl)-1H-indazol-5-yl)pyridin-3-yl)butanamide 224.

White solid (30.4 mg, 0.06 mmol). $^1$H NMR (DMSO-d$_6$, 400 MHz) δ ppm 1.07 (s, 9H), 2.41 (s, 2H), 2.89 (brs, 3H), 3.42-3.53 (m, 2H), 3.70-3.80 (m, 2H), 3.91-4.03 (m, 2H), 5.33-5.46 (m, 2H), 7.26 (d, J=6.53 Hz, 1H), 7.80-7.94 (m, 3H), 8.61 (s, 1H), 8.92 (brs, 1H), 8.96 (s, 1H), 9.14 (brs, 1H), 11.29 (brs, 1H), 11.49 (brs, 1H), 14.31 (s, 1H), 14.49 (s, 1H); ESIMS found for C$_{29}$H$_{33}$N$_9$O m/z 524.2 (M+1).

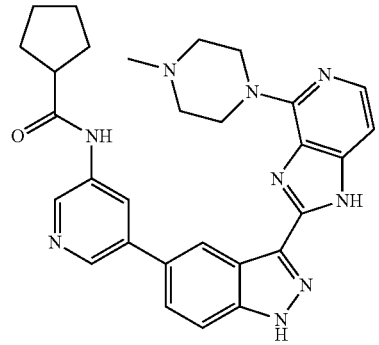

229

N-(5-(3-(4-(4-Methylpiperazin-1-yl)-1H-imidazo[4,5-c]pyridin-2-yl)-1H-indazol-5-yl)pyridin-3-yl)cyclopentanecarboxamide 229.

White solid (19.4 mg, 0.04 mmol). $^1$H NMR (DMSO-d$_6$, 400 MHz) δ ppm 1.52-1.65 (m, 2H), 1.65-1.84 (m, 4H), 1.85-1.97 (m, 2H), 2.23 (s, 3H), 2.42-2.49 (m, 4H), 2.86 (quin, J=7.91 Hz, 2H), 4.20 (brs, 4H), 6.86 (d, J=5.77 Hz, 1H), 7.79-7.82 (m, 2H), 7.83 (s, 1H), 8.17 (s, 1H), 8.59 (t, J=2.01 Hz, 1H), 8.62 (d, J=1.76 Hz, 1H), 8.68 (d, J=2.01 Hz, 1H), 8.70 (s, 1H), 10.27 (s, 1H), 13.27 (brs, 1H), 13.79 (brs, 1H); ESIMS found for C$_{29}$H$_{31}$N$_9$O m/z 522.3 (M+1).

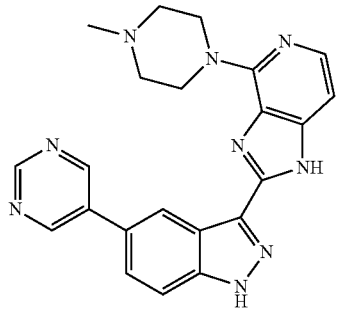

234

4-(4-Methylpiperazin-1-yl)-2-(5-(pyrimidin-5-yl)-1H-indazol-3-yl)-1H-imidazo[4,5-c]pyridine 234.

White solid (23.5 mg, 0.06 mmol). $^1$H NMR (DMSO-d$_6$, 400 MHz) δ ppm 2.85 (s, 3H), 3.61-3.70 (m, 4H), 3.88-4.03 (m, 2H), 5.30-5.45 (m, 2H), 7.28 (d, J=6.78 Hz, 1H), 7.83-7.87 (m, 1H), 7.89 (s, 1H), 7.92-7.98 (m, 1H), 8.63 (s, 1H), 9.22-9.28 (m, 3H), 14.24 (brs, 1H), 14.48 (brs, 1H); ESIMS found for C$_{22}$H$_{22}$N$_9$ m/z 412.1 (M+1).

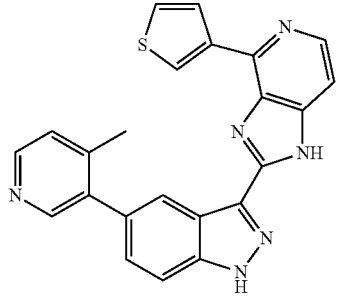

239

2-(5-(4-Methylpyridin-3-yl)-1H-indazol-3-yl)-4-(thiophen-3-yl)-1H-imidazo[4,5-c]pyridine 239.

White solid (39.4 mg, 0.10 mmol). $^1$H NMR (DMSO-d$_6$, 400 MHz) δ ppm 2.43 (s, 3H), 7.41-7.48 (m, 2H), 7.60 (d, J=8.78 Hz, 1H), 7.64 (dd, J=4.89, 3.14 Hz, 1H), 7.82 (d, J=8.78 Hz, 1H), 8.30 (d, J=4.77 Hz, 1H), 8.35 (d, J=5.52 Hz, 1H), 8.50 (d, J=5.02 Hz, 1H), 8.56 (s, 1H), 8.60 (s, 1H), 8.87 (d, J=1.76 Hz, 1H), 14.01 (brs, 1H); ESIMS found for C₂₃H₁₆N₆S m/z 409.0 (M+1).

242

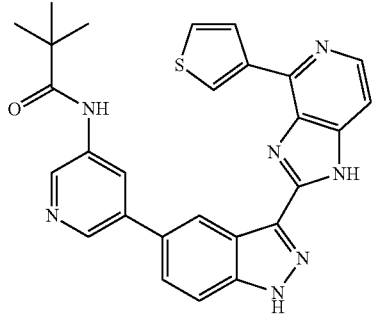

N-(5-(3-(4-(Thiophen-3-yl)-1H-imidazo[4,5-c]pyridin-2-yl)-1H-indazol-5-yl) pyridin-3-yl)pivalamide 242.

White solid (22.8 mg, 0.05 mmol). ¹H NMR (DMSO-d₆, 400 MHz) δ ppm 1.32 (s, 9H), 7.91 (d, J=6.02 Hz, 1H), 7.93-8.01 (m, 3H), 8.49 (d, J=6.53 Hz, 1H), 8.52 (d, J=4.77 Hz, 1H), 8.85 (s, 1H), 8.90 (s, 1H), 8.94 (d, J=1.51 Hz, 1H), 9.11 (s, 1H), 9.35 (brs, 1H), 10.04 (brs, 1H), 14.43 (s, 1H), 14.85 (brs, 1H); ESIMS found for C₂₇H₂₃N₇OS m/z 494.2 (M+1).

244

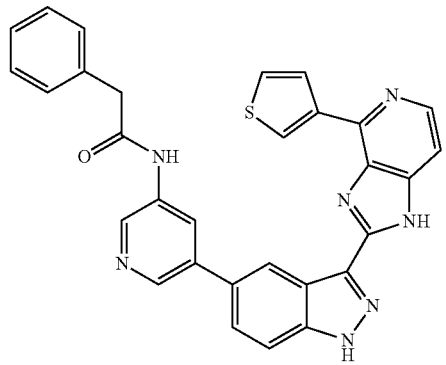

2-Phenyl-N-(5-(3-(4-(thiophen-3-yl)-1H-imidazo[4,5-c]pyridin-2-yl)-1H-indazol-5-yl)pyridin-3-yl)acetamide 244.

White solid (11.9 mg, 0.02 mmol). ¹H NMR (DMSO-d₆, 400 MHz) δ ppm 3.85 (s, 2H), 7.25-7.32 (m, 1H), 7.36 (t, J=7.40 Hz, 2H), 7.40-7.46 (m, 2H), 7.79 (dd, J=5.14, 2.89 Hz, 1H), 7.86 (d, J=6.27 Hz, 1H), 7.90 (s, 2H), 8.44 (d, J=6.53 Hz, 1H), 8.54 (d, J=5.02 Hz, 1H), 8.74 (s, 1H), 8.83 (s, 1H), 8.87 (brs, 2H), 9.28 (d, J=1.25 Hz, 1H), 11.15 (brs, 1H), 14.40 (s, 1H), 14.78 (brs, 1H); ESIMS found for C₃₀H₂₁N₇OS m/z 528.1 (M+1).

245

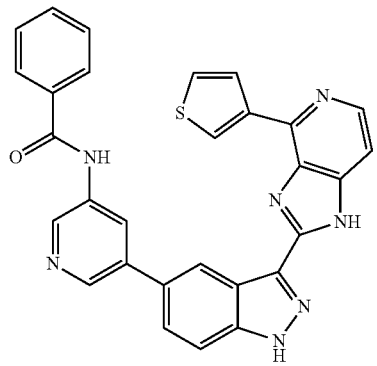

N-(5-(3-(4-(Thiophen-3-yl)-1H-imidazo[4,5-c]pyridin-2-yl)-1H-indazol-5-yl)pyridin-3-yl)benzamide 245.

White solid (40.2 mg, 0.08 mmol). ¹H NMR (DMSO-d₆, 400 MHz) δ ppm 7.43-7.49 (m, 1H), 7.57-7.69 (m, 4H), 7.83-7.90 (m, 1H), 7.90-7.96 (m, 1H), 8.05-8.11 (m, 2H), 8.17 (s, 1H), 8.28-8.34 (m, 1H), 8.35-8.40 (m, 1H), 8.77-8.84 (m, 2H), 8.93-9.04 (m, 3H), 10.67 (d, J=3.01 Hz, 1H), 13.64 (brs, 1H), 14.00 (brs, 1H); ESIMS found for C₂₉H₁₉N₇OS m/z 514.2 (M+1).

251

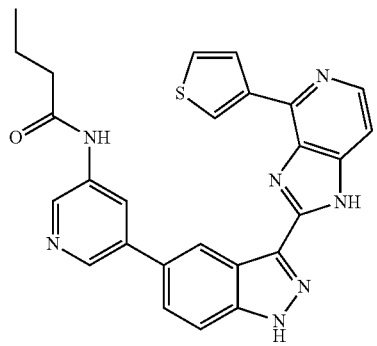

N-(5-(3-(4-(Thiophen-3-yl)-1H-imidazo[4,5-c]pyridin-2-yl)-1H-indazol-5-yl)pyridin-3-yl)butyramide 251.

White solid (14.9 mg, 0.03 mmol). ¹H NMR (DMSO-d₆, 400 MHz) δ ppm 0.97 (t, J=7.40 Hz, 3H), 1.69 (sxt, J=7.24 Hz, 2H), 2.42 (t, J=7.28 Hz, 3H), 7.45 (d, J=5.52 Hz, 1H), 7.68 (dd, J=4.89, 2.89 Hz, 1H), 7.86 (s, 2H), 8.26 (s, 1H), 8.32 (d, J=5.02 Hz, 1H), 8.37 (d, J=5.27 Hz, 1H), 8.66 (brs, 1H), 8.70 (d, J=1.76 Hz, 1H), 8.72 (d, J=2.01 Hz, 1H), 8.88 (s, 1H), 8.96 (d, J=2.76 Hz, 1H), 10.33 (s, 1H); ESIMS found for C₂₆H₂₁N₇OS m/z 480.2 (M+1).

253

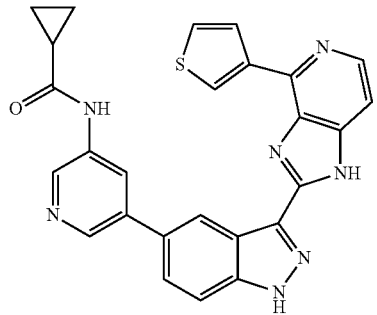

N-(5-(3-(4-(Thiophen-3-yl)-1H-imidazo[4,5-c]pyridin-2-yl)-1H-indazol-5-yl)pyridin-3-yl)cyclopropanecarboxamide 253.

White solid (9.0 mg, 0.02 mmol). ¹H NMR (DMSO-d₆, 400 MHz) δ ppm 0.92 (d, J=5.77 Hz, 4H), 1.87-1.99 (m, 1H), 7.84-8.01 (m, 4H), 8.44-8.53 (m, 2H), 8.77-8.88 (m, 4H), 9.26-9.36 (m, 1H), 11.03 (brs, 1H), 14.40 (s, 1H), 14.84 (brs, 1H); ESIMS found for $C_{26}H_{19}N_7OS$ m/z 478.1 (M+1).

255

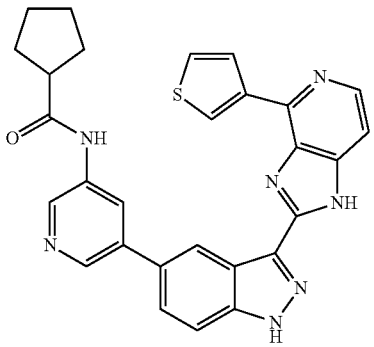

N-(5-(3-(4-(Thiophen-3-yl)-1H-imidazo[4,5-c]pyridin-2-yl)-1H-indazol-5-yl)pyridin-3-yl)cyclopentanecarboxamide 255.

White solid (14.5 mg, 0.03 mmol). $^1$H NMR (DMSO-d$_6$, 400 MHz) δ ppm 1.53-1.75 (m, 4H), 1.76-1.88 (m, 2H), 1.90-2.02 (m, 2H), 2.99 (quin, J=8.00 Hz, 1H), 7.91 (d, J=6.53 Hz, 1H), 7.95 (s, 2H), 7.99 (dd, J=4.64, 3.14 Hz, 1H), 8.47 (d, J=6.53 Hz, 1H), 8.59 (d, J=5.27 Hz, 1H), 8.84 (s, 1H), 9.01 (s, 1H), 9.04 (s, 1H), 9.12 (s, 1H), 9.39 (brs, 1H), 11.21 (s, 1H), 14.53 (brs, 1H), 14.89 (brs, 1H); ESIMS found for $C_{28}H_{23}N_7OS$ m/z 506.1 (M+1).

357

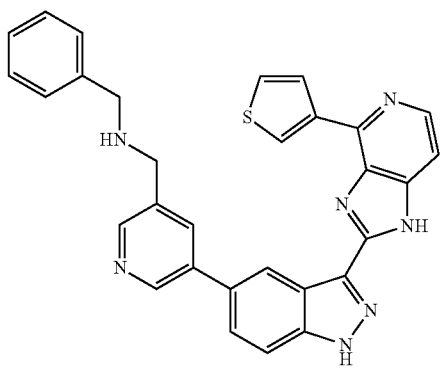

N-Benzyl-1-(5-(3-(4-(thiophen-3-yl)-1H-imidazo[4,5-c]pyridin-2-yl)-1H-indazol-5-yl)pyridin-3-yl)methanamine 257.

White solid (33.5 mg, 0.07 mmol). $^1$H NMR (DMSO-d$_6$, 400 MHz) δ 4.28 (s, 2H), 4.37 (s, 2H), 7.36-7.51 (m, 4H), 7.54-7.62 (m, 2H), 7.67 (dd, J=4.89, 2.89 Hz, 1H), 7.89 (d, J=8.8 Hz, 1H), 7.96 (dd, J=9.04 Hz, J=1.52 Hz, 1H), 8.33 (d, J=6.02 Hz, 1H), 8.37 (d, J=5.27 Hz, 1H), 8.51 (br. s., 1H), 8.75 (d, J=1.25 Hz, 1H), 8.96 (s, 1H), 9.04 (d, J=3.0 Hz, 1H), 9.09 (d, J=1.51 Hz, 1H), 13.69 (s, 1H), 14.10 (s, 1H); ESIMS found for $C_{30}H_{23}N_7S$ m/z 514.2 (M+1).

266

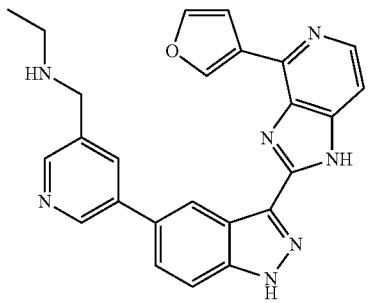

N-((5-(3-(4-(Furan-3-yl)-1H-imidazo[4,5-c]pyridin-2-yl)-1H-indazol-5-yl)pyridin-3-yl)methyl)ethanamine 266.

White solid (40.7 mg, 0.09 mmol). $^1$H NMR (DMSO-d$_6$, 400 MHz) 1H NMR (400 MHz, DMSO) δ 1.30 (t, J=7.28 Hz, 3H), 3.05 (q, J=7.03 Hz, 2H), 4.31 (s, 2H), 7.42 (s, 1H), 7.45 (d, J=5.52 Hz, 1H), 7.83-7.92 (m, 2H), 7.96 (dd, J=8.76 Hz, J=1.48 Hz, 1H), 8.35 (d, J=5.52 Hz, 1H), 8.57 (s, 1H), 8.79 (d, J=1.26 Hz, 1H), 8.92 (s, 1H), 8.99 (s, 1H), 9.08 (d, J=2.01 Hz, 1H), 9.64 (brs, 2H), 13.65 (brs, 1H), 14.18 (s, 1H); ESIMS found for $C_{25}H_{21}N_7O$ m/z 436.2 (M+1).

272

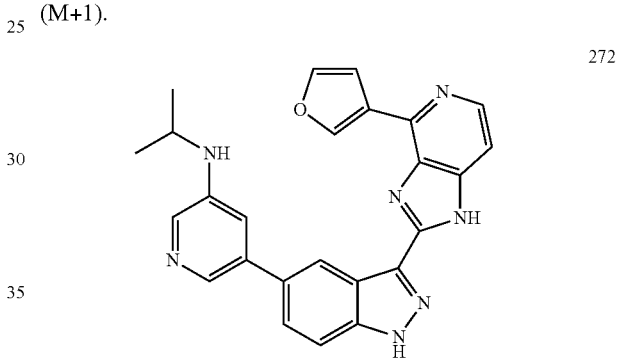

5-(3-(4-(Furan-3-yl)-1H-imidazo[4,5-c]pyridin-2-yl)-1H-indazol-5-yl)-N-isopropylpyridin-3-amine 272.

White solid (23.2 mg, 0.05 mmol). $^1$H NMR (DMSO-d$_6$, 400 MHz) δ ppm 1.22 (d, J=6.27 Hz, 5H), 3.74 (spt, J=7.03 Hz, 1H), 5.92 (d, J=7.78 Hz, 1H), 7.22 (t, J=2.26 Hz, 1H), 7.40 (d, J=1.51 Hz, 1H), 7.42 (d, J=5.27 Hz, 1H), 7.81 (d, J=1.00 Hz, 2H), 7.85 (t, J=1.63 Hz, 1H), 8.01 (d, J=2.51 Hz, 1H), 8.14 (d, J=1.76 Hz, 1H), 8.34 (d, J=5.52 Hz, 1H), 8.78 (s, 1H), 8.92 (d, J=1.00 Hz, 1H), 13.58 (s, 1H), 13.98 (s, 1H); ESIMS found for $C_{25}H_{22}N_7O$ m/z 436.3 (M+1).

278

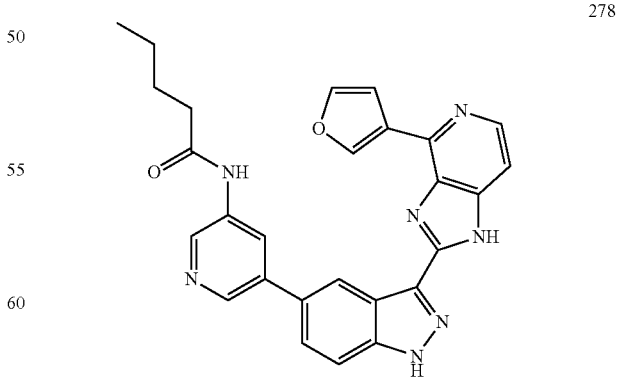

N-(5-(3-(4-(Furan-3-yl)-1H-imidazo[4,5-c]pyridin-2-yl)-1H-indazol-5-yl)pyridin-3-yl)pentanamide 278.

White solid (36.6 mg, 0.08 mmol). $^1$H NMR (DMSO-d$_6$, 400 MHz) δ ppm 0.92 (t, J=7.40 Hz, 3H), 1.37 (sxt, J=7.52

Hz, 2H), 1.63 (quin, J=7.28, 2H), 2.42 (t, J=7.40 Hz, 2H), 7.53 (br. s., 2H), 7.82-7.93 (m, 3H), 8.37 (d, J=5.77 Hz, 1H), 8.62 (s, 1H), 8.70 (d, J=1.76 Hz, 1H), 8.73 (d, J=2.01 Hz, 1H), 8.82 (s, 1H), 8.97 (brs, 1H), 10.34 (s, 1H), 13.88 (brs, 1H), 14.10 (brs, 1H); ESIMS found for $C_{27}H_{23}N_7O_2$ m/z 478.2 (M+1).

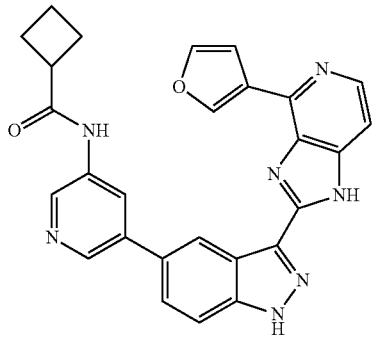

280

N-(5-(3-(4-(Furan-3-yl)-1H-imidazo[4,5-c]pyridin-2-yl)-1H-indazol-5-yl)pyridin-3-yl)cyclobutanecarboxamide 280.

White solid (11.8 mg, 0.02 mmol). $^1$H NMR (DMSO-d$_6$, 400 MHz) δ ppm 1.80-1.91 (m, 1H), 1.94-2.09 (m, 1H), 2.13-2.24 (m, 2H), 2.25-2.37 (m, 2H), 3.40 (quin, J=8.56 Hz, 1H), 7.83 (d, J=6.27 Hz, 1H), 7.89 (s, 3H), 8.06 (s, 1H), 8.41 (d, J=6.52 Hz, 1H), 8.74 (s, 1H), 8.98 (s, 2H), 9.05 (brs, 1H), 9.28 (s, 1H), 10.93 (s, 1H), 14.46 (brs, 1H), 14.78 (brs, 1H); ESIMS found for $C_{27}H_{21}N_7O_2$ m/z 476.2 (M+1).

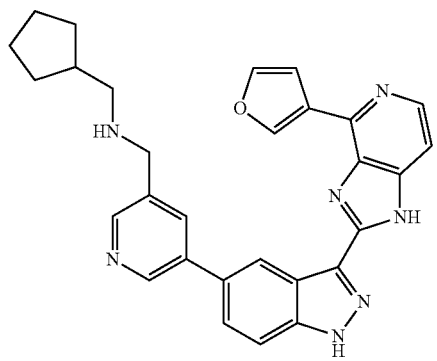

284

1-Cyclopentyl-N-((5-(3-(4-(furan-3-yl)-1H-imidazo[4,5-c]pyridin-2-yl)-1H-indazol-5-yl)pyridin-3-yl)methyl)methanamine 284.

White solid (14.9 mg, 0.03 mmol). $^1$H NMR (DMSO-d$_6$, 400 MHz) δ ppm 1.17-1.38 (m, 2H), 1.43-1.70 (m, 4H), 1.72-1.89 (m, 2H), 2.30 (dd, J=15.43, 8.16 Hz, 1H), 2.92-3.07 (m, 2H), 4.39 (t, J=5.52 Hz, 2H), 7.82-7.94 (m, 2H), 7.94-8.08 (m, 2H), 8.12 (s, 1H), 8.47 (d, J=6.53 Hz, 1H), 8.85 (brs, 1H), 8.89 (brs, 2H), 9.24 (s, 1H), 9.43 (s, 1H), 9.46-9.60 (m, 2H), 14.49 (brs, 1H), 14.86 (brs, 1H); ESIMS found for $C_{29}H_{27}N_7O$ m/z 490.2 (M+1).

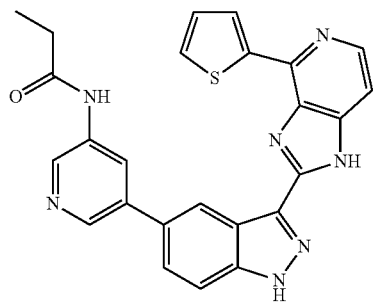

287

N-(5-(3-(4-(Thiophen-2-yl)-1H-imidazo[4,5-c]pyridin-2-yl)-1H-indazol-5-yl)pyridin-3-yl)propionamide 287.

White solid (6.0 mg, 0.01 mmol). $^1$H NMR (DMSO-d$_6$, 400 MHz) δ ppm 1.15 (t, J=7.53 Hz, 3H), 2.46 (q, J=7.52 Hz, 2H), 7.29 (dd, J=5.02, 3.76 Hz, 1H), 7.44 (d, J=5.27 Hz, 1H), 7.69 (dd, J=5.04 Hz, J=1.00 Hz, 1H), 7.87 (s, 2H), 8.30 (d, J=5.52 Hz, 1H), 8.66-8.71 (m, 2H), 8.71-8.74 (m, 1H), 8.75 (d, J=2.76 Hz, 1H), 8.92 (s, 1H), 10.41 (s, 1H), 13.68 (brs, 1H), 14.07 (brs, 1H); ESIMS found for $C_{25}H_{19}N_7OS$ m/z 466.2 (M+1).

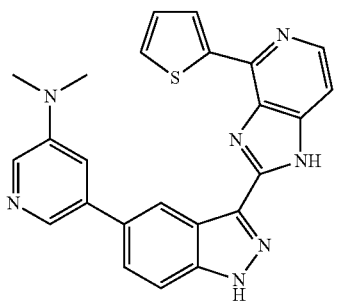

293

N,N-Dimethyl-5-(3-(4-(thiophen-2-yl)-1H-imidazo[4,5-c]pyridin-2-yl)-1H-indazol-5-yl)pyridin-3-amine 293.

White solid (11.4 mg, 0.03 mmol). $^1$H NMR (DMSO-d$_6$, 400 MHz) δ ppm 3.11 (s, 6H), 7.22-7.27 (m, 1H), 7.45 (d, J=5.52 Hz, 1H), 7.54 (brs, 1H), 7.73 (d, J=5.02 Hz, 1H), 7.84 (d, J=8.56 Hz, 1H), 7.93 (dd, J=8.53 Hz, J=1.48 Hz, 1H), 8.13 (s, 1H), 8.21 (d, J=2.26 Hz, 1H), 8.31 (d, J=5.52 Hz, 1H), 8.38 (s, 1H), 8.73 (d, J=3.26 Hz, 1H), 8.95 (s, 1H), 13.68 (brs, 1H), 13.98 (s, 1H); ESIMS found for $C_{24}H_{19}N_7S$ m/z 438.1 (M+1).

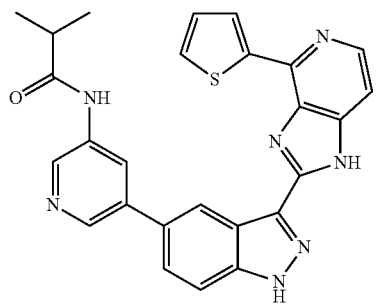

295

N-(5-(3-(4-(Thiophen-2-yl)-1H-imidazo[4,5-c]pyridin-2-yl)-1H-indazol-5-yl)pyridin-3-yl)isobutyramide 295.

White solid (32.4 mg, 0.07 mmol). $^1$H NMR (DMSO-d$_6$, 400 MHz) δ ppm 1.18 (d, J=6.78 Hz, 6H), 2.75 (spt, J=6.76

Hz, 1H), 7.39 (t, J=4.39 Hz, 1H), 7.65 (d, J=5.77 Hz, 1H), 7.89 (s, 2H), 7.95 (brs, 1H), 8.37 (d, J=6.02 Hz, 1H), 8.72-8.77 (m, 2H), 8.78-8.84 (m, 2H), 8.93 (s, 1H), 10.55 (s, 1H), 14.27 (brs, 2H); ESIMS found for $C_{26}H_{21}N_7OS$ m/z 480.1 (M+1).

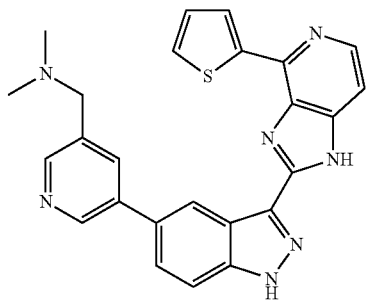

299

N,N-Dimethyl-1-(5-(3-(4-(thiophen-2-yl)-1H-imidazo[4,5-c]pyridin-2-yl)-1H-indazol-5-yl)pyridin-3-yl)methanamine 299.

White solid (32.9 mg, 0.07 mmol). $^1$H NMR (DMSO-$d_6$, 400 MHz) δ ppm 2.35 (s, 6H), 3.75 (brs, 2H), 7.27 (dd, J=5.00 Hz, J=3.52 Hz, 1H), 7.44 (d, J=5.52 Hz, 1H), 7.73 (dd, J=5.02, 1.00 Hz, 1H), 7.83-7.90 (m, 1H), 7.93 (dd, J=8.52 Hz, J=1.28 Hz, 1H), 8.14 (s, 1H), 8.17 (s, 1H), 8.31 (d, J=5.52 Hz, 1H), 8.58 (d, J=1.51 Hz, 1H), 8.75 (dd, J=3.51, 1.00 Hz, 1H), 8.96 (s, 1H), 8.99 (d, J=2.01 Hz, 1H), 13.67 (s, 1H), 13.99 (s, 1H); ESIMS found for $C_{25}H_{21}N_7S$ m/z 452.2 (M+1).

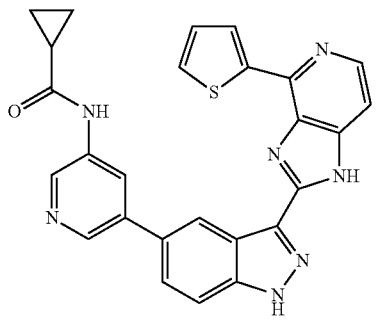

305

N-(5-(3-(4-(Thiophen-2-yl)-1H-imidazo[4,5-c]pyridin-2-yl)-1H-indazol-5-yl)pyridin-3-yl)cyclopropanecarboxamide 305.

White solid (13.7 mg, 0.03 mmol). $^1$H NMR (DMSO-$d_6$, 400 MHz) δ ppm 0.87-0.97 (m, 4H), 1.90-1.99 (m, 1H), 7.43-7.49 (m, 1H), 7.74-7.80 (m, 1H), 7.93 (d, J=1.00 Hz, 2H), 8.05-8.10 (m, 1H), 8.43 (d, J=6.27 Hz, 1H), 8.73 (d, J=4.02 Hz, 2H), 8.83 (s, 2H), 8.86 (brs, 1H), 8.96 (s, 1H), 11.06 (brs, 1H), 14.34 (s, 1H), 14.66 (brs, 1H); ESIMS found for $C_{26}H_{19}N_7OS$ m/z 478.2 (M+1).

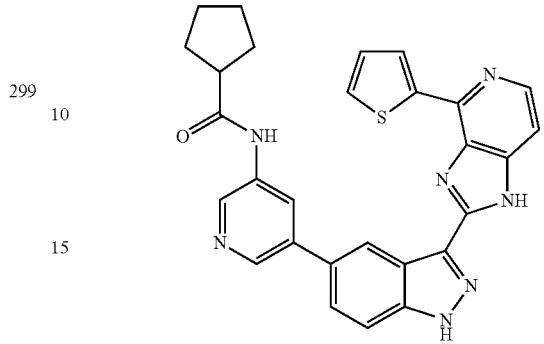

307

N-(5-(3-(4-(Thiophen-2-yl)-1H-imidazo[4,5-c]pyridin-2-yl)-1H-indazol-5-yl)pyridin-3-yl)cyclopentanecarboxamide 307.

White solid (14.2 mg, 0.03 mmol). $^1$H NMR (DMSO-$d_6$, 400 MHz) δ ppm 1.55-1.65 (m, 2H), 1.66-1.74 (m, 2H), 1.75-1.86 (m, 2H), 1.91-2.02 (m, 2H), 2.99 (spt, J=7.76 Hz, 1H), 7.44 (t, J=4.39 Hz, 1H), 7.77 (d, J=6.27 Hz, 1H), 7.90 (s, 2H), 8.19 (d, J=5.27 Hz, 1H), 8.40 (d, J=6.53 Hz, 1H), 8.78 (d, J=3.26 Hz, 1H), 8.87 (s, 1H), 8.90 (s, 1H), 8.98 (s, 1H), 9.05 (s, 1H), 11.11 (brs, 1H), 14.42 (s, 1H), 14.74 (brs, 1H); ESIMS found for $C_{28}H_{23}N_7OS$ m/z 506.1 (M+1).

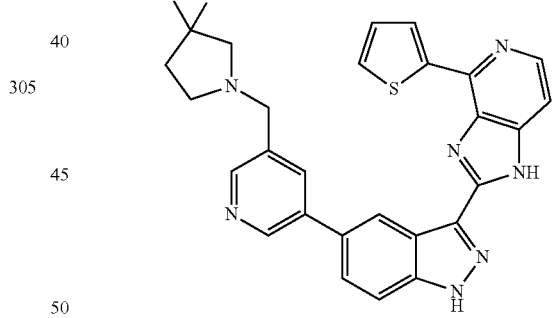

311

2-(5-(5-((3,3-Difluoropyrrolidin-1-yl)methyl)pyridin-3-yl)-1H-indazol-3-yl)-4-(thiophen-2-yl)-1H-imidazo[4,5-c]pyridine 311.

White solid (60.5 mg, 0.12 mmol). $^1$H NMR (DMSO-$d_6$, 400 MHz) δ ppm 2.20-2.31 (m, 2H), 2.79 (t, J=7.03 Hz, 2H), 2.98 (t, J=13.30 Hz, 2H), 3.82 (s, 2H), 7.28 (dd, J=5.02, 3.76 Hz, 1H), 7.44 (d, J=5.52 Hz, 1H), 7.73 (dd, J=5.02, 1.25 Hz, 1H), 7.86 (d, J=8.53 Hz, 1H), 7.92 (dd, J=8.76 Hz, J=1.48 Hz, 1H), 8.13 (t, J=2.01 Hz, 1H), 8.17 (s, 1H), 8.31 (d, J=5.52 Hz, 1H), 8.58 (d, J=1.76 Hz, 1H), 8.76 (d, J=2.76 Hz, 1H), 8.97 (d, J=1.76 Hz, 2H), 13.67 (brs, 1H), 13.98 (brs, 1H); ESIMS found for $C_{27}H_{21}F_2N_7S$ m/z 514.2 (M+1).

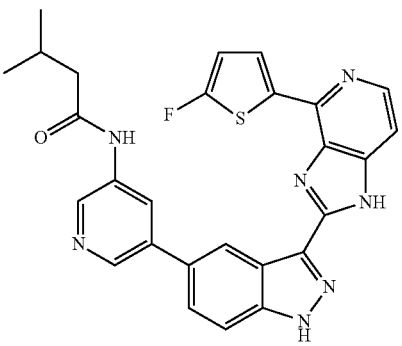

N-(5-(3-(4-(5-Fluorothiophen-2-yl)-1H-imidazo[4,5-c]pyridin-2-yl)-1H-indazol-5-yl)pyridin-3-yl)-3-methylbutanamide 314.

White solid (2.7 mg, 0.005 mmol). $^1$H NMR (CD$_3$OD, 400 MHz) δ ppm 1.06 (d, J=6.65 Hz, 6H), 2.24 (non, J=6.92 Hz, 1H), 2.43 (d, J=7.15 Hz, 2H), 6.96 (d, J=3.76 Hz, 1H), 7.80 (d, J=6.65 Hz, 1H), 7.84-7.94 (m, 2H), 8.16 (t, J=4.02 Hz, 1H), 8.32 (d, J=6.53 Hz, 1H), 8.90 (s, 1H), 8.95 (s, 1H), 9.09 (s, 1H), 9.26 (s, 1H); ESIMS found for C$_{27}$H$_{22}$FN$_7$OS m/z 512.1 (M+1).

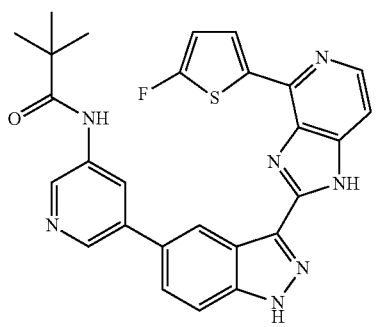

N-(5-(3-(4-(5-Fluorothiophen-2-yl)-1H-imidazo[4,5-c]pyridin-2-yl)-1H-indazol-5-yl)pyridin-3-yl)pivalamide 320.

White solid (17.1 mg, 0.03 mmol). $^1$H NMR (DMSO-d$_6$, 400 MHz) δ ppm 1.26-1.30 (m, 9H), 7.12 (d, J=4.27 Hz, 1H), 7.84 (d, J=6.53 Hz, 1H), 7.92-8.00 (m, 2H), 8.38 (d, J=6.52 Hz, 1H), 8.66 (t, J=3.52 Hz, 1H), 8.88 (s, 1H), 9.05 (s, 1H), 9.41 (d, J=1.51 Hz, 1H), 9.45 (s, 1H), 10.76 (s, 1H), 14.69 (brs, 1H), 14.96 (brs, 1H); ESIMS found for C$_{27}$H$_{22}$FN$_7$OS m/z 512.1 (M+1).

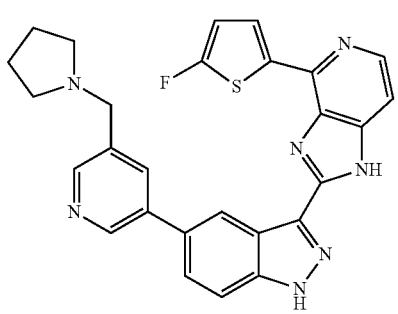

4-(5-Fluorothiophen-2-yl)-2-(5-(5-(pyrrolidin-1-ylmethyl)pyridin-3-yl)-1H-indazol-3-yl)-1H-imidazo[4,5-c]pyridine 326.

White solid (13.0 mg, 0.03 mmol). $^1$H NMR (DMSO-d$_6$, 400 MHz) δ ppm 1.86-1.98 (m, 2H), 2.01-2.11 (m, 2H), 3.10-3.22 (m, 4H), 4.54 (d, J=5.02 Hz, 2H), 7.06 (d, J=2.64 Hz, 1H), 7.66 (d, J=5.77 Hz, 1H), 7.89-7.94 (m, 1H), 8.00 (dd, J=8.66, 1.63 Hz, 1H), 8.36 (d, J=6.15 Hz, 1H), 8.49-8.54 (m, 1H), 8.66 (br. s., 1H), 8.86 (d, J=1.38 Hz, 1H), 8.92 (s, 1H), 9.13 (d, J=2.13 Hz, 1H), 11.30 (brs, 1H), 14.30 (brs, 1H), 14.37 (brs, 1H); ESIMS found for C$_{27}$H$_{22}$FN$_7$S m/z 496.1 (M+1).

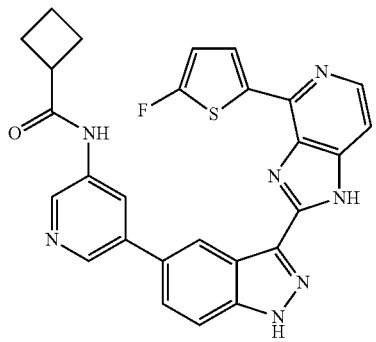

N-(5-(3-(4-(5-Fluorothiophen-2-yl)-1H-imidazo[4,5-c]pyridin-2-yl)-1H-indazol-5-yl)pyridin-3-yl)cyclobutanecarboxamide 332.

White solid (5.1 mg, 0.01 mmol). $^1$H NMR (DMSO-d$_6$, 400 MHz) δ ppm 1.79-1.92 (m, 1H), 1.94-2.07 (m, 1H), 2.13-2.24 (m, 2H), 2.24-2.36 (m, 2H), 3.21-3.30 (m, 1H), 6.88-6.94 (m, 1H), 7.43 (d, J=5.52 Hz, 1H), 7.83-7.94 (m, 2H), 8.27 (d, J=5.40 Hz, 1H), 8.42 (t, J=4.02 Hz, 1H), 8.69 (s, 2H), 8.72 (brs, 1H), 8.87 (s, 1H), 10.18 (s, 1H), 13.70 (brs, 1H), 14.01 (brs, 1H); ESIMS found for C$_{27}$H$_{20}$FN$_7$OS m/z 510.1 (M+1).

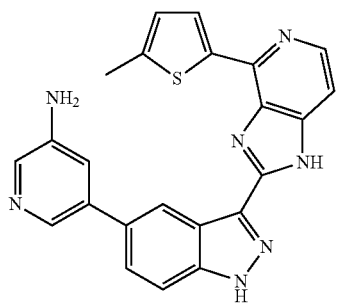

5-(3-(4-(5-Methylthiophen-2-yl)-1H-imidazo[4,5-c]pyridin-2-yl)-1H-indazol-5-yl)pyridin-3-amine 341.

White solid (9.0 mg, 0.02 mmol). $^1$H NMR (DMSO-d$_6$, 400 MHz) δ ppm 2.63 (s, 3H), 7.14 (d, J=2.51 Hz, 1H), 7.69 (d, J=6.27 Hz, 1H), 7.81-7.86 (m, 1H), 7.87-7.93 (m, 1H), 7.99 (brs, 1H), 8.10 (d, J=1.00 Hz, 1H), 8.32 (d, J=6.27 Hz, 1H), 8.41 (s, 1H), 8.59 (d, J=3.76 Hz, 1H), 8.85 (s, 1H), 14.41 (brs, 1H), 14.69 (brs, 1H); ESIMS found for C$_{23}$H$_{17}$N$_7$S m/z 424.1 (M+1).

347

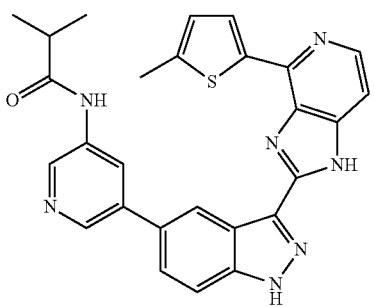

N-(5-(3-(4-(5-Methylthiophen-2-yl)-1H-imidazo[4,5-c]pyridin-2-yl)-1H-indazol-5-yl)pyridin-3-yl)isobutyramide 347.

White solid (27.0 mg, 0.05 mmol). $^1$H NMR (DMSO-$d_6$, 400 MHz) δ ppm 1.18 (d, J=6.78 Hz, 6H), 2.53 (s, 3H), 2.64-2.81 (m, 2H), 6.98 (d, J=2.76 Hz, 1H), 7.39 (d, J=5.52 Hz, 1H), 7.85 (s, 2H), 8.26 (d, J=5.52 Hz, 1H), 8.52 (d, J=3.26 Hz, 1H), 8.64 (s, 1H), 8.71 (d, J=1.76 Hz, 1H), 8.79 (d, J=2.26 Hz, 1H), 8.95 (s, 1H), 10.38 (s, 1H); ESIMS found for $C_{27}H_{23}N_7OS$ m/z 494.2 (M+1).

353

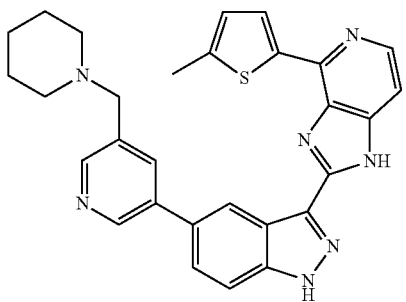

4-(5-Methylthiophen-2-yl)-2-(5-(5-(piperidin-1-ylmethyl)pyridin-3-yl)-1H-indazol-3-yl)-1H-imidazo[4,5-c]pyridine 353.

White solid (39.6 mg, 0.08 mmol). $^1$H NMR (DMSO-$d_6$, 400 MHz) δ ppm 1.32-1.91 (m, 6H), 2.58 (s, 3H), 4.26-4.51 (m, 4H), 6.97 (d, J=2.63 Hz, 1H), 7.41 (d, J=5.52 Hz, 1H), 7.88-7.95 (m, 2H), 8.14 (s, 1H), 8.28 (d, J=5.52 Hz, 1H), 8.36 (brs, 1H), 8.50 (d, J=3.26 Hz, 1H), 8.73 (s, 1H), 9.03 (s, 1H), 9.15 (s, 1H), 13.65 (s, 1H), 14.03 (s, 1H); ESIMS found for $C_{29}H_{27}N_7S$ m/z 506.3 (M+1).

354

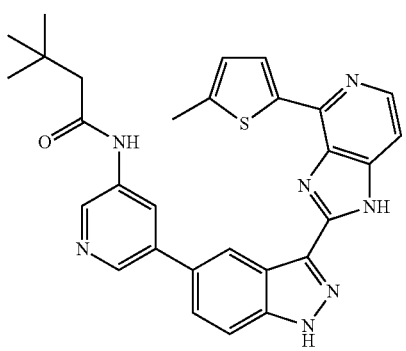

3,3-Dimethyl-N-(5-(3-(4-(5-methylthiophen-2-yl)-1H-imidazo[4,5-c]pyridin-2-yl)-1H-indazol-5-yl)pyridin-3-yl)butanamide 354.

White solid (44.0 mg, 0.08 mmol). $^1$H NMR (DMSO-$d_6$, 400 MHz) δ ppm 1.05 (s, 9H), 2.32 (s, 2H), 2.60 (s, 3H), 7.16 (d, J=3.76 Hz, 1H), 7.75 (d, J=6.27 Hz, 1H), 7.87 (dd, J=8.76 Hz, J=1.52 Hz, 1H), 7.93 (d, J=8.68 Hz, 1H), 8.37 (d, J=6.40 Hz, 1H), 8.55 (d, J=1.13 Hz, 1H), 8.71 (brs, 1H), 8.87 (s, 1H), 8.98 (s, 1H), 9.00 (brs, 1H), 10.71 (brs, 1H), 14.36 (s, 1H), 14.76 (brs, 1H); ESIMS found for $C_{29}H_{27}N_7OS$ m/z 522.2 (M+1).

358

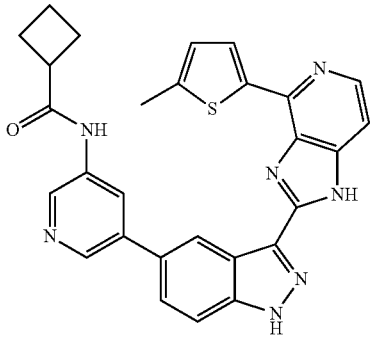

N-(5-(3-(4-(5-Methylthiophen-2-yl)-1H-imidazo[4,5-c]pyridin-2-yl)-1H-indazol-5-yl)pyridin-3-yl)cyclobutanecarboxamide 358.

White solid (14.9 mg, 0.03 mmol). $^1$H NMR (DMSO-$d_6$, 400 MHz) δ ppm 1.78-1.89 (m, 1H), 1.95-2.05 (m, 1H), 2.12-2.22 (m, 2H), 2.22-2.30 (m, 2H), 2.59 (s, 3H), 3.35 (spt, J=8.28 Hz, 1H), 7.17 (d, J=3.26 Hz, 1H), 7.75 (d, J=6.53 Hz, 1H), 7.89 (dd, J=9.00 Hz, J=1.52 Hz, 1H), 7.93 (d, J=8.52 Hz, 1H), 8.38 (d, J=6.27 Hz, 1H), 8.57 (d, J=4.02 Hz, 1H), 8.73 (s, 1H), 8.85 (s, 1H), 9.00 (brs, 2H), 10.57 (brs, 1H), 14.35 (s, 1H), 14.75 (brs, 1H); ESIMS found for $C_{28}H_{23}N_7OS$ m/z 506.1 (M+1).

359

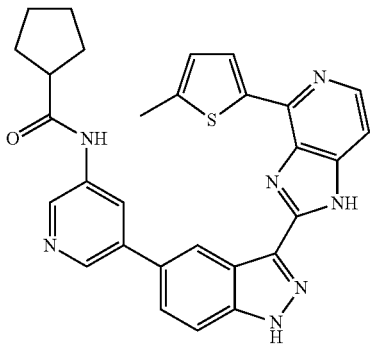

N-(5-(3-(4-(5-Methylthiophen-2-yl)-1H-imidazo[4,5-c]pyridin-2-yl)-1H-indazol-5-yl)pyridin-3-yl)cyclopentanecarboxamide 359.

White solid (9.0 mg, 0.02 mmol). $^1$H NMR (DMSO-$d_6$, 400 MHz) δ ppm 1.53-1.66 (m, 2H), 1.66-1.76 (m, 2H), 1.76-1.86 (m, 2H), 1.88-1.99 (m, 2H), 2.53 (s, 3H), 2.83-2.94 (m, 1H), 6.95-7.00 (m, 1H), 7.39 (d, J=5.52 Hz, 1H), 7.83-7.89 (m, 2H), 8.23-8.31 (m, 2H), 8.50-8.55 (m, 1H), 8.62-8.68 (m, 1H), 8.69-8.73 (m, 1H), 8.74-8.78 (m, 1H), 8.93-8.99 (m, 1H), 10.29-10.35 (m, 1H), 13.64 (brs, 1H), 14.01 (brs, 1H); ESIMS found for $C_{29}H_{25}N_7OS$ m/z 520.3 (M+1).

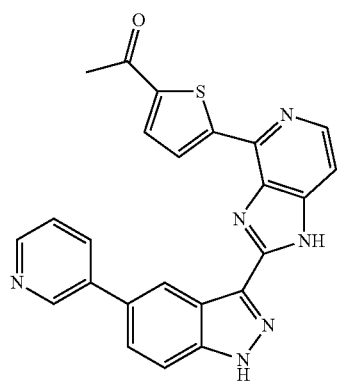

1-(5-(2-(5-(Pyridin-3-yl)-1H-indazol-3-yl)-1H-imidazo[4,5-c]pyridin-4-yl)thiophen-2-yl)ethan-1-one 368.

White solid (41.1 mg, 0.09 mmol). $^1$H NMR (DMSO-d$_6$, 300 MHz) δ ppm 2.63 (s, 3H), 7.57 (d, J=5.65 Hz, 1H), 7.79-7.93 (m, 2H), 7.99 (dd, J=8.67 Hz, J=1.11 Hz, 1H), 8.06 (d, J=3.77 Hz, 1H), 8.40 (d, J=5.27 Hz, 1H), 8.52 (d, J=7.91 Hz, 1H), 8.64 (d, J=3.77 Hz, 1H), 8.70-8.87 (m, 1H), 8.99 (s, 1H), 9.17 (brs, 1H), 13.92 (brs, 1H), 14.11 (s, 1H); ESIMS found for C$_{24}$H$_{16}$N$_6$OS m/z 437.2 (M+1).

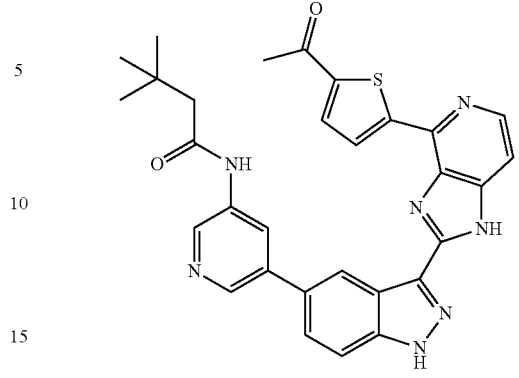

N-(5-(3-(4-(5-Acetylthiophen-2-yl)-1H-imidazo[4,5-c]pyridin-2-yl)-1H-indazol-5-yl)pyridin-3-yl)-3,3-dimethylbutanamide 380.

White solid (16.6 mg, 0.03 mmol). $^1$H NMR (DMSO-d$_6$, 400 MHz) δ ppm 1.05 (s, 9H), 2.32 (s, 2H), 2.58 (s, 3H), 7.55 (d, J=5.27 Hz, 1H), 7.87 (s, 2H), 8.03 (d, J=3.51 Hz, 1H), 8.37 (d, J=5.27 Hz, 1H), 8.64 (brs, 1H), 8.70 (brs, 1H), 8.74-8.82 (m, 2H), 8.84 (s, 1H), 10.35 (s, 1H), 13.82 (brs, 1H), 14.15 (brs, 1H); ESIMS found for C$_{30}$H$_{27}$N$_7$O$_2$S m/z 550.2 (M+1).

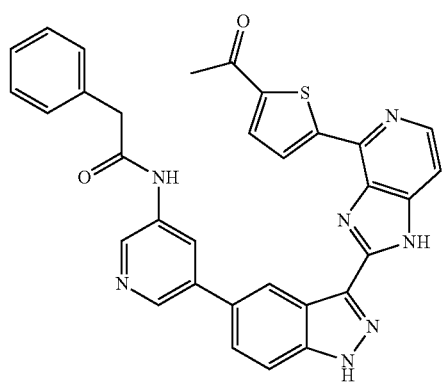

N-(5-(3-(4-(5-Acetylthiophen-2-yl)-1H-imidazo[4,5-c]pyridin-2-yl)-1H-indazol-5-yl)pyridin-3-yl)-2-phenylacetamide 374.

White solid (11.1 mg, 0.02 mmol). $^1$H NMR (DMSO-d$_6$, 400 MHz) δ ppm 2.52 (s, 3H), 3.79 (s, 2H), 7.18-7.46 (m, 5H), 7.63 (d, J=5.52 Hz, 1H), 7.85-7.95 (m, 2H), 8.08 (d, J=4.02 Hz, 1H), 8.37-8.46 (m, 1H), 8.73 (d, J=2.01 Hz, 1H), 8.75 (d, J=4.02 Hz, 1H), 8.86 (d, J=2.01 Hz, 1H), 8.92 (s, 1H), 8.94 (d, J=2.01 Hz, 1H), 10.85-10.95 (m, 1H), 14.06 (brs, 1H), 14.19 (brs, 1H); ESIMS found for C$_{32}$H$_{23}$N$_7$O$_2$S m/z 570.1 (M+1).

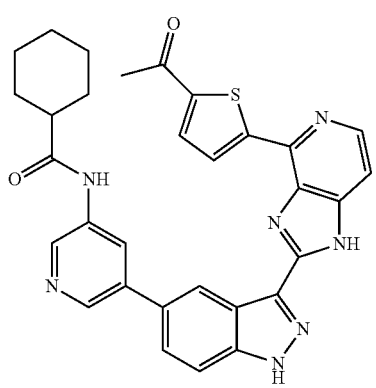

N-(5-(3-(4-(5-Acetylthiophen-2-yl)-1H-imidazo[4,5-c]pyridin-2-yl)-1H-indazol-5-yl)pyridin-3-yl)cyclohexanecarboxamide 386.

White solid (27.4 mg, 0.05 mmol). $^1$H NMR (DMSO-d$_6$, 400 MHz) δ ppm 1.15-1.38 (m, 3H), 1.40-1.56 (m, 2H), 1.67 (dd, J=11.67, 2.64 Hz, 1H), 1.72-1.83 (m, 2H), 1.90 (d, J=12.30 Hz, 2H), 2.43 (tt, J=11.89, 3.92 Hz, 1H), 2.57 (s, 3H), 7.54 (d, J=5.52 Hz, 1H), 7.87 (d, J=1.00 Hz, 2H), 8.02 (d, J=4.02 Hz, 1H), 8.38 (d, J=5.28 Hz, 1H), 8.65 (d, J=2.01 Hz, 1H), 8.68 (d, J=2.01 Hz, 1H), 8.73 (d, J=2.26 Hz, 1H), 8.79 (d, J=3.76 Hz, 1H), 8.84 (s, 1H), 10.23 (s, 1H), 13.78 (brs, 1H), 14.06 (brs, 1H); ESIMS found for C$_{31}$H$_{27}$N$_7$O$_2$S m/z 562.2 (M+1).

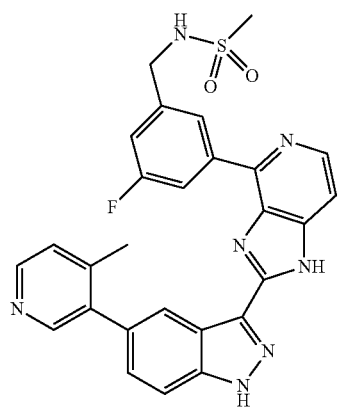

N-(3-Fluoro-5-(2-(5-(4-methylpyridin-3-yl)-1H-indazol-3-yl)-1H-imidazo[4,5-c]pyridin-4-yl)benzyl)methanesulfonamide 395.

White solid (12.6 mg, 0.02 mmol). $^1$H NMR (DMSO-d$_6$, 400 MHz) δ 2.39 (s, 3H), 2.91 (s, 3H), 4.22 (d, J=6.27 Hz, 2H), 7.24 (d, J=9.54 Hz, 1H), 7.42 (d, J=5.02 Hz, 1H), 7.55 (d, J=5.52 Hz, 1H), 7.57-7.63 (m, 1H), 7.72 (t, J=6.40 Hz, 1H), 7.78-7.87 (m, 1H), 8.18 (s, 1H), 8.45 (d, J=5.52 Hz, 1H), 8.49 (d, J=5.02 Hz, 1H), 8.53-8.59 (m, 2H), 8.61 (s, 1H), 8.85 (d, J=9.29 Hz, 1H), 13.74 (brs, 1H), 14.02 (brs, 1H); ESIMS found for C$_{27}$H$_{22}$FN$_7$O$_2$S m/z 528.2 (M+1).

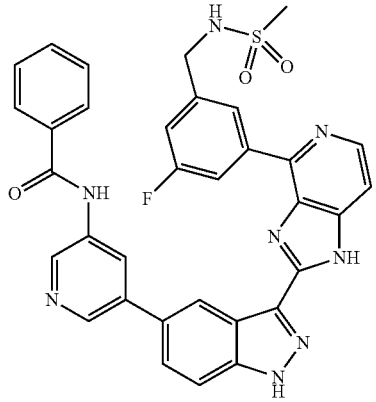

N-(5-(3-(4-(3-Fluoro-5-(methylsulfonamidomethyl)phenyl)-1H-imidazo[4,5-c]pyridin-2-yl)-1H-indazol-5-yl)pyridin-3-yl)benzamide 401.

White solid (10.0 mg, 0.02 mmol). $^1$H NMR (DMSO-d$_6$, 400 MHz) δ ppm 2.90 (s, 3H), 4.28 (d, J=6.02 Hz, 2H), 7.06-7.15 (m, 1H), 7.56-7.69 (m, 3H), 7.74 (t, J=6.53 Hz, 1H), 7.91 (s, 2H), 8.03 (d, J=7.28 Hz, 2H), 8.28 (d, J=1.00 Hz, 1H), 8.48 (d, J=5.27 Hz, 1H), 8.63 (d, J=13.05 Hz, 2H), 8.81 (d, J=1.25 Hz, 1H), 8.89-9.04 (m, 2H), 9.07 (d, J=2.01 Hz, 1H), 10.61 (s, 1H), 13.78 (brs, 1H), 14.08 (brs, 1H); ESIMS found for C$_{33}$H$_{25}$FN$_5$O$_3$S m/z 633.2 (M+1).

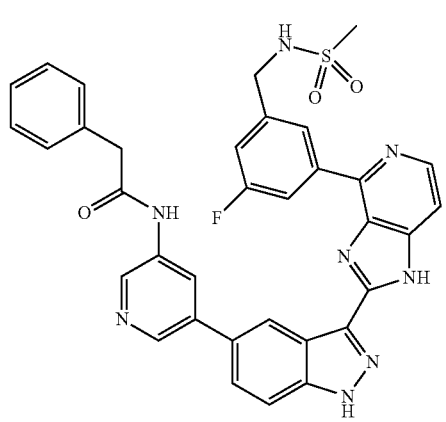

N-(5-(3-(4-(3-Fluoro-5-(methylsulfonamidomethyl)phenyl)-1H-imidazo[4,5-c]pyridin-2-yl)-1H-indazol-5-yl)pyridin-3-yl)-2-phenylacetamide 400.

White solid (13.7 mg, 0.02 mmol). $^1$H NMR (DMSO-d$_6$, 400 MHz) δ ppm 2.90 (s, 3H), 3.80 (brs, 2H), 4.32 (d, J=6.02 Hz, 2H), 7.25-7.31 (m, 1H), 7.32-7.42 (m, 4H), 7.45-7.52 (m, 1H), 7.80 (t, J=6.27 Hz, 1H), 7.85-7.90 (m, 1H), 7.95 (d, J=8.53 Hz, 2H), 8.48 (d, J=2.51 Hz, 1H), 8.51-8.57 (m, 1H), 8.60 (d, J=6.52 Hz, 1H), 8.63-8.71 (m, 1H), 8.81 (s, 1H), 8.84-8.89 (m, 1H), 8.95-9.02 (m, 1H), 11.04 (brs, 1H), 14.41 (s, 1H), 14.78 (brs, 1H); ESIMS found for C$_{34}$H$_{27}$FN$_8$O$_3$S m/z 647.2 (M+1).

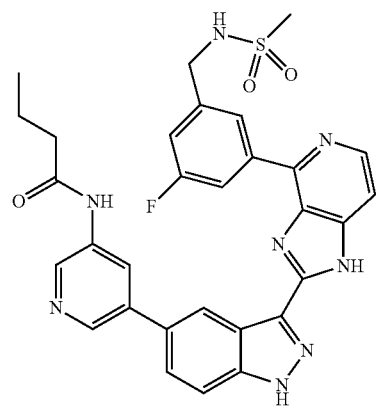

N-(5-(3-(4-(3-Fluoro-5-(methylsulfonamidomethyl)phenyl)-1H-imidazo[4,5-c]pyridin-2-yl)-1H-indazol-5-yl)pyridin-3-yl)butyramide 407.

White solid (10.9 mg, 0.02 mmol). $^1$H NMR (DMSO-d$_6$, 400 MHz) δ ppm 0.95 (t, J=7.28 Hz, 3H), 1.65 (dq, J=14.62, 7.17 Hz, 2H), 2.37 (t, J=7.40 Hz, 2H), 2.88 (s, 3H), 4.29 (d, J=6.00 Hz, 2H), 7.26 (d, J=9.79 Hz, 1H), 7.57 (d, J=5.52 Hz, 1H), 7.75 (t, J=6.28 Hz, 1H), 7.82 (dd, J=8.28 Hz, J=1.52 Hz, 1H), 7.88 (d, J=9.04 Hz, 1H), 8.32 (brs, 1H), 8.44-8.50 (m, 2H), 8.63 (brs, 1H), 8.71 (d, J=2.01 Hz, 1H), 8.79 (d, J=2.26 Hz, 1H), 8.87-8.91 (m, 1H), 8.92-9.01 (m, 1H), 10.25 (s, 1H), 13.77 (brs, 1H), 14.08 (brs, 1H); ESIMS found for C$_{30}$H$_{27}$FN$_8$O$_3$S m/z 599.3 (M+1).

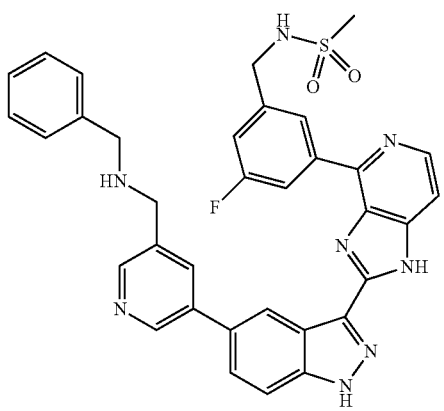

N-(3-(2-(5-(5-((Benzylamino)methyl)pyridin-3-yl)-1H-indazol-3-yl)-1H-imidazo[4,5-c]pyridin-4-yl)-5-fluorobenzyl)methanesulfonamide 413.

White solid (38.1 mg, 0.06 mmol). $^1$H NMR (DMSO-d$_6$, 400 MHz) δ ppm 2.91 (s, 3H), 3.77-4.08 (m, 4H), 4.23-4.38 (m, 2H), 7.18-7.38 (m, 4H), 7.38-7.50 (m, 2H), 7.57 (d, J=5.27 Hz, 1H), 7.74-7.84 (m, 1H), 7.84-8.01 (m, 2H), 8.16-8.32 (m, 1H), 8.47 (d, J=5.52 Hz, 1H), 8.57-8.70 (m, 2H), 8.91 (s, 1H), 8.94-9.09 (m, 2H), 13.78 (brs, 1H), 14.13 (brs, 1H); ESIMS found for $C_{34}H_{29}FN_8O_2S$ m/z 633.3 (M+1).

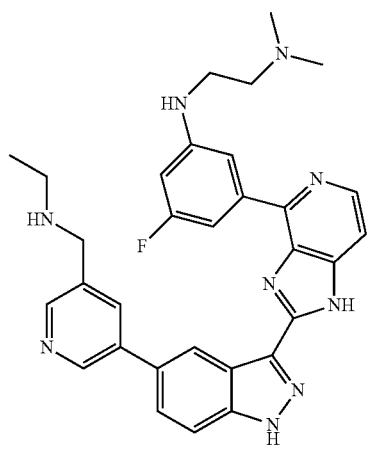

$N^1$-(3-(2-(5-(5-((Ethylamino)methyl)pyridin-3-yl)-1H-indazol-3-yl)-1H-imidazo[4,5-c]pyridin-4-yl)-5-fluorophenyl)-$N^2$,$N^2$-dimethylethane-1,2-diamine 422.

White solid (21.0 mg, 0.04 mmol). $^1$H NMR (DMSO-d$_6$, 400 MHz) δ ppm 1.29 (t, J=7.15 Hz, 3H), 2.76-2.95 (m, 6H), 2.96-3.12 (m, 2H), 3.29-3.44 (m, 2H), 3.55-3.76 (m, 2H), 3.91-4.08 (m, 2H), 6.83 (d, J=11.8 Hz, 1H), 7.74 (s, 1H), 7.83-8.11 (m, 4H), 8.55 (d, J=6.52 Hz, 1H), 8.71-8.93 (m, 2H), 8.98 (s, 2H), 9.13-9.34 (m, 2H), 9.85-10.10 (m, 2H), 10.67 (brs, 1H), 14.60 (brs, 1H), 14.99 (brs, 1H); ESIMS found for $C_{31}H_{32}FN_9$ m/z 550.2 (M+1).

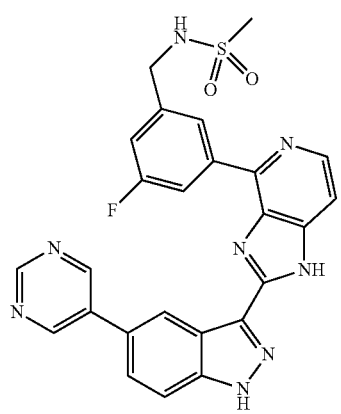

N-(3-Fluoro-5-(2-(5-(pyrimidin-5-yl)-1H-indazol-3-yl)-1H-imidazo[4,5-c]pyridin-4-yl)benzyl)methanesulfonamide 416.

White solid (6.6 mg, 0.01 mmol). $^1$H NMR (DMSO-d$_6$, 400 MHz) δ ppm 2.98 (s, 2H), 4.37 (d, J=5.52 Hz, 2H), 7.56 (d, J=8.53 Hz, 1H), 7.86 (d, J=8.53 Hz, 2H), 7.90-8.00 (m, 2H), 8.44 (s, 1H), 8.50 (d, J=9.54 Hz, 1H), 8.55 (d, J=6.27 Hz, 1H), 8.73 (s, 1H), 9.2 s (d, J=4.04 Hz, 2H), 14.46 (brs, 1H), 14.93 (brs, 1H); ESIMS found for $C_{25}H_{19}FN_5O_2S$ m/z 515.2 (M+1).

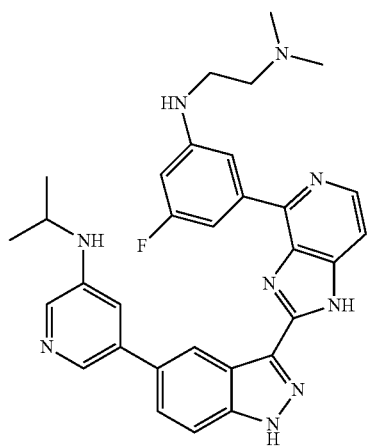

$N^1$-(3-Fluoro-5-(2-(5-(5-(isopropylamino)pyridin-3-yl)-1H-indazol-3-yl)-1H-imidazo[4,5-c]pyridin-4-yl)phenyl)-$N^2$,$N^2$-dimethylethane-1,2-diamine 428.

White solid (36.8 mg, 0.07 mmol). $^1$H NMR (DMSO-d$_6$, 400 MHz) δ ppm 1.19 (d, J=6.28 Hz, 6H), 2.81 (s, 6H), 3.21-3.32 (m, 2H), 3.50-3.60 (m, 2H), 3.72-3.86 (m, 1H), 6.41-6.58 (m, 2H), 6.64 (dd, J=10.54, 2.51 Hz, 1H), 7.51 (d, J=2.26 Hz, 1H), 7.65 (d, J=3.76 Hz, 1H), 7.75-7.96 (m, 3H), 8.06 (d, J=2.26 Hz, 1H), 8.09-8.22 (m, 1H), 8.30 (s, 1H), 8.46 (d, J=5.52 Hz, 1H), 8.80 (s, 1H), 10.48 (brs, 1H), 14.01 (brs, 1H) 14.23 (brs, 1H); ESIMS found for $C_{31}H_{32}FN_9$ m/z 550.3 (M+1).

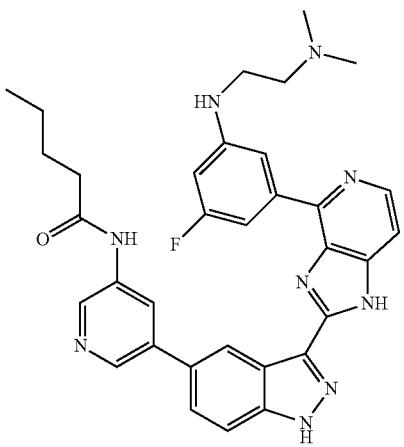

N-(5-(3-(4-(3-((2-(Dimethylamino)ethyl)amino)-5-fluorophenyl)-1H-imidazo[4,5-c]pyridin-2-yl)-1H-indazol-5-yl)pyridin-3-yl)pentanamide 434.

White solid (13.0 mg, 0.02 mmol). $^1$H NMR (DMSO-d$_6$, 400 MHz) δ ppm 0.92 (t, J=6.80 Hz, 3H), 1.30-1.43 (m, 2H), 1.56-1.69 (m, 2H), 2.12 (s, 6H), 2.27-2.43 (m, 4H), 3.06-3.18 (m, 2H), 5.77-5.87 (m, 1H), 6.44-6.54 (m, 1H), 7.48-7.55 (m, 1H), 7.76-7.91 (m, 2H), 7.94-8.02 (m, 1H), 8.05-8.13 (m, 1H), 8.17-8.24 (m, 1H), 8.37-8.47 (m, 2H), 8.64-8.71 (m, 1H), 8.79-8.89 (m, 2H), 10.20-10.28 (m, 1H); ESIMS found for C$_{33}$H$_{34}$FN$_9$O m/z 592.3 (M+1).

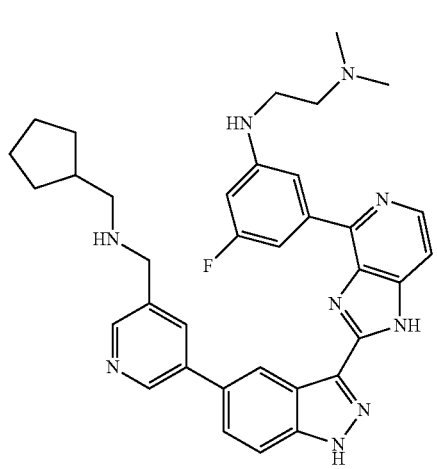

N$^1$-(3-(2-(5-(5-((((Cyclopentylmethyl)amino)methyl)pyridin-3-yl)-1H-indazol-3-yl)-1H-imidazo[4,5-c]pyridin-4-yl)-5-fluorophenyl)-N$^2$,N$^2$-dimethylethane-1,2-diamine 440.

White solid (14.5 mg, 0.02 mmol). $^1$H NMR (DMSO-d$_6$, 400 MHz) δ ppm 1.17-1.36 (m, 2H), 1.41-1.65 (m, 4H), 1.71-1.91 (m, 2H), 2.18-2.37 (m, 2H), 2.79-3.01 (m, 6H), 3.32-3.45 (m, 3H), 3.59-3.77 (m, 2H), 4.24-4.40 (m, 2H), 6.70-6.97 (m, 2H), 7.77 (d, J=1.76 Hz, 1H), 7.88-8.07 (m, 3H), 8.51-8.72 (m, 2H), 8.76-8.93 (m, 2H), 9.14 (s, 1H), 9.53 (brs, 2H), 10.56 (brs, 1H), 14.47 (brs, 1H), 14.89 (brs, 1H); ESIMS found for C$_{35}$H$_{38}$FN$_9$ m/z 604.3 (M+1).

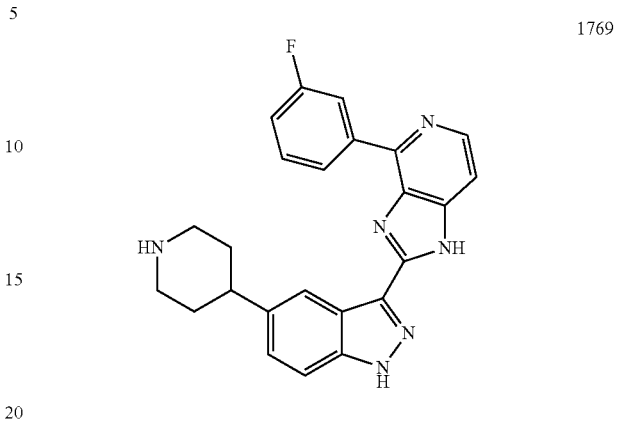

4-(3-Fluorophenyl)-2-(5-(piperidin-4-yl)-1H-indazol-3-yl)-1H-imidazo[4,5-c]pyridine 1769.

Brown solid (7.0 mg, 0.02 mmol). $^1$H NMR (DMSO-d$_6$, 500 MHz) δ ppm 1.68 (qd, J=12.35, 4.12 Hz, 2H), 1.94 (br d, J=12.35 Hz, 2H), 2.66-2.75 (m, 2H), 2.81 (br t, J=12.08 Hz, 1H), 3.13 (br d, J=12.35 Hz, 2H), 7.33 (td, J=8.23, 2.20 Hz, 1H), 7.42 (dd, J=8.51, 1.37 Hz, 1H), 7.52 (d, J=5.21 Hz, 1H), 7.59-7.66 (m, 2H), 8.42 (d, J=5.21 Hz, 1H), 8.53 (s, 1H), 8.81 (d, J=7.96 Hz, 1H), 8.96 (br d, J=11.25 Hz, 1H), 13.68 (s, 1H); ESIMS found for C$_{24}$H$_{21}$FN$_6$ m/z 413.2 (M+1).

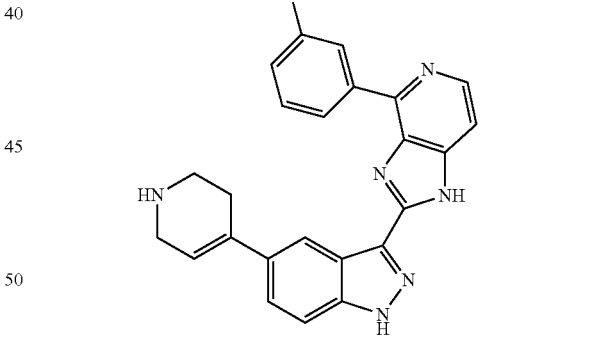

4-(3-Fluorophenyl)-2-(5-(1,2,3,6-tetrahydropyridin-4-yl)-1H-indazol-3-yl)-1H-imidazo[4,5-c]pyridine 1770.

White solid (11.0 mg, 0.03 mmol). $^1$H NMR (DMSO-d$_6$, 500 MHz) δ ppm 2.60 (br s, 2H), 3.05 (t, J=5.63 Hz, 2H), 3.47 (br d, J=2.74 Hz, 2H), 6.40 (br s, 1H), 7.34 (td, J=8.37, 2.20 Hz, 1H), 7.53 (d, J=5.21 Hz, 1H), 7.60 (td, J=7.96, 6.31 Hz, 1H), 7.63-7.67 (m, 1H), 7.72 (dd, J=9.06, 1.65 Hz, 1H), 8.44 (d, J=5.49 Hz, 1H), 8.71 (s, 1H), 8.75 (d, J=7.68 Hz, 1H), 8.99 (br d, J=10.43 Hz, 1H); ESIMS found for C$_{24}$H$_{19}$FN$_6$ m/z 411.2 (M+1).

697

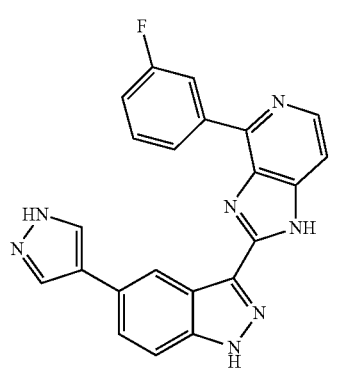

1771

2-(5-(1H-Pyrazol-4-yl)-1H-indazol-3-yl)-4-(3-fluorophenyl)-1H-imidazo[4,5-c]pyridine 1771.

Pink solid (7.7 mg, 0.02 mmol). $^1$H NMR (DMSO-d$_6$, 500 MHz) δ ppm 7.37 (br t, J=7.41 Hz, 1H), 7.54 (br d, J=4.94 Hz, 1H), 7.61-7.68 (m, 1H), 7.70 (br d, J=8.23 Hz, 1H), 7.81 (br d, J=9.06 Hz, 1H), 8.02 (br s, 1H), 8.22 (br s, 1H), 8.45 (d, J=5.21 Hz, 1H), 8.74 (br d, J=7.96 Hz, 1H), 8.79 (s, 1H), 9.08 (br d, J=11.53 Hz, 1H), 13.06 (br s, 1H), 13.62 (br s, 1H), 13.80 (br s, 1H); ESIMS found for C$_{22}$H$_{14}$FN$_7$ m/z 396.2 (M+1).

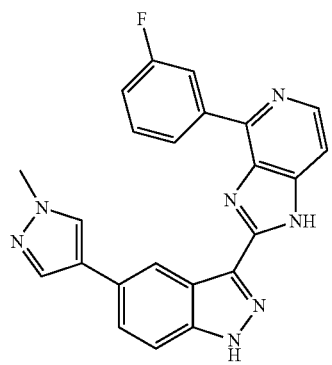

1772

4-(3-Fluorophenyl)-2-(5-(1-methyl-1H-pyrazol-4-yl)-1H-indazol-3-yl)-1H-imidazo[4,5-c]pyridine 1772.

Yellow solid (7.3 mg, 0.02 mmol). $^1$H NMR (DMSO-d$_6$, 500 MHz) δ ppm 3.94 (s, 3H), 7.38 (td, J=8.37, 2.47 Hz, 1H), 7.54 (d, J=5.21 Hz, 1H), 7.62-7.68 (m, 1H), 7.68-7.73 (m, 1H), 7.73-7.78 (m, 1H), 7.94 (s, 1H), 8.17 (s, 1H), 8.45 (d, J=5.21 Hz, 1H), 8.72 (br d, J=7.96 Hz, 1H), 8.78 (s, 1H), 9.08 (br d, J=11.53 Hz, 1H), 13.66 (br s, 1H), 13.79 (br s, 1H); ESIMS found for C$_{23}$H$_{16}$FN$_7$ m/z 410.2 (M+1).

698

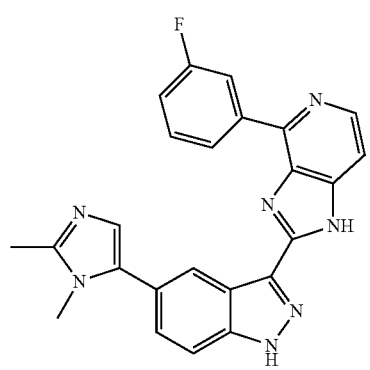

1773

2-(5-(1,2-Dimethyl-1H-imidazol-5-yl)-1H-indazol-3-yl)-4-(3-fluorophenyl)-1H-imidazo[4,5-c]pyridine 1773.

Yellow solid (4.5 mg, 0.01 mmol). $^1$H NMR (DMSO-d$_6$, 500 MHz) δ ppm 2.43 (s, 3H), 3.68 (s, 3H), 7.01 (s, 1H), 7.33 (td, J=8.23, 2.20 Hz, 1H), 7.54 (d, J=5.21 Hz, 1H), 7.57-7.64 (m, 2H), 7.79 (d, J=8.78 Hz, 1H), 8.45 (d, J=5.21 Hz, 1H), 8.63 (s, 1H), 8.72 (d, J=7.68 Hz, 1H), 8.84 (br d, J=10.43 Hz, 1H), 13.67 (br s, 1H), 13.94 (s, 1H); ESIMS found for C$_{24}$H$_{18}$FN$_7$ m/z 424 (M+1).

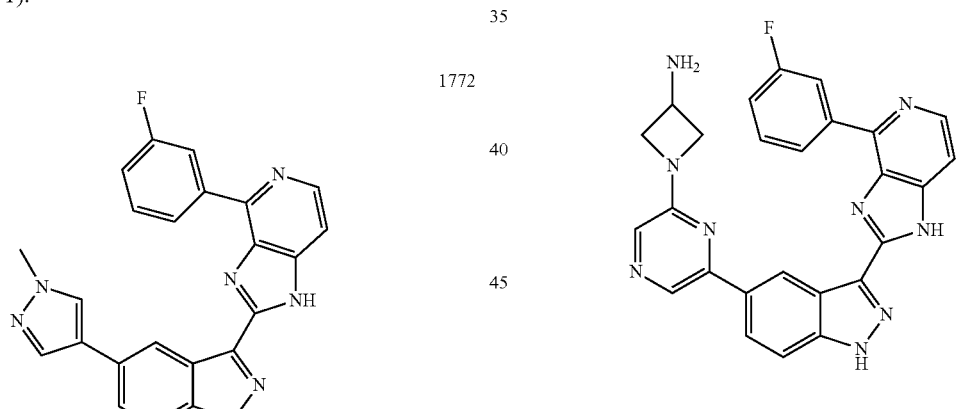

1774

1-(6-(3-(4-(3-Fluorophenyl)-1H-imidazo[4,5-c]pyridin-2-yl)-1H-indazol-5-yl)pyrazin-2-yl)azetidin-3-amine 1774.

Yellow solid (3.7 mg, 0.008 mmol). $^1$H NMR (DMSO-d$_6$, 500 MHz) δ ppm 3.44-3.52 (m, 1H), 3.44-3.52 (m, 1H), 3.58 (dt, J=13.65, 5.52 Hz, 1H), 4.01-4.11 (m, 2H), 4.31-4.39 (m, 1H), 7.31-7.39 (m, 2H), 7.56 (d, J=5.21 Hz, 1H), 7.62 (td, J=7.96, 6.31 Hz, 1H), 7.78 (s, 1H), 7.81 (d, J=8.78 Hz, 1H), 7.98 (s, 1H), 8.28 (dd, J=8.78, 1.65 Hz, 1H), 8.42-8.49 (m, 2H), 8.81 (d, J=7.96 Hz, 1H), 8.88-8.94 (m, 1H), 9.22 (s, 1H), 13.70 (br s, 1H), 13.96 (s, 1H); ESIMS found for C$_{26}$H$_{20}$FN$_9$ m/z 520.2 (M+MeCN).

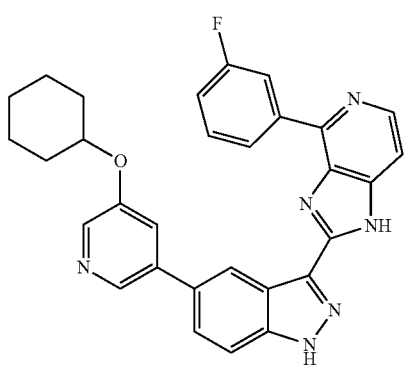

2-(5-(5-(Cyclohexyloxy)pyridin-3-yl)-1H-indazol-3-yl)-4-(3-fluorophenyl)-1H-imidazo[4,5-c]pyridine 1775.

Yellow solid (20 mg, 0.038 mmol, 31.7% yield). $^1$H NMR (DMSO-d$_6$, 500 MHz) δ ppm 1.25-1.35 (m, 1H), 1.35-1.46 (m, 2H), 1.47-1.59 (m, 3H), 168-1.78 (m, 2H), 1.95-2.05 (m, 2H), 4.57-4.66 (m, 1H), 7.30 (td, J=8.30, 2.06 Hz, 1H), 7.55 (d, J=5.21 Hz, 1H), 7.61 (td, J=8.10, 6.31 Hz, 1H), 7.73 (t, J=2.33 Hz, 1H), 7.83 (d, J=8.78 Hz, 1H), 7.91 (dd, J=8.64, 1.78 Hz, 1H), 8.34 (d, J=2.74 Hz, 1H), 8.44 (d, J=5.49 Hz, 1H), 8.62 (d, J=1.92 Hz, 1H), 8.81-8.89 (m, 2H), 8.95 (d, J=0.82 Hz, 1H); ESIMS found for C$_{30}$H$_{25}$FN$_6$O m/z 505.2 (M+1).

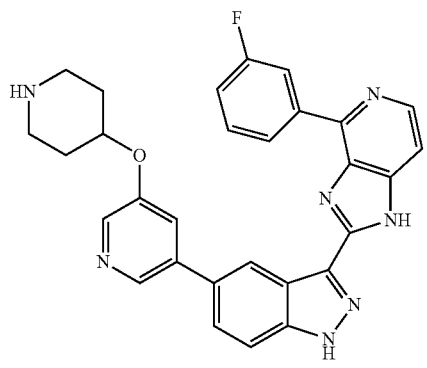

4-(3-Fluorophenyl)-2-(5-(5-(piperidin-4-yloxy)pyridin-3-yl)-1H-indazol-3-yl)-1H-imidazo[4,5-c]pyridine 1776.

Yellow solid (12 mg, 0.021 mmol, 60.4% yield). $^1$H NMR (DMSO-d$_6$, 500 MHz) δ ppm 1.86-1.99 (m, 2H), 2.13-2.23 (m, 2H), 3.06-3.17 (m, 2H), 3.27-3.33 (m, 2H), 4.93 (dt, J=7.34, 3.88 Hz, 1H), 7.36 (td, J=8.23, 2.47 Hz, 1H), 7.57 (d, J=5.21 Hz, 1H), 7.59-7.66 (m, 1H), 7.82-7.88 (m, 2H), 7.93 (dd, J=8.78, 1.65 Hz, 1H), 8.44 (d, J=2.47 Hz, 1H), 8.47 (d, J=5.49 Hz, 1H), 8.52 (br s, 2H), 8.69 (d, J=1.37 Hz, 1H), 8.83 (br d, J=7.96 Hz, 1H), 8.87 (br d, J=10.98 Hz, 1H), 8.95 (s, 1H), 13.77 (br s, 1H), 14.02 (s, 1H); ESIMS found for C$_{29}$H$_{24}$FN$_7$O m/z 507.2 (M+1).

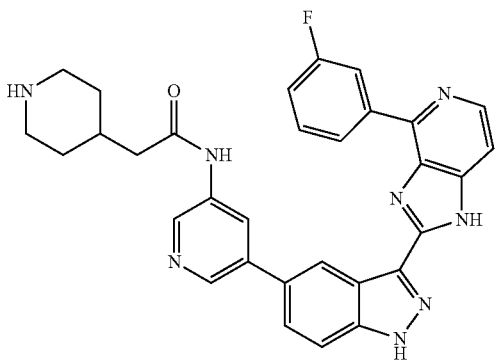

N-(5-(3-(4-(3-Fluorophenyl)-1H-imidazo[4,5-c]pyridin-2-yl)-1H-indazol-5-yl)pyridin-3-yl)-2-(piperidin-4-yl)acetamide 1777.

Yellow solid (5.5 mg, 0.01 mmol). $^1$H NMR (DMSO-d$_6$, 500 MHz) δ ppm 1.00-1.11 (m, 1H) 1.13-1.22 (m, 1H) 1.68-1.80 (m, 2H) 2.01-2.10 (m, 1H) 2.35 (dd, J=7.00, 2.33 Hz, 2H) 2.52-2.58 (m, 1H) 2.97-3.06 (m, 1H) 3.78 (br d, J=14.27 Hz, 1H) 4.35 (br d, J=12.90 Hz, 1H) 7.08-7.15 (m, 1H) 7.39 (d, J=5.21 Hz, 1H) 7.46-7.53 (m, 1H) 7.64 (br d, J=8.51 Hz, 1H) 7.68-7.74 (m, 1H) 8.06 (br d, J=4.67 Hz, 1H) 8.42 (br d, J=2.20 Hz, 1H) 8.69 (d, J=1.92 Hz, 1H) 8.80 (d, J=2.20 Hz, 1H) 8.98 (br d, J=7.68 Hz, 1H) 9.06 (br d, J=11.25 Hz, 1H) 9.10 (br s, 1H) 10.29 (s, 1H); ESIMS found for C$_{31}$H$_{27}$FN$_8$O m/z 547.2 (M+1).

4-(3-Fluorophenyl)-2-(5-(5-(2-(pyrrolidin-1-yl)ethoxy)pyridin-3-yl)-1H-indazol-3-yl)-1H-imidazo[4,5-c]pyridine 1778.

Brown solid (18 mg, 0.033 mmol, 52.2% yield). $^1$H NMR (DMSO-d$_6$, 500 MHz) δ ppm 1.68 (dt, J=6.72, 3.22 Hz, 4H), 2.55 (br s, 4H), 2.87 (t, J=5.76 Hz, 2H), 4.28 (t, J=5.76 Hz, 2H), 7.31 (td, J=8.23, 2.47 Hz, 1H), 7.55 (d, J=5.49 Hz, 1H), 7.60 (td, J=7.96, 6.31 Hz, 1H), 7.76 (t, J=2.33 Hz, 1H), 7.84 (d, J=8.51 Hz, 1H), 7.94 (dd, J=8.78, 1.65 Hz, 1H), 8.36 (d, J=2.74 Hz, 1H), 8.46 (d, J=5.49 Hz, 1H), 8.65 (d, J=1.65 Hz, 1H), 8.79-8.88 (m, 2H), 8.95 (s, 1H), 13.71 (br s, 1H), 13.97 (br s, 1H); ESIMS found for C$_{30}$H$_{26}$FN$_7$O m/z 520.2 (M+1).

701

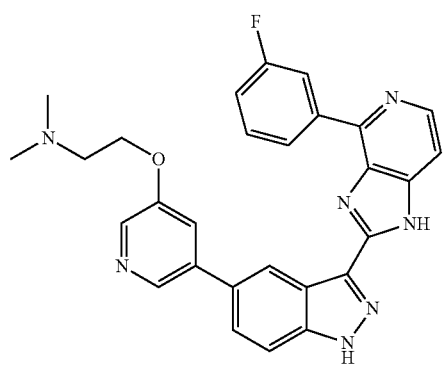

2-((5-(3-(4-(3-Fluorophenyl)-1H-imidazo[4,5-c]pyridin-2-yl)-1H-indazol-5-yl)pyridin-3-yl)oxy)-N,N-dimethyl-ethan-1-amine 1779.

Yellow solid (4.3 mg, 0.009 mmol). $^1$H NMR (DMSO-d$_6$, 500 MHz) δ ppm 2.21-2.27 (m, 1H) 2.25 (s, 5H) 2.70 (t, J=5.76 Hz, 2H) 4.26 (t, J=5.76 Hz, 2H) 7.28-7.35 (m, 1H) 7.55 (d, J=5.49 Hz, 1H) 7.58-7.65 (m, 1H) 7.73-7.77 (m, 1H) 7.83 (d, J=8.78 Hz, 1H) 7.93 (dd, J=8.78, 1.65 Hz, 1H) 8.36 (d, J=2.47 Hz, 1H) 8.45 (d, J=5.21 Hz, 1H) 8.64 (d, J=1.92 Hz, 1H) 8.80-8.88 (m, 2H) 8.95 (s, 1H) 13.83 (br s, 1H); ESIMS found for C$_{28}$H$_{24}$FN$_7$O m/z 494.3 (M+1).

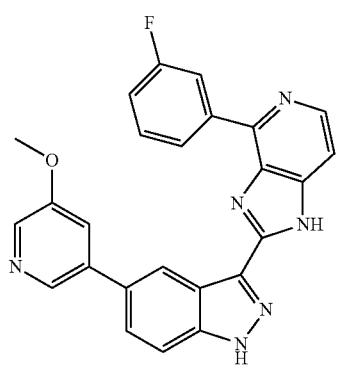

4-(3-Fluorophenyl)-2-(5-(5-methoxypyridin-3-yl)-1H-indazol-3-yl)-1H-imidazo[4,5-c]pyridine 1780.

Brown solid (25.6 mg, 0.06 mmol). $^1$H NMR (DMSO-d$_6$, 500 MHz) δ ppm 3.96 (s, 3H) 7.38 (td, J=8.23, 2.20 Hz, 1H) 7.59-7.66 (m, 2H) 7.73-7.77 (m, 1H) 7.85 (d, J=8.78 Hz, 1H) 7.93 (dd, J=8.78, 1.65 Hz, 1H) 8.37 (d, J=2.74 Hz, 1H) 8.48 (d, J=5.49 Hz, 1H) 8.65 (d, J=1.65 Hz, 1H) 8.74 (br d, J=7.68 Hz, 1H) 8.81 (br d, J=10.98 Hz, 1H) 8.92 (s, 1H) 13.89 (br s, 1H) 14.03 (s, 1H); ESIMS found for C$_{25}$H$_{17}$FN$_6$O m/z 437.1 (M+1).

702

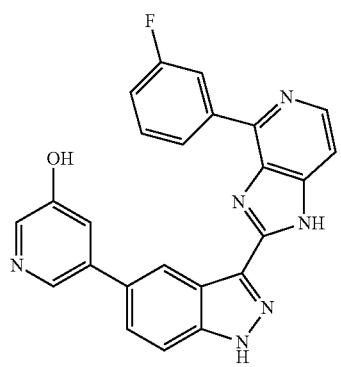

5-(3-(4-(3-Fluorophenyl)-1H-imidazo[4,5-c]pyridin-2-yl)-1H-indazol-5-yl)pyridin-3-ol 1781.

Yellow solid (1.3 mg, 0.003 mmol). $^1$H NMR (DMSO-d$_6$, 500 MHz) δ ppm 7.31 (br d, J=5.76 Hz, 1H) 7.50-7.56 (m, 2H) 7.61 (br d, J=6.59 Hz, 1H) 7.82 (br s, 2H) 8.20 (br s, 1H) 8.43 (br s, 1H) 8.51 (s, 1H) 8.78-8.90 (m, 2H) 8.93 (br s, 1H) 13.74 (brs, 1H); ESIMS found for C$_{24}$H$_{15}$FN$_6$O m/z 423.1 (M+1).

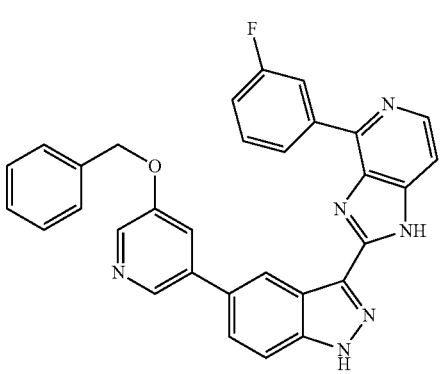

2-(5-(5-(Benzyloxy)pyridin-3-yl)-1H-indazol-3-yl)-4-(3-fluorophenyl)-1H-imidazo[4,5-c]pyridine 1782.

White solid (42 mg, 0.078 mmol, 39.7% yield). $^1$H NMR (DMSO-d$_6$, 500 MHz) δ ppm 5.32 (s, 2H), 7.19 (td, J=7.82, 1.92 Hz, 1H), 7.35-7.40 (m, 1H), 7.42-7.48 (m, 2H), 7.52-7.56 (m, 3H), 7.56-7.63 (m, 1H), 7.82-7.88 (m, 2H), 7.94 (dd, J=8.78, 1.65 Hz, 1H), 8.44 (d, J=2.74 Hz, 1H), 8.46 (d, J=5.21 Hz, 1H), 8.68 (d, J=1.65 Hz, 1H), 8.83 (br s, 1H), 8.84 (br s, 1H), 8.97 (s, 1H), 13.74 (br s, 1H), 13.96 (br s, 1H); ESIMS found for C$_{31}$H$_{21}$FN$_6$O m/z 513.2 (M+1).

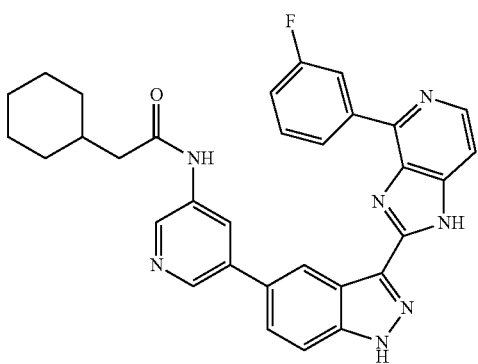

2-Cyclohexyl-N-(5-(3-(4-(3-fluorophenyl)-1H-imidazo[4,5-c]pyridin-2-yl)-1H-indazol-5-yl)pyridin-3-yl)acetamide 1783.

White solid (21 mg, 0.037 mmol, 46.1% yield). $^1$H NMR (DMSO-d$_6$, 500 MHz) δ ppm 0.95-1.06 (m, 2H), 1.09-1.30 (m, 3H), 1.62 (br d, J=11.80 Hz, 1H), 1.64-1.71 (m, 2H), 1.74 (br d, J=13.17 Hz, 2H), 1.81 (dtd, J=14.51, 7.22, 7.22, 3.70 Hz, 1H), 2.29 (d, J=7.14 Hz, 2H), 7.23-7.31 (m, 1H), 7.55 (d, J=5.21 Hz, 1H), 7.57-7.65 (m, 1H), 7.81-7.90 (m, 2H), 8.46 (d, J=5.21 Hz, 1H), 8.54 (s, 1H), 8.70 (d, J=1.92 Hz, 1H), 8.76 (d, J=2.20 Hz, 1H), 8.83 (br s, 1H), 8.85 (br s, 1H), 8.90 (s, 1H), 10.24 (s, 1H), 13.73 (br s, 1H), 13.99 (br s, 1H); ESIMS found for C$_{32}$H$_{28}$FN$_7$O m/z 546.3 (M+1).

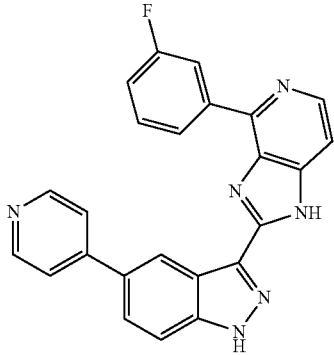

4-(3-Fluorophenyl)-2-(5-(pyridin-4-yl)-1H-indazol-3-yl)-1H-imidazo[4,5-c]pyridine 1784.

White solid (60.0 mg, 0.14 mmol). $^1$H NMR (DMSO-d$_6$, 500 MHz) δ 7.37 (td, J=8.30, 2.61 Hz, 1H) 7.56 (d, J=5.49 Hz, 1H) 7.61-7.68 (m, 1H) 7.84-7.90 (m, 3H) 8.00 (dd, J=8.78, 1.65 Hz, 1H) 8.47 (d, J=5.49 Hz, 1H) 8.70-8.76 (m, 3H) 9.01 (br d, J=11.25 Hz, 1H) 9.11 (s, 1H) 13.75 (s, 1H) 14.01 (s, 1H); ESIMS found for C$_{24}$H$_{15}$FN$_6$ m/z 407.1 (M+1).

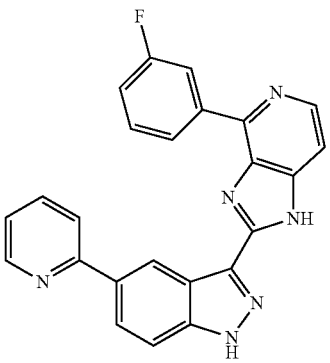

4-(3-Fluorophenyl)-2-(5-(pyridin-2-yl)-1H-indazol-3-yl)-1H-imidazo[4,5-c]pyridine 1785.

Light yellow solid (22 mg, 0.051 mmol, 71.0% yield). $^1$H NMR (DMSO-d$_6$, 500 MHz) δ ppm 7.37 (td, J=8.37, 2.47 Hz, 1H), 7.41 (dd, J=7.41, 4.94 Hz, 1H), 7.56 (d, J=5.21 Hz, 1H), 7.65 (td, J=7.96, 6.31 Hz, 1H), 7.81 (d, J=8.78 Hz, 1H), 7.96 (td, J=7.68, 1.65 Hz, 1H), 8.11 (d, J=7.96 Hz, 1H), 8.32 (dd, J=8.78, 1.65 Hz, 1H), 8.47 (d, J=5.21 Hz, 1H), 8.76 (d, J=4.67 Hz, 1H), 8.81 (br d, J=7.68 Hz, 1H), 9.01 (br d, J=10.98 Hz, 1H), 9.43 (s, 1H), 13.74 (brs, 1H), 13.95 (brs, 1H); ESIMS found for C$_{24}$H$_{15}$FN$_6$ m/z 407.1 (M+1).

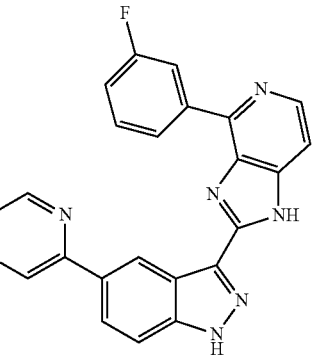

4-(3-Fluorophenyl)-2-(5-(pyrazin-2-yl)-1H-indazol-3-yl)-1H-imidazo[4,5-c]pyridine 1786.

Pink solid (45 mg, 0.105 mmol, 48.7% yield). $^1$H NMR (DMSO-d$_6$, 500 MHz) δ ppm 7.33-7.40 (m, 1H), 7.56 (d, J=5.21 Hz, 1H), 7.64 (td, J=8.03, 6.17 Hz, 1H), 7.86 (d, J=8.78 Hz, 1H), 8.33 (dd, J=8.78, 1.65 Hz, 1H), 8.47 (d, J=5.49 Hz, 1H), 8.66 (d, J=2.47 Hz, 1H), 8.80 (dd, J=2.33, 1.51 Hz, 1H), 8.83 (d, J=7.96 Hz, 1H), 8.95 (br d, J=10.70 Hz, 1H), 9.38 (d, J=1.65 Hz, 1H), 9.49 (s, 1H), 13.75 (brs, 1H), 14.01 (brs, 1H); ESIMS found for C$_{23}$H$_{14}$FN$_7$ m/z 408.1 (M+1).

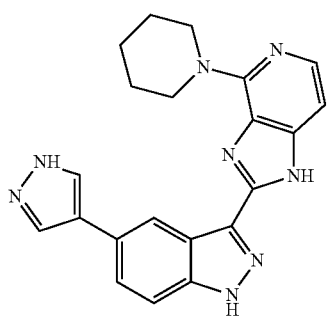

2-(5-(1H-pyrazol-4-yl)-1H-indazol-3-yl)-4-(piperidin-1-yl)-1H-imidazo[4,5-c]pyridine 1879.

Light yellow solid (63.9 mg, 0.166 mmol, 43.2% yield). $^1$H NMR (DMSO-$d_6$, 500 MHz) δ ppm 1.73 (br s, 6H), 4.22 (br s, 4H), 6.80 (d, J=5.49 Hz, 1H), 7.64 (d, J=8.51 Hz, 1H), 7.74 (dd, J=8.64, 1.51 Hz, 1H), 7.80 (d, J=5.49 Hz, 1H), 7.88 (br s, 1H), 8.15 (br s, 1H), 8.60 (s, 1H), 12.99 (br s, 2H), 13.54 (br s, 1H); ESIMS found for $C_{21}H_{20}N_8$ m/z 385.2 (M+1).

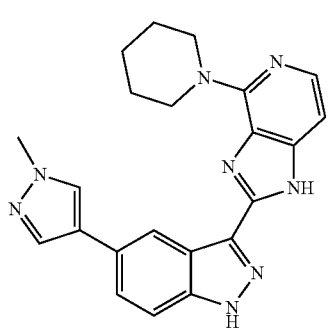

2-(5-(1-Methyl-1H-pyrazol-4-yl)-1H-indazol-3-yl)-4-(piperidin-1-yl)-1H-imidazo[4,5-c]pyridine 1880.

Orange-yellow solid (44.6 mg, 0.112 mmol, 37.1% yield). $^1$H NMR (DMSO-$d_6$, 500 MHz) δ ppm 1.73 (br s, 6H), 4.21 (br s, 4H), 6.80 (d, J=5.49 Hz, 1H), 7.62-7.66 (m, 1H), 7.66-7.71 (m, 1H), 7.79 (s, 1H), 7.80 (d, J=5.49 Hz, 1H), 8.10 (s, 1H), 8.57 (s, 1H), 13.11 (br s, 1H), 13.56 (br s, 1H); ESIMS found for $C_{22}H_{22}N_8$ m/z 399.2 (M+1).

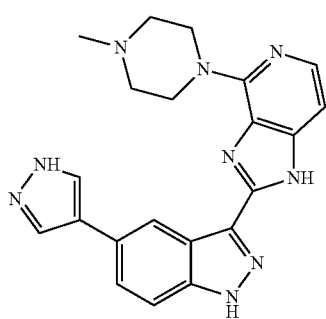

2-(5-(1H-pyrazol-4-yl)-1H-indazol-3-yl)-4-(4-methylpiperazin-1-yl)-1H-imidazo[4,5-c]pyridine 1915.

Off-white solid (45.5 mg, 0.114 mmol, 39.2% yield). $^1$H NMR (DMSO-$d_6$, 500 MHz) δ ppm 2.29 (s, 3H), 2.57 (br s, 4H), 4.22 (br s, 4H), 6.86 (d, J=5.49 Hz, 1H), 7.64 (d, J=8.78 Hz, 1H), 7.74 (dd, J=8.78, 1.65 Hz, 1H), 7.82 (d, J=5.49 Hz, 1H), 7.88 (br s, 1H), 8.16 (br s, 1H), 8.56 (s, 1H), 13.00 (br s, 1H), 13.16 (s, 1H), 13.57 (s, 1H); ESIMS found for $C_{21}H_{21}N_9$ m/z 400 (M+1).

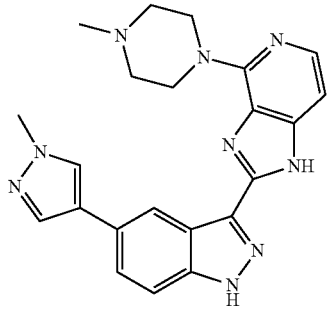

2-(5-(1-Methyl-1H-pyrazol-4-yl)-1H-indazol-3-yl)-4-(4-methylpiperazin-1-yl)-1H-imidazo[4,5-c]pyridine 1916.

Beige solid (47.7 mg, 0.115 mmol, 60.6% yield). $^1$H NMR (DMSO-$d_6$, 500 MHz) δ ppm 2.28 (s, 3H), 2.56 (t, J=4.94 Hz, 4H), 3.91 (s, 3H), 4.21 (br s, 4H), 6.86 (d, J=5.49 Hz, 1H), 7.62-7.71 (m, 2H), 7.80 (s, 1H), 7.82 (d, J=5.49 Hz, 1H), 8.10 (s, 1H), 8.54 (s, 1H), 13.16 (br s, 1H), 13.57 (br s, 1H); ESIMS found for $C_{22}H_{23}N_9$ m/z 414.1 (M+1).

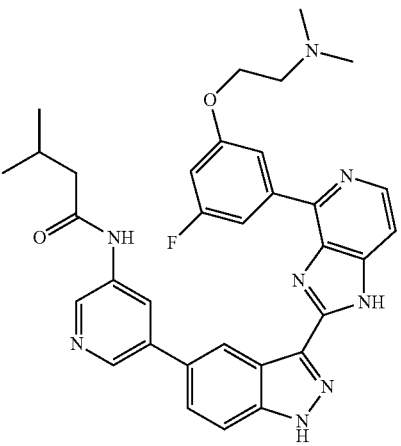

N-(5-(3-(4-(3-(2-(Dimethylamino)ethoxy)-5-fluorophenyl)-1H-imidazo[4,5-c]pyridin-2-yl)-1H-indazol-5-yl)pyridin-3-yl)-3-methylbutanamide 2076.

Yellow solid (17.7 mg, 0.030 mmol, 44.9% yield). $^1$H NMR (DMSO-$d_6$, 500 MHz) δ ppm 0.97 (d, J=6.86 Hz, 6H), 2.06-2.17 (m, 1H), 2.28 (d, J=6.86 Hz, 2H), 2.85 (br s, 6H), 3.54 (br s, 2H), 4.48 (br s, 2H), 7.08 (br s, 1H), 7.67 (br s, 1H), 7.79-7.84 (m, 1H), 7.87-7.93 (m, 1H), 8.37 (br s, 1H), 8.45 (s, 1H), 8.49 (br d, J=5.49 Hz, 1H), 8.56 (br s, 1H), 8.75 (s, 1H), 8.86 (br s, 2H), 9.79 (br s, 1H), 10.29 (s, 1H), 14.12 (br s, 1H); ESIMS found for $C_{33}H_{33}FN_8O_2$ m/z 593.3 (M+1).

1H), 8.89 (s, 1H), 9.97 (br s, 1H), 10.17 (s, 1H), 13.67 (br s, 1H), 13.98 (br s, 1H); ESIMS found for $C_{29}H_{24}FN_7O_2$ m/z 522.2 (M+1).

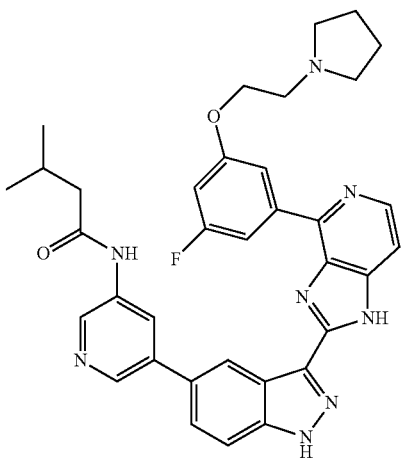

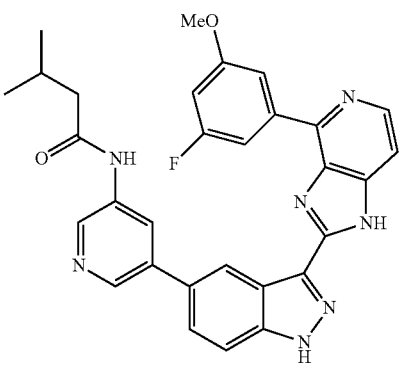

N-(5-(3-(4-(3-Fluoro-5-(2-(pyrrolidin-1-yl)ethoxy)phenyl)-1H-imidazo[4,5-c]pyridin-2-yl)-1H-indazol-5-yl)pyridin-3-yl)-3-methylbutanamide 2120.

Yellow solid (8.3 mg, 0.013 mmol, 20.95% yield). $^1$H NMR (DMSO-$d_6$, 500 MHz) δ ppm 0.96 (d, J=6.59 Hz, 6H), 1.61 (br s, 4H), 2.10 (dquin, J=13.60, 6.69, 6.69, 6.69, 6.69 Hz, 1H), 2.26 (d, J=7.14 Hz, 2H), 2.44 (br s, 3H), 2.56-2.67 (m, 2H), 4.06-4.16 (m, 2H), 6.89 (br d, J=10.43 Hz, 1H), 7.55 (d, J=5.21 Hz, 1H), 7.80 (dd, J=8.78, 1.65 Hz, 1H), 7.85-7.91 (m, 1H), 8.39 (br d, J=11.25 Hz, 1H), 8.43 (t, J=2.06 Hz, 1H), 8.45 (d, J=5.21 Hz, 1H), 8.49 (s, 1H), 8.67 (d, J=2.20 Hz, 1H), 8.82 (d, J=2.20 Hz, 1H), 8.83 (s, 1H), 10.22 (s, 1H), 13.71 (br s, 1H), 14.01 (br s, 1H); ESIMS found for $C_{35}H_{35}FN_8O_2$ m/z 619.3 (M+1).

N-(5-(3-(4-(3-Fluoro-5-methoxyphenyl)-1H-imidazo[4,5-c]pyridin-2-yl)-1H-indazol-5-yl)pyridin-3-yl)-3-methylbutanamide 2208.

Yellow solid 33.6 mg, 0.063 mmol, 51.8% yield). $^1$H NMR (DMSO-$d_6$, 500 MHz) δ ppm 0.96 (d, J=6.59 Hz, 6H), 2.11 (dquin, J=13.64, 6.81, 6.81, 6.81, 6.81 Hz, 1H), 2.27 (d, J=7.14 Hz, 2H), 3.81 (s, 3H), 6.89 (dt, J=10.50, 2.30 Hz, 1H), 7.56 (d, J=5.49 Hz, 1H), 7.80 (dd, J=8.78, 1.65 Hz, 1H), 7.85-7.90 (m, 1H), 8.36 (br d, J=10.15 Hz, 1H), 8.42-8.48 (m, 2H), 8.58 (s, 1H), 8.69 (d, J=1.92 Hz, 1H), 8.82 (d, J=2.20 Hz, 1H), 8.86 (s, 1H), 10.22 (s, 1H), 13.73 (s, 1H), 14.01 (s, 1H); ESIMS found for $C_{30}H_{26}FN_7O_2$ m/z 536.2 (M+1).

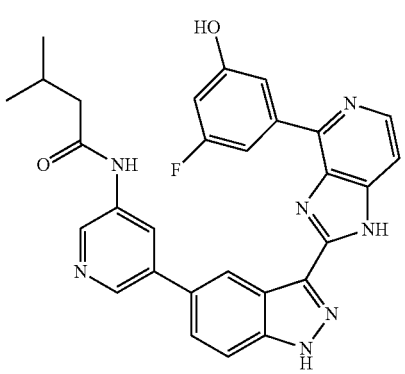

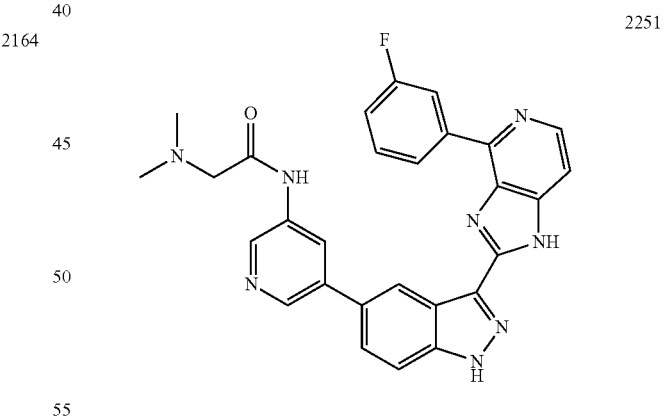

N-(5-(3-(4-(3-Fluoro-5-hydroxyphenyl)-1H-imidazo[4,5-c]pyridin-2-yl)-1H-indazol-5-yl)pyridin-3-yl)-3-methylbutanamide 2164.

Yellow solid (12.6 mg, 0.024 mmol, 17.23% yield). $^1$H NMR (DMSO-$d_6$, 500 MHz) δ ppm 0.97 (d, J=6.59 Hz, 6H), 2.12 (dquin, J=13.64, 6.81, 6.81, 6.81, 6.81 Hz, 1H), 2.27 (d, J=7.14 Hz, 2H), 6.60-6.68 (m, 1H), 7.53 (d, J=5.21 Hz, 1H), 7.79-7.89 (m, 2H), 8.16 (s, 1H), 8.40-8.45 (m, 2H), 8.45-8.51 (m, 1H), 8.72 (d, J=1.92 Hz, 1H), 8.81 (d, J=2.20 Hz, 2-(Dimethylamino)-N-(5-(3-(4-(3-fluorophenyl)-1H-imidazo[4,5-c]pyridin-2-yl)-1H-indazol-5-yl)pyridin-3-yl)acetamide 2251.

Yellow solid (3.6 mg, 0.007 mmol). $^1$H NMR (DMSO-$d_6$, 500 MHz) δ ppm 2.33 (s, 6H) 3.17 (s, 2H) 7.28 (td, J=8.44, 2.33 Hz, 1H) 7.55 (d, J=5.21 Hz, 1H) 7.57-7.64 (m, 1H) 7.82-7.89 (m, 2H) 8.45 (d, J=5.49 Hz, 1H) 8.58 (t, J=2.06 Hz, 1H) 8.73 (d, J=1.92 Hz, 1H) 8.81-8.89 (m, 2H) 8.89-8.95 (m, 2H) 10.10 (s, 1H) 13.90 (br s, 2H); ESIMS found for $C_{28}H_{23}FN_8O$ m/z 507.2 (M+1).

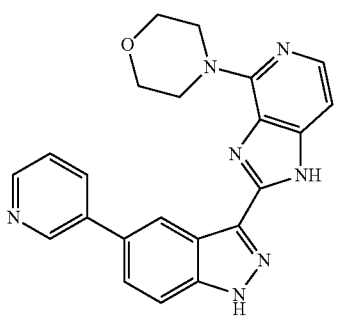

4-(2-(5-(Pyridin-3-yl)-1H-indazol-3-yl)-1H-imidazo[4,5-c]pyridin-4-yl)morpholine 2272.

White solid (46 mg, 0.116 mmol, 76.3% yield). $^1$H NMR (DMSO-d$_6$, 500 MHz) δ ppm 3.78-3.88 (m, 4H), 4.12-4.21 (m, 4H), 6.91 (d, J=5.49 Hz, 1H), 7.56 (dd, J=7.96, 4.94 Hz, 1H), 7.79 (d, J=8.78 Hz, 1H), 7.85 (d, J=5.49 Hz, 1H), 7.87 (dd, J=8.64, 1.78 Hz, 1H), 8.14 (dt, J=8.10, 1.85 Hz, 1H), 8.60 (dd, J=4.67, 1.37 Hz, 1H), 8.74 (s, 1H), 8.96 (d, J=1.92 Hz, 1H), 13.29 (s, 1H), 13.75 (s, 1H); ESIMS found for C$_{22}$H$_{19}$N$_7$O m/z 398.2 (M+1).

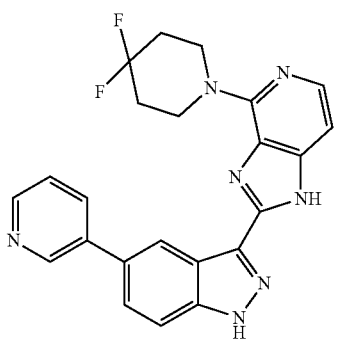

4-(4,4-Difluoropiperidin-1-yl)-2-(5-(pyridin-3-yl)-1H-indazol-3-yl)-1H-imidazo[4,5-c]pyridine 2273.

White solid (31 mg, 0.072 mmol, 70.2% yield). $^1$H NMR (DMSO-d$_6$, 500 MHz) δ ppm 2.06-2.18 (m, 4H), 4.35 (br t, J=5.63 Hz, 4H), 6.92 (d, J=5.49 Hz, 1H), 7.55 (dd, J=8.10, 4.53 Hz, 1H), 7.77-7.82 (m, 1H), 7.86 (s, 1H), 7.86-7.89 (m, 1H), 8.12-8.19 (m, 1H), 8.61 (dd, J=4.80, 1.51 Hz, 1H), 8.73 (s, 1H), 8.97 (d, J=1.92 Hz, 1H), 13.32 (s, 1H), 13.77 (s, 1H); ESIMS found for C$_{23}$H$_{19}$F$_2$N$_7$ m/z 432.1 (M+1).

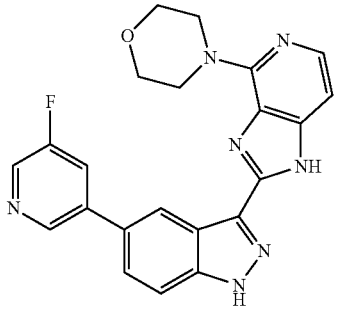

4-(2-(5-(5-Fluoropyridin-3-yl)-1H-indazol-3-yl)-1H-imidazo[4,5-c]pyridin-4-yl)morpholine 2275.

White solid (65 mg, 0.156 mmol, 99.1% yield). $^1$H NMR (DMSO-d$_6$, 500 MHz) δ ppm 3.78-3.88 (m, 4H), 4.17 (br s, 4H), 6.91 (d, J=5.49 Hz, 1H), 7.80 (d, J=8.78 Hz, 1H), 7.85 (d, J=5.49 Hz, 1H), 7.92 (dd, J=8.64, 1.78 Hz, 1H), 8.11 (dt, J=10.22, 2.30 Hz, 1H), 8.61 (d, J=2.74 Hz, 1H), 8.79 (s, 1H), 8.86 (s, 1H), 13.32 (br s, 1H), 13.76 (br s, 1H); ESIMS found for C$_{22}$H$_{18}$FN$_7$O m/z 416.1 (M+1).

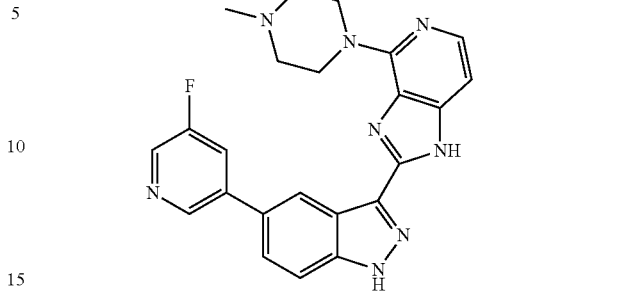

2-(5-(5-Fluoropyridin-3-yl)-1H-indazol-3-yl)-4-(4-methylpiperazin-1-yl)-1H-imidazo[4,5-c]pyridine 2276.

White solid (21 mg, 0.049 mmol, 32.9% yield). $^1$H NMR (DMSO-d$_6$, 500 MHz) δ ppm 2.31 (br s, 3H), 2.55-2.70 (m, 4H), 4.21 (br s, 4H), 6.88 (d, J=5.49 Hz, 1H), 7.80 (d, J=8.51 Hz, 1H), 7.83 (d, J=5.49 Hz, 1H), 7.93 (dd, J=8.78, 1.65 Hz, 1H), 8.10 (dt, J=10.29, 2.26 Hz, 1H), 8.62 (d, J=2.74 Hz, 1H), 8.81 (s, 1H), 8.85-8.90 (m, 1H), 13.28 (s, 1H), 13.78 (s, 1H); ESIMS found for C$_{23}$H$_{21}$FN$_8$ m/z 429.2 (M+1).

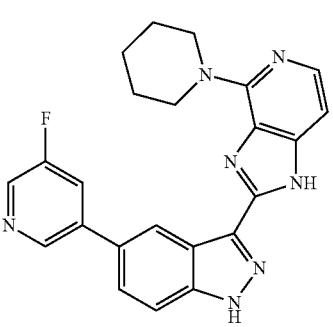

4-(4,4-Difluoropiperidin-1-yl)-2-(5-(5-fluoropyridin-3-yl)-1H-indazol-3-yl)-1H-imidazo[4,5-c]pyridine 2277.

Off-white solid (25 mg, 0.056 mmol, 63.1% yield). $^1$H NMR (DMSO-d$_6$, 500 MHz) δ ppm 2.07-2.19 (m, 4H), 4.35 (br s, 4H), 6.92 (d, J=5.49 Hz, 1H), 7.80 (d, J=8.78 Hz, 1H), 7.85 (d, J=5.76 Hz, 1H), 7.90 (dd, J=8.64, 1.78 Hz, 1H), 8.12 (dt, J=10.22, 2.30 Hz, 1H), 8.61 (d, J=2.47 Hz, 1H), 8.79 (d, J=0.82 Hz, 1H), 8.87 (t, J=1.65 Hz, 1H); ESIMS found for C$_{23}$H$_{18}$F$_3$N$_7$ m/z 450.1 (M+1).

2-(5-(5-Fluoropyridin-3-yl)-1H-indazol-3-yl)-4-(piperidin-1-yl)-1H-imidazo[4,5-c]pyridine 2279.

Tan solid (44.6 mg, 0.108 mmol, 36.4% yield). $^1$H NMR (DMSO-d$_6$, 500 MHz) δ ppm 1.70 (br s, 6H), 4.19 (br s, 4H), 6.81 (d, J=5.76 Hz, 1H), 7.77-7.83 (m, 2H), 7.91 (dd, J=8.78, 1.92 Hz, 1H), 8.09 (dt, J=10.36, 2.23 Hz, 1H), 8.60

(d, J=2.47 Hz, 1H), 8.83 (s, 1H), 8.86 (t, J=1.65 Hz, 1H), 13.21 (s, 1H), 13.75 (s, 1H); ESIMS found for C₂₃H₂₀FN₇ m/z 414.1 (M+1).

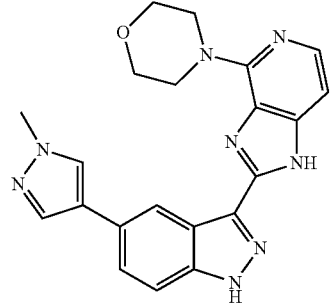

4-(2-(5-(1-Methyl-1H-pyrazol-4-yl)-1H-indazol-3-yl)-1H-imidazo[4,5-c]pyridin-4-yl)morpholine 2280.

White solid (25 mg, 0.062 mmol, 48.9% yield). ¹H NMR (DMSO-d₆, 500 MHz) δ ppm 3.84-3.90 (m, 4H), 3.91 (s, 3H), 4.16-4.22 (m, 4H), 6.91 (d, J=5.49 Hz, 1H), 7.63-7.71 (m, 2H), 7.81 (s, 1H), 7.84 (d, J=5.49 Hz, 1H), 8.10 (s, 1H), 8.50 (s, 1H), 13.25 (br s, 1H), 13.61 (s, 1H); ESIMS found for C₂₁H₂₀N₈O m/z 401.2 (M+1).

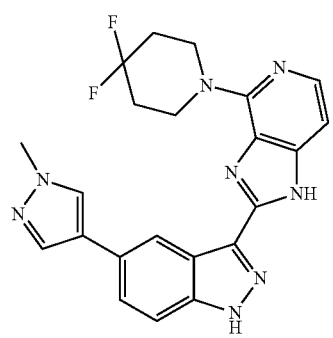

4-(4,4-Difluoropiperidin-1-yl)-2-(5-(1-methyl-1H-pyrazol-4-yl)-1H-indazol-3-yl)-1H-imidazo[4,5-c]pyridine 2281.

White solid (41 mg, 0.094 mmol, 65.2% yield). ¹H NMR (DMSO-d₆, 500 MHz) δ ppm 2.09-2.21 (m, 4H), 4.37 (br s, 4H), 6.92 (d, J=5.76 Hz, 1H), 7.62-7.71 (m, 2H), 7.83 (s, 1H), 7.86 (d, J=5.49 Hz, 1H), 8.13 (s, 1H), 8.52 (s, 1H), 13.24 (br s, 1H), 13.61 (br s, 1H); ESIMS found for C₂₂H₂₀F₂N₈ m/z 435.2 (M+1).

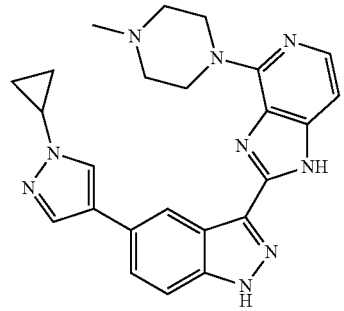

2-(5-(1-Cyclopropyl-1H-pyrazol-4-yl)-1H-indazol-3-yl)-4-(4-methylpiperazin-1-yl)-1H-imidazo[4,5-c]pyridine 2284.

White solid (42.4 mg, 0.096 mmol, 56.5% yield). ¹H NMR (DMSO-d₆, 500 MHz) δ ppm 0.97-1.04 (m, 2H), 1.10-1.15 (m, 2H), 2.30 (s, 3H), 2.58 (br t, J=4.67 Hz, 4H), 3.78 (tt, J=7.34, 3.77 Hz, 1H), 4.20 (br s, 4H), 6.86 (d, J=5.49 Hz, 1H), 7.61-7.66 (m, 1H), 7.72 (dd, J=8.64, 1.51 Hz, 1H), 7.81 (d, J=0.55 Hz, 1H), 7.82 (d, J=5.49 Hz, 1H), 8.17 (s, 1H), 8.55 (s, 1H), 13.16 (br s, 1H), 13.58 (br s, 1H); ESIMS found for C₂₄H₂₅N₉ m/z 440.2 (M+1).

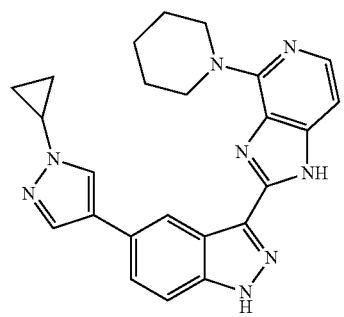

2-(5-(1-Cyclopropyl-1H-pyrazol-4-yl)-1H-indazol-3-yl)-4-(piperidin-1-yl)-1H-imidazo[4,5-c]pyridine 2287.

Off-white solid (71.1 mg, 0.167 mmol, 68.0% yield). ¹H NMR (DMSO-d₆, 500 MHz) δ ppm 0.97-1.04 (m, 2H), 1.08-1.14 (m, 2H), 1.74 (br s, 6H), 3.78 (tt, J=7.34, 3.77 Hz, 1H), 4.21 (br s, 4H), 6.81 (d, J=5.49 Hz, 1H), 7.61-7.66 (m, 1H), 7.69-7.74 (m, 1H), 7.77-7.83 (m, 2H), 8.19 (s, 1H), 8.58 (s, 1H), 13.13 (br s, 1H), 13.53 (br s, 1H); ESIMS found for C₂₄H₂₄N₈ m/z 425.2 (M+1).

Example 2

Preparation of intermediate 5-(5-((dimethylamino)methyl)pyridin-3-yl)-6-fluoro-1H-indazole-3-carbaldehyde (CXXXII) is depicted below in Scheme 26.

Scheme 26

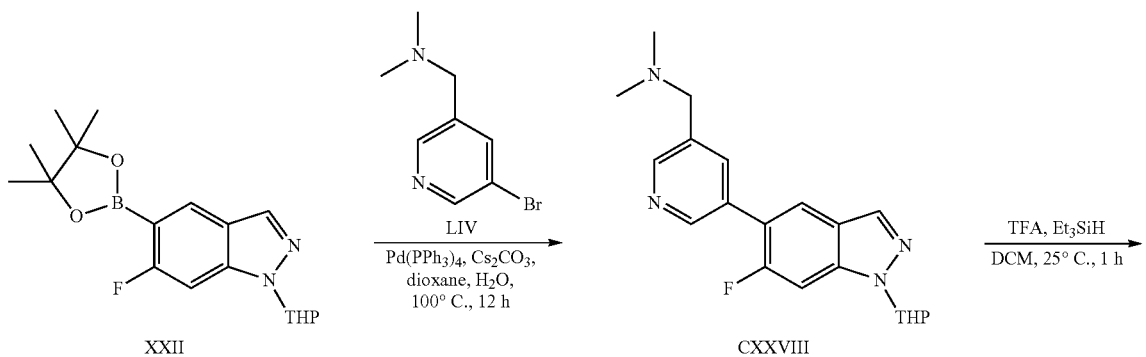

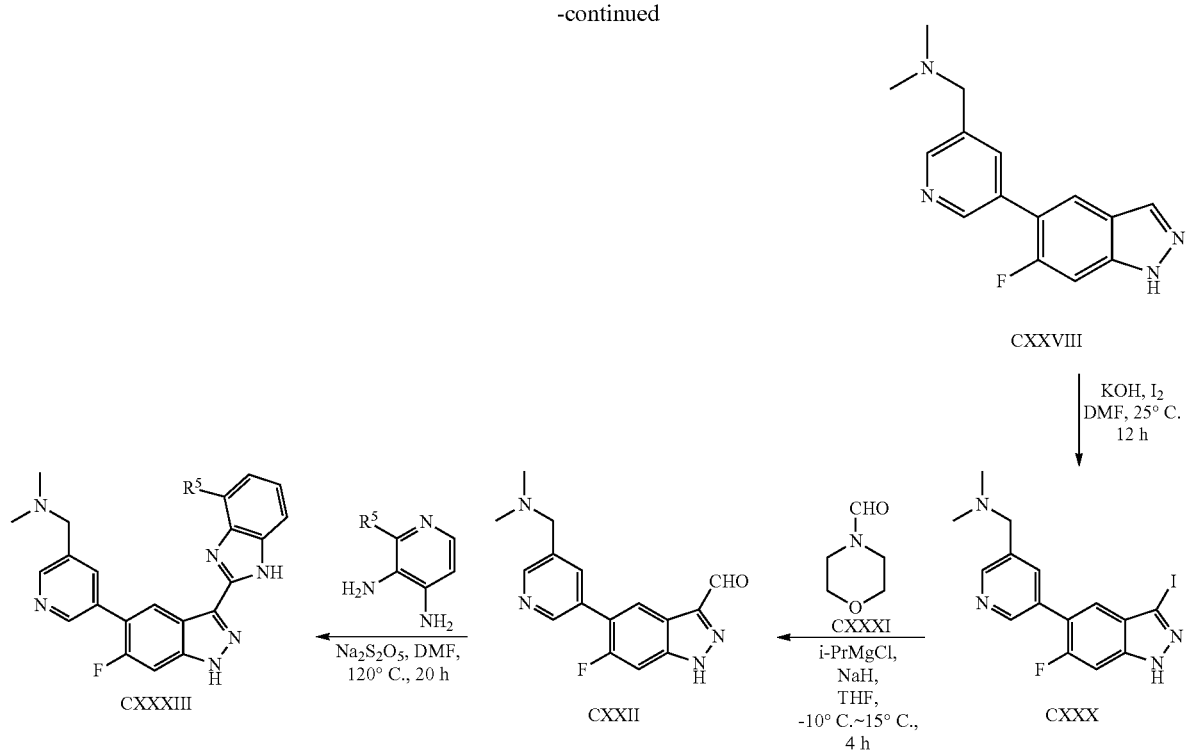

Step 1

A solution of 6-fluoro-1-(tetrahydro-2H-pyran-2-yl)-5-(4,4,5,5-tetramethyl-1,3,2-dioxaborolan-2-yl)-1H-indazole (XXII) (19.5 g, 56.3 mmol, 1.0 eq) in DME (215 mL) was added 1-(5-bromopyridin-3-yl)-N,N-dimethylmethanamine (LIV) (11.5 g, 53.5 mmol, 1.0 eq), Pd(PPh$_3$)$_4$ (1.95 g, 1.69 mmol, 0.03 eq), aq. Na$_2$CO$_3$ (2 M, 56 mL, 2.00 eq). The mixture was stirred at 100° C. for 12 h under N$_2$. TLC (DCM:MeOH=10:1, Rf=0.9) showed (XXII) was consumed completely. The solvent was concentrated under reduce pressure. The residue was dissolved in water (500 ml) and the aqueous phase was extracted with EtOAc (200 ml). The organic layer was washed with brine (100 mL), dried over anhydrous Na$_2$SO$_4$ and filtered. The filtrate was concentrated to give crude product which was purified by silica gel column (DCM:MeOH=30:1) to give 1-(5-(6-fluoro-1-(tetrahydro-2H-pyran-2-yl)-1H-indazol-5-yl)pyridin-3-yl)-N,N-dimethylmethanamine (CXXVIII) as a brown oil (18 g, 50.8 mmol, 94.9% yield). $^1$H NMR (CDCl$_3$, 400 MHz) δ ppm 1.85-1.74 (m, 3H), 2.32-2.15 (m, 2H), 2.32 (s, 6H), 2.60-2.51 (m, 1H), 3.55 (s, 2H), 3.81-3.76 (m, 1H), 4.06 (d, J=11.8 Hz, 1H), 5.71 (d, J=8.8 Hz, 1H), 7.42 (d, J=11.8 Hz, 1H), 7.80 (s, 1H), 7.89 (s, 1H), 8.07 (s, 1H), 8.54 (s, 1H), 8.71 (s, 1H); ESIMS found C$_{20}$H$_{23}$FN$_4$O m/z 355.1 (M+1).

Step 2

To a solution of 1-(5-(6-fluoro-1-(tetrahydro-2H-pyran-2-yl)-1H-indazol-5-yl)pyridin-3-yl)-N,N-dimethylmethanamine (CXXVIII) (18 g, 50.8 mmol, 1.0 eq) in DCM (50 mL) was added Et$_3$SiH (13.2 g, 113 mmol, 2.5 eq) and TFA (51 g, 454 mmol, 10 eq). The mixture was stirred at 25° C. for 12 h. LC/MS showed (CXXVIII) was consumed. The reaction mixture was concentrated in vacuo. The residue was diluted with TBME (200 mL). The mixture was stirred for 0.5 h at −65° C., 1 h at 25° C. The precipitate was filtered and the solid was concentrated in vacuo. The residue was dissolve in MeOH (200 mL), weakly basic resin was added. The mixture was stirred for 0.5 h, pH=7. The solid was filtered and dried in vacuo to give 1-(5-(6-fluoro-1H-indazol-5-yl)pyridin-3-yl)-N,N-dimethylmethanamine (CXXIX) as white solid (12.0 g, 44.4 mmol, 88.3% yield). $^1$H NMR (CDCl$_3$, 400 MHz) δ ppm 2.96 (s, 6H), 4.52 (s, 2H), 7.42 (d, J=11.2 Hz, 1H), 8.02 (d, J=7.2 Hz, 1H), 8.16 (s, 1H), 8.27 (s, 1H), 8.73 (s, 1H), 8.89 (s, 1H); ESIMS found Cl$_5$H$_{15}$FN$_4$ m/z 271.1 (M+1).

Step 3

To a solution of 1-(5-(6-fluoro-1H-indazol-5-yl)pyridin-3-yl)-N,N-dimethylmethanamine (CXXIX) (12.0 g, 44.4 mmol, 1.0 eq) in DMF (70 mL) was added KOH (7.4 g, 133.2 mmol, 3.0 eq) and I$_2$ (16.9 g, 66.6 mmol, 1.5 eq) at 25° C. The reaction mixture was stirred at 25° C. for 1 h. LC/MS showed (CXXIX) was consumed. The reaction mixture was quenched with 10% aqueous Na$_2$SO$_3$ (100 mL) and diluted with water (300 mL) and EtOAc (200 mL). The precipitated solid was filtered, dried to afford product. The solution was separated, and the organic layer was washed with water (100 mL) and sat NaCl (100 mL), then dried over anhydrous Na$_2$SO$_4$ and concentrated to afford 1-(5-(6-fluoro-3-iodo-1H-indazol-5-yl)pyridin-3-yl)-N,N-dimethylmethanamine (CXXX) as a yellow solid (10.0 g, 25.2 mmol, 56.8% yield). $^1$H NMR (CDCl$_3$, 400 MHz) δ ppm 2.31 (s, 6H), 4.02 (d, J=7.2 Hz, 2H), 7.59-7.55 (m, 2H), 7.92 (s, 1H), 8.53 (s, 1H), 8.69 (s, 1H), 13.71 (br, 1H); ESIMS found C$_{15}$H$_{14}$F$_1$N$_4$ m/z 397.1 (M+1).

Step 4

To a solution of 1-(5-(6-fluoro-3-iodo-1H-indazol-5-yl)pyridin-3-yl)-N,N-dimethylmethanamine (CXXX) (1.50 g, 3.79 mmol, 1.00 eq) in THF (20 mL) was added NaH (181 mg, 4.55 mmol, 1.20 eq) portion-wise at 0° C. The reaction mixture was stirred at 20° C. for 10 min then cooled to −10° C. and i-PrMgCl (2 M, 11.37 mL, 6.00 eq) was added. The reaction mixture was stirred at −10° C. for 1 h then morpholine-4-carbaldehyde (CXXXI) (3.49 g, 30.32 mmol, 8.00 eq) was slowly added. The mixture was stirred at −10° C. for 20 min then at 20° C. for 3 h. TLC (DCM:MeOH=5/1, $R_f$=0.55) show the reaction is complete. The reaction mixture was quenched with water (3 mL). The mixture was acidified with HCl (1N, 20 mL) to pH=7 and then concentrated to give crude product, which was further purified by silica gel on column chromatography (DCM/MeOH=50:1→3:1) to give 5-(5-((dimethylamino)methyl)pyridin-3-yl)-6-fluoro-1H-indazole-3-carbaldehyde (CXXXII) (2.9 g, 50% TLC purity) as yellow solid. The crude product was used for step 5 without further purification. ESIMS found $C_{16}H_{15}FN_4O$ m/z 299.1 (M+1).

Step 5

Preparation of the following compounds were performed following the procedure listed in Scheme 25, Step 2.

The following compounds were prepared in accordance with the procedure described in the above Example 2.

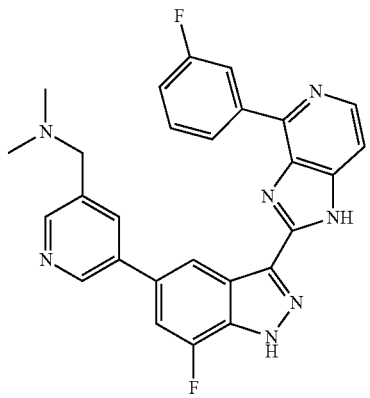

456

1-(5-(7-Fluoro-3-(4-(3-fluorophenyl)-1H-imidazo[4,5-c]pyridin-2-yl)-1H-indazol-5-yl)pyridin-3-yl)-N,N-dimethylmethanamine 456.

White solid (39.8 mg, 0.08 mmol). ESIMS found for $C_{27}H_{21}F_2N_7$ m/z 482.1 (M+1).

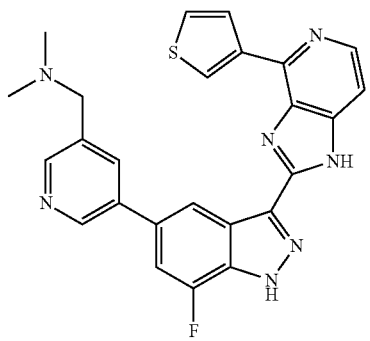

688

1-(5-(7-Fluoro-3-(4-(thiophen-3-yl)-1H-imidazo[4,5-c]pyridin-2-yl)-1H-indazol-5-yl)pyridin-3-yl)-N,N-dimethylmethanamine 688.

White solid (30.8 mg, 0.07 mmol). $^1$H NMR (DMSO-d$_6$, 400 MHz) δ ppm 2.82 (br d, J=3.76 Hz, 6H), 4.52 (br d, J=3.28 Hz, 2H), 7.83 (br d, J=10.54 Hz, 1H), 7.93 (br d, J=6.02 Hz, 2H), 8.47 (br d, J=6.52 Hz, 1H), 8.58-8.66 (m, 2H), 8.71 (br d, J=7.28 Hz, 1H), 8.96 (s, 1H), 9.07 (br s, 1H), 9.47 (br s, 1H), 11.46 (br s, 1H), 14.59 (br s, 1H), 14.92 (br s, 1H); ESIMS found for $C_{25}H_{20}FN_7S$ m/z 470.1 (M+1).

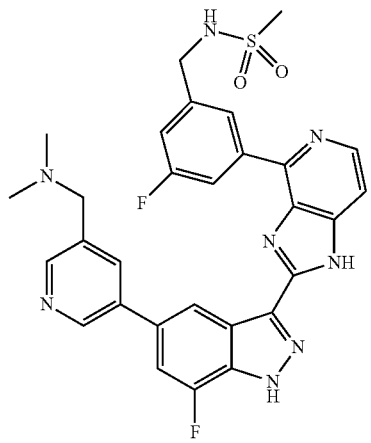

844

N-(3-(2-(5-(5-((Dimethylamino)methyl)pyridin-3-yl)-7-fluoro-1H-indazol-3-yl)-1H-imidazo[4,5-c]pyridin-4-yl)-5-fluorobenzyl)methanesulfonamide 844.

White solid (36.5 mg, 0.06 mmol). $^1$H NMR (DMSO-d$_6$, 400 MHz) δ ppm 2.82 (br s, 6H), 2.94 (s, 3H), 4.31 (br s, 2H), 4.64 (br s, 2H), 7.52 (br d, J=9.03 Hz, 1H), 7.66 (d, J=10.54 Hz, 1H), 7.88 (br d, J=6.27 Hz, 2H), 8.40 (br d, J=9.79 Hz, 1H), 8.43-8.51 (m, 3H), 8.90 (br s, 1H), 9.15 (br s, 1H), 9.20 (br s, 1H), 11.67 (br s, 1H), 14.63 (br s, 1H); ESIMS found for $C_{29}H_{26}F_2N_5O_2S$ m/z 589.1 (M+1).

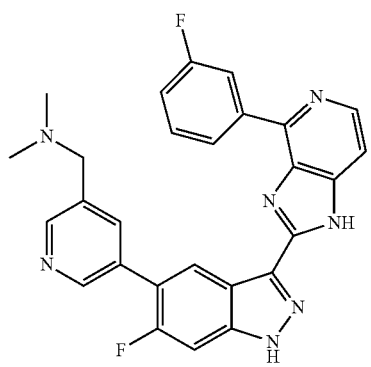

898

1-(5-(6-Fluoro-3-(4-(3-fluorophenyl)-1H-imidazo[4,5-c]pyridin-2-yl)-1H-indazol-5-yl)pyridin-3-yl)-N,N-dimethylmethanamine 898.

White solid (27.2 mg, 0.06 mmol). $^1$H NMR (DMSO-d$_6$, 400 MHz) δ ppm 2.84 (br s, 6H), 4.60 (br s, 2H), 7.47 (br t, J=7.40 Hz, 1H), 7.65-7.73 (m, 1H), 7.75-7.82 (m, 2H), 8.27 (s, 1H), 8.41 (br d, J=6.27 Hz, 1H), 8.44-8.52 (m, 2H), 8.88 (br s, 1H), 8.96 (s, 1H), 9.03 (s, 1H), 11.71 (br s, 1H), 14.78 (br s, 1H); ESIMS found for $C_{27}H_{21}F_2N_7$ m/z 482.3 (M+1).

717

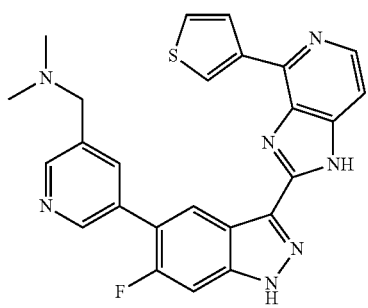

1-(5-(6-Fluoro-3-(4-(thiophen-3-yl)-1H-imidazo[4,5-c]pyridin-2-yl)-1H-indazol-5-yl)pyridin-3-yl)-N,N-dimethylmethanamine 1132.

White solid (5.3 mg, 0.01 mmol). $^1$H NMR (DMSO-$d_6$, 400 MHz) δ ppm 2.82 (br d, J=2.76 Hz, 6H), 4.53 (br s, 2H), 7.87 (d, J=6.52 Hz, 1H), 7.92-8.00 (m, 2H), 8.43 (d, J=6.53 Hz, 1H), 8.60 (d, J=5.02 Hz, 1H), 8.63 (s, 1H), 8.89 (br s, 1H), 8.92 (br s, 1H), 9.22 (d, J=1.76 Hz, 1H), 9.45 (d, J=1.76 Hz, 1H), 11.60 (br s, 1H), 14.90 (br s, 1H), 14.96 (br s, 1H); ESIMS found for $C_{25}H_{20}FN_7S$ m/z 470.1 (M+1).

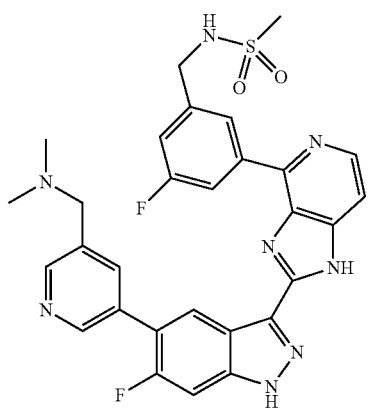

N-(3-(2-(5-(5-((Dimethylamino)methyl)pyridin-3-yl)-6-fluoro-1H-indazol-3-yl)-1H-imidazo[4,5-c]pyridin-4-yl)-5-fluorobenzyl)methanesulfonamide 1288.

White solid (35.0 mg, 0.06 mmol). $^1$H NMR (DMSO-$d_6$, 400 MHz) δ ppm 2.84 (br s, 6H), 2.98 (s, 3H), 4.34 (br s, 2H), 4.61 (br s, 2H), 7.50 (br d, J=8.78 Hz, 1H), 7.76-7.84 (m, 2H), 7.90 (br s, 1H), 8.28 (s, 1H), 8.37-8.46 (m, 3H), 8.93 (br s, 1H), 9.01 (s, 1H), 9.15 (s, 1H), 11.68 (br s, 1H), 14.82 (br s, 1H); ESIMS found for $C_{29}H_{26}F_2N_8O_2S$ m/z 589.3 (M+1).

718

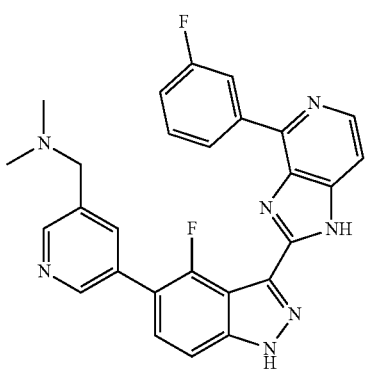

1-(5-(4-Fluoro-3-(4-(3-fluorophenyl)-1H-imidazo[4,5-c]pyridin-2-yl)-1H-indazol-5-yl)pyridin-3-yl)-N,N-dimethylmethanamine 1339.

White solid (53.8 mg, 0.11 mmol). ESIMS found for $C_{27}H_{21}F_2N_7$ m/z 482.1 (M+1).

1-(5-(4-Fluoro-3-(4-(thiophen-3-yl)-1H-imidazo[4,5-c]pyridin-2-yl)-1H-indazol-5-yl)pyridin-3-yl)-N,N-dimethylmethanamine 1573.

White solid (3.9 mg, 0.008 mmol). $^1$H NMR (DMSO-$d_6$, 400 MHz) δ ppm 2.80 (br d, J=3.76 Hz, 6H), 4.51 (br d, J=3.80 Hz, 2H), 7.74 (d, J=8.53 Hz, 1H), 7.80-7.87 (m, 1H), 7.89 (d, J=6.78 Hz, 1H), 7.91-7.95 (m, 1H), 8.44 (d, J=6.53 Hz, 1H), 8.62 (br s, 1H), 8.71 (br d, J=5.02 Hz, 1H), 8.90 (s, 1H), 9.07 (s, 1H), 9.48 (br s, 1H), 11.49 (br s, 1H), 14.75 (br s, 1H), 14.84 (br s, 1H); ESIMS found for $C_{25}H_{20}FN_7S$ m/z 470.1 (M+1).

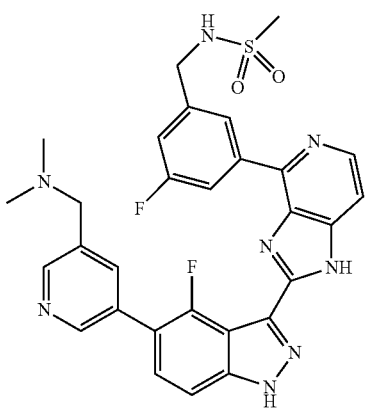

N-(3-(2-(5-(5-((Dimethylamino)methyl)pyridin-3-yl)-4-fluoro-1H-indazol-3-yl)-1H-imidazo[4,5-c]pyridin-4-yl)-5-fluorobenzyl)methanesulfonamide 1729.

White solid (6.9 mg, 0.01 mmol). $^1$H NMR (DMSO-$d_6$, 400 MHz) δ ppm 2.78 (br s, 6H), 2.94 (br d, J=3.26 Hz, 3H), 4.32 (br s, 2H), 4.52 (br s, 2H), 7.53 (br d, J=8.53 Hz, 1H), 7.73 (br dd, J=8.78, 3.76 Hz, 1H), 7.84 (br s, 2H), 7.98 (br s, 1H), 8.55 (br s, 1H), 8.60-8.71 (m, 3H), 8.93 (br s, 1H), 9.11 (br s, 1H), 11.58 (br s, 1H), 14.90 (br s, 1H); ESIMS found for $C_{29}H_{26}F_2N_8O_2S$ m/z 589.2 (M+1).

Example 3

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 µg/ml of hygromycin for 7 days. These stably transduced SW480 cells were expanded in cell culture and used for all further screening activities. For Sp5-Luc reporter gene assays, the cells were plated at 10,000 cells/well in 96-well plates with growth medium containing 10% fetal calf serum and incubated overnight at 37° C. and 5% $CO_2$. Each compound was dissolved in DMSO as a 10 mM stock in standard j-vials and used to prepare compound source plates in dose-response format with 3-fold serial dilutions and a 10 mM top concentration. Compound transfer from serially diluted source plates to assay plates containing the cells was accomplished using a pintool (Multimek 96, Beckman equipped with V&P Scientific FP1S50H pins) based liquid handling protocol. This protocol used a slotted pin to transfer 50 nl of compound from a source plate well to an assay plate well containing 50 µl of cells in growth medium. The 1000-fold dilution resulted in a final DMSO concentration of 0.1% on the cells in each well. Control wells received 50 nl of DMSO treatment for normalization and calculating $IC_{50}$ values. The treated cells were incubated at 37° C. and 5% $CO_2$ for an additional forty-two hours. Following incubation, the growth medium was removed and 50 µl of BrightGlo luminescence reagent (Promega) was added to each well of the 96-well assay plates. The plates were placed on an orbital shaker for 5 min and then luminescence was quantified on the Victor3 (Perkin Elmer) plate reader. Readings were normalized to DMSO only treated cells, and normalized activities were utilized for $IC_{50}$ calculations using the dose-response log (inhibitor) vs. response-variable slope (four parameters) nonlinear regression feature available in GraphPad Prism 5.0 or 6.0. Table 2 shows the measured activity for selected compounds of Formula I as described herein.

TABLE 2

| Compound | $IC_{50}$ (µM) | Compound | $IC_{50}$ (µM) | Compound | $IC_{50}$ (µM) |
|---|---|---|---|---|---|
| 1 | 0.001 | 223 | 0.172 | 428 | 0.006 |
| 2 | 0.005 | 224 | 0.6729 | 434 | 0.016 |
| 7 | 0.004 | 229 | 0.711 | 440 | 0.5392 |
| 13 | 0.001 | 234 | 0.021 | 456 | 0.090 |
| 19 | 0.001 | 239 | 0.003 | 688 | 0.415 |
| 21 | 0.0128 | 242 | 0.0274 | 844 | 0.096 |
| 25 | 0.010 | 244 | 0.0691 | 898 | 1.453 |
| 28 | 0.009 | 245 | 0.040 | 1132 | 3.680 |
| 34 | 0.013 | 251 | 0.001 | 1288 | 0.637 |
| 38 | 0.0429 | 253 | 0.1265 | 1339 | 1.180 |
| 40 | 0.075 | 255 | 0.0594 | 1573 | 3.055 |
| 46 | 0.010 | 257 | 0.007 | 1729 | 1.095 |
| 52 | 0.025 | 266 | 0.036 | 1769 | 2.336 |
| 55 | 0.0041 | 272 | <0.001 | 1770 | 0.658 |

TABLE 2-continued

| Compound | $IC_{50}$ (µM) | Compound | $IC_{50}$ (µM) | Compound | $IC_{50}$ (µM) |
|---|---|---|---|---|---|
| 59 | 0.0094 | 278 | 0.015 | 1771 | 0.004 |
| 61 | 0.005 | 280 | 0.0279 | 1772 | 0.011 |
| 68 | 0.020 | 284 | >10 | 1773 | 0.023 |
| 69 | 0.005 | 287 | 0.010 | 1774 | 0.171 |
| 73 | 0.008 | 293 | 0.009 | 1775 | 0.252 |
| 82 | 0.008 | 295 | 0.0308 | 1776 | 0.778 |
| 86 | 0.0179 | 299 | 0.332 | 1777 | 0.243 |
| 87 | 0.003 | 305 | 0.004 | 1778 | 0.280 |
| 90 | 0.004 | 307 | 0.0348 | 1779 | 0.192 |
| 93 | 0.318 | 311 | 0.320 | 1780 | 0.025 |
| 101 | 0.047 | 314 | 0.0447 | 1781 | 0.006 |
| 109 | 0.0405 | 320 | 0.0052 | 1782 | 0.575 |
| 114 | 0.036 | 326 | 0.2837 | 1783 | 0.505 |
| 121 | 0.102 | 332 | 0.0326 | 1784 | >10 |
| 126 | 1.187 | 341 | 0.0013 | 1785 | 0.633 |
| 136 | 3.058 | 347 | 0.007 | 1786 | 0.035 |
| 141 | >10 | 353 | 0.844 | 1915 | 0.070 |
| 148 | 0.2484 | 354 | 0.0127 | 1916 | 0.065 |
| 150 | 0.0514 | 358 | 0.009 | 2076 | 0.370 |
| 154 | 0.061 | 359 | 0.005 | 2120 | 0.305 |
| 157 | 0.183 | 368 | <0.001 | 2164 | 0.035 |
| 163 | 0.003 | 374 | 0.009 | 2208 | 0.020 |
| 168 | 0.0881 | 380 | 0.187 | 2251 | 0.124 |
| 169 | 4.018 | 386 | 0.4755 | 2272 | 0.020 |
| 175 | 0.278 | 395 | 0.085 | 2273 | 0.050 |
| 181 | 0.067 | 400 | >10 | 2275 | 0.080 |
| 184 | 0.002 | 401 | 0.032 | 2276 | 0.439 |
| 190 | 0.005 | 407 | 0.024 | 2277 | 0.315 |
| 202 | <0.001 | 413 | 0.187 | 2280 | 0.015 |
| 211 | 0.0971 | 416 | <0.001 | 2281 | 0.020 |
| 212 | 0.065 | 422 | 0.108 | 2284 | 0.090 |
| 217 | 0.245 | | | | |

Example 4

The above synthesized compounds were screened using primary human mesenchymal stem cells (hMSCs) to determine their ability to induce chondrogenesis (process by which cartilage is developed).

Human Mesenchymal Stem Cell Culture: Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening: Each compound was dissolved in DMSO as a 10 mM stock and used to prepare compound source plates. Serial dilution (1:3, 6-point dose-response curves from 2700 nM to 10 nM) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.03%. hMSCs were plated at 20,000 cells/well in 250 µL/well Incomplete Chondrogenic Induction Medium (Lonza; DMEM, dexamethasone, ascorbate, insulin-transferrin-selenium [ITS supplement], gentamycin-amphotericin [GA-1000], sodium pyruvate, proline and L-glutamine). TGF-β3 (10 ng/mL) was used as a positive control for differentiation while negative control wells were treated with 75 nL DMSO for normalization and calculating $EC_{50}$ values. Cells were incubated at 37° C. and 5% $CO_2$ for 6 days. To image chondrogenic nodules, the cells were fixed using 4% formaldehyde (Electron Microscopy Sciences), and stained with 2 µg/mL Rhodamine B (Sigma-Aldrich) and 20 µM Nile Red (Sigma-Aldrich) [Johnson K., et. al, A Stem Cell-Based Approach to Cartilage Repair, Science, (2012), 336(6082), 717-721]. The nodules imaged (4 images per well at 4× magnification) by excitation at 531 nm and emission at 625 nm and quantified using the CellInsight CX5 (Thermo Scientific). Number of nodules in each well was normalized to the average of 3 DMSO treated wells on the same plate using Excel (Microsoft Inc.). The normalized averages (fold change over DMSO) of 3 replicate wells for each compound concentration were calculated. Due to solubility limitations of some of the compounds, curve fitting was incomplete leading to inaccurate $EC_{50}$ determinations.

Using TGF-β3 as a positive control, the concentration of test compounds required to induce equivalent levels of chondrogenesis is reported. In addition, the maximum activity of each compound and the respective dose that each compound reached maximum chondrogenesis activity is reported. Table 3 shows the activity of selected compounds as provided herein.

TABLE 3

| Compound | Conc (nM) of Max. activity | Max. Activity as 70% TGF-β3 activity | Conc (nM) of 100% TGF-β3 activity | Compound | Conc (nM) of Max. activity | Max. Activity as 70% TGF-β3 activity | Conc (nM) of 100% TGF-β3 activity |
|---|---|---|---|---|---|---|---|
| 1 | 300 | N/A | 60.96 | 234 | 30 | 30 | 87.3 |
| 13 | 900 | 900 | 129.9 | 239 | 300 | 10 | 155.7 |
| 19 | 300 | 10 | 112.5 | 272 | 300 | 30 | 90.2 |
| 55 | 100 | 100 | 61.9 | 320 | 2700 | 2700 | 96.4 |
| 87 | 900 | N/A | 68.3 | 341 | 10 | 2700 | 163.1 |
| 114 | 900 | N/A | 48.2 | 368 | 10 | 10 | 105.8 |
| 163 | 10 | N/A | 62.8 | 416 | 30 | 30 | 73.1 |
| 184 | 30 | 30 | 73.7 | 428 | 30 | 30 | 85.1 |
| 202 | 30 | 30 | 76.2 | 2251 | 300 | N/A | 36.1 |

Example 5

The above synthesized compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and Penicillin/Streptomycin.

Compound Screening:

Each compound was dissolved in DMSO as a 10 mM stock and used to prepare compound source plates. Serial dilution (1:2, 11-point dose-response curves from 10 M to 1.87 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 80 l/well $F_{12}$ medium supplemented with 1% Fetal Bovine Serum. One hour after addition of the cells, TGF-31 (Peprotech; 20 ng/mL) was added to the plates to induce fibrosis (ref. 1 and 2 above). Wells treated with TGF-β1 and containing DMSO were used as controls. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 uM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and $EC_{50}$ values were calculated using non-linear regression curve fit in the Dotmatics' Studies Software. The $EC_{50}$ values are reported.

Table 4 shows the activity of selected compounds as provided herein.

TABLE 4

| Compound | Inhibition of fibrosis $EC_{50}$ (μM) | Compound | Inhibition of fibrosis $EC_{50}$ (μM) | Compound | Inhibition of fibrosis $EC_{50}$ (μM) |
|---|---|---|---|---|---|
| 1 | 0.020 | 181 | 0.0805 | 347 | 0.038 |
| 2 | 0.009 | 184 | 0.049 | 353 | 0.009 |
| 7 | 0.009 | 190 | 0.050 | 354 | 0.086 |
| 13 | 0.009 | 202 | 0.013 | 358 | 0.021 |
| 19 | 0.009 | 217 | 4.452 | 359 | 0.041 |
| 21 | 0.317 | 223 | 1.113 | 368 | 0.014 |
| 25 | 0.056 | 224 | 1.094 | 374 | 0.009 |
| 28 | 0.009 | 229 | 9.990 | 386 | 0.536 |
| 34 | 0.009 | 234 | 0.280 | 395 | 0.026 |
| 38 | 0.126 | 239 | 0.060 | 400 | 0.009 |
| 40 | 0.024 | 242 | 1.179 | 401 | 9.990 |
| 46 | 0.009 | 244 | 0.203 | 407 | 0.019 |
| 52 | 0.539 | 245 | 0.017 | 413 | 0.009 |
| 55 | 0.017 | 251 | 0.018 | 416 | 0.027 |
| 59 | 0.018 | 253 | 0.544 | 422 | 0.108 |
| 61 | 0.079 | 255 | 1.221 | 428 | 0.009 |
| 68 | 0.009 | 257 | 0.009 | 434 | 0.459 |
| 69 | 0.074 | 266 | 0.009 | 440 | 0.009 |
| 73 | 0.009 | 272 | 0.009 | 1769 | 0.670 |
| 82 | 0.009 | 278 | 0.291 | 1770 | 9.990 |
| 86 | 0.993 | 280 | 1.244 | 1771 | 9.990 |
| 87 | 0.295 | 284 | 0.009 | 1772 | 9.990 |
| 90 | 0.009 | 287 | 0.062 | 1774 | 0.102 |
| 93 | 0.388 | 293 | 0.036 | 1775 | 0.009 |
| 101 | 2.432 | 295 | 0.186 | 1776 | 0.038 |
| 109 | >10 | 299 | 0.608 | 1777 | 0.107 |
| 126 | 9.990 | 305 | 0.022 | 1779 | 0.041 |
| 136 | 0.009 | 307 | 0.422 | 1780 | 0.019 |
| 150 | 1.518 | 311 | 0.083 | 1781 | 0.079 |
| 154 | 0.061 | 314 | 0.665 | 1784 | 9.990 |
| 157 | 0.071 | 320 | 0.115 | 1785 | 0.009 |
| 163 | 1.548 | 326 | 0.940 | 1786 | 0.009 |
| 169 | 0.171 | 332 | 0.363 | 2251 | 0.075 |
| 175 | 0.115 | 341 | 0.009 | | |

Example 6

The above synthesized compounds were screened using ARPE-19 cells [a spontaneously arising retinal pigment epithelia (RPE) cell line] to determine their ability to transdifferentiate ARPE-19 into eye neuronal cells [photoreceptors].

ARPE-19 Cell Culture: ARPE-19 cells are cultured in standard culture medium containing Dulbecco's Modified Eagle's Medium and Ham's $F_{12}$ Nutrient Mixture (DMEM/$F_{12}$) mix (1:1)+GlutaMax with 1% penicillin-Streptomycin and 10% FBS (Fetal Bovine Serum). Cells are incubated at 37° C. with 5% $CO_2$. Cells are trypsinized and plated onto 384-well pre-spotted plate at a density of 3000 cells/well in 50 uL of media. Plating media: DMEM/$F_{12}$ (1:1)+3% charcoal filtered-FBS+GlutaMax+1% pen/Strep. Cells are incubated at 37° C. with 5% $CO_2$. At 40 hours, cells were fixed for 15 min with 10% Buffered Formalin. Cells were then washed 3 times with PBS for 5 min each, permeablize using 0.3% Triton X-100 in 1×PBS for 30 min, block for 1 h with 2% BSA in 1×PBS with 0.1% Triton X-100. The primary antibody (1:100 PAX6 Santa Cruz Biotech; sc-81649) was diluted and 10 μL/well was added to the cells. The cells were incubated overnight at 4° C. The plates were washed 3× with PBS before applying the secondary antibody (goat Anti-mouse 488), shake for 1 h in complete darkness, aspirate secondary, add 10 μL of DAPI (diamidino-2-phenylindole) (1 μg/mL), shake for 10 min. Wash 3× in PBS and scan on Thermo Fisher Scientific cell-Insight CX5. Readings were normalized to DMSO only treated cells, and normalized activities were utilized for $EC_{50}$ calculations using the dose-response log (activator) vs. response-variable slope (four parameters) nonlinear regression feature available in GraphPad Prism 5.0 or 6.0.

Table 5 shows the activity of selected compounds as provided herein.

TABLE 5

| Compound | PAX6 $EC_{50}$ (μM) |
|---|---|
| 1916 | 0.0037 |
| 2275 | 0.0434 |
| 2280 | 0.002 |
| 2284 | 0.006 |

What is claimed is:

1. A method of treating a bone or cartilage disease in a subject, wherein the bone or cartilage disease is selected from the group consisting of osteoarthritis, bone spur (osteophytes), craniosynostosis, fibrodysplasia ossificans progressive, fibrous dysplasia, giant cell tumor of bone, hip labral tear, meniscal tears, bone/osteoporotic fractures, articular cartilage (chondral) defects, degenerative disc disease, osteochondritis dissecans, osteochondroma, osteopetrosis, relapsing polychondritis, and Salter-Harris fractures, the method comprising administering to the subject a therapeutically effective amount of a compound of Formula I, or a pharmaceutically acceptable salt thereof:

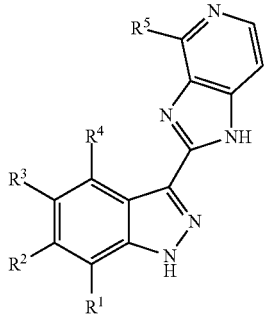

I wherein:
$R^1$, $R^2$, and $R^4$ are independently selected from the group consisting of H and halide;

$R^3$ is selected from the group consisting of -heteroaryl$(R^6)_q$ and -heterocyclyl$(R^7)_h$;
$R^5$ is selected from the group consisting of -heteroaryl$(R^8)_q$, -heterocyclyl$(R^9)_h$, and -aryl$(R^{10})_k$;
each $R^6$ is one substituent attached to the heteroaryl and is independently selected from the group consisting of halide, —$(C_{1-6}$ alkyl), —$(C_{1-4}$ alkylene$)_p$heterocyclyl$(R^{11})_h$, —$(C_{1-4}$ alkylene$)_p$carbocyclyl$(R^{12})_j$, —$(C_{1-4}$ alkylene$)_p$aryl$(R^{13})_k$, —NHC(=O)$R^{14}$, —$NR^{15}R^{16}$, —$(C_{1-6}$ alkylene)$NR^{17}R^{18}$, and —$OR^{24}$;
each $R^7$ is one substituent attached to the heterocyclyl and is independently selected from the group consisting of —$(C_{1-4}$ alkyl), halide, —$CF_3$, and —CN;
each $R^8$ is one substituent attached to the heteroaryl and is independently selected from the group consisting of —$(C_{1-6}$ alkyl), halide, —$CF_3$, —$OCH_3$, —CN, and —C(=O)$R^{19}$;
each $R^9$ is one substituent attached to the heterocyclyl and is independently selected from the group consisting of —$(C_{1-6}$ alkyl), halide, —$CF_3$, —CN, and —$OCH_3$;
each $R^{10}$ is one substituent attached to the aryl and is independently selected from the group consisting of —$(C_{1-6}$ alkyl), halide, —$CF_3$, —CN, —$OCH_3$, —$(C_{1-6}$ alkylene$)_p$$NHSO_2R^{19}$, —$NR^{15}(C_{1-6}$ alkylene)$NR^{15}R^{16}$, —$(C_{1-6}$ alkylene$)_p$$NR^{15}R^{16}$, and —$OR^{27}$;
each $R^{11}$ is one substituent attached to the heterocyclyl and is independently selected from the group consisting of amino, —$(C_{1-4}$ alkyl), halide, —$CF_3$, and —CN;
each $R^{12}$ is one substituent attached to the carbocyclyl and is independently selected from the group consisting of —$(C_{1-4}$ alkyl), halide, —$CF_3$, and —CN;
each $R^{13}$ is one substituent attached to the aryl and is independently selected from the group consisting of —$(C_{1-4}$ alkyl), halide, —$CF_3$, and —CN;
each $R^{14}$ is independently selected from the group consisting of —$(C_{1-9}$ alkyl), -heteroaryl$(R^{20})_q$, -aryl$(R^{21})_k$, —$CH_2$aryl$(R^{21})_k$, -carbocyclyl$(R^{22})_j$, —$CH_2$carbocyclyl$(R^{22})_j$, —$(C_{1-4}$ alkylene$)_p$$NR^{25}R^{26}$, -heterocyclyl$(R^{23})_h$, and —$CH_2$heterocyclyl$(R^{23})_h$;
each $R^{15}$ is independently selected from the group consisting of H and —$(C_{1-6}$ alkyl);
each $R^{16}$ is independently selected from the group consisting of H, —$(C_{1-6}$ alkyl), —$CH_2$aryl$(R^{21})_k$, and —$CH_2$carbocyclyl$(R^{22})_j$;
each $R^{17}$ is independently selected from the group consisting of H and —$(C_{1-6}$ alkyl);
each $R^{18}$ is independently selected from the group consisting of H, —$(C_{1-6}$ alkyl), —$CH_2$aryl$(R^{21})_k$, and —$CH_2$carbocyclyl$(R^{22})_j$;
each $R^{19}$ is a —$(C_{1-6}$ alkyl);
each $R^{20}$ is one substituent attached to the heteroaryl and is independently selected from the group consisting of —$(C_{1-4}$ alkyl), halide, —$CF_3$, and —CN;
each $R^{21}$ is one substituent attached to the aryl and is independently selected from the group consisting of —$(C_{1-4}$ alkyl), halide, —$CF_3$, and —CN;
each $R^{22}$ is one substituent attached to the carbocyclyl and is independently selected from the group consisting of —$(C_{1-4}$ alkyl), halide, —$CF_3$, and —CN;
each $R^{23}$ is one substituent attached to the heterocyclyl and is independently selected from the group consisting of —$(C_{1-4}$ alkyl), halide, —$CF_3$, and —CN;
$R^{24}$ is selected from the group consisting of H, —$(C_{1-6}$ alkyl), —$(C_{1-4}$ alkylene$)_p$heterocyclyl$(R^{23})_h$, —$(C_{1-4}$ alkylene$)_p$carbocyclyl$(R^{22})_j$, —$(C_{1-4}$ alkylene$)_p$aryl$(R^{21})_k$, and —$(C_{1-6}$ alkylene$)_p$$NR^{25}R^{26}$;

each $R^{25}$ is independently selected from the group consisting of H and —$(C_{1-6}$ alkyl);

each $R^{26}$ is independently selected from the group consisting of H and —$(C_{1-6}$ alkyl);

$R^{27}$ is selected from the group consisting of H, —$(C_{1-6}$ alkyl), —$(C_{1-4}$ alkylene)$_p$heterocyclyl($R^{23})_h$, and —$(C_{1-6}$ alkylene)$_p$NR$^{25}$R$^{26}$;

each p is independently 0 or 1;
each q is independently 0 to 4;
each h is independently 0 to 10;
each k is independently 0 to 5; and
each j is independently 0 to 12.

2. The method of claim 1, wherein $R^3$ is -heteroaryl($R^6)_q$.

3. The method of claim 2, wherein $R^3$ is selected from the group consisting of -pyridinyl($R^6)_q$, -pyrimidinyl($R^6)_q$, -pyrazolyl($R^6)_q$, and -imidazolyl($R^6)_q$.

4. The method of claim 2, wherein q is 0, 1 or 2.

5. The method of claim 2, wherein $R^6$ is selected from the group consisting of —$(C_{1-3}$ alkyl), —CH$_2$heterocyclyl($R^{11})_h$, —NHC(=O)R$^{14}$, —NR$^{15}$R$^{16}$, —CH$_2$NR$^{17}$R$^{18}$, and —OR$^{24}$.

6. The method of claim 1, wherein $R^5$ is -aryl($R^{10})_k$.

7. The method of claim 6, wherein $R^5$ is -phenyl($R^{10})_k$.

8. The method of claim 6, wherein k is 1 or 2.

9. The method of claim 8, wherein each $R^{10}$ is independently selected from the group consisting of halide and is —CH$_2$NHSO$_2$R$^{19}$.

10. The method of claim 1, wherein $R^5$ is -heteroaryl($R^8)_q$.

11. The method of claim 10, wherein $R^5$ is selected from the group consisting of -pyridinyl($R^8)_q$, -imidazolyl($R^8)_q$, -furanyl($R^8)_q$, and -thiophenyl($R^8)_q$.

12. The method of claim 10, wherein q is 0 or 1.

13. The method of claim 12, wherein q is 1 and $R^8$ is selected from the group consisting of halide, —$(C_{1-3}$ alkyl), and —C(=O)R$^{19}$.

14. The method of claim 1, wherein $R^5$ is -heterocyclyl($R^9)_h$.

15. The method of claim 14, wherein $R^5$ is selected from the group consisting of -piperidinyl($R^9)_h$, -morpholinyl($R^9)_h$, and -piperazinyl($R^9)_h$.

16. The method of claim 14, wherein h is 0, 1, or 2.

17. The method of claim 16, wherein h is 1 or 2 and each $R^9$ is independently selected from the group consisting of a halide and —$(C_{1-3}$ alkyl).

18. The method of claim 1, wherein $R^1$, $R^2$, and $R^4$ are H.

19. The method of claim 1, wherein the compound of Formula I is selected from the group consisting of:

N-(5-(3-(4-(3-fluorophenyl)-1H-imidazo[4,5-c]pyridin-2-yl)-1H-indazol-5-yl)pyridin-3-yl)propionamide [1];

N-(5-(3-(4-(3-fluorophenyl)-1H-imidazo[4,5-c]pyridin-2-yl)-1H-indazol-5-yl)pyridin-3-yl)-3-methylbutanamide [2];

5-(3-(4-(3-fluorophenyl)-1H-imidazo[4,5-c]pyridin-2-yl)-1H-indazol-5-yl)pyridin-3-amine [3];

4-(3-fluorophenyl)-2-(5-(pyridin-3-yl)-1H-indazol-3-yl)-1H-imidazo[4,5-c]pyridine [4];

4-(3-fluorophenyl)-2-(5-(4-methylpyridin-3-yl)-1H-indazol-3-yl)-1H-imidazo[4,5-c]pyridine [5];

N-((5-(3-(4-(3-fluorophenyl)-1H-imidazo[4,5-c]pyridin-2-yl)-1H-indazol-5-yl)pyridin-3-yl)methyl)ethanamine [6];

5-(3-(4-(3-fluorophenyl)-1H-imidazo[4,5-c]pyridin-2-yl)-1H-indazol-5-yl)-N,N-dimethylpyridin-3-amine [7];

N-(5-(3-(4-(3-fluorophenyl)-1H-imidazo[4,5-c]pyridin-2-yl)-1H-indazol-5-yl)pyridin-3-yl)pivalamide [8];

N-(5-(3-(4-(3-fluorophenyl)-1H-imidazo[4,5-c]pyridin-2-yl)-1H-indazol-5-yl)pyridin-3-yl)isobutyramide [9];

N-(5-(3-(4-(3-fluorophenyl)-1H-imidazo[4,5-c]pyridin-2-yl)-1H-indazol-5-yl)pyridin-3-yl)-2-phenylacetamide [10];

N-(5-(3-(4-(3-fluorophenyl)-1H-imidazo[4,5-c]pyridin-2-yl)-1H-indazol-5-yl)pyridin-3-yl)benzamide [11];

5-(3-(4-(3-fluorophenyl)-1H-imidazo[4,5-c]pyridin-2-yl)-1H-indazol-5-yl)-N-isopropylpyridin-3-amine [12];

1-(5-(3-(4-(3-fluorophenyl)-1H-imidazo[4,5-c]pyridin-2-yl)-1H-indazol-5-yl)pyridin-3-yl)-N,N-dimethylmethanamine [13];

4-(3-fluorophenyl)-2-(5-(5-(pyrrolidin-1-ylmethyl)pyridin-3-yl)-1H-indazol-3-yl)-1H-imidazo[4,5-c]pyridine [14];

4-(3-fluorophenyl)-2-(5-(5-(piperidin-1-ylmethyl)pyridin-3-yl)-1H-indazol-3-yl)-1H-imidazo[4,5-c]pyridine [15];

N-(5-(3-(4-(3-fluorophenyl)-1H-imidazo[4,5-c]pyridin-2-yl)-1H-indazol-5-yl)pyridin-3-yl)-3,3-dimethylbutanamide [16];

N-(5-(3-(4-(3-fluorophenyl)-1H-imidazo[4,5-c]pyridin-2-yl)-1H-indazol-5-yl)pyridin-3-yl)butyramide [17];

N-(5-(3-(4-(3-fluorophenyl)-1H-imidazo[4,5-c]pyridin-2-yl)-1H-indazol-5-yl)pyridin-3-yl)pentanamide [18];

N-(5-(3-(4-(3-fluorophenyl)-1H-imidazo[4,5-c]pyridin-2-yl)-1H-indazol-5-yl)pyridin-3-yl)cyclopropanecarboxamide [19];

N-(5-(3-(4-(3-fluorophenyl)-1H-imidazo[4,5-c]pyridin-2-yl)-1H-indazol-5-yl)pyridin-3-yl)cyclobutanecarboxamide [20];

N-(5-(3-(4-(3-fluorophenyl)-1H-imidazo[4,5-c]pyridin-2-yl)-1H-indazol-5-yl)pyridin-3-yl)cyclopentanecarboxamide [21];

N-(5-(3-(4-(3-fluorophenyl)-1H-imidazo[4,5-c]pyridin-2-yl)-1H-indazol-5-yl)pyridin-3-yl)cyclohexanecarboxamide [22];

N-benzyl-1-(5-(3-(4-(3-fluorophenyl)-1H-imidazo[4,5-c]pyridin-2-yl)-1H-indazol-5-yl)pyridin-3-yl)methanamine [23];

1-cyclopentyl-N-((5-(3-(4-(3-fluorophenyl)-1H-imidazo[4,5-c]pyridin-2-yl)-1H-indazol-5-yl)pyridin-3-yl)methyl)methanamine [24];

2-(5-(5-((3,3-difluoropyrrolidin-1-yl)methyl)pyridin-3-yl)-1H-indazol-3-yl)-4-(3-fluorophenyl)-1H-imidazo[4,5-c]pyridine [25];

4-(3-fluorophenyl)-2-(5-(pyrimidin-5-yl)-1H-indazol-3-yl)-1H-imidazo[4,5-c]pyridine [26];

N-(5-(3-(4-(4-fluorophenyl)-1H-imidazo[4,5-c]pyridin-2-yl)-1H-indazol-5-yl)pyridin-3-yl)propionamide [27];

N-(5-(3-(4-(4-fluorophenyl)-1H-imidazo[4,5-c]pyridin-2-yl)-1H-indazol-5-yl)pyridin-3-yl)-3-methylbutanamide [28];

5-(3-(4-(4-fluorophenyl)-1H-imidazo[4,5-c]pyridin-2-yl)-1H-indazol-5-yl)pyridin-3-amine [29];

4-(4-fluorophenyl)-2-(5-(pyridin-3-yl)-1H-indazol-3-yl)-1H-imidazo[4,5-c]pyridine [30];

4-(4-fluorophenyl)-2-(5-(4-methylpyridin-3-yl)-1H-indazol-3-yl)-1H-imidazo[4,5-c]pyridine [31];

N-((5-(3-(4-(4-fluorophenyl)-1H-imidazo[4,5-c]pyridin-2-yl)-1H-indazol-5-yl)pyridin-3-yl)methyl)ethanamine [32];

5-(3-(4-(4-fluorophenyl)-1H-imidazo[4,5-c]pyridin-2-yl)-1H-indazol-5-yl)-N,N-dimethylpyridin-3-amine [33];

N-(5-(3-(4-(4-fluorophenyl)-1H-imidazo[4,5-c]pyridin-2-yl)-1H-indazol-5-yl)pyridin-3-yl)pivalamide [34];
N-(5-(3-(4-(4-fluorophenyl)-1H-imidazo[4,5-c]pyridin-2-yl)-1H-indazol-5-yl)pyridin-3-yl)isobutyramide [35];
N-(5-(3-(4-(4-fluorophenyl)-1H-imidazo[4,5-c]pyridin-2-yl)-1H-indazol-5-yl)pyridin-3-yl)-2-phenylacetamide [36];
N-(5-(3-(4-(4-fluorophenyl)-1H-imidazo[4,5-c]pyridin-2-yl)-1H-indazol-5-yl)pyridin-3-yl)benzamide [37];
5-(3-(4-(4-fluorophenyl)-1H-imidazo[4,5-c]pyridin-2-yl)-1H-indazol-5-yl)-N-isopropylpyridin-3-amine [38];
1-(5-(3-(4-(4-fluorophenyl)-1H-imidazo[4,5-c]pyridin-2-yl)-1H-indazol-5-yl)pyridin-3-yl)-N,N-dimethylmethanamine [39];
4-(4-fluorophenyl)-2-(5-(5-(pyrrolidin-1-ylmethyl)pyridin-3-yl)-1H-indazol-3-yl)-1H-imidazo[4,5-c]pyridine [40];
4-(4-fluorophenyl)-2-(5-(5-(piperidin-1-ylmethyl)pyridin-3-yl)-1H-indazol-3-yl)-1H-imidazo[4,5-c]pyridine [41];
N-(5-(3-(4-(4-fluorophenyl)-1H-imidazo[4,5-c]pyridin-2-yl)-1H-indazol-5-yl)pyridin-3-yl)-3,3-dimethylbutanamide [42];
N-(5-(3-(4-(4-fluorophenyl)-1H-imidazo[4,5-c]pyridin-2-yl)-1H-indazol-5-yl)pyridin-3-yl)butyramide [43];
N-(5-(3-(4-(4-fluorophenyl)-1H-imidazo[4,5-c]pyridin-2-yl)-1H-indazol-5-yl)pyridin-3-yl)pentanamide [44];
N-(5-(3-(4-(4-fluorophenyl)-1H-imidazo[4,5-c]pyridin-2-yl)-1H-indazol-5-yl)pyridin-3-yl)cyclopropanecarboxamide [45];
N-(5-(3-(4-(4-fluorophenyl)-1H-imidazo[4,5-c]pyridin-2-yl)-1H-indazol-5-yl)pyridin-3-yl)cyclobutanecarboxamide [46];
N-(5-(3-(4-(4-fluorophenyl)-1H-imidazo[4,5-c]pyridin-2-yl)-1H-indazol-5-yl)pyridin-3-yl)cyclopentanecarboxamide [47];
N-(5-(3-(4-(4-fluorophenyl)-1H-imidazo[4,5-c]pyridin-2-yl)-1H-indazol-5-yl)pyridin-3-yl)cyclohexanecarboxamide [48];
N-benzyl-1-(5-(3-(4-(4-fluorophenyl)-1H-imidazo[4,5-c]pyridin-2-yl)-1H-indazol-5-yl)pyridin-3-yl)methanamine [49];
1-cyclopentyl-N-((5-(3-(4-(4-fluorophenyl)-1H-imidazo[4,5-c]pyridin-2-yl)-1H-indazol-5-yl)pyridin-3-yl)methyl)methanamine [50];
2-(5-(5-((3,3-difluoropyrrolidin-1-yl)methyl)pyridin-3-yl)-1H-indazol-3-yl)-4-(4-fluorophenyl)-1H-imidazo[4,5-c]pyridine [51];
4-(4-fluorophenyl)-2-(5-(pyrimidin-5-yl)-1H-indazol-3-yl)-1H-imidazo[4,5-c]pyridine [52];
N-(5-(3-(4-(2-fluorophenyl)-1H-imidazo[4,5-c]pyridin-2-yl)-1H-indazol-5-yl)pyridin-3-yl)propionamide [53];
N-(5-(3-(4-(2-fluorophenyl)-1H-imidazo[4,5-c]pyridin-2-yl)-1H-indazol-5-yl)pyridin-3-yl)-3-methylbutanamide [54];
5-(3-(4-(2-fluorophenyl)-1H-imidazo[4,5-c]pyridin-2-yl)-1H-indazol-5-yl)pyridin-3-amine [55];
4-(2-fluorophenyl)-2-(5-(pyridin-3-yl)-1H-indazol-3-yl)-1H-imidazo[4,5-c]pyridine [56];
4-(2-fluorophenyl)-2-(5-(4-methylpyridin-3-yl)-1H-indazol-3-yl)-1H-imidazo[4,5-c]pyridine [57];
N-((5-(3-(4-(2-fluorophenyl)-1H-imidazo[4,5-c]pyridin-2-yl)-1H-indazol-5-yl)pyridin-3-yl)methyl)ethanamine [58];
5-(3-(4-(2-fluorophenyl)-1H-imidazo[4,5-c]pyridin-2-yl)-1H-indazol-5-yl)-N,N-dimethylpyridin-3-amine [59];
N-(5-(3-(4-(2-fluorophenyl)-1H-imidazo[4,5-c]pyridin-2-yl)-1H-indazol-5-yl)pyridin-3-yl)pivalamide [60];
N-(5-(3-(4-(2-fluorophenyl)-1H-imidazo[4,5-c]pyridin-2-yl)-1H-indazol-5-yl)pyridin-3-yl)isobutyramide [61];
N-(5-(3-(4-(2-fluorophenyl)-1H-imidazo[4,5-c]pyridin-2-yl)-1H-indazol-5-yl)pyridin-3-yl)-2-phenylacetamide [62];
N-(5-(3-(4-(2-fluorophenyl)-1H-imidazo[4,5-c]pyridin-2-yl)-1H-indazol-5-yl)pyridin-3-yl)benzamide [63];
5-(3-(4-(2-fluorophenyl)-1H-imidazo[4,5-c]pyridin-2-yl)-1H-indazol-5-yl)-N-isopropylpyridin-3-amine [64];
1-(5-(3-(4-(2-fluorophenyl)-1H-imidazo[4,5-c]pyridin-2-yl)-1H-indazol-5-yl)pyridin-3-yl)-N,N-dimethylmethanamine [65];
4-(2-fluorophenyl)-2-(5-(5-(pyrrolidin-1-ylmethyl)pyridin-3-yl)-1H-indazol-3-yl)-1H-imidazo[4,5-c]pyridine [66];
4-(2-fluorophenyl)-2-(5-(5-(piperidin-1-ylmethyl)pyridin-3-yl)-1H-indazol-3-yl)-1H-imidazo[4,5-c]pyridine [67];
N-(5-(3-(4-(2-fluorophenyl)-1H-imidazo[4,5-c]pyridin-2-yl)-1H-indazol-5-yl)pyridin-3-yl)-3,3-dimethylbutanamide [68];
N-(5-(3-(4-(2-fluorophenyl)-1H-imidazo[4,5-c]pyridin-2-yl)-1H-indazol-5-yl)pyridin-3-yl)butyramide [69];
N-(5-(3-(4-(2-fluorophenyl)-1H-imidazo[4,5-c]pyridin-2-yl)-1H-indazol-5-yl)pyridin-3-yl)pentanamide [70];
N-(5-(3-(4-(2-fluorophenyl)-1H-imidazo[4,5-c]pyridin-2-yl)-1H-indazol-5-yl)pyridin-3-yl)cyclopropanecarboxamide [71];
N-(5-(3-(4-(2-fluorophenyl)-1H-imidazo[4,5-c]pyridin-2-yl)-1H-indazol-5-yl)pyridin-3-yl)cyclobutanecarboxamide [72];
N-(5-(3-(4-(2-fluorophenyl)-1H-imidazo[4,5-c]pyridin-2-yl)-1H-indazol-5-yl)pyridin-3-yl)cyclopentanecarboxamide [73];
N-(5-(3-(4-(2-fluorophenyl)-1H-imidazo[4,5-c]pyridin-2-yl)-1H-indazol-5-yl)pyridin-3-yl)cyclohexanecarboxamide [74];
N-benzyl-1-(5-(3-(4-(2-fluorophenyl)-1H-imidazo[4,5-c]pyridin-2-yl)-1H-indazol-5-yl)pyridin-3-yl)methanamine [75];
1-cyclopentyl-N-((5-(3-(4-(2-fluorophenyl)-1H-imidazo[4,5-c]pyridin-2-yl)-1H-indazol-5-yl)pyridin-3-yl)methyl)methanamine [76];
2-(5-(5-((3,3-difluoropyrrolidin-1-yl)methyl)pyridin-3-yl)-1H-indazol-3-yl)-4-(2-fluorophenyl)-1H-imidazo[4,5-c]pyridine [77];
4-(2-fluorophenyl)-2-(5-(pyrimidin-5-yl)-1H-indazol-3-yl)-1H-imidazo[4,5-c]pyridine [78];
N-(5-(3-(4-(pyridin-3-yl)-1H-imidazo[4,5-c]pyridin-2-yl)-1H-indazol-5-yl)pyridin-3-yl)propionamide [79];
3-methyl-N-(5-(3-(4-(pyridin-3-yl)-1H-imidazo[4,5-c]pyridin-2-yl)-1H-indazol-5-yl)pyridin-3-yl)butanamide [80];
5-(3-(4-(pyridin-3-yl)-1H-imidazo[4,5-c]pyridin-2-yl)-1H-indazol-5-yl)pyridin-3-amine [81];
4-(pyridin-3-yl)-2-(5-(pyridin-3-yl)-1H-indazol-3-yl)-1H-imidazo[4,5-c]pyridine [82];
2-(5-(4-methylpyridin-3-yl)-1H-indazol-3-yl)-4-(pyridin-3-yl)-1H-imidazo[4,5-c]pyridine [83];

N-((5-(3-(4-(pyridin-3-yl)-1H-imidazo[4,5-c]pyridin-2-yl)-1H-indazol-5-yl)pyridin-3-yl)methyl)ethanamine [84];
N,N-dimethyl-5-(3-(4-(pyridin-3-yl)-1H-imidazo[4,5-c]pyridin-2-yl)-1H-indazol-5-yl)pyridin-3-amine [85];
N-(5-(3-(4-(pyridin-3-yl)-1H-imidazo[4,5-c]pyridin-2-yl)-1H-indazol-5-yl)pyridin-3-yl)pivalamide [86];
N-(5-(3-(4-(pyridin-3-yl)-1H-imidazo[4,5-c]pyridin-2-yl)-1H-indazol-5-yl)pyridin-3-yl)isobutyramide [87];
2-phenyl-N-(5-(3-(4-(pyridin-3-yl)-1H-imidazo[4,5-c]pyridin-2-yl)-1H-indazol-5-yl)pyridin-3-yl)acetamide [88];
N-(5-(3-(4-(pyridin-3-yl)-1H-imidazo[4,5-c]pyridin-2-yl)-1H-indazol-5-yl)pyridin-3-yl)benzamide [89];
N-isopropyl-5-(3-(4-(pyridin-3-yl)-1H-imidazo[4,5-c]pyridin-2-yl)-1H-indazol-5-yl)pyridin-3-amine [90];
N,N-dimethyl-1-(5-(3-(4-(pyridin-3-yl)-1H-imidazo[4,5-c]pyridin-2-yl)-1H-indazol-5-yl)pyridin-3-yl)methanamine [91];
4-(pyridin-3-yl)-2-(5-(5-(pyrrolidin-1-ylmethyl)pyridin-3-yl)-1H-indazol-3-yl)-1H-imidazo[4,5-c]pyridine [92];
2-(5-(5-(piperidin-1-ylmethyl)pyridin-3-yl)-1H-indazol-3-yl)-4-(pyridin-3-yl)-1H-imidazo[4,5-c]pyridine [93];
3,3-dimethyl-N-(5-(3-(4-(pyridin-3-yl)-1H-imidazo[4,5-c]pyridin-2-yl)-1H-indazol-5-yl)pyridin-3-yl)butanamide [94];
N-(5-(3-(4-(pyridin-3-yl)-1H-imidazo[4,5-c]pyridin-2-yl)-1H-indazol-5-yl)pyridin-3-yl)butyramide [95];
N-(5-(3-(4-(pyridin-3-yl)-1H-imidazo[4,5-c]pyridin-2-yl)-1H-indazol-5-yl)pyridin-3-yl)pentanamide [96];
N-(5-(3-(4-(pyridin-3-yl)-1H-imidazo[4,5-c]pyridin-2-yl)-1H-indazol-5-yl)pyridin-3-yl)cyclopropanecarboxamide [97];
N-(5-(3-(4-(pyridin-3-yl)-1H-imidazo[4,5-c]pyridin-2-yl)-1H-indazol-5-yl)pyridin-3-yl)cyclobutanecarboxamide [98];
N-(5-(3-(4-(pyridin-3-yl)-1H-imidazo[4,5-c]pyridin-2-yl)-1H-indazol-5-yl)pyridin-3-yl)cyclopentanecarboxamide [99]; and
N-(5-(3-(4-(pyridin-3-yl)-1H-imidazo[4,5-c]pyridin-2-yl)-1H-indazol-5-yl)pyridin-3-yl)cyclohexanecarboxamide [100]; or a pharmaceutically acceptable salt thereof.

20. The method of claim 1, wherein the compound of Formula I is selected from the group consisting of:
N-benzyl-1-(5-(3-(4-(pyridin-3-yl)-1H-imidazo[4,5-c]pyridin-2-yl)-1H-indazol-5-yl)pyridin-3-yl)methanamine [101];
1-cyclopentyl-N-((5-(3-(4-(pyridin-3-yl)-1H-imidazo[4,5-c]pyridin-2-yl)-1H-indazol-5-yl)pyridin-3-yl)methyl)methanamine [102];
2-(5-(5-((3,3-difluoropyrrolidin-1-yl)methyl)pyridin-3-yl)-1H-indazol-3-yl)-4-(pyridin-3-yl)-1H-imidazo[4,5-c]pyridine [103];
4-(pyridin-3-yl)-2-(5-(pyrimidin-5-yl)-1H-indazol-3-yl)-1H-imidazo[4,5-c]pyridine [104];
N-(5-(3-(4-(pyridin-4-yl)-1H-imidazo[4,5-c]pyridin-2-yl)-1H-indazol-5-yl)pyridin-3-yl)propionamide [105];
3-methyl-N-(5-(3-(4-(pyridin-4-yl)-1H-imidazo[4,5-c]pyridin-2-yl)-1H-indazol-5-yl)pyridin-3-yl)butanamide [106];
5-(3-(4-(pyridin-4-yl)-1H-imidazo[4,5-c]pyridin-2-yl)-1H-indazol-5-yl)pyridin-3-amine [107];
2-(5-(pyridin-3-yl)-1H-indazol-3-yl)-4-(pyridin-4-yl)-1H-imidazo[4,5-c]pyridine [108];
2-(5-(4-methylpyridin-3-yl)-1H-indazol-3-yl)-4-(pyridin-4-yl)-1H-imidazo[4,5-c]pyridine [109];
N-((5-(3-(4-(pyridin-4-yl)-1H-imidazo[4,5-c]pyridin-2-yl)-1H-indazol-5-yl)pyridin-3-yl)methyl)ethanamine [110];
N,N-dimethyl-5-(3-(4-(pyridin-4-yl)-1H-imidazo[4,5-c]pyridin-2-yl)-1H-indazol-5-yl)pyridin-3-amine [111];
N-(5-(3-(4-(pyridin-4-yl)-1H-imidazo[4,5-c]pyridin-2-yl)-1H-indazol-5-yl)pyridin-3-yl)pivalamide [112];
N-(5-(3-(4-(pyridin-4-yl)-1H-imidazo[4,5-c]pyridin-2-yl)-1H-indazol-5-yl)pyridin-3-yl)isobutyramide [113];
2-phenyl-N-(5-(3-(4-(pyridin-4-yl)-1H-imidazo[4,5-c]pyridin-2-yl)-1H-indazol-5-yl)pyridin-3-yl)acetamide [114];
N-(5-(3-(4-(pyridin-4-yl)-1H-imidazo[4,5-c]pyridin-2-yl)-1H-indazol-5-yl)pyridin-3-yl)benzamide [115];
N-isopropyl-5-(3-(4-(pyridin-4-yl)-1H-imidazo[4,5-c]pyridin-2-yl)-1H-indazol-5-yl)pyridin-3-amine [116];
N,N-dimethyl-1-(5-(3-(4-(pyridin-4-yl)-1H-imidazo[4,5-c]pyridin-2-yl)-1H-indazol-5-yl)pyridin-3-yl)methanamine [117];
4-(pyridin-4-yl)-2-(5-(5-(pyrrolidin-1-ylmethyl)pyridin-3-yl)-1H-indazol-3-yl)-1H-imidazo[4,5-c]pyridine [118];
2-(5-(5-(piperidin-1-ylmethyl)pyridin-3-yl)-1H-indazol-3-yl)-4-(pyridin-4-yl)-1H-imidazo[4,5-c]pyridine [119];
3,3-dimethyl-N-(5-(3-(4-(pyridin-4-yl)-1H-imidazo[4,5-c]pyridin-2-yl)-1H-indazol-5-yl)pyridin-3-yl)butanamide [120];
N-(5-(3-(4-(pyridin-4-yl)-1H-imidazo[4,5-c]pyridin-2-yl)-1H-indazol-5-yl)pyridin-3-yl)butyramide [121];
N-(5-(3-(4-(pyridin-4-yl)-1H-imidazo[4,5-c]pyridin-2-yl)-1H-indazol-5-yl)pyridin-3-yl)pentanamide [122];
N-(5-(3-(4-(pyridin-4-yl)-1H-imidazo[4,5-c]pyridin-2-yl)-1H-indazol-5-yl)pyridin-3-yl)cyclopropanecarboxamide [123];
N-(5-(3-(4-(pyridin-4-yl)-1H-imidazo[4,5-c]pyridin-2-yl)-1H-indazol-5-yl)pyridin-3-yl)cyclobutanecarboxamide [124];
N-(5-(3-(4-(pyridin-4-yl)-1H-imidazo[4,5-c]pyridin-2-yl)-1H-indazol-5-yl)pyridin-3-yl)cyclopentanecarboxamide [125];
N-(5-(3-(4-(pyridin-4-yl)-1H-imidazo[4,5-c]pyridin-2-yl)-1H-indazol-5-yl)pyridin-3-yl)cyclohexanecarboxamide [126];
N-benzyl-1-(5-(3-(4-(pyridin-4-yl)-1H-imidazo[4,5-c]pyridin-2-yl)-1H-indazol-5-yl)pyridin-3-yl)methanamine [127];
1-cyclopentyl-N-((5-(3-(4-(pyridin-4-yl)-1H-imidazo[4,5-c]pyridin-2-yl)-1H-indazol-5-yl)pyridin-3-yl)methyl)methanamine [128];
2-(5-(5-((3,3-difluoropyrrolidin-1-yl)methyl)pyridin-3-yl)-1H-indazol-3-yl)-4-(pyridin-4-yl)-1H-imidazo[4,5-c]pyridine [129];
4-(pyridin-4-yl)-2-(5-(pyrimidin-5-yl)-1H-indazol-3-yl)-1H-imidazo[4,5-c]pyridine [130];
N-(5-(3-(4-(pyridin-2-yl)-1H-imidazo[4,5-c]pyridin-2-yl)-1H-indazol-5-yl)pyridin-3-yl)propionamide [131];
3-methyl-N-(5-(3-(4-(pyridin-2-yl)-1H-imidazo[4,5-c]pyridin-2-yl)-1H-indazol-5-yl)pyridin-3-yl)butanamide [132];
5-(3-(4-(pyridin-2-yl)-1H-imidazo[4,5-c]pyridin-2-yl)-1H-indazol-5-yl)pyridin-3-amine [133];
4-(pyridin-2-yl)-2-(5-(pyridin-3-yl)-1H-indazol-3-yl)-1H-imidazo[4,5-c]pyridine [134];

2-(5-(4-methylpyridin-3-yl)-1H-indazol-3-yl)-4-(pyridin-2-yl)-1H-imidazo[4,5-c]pyridine [135];
N-((5-(3-(4-(pyridin-2-yl)-1H-imidazo[4,5-c]pyridin-2-yl)-1H-indazol-5-yl)pyridin-3-yl)methyl)ethanamine [136];
N,N-dimethyl-5-(3-(4-(pyridin-2-yl)-1H-imidazo[4,5-c]pyridin-2-yl)-1H-indazol-5-yl)pyridin-3-amine [137];
N-(5-(3-(4-(pyridin-2-yl)-1H-imidazo[4,5-c]pyridin-2-yl)-1H-indazol-5-yl)pyridin-3-yl)pivalamide [138];
N-(5-(3-(4-(pyridin-2-yl)-1H-imidazo[4,5-c]pyridin-2-yl)-1H-indazol-5-yl)pyridin-3-yl)isobutyramide [139];
2-phenyl-N-(5-(3-(4-(pyridin-2-yl)-1H-imidazo[4,5-c]pyridin-2-yl)-1H-indazol-5-yl)pyridin-3-yl)acetamide [140];
N-(5-(3-(4-(pyridin-2-yl)-1H-imidazo[4,5-c]pyridin-2-yl)-1H-indazol-5-yl)pyridin-3-yl)benzamide [141];
N-isopropyl-5-(3-(4-(pyridin-2-yl)-1H-imidazo[4,5-c]pyridin-2-yl)-1H-indazol-5-yl)pyridin-3-amine [142];
N,N-dimethyl-1-(5-(3-(4-(pyridin-2-yl)-1H-imidazo[4,5-c]pyridin-2-yl)-1H-indazol-5-yl)pyridin-3-yl)methanamine [143];
4-(pyridin-2-yl)-2-(5-(5-(pyrrolidin-1-ylmethyl)pyridin-3-yl)-1H-indazol-3-yl)-1H-imidazo[4,5-c]pyridine [144];
2-(5-(5-(piperidin-1-ylmethyl)pyridin-3-yl)-1H-indazol-3-yl)-4-(pyridin-2-yl)-1H-imidazo[4,5-c]pyridine [145];
3,3-dimethyl-N-(5-(3-(4-(pyridin-2-yl)-1H-imidazo[4,5-c]pyridin-2-yl)-1H-indazol-5-yl)pyridin-3-yl)butanamide [146];
N-(5-(3-(4-(pyridin-2-yl)-1H-imidazo[4,5-c]pyridin-2-yl)-1H-indazol-5-yl)pyridin-3-yl)butyramide [147];
N-(5-(3-(4-(pyridin-2-yl)-1H-imidazo[4,5-c]pyridin-2-yl)-1H-indazol-5-yl)pyridin-3-yl)pentanamide [148];
N-(5-(3-(4-(pyridin-2-yl)-1H-imidazo[4,5-c]pyridin-2-yl)-1H-indazol-5-yl)pyridin-3-yl)cyclopropanecarboxamide [149];
N-(5-(3-(4-(pyridin-2-yl)-1H-imidazo[4,5-c]pyridin-2-yl)-1H-indazol-5-yl)pyridin-3-yl)cyclobutanecarboxamide [150];
N-(5-(3-(4-(pyridin-2-yl)-1H-imidazo[4,5-c]pyridin-2-yl)-1H-indazol-5-yl)pyridin-3-yl)cyclopentanecarboxamide [151];
N-(5-(3-(4-(pyridin-2-yl)-1H-imidazo[4,5-c]pyridin-2-yl)-1H-indazol-5-yl)pyridin-3-yl)cyclohexanecarboxamide [152];
N-benzyl-1-(5-(3-(4-(pyridin-2-yl)-1H-imidazo[4,5-c]pyridin-2-yl)-1H-indazol-5-yl)pyridin-3-yl)methanamine [153];
1-cyclopentyl-N-((5-(3-(4-(pyridin-2-yl)-1H-imidazo[4,5-c]pyridin-2-yl)-1H-indazol-5-yl)pyridin-3-yl)methyl)methanamine [154];
2-(5-(5-((3,3-difluoropyrrolidin-1-yl)methyl)pyridin-3-yl)-1H-indazol-3-yl)-4-(pyridin-2-yl)-1H-imidazo[4,5-c]pyridine [155];
4-(pyridin-2-yl)-2-(5-(pyrimidin-5-yl)-1H-indazol-3-yl)-1H-imidazo[4,5-c]pyridine [156];
N-(5-(3-(4-(piperidin-1-yl)-1H-imidazo[4,5-c]pyridin-2-yl)-1H-indazol-5-yl)pyridin-3-yl)propionamide [157];
3-methyl-N-(5-(3-(4-(piperidin-1-yl)-1H-imidazo[4,5-c]pyridin-2-yl)-1H-indazol-5-yl)pyridin-3-yl)butanamide [158];
5-(3-(4-(piperidin-1-yl)-1H-imidazo[4,5-c]pyridin-2-yl)-1H-indazol-5-yl)pyridin-3-amine [159];
4-(piperidin-1-yl)-2-(5-(pyridin-3-yl)-1H-indazol-3-yl)-1H-imidazo[4,5-c]pyridine [160];

2-(5-(4-methylpyridin-3-yl)-1H-indazol-3-yl)-4-(piperidin-1-yl)-1H-imidazo[4,5-c]pyridine [161];
N-((5-(3-(4-(piperidin-1-yl)-1H-imidazo[4,5-c]pyridin-2-yl)-1H-indazol-5-yl)pyridin-3-yl)methyl)ethanamine [162];
N,N-dimethyl-5-(3-(4-(piperidin-1-yl)-1H-imidazo[4,5-c]pyridin-2-yl)-1H-indazol-5-yl)pyridin-3-amine [163];
N-(5-(3-(4-(piperidin-1-yl)-1H-imidazo[4,5-c]pyridin-2-yl)-1H-indazol-5-yl)pyridin-3-yl)pivalamide [164];
N-(5-(3-(4-(piperidin-1-yl)-1H-imidazo[4,5-c]pyridin-2-yl)-1H-indazol-5-yl)pyridin-3-yl)isobutyramide [165];
2-phenyl-N-(5-(3-(4-(piperidin-1-yl)-1H-imidazo[4,5-c]pyridin-2-yl)-1H-indazol-5-yl)pyridin-3-yl)acetamide [166];
N-(5-(3-(4-(piperidin-1-yl)-1H-imidazo[4,5-c]pyridin-2-yl)-1H-indazol-5-yl)pyridin-3-yl)benzamide [167];
N-isopropyl-5-(3-(4-(piperidin-1-yl)-1H-imidazo[4,5-c]pyridin-2-yl)-1H-indazol-5-yl)pyridin-3-amine [168];
N,N-dimethyl-1-(5-(3-(4-(piperidin-1-yl)-1H-imidazo[4,5-c]pyridin-2-yl)-1H-indazol-5-yl)pyridin-3-yl)methanamine [169];
4-(piperidin-1-yl)-2-(5-(5-(pyrrolidin-1-ylmethyl)pyridin-3-yl)-1H-indazol-3-yl)-1H-imidazo[4,5-c]pyridine [170];
4-(piperidin-1-yl)-2-(5-(5-(piperidin-1-ylmethyl)pyridin-3-yl)-1H-indazol-3-yl)-1H-imidazo[4,5-c]pyridine [171];
3,3-dimethyl-N-(5-(3-(4-(piperidin-1-yl)-1H-imidazo[4,5-c]pyridin-2-yl)-1H-indazol-5-yl)pyridin-3-yl)butanamide [172];
N-(5-(3-(4-(piperidin-1-yl)-1H-imidazo[4,5-c]pyridin-2-yl)-1H-indazol-5-yl)pyridin-3-yl)butyramide [173];
N-(5-(3-(4-(piperidin-1-yl)-1H-imidazo[4,5-c]pyridin-2-yl)-1H-indazol-5-yl)pyridin-3-yl)pentanamide [174];
N-(5-(3-(4-(piperidin-1-yl)-1H-imidazo[4,5-c]pyridin-2-yl)-1H-indazol-5-yl)pyridin-3-yl)cyclopropanecarboxamide [175];
N-(5-(3-(4-(piperidin-1-yl)-1H-imidazo[4,5-c]pyridin-2-yl)-1H-indazol-5-yl)pyridin-3-yl)cyclobutanecarboxamide [176];
N-(5-(3-(4-(piperidin-1-yl)-1H-imidazo[4,5-c]pyridin-2-yl)-1H-indazol-5-yl)pyridin-3-yl)cyclopentanecarboxamide [177];
N-(5-(3-(4-(piperidin-1-yl)-1H-imidazo[4,5-c]pyridin-2-yl)-1H-indazol-5-yl)pyridin-3-yl)cyclohexanecarboxamide [178];
N-benzyl-1-(5-(3-(4-(piperidin-1-yl)-1H-imidazo[4,5-c]pyridin-2-yl)-1H-indazol-5-yl)pyridin-3-yl)methanamine [179];
1-cyclopentyl-N-((5-(3-(4-(piperidin-1-yl)-1H-imidazo[4,5-c]pyridin-2-yl)-1H-indazol-5-yl)pyridin-3-yl)methyl)methanamine [180];
2-(5-(5-((3,3-difluoropyrrolidin-1-yl)methyl)pyridin-3-yl)-1H-indazol-3-yl)-4-(piperidin-1-yl)-1H-imidazo[4,5-c]pyridine [181];
4-(piperidin-1-yl)-2-(5-(pyrimidin-5-yl)-1H-indazol-3-yl)-1H-imidazo[4,5-c]pyridine [182];
N-(5-(3-(4-(4-methyl-1H-imidazo-1-yl)-1H-imidazo[4,5-c]pyridin-2-yl)-1H-indazol-5-yl)pyridin-3-yl)propionamide [183];
3-methyl-N-(5-(3-(4-(4-methyl-1H-imidazo-1-yl)-1H-imidazo[4,5-c]pyridin-2-yl)-1H-indazol-5-yl)pyridin-3-yl)butanamide [184];
5-(3-(4-(4-methyl-1H-imidazo-1-yl)-1H-imidazo[4,5-c]pyridin-2-yl)-1H-indazol-5-yl)pyridin-3-amine [185];

4-(4-methyl-1H-imidazol-1-yl)-2-(5-(pyridin-3-yl)-1H-indazol-3-yl)-1H-imidazo[4,5-c]pyridine [186];
4-(4-methyl-1H-imidazol-1-yl)-2-(5-(4-methylpyridin-3-yl)-1H-indazol-3-yl)-1H-imidazo[4,5-c]pyridine [187];
N-((5-(3-(4-(4-methyl-1H-imidazol-1-yl)-1H-imidazo[4,5-c]pyridin-2-yl)-1H-indazol-5-yl)pyridin-3-yl)methyl)ethanamine [188];
N,N-dimethyl-5-(3-(4-(4-methyl-1H-imidazol-1-yl)-1H-imidazo[4,5-c]pyridin-2-yl)-1H-indazol-5-yl)pyridin-3-amine [189];
N-(5-(3-(4-(4-methyl-1H-imidazo-1-yl)-1H-imidazo[4,5-c]pyridin-2-yl)-1H-indazol-5-yl)pyridin-3-yl)pivalamide [190];
N-(5-(3-(4-(4-methyl-1H-imidazo-1-yl)-1H-imidazo[4,5-c]pyridin-2-yl)-1H-indazol-5-yl)pyridin-3-yl)isobutyramide [191];
N-(5-(3-(4-(4-methyl-1H-imidazol-1-yl)-1H-imidazo[4,5-c]pyridin-2-yl)-1H-indazol-5-yl)pyridin-3-yl)-2-phenylacetamide [192];
N-(5-(3-(4-(4-methyl-1H-imidazol-1-yl)-1H-imidazo[4,5-c]pyridin-2-yl)-1H-indazol-5-yl)pyridin-3-yl)benzamide [193];
N-isopropyl-5-(3-(4-(4-methyl-1H-imidazol-1-yl)-1H-imidazo[4,5-c]pyridin-2-yl)-1H-indazol-5-yl)pyridin-3-amine [194];
N,N-dimethyl-1-(5-(3-(4-(4-methyl-1H-imidazol-1-yl)-1H-imidazo[4,5-c]pyridin-2-yl)-1H-indazol-5-yl)pyridin-3-yl)methanamine [195];
4-(4-methyl-1H-imidazol-1-yl)-2-(5-(5-(pyrrolidin-1-ylmethyl)pyridin-3-yl)-1H-indazol-3-yl)-1H-imidazo[4,5-c]pyridine [196];
4-(4-methyl-1H-imidazol-1-yl)-2-(5-(5-(piperidin-1-ylmethyl)pyridin-3-yl)-1H-indazol-3-yl)-1H-imidazo[4,5-c]pyridine [197];
3,3-dimethyl-N-(5-(3-(4-(4-methyl-1H-imidazol-1-yl)-1H-imidazo[4,5-c]pyridin-2-yl)-1H-indazol-5-yl)pyridin-3-yl)butanamide [198];
N-(5-(3-(4-(4-methyl-1H-imidazo-1-yl)-1H-imidazo[4,5-c]pyridin-2-yl)-1H-indazol-5-yl)pyridin-3-yl)butyramide [199]; and
N-(5-(3-(4-(4-methyl-1H-imidazo-1-yl)-1H-imidazo[4,5-c]pyridin-2-yl)-1H-indazol-5-yl)pyridin-3-yl)pentanamide [200]; or a pharmaceutically acceptable salt thereof.

21. The method of claim 1, wherein the compound of Formula I is selected from the group consisting of:
N-(5-(3-(4-(4-methyl-1H-imidazo-1-yl)-1H-imidazo[4,5-c]pyridin-2-yl)-1H-indazol-5-yl)pyridin-3-yl)cyclopropanecarboxamide [201];
N-(5-(3-(4-(4-methyl-1H-imidazo-1-yl)-1H-imidazo[4,5-c]pyridin-2-yl)-1H-indazol-5-yl)pyridin-3-yl)cyclobutanecarboxamide [202];
N-(5-(3-(4-(4-methyl-1H-imidazol-1-yl)-1H-imidazo[4,5-c]pyridin-2-yl)-1H-indazol-5-yl)pyridin-3-yl)cyclopentanecarboxamide [203];
N-(5-(3-(4-(4-methyl-1H-imidazol-1-yl)-1H-imidazo[4,5-c]pyridin-2-yl)-1H-indazol-5-yl)pyridin-3-yl)cyclohexanecarboxamide [204];
N-benzyl-1-(5-(3-(4-(4-methyl-1H-imidazol-1-yl)-1H-imidazo[4,5-c]pyridin-2-yl)-1H-indazol-5-yl)pyridin-3-yl)methanamine [205];
1-cyclopentyl-N-((5-(3-(4-(4-methyl-1H-imidazol-1-yl)-1H-imidazo[4,5-c]pyridin-2-yl)-1H-indazol-5-yl)pyridin-3-yl)methyl)methanamine [206];
2-(5-(5-((3,3-difluoropyrrolidin-1-yl)methyl)pyridin-3-yl)-1H-indazol-3-yl)-4-(4-methyl-1H-imidazol-1-yl)-1H-imidazo[4,5-c]pyridine [207];
4-(4-methyl-1H-imidazol-1-yl)-2-(5-(pyrimidin-5-yl)-1H-indazol-3-yl)-1H-imidazo[4,5-c]pyridine [208];
N-(5-(3-(4-(4-methylpiperazin-1-yl)-1H-imidazo[4,5-c]pyridin-2-yl)-1H-indazol-5-yl)pyridin-3-yl)propionamide [209];
3-methyl-N-(5-(3-(4-(4-methylpiperazin-1-yl)-1H-imidazo[4,5-c]pyridin-2-yl)-1H-indazol-5-yl)pyridin-3-yl)butanamide [210];
5-(3-(4-(4-methylpiperazin-1-yl)-1H-imidazo[4,5-c]pyridin-2-yl)-1H-indazol-5-yl)pyridin-3-amine [211];
4-(4-methylpiperazin-1-yl)-2-(5-(pyridin-3-yl)-1H-indazol-3-yl)-1H-imidazo[4,5-c]pyridine [212];
4-(4-methylpiperazin-1-yl)-2-(5-(4-methylpyridin-3-yl)-1H-indazol-3-yl)-1H-imidazo[4,5-c]pyridine [213];
N-((5-(3-(4-(4-methylpiperazin-1-yl)-1H-imidazo[4,5-c]pyridin-2-yl)-1H-indazol-5-yl)pyridin-3-yl)methyl)ethanamine [214];
N,N-dimethyl-5-(3-(4-(4-methylpiperazin-1-yl)-1H-imidazo[4,5-c]pyridin-2-yl)-1H-indazol-5-yl)pyridin-3-amine [215];
N-(5-(3-(4-(4-methylpiperazin-1-yl)-1H-imidazo[4,5-c]pyridin-2-yl)-1H-indazol-5-yl)pyridin-3-yl)pivalamide [216];
N-(5-(3-(4-(4-methylpiperazin-1-yl)-1H-imidazo[4,5-c]pyridin-2-yl)-1H-indazol-5-yl)pyridin-3-yl)isobutyramide [217];
N-(5-(3-(4-(4-methylpiperazin-1-yl)-1H-imidazo[4,5-c]pyridin-2-yl)-1H-indazol-5-yl)pyridin-3-yl)-2-phenylacetamide [218];
N-(5-(3-(4-(4-methylpiperazin-1-yl)-1H-imidazo[4,5-c]pyridin-2-yl)-1H-indazol-5-yl)pyridin-3-yl)benzamide [219];
N-isopropyl-5-(3-(4-(4-methylpiperazin-1-yl)-1H-imidazo[4,5-c]pyridin-2-yl)-1H-indazol-5-yl)pyridin-3-amine [220];
N,N-dimethyl-1-(5-(3-(4-(4-methylpiperazin-1-yl)-1H-imidazo[4,5-c]pyridin-2-yl)-1H-indazol-5-yl)pyridin-3-yl)methanamine [221];
4-(4-methylpiperazin-1-yl)-2-(5-(5-(pyrrolidin-1-ylmethyl)pyridin-3-yl)-1H-indazol-3-yl)-1H-imidazo[4,5-c]pyridine [222];
4-(4-methylpiperazin-1-yl)-2-(5-(5-(piperidin-1-ylmethyl)pyridin-3-yl)-1H-indazol-3-yl)-1H-imidazo[4,5-c]pyridine [223];
3,3-dimethyl-N-(5-(3-(4-(4-methylpiperazin-1-yl)-1H-imidazo[4,5-c]pyridin-2-yl)-1H-indazol-5-yl)pyridin-3-yl)butanamide [224];
N-(5-(3-(4-(4-methylpiperazin-1-yl)-1H-imidazo[4,5-c]pyridin-2-yl)-1H-indazol-5-yl)pyridin-3-yl)butyramide [225];
N-(5-(3-(4-(4-methylpiperazin-1-yl)-1H-imidazo[4,5-c]pyridin-2-yl)-1H-indazol-5-yl)pyridin-3-yl)pentanamide [226];
N-(5-(3-(4-(4-methylpiperazin-1-yl)-1H-imidazo[4,5-c]pyridin-2-yl)-1H-indazol-5-yl)pyridin-3-yl)cyclopropanecarboxamide [227];
N-(5-(3-(4-(4-methylpiperazin-1-yl)-1H-imidazo[4,5-c]pyridin-2-yl)-1H-indazol-5-yl)pyridin-3-yl)cyclobutanecarboxamide [228];
N-(5-(3-(4-(4-methylpiperazin-1-yl)-1H-imidazo[4,5-c]pyridin-2-yl)-1H-indazol-5-yl)pyridin-3-yl)cyclopentanecarboxamide [229];
N-(5-(3-(4-(4-methylpiperazin-1-yl)-1H-imidazo[4,5-c]pyridin-2-yl)-1H-indazol-5-yl)pyridin-3-yl)cyclohexanecarboxamide [230];

N-benzyl-1-(5-(3-(4-(4-methylpiperazin-1-yl)-1H-imidazo[4,5-c]pyridin-2-yl)-1H-indazol-5-yl)pyridin-3-yl)methanamine [231];

1-cyclopentyl-N-((5-(3-(4-(4-methylpiperazin-1-yl)-1H-imidazo[4,5-c]pyridin-2-yl)-1H-indazol-5-yl)pyridin-3-yl)methyl)methanamine [232];

2-(5-(5-((3,3-difluoropyrrolidin-1-yl)methyl)pyridin-3-yl)-1H-indazol-3-yl)-4-(4-methylpiperazin-1-yl)-1H-imidazo[4,5-c]pyridine [233];

4-(4-methylpiperazin-1-yl)-2-(5-(pyrimidin-5-yl)-1H-indazol-3-yl)-1H-imidazo[4,5-c]pyridine [234];

N-(5-(3-(4-(thiophen-3-yl)-1H-imidazo[4,5-c]pyridin-2-yl)-1H-indazol-5-yl)pyridin-3-yl)propionamide [235];

3-methyl-N-(5-(3-(4-(thiophen-3-yl)-1H-imidazo[4,5-c]pyridin-2-yl)-1H-indazol-5-yl)pyridin-3-yl)butanamide [236];

5-(3-(4-(thiophen-3-yl)-1H-imidazo[4,5-c]pyridin-2-yl)-1H-indazol-5-yl)pyridin-3-amine [237];

2-(5-(pyridin-3-yl)-1H-indazol-3-yl)-4-(thiophen-3-yl)-1H-imidazo[4,5-c]pyridine [238];

2-(5-(4-methylpyridin-3-yl)-1H-indazol-3-yl)-4-(thiophen-3-yl)-1H-imidazo[4,5-c]pyridine [239];

N-((5-(3-(4-(thiophen-3-yl)-1H-imidazo[4,5-c]pyridin-2-yl)-1H-indazol-5-yl)pyridin-3-yl)methyl)ethanamine [240];

N,N-dimethyl-5-(3-(4-(thiophen-3-yl)-H-imidazo[4,5-c]pyridin-2-yl)-1H-indazol-5-yl)pyridin-3-amine [241];

N-(5-(3-(4-(thiophen-3-yl)-1H-imidazo[4,5-c]pyridin-2-yl)-1H-indazol-5-yl)pyridin-3-yl)pivalamide [242];

N-(5-(3-(4-(thiophen-3-yl)-1H-imidazo[4,5-c]pyridin-2-yl)-1H-indazol-5-yl)pyridin-3-yl)isobutyramide [243];

2-phenyl-N-(5-(3-(4-(thiophen-3-yl)-1H-imidazo[4,5-c]pyridin-2-yl)-1H-indazol-5-yl)pyridin-3-yl)acetamide [244];

N-(5-(3-(4-(thiophen-3-yl)-1H-imidazo[4,5-c]pyridin-2-yl)-1H-indazol-5-yl)pyridin-3-yl)benzamide [245];

N-isopropyl-5-(3-(4-(thiophen-3-yl)-1H-imidazo[4,5-c]pyridin-2-yl)-1H-indazol-5-yl)pyridin-3-amine [246];

N,N-dimethyl-1-(5-(3-(4-(thiophen-3-yl)-1H-imidazo[4,5-c]pyridin-2-yl)-1H-indazol-5-yl)pyridin-3-yl)methanamine [247];

2-(5-(5-(pyrrolidin-1-ylmethyl)pyridin-3-yl)-1H-indazol-3-yl)-4-(thiophen-3-yl)-1H-imidazo[4,5-c]pyridine [248];

2-(5-(5-(piperidin-1-ylmethyl)pyridin-3-yl)-1H-indazol-3-yl)-4-(thiophen-3-yl)-1H-imidazo[4,5-c]pyridine [249];

3,3-dimethyl-N-(5-(3-(4-(thiophen-3-yl)-1H-imidazo[4,5-c]pyridin-2-yl)-1H-indazol-5-yl)pyridin-3-yl)butanamide [250];

N-(5-(3-(4-(thiophen-3-yl)-1H-imidazo[4,5-c]pyridin-2-yl)-1H-indazol-5-yl)pyridin-3-yl)butyramide [251];

N-(5-(3-(4-(thiophen-3-yl)-1H-imidazo[4,5-c]pyridin-2-yl)-1H-indazol-5-yl)pyridin-3-yl)pentanamide [252];

N-(5-(3-(4-(thiophen-3-yl)-1H-imidazo[4,5-c]pyridin-2-yl)-1H-indazol-5-yl)pyridin-3-yl)cyclopropanecarboxamide [253];

N-(5-(3-(4-(thiophen-3-yl)-1H-imidazo[4,5-c]pyridin-2-yl)-1H-indazol-5-yl)pyridin-3-yl)cyclobutanecarboxamide [254];

N-(5-(3-(4-(thiophen-3-yl)-1H-imidazo[4,5-c]pyridin-2-yl)-1H-indazol-5-yl)pyridin-3-yl)cyclopentanecarboxamide [255];

N-(5-(3-(4-(thiophen-3-yl)-1H-imidazo[4,5-c]pyridin-2-yl)-1H-indazol-5-yl)pyridin-3-yl)cyclohexanecarboxamide [256];

N-benzyl-1-(5-(3-(4-(thiophen-3-yl)-1H-imidazo[4,5-c]pyridin-2-yl)-1H-indazol-5-yl)pyridin-3-yl)methanamine [257];

1-cyclopentyl-N-((5-(3-(4-(thiophen-3-yl)-1H-imidazo[4,5-c]pyridin-2-yl)-1H-indazol-5-yl)pyridin-3-yl)methyl)methanamine [258];

2-(5-(5-((3,3-difluoropyrrolidin-1-yl)methyl)pyridin-3-yl)-1H-indazol-3-yl)-4-(thiophen-3-yl)-1H-imidazo[4,5-c]pyridine [259];

2-(5-(pyrimidin-5-yl)-1H-indazol-3-yl)-4-(thiophen-3-yl)-1H-imidazo[4,5-c]pyridine [260];

N-(5-(3-(4-(furan-3-yl)-1H-imidazo[4,5-c]pyridin-2-yl)-1H-indazol-5-yl)pyridin-3-yl)propionamide [261];

N-(5-(3-(4-(furan-3-yl)-1H-imidazo[4,5-c]pyridin-2-yl)-1H-indazol-5-yl)pyridin-3-yl)-3-methylbutanamide [262]

5-(3-(4-(furan-3-yl)-1H-imidazo[4,5-c]pyridin-2-yl)-1H-indazol-5-yl)pyridin-3-amine [263];

4-(furan-3-yl)-2-(5-(pyridin-3-yl)-1H-indazol-3-yl)-1H-imidazo[4,5-c]pyridine [264];

4-(furan-3-yl)-2-(5-(4-methylpyridin-3-yl)-1H-indazol-3-yl)-1H-imidazo[4,5-c]pyridine [265];

N-((5-(3-(4-(furan-3-yl)-1H-imidazo[4,5-c]pyridin-2-yl)-1H-indazol-5-yl)pyridin-3-yl)methyl)ethanamine [266];

5-(3-(4-(furan-3-yl)-1H-imidazo[4,5-c]pyridin-2-yl)-1H-indazol-5-yl)-N,N-dimethylpyridin-3-amine [267];

N-(5-(3-(4-(furan-3-yl)-1H-imidazo[4,5-c]pyridin-2-yl)-1H-indazol-5-yl)pyridin-3-yl)pivalamide [268];

N-(5-(3-(4-(furan-3-yl)-1H-imidazo[4,5-c]pyridin-2-yl)-1H-indazol-5-yl)pyridin-3-yl)isobutyramide [269];

N-(5-(3-(4-(furan-3-yl)-1H-imidazo[4,5-c]pyridin-2-yl)-1H-indazol-5-yl)pyridin-3-yl)-2-phenylacetamide [270];

N-(5-(3-(4-(furan-3-yl)-1H-imidazo[4,5-c]pyridin-2-yl)-1H-indazol-5-yl)pyridin-3-yl)benzamide [271];

5-(3-(4-(furan-3-yl)-1H-imidazo[4,5-c]pyridin-2-yl)-1H-indazol-5-yl)-N-isopropylpyridin-3-amine [272];

1-(5-(3-(4-(furan-3-yl)-1H-imidazo[4,5-c]pyridin-2-yl)-1H-indazol-5-yl)pyridin-3-yl)-N,N-dimethylmethanamine [273];

4-(furan-3-yl)-2-(5-(5-(pyrrolidin-1-ylmethyl)pyridin-3-yl)-1H-indazol-3-yl)-1H-imidazo[4,5-c]pyridine [274];

4-(furan-3-yl)-2-(5-(5-(piperidin-1-ylmethyl)pyridin-3-yl)-1H-indazol-3-yl)-1H-imidazo[4,5-c]pyridine [275];

N-(5-(3-(4-(furan-3-yl)-1H-imidazo[4,5-c]pyridin-2-yl)-1H-indazol-5-yl)pyridin-3-yl)-3,3-dimethylbutanamide [276];

N-(5-(3-(4-(furan-3-yl)-1H-imidazo[4,5-c]pyridin-2-yl)-1H-indazol-5-yl)pyridin-3-yl)butyramide [277];

N-(5-(3-(4-(furan-3-yl)-1H-imidazo[4,5-c]pyridin-2-yl)-1H-indazol-5-yl)pyridin-3-yl)pentanamide [278];

N-(5-(3-(4-(furan-3-yl)-1H-imidazo[4,5-c]pyridin-2-yl)-1H-indazol-5-yl)pyridin-3-yl)cyclopropanecarboxamide [279];

N-(5-(3-(4-(furan-3-yl)-1H-imidazo[4,5-c]pyridin-2-yl)-1H-indazol-5-yl)pyridin-3-yl)cyclobutanecarboxamide [280];

N-(5-(3-(4-(furan-3-yl)-1H-imidazo[4,5-c]pyridin-2-yl)-1H-indazol-5-yl)pyridin-3-yl)cyclopentanecarboxamide [281];

N-(5-(3-(4-(furan-3-yl)-1H-imidazo[4,5-c]pyridin-2-yl)-1H-indazol-5-yl)pyridin-3-yl)cyclohexanecarboxamide [282];

N-benzyl-1-(5-(3-(4-(furan-3-yl)-1H-imidazo[4,5-c]pyridin-2-yl)-1H-indazol-5-yl)pyridin-3-yl)methanamine [283];

1-cyclopentyl-N-((5-(3-(4-(furan-3-yl)-1H-imidazo[4,5-c]pyridin-2-yl)-1H-indazol-5-yl)pyridin-3-yl)methyl)methanamine [284];
2-(5-(5-((3,3-difluoropyrrolidin-1-yl)methyl)pyridin-3-yl)-1H-indazol-3-yl)-4-(furan-3-yl)-1H-imidazo[4,5-c]pyridine [285];
4-(furan-3-yl)-2-(5-(pyrimidin-5-yl)-1H-indazol-3-yl)-1H-imidazo[4,5-c]pyridine [286];
N-(5-(3-(4-(thiophen-2-yl)-1H-imidazo[4,5-c]pyridin-2-yl)-1H-indazol-5-yl)pyridin-3-yl)propionamide [287];
3-methyl-N-(5-(3-(4-(thiophen-2-yl)-1H-imidazo[4,5-c]pyridin-2-yl)-1H-indazol-5-yl)pyridin-3-yl)butanamide [288];
5-(3-(4-(thiophen-2-yl)-1H-imidazo[4,5-c]pyridin-2-yl)-1H-indazol-5-yl)pyridin-3-amine [289];
2-(5-(pyridin-3-yl)-1H-indazol-3-yl)-4-(thiophen-2-yl)-1H-imidazo[4,5-c]pyridine [290];
2-(5-(4-methylpyridin-3-yl)-1H-indazol-3-yl)-4-(thiophen-2-yl)-1H-imidazo[4,5-c]pyridine [291];
N-((5-(3-(4-(thiophen-2-yl)-1H-imidazo[4,5-c]pyridin-2-yl)-1H-indazol-5-yl)pyridin-3-yl)methyl)ethanamine [292];
N,N-dimethyl-5-(3-(4-(thiophen-2-yl)-1H-imidazo[4,5-c]pyridin-2-yl)-1H-indazol-5-yl)pyridin-3-amine [293];
N-(5-(3-(4-(thiophen-2-yl)-1H-imidazo[4,5-c]pyridin-2-yl)-1H-indazol-5-yl)pyridin-3-yl)pivalamide [294];
N-(5-(3-(4-(thiophen-2-yl)-1H-imidazo[4,5-c]pyridin-2-yl)-1H-indazol-5-yl)pyridin-3-yl)isobutyramide [295];
2-phenyl-N-(5-(3-(4-(thiophen-2-yl)-1H-imidazo[4,5-c]pyridin-2-yl)-1H-indazol-5-yl)pyridin-3-yl)acetamide [296];
N-(5-(3-(4-(thiophen-2-yl)-1H-imidazo[4,5-c]pyridin-2-yl)-1H-indazol-5-yl)pyridin-3-yl)benzamide [297];
N-isopropyl-5-(3-(4-(thiophen-2-yl)-1H-imidazo[4,5-c]pyridin-2-yl)-1H-indazol-5-yl)pyridin-3-amine [298];
N,N-dimethyl-1-(5-(3-(4-(thiophen-2-yl)-1H-imidazo[4,5-c]pyridin-2-yl)-1H-indazol-5-yl)pyridin-3-yl)methanamine [299]; and
2-(5-(5-(pyrrolidin-1-ylmethyl)pyridin-3-yl)-1H-indazol-3-yl)-4-(thiophen-2-yl)-1H-imidazo[4,5-c]pyridine [300]; or a pharmaceutically acceptable salt thereof.

22. The method of claim 1, wherein the compound of Formula I is selected from the group consisting of:
2-(5-(5-(piperidin-1-ylmethyl)pyridin-3-yl)-1H-indazol-3-yl)-4-(thiophen-2-yl)-1H-imidazo[4,5-c]pyridine [301];
3,3-dimethyl-N-(5-(3-(4-(thiophen-2-yl)-1H-imidazo[4,5-c]pyridin-2-yl)-1H-indazol-5-yl)pyridin-3-yl)butanamide [302];
N-(5-(3-(4-(thiophen-2-yl)-1H-imidazo[4,5-c]pyridin-2-yl)-1H-indazol-5-yl)pyridin-3-yl)butyramide [303];
N-(5-(3-(4-(thiophen-2-yl)-1H-imidazo[4,5-c]pyridin-2-yl)-1H-indazol-5-yl)pyridin-3-yl)pentanamide [304];
N-(5-(3-(4-(thiophen-2-yl)-1H-imidazo[4,5-c]pyridin-2-yl)-1H-indazol-5-yl)pyridin-3-yl)cyclopropanecarboxamide [305];
N-(5-(3-(4-(thiophen-2-yl)-1H-imidazo[4,5-c]pyridin-2-yl)-1H-indazol-5-yl)pyridin-3-yl)cyclobutanecarboxamide [306];
N-(5-(3-(4-(thiophen-2-yl)-1H-imidazo[4,5-c]pyridin-2-yl)-1H-indazol-5-yl)pyridin-3-yl)cyclopentanecarboxamide [307];
N-(5-(3-(4-(thiophen-2-yl)-1H-imidazo[4,5-c]pyridin-2-yl)-1H-indazol-5-yl)pyridin-3-yl)cyclohexanecarboxamide [308];
N-benzyl-1-(5-(3-(4-(thiophen-2-yl)-1H-imidazo[4,5-c]pyridin-2-yl)-1H-indazol-5-yl)pyridin-3-yl)methanamine [309];
1-cyclopentyl-N-((5-(3-(4-(thiophen-2-yl)-1H-imidazo[4,5-c]pyridin-2-yl)-1H-indazol-5-yl)pyridin-3-yl)methyl)methanamine [310];
2-(5-(5-((3,3-difluoropyrrolidin-1-yl)methyl)pyridin-3-yl)-1H-indazol-3-yl)-4-(thiophen-2-yl)-1H-imidazo[4,5-c]pyridine [311];
2-(5-(pyrimidin-5-yl)-1H-indazol-3-yl)-4-(thiophen-2-yl)-1H-imidazo[4,5-c]pyridine [312];
N-(5-(3-(4-(5-fluorothiophen-2-yl)-1H-imidazo[4,5-c]pyridin-2-yl)-1H-indazol-5-yl)pyridin-3-yl)propionamide [313];
N-(5-(3-(4-(5-fluorothiophen-2-yl)-1H-imidazo[4,5-c]pyridin-2-yl)-1H-indazol-5-yl)pyridin-3-yl)-3-methylbutanamide [314];
5-(3-(4-(5-fluorothiophen-2-yl)-1H-imidazo[4,5-c]pyridin-2-yl)-1H-indazol-5-yl)pyridin-3-amine [315];
4-(5-fluorothiophen-2-yl)-2-(5-(pyridin-3-yl)-1H-indazol-3-yl)-1H-imidazo[4,5-c]pyridine [316];
4-(5-fluorothiophen-2-yl)-2-(5-(4-methylpyridin-3-yl)-1H-indazol-3-yl)-1H-imidazo[4,5-c]pyridine [317];
N-((5-(3-(4-(5-fluorothiophen-2-yl)-1H-imidazo[4,5-c]pyridin-2-yl)-1H-indazol-5-yl)pyridin-3-yl)methyl)ethanamine [318];
5-(3-(4-(5-fluorothiophen-2-yl)-1H-imidazo[4,5-c]pyridin-2-yl)-1H-indazol-5-yl)-N,N-dimethylpyridin-3-amine [319];
N-(5-(3-(4-(5-fluorothiophen-2-yl)-1H-imidazo[4,5-c]pyridin-2-yl)-1H-indazol-5-yl)pyridin-3-yl)pivalamide [320];
N-(5-(3-(4-(5-fluorothiophen-2-yl)-1H-imidazo[4,5-c]pyridin-2-yl)-1H-indazol-5-yl)pyridin-3-yl)isobutyramide [321];
N-(5-(3-(4-(5-fluorothiophen-2-yl)-1H-imidazo[4,5-c]pyridin-2-yl)-1H-indazol-5-yl)pyridin-3-yl)-2-phenylacetamide [322];
N-(5-(3-(4-(5-fluorothiophen-2-yl)-1H-imidazo[4,5-c]pyridin-2-yl)-1H-indazol-5-yl)pyridin-3-yl)benzamide [323];
5-(3-(4-(5-fluorothiophen-2-yl)-1H-imidazo[4,5-c]pyridin-2-yl)-1H-indazol-5-yl)-N-isopropylpyridin-3-amine [324];
1-(5-(3-(4-(5-fluorothiophen-2-yl)-1H-imidazo[4,5-c]pyridin-2-yl)-1H-indazol-5-yl)pyridin-3-yl)-N,N-dimethylmethanamine [325];
4-(5-fluorothiophen-2-yl)-2-(5-(5-(pyrrolidin-1-ylmethyl)pyridin-3-yl)-1H-indazol-3-yl)-1H-imidazo[4,5-c]pyridine [326];
4-(5-fluorothiophen-2-yl)-2-(5-(5-(piperidin-1-ylmethyl)pyridin-3-yl)-1H-indazol-3-yl)-1H-imidazo[4,5-c]pyridine [327];
N-(5-(3-(4-(5-fluorothiophen-2-yl)-1H-imidazo[4,5-c]pyridin-2-yl)-1H-indazol-5-yl)pyridin-3-yl)-3,3-dimethylbutanamide [328];
N-(5-(3-(4-(5-fluorothiophen-2-yl)-1H-imidazo[4,5-c]pyridin-2-yl)-1H-indazol-5-yl)pyridin-3-yl)butyramide [329];
N-(5-(3-(4-(5-fluorothiophen-2-yl)-1H-imidazo[4,5-c]pyridin-2-yl)-1H-indazol-5-yl)pyridin-3-yl)pentanamide [330];
N-(5-(3-(4-(5-fluorothiophen-2-yl)-1H-imidazo[4,5-c]pyridin-2-yl)-1H-indazol-5-yl)pyridin-3-yl)cyclopropanecarboxamide [331];

N-(5-(3-(4-(5-fluorothiophen-2-yl)-1H-imidazo[4,5-c]pyridin-2-yl)-1H-indazol-5-yl)pyridin-3-yl)cyclobutanecarboxamide [332];

N-(5-(3-(4-(5-fluorothiophen-2-yl)-1H-imidazo[4,5-c]pyridin-2-yl)-1H-indazol-5-yl)pyridin-3-yl)cyclopentanecarboxamide [333];

N-(5-(3-(4-(5-fluorothiophen-2-yl)-1H-imidazo[4,5-c]pyridin-2-yl)-1H-indazol-5-yl)pyridin-3-yl)cyclohexanecarboxamide [334];

N-benzyl-1-(5-(3-(4-(5-fluorothiophen-2-yl)-1H-imidazo[4,5-c]pyridin-2-yl)-1H-indazol-5-yl)pyridin-3-yl)methanamine [335];

1-cyclopentyl-N-((5-(3-(4-(5-fluorothiophen-2-yl)-1H-imidazo[4,5-c]pyridin-2-yl)-1H-indazol-5-yl)pyridin-3-yl)methyl)methanamine [336];

2-(5-(5-((3,3-difluoropyrrolidin-1-yl)methyl)pyridin-3-yl)-1H-indazol-3-yl)-4-(5-fluorothiophen-2-yl)-1H-imidazo[4,5-c]pyridine [337];

4-(5-fluorothiophen-2-yl)-2-(5-(pyrimidin-5-yl)-1H-indazol-3-yl)-1H-imidazo[4,5-c]pyridine [338];

N-(5-(3-(4-(5-methylthiophen-2-yl)-1H-imidazo[4,5-c]pyridin-2-yl)-1H-indazol-5-yl)pyridin-3-yl)propionamide [339];

3-methyl-N-(5-(3-(4-(5-methylthiophen-2-yl)-1H-imidazo[4,5-c]pyridin-2-yl)-1H-indazol-5-yl)pyridin-3-yl)butanamide [340];

5-(3-(4-(5-methylthiophen-2-yl)-1H-imidazo[4,5-c]pyridin-2-yl)-1H-indazol-5-yl)pyridin-3-amine [341];

4-(5-methylthiophen-2-yl)-2-(5-(pyridin-3-yl)-1H-indazol-3-yl)-1H-imidazo[4,5-c]pyridine [342];

2-(5-(4-methylpyridin-3-yl)-1H-indazol-3-yl)-4-(5-methylthiophen-2-yl)-1H-imidazo[4,5-c]pyridine [343];

N-((5-(3-(4-(5-methylthiophen-2-yl)-1H-imidazo[4,5-c]pyridin-2-yl)-1H-indazol-5-yl)pyridin-3-yl)methyl)ethanamine [344];

N,N-dimethyl-5-(3-(4-(5-methylthiophen-2-yl)-1H-imidazo[4,5-c]pyridin-2-yl)-1H-indazol-5-yl)pyridin-3-amine [345];

N-(5-(3-(4-(5-methylthiophen-2-yl)-1H-imidazo[4,5-c]pyridin-2-yl)-1H-indazol-5-yl)pyridin-3-yl)pivalamide [346];

N-(5-(3-(4-(5-methylthiophen-2-yl)-1H-imidazo[4,5-c]pyridin-2-yl)-1H-indazol-5-yl)pyridin-3-yl)isobutyramide [347];

N-(5-(3-(4-(5-methylthiophen-2-yl)-1H-imidazo[4,5-c]pyridin-2-yl)-1H-indazol-5-yl)pyridin-3-yl)-2-phenylacetamide [348];

N-(5-(3-(4-(5-methylthiophen-2-yl)-1H-imidazo[4,5-c]pyridin-2-yl)-1H-indazol-5-yl)pyridin-3-yl)benzamide [349];

N-isopropyl-5-(3-(4-(5-methylthiophen-2-yl)-1H-imidazo[4,5-c]pyridin-2-yl)-1H-indazol-5-yl)pyridin-3-amine [350];

N,N-dimethyl-1-(5-(3-(4-(5-methylthiophen-2-yl)-1H-imidazo[4,5-c]pyridin-2-yl)-1H-indazol-5-yl)pyridin-3-yl)methanamine [351];

4-(5-methylthiophen-2-yl)-2-(5-(5-(pyrrolidin-1-ylmethyl)pyridin-3-yl)-1H-indazol-3-yl)-1H-imidazo[4,5-c]pyridine [352];

4-(5-methylthiophen-2-yl)-2-(5-(5-(piperidin-1-ylmethyl)pyridin-3-yl)-1H-indazol-3-yl)-1H-imidazo[4,5-c]pyridine [353];

3,3-dimethyl-N-(5-(3-(4-(5-methylthiophen-2-yl)-1H-imidazo[4,5-c]pyridin-2-yl)-1H-indazol-5-yl)pyridin-3-yl)butanamide [354];

N-(5-(3-(4-(5-methylthiophen-2-yl)-1H-imidazo[4,5-c]pyridin-2-yl)-1H-indazol-5-yl)pyridin-3-yl)butyramide [355];

N-(5-(3-(4-(5-methylthiophen-2-yl)-1H-imidazo[4,5-c]pyridin-2-yl)-1H-indazol-5-yl)pyridin-3-yl)pentanamide [356];

N-(5-(3-(4-(5-methylthiophen-2-yl)-1H-imidazo[4,5-c]pyridin-2-yl)-1H-indazol-5-yl)pyridin-3-yl)cyclopropanecarboxamide [357];

N-(5-(3-(4-(5-methylthiophen-2-yl)-1H-imidazo[4,5-c]pyridin-2-yl)-1H-indazol-5-yl)pyridin-3-yl)cyclobutanecarboxamide [358];

N-(5-(3-(4-(5-methylthiophen-2-yl)-1H-imidazo[4,5-c]pyridin-2-yl)-1H-indazol-5-yl)pyridin-3-yl)cyclopentanecarboxamide [359];

N-(5-(3-(4-(5-methylthiophen-2-yl)-1H-imidazo[4,5-c]pyridin-2-yl)-1H-indazol-5-yl)pyridin-3-yl)cyclohexanecarboxamide [360];

N-benzyl-1-(5-(3-(4-(5-methylthiophen-2-yl)-1H-imidazo[4,5-c]pyridin-2-yl)-1H-indazol-5-yl)pyridin-3-yl)methanamine [361];

1-cyclopentyl-N-((5-(3-(4-(5-methylthiophen-2-yl)-1H-imidazo[4,5-c]pyridin-2-yl)-1H-indazol-5-yl)pyridin-3-yl)methyl)methanamine [362];

2-(5-(5-((3,3-difluoropyrrolidin-1-yl)methyl)pyridin-3-yl)-1H-indazol-3-yl)-4-(5-methylthiophen-2-yl)-1H-imidazo[4,5-c]pyridine [363];

4-(5-methylthiophen-2-yl)-2-(5-(pyrimidin-5-yl)-1H-indazol-3-yl)-1H-imidazo[4,5-c]pyridine [364];

N-(5-(3-(4-(5-acetylthiophen-2-yl)-1H-imidazo[4,5-c]pyridin-2-yl)-1H-indazol-5-yl)pyridin-3-yl)propionamide [365];

N-(5-(3-(4-(5-acetylthiophen-2-yl)-1H-imidazo[4,5-c]pyridin-2-yl)-1H-indazol-5-yl)pyridin-3-yl)-3-methylbutanamide [366];

1-(5-(2-(5-(5-aminopyridin-3-yl)-1H-indazol-3-yl)-1H-imidazo[4,5-c]pyridin-4-yl)thiophen-2-yl)ethan-1-one [367];

1-(5-(2-(5-(pyridin-3-yl)-1H-indazol-3-yl)-1H-imidazo[4,5-c]pyridin-4-yl)thiophen-2-yl)ethan-1-one [368];

1-(5-(2-(5-(4-methylpyridin-3-yl)-1H-indazol-3-yl)-1H-imidazo[4,5-c]pyridin-4-yl)thiophen-2-yl)ethan-1-one [369];

1-(5-(2-(5-(5-((ethylamino)methyl)pyridin-3-yl)-1H-indazol-3-yl)-1H-imidazo[4,5-c]pyridin-4-yl)thiophen-2-yl)ethan-1-one [370];

1-(5-(2-(5-(5-(dimethylamino)pyridin-3-yl)-1H-indazol-3-yl)-1H-imidazo[4,5-c]pyridin-4-yl)thiophen-2-yl)ethan-1-one [371];

N-(5-(3-(4-(5-acetylthiophen-2-yl)-1H-imidazo[4,5-c]pyridin-2-yl)-1H-indazol-5-yl)pyridin-3-yl)pivalamide [372];

N-(5-(3-(4-(5-acetylthiophen-2-yl)-1H-imidazo[4,5-c]pyridin-2-yl)-1H-indazol-5-yl)pyridin-3-yl)isobutyramide [373];

N-(5-(3-(4-(5-acetylthiophen-2-yl)-1H-imidazo[4,5-c]pyridin-2-yl)-1H-indazol-5-yl)pyridin-3-yl)-2-phenylacetamide [374];

N-(5-(3-(4-(5-acetylthiophen-2-yl)-1H-imidazo[4,5-c]pyridin-2-yl)-1H-indazol-5-yl)pyridin-3-yl)benzamide [375];

1-(5-(2-(5-(5-(isopropylamino)pyridin-3-yl)-1H-indazol-3-yl)-1H-imidazo[4,5-c]pyridin-4-yl)thiophen-2-yl)ethan-1-one [376];

1-(5-(2-(5-(5-((dimethylamino)methyl)pyridin-3-yl)-1H-indazol-3-yl)-1H-imidazo[4,5-c]pyridin-4-yl)thiophen-2-yl)ethan-1-one [377];

1-(5-(2-(5-(5-(pyrrolidin-1-ylmethyl)pyridin-3-yl)-1H-indazol-3-yl)-1H-imidazo[4,5-c]pyridin-4-yl)thiophen-2-yl)ethan-1-one [378];

1-(5-(2-(5-(5-(piperidin-1-ylmethyl)pyridin-3-yl)-1H-indazol-3-yl)-1H-imidazo[4,5-c]pyridin-4-yl)thiophen-2-yl)ethan-1-one [379];

N-(5-(3-(4-(5-acetylthiophen-2-yl)-1H-imidazo[4,5-c]pyridin-2-yl)-1H-indazol-5-yl)pyridin-3-yl)-3,3-dimethylbutanamide [380];

N-(5-(3-(4-(5-acetylthiophen-2-yl)-1H-imidazo[4,5-c]pyridin-2-yl)-1H-indazol-5-yl)pyridin-3-yl)butyramide [381];

N-(5-(3-(4-(5-acetylthiophen-2-yl)-1H-imidazo[4,5-c]pyridin-2-yl)-1H-indazol-5-yl)pyridin-3-yl)pentanamide [382];

N-(5-(3-(4-(5-acetylthiophen-2-yl)-1H-imidazo[4,5-c]pyridin-2-yl)-1H-indazol-5-yl)pyridin-3-yl)cyclopropanecarboxamide [383];

N-(5-(3-(4-(5-acetylthiophen-2-yl)-1H-imidazo[4,5-c]pyridin-2-yl)-1H-indazol-5-yl)pyridin-3-yl)cyclobutanecarboxamide [384];

N-(5-(3-(4-(5-acetylthiophen-2-yl)-1H-imidazo[4,5-c]pyridin-2-yl)-1H-indazol-5-yl)pyridin-3-yl)cyclopentanecarboxamide [385];

N-(5-(3-(4-(5-acetylthiophen-2-yl)-1H-imidazo[4,5-c]pyridin-2-yl)-1H-indazol-5-yl)pyridin-3-yl)cyclohexanecarboxamide [386];

1-(5-(2-(5-(5-((benzylamino)methyl)pyridin-3-yl)-1H-indazol-3-yl)-1H-imidazo[4,5-c]pyridin-4-yl)thiophen-2-yl)ethan-1-one [387];

1-(5-(2-(5-(5-(((cyclopentylmethyl)amino)methyl)pyridin-3-yl)-1H-indazol-3-yl)-1H-imidazo[4,5-c]pyridin-4-yl)thiophen-2-yl)ethan-1-one [388];

1-(5-(2-(5-(5-((3,3-difluoropyrrolidin-1-yl)methyl)pyridin-3-yl)-1H-indazol-3-yl)-1H-imidazo[4,5-c]pyridin-4-yl)thiophen-2-yl)ethan-1-one [389];

1-(5-(2-(5-(pyrimidin-5-yl)-1H-indazol-3-yl)-1H-imidazo[4,5-c]pyridin-4-yl)thiophen-2-yl)ethan-1-one [390];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)propionamide [391];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)-3-methylbutanamide [392];

N-(3-(2-(5-(5-aminopyridin-3-yl)-1H-indazol-3-yl)-1H-imidazo[4,5-c]pyridin-4-yl)-5-fluorobenzyl)methanesulfonamide [393];

N-(3-fluoro-5-(2-(5-(pyridin-3-yl)-1H-indazol-3-yl)-1H-imidazo[4,5-c]pyridin-4-yl)benzyl)methanesulfonamide [394];

N-(3-fluoro-5-(2-(5-(4-methylpyridin-3-yl)-1H-indazol-3-yl)-1H-imidazo[4,5-c]pyridin-4-yl)benzyl)methanesulfonamide [395];

N-(3-(2-(5-(5-((ethylamino)methyl)pyridin-3-yl)-1H-indazol-3-yl)-1H-imidazo[4,5-c]pyridin-4-yl)-5-fluorobenzyl)methanesulfonamide [396];

N-(3-(2-(5-(5-(dimethylamino)pyridin-3-yl)-1H-indazol-3-yl)-1H-imidazo[4,5-c]pyridin-4-yl)-5-fluorobenzyl)methanesulfonamide [397];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)pivalamide [398];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)isobutyramide [399]; and N-(5-(3-(4-(3-fluoro-5-(methylsulfonamidomethyl)phenyl)-1H-imidazo[4,5-c]pyridin-2-yl)-1H-indazol-5-yl)pyridin-3-yl)-2-phenylacetamide [400]; or a pharmaceutically acceptable salt thereof.

23. The method of claim 1, wherein the compound of Formula I is selected from the group consisting of:

N-(5-(3-(4-(3-fluoro-5-(methylsulfonamidomethyl)phenyl)-1H-imidazo[4,5-c]pyridin-2-yl)-1H-indazol-5-yl)pyridin-3-yl)benzamide [401];

N-(3-fluoro-5-(2-(5-(5-(isopropylamino)pyridin-3-yl)-1H-indazol-3-yl)-1H-imidazo[4,5-c]pyridin-4-yl)benzyl)methanesulfonamide [402];

N-(3-(2-(5-(5-((dimethylamino)methyl)pyridin-3-yl)-1H-indazol-3-yl)-1H-imidazo[4,5-c]pyridin-4-yl)-5-fluorobenzyl)methanesulfonamide [403];

N-(3-fluoro-5-(2-(5-(5-(pyrrolidin-1-ylmethyl)pyridin-3-yl)-1H-indazol-3-yl)-1H-imidazo[4,5-c]pyridin-4-yl)benzyl)methanesulfonamide [404];

N-(3-fluoro-5-(2-(5-(5-(piperidin-1-ylmethyl)pyridin-3-yl)-1H-indazol-3-yl)-1H-imidazo[4,5-c]pyridin-4-yl)benzyl)methanesulfonamide [405];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)-3,3-dimethylbutanamide [406];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)butyramide [407];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)pentanamide [408];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)cyclopropanecarboxamide [409];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)cyclobutanecarboxamide [410];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)cyclopentanecarboxamide [411];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)cyclohexanecarboxamide [412];

N-(3-(2-(5-(5-((benzylamino)methyl)pyridin-3-yl)-1H-indazol-3-yl)-1H-imidazo[4,5-c]pyridin-4-yl)-5-fluorobenzyl)methanesulfonamide [413];

N-(3-(2-(5-(5-(((cyclopentylmethyl)amino)methyl)pyridin-3-yl)-1H-indazol-3-yl)-1H-imidazo[4,5-c]pyridin-4-yl)-5-fluorobenzyl)methanesulfonamide [414];

N-(3-(2-(5-(5-((3,3-difluoropyrrolidin-1-yl)methyl)pyridin-3-yl)-1H-indazol-3-yl)-1H-imidazo[4,5-c]pyridin-4-yl)-5-fluorobenzyl)methanesulfonamide [415];

N-(3-fluoro-5-(2-(5-(pyrimidin-5-yl)-1H-indazol-3-yl)-1H-imidazo[4,5-c]pyridin-4-yl)benzyl)methanesulfonamide [416];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)propionamide [417];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)-3-methylbutanamide [418];

$N^1$-(3-(2-(5-(5-aminopyridin-3-yl)-1H-indazol-3-yl)-1H-imidazo[4,5-c]pyridin-4-yl)-5-fluorophenyl)-$N^2$,$N^2$-dimethylethane-1,2-diamine [419];

$N^1$-(3-fluoro-5-(2-(5-(pyridin-3-yl)-1H-indazol-3-yl)-1H-imidazo[4,5-c]pyridin-4-yl)phenyl)-$N^2$,$N^2$-dimethylethane-1,2-diamine [420];

N$^1$-(3-fluoro-5-(2-(5-(4-methylpyridin-3-yl)-1H-indazol-3-yl)-1H-imidazo[4,5-c]pyridin-4-yl)phenyl)-N$^2$,N$^2$-dimethylethane-1,2-diamine [421];

N$^1$-(3-(2-(5-(5-((ethylamino)methyl)pyridin-3-yl)-1H-indazol-3-yl)-1H-imidazo[4,5-c]pyridin-4-yl)-5-fluorophenyl)-N$^2$,N$^2$-dimethylethane-1,2-diamine [422];

N$^1$-(3-(2-(5-(5-(dimethylamino)pyridin-3-yl)-1H-indazol-3-yl)-1H-imidazo[4,5-c]pyridin-4-yl)-5-fluorophenyl)-N$^2$,N$^2$-dimethylethane-1,2-diamine [423];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)pivalamide [424];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)isobutyramide [425];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)-2-phenylacetamide [426];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)benzamide [427];

N$^1$-(3-fluoro-5-(2-(5-(5-(isopropylamino)pyridin-3-yl)-1H-indazol-3-yl)-1H-imidazo[4,5-c]pyridin-4-yl)phenyl)-N$^2$,N$^2$-dimethylethane-1,2-diamine [428];

N$^1$-(3-(2-(5-(5-((dimethylamino)methyl)pyridin-3-yl)-1H-indazol-3-yl)-1H-imidazo[4,5-c]pyridin-4-yl)-5-fluorophenyl)-N$^2$,N$^2$-dimethylethane-1,2-diamine [429];

N$^1$-(3-fluoro-5-(2-(5-(5-(pyrrolidin-1-ylmethyl)pyridin-3-yl)-1H-indazol-3-yl)-1H-imidazo[4,5-c]pyridin-4-yl)phenyl)-N$^2$,N$^2$-dimethylethane-1,2-diamine [430];

N$^1$-(3-fluoro-5-(2-(5-(5-(piperidin-1-ylmethyl)pyridin-3-yl)-1H-indazol-3-yl)-1H-imidazo[4,5-c]pyridin-4-yl)phenyl)-N$^2$,N$^2$-dimethylethane-1,2-diamine [431];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)-3,3-dimethylbutanamide [432];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)butyramide [433];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)pentanamide [434];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)cyclopropanecarboxamide [435];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)cyclobutanecarboxamide [436];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)cyclopentanecarboxamide [437];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)cyclohexanecarboxamide [438];

N$^1$-(3-(2-(5-(5-((benzylamino)methyl)pyridin-3-yl)-1H-indazol-3-yl)-1H-imidazo[4,5-c]pyridin-4-yl)-5-fluorophenyl)-N$^2$,N$^2$-dimethylethane-1,2-diamine [439];

N$^1$-(3-(2-(5-(5-(((cyclopentylmethyl)amino)methyl)pyridin-3-yl)-1H-indazol-3-yl)-1H-imidazo[4,5-c]pyridin-4-yl)-5-fluorophenyl)-N$^2$,N$^2$-dimethylethane-1,2-diamine [440];

N$^1$-(3-(2-(5-(5-((3,3-difluoropyrrolidin-1-yl)methyl)pyridin-3-yl)-1H-indazol-3-yl)-1H-imidazo[4,5-c]pyridin-4-yl)-5-fluorophenyl)-N$^2$,N$^2$-dimethylethane-1,2-diamine [441];

N$^1$-(3-fluoro-5-(2-(5-(pyrimidin-5-yl)-1H-indazol-3-yl)-1H-imidazo[4,5-c]pyridin-4-yl)phenyl)-N$^2$,N$^2$-dimethylethane-1,2-diamine [442];

1-(5-(7-fluoro-3-(4-(3-fluorophenyl)-1H-imidazo[4,5-c]pyridin-2-yl)-1H-indazol-5-yl)pyridin-3-yl)-N,N-dimethylmethanamine [456];

1-(5-(7-fluoro-3-(4-(thiophen-3-yl)-1H-imidazo[4,5-c]pyridin-2-yl)-1H-indazol-5-yl)pyridin-3-yl)-N,N-dimethylmethanamine [688];

N-(3-(2-(5-(5-((dimethylamino)methyl)pyridin-3-yl)-7-fluoro-1H-indazol-3-yl)-1H-imidazo[4,5-c]pyridin-4-yl)-5-fluorobenzyl)methanesulfonamide [844];

1-(5-(6-fluoro-3-(4-(3-fluorophenyl)-1H-imidazo[4,5-c]pyridin-2-yl)-1H-indazol-5-yl)pyridin-3-yl)-N,N-dimethylmethanamine [898];

1-(5-(6-fluoro-3-(4-(thiophen-3-yl)-1H-imidazo[4,5-c]pyridin-2-yl)-1H-indazol-5-yl)pyridin-3-yl)-N,N-dimethylmethanamine [1132];

N-(3-(2-(5-(5-((dimethylamino)methyl)pyridin-3-yl)-6-fluoro-1H-indazol-3-yl)-1H-imidazo[4,5-c]pyridin-4-yl)-5-fluorobenzyl)methanesulfonamide [1288];

1-(5-(4-fluoro-3-(4-(3-fluorophenyl)-1H-imidazo[4,5-c]pyridin-2-yl)-1H-indazol-5-yl)pyridin-3-yl)-N,N-dimethylmethanamine [1339];

1-(5-(4-fluoro-3-(4-(thiophen-3-yl)-1H-imidazo[4,5-c]pyridin-2-yl)-1H-indazol-5-yl)pyridin-3-yl)-N,N-dimethylmethanamine [1573];

N-(3-(2-(5-(5-((dimethylamino)methyl)pyridin-3-yl)-4-fluoro-1H-indazol-3-yl)-1H-imidazo[4,5-c]pyridin-4-yl)-5-fluorobenzyl)methanesulfonamide [1729];

4-(3-fluorophenyl)-2-(5-(piperidin-4-yl)-1H-indazol-3-yl)-1H-imidazo[4,5-c]pyridine [1769];

4-(3-fluorophenyl)-2-(5-(1,2,3,6-tetrahydropyridin-4-yl)-1H-indazol-3-yl)-1H-imidazo[4,5-c]pyridine [1770];

2-(5-(1H-pyrazol-4-yl)-1H-indazol-3-yl)-4-(3-fluorophenyl)-1H-imidazo[4,5-c]pyridine [1771];

4-(3-fluorophenyl)-2-(5-(1-methyl-1H-pyrazol-4-yl)-1H-indazol-3-yl)-1H-imidazo[4,5-c]pyridine [1772];

2-(5-(1,2-dimethyl-1H-imidazol-5-yl)-1H-indazol-3-yl)-4-(3-fluorophenyl)-1H-imidazo[4,5-c]pyridine [1773];

1-(6-(3-(4-(3-fluorophenyl)-1H-imidazo[4,5-c]pyridin-2-yl)-1H-indazol-5-yl)pyrazin-2-yl)azetidin-3-amine [1774];

2-(5-(5-(cyclohexyloxy)pyridin-3-yl)-1H-indazol-3-yl)-4-(3-fluorophenyl)-1H-imidazo[4,5-c]pyridine [1775];

4-(3-fluorophenyl)-2-(5-(5-(piperidin-4-yloxy)pyridin-3-yl)-1H-indazol-3-yl)-1H-imidazo[4,5-c]pyridine [1776];

N-(5-(3-(4-(3-fluorophenyl)-1H-imidazo[4,5-c]pyridin-2-yl)-1H-indazol-5-yl)pyridin-3-yl)-2-(piperidin-4-yl)acetamide [1777];

4-(3-fluorophenyl)-2-(5-(5-(2-(pyrrolidin-1-yl)ethoxy)pyridin-3-yl)-1H-indazol-3-yl)-1H-imidazo[4,5-c]pyridine [1778];

2-((5-(3-(4-(3-fluorophenyl)-1H-imidazo[4,5-c]pyridin-2-yl)-1H-indazol-5-yl)pyridin-3-yl)oxy)-N,N-dimethylethan-1-amine [1779];

4-(3-fluorophenyl)-2-(5-(5-methoxypyridin-3-yl)-1H-indazol-3-yl)-1H-imidazo[4,5-c]pyridine [1780];

5-(3-(4-(3-fluorophenyl)-1H-imidazo[4,5-c]pyridin-2-yl)-1H-indazol-5-yl)pyridin-3-ol [1781];

2-(5-(5-(benzyloxy)pyridin-3-yl)-1H-indazol-3-yl)-4-(3-fluorophenyl)-1H-imidazo[4,5-c]pyridine [1782];

2-cyclohexyl-N-(5-(3-(4-(3-fluorophenyl)-1H-imidazo[4,5-c]pyridin-2-yl)-1H-indazol-5-yl)pyridin-3-yl)acetamide [1783];

4-(3-fluorophenyl)-2-(5-(pyridin-4-yl)-1H-indazol-3-yl)-
1H-imidazo[4,5-c]pyridine [1784];
4-(3-fluorophenyl)-2-(5-(pyridin-2-yl)-1H-indazol-3-yl)-
1H-imidazo[4,5-c]pyridine [1785];
4-(3-fluorophenyl)-2-(5-(pyrazin-2-yl)-1H-indazol-3-yl)-
1H-imidazo[4,5-c]pyridine [1786];
4-(4-fluorophenyl)-2-(5-(piperidin-4-yl)-1H-indazol-3-
yl)-1H-imidazo[4,5-c]pyridine [1787];
4-(4-fluorophenyl)-2-(5-(1,2,3,6-tetrahydropyridin-4-yl)-
1H-indazol-3-yl)-1H-imidazo[4,5-c]pyridine [1788];
2-(5-(1H-pyrazol-4-yl)-1H-indazol-3-yl)-4-(4-fluorophe-
nyl)-1H-imidazo[4,5-c]pyridine [1789];
4-(4-fluorophenyl)-2-(5-(1-methyl-1H-pyrazol-4-yl)-1H-
indazol-3-yl)-1H-imidazo[4,5-c]pyridine [1790];
2-(5-(1,2-dimethyl-1H-imidazol-5-yl)-1H-indazol-3-yl)-
4-(4-fluorophenyl)-1H-imidazo[4,5-c]pyridine [1791];
1-(6-(3-(4-(4-fluorophenyl)-1H-imidazo[4,5-c]pyridin-2-
yl)-1H-indazol-5-yl)pyrazin-2-yl)azetidin-3-amine
[1792];
2-(5-(5-(cyclohexyloxy)pyridin-3-yl)-1H-indazol-3-yl)-
4-(4-fluorophenyl)-1H-imidazo[4,5-c]pyridine [1793];
4-(4-fluorophenyl)-2-(5-(5-(piperidin-4-yloxy)pyridin-3-
yl)-1H-indazol-3-yl)-1H-imidazo[4,5-c]pyridine
[1794];
N-(5-(3-(4-(4-fluorophenyl)-1H-imidazo[4,5-c]pyridin-
2-yl)-1H-indazol-5-yl)pyridin-3-yl)-2-(piperidin-4-yl)
acetamide [1795];
4-(4-fluorophenyl)-2-(5-(5-(2-(pyrrolidin-1-yl)ethoxy)
pyridin-3-yl)-1H-indazol-3-yl)-1H-imidazo[4,5-c]
pyridine [1796];
2-((5-(3-(4-(4-fluorophenyl)-1H-imidazo[4,5-c]pyridin-
2-yl)-1H-indazol-5-yl)pyridin-3-yl)oxy)-N,N-dim-
ethylethan-1-amine [1797];
4-(4-fluorophenyl)-2-(5-(5-methoxypyridin-3-yl)-1H-in-
dazol-3-yl)-1H-imidazo[4,5-c]pyridine [1798];
5-(3-(4-(4-fluorophenyl)-1H-imidazo[4,5-c]pyridin-2-
yl)-1H-indazol-5-yl)pyridin-3-ol [1799]; and
2-(5-(5-(benzyloxy)pyridin-3-yl)-1H-indazol-3-yl)-4-(4-
fluorophenyl)-1H-imidazo[4,5-c]pyridine [1800]; or a
pharmaceutically acceptable salt thereof.

24. The method of claim 1, wherein the compound of Formula I is selected from the group consisting of:
2-cyclohexyl-N-(5-(3-(4-(4-fluorophenyl)-1H-imidazo[4,
5-c]pyridin-2-yl)-1H-indazol-5-yl)pyridin-3-yl)acet-
amide [1801];
4-(4-fluorophenyl)-2-(5-(pyridin-4-yl)-1H-indazol-3-yl)-
1H-imidazo[4,5-c]pyridine [1802];
4-(4-fluorophenyl)-2-(5-(pyridin-2-yl)-1H-indazol-3-yl)-
1H-imidazo[4,5-c]pyridine [1803];
4-(4-fluorophenyl)-2-(5-(pyrazin-2-yl)-1H-indazol-3-yl)-
1H-imidazo[4,5-c]pyridine [1804];
4-(2-fluorophenyl)-2-(5-(piperidin-4-yl)-1H-indazol-3-
yl)-1H-imidazo[4,5-c]pyridine [1805];
4-(2-fluorophenyl)-2-(5-(1,2,3,6-tetrahydropyridin-4-yl)-
1H-indazol-3-yl)-1H-imidazo[4,5-c]pyridine [1806];
2-(5-(1H-pyrazol-4-yl)-1H-indazol-3-yl)-4-(2-fluorophe-
nyl)-1H-imidazo[4,5-c]pyridine [1807];
4-(2-fluorophenyl)-2-(5-(1-methyl-1H-pyrazol-4-yl)-1H-
indazol-3-yl)-1H-imidazo[4,5-c]pyridine [1808];
2-(5-(1,2-dimethyl-1H-imidazol-5-yl)-1H-indazol-3-yl)-
4-(2-fluorophenyl)-1H-imidazo[4,5-c]pyridine [1809];
1-(6-(3-(4-(2-fluorophenyl)-1H-imidazo[4,5-c]pyridin-2-
yl)-1H-indazol-5-yl)pyrazin-2-yl)azetidin-3-amine
[1810];
2-(5-(5-(cyclohexyloxy)pyridin-3-yl)-1H-indazol-3-yl)-
4-(2-fluorophenyl)-1H-imidazo[4,5-c]pyridine [1811];
4-(2-fluorophenyl)-2-(5-(5-(piperidin-4-yloxy)pyridin-3-
yl)-1H-indazol-3-yl)-1H-imidazo[4,5-c]pyridine
[1812];
N-(5-(3-(4-(2-fluorophenyl)-1H-imidazo[4,5-c]pyridin-
2-yl)-1H-indazol-5-yl)pyridin-3-yl)-2-(piperidin-4-yl)
acetamide [1813];
4-(2-fluorophenyl)-2-(5-(5-(2-(pyrrolidin-1-yl)ethoxy)
pyridin-3-yl)-1H-indazol-3-yl)-1H-imidazo[4,5-c]
pyridine [1814];
2-((5-(3-(4-(2-fluorophenyl)-1H-imidazo[4,5-c]pyridin-
2-yl)-1H-indazol-5-yl)pyridin-3-yl)oxy)-N,N-dim-
ethylethan-1-amine [1815];
4-(2-fluorophenyl)-2-(5-(5-methoxypyridin-3-yl)-1H-in-
dazol-3-yl)-1H-imidazo[4,5-c]pyridine [1816];
5-(3-(4-(2-fluorophenyl)-1H-imidazo[4,5-c]pyridin-2-
yl)-1H-indazol-5-yl)pyridin-3-ol [1817];
2-(5-(5-(benzyloxy)pyridin-3-yl)-1H-indazol-3-yl)-4-(2-
fluorophenyl)-1H-imidazo[4,5-c]pyridine [1818];
2-cyclohexyl-N-(5-(3-(4-(2-fluorophenyl)-1H-imidazo[4,
5-c]pyridin-2-yl)-1H-indazol-5-yl)pyridin-3-yl)acet-
amide [1819];
4-(2-fluorophenyl)-2-(5-(pyridin-4-yl)-1H-indazol-3-yl)-
1H-imidazo[4,5-c]pyridine [1820];
4-(2-fluorophenyl)-2-(5-(pyridin-2-yl)-1H-indazol-3-yl)-
1H-imidazo[4,5-c]pyridine [1821];
4-(2-fluorophenyl)-2-(5-(pyrazin-2-yl)-1H-indazol-3-yl)-
1H-imidazo[4,5-c]pyridine [1822];
2-(5-(piperidin-4-yl)-1H-indazol-3-yl)-4-(pyridin-3-yl)-
1H-imidazo[4,5-c]pyridine [1823];
4-(pyridin-3-yl)-2-(5-(1,2,3,6-tetrahydropyridin-4-yl)-
1H-indazol-3-yl)-1H-imidazo[4,5-c]pyridine [1824];
2-(5-(1H-pyrazol-4-yl)-1H-indazol-3-yl)-4-(pyridin-3-
yl)-1H-imidazo[4,5-c]pyridine [1825];
2-(5-(1-methyl-1H-pyrazol-4-yl)-1H-indazol-3-yl)-4-
(pyridin-3-yl)-1H-imidazo[4,5-c]pyridine [1826];
2-(5-(1,2-dimethyl-1H-imidazol-5-yl)-1H-indazol-3-yl)-
4-(pyridin-3-yl)-1H-imidazo[4,5-c]pyridine [1827];
1-(6-(3-(4-(pyridin-3-yl)-1H-imidazo[4,5-c]pyridin-2-
yl)-1H-indazol-5-yl)pyrazin-2-yl)azetidin-3-amine
[1828];
2-(5-(5-(cyclohexyloxy)pyridin-3-yl)-1H-indazol-3-yl)-
4-(pyridin-3-yl)-1H-imidazo[4,5-c]pyridine [1829];
2-(5-(5-(piperidin-4-yloxy)pyridin-3-yl)-1H-indazol-3-
yl)-4-(pyridin-3-yl)-1H-imidazo[4,5-c]pyridine
[1830];
2-(piperidin-4-yl)-N-(5-(3-(4-(pyridin-3-yl)-1H-imidazo
[4,5-c]pyridin-2-yl)-1H-indazol-5-yl)pyridin-3-yl)ac-
etamide [1831];
4-(pyridin-3-yl)-2-(5-(5-(2-(pyrrolidin-1-yl)ethoxy)pyri-
din-3-yl)-1H-indazol-3-yl)-1H-imidazo[4,5-c]pyridine
[1832];
N,N-dimethyl-2-((5-(3-(4-(pyridin-3-yl)-1H-imidazo[4,
5-c]pyridin-2-yl)-1H-indazol-5-yl)pyridin-3-yl)oxy)
ethan-1-amine [1833];
2-(5-(5-methoxypyridin-3-yl)-1H-indazol-3-yl)-4-(pyri-
din-3-yl)-1H-imidazo[4,5-c]pyridine [1834];
5-(3-(4-(pyridin-3-yl)-1H-imidazo[4,5-c]pyridin-2-yl)-
1H-indazol-5-yl)pyridin-3-ol [1835];
2-(5-(5-(benzyloxy)pyridin-3-yl)-1H-indazol-3-yl)-4-
(pyridin-3-yl)-1H-imidazo[4,5-c]pyridine [1836];
2-cyclohexyl-N-(5-(3-(4-(pyridin-3-yl)-1H-imidazo[4,5-
c]pyridin-2-yl)-1H-indazol-5-yl)pyridin-3-yl)acet-
amide [1837];
4-(pyridin-3-yl)-2-(5-(pyridin-4-yl)-1H-indazol-3-yl)-
1H-imidazo[4,5-c]pyridine [1838];
2-(5-(pyridin-2-yl)-1H-indazol-3-yl)-4-(pyridin-3-yl)-
1H-imidazo[4,5-c]pyridine [1839];

2-(5-(pyrazin-2-yl)-1H-indazol-3-yl)-4-(pyridin-3-yl)-1H-imidazo[4,5-c]pyridine [1840];

2-(5-(piperidin-4-yl)-1H-indazol-3-yl)-4-(pyridin-4-yl)-1H-imidazo[4,5-c]pyridine [1841];

4-(pyridin-4-yl)-2-(5-(1,2,3,6-tetrahydropyridin-4-yl)-1H-indazol-3-yl)-1H-imidazo[4,5-c]pyridine [1842];

2-(5-(1H-pyrazol-4-yl)-1H-indazol-3-yl)-4-(pyridin-4-yl)-1H-imidazo[4,5-c]pyridine [1843];

2-(5-(1-methyl-1H-pyrazol-4-yl)-1H-indazol-3-yl)-4-(pyridin-4-yl)-1H-imidazo[4,5-c]pyridine [1844];

2-(5-(1,2-dimethyl-1H-imidazol-5-yl)-1H-indazol-3-yl)-4-(pyridin-4-yl)-1H-imidazo[4,5-c]pyridine [1845];

1-(6-(3-(4-(pyridin-4-yl)-1H-imidazo[4,5-c]pyridin-2-yl)-1H-indazol-5-yl)pyrazin-2-yl)azetidin-3-amine [1846];

2-(5-(5-(cyclohexyloxy)pyridin-3-yl)-1H-indazol-3-yl)-4-(pyridin-4-yl)-1H-imidazo[4,5-c]pyridine [1847];

2-(5-(5-(piperidin-4-yloxy)pyridin-3-yl)-1H-indazol-3-yl)-4-(pyridin-4-yl)-1H-imidazo[4,5-c]pyridine [1848];

2-(piperidin-4-yl)-N-(5-(3-(4-(pyridin-4-yl)-1H-imidazo[4,5-c]pyridin-2-yl)-1H-indazol-5-yl)pyridin-3-yl)acetamide [1849];

4-(pyridin-4-yl)-2-(5-(5-(2-(pyrrolidin-1-yl)ethoxy)pyridin-3-yl)-1H-indazol-3-yl)-1H-imidazo[4,5-c]pyridine [1850];

N,N-dimethyl-2-((5-(3-(4-(pyridin-4-yl)-1H-imidazo[4,5-c]pyridin-2-yl)-1H-indazol-5-yl)pyridin-3-yl)oxy)ethan-1-amine [1851];

2-(5-(5-methoxypyridin-3-yl)-1H-indazol-3-yl)-4-(pyridin-4-yl)-1H-imidazo[4,5-c]pyridine [1852];

5-(3-(4-(pyridin-4-yl)-1H-imidazo[4,5-c]pyridin-2-yl)-1H-indazol-5-yl)pyridin-3-ol [1853];

2-(5-(5-(benzyloxy)pyridin-3-yl)-1H-indazol-3-yl)-4-(pyridin-4-yl)-1H-imidazo[4,5-c]pyridine [1854];

2-cyclohexyl-N-(5-(3-(4-(pyridin-4-yl)-1H-imidazo[4,5-c]pyridin-2-yl)-1H-indazol-5-yl)pyridin-3-yl)acetamide [1855];

4-(pyridin-4-yl)-2-(5-(pyridin-4-yl)-1H-indazol-3-yl)-1H-imidazo[4,5-c]pyridine [1856];

2-(5-(pyridin-2-yl)-1H-indazol-3-yl)-4-(pyridin-4-yl)-1H-imidazo[4,5-c]pyridine [1857];

2-(5-(pyrazin-2-yl)-1H-indazol-3-yl)-4-(pyridin-4-yl)-1H-imidazo[4,5-c]pyridine [1858];

2-(5-(piperidin-4-yl)-1H-indazol-3-yl)-4-(pyridin-2-yl)-1H-imidazo[4,5-c]pyridine [1859];

4-(pyridin-2-yl)-2-(5-(1,2,3,6-tetrahydropyridin-4-yl)-1H-indazol-3-yl)-1H-imidazo[4,5-c]pyridine [1860];

2-(5-(1H-pyrazol-4-yl)-1H-indazol-3-yl)-4-(pyridin-2-yl)-1H-imidazo[4,5-c]pyridine [1861];

2-(5-(1-methyl-1H-pyrazol-4-yl)-1H-indazol-3-yl)-4-(pyridin-2-yl)-1H-imidazo[4,5-c]pyridine [1862];

2-(5-(1,2-dimethyl-1H-imidazol-5-yl)-1H-indazol-3-yl)-4-(pyridin-2-yl)-1H-imidazo[4,5-c]pyridine [1863];

1-(6-(3-(4-(pyridin-2-yl)-1H-imidazo[4,5-c]pyridin-2-yl)-1H-indazol-5-yl)pyrazin-2-yl)azetidin-3-amine [1864];

2-(5-(5-(cyclohexyloxy)pyridin-3-yl)-1H-indazol-3-yl)-4-(pyridin-2-yl)-1H-imidazo[4,5-c]pyridine [1865];

2-(5-(5-(piperidin-4-yloxy)pyridin-3-yl)-1H-indazol-3-yl)-4-(pyridin-2-yl)-1H-imidazo[4,5-c]pyridine [1866];

2-(piperidin-4-yl)-N-(5-(3-(4-(pyridin-2-yl)-1H-imidazo[4,5-c]pyridin-2-yl)-1H-indazol-5-yl)pyridin-3-yl)acetamide [1867];

4-(pyridin-2-yl)-2-(5-(5-(2-(pyrrolidin-1-yl)ethoxy)pyridin-3-yl)-1H-indazol-3-yl)-1H-imidazo[4,5-c]pyridine [1868];

N,N-dimethyl-2-((5-(3-(4-(pyridin-2-yl)-1H-imidazo[4,5-c]pyridin-2-yl)-1H-indazol-5-yl)pyridin-3-yl)oxy)ethan-1-amine [1869];

2-(5-(5-methoxypyridin-3-yl)-1H-indazol-3-yl)-4-(pyridin-2-yl)-1H-imidazo[4,5-c]pyridine [1870];

5-(3-(4-(pyridin-2-yl)-1H-imidazo[4,5-c]pyridin-2-yl)-1H-indazol-5-yl)pyridin-3-ol [1871];

2-(5-(5-(benzyloxy)pyridin-3-yl)-1H-indazol-3-yl)-4-(pyridin-2-yl)-1H-imidazo[4,5-c]pyridine [1872];

2-cyclohexyl-N-(5-(3-(4-(pyridin-2-yl)-1H-imidazo[4,5-c]pyridin-2-yl)-1H-indazol-5-yl)pyridin-3-yl)acetamide [1873];

4-(pyridin-2-yl)-2-(5-(pyridin-4-yl)-1H-indazol-3-yl)-1H-imidazo[4,5-c]pyridine [1874];

4-(pyridin-2-yl)-2-(5-(pyridin-2-yl)-1H-indazol-3-yl)-1H-imidazo[4,5-c]pyridine [1875];

2-(5-(pyrazin-2-yl)-1H-indazol-3-yl)-4-(pyridin-2-yl)-1H-imidazo[4,5-c]pyridine [1876];

4-(piperidin-1-yl)-2-(5-(piperidin-4-yl)-1H-indazol-3-yl)-1H-imidazo[4,5-c]pyridine [1877];

4-(piperidin-1-yl)-2-(5-(1,2,3,6-tetrahydropyridin-4-yl)-1H-indazol-3-yl)-1H-imidazo[4,5-c]pyridine [1878];

2-(5-(1H-pyrazol-4-yl)-1H-indazol-3-yl)-4-(piperidin-1-yl)-1H-imidazo[4,5-c]pyridine [1879];

2-(5-(1-methyl-1H-pyrazol-4-yl)-1H-indazol-3-yl)-4-(piperidin-1-yl)-1H-imidazo[4,5-c]pyridine [1880];

2-(5-(1,2-dimethyl-1H-imidazol-5-yl)-1H-indazol-3-yl)-4-(piperidin-1-yl)-1H-imidazo[4,5-c]pyridine [1881];

1-(6-(3-(4-(piperidin-1-yl)-1H-imidazo[4,5-c]pyridin-2-yl)-1H-indazol-5-yl)pyrazin-2-yl)azetidin-3-amine [1882];

2-(5-(5-(cyclohexyloxy)pyridin-3-yl)-1H-indazol-3-yl)-4-(piperidin-1-yl)-1H-imidazo[4,5-c]pyridine [1883];

4-(piperidin-1-yl)-2-(5-(5-(piperidin-4-yloxy)pyridin-3-yl)-1H-indazol-3-yl)-1H-imidazo[4,5-c]pyridine [1884];

N-(5-(3-(4-(piperidin-1-yl)-1H-imidazo[4,5-c]pyridin-2-yl)-1H-indazol-5-yl)pyridin-3-yl)-2-(piperidin-4-yl)acetamide [1885];

4-(piperidin-1-yl)-2-(5-(5-(2-(pyrrolidin-1-yl)ethoxy)pyridin-3-yl)-1H-indazol-3-yl)-1H-imidazo[4,5-c]pyridine [1886];

N,N-dimethyl-2-((5-(3-(4-(piperidin-1-yl)-1H-imidazo[4,5-c]pyridin-2-yl)-1H-indazol-5-yl)pyridin-3-yl)oxy)ethan-1-amine [1887];

2-(5-(5-methoxypyridin-3-yl)-1H-indazol-3-yl)-4-(piperidin-1-yl)-1H-imidazo[4,5-c]pyridine [1888];

5-(3-(4-(piperidin-1-yl)-1H-imidazo[4,5-c]pyridin-2-yl)-1H-indazol-5-yl)pyridin-3-ol [1889];

2-(5-(5-(benzyl oxy)pyridin-3-yl)-1H-indazol-3-yl)-4-(piperidin-1-yl)-1H-imidazo[4,5-c]pyridine [1890];

2-cyclohexyl-N-(5-(3-(4-(piperidin-1-yl)-1H-imidazo[4,5-c]pyridin-2-yl)-1H-indazol-5-yl)pyridin-3-yl)acetamide [1891];

4-(piperidin-1-yl)-2-(5-(pyridin-4-yl)-1H-indazol-3-yl)-1H-imidazo[4,5-c]pyridine [1892];

4-(piperidin-1-yl)-2-(5-(pyridin-2-yl)-1H-indazol-3-yl)-1H-imidazo[4,5-c]pyridine [1893];

4-(piperidin-1-yl)-2-(5-(pyrazin-2-yl)-1H-indazol-3-yl)-1H-imidazo[4,5-c]pyridine [1894];

4-(4-methyl-1H-imidazol-1-yl)-2-(5-(piperidin-4-yl)-1H-indazol-3-yl)-1H-imidazo[4,5-c]pyridine [1895];

4-(4-methyl-1H-imidazol-1-yl)-2-(5-(1,2,3,6-tetrahydro-pyridin-4-yl)-1H-indazol-3-yl)-1H-imidazo[4,5-c]pyridine [1896];

2-(5-(1H-pyrazol-4-yl)-1H-indazol-3-yl)-4-(4-methyl-1H-imidazo-1-yl)-1H-imidazo[4,5-c]pyridine [1897];

4-(4-methyl-1H-imidazol-1-yl)-2-(5-(1-methyl-1H-pyrazol-4-yl)-1H-indazol-3-yl)-1H-imidazo[4,5-c]pyridine [1898];

2-(5-(1,2-dimethyl-1H-imidazol-5-yl)-1H-indazol-3-yl)-4-(4-methyl-1H-imidazol-1-yl)-1H-imidazo[4,5-c]pyridine [1899]; and 1-(6-(3-(4-(4-methyl-1H-imidazol-1-yl)-1H-imidazo[4,5-c]pyridin-2-yl)-1H-indazol-5-yl)pyrazin-2-yl)azetidin-3-amine [1900]; or a pharmaceutically acceptable salt thereof.

25. The method of claim 1, wherein the compound of Formula I is selected from the group consisting of:

2-(5-(5-(cyclohexyloxy)pyridin-3-yl)-1H-indazol-3-yl)-4-(4-methyl-1H-imidazol-1-yl)-1H-imidazo[4,5-c]pyridine [1901];

4-(4-methyl-1H-imidazol-1-yl)-2-(5-(5-(piperidin-4-yloxy)pyridin-3-yl)-1H-indazol-3-yl)-1H-imidazo[4,5-c]pyridine [1902];

N-(5-(3-(4-(4-methyl-1H-imidazol-1-yl)-1H-imidazo[4,5-c]pyridin-2-yl)-1H-indazol-5-yl)pyridin-3-yl)-2-(piperidin-4-yl)acetamide [1903];

4-(4-methyl-1H-imidazol-1-yl)-2-(5-(5-(2-(pyrrolidin-1-yl)ethoxy)pyridin-3-yl)-1H-indazol-3-yl)-1H-imidazo[4,5-c]pyridine [1904];

N,N-dimethyl-2-((5-(3-(4-(4-methyl-1H-imidazol-1-yl)-1H-imidazo[4,5-c]pyridin-2-yl)-1H-indazol-5-yl)pyridin-3-yl)oxy)ethan-1-amine [1905];

2-(5-(5-methoxypyridin-3-yl)-1H-indazol-3-yl)-4-(4-methyl-1H-imidazol-1-yl)-1H-imidazo[4,5-c]pyridine [1906];

5-(3-(4-(4-methyl-1H-imidazol-1-yl)-1H-imidazo[4,5-c]pyridin-2-yl)-1H-indazol-5-yl)pyridin-3-ol [1907];

2-(5-(5-(benzyloxy)pyridin-3-yl)-1H-indazol-3-yl)-4-(4-methyl-1H-imidazol-1-yl)-1H-imidazo[4,5-c]pyridine [1908];

2-cyclohexyl-N-(5-(3-(4-(4-methyl-1H-imidazol-1-yl)-1H-imidazo[4,5-c]pyridin-2-yl)-1H-indazol-5-yl)pyridin-3-yl)acetamide [1909];

4-(4-methyl-1H-imidazol-1-yl)-2-(5-(pyridin-4-yl)-1H-indazol-3-yl)-1H-imidazo[4,5-c]pyridine [1910];

4-(4-methyl-1H-imidazol-1-yl)-2-(5-(pyridin-2-yl)-1H-indazol-3-yl)-1H-imidazo[4,5-c]pyridine [1911];

4-(4-methyl-1H-imidazol-1-yl)-2-(5-(pyrazin-2-yl)-1H-indazol-3-yl)-1H-imidazo[4,5-c]pyridine [1912];

4-(4-methylpiperazin-1-yl)-2-(5-(piperidin-4-yl)-1H-indazol-3-yl)-1H-imidazo[4,5-c]pyridine [1913];

4-(4-methylpiperazin-1-yl)-2-(5-(1,2,3,6-tetrahydropyridin-4-yl)-1H-indazol-3-yl)-1H-imidazo[4,5-c]pyridine [1914];

2-(5-(1H-pyrazol-4-yl)-1H-indazol-3-yl)-4-(4-methylpiperazin-1-yl)-1H-imidazo[4,5-c]pyridine [1915];

2-(5-(1-methyl-1H-pyrazol-4-yl)-1H-indazol-3-yl)-4-(4-methylpiperazin-1-yl)-1H-imidazo[4,5-c]pyridine [1916];

2-(5-(1,2-dimethyl-1H-imidazol-5-yl)-1H-indazol-3-yl)-4-(4-methylpiperazin-1-yl)-1H-imidazo[4,5-c]pyridine [1917];

1-(6-(3-(4-(4-methylpiperazin-1-yl)-1H-imidazo[4,5-c]pyridin-2-yl)-1H-indazol-5-yl)pyrazin-2-yl)azetidin-3-amine [1918];

2-(5-(5-(cyclohexyloxy)pyridin-3-yl)-1H-indazol-3-yl)-4-(4-methylpiperazin-1-yl)-1H-imidazo[4,5-c]pyridine [1919];

4-(4-methylpiperazin-1-yl)-2-(5-(5-(piperidin-4-yloxy)pyridin-3-yl)-1H-indazol-3-yl)-1H-imidazo[4,5-c]pyridine [1920];

N-(5-(3-(4-(4-methylpiperazin-1-yl)-1H-imidazo[4,5-c]pyridin-2-yl)-1H-indazol-5-yl)pyridin-3-yl)-2-(piperidin-4-yl)acetamide [1921];

4-(4-methylpiperazin-1-yl)-2-(5-(5-(2-(pyrrolidin-1-yl)ethoxy)pyridin-3-yl)-1H-indazol-3-yl)-1H-imidazo[4,5-c]pyridine [1922];

N,N-dimethyl-2-((5-(3-(4-(4-methylpiperazin-1-yl)-1H-imidazo[4,5-c]pyridin-2-yl)-1H-indazol-5-yl)pyridin-3-yl)oxy)ethan-1-amine [1923];

2-(5-(5-methoxypyridin-3-yl)-1H-indazol-3-yl)-4-(4-methylpiperazin-1-yl)-1H-imidazo[4,5-c]pyridine [1924];

5-(3-(4-(4-methylpiperazin-1-yl)-1H-imidazo[4,5-c]pyridin-2-yl)-1H-indazol-5-yl)pyridin-3-ol [1925];

2-(5-(5-(benzyloxy)pyridin-3-yl)-1H-indazol-3-yl)-4-(4-methylpiperazin-1-yl)-1H-imidazo[4,5-c]pyridine [1926];

2-cyclohexyl-N-(5-(3-(4-(4-methylpiperazin-1-yl)-1H-imidazo[4,5-c]pyridin-2-yl)-1H-indazol-5-yl)pyridin-3-yl)acetamide [1927];

4-(4-methylpiperazin-1-yl)-2-(5-(pyridin-4-yl)-1H-indazol-3-yl)-1H-imidazo[4,5-c]pyridine [1928];

4-(4-methylpiperazin-1-yl)-2-(5-(pyridin-2-yl)-1H-indazol-3-yl)-1H-imidazo[4,5-c]pyridine [1929];

4-(4-methylpiperazin-1-yl)-2-(5-(pyrazin-2-yl)-1H-indazol-3-yl)-1H-imidazo[4,5-c]pyridine [1930];

2-(5-(piperidin-4-yl)-1H-indazol-3-yl)-4-(thiophen-3-yl)-1H-imidazo[4,5-c]pyridine [1931];

2-(5-(1,2,3,6-tetrahydropyridin-4-yl)-1H-indazol-3-yl)-4-(thiophen-3-yl)-1H-imidazo[4,5-c]pyridine [1932];

2-(5-(1H-pyrazol-4-yl)-1H-indazol-3-yl)-4-(thiophen-3-yl)-1H-imidazo[4,5-c]pyridine [1933];

2-(5-(1-methyl-1H-pyrazol-4-yl)-1H-indazol-3-yl)-4-(thiophen-3-yl)-1H-imidazo[4,5-c]pyridine [1934];

2-(5-(1,2-dimethyl-1H-imidazol-5-yl)-1H-indazol-3-yl)-4-(thiophen-3-yl)-1H-imidazo[4,5-c]pyridine [1935];

1-(6-(3-(4-(thiophen-3-yl)-1H-imidazo[4,5-c]pyridin-2-yl)-1H-indazol-5-yl)pyrazin-2-yl)azetidin-3-amine [1936];

2-(5-(5-(cyclohexyloxy)pyridin-3-yl)-1H-indazol-3-yl)-4-(thiophen-3-yl)-1H-imidazo[4,5-c]pyridine [1937];

2-(5-(5-(piperidin-4-yloxy)pyridin-3-yl)-1H-indazol-3-yl)-4-(thiophen-3-yl)-1H-imidazo[4,5-c]pyridine [1938];

2-(piperidin-4-yl)-N-(5-(3-(4-(thiophen-3-yl)-1H-imidazo[4,5-c]pyridin-2-yl)-1H-indazol-5-yl)pyridin-3-yl)acetamide [1939];

2-(5-(5-(2-(pyrrolidin-1-yl)ethoxy)pyridin-3-yl)-1H-indazol-3-yl)-4-(thiophen-3-yl)-1H-imidazo[4,5-c]pyridine [1940];

N,N-dimethyl-2-((5-(3-(4-(thiophen-3-yl)-1H-imidazo[4,5-c]pyridin-2-yl)-1H-indazol-5-yl)pyridin-3-yl)oxy)ethan-1-amine [1941];

2-(5-(5-methoxypyridin-3-yl)-1H-indazol-3-yl)-4-(thiophen-3-yl)-1H-imidazo[4,5-c]pyridine [1942];

5-(3-(4-(thiophen-3-yl)-1H-imidazo[4,5-c]pyridin-2-yl)-1H-indazol-5-yl)pyridin-3-ol [1943];

2-(5-(5-(benzyloxy)pyridin-3-yl)-1H-indazol-3-yl)-4-(thiophen-3-yl)-1H-imidazo[4,5-c]pyridine [1944];

2-cyclohexyl-N-(5-(3-(4-(thiophen-3-yl)-1H-imidazo[4,5-c]pyridin-2-yl)-1H-indazol-5-yl)pyridin-3-yl)acetamide [1945];

2-(5-(pyridin-4-yl)-1H-indazol-3-yl)-4-(thiophen-3-yl)-1H-imidazo[4,5-c]pyridine [1946];

2-(5-(pyridin-2-yl)-1H-indazol-3-yl)-4-(thiophen-3-yl)-1H-imidazo[4,5-c]pyridine [1947];

2-(5-(pyrazin-2-yl)-1H-indazol-3-yl)-4-(thiophen-3-yl)-1H-imidazo[4,5-c]pyridine [1948];

4-(furan-3-yl)-2-(5-(piperidin-4-yl)-1H-indazol-3-yl)-1H-imidazo[4,5-c]pyridine [1949];

4-(furan-3-yl)-2-(5-(1,2,3,6-tetrahydropyridin-4-yl)-1H-indazol-3-yl)-1H-imidazo[4,5-c]pyridine [1950];

2-(5-(1H-pyrazol-4-yl)-1H-indazol-3-yl)-4-(furan-3-yl)-1H-imidazo[4,5-c]pyridine [1951];

4-(furan-3-yl)-2-(5-(1-methyl-1H-pyrazol-4-yl)-1H-indazol-3-yl)-1H-imidazo[4,5-c]pyridine [1952];

2-(5-(1,2-dimethyl-1H-imidazol-5-yl)-1H-indazol-3-yl)-4-(furan-3-yl)-1H-imidazo[4,5-c]pyridine [1953];

1-(6-(3-(4-(furan-3-yl)-1H-imidazo[4,5-c]pyridin-2-yl)-1H-indazol-5-yl)pyrazin-2-yl)azetidin-3-amine [1954];

2-(5-(5-(cyclohexyloxy)pyridin-3-yl)-1H-indazol-3-yl)-4-(furan-3-yl)-1H-imidazo[4,5-c]pyridine [1955];

4-(furan-3-yl)-2-(5-(5-(piperidin-4-yloxy)pyridin-3-yl)-1H-indazol-3-yl)-1H-imidazo[4,5-c]pyridine [1956];

N-(5-(3-(4-(furan-3-yl)-1H-imidazo[4,5-c]pyridin-2-yl)-1H-indazol-5-yl)pyridin-3-yl)-2-(piperidin-4-yl)acetamide [1957];

4-(furan-3-yl)-2-(5-(5-(2-(pyrrolidin-1-yl)ethoxy)pyridin-3-yl)-1H-indazol-3-yl)-1H-imidazo[4,5-c]pyridine [1958];

2-((5-(3-(4-(furan-3-yl)-1H-imidazo[4,5-c]pyridin-2-yl)-1H-indazol-5-yl)pyridin-3-yl)oxy)-N,N-dimethylethan-1-amine [1959];

4-(furan-3-yl)-2-(5-(5-methoxypyridin-3-yl)-1H-indazol-3-yl)-1H-imidazo[4,5-c]pyridine [1960];

5-(3-(4-(furan-3-yl)-1H-imidazo[4,5-c]pyridin-2-yl)-1H-indazol-5-yl)pyridin-3-ol [1961];

2-(5-(5-(benzyloxy)pyridin-3-yl)-1H-indazol-3-yl)-4-(furan-3-yl)-1H-imidazo[4,5-c]pyridine [1962];

2-cyclohexyl-N-(5-(3-(4-(furan-3-yl)-1H-imidazo[4,5-c]pyridin-2-yl)-1H-indazol-5-yl)pyridin-3-yl)acetamide [1963];

4-(furan-3-yl)-2-(5-(pyridin-4-yl)-1H-indazol-3-yl)-1H-imidazo[4,5-c]pyridine [1964];

4-(furan-3-yl)-2-(5-(pyridin-2-yl)-1H-indazol-3-yl)-1H-imidazo[4,5-c]pyridine [1965];

4-(furan-3-yl)-2-(5-(pyrazin-2-yl)-1H-indazol-3-yl)-1H-imidazo[4,5-c]pyridine [1966];

2-(5-(piperidin-4-yl)-1H-indazol-3-yl)-4-(thiophen-2-yl)-1H-imidazo[4,5-c]pyridine [1967];

2-(5-(1,2,3,6-tetrahydropyridin-4-yl)-1H-indazol-3-yl)-4-(thiophen-2-yl)-1H-imidazo[4,5-c]pyridine [1968];

2-(5-(1H-pyrazol-4-yl)-1H-indazol-3-yl)-4-(thiophen-2-yl)-1H-imidazo[4,5-c]pyridine [1969];

2-(5-(1-methyl-1H-pyrazol-4-yl)-1H-indazol-3-yl)-4-(thiophen-2-yl)-1H-imidazo[4,5-c]pyridine [1970];

2-(5-(1,2-dimethyl-1H-imidazol-5-yl)-1H-indazol-3-yl)-4-(thiophen-2-yl)-1H-imidazo[4,5-c]pyridine [1971];

1-(6-(3-(4-(thiophen-2-yl)-1H-imidazo[4,5-c]pyridin-2-yl)-1H-indazol-5-yl)pyrazin-2-yl)azetidin-3-amine [1972];

2-(5-(5-(cyclohexyloxy)pyridin-3-yl)-1H-indazol-3-yl)-4-(thiophen-2-yl)-1H-imidazo[4,5-c]pyridine [1973];

2-(5-(5-(piperidin-4-yloxy)pyridin-3-yl)-1H-indazol-3-yl)-4-(thiophen-2-yl)-1H-imidazo[4,5-c]pyridine [1974];

2-(piperidin-4-yl)-N-(5-(3-(4-(thiophen-2-yl)-1H-imidazo[4,5-c]pyridin-2-yl)-1H-indazol-5-yl)pyridin-3-yl)acetamide [1975];

2-(5-(5-(2-(pyrrolidin-1-yl)ethoxy)pyridin-3-yl)-1H-indazol-3-yl)-4-(thiophen-2-yl)-1H-imidazo[4,5-c]pyridine [1976];

N,N-dimethyl-2-((5-(3-(4-(thiophen-2-yl)-1H-imidazo[4,5-c]pyridin-2-yl)-1H-indazol-5-yl)pyridin-3-yl)oxy)ethan-1-amine [1977];

2-(5-(5-methoxypyridin-3-yl)-1H-indazol-3-yl)-4-(thiophen-2-yl)-1H-imidazo[4,5-c]pyridine [1978];

5-(3-(4-(thiophen-2-yl)-1H-imidazo[4,5-c]pyridin-2-yl)-1H-indazol-5-yl)pyridin-3-ol [1979];

2-(5-(5-(benzyloxy)pyridin-3-yl)-1H-indazol-3-yl)-4-(thiophen-2-yl)-1H-imidazo[4,5-c]pyridine [1980];

2-cyclohexyl-N-(5-(3-(4-(thiophen-2-yl)-1H-imidazo[4,5-c]pyridin-2-yl)-1H-indazol-5-yl)pyridin-3-yl)acetamide [1981];

2-(5-(pyridin-4-yl)-1H-indazol-3-yl)-4-(thiophen-2-yl)-1H-imidazo[4,5-c]pyridine[1982];

2-(5-(pyridin-2-yl)-1H-indazol-3-yl)-4-(thiophen-2-yl)-1H-imidazo[4,5-c]pyridine [1983];

2-(5-(pyrazin-2-yl)-1H-indazol-3-yl)-4-(thiophen-2-yl)-1H-imidazo[4,5-c]pyridine [1984];

4-(5-fluorothiophen-2-yl)-2-(5-(piperidin-4-yl)-1H-indazol-3-yl)-1H-imidazo[4,5-c]pyridine [1985];

4-(5-fluorothiophen-2-yl)-2-(5-(1,2,3,6-tetrahydropyridin-4-yl)-1H-indazol-3-yl)-1H-imidazo[4,5-c]pyridine [1986];

2-(5-(1H-pyrazol-4-yl)-1H-indazol-3-yl)-4-(5-fluorothiophen-2-yl)-1H-imidazo[4,5-c]pyridine [1987];

4-(5-fluorothiophen-2-yl)-2-(5-(1-methyl-1H-pyrazol-4-yl)-1H-indazol-3-yl)-1H-imidazo[4,5-c]pyridine [1988];

2-(5-(1,2-dimethyl-1H-imidazol-5-yl)-1H-indazol-3-yl)-4-(5-fluorothiophen-2-yl)-1H-imidazo[4,5-c]pyridine [1989];

1-(6-(3-(4-(5-fluorothiophen-2-yl)-1H-imidazo[4,5-c]pyridin-2-yl)-1H-indazol-5-yl)pyrazin-2-yl)azetidin-3-amine [1990];

2-(5-(5-(cyclohexyloxy)pyridin-3-yl)-1H-indazol-3-yl)-4-(5-fluorothiophen-2-yl)-1H-imidazo[4,5-c]pyridine [1991];

4-(5-fluorothiophen-2-yl)-2-(5-(5-(piperidin-4-yloxy)pyridin-3-yl)-1H-indazol-3-yl)-1H-imidazo[4,5-c]pyridine [1992];

N-(5-(3-(4-(5-fluorothiophen-2-yl)-1H-imidazo[4,5-c]pyridin-2-yl)-1H-indazol-5-yl)pyridin-3-yl)-2-(piperidin-4-yl)acetamide [1993];

4-(5-fluorothiophen-2-yl)-2-(5-(5-(2-(pyrrolidin-1-yl)ethoxy)pyridin-3-yl)-1H-indazol-3-yl)-1H-imidazo[4,5-c]pyridine [1994];

2-((5-(3-(4-(5-fluorothiophen-2-yl)-1H-imidazo[4,5-c]pyridin-2-yl)-1H-indazol-5-yl)pyridin-3-yl)oxy)-N,N-dimethylethan-1-amine [1995];

4-(5-fluorothiophen-2-yl)-2-(5-(5-methoxypyridin-3-yl)-1H-indazol-3-yl)-1H-imidazo[4,5-c]pyridine [1996];

5-(3-(4-(5-fluorothiophen-2-yl)-1H-imidazo[4,5-c]pyridin-2-yl)-1H-indazol-5-yl)pyridin-3-ol [1997];

2-(5-(5-(benzyloxy)pyridin-3-yl)-1H-indazol-3-yl)-4-(5-fluorothiophen-2-yl)-1H-imidazo[4,5-c]pyridine [1998];

2-cyclohexyl-N-(5-(3-(4-(5-fluorothiophen-2-yl)-1H-imidazo[4,5-c]pyridin-2-yl)-1H-indazol-5-yl)pyridin-3-yl)acetamide [1999]; and 4-(5-fluorothiophen-2-yl)-2-(5-(pyridin-4-yl)-1H-indazol-3-yl)-1H-imidazo[4,5-c]pyridine [2000]; or a pharmaceutically acceptable salt thereof.

26. The method of claim 1, wherein the compound of Formula I is selected from the group consisting of:

4-(5-fluorothiophen-2-yl)-2-(5-(pyridin-2-yl)-1H-indazol-3-yl)-1H-imidazo[4,5-c]pyridine [2001];
4-(5-fluorothiophen-2-yl)-2-(5-(pyrazin-2-yl)-1H-indazol-3-yl)-1H-imidazo[4,5-c]pyridine [2002];
4-(5-methylthiophen-2-yl)-2-(5-(piperidin-4-yl)-1H-indazol-3-yl)-1H-imidazo[4,5-c]pyridine [2003];
4-(5-methylthiophen-2-yl)-2-(5-(1,2,3,6-tetrahydropyridin-4-yl)-1H-indazol-3-yl)-1H-imidazo[4,5-c]pyridine [2004];
2-(5-(1H-pyrazol-4-yl)-1H-indazol-3-yl)-4-(5-methylthiophen-2-yl)-1H-imidazo[4,5-c]pyridine [2005];
2-(5-(1-methyl-1H-pyrazol-4-yl)-1H-indazol-3-yl)-4-(5-methylthiophen-2-yl)-1H-imidazo[4,5-c]pyridine [2006];
2-(5-(1,2-dimethyl-1H-imidazol-5-yl)-1H-indazol-3-yl)-4-(5-methylthiophen-2-yl)-1H-imidazo[4,5-c]pyridine [2007];
1-(6-(3-(4-(5-methylthiophen-2-yl)-1H-imidazo[4,5-c]pyridin-2-yl)-1H-indazol-5-yl)pyrazin-2-yl)azetidin-3-amine [2008];
2-(5-(5-(cyclohexyloxy)pyridin-3-yl)-1H-indazol-3-yl)-4-(5-methylthiophen-2-yl)-1H-imidazo[4,5-c]pyridine [2009];
4-(5-methylthiophen-2-yl)-2-(5-(5-(piperidin-4-yloxy)pyridin-3-yl)-1H-indazol-3-yl)-1H-imidazo[4,5-c]pyridine [2010];
N-(5-(3-(4-(5-methylthiophen-2-yl)-1H-imidazo[4,5-c]pyridin-2-yl)-1H-indazol-5-yl)pyridin-3-yl)-2-(piperidin-4-yl)acetamide [2011];
4-(5-methylthiophen-2-yl)-2-(5-(5-(2-(pyrrolidin-1-yl)ethoxy)pyridin-3-yl)-1H-indazol-3-yl)-1H-imidazo[4,5-c]pyridine [2012];
N,N-dimethyl-2-((5-(3-(4-(5-methylthiophen-2-yl)-1H-imidazo[4,5-c]pyridin-2-yl)-1H-indazol-5-yl)pyridin-3-yl)oxy)ethan-1-amine [2013];
2-(5-(5-methoxypyridin-3-yl)-1H-indazol-3-yl)-4-(5-methylthiophen-2-yl)-1H-imidazo[4,5-c]pyridine [2014];
5-(3-(4-(5-methylthiophen-2-yl)-1H-imidazo[4,5-c]pyridin-2-yl)-1H-indazol-5-yl)pyridin-3-ol [2015];
2-(5-(5-(benzyloxy)pyridin-3-yl)-1H-indazol-3-yl)-4-(5-methylthiophen-2-yl)-1H-imidazo[4,5-c]pyridine [2016];
2-cyclohexyl-N-(5-(3-(4-(5-methylthiophen-2-yl)-1H-imidazo[4,5-c]pyridin-2-yl)-1H-indazol-5-yl)pyridin-3-yl)acetamide [2017];
4-(5-methylthiophen-2-yl)-2-(5-(pyridin-4-yl)-1H-indazol-3-yl)-1H-imidazo[4,5-c]pyridine [2018];
4-(5-methylthiophen-2-yl)-2-(5-(pyridin-2-yl)-1H-indazol-3-yl)-1H-imidazo[4,5-c]pyridine [2019];
4-(5-methylthiophen-2-yl)-2-(5-(pyrazin-2-yl)-1H-indazol-3-yl)-1H-imidazo[4,5-c]pyridine [2020];
1-(5-(2-(5-(piperidin-4-yl)-1H-indazol-3-yl)-1H-imidazo[4,5-c]pyridin-4-yl)thiophen-2-yl)ethan-1-one [2021];
1-(5-(2-(5-(1,2,3,6-tetrahydropyridin-4-yl)-1H-indazol-3-yl)-1H-imidazo[4,5-c]pyridin-4-yl)thiophen-2-yl)ethan-1-one [2022];
1-(5-(2-(5-(1H-pyrazol-4-yl)-1H-indazol-3-yl)-1H-imidazo[4,5-c]pyridin-4-yl)thiophen-2-yl)ethan-1-one [2023];
1-(5-(2-(5-(1-methyl-1H-pyrazol-4-yl)-1H-indazol-3-yl)-1H-imidazo[4,5-c]pyridin-4-yl)thiophen-2-yl)ethan-1-one [2024];
1-(5-(2-(5-(1,2-dimethyl-1H-imidazol-5-yl)-1H-indazol-3-yl)-1H-imidazo[4,5-c]pyridin-4-yl)thiophen-2-yl)ethan-1-one [2025];
1-(5-(2-(5-(6-(3-aminoazetidin-1-yl)pyrazin-2-yl)-1H-indazol-3-yl)-1H-imidazo[4,5-c]pyridin-4-yl)thiophen-2-yl)ethan-1-one [2026];
1-(5-(2-(5-(5-(cyclohexyloxy)pyridin-3-yl)-1H-indazol-3-yl)-1H-imidazo[4,5-c]pyridin-4-yl)thiophen-2-yl)ethan-1-one [2027];
1-(5-(2-(5-(5-(piperidin-4-yloxy)pyridin-3-yl)-1H-indazol-3-yl)-1H-imidazo[4,5-c]pyridin-4-yl)thiophen-2-yl)ethan-1-one [2028];
N-(5-(3-(4-(5-acetylthiophen-2-yl)-1H-imidazo[4,5-c]pyridin-2-yl)-1H-indazol-5-yl)pyridin-3-yl)-2-(piperidin-4-yl)acetamide [2029];
1-(5-(2-(5-(5-(2-(pyrrolidin-1-yl)ethoxy)pyridin-3-yl)-1H-indazol-3-yl)-1H-imidazo[4,5-c]pyridin-4-yl)thiophen-2-yl)ethan-1-one [2030];
1-(5-(2-(5-(5-(2-(dimethylamino)ethoxy)pyridin-3-yl)-1H-indazol-3-yl)-1H-imidazo[4,5-c]pyridin-4-yl)thiophen-2-yl)ethan-1-one [2031];
1-(5-(2-(5-(5-methoxypyridin-3-yl)-1H-indazol-3-yl)-1H-imidazo[4,5-c]pyridin-4-yl)thiophen-2-yl)ethan-1-one [2032];
1-(5-(2-(5-(5-hydroxypyridin-3-yl)-1H-indazol-3-yl)-1H-imidazo[4,5-c]pyridin-4-yl)thiophen-2-yl)ethan-1-one [2033];
1-(5-(2-(5-(5-(benzyloxy)pyridin-3-yl)-1H-indazol-3-yl)-1H-imidazo[4,5-c]pyridin-4-yl)thiophen-2-yl)ethan-1-one [2034];
N-(5-(3-(4-(5-acetylthiophen-2-yl)-1H-imidazo[4,5-c]pyridin-2-yl)-1H-indazol-5-yl)pyridin-3-yl)-2-cyclohexylacetamide [2035];
1-(5-(2-(5-(pyridin-4-yl)-1H-indazol-3-yl)-1H-imidazo[4,5-c]pyridin-4-yl)thiophen-2-yl)ethan-1-one [2036];
1-(5-(2-(5-(pyridin-2-yl)-1H-indazol-3-yl)-1H-imidazo[4,5-c]pyridin-4-yl)thiophen-2-yl)ethan-1-one [2037];
1-(5-(2-(5-(pyrazin-2-yl)-1H-indazol-3-yl)-1H-imidazo[4,5-c]pyridin-4-yl)thiophen-2-yl)ethan-1-one [2038];
N-(3-fluoro-5-(2-(5-(piperidin-4-yl)-1H-indazol-3-yl)-1H-imidazo[4,5-c]pyridin-4-yl)benzyl)methanesulfonamide [2039];
N-(3-fluoro-5-(2-(5-(1,2,3,6-tetrahydropyridin-4-yl)-1H-indazol-3-yl)-1H-imidazo[4,5-c]pyridin-4-yl)benzyl)methanesulfonamide [2040];
N-(3-(2-(5-(1H-pyrazol-4-yl)-1H-indazol-3-yl)-1H-imidazo[4,5-c]pyridin-4-yl)-5-fluorobenzyl)methanesulfonamide [2041];
N-(3-fluoro-5-(2-(5-(1-methyl-1H-pyrazol-4-yl)-1H-indazol-3-yl)-1H-imidazo[4,5-c]pyridin-4-yl)benzyl)methanesulfonamide [2042];
N-(3-(2-(5-(1,2-dimethyl-1H-imidazol-5-yl)-1H-indazol-3-yl)-1H-imidazo[4,5-c]pyridin-4-yl)-5-fluorobenzyl)methanesulfonamide [2043];
N-(3-(2-(5-(6-(3-aminoazetidin-1-yl)pyrazin-2-yl)-1H-indazol-3-yl)-1H-imidazo[4,5-c]pyridin-4-yl)-5-fluorobenzyl)methanesulfonamide [2045];
N-(3-(2-(5-(5-(cyclohexyloxy)pyridin-3-yl)-1H-indazol-3-yl)-1H-imidazo[4,5-c]pyridin-4-yl)-5-fluorobenzyl)methanesulfonamide [2045];
N-(3-fluoro-5-(2-(5-(5-(piperidin-4-yloxy)pyridin-3-yl)-1H-indazol-3-yl)-1H-imidazo[4,5-c]pyridin-4-yl)benzyl)methanesulfonamide [2046];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)-2-(piperidin-4-yl)acetamide [2047];

N-(3-fluoro-5-(2-(5-(5-(2-(pyrrolidin-1-yl)ethoxy)pyridin-3-yl)-1H-indazol-3-yl)-1H-imidazo[4,5-c]pyridin-4-yl)benzyl)methanesulfonamide [2048];

N-(3-(2-(5-(5-(2-(dimethylamino)ethoxy)pyridin-3-yl)-1H-indazol-3-yl)-1H-imidazo[4,5-c]pyridin-4-yl)-5-fluorobenzyl)methanesulfonamide [2049];

N-(3-fluoro-5-(2-(5-(5-methoxypyridin-3-yl)-1H-indazol-3-yl)-1H-imidazo[4,5-c]pyridin-4-yl)benzyl)methanesulfonamide [2050];

N-(3-fluoro-5-(2-(5-(5-hydroxypyridin-3-yl)-1H-indazol-3-yl)-1H-imidazo[4,5-c]pyridin-4-yl)benzyl)methanesulfonamide [2051];

N-(3-(2-(5-(5-(benzyloxy)pyridin-3-yl)-1H-indazol-3-yl)-1H-imidazo[4,5-c]pyridin-4-yl)-5-fluorobenzyl)methanesulfonamide [2052];

2-cyclohexyl-N-(5-(3-(4-(3-fluoro-5-(methylsulfonamidomethyl)phenyl)-1H-imidazo[4,5-c]pyridin-2-yl)-1H-indazol-5-yl)pyridin-3-yl)acetamide [2053];

N-(3-fluoro-5-(2-(5-(pyridin-4-yl)-1H-indazol-3-yl)-1H-imidazo[4,5-c]pyridin-4-yl)benzyl)methanesulfonamide [2054];

N-(3-fluoro-5-(2-(5-(pyridin-2-yl)-1H-indazol-3-yl)-1H-imidazo[4,5-c]pyridin-4-yl)benzyl)methanesulfonamide [2055];

N-(3-fluoro-5-(2-(5-(pyrazin-2-yl)-1H-indazol-3-yl)-1H-imidazo[4,5-c]pyridin-4-yl)benzyl)methanesulfonamide [2056];

$N^1$-(3-fluoro-5-(2-(5-(piperidin-4-yl)-1H-indazol-3-yl)-1H-imidazo[4,5-c]pyridin-4-yl)phenyl)-$N^2$,$N^2$-dimethylethane-1,2-diamine [2057];

$N^1$-(3-fluoro-5-(2-(5-(1,2,3,6-tetrahydropyridin-4-yl)-1H-indazol-3-yl)-1H-imidazo[4,5-c]pyridin-4-yl)phenyl)-$N^2$,$N^2$-dimethylethane-1,2-diamine [2058];

$N^1$-(3-(2-(5-(1H-pyrazol-4-yl)-1H-indazol-3-yl)-1H-imidazo[4,5-c]pyridin-4-yl)-5-fluorophenyl)-$N^2$,$N^2$-dimethylethane-1,2-diamine [2059];

$N^1$-(3-fluoro-5-(2-(5-(1-methyl-1H-pyrazol-4-yl)-1H-indazol-3-yl)-1H-imidazo[4,5-c]pyridin-4-yl)phenyl)-$N^2$,$N^2$-dimethylethane-1,2-diamine [2060];

$N^1$-(3-(2-(5-(1,2-dimethyl-1H-imidazol-5-yl)-1H-indazol-3-yl)-1H-imidazo[4,5-c]pyridin-4-yl)-5-fluorophenyl)-$N^2$,$N^2$-dimethylethane-1,2-diamine [2061];

$N^1$-(3-(2-(5-(6-(3-aminoazetidin-1-yl)pyrazin-2-yl)-1H-indazol-3-yl)-1H-imidazo[4,5-c]pyridin-4-yl)-5-fluorophenyl)-$N^2$,$N^2$-dimethylethane-1,2-diamine [2062];

$N^1$-(3-(2-(5-(5-(cyclohexyloxy)pyridin-3-yl)-1H-indazol-3-yl)-1H-imidazo[4,5-c]pyridin-4-yl)-5-fluorophenyl)-$N^2$,$N^2$-dimethylethane-1,2-diamine [2063];

$N^1$-(3-fluoro-5-(2-(5-(5-(piperidin-4-yloxy)pyridin-3-yl)-1H-indazol-3-yl)-1H-imidazo[4,5-c]pyridin-4-yl)phenyl)-$N^2$,$N^2$-dimethylethane-1,2-diamine [2064];

N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)-2-(piperidin-4-yl)acetamide [2065];

$N^1$-(3-fluoro-5-(2-(5-(5-(2-(pyrrolidin-1-yl)ethoxy)pyridin-3-yl)-1H-indazol-3-yl)-1H-imidazo[4,5-c]pyridin-4-yl)phenyl)-$N^2$,$N^2$-dimethylethane-1,2-diamine [2066];

$N^1$-(3-(2-(5-(5-(2-(dimethylamino)ethoxy)pyridin-3-yl)-1H-indazol-3-yl)-1H-imidazo[4,5-c]pyridin-4-yl)-5-fluorophenyl)-$N^2$,$N^2$-dimethylethane-1,2-diamine [2067];

$N^1$-(3-fluoro-5-(2-(5-(5-methoxypyridin-3-yl)-1H-indazol-3-yl)-1H-imidazo[4,5-c]pyridin-4-yl)phenyl)-$N^2$,$N^2$-dimethylethane-1,2-diamine [2068];

5-(3-(4-(3-((2-(dimethylamino)ethyl)amino)-5-fluorophenyl)-1H-imidazo[4,5-c]pyridin-2-yl)-1H-indazol-5-yl)pyridin-3-ol [2069];

$N^1$-(3-(2-(5-(5-(benzyloxy)pyridin-3-yl)-1H-indazol-3-yl)-1H-imidazo[4,5-c]pyridin-4-yl)-5-fluorophenyl)-$N^2$,$N^2$-dimethylethane-1,2-diamine [2070];

2-cyclohexyl-N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)acetamide [2071];

$N^1$-(3-fluoro-5-(2-(5-(pyridin-4-yl)-1H-indazol-3-yl)-1H-imidazo[4,5-c]pyridin-4-yl)phenyl)-$N^2$,$N^2$-dimethylethane-1,2-diamine [2072];

$N^1$-(3-fluoro-5-(2-(5-(pyridin-2-yl)-1H-indazol-3-yl)-1H-imidazo[4,5-c]pyridin-4-yl)phenyl)-$N^2$,$N^2$-dimethylethane-1,2-diamine [2073];

$N^1$-(3-fluoro-5-(2-(5-(pyrazin-2-yl)-1H-indazol-3-yl)-1H-imidazo[4,5-c]pyridin-4-yl)phenyl)-$N^2$,$N^2$-dimethylethane-1,2-diamine [2074];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)propionamide [2075];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)-3-methylbutanamide [2076];

5-(3-(4-(3-(2-(dimethylamino)ethoxy)-5-fluorophenyl)-1H-imidazo[4,5-c]pyridin-2-yl)-1H-indazol-5-yl)pyridin-3-amine [2077];

2-(3-fluoro-5-(2-(5-(pyridin-3-yl)-1H-indazol-3-yl)-1H-imidazo[4,5-c]pyridin-4-yl)phenoxy)-N,N-dimethylethan-1-amine [2078];

2-(3-fluoro-5-(2-(5-(4-methylpyridin-3-yl)-1H-indazol-3-yl)-1H-imidazo[4,5-c]pyridin-4-yl)phenoxy)-N,N-dimethylethan-1-amine [2079];

2-(3-(2-(5-(5-((ethylamino)methyl)pyridin-3-yl)-1H-indazol-3-yl)-1H-imidazo[4,5-c]pyridin-4-yl)-5-fluorophenoxy)-N,N-dimethylethan-1-amine [2080];

5-(3-(4-(3-(2-(dimethylamino)ethoxy)-5-fluorophenyl)-1H-imidazo[4,5-c]pyridin-2-yl)-1H-indazol-5-yl)-N,N-dimethylpyridin-3-amine [2081];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)pivalamide [2082];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)isobutyramide [2083];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)-2-phenylacetamide [2084];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)benzamide [2085];

5-(3-(4-(3-(2-(dimethylamino)ethoxy)-5-fluorophenyl)-1H-imidazo[4,5-c]pyridin-2-yl)-1H-indazol-5-yl)-N-isopropylpyridin-3-amine [2086];

2-(3-(2-(5-(5-((dimethylamino)methyl)pyridin-3-yl)-1H-indazol-3-yl)-1H-imidazo[4,5-c]pyridin-4-yl)-5-fluorophenoxy)-N,N-dimethylethan-1-amine [2087];

2-(3-fluoro-5-(2-(5-(5-(pyrrolidin-1-ylmethyl)pyridin-3-yl)-1H-indazol-3-yl)-1H-imidazo[4,5-c]pyridin-4-yl)phenoxy)-N,N-dimethylethan-1-amine [2088];

2-(3-fluoro-5-(2-(5-(5-(piperidin-1-ylmethyl)pyridin-3-yl)-1H-indazol-3-yl)-1H-imidazo[4,5-c]pyridin-4-yl)phenoxy)-N,N-dimethylethan-1-amine [2089];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)-3,3-dimethylbutanamide [2090];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)butyramide [2091];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)pentanamide [2092];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)cyclopropanecarboxamide [2093];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)cyclobutanecarboxamide [2094];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)cyclopentanecarboxamide [2095];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)cyclohexanecarboxamide [2096];

2-(3-(2-(5-(5-((benzylamino)methyl)pyridin-3-yl)-1H-indazol-3-yl)-1H-imidazo[4,5-c]pyridin-4-yl)-5-fluorophenoxy)-N,N-dimethylethan-1-amine [2097];

2-(3-(2-(5-(5-(((cyclopentylmethyl)amino)methyl)pyridin-3-yl)-1H-indazol-3-yl)-1H-imidazo[4,5-c]pyridin-4-yl)-5-fluorophenoxy)-N,N-dimethylethan-1-amine [2098];

2-(3-(2-(5-(5-((3,3-difluoropyrrolidin-1-yl)methyl)pyridin-3-yl)-1H-indazol-3-yl)-1H-imidazo[4,5-c]pyridin-4-yl)-5-fluorophenoxy)-N,N-dimethylethan-1-amine [2099]; and 2-(3-fluoro-5-(2-(5-(pyrimidin-5-yl)-1H-indazol-3-yl)-1H-imidazo[4,5-c]pyridin-4-yl)phenoxy)-N,N-dimethylethan-1-amine [2100]; or a pharmaceutically acceptable salt thereof.

27. The method of claim 1, wherein the compound of Formula I is selected from the group consisting of:

2-(3-fluoro-5-(2-(5-(pyridin-2-yl)-1H-indazol-3-yl)-1H-imidazo[4,5-c]pyridin-4-yl)phenoxy)-N,N-dimethylethan-1-amine [2101];

2-(3-fluoro-5-(2-(5-(piperidin-4-yl)-1H-indazol-3-yl)-1H-imidazo[4,5-c]pyridin-4-yl)phenoxy)-N,N-dimethylethan-1-amine [2102];

2-(3-fluoro-5-(2-(5-(1,2,3,6-tetrahydropyridin-4-yl)-1H-indazol-3-yl)-1H-imidazo[4,5-c]pyridin-4-yl)phenoxy)-N,N-dimethylethan-1-amine [2103];

2-(3-(2-(5-(1H-pyrazol-4-yl)-1H-indazol-3-yl)-1H-imidazo[4,5-c]pyridin-4-yl)-5-fluorophenoxy)-N,N-dimethylethan-1-amine [2104];

2-(3-fluoro-5-(2-(5-(1-methyl-1H-pyrazol-4-yl)-1H-indazol-3-yl)-1H-imidazo[4,5-c]pyridin-4-yl)phenoxy)-N,N-dimethylethan-1-amine [2105];

2-(3-(2-(5-(1,2-dimethyl-1H-imidazol-5-yl)-1H-indazol-3-yl)-1H-imidazo[4,5-c]pyridin-4-yl)-5-fluorophenoxy)-N,N-dimethylethan-1-amine [2106];

1-(6-(3-(4-(3-(2-(dimethylamino)ethoxy)-5-fluorophenyl)-1H-imidazo[4,5-c]pyridin-2-yl)-1H-indazol-5-yl)pyrazin-2-yl)azetidin-3-amine [2107];

2-(3-(2-(5-(5-(cyclohexyloxy)pyridin-3-yl)-1H-indazol-3-yl)-1H-imidazo[4,5-c]pyridin-4-yl)-5-fluorophenoxy)-N,N-dimethylethan-1-amine [2108];

2-(3-fluoro-5-(2-(5-(5-(piperidin-4-yloxy)pyridin-3-yl)-1H-indazol-3-yl)-1H-imidazo[4,5-c]pyridin-4-yl)phenoxy)-N,N-dimethylethan-1-amine [2109];

N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)-2-(piperidin-4-yl)acetamide [2110];

2-(3-fluoro-5-(2-(5-(5-(2-(pyrrolidin-1-yl)ethoxy)pyridin-3-yl)-1H-indazol-3-yl)-1H-imidazo[4,5-c]pyridin-4-yl)phenoxy)-N,N-dimethylethan-1-amine [2111];

2-((5-(3-(4-(3-(2-(dimethylamino)ethoxy)-5-fluorophenyl)-1H-imidazo[4,5-c]pyridin-2-yl)-1H-indazol-5-yl)pyridin-3-yl)oxy)-N,N-dimethylethan-1-amine [2112];

2-(3-fluoro-5-(2-(5-(5-methoxypyridin-3-yl)-1H-indazol-3-yl)-1H-imidazo[4,5-c]pyridin-4-yl)phenoxy)-N,N-dimethylethan-1-amine [2113];

5-(3-(4-(3-(2-(dimethylamino)ethoxy)-5-fluorophenyl)-1H-imidazo[4,5-c]pyridin-2-yl)-1H-indazol-5-yl)pyridin-3-ol [2114];

2-(3-(2-(5-(5-(benzyloxy)pyridin-3-yl)-1H-indazol-3-yl)-1H-imidazo[4,5-c]pyridin-4-yl)-5-fluorophenoxy)-N,N-dimethylethan-1-amine [2115];

2-cyclohexyl-N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)acetamide [2116];

2-(3-fluoro-5-(2-(5-(pyridin-4-yl)-1H-indazol-3-yl)-1H-imidazo[4,5-c]pyridin-4-yl)phenoxy)-N,N-dimethylethan-1-amine [2117];

2-(3-fluoro-5-(2-(5-(pyrazin-2-yl)-1H-indazol-3-yl)-1H-imidazo[4,5-c]pyridin-4-yl)phenoxy)-N,N-dimethylethan-1-amine [2118];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)propionamide [2119];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)-3-methylbutanamide [2120];

5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-amine [2121];

4-(3-fluoro-5-(2-(pyrrolidin-1-yl)ethoxy)phenyl)-2-(5-(pyridin-3-yl)-1H-indazol-3-yl)-1H-imidazo[4,5-c]pyridine [2122];

4-(3-fluoro-5-(2-(pyrrolidin-1-yl)ethoxy)phenyl)-2-(5-(4-methylpyridin-3-yl)-1H-indazol-3-yl)-1H-imidazo[4,5-c]pyridine [2123];

N-((5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)methyl)ethanamine [2124];

5-(3-(4-(3-fluoro-5-(2-(pyrrolidin-1-yl)ethoxy)phenyl)-1H-imidazo[4,5-c]pyridin-2-yl)-1H-indazol-5-yl)-N,N-dimethylpyridin-3-amine [2125];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)pivalamide [2126];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)isobutyramide [2127];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)-2-phenylacetamide [2128];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)benzamide [2129];

5-(3-(4-(3-fluoro-5-(2-(pyrrolidin-1-yl)ethoxy)phenyl)-1H-imidazo[4,5-c]pyridin-2-yl)-1H-indazol-5-yl)-N-isopropylpyridin-3-amine [2130];

1-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)-N,N-dimethylmethanamine [2131];

4-(3-fluoro-5-(2-(pyrrolidin-1-yl)ethoxy)phenyl)-2-(5-(5-(pyrrolidin-1-ylmethyl)pyridin-3-yl)-1H-indazol-3-yl)-1H-imidazo[4,5-c]pyridine [2132];

4-(3-fluoro-5-(2-(pyrrolidin-1-yl)ethoxy)phenyl)-2-(5-(5-(piperidin-1-ylmethyl)pyridin-3-yl)-1H-indazol-3-yl)-1H-imidazo[4,5-c]pyridine [2133];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)-3,3-dimethylbutanamide [2134];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)butyramide [2135];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)pentanamide [2136];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)cyclopropanecarboxamide [2137];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)cyclobutanecarboxamide [2138];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)cyclopentanecarboxamide [2139];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)cyclohexanecarboxamide [2140];

N-benzyl-1-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)methanamine [2141];

1-cyclopentyl-N-((5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)methyl)methanamine [2142];

2-(5-(5-((3,3-difluoropyrrolidin-1-yl)methyl)pyridin-3-yl)-1H-indazol-3-yl)-4-(3-fluoro-5-(2-(pyrrolidin-1-yl)ethoxy)phenyl)-1H-imidazo[4,5-c]pyridine [2143];

4-(3-fluoro-5-(2-(pyrrolidin-1-yl)ethoxy)phenyl)-2-(5-(pyrimidin-5-yl)-1H-indazol-3-yl)-1H-imidazo[4,5-c]pyridine [2144];

4-(3-fluoro-5-(2-(pyrrolidin-1-yl)ethoxy)phenyl)-2-(5-(pyridin-2-yl)-1H-indazol-3-yl)-1H-imidazo[4,5-c]pyridine [2145];

4-(3-fluoro-5-(2-(pyrrolidin-1-yl)ethoxy)phenyl)-2-(5-(piperidin-4-yl)-1H-indazol-3-yl)-1H-imidazo[4,5-c]pyridine [2146];

4-(3-fluoro-5-(2-(pyrrolidin-1-yl)ethoxy)phenyl)-2-(5-(1,2,3,6-tetrahydropyridin-4-yl)-1H-indazol-3-yl)-1H-imidazo[4,5-c]pyridine [2147];

2-(5-(1H-pyrazol-4-yl)-1H-indazol-3-yl)-4-(3-fluoro-5-(2-(pyrrolidin-1-yl)ethoxy)phenyl)-1H-imidazo[4,5-c]pyridine [2148];

4-(3-fluoro-5-(2-(pyrrolidin-1-yl)ethoxy)phenyl)-2-(5-(1-methyl-1H-pyrazol-4-yl)-1H-indazol-3-yl)-1H-imidazo[4,5-c]pyridine [2149];

2-(5-(1,2-dimethyl-1H-imidazol-5-yl)-1H-indazol-3-yl)-4-(3-fluoro-5-(2-(pyrroliddin-1-yl)ethoxy)phenyl)-1H-imidazo[4,5-c]pyridine [2150];

1-(6-(3-(4-(3-fluoro-5-(2-(pyrrolidin-1-yl)ethoxy)phenyl)-1H-imidazo[4,5-c]pyridin-2-yl)-1H-indazol-5-yl)pyrazin-2-yl)azetidin-3-amine [2151];

2-(5-(5-(cyclohexyloxy)pyridin-3-yl)-1H-indazol-3-yl)-4-(3-fluoro-5-(2-(pyrrolidin-1-yl)ethoxy)phenyl)-1H-imidazo[4,5-c]pyridine [2152];

4-(3-fluoro-5-(2-(pyrrolidin-1-yl)ethoxy)phenyl)-2-(5-(5-(piperidin-4-yloxy)pyridin-3-yl)-1H-indazol-3-yl)-1H-imidazo[4,5-c]pyridine [2153];

N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)-2-(piperidin-4-yl)acetamide [2154];

4-(3-fluoro-5-(2-(pyrrolidin-1-yl)ethoxy)phenyl)-2-(5-(5-(2-(pyrrolidin-1-yl)ethoxy)pyridin-3-yl)-1H-indazol-3-yl)-1H-imidazo[4,5-c]pyridine [2155];

2-((5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)oxy)-N,N-dimethylethan-1-amine [2156];

4-(3-fluoro-5-(2-(pyrrolidin-1-yl)ethoxy)phenyl)-2-(5-(5-methoxypyridin-3-yl)-1H-indazol-3-yl)-1H-imidazo[4,5-c]pyridine [2157];

5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-ol [2158];

2-(5-(5-(benzyloxy)pyridin-3-yl)-1H-indazol-3-yl)-4-(3-fluoro-5-(2-(pyrrolidin-1-yl)ethoxy)phenyl)-1H-imidazo[4,5-c]pyridine [2159];

2-cyclohexyl-N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)acetamide [2160];

4-(3-fluoro-5-(2-(pyrrolidin-1-yl)ethoxy)phenyl)-2-(5-(pyridin-4-yl)-1H-indazol-3-yl)-1H-imidazo[4,5-c]pyridine [2161];

4-(3-fluoro-5-(2-(pyrrolidin-1-yl)ethoxy)phenyl)-2-(5-(pyrazin-2-yl)-1H-indazol-3-yl)-1H-imidazo[4,5-c]pyridine [2162];

N-(5-(3-(4-(3-fluoro-5-hydroxyphenyl)-1H-imidazo[4,5-c]pyridin-2-yl)-1H-indazol-5-yl)pyridin-3-yl)propionamide [2163];

N-(5-(3-(4-(3-fluoro-5-hydroxyphenyl)-1H-imidazo[4,5-c]pyridin-2-yl)-1H-indazol-5-yl)pyridin-3-yl)-3-methylbutanamide [2164];

3-(2-(5-(5-aminopyridin-3-yl)-1H-indazol-3-yl)-1H-imidazo[4,5-c]pyridin-4-yl)-5-fluorophenol [2165];

3-fluoro-5-(2-(5-(pyridin-3-yl)-1H-indazol-3-yl)-1H-imidazo[4,5-c]pyridin-4-yl)phenol [2166];

3-fluoro-5-(2-(5-(4-methylpyridin-3-yl)-1H-indazol-3-yl)-1H-imidazo[4,5-c]pyridin-4-yl)phenol [2167];

3-(2-(5-(5-((ethylamino)methyl)pyridin-3-yl)-1H-indazol-3-yl)-1H-imidazo[4,5-c]pyridin-4-yl)-5-fluorophenol [2168];

3-(2-(5-(5-(dimethylamino)pyridin-3-yl)-1H-indazol-3-yl)-1H-imidazo[4,5-c]pyridin-4-yl)-5-fluorophenol [2169];

N-(5-(3-(4-(3-fluoro-5-hydroxyphenyl)-1H-imidazo[4,5-c]pyridin-2-yl)-1H-indazol-5-yl)pyridin-3-yl)pivalamide [2170];

N-(5-(3-(4-(3-fluoro-5-hydroxyphenyl)-1H-imidazo[4,5-c]pyridin-2-yl)-1H-indazol-5-yl)pyridin-3-yl)isobutyramide [2171];

N-(5-(3-(4-(3-fluoro-5-hydroxyphenyl)-1H-imidazo[4,5-c]pyridin-2-yl)-1H-indazol-5-yl)pyridin-3-yl)-2-phenylacetamide [2172];

N-(5-(3-(4-(3-fluoro-5-hydroxyphenyl)-1H-imidazo[4,5-c]pyridin-2-yl)-1H-indazol-5-yl)pyridin-3-yl)benzamide [2173];

3-fluoro-5-(2-(5-(5-(isopropylamino)pyridin-3-yl)-1H-indazol-3-yl)-1H-imidazo[4,5-c]pyridin-4-yl)phenol [2174];

3-(2-(5-(5-((dimethylamino)methyl)pyridin-3-yl)-1H-indazol-3-yl)-1H-imidazo[4,5-c]pyridin-4-yl)-5-fluorophenol [2175];

3-fluoro-5-(2-(5-(5-(pyrrolidin-1-ylmethyl)pyridin-3-yl)-1H-indazol-3-yl)-1H-imidazo[4,5-c]pyridin-4-yl)phenol [2176];

3-fluoro-5-(2-(5-(5-(piperidin-1-ylmethyl)pyridin-3-yl)-1H-indazol-3-yl)-1H-imidazo[4,5-c]pyridin-4-yl)phenol [2177];

N-(5-(3-(4-(3-fluoro-5-hydroxyphenyl)-1H-imidazo[4,5-c]pyridin-2-yl)-1H-indazol-5-yl)pyridin-3-yl)-3,3-dimethylbutanamide [2178];

N-(5-(3-(4-(3-fluoro-5-hydroxyphenyl)-1H-imidazo[4,5-c]pyridin-2-yl)-1H-indazol-5-yl)pyridin-3-yl)butyramide [2179];

N-(5-(3-(4-(3-fluoro-5-hydroxyphenyl)-1H-imidazo[4,5-c]pyridin-2-yl)-1H-indazol-5-yl)pyridin-3-yl)pentanamide [2180];

N-(5-(3-(4-(3-fluoro-5-hydroxyphenyl)-1H-imidazo[4,5-c]pyridin-2-yl)-1H-indazol-5-yl)pyridin-3-yl)cyclopropanecarboxamide [2181];

N-(5-(3-(4-(3-fluoro-5-hydroxyphenyl)-1H-imidazo[4,5-c]pyridin-2-yl)-1H-indazol-5-yl)pyridin-3-yl)cyclobutanecarboxamide [2182];

N-(5-(3-(4-(3-fluoro-5-hydroxyphenyl)-1H-imidazo[4,5-c]pyridin-2-yl)-1H-indazol-5-yl)pyridin-3-yl)cyclopentanecarboxamide [2183];

N-(5-(3-(4-(3-fluoro-5-hydroxyphenyl)-1H-imidazo[4,5-c]pyridin-2-yl)-1H-indazol-5-yl)pyridin-3-yl)cyclohexanecarboxamide [2184];

3-(2-(5-(5-((benzylamino)methyl)pyridin-3-yl)-1H-indazol-3-yl)-1H-imidazo[4,5-c]pyridin-4-yl)-5-fluorophenol [2185];

3-(2-(5-(5-(((cyclopentylmethyl)amino)methyl)pyridin-3-yl)-1H-indazol-3-yl)-1H-imidazo[4,5-c]pyridin-4-yl)-5-fluorophenol [2186];

3-(2-(5-(5-((3,3-difluoropyrrolidin-1-yl)methyl)pyridin-3-yl)-1H-indazol-3-yl)-1H-imidazo[4,5-c]pyridin-4-yl)-5-fluorophenol [2187];

3-fluoro-5-(2-(5-(pyrimidin-5-yl)-1H-indazol-3-yl)-1H-imidazo[4,5-c]pyridin-4-yl)phenol [2188];

3-fluoro-5-(2-(5-(pyridin-2-yl)-1H-indazol-3-yl)-1H-imidazo[4,5-c]pyridin-4-yl)phenol [2189];

3-fluoro-5-(2-(5-(piperidin-4-yl)-1H-indazol-3-yl)-1H-imidazo[4,5-c]pyridin-4-yl)phenol [2190];

3-fluoro-5-(2-(5-(1,2,3,6-tetrahydropyridin-4-yl)-1H-indazol-3-yl)-1H-imidazo[4,5-c]pyridin-4-yl)phenol [2191];

3-(2-(5-(1H-pyrazol-4-yl)-1H-indazol-3-yl)-1H-imidazo[4,5-c]pyridin-4-yl)-5-fluorophenol [2192];

3-fluoro-5-(2-(5-(1-methyl-1H-pyrazol-4-yl)-1H-indazol-3-yl)-1H-imidazo[4,5-c]pyridin-4-yl)phenol [2193];

3-(2-(5-(1,2-dimethyl-1H-imidazol-5-yl)-1H-indazol-3-yl)-1H-imidazo[4,5-c]pyridin-4-yl)-5-fluorophenol [2194];

3-(2-(5-(6-(3-aminoazetidin-1-yl)pyrazin-2-yl)-1H-indazol-3-yl)-1H-imidazo[4,5-c]pyridin-4-yl)-5-fluorophenol [2195];

3-(2-(5-(5-(cyclohexyloxy)pyridin-3-yl)-1H-indazol-3-yl)-1H-imidazo[4,5-c]pyridin-4-yl)-5-fluorophenol [2196];

3-fluoro-5-(2-(5-(5-(piperidin-4-yloxy)pyridin-3-yl)-1H-indazol-3-yl)-1H-imidazo[4,5-c]pyridin-4-yl)phenol [2197];

N-(5-(3-(4-(3-fluoro-5-hydroxyphenyl)-1H-imidazo[4,5-c]pyridin-2-yl)-1H-indazol-5-yl)pyridin-3-yl)-2-(piperidin-4-yl)acetamide [2198];

3-fluoro-5-(2-(5-(5-(2-(pyrrolidin-1-yl)ethoxy)pyridin-3-yl)-1H-indazol-3-yl)-1H-imidazo[4,5-c]pyridin-4-yl)phenol [2199]; and 3-(2-(5-(5-(2-(dimethylamino)ethoxy)pyridin-3-yl)-1H-indazol-3-yl)-1H-imidazo[4,5-c]pyridin-4-yl)-5-fluorophenol [2200]; or a pharmaceutically acceptable salt thereof.

28. The method of claim 1, wherein the compound of Formula I is selected from the group consisting of:

3-fluoro-5-(2-(5-(5-methoxypyridin-3-yl)-1H-indazol-3-yl)-1H-imidazo[4,5-c]pyridin-4-yl)phenol [2201];

5-(3-(4-(3-fluoro-5-hydroxyphenyl)-1H-imidazo[4,5-c]pyridin-2-yl)-1H-indazol-5-yl)pyridin-3-ol [2202];

3-(2-(5-(5-(benzyloxy)pyridin-3-yl)-1H-indazol-3-yl)-1H-imidazo[4,5-c]pyridin-4-yl)-5-fluorophenol [2203];

2-cyclohexyl-N-(5-(3-(4-(3-fluoro-5-hydroxyphenyl)-1H-imidazo[4,5-c]pyridin-2-yl)-1H-indazol-5-yl)pyridin-3-yl)acetamide [2204];

3-fluoro-5-(2-(5-(pyridin-4-yl)-1H-indazol-3-yl)-1H-imidazo[4,5-c]pyridin-4-yl)phenol [2205];

3-fluoro-5-(2-(5-(pyrazin-2-yl)-1H-indazol-3-yl)-1H-imidazo[4,5-c]pyridin-4-yl)phenol [2206];

N-(5-(3-(4-(3-fluoro-5-methoxyphenyl)-1H-imidazo[4,5-c]pyridin-2-yl)-1H-indazol-5-yl)pyridin-3-yl)propionamide [2207];

N-(5-(3-(4-(3-fluoro-5-methoxyphenyl)-1H-imidazo[4,5-c]pyridin-2-yl)-1H-indazol-5-yl)pyridin-3-yl)-3-methylbutanamide [2208];

5-(3-(4-(3-fluoro-5-methoxyphenyl)-1H-imidazo[4,5-c]pyridin-2-yl)-1H-indazol-5-yl)pyridin-3-amine [2209];

4-(3-fluoro-5-methoxyphenyl)-2-(5-(pyridin-3-yl)-1H-indazol-3-yl)-1H-imidazo[4,5-c]pyridine [2210];

4-(3-fluoro-5-methoxyphenyl)-2-(5-(4-methylpyridin-3-yl)-1H-indazol-3-yl)-1H-imidazo[4,5-c]pyridine [2211];

N-((5-(3-(4-(3-fluoro-5-methoxyphenyl)-1H-imidazo[4,5-c]pyridin-2-yl)-1H-indazol-5-yl)pyridin-3-yl)methyl)ethanamine [2212];

5-(3-(4-(3-fluoro-5-methoxyphenyl)-1H-imidazo[4,5-c]pyridin-2-yl)-1H-indazol-5-yl)-N,N-dimethylpyridin-3-amine [2213];

N-(5-(3-(4-(3-fluoro-5-methoxyphenyl)-1H-imidazo[4,5-c]pyridin-2-yl)-1H-indazol-5-yl)pyridin-3-yl)pivalamide [2214];

N-(5-(3-(4-(3-fluoro-5-methoxyphenyl)-1H-imidazo[4,5-c]pyridin-2-yl)-1H-indazol-5-yl)pyridin-3-yl)isobutyramide [2215];

N-(5-(3-(4-(3-fluoro-5-methoxyphenyl)-1H-imidazo[4,5-c]pyridin-2-yl)-1H-indazol-5-yl)pyridin-3-yl)-2-phenylacetamide [2216];

N-(5-(3-(4-(3-fluoro-5-methoxyphenyl)-1H-imidazo[4,5-c]pyridin-2-yl)-1H-indazol-5-yl)pyridin-3-yl)benzamide [2217];

5-(3-(4-(3-fluoro-5-methoxyphenyl)-1H-imidazo[4,5-c]pyridin-2-yl)-1H-indazol-5-yl)-N-isopropylpyridin-3-amine [2218];

1-(5-(3-(4-(3-fluoro-5-methoxyphenyl)-1H-imidazo[4,5-c]pyridin-2-yl)-1H-indazol-5-yl)pyridin-3-yl)-N,N-dimethylmethanamine [2219];

4-(3-fluoro-5-methoxyphenyl)-2-(5-(5-(pyrrolidin-1-ylmethyl)pyridin-3-yl)-1H-indazol-3-yl)-1H-imidazo[4,5-c]pyridine [2220];

4-(3-fluoro-5-methoxyphenyl)-2-(5-(5-(piperidin-1-ylmethyl)pyridin-3-yl)-1H-indazol-3-yl)-1H-imidazo[4,5-c]pyridine [2221];

N-(5-(3-(4-(3-fluoro-5-methoxyphenyl)-1H-imidazo[4,5-c]pyridin-2-yl)-1H-indazol-5-yl)pyridin-3-yl)-3,3-dimethylbutanamide [2222];

N-(5-(3-(4-(3-fluoro-5-methoxyphenyl)-1H-imidazo[4,5-c]pyridin-2-yl)-1H-indazol-5-yl)pyridin-3-yl)butyramide [2223];

N-(5-(3-(4-(3-fluoro-5-methoxyphenyl)-1H-imidazo[4,5-c]pyridin-2-yl)-1H-indazol-5-yl)pyridin-3-yl)pentanamide [2224];

N-(5-(3-(4-(3-fluoro-5-methoxyphenyl)-1H-imidazo[4,5-c]pyridin-2-yl)-1H-indazol-5-yl)pyridin-3-yl)cyclopropanecarboxamide [2225];

N-(5-(3-(4-(3-fluoro-5-methoxyphenyl)-1H-imidazo[4,5-c]pyridin-2-yl)-1H-indazol-5-yl)pyridin-3-yl)cyclobutanecarboxamide [2226];

N-(5-(3-(4-(3-fluoro-5-methoxyphenyl)-1H-imidazo[4,5-c]pyridin-2-yl)-1H-indazol-5-yl)pyridin-3-yl)cyclopentanecarboxamide [2227];

N-(5-(3-(4-(3-fluoro-5-methoxyphenyl)-1H-imidazo[4,5-c]pyridin-2-yl)-1H-indazol-5-yl)pyridin-3-yl)cyclohexanecarboxamide [2228];

N-benzyl-1-(5-(3-(4-(3-fluoro-5-methoxyphenyl)-1H-imidazo[4,5-c]pyridin-2-yl)-1H-indazol-5-yl)pyridin-3-yl)methanamine [2229];

1-cyclopentyl-N-((5-(3-(4-(3-fluoro-5-methoxyphenyl)-1H-imidazo [4,5-c]pyridin-2-yl)-1H-indazol-5-yl)pyridin-3-yl)methyl)methanamine [2230];

2-(5-(5-((3,3-difluoropyrrolidin-1-yl)methyl)pyridin-3-yl)-1H-indazol-3-yl)-4-(3-fluoro-5-methoxyphenyl)-1H-imidazo[4,5-c]pyridine [2231];

4-(3-fluoro-5-methoxyphenyl)-2-(5-(pyrimidin-5-yl)-1H-indazol-3-yl)-1H-imidazo[4,5-c]pyridine [2232];

4-(3-fluoro-5-methoxyphenyl)-2-(5-(pyridin-2-yl)-1H-indazol-3-yl)-1H-imidazo[4,5-c]pyridine [2233];

4-(3-fluoro-5-methoxyphenyl)-2-(5-(piperidin-4-yl)-1H-indazol-3-yl)-1H-imidazo[4,5-c]pyridine [2234];

4-(3-fluoro-5-methoxyphenyl)-2-(5-(1,2,3,6-tetrahydropyridin-4-yl)-1H-indazol-3-yl)-1H-imidazo[4,5-c]pyridine [2235];

2-(5-(1H-pyrazol-4-yl)-1H-indazol-3-yl)-4-(3-fluoro-5-methoxyphenyl)-1H-imidazo[4,5-c]pyridine [2236];

4-(3-fluoro-5-methoxyphenyl)-2-(5-(1-methyl-1H-pyrazol-4-yl)-1H-indazol-3-yl)-1H-imidazo[4,5-c]pyridine [2237];

2-(5-(1,2-dimethyl-1H-imidazol-5-yl)-1H-indazol-3-yl)-4-(3-fluoro-5-methoxyphenyl)-1H-imidazo[4,5-c]pyridine [2238];

1-(6-(3-(4-(3-fluoro-5-methoxyphenyl)-1H-imidazo[4,5-c]pyridin-2-yl)-1H-indazol-5-yl)pyrazin-2-yl)azetidin-3-amine [2239];

2-(5-(5-(cyclohexyloxy)pyridin-3-yl)-1H-indazol-3-yl)-4-(3-fluoro-5-methoxyphenyl)-1H-imidazo[4,5-c]pyridine [2240];

4-(3-fluoro-5-methoxyphenyl)-2-(5-(5-(piperidin-4-yloxy)pyridin-3-yl)-1H-indazol-3-yl)-1H-imidazo[4,5-c]pyridine [2241];

N-(5-(3-(4-(3-fluoro-5-methoxyphenyl)-1H-imidazo[4,5-c]pyridin-2-yl)-1H-indazol-5-yl)pyridin-3-yl)-2-(piperidin-4-yl)acetamide [2242];

4-(3-fluoro-5-methoxyphenyl)-2-(5-(5-(2-(pyrrolidin-1-yl)ethoxy)pyridin-3-yl)-1H-indazol-3-yl)-1H-imidazo[4,5-c]pyridine [2243];

2-((5-(3-(4-(3-fluoro-5-methoxyphenyl)-1H-imidazo[4,5-c]pyridin-2-yl)-1H-indazol-5-yl)pyridin-3-yl)oxy)-N,N-dimethylethan-1-amine [2244];

4-(3-fluoro-5-methoxyphenyl)-2-(5-(5-methoxypyridin-3-yl)-1H-indazol-3-yl)-1H-imidazo[4,5-c]pyridine [2245];

5-(3-(4-(3-fluoro-5-methoxyphenyl)-1H-imidazo[4,5-c]pyridin-2-yl)-1H-indazol-5-yl)pyridin-3-ol [2246];

2-(5-(5-(benzyloxy)pyridin-3-yl)-1H-indazol-3-yl)-4-(3-fluoro-5-methoxyphenyl)-1H-imidazo[4,5-c]pyridine [2247];

2-cyclohexyl-N-(5-(3-(4-(3-fluoro-5-methoxyphenyl)-1H-imidazo[4,5-c]pyridin-2-yl)-1H-indazol-5-yl)pyridin-3-yl)acetamide [2248];

4-(3-fluoro-5-methoxyphenyl)-2-(5-(pyridin-4-yl)-1H-indazol-3-yl)-1H-imidazo[4,5-c]pyridine [2249];

4-(3-fluoro-5-methoxyphenyl)-2-(5-(pyrazin-2-yl)-1H-indazol-3-yl)-1H-imidazo[4,5-c]pyridine [2250];

2-(dimethylamino)-N-(5-(3-(4-(3-fluorophenyl)-1H-imidazo[4,5-c]pyridin-2-yl)-1H-indazol-5-yl)pyridin-3-yl)acetamide [2251];

2-(dimethylamino)-N-(5-(3-(4-(4-fluorophenyl)-1H-imidazo[4,5-c]pyridin-2-yl)-1H-indazol-5-yl)pyridin-3-yl)acetamide [2252];

2-(dimethylamino)-N-(5-(3-(4-(2-fluorophenyl)-1H-imidazo[4,5-c]pyridin-2-yl)-1H-indazol-5-yl)pyridin-3-yl)acetamide [2253];

2-(dimethylamino)-N-(5-(3-(4-(pyridin-3-yl)-1H-imidazo[4,5-c]pyridin-2-yl)-1H-indazol-5-yl)pyridin-3-yl)acetamide [2254];

2-(dimethylamino)-N-(5-(3-(4-(pyridin-4-yl)-1H-imidazo[4,5-c]pyridin-2-yl)-1H-indazol-5-yl)pyridin-3-yl)acetamide [2255];

2-(dimethylamino)-N-(5-(3-(4-(pyridin-2-yl)-1H-imidazo[4,5-c]pyridin-2-yl)-1H-indazol-5-yl)pyridin-3-yl)acetamide [2256];

2-(dimethylamino)-N-(5-(3-(4-(piperidin-1-yl)-1H-imidazo[4,5-c]pyridin-2-yl)-1H-indazol-5-yl)pyridin-3-yl)acetamide [2257];

2-(dimethylamino)-N-(5-(3-(4-(4-methyl-1H-imidazol-1-yl)-1H-imidazo[4,5-c]pyridin-2-yl)-1H-indazol-5-yl)pyridin-3-yl)acetamide [2258];

2-(dimethylamino)-N-(5-(3-(4-(4-methylpiperazin-1-yl)-1H-imidazo[4,5-c]pyridin-2-yl)-1H-indazol-5-yl)pyridin-3-yl)acetamide [2259];

2-(dimethylamino)-N-(5-(3-(4-(thiophen-3-yl)-1H-imidazo[4,5-c]pyridin-2-yl)-1H-indazol-5-yl)pyridin-3-yl)acetamide [2260];

2-(dimethylamino)-N-(5-(3-(4-(furan-3-yl)-1H-imidazo[4,5-c]pyridin-2-yl)-1H-indazol-5-yl)pyridin-3-yl)acetamide [2261];

2-(dimethylamino)-N-(5-(3-(4-(thiophen-2-yl)-1H-imidazo[4,5-c]pyridin-2-yl)-1H-indazol-5-yl)pyridin-3-yl)acetamide [2262];

2-(dimethylamino)-N-(5-(3-(4-(5-fluorothiophen-2-yl)-1H-imidazo[4,5-c]pyridin-2-yl)-1H-indazol-5-yl)pyridin-3-yl)acetamide [2263];

2-(dimethylamino)-N-(5-(3-(4-(5-methylthiophen-2-yl)-1H-imidazo[4,5-c]pyridin-2-yl)-1H-indazol-5-yl)pyridin-3-yl)acetamide [2264];

N-(5-(3-(4-(5-acetylthiophen-2-yl)-1H-imidazo[4,5-c]pyridin-2-yl)-1H-indazol-5-yl)pyridin-3-yl)-2-(dimethylamino)acetamide [2265];

2-(dimethylamino)-N-(5-(3-(4-(3-fluoro-5-(methylsulfonamidomethyl)phenyl)-1H-imidazo[4,5-c]pyridin-2-yl)-1H-indazol-5-yl)pyridin-3-yl)acetamide [2266];

2-(dimethylamino)-N-(5-(3-(4-(3-((2-(dimethylamino)ethyl)amino)-5-fluorophenyl)-1H-imidazo[4,5-c]pyridin-2-yl)-1H-indazol-5-yl)pyridin-3-yl)acetamide [2267];

2-(dimethylamino)-N-(5-(3-(4-(3-(2-(dimethylamino)ethoxy)-5-fluorophenyl)-1H-imidazo[4,5-c]pyridin-2-yl)-1H-indazol-5-yl)pyridin-3-yl)acetamide [2268];

2-(dimethylamino)-N-(5-(3-(4-(3-fluoro-5-(2-(pyrrolidin-1-yl)ethoxy)phenyl)-1H-imidazo[4,5-c]pyridin-2-yl)-1H-indazol-5-yl)pyridin-3-yl)acetamide [2269];

2-(dimethylamino)-N-(5-(3-(4-(3-fluoro-5-hydroxyphenyl)-1H-imidazo[4,5-c]pyridin-2-yl)-1H-indazol-5-yl)pyridin-3-yl)acetamide [2270];

2-(dimethylamino)-N-(5-(3-(4-(3-fluoro-5-methoxyphenyl)-1H-imidazo[4,5-c]pyridin-2-yl)-1H-indazol-5-yl)pyridin-3-yl)acetamide [2271];

4-(2-(5-(pyridin-3-yl)-1H-indazol-3-yl)-1H-imidazo[4,5-c]pyridin-4-yl)morpholine [2272];

4-(4,4-difluoropiperidin-1-yl)-2-(5-(pyridin-3-yl)-1H-indazol-3-yl)-1H-imidazo[4,5-c]pyridine [2273];

4-(1-methylpiperidin-4-yl)-2-(5-(pyridin-3-yl)-1H-indazol-3-yl)-1H-imidazo[4,5-c]pyridine [2274];

4-(2-(5-(5-fluoropyridin-3-yl)-1H-indazol-3-yl)-1H-imidazo[4,5-c]pyridin-4-yl) morpholine [2275];

2-(5-(5-fluoropyridin-3-yl)-1H-indazol-3-yl)-4-(4-methylpiperazin-1-yl)-1H-imidazo[4,5-c]pyridine [2276];

4-(4,4-difluoropiperidin-1-yl)-2-(5-(5-fluoropyridin-3-yl)-1H-indazol-3-yl)-1H-imidazo[4,5-c]pyridine [2277];

2-(5-(5-fluoropyridin-3-yl)-1H-indazol-3-yl)-4-(1-methylpiperidin-4-yl)-1H-imidazo[4,5-c]pyridine [2278];

2-(5-(5-fluoropyridin-3-yl)-1H-indazol-3-yl)-4-(piperidin-1-yl)-1H-imidazo[4,5-c]pyridine [2278];

4-(2-(5-(1-methyl-1H-pyrazol-4-yl)-1H-indazol-3-yl)-1H-imidazo[4,5-c]pyridin-4-yl) morpholine [2280];

4-(4,4-difluoropiperidin-1-yl)-2-(5-(1-methyl-1H-pyrazol-4-yl)-1H-indazol-3-yl)-1H-imidazo[4,5-c]pyridine [2281];

2-(5-(1-methyl-1H-pyrazol-4-yl)-1H-indazol-3-yl)-4-(1-methylpiperidin-4-yl)-1H-imidazo[4,5-c]pyridine [2282];

4-(2-(5-(1-cyclopropyl-1H-pyrazol-4-yl)-1H-indazol-3-yl)-1H-imidazo[4,5-c]pyridin-4-yl)morpholine [2283];

2-(5-(1-cyclopropyl-1H-pyrazol-4-yl)-1H-indazol-3-yl)-4-(4-methylpiperazin-1-yl)-1H-imidazo[4,5-c]pyridine [2284];

2-(5-(1-cyclopropyl-1H-pyrazol-4-yl)-1H-indazol-3-yl)-4-(4,4-difluoropiperidin-1-yl)-1H-imidazo[4,5-c]pyridine [2285];

2-(5-(1-cyclopropyl-1H-pyrazol-4-yl)-1H-indazol-3-yl)-4-(1-methylpiperidin-4-yl)-1H-imidazo[4,5-c]pyridine [2286];

2-(5-(1-cyclopropyl-1H-pyrazol-4-yl)-1H-indazol-3-yl)-4-(piperidin-1-yl)-1H-imidazo[4,5-c]pyridine [2287];

4-(2-(5-(1H-pyrazol-4-yl)-1H-indazol-3-yl)-1H-imidazo[4,5-c]pyridin-4-yl)morpholine [2288];

2-(5-(1H-pyrazol-4-yl)-1H-indazol-3-yl)-4-(4,4-difluoropiperidin-1-yl)-1H-imidazo[4,5-c]pyridine [2289]; and 2-(5-(1H-pyrazol-4-yl)-1H-indazol-3-yl)-4-(1-methylpiperidin-4-yl)-1H-imidazo[4,5-c]pyridine [2290]; or a pharmaceutically acceptable salt thereof.

29. The method of claim 1, wherein the compound of Formula I is selected from the group consisting of:

N-(5-(3-(4-(3-fluorophenyl)-1H-imidazo[4,5-c]pyridin-2-yl)-1H-indazol-5-yl)pyridin-3-yl)propionamide [1];

N-(5-(3-(4-(3-fluorophenyl)-1H-imidazo[4,5-c]pyridin-2-yl)-1H-indazol-5-yl)pyridin-3-yl)-3-methylbutanamide [2];

5-(3-(4-(3-fluorophenyl)-1H-imidazo[4,5-c]pyridin-2-yl)-1H-indazol-5-yl)-N,N-dimethylpyridin-3-amine [7];

1-(5-(3-(4-(3-fluorophenyl)-1H-imidazo[4,5-c]pyridin-2-yl)-1H-indazol-5-yl)pyridin-3-yl)-N,N-dimethylmethanamine [13];

N-(5-(3-(4-(3-fluorophenyl)-1H-imidazo[4,5-c]pyridin-2-yl)-1H-indazol-5-yl)pyridin-3-yl)cyclopropanecarboxamide [19];

N-(5-(3-(4-(4-fluorophenyl)-1H-imidazo[4,5-c]pyridin-2-yl)-1H-indazol-5-yl)pyridin-3-yl)-3-methylbutanamide [28];

N-(5-(3-(4-(4-fluorophenyl)-1H-imidazo[4,5-c]pyridin-2-yl)-1H-indazol-5-yl)pyridin-3-yl)pivalamide [34];

N-(5-(3-(4-(4-fluorophenyl)-1H-imidazo[4,5-c]pyridin-2-yl)-1H-indazol-5-yl)pyridin-3-yl)cyclobutanecarboxamide [46];

5-(3-(4-(2-fluorophenyl)-1H-imidazo[4,5-c]pyridin-2-yl)-1H-indazol-5-yl)pyridin-3-amine [55];

N-(5-(3-(4-(2-fluorophenyl)-1H-imidazo[4,5-c]pyridin-2-yl)-1H-indazol-5-yl)pyridin-3-yl)isobutyramide [61];

N-(5-(3-(4-(2-fluorophenyl)-1H-imidazo[4,5-c]pyridin-2-yl)-1H-indazol-5-yl)pyridin-3-yl)-3,3-dimethylbutanamide [68];

N-(5-(3-(4-(2-fluorophenyl)-1H-imidazo[4,5-c]pyridin-2-yl)-1H-indazol-5-yl)pyridin-3-yl)butyramide [69];

N-(5-(3-(4-(2-fluorophenyl)-1H-imidazo[4,5-c]pyridin-2-yl)-1H-indazol-5-yl)pyridin-3-yl)cyclopentanecarboxamide [73];

4-(pyridin-3-yl)-2-(5-(pyridin-3-yl)-1H-indazol-3-yl)-1H-imidazo[4,5-c]pyridine [82];

N-(5-(3-(4-(pyridin-3-yl)-1H-imidazo[4,5-c]pyridin-2-yl)-1H-indazol-5-yl)pyridin-3-yl)isobutyramide [87];

N-isopropyl-5-(3-(4-(pyridin-3-yl)-1H-imidazo[4,5-c]pyridin-2-yl)-1H-indazol-5-yl)pyridin-3-amine [90];

N-((5-(3-(4-(pyridin-2-yl)-1H-imidazo[4,5-c]pyridin-2-yl)-1H-indazol-5-yl)pyridin-3-yl)methyl)ethanamine [136];

N,N-dimethyl-5-(3-(4-(piperidin-1-yl)-1H-imidazo[4,5-c]pyridin-2-yl)-1H-indazol-5-yl)pyridin-3-amine [163];

3-methyl-N-(5-(3-(4-(4-methyl-1H-imidazo-1-yl)-1H-imidazo[4,5-c]pyridin-2-yl)-1H-indazol-5-yl)pyridin-3-yl)butanamide [184];

N-(5-(3-(4-(4-methyl-1H-imidazo-1-yl)-1H-imidazo[4,5-c]pyridin-2-yl)-1H-indazol-5-yl)pyridin-3-yl)pivalamide [190];

N-(5-(3-(4-(4-methyl-1H-imidazo-1-yl)-1H-imidazo[4,5-c]pyridin-2-yl)-1H-indazol-5-yl) pyridin-3-yl)cyclobutanecarboxamide [202];

4-(4-methylpiperazin-1-yl)-2-(5-(pyrimidin-5-yl)-1H-indazol-3-yl)-1H-imidazo[4,5-c]pyridine [234];

2-(5-(4-methylpyridin-3-yl)-1H-indazol-3-yl)-4-(thiophen-3-yl)-1H-imidazo[4,5-c]pyridine [239];

N-(5-(3-(4-(thiophen-3-yl)-1H-imidazo[4,5-c]pyridin-2-yl)-1H-indazol-5-yl)pyridin-3-yl) butyramide [251];

N-benzyl-1-(5-(3-(4-(thiophen-3-yl)-1H-imidazo[4,5-c]pyridin-2-yl)-1H-indazol-5-yl)pyridin-3-yl)methanamine [257];

N-((5-(3-(4-(furan-3-yl)-1H-imidazo[4,5-c]pyridin-2-yl)-1H-indazol-5-yl)pyridin-3-yl)methyl)ethanamine [266];

5-(3-(4-(furan-3-yl)-1H-imidazo[4,5-c]pyridin-2-yl)-1H-indazol-5-yl)-N-isopropylpyridin-3-amine [272];

1-cyclopentyl-N-((5-(3-(4-(furan-3-yl)-1H-imidazo[4,5-c]pyridin-2-yl)-1H-indazol-5-yl)pyridin-3-yl)methyl)methanamine [284];

N-(5-(3-(4-(thiophen-2-yl)-1H-imidazo[4,5-c]pyridin-2-yl)-1H-indazol-5-yl)pyridin-3-yl)cyclopropanecarboxamide [305];

N-(5-(3-(4-(5-fluorothiophen-2-yl)-1H-imidazo[4,5-c]pyridin-2-yl)-1H-indazol-5-yl)pyridin-3-yl)pivalamide [320];

5-(3-(4-(5-methylthiophen-2-yl)-1H-imidazo[4,5-c]pyridin-2-yl)-1H-indazol-5-yl)pyridin-3-amine [341];

4-(5-methylthiophen-2-yl)-2-(5-(5-(piperidin-1-ylmethyl)pyridin-3-yl)-1H-indazol-3-yl)-1H-imidazo[4,5-c]pyridine [353];

N-(5-(3-(4-(5-methylthiophen-2-yl)-1H-imidazo[4,5-c]pyridin-2-yl)-1H-indazol-5-yl)pyridin-3-yl)cyclopentanecarboxamide [359];

1-(5-(2-(5-(pyridin-3-yl)-1H-indazol-3-yl)-1H-imidazo[4,5-c]pyridin-4-yl)thiophen-2-yl)ethan-1-one [368];

N-(5-(3-(4-(5-acetylthiophen-2-yl)-1H-imidazo[4,5-c]pyridin-2-yl)-1H-indazol-5-yl)pyridin-3-yl)-2-phenylacetamide [374];

N-(5-(3-(4-(3-fluoro-5-(methylsulfonamidomethyl)phenyl)-1H-imidazo[4,5-c]pyridin-2-yl)-1H-indazol-5-yl)pyridin-3-yl)-2-phenylacetamide [400];

N-(3-(2-(5-(5-((benzylamino)methyl)pyridin-3-yl)-1H-indazol-3-yl)-1H-imidazo[4,5-c]pyridin-4-yl)-5-fluorobenzyl)methanesulfonamide [413];

N-(3-fluoro-5-(2-(5-(pyrimidin-5-yl)-1H-indazol-3-yl)-1H-imidazo[4,5-c]pyridin-4-yl)benzyl)methanesulfonamide [416];

$N^1$-(3-fluoro-5-(2-(5-(5-(isopropylamino)pyridin-3-yl)-1H-indazol-3-yl)-1H-imidazo[4,5-c]pyridin-4-yl)phenyl)-$N^2$,$N^2$-dimethylethane-1,2-diamine [428];

$N^1$-(3-(2-(5-(5-(((cyclopentylmethyl)amino)methyl)pyridin-3-yl)-1H-indazol-3-yl)-1H-imidazo[4,5-c]pyridin-4-yl)-5-fluorophenyl)-$N^2$,$N^2$-dimethylethane-1,2-diamine [440];

2-(5-(1H-pyrazol-4-yl)-1H-indazol-3-yl)-4-(3-fluorophenyl)-1H-imidazo[4,5-c]pyridine [1771];

2-(5-(5-(cyclohexyloxy)pyridin-3-yl)-1H-indazol-3-yl)-4-(3-fluorophenyl)-1H-imidazo[4,5-c]pyridine [1775];

5-(3-(4-(3-fluorophenyl)-1H-imidazo[4,5-c]pyridin-2-yl)-1H-indazol-5-yl)pyridin-3-ol [1781];

4-(3-fluorophenyl)-2-(5-(pyridin-2-yl)-1H-indazol-3-yl)-1H-imidazo[4,5-c]pyridine [1785];

4-(3-fluorophenyl)-2-(5-(pyrazin-2-yl)-1H-indazol-3-yl)-1H-imidazo[4,5-c]pyridine [1786];

2-(5-(1-methyl-1H-pyrazol-4-yl)-1H-indazol-3-yl)-4-(4-methylpiperazin-1-yl)-1H-imidazo[4,5-c]pyridine [1916];

4-(2-(5-(1-methyl-1H-pyrazol-4-yl)-1H-indazol-3-yl)-1H-imidazo[4,5-c]pyridin-4-yl)morpholine [2280]; and 2-(5-(1-cyclopropyl-1H-pyrazol-4-yl)-1H-indazol-3-yl)-4-(4-methylpiperazin-1-yl)-1H-imidazo[4,5-c]pyridine [2284]; or a pharmaceutically acceptable salt thereof.

30. The method of claim 1, wherein the compound of Formula I is selected from the group consisting of:

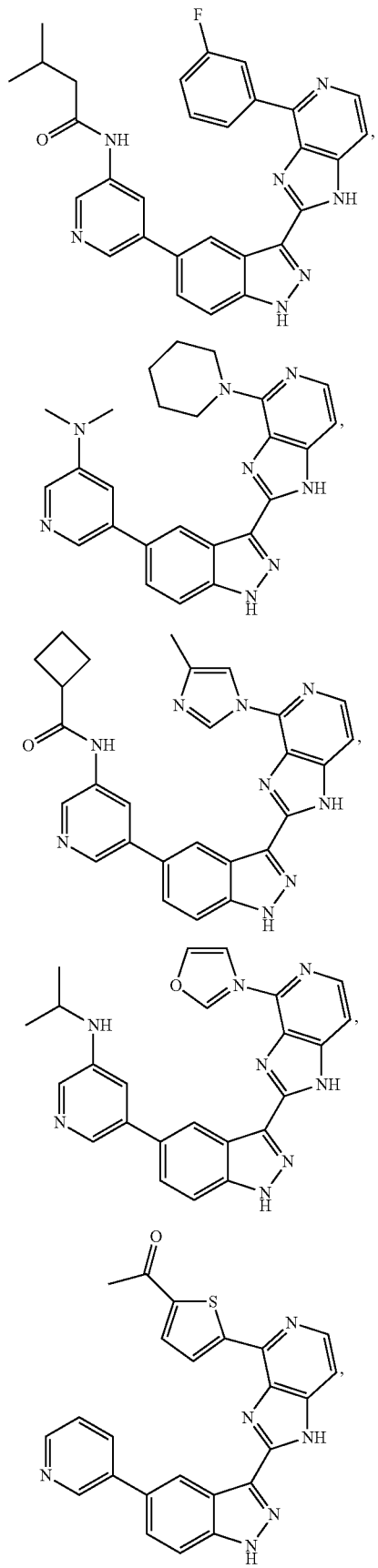

-continued

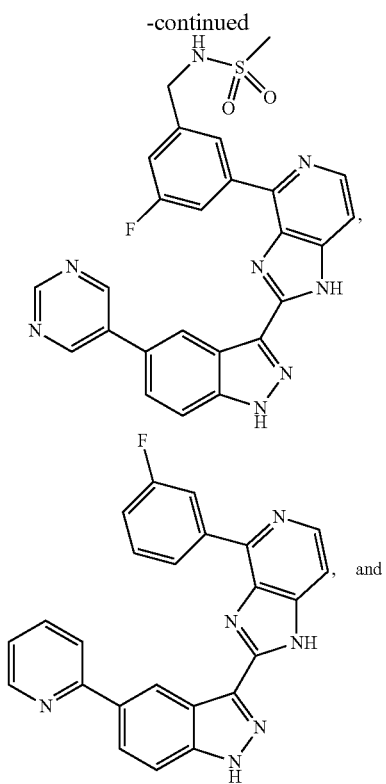

-continued

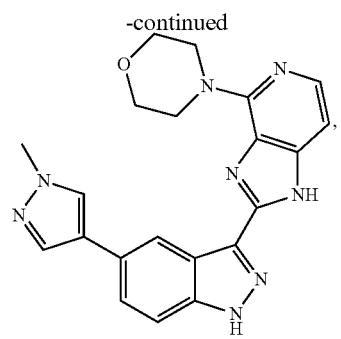

or a pharmaceutically acceptable salt thereof.

31. The method of claim 1, wherein the bone or cartilage disease is osteoarthritis.

32. The method of claim 1, wherein the bone or cartilage disease is articular cartilage (chondral) defects.

33. The method of claim 1, wherein the bone or cartilage disease is degenerative disc disease.

34. The method of claim 1, wherein the bone or cartilage disease is relapsing polychondritis.

35. The method of claim 1, wherein the bone or cartilage disease is osteochondritis dissecans.

36. The method of claim 1, wherein the subject is a human.

* * * * *

UNITED STATES PATENT AND TRADEMARK OFFICE
CERTIFICATE OF CORRECTION

PATENT NO. : 9,828,372 B2
APPLICATION NO. : 15/298346
DATED : November 28, 2017
INVENTOR(S) : Sunil Kumar KC et al.

Page 1 of 2

It is certified that error appears in the above-identified patent and that said Letters Patent is hereby corrected as shown below:

In the Claims

Column 724, Line 25, in Claim 1, delete "–NR$^{15}$(C$_{1-6}$  alkylene)" and insert
-- –NR$^{15}$(C$_{1-6}$ alkylene) --, therefor.
Column 725, Line 18, in Claim 5, delete "claim 2," and insert -- claim 4, --, therefor.
Column 732, Line 60, in Claim 20, delete "imidazo" and insert -- imidazol --, therefor.
Column 732, Line 63, in Claim 20, delete "imidazo" and insert -- imidazol --, therefor.
Column 733, Line 11, in Claim 20, delete "imidazo" and insert -- imidazol --, therefor.
Column 733, Line 14, in Claim 20, delete "imidazo" and insert -- imidazol --, therefor.
Column 733, Line 17, in Claim 20, delete "imidazo" and insert -- imidazol --, therefor.
Column 733, Line 20, in Claim 20, delete "imidazo" and insert -- imidazol --, therefor.
Column 733, Line 47, in Claim 21, delete "imidazo" and insert -- imidazol --, therefor.
Column 733, Line 50, in Claim 21, delete "imidazo" and insert -- imidazol --, therefor.
Column 735, Line 27, in Claim 21, delete "3-yl)-H-imidazo[4,5-c]" and insert
-- 3-yl)-1H-imidazo[4,5-c] --, therefor.
Column 736, Line 16, in Claim 21, after "[262]" insert -- ; --.
Column 748, Line 55, in Claim 24, delete "(benzyl oxy)" and insert -- (benzyloxy) --, therefor.
Column 749, Line 5, in Claim 24, delete "imidazo" and insert -- imidazol --, therefor.
Column 749, Line 6, in Claim 24, delete "(1 -methyl-1H" and insert -- (1-methyl-1H --, therefor.
Column 754, Line 61, in Claim 26, delete "[2045];" and insert -- [2044]; --, therefor.
Column 759, Line 57, in Claim 27, delete "(pyrroliddin" and insert -- (pyrrolidin --, therefor.
Column 763, Line 23, in Claim 28, delete "1H-imidazo [4,5-c]" and insert -- 1H-imidazo[4,5-c] --, therefor.
Column 765, Line 18, in Claim 28, delete "4-yl) morpholine" and insert -- 4-yl)morpholine --, therefor.
Column 765, Line 27, in Claim 28, delete "[2278];" and insert -- [2279]; --, therefor.
Column 766, Line 42, in Claim 29, delete "imidazo" and insert -- imidazol --, therefor.
Column 766, Line 45, in Claim 29, delete "imidazo" and insert -- imidazol --, therefor.
Column 766, Line 48, in Claim 29, delete "imidazo" and insert -- imidazol --, therefor.

Signed and Sealed this
Twenty-ninth Day of December, 2020

Andrei Iancu
*Director of the United States Patent and Trademark Office*

CERTIFICATE OF CORRECTION (continued)
U.S. Pat. No. 9,828,372 B2

Column 766, Line 49, in Claim 29, delete "5-yl) pyridin-3-yl)" and insert -- 5-yl)pyridin-3-yl) --, therefor.
Column 766, Line 56, in Claim 29, delete "3-yl) butyramide" and insert -- 3-yl)butyramide --, therefor.

Column 768, Line 45, in Claim 30, delete " 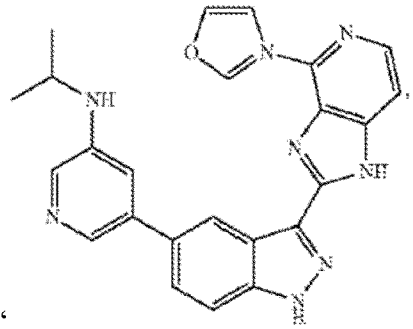 " and insert -- 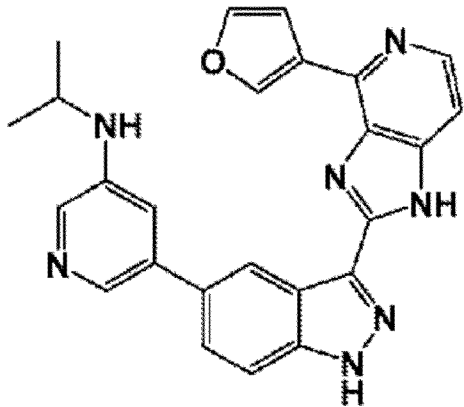 --, therefor.